US008816152B2

(12) United States Patent
Elich et al.

(10) Patent No.: US 8,816,152 B2
(45) Date of Patent: Aug. 26, 2014

(54) REGULATORY POLYNUCLEOTIDES AND USES THEREOF

(75) Inventors: Tedd D. Elich, Durham, NC (US); Philip N. Benfey, Chapel Hill, NC (US); Ai-Jiuan Wu, Carrboro, NC (US); David A. Orlando, Durham, NC (US); Ian Davis, Durham, NC (US)

(73) Assignee: Monsanto Technology LLC, St. Louis, MO (US)

(*) Notice: Subject to any disclaimer, the term of this patent is extended or adjusted under 35 U.S.C. 154(b) by 0 days.

(21) Appl. No.: 13/528,515

(22) Filed: Jun. 20, 2012

(65) Prior Publication Data

US 2012/0284880 A1 Nov. 8, 2012

Related U.S. Application Data

(63) Continuation of application No. PCT/US2010/061793, filed on Dec. 22, 2010.

(60) Provisional application No. 61/289,771, filed on Dec. 23, 2009, provisional application No. 61/298,765, filed on Jan. 27, 2010, provisional application No. 61/299,053, filed on Jan. 28, 2010, provisional application No. 61/385,243, filed on Sep. 22, 2010.

(51) Int. Cl.

| | |
|---|---|
| ***C12N 15/113*** | (2010.01) |
| ***C12N 15/63*** | (2006.01) |
| ***C12N 15/82*** | (2006.01) |
| ***C07H 21/00*** | (2006.01) |

(52) U.S. Cl.

USPC ........... 800/278; 800/298; 800/306; 800/312; 800/314; 800/317.2; 800/320; 800/320.1; 800/320.3; 435/410; 435/320.1; 435/419; 536/24.1

(58) Field of Classification Search

None

See application file for complete search history.

(56) References Cited

U.S. PATENT DOCUMENTS

| | | | | |
|---|---|---|---|---|
| 6,462,258 | B1 * | 10/2002 | Fincher et al. | 800/300 |
| 2007/0020621 | A1 * | 1/2007 | Boukharov et al. | 435/6 |
| 2008/0114160 | A1 | 5/2008 | Boukharov et al. | |
| 2008/0141585 | A1 | 6/2008 | Benfey et al. | |

FOREIGN PATENT DOCUMENTS

| | | | | |
|---|---|---|---|---|
| EP | WO03000898 | * | 3/2003 | C07K 14/415 |
| WO | WO 2008/064128 | | 5/2008 | |
| WO | WO 2011/079197 | | 6/2011 | |

OTHER PUBLICATIONS

Rombauts et al. Computational appraoches to identify promoters and cis-regulatory elements in plant genomes. Plant Physiology. 2003. 132: 1162-1176.*

Kim et al. A 20 nucleotide upstream element is essential for the nopaline synthase (nos) promoter activity. Plant Molecular Biology. 1994. 24: 105-117.*

SnapGene. pBeloBAC11 plasmid vector. 2013.*

Random House Dictionary. Derive. 2013. http://dictionary.reference.com/browse/derive?s=t&path=/.*

Clontech. Genome Walker User Manual. 2007.*

Brady et al., "A High-Resolution Root Spatiotemporal Map Reveals Dominant Expresson Patterns," *Science*, 318:801-806 (2007).

Schmid et al., "A Gene Expression Map of *Arabidopsis thaliana* Development," *Nat. Genet.*, 37(5):501-506 (2005).

AtGeneExpress Expression Atlas of *Arabidopsis thaliana* (Laubinger, Schmid, Weigel), available on the World Wide Web at weigelworld.org/resources/microarray/AtGenExpress, printed Jul. 25, 2012.

Kilian et al., "The AtGenExpress Global Stress Expression Data Set: Protocols, Evaluation and Model Data Analysis of UV-B Light, Drought and Cold Stress Responses," *Plant J.*, 50:347-363 (2007).

Lee et al., "Transcriptional and Posttranscriptional Regulation of Transcription Factor Expression in *Arabidopsis* Roots," *Proc Natl Acad Sci U S A*, 103(15):6055-6060 (2006).

Clough and Bent, "Floral Dip: A Simplified Method for Agrobacterium-Mediated Transformation of *Arabidopsis thaliana*," *Plant J*, 16(6), 735-743 (1998).

Hirose et al., "Overexpression of a Type-A Response Regulator Alters Rice Morphology and Cytokinin Metabolism," *Plant Cell Physiol.*, 48(3):523-539 (2007).

Jain et al., F-Box Proteins in Rice. Genome-Wide Analysis, Classification, Temporal and Spatial Gene Expression during Panicle and Seed Development, and Regulation by Light and Abiotic Stress[1[W][OA]], *Plant Physiol.*, 143:1467-1483 (2007).

Rice Genome Annotation Project, available on the worldwide web at rice.plantbiology.msu.edu/index.shtml, printed Jul. 25, 2012.

Moreno-Hagelsieb and Latimer, "Choosing BLAST Options for Better Detection of Orthologs as Reciprocal Best Hits," *Bioinformatics*, 24(3):319-324 (2008).

McElroy et. al., "Isolation of an Efficient Actin Promoter for Use in Rice Transformation," *Plant Cell*, 2:163-171 (1990).

Jefferson et al., "GUS Fusions: β-glucuronidase as a Sensitive and Versatile Gene Fusion Marker in Higher Plants," *EMBO J.*, 6(13):3901-3907 (1987).

International Search Report dated Dec. 11, 2011 issued in PCT Application No. PCT/US2010/61793.

* cited by examiner

*Primary Examiner* — Cathy Kingdon Worley
*Assistant Examiner* — Ashley K Buran
(74) *Attorney, Agent, or Firm* — Dentons US LLP; Carine M. Doyle Esq.

(57) ABSTRACT

The present disclosure provides compositions and methods for regulating expression of transcribable polynucleotides in plant cells, plant tissues, and plants. Compositions include regulatory polynucleotide molecules capable of providing expression in plant tissues and plants. Methods for expressing polynucleotides in a plant cell, plant tissue, or plants using the regulatory polynucleotide molecules disclosed herein are also provided.

17 Claims, 319 Drawing Sheets

Figure 1 (SEQ ID NO: 1) AT1G02780 tttctaagtggcaaaatatctctttcataaaaaaaaaaggaaagaataataaataaaaatatctct
ttcattctaacttggcattaaaatttagcaaaaactatttgtggacttgaaaaaaatattactag
ctcagacttaaacttaaatagtaacaagcatattaaaagtcatgctaactgagatattgatttcct
catctcaagaaactatcttatgaatctgtttccgattattttagtttcccatcaatcatctttaat
ttctaggaagtttgatttttttgaaaatttctccacctgcttaaatttcattacaattttttaatctt
agataaacaactgtaatttatgcaaaatgaactgattatataagtcgttatgaatatttatatttt
ttaaaaacatttcagcaaaactgatatactttttttttttttttttttgcaagcaaataaacaaac
ttccttgaataaaacgtgaaaaataataagagtctttaaagataaacgttgttcatatacattacg
tcatataatatatataacaattaagacaatacaaacatatatacaattctcattgggttgaaacat
tataaagataagataaacatctgtatatatacattggtatacaatatttttcataaattttttttt
ctctaatcgacagttatatatatacagaaccataattttaaagcatgctttccaatgcgttttttt
ttttttttttttttttttgtaaaccaaagccgtgtttctaaacctcaatttataaatttggtgtag
cttttcaaccttgatgaaattattacatagaatcattcgttaaaagacttataattgggtttagaa
aagcccattttaaatttaaagcccaatatactgctcgaaaaggaggaaaccctagaaacattgtgg
tAtataaattcttttcgtctcgttcgctaatcagttctccgccacaccaatctccagaaaagggga
gaagcaaaa Figure 2 (SEQ ID NO: 2) AT3G01280 cgtttacattctcatgatgcatctaaaagtagtgaaaatgtcagactgcttgtagtataaattgct
accataacggagacttgactaatcgtttactatatcagccgctaactagttgggatatttttctga
aaatagtttgataaatatgtaaaaatcacgatttcaccatcacattcgattactcattcatgacta
aaataaaggatgaaatagctaaatttatgcgactaatcatcaagggaaaaaaacgatttttctcatt
ttaggcgtggaaagaaaaatgtgttattaaacgacgccgtttagttgccacgtaataaatgagaat
aaatttcttggtgagtggggaataaatatatggacggctgtggataaggaatactgaagcaagcga
gtctccatccaacggctgataaaattatgcttgataaacaggaaaactcttCtttctctgataata
ttcggaaataaaaaacattttagggttttcctcagtctctctctcttatagacgccaaccacgttt
tccagctcttgttctttcgattctcagagaagacttttcagaacatcctccaactttctcagataa
gcaaca Figure 3 (SEQ ID NO: 3) AT1G43170 catgagcggagtaagaggtgttgtactagactaaagattagtttagcgatttagaattagcaaata
gtgttaaaaatgacacaaagaaaaatttgaatgtataatctaatacatgattctcaagcctctaa
atgagaaatattaaatctagattaagtttaaatatataaaatttagcttaaatctaaatttcaaaa
tgataggaactactataaaatcatatagtaacaagatacaaaaaaacatccatgtgttaccttaag
ttatatttattccctttagtaaccaacaaattttaactttctttcacgacaaaacttttgccgtct
acaattcacacacacttccaactttgaagcttacatacaatacggtggcagcagtaacacacacca
ttatactacaaacatcgataaatttttatcaataaccatatcgatcatttgacaaaaccacccacg
gagtaaccatatcattataagtaaacataatgaaatttttgcttcaagtgaactgtgaacatgtga
gtgtgttatcggatttagctgttgtcttttctttttatacgaaacaaaaaataaataaaacccttta
tcaaatttgtacaaacctctgggctttatttaggcccaataacaaaattcggcccatatttgagaa
ttcacaaaacctagatactcttactataaattggaacatcattgatctaatacaattaattactgt
gttaatattatttatactcaatctgaaatgtctttttttagctgtccaccagtttccaatctttga
aatacgaaacaaaaaataaataaaagtataaaacctttatctaatttgtaaaaacatttgttgggc
tttaggcccaaaacaaaagtcggcccatatttgagtgttcacaaaacctagatactcttactataa
attcAaactagggttttaaagctcatttctctcttgcagtcctcatcgttggagcttagaagccgt
cggcacaaggttcgtctttctctcatccctttcctcttcctttgcgtgaattcaccagaaaatgta
tatctaccttagcgagtctgtctagtttagcgaatctaggataatctccggaagacactttgaat
catcactgttttgatctctgtttctttctctaattgtgttgttgtattactgttgatgtagaaga
agaagaagaaga Figure 4 (SEQ ID NO: 4) AT1G67430 tgggaaagtttttttttttttgacatcggaaccgcatactctatttatacctaaatcatactaaca
tgagcaagtcttaagtacattttctttgttgatatagtaattgtgtacatttacttggttctttga
taatttataatcttatactttgattggtgcaactatagtcttatatccttaatttaactttatcct
taatttaacttcatgatcaaaagatatagtcttgtttttttgttttgttgagaagtttcattagcat
tattgtctaccgagagtaataccacaaattgatagtttctctgcatttttaagagaataagctaaa
taacggacctaaatacaagtggtccttacaattgcaatttgcaaatgaaaaaatttaaaagagtaa
gctaaacaaccgtactgacctaaataacaaacacatgaaaaaccacataaataacaaacacatgaa
aaaccaatagaagtgtctgttacaattacaaagtccacgtacatgccacgaggtaatgaataagtc
taattgcaacaaaataaataatattgtttcatataaataatttttcaaaatattgtttttattttt
ttcgttatcttttggactcaaatatgtgacaagagtaagactctataaacgacagctattttatcg
tggtgcgccatcaaataatgtgtcctatcatttctaagttgagccacgaaggtcaacgtttccgat
gcataccaccaaaactcctccctcgtggtgcaccatcaaataatcgtcaatccactcgttaatatg
tgtgatgatacgcttatcagcgatatcagtagatgttgaatcaactcttcaggtttcaatgatatc
gatagtatacttagctagtttctccccccatgaaatcgatagagcttcctcccaaggtattcaagat
cttattggcttctacatatgaagcaatcattactcatgtagcaaacttgttaatcttctatatttt
cattacatataatattttacgtacaagtaagtcaaatgacatgacatgacatatgatataactgag
taagtaagaaattacgtataacaattaagtcaaatgacatagtaaccattcgtgattgttgtctca
tatttatatatataaaacaaaaaatgaagttttaagcaaatgatctacaactaaaacaacatactc
caccaatatatacaaaatacgtacacttttttttgataagtaagtagaattctattgaacctgatg
agagttgagcataactctattcttagacccgaaaactactcaccatgtttattttagagatttaat
gatggattggacagtttttaggccatattacatagtaacaactaatttcaactaaaagaatgcaag
ttggttagtttaatacaaaacaaaatagtgaaaattggatctctagctcattttccgattaattaa
cttattttcaaaaaaattgtggttataagaacgaattaatcaattgcatttcttataaaaaaaagt
aatgaagagagatttacttacataaaataaatacatctggcctgatgaaacaaaaatgagtaagg
atatcaacctttgtaataagtaattgttaattaccaattcatagtcttgatgggcattattagaaa
gcccattaaaaatggacaaggcccatttaaacctaggtttcgcagggtttattgcttcactcttat
ataaaaactctcgTcttcacaaatctcacatctcttctgcagccgattcttctattagccgcc Figure 5 (SEQ ID NO: 5) AT1G76200 ccatttggagtaattgttaactttttttggagaagggttgttctattttgtgtataccaacatgat
cttgtaataaattaattattgtaatgtatcaatgatacagtatcatcatttgattttgagtctttt
tttgacggttaaaacaacgatttgggacgaagttataggccctgaatggatgctgattttggattc
agtttttgaatttagattttagtttatagattttagattttagtttcagattttattattatatt
tttgtttcaaaaaccccaaaaaattggtttttggtttttgagaaaaataacgttgattgagtaaaa
actagatttcctaaattttaggagaactaaaaaactaaaatcatgaatggaaaactacaagaaaat
aatttttctaaattgtagggaaaccaaaattttaaaatcttgattggtatgaaaataagtttttgg
aaaacaaaaaccaaaaactcttacaaaatctacaaaacattcaattcatgtatccaaacttcttaa
agggcccaaaaaggaagaaaacattgtgaaagaaacagatatagaaatgggcctttggtctttaaa
ttgggcctaagccttttaattgaggccttactaaaagtgacgactcacatggttgaatcAaatctc
aggtagtaaattgtcaaagctgaggagaaagaaagctttttcggtctgaaattgaagtgcgaatcg
gggaatctagggtttcgagagagagata Figure 6 (SEQ ID NO: 6) AT2G16850 gatcaaattttgtaaaaaattacaaatttgtaaaatatctccataaattaataattattaattta
tcgataaattaatatctctctaaattaaaaaaaatttggtcctgacattattaatttatagaggt
tttactgtagttacaaactgcgcatggtttgtcaaattctaaaacatgctttgtttattttgaaaa
taaaataaaatgatactagatgaaacaaatataatgaaaaggatatttaccaattgattattctta
tatttccatatttttttattttagctactatttttgaaaacttccattaactctttcactaagagc
tgtgatagtacacaaaaaaaaaagctgtgattcaagtttttctactcataaaatatgtctttgatt
ttttgtagtaattataggccgtaggccaatctttcaatatcatacacgtaggcacgggctagtgct
ggcccaaattggagatggtcttagtggttagaaacgaatgtttaaattcttaattaacttttgtaa
aacaccagatagtttgtaatatacgacgagatagttgaaacttatgtccaaaaaagaaacaaaaga
aagagagtatgttcatatagtaatagggaaaagaaagaaatataaccgttggtgattagtcattta
gttggatgacaaatctctctcaccttcacatggaccaacggcttctatgtcccaccaatttgtact
ctcaatctcctttaccttatttattcattacaccaaagctacgacacgacatggcttttgttttat
tttcattatatttatgttatttaatgttacagtacatacaatatttagcttttatgtcatgcattg
gttattagtattttgtattactagtaagattgaaaacggttttaagaatgtaggagtgtgtttcac
aaaattgagagtattgcaattacatgagagtgttcagacttcagagtattacaaacctaacaaacc
tggatattgtgatatgactggcttttaggttttgtaggtctcccatttgattataaacaaaatgta
tttattacctatattccaaaagtacccttatgttccatgttctcttcttataaagcaacacacaag
atgcaagaaatcTccataactagagagagaaactaatctttttagtgagagagaaatcttagagct
gagctaagaaaa Figure 7 (SEQ ID NO: 7) AT2G31490 gtaagaaccaaacctagctttcaaaacatgaaataacaataagaaacctttttcgattgaacggcg
aaatatatccattgaagatgttgagagtgagaatcgaagacgaagaggtgcaattactcgcagttt
ttttttttttgtaagttaattattaattttgacttcattaaagttaattatttgctgaaaaaaa
aaaaaaaaaagttaattatttagtatcttcaaatataatatttaaaaaatctagccatcttaatg
cattttaatgaaaatcctacccaagtttttaaaggtcaatttaaaaagtatcagttttgattttt
aattatattcaatatttgttaaattttgtttcatatgttaatattaaaaacacaatctatttccta
aacatttatatacagatctttttaaaaaggttagtcaaaaactgttggaaaagctaatcttttt
ttaacaaaaatagtaaaatactcatatacgtaactttgggcctttcttaaatggctttgggccttt
cgtaaatgggcttatgggcttaagtacttcaaatctgatagtatttggtttattgcaacaaaaaca
ataaatggaaatagcgatctgagctgaccAaccacagtcgcggacagagctaaaaccaccatttga
agaaggagaagaagaagaagacgattcggtgaaagcgaag Figure 8 (SEQ ID NO: 8) AT4G00860 atcttatgcgtgcagaataaatattggtgttatgtgcatttgaagctttaggctttagcactttct
aaaacctcgttttgagcaaagtcattcaaaaggaactcttaatatttttacaaattgaaatagcaa
ttgtaatttaatcagtaaaacctctataaattatcatgtttattaatttatagagacaatatttgg
gctaaaatatcaatttgagaacggaagaaaattattaatttaatgagatattaatttattgaatat
taatttatagatttttgactgtatatattctaagctttgttttaagaaaatttaatccgtttaaaa
agatttatcttcattaaccccaaaagaaatgatttgttttagcttggccaatagtcatgtatggcc
caatctggtataaaatctcataaaaagttttatcttcattaacccaaagaaatgatttgtattaag
atgggccaatagtcaagtgtggcccaattaggagtaaaatctcataaacgaaatgggcccataatg
gcccaatatttgtacaccacaatcggaaacccctttttgggtcatttcAagtttgacgagaaacgta
aatcgctatttcttctattcctccctaaaaatctaccaacgagattcttctcgaaaatttcctgcg
cctctccgtgtctgtgaaatcgattcaggtaaatcactcttctcgaatcgatgcttgttttgtgaa
ataccgattctatcagatctatttgataaatttgttgttgttgttagtcgtctgtgtagtttattc
accttttgtttcgatttttgggtcctcacgagatctatgaatcgttatctgaaacaaaactcgaaa
ctagcagatgatatgttatttagcgcgattaggaagaataaaacgagatttgttggtagcagtgag
tttcttagatcggttttttatcgattgtgtgaaaaaattcaccattcagatgcttttattgattt
gtgtcttctataattgaattgaattgtttgattcagcagcttaattatctaatggttttatgtgat
tgtattggcttgattagggttgaatatgccttgaaacttcatttcaatcccactatacactatagc
tataatctgatataagttcgttttctccttttgtgtggcttgattatgtttgatatatctatgtac
ttcaggttaagg Figure 9 (SEQ ID NO: 9) AT5G08690 aaatgctgcaagtcttggtacgccaagcaagtataattatatctaatgtccgaaaagacaagcaaa
atagcatcccataattcgaaaaatatcacgatattcaagtattgcatctacgtatatactactgca
gcactacatgcattgttcattataaagtgtgttgtatatagatgactggttaagcaagtcttgcat
atgatgatttattgatctcaggctctttgttttatcaagcaaaatagcatctcataattcgaggaa
atatcaccaccatattaaaatattgcatacaacgacggcagcactacattgctcaggataaaatgt
gttgcatatctcggtattttaccaaaaatatgttgattttatttgaaaaataaaatacatactat
cattttaatatttatcgtgtctaaatgtatttttttaaaaattatctttatacttttctaaagata
gttaaatgaaagcaacttggaaatcttaaaccatcaaaaatatttgtgtttaataaaactttgac
cttgcaaaatatatttttgttaactaaaaatctcaaccgatcccccaaaggtcaacctcatctttt
tttttttttttttatcctttagtttctattatgataaagacccaaataaataagcccattattctg
ttttgttcaaaataagcccattatctgagcccaccaaacattggaaagtttgagcttagattcagg
tgctgtagttaccctagcttGcatttcctcttccacacacccactc Figure 10 (SEQ ID NO: 10) AT5G53560 aattctatttaaaaatccatgtcccaagtaacttctccccaaaaagaaactcaatattttagaata
aggtcaaatggaattaaattccagaagatatttgccaaaatagtgataaaaatacggttaaattgg
tatatgtttttactgacaaaaggcaagattcttctattttaagatttatttctttctttgaaatct
gctaaacgttgttagatcacactttatgtgtctgtttttttttttgtcaattcagcacacgtcata
tttgtatttttcaaagtaccaaacgtggaccaaaataaaatctcgtcaaaaatggaaaccaaattt
taatttgatttgcacaaagcccaatttgatttgtttaaagtcaaagcccaacttgaccaaaactac
ccctgctcatccaaaccctaagcaaaatatcgagggtagtttcgtattttgttTatattgaacaca
attaagtaggtgaggaacctctatttcttccgtcttctgctgatttctgagcttcggagctatcga
aaattctgaatctgaaagggtaaagatcccatctttttccaaaaatcgataagggaattagtatat
tcgttcattcatcatcgttctgatgatttcgatttgaatctgtatctagtactctgtattatcaga
aattttgattagtagctttgatgtgttcttgttttgcagtttgagtgaag Figure 11 (SEQ ID NO: 11) AT1G07600
taggaaaaaagtttatattcctacccaaactttcggcaccagagacaaattaggtttgttcagaaa
atcagtcgctcatcgacagacttaacaccacaaaatcatcagaatttctttgggacaaaatggaaa
atgttcttcacggctccacctaccaaaatttcgatatcaagctcaaaagcatacacaaactataac
taattccatagttacgtaatcttaacttcgaattcaacaacacatgcatgcatcgactgaatcttc
aacaaatgcaatcaaacacacaaaattgctaccaaaaaaatatgattttttttttatgatttcaat
tttcatccggcacttagtccaaaactttttttgtgtgtcaacatttttaaaaaaatctttaaacg
gatatctgatctaagagcatgttcataggtgatacttacaaaatattttaagaaatttttttagta
ttatttataatgtttgtttaataaatatatataagatttttttgctttttatcaaatgtgaccaatca
gaagaaaccacgtcagatgatactgatatgacaaatatgatactgatcaaacatattctaattgct
ttactaatataaaaataatttttggacttgtgatactctaaaaatatcacccatatacatggtcta
atatatggatcgtaaaaaactcatatataatattaataagtagtagaagagcgtagaccatgtcct
gggtcgtcgtccaaatgaccacaagaagatttcaaaacagaggaaaatatttctcattaaataagt
tttcctgacgcataagataacattattacaagattcagaaaaagaaaggtgaaaggataatgtttc
tcctactatataagatgtgtacatctgaaaaaatatgaatatatttgtaacgtttgactgttatta
catgattaatacgatataaatattaacattttttttcaaaataaaagtaatatagtaaggaaatga
aaagaggcatgaagcatgcctctttttttggtcggctgccgtttacaattgccaattgcgatagtt
actcttcttgcgtgtacgacttttgtttttttttacatattcgccaataatttgacgttttctatt
agtttgtttgatactctgttgtcttgctaaaactcaataaaacattaaattactttcttgaatgaa
gctggaacaaatctaacataaatagaaaatgatgggcaagttgatgttattcgtaaatttatttag
attatattatataaaaagcaatccaattatatatctcatatatacaatttcttatcttactttgtc
aatgtcatatacgtaactaaaacttgcggaaatagaaaatgccacgtgtatggtggacataatccg
aatctctctctttcttctataaatagtggccattcccattggttgaaatcacaaaagcatcataag
aagaagaagaaactacaatagttaatcaatcaaagagaagtaagagaa Figure 12 (SEQ ID NO: 12) AT1G67350
attgacacatttaataagtagctttcgatagcaaacaaatctattggaactttctgttcatttacc
ttctttttggggtcagaaaataaatgtatcagcttaattgaactttgaacgataaaaagtagattc
atggtgagggtggggtgctacaaagaggtccagcccatttattgctagttgttagaatttgccagc
ttttggttcaaaatgatatacacacatatgtagttgttgcatattaagtagaaagagaaattcaat
gttgtgaattttcaaaaaagttgtaataatatatgatactcgatccttattaacatgtaatattag
gccttggctgaaccggattgttcggatcggtttgtttggtttgggagaaattcggttttcaaaaaa
tctcagatccgtattaacctttccggaatagatccatattaacctttacccgactcaaaaattat
atataccttttttttaaagacggatactaaatggataacggatcaaatacttgtaactggtatatc
agtgcccagcagtctagcactagtttAgttgtagccatatatttgacagctgaataggtttggtca
aattttggccacggcattccgtaaagggaggcataaacagggtggagttttttgttacagaaaacgt
cttgtttctttattctcagtacaaaacaacacgcagtttctattcctatcagatttttgttttctt
cttcatcaacactcgctctgcgctgcgttcgaatccagaactctctgaccatcccaaagcaaaagc
ttcaccgatcttcctcgtttggtctcgaatattaaggtaagttccatttattgtatggatcctag
aaacttaacctagatctagattaagaacccaatttgtggaaatcaatgcgtcgatttgatagaaac
cctaatttctggtgatttccatggttaagctgttggcttgcattaagtaaataacgagatggttt
cagaaatttaggtcacagagtccaatttatggattcaatgcttcgatttgattttaaaaaaccaat
cttcgggttaaattgaatgtaagaagtgtgtgtttttgagtttgcagtgaaatatgggtttcataa
tggaattcgcggagaatttggtgttaaggttaatggagaatccagaggaacgagacaggaaagcga
gg Figure 13 (SEQ ID NO: 13) AT1G78380 agtcaactatttgtgtatattgtaagatgtatcatgttatgacatgagtatgttgctacgtgtcg
tgagatatcgaacccaacgcagatatgagtatgttgagctagtttcttcttatgaaacaatcatat
atgtctataatgaatagatcacattatctgcctgaaaaaatcccgtatattactcgacgaaatat
aaatacccaatgtagctgattttgctttctctggtgacatatccaatttggctaaatttgttaact
agtctattataggtttataatagatctagctatgttaaagatactaaagcatcagttacataaatt
tttggcgcgagtttatatcttttggaattaaaaataagagaatttaaaaataagaagatcattttg
tttggccacaggagttctgaaaggtcaggtatgatttttttcttgctcgctcttatgattttgttt
ttattaatgggttttcaaataagaaaaactgtttttcgaagcccggttcagatccattgtttttg
taaaatataggcccaattcaccataagtccatgaccaaaacaaaaataagatagaaccaatactga
accaggatcttctctcgctttcgtgatcaatgtcgccaagcttctcgagatcatgtggtcacgtca
attgtataaatacaattattgacgtaacacaatctctacagttccatcgaaatatctcgaaaattt
ccagttaattctggtaacgtgaacgtatcttccacctcttcaacctacacagctttctagaaattt
ggctcgctttctaagtcctctgtattttttgcacgtttttcaactaagtttcaatatgaatcat
ttcttctataaataaatgatattttcatcaggtaatgatacattgtgccgaaataaaacgtcaata
ctcattagtcaaattaattgttcacataatttaaaactgtgttaatccatccagttattttcttac
aacaaaataatcttttccatcaacttttaaaataattaaacgcagtgctaagaaatctaaaatctt
gatttagaaatccattatggtttctggtcaactgaaatccataatttcctttaacatccaaaatcc
aaatttgctactatgataatagatttcagacgatttttttctttttttcaatcatagagtccacac
gaatatttgcaagttactatataaaacactataatggtcaacagataaaaaaaaggcgaatgaaga
tatgttacgtaaaaagaaaatactgtaattataaattattactttaaaaagctttaaaatctggcc
acatgtttttaaagagtggtgtgacgtaacgactagagtcagcacaatccattattgtatcataaa
tattctcatctataaattacctaaaccCttacaggtagtgtcccaaccaaacaaatcgagaaagac
gaacacttacaaaaaaaaatctctttgtgagctttagcgatcgtaaca Figure 14 (SEQ ID NO: 14) AT1G76200, +intron ccatttggagtaattgttaactttttttggagaagggttgttctattttgtgtataccaacatgat
cttgtaataaattaattattgtaatgtatcaatgatacagtatcatcatttgattttgagtctttt
tttgacggttaaaacaacgatttgggacgaagttataggccctgaatggatgctgattttggattc
agtttttgaatttagattttagtttatagattttagattttagtttcagatttttattattatatt
tttgtttcaaaaaccccaaaaaattggtttttggtttttgagaaaaataacgttgattgagtaaaa
actagatttcctaaattttaggagaactaaaaaactaaaatcatgaatggaaaactacaagaaaat
aatttttctaaattgtagggaaaccaaaattttaaaatcttgattggtatgaaaataagtttttgg
aaaacaaaaaccaaaaactcttacaaaatctacaaaacattcaattcatgtatccaaacttcttaa
agggcccaaaaaggaagaaaacattgtgaaagaaacagatatagaaatgggcctttggtctttaaa
ttgggcctaagccttttaattgaggccttactaaaagtgacgactcacatggttgaatcAaatctc
aggtagtaaattgtcaaagctgaggagaaagaaagctttttcggtctgaaattgaagtgcgaatcg
gggaatctagggtttcgagagagagata*cag*gtacatttctgatttctctctttcacctaattcgc
ttttgattttgggacctagctaatctcgatcgtagctagatctcgccatggggattttgggctaat
tgatcatctgaggaattttgtatatagaatccatttgaatcaaaaaattggatttgtcaaattagt
atcggagctaatcaggtagatgttaatttgaatcagatattgcttatgtcaatttcagttcgatga
gaatggttgaagaagtaatcgcacataggttttaactttccctagcattcacatcttaaaaactca
atttttggtattttcag*gt*

Figure 15 (SEQ ID NO: 15) AT1G78380, +intron agtcaactattttgtgtatattgtaagatgtatcatgttatgacatgagtatgttgctacgtgtcg
tgagatatcgaacccaacgcagatatgagtatgttgagctagtttcttcttatgaaacaatcatat
atgtctataatgaatagatcacattatctgcctgaaaaaatcccgtatattactcgacgaaatat
aaatacccaatgtagctgattttgctttctctggtgacatatccaatttggctaaatttgttaact
agtctattataggtttataatagatctagctatgttaaagatactaaagcatcagttacataaatt
tttggcgcgagtttatatcttttggaattaaaaataagagaatttaaaaataagaagatcattttg
tttggccacaggagttctgaaaggtcaggtatgatttttttcttgctcgctcttatgattttgttt
ttattaatgggttttcaaataagaaaaactgtttttcgaagcccggttcagatccattgtttttg
taaaatataggcccaattcaccataagtccatgaccaaaacaaaaataagatagaaccaatactga
accaggatcttctctcgctttcgtgatcaatgtcgccaagcttctcgagatcatgtggtcacgtca
attgtataaatacaattattgacgtaacacaatctctacagttccatcgaaatatctcgaaaattt
ccagttaattctggtaacgtgaacgtatcttccacctcttcaacctacacagctttctagaaattt
ggctcgctttctaagtcctctgtatttttttgcacgtttttcaactaagtttcaatatgaatcat
ttcttctataaataaatgatattttcatcaggtaatgatacattgtgccgaaataaaacgtcaata
ctcattagtcaaattaattgttcacataatttaaaactgtgttaatccatccagttattttcttac
aacaaaataatcttttccatcaacttttaaaataattaaacgcagtgctaagaaatctaaaatctt
gatttagaaatccattatggtttctggtcaactgaaatccataatttcctttaacatccaaaatcc
aaatttgctactatgataatagatttcagacgatttttttttctttttttcaatcatagagtccacac
gaatatttgcaagttactatataaaacactataatggtcaacagataaaaaaaaaggcgaatgaaga
tatgttacgtaaaaagaaaatactgtaattataaattattactttaaaaagctttaaaatctggcc
acatgtttttaaagagtggtgtgacgtaacgactagagtcagcacaatccattattgtatcataaa
tattctcatctataaattacctaaaccCttacaggtagtgtcccaaccaaacaaatcgagaaagac
gaacacttacaaaaaaaaatctctttgtgagctttagcgatcgtaaca*cag*gtatcttatttcctt
tgtgcccttgattgaataatgttgaaattgaacttgggatttcataaaaattgaaactttagttga
gtttgctagtgattggctcaaatttagggttttgcttgtagactcgtctttgagcttgtatgggtt
tgtctgatgttataatattacttgagtttgtagttgttagggttagagatctcacctccaaatttc
agatttttcttgtggactcatctctgagctagtcagggtttgtcttcttagatagtttaatgttat
gttacttgtgcaatttgaggtttttacatactagtttcgctagtagatatcatctttgagctttgt
ttgggttcatcttagatagtttgatgatatgtttcttttgcaatttgggggtctctaggactggtt
ttgctttgtagacatcatctttgagctttgtttgggttcgactgagttctgacatagcttggtgtt
atgttactctgtgcaatgtttcag*gt*

Figure 16 (SEQ ID NO: 16) AT1G02780, +intron tttctaagtggcaaaatatctctttcataaaaaaaaaaggaaagaataataaataaaaatatctct
ttcattctaacttggcattaaatttagcaaaaactatttgtggaacttgaaaaaaaatattactag
ctcagacttaaacttaaatagtaacaagcatattaaaagtcatgctaactgagatattgatttcct
catctcaagaaactatcttatgaatctgtttccgattattttagtttcccatcaatcatctttaat
ttctaggaagtttgatttttttgaaatttctccacctgcttaaatttcattacaattttaatctt
agataaacaactgtaatttatgcaaaatgaactgattatataagtcgttatgaatatttatatttt
ttaaaaacatttcagcaaaactgatatactttttttttttttttttttgcaagcaaataaacaaac
ttccttgaataaaacgtgaaaaataataagagtctttaaagataaacgttgttcatatacattacg
tcatataatatatataacaattaagacaatacaaacatatatacaattctcattggttgaaacat
tataaagataagataaacatctgtatatatacattggtatacaatatttttcataaattttttttt
ctctaatcgacagttatatatatacagaaccataattttaaagcatgctttccaatgcgttttttt
ttttttttttttttttttgtaaaccaaagccgtgtttctaaacctcaatttataaatttggtgtag
cttttcaaccttgatgaaattattacatagaatcattcgttaaaagacttataattgggtttagaa
aagcccattttaaatttaaagcccaatatactgctcgaaaaggaggaaaccctagaaacattgtgg
tAtataaattcttttcgtctcgttcgctaatcagttctccgccacaccaatctccagaaaaggggga
gaagcaaaa*cag*gtatgttgttgctttttttcttcatcctttttactttttattgttgtcctgtgtttg
tctgcgacggtggtagacggtcttaggtgttgaatcactgtgtttgtttccgatctgaaatttag
agcttgtaggtgttgttacggtttcatttctctagttataggccttgtagaactgtgatttgtctc
gtgaatcaaagctagaggatttgatttctgatattgcttcttaatagactgaggatttgaatgatg
ttccatttcgagtattgttgttatatatttgaagatctttgtagcttcaaatattaagaatgtgat
gattggtgttgaacttattgtag*gt*

Figure 17 (SEQ ID NO: 17) AT5G08690, +intron aaatgctgcaagtcttggtacgccaagcaagtataattatatctaatgtccgaaaagacaagcaaa
atagcatcccataattcgaaaaatatcacgatattcaagtattgcatctacgtatatactactgca
gcactacatgcattgttcattataaagtgtgttgtatatagatgactggttaagcaagtcttgcat
atgatgatttattgatctcaggctctttgttttatcaagcaaaatagcatctcataattcgaggaa
atatcaccaccatattaaaatattgcatacaacgacggcagcactacattgctcaggataaaatgt
gttgcatatctcggtattttaccaaaaatatgttgatttttatttgaaaaataaaatacatactat
cattttaatatttatcgtgtctaaatgtatttttttaaaaattatctttatacttttctaaagata
gttaaatgaaagcaacttggaaatcttaaaaccatcaaaaatatttgtgtttaataaaactttgac
cttgcaaaatatatttttgttaactaaaaatctcaaccgatcccccaaaggtcaacctcatctttt
ttttttttttttatcctttagtttctattatgataaagacccaaataaataagcccattattctg
ttttgttcaaaataagcccattatctgagcccaccaaacattggaaagtttgagcttagattcagg
tgctgtagttaccctagcttGcatttcctcttccacacacccactc*cag*gtaagtggcttctctgt
ctagatccttctatctttgttgctgatccgtaaaacaagccattactaggtatagatctgtgaatt
cgttgattggatttgcatagtctcgccggtgtctgttcgtgtttcctcaacgttgactttccccaa
tctcactttttttctttaaaagtctattcattaccaaggaactctacgtccggatgatttcgtgaat
ttgaatgactaatcaattccttgatacattaatctgaataagttgcgattgtcaaaaatgactttt
ttgcttgttctcactgttaag*gt*

Figure 18 (SEQ ID NO: 18) AT1G67430, +intron tgggaaagtttttttttttttgacatcggaaccgcatactctatttatacctaaatcatactaaca
tgagcaagtcttaagtacattttctttgttgatatagtaattgtgtacatttacttggttctttga
taatttataatcttatactttgattggtgcaactatagtcttatatccttaatttaactttatcct
taatttaacttcatgatcaaaagatatagtcttgttttttgttttgttgagaagtttcattagcat
tattgtctaccgagagtaataccacaaattgatagtttctctgcattttaagagaataagctaaa
taacggacctaaatacaagtggtccttacaattgcaatttgcaaatgaaaaaatttaaaagagtaa
gctaaacaaccgtactgacctaaataacaaacacatgaaaaaccacataaataacaaacacatgaa
aaaccaatagaagtgtctgttacaattacaaagtccacgtacatgccacgaggtaatgaataagtc
taattgcaacaaaataaataatattgtttcatataaataatttttcaaaatattgtttttattttt
ttcgttatcttttggactcaaatatgtgacaagagtaagactctataaacgacagctattttatcg
tggtgcgccatcaaataatgtgtcctatcatttctaagttgagccacgaaggtcaacgtttccgat
gcataccaccaaaactcctccctcgtggtgcaccatcaaataatcgtcaatccactcgttaatatg
tgtgatgatacgcttatcagcgatatcagtagatgttgaatcaactcttcaggtttcaatgatatc
gatagtatacttagctagtttctcccccatgaaatcgatagagcttcctcccaaggtattcaagat
cttattggcttctacatatgaagcaatcattactcatgtagcaaacttgttaatcttctatatttt
cattacatataatattttacgtacaagtaagtcaaatgacatgacatgacatatgatataactgag
taagtaagaaattacgtataacaattaagtcaaatgacatagtaaccattcgtgattgttgtctca
tatttatatatataaaacaaaaaatgaagttttaagcaaatgatctacaactaaaacaacatactc
caccaatatatacaaaatacgtacacttttttttgataagtaagtagaattctattgaacctgatg
agagttgagcataactctattcttagacccgaaaactactcaccatgtttattttagagatttaat
gatggattggacagttttttaggccatattacatagtaacaactaatttcaactaaaagaatgcaag
ttggttagtttaatacaaaacaaaatagtgaaaattggatctctagctcattttccgattaattaa
cttattttcaaaaaaattgtggttataagaacgaattaatcaattgcatttcttataaaaaaaagt
aatgaagagagattttacttacataaaataaatacatctggcctgatgaaacaaaaatgagtaagg
atatcaacctttgtaataagtaattgttaattaccaattcatagtcttgatgggcattattagaaa
gcccattaaaaatggacaaggcccatttaaacctaggtttcgcagggtttattgcttcactcttat
ataaaaactctcgTcttcacaaatctcacatctcttctgcagccgattcttctattagccgcc*cag*
gtaattgcttaattgcttaagcttctcaaactccatctctcttctcgctgatttgacctagaaatc
ttcttccctaattttctttaccctgtctttgctgatttcgcag*gt*

Figure 19 (SEQ ID NO: 19) AT2G16850, +intron gatcaaattttgtaaaaattacaaatttgtaaaatatctccataaattaataattattaattta
tcgataaattaatatctctctaaattaaaaaaaatttggtcctgacattattaatttatagaggt
tttactgtagttacaaactgcgcatggtttgtcaaattctaaaacatgctttgtttattttgaaaa
taaaataaaatgatactagatgaaacaaatataatgaaaaggatatttaccaattgattattctta
tatttccatatttttttattttagctactattttgaaaacttccattaactctttcactaagagc
tgtgatagtacacaaaaaaaaaagctgtgattcaagttttctactcataaaatatgtctttgatt
ttttgtagtaattataggccgtaggccaatctttcaatatcatacacgtaggcacgggctagtgct
ggcccaaattggagatggtcttagtggttagaaacgaatgtttaaattcttaattaacttttgtaa
aacaccagatagtttgtaatatacgacgagatagttgaaacttatgtccaaaaaagaaacaaaaga
aagagagtatgttcatatagtaatagggaaaagaaagaaatataaccgttggtgattagtcattta
gttggatgacaaatctctctcaccttcacatggaccaacggcttctatgtcccaccaatttgtact
ctcaatctcctttaccttatttattcattacaccaaagctacgacacgacatggcttttgttttat
tttcattatatttatgttatttaatgttacagtacatacaatatttagcttttatgtcatgcattg
gttattagtatttgtattactagtaagattgaaaacggttttaagaatgtaggagtgtgtttcac
aaaattgagagtattgcaattacatgagagtgttcagacttcagagtattacaaacctaacaaacc
tggatattgtgatatgactggcttttaggttttgtaggtctcccatttgattataaacaaaatgta
tttattacctatattccaaaagtacccttatgttccatgttctcttcttataaagcaacacacaag
atgcaagaaatcTccataactagagagagaaactaatctttttagtgagagagaaatcttagagct
gagctaagaaaa*cag*gtaaatatttccacaaaaaccacaaaaatttccataaacttcagtttcaag
atcttaatatgaagttgtttagcaatgatacatttataattcaaagatacatttttagcaagtttt
tgtttggtaaaataccttttagcaagttggtaaaatatttcaacaaactttatcctaaaattac
taaaccttaatcttcaacaacttaatatggagttgttaacttgcag*gt*

Figure 20 (SEQ ID NO: 20) AT2G31490, +intron gtaagaaccaaacctagctttcaaaacatgaaataacaataagaaacctttttcgattgaacggcg
aaatatatccattgaagatgttgagagtgagaatcgaagacgaagaggtgcaattactcgcagttt
tttttttttgtaagttaattattaattttgacttcattaaagttaattatttgctgaaaaaaa
aaaaaaaaaagttaattatttagtatcttcaaatataatatttaaaaaatctagccatcttaatg
cattttaatgaaaatcctacccaagtttttaaaggtcaatttaaaaagtatcagttttgattttt
aattatattcaatatttgttaaattttgtttcatatgttaatattaaaaacacaatctatttccta
aacatttatatacagatctttttttaaaaaaggttagtcaaaaactgttggaaaagctaatcttttt
ttaacaaaaatagtaaaatactcatatacgtaactttgggcctttcttaaatggctttgggccttt
cgtaaatgggcttatgggcttaagtacttcaaatctgatagtatttggtttattgcaacaaaaaca
ataaatggaaatagcgatctgagctgaccAaccacagtcgcggacagagctaaaaccaccatttga
agaaggagaagaagaagaagacgattcggtgaaagcgaag*cag*gtgagtttaaatctctctatctc
tatctcattctcgatcctatttgcatttcgaatcctcccgagttagatatctgttttgtgccctaa
tttttcatgtatcgtatggaattggatcgtttgatacatttgaaattggggtttaattttagctgt
agatgcatttgaattagattagttcttttgctgcaacgattggattcggaactggatttcaatttt
cacctccatactagtattcttaggtgatgatggttcgatttcagattgattataactcaaaatttt
cgagaccgaccaatgaaagtctaagattggagttagggcagaagaaatttagttctcttttagctt
gtaaaaattggatctttggctaaaaaaatggttttaactgctttctattgttctgagtttgagtct
gagctgatttggttatgaaaaattatgtatagtggactttcaaggttcttaatctctcagcagttc
attgctacaatccttgaggattcttcctccatagtagtttctactctgtgtccttgaatatagatt
cttgttaggaccatgtttatgtggttgatgatctatgccatcccttgttagtggaatttgtctatg
acgattgagatggaaatttttttatgtgttacttccaatacaattgtgtagttattgtgattaat
atactaagttcaatctaatggactctaaactcatttttttgatag*gt*

Figure 21 (SEQ ID NO: 21) AT3G01280, +intron cgtttacattctcatgatgcatctaaaagtagtgaaaatgtcagactgcttgtagtataaattgct
accataacggagacttgactaatcgtttactatatcagccgctaactagttgggatatttttctga
aaatagtttgataaatatgtaaaaatcacgatttcaccatcacattcgattactcattcatgacta
aaataaaggatgaaatagctaaatttatgcgactaatcatcaagggaaaaaaacgattttctcatt
ttaggcgtggaaagaaaaatgtgttattaaacgacgccgtttagttgccacgtaataaatgagaat
aaatttcttggtgagtggggaataaatatatggacggctgtggataaggaatactgaagcaagcga
gtctccatccaacggctgataaaattatgcttgataaacaggaaaactcttCtttctctgataata
ttcggaaataaaaaacattttagggtttcctcagtctctctctcttatagacgccaaccacgttt
tccagctcttgttctttcgattctcagagaagacttttcagaacatcctccaactttctcagataa
gcaaca*cag*gtatctttttattatctccctcacttcttctctttcatttcgttcaattaaatctgt
ttatggcgtagacgatctgattgttgctacttagtgtcccgttctgtcttctaatctggactttct
tttgattccttaggatttttgattcatttgctcatctcttagattttccttttcccggtcccgatt
tggctaccgggatagatcatagatgcatgcgtagatttcgagtattcgatcgggtagagattcata
agtaatggatttcaatcattggtgctgatatgagtaattccttgggttcaatgtctccgtcactct
cgtttaagctctctacctttctcaatagaccctgttttgtttatcgttgatctggaatagccaatt
tgaatgctgtgattctctttcatgtttagcatttctcaccatttaagtcccctttgagaatgtttt
gttaataagctgtctaaaactgttgctctgctctgtgtatttgcag*gt*

Figure 22 (SEQ ID NO: 22) AT1G07600, +intron taggaaaaaagtttatattcctacccaaactttcggcaccagagacaaattaggtttgttcagaaa
atcagtcgctcatcgacagacttaacaccacaaaatcatcagaatttctttgggacaaaatggaaa
atgttcttcacggctccacctaccaaaatttcgatatcaagctcaaaagcatacacaaactataac
taattccatagttacgtaatcttaacttcgaattcaacaacacatgcatgcatcgactgaatcttc
aacaaatgcaatcaaacacacaaaattgctaccaaaaaaatatgattttttttttatgatttcaat
tttcatccggcacttagtccaaaactttttttgtgtgtcaacatttttaaaaaaatctttaaacg
gatatctgatctaagagcatgttcataggtgatacttacaaaatatttttaagaaatttttagta
ttatttataatgtttgtttaataaatatatataagatttttgcttttatcaaatgtgaccaatca
gaagaaaccacgtcagatgatactgatatgacaaatatgatactgatcaaacatattctaattgct
ttactaatataaaaataatttttggacttgtgatactctaaaaatatcacccatatacatggtcta
atatatggatcgtaaaaaactcatatataatattaataagtagtagaagagcgtagaccatgtcct
gggtcgtcgtccaaatgaccacaagaagatttcaaaacagaggaaaatatttctcattaaataagt
tttcctgacgcataagataacattattacaagattcagaaaaagaaaggtgaaaggataatgtttc
tcctactatataagatgtgtacatctgaaaaaatatgaatatatttgtaacgtttgactgttatta
catgattaatacgatataaatattaacatttttttcaaaataaaagtaatatagtaaggaaatga
aaagaggcatgaagcatgcctctttttttggtcggctgccgtttacaattgccaattgcgatagtt
actcttcttgcgtgtacgactttgtttttttttacatattcgccaataatttgacgttttctatt
agtttgtttgatactctgttgtcttgctaaaactcaataaaacattaaattactttcttgaatgaa
gctggaacaaatctaacataaatagaaaatgatgggcaagttgatgttattcgtaaatttatttag
attatattatataaaaagcaatccaattatatatctcatatatacaatttcttatcttactttgtc
aatgtcatatacgtaactaaaacttgcggaaatagaaaatgccacgtgtatggtggacataatccg
aatctctctctttcttctataaatagtggccattcccattggttgaaatcacaaaagcatcataag
aagaagaagaaactacaatagttaatcaatcaaagagaagtaagagaa*Cag*gtaaacccctagatt
ctctcttctttacatttatatgcatatatgtagactatgtagttcgagcttcatggtacaaaattc
aataaactcttcttatgacttcgtttacaattgtgtttgtgaatagacacaaaagattagttttgt
ttactttagattcaaaacacttcgggcctatcctgtatatatgctgatcagatgcatgtggttgat
taatctttaatctcatcatattaattactaatttttgtttgtttgattaatttgtgtgtggtaaa
g*gt*

Figure 23 (SEQ ID NO: 23) AT4G05320 gttttgtgtatcattcttgttacattgttattaatgaaaaaatattattggtcattggactgaaca
cgagtgttaaatatggaccaggccccaaataagatccattgatatatgaattaaataacaagaata
aatcgagtcaccaaaccacttgcctttttttaacgagacttgttcaccaacttgatacaaaagtcat
tatcctatgcaaatcaataatcatacaaaaatatccaataacactaaaaaattaaaagaaatggat
aatttcacaatatgttatacgataaagaagttacttttccaagaaattcactgattttataagccc
acttgcattagataaatggcaaaaaaaaacaaaaaggaaaagaaataaagcacgaagaattctaga
aaatacgaaatacgcttcaatgcagtgggacccacggttcaattattgccaatttcagctccacc
gtatatttaaaaaataaaacgataatgctaaaaaaatataaatcgtaacgatcgttaaatctcaac
ggctggatcttatgacgaccgttagaaattgtggttgtcgacgagtcagtaataaacggcgtcaaa
gtggttgcagccggcacacacgagtcgtgtttatcaactcaaagcacaaatactttcctcaacct
aaaaataaggcaattagccaaaaacaactttgcgtgtaaacaacgctcaatacacgtgtcatttta
ttattagctattgcttcaccgccttagctttctcgtgacctagtcgtcctcgtcttttcttcttct
tcttctataaaacaataccCaaagagctcttcttcttcacaattcagatttcaatttctcaaaatc
ttaaaactttctctcaattctctctaccgtgatcaaggtaaatttctgtgttccttattctctca
aaatcttcgattttgttttcgttcgatcccaatttcgtatatgttctttggtttagattctgttaa
tcttagatcgaagacgattttctgggtttgatcgttagatatcatcttaattctcgattagggttt
catagatatcatccgatttgttcaaataatttgagttttgtcgaataattactcttcgatttgtga
tttctatctagatctggtgttagtttctagtttgtgcgatcgaatttgtcgattaatctgagtttt
tctgattaacag*gt*

Figure 24 (SEQ ID NO: 24) AT5G20290 tgataacttatgtgcaagagtctctcgttggtcagtgtgaaatgtttatgttgttagaacagattt
tggctctcaaacccaacacgttttcaataaaatatgcacggttagattcacccaaccctagttcaa
tctgccaggatctatctcttttttttttacgatttcttcaaccaaaacaatgaaataacacacaa
aattattatcactagaccaaattttatttataacataaaacggccggaagctgatgcttcatgggc
ttggcccaaaggccggctctggatgggccagatgataacctagggtttatactccctatatattta
tatttaagctcttcgttcaCtcctctcaactccgcgcagctaaactttattggagaaaccctaatc
ggcgaca Figure 25 (SEQ ID NO: 25) AT5G42980 caaaacttttttggaatggtagacatcccattgaaagaaaacaaattgccatggtatggaattcat
gataatgatttaactcgttatagtctggacaaattgtcatggtagggtttcattgctctttctttg
ggtagttacctcaagatatctctttgttcttccttgtgatagttccaccttgatatgtacaacccc
acattaatctgctcatttcaacattaatttctctattgtttttaaattgtgtgtataagattatt
tcactaactaggaaaacaatccatttctttgacacatgggctttacttaaacaaaagcccaataac
ttgtgtttagaagtcacatgatcaaatctcaagacctattataaattaacaaatttcatattgata
aattttaaaagatttcctattacaatatttaaagttgctacaaattatagattcttttgatctttt
ctgatattgtttctcaaataaaatataggaataccaaattacaatatgaaagttgcttcaaattat
agattcttttctgattttgtttctcaaataaaatataggactgaactaccaaaggcaataatattc
aatgtgaccaacaaaaaaaaaataaaaaataaaaagaaatactcaaatctcataacctttttgact
aaatatatcaatttcttctattttcaatgagcataaattacacgcgtcctcagaagctgaatccga
tttgcaattcttcaatctcaaccgttagatcaacaaatccggcatcgaattcctccgcgtggtttg
gtccatttttttaatttgagtattaattcttttcctatttgacAacttgttttattaattattatt
attattccatttgcattaaaatataataaaaagttgtaagattctctccgcctccttctctctata
agaaccgacacagagacgaagaagaataatcactcgaaaactcatcaaatcaaaaatcaaacacag
agaagagaaa Figure 26 (SEQ ID NO: 26) AT3G60245 atttctgtgtttaaccttttcgtacatcagttttaaagcacagagagctcaatgttcttccaatat
cgttattaataaattttgattaaattcaatcaaatcggagttatattaccacatgaggttaaaggg
ccatattaaaaagtctgcacttcatatgagcaacaaggcttttatgtctttatggttgatttgatg
gcccatatatgatagttcaaaggcccatattaaaaaatgccctaacatgattcgattcgtatataa
agacgcttaatgtgacaagcgaacttGctcattagggtttctcatctacgacggcgtggtgttcct
ccttcctgctctgaaaa Figure 27 (SEQ ID NO: 27) AT3G17390 ccgacactactaaaaagcaaacaaaagaagaattctatgttgtcattttaccggtggcaagtggac
ccttctataaaagagtaaagagacagcctgtgtgtgtataatctctaattatgttcaccgacacaa
tcacacaaacccttctctaatcacacaacttcttcatgatttacgacattaattatcattaactct
ttaaattcactttacatgctcaaaaatatctaatttgcagcattaatttgagtaccgataactatt
attataatcgtcgtgattcgcaatcttcttcattagatgctgtcaagttgtactcgcacgcggtgg
tccagtgaagcaaatccaacggtttaaaaccttcttacatttctagatctaatctgaaccgtcaga
tatCtagatctcattgtctgaacacagttagttgaaactgggattgaatctggacgaaattacgat
cttacaccaaccccctcgacgagctcgtatatataaagcttatacgctcctccttcaccttcgtac
tactactaccaccacatttctttagctcaaccttcattactaatctcctttttaaggtatgttcact
tttcttcgattcatactttctcaagattcctgcatttctgtagaatttgaaccaagtgtcgatttt
tgtttgagagaagtgttgatttatagatctggttattgaatctagattccaatttttaattgattc
gagtttgttatgtgtgtttatactacttctcattgatcttgtttgatttctctgctctgtattagg
tttctttcgtgaatcagatcggaaaa Figure 28 (SEQ ID NO: 28) AT3G04400 agattgaaggaggacttaataattagaacaaggttatataattagatatattcttttttttttttaa
ggttatataattagatatattcgttttttttaaaaggttatagaataagatttcattgcatcttaaa
accagacaactttcagaactgaagaatgacgaaaaattaataatagaggaggagaggaggagctac
atcaacattatttctattttttcagccaatcagagcgctccggacttcgcccactcgcaccaacct
cgcgccacgcgctccattccatgcccactcgcaccaacctcgcgttgaacgcgtgtcgtcgatttc
tgtaggggtaaacccacaaaatcatgcctattttacatctactcgctttgtttccaaaacagcctc
gagtgacttttttcttttgttttttttctcaaaaccgtattaattctaatgcaaaccgaaccaaaa
ttaatttttatttcaaaaccatctaaaccaaacagaaatcacatgtaatttcaaacccgaaccgaa
atcaattgtcatttcatcaaaaccatgtaaaaagcttctacgattgttttaacttgcaactgaaaa
tagcaatcctaatttatcaacagataaagatagatacatgcaacactttacttttttatttttggt
tttgagaagatgattacagttgtgattttggtggagacaaaaatgtccatctctgtatgttgctag
ccgatcaaattttacattcaaaatcctttttgataaaaaaaataaaaaaattcaaaatcctttatg
atatattggcctaagatgatttccaaaaaaaaaagatgatgagaaagaaagagaacattattgggc
ttattgttaaattatttcggcccataaaataaagtccaggtcagctcacaatacatgaagaaaacc
ctagttcaagcgtAtataaaccctctcggcgctgccattgaaactctttcaaggagagagctgcta
ctctgcaacc Figure 29 (SEQ ID NO: 29) AT5G20290, +intron tgataacttatgtgcaagagtctctcgttggtcagtgtgaaatgtttatgttgttagaacagattt
tggctctcaaacccaacacgttttcaataaaatatgcacggttagattcacccaaccctagttcaa
tctgccaggatctatctctttttttttttacgatttcttcaaccaaaacaatgaaataacacacaa
aattattatcactagaccaaattttatttataacataaaacggccggaagctgatgcttcatgggc
ttggcccaaaggccggctctggatgggccagatgataacctagggtttatactccctatatattta
tatttaagctcttcgttcaCtcctctcaactccgcgcagctaaactttattggagaaaccctaatc
ggcgaca*cag*gtacgaacaatctctcctcgctttctctttgatttctccactccttcgatctcgtt
tctgtgttatgctattgttgtttagattctgatatatggattctggtttctcttag*gt*

Figure 30 (SEQ ID NO: 30) AT5G42980, +intron caaaacttttttggaatggtagacatcccattgaaagaaaacaaattgccatggtatggaattcat
gataatgatttaactcgttatagtctggacaaattgtcatggtagggtttcattgctctttctttg
ggtagttacctcaagatatctctttgttcttccttgtgatagttccaccttgatatgtacaacccc
acattaatctgctcatttcaacattaatttctctattgtttttaaattgtgtgtataagattatt
tcactaactaggaaaacaatccatttctttgacacatgggctttacttaaacaaaagcccaataac
ttgtgtttagaagtcacatgatcaaatctcaagacctattataaattaacaaatttcatattgata
aattttaaaagatttcctattacaatatttaaagttgctacaaattatagattcttttgatctttt
ctgatattgtttctcaaataaaatataggaataccaaattacaatatgaaagttgcttcaaattat
agattcttttctgattttgtttctcaaataaaatataggactgaactaccaaaggcaataatattc
aatgtgaccaacaaaaaaaaaataaaaaataaaaagaaatactcaaatctcataacctttttgact
aaatatatcaatttcttctattttcaatgagcataaattacacgcgtcctcagaagctgaatccga
tttgcaattcttcaatctcaaccgttagatcaacaaatccggcatcgaattcctccgcgtggtttg
gtccatttttttaatttgagtattaattcttttcctatttgacAacttgttttattaattattatt
attattccatttgcattaaatataataaaaagttgtaagattctctccgcctccttctctctata
agaaccgacacagagacgaagaagaataatcactcgaaaactcatcaaatcaaaaatcaaacacag
agaagagaaa*cag*gtaaaaactctcgatctaaggttttaaatgtttctttctgattgatttcgctg
ctttatcgtttctgatcttggtccttttgattagaatatgacggattcagaattaggtttgaattg
tccccaatcgaattttgagctccttaatgtcaaatttatgaaccctaatagtttaattgattgtt
taggaacccagaatctcagaaattgaaaccctaagaacttgatagaagcatcattggataaaaaca
tgttatgtgaatctctcaactatgcatattcaattttatgaatcatctgctagagatcacatgaaa
attgtctttagtgaacccatttgtatctatgtttgtattattatccatgttctgtgaagcacatg
aaatgcatacatttgttatcttaatgatgaaccgatgtcgtatctattgtttgaattatcgatcgg
tgtagcttgttttcttaaatatggttgtgtggaaatgacacag*gt*

Figure 31 (SEQ ID NO: 31) AT3G60245, +intron
atttctgtgtttaaccttttcgtacatcagttttaaagcacagagagctcaatgttcttccaatat
cgttattaataaattttgattaaattcaatcaaatcggagttatattaccacatgaggttaaaggg
ccatattaaaaagtctgcacttcatatgagcaacaaggcttttatgtctttatggttgatttgatg
gcccatatatgatagttcaaaggcccatattaaaaaatgccctaacatgattcgattcgtatataa
agacgcttaatgtgacaagcgaacttGctcattagggtttctcatctacgacggcgtggtgttcct
ccttcctgctctgaaaa*cag*gtgaaaaacctaatcctttctttttgttattgttcttgaatctctg
taattccatagcaagttattcgagtatacttccttctgtctcgttctagctttcgttttgagattt
caagtttcatagttgatctgtggattctgatagaagtctagttttgtgattttgtcttttgactct
attactctttttcgatgtttcacag*gt*

Figure 32 (SEQ ID NO: 32) AT3G04400, +intron
agattgaaggaggacttaataattagaacaaggttatataattagatatattcttttttttttaa
ggttatataattagatatattcgtttttttaaaaggttatagaataagatttcattgcatcttaaa
accagacaactttcagaactgaagaatgacgaaaaattaataatagaggaggagaggaggagctac
atcaacattatttctatttttcagccaatcagagcgctccggacttcgcccactcgcaccaacct
cgcgccacgcgctccattccatgcccactcgcaccaacctcgcgttgaacgcgtgtcgtcgatttc
tgtaggggtaaacccacaaaatcatgcctattttacatctactcgctttgtttccaaaacagcctc
gagtgactttttttcttttgttttttttctcaaaaccgtattaattctaatgcaaaccgaaccaaaa
ttaatttttatttcaaaaccatctaaaccaaacagaaatcacatgtaatttcaaacccgaaccgaa
atcaattgtcatttcatcaaaaccatgtaaaaagcttctacgattgttttaacttgcaactgaaaa
tagcaatcctaatttatcaacagataaagatagatacatgcaacactttactttttttatttttggt
tttgagaagatgattacagttgtgattttggtggagacaaaaatgtccatctctgtatgttgctag
ccgatcaaattttacattcaaaatcctttttgataaaaaaaataaaaaaattcaaaatcctttatg
atatattgggcctaagatgatttccaaaaaaaagatgatgagaaaagaaagagaacattattgggc
ttattgttaaattatttcggcccataaaataaagtccaggtcagctcacaatacatgaagaaaacc
ctagttcaagcgtAtataaaccctctcggcgctgccattgaaactctttcaaggagagagctgcta
ctctgcaacc*cag*gtaaaaaaacgtttcttcatctctaattcgcttaacctaatctgtgtacatct
cgtatgaatcatatcctgttttcgcttattttcttcatttcactttcaatgacaatggttttaccc
taatttctattagtaaagcttctggatcatgaatattagtcttatatgtctctactttggttgata
gtgtttagatctgtaactttgtgtttgttttttgtgaatag*gt*

Figure 33 (SEQ ID NO: 33) AT2G47170 ttcagacacaaggaccgaccaattcgaaaacaatgaatggatatgattcatccttatgaaagcttg
acaacaaactcggttttggctggttaacctagactcggtttatttaaaccagacaataatttcttt
cgtcgtcgttttatttgaataggtgcgtcaaaaataaaagctgaaattcttggttgcaaaagccca
acaggcctgtggagatagctttttagattgattaaatgggccgaattgggctgacacatgacgaga
atgtggctatagaaattgttagtgagagggtccgggtccaaaaatgttgcagaagtgatatagtat
ttatttaattaaaaacatattattcgacgTatttttaacgctcactggatttataagtagagattt
tttgtgtctcacaaaaacaaaaaaatcatcgtgaaacgttcgaaggccattttctttggacgacca
tcggcgttaaggagagagcttagatctcgtgccgtcgtgcgacgttgttttccggtacgtttattc
ctgttgattccttctctgtctctctcgattcactgctacttctgtttggattcctttcgcgcgatc
tctggatccgtgcgttattcattggctcgtcgttttcagatctgttgcgtttcttctgttttctgt
tatgagtggatgcgttttcttgtgattcgcttgtttgtaatgctggatctgtatctgcgtcgtggg
aattcaaagtgatagtagttgatatttttttccagatcaggcatgttctcgtataatcaggtctaat
ggttgatgattctgcggaattatagatctaagatcttgattgatttagatttgaggatatgaatga
gattcgtaggtccacaaaggtcttgttatctctgctgctagatagatgattatccaattgcgtttc
gtagttattttatggattcaaggaattgcgtgtaattgagagttttactctgttttgtgaacagg
cttgatcaaa Figure 34 (SEQ ID NO: 34) AT1G65930 aataacaatatatatatatatatatatttatttatttatagatattcatatatatatataagaaaa
tatatagatatggtcatatggatatggttgtggacttgtgatgcgacaaaaaaaaattgaacaaag
tggatctggttaggtggccagcatcttttacggaagggaaaagttggatatattacaatattttg
gtggaccatgagcaaccccaccacaaagtgcatgtgaagtgaccacttttctgcgagctgatccaa
ctaatcaataatggtaacaaatacaaaaaataaacgctctaattttatttcagtcaaatgtttta
ataattttccatgtccgaaaactttaaaatcttttattattactaagttaagaaaattgcaaatgt
aagaattatttgtttctaaatagataatattaataccaaattgatattccaaaacatattattttc
ttgtttgatttgattgataatctattaactgataaacaacaatgatagaaatatgttctctaattc
ttcttctctagcattcaaaaattcacatccaacaaaaccataaattttgtaattttagatacaatt
ttacactaaaaattaataattgtaaagcttgtaattatattcccaaactttattctataaattaaa
acttagcattcatattgttgaatatgacttttgaattttgttagtgggacccttttatacaataag
tggcggctacaacgaaaaatcaaagtagggaccaaaatgatacaaatcgtaataacggggtcaaaa
taacatAatccaaacttttaaatagcataaatacaacaactctcaagacctgtacaagctatttca
cctacttcatcactcatcaccagcttcgcatcttcttctccggcttgatcttctctcgtttctaga
tctccgacgatcggaatatcaaatccgatcgattaattctgtcaatcacacaaaaaccgaaaacca
aaaaaaaacc Figure 35 (SEQ ID NO: 35) AT1G02500 tgaaaacgttttccttatctcacttgtatcaaaccaaacgaaactaaaaagactattgtttgata
taatttttgatgtgtaacccggtccaacaatttcatatggtatttatttgaatttttatagtcctt
ttttcctaaattacagtcttacagacacaattattttctttgaaatgaaaaatccgattggttcac
gttatataacaagtcggaccaatcggtccccaatagtcagaaaattttgaaaataatgccaaaaaa
tagtaaatattggtaggccaactccaaagccaaatacatatatatttctttacaagtccaaagtag
ggtggtttaaccaaataaaccggtgaccagtcattagtgaaccgtaaaaggcctataaataaccaa
cgtgttctgactcactttCtcgtctcaaaccgttccttctcttttaacacttgttcttttaaggca
aaaaggctcgagccacagagatctgagtttctcttcttcgagatctgatcgccgaatctcataatc
tcccatcgaagcaggtattgttcttcgtattcgcttctcgtttctctctcgatgtattgttcattt
ttgttttccagttgattttcaagtctgacgtgcgtatttttttccgatttgacgatggaagtagatt
taagggactattgactgtatctatggtttttaattagatttcagctactctttaaccattttgtta
ttggatcagcagcgatttcgttatagattctcaaaaatattctcagatgtgtgggatttgagtaga
gtttatgttgcgttggcatgatttgaatagtatgcaagatttttgagattttgaattcgttcatgt
gtgtatgtgtgattgtagcttgatatgatttaacctgttagttaaatgtgcatagacaataagtaa
catacgaagcgagtcactaagcataagagtcaacttgttttgctgaaaagatatcacttatgattt
tcgaatcatttttagctttttttgtcacttgagcttaatgattcttctgaaattcgattctttgtttg
gtttatgtcacattctttagaattgagaatctaagaaaagcttacaggatatggtgaaactattct
tttaagatagcatgatgcttcttttatgattctacagtggctaagtcatttttttttgttctatt
ctttgtagcaga Figure 36 (SEQ ID NO: 36) AT2G45960 attttacacattcatggtgaaactacttggtatatatatgcaaatgaatatgcatgtggatggtac
atggcgtttgattttgcatataggcaatttattgatcaatacttggtgtagttggtacattaaagt
tgcattatagacaaacaaaattcggctgtcatgcttgattgatctatagatgatttcataataaaa
aaatattgtcatggataaaaatagtgaagatgataacaaaaagaacagaacacaaagaagaatctc
atttctttttttgattaataaaaggatataaagtcattagtttttttattcgtctcactcgacacta
ataataactaaaattgttggagaattaaaagtaagaaagcaatgctataaaataaagtaattgttg
ggaatggagcatgtaaaattatcactcataactaaaattagcaatgttataaagtatttaagtaag
aaaatgttgtagataatttgttaaatgaggtgtccctatgtcttttaggtgcggtgagtccatgtg
cttatcctgacagcggtccaacttaaccggcggttcatctcgaccacatattcaactgcttttta
atatgattttctgtattttcttacctgtcataatctacatttaaacgttaaaaaatgtccacaatt
ttatttattttattagggtacaataacgacatttgattagagtaaagaaaatagttgcaaagcggg
atttgaaactctgtccacatactttaattatcattaatcaataacaagcattatcagtattcagca
gcagcaaagatgataacgttaattatactatcatgcaattaagttaactaattAactatcatcttg
tttttgttttaatttgtttccatcatcttccaaccttgagtttcggtcactataaaaagccacca
ctctctctgcttctctgcaacacataacccactcacagaaaaacctagaaagctctagagagaaag
agagagagag Figure 37 (SEQ ID NO: 37) AT5G02380

Cgaaaaaagaggagagattcgattcaaatacccacatagaacggacaaggtcaataatgggcccac
tattcttttgagagcccatctcaacaagttgaatcatctttttgtgtactctcacttcaccttttt
gacaaaaagtcatggaagccaaactttggaacactactttactttgccaacatcttgttttgttga
ataccttttcaaattggaaaccaaagacatatctaaagggaaaacctgtaggacaataaaacaaa
gaagtgatagctaaagtctaaactaatctcaatatatgtaaatcaaagagataactaatgaaaaat
atgaaaattttcgcgaggattaatgaacaaaggaattttttttttccttctaaaatttttatta
gacaattggtattacaatgacaactacgaagctaatacaaaacttcggaaaccaacttattacata
agcaaaattatgtgtcatatactgaaaattacgaaactgaaaaagtgaatttaacgattttcctt
tcgataagctttattcgctaacatgttaacatgttagaacatagaaaatattgaaaaaaaatttat
gtttaaattgtcaaatggaaatatactttacacttttatttgtattaattgttactttgctctcct
agttataaagaagtaaagtctatgattttgttacttcttttttcttgtaaatctttatacatgta
aaaagcttttgtttccaactctaatcctcaatattttatttttctgtttattggaaaagggctgta
aactaaaattatttacttgaggaacgattatttaggtgataagagtggacaaagatcgttgacacg
tggacggtctacaaattctaattttgcctataaatatcaaagctcctgaatatgtaagtttcAttc
actgattatcgtttaaggcaaattaagatcatcttcataaatcttctcagatctcttccaatttc
tagaaaaaac Figure 38 (SEQ ID NO: 38) AT1G15930 agttgtttacaccctttgtttgtcaaccacaacttttccaatgattccactaatccacgttgctgc
caatgtctaatatcgtatcaattatcaaaattgtgggagagaagggaaccaccgaaataataatgt
ccttacacaacgtcgtctagcccaattaataggcccatttaagcccaaataatacagaattgtggc
cctggtccgctacgatccgttaaaatctgaaattagggttttagtttaactcTccatataaattgt
tccaaatttcattcgtatcctttccgctgctgccgtcttcgtctctgaggtcagtgtttcagctcc
ttgaacgatatatacgatcttatcgatttcgcattattctatcttaggctatgtatatgactgtcg
aacttagttttaccgccgccgatttggcttcgttatattttccctagtagaattaattgtttaggt
gtttgctaagctcatttgcatgacttatattggcagataataaggacttgtgtatttttccatcgt
taaaaggcatttcaaagagacaat Figure 39 (SEQ ID NO: 39) AT4G33865 tctctcttttaccactttagcggactcctgttgataagatttgattttgttttcgaatatatgtag
taactgaattgaggattttgagtttgatttcagaaggctgataaataagttgagagttcaatcccct
cattgtgtatgataaccatcaccaatttttctactacatttttggctctgacctcatttatcaaa
ttttgataggaaaatgtcactttggtttgtgccaaaaaagggcaggctctgttatattattgacgg
cagaaaatggtaggcatgcttaaacgtatgagttagtgttaaattaggtagaaaaatgacaagctt
ggtatataacgttcaataatataaggaagatgtggcagagttagtgttgagaatgggctagtctac
ttgtgtttaggcccatatatataaggcccatatatatttgaagaccacaaataactagggtttaca
aatttggttatAtagctctctctctcgagccgcacatatttcgtcttcttgatctaatcgctttga
gctgttagcagagagcagtcgacaatc Figure 40 (SEQ ID NO: 40) AT2G18020 atcatcattttatatatcaatctatatatttatcatatgactcagactatcatgagacgcattttt
tttaagtattatgaataatataccacttgttcacgttttaacgtttgaaaaacatgattttgctac
tttttacgattcaaagtatttattaagaatttacgttcttgaaaagtgattatactgtatatataa
ctataagtaaataaaactttttcgacgaaatttctgatgataaataaaaggtcggatatatttga
ctttttttttttttttaattatttttgacgataaatttttcgttgaaaaatcatcgaaattttcg
acggattccaatgatcaaaaattcgtcaataatttccaacgatattctgactaaactaaatctgat
gaaatatttttgacggctttccaaccaaaatatttcgttgtgacttgtcaaaaatccgttagaata
ctaagcaacttttcgacagattttcagcaaaaatattcggtaatataacgtgttaaaaatatgata
aaaaaaaaaacttgatgaatctactaaaactaaattttcaatcatatatatctattattcatatat
ttcattcattttattatttttctcttaacaattatttagttattctggtatcgtgtaattatattc
atatgatttattctgatattgattcggttagcatccggataaatctgggttgggctttttaacttg
gtttttctaagaaaaattctaatatgatttggttagcatccggattagtctagtttggtaggcctg
cctttgtgattcttaactcggtcttttgtatgggtttgaacaattactacaccatttagattcttc
tgacccatatcaaataaagatccacttaggcccattagggttagaacaaacatgaggttgcagaat
aaaaagggttcattttcctcactctcaAgttggatctcaaaaccctaatatctgaacttcgccgtc
gagagcatcc Figure 41 (SEQ ID NO: 41) AT4G34050 taaaaaaatttgttcggaaaatatcacatttctttcactagacaagccttgttaccacacaatgta
tcaatatgatctaaagggcaaacgaaagatcctgacatgaaacgtttaattctcattttctccaaa
ttttatttttatgtgaagtagataaattagtatatatatatatataccaaactagtgtgttatgt
tatggcaaatgttatatcaattcgaaggttccgctattgcaatattcattaatttttcataccaa
tactatttttctttctcttttattttgtttttaataaataaaagaaattaaggatgattagtaag
gaagtcgcctaccaagagattcacctaccacggtacacttcaacaccgaagcagagttgttgaatc
cacttttattcccttctctaatctctactcaccaagtctccactttttttctctttattatata
catttaaattatttaatatacgccaactacatacatatccagtgtaatttctcgttacgtcacacc
cctttcgtaatcgtctaatttcagaaaaatatccagaggtttaaatacatattcccatcattaaat
ctagacataaacacatcatactcacaaaatttggcagcaaacagttactacagacccataaatgaa
aaaacgtattcacttgttttcaattttcacataaccacttccctgagtttggtctcaatttgattg
ccccgccgaggcattactacgccaagtgcgattaaggtcccatacagtgtaacgggacccactata
agacagcgaccgaccaattgcgtgttaggagagtttcaccaaccccggaccggtttttaccggata
taacagaaccggtacgaaccggtctcattatcttccatcttctttatatagacctcatgccatgtg
tgtgactCaccaagaaaaacacaatcgtttaatctcacccaagaagacaaaaacacagagagagaa
agagagagaa Figure 42 (SEQ ID NO: 42) AT3G09840 atatttgtggtaatgtgttaagagttcctattaattaccataagtaaatcacaaacataaataaaa
tgaaaataattatgggctttaaggtctggaggactactgaaatttgggagaagtagttggaaaaag
aatattagtcgataggtaggaaattgatattgcttgtggaatggaggaaaaaattgaacgaaaaag
aagtttctagaattctaatcacataacataaatagggtgaatatttgggaaaagtaaaacaatagg
ggtcggtttgatattactagaagataagaaacaaaaaggaaaataagaataaaggaaaaaaaaaga
gctctcttttccaacaagaaacgtagAgagatataattagagaaaatctgtgctctttcagatccc
attatcacaaatccatctctctctctctcagagaagaaaccaaagaagaagaaaaagctctcaa
ctttcttcgatttctcagggaactctttcgttaatctcaaactcaatc Figure 43 (SEQ ID NO: 43) AT2G45070 gaaacaatgatgtggacctaatttcggttggaagatattttgtttatctggcttagattttgtcct
ttgatttagggaatcaaaagaaagtcataaacattaattttgcctgtaaaatcacacatttcagat
ttgttctcgtatgacctacaaataaagtatatgattacacaatcaatctttagattcaagaacttt
gtccctacttcattatattcagctaacatttctttttaattctctgtcgtgcgaaaggttgttgac
aatataaatgatatatgtacttgtacgcgtaatgctgctaatacatttaatttgggcttcttctg
ggccttaatatttgggctttaaataagttatctctcccacttacgcatgTaaacacagctctgata
attacgctgaggtggcatttttaattggctattgcattaagagttgcgtggcgagaaatttcccc
tcctataaaaattgttgaagagtccggtcaactccgaaagtcttcaaatctctccgtcacgaatcg
ttctctcgtcgtcatcaaaatctgttagccgaatcaggtgagccctttgttattttgttgtttat
gatctggatctctgttgattgaggaaattggtagatctatggatttgttagatgagcgtgtgcgta
gatctgaaaatgagatctcgatgttgaatctgaatcgcggctggtatacgattcccgatctggata
cgattcaacatgcatagcatctgagaattttacatagaattttgcatgttcaattttgtctcgct
gatttgagaattttaggattgcttcatctaatttagttttgttgactcgatgctgaaattagtttt
ctgcgtttgagagtttcgaatcttccatctcctgaaaatgcagctcaaactcatatagtatatgtc
aaattgaaacaagtttttcaattacgtttctaagaactcttgctaaccagaacaggattgtacca
agtaatttacatgattaaacctgaatttgtactgatttgagcttacggataaatggaaacaatgtg
atagtagtatataaatttgggtatacgtagttgccttgtgggaagcaaatcttttaccagaggttt
ctagtatcatatagaatgtatgaccatggaaaactaaacatgagcttaatggtgtttagatgtctc
ctattatttcatttgcttaataattctctgtttttttttatatatgatcgctcttttgcttccgat
ttcctaaaggccaaccattattctcagatagagaaaagaagaaaga Figure 44 (SEQ ID NO: 44) AT5G43940 tgctaaacctcagcaaaatcatgtgttgtgataagacagtggcattagccaatagcttaaacaaaa
aaaagtactagagtacaacctcttattattgttttcaatgttttgtttttatatttttttcagaat
aaaatatataatggttcgacgcatatttttcaattttcttttggtttaattaatgataaaatgatt
gcaactctataaatatacataattgtgaaataaacctaattgctatgttcttaattgtcaagaatt
tatcttcgaatgacacgaaaatcgaatttgaagtacgagacatgatttgatctgtgtatattgtac
atgtcctggatcgataaggttcccagtctagctacgtacactagtttggtcagggatagctttatg
gtaacgagaaagaaaggaagtgtatccaatcacgatgaatcgttttctaatctatttctttcagtc
ctattcaactgattacacatgtcacatgtgcgccaattggatgctgttgaaactttgaaaatgcac
cactatagtgttaacaatgagccggcgtgataccatgttttctttattttcgaaaggtgtatccat
tattgtaattttggaccaaagcatatgacattgatgtgtctctgggcctactttaaatcaaatcgg
acttttctcactcgattattaacgacccgacccgactcgacccggctcggaccggataattacatt
tgtagctatgagaagaaaAagaagaccacactactctctctatctctctttctctctatctctctc
tatctctctcatttcttcctgcgtca Figure 45 (SEQ ID NO: 45) AT5G64350 atattgctctgtcttcttgaccatgtatctttcaaaaatgcgaaggaaattttgatagctacaagt
ctgggcttgaatttgatgaatccgaagtaaaaaatagttttgggctagattctgcttcttaattcg
gtctggtacagtattatattatccacctttgagaaagaataaataatgggcctaaatttcatcgaa
ttgggttttggattattgttaggcccagatagggtttagatcaaacagcatgataattgataaata
acaaAatatatataggcaaaagctactccgagattcgaagctgcaaagaacgcgaaacagtgagagag
acagagagaagatatagag Figure 46 (SEQ ID NO: 46) AT5G48810 ttttaaaatgaatcactaaacaagattcattttctttctaaatagtgtaaagacgagtgatgcatg
caactgctctcctttccgttggtcccttgtcaaaatatacgaccgtgaataattcttcccatcata
tttatctgtcggagagttccaacctcaaaacattctccttctcttatcaattctttctaaaatcat
aaaccaacaaactgggcctatgatcaattattcatattcaatttagcctataactaaaaccacact
gctttcgttacactggccttccgacaagtctctttgactgttttatcttaagcgccatcaagttt
taaagaagacaaccccatatctttcctcccatgaatcatcgtgtccatattgctatagttcatgaa
aaaactaaatactatcgacaactgaagaaaagatccggatcttgtggaccgagtgaatggttgggc
ccaattagaatggtctaccctaacatctagccgtctacacgattgatcatacgtctaagagggcga
aaccaccaaacgtttggattttatctaaattgatgtacataaagctaacatgattttagtataaac
attataagcatcatggaaatcaataagctaacatgattttagtagaaacattatcagctaacatga
attactaaaacatttattttattttaaggaaaaacatacaatactaagatttttataacatttt
ttctttgtaacattataaattgttttagtttctacattaattaaatatataaaataaattcattta
aataatataagaaaacggaatctttgattaactgctgattattggccactgattAatttccgaccc
catcaatagttgagatcagacatacacaacttaagtagaccaaaaaagcggttggtgtaagatccc
aaactcacagattcccaaataatagtaatactcttcctcttctcaactctcaccagtcaccagcag
atcatcggag Figure 47 (SEQ ID NO: 47) AT5G19760 aacgttctgtatatgctttgttgtcgtatcagctaataatacatttatgagattcaactaatgtta
acaaaccacgttgatcttcacaaaagggcatcagaattatcaaattgcatcagaaatactgctcca
ctggtccactatctaaaatacggcgtgaaaaatgccaaaaattattgaacaaatacaaaatacaaa
tacagaagatcaatttttttaaaaaattagaatttattggacccaaaaaattcagaatactaacga
ttttcaacttcatactagaaaattagaaatggacgaatgtcaaatctaaaattcatatgaatgcgt
aataaataactctaaatatttggattgcgtaaaatccgaatggtgaaaagtaaagtccaaattaat
aaatttagaaaatatgtctggcttagatcagatctcatatgcaaatggaaaaaaataaaaattaaa
aaggcaagggtttggtgcaatttagtttcAgttgggtggtgttaatataaaaggcccataagcttc
acacttcatcgtctcctctccaccaagtgaatctctttctctctctcttttctccgcggaaggaa
tctcttcttctggttgcgtttgagtccgtacgaaaacaaaagaaaagagagag Figure 48 (SEQ ID NO: 48) AT2G28910 taagctaatgcgcagttttgtttgtttttatctggagtttttttgtttcagttactatttgatg
atggatgattacagcagtaaaaaagaaaaacacatattaactactcagccaggcccagcccaaatc
cctctcaacgcagccaggcccagccgaattatgtgacaaaactaaaaatgatgaaatacacaaaat
ttggaggatataaatgtaaaataacaaaagctaaagggcggttccaactatttcccaatctttata
atataccctcgagactttccaatctttcCtttttgcctcagaggccattggcgaagaacaaagttt
gaacctttcttcatccatctctctccgtcgcttcttcctaacgattccttcactcgaatcaggta
aactatttactcttctctttctctttaggatcgattggaaccctaggatctctgagtttttctttc
acatttaggatctatccctttaatcggcaaattagtatgtgagcttttgatgatttggggcttgaa
accctagatttcagcttaatctgggtaatttcattgggttgtgaaatttctgtgtaattgtatttt
ggagaagatattgatttggttaggtattaatcaatctatatttctctgttattggtttaggtttgt
gaaggtttttctagggtttcgaaaag Figure 49 (SEQ ID NO: 49) AT2G23090 gttttggccgaaaagaatatgatgaaatcatatgttagatgtcaaaattacggaatcatctagaaa
aaatcaaaatgaattcttctagaagttaacaatagaaaccactcattcgccgggtgaaatcaattg
actgacgagttgtctactaaacgagcgttagtgtgagttaaacctctaaagtttgatagctcgaac
tactatcgagattcttcggacaatctttcttagtatcatctcgatgttcattgctataccatcatt
tgctctcttatactcaatagacaaggtagtagttagctcgtgcaatcaataaaaagcggtcatatt
ttgtgtgagtgagtgactcattttttttgaagaagataaatcgtgtaggttatagcttatagagac
ctaataaaattgacatttactagagtctgtcctaaaacaacaaaaaaataattttcctttattttt
aatttttaattgtaaattctgttttgttttagtttttttagaagttaacaatataaaccactcac
tccctgaataatattaatcctatcattttgcatgaatgagtgagtgtctcaattcctttgaataag
ataaactgtacaggttatcaattagcaaaaaagaatctttttcttggtttagattgaaaacatatt
tgtgtgttggtcaactgatttattcagaccaaaaaaaaaaaaaaaacctcagtcgtttaaacgtta
aaggttcttgttttaacgggccttaaatggataataagtccgaaggcccattatgttgaattatct
agaatccaaaataactttaggtgattggtgagtaggcgaattaaatgtaagtggacattacagaaa
aagaatCaagtggcatcgtttttttctttctcatataaatcttttcacattagagtcggcataaaa
attccatttcgtatttttctcttcttcctcttctgaaaaattagggtttgagttcttcttctaatc
gatcagaaag Figure 50 (SEQ ID NO: 50) AT5G02960 tacagccggttccgtaaggattacgggttatgctgatgtggcggaagtatttattcccagtattaa
ttagcatcagagtatacgtgtatgtcatctaatgcgtccattagatccaacggtttagagttcagc
ttttaaaagcccaaaagaatgatgagaagttgagacaattatagtcaatttttttaaaagcccatga
cttaatgggcctactaattgatgggccaagtattagaaatccgcggaggtagaaccagcttcgcat
Atattaagagtcactgccttcactaggtttagggttttctcagccgcttaagagcttatcatcttt
gtgcttcctgcaaatagctctttgctgttgatctttctcctccatcaacaaac Figure 51 (SEQ ID NO: 51) AT3G09500 tattgatttttgtttgtgattttaacactttgtacaaagattgggtgagtatttgtcatttgagaa
gcggaagcttcattgtgataataaagacaagatgaaattagatgatgcaatgtgactgaaaccata
aaggtcacgtgcgtttatttgctttaggcttctcgtaatgaaagtgataatacatgggctaaggcc
cattaagtatttctcttaagttaagctattgggtatgaataatgagctttataccacccaataagg
agactcgtcatataTaattgaccactcctccgttattagggtttctgattctcggagctaaaagaa
gagcaagcagcggcgcagaagttgaacacaagtgaagctcaca Figure 52 (SEQ ID NO: 52) AT1G66410 aatgttcacacacattgatggaaaacatgccattacaaaagatgtatatagataattttgaaatca
gttaacatacctataagtgttcaaatgatagtattaggttagttaaaatgttggcttaactaattt
tgtttttagtaaatcatagatttggaggtaaattttgtagtccccgagatttaaaataataacaga
ttttaatcttcatctgaagaaaattgaacagttgttttgttcctatctttagaaactactagttca
atcctttttttattatacagtaagtaatgtcaacttttactataagattaggtctttactctttag
gataaaactgtttttaagtaaacacaattttattttaaactcaaaagtaaatatttgcttttcagg
gatgtcaaataaaatgatgatctgaataataaaacaatggtaattttggaaaacttacagcttaaa
acttaagtactattgtattattgaggattgtcttatttatcattcaaaattgaaaaatcattactt
tttaaatatgtaaattgttttattaaaacattttaagccttaatgtgtatccaagggccctttgg
gcttcctctcaagtcccacatccactaatcacatgattagctaaaaacccaactagtaaattatta
ttattatcttccgtaaacatttaatttcgttttaactttttcctcattgtCgtataattgtttttg
tcggtcgctaagatattttcacagcttcggagacttcaggaaaaaaaaaaatcatttcttctctga
aacgaaaaaccaaagaaacgagaagaagaagct Figure 53 (SEQ ID NO: 53) AT1G04270 ttgatcctatcgtatataacttcgatttaacaaacacaagtcgtaatttctaaaaaacaattaact
caatttgtttgaaaataaaagtttcctttttcttcgtaacaagtgaagtcaaatgtttttcactcg
tatctcttacaacgttttgatgagatgataagagaagagtgggcccacatatttgcttaacaatac
acgttttagggttacgtgtcactaatgttattgggttcatttaatctgggcttaaaagaggcgtgt
atcatgttgtaatattcccatttgggctttcatataatgaagttgggccgacaaaaaaaaaaagga
ctagggttcccaagtatcccactatatataattttagtcgaagaaaattcttTtatttttctcttg
caaagacctctcagcagccaacgacagttatcaaagcttaagccgttttagggttttatcctttg
ctgagatccaatc Figure 54 (SEQ ID NO: 54) AT2G46330 atagagagagagagagactgactaatgagtcacatatgacgaatgagtccagtttggctgccagtc
tgtcagcccctaccattacaccacctctaaagatttgtattttatcataatccaaccaaacaatgc
ttacaaaaaaaagataatcacatcacatcacatggccttcttcgtcgctgtaacgtttaattaaac
tagccgccaatttcttttaaagatttttttgttttgtttttgggcttatgtttaaaccatataatc
cataacttcatttctattgctatttttgaatttaccctataaagctaccaatattgaatttttgta
attcatttaagtttattacataaataatttatttacttatatgattataattttttttatcggcta
tatgattgtaatttagatcagtacctaatcaagtttctatctttttctatccgttgacagaaaaaa
gaaaacaattttctatcaacaattcacaaatcaaattggattagagatacaacaactttagtcaaa
attctaacacaacaattcatacttttgatcattcaaacatgattttatttttttatttatctagaaa
catagtaatgtcaattttgacaattattcattcaaaaaaaaatgtcaattttgacaagaaaactag
gaaaaaaaagaacaatagaggaatggtcaaaaaagaataaaagaaaattcgaggaaaatcatgctt
cttagaagtttttttgtttaattagcttgactagtaaatagatttgaccggataaataaccggttga
aaccggtaacctttaaccggtcttcatactataagaacaccttaaacaagtcgtctccttcCactt
cttgctttattcctctcataccgttttctctctctcctccgtcgtctctgcagaatcactctctcg
ccggagtttttcacctgcagagctctcgatttttttctctcgagcatcatcattttcgtcggatcaa
tcaccaagag Figure 55 (SEQ ID NO: 55) AT5G42300 atccggagttgatatggcggtgaatgatagttggttcgatttgatggtgttcttgttcgtgagaca
gatttttttcgagtagttaagcttcgctccttgtctttgatttgcatatttggtagtgatttgata
gcgttttgtagaattttatttagacgtaaattggtggcatatttattgtaattttacatatcagat
tatgagtttgaatggtaacacaatacagctttatataattttgtacaactttcacagttaccaata
acaaaaactttattaaaagtgttataaaaagtttactctcagctttttttgtacaactctttctaac
agctttgcactattcaaataaagctaacagctaaaaaacttgtacagcttttggttaccaatcaga
cactatgtaaatttttggtttttgctttgttacttttgagaggtcggctcttttcttgataggat
aaaattgttgttatttttgagtttgctagcatcaataatcacaattaagatgtatcttattttgag
aggtcggctctttctttgataggataaaattgttgttatttttaagtttgctgagagaattcaaga
tgataaaaaaattaaaaaaatcacaatcacaaggttttaataataaggtttcaaatataaactttt
ttttttttgcacaaactttcaaatataaacaaaaaaataattttaatacaaagtctatatatggag
aaaataggaagccaaaattgataattcacaaaattaaagtaaaatctattagccgacaaaaaaaaa
ggtaaaatctattaaaatatagataaggttctagaaattaaataaatctattaccaattctcaaac
cgacataagtacgaccaaaaaaaaagtttataaataaaagtcacaAcgagccttaacgcgtagaatc
ttcccgtactttacttttccggaggaatagaaaattgggggctagggttcgcaattgtagttttcg
agcgaagaag Figure 56 (SEQ ID NO: 56) AT5G47930 tactctgttgaaagaagttgtaagctttaatgataccatggattactgtgttctatatgcgacaaa
tgcaagtgtagatattagaaccaattgtggcagaaatccaatgacgtggagaaaaaaagttatgcg
ctaggactcagaccagtacgttgccactcgacttcttagtacgatttgttaggatagatagactat
agcaaagaattgaccatcttgaggaagggttaggggagttggtctgccgcatagagtaaaccaacg
tgacttggagctatgagggaacactaatgtgacataaagacaactctcagtgagacctaagtttaa
gttgtacatattgagaggatatctagtttattgttacaaatctatccttttcaattaatcttttgg
ggttaatggtgataaatattcaactatacataacactttttgtttacgtttttttagttttccaaag
taagagcatacaaattgctaagccgaatttctcccactcctacttgtttatatgtacaatgggctg
ggcctataaggcccaatgttttgtgtgtcacatttcgtcacccacagacatatatacttagattga
agctaaagctGcagtctccgtctcttcgcttctagggtttcatcaaccaaattcgctttcgccgcc
tttccacaagcaatc Figure 57 (SEQ ID NO: 57) AT2G33040 ggatcaaatgaacgcacattaatatgacgtaacgatgatgacaattctgtttaatagtatcttatt
gtttacagatacagaaaaataaattaagtgggcctttcaataattaataggttggtgaaatgttac
cttctcttgatattttttttaattttcatttattatgagtatgttgcgttatgaaacaactcgcatt
aatttggttatagattggagaaagaagaagtcatggtcaaaactcaaaaatgtaaaaggaaacaag
acgtgtatgacgacgtgattgataatctgaggagatacctttgggccttataagatgggccgaaaa
agtaatagtattagcctctattcggcccgattaatttcaggggaaattttggtaataaagtggaaa
cgacgtcgtgacaaaactActgtgtagactgagaaataaagaagcccttgattttgcccattgcag
tcatctctctcgaatctctctctataatccgatctgagaaatttcgccggagctaggttttgttgt
ttaccgatcaatcctttaatca Figure 58 (SEQ ID NO: 58) AT5G14030 tgtgaattcttattctatgtccccacccacttgcctacttttattggctctcctgttttagtttt
agtacttccttcctcgttgacttctttccttaactttcccgccaccttgattaattgaatcaaatc
aactttatcagtttttaccctcttttcttactccaaccaaaagattgttagaaatgaaaatgagat
tatggtaacaaaacctccattgattcgagtcaatatgtcttttgaatgatatgaatcgttggctat
tacatcttaagtagactttataattagacgagataattaatagacaaagtcatctatgattataaa
agtattagagaatatttggatccaatcgaaatgtggtgtgggaaaagaaacatgttagattgtggc
aggagacaggctgtgttatcttcattgttctactgcaagtgcaaacacacttcccttctttaattt
ggacggtatattaatacactttattattagaatgggcttttataagtaggcccattatcaggtgaa
aaacaattgggcccatcattgactttttttgttaatgggtggtggtggtggtgattaAtatcgtcg
tcggaggtttcttgagctgaagaaaacattcgtagatctatttccgcatctgcttaaacacctaca
tcgtcgtagatcgcaaacc Figure 59 (SEQ ID NO: 59) AT1G77940 aacgaaggtgcctctcgatgaaggagcttcaaaaggaagcaaattaggttagggctctatggaata
attcttgatgttaccatatattttatagaaatattgtacatgacgaccacctggtctcagtttacg
acacgtgggggatttgtttgtttgtgttgtctcggtcgttgttgttacgtgccgacaaggggaatg
atattaacatagagggggaaaaaagagagagatcttcaatgtgaagtttgctctgtgtatataaat
atttttacatctttcgacttattctattaattcttcaaatcataataaaaattaaaccacttttga
ttacttgtttcttaatttccaagataattaattataatttatctattaatatttgtctaccaaaat
ctaacacttaaaattagcaatttatcttaattaaataaatattgttaaactttgtcttttgtcaca
ctagtcataactgagattgatcagttcgttccatttctatagaattcaacttatacgttgaatccg
atagaaagaaaatagaaaagtaatttgaattttttttcatccacaaacaaaacttgttgaaacttg
aaacattgaataatctaataaaagtataaaaaaaaatataaaaaatatatgtttaccaattatcca
atttatttctgcatattttgtaaattaaaaagtaattcaaatacgtttcatgtcgacaaaatgttg
aatgtacaagtggtttatgctaatttaatcactgtcaattcactgaaacgaataaatcgagtaatt
actttttaattgacaaattacaaaactatagaaacattaagggcataattgaaatttccaataaa
ttgaagagcaaaaaccctagaaaattgacacggactataaaaaggtgaCgaagcggcgctttttcg
gtttggtcatcgtgctcctcttctcctccaccgcacagatccaagacattttgattacactccatc
gccggcgaaa Figure 60 (SEQ ID NO: 60) AT4G36130 cgagtccttcacattaaacctgatcataatcatcatcagctaccacagtatcgcacttagaacaca
cacaatcaaattcaaacaaactttcgcttgacaatttcaatcgaaaccatatcttttcaagtttag
ctaactatcggaaagaaattacataccgagactaatgattccacagacttgagagagcgcaaagat
cgaagaacattcgtcgagagaaagaagaagaaagtgggaggagcgtgtatgtgccagagaagaagg
agcagtggatgatttatgcgcttgggctgtcgctttttttcaactttgacgctccacaaagacaca
acaacgacatctctctatttcaaaaaagtttatttttttattcatttaaatacattttaaaaaa
attaacaaataaatcgccatttgttgttctttttttcaaaaacggaatacgagggtgcagttatcct
ctacgagcaggtgcatgtaataccatctgatggatttgacttatcgtttatccacaaaagattcaa
aatcttcccggtttttaagtttgggcttcataaggcccaattagtggcaaatccatcacagtccac
tagggtttttgagagactggatataaaatttgattttgttcattgttgtcattcGccgtaatctga
agaagacgaagcaatcctcccacaaagaatcatcc Figure 61 (SEQ ID NO: 61) AT2G36530 aacaccacattttgataagaattatagaactagtgatttgcattttaaatgttgatacatatagaa
taagcataatcaaacaatgattactgaaaaatatggtccattaatatcgtataaaaatggttgatg
gacattgaaaccctagtggagaatttgtcacataagtaaggcccaaagtttttgacccacaaacat
atccattaagttatagtttagcgaaacccctttaacaaaaaagaaaattttcaactagtgaattgt
ttctagagagttctgtacaaccatccaaatttcaaacatggtataaaagatgttattgacaaaata
aaaatggaaacagtgaaacgtatagtcggaaaatggaataaaatctagatgccatatattattctt
acttgttctaaagtctttaataaaaatagtcggtattacttggacaaggagcaaaacaatatggaa
aaaactcttctattctgcaaaaggcgtgcagcgcatcgttttggcttcttgcatcagagctgactg
ttctcatccaacggctgttattaaaacaatccaacggttttggctaaatccgtgacgtctttatat
atcgaaccagaccaccaacccatTtcctcagctactactgttgaagcgattctcactaaaccctc
gaacacatcgcctttatctctttctctagatctactcgct Figure 62 (SEQ ID NO: 62) AT5G15200 acgttaggttaatatgattggagacaccactcacttataatatattcttgctgttctattaaggca
agactggtaaaacatctcaacaaaatattgcaattatttgtttttacgatataatctttttttttt
catcaactttttaatgatataatctaaatgccaaaagacatgtaaaatgacattttttttttttgt
tcaaatgacatttctaggtaccactattcagtgcataaaaataattttatgattaagaaaataaat
tcgagcccaagcgcaagactcaaaaataaatcgacatctcaaaacgggcccaatataaagccataa
ttcgtaaaggcccaatataaagccttaattcgtaaaggcccaataaagaaagtgagagtgtagcgt
tagggttttaagaaatcctataaattagttCattcgtctctttcgttcctctctgcgtgccctagt
tattcagatcgccgaatttgcagtaaggagacgaaaat Figure 63 (SEQ ID NO: 63) AT1G65930, +intron aataacaatatatatatatatatatatttatttatttatagatattcatatatatatataagaaaa
tatatagatatggtcatatggatatggttgtggacttgtgatgcgacaaaaaaaaattgaacaaag
tggatctggttaggtggccagcatcttttacggaagggaaaagttggatatattacaatattttg
gtggaccatgagcaaccccaccacaaagtgcatgtgaagtgaccacttttctgcgagctgatccaa
ctaatcaataatggtaacaaatacaaaaaataaacgctctaattttatttcagtcaaatgtttta
ataattttccatgtccgaaaactttaaaatcttttattattactaagttaagaaaattgcaaatgt
aagaattatttgtttctaaatagataatattaataccaaattgatattccaaaacatattattttc
ttgtttgatttgattgataatctattaactgataaacaacaatgatagaaatatgttctctaattc
ttcttctctagcattcaaaaattcacatccaacaaaaccataaattttgtaattttagatacaatt
ttacactaaaattaataattgtaaagcttgtaattatattcccaaactttattctataaattaaa
acttagcattcatattgttgaatatgacttttgaattttgttagtgggacccttttatacaataag
tggcggctacaacgaaaaatcaaagtagggaccaaaatgatacaaatcgtaataacggggtcaaaa
taacatAatccaaacttttaaatagcataaatacaacaactctcaagacctgtacaagctatttca
cctacttcatcactcatcaccagcttcgcatcttcttctccggcttgatcttctctcgtttctaga
tctccgacgatcggaatatcaaatccgatcgattaattctgtcaatcacacaaaaaccgaaaacca
aaaaaaaaccaggtgagatcttacttctccttctcctctctcgatctctttcgctatctataatca
gatattttcgttgattggatacgaaatgatttactttcgcttgcctagattgtaacgaagtttcgt
tgtttgttctgatctgatctctggaatctacgcatgtgtaaactcgttgattgatttggttttggt
gtatgattacgttacagatcgataaaatcgataaaacctttaagctctgttcatgagattgattga
tttatgaaaaatctggactcgatttcaagtgtggatttgatttacagctttgattcggcgaaatag
tttcgatatttaagcttcattggtttgtgtaatgtaggt

Figure 64 (SEQ ID NO: 64) AT2G45960, +intron attttacacattcatggtgaaactacttggtatatatatgcaaatgaatatgcatgtggatggtac
atggcgtttgattttgcatataggcaatttattgatcaatacttggtgtagttggtacattaaagt
tgcattatagacaaacaaaattcggctgtcatgcttgattgatctatagatgatttcataataaaa
aaatattgtcatggataaaaatagtgaagatgataacaaaaagaacagaacacaaagaagaatctc
atttctttttttgattaataaaaggatataaagtcattagtttttttattcgtctcactcgacacta
ataataactaaaattgttggagaattaaaagtaagaaagcaatgctataaaataaagtaattgttg
ggaatggagcatgtaaaattatcactcataactaaaattagcaatgttataaagtatttaagtaag
aaaatgttgtagataatttgttaaatgaggtgtccctatgtcttttaggtgcggtgagtccatgtg
cttatcctgacagcggtccaacttaaccggcggttcatctcgaccacatattcaactgcttttta
atatgattttctgtattttcttacctgtcataatctacatttaaacgttaaaaaatgtccacaatt
ttatttattttattagggtacaataacgacatttgattagagtaaagaaaatagttgcaaagcggg
atttgaaactctgtccacatactttaattatcattaatcaataacaagcattatcagtattcagca
gcagcaaagatgataacgttaattatactatcatgcaattaagttaactaattAactatcatcttg
tttttgttttaatttgtttccatcatcttccaaccttgagtttcggtcactataaaagccacca
ctctctctgcttctctgcaacacataacccactcacagaaaaacctagaaagctctagagagaaag
agagagagagcaggtaagttcactggtttctccgatctaacgatttcgaatatagatcctgtgtta
gctaggtagcgtaattcaaatcttagcatgtttaggattcaatcaggaacaaattagggtttacaa
actcagtaaatggggggactttgatgttagttccagctttgttctgcttggaatcatttgatttgca
gatgttttaatctgtgtttgtgtatgttatgacctttcaggt

Figure 65 (SEQ ID NO: 65) AT5G02380, +intron cgaaaaaagaggagagattcgattcaaatacccacatagaacggacaaggtcaataatgggcccac
tattcttttgagagcccatctcaacaagttgaatcatcttttttgtgtactctcacttcaccttt t
gacaaaaagtcatggaagccaaactttggaacactactttactttgccaacatcttgttttgttga
atacctttttcaaattggaaaccaaagacatatctaaagggaaaacctgtaggacaataaaacaaa
gaagtgatagctaaagtctaaactaatctcaatatatgtaaatcaaagagataactaatgaaaat
atgaaaattttcgcgaggattaatgaacaaaggaatttttttttttccttctaaaatttttttatta
gacaattggtattacaatgacaactacgaagctaatacaaaacttcggaaaccaacttattacata
agcaaaattatgtgtcatatactgaaaattacgaaactgaaaaagtgaatttaacgatttttcctt
tcgataagctttattcgctaacatgttaacatgttagaacatagaaaatattgaaaaaaaatttat
gtttaaattgtcaaatggaaatatactttacactttatttgtattaattgttactttgctctcct
agttataaagaagtaaagtctatgattttgttacttctttttttcttgtaaatctttatacatgta
aaaagcttttgtttccaactctaatcctcaatatttatttttctgtttattggaaaagggctgta
aactaaaattatttacttgaggaacgattatttaggtgataagagtggacaaagatcgttgacacg
tggacggtctacaaattctaattttgcctataaatatcaaagctcctgaatatgtaagtttcAttc
actgattatcgtttaaggcaaattaagatcatcttcataaatcttctcagatctcttccaattttc
tagaaaaaacaggtacgcgtttctcgatctctcataattctgattcttctggtgtttcttgtgatt
ttctgaatcaaaaaccctaatttctcgatgagattataatacaatttaatcaaatctttctggtt
ttaattattcatcatttttaacccatgatctttattttttttggggctttgtacaggt

Figure 66 (SEQ ID NO: 66) AT4G33865, +intron
tctctcttttaccactttagcggactcctgttgataagatttgatttgttttcgaatatatgtag
taactgaattgaggattttgagtttgatttcagaaggctgataaataagttgagagttcaatccct
cattgtgtatgataaccatcaccaatttttctactacatttttggctctgacctcatttatcaaa
ttttgataggaaaatgtcactttggtttgtgccaaaaaagggcaggctctgttatattattgacgg
cagaaaatggtaggcatgcttaaacgtatgagttagtgttaaattaggtagaaaaatgacaagctt
ggtatataacgttcaataatataaggaagatgtggcagagttagtgttgagaatgggctagtctac
ttgtgtttaggcccatatatataaggcccatatatatttgaagaccacaaataactagggtttaca
aatttggttatAtagctctctctctcgagccgcacatatttcgtcttcttgatctaatcgctttga
gctgttagcagagagcagtcgacaatcaggtactatctttttctcatctctcggctttctttctt
ttaaaataaaaattctgtttagtttagagaaattgggattgcctaagaactttatcatgtttatc
attcgaaagatttcaacataggaagatttttatctgaacctgatccttattgattatgtgaaac
ttttgatgtgaaattttgcttagggatagttaagtgtggtggtttaggtgtgtaaagcagaacact
ttatccatgaagatcttgtattaatcttaatagtttccatgggatagaaaattgatatgttcctcc
gctctgtttgagttgacttgttagatttcttcattccatttttactttagtttacgttaaaacat
tgttttgtgaataaatatatggattactgttaatagttgtgttgatttggagcatcttaaacattc
atgtatttgttttgtaggt

Figure 67 (SEQ ID NO: 67) AT2G18020, +intron
atcatcatttatatatcaatctatatatttatcatatgactcagactatcatgagacgcattttt
tttaagtattatgaataatataccacttgttcacgttttaacgtttgaaaaacatgattttgctac
tttttacgattcaaagtatttattaagaatttacgttcttgaaaagtgattatactgtatatataa
ctataagtaaataaaacttttttcgacgaaatttctgatgataaataaaaggtcggatatatttga
ctttttttttttttttaattatttttttgacgataaatttttcgttgaaaaatcatcgaaattttcg
acggattccaatgatcaaaaattcgtcaataatttccaacgatattctgactaaactaaatctgat
gaaatatttttgacggctttccaaccaaaatatttcgttgtgacttgtcaaaaatccgttagaata
ctaagcaacttttcgacagattttcagcaaaaatattcggtaatataacgtgttaaaaatatgata
aaaaaaaaaacttgatgaatctactaaaactaaattttcaatcatatatatctattattcatatat
ttcattcattttattatttttctcttaacaattatttagttattctggtatcgtgtaattatattc
atatgatttattctgatattgattcggttagcatccggataaatctgggttgggcttttttaacttg
gtttttctaagaaaaattctaatatgatttggttagcatccggattagtctagtttggtaggcctg
cctttgtgattcttaactcggtcttttgtatgggtttgaacaattactacaccatttagattcttc
tgacccatatcaaataaagatccacttaggcccattagggttagaacaaacatgaggttgcagaat
aaaaagggttcattttcctcactctcaAgttggatctcaaaaccctaatatctgaacttcgccgtc
gagagcatccaggtttgtttctcttatccaaaaatcttctgaggcttataaacattttcagatctg
ttgattgtttgttgtagattatgatgatcttaatcagattaattagaaaatgcttatgtatcattg
gttatttagtgtagtttatgatgatgttaatggaatcatttcgttaattagaaatgcttgtggtat
agttgttgtagtcttgtgaatgatgatttgagtatatgtttgcgcaggt

Figure 68 (SEQ ID NO: 68) AT4G34050, +intron taaaaaaatttgttcggaaaatatcacatttctttcactagacaagccttgttaccacacaatgta
tcaatatgatctaaagggcaaacgaaagatcctgacatgaaacgtttaattctcattttctccaaa
ttttatttttatgtgaagtagataaattagtatatatatatataccaaactagtgtgttatgt
tatggcaaatgttatatcaattcgaaggttccgctattgcaatattcattaatttttcataccaa
tactatttttctttctctttttatttgtttttaataaataaaagaaattaaggatgattagtaag
gaagtcgcctaccaagagattcacctaccacggtacacttcaacaccgaagcagagttgttgaatc
cactttttattcccttctctaatctctactcaccaagtctccactttttttctctttattatata
catttaaattatttaatatacgccaactacatacatatccagtgtaatttctcgttacgtcacacc
cctttcgtaatcgtctaatttcagaaaaatatccagaggtttaaatacatattcccatcattaaat
ctagacataaacacatcatactcacaaaatttggcagcaaacagttactacagacccataaatgaa
aaaacgtattcacttgttttcaattttcacataaccacttccctgagtttggtctcaatttgattg
ccccgccgaggcattactacgccaagtgcgattaaggtcccatacagtgtaacggacccactata
agacagcgaccgaccaattgcgtgttaggagagtttcaccaaccccggaccggtttttaccggata
taacagaaccggtacgaaccggtctcattatcttccatcttctttatatagacctcatgccatgtg
tgtgactCaccaagaaaaacacaatcgtttaatctcacccaagaagacaaaaacacagagagagaa
agagagagaacaggtctgtttttttgttttactcaaaaactctgcttttcaattcaatttcagcaa
tctaaatctcaattaaaaaaatcaacacaggt

Figure 69 (SEQ ID NO: 69) AT3G09840, +intron atatttgtggtaatgtgttaagagttcctattaattaccataagtaaatcacaaacataaataaaa
tgaaaataattatgggctttaaggtctggaggactactgaaatttgggagaagtagttggaaaaag
aatattagtcgataggtaggaaattgatattgcttgtggaatggaggaaaaaattgaacgaaaaag
aagtttctagaattctaatcacataacataaatagggtgaatatttgggaaaagtaaaacaatagg
ggtcggtttgatattactagaagataagaaacaaaaaggaaaataagaataaaggaaaaaaaaaga
gctctcttttccaacaagaaacgtagAgagatataattagagaaaatctgtgctctttcagatccc
attatcacaaatccatctctctctctctctcagagaagaaaccaaagaagaagaaaaagctctcaa
ctttcttcgatttctcagggaactctttcgttaatctcaaactcaatcaggtaagtacccagatct
ctgattttggttttccgatcgggatttttttcggatcttcttaaagtctgggtttttcgattttgg
ggattagggttttggttgatcttgtgtttctatagttgaatcttaatcttctttgttgttgttaca
ggt

Figure 70 (SEQ ID NO: 70) AT5G43940, +intron tgctaaacctcagcaaaatcatgtgttgtgataagacagtggcattagccaatagcttaaacaaaa
aaaagtactagagtacaacctcttattattgttttcaatgttttgtttttatatttttttcagaat
aaaatatataatggttcgacgcatatttttcaattttcttttggtttaattaatgataaaatgatt
gcaactctataaatatacataattgtgaaataaacctaattgctatgttcttaattgtcaagaatt
tatcttcgaatgacacgaaaatcgaatttgaagtacgagacatgatttgatctgtgtatattgtac
atgtcctggatcgataaggttcccagtctagctacgtacactagtttggtcagggatagctttatg
gtaacgagaaagaaaggaagtgtatccaatcacgatgaatcgttttctaatctatttctttcagtc
ctattcaactgattacacatgtcacatgtgcgccaattggatgctgttgaaactttgaaaatgcac
cactatagtgttaacaatgagccggcgtgataccatgttttctttattttcgaaaggtgtatccat
tattgtaattttggaccaaagcatatgacattgatgtgtctctgggcctactttaaatcaaatcgg
acttttctcactcgattattaacgacccgacccgactcgacccggctcggaccggataattacatt
tgtagctatgagaagaaaAagaagaccacactactctctctatctctctttctctctatctctctc
tatctctctcatttcttcctgcgtcaggtacctttatcctcgatcctcgcactctcactatctgta
gacatgttattgaaaaaccctatctccgattattagttttctgattttcatttcattttgacgccg
attcacataggt

Figure 71 (SEQ ID NO: 71) AT5G64350, +intron atattgctctgtcttcttgaccatgtatctttcaaaaatgcgaaggaaattttgatagctacaagt
ctgggcttgaatttgatgaatccgaagtaaaaaatagttttgggctagattctgcttcttaattcg
gtctggtacagtattatattatccacctttgagaaagaataaataatgggcctaaatttcatcgaa
ttgggttttggattattgttaggcccagatagggtttagatcaaacagcatgataattgataaata
acaaAatatataggcaaaagctactccgagattcgaagctgcaaagaacgcgaaacagtgagagag
acagagagaagatatagagcaggtaactttcctctgcatatttatatctttgaaaattccatgata
ggctaaatcgatctatacaaatctgctttgttgaagagctatttgatgtgttgtggtagtcgtact
cgctatttgtttgttttctatgatgtgaaatagatttaattagggtttatgttctattctgggtgg
tgatagtaacacttaggtcataattaatctgtaattttgctgttctgcgagattatttgtctgctc
atctgaaacttcatacgaatagatctcttgtttagatttctatttgtaggtttaattaaagaatc
ttgtttatcttataatccagtttcttgtgtggaattgaaatgaatttgtttgagaatcttatttct
cttgtgtgtgtgtttttttttggcaggt

Figure 72 (SEQ ID NO: 72) AT5G48810, +intron ttttaaaatgaatcactaaacaagattcattttctttctaaatagtgtaaagacgagtgatgcatg
caactgctctcctttccgttggtcccttgtcaaaatatacgaccgtgaataattcttcccatcata
tttatctgtcggagagttccaacctcaaaacattctccttctcttatcaattctttctaaaatcat
aaaccaacaaactgggcctatgatcaattattcatattcaatttagcctataactaaaaccacact
gctttcgttacactggccttccgacaagtctctttgactgtttttatcttaagcgccatcaagttt
taaagaagacaaccccatatctttcctcccatgaatcatcgtgtccatattgctatagttcatgaa
aaaactaaatactatcgacaactgaagaaaagatccggatcttgtggaccgagtgaatggttgggc
ccaattagaatggtctaccctaacatctagccgtctacacgattgatcatacgtctaagagggcga
aaccaccaaacgtttggattttatctaaattgatgtacataaagctaacatgattttagtataaac
attataagcatcatggaaatcaataagctaacatgattttagtagaaacattatcagctaacatga
attactaaaaacatttattttattttaaggaaaaacatacaatactaagatttttttataacatttt
ttctttgtaacattataaattgttttagtttctacattaattaaatatataaaataaattcattta
aataatataagaaaacggaatctttgattaactgctgattattggccactgattAatttccgaccc
catcaatagttgagatcagacatacacaacttaagtagaccaaaaaagcggttggtgtaagatccc
aaactcacagattcccaaataatagtaatactcttcctcttctcaactctcaccagtcaccagcag
atcatcggagcaggtcctacatctccgatcccagtttctcattcgattttccgttttcccttagat
tttgcatcttatcttcgtgagatccgaaattcttgagttgtgttgacttggatttataaatctaga
gttatgtagtaacaagtttggggatagatctgatctgatttgctagattaatgttacttttctaag
tctaaatcacagagaaattgctaaaaacttacgtctttataattgaatgtgatagttggtgctgct
taagatgtctctgtgtgatcttgtatctgtagttaaagctagtaaggttcatgtagttcatgtatg
ttctgatgtatgaacttttgataacccacttaatctaggtctctgattgtgtggaattagggactt
atatgacaaagtttacatttttttgtgtgtttcattttgatggttatatatataggt

Figure 73 (SEQ ID NO: 73) AT5G19760, +intron aacgttctgtatatgctttgttgtcgtatcagctaataatacatttatgagattcaactaatgtta
acaaaccacgttgatcttcacaaaagggcatcagaattatcaaattgcatcagaaatactgctcca
ctggtccactatctaaaatacggcgtgaaaaatgccaaaaattattgaacaaatacaaaatacaaa
tacagaagatcaatttttttaaaaaattagaatttattggacccaaaaaattcagaatactaacga
ttttcaacttcatactagaaaattagaaatggacgaatgtcaaatctaaaattcatatgaatgcgt
aataaataactctaaatatttggattgcgtaaaatccgaatggtgaaaagtaaagtccaaattaat
aaatttagaaaatatgtctggcttagatcagatctcatatgcaaatggaaaaaaataaaaattaaa
aaggcaagggtttggtgcaatttagtttcAgttgggtggtgttaatataaaaggcccataagcttc
acacttcatcgtctcctctccaccaagtgaatctctttctctctctcttttttctccgcggaaggaa
tctcttcttctggttgcgtttgagtccgtacgaaaacaaaagaaaagagagagcaggtctgtcaaa
tgtttacggatacacgtttctgtatcacccatctctatgtctaagctcgttagtattaacaattct
tgcttgatttgctggtattgatacctacgaaatccgtaaatgttgttcatcagatccgagtctgta
gattttatctctcagatctgagtttttgttttggcttattataatcaaatttcattgctcggaaca
tagtcagactcgtttgagtgtgaattgttgctattgatacatgtttagatgaaatgttctagttca
gatctggattttgattagaataacgttcttaggttcatcacaatgtgtgattcttcgcctgtgttc
ataggattttttaaatgatgtgaatgtaattaactaatactttgttttgtttctggttggtgaaggt

Figure 74 (SEQ ID NO: 74) AT2G23090, +intron gttttggccgaaaagaatatgatgaaatcatatgttagatgtcaaaattacggaatcatctagaaa
aaatcaaaatgaattcttctagaagttaacaatagaaaccactcattcgccgggtgaaatcaattg
actgacgagttgtctactaaacgagcgttagtgtgagttaaacctctaaagtttgatagctcgaac
tactatcgagattcttcggacaatctttcttagtatcatctcgatgttcattgctataccatcatt
tgctctcttatactcaatagacaaggtagtagttagctcgtgcaatcaataaaaagcggtcatatt
ttgtgtgagtgagtgactcatttttttgaagaagataaatcgtgtaggttatagcttatagagac
ctaataaaattgacatttactagagtctgtcctaaaacaacaaaaaaataattttcctttattttt
aatttttaattgtaaattctgttttgttttagtttttttagaagttaacaatataaaccactcac
tccctgaataatattaatcctatcattttgcatgaatgagtgagtgtctcaattcctttgaataag
ataaactgtacaggttatcaattagcaaaaaagaatctttttcttggtttagattgaaaacatatt
tgtgtgttggtcaactgatttattcagaccaaaaaaaaaaaaaaaacctcagtcgtttaaacgtta
aaggttcttgttttaacggccttaaatggataataagtccgaaggcccattatgttgaattatct
agaatccaaaataactttaggtgattggtgagtaggcgaattaaatgtaagtggacattacagaaa
aagaatCaagtggcatcgtttttttctttctcatataaatcttttcacattagagtcggcataaaa
attccatttcgtatttttctcttcttcctcttctgaaaaattagggtttgagttcttcttctaatc
gatcagaaagcaggtaacaaccagattcaattttaggggtttttagtcaatttcaaagatggagat
tttagccgtaaaatcgtgtttcttaatgatttttgtatttgatctctcttataggt

Figure 75 (SEQ ID NO: 75) AT5G02960, +intron tacagccggttccgtaaggattacgggttatgctgatgtggcggaagtatttattcccagtattaa
ttagcatcagagtatacgtgtatgtcatctaatgcgtccattagatccaacggtttagagttcagc
ttttaaaagcccaaaagaatgatgagaagttgagacaattatagtcaatttttaaaagcccatga
cttaatgggcctactaattgatgggccaagtattagaaatccgcggaggtagaaccagcttcgcat
Atattaagagtcactgccttcactaggtttagggttttctcagccgcttaagagcttatcatcttt
gtgcttcctgcaaatagctctttgctgttgatctttctcctccatcaacaaacaggtacgtttctc
ctctattagatctatccttcgtgttcctatctcatttctctgtttagcgttttatttatctgattc
acttgctgtttccatgaattatgaaggattctatagagtctgctgtgtttttttttgtttgaaat
tgttacatgttttcgacttttgattgtggtttttgattggaactgattctatagcaaatgcgtctt
catttctggatatgtttgctaaatgtttttatgtatagatccacaatagattgtgtaaattttga
gctactctggagttctagtatggttgataactggagatttaaaattcgctgtatgagtatctatgg
tctcttgggttttgaagctcacttttgctgatgtattagagataaatcttctatcgtcttgttatt
atttagatgaatttcttattgattttctgagttttaactatggtttatcgagtgaagttgttctca
aatgttattttgtgatgatttgttaacaggt

Figure 76 (SEQ ID NO: 76) AT3G09500, +intron tattgatttttgtttgtgattttaacactttgtacaaagattgggtgagtatttgtcatttgagaa
gcggaagcttcattgtgataataaagacaagatgaaattagatgatgcaatgtgactgaaaccata
aaggtcacgtgcgtttatttgctttaggcttctcgtaatgaaagtgataatacatgggctaaggcc
cattaagtatttctcttaagttaagctattgggtatgaataatgagctttataccacccaataagg
agactcgtcatataTaattgaccactcctccgttattagggtttctgattctcggagctaaaagaa
gagcaagcagcggcgcagaagttgaacacaagtgaagctcacaggtatggcaatggctaatcccta
aatgtcttctaatctgtttcgttttcatcggagaattacgtctaattaatatttgtttggttctgt
tttgtaggt

Figure 77 (SEQ ID NO: 77) AT1G66410, +intron aatgttcacacacattgatggaaaacatgccattacaaaagatgtatatagataattttgaaatca
gttaacatacctataagtgttcaaatgatagtattaggttagttaaaatgttggcttaactaattt
tgtttttagtaaatcatagatttggaggtaaattttgtagtccccgagatttaaaataataacaga
ttttaatcttcatctgaagaaaattgaacagttgttttgttcctatctttagaaactactagttca
atcctttttttattatacagtaagtaatgtcaacttttactataagattaggtctttactctttag
gataaaactgtttttaagtaaacacaattttatttaaactcaaaagtaaatatttgcttttcagg
gatgtcaaataaaatgatgatctgaataataaaacaatggtaattttggaaacttacagcttaaa
acttaagtactattgtattattgaggattgtcttatttatcattcaaaattgaaaaatcattactt
tttaaatatgtaaattgttttattaaaacattttaagccttaatgtgtatccaagggccctttgg
gcttcctctcaagtcccacatccactaatcacatgattagctaaaaacccaactagtaaattatta
ttattatcttccgtaaacatttaatttcgttttaactttttcctcattgtCgtataattgtttttg
tcggtcgctaagatattttcacagcttcggagacttcaggaaaaaaaaaaatcatttcttctctga
aacgaaaaaccaaagaaacgagaagaagaagctcaggttagtctcaatctcatcttcttctttaa
atctctcttgatcgttgttaaaaccataacggatctcatttttccgatttcgtctgcgatcagct
tcagattcagaaaatatttgagtctgattctttgatacgctttggatttggtctaatctctggttt
tgctagattcgatctctgattcaggtgattcgtgtggtgaattgttacttcgttgttgattgaatc
gtttgattgtctcttttgatgtagttttgttccatctctaagcatggatttgtgattttgatgttt
ctttgaaggtgacttatattgaaatgttactagctttgtgcagaatatcatgttcctgattcttgt
tctgaatcgtcttttgtgtcattcttctgtagtttaagtaggtatattgctatagatttcagttc
aaagatactgtttagttttagcacctgtcatgcttttccatagccaaagatattcagattctagt
gttttatgagattcatttaatggtcatgtttttggttgattagtggcttttttttgctcaaaaac
gtttaaacaaaagacctggtttcattcatgtttcgtatgtatatcaatctgactttgttatgggaa
tctacttgtaaggtggtatgtagctacaggtttaagttctctgataatatttagtttcgtatgaga
agcaaacagtcatgtatagtcatgtatgttttagaacagatcatgagttttccataatgaaagatt
ccagagtctagtgcttttttttctggcatccattgatggtcatgtgtttagctgtttgttggctc
ttgtagcttaaaaaagttttattggagacttatttatcacaagacctggtttttattcatgttatc
ttttactgattgaacaggt

Figure 78 (SEQ ID NO: 78) AT1G04270, +intron ttgatcctatcgtatataacttcgatttaacaaacacaagtcgtaatttctaaaaaacaattaact
caatttgtttgaaaataaaagtttcctttttcttcgtaacaagtgaagtcaaatgtttttcactcg
tatctcttacaacgttttgatgagatgataagagaagagtgggcccacatatttgcttaacaatac
acgttttagggttacgtgtcactaatgttattgggttcatttaatctgggcttaaaagaggcgtgt
atcatgttgtaatattcccatttgggctttcatataatgaagttgggccgacaaaaaaaaaaagga
ctagggttcccaagtatcccactatatataatttagtcgaagaaaattcttTtatttttctcttg
caaagacctctcagcagccaacgacagttatcaaagcttaagccgttttagggtttatcctttg
ctgagatccaatcaggtgagttcttcagtctcaatatctgactgaatcttcttctctgatttacat
tttccgattgctgaacaattaatggtgaatgttgtaggt

Figure 79 (SEQ ID NO: 79) AT5G42300, +intron atccggagttgatatggcggtgaatgatagttggttcgatttgatggtgttcttgttcgtgagaca
gatttttttcgagtagttaagcttcgctccttgtctttgatttgcatatttggtagtgatttgata
gcgttttgtagaattttatttagacgtaaattggtggcatatttattgtaattttacatatcagat
tatgagtttgaatggtaacacaatacagctttatataatttgtacaactttcacagttaccaata
acaaaaactttattaaaagtgttataaaaagtttactctcagctttttttgtacaactctttctaac
agctttgcactattcaaataaagctaacagctaaaaaacttgtacagcttttggttaccaatcaga
cactatgtaaattttggtttttgcttttgttacttttgagaggtcggctcttttcttgataggat
aaaattgttgttatttttgagtttgctagcatcaataatcacaattaagatgtatcttattttgag
aggtcggctctttctttgataggataaaattgttgttatttttaagtttgctgagagaattcaaga
tgataaaaaaattaaaaaaatcacaatcacaaggttttaataataaggtttcaaatataaactttt
ttttttttgcacaaactttcaaatataaacaaaaaaataattttaatacaaagtctatatatggag
aaaataggaagccaaaattgataattcacaaaattaaagtaaaatctattagccgacaaaaaaaa
ggtaaaatctattaaaatatagataaggttctagaaattaaataaatctattaccaattctcaaac
cgacataagtacgaccaaaaaaaagtttataaataaaagtcacaAcgagccttaacgcgtagaatc
ttcccgtactttacttttccggaggaatagaaaattgggggctagggttcgcaattgtagttttcg
agcgaagaagcaggttttacatctttcttattgtttgcgattacgattgattatctttcggttttt
gtggtatgtgatttgtttgagtatggagctttatttttggcttaagattttgatttttctgaagat
tttgcggaattgagatgttgttgttagttgtggaccctgtgattgcagaatttggagatttaattg
gaattttggaaccttgaaaagccattgttattaaaaactgaagcttgttattgtttgattttgtag
taagtaaacccttaaggagaatccaaacctttaattataatgttttggaatagcctagttgctaaa
ccttaagagacgccataagtgaatagctgaccaatgtgtttccttaaagtttttggtttttcagaa
actttagcaaattcagaggttgtagttagttgcagacctgtgaaaagtagaactctaaagctttag
ttggacccatcaaaatccattgttatacaaaattgaagcttttaaggattttgattttgttccaca
gtatcctaagcatagatagatatgttgaggctcctttagtacaaagaagatatgattgctcgtaat
gaaatagattggttggttaaaaagattctctattatcattcttcttccactgaaatgtgttttgat
ctttcctaatcgtttgtgtaatgagaaggtcttagaaagacatggaacctttgcttcctcccattg
agacacccccttgtctctattggaacatgattgataactctgaataagttgctattaatactgaac
agtaaagtcgccaaacattccattcaattgttttatataataaataactcacatggtaacttgagg
tagacaatatgcagttttccaatgaacctctgacatgtctattttcatgatcgtttgcgcattgtc
ctaatctgattatgattctattcttcgattggtatacacgagcttcattgtttatttgctttttct
atctggtccaggt

Figure 80 (SEQ ID NO: 80) AT5G47930, +intron tactctgttgaaagaagttgtaagctttaatgataccatggattactgtgttctatatgcgacaaa
tgcaagtgtagatattagaaccaattgtggcagaaatccaatgacgtggagaaaaaaagttatgcg
ctaggactcagaccagtacgttgccactcgacttcttagtacgatttgttaggatagatagactat
agcaaagaattgaccatcttgaggaagggttaggggagttggtctgccgcatagagtaaaccaacg
tgacttggagctatgagggaacactaatgtgacataaagacaactctcagtgagacctaagtttaa
gttgtacatattgagaggatatctagtttattgttacaaatctatccttttcaattaatcttttgg
ggttaatggtgataaatattcaactatacataacacttttttgtttacgtttttttagttttccaaag
taagagcatacaaattgctaagccgaatttctcccactcctacttgtttatatgtacaatgggctg
ggcctataaggcccaatgttttgtgtgtcacatttcgtcacccacagacatatatacttagattga
agctaaagctGcagtctccgtctcttcgcttctagggtttcatcaaccaaattcgctttcgccgcc
tttccacaagcaatcaggtgaaatatctctccttgttcttgatttcctctctctttcactttcct
ctgtaatctctgagtttttttttttatggatctgttgattaggt

Figure 81 (SEQ ID NO: 81) AT2G33040, +intron
ggatcaaatgaacgcacattaatatgacgtaacgatgatgacaattctgtttaatagtatcttatt
gtttacagatacagaaaaataaattaagtgggcctttcaataattaataggttggtgaaatgttac
cttctcttgatatttttttaattttcatttattatgagtatgttgcgttatgaaacaactcgcatt
aatttggttatagattggagaaagaagaagtcatggtcaaaactcaaaaatgtaaaaggaaacaag
acgtgtatgacgacgtgattgataatctgaggagatacctttgggccttataagatgggccgaaaa
agtaatagtattagcctctattcggcccgattaatttcaggggaaattttggtaataaagtggaaa
cgacgtcgtgacaaaactActgtgtagactgagaaataaagaagcccttgattttgcccattgcag
tcatctctctcgaatctctctctataatccgatctgagaaatttcgccggagctaggttttgttgt
ttaccgatcaatcctttaatcaggtgagatctctttctcattcatcttatccttgcgtataaacac
acatttcgctgttcctctgtgatgcttttctgaatttgaaatcgtttgatttaattgagtcgttga
tgttttcatttccttgaaattcgaatcgacgaaaatttatggaaattgtgttgtttgactcgggag
ctgctaatgagtgaggtgtttttgttcgtctatttggagttttgagactcggaaatgtcctgttaa
gctcgtttcgttgaatttcctattgcaagaccaatttgatttcctcgtagaagagactttgtgat
atgttgtctaagctcgtcagatttaatcagcttttacctgcaaaactttgtgatatttaggatgat
gaggactaaacttgtatttgatttgtaggt

Figure 82 (SEQ ID NO: 82) AT5G14030, +intron
tgtgaattcttattctatgtccccacccacttgcctactttttattggctctcctgttttagtttt
agtacttccttcctcgttgacttctttccttaactttcccgccaccttgattaattgaatcaaatc
aactttatcagtttttaccctcttttcttactccaaccaaaagattgttagaaatgaaaatgagat
tatggtaacaaaacctccattgattcgagtcaatatgtcttttgaatgatatgaatcgttggctat
tacatcttaagtagactttataattagacgagataattaatagacaaagtcatctatgattataaa
agtattagagaatatttggatccaatcgaaatgtggtgtgggaaaagaaacatgttagattgtggc
aggagacaggctgtgttatcttcattgttctactgcaagtgcaaacacacttcccttctttaattt
ggacggtatattaatacactttattattagaatgggcttttataagtaggcccattatcaggtgaa
aaacaattgggcccatcattgactttttttgttaatgggtggtggtggtggtgattaAtatcgtcg
tcggaggtttcttgagctgaagaaaacattcgtagatctatttccgcatctgcttaaacacctaca
tcgtcgtagatcgcaaaccaggttagttctctatccttcatctagttatttcccgaatccgtttga
tttctccattttcatttccgatccgtgttaatttctgattgcatggagagattggtcaatgtagaa
ttaggagattatgcttgagctatcattagatctaccgtatgcgtatcagttaaacgaaacgccatt
tgatctgatctcattgtttatcggaattttggatttggtttgtgaattttgtatctgccggctacg
atgactttgagatttttaatgaatgtcagctaaaagcgtcagatatttgtggtgtttgctctcagg
t

Figure 83 (SEQ ID NO: 83) AT1G77940, +intron aacgaaggtgcctctcgatgaaggagcttcaaaaggaagcaaattaggttagggctctatggaata
attcttgatgttaccatatattttatagaaatattgtacatgacgaccacctggtctcagtttacg
acacgtggggatttgtttgtttgtgttgtctcggtcgttgttgttacgtgccgacaaggggaatg
atattaacatagaggggaaaaaagagagagatcttcaatgtgaagtttgctctgtgtatataaat
atttttacatctttcgacttattctattaattcttcaaatcataataaaaattaaaccacttttga
ttacttgtttcttaatttccaagataattaattataatttatctattaatatttgtctaccaaaat
ctaacacttaaaattagcaatttatcttaattaaataaatattgttaaactttgtcttttgtcaca
ctagtcataactgagattgatcagttcgttccatttctatagaattcaacttatacgttgaatccg
atagaaagaaaatagaaaagtaatttgaatttttttcatccacaaacaaaacttgttgaaacttg
aaacattgaataatctaataaaagtataaaaaaaaatataaaaaatatatgtttaccaattatcca
atttatttctgcatattttgtaaattaaaaagtaattcaaatacgtttcatgtcgacaaaatgttg
aatgtacaagtggtttatgctaatttaatcactgtcaattcactgaaacgaataaatcgagtaatt
actttttaattgacaaattacaaaactatagaaacattaagggcataattgaaatttccaataaa
ttgaagagcaaaaaccctagaaaattgacacggactataaaaaggtgaCgaagcggcgctttttcg
gtttggtcatcgtgctcctcttctcctccaccgcacagatccaagacattttgattacactccatc
gccggcgaaacaggtgcgccttattctctcccatcaaagttttatccctttcctcatcatctaga
tatcgtttacgatctcaatgtactaatatgtttctgggtttattgcttaattgcaggt

Figure 84 (SEQ ID NO: 84) AT4G36130, +intron cgagtccttcacattaaacctgatcataatcatcatcagctaccacagtatcgcacttagaacaca
cacaatcaaattcaaacaaactttcgcttgacaatttcaatcgaaaccatatcttttcaagtttag
ctaactatcggaaagaaattacataccgagactaatgattccacagacttgagagagcgcaaagat
cgaagaacattcgtcgagagaaagaagaagaaagtgggaggagcgtgtatgtgccagagaagaagg
agcagtggatgatttatgcgcttgggctgtcgctttttttcaactttgacgctccacaaagacaca
acaacgacatctctctatttcaaaaaagttttatttttttattcattttaaatacattttaaaaaa
attaacaaataaatcgccatttgttgttctttttttcaaaaacggaatacgagggtgcagttatcct
ctacgagcaggtgcatgtaataccatctgatggatttgacttatcgtttatccacaaaagattcaa
aatcttcccggttttaagtttgggcttcataaggcccaattagtggcaaatccatcacagtccac
tagggttttgagagactggatataaaatttgattttgttcattgttgtcattcGccgtaatctga
agaagacgaagcaaatcctcccacaaagaatcatccaggtttgttgtattcaataccttttctggt
gattcgattgattaatgatgtataatgtaatgttttgttctactgaattgttttgtgtgactgaat
atgatatatatctcatagaccagttggcttagctctgctgaattgtatcatgaaaattgtgtttag
tataccatttcagttttctgattgcgtagaattgcagtgaacacaatttttacttacgagcattgt
tctcagtctcacagttacgaatttgcgcatgattttgataggt

Figure 85 (SEQ ID NO: 85) AT2G36530, +intron aacaccacattttgataagaattatagaactagtgatttgcattttaaatgttgatacatatagaa
taagcataatcaaacaatgattactgaaaaatatggtccattaatatcgtataaaaatggttgatg
gacattgaaaccctagtggagaatttgtcacataagtaaggcccaaagtttttgacccacaaacat
atccattaagttatagtttagcgaaacccctttaacaaaaaagaaaattttcaactagtgaattgt
ttctagagagttctgtacaaccatccaaatttcaaacatggtataaaagatgttattgacaaaata
aaaatggaaacagtgaaacgtatagtcggaaaatggaataaaatctagatgccatatattattctt
acttgttctaaagtctttaataaaaatagtcggtattacttggacaaggagcaaaacaatatggaa
aaaactcttctattctgcaaaaggcgtgcagcgcatcgttttggcttcttgcatcagagctgactg
ttctcatccaacggctgttattaaaacaatccaacggttttggctaaatccgtgacgtctttatat
atcgaaccagaccaccaacccatTtcctcagctactactgttgaagcgattctcactaaaaccctc
gaacacatcgcctttatctctttctctagatctactcgctcaggttagtttctccgatcactttg
tatttcccagtcactttccggctttgtacagtattcgtgacggatctgtttgtttgatgactatcc
gatgctaaaaccactattcaatcgtttttttgtaaacctgaattgatctagtagtcgtacgtgaat
gagatttggtttttgtgaacgatgatcggtgatttgatctcggcgatttggatcgtgagttgtcga
tgatggagttgattttgtttatatgatttttgcgacggatctatttatttccatctggtttttacg
atttcgattgtttgctaatgacgaatttgaaaagaaagctaatgatttctctgatgatgttggttt
aggt

Figure 86 (SEQ ID NO: 86) AT5G15200, +intron acgttaggttaatatgattggagacaccactcacttataatatattcttgctgttctattaaggca
agactggtaaaacatctcaacaaaatattgcaattatttgtttttacgatataatcttttttttt
catcaactttttaatgatataatctaaatgccaaaagacatgtaaaatgacatttttttttttgt
tcaaatgacatttctaggtaccactattcagtgcataaaaataattttatgattaagaaaataaat
tcgagcccaagcgcaagactcaaaaataaatcgacatctcaaaacgggcccaatataaagccataa
ttcgtaaaggcccaatataaagccttaattcgtaaaggcccaataaagaaagtgagagtgtagcgt
tagggttttaagaaatcctataaattagttCattcgtctctttcgttcctctctgcgtgccctagt
tattcagatcgccgaatttgcagtaaggagacgaaaatcaggtaagcttcttctctccttttcgtc
gtttatatcacagctcattttcgattcgatctacgtagtgatttctctcaatatcaaatgatagat
tagggattatctgaggtttttgattgtgttatatatatagattgtgaatctgggttgttgtaactt
ttgaggttttagtttctgaaatgaatcaatcttagatacgagcctcaaagatctaacctttatgct
gataattttgtatgaatgtgtgtgtttgttgttgaataggt

Figure 87 (SEQ ID NO: 87) Os03g21940 ctgcatgtaataagttaatgtagcaaccatgcccgtggaaatattatcacatttgacttgagaaca
aatgaatgaaatatatttggattatgtttatttttaagaaaatagattaaacctgcctctacaac
catagtggatgtacacaaccaaggattatatgtttctatgtctgtcgtttcacttttctgaatata
agctagtataaaatgcaggtgtggttcaatgtgtagtaaaatgcacctgaggtaccaaaacttatg
ctgccgattagttactaatcctgcaaacaatttagagtttagatgagttacaggcatgggcagaaa
atgacatactggtctactactacatcgatatcaccttgactaatctacgctcacttctaaatgctc
cctccgattcatgttaagacgttataactttcaaaagttaaacttatttaagattacgagaaatat
agcaacctttttaatacaaaacaaataaaaacatgttatcaacttctactttcttatttttcacgt
gcacacttttcaaactgttaaatattataattttttttagggacaacgcagacactcacaacacgc
gcacgctaaccaaaggcacacgctaaccttctaagagcacattcagaagactagatatatctatga
gcacatccgaaaggctaggcatatcttaagattaatgaagttaccacggacgtctcgttgtcgatg
attgtattgtctatcactgaaaaaaaattagccgtaaatgtgaatacccgtgctaaatttagaatt
ttgaaggcccacttcgcagtgtcacagttttaaaaacatattaatcaatttttaagtttttataac
taatacttaattactgatctgttaatgagccattcgttttaatgtgcacgttagagaagtttctaa
tcttcgcttctgaacccacactgatcctgatactgtaatgcaaaagagagagtacattttaagtat
ctcttttcatttttttttttcagaaaaaacttttaagtatctcacagaaattggagccatcaaatca
tcaatatagtttactcatttatgaaagcttcaaatgtccggcgtccagagtttcagaaaattcact
caggagtatgctagactattctcttctccatgattccgcaaaaagctttttcgttaaaacctaaat
aaacctcgtcaaaaaaaaaaagccggcgacaaatccaagtcctccacgtcatcccatccccgacag
cgacacgctccactcactcgagccttctgggcggtggaacctacaccaaccactgatgggccgacg
gcccagcccagccagctcgcgctgaaaccctagccccatcacaggagggggctatataagccctc
cgcgccgcccctcgccaacCcttgcaccccctcgcgcctccaccacacactcccacccaggtaagg
agagggaggaggaagggaacctcgaaggcggcggcggcggcggag Figure 88 (SEQ ID NO: 88) Os04g35300
tcgttctgggttatcaaaactcaaaaaggaactctcaaggtatcagtgtcagtgtgtcaagtgtga
tcgttccatggcatatatggcttcaaacatttggttcttggcacttggcagaattgaagtgtgcag
tgaaaagaactgaaattgcaatgtgctggaagcatggagcagacgaggaggaagagaaggaaggaa
aggaagcctttcaactcgtctggtttgttttcctttcttcttttatttcaggcccatggaggccc
acacggcccatgttacagcgctggggcccaaggtacgaagcccactcacactccccccgcatctct
cgggagtggtgagattgacctaaccggtagtggagccAagatcagcgaaaccgcggcacccaaccc
caacccaaaccaccagaccggcggcggcgggggcgacctaaggcgagaacacgagcgaaaccagag
agggggcg Figure 89 (SEQ ID NO: 89) Os05g45950
ggcgatggtcagaattaggcatctacaattctacatggcaaagccagcatacatggcaatttgatt
ctaaggtattgatcagatcagatttgatgcaacctgtttggaagtcaggcccctttgactttgagg
tgcaaattaatcttttgcttgtctcctagcttagaatcgcctatggactgttgctgtttataactt
aaggctggccaaacaattagttttgtcctctatgcatcaaaccttgagacatctcatcatttgttc
atgaagagtagattagtttcaagccatccggacaggaataagcctgtgcttaactgaagtttcttc
agcaagcctccttcggcctgttcagtattggaatggtggtgtcacaagacttcatcagaaaagatg
caaagaaaagggctcaggaccctcttcttgctggtctgctggggaatttggacggaacgaaacaat
agaaacttcgagaaagagggatggtcaattcagcgaattgtcgacaaattctttttttatgagatca
agcagtggaccagctacagagaaaaaaggctggtatagttctctcgaagagagagctgttttttttg
ttagtttgtaactttgtatagcctctggcttcagttctattttgttccctcctatcaaaattcgta
caaaacagacagatcatacccataattacaagtaccgattatgttggttatatctttttttacaatt
acacaggatatatattttataaatttggttgaataaattattttggtagatatagtttccaaac
tttcaatgtatccctatgatatattttatgaaaaacgtgtattgcacgtgcacgattactagtgcc
cagataaattagtactgatcttgtcccgctcaaggcctcaaacctcggtaaaaataatttcacggc
ggtaaaaataaaacatggcaccatctttttactcaagaaagaaggcaaaaatcctgtcgctattca
ccaatcacgcaaaacccttctctccaagaacacggcgccctcacctcacatctcacatcaattttg
ataccattttcaaccttaccaaattttaataaagttataaaaaaatggctgcatttagtttgttac
catattttaatacttatagaaatcctactaaaatttagcaagttatcaaaatttgacaactatat
tgctaaaatttggtaaggttttttttacatcaaagtgaacagtcccaaaagttcaccctgcgcaac
aattaaattaagcaaattaaatcatttttggcatcttcttcctccccaagaaaaaggccaggata
agcccatccgacggcgcaggcgagccgagagccccgcgagcgcagatctgggccgtccgcccgccg
ataaataccagctctctcctccactccgcttcAcccccaaatcaaatccccttctcccatttttcc
tctcctcgcttctcgccgcagccgccgccgcctcctcctcctctcgcc Figure 90 (SEQ ID NO: 90) Os11g47760
agcaccatcagacgccgccacatctccggcgcccgtcgcctcctccatccctcccaactcgcttga
gcggacacgagcagccgcaggagctcctccagctccggccaccggcgtggtgctcgtgctccgccg
cggcactctcgccggaaaaagaacgaagagaagagagagagagaggaggaaccgaggaagaggagagg
gaggggagagatgacatggcatatatgtgggggtcccacgctgactcaactgtcacataggacaaa
accaagatcaaaaccatagaggatctattgtgaacgggttttgattagttaagagaccccaaatat
tttttcagttgaggtacgattttgtaactcgatgacaagttgagggacctttggtgtactttttcc
tagccaaaaggcctcggcccatgtattaaggtgacggcccacttgtgccgtcctcgaagacggccg
acagaccaacattcatttacagcccaaaaattacgaaaacctagctgcatcgcatcttcttctcct
ttccccaggcggagcaccgtccgatgagcatccaacggctacggtcagcaccctcggaaccttcga
gaacaccctccccgctataaattcccgcctttccggtagcatcTagtcttcctctcccactcttcc
tcctccccaaaccctagccgccgccgccggcgtactcgagagaaacatcagcatcc Figure 91 (SEQ ID NO: 91) Os02g02130
tatttagctcgttaagaaaagtatataaaaatttattcataaattatttttaatttgcaaatata
tcgttccgttctttcgtccaatatgctaaacagggccggagagatttgccggacccaatggtatcc
atgttgccttcgattgggtcaagtcatgggaagaagaatccaaaagagggagactgatgaccattg
gcatcgatgattaaagagagggctcgtactaagtgctagtgatagacattgacgccaattgataga
gcaacttttgaccacaagttgatcccgcttgccgattgtaaagaaattgagcatagtgtgctctct
ctgtcctataagtacaacctaatataaatgtgatcacatctatattatattgtatttatattagag
cggaaggagtactccctccattccattttaaacataaccatgagtttccgtgtcctagcgatcaag
gtgctaactcgagcctacccttcaagcagactgatgttgtagatctccactcggcttgtggagtta
tgcataaaagtgcggttatactcacatgaaacgtcgaaaccttctttgtagaagcaaccagtatca
atgccgaacgggtagggacgagctaacaataatgctgaactggtcttgagattcatgctatttcca
cgcgttgcgtgatgctatttggcatctacgcggatacaaacaaactgaattttggaagactcgtag
acttgcgttttgccgtgaagtacttgaaggcggatcgctattgaaggacgacggcaagacgcgctt
cgcgaaggttacgagtcaattttcaggactttagtactgtaggtctaattgggtcaagtcgttgcc
tttgtgtgatatctttcgtccgaaagagcgtcgttgttttacttatgtttataggtaggatttaaa
ttttaaaatttaattttaaagttgacttagggagtttttttctaatttattttacaccatttgctt
ttgaatatccgaaaacatatatatagaagttttatatacaaattaagttttagttgctaataagat
aaacataagagaatgctatgaatgtaacatctcctatcaggctatcactccaaaaataatgaacaa
caaattgtagatagcttgtttgtgcataatccttttgttttgtttacggtgaatctggatttaaaa
ttactaaaacaatgtgatcatcatatgcaggcttcggccattcggagcgacccaactttcgttgac
gggccgacgtcgctggctgaaggtgaatggaacagcccatgttccattatattggcccagaacgga
atcgtaactattggttcctaatatcggcccaatcaattgcgttggttatgaatggcccatggaagc
ccactattgctgctcccgtgctccctataaatagctagggttttacgccacttcccccatctccgc
cgccgccgccccactctccaaccctagccgagaggagcagaccaagca Figure 92 (SEQ ID NO: 92) Os03g56190 aattgtaaatttgaatatgattgaattctatgtgttttaaatatttctgtttgaattattttggtg
ctaaactaggtataaatatagtgtatacaaaatagaagagaatgagaaatgtggcctgagaaatgg
gggttgttgctgaagtacaagtcaacttttggatcctcggacagcctccattagatcttttaaggg
ctttacaatttacaatataagttattgctggagatgcttggcagcatcatagtttctcccaccttc
gtcggaaagtagattccgccaaatgcatggtttatttgatttgccattataccaaaatgttgcagt
gctaaaatctaggtaattttaagtactgctatttttttaaaccggtgtatattatcggcacatctt
aatagcaaattaaacaataacaaaatactctttaaagtgctaacaattcaacacggcacattttgg
attcaaacgagaatgcttgcatgggcataatcacttaacgtgtatttggtctggtgacaagatgag
atgggttaggctcatccctcttttttttttttttaaggatatgttttcatcagtacacgtttggt
agataactttctctttaaagaaatgagagaatgtggcccaatgagagagagtggattagattagtt
atgtcgattttttaagtacaaaactgaacccgatctagagagtattccctttttagggatcaatgtat
cccacctatccccgaatcaaatacactgaagaataagttcacccttattgatcatcccattatgtc
cctttcaacttaaaaatatgtttatagttggaattagggtagtatgatttaaaggtgaaaaaaatg
tattcaacgtagctttgaaaaggtaaagaaaagtgtattcggacttgttcttgtcaaacactttat
attagtcaattgccgttgcattgtattttgaaaacagttatactcctaccttaggaattactacta
ggagttaggtcctaacttcaataactcctatggagattttagcgcacacaaaaagagaaaactcat
taacatatgattaattaactattaactattataaacttgaagatcaaatttatttaatttttctta
agaaaacatttttatatattaaaaaattcgtatattttaaatatttaaaaatcgtgctaacagaa
aacgagtacaggttagagtttgaagttgaagaaaaaaacaatgacagtggttgaaatttcctactt
cctctgtcctaaaatattgctacatgacccacaaattcgttgttttacgatggtagcaacattttg
ggaccgatgtagtatctgtgatttcaactcaacggcccaacaattgaagcccacaaaccgcaaagc
ccacgaagaccaccagcaaaaataaagaagaaaccggaggtcagtttcctAtctaatctcgatctc
tccacccgtttcccccaaaaccagcggcgccaccacccaccttccccc Figure 93 (SEQ ID NO: 93) Os05g47980 tgtgggtcccatctttttttattattattttatgtgactgacatgtgggtcccacagattttattat
ttttctagatcggattgccacgtaagcaccacgtcagtaccacatcaaatgaagaccgagtcaaaa
tggacacgtaggcgctacgtcagccaaaaccacccttaaaatcgtcaaggtacctcgtttgtccgg
ttttcgtaagttggggacgggtcgtaccggttttgcagttcagggacgaaaatcagactgggcgac
aaatagagggacctaaaatgaacttattccttcaacgtttgtgtgctgacagagtgacgagcctcg
attttctaaaaaagaaaaggttacaggcctcgaacaagatgctgttaccaaagttagccacgaatt
tggactagaaaatagctaaacatgacggcttgatcgaagattacgcaaagttttagttcgactttc
gaacttataatagttcaaaataatcatctgctgtcatcatctactcaataaaaaccgaaatcctct
gtcaccatcaaaacatagcaaaaatcaaatgccattaaaaagtgccaaatgacagttgacagccca
aaataaaaaagaagaaaaaaaaaggaacactattatattccagatttccagctgcaatatcaagct
accaaatggatccccaaaaaaattgcaatccattccatgaactgagcccaccatgcaccacacaac
ccccgctcctccacgcttctcgggctcccgtagaccgggtccacccgccaatccccccacacgtcg
atatctccagcacccaccgcacccactctcctcctcActccgctcccctcctctcctcctcccttc
tcgcggaggccgccgcaaccaaaaaaaaaaaagtctaaccctagatccaggccccgcgtctccggc
gatctcccggcc Figure 94 (SEQ ID NO: 94) Os01g46610
gtgacaaatgtttctttcattctatctttttttttttgagaggtttcattctatcgttttcccttt
gagtttgagaggagagcagtgtttttgttttacacgtaggaatgggctatggagtatggagtatgg
agttggtaacgtggcaactgggaaggaaatagtaggagtaggtgggaaatttgctttgcgctgcat
gactgcatcccacttgatagagatgttaattgacttgatgttgtttgcacatgaatactgacacat
ggggccactaccttgtgggcctacttctcagttctcagtcccacctaaactgattttacgaacgga
tttcacgtaggattaggggcccaaaaaggtcgtttttacgattttatttctgatcagaggctttca
gctaataaaattaaattgctgagaggtttagtagagtctatacatattcttttgcagtttgttgta
acagcaatgcagaggatcctcgttgatagtactacacacaaacacattttgtgagctgtgtgacga
taattaggggcctgttcactttgatgctatttttaaccttaccaaattttggtaaagataaaaaaa
agtggctatatttaatttgctgccaaattttaattactatataaaaaatcctgttaaaatttagac
aagttgtcaaaattttgacacctataccaagtgaacaggccctaggtgcagacaataacctacctc
cccggcccaaaatgctcgtggagtcgttgtgttcatgtcatttgagaatctcatacccgtgacgtg
ctaatgctagggttaaacgcctaaactacggcgcggccatgcatgtgcgcggcggattggtcacgc
gctgcgtgtcgggtgctatcaattttgttggatttgattgcaatctcacactctcacagggtcaca
ccgtttttggatttgggaagaaaaatactgaggattagagagagagagattaatttcgaggtgtca
cgagagagagactactatttctccagatagtagtagtaactcttacgtcatggacactccaataca
ccaaatggagtttctactagtaccacctaatccaaatgattggtcaaacaagagacatctaccaaa
actaatcgctgcaaaaatcaccactcctcgaataatactcgccgtgccaaacgctttggccgccgg
agtccatcgccctacattgcccaccaaccgcacgcacccagattcacattcaagtgggccccacgc
tctgatcccataaccaacaattatgcaggcgaaaaatattactaacaaatgtagtgtctcaatgac
aggtgggacccatacctcccacccgtctgttctttaaatgcgctcgcccaactgctcgcatctTtc
tctctgcccgtgccaatcttcctttcccacatcctcctccgccgccggctgcttcccaccggctcc
cgatctccgaggcaagcagcgccgcacccggccgctgccgccgccgcc Figure 95 (SEQ ID NO: 95) Os02g52290 aaaagtttttttaatgtgtttgtattatgagcgtctgcgtttacacaatagaagttattaatcatg
cattgatcattgtatatttgtattgtaccatggtgcagttaattttagagaaaaaattcaaagaaa
aactagcgatccaaaccaatatattggtgttgatacttgttctaccaccataacgatatattggtg
ttggacgtgctagtgtgttttgaacaagatttttttagcgaggttaaaaatcccatattcaagcct
tgttacttctttcttaggttaagcacatcatttattaatattgccatctattactggataggatac
atcatagtactacgaatcggatacatcactatattatatagtactaaattgttatattatgggatg
gagagagtattctataacacacattttgttttctcataagcaattatcatttcttctttttgttatg
acgatcaagcaagagagattacatgagaggcatcatatgttgttattaggaagattatgggttgtt
tggttgatacctaactttgacataactaaggttagacaagtaatatgtctaagaaatagttggtta
tagcccgcagggggggatttacaattatgacattgcaaacattaacctttgctataataacactagg
ctcacattttatagacacagatggacccatttgtcatccactcggagtgtcaaaacagcgaagctc
tcgtgtttgcagtcccaatattacaaatttctcgcccgcatgtgtgatatgtttagttacaaattt
gaaagtgcgggtaggtcttaagagtaagaaagtgtgcataattgtgaagtgaaacaatcacatgac
taaataatcgtgatatgactaaagtgtggtatggtaaagtgagacaaccaacccatcacccccttaa
gtcaatggccggtcagcagcttaatacggcatttgtagcctcacgactaatattgtatggttcttt
taataggttttcataggacgacacaaaatatattttcgagatcgttataggaatgtaacaaaat
atcgtacgcatagtattttccgttatgtttaccgttatgtttatgttattccagtttctttcccat
gtttttatttttttgagcggtttcccatgtttttatggttgtgcgcaacctatatacgtagaggtcg
gatgcaattttattgcgaaaaaaaagaagaaaaccattgaagctggaccgtaggactgaaaagatc
gtctctccatccaacggcccaggagacgccggaacaattacaccaccagaaagtcgtgtaataaaa
aaaagtagtggattggtggtgtaataaaaaaggaatctactagcgctctataagggcgagccgcac
gGcaccaccaatccaccactgatcatactagcacagagcgccgccgccgaggagagtccaatcgag
aagaagggaggagaggcaagcggagaggaagaagaagaagaagagagg Figure 96 (SEQ ID NO: 96) Os04g28180 atcggcttatactaaggggagaatatatgctgggaagagaacttgaaggggactaattctgattat
ttattgctaaattccaaagactagctaaataccctatatatagagccgacacctgcaactcaatct
aatctaatcctacttttaagcaacagagtatatgtaacacgcgctgcattggaggcatggaggcat
tatatctaacacccaccttgtttccctgcatggaggcattccctagtttactagcttgctcagtcc
gttttgctcctttcaatctcaaaattatatagatccttatgtttgatgttatttttgtcattaccg
gtctcttcacgttattccattatgttaggtgccaagaagagtatgttggaccattagagtggacat
gattagggatgcaagtggatagttcctctactcgcaaaaaaacccgtttgctagttcatttcttac
atgatagtataaaatttagaagaaaaaatgaagtagaagtgagattagcgggctaaagaaacccgc
ttgcatccctagacatgatccatccaccttcttattattaggttgtaggctgccatttttctacca
gccatttacaagattgccaaccagattcgctctgctctcgtagccactttacaccactacgcagaa
ctacaaatctacaggatggatttgcattgcgagcatgatgtccccaactttaatacaaaactgcca
atatataatgagttcagcaacgtgttagggtaaagtttttttttttttttgcgcagaggcagttg
gaaaaaaaaacctaagacccctatcccatataaaaaaaaccaacttgtagcttacaaacctagata
ataagctagaagtttatttttttatgagtaaaacaggtggcttgacagtaattctgatggcagtgtt
cttttgaagggattggagcatatcccactcgcacgcaaacaaagtgacaaattaatgcacgattaa
ttaagtattagcttaaaaagtttgaaaaatgaattaatttgatttttacagtaacttttgtgtaat
tttttttaaaaaaagtgcaccatttaaccgtttgggatatgtgcatgtggaaaacaagaaatatgt
ggttgaaaccttgagggagaacacagccaaaacaaaaaaaaatctgatggaatcaagaaggccaac
gttggtgtgggccgggcccaatgcatcatttccttcgtacgttgcaatctaggcccaacggactgc
ccaccacccccctcgcctgaagaatggggtggatcagatggcaggctcattcccagccgtcggatc
gacccgatcaccgcctgcgaagtaaaccctaagccacggccgcctccctatataagcccacccact
agggtttcgcccGcctctcctcccccccgctagttcccaaccagcagctgcggcggcgcgagcaca
cgaagaggaggcggagcagccggagccacctccgccgccgccgccacc Figure 97 (SEQ ID NO: 97) Os05g01820 cttccaaattatgatctactcactccagaagcttctgttgtcctgttaactgatagcatcttctct
tctaatgttctgtggactgtgtttaatttagcactagcatttaatttggggcctacttgaatatca
ttatattatattgctaaaatttgatggtttgccatttaatttgtttgtaagttcactgaatcatgt
gtaatctagatagtactaagttagtggtaggtgtgttagctccctccaactgaagaagatgagaca
tgcaaagcaccctgcgtcatgtacaacccacaaagttctaattaacgttcttaactatatataaaa
tatcataacaataactccttaatgtgaaaggtaaatagcctctttgagtaatccacatgaagatgt
ggatctgaaagacaaatgaggatgtagatctgaaaacaattgtaaataaattcataggataagaaa
aagacaatgcttgatttgatactgctatggtcactagtcataagagaaaatgacttcaaagttgga
atatgttttggattgtcaataggtgcttcaattggactctcagctgagccaccaaccttacaactt
ttgagcggctaacataatattcctttctccaaataagcaagaataaaaccagagttcaaatacaa
ttagaaaagattaacatttacttgctcggttttacgattccaaaaagaaaaaaattctactatgt
tttctcgcatggttattacgacaacgtctaccacatcatgcatgctttttttcattaacggtttg
ggtgggacaaatatactccttccgtcctcaaatataagagatttgatatttccttgtactgttt
caccattcgtcttatttaaaatttttaaaattattatttattttatttgtgacttactttattat
ccaaaatacttaaaccacaacttttcgttttatatttgtacaatttttttagaataagatgagtgg
tcaaacgttataagaaaatagtgaatattccttatattaggggacggagctagtagcatatattcg
attaaggattttaagcagtgacagtgattatagaccaatccctttggaattatgataatagaaatt
gaattgaaaagggaaaaggtgaaggaaaagaggtgtgggtttagccgtttattgaaaggtgagatg
ggggtaggtaagctaatataagctctccactcctacaccaAcacaacacaaactccgatcttgttt
ctctctctctctctcccttgtttcagtggctcagaaattttcctcttttcttattattgctttcct
ttatttaaggaaggagttgggctctctctctttctctgagtctgaatccccacgagacgagaaacc
tagcaaaaatctcgtctttcgccgcgctctccctcctctgattcctgctgttcttgatcttggatc
tcaattcccaaccaagaacacacagacagagaaaggaaggagaagaag Figure 98 (SEQ ID NO: 98) Os07g46750 cgcataaacagatactagggggtgggaggtagagacgaccttgcgttggatttcgcagatgcgatg
tagaccgttgcgtgaggaacgaaagaacgagtgaccagtaaaatcatttgttgggtagattacttt
ttcttcgtattctttttttttacttttttttcttatttttacttctattagaaaaaatgcacgtgcg
ttgcatcgggataaaaacgtttttatgatacaaccgttattagaaactgagcaatgaagaaacatt
aggatcactattcattataattgaaaaaattaatgaaaattatttcttggttttgggcctacagcc
cattatttccttccttttctatcctaacccagcccgctacctctctcgcctgcctcttttctatcc
agcccacaagtggaactacatgctcctccctattaaattcggtcgaatctttttttttatctctcaa
aattggttaagaacttatacactcaatatcctcttttcgttttcccaaaaccaaaatgaattcaca
aagttgggataaaaaggtcggccaaccataattagtgactgataaatctagatatttaaaaccgaa
tcgaaaggagaagtcatgagaaaaatgatgagagaggagtggagaatcgatttttacaatcagttg
aaggagaaaacacatggggagacagatcaaagtggcggcggcgtaagggtttggtccagcgacgga
agcatgcaacagatcggatgagataaaaaaccgggtaaaaaaagcgaaaaagaaacctagaaaaaa
accgaatagggaaaaatcaaacaacgaagaaaaagaaaccggataaaaacagcaaaaaaaaaacac
gacaaaacgaatcgaaaaaaaaggagacacgaaaaaaaacgaatagtaggcgacgatgcgttatgg
tcatgagaaaaaaaaaagggaacatatgcttaggctgaaaaaaaacgacgacggaagcgattggga
ttctaattgacggaccaaataatctggcaaaaacattaaacttttataataggtaaagaaaaggta
attcaagtgatgatgaaaagctcagaatccgggccgtacactgcctcgagatccgatccgacggcc
aggaggctcccagcggtgcccccgggaatatccccaccgtagatgcctcatcccacgggtagaagg
ctagatgccgcgggagccggggtataaataggccactcgtccttctcctctcGgtctctagggttt
gggattttagccgccgccgccgccgccgctcacccgcgccttcgacgagctccagcccgtaga
cctcgccggatctccccg Figure 99 (SEQ ID NO: 99) Os11g11390 cacatgcatgctatcccatgaggtgggtttttgtgatatttcaaagaattaattttcgaataggcc
ttagcccatctattaattccaatattaattccaacagtaataagctagctgatgctatagcatcga
tcggatgtaacagtccccaaaacaccgatctcctttgggacagtgcacctccgggtgttgagggtt
tggtcgccagtgattctgccgcgtccatgggttaatggaaacatgaagtcttctttaaaaaaaact
attgggttaatcggtacgcacccatatgtccatctcactcccacctctagtcgagatcccatttga
tttagattattgaatggaccatttacttgaatattgggatatattaagtattttaagagataatct
taacaaatagcttacaacaaatgacctaagcaagcagtaaaatttctgttaagaaaatgtattttt
tgaagtggaggctagagagcaaacatatatccggttggatgtagaggccgggtaaaaaaaaaagtt
attactgcttatctttttcaccgtatgtctctgggtaaaaaaaaaaacttctcttaaaaaagtgtt
atcgctgcttatcattttcaccgtatgtctctgagtaaaaaaaaaaccttctctaaaaaatccggt
tggatgtagaggccgggtaaaaaaatacccttctccagaaaaagtattattgctgcttatcttttt
caccgtatgtctctgggtaaaacaaaaaaccccttctttaaaaaaattcggttggatatagagacc
gggtaaaataaataaaaaacccttctcttaaaaaaagtgatttgctacttatctttttcaccgtat
gtgttaggttaaaaaaaaaaccccttctctaaaacaaggtaaaaatgtgttattgatgtttatcttt
ttcaccgtatgtctctaagttaaaaaaaaaccattctcttaaaaaaatgtattattactgcttatc
gcttatgtgtcttggatccaactggtaacggtggtgggaaaggaggcaagaagcatagcaaaattc
ctgatgcaaatgcgcaacaccctgaaaatattgaaagtaggaatgccccccctttttttaaaacaa
taaaaatcatttcaacgaaaatttgactaactggtacacaatacaagaaaatttatttcaccgtct
cttgcgtcatgatagaaaccatcgaaaaaacaagttttagacattcgcgaaagaggactaccagct
cactcttttacggaattgccctttttgaggaaccgttgttatggttatgggccttatgaactgggc
ccaatatccacgcggccatacggcccgaagcccaggcccatttcgcaggcagccacacctattgct
ccccctccgcagtatttaagcttcacccccctccaaccctagcgcCcccattcctcaggtttcccct
cgccgacgcctccatcgccctccgggctccgcctccgccgccgcc Figure 100 (SEQ ID NO: 100) Os03g56190, +intron aattgtaaatttgaatatgattgaattctatgtgttttaaatatttctgtttgaattattttggtg
ctaaactaggtataaatatagtgtatacaaaatagaagagaatgagaaatgtggcctgagaaatgg
gggttgttgctgaagtacaagtcaacttttggatcctcggacagcctccattagatcttttaaggg
ctttacaatttacaatataagttattgctggagatgcttggcagcatcatagtttctcccaccttc
gtcggaaagtagattccgccaaatgcatggtttatttgatttgccattataccaaaatgttgcagt
gctaaaatctaggtaattttaagtactgctatttttttaaaccggtgtatattatcggcacatctt
aatagcaaattaaacaataacaaaatactctttaaagtgctaacaattcaacacggcacattttgg
attcaaacgagaatgcttgcatgggcataatcacttaacgtgtatttggtctggtgacaagatgag
atgggttaggctcatccctctttttttttttttttaaggatatgttttcatcagtacacgtttggt
agataactttctctttaaagaaatgagagaatgtggcccaatgagagagagtggattagattagtt
atgtcgattttaagtacaaaactgaacccgatctagagagtattccctttagggatcaatgtat
cccacctatccccgaatcaaatacactgaagaataagttcacccttattgatcatcccattatgtc
cctttcaacttaaaaatatgtttatagttggaattagggtagtatgatttaaaggtgaaaaaaatg
tattcaacgtagctttgaaaaggtaaagaaaagtgtattcggacttgttcttgtcaaacactttat
attagtcaattgccgttgcattgtattttgaaaacagttatactcctaccttaggaattactacta
ggagttaggtcctaacttcaataactcctatggagattttagcgcacacaaaaagagaaaactcat
taacatatgattaattaactattaactattataaacttgaagatcaaatttatttaatttttctta
agaaaacatttttatatattaaaaaattcgtatattttaaatatttaaaaatcgtgctaacagaa
aacgagtacaggttagagtttgaagttgaagaaaaaaacaatgacagtggttgaaatttcctactt
cctctgtcctaaaatattgctacatgacccacaaattcgttgttttacgatggtagcaacattttg
ggaccgatgtagtatctgtgatttcaactcaacggcccaacaattgaagcccacaaaccgcaaagc
ccacgaagaccaccagcaaaaataaagaagaaaccggaggtcagtttcctAtctaatctcgatctc
tccacccgtttcccccaaaaccagcggcgccaccacccaccttcccccc*cag*<u>gtgagtcgtcccacc</u>
<u>tcccgtctcctcttccccgttttgtgtggttttctcgttgacccatgattggcttctgattcgcgt</u>
<u>ttcgatctccctatccccctccccctcgcag</u>*gt*

Figure 101 (SEQ ID NO: 101) Os04g35300, +intron tcgttctgggttatcaaaactcaaaaaggaactctcaaggtatcagtgtcagtgtgtcaagtgtga
tcgttccatggcatatatggcttcaaacatttggttcttggcacttggcagaattgaagtgtgcag
tgaaaagaactgaaattgcaatgtgctggaagcatggagcagacgaggaggaagagaaggaaggaa
aggaagcctttcaactcgtctggtttgttttcctttcttcttttattttcaggcccatggaggccc
acacggcccatgttacagcgctggggcccaaggtacgaagcccactcacactcccccgcatctct
cgggagtggtgagattgacctaaccggtagtggagccAagatcagcgaaaccgcggcacccaaccc
caacccaaaccaccagaccggcggcggcgggggcgacctaaggcgagaacacgagcgaaaccagag
agggggcg*caggt*gcaagcgctccctacccctcccttctcctccccaatcccctcgagctgcgtcg
cgttgaccgcgcgaggcggcctggttagggtttcggcgccgggcggcgagcgattcgcctcgatgg
atgcatatgttcccgtttctctttgttcgggtggtggtttggatgcgttggacggtagatccgcga
ctcctggaaaagcgaatcgggggtttggcgatcgaaatgtttctagggctgatggatcttgggccg
ctgtgatttggtttgcgtaggcgtttattagatcaatcgctacatcattctcgtttggatgaatcc
cgcgatggaccatgttggtggttgatttttgggctagcctgtggtgactgaatcgaccgtaggccg
gtggaatgtgaatctgcgatatgccgtcactgtgaaatgatcaaacggatggccatcttgtgaact
gtgatgaaattctgatgtccaaattctgtgcgtcgggcggcggcggtgacgtgcgcgtgcgttgct
ggctgcggcggtgcgcgtgtgcgtcggacggcagcggcggcggcgcgcgtacgtcaggcggtg
gcggcggcgcgttcgcctccgccgcctcctgccggtgccgccgctcgccgaacgccaccgtcactg
tcgttcgccgaaagccgctgtgccagcgacgtcctcgctgctccgtgccatggactgacccaacag
caagcagctccacatgcccaggcgaggagaacgagggtaatttggtcccgtatagcattgtagctt
gtagccacgggttgagattggcattttaacgaatcccttttgcggagtggcattttggcaaaacct
agttttggcaatggcagaatgtccaatttctcgttttggttgccctggtttcatctgtgcagagga
gagtattgtgcaaataacctgtttttctcacaaaatgtctagtcacctgctcgctgccgtttttta
actagtttatttgtctgtgatgttaatgatgagcagtattactaatggttttctgccaagggtcga
aatacgtgtccatcttgtcatgctatatgtatctatggtgcattctagcgaatcttagagataatc
agagtagcttggatgggggaagagtggagacctggaattgttggctattggattggatgtgtattt
gcgtttcagatgtttggcttgttcttcttttaatgtttagtagtatcatcaaatatatctttgat
gtttggcttgttcttttttattgtttagtagtatcttcaaatatagttattggtttggatgtgta
tttgccttcgagatgtttggcttgttcctgtatcatcaaattgtgaactctactattttagttcac
ttctgattgctgaattctcttctctgtgcatataacag*gt*

Figure 102 (SEQ ID NO: 102) Os02g02130, +intron tatttagctcgttaagaaaagtatataaaaatttattcataaattatttttaatttgcaaatata
tcgttccgttctttcgtccaatatgctaaacagggccggagagatttgccggacccaatggtatcc
atgttgccttcgattgggtcaagtcatgggaagaagaatccaaaagagggagactgatgaccattg
gcatcgatgattaaagagagggctcgtactaagtgctagtgatagacattgacgccaattgataga
gcaacttttgaccacaagttgatcccgcttgccgattgtaaagaaattgagcatagtgtgctctct
ctgtcctataagtacaacctaatataaatgtgatcacatctatattatattgtatttatattagag
cggaaggagtactccctccattccattttaaacataaccatgagtttccgtgtcctagcgatcaag
gtgctaactcgagcctacccttcaagcagactgatgttgtagatctccactcggcttgtggagtta
tgcataaaagtgcggttatactcacatgaaacgtcgaaaccttctttgtagaagcaaccagtatca
atgccgaacgggtagggacgagctaacaataatgctgaactggtcttgagattcatgctatttcca
cgcgttgcgtgatgctatttggcatctacgcggatacaaacaaactgaattttggaagactcgtag
acttgcgttttgccgtgaagtacttgaaggcggatcgctattgaaggacgacggcaagacgcgctt
cgcgaaggttacgagtcaattttcaggactttagtactgtaggtctaattgggtcaagtcgttgcc
tttgtgtgatatctttcgtccgaaagagcgtcgttgttttacttatgtttataggtaggatttaaa
ttttaaaatttaattttaaagttgacttagggagtttttttctaatttattttacaccatttgctt
ttgaatatccgaaaacatatatatagaagttttatatacaaattaagttttagttgctaataagat
aaacataagagaatgctatgaatgtaacatctcctatcaggctatcactccaaaaataatgaacaa
caaattgtagatagcttgtttgtgcataatccttttgttttgtttacggtgaatctggatttaaaa
ttactaaaacaatgtgatcatcatatgcaggcttcggccattcggagcgacccaactttcgttgac
gggccgacgtcgctggctgaaggtgaatggaacagcccatgttccattatattggcccagaacgga
atcgtaactattggttcctaatatcggcccaatcaattgcgttggttatgaatggcccatggaagc
ccactattgctgctcccgtgctccctataaatagctagggttttacgccacttcccccatctccgc
cgccgccgccccactctccaaccctagccgagaggagcagaccaagca*Cag*gtaaccttcgcgccg
ccgccgcctcattgcttcttcctcgtctactcctagctctaacatggtgatcttcttgtggctcgc
ag*gt*

Figure 103 (SEQ ID NO: 103) Os01g46610, +intron gtgacaaatgtttctttcattctatcttttttttttgagaggtttcattctatcgttttcccttt
gagtttgagaggagagcagtgtttttgttttacacgtaggaatgggctatggagtatggagtatgg
agttggtaacgtggcaactgggaaggaaatagtaggagtaggtgggaaatttgctttgcgctgcat
gactgcatcccacttgatagagatgttaattgacttgatgttgtttgcacatgaatactgacacat
ggggccactaccttgtgggcctacttctcagttctcagtcccacctaaactgattttacgaacgga
tttcacgtaggattaggggcccaaaaaggtcgtttttacgattttatttctgatcagaggctttca
gctaataaaattaaattgctgagaggtttagtagagtctatacatattcttttgcagtttgttgta
acagcaatgcagaggatcctcgttgatagtactacacacaaacacattttgtgagctgtgtgacga
taattaggggcctgttcactttgatgctattttaaccttaccaaattttggtaaagataaaaaaa
agtggctatatttaatttgctgccaaattttaattactatataaaaaatcctgttaaaatttagac
aagttgtcaaaattttgacacctataccaagtgaacaggccctaggtgcagacaataacctacctc
cccggcccaaaatgctcgtggagtcgttgtgttcatgtcatttgagaatctcatacccgtgacgtg
ctaatgctagggttaaacgcctaaactacggcgcggccatgcatgtgcgcggcggattggtcacgc
gctgcgtgtcgggtgctatcaattttgttggatttgattgcaatctcacactctcacagggtcaca
ccgtttttggatttgggaagaaaaatactgaggattagagagagagagattaatttcgaggtgtca
cgagagagagactactatttctccagatagtagtagtaactcttacgtcatggacactccaataca
ccaaatggagtttctactagtaccacctaatccaaatgattggtcaaacaagagacatctaccaaa
actaatcgctgcaaaaatcaccactcctcgaataatactcgccgtgccaaacgctttggccgccgg
agtccatcgccctacattgcccaccaaccgcacgcacccagattcacattcaagtgggccccacgc
tctgatcccataaccaacaattatgcaggcgaaaaatattactaacaaatgtagtgtctcaatgac
aggtgggacccatacctcccacccgtctgttctttaaatgcgctcgcccaactgctcgcatctTtc
tctctgcccgtgccaatcttcctttcccacatcctcctccgccgccggctgcttcccaccggctcc
cgatctccgaggcaagcagcgccgcacccggccgctgccgccgccgcc*cag*gttagatcccccgct
tccctctccgcaccagcagatctgtcccgcggacgaggcgccgttcgcatgcgctgggttttgata
tttttggttcgtgggtgtcgcggagagatccgcgtgatccggcaaatcgctgttgttttcccgtc
gaggttgcttttgtttaggctaggcgatggtgcgtcgagttcgtgcgcgtaggattttagcgcgta
atcactctgtggagccgagctgccgctgtattagtttgtggacacgcgggagacgatttgctgccg
tgttagaggccggatttaagcatgtagagatatatgcatatatgcgatgccccgatggatgatcta
tgtgcagctgacgaaagtattgtgaattggatgcatgatgtgaaaattttgaatagtgggtttgga
gtccagaattctggttgtcgtttagatattggttatgtacttttgtgaggctatttccatatgcaa
ttgatcatgtttgatgtccaaacatcatcaggactcgtccgaactgttcctttgtttttaaatat
aacgaagggaagatctctaatgaaaaattgttgcaaacactgcacatacttataagtatatcagga
attaagggtatacggcactgtgtttgtaatgagtcagagattatttgcacataatatatcagtgag
cctctgtttcatcttatggaactaactgatttgtaattcacctactccag*gt*

Figure 104 (SEQ ID NO: 104) Os05g01820, +intron cttccaaattatgatctactcactccagaagcttctgttgtcctgttaactgatagcatcttctct
tctaatgttctgtggactgtgtttaatttagcactagcatttaatttggggcctacttgaatatca
ttatattatattgctaaaatttgatggtttgccatttaatttgtttgtaagttcactgaatcatgt
gtaatctagatagtactaagttagtggtaggtgtgttagctccctccaactgaagaagatgagaca
tgcaaagcaccctgcgtcatgtacaacccacaaagttctaattaacgttcttaactatatataaaa
tatcataacaataactccttaatgtgaaaggtaaatagcctctttgagtaatccacatgaagatgt
ggatctgaaagacaaatgaggatgtagatctgaaaacaattgtaaataaattcataggataagaaa
aagacaatgcttgatttgatactgctatggtcactagtcataagagaaaatgacttcaaagttgga
atatgttttggattgtcaataggtgcttcaattggactctcagctgagccaccaaccttacaactt
ttgagcggctaacataatattcctttctccaaataagcaagaataaaaaccagagttcaaatacaa
ttagaaaagattaacatttacttgctcggttttacgattccaaaaagaaaaaaaattctactatgt
tttctcgcatggttattacgacaacgtctaccacatcatgcatgctttttttttcattaacggtttg
ggtgggacaaatatactccttccgtcctcaaatataagagattttgatattttccttgtactgttt
caccattcgtcttatttaaaatttttaaaattattatttattttatttgtgacttactttattat
ccaaaatacttaaaccacaacttttcgttttatatttgtacaatttttttagaataagatgagtgg
tcaaacgttataagaaaatagtgaatattccttatattaggggacggagctagtagcatatattcg
attaaggattttaagcagtgacagtgattatagaccaatccctttggaattatgataatagaaatt
gaattgaaaagggaaaaggtgaaggaaaagaggtgtgggtttagccgtttattgaaaggtgagatg
ggggtaggtaagctaatataagctctccactcctacaccaAcacaacacaaactccgatcttgttt
ctctctctctctctcccttgtttcagtggctcagaaattttcctcttttcttattattgctttcct
ttatttaaggaaggagttgggctctctctctttctctgagtctgaatccccacgagacgagaaacc
tagcaaaaatctcgtctttcgccgcgctctccctcctctgattcctgctgttcttgatcttggatc
tcaattcccaaccaagaacacacagacagagaaaggaaggagaagaag*cag*gtctcatcttttgtt
tttcttttcttttcacgcttttacttacttgtactattcgatttcatgtttcgattcgtttcgttg
gttcttggttccctatcctccaacaacgtcctgagacctcgatctggtcggagtccacgaccagat
cttggccgcggcgcagatctggccctccagccgccggcgtggggaccttgccagatctggtcttct
ccgacggtggccaacttctcttgtcccttggttgcagccaccaaacctcttcctcccctcctcgat
ccaaccttggtcttgttcatcgactggccactaaaccccaaataagcgagatagaatttggattcg
tttcgttggttattgtttctctgatgctgtgatggtggctagatcatggcagatctgcccagtaaa
gtcgaattttgtttgattccaccgcacctcctgaggaatcggtccaatcctgtgaattcttctctt
ctttcctgctgattggattgtctacatgggctttacctggaaacaggggtgagtgctagcagattc
aaacatcatggactgactgctcctaaacaagttccatatgaaaacctgttctacatgctttttttc
ttttactcttcactcgttgtcagtcaaacactgcaaaatttgtccctgcgcctattctgcaagagc
ttcttgttagtacaactgaagaatcaatcctctgttccaacttggcatctggacagaataatgaat
gtttcataggaaaggctcagctcaactaagtaaatcatgttgattggccttaaaacacacttcatt
aagagtctgtttttttttatattggacatgataagaataatatggctgtttttttattattaatgttt
tttcttggtaacagtgcttctattgatgaacctaccctgtttacctgatctcaccagtgttctgca
atactatccag*gt*

Figure 105 (SEQ ID NO: 105) Os07g46750, +intron cgcataaacagatactagggggtgggaggtagagacgaccttgcgttggatttcgcagatgcgatg
tagaccgttgcgtgaggaacgaaagaacgagtgaccagtaaaatcatttgttgggtagattacttt
ttcttcgtattctttttttacttttttttcttatttttacttctattagaaaaaatgcacgtgcg
ttgcatcgggataaaaacgtttttatgatacaaccgttattagaaactgagcaatgaagaaacatt
aggatcactattcattataattgaaaaaattaatgaaaattatttcttggttttgggcctacagcc
cattatttccttccttttctatcctaacccagcccgctacctctctcgcctgcctcttttctatcc
agcccacaagtggaactacatgctcctccctattaaattcggtcgaatctttttttatctctcaa
aattggttaagaacttatacactcaatatcctcttttcgttttcccaaaaccaaaatgaattcaca
aagttgggataaaaaggtcggccaaccataattagtgactgataaatctagatatttaaaaccgaa
tcgaaaggagaagtcatgagaaaaatgatgagagaggagtggagaatcgatttttacaatcagttg
aaggagaaaacacatggggagacagatcaaagtggcggcggcgtaagggtttggtccagcgacgga
agcatgcaacagatcggatgagataaaaaaccgggtaaaaaaagcgaaaaagaaacctagaaaaaa
accgaatagggaaaaatcaaacaacgaagaaaaagaaaccggataaaaacagcaaaaaaaaaacac
gacaaaacgaatcgaaaaaaaaggagacacgaaaaaaaacgaatagtaggcgacgatgcgttatgg
tcatgagaaaaaaaaaagggaacatatgcttaggctgaaaaaaaacgacgacggaagcgattggga
ttctaattgacggaccaaataatctggcaaaaacattaaacttttataataggtaaagaaaaggta
attcaagtgatgatgaaaagctcagaatccgggccgtacactgcctcgagatccgatccgacggcc
aggaggctcccagcggtgcccccgggaatatccccaccgtagatgcctcatcccacgggtagaagg
ctagatgccgcgggagccggggtataaataggccactcgtccttctcctctcGgtctctagggttt
gggattttagccgccgccgccgccgccgctcacccgcgccttcgacgagctccagcccgtaga
cctcgccggatctccccg*cag*gtgagcccccaatttcacacccttcgcgcttgcaatttggtgatt
agatctgttgacgacgacgacgacgatgcgcttgttgtgttgacgcgtgctgatttgcgtgggcat
attaaattggatgatgttgtgtgtttttgccatgatgatatcgtacgggggtaggattagatcttg
ctgcgtccatttcaatttagtaaatatggtgattcgcgatgcgggcgtgctcacttggtagtgttt
gttcttgtgatctagtatttgttgtggtgattgtgcagcaattggtagtatttgttgtggtgattg
tgcagcaattggtgtggtggtatctgttctggcaatctgcgatgaggctgtgctcacttttttactt
atctgtgatgattgaacag*gt*

Figure 106 (SEQ ID NO: 106) Os04g28180, +intron atcggcttatactaaggggagaatatatgctgggaagagaacttgaaggggactaattctgattat
ttattgctaaattccaaagactagctaaataccctatatatagagccgacacctgcaactcaatct
aatctaatcctacttttaagcaacagagtatatgtaacacgcgctgcattggaggcatggaggcat
tatatctaacacccaccttgtttccctgcatggaggcattccctagtttactagcttgctcagtcc
gttttgctcctttcaatctcaaaattatatagatccttatgtttgatgttatttttgtcattaccg
gtctcttcacgttattccattatgttaggtgccaagaagagtatgttggaccattagagtggacat
gattagggatgcaagtggatagttcctctactcgcaaaaaaacccgtttgctagttcatttcttac
atgatagtataaaatttagaagaaaaaatgaagtagaagtgagattagcgggctaaagaaacccgc
ttgcatccctagacatgatccatccaccttcttattattaggttgtaggctgccatttttctacca
gccatttacaagattgccaaccagattcgctctgctctcgtagccactttacaccactacgcagaa
ctacaaatctacaggatggatttgcattgcgagcatgatgtccccaactttaatacaaaactgcca
atatataatgagttcagcaacgtgttagggtaaagttttttttttttttttgcgcagaggcagttg
gaaaaaaaaacctaagacccctatcccatataaaaaaaaccaacttgtagcttacaaacctagata
ataagctagaagtttatttttatgagtaaaacaggtggcttgacagtaattctgatggcagtgtt
cttttgaagggattggagcatatcccactcgcacgcaaacaaagtgacaaattaatgcacgattaa
ttaagtattagcttaaaaagtttgaaaaatgaattaatttgatttttacagtaacttttgtgtaat
tttttttaaaaaaagtgcaccatttaaccgtttgggatatgtgcatgtggaaaacaagaaatatgt
ggttgaaaccttgagggagaacacagccaaaacaaaaaaaaatctgatggaatcaagaaggccaac
gttggtgtgggccgggcccaatgcatcatttccttcgtacgttgcaatctaggcccaacggactgc
ccaccaccccccctcgcctgaagaatggggtggatcagatggcaggctcattcccagccgtcggatc
gacccgatcaccgcctgcgaagtaaaccctaagccacggccgcctccctatataagcccacccact
agggtttcgcccGcctctcctcccccccgctagttcccaaccagcagctgcggcggcgcgagcaca
cgaagaggaggcggagcagccggagccacctccgccgccgccgccacc*cag*gtaaggcacgcccgc
aacccgggtgctcaaccttcctcctccgcttacccccatccgcgtgggggttgtggagttcgttg
tttgggtttttttgcgtgtgtgtgtgctgatggattgatggggtgcggtgatggctgtgcag*gt*

Figure 107 (SEQ ID NO: 107) Os03g21940, +intron ctgcatgtaataagttaatgtagcaaccatgcccgtggaaatattatcacatttgacttgagaaca
aatgaatgaaatatatttggattatgtttatttttaagaaaatagattaaacctgcctctacaac
catagtggatgtacacaaccaaggattatatgtttctatgtctgtcgtttcacttttctgaatata
agctagtataaaatgcaggtgtggttcaatgtgtagtaaaatgcacctgaggtaccaaaacttatg
ctgccgattagttactaatcctgcaaacaatttagagtttagatgagttacaggcatgggcagaaa
atgacatactggtctactactacatcgatatcaccttgactaatctacgctcacttctaaatgctc
cctccgattcatgttaagacgttataactttcaaaagttaaacttatttaagattacgagaaatat
agcaaccttttaatacaaaacaaataaaaacatgttatcaacttctactttcttattttcacgt
gcacactttcaaactgttaaatattataattttttttagggacaacgcagacactcacaacacgc
gcacgctaaccaaaggcacacgctaaccttctaagagcacattcagaagactagatatatctatga
gcacatccgaaaggctaggcatatcttaagattaatgaagttaccacggacgtctcgttgtcgatg
attgtattgtctatcactgaaaaaaaattagccgtaaatgtgaatacccgtgctaaatttagaatt
ttgaaggcccacttcgcagtgtcacagttttaaaaacatattaatcaattttaagttttataac
taatacttaattactgatctgttaatgagccattcgttttaatgtgcacgttagagaagtttctaa
tcttcgcttctgaacccacactgatcctgatactgtaatgcaaaagagagagtacattttaagtat
ctcttttcatttttttttcagaaaaaactttaagtatctcacagaaattggagccatcaaatca
tcaatatagtttactcatttatgaaagcttcaaatgtccggcgtccagagtttcagaaaattcact
caggagtatgctagactattctcttctccatgattccgcaaaaagctttttcgttaaaacctaaat
aaacctcgtcaaaaaaaaaaagccggcgacaaatccaagtcctccacgtcatcccatccccgacag
cgacacgctccactcactcgagccttctgggcggtggaacctacaccaaccactgatgggccgacg
gcccagcccagccagctcgcgctgaaaccctagccccatcacaggagggggctatataagccctc
cgcgccgcccctcgccaacCcttgcacccccctcgcgcctccaccacacactcccacccaggtaagg
agagggaggaggaagggaacctcgaaggcggcggcggcggcggag*cag*gtaagaactcccctc
aactcccgtttgatatcatctttgtgtgcgattggtagtttgtgttgcgcgtgatttcctttagat
ctggagctatagtgctagtctgcggcgcgaaactgttgccgtggcgattccgatgtggagtttcgt
ttggttcgcttagtcggagtagttttgatgtgttctaggtagtgtgttgtttaatttagttgcgga
ggaagttgcttcatgggacttaaaccgttgcctgttgcagtttttctaggttcgtttttgtgatgg
atgcatagaggtagaaaagtttcgagaaatgatttatacatggaacttagggttagggtttagatt
gatcttaggggttctgtcaaatccacggtgctgttctggggatgtgtgtgcttattatcctccatt
agatgaaaaatagacatgatatagacatgatatgtgatgcttgatgtattacttattcttgttcgt
cacctatgccaggtaggatgaagactgcaattcatgcacacaggattattaatagggaatgcccac
acggttatcaataggggaacattcctttgtctgttgaaattacaattctataacatctaagttcat
tcggttcatttcgattgttcatcaccatttgtagaactgcagtatgatactgtgtaaatgtatgca
ttgtggtttgtttacttgcaagttttgttgtgctaattataagatatattgtttgctatgctatgt
tgggtatcgtgcatactttcataaacaaagtctatgttctgttctgtttggagtataaatactcat
ttccgatggtctagtaattatttactatcgtcttgaaaagctgttctagatacttggttttatttc
cctgtgacttgtatatgtgcttgcatggtgatgaactttgatttctataacacgttcctgaaatgc
tgggaaagctatctgatgttctgttccttcctacttgcag*gt*

Figure 108 (SEQ ID NO: 108) Os05g45950, +intron ggcgatggtcagaattaggcatctacaattctacatggcaaagccagcatacatggcaatttgatt
ctaaggtattgatcagatcagatttgatgcaacctgtttggaagtcaggcccctttgactttgagg
tgcaaattaatcttttgcttgtctcctagcttagaatcgcctatggactgttgctgtttataactt
aaggctggccaaacaattagttttgtcctctatgcatcaaaccttgagacatctcatcatttgttc
atgaagagtagattagtttcaagccatccggacaggaataagcctgtgcttaactgaagtttcttc
agcaagcctccttcggcctgttcagtattggaatggtggtgtcacaagacttcatcagaaaagatg
caaagaaaagggctcaggaccctcttcttgctggtctgctggggaatttggacggaacgaaacaat
agaaacttcgagaaagagggatggtcaattcagcgaattgtcgacaaattcttttttatgagatca
agcagtggaccagctacagagaaaaaaggctggtatagttctctcgaagagagagctgtttttttg
ttagtttgtaactttgtatagcctctggcttcagttctattttgttccctcctatcaaaattcgta
caaaacagacagatcatacccataattacaagtaccgattatgttggttatatctttttttacaatt
acacaggatatatattttataaattttggttgaataaattatttttggtagatatagtttccaaac
tttcaatgtatccctatgatatattttatgaaaaacgtgtattgcacgtgcacgattactagtgcc
cagataaattagtactgatcttgtcccgctcaaggcctcaaacctcggtaaaaataatttcacggc
ggtaaaaataaaacatggcaccatctttttactcaagaaagaaggcaaaaatcctgtcgctattca
ccaatcacgcaaaacccttctctccaagaacacggcgccctcacctcacatctcacatcaatttg
ataccattttcaaccttaccaaattttaataaagttataaaaaaatggctgcatttagtttgttac
catattttaatacttatagaaatcctactaaaattttagcaagttatcaaaatttgacaactatat
tgctaaaatttggtaaggttttttttacatcaaagtgaacagtcccaaaagttcaccctgcgcaac
aattaaattaagcaaattaaatcattttttggcatcttcttcctccccaagaaaaaggccaggata
agcccatccgacggcgcaggcgagccgagagccccgcgagcgcagatctgggccgtccgcccgccg
ataaataccagctctctcctccactccgcttcAcccccaaatcaaatccccttctcccattttttcc
tctcctcgcttctcgccgcagccgccgccgcctcctcctcctctcgcc*cag*gttcggggatgctgc
gtcgttgctggttctttttgtggggtgtttttgtggttggggttttgtgatttgttgccctttttg
cttggggttgtttcttggtttcttgggtgtttgctgacgctggttgttttttttttctggtgggat
ttgcag*gt*

Figure 109 (SEQ ID NO: 109) Os02g52290, +intron aaaagtttttttaatgtgtttgtattatgagcgtctgcgtttacacaatagaagttattaatcatg
cattgatcattgtatatttgtattgtaccatggtgcagttaattttagagaaaaaattcaaagaaa
aactagcgatccaaaccaatatattggtgttgatacttgttctaccaccataacgatatattggtg
ttggacgtgctagtgtgttttgaacaagatttttttagcgaggttaaaaatcccatattcaagcct
tgttacttctttcttaggttaagcacatcatttattaatattgccatctattactggataggatac
atcatagtactacgaatcggatacatcactatattatatagtactaaattgttatattatgggatg
gagagagtattctataacacacattttgttttctcataagcaattatcatttcttcttttgttatg
acgatcaagcaagagagattacatgagaggcatcatatgttgttattaggaagattatgggttgtt
tggttgatacctaactttgacataactaaggttagacaagtaatatgtctaagaaatagttggtta
tagcccgcagggggatttacaattatgacattgcaaacattaacctttgctataataacactagg
ctcacattttatagacacagatggacccatttgtcatccactcggagtgtcaaaacagcgaagctc
tcgtgtttgcagtcccaatattacaaatttctcgcccgcatgtgtgatatgtttagttacaaattt
gaaagtgcgggtaggtcttaagagtaagaaagtgtgcataattgtgaagtgaaacaatcacatgac
taaataatcgtgatatgactaaagtgtggtatggtaaagtgagacaaccaacccatcaccccctta
gtcaatggccggtcagcagcttaatacggcatttgtagcctcacgactaatattgtatggttcttt
taataggtttttcataggacgacacaaaatatatttttcgagatcgttataggaatgtaacaaaat
atcgtacgcatagtattttccgttatgtttaccgttatgtttatgttattccagtttctttcccat
gtttttatttttttgagcggtttcccatgtttttatggttgtgcgcaacctatatacgtagaggtcg
gatgcaattttattgcgaaaaaaaagaagaaaaccattgaagctggaccgtaggactgaaaagatc
gtctctccatccaacggcccaggagacgccggaacaattacaccaccagaaagtcgtgtaataaaa
aaaagtagtggattggtggtgtaataaaaaaggaatctactagcgctctataagggcgagccgcac
gGcaccaccaatccaccactgatcatactagcacagagcgccgccgccgaggagagtccaatcgag
aagaagggaggagaggcaagcggagaggaagaagaagaagaagagagg*cag*gttcgccgctttcct
ccctccctatctcccccagaacatttcctttcatgctttttcttttcttggatccgtgcgtgtgct
tagctgaatcaacctgagcggtaagaacaaggtggttcgttcccagatccatttcttgttggatct
catgtttgatgccaggattgtcttttggatagatggtttagattcaaatcgcagctgctagtttac
ctctgtccggtttgtggatagatttctgagtttctgttttggagtagttaagcctaacttggtttc
cttgccatgctgctttcttttctgcag*gt*

Figure 110 (SEQ ID NO: 110) Os05g47980, +intron tgtgggtcccatctttttttattattatttatgtgactgacatgtgggtcccacagattttattat
ttttctagatcggattgccacgtaagcaccacgtcagtaccacatcaaatgaagaccgagtcaaaa
tggacacgtaggcgctacgtcagccaaaaccacccttaaaatcgtcaaggtacctcgtttgtccgg
ttttcgtaagttggggacgggtcgtaccggttttgcagttcagggacgaaaatcagactgggcgac
aaatagagggacctaaaatgaacttattccttcaacgtttgtgtgctgacagagtgacgagcctcg
attttctaaaaaagaaaaggttacaggcctcgaacaagatgctgttaccaaagttagccacgaatt
tggactagaaaatagctaaacatgacggcttgatcgaagattacgcaaagttttagttcgactttc
gaacttataatagttcaaaataatcatctgctgtcatcatctactcaataaaaaccgaaatcctct
gtcaccatcaaaacatagcaaaaatcaaatgccattaaaaagtgccaaatgacagttgacagccca
aaataaaaaagaagaaaaaaaaaaggaacactattatattccagatttccagctgcaatatcaagct
accaaatggatccccaaaaaaattgcaatccattccatgaactgagcccaccatgcaccacacaac
ccccgctcctccacgcttctcgggctcccgtagaccgggtccacccgccaatccccccacacgtcg
atatctccagcacccaccgcacccactctcctcctcActccgctcccctcctctcctcctcccttc
tcgcggaggccgccgcaaccaaaaaaaaaaaaagtctaaccctagatccaggccccgcgtctccggc
gatctcccggcc*cag*gtaatgcccccccgcccgtcttctcatccttgtttgcgatcgtacatttca
tttcgtgttgtctccgaccagatctgacgaaatgtggatctactgctgtcagatttgatctaggtg
tacagttctgagtggcgagcgatcgcccttccatttcgttcattttatcggtagactgttggctgc
tttgtggtggtctgttcgtgctagtgaagaaattgacttttttttccccctataaagtgctgcctttt
ggtttgtggtggtcatctagagtctattagaattcattatgttcaccagtgttgcatttccgtatt
ggcgtattgtgaggttaacatgcattggttggtataacttttccactgtttgcttgaatgaaaatt
gtcgtcatagtctaggaatccattccagtttttgtttatttaatacccttgccaattgtttagcat
aaaatgggcattactgaattcagagaactgctgatgcattcgtgtaaattctgattataattagag
ttgctgaaccttgtatctgtagcattgtcttggaagttgaaactaatcatatataatgtgttctac
tatgtttttgacttggaagttattcttctttgtag*gt*

Figure 111 (SEQ ID NO: 111) Os11g11390, +intron cacatgcatgctatcccatgaggtgggttttgtgatatttcaaagaattaatttcgaataggcc
ttagcccatctattaattccaatattaattccaacagtaataagctagctgatgctatagcatcga
tcggatgtaacagtccccaaaacaccgatctcctttgggacagtgcacctccgggtgttgagggtt
tggtcgccagtgattctgccgcgtccatgggttaatggaaacatgaagtcttctttaaaaaaact
attgggttaatcggtacgcacccatatgtccatctcactcccacctctagtcgagatcccatttga
tttagattattgaatggaccatttacttgaatattgggatatattaagtattttaagagataatct
taacaaatagcttacaacaaatgacctaagcaagcagtaaatttctgttaagaaatgtattttt
tgaagtggaggctagagagcaaacatatatccggttggatgtagaggccgggtaaaaaaaaagtt
attactgcttatctttttcaccgtatgtctctgggtaaaaaaaaaacttctcttaaaaagtgtt
atcgctgcttatcattttcaccgtatgtctctgagtaaaaaaaaaccttctctaaaaaatccggt
tggatgtagaggccgggtaaaaaatacccttctccagaaaaagtattattgctgcttatcttttt
caccgtatgtctctgggtaaaacaaaaacccccttctttaaaaaaattcggttggatatagagacc
gggtaaaataaataaaaaacccttctcttaaaaaaagtgatttgctacttatctttttcaccgtat
gtgttaggttaaaaaaaaaccccttctctaaaacaaggtaaaaatgtgttattgatgtttatcttt
ttcaccgtatgtctctaagttaaaaaaaaccattctcttaaaaaaatgtattattactgcttatc
gcttatgtgtcttggatccaactggtaacggtggtgggaaaggaggcaagaagcatagcaaaattc
ctgatgcaaatgcgcaacaccctgaaaatattgaaagtaggaatgcccccccttttttaaaacaa
taaaaatcatttcaacgaaaatttgactaactggtacacaatacaagaaaatttatttcaccgtct
cttgcgtcatgatagaaaccatcgaaaaaacaagttttagacattcgcgaaagaggactaccagct
cactcttttacggaattgcccttttgaggaaccgttgttatggttatgggccttatgaactgggc
ccaatatccacgcggccatacggcccgaagcccaggcccatttcgcaggcagccacacctattgct
cccccctccgcagtatttaagcttcacccccctccaaccctagcgcCcccattcctcaggtttcccct
cgccgacgcctccatcgccctccgggctccgcctccgccgccgccgcc*cag*gtaagctcgctcgct
cgctcgatctctcacatcccttcatcatctctccctctccctctctcgctcgctcgctcgtacggt
tgctctctcttcgatcggctgcgcggtgtcttggctcggctctgcgctagggtttcgctccggtga
actaggtccgtgtcttagatcccgtggcgcgcgcgcctcctcggtgcgagatttgcgaaattcggt
cggggtaatcgagcggattgtaggatttgtttctcgtggtggtgttgactcggtgggcggtttgac
ttttcttgttttcgtgaatgttataaggcgagtaatcgggaaatctccgggtttgttcagtttagc
atgttaaatttggtctataatcggttatgtagggcgtgtaagagctgcaggatcagcaatatacat
gtataggattgctttcttagaagatatgtttggtggcgtgtgatttgttgcgccatgtaatgcata
aacttgttaggttagtattggtcgttgttgggatgccacagtatcttgtaattttggcaatctgtt
gtggtgctacatgtcctagtattgtagatttacatctgacaaactagatataaatggtttctgttg
aattttgtttatggcatacgttcatgtagtttgattgtcattctgtggcttatattacggtacatc
atgtgtatacttttcatttacggtgtattcccattcctaagaatgtttcatgttgtgaatcacccct
caatctcaaaattatgatgagatatggactaactaggattttattatctattagtgatacacata
tgtgctatttagggtttaatctttttggtactatctttgaagcttaatttgcatcattgactccat
acttaatgtaatctgctgagaatctgtctcgaacatcacatgtttctttcttgttttgctattgt
caagattgtttgttgtctttgctacctttgtatgtatttcaaattataatgcaatcattgtcatg
tatgcatatatgcctggttatgatgtatgatgcagatacacatttacttgagctttttggccaa
tttgttgaatttcactttcttttgattctgtactcatgatttcctcagctagaaacattgcctt
gttcagattatactgagatacttaatatctttcattttcatctttggatgctggtcactagtttag
acctattatcttgttaattagagtttgtatacttgaatgaaccacatgtgagttgtgttattctaa
cttgtgcactgctgttctcttaccag*gt*

Figure 112 (SEQ ID NO: 112) Os11g47760, +intron agcaccatcagacgccgccacatctccggcgcccgtcgcctcctccatccctcccaactcgcttga
gcggacacgagcagccgcaggagctcctccagctccggccaccggcgtggtgctcgtgctccgccg
cggcactctcgccggaaaaagaacgaagagaagagagagagaggaggaaccgaggaagaggagagg
gaggggagagatgacatggcatatatgtgggggtcccacgctgactcaactgtcacataggacaaa
accaagatcaaaaccatagaggatctattgtgaacgggttttgattagttaagagaccccaaatat
tttttcagttgaggtacgattttgtaactcgatgacaagttgagggacctttggtgtactttttcc
tagccaaaaggcctcggcccatgtattaaggtgacggcccacttgtgccgtcctcgaagacggccg
acagaccaacattcatttacagcccaaaaattacgaaaacctagctgcatcgcatcttcttctcct
ttccccaggcggagcaccgtccgatgagcatccaacggctacggtcagcaccctcggaaccttcga
gaacaccctccccgctataaattcccgcctttccggtagcatcTagtcttcctctcccactcttcc
tcctccccaaaccctagccgccgccgccggcgtactcgagagaaacatcagcatcc*cag*gtaacta
cttattccctgctcctcagtcctctctctttctctctctcccccccttagatctcatctctaaggtc
ttcgtcgtcgtcgtatgctagatctactcttgcccagctcgttcagatctgttagatttgtgtggg
atgctctaattaattactaccaacttagtagatctggaactcttttgacttgcagatcttgctcca
ctcctgttgcattttgaatctgtgttgatgtgatttaagttgttggcagtgctttttgcatactat
ttgaatttgtggatggttagcagtcagtacactaggatttattactggatctggacagatatgctc
gtttcaatcggctcgatttgctatgttgatagctaacatgttgtgcttgtcctactgccctggcgc
aaatttgatccatgcattcttttcgttaaatgatttgtcaagtagtaatgcttgtttgaaaatgat
attattattattattattatttaaataaatatagcctgaaacattcttagtttcgaggagaagtg
atgatgtcttatccataccacatgtctgcatctcatatgatgattaatctacatcatgcactacca
tctgatctcctctagctcatacagcttttaacaagttaggcgatagatgtttgctacaaacagtca
actggatttgctttcttgaaagaaaaaaatgaaccgtgtagtttgcaacctgtgatgtaaattaa
cccatttactgaactacattgattatttcagtaaaatcaccatctttcggctgaggttgcatgctt
agttattatatttttaccaatgatgattttgttatgtagccagatactgtactttcttatgccatt
tggtatctgactcattgtctactttttgtgactatgtgtctcgaaatatggcatataataaggggga
acggatcttgcgacattgatggctcctgtatgagcctccaattactatatagccgtttacatgttc
ttatcatgttacttttccaaattagtgctgcacatcttgtctgtttgcaagtttgggttcattcat
attgctgtgggcattttaatacatcttaactataatgtaaatttcttgtacatcgctaaaatttc
tgccttgattgagtagactcttagatgacatctatcttaccttatgcacttgattcgtatttctgt
tacaacattttgattacttgatgtagttcacacaagcatgacacatctctttgaaaaaaagatttc
atttttaaagcaagcctaatgctttagggtgggagaagtgatgatacttaatccatacaacattt
ctgcatctcagatgatgatcaatctacatcatgcactaccatctgatctccccatcatacaatttt
ttattttgttttgttggattatataactttaacatttgataaagtgccaacagattttttatacaca
atttcttatagatattaccatgacagcttgcagcctgtgatgcaaaagtacccattaaactgaatt
acactgattattccaaacaaatcaccatctttcggctgaggttgcttgcttgtttaaaattatgaa
tgcttcttgcacaaccatttaggactttcggtagtttgtaatgccatttggtatctgacacatggt
ctgcgcttgtgactatttgtcttgaaatatggcataaaacaagggggaacggatcttgcgacattg
gtggttcctctatgatcctccaattactatatagctgtttacaatttgttaagttaggagcatacc
ttttgctttgtcatcaaagtcttggttcctttgtatttctagttcagattcatttttcttcagctt
ttgaaacataaactcagtatatttttactgtaattgctgacattgagtcttctctgcag*gt*

Figure 113 (SEQ ID NO: 113) Os07g02210 atatgttcaaccattttctattgacaaaaatgaattctagaccttgtgctagcgtttcgtattttc
cagtacaaaacatgagtaaaaaactaagaacttcctcgcattccagattttactctaactgttgta
ctagtagccccatttggagaacaaagtttaactaaaaactgtatgaagcaattaaactctcacaca
atcaaatcaagatagatatacaattgtaaaaaaaaacatatctttaacctggaagtgaggaggaga
tccaaggtcaatgaaagaagacaggtagggagggccatgtgaggagatgcctctccatttgcccct
ttatttccgacaatgccactcaagttgatcagtatcttcttcatggcaccagtagctgtgtactcc
atgagtgtaattaactttcttcttctctccaactgcttcagctaactttcttattaatgagcacca
tttttctgctctcattatatcatgtggtttgcttctgttacctgctgacctgtgtttgtgtgtgat
ctactatctgcagactgcagctaccacttgggcttgctttgtcacatgcagttttacaccttttat
ttctccttaatacaaggtaagtgttggatcagtagcttgctcaatgctcactcatcctgccaaaga
gagactacagacttgttctgaactgtaaagtctgttgtttggatcctctgcatattgttcagtctt
gtccttttgctttacagcccttttgcaaatgcaggaaccgtgtgataaaacagtagtagaagtttc
atcaggctcatggttgaagtaacagtgaggatggagccagggcgaagccatgattcttcgagtgca
tggctagaaaataataaaatgcatttttttcatttagatattcttagcttaaaatcgcttactctg
cattggaaaattctgctgccacatgtagtgttactctgcattagccaaaaaaaaagaagcaaaagc
aaaaattaacaggtgcctcaagatttgtgttaagtgatatcacagtaatgttaacctatccaatgt
agtattagttagtcatattctaactggatgattggattgattatggacagatttaaatttgctcgt
atggatgaataaagcaagggacgtgtgaaaattgtacaaaattttgatgggcctgatctgggccac
tttgggccttgacactctaggcggactagtgcaacatatgccccggcccatttacaccgccccgcg
ataaaaactgggtgagggcgaccaagaaccctaggctgtcGcggatccatcccatcccatctcttc
ctcgtctcccactcctccggtgagccttgcctccctttttcctcgattcagttcatcagatctttc
ggtaaatccaatcgagttgatagggtttgatgtcctaatctatctatctctctctgtgctgctgct
gttgttgggggtggcaggattctttctgttcttggttgattgccggag Figure 114 (SEQ ID NO: 114) Os12g07010 ggtgttcgtcatgttggcgaggatgatgcagagggagacgaacaaaagcagtcgcacgtagcgctc
cccaaaaacttaatcgcccgcctacccgtgcaggttctcaagcggatgaagtttcggaggcacctg
ctcgttccgatctaccgtacgtgcgggatggacagaaccggggaaacagagagacaacgcaggaac
aaaaggagaatatcgccaaggaacatcagcaggaggaagactcaatctttgagagccttttccttt
gcgttatttatatagagagatctccattaccacacaaataaatctcatttgttgtgaaggttacca
cacaatgaatctatttgttgtagaggttacaacaaataaatctctatttgttgtggaggttacaac
acaatgaatctctcatttgttgtgtaggttacaacacacaatgaatttcatttgttaatggtgact
ttattttcgtctgttacaaaacggaagagcaacaagaggcttggctcggcaggccgcctcgcctcg
ccacgcccacggccgaggccgactcggcgcgcgcgtgtggcagtccaaccatcacctcaaccgg
tcaacatggattctccaatatcactctatttaagttgaggttattccacataaattttcaaggtag
tattattgtctctaacaatacttatgggatcttaagattttaattaaattaaatttggcctaacct
atttattccaacagaatataaacaattttagtttttttagcagatattagacttgaggataaaaa
ggctttgacatgtatcataaaatgaagtatgtttgggattagaaggattactgagagtaagatgga
aagaaattaaaacgtgaggtgattgatgaagcaattactattctaaaatctttatatctgtgaac
aaatttaaaaaacataaaatgtttatatttgtgaacagataaagtacacaatattccactgtcata
atacaaaacactcagaaagagacgtatttgggccgtaagcaagttggtgtggtcgtgtccaagcga
tccagtccaaaagcccattcgctttacctagtgtgaggcccagtctgcgacctccacacaaagccc
tagcattcaagcccattcctacatttccgcccgacccagcgaaaccctccattcggtagccgccta
taaataccacccctagggtttacctccctcGcctctgcactcagctcgcgccgccgccgccgtcgc
cgtcactctcctcaggtaagctcctcccctcctcatcctccaatccccgcttcgattcagatttg
cctccgctccgtgtccgcaatccgccattagttgttagtgagctagctgggagatcgaattctcgt
cgctggtgctgtagtttgatcgctgtggcttgcgattggtgattttacgggcattttcttggttgc
ggatctcatggcttgtgtgggtttcgtttgcaggtaaggaggaggaag Figure 115 (SEQ ID NO: 115) Os09g08430 acttcaccaccacaccaaagggtgttgtactctcttactctgcaccttttaaaatactcttactcc
gcacctttcaaaatacatgcccatatcttctctttgcaaaatttcagcttttctgtagttaaatga
tttaaccaataaaatgtggttgtatcatacaaagaaattaatggtgtaaaatgaatttggacgtat
tctagtcatgttacttacataatcgagcttatgaggtatttgagcttaagaaagattatgagttgg
gacataggctatggtcaaaagtgacaagtaatctgaacatcaagtatgtgatttcaactcttggca
attgacatttgacaactacttctatacagcatgtaaagctatgttgtccatctgtagtactattag
ttggcagatcaagttgctaggagcccgttgttcgttgatgattaagattgtgatcgcacggtcatc
tagcctaaaaggacggttgaacacatatgattttatccaggttcaggtcttccagaagataatagg
tctactcactaactagagatattatcttgatgggattgcttgggtacccctgttcgctcaaggtgg
ctaagctctacactcctatagcttctctgtgttgtaatgaaccaaacctctggtgtagaccagact
ggtcctcataatcgctcaaggtggctaacccttgcaatcttatatatccccaggtctacctaacca
ccatagagacactgagctactgtcacgctgcttgtcctggtcattcttctttgccatgttggcatg
ttgcacggtaccaccttgagcttccattttgatggaaaggggagcttgagagatatattattttcc
gtgaggaatttagttttatttatgtatatgaaatttaaaattagttattagcaagatgcagttaca
cggacttttctcctaaactatcattatacaattagaaaataaaccaatatatttatcaatcataa
gattaatatttaatatttaatatatttatcatatgactaaaattttaatatttatcaataataa
ttgcccgtgcaaagcatgagttgatggcataaataattattcaaaataaatagtatttatatatat
agtagtgggtggcaataaccaggaggggaaatttgaacgccatagttttctctcatctacacattt
ttcaatacaatgaaaaaaatacagtaacataaattggcaatcccttaaaaatgatttacagaaatt
acctcacattgtttttgaaaagaaagaatgtacagcatcggtttgggctgagggagtcgttgccat
cttgggccgcgcgcaaacagcccataccttggcccattagggttttgctccctaggtttcgtctcc
cccctatataaatgcttctcctgcgccgtcgtttcCctcttccatccttcgctcgctccgccgccg
ccgccgccgcctcctcctcctcggcgcctctccgccgccgcctcagcc Figure 116 (SEQ ID NO: 116) Os08g03290 gacaaccgatgtagatgaatacttcctcggtttaggaattgggattttatttataagttatacaaa
gtaaatataaaatggacggtgcatattgattgaggtagaatattagtactactgtttcttcttttt
ggaatatactgcaaaacaacactaatgtaatgttcggacaaaacttaaacgtcattatgaatatta
ttagctcttaataatcggcaatagccaataggtcagagacaaacacccatcagaggatccggattc
gatcaggtgagtgccggacaaacagtatgcggcgccatcgcccgtcgccgccgccggctactttct
gttagagcacgggcctgtttagttcaagaaaaaaaaattattttttgaatgtcacattggacgttta
actagatatcgaaatagatttttggacacgaataaaaaaactaatttcataactcgtctggaaaca
gcgagacgaatcatttgagcctaattaatccgtcgttagtatacgtaggttaatgtagcacttatg
gctaatcatgaactaattagactcaaaagattcgtctcgtgatttcctccctaactgtgcaattag
tttttgtttttatctatatttaatgtttcatgtatgtgtccaaagattcgatgtaatgtttttagg
aaaaaaatctgtgaactaaacagggcccaagtttagccaactactaactccaaatcacatatagtc
aacttaatagttaattcatacaatagttacatactacactattaatacctgatcccacctgtcata
catacactgtctcttgaagtccatgctacagctggctacaaatctttagctcgctgctcttctctt
tcttattttattttcttaaaatatgttaccaaacgacgacacgtagccagaaacacctcgacacga
acacccccatgtcacaccacaccacaacacgatcagttcaacttttttttttctctttttttcaaaat
ttcacatccttttccatcaatttttctttaccccgcattattgcagaagcaagaaggagcaaatat
gcccttttctatttctttcacctcccctgattctttcttgggcgacaaaccacaacctgccacgta
ctctactctacccgccgcgcgtcactagctaatgacacgtgggcctcgcccatgcccgggcccaca
cgtcagcgggacacctcacctgcctgcccctgcgctgcgccggctgcgccttctggagaaaaggta
aagaaagacaggtcacccacgcacctcgcgcttaatttatttgtttccattttttatTtttaatttt
ttttcctcacgctttctcggttccatttggctttattaataattaattagacttttttcctcttggc
tttataaaagagagcgcttaaaccctctccacctctccatatccggcttccagacgcttctctcct
cctctaatctcaagtctctgtctcgtcgtcctcgcatctccactcgcc Figure 117 (SEQ ID NO: 117) Os10g22590
agacataccttctatcctagaagtcataaagtatgcggatacattatatcttcaagtaaacggaaa
ggatccatttgaattaaggaaattgatgagtccttacgaaaataatatctacgaacaggggatatc
agagtcctacttataggggataattaatgacgttgtcatatcgtgcggggtctgttgtctccaagt
tctacttggagaccaaggtgatctgcggtataaatagataccccctgagaggtatagggcatcgaa
tcttagtgcaagacacccgccaccacataagcaatccggaggacttgaagccaattcatcgataga
tctcgtcgaggctctctcgacaagaatctcgtcggtaatcttggagttatgttgttctctgttgta
ctctgtggattcttctataatcccatataaactggattaagaatattaccttgtgaggtgcctgaa
ccagtataattcctatctttttatgtgctcgatgtcgtatcgtgtagatcctcgtaccaacatacc
ccgatacccatagaatacggtccgtgggaatcccgtcgacattataaatttatagagttcaagaaa
acttagatccagtgttgtgctaaaacaatcttaatatgacttatatttacaatatcttattaaaca
ttgcttgtgttaaaacttagccaaagtttaacagtagacaaccaaaccgacactaagtatatcttt
aagagcgagtaagtaataactttggtatatggcgttattccacatttcctaagttcgaaaactatt
ttgtaataatacacgtaagttcaaaaactatgtctacaacattcaacgttacaatgtcatataacc
tcacaaattattgctgctgtagcggttccaatcgaaaaacatcaaatttcgtcttggagcaactcg
atagattatggagaaaatctcaaaccccctaagtagaatcataaaaaaaagaatgcgagagaccaga
tcagataaagagtctatttgagagagtttatggtcctgtagtttcctatctggccttaggttataa
gtcctcagctatttgtcatcttgcttaaaactgtaatctttctcagactgtaatcttttatgaatt
aataaagctccttgtattcgtcgaaaaaaaaagctttctcaaaaaatttagattttcgttcaaatt
aaaaaatatatagtcaaataaaaataattgtacgatagaaaccgagaaacccaatttgttagattt
tcagaaaatgattagcaacgagctttgcctttgattctcctgggtcctggccatcaccgactcacc
gtgcggtgctcgcacccccacaaaaccggtcacatgctgcgcataaatccatccaccccatcacgc
Gaccccacacgaccattattcctcctcctctctggagtctagtctcctctcctcactcctcactcg
ccccactccgccgcttcactcgcgagctcgtcgttggcgccggcggca Figure 118 (SEQ ID NO: 118) Os03g45280
tgtaaattgtgtaattagtttttattttatctatatttaatgctctatgcatgtatttaaagatt
cgatgtggtgtttttaaaaaaataaaattgagaagtaaacaaggccttacatttgagaaagcttcc
attggagctagccgtggaagtccaacctgcaggctcaggctgcagatcgcccaaggcgcacttgcc
tccacgatggcttgtcctcaaccgctcggaaggcgagatccaattggcaatttgttcaacgcaggg
agagaggaggagactggaacgggatcattggacattggttgatgaattgcaatttggatgacgagg
ccgcgagggtcagaccgtcggagagtgagatgatggttatacaagtgtactagtaggacggacggt
ggcaccggccagaagcagcagattttgtgcaaacgttgagcccgcaacacgtggccggcatcgacc
cgctacgacggacgcagcgccccccccccccccccccgcggacccacgcgggccggccgc
gctgtcgccgtgctgccgactacgccgtcgaaatcaacgcgtccgcctcgatcctcccctgccgac
gctgtacaagtggcgaccagaaacaccatgtagtatttgatctcgtctaagagcaagtttaatac
tatagtccactattagctccaatttatttataactgatctaatagccaattcacacaataattgct
tactatactattaatatatggtctcacatgtcatacacatattccgtcttggagttcgtgctgcag
ctggctacagatctgtagcccgctgctcttctctctcagagcgagtataatagtacaaactggact
ggcgataggagaaacacgtcagctacagtgttgagctggatgagtgagaagaggagagagagtgag
agtgggcgacaattttatcgccggctctagcaccagcttcgagagaaaagtggtgagcgcagaggt
tgtgagctgcatgtgtgagacgaagcttaagttattttattatgatgtgaagttgatgggtccagc
gttgcaggtcatttattgtattcacaagatgcaaagagagctactagctgagttggatggaattaa
cgccggctgtctacgctactattaaccttgctctcatcttttatctcatcaaaatatatttatagc
tggctaatagtctgctatcgtacctgctctaatgcatacgtttttctctctgtggcaaaacggtt
ggtgcgttacacggggtgcacgaagccatgcatcaccctgctcaacccgtctcctttttagccta
atcttttcctccttatccgatgggccttccgtttctcaagacacccccacaccgccccggccctct
ataaataccaaccacgacgagccaagcGaacatcaccacagctagatcattagcaatccattccga
tccatcaaatttctcttgagaccgtagagagagagagaggcgccaacc Figure 119 (SEQ ID NO: 119) Os06g07969
ggtttctttgaactgcaattttgcaaccactgacagtgatgcaaggattgaaagaacagtgtttgt
acataccattggatgttagcctcttaccttgcacgcaacttgtttgtctacattgcatatttgcat
gtgagctttggtcaaccttgttgagttgtttgtgaggcaacaagggatttcacaaatatgttaaca
atcctaagaagtgagaactctaatgctaggtttggaatacaagaactatgcagaaattcataggga
actgactgtaattcccacgcgaatcaatgccaagttccaagtggtaaggtgtcttaggtgaccaag
tttatgaaaaaagatagcaacattctaaacatattcaatagtaggtataattaaattaatttggtg
tttttctataaacttggttaaacttgaggatgtttaactcaagacaaaaacaaaacaccttacatt
ttaaaaatgatttcgaaaaactaatataattctttttcccagtgaacaatcatgctaccaaaccgc
atctgcacagttaggtctaccagtatcgtttatcaaggtcttcagagttcacatctacgatttggt
tgcttgcattctcgccatggtagagattataattcgctcttctgaaatttactcaaaaaatcgctg
tgtaattgggccgggcccaagaggccaagtttgtgattgggccaaagcccaataccccaacacacg
acgacttctatccatcctatataccgaaccctagctgacgaacaatccAgaagcccatcgatcgat
cggcgtgtagaggtgatcggaggcgagcgcaccggagcacaccaccgaggcggcggcggcggc
gagggagggagaggaag Figure 120 (SEQ ID NO: 120) Os07g30970 cttttcactgcttgaacctgcaggggacacatgatttcaagctcagtctcagaattgggaccatat
atacagcaacgctggtgaaagttcctcatattaactgtacatgctgtacatatcgatgtacttttc
ccgtggacatggtgtggttagagcaaacgtcttgttacattaccaggctgttcttgggccacaagg
gccaaccaagaaacgaaccgggccttctctttggggaatctggctcggcccacaaaataaccagct
atgggagactcagtcacatccctcatgcaacgtacatcctccgtcttgtaaaaaaaatatcaactt
ctagctatgtactttatgggatggattgagtacgggttatgtgatcattgcctcttgtttttgcga
tgatccttgtacgctagtgcctagtggtataaaatgagctttgtatataatttggtccattttttt
taaaaaaataaacctgcaataaaacgttttctagaaactggacctacaatatggggccgtgatatt
caatgtgatgtgcatacagcatggtgttgtataatttggacgtcgatgtaggatattttgtgagac
cattatacgcggttgcctacatagcctcaaattatgtgacacggtgccaatgtgccataaacatct
ctatctctaaaatgctaccgacggtctagaatatatatgatgtttaggagaaccaaaattgactta
aatgttgttatatttttctgtcctaaacgtcgtatatgatcatgattggatggagtattttattag
aggcccacatgtaaaagatatttaagaaaaaaaaagactaaattaccaaaactaccccgctatgta
ctcctatactgcccagtctgccctacaagaaactcgtgcgtgaacttctactgtcactgcactctt
cctctgcacacacgtttcagtctctcatcagcccgacgtttctgctgcaaaaccacggcctgattc
cgattcacgcaaatcgcggccaaatctcgcaaaccaaaaccaaaatcgccacctgtaatgtaaaga
aaagaaaaacaaaaacaaacaaaagtgaaaaacagccaaaccgacggcccaaaaagaagccgcagc
ggtgcgtttccatgtggcgaatatttccaggatgattccaatcggcgcacggcacctcagcacatc
acaccagatatataattaaccaccccgtctctttcAcgacccactccgcctcgcctccactcctct
cctctccgcatcctcctcatcgcctccgcttctgcttttttttttcttttttctcgttgatcggtt
tgttcgatcagatcggttctttggagag Figure 121 (SEQ ID NO: 121) Os09g33500 tacaaaataatttatgagtaaaacttttatatgtgtctctagcgacttaaagatcaatgctgaaaa
gaaaacaaagtccaaaataccttaaaatcaactccacaatcaagctttaaattttaaattttggcc
gcgactgattcgttgtaagataaacgatgatgcttgagacaaatggcctccctgaactggagagag
agaaaaaaaactttgcagctttcaagaggcgaaatgagaagtttgatcagcggaaggaaggaagg
gaggaaagaaggacgggtcccccctggctcgagcgagtcaagtgagagtgagtgacagacacctgcg
aatccaccgcgagatcctggcgttgaatcgcggggcgctctgccgatcacgtcgccaacagtgtga
cagttcagcaaagatggcgatctttcttttgctctcgagtggcctcggtactctgaactcttctga
agtctgaagtctgaactccttcaagtggcgatctgcatatagatactagaggttgtctcattattt
atttgctcccgattactgtgaatagtaacaagaagtagtattatagtagtatgaatatatttttct
gaagaattgtgacatctagtatagaaaagaacgcagtaaaagttgagaaaccagaagtttgcaggc
attatttttatccagaggcaaatgcatataaggaagtgagggagaaggtttggtctgtacagtta
aactgattccgctccctttgtcgtgaaaatacaatctcaaagacatgtttatgttcttacattaaa
aaaaacctcaaaaacttgtttatgttcttaagacaaaaattactcgtccctacacaaaagtcaatc
cacgaattactcctttaaatattccttatggtggttttctaaatgtatagttgtagcggtagagtc
acgagtgcatgattctactcaccagagtttaattccttgtgtccataaatatggttatgttcatcc
tcgttgatgtagagatgggagttatacatttttcccctttttttttgggatatacagttcccctcg
caaaattcaggtcgttaattggaaaaacatttatgctaaacaggccgtcattacggtgatagcaat
acgaaagcccatcacagcagtctcccctttgacgggccggcccaattactcccacaaaccaggctg
ggcctttgggccaatatgtaattacagtaattattccttatactaataataaatgcgcattaagct
gggggctttcctgcaaaagagcgcggaaaataaaaatctcgcacagaggcgtatccacGctttcc
ttctcccctcccaccaactaatcgatctcctctctctctctctctccctctctatcccattcgc
gaggcggcgtctcctcctcctccccgtctctctcgcttccccccaaatccggcggcgaatccagg
gccccgcgccgcgccgacgaccaccgccgatcgcgaccaggagggagg Figure 122 (SEQ ID NO: 122) Os10g33800
tgtgtagccatatatataggacatcttcaactagtggttcccttatcatcgttgtacccctcctcg
gtaataggttagttaccgagcaaaacagataaaagctaaaatgctagaaaaggttaattaaaaact
tttttaaattcgtaacaaacattttcgttatttagccttggtggtaaactatggtgaccgatggt
caaaccttggtttcaacgaagccacccattgtagtgtaaaaatatttctgtagcttaatttagggg
ttgtttggttggtgaccgcaatttgctataccaaaatcttagacacagttgaattaagctacactt
tattagcacattggcccgtgcgttatattgtcattttctagccaaagtttgccataattgtggcta
acaaattgttggccacattttggctacgttcgataggacatgttcccaacttctccttctcgtttt
tcgcgcgtacgctttttcaaactgttaaacggtgtgtttttttgcaaaatatttttttacgaaagtt
gcttaaaaaattatattaatctattttttttaaaaaaagtagctaaaacttaattaatctcacgct
agacgctgcttcgttttacgtgtcgggtacccaaccctcactcccgaacacagcctttgtgtggtt
tactacagttatagtaaagctagtctccatccaaacaatcctttagtccatataacttcgtatact
ccaaaattccactcgttctacggacatcactaatacgaagatcaagtggaagatagatatttttaa
tgacatgttattttcagtgaacacttgaggtcctcacgatccacaaacacacattttcgtagataa
gttctgaaatactccatacggcggttgtcacgatgtcatgatcgtcgttacccaaggaagaagaaa
agagtggcatcttctccacgccagtgttcccaacggagcatcttttcttcccccacacggcatcga
cgtcacactttctggtgcaaactttaataattagtccaaaaacaaaaaaagaatttcggccacatc
ttctcccgaaacgccaggtgggccccacctgcatcactgacagcctgtccccacaacgcgcagtcg
tgtccccacctgtcaggatgttagcgtctccgttgcaggtttcccagatcccatcgccgatctgtg
ggccagcgcccacggtgtcacgcccgcgcacacctggctccaacccacccaccccacgcgctccgt
cgccgacagcgtggacccacctaggtggggcccaccgtcagtgggagatgggtaggggagcccccca
cgtgggagcaacggggggttctccgggctccccgtcgccgcgaggttaaataacggccacccgtttc
cccctctCtcgcaaaactcacccaaaagagcagcgtcgcctctcctcctccctaacccctacg
cttccagaaccttctcgaagctcccgctcccccccccttccgctcca Figure 123 (SEQ ID NO: 123) Os11g38959 atgtgatcgacaaattttgaagaagtgtcatcaaaatccatcgaattccatcaaaaacctgttact
gatggcattattcagaagattttcctcctgttctttttgcgtttcaatactctgctcgaaatttt
tttcccctcctatttttttgtatttcaactgatatcaccatcatcctgatgtgataatcagagcaa
tgtacaaaattctctcaaacattaatgaggttcagaaaatttctccttttgcatttcaaaatcagt
aaacaacaatgattcattcactatgcatcctgggaagaaaagaaaagaggaggcagcggcgaacgg
gtagcagcagcatagccaacaccggctggtcatgtaggcgtatggcctcctatgcacatatagcaa
aggaggaaaatgagcagctaaccattcatacatgcaaagatatttttttaaagcataggcaagaaat
caccacagtaggcaagaaaaaatggttgccagatttgccaggtccgcgtaacatagaacacatgtc
aggcagatgggagcaacactgctattacagcatcaaaattcaccggctcgacggcgatcgccgcgc
gcggccgcggcagtcgcccgtcgagcaggtaagctgcgaccccggaggtggaggtggagcccgtgg
aagatggagcgaggtgccggaggagcatgaggccgtggcggctgccccgaccgcgagctccatgga
tgcccgtgatctggaagaagaagtcgaggcaggggttgtcggagtcggcataggtggcggatcgag
tcgttctcggtgcaggccttccatggcttttggtttctatccggaggtcctcccgctccttcgcgg
cctgtccgtcgccgccaagaagctcgcttacggctgccatggcgcctgcctccacctctgcgcccg
tcgccgcggcgcccggcctcgccttagcctccacacccaccgccgcggcgccccacctgcgcccgg
ccagccgtcgccaccgctccaccgcgccgcccgtatgttgtaaaaaatgagagagaggaggaaggg
agagaagggagagagatgatgacgtggtcacatgacgtgtgggactcatgctgactctgttgctac
gtaggataaaaccggggtcaaaaccagccaagaatataaagtgaacggttttgttagttgagggac
gtatctgcttttacggttgaggcacgattttgtatctggatgataagttgagggaccttttggtgt
actttttccttgcaaatatgggccttctcaccgaaggcccatttatgatctcgatatgtgggccta
attgccacccgtgcgttaatgggccgagaaatctcggcccatttaacctagccctcaagctagggt
ttcctctcgtcgccgcatataaaagcgctctcctcttcactcctcctccCctcgggaaaccatagc
tccagcaatcggcggcggcggcgacgcgggagaggcggtccggcgacg Figure 124 (SEQ ID NO: 124) Os11g38959, +intron atgtgatcgacaaattttgaagaagtgtcatcaaaatccatcgaattccatcaaaaacctgttact
gatggcattattcagaagattttcctcctgttctttttgcgtttcaatactctgctcgaatttt
tttcccctcctatttttttgtatttcaactgatatcaccatcatcctgatgtgataatcagagcaa
tgtacaaaattctctcaaacattaatgaggttcagaaaatttctccttttgcatttcaaaatcagt
aaacaacaatgattcattcactatgcatcctgggaagaaaagaaaagaggaggcagcggcgaacgg
gtagcagcagcatagccaacaccggctggtcatgtaggcgtatggcctcctatgcacatatagcaa
aggaggaaaatgagcagctaaccattcatacatgcaaagatatttttaaagcataggcaagaaat
caccacagtaggcaagaaaaaatggttgccagatttgccaggtccgcgtaacatagaacacatgtc
aggcagatgggagcaacactgctattacagcatcaaaattcaccggctcgacggcgatcgccgcgc
gcggccgcggcagtcgcccgtcgagcaggtaagctgcgaccccggaggtggaggtggagcccgtgg
aagatggagcgaggtgccggaggagcatgaggccgtggcggctgccccgaccgcgagctccatgga
tgcccgtgatctggaagaagaagtcgaggcaggggttgtcggagtcggcataggtggcggatcgag
tcgttctcggtgcaggccttccatggcttttggtttctatccggaggtcctcccgctccttcgcgg
cctgtccgtcgccgccaagaagctcgcttacggctgccatggcgcctgcctccacctctgcgcccg
tcgccgcggcgcccggcctcgccttagcctccacacccaccgccgcggcgccccacctgcgcccgg
ccagccgtcgccaccgctccaccgcgccgcccgtatgttgtaaaaaatgagagagaggaggaaggg
agagaagggagagagatgatgacgtggtcacatgacgtgtgggactcatgctgactctgttgctac
gtaggataaaaccggggtcaaaaccagccaagaatataaagtgaacggttttgttagttgagggac
gtatctgcttttacggttgaggcacgattttgtatctggatgataagttgagggaccttttggtgt
actttttccttgcaaatatgggccttctcaccgaaggcccatttatgatctcgatatgtgggccta
attgccacccgtgcgttaatgggccgagaaatctcggcccatttaacctagccctcaagctagggt
ttcctctcgtcgccgcatataaaagcgctctcctcttcactcctcctccCctcgggaaaccatagc
tccagcaatcggcggcggcggcgacgcgggagaggcggtccggcgacg*cag*gtacgtagctcctcc
tcctcctctccctctctctcgtccaagaacggcgcgtcgtcttggttggtgctagtgcgatttggc
gcagcgagagaatgttcttttcttttttttttatctcttttcttgcttcggtgtgttagttgatta
gcgagtggcggttagttaatgaggggatggctggttcggttggcgagatgatctggatcaagattt
gcctcgacgcggtctgttcccgtagctttgttcatattctcgtttccattgcgttggatccgtacc
tatgccgattagttcgtgctgatttcgactgactgcgcattctgttgttgaaacttgtgtggtgcg
gatttaatttcgagatatgtagattttgggggggttttaactagaatgctaagatgtgttgattag
tactgaggaatgaggacatgtttactcatttggcatttggtactatgtagcttgaaaatggttgtt
tctgttatggtacaaaatttgataatttacctgttttaaggactggaaatatgagtttcattagct
agagtttttttgttctcaagtattctgtttgatcactcatttggtggaatggagttatgcataagc
ttgtgaattttgttacgaaaatgaatcatggagcttaatatagaggactatatacttgtaatgcac
taactgtttgtttatacatagagtggtccatcgagaactatatttgttatttttttttaaaatttct
gtgtaagttgtagtatgctaattgtattctatatgtatattttcttaaatatattatatgatagtt
cctgatgagatctttcaagtattgtcgctttaggtcatgaattccattttacagtagaacaaataa
tttaggtatgtatgatatggctaaccagggataacacagcaaaactaaatctggcatgtaagctat
ttatgggttaatcagacacaatgttatgaattgttttataaatccttgtcaaacatggttgtatat
ctgaagctcttatagtatttactgtacacaagatccctactactatttgtcttgaatatccatact
attattgggcgtaatctcaacaactactgtagtttctttatttgtgttgttgcattgtctttctg
ggttgtgtgtgcagttgctttcttgctttgtatattttggggtcaggatataaggaatttgggac
tgtagggcttctttctatgttattgtttggttcttatgaacaactatactatctacagtggtttct
ttctctgtcaagtgttatgaacaaatttattacttcattgcag*gt*

Figure 125 (SEQ ID NO: 125) Os06g07969, +intron ggtttctttgaactgcaattttgcaaccactgacagtgatgcaaggattgaaagaacagtgtttgt
acataccattggatgttagcctcttaccttgcacgcaacttgtttgtctacattgcatatttgcat
gtgagctttggtcaaccttgttgagttgtttgtgaggcaacaagggatttcacaaatatgttaaca
atcctaagaagtgagaactctaatgctaggtttggaatacaagaactatgcagaaattcatagga
actgactgtaattcccacgcgaatcaatgccaagttccaagtggtaaggtgtcttaggtgaccaag
tttatgaaaaaagatagcaacattctaaacatattcaatagtaggtataattaaattaatttggtg
tttttctataaacttggttaaacttgaggatgtttaactcaagacaaaaacaaaacaccttacatt
ttaaaaatgatttcgaaaaactaatataattctttttcccagtgaacaatcatgctaccaaaccgc
atctgcacagttaggtctaccagtatcgtttatcaaggtcttcagagttcacatctacgatttggt
tgcttgcattctcgccatggtagagattataattcgctcttctgaaatttactcaaaaaatcgctg
tgtaattgggccgggcccaagaggccaagtttgtgattgggccaaagcccaataccccaacacacg
acgacttctatccatcctatataccgaaccctagctgacgaacaatccAgaagcccatcgatcgat
cggcgtgtagaggtgatcggaggcgagcgcaccggagcacaccaccgaggcggcggcggcggc
gagggagggagaggaag*cag*gtacgcctcccccatcctcttccctccactccccccctcctctcgcg
cgcatgcggtttcggcggatctgggcggatctagggttgttaggcatggttagcttcggtggctct
ggttggatcggtcttctcgttgcggtttcggttgattcgttaggtctgcgatgcggggatgagttt
ctctgtatttgctcccatttcgtcggaattattgtgcagatttcgcgtgaattgatgcgtgtcaac
gttgcatcgggttgtcatttgactcgggaaacgcgtgccccgtcgatccaattaggttaggcagaa
tttggagcagtggactcgctgcaaattatttgctgtgaggttatatttgtatttgttctcacaacg
attttgctgtttcaatcgagagttccagacccaaattgatttggtattctgtatggtcatgatgct
gatccaatcatgttagctaagtacttctcttgtactgtattatttagttgaatttgcctctaatat
tgattggctttgttactgtttccaaactgaatgttttgagcgccacatatagcttttgtactcaca
tgtctcctggagaatctatgcccaagcttgagatatgcaaaactagattatgtcttcggatgaatg
cctgaatgatcagttagcctattatactatttttttccaacatggattttcagtgatttagcttt
atgtgaacttgttaaactgcatgttacagcttgttggcgttgtgagctcactatgtgtcgaagcct
gaagaaataccatctgaatgttgtttgtttaccttgtaccataggattttgggaagttgtcttaa
gtagatgcaatatgctatgttttgaccattgatgcagcttatcatatagtctccatggttcttagt
actgatgagttacctttttttttttttgcctggcagttataggcatgcttgtttttcctaatatc
aggaaaccctcacctcggattgtgaattattgaaaacaatgagcctaacgattgaaatgtttttg
agaacttgaattgaaaagaggagttgggttggcagggctggcctcttaagttcctagtgctgccta
ggtactccaagagattagcaacatattacatgctaaacaatatagcactaaaatagtaacacaaga
gcactctagccgcctattgcaccatctaattgctaaacacggtggctacctggcgcctgctaactt
ttagaacactgagtcgctgacagcattcactctttttgcctttcgtgagggaaatgcaagtaggcc
ttcttttcaatccaaggatggaggaacatggtggagtgtgtatactgctggttcacgttgtaaaca
attgatgacttcctttgtgtttctttgtgtgcagtaacactgtttccttgacattgatgactatc
agttttcttgacagcatcacaaacaatataacctggtctattttgatggctatgcag*gt*

Figure 126 (SEQ ID NO: 126) Os09g33500, +intron tacaaaataatttatgagtaaaacttttatatgtgtctctagcgacttaaagatcaatgctgaaaa
gaaaacaaagtccaaaataccttaaaatcaactccacaatcaagctttaaattttaaattttggcc
gcgactgattcgttgtaagataaacgatgatgcttgagacaaatggcctccctgaactggagagag
agaaaaaaaacttttgcagctttcaagaggcgaaatgagaagtttgatcagcggaaggaaggaagg
gaggaaagaaggacgggtccccctggctcgagcgagtcaagtgagagtgagtgacagacacctgcg
aatccaccgcgagatcctggcgttgaatcgcggggcgctctgccgatcacgtcgccaacagtgtga
cagttcagcaaagatggcgatctttcttttgctctcgagtggcctcggtactctgaactcttctga
agtctgaagtctgaactccttcaagtggcgatctgcatatagatactagaggttgtctcattattt
atttgctcccgattactgtgaatagtaacaagaagtagtattatagtagtatgaatatatttttct
gaagaattgtgacatctagtatagaaaagaacgcagtaaaagttgagaaaccagaagtttgcaggc
attatttttatccagaggcaaatgcatataaggaagtgagggagaaggtttggtctgtacagtta
aactgattccgctccctttgtcgtgaaaatacaatctcaaagacatgtttatgttcttacattaaa
aaaaacctcaaaaacttgtttatgttcttaagacaaaaattactcgtccctacacaaaagtcaatc
cacgaattactcctttaaatattccttatggtggttttctaaatgtatagttgtagcggtagagtc
acgagtgcatgattctactcaccagagtttaattccttgtgtccataaatatggttatgttcatcc
tcgttgatgtagagatgggagttatacatttttcccctttttttttgggatatacagttcccctcg
caaaattcaggtcgttaattggaaaaacatttatgctaaacaggccgtcattacggtgatagcaat
acgaaagcccatcacagcagtctcccctttgacgggccggcccaattactcccacaaaccaggctg
ggcctttgggccaatatgtaattacagtaattattccttatactaataataaatgcgcattaagct
gggggctttcctgcaaaagagcgcggaaaataaaaatctcgcacagaggcgtatccacGctttcc
ttctcccctcccaccaactaatcgatctcctctctctctctctctccctctctatcccattcgc
gaggcggcgtctcctcctcctccccgtctctctcgcttcccccccaaatccggcggcgaatccagg
gccccgcgccgcgccgacgaccaccgccgatcgcgaccaggagggagg*cag*gtgagtgccgacgac
ctcctcggtttttttcctcgctcgctcgcccgcccgccatccctcggatttcccggggtttggtg
cggttgggtttcgatctgtgatttggggggtcgctgacgggtaatggatggcgtgtgtgggggttg
cag*gt*

Figure 127 (SEQ ID NO: 127) Os07g30970, +intron cttttcactgcttgaacctgcaggggacacatgatttcaagctcagtctcagaattgggaccatat
atacagcaacgctggtgaaagttcctcatattaactgtacatgctgtacatatcgatgtacttttc
ccgtggacatggtgtggttagagcaaacgtcttgttacattaccaggctgttcttgggccacaagg
gccaaccaagaaacgaaccgggccttctctttggggaatctggctcggcccacaaaataaccagct
atgggagactcagtcacatccctcatgcaacgtacatcctccgtcttgtaaaaaaaatatcaactt
ctagctatgtactttatgggatggattgagtacgggttatgtgatcattgcctcttgttttttgcga
tgatccttgtacgctagtgcctagtggtataaaatgagctttgtatataatttggtccattttttt
taaaaaaataaacctgcaataaaacgttttctagaaactggacctacaatatggggccgtgatatt
caatgtgatgtgcatacagcatggtgttgtataatttggacgtcgatgtaggatattttgtgagac
cattatacgcggttgcctacatagcctcaaattatgtgacacggtgccaatgtgccataaacatct
ctatctctaaaatgctaccgacggtctagaatatatatgatgtttaggagaaccaaaattgactta
aatgttgttatatttttctgtcctaaacgtcgtatatgatcatgattggatggagtattttattag
aggcccacatgtaaaagatatttaagaaaaaaaaagactaaattaccaaaactaccccgctatgta
ctcctatactgcccagtctgccctacaagaaactcgtgcgtgaacttctactgtcactgcactctt
cctctgcacacacgtttcagtctctcatcagcccgacgtttctgctgcaaaaccacggcctgattc
cgattcacgcaaatcgcggccaaatctcgcaaaccaaaaccaaaatcgccacctgtaatgtaaaga
aaagaaaaacaaaaacaaacaaaagtgaaaaacagccaaaccgacggcccaaaaagaagccgcagc
ggtgcgtttccatgtggcgaatatttccaggatgattccaatcggcgcacggcacctcagcacatc
acaccagatatataattaaccaccccgtctctttcAcgacccactccgcctcgcctccactcctct
cctctccgcatcctcctcatcgcctccgcttctgctttttttttttctttttttctcgttgatcggtt
tgttcgatcagatcggttctttggagag*cag*gtaatctgacttctttttttcttttaatgttcttc
ttgtcgttttggccatcgattttcgagaggaattttgcggtttcggatcggttaaatagcgtagtt
gattggtgtttgtttgtgagattttgagttgttttggtaactttttgtaccgttttgcgtggtttt
taatggggaattttgattttctgttctgcag*gt*

Figure 128 (SEQ ID NO: 128) Os08g03290, +intron gacaaccgatgtagatgaatacttcctcggtttaggaattgggattttatttataagttatacaaa
gtaaatataaaatggacggtgcatattgattgaggtagaatattagtactactgtttcttctttt
ggaatatactgcaaaacaacactaatgtaatgttcggacaaaacttaaacgtcattatgaatatta
ttagctcttaataatcggcaatagccaataggtcagagacaaacacccatcagaggatccggattc
gatcaggtgagtgccggacaaacagtatgcggcgccatcgcccgtcgccgccgccggctactttct
gttagagcacgggcctgtttagttcaagaaaaaaaaattattttgaatgtcacattggacgttta
actagatatcgaaatagatttttggacacgaataaaaaaactaatttcataactcgtctggaaaca
gcgagacgaatcatttgagcctaattaatccgtcgttagtatacgtaggttaatgtagcacttatg
gctaatcatgaactaattagactcaaaagattcgtctcgtgatttcctccctaactgtgcaattag
tttttgtttttatctatatttaatgtttcatgtatgtgtccaaagattcgatgtaatgtttttagg
aaaaaaatctgtgaactaaacagggcccaagtttagccaactactaactccaaatcacatatagtc
aacttaatagttaattcatacaatagttacatactacactattaatacctgatcccacctgtcata
catacactgtctcttgaagtccatgctacagctggctacaaatctttagctcgctgctcttctctt
tcttattttattttcttaaaatatgttaccaaacgacgacacgtagccagaaacacctcgacacga
acacccccatgtcacaccacaccacaacacgatcagttcaactttttttttctctttttttcaaaat
ttcacatccttttccatcaatttttctttaccccgcattattgcagaagcaagaaggagcaaatat
gccctttttctatttctttcacctcccctgattctttcttgggcgacaaaccacaacctgccacgta
ctctactctacccgccgcgcgtcactagctaatgacacgtgggcctcgcccatgcccgggcccaca
cgtcagcgggacacctcacctgcctgcccctgcgctgcgccggctgcgccttctggagaaaggta
aagaaagacaggtcacccacgcacctcgcgcttaatttatttgtttccatttttatTtttaatttt
ttttcctcacgctttctcggttccatttggctttattaataattaattagactttttcctcttggc
tttataaaagagagcgcttaaaccctctccacctctccatatccggcttccagacgcttctctcct
cctctaatctcaagtctctgtctcgtcgtcctcgcatctccactcgccc*cag*gtaattatgctcacc
tccgaatcgaattaattcccccgtttgattactgctggtgcttcgcgtcctgatctgattgatgtt
tttttttctgatttttttggtgaattttctggtggtgtttttggggacgcag*gt*

Figure 129 (SEQ ID NO: 129) Os09g08430, +intron acttcaccaccacaccaaagggtgttgtactctcttactctgcaccttttaaaatactcttactcc
gcacctttcaaaatacatgcccatatcttctctttgcaaaatttcagcttttctgtagttaaatga
tttaaccaataaaatgtggttgtatcatacaaagaaattaatggtgtaaaatgaatttggacgtat
tctagtcatgttacttacataatcgagcttatgaggtatttgagcttaagaaagattatgagttgg
gacataggctatggtcaaaagtgacaagtaatctgaacatcaagtatgtgatttcaactcttggca
attgacatttgacaactacttctatacagcatgtaaagctatgttgtccatctgtagtactattag
ttggcagatcaagttgctaggagcccgttgttcgttgatgattaagattgtgatcgcacggtcatc
tagcctaaaaggacggttgaacacatatgattttatccaggttcaggtcttccagaagataatagg
tctactcactaactagagatattatcttgatgggattgcttgggtacccctgttcgctcaaggtgg
ctaagctctacactcctatagcttctctgtgttgtaatgaaccaaacctctggtgtagaccagact
ggtcctcataatcgctcaaggtggctaacccttgcaatcttatatatccccaggtctacctaacca
ccatagagacactgagctactgtcacgctgcttgtcctggtcattcttctttgccatgttggcatg
ttgcacggtaccaccttgagcttccattttgatggaaaggggagcttgagagatatattattttcc
gtgaggaatttagttttatttatgtatatgaaatttaaaattagttattagcaagatgcagttaca
cggactttttctcctaaactatcattatacaattagaaaataaaccaatatatttatcaatcataa
gattaatattttaatatttaatatatttatcatatgactaaaattttaatattttatcaataataa
ttgcccgtgcaaagcatgagttgatggcataaataattattcaaaataaatagtatttatatatat
agtagtgggtggcaataaccaggaggggaaatttgaacgccatagttttctctcatctacacattt
ttcaatacaatgaaaaaaatacagtaacataaattggcaatcccttaaaaatgatttacagaaatt
acctcacattgtttttgaaaagaaagaatgtacagcatcggtttgggctgagggagtcgttgccat
cttgggccgcgcgcaaacagcccataccttggcccattagggttttgctccctaggtttcgtctcc
cccctatataaatgcttctcctgcgccgtcgtttcCctcttccatccttcgctcgctccgccgccg
ccgccgccgcctcctcctcctcggcgcctctccgccgccgcctcagcc*cag*gtgagcctccctctc
cctctctcatctcgccgcgacatctctctctccgccgccttctcaccgatgcttctctcggtat
ggctctcttctgactcgcgattccgttgttgttcttggtggttcgcag*gt*

Figure 130 (SEQ ID NO: 130) Os10g08550 attaaattcaagaaagccattaagatgataagttgttggattgaaatatgcctatcaaaaataaat
ttttcagatttggaaatataactatcaaaagtagaaaagtagatggagggagtattaaataatttc
tatttctccccacatggccacatgtttccatgttatcatcaatttacaactactggacccactttg
atatgaagtataaccgttcaatttgtgacggacatgtggatcgcactaatatgtagatgctacgtg
gcaccccacgttagtttacggaaacccatttgaacttgcataacacccaaaacatgtttaggcact
aaaaatatttttgagagttcaggacctagatatcacacccgcttaagtttatgtactgttcattta
cttcactctttaaaacattccatggtttgttattagacatcttttctagtcttatttgttctaaca
ggagttggatgtacctttacataccattcgaacctatgttatattgattcatttgtcaacaaacgc
aacaactctcccttcggtctattcacaaatcatgctgagaccaactcaacaaaccctcttcattt
tgaaactaaatctcatcgataaaggtgtggagtcacttcggtgttaggcgcatgcataggtggaga
ttgcaatgatgctatttactcatgcgctaataaacgaacacactgattagttgttgatcgtctaaa
aaatatgtggccatgaccaaacacatgaataaaaaaactattcacattcaccctctgtcccaaaat
ataagagcttttgagtatacgtggaatcattaatatttcttatcaaaattttcagatgacaaggga
acattccttttgatttgatgattaaaattgtttccctaataatgcttaaatctttttgtcaacgaa
tcaggatcctctatagtcaatgcaccgtgcttttatcactaacatataagtctaatgtgttgttgg
ctccatgtgataaaagcgcggtgaaatataccgttgagtatttcaaattctcaatcccttgtcaac
tgcccaatgcgccagggcttcattcggccttcgcgtccatcgcttccatctggctggacccaccgt
actaatggcacgacccccctcagccgcctagaagcaagaaaaaaaaaacgagaccagccaggaaacc
ggtgctctcctctctctcccaacttttcaaaatccgacggctggcgaagacctccttccatcggcg
ggccgcgacgcgagggcggcgccgatttccatcacgcccacaagtttccgcatcgagaacatcgac
aaccccacctccacgtgggaccacaccccaatcccaccccaaaccgggcccactgtcagcgacact
gcacgtcgaccctcctcgtgaccgtaactattagggctgcttccaactcaccaccctccattataa
atgggcggtctGccctaattgtctcgcatccatcgaaaccccactttattagcaccaaccccgtct
ccttcctccattcctccgctgctagaaccttctagaagctctcctcctcctcccttggcggcgacg
atcgtgtccgtcaaggcgcgccagatcttcgacagcaggggcaaccccaccgtcgaggtacgtacc
gccgccgagacgagctttctctctccctcccgctgccgatctgatctcttcctcctctcgcggcct
ccctgcttcgatctggccagatgggccgttccggtgtggtgattccgtcgatctcgcggggtgggg
ggcgctgaggccgtcgcgatgaccgtggattcgtttttttccggcgaggttgtttggggggtttaggc
gatttgcggggttgtttgcggaatttggtgcagggtttaaccccttttcgcgaggggttttgtgga
gggtaggtgggatctggagacagtgaacgactgttgtgttggatttaaagcgagggttaaggtatc
gcctagatttaatgcgaatattgatttatcgcctagatcaattagatgctgcgccgtgcacgaatt
cccccacctgtcatacatttttctacggatttgaaggatgcatggtacagatctgtgggtcctgca
cttgctcgtggcttcattattgtcgaagcattgttgaccgtgggtgtggtaattgtgatgtgggtc
gatagttctaaatccaactcttaccatgtatacagtaaatgtttcattttgttttcatgctgttgc
gacaaaatgttatttggttgctagtataatttatgatacatatgtgcatcaggtcg Figure 131 (SEQ ID NO: 131) Os04g32710, +intron ttgggtcatttgtcttcaatttttttatcaatttaatgttttatttttttgggtcatttgtcttc
aatttttttgtgttttatttttgggtttttgggtcatttgtcttcaatttttttatcaattta
atgttttatttctgggtcatttgtcttcaatttttttgtgttttatttttgggtcatttgtct
tcaatttttttatcaatttaatttttgggtcatttgattctcttcggaaagaaaccaacattct
ggactaaatcaacattctggataaaatccttgggaagtaatagtcactactagaaaaattatttgt
cacttcgtagaagttctgaattaaagtgagatctctttaaaagaaaccaacgttctggataaaatc
cttgggaagtaataggtactcccagataccaacattcaacagcacagcaattcgcccttgtatcat
ccgaaacgcacccttacatatattcatcattaagaagtccaaaatttaaatttgaaaaaaaaaacc
agaccatattcgctccactttatgttctatattccttgtgcaaatacaacagagatggcagaagat
gaacaaaaaagaaaaaatcagagacggcccaacaataaacagcccatcccttttgggcctccact
atccagacccacggcccagcagtagaagcccccacgggagatctcgtcgcgtcccatccatccgac
ggcgcagaccacctcacgcctcccctataaataccacgcctccaaccctaaAccctctctcactct
cttcctccgccgccgccctcctctccgggaagaagagaccagagcgagcgcgcgcgccgccggagc
aaacccctcctcctacccttcagccaggtacgctcgccgcggtccccacccgtctcttcgccggat
ttcgctggatcgatgatcggtgtggttttcaaccgtttgtttttttttgcgtttgcaggt

Figure 132 (SEQ ID NO: 132) Os04g30730, +intron atttttcctgtaaaataccattgactattatgtaggagtatgtattattgtttgtcattagcaatc
ttaagttatgcatagacaatcttgaaagctcttctacggcgtggattcaaagtgagccaaaatgcg
tcacaaaaataagaacaagggttaaaacattaaaaaaataatcctgctatatgcaatgatttagag
aggcaatgcacaatgatttagttctccttcaggctttagtcactttatacaaaaacacaaaaaaga
ccaaaaaggaaaaaagaaaaccaaaactattttatatataaaaggcccactacaagtaattaccca
ctaggcccataaaggaccactacaagtcattacccattaggcccatcaaggcccatctaaaatttc
tagggtttcctcatcctcgatggggtttatccTtcgagcacatatataatccgcacgccgccgcct
ccctctctgcttcgcactccatttccctctccccgctcgccgccgccgccgccgccagccaagct
cgccgctcgccaggtaagcctcccccctcctctccctctctccggttcatctcgattagttttagct
ctcaatcccttccggatctgaccgtttcttggacaaatgtcaggt

Figure 133 (SEQ ID NO: 133) Os02g30050, +intron taaaatacaatcgtaaccgactaggatcttgggtattaccttgacatacaagtttagaatttaacc
caagtcattttaaagatattctatctatatatagcactccatacccagtcaaactatacatgccgt
gtatgtatggggtatccatgatctccacaattcatttgtcaagtaagtacttcaatagtacaattc
tgatagtgcgagcatagtcgtgaaatacgacattcacaaaaccgatgataactgctcgaaaaccac
aggtatcatcagctttattgctccggctcaagctaaaagttcactaaaatccggtcaagtatataa
aaactcaagctaaaacttaaattttgcattaaactgtcatctccgagctgttaacatcaaaaccga
caaatccaaatcctcgaatccttatgggaagcccatttcaactcaccttaaacagtcaatgggccc
agccatctatcataaagcccaacaaggcccatgaaagcccatctcaactcagcctagggtttttt
ccactccgcggcgtctcgctgtctctctctcctctatatataagcctccgccgccgcctcctcacc
tcTtccccttcctagcaccgccgccgccgccgccgccgccgccgcccgccgcgccgcctccgtcgc
caggtaagctacaacattccgttcttctctcctcccgctcgcctgcggatctaaccgtgcgtgtgt
ggtgcaggt

Figure 134 (SEQ ID NO: 134) Os05g11780, +intron atttatagtctcatgctaaattaaattgttgaccgaaatatgaacaactatcttagtcctcattgg
ttacatgcatagtataattcattagtttctggtgggttttgtttttataatttttagaagtctcgt
caaacactatcactatagtccgctacggtccatccgctgccttatctatttattgtcattgtgatt
ttaaaaattgaacataattatcgtttgagtttattatttactctctataagtctagtaaaatcat
tagcggcttcgtcattatactcctctacagcttgcccgctgcttccgctctttattgcttttgaga
ttgtaaaagtccaacattattatcattggggtttatttttttactttccagaagttccactaatcg
tcgtgactggtgctgcttaatggcatgctcgttgttcctcctcttaatcatcatagggattcaatt
tgggactctgtttatagttttagatgttccatcaatcaccactaccctgcttcattaccttctcc
catcttttattgccatttgtcattactgttctagatgtttttttttgaaaatttcatattttca
ttcctatattttttatttatataaattgtattcctacataaactcttataattattcttctatttt
ctaaatttattttatttattatttcgaattttattgatcgtgttttagatggtcatttctttcaat
agtttttatttttaattataaatttagctatttataaattgtattcctagttgaactcttattt
atttaaattttggaattcattttatttttatttcaaattttaatttaacaataactgaaattca
caattaaaaataagcaatattttaatcccaaattttaatttccgagtcgtaactgcggcggcaacg
acactccgacggcgacggcagcaaatccccccctcccccgccgccgtccggtgacgtggccttcctc
ctcttcccaccgcagcctcaagttgggggcgtggcccacgcactgggccccacacccgcccaccat
agctggtgcccacactccaacctcccaattcctccatgaacgtagcccaccatacaccacccctct
cacaagttcacaacacctcacccacgggcccacctgtcagtcactcaaccatccccacccatccgt
agagcgggtccacccgcccagtccaccatcgtcgtcacccacgaggagacgccgcagcacgggaac
actctttttttcttcaatttcacaggaaataacattttttGtaatttcttttataattttttttatt
gcgcgtcggcgttaataaagcgcaacggcaggcagcgatctaggcgcccgtcgtccactcctcctc
gccttcctcgccttcctcgcttttatcgccgccgccgccgccgcctccgccgccgccgaggag
taggagtagtaggaggaggaagccggtagccggaggaggagcggggagcaggtactggacgctgtg
cttcctcctcctccctagggtctgaggttggcgacgggatcggggttttggggtgggtcgggttgc
ttgctcggggtggagggcttggatccgttgtaatggagggggatctggtgggtagctgcgtaggag
tgggttggatctgatgatgcgtgggttcgagtggtgcagtggagctcgcttataggggtggctggg
tgtggatcgctttagatctgttgcaatttgtcgatggcgtccgcgcggatgcttgggaactcattt
ccgttagctaattattgtctcggatggagttcggtcgccacgatctattagatccgtggagtttgg
gttttacgtgatgcggattgtagtagagccgggccagtttggtgttgctcgctgttctctgtgctt
tcttgaggtatttcatatcgccatcttaggtaaatttgtcagtggattgtgtagtaaattgcctaa
ttggtcgatcctgagatgatccattaacatttaatctgtgaaaattgtagcagtagcagatttagt
gtatggctctacatttgtgcagcggcatgcaaacgtgctaatttttttagtctggtgggcggagaag
atgcattccttgctattccttttcgtgatctgttatcgattagtagcacaaaatggggaaaaaaat
gtcagcaagatctgttggaacatgggaattggctagtagccatcactatcaatgtgctgatggctt
ggtttatggttggtacctactttatttagcacgtgagcttcctgtacataattcttccttttattt
tgatttcaggt

Figure 135 (SEQ ID NO: 135) Os03g14450, +intron tgttccaaattcagagcagcttcatatctgtatgagcattattcaggaatgcagactgccatagcc
catagactaccgacaggtaaaacaaaatactgctccgtgatgttattaagcaactagacacctgaa
atctgaattcgatgatacacatttgaacatctccaagcacgaggagatatcgatccgtccaagtac
caacagtgcagtgtgcaccatatgcaggttggatatgcatattttgacaactatagacttggaaaa
cccgtttcagtggaacctgtgaaaaaacggtgcagatccttatgctttttttgaatccacaagtgtg
ctcaagctaagagatggaagcgtctctatgctcgactgagcggccatgtttttctccgtttcagaa
ggattggaattcggaggaggttgcaaagaaacagccaagcaaatggcaggagtccaggagatatca
gtagcagatcctcgggttttctcactcgatgcagtgacatgtgtgtgcttcccatctgtgtactcc
aatcttaccaagatcagataaatattcgacgtgattcaaatttcgaagtaccaaaagaaaaaactt
aacttgcaacatcacgtatagtgaccccagattggcattcatcgacacgaacgaacagtaatacag
cccaagatgtgaagctgcggccctgctgcggcggttccccgtgggctggactaccagctgcaagga
gataggaataagttcagatatcatccctcaactttacgtcgagtttgtatgacatccctaatcttc
aataccagaaatcttcacccataaactatacaaaaccgtgtggttctcacagcagtatgattaggg
atgaagatttgaagagtgaagatttctggtattagggattagggatgtcatactgattcagcataa
agttgagcgatgaaaggtgaacttattcccaaggagatacgcatgcaacgacgccAccacaaacgg
gccaccacaccaacggcccggcaattgcggcgttgcagtccccgcggcgcgggcgaatttgctctc
cgcaggacggcgttgccacttcttcggttatcgggtgggccctcacttcctccgccgaaagccacg
cacacgctgcccataaaaaggcgacgctgttctcaaaacctcagaaaattcctatatcctctgttc
gtcactgccttcctctccaagtccatccccttccccgatctaagatccatccgatccaggccaggt
acgccgcgggtccagtttcgttctgtctagggcgtcgcggcgattgaatcgggtgctttcttagcg
cgatgccgcgatcttggtctgttggttagagcggttcggattggagtttccgcgatcttggtctgt
tggttagagcggttcggattggagttcccgtagtagggtttgtttaatcactgtgtgcgatgtggc
taaccggcttagagtcctgaattgtgtggtttgtgaattgtaaatgttgatgccccctgctccgat
ttggccatgcgaagggtggattgggctctgatcggtttatttctgtcggctcagtcggctttggct
ttgagttatgctcgatccctactcgatccaatctactgctgtgtacctagagattagttgcacgtc
gaactgcgctttgattttggaatttgcgctatatctgcaacagatggttgctttgaacatattgcc
actgttagatatcgtgttgcttggtgcttttgttccaggatttcatgatatgagcatacagttgtt
acagaattcgtttgttttattggactaaatcaatagttttgaatggttttggcaactaaatggtct
tactaaaatatgatgcttgtgttgccaggt

Figure 136 (SEQ ID NO: 136) Os01g17190, +intron gctagagcatgtctttgcactgctcgttttaagttgctatgtagcttgtgcatggaccctacttga
gaccacatacattatggagtatatgtctgttcgatcagtgtattggccctacatcttgttgaggtc
tagctaaagcatatcttgcattgttcttgccctaagttgctctagacaatgtgtacatggacttgt
tgacctcgtctgatgcacatgacacatgctaattttgtttttaattactaaagcccatataggag
aaatgacgtcacccccctagcccaatagttagagcaaatcgtgtgctatcagactgcagaatgaaaa
agcccatcaagtagcctagaatggccagacacgcactaaagaacaaaagatgcctgctcgatcgag
ttctcttcttcttcgtctaggcaagaagatgaaggcaaggagtctccttttctttcctacaccact
gaccagcaagctctcaatttgcaaagagaacacaccactttaagtgacaacgtgatcaatctcagc
gaaggatcctatagaccccctagcaccctcctcccaccttggccacccagtttacactatattttat
gtcgacgacaacatctagctatttcttatgcagagaaacaagtttcaagcattcaaattgaatgta
gtttcaatttatttataatagctatctttatctcagtttcttaattagggatttcatttaatcagt
tttcccccaaaacatagggtttctaatttgacaattcatttgaaagcaattgataaacaaatggta
gagtttggaggatgaatgcttgaagcttgataaacatgtactaccaaacttttgctaaggcaacat
ttagctctacaataacaaaccctacaaatcactattaaatataaattgcttgatatgtcaagtact
agatagttttattgtgatatactattatgtttgggacaccagatcattttcgttttggatttacta
tgattgtttaggatcctacttgagaccacatacacataatacatagtatttgagacctagctagtg
catgtactctgtccattcccattccaaaatagaggccgcttttggattaaaaagttttcaaaaaaa
aaggagtttagaagtaccttttatcacatcaattcaaaattttctctatcctaccccttaaatata
ggtattacagtaatttttttaagcattattttttctatataacttggatcgataactatagaatag
aaggtagtaccgaaccgttcctcctacaggcaattccctcaacctaaaccattggaagaacgtgcc
aagttggaagcctaacctagcactagtcttagaaaaaacagtagaaatcgtgagttatctctgcaa
taaaaaaGgaggtaagcctacccacactgcaagtctccaactcgggcaagctctcctcccccacga
ctcccctctccttcctctctctctcgctcgcgcgcgcctgcgtcgccag<u>gtaacccctgcctcacc</u>
<u>tccctccctccctctcgtaattttgttgcgggaaccagatcgataggctgtccgaagcgagatcgg</u>
<u>cgatctttttcttgggggttaattaaatcgaacgccctgatccgtcgtctccgtgtcccgattctt</u>
<u>ggtttgctgtagggatccggttgggatgcgtttagctgctctgaaatctccggatcttttgataat</u>
<u>ataggcgttgctcgtcggtttgggagtagatgctggtcggtcaatcgcgtgatccagcgtaatttt</u>
<u>ctggccttttttgagatttggggcactggctagtgcctgttcgtaatgattcgtgcttgattaggtt</u>
<u>tagatgggataattctcacgagtcctcgttttcattcccattgcaatagtgtagtaatttgggtta</u>
<u>gtcatctcgtatgataatacgacgacactgtcctggtgtttttcttggattttctacagaagatct</u>
<u>gtggtggtagaggataagaagtttacaattagcactaacatgagctactactgttttcgataatct</u>
<u>ttacatatatgatcagggagtaataattaagcaatttagataacacttcgattctgttcatttca</u>
<u>agtagtgctcagcttttggtcttgtttctctttcttttatcagtttgtaaacagcgacaagccttg</u>
<u>atgatctaaagcagtactgtgaatactatgtagtgatacactgacacctcgagttgaacgatttttt</u>
<u>agactttgagtgacatagataaagttattttcttccag</u>gt

Figure 137 (SEQ ID NO: 137) Os10g17280, +intron gccggaaccacgctggcagaccagcaggggtcggtgcccgaagcaatagatatgaaattacatttg
cttagcttagataattaaaacccatagaaagtcctctctagcctagcctgcctaccatctgttgtt
gttcttggatagtcttagccttatgtagattacacacgttctctgagtttgatatccttttggagt
cacccgaaggtgaagtgctacagcggtattccgtgcgcttgcggatttatcagtggtcgtaagaaa
taccaacacgggccggccaaacaagggaacggcatgggaaaggagttgggccgacggcccaagaaa
gaaaaagaagaaaaggaaaaagaggaaaaagaaaaagggattcatgtgatttatatattgcataga
attgattttaatcggttaaaattatttccgaggcgctgaaaatttcgctaaaaatcctgttaatgt
attgtgacatgtggaacttaagaaaaattccacgataccaattgcatttattagttaaggttcatc
tctaggttaaattaaacaatttcttcagataatttattaaataaattttaaagctagaaaggggaa
ctttaggggcatgatacatgaccataggatatagggtatgcattatcccctgacagaaaactctat
tcatcccttaaggaatatacccttatttttgcatgtcacttaaaagttatcaaaaagaatttgaa
acaaattagtaagatagatcattatgtgatatgtcactccacaaacatgcacgttcaaattcaact
tatacaagtagaaacaaaaataaaaaattttgactattcaatatgaataaaatgtgtaatttgcga
tcaaaattgttagaattgtataagtcgaaattcaacttgcatgttcgtggaaaaatatatcatatg
ttgatctatatatttttatttttttatgactttttttatgattactgcaattgttttaaaattgaga
aagtaccaaaataacaaataatgatacagaaggtggtaatcagggaaataaactagtaaaacattg
ataagtgtgaaataaaataatacaaaagttgatatgaagaataaactagtagtacatattgtggta
gttgggaaataaattaataatgtgtctaaatcacaaaatttatatattgtgacaaatttgaaagat
aaaatcatctatcctgagacagactgacggagggatcggagtaccccgtaacaaataaagaagaag
aagaaaataataacaataatagtaatagtaaaagaagaaaaaggcctatttcacttcttggaggcc
cattagcaacaagcggcccattcccaagctggcatgaggcatcttagggcttgtgccggtgtgccc
tcacctGctgccctcccaccccaccactctccctcctctctctttcctcccaacctcttgcggcca
cacgagccaagcagcgagacccccggatcgaaacgcacaccggcggcgcaggtaagatcccctttc
ccttttcccgctccgcctccccccctctctctctccgccagatccgcctccggttcgattcgtcc
gtctccgctggatctggctgcggatctggtgttcccgtgggcgagtttattgggcgaccagtggat
tcattaccctcggatttgaggcgcatctagggcgaattggagttggtgcttgcggctgcgaaatgt
atgtgtgggtgtgttatgggttgtggtggtgattgcgtagacgaaggatttgtagtctccttttct
tttcccacctttagtggacgagattggaatccgtatgaactttggctgcatccccttatggattat
gaaatggatgtgaatgctggaaaagggttctgatgcactgctacaagggagaaaaaaaatccatat
gtagttgtaactttaatctcacatgctgttgactggttcggcatgttgtttggtttgtgattgtcc
acacggattgcaaccgctcataaagtatgacttgtatagaaaccactcatgtttctggtgggtttt
actctcattgtcttgcattgaatgattagtacgaaatgtgcagtgtcatagatgtcatttcttgtt
tgttaaaattgtagcctcgtatagctggttacttttgttgcaaacaatatgacattatattgttaa
ttgcacattttttatcgtgcatgtaagtatttacaccaaattccttggaattatctctctgcatgat
ccatgcttttgttatacatgactgctcgatttctctttaaattattcgcttcttgcttccactatg
tattactttctaactgaatatactgcgtatttaaaaaccaggt

Figure 138 (SEQ ID NO: 138) Os11g06890, +intron tacttgatatgttgattttgagatgtttggtagcactctaaatccataatatgctatattagaaat
ttatggcttcctcaatacaaagattggatgacaaaatatctccaccaccgtcaaatcttaggagta
caatctgcattcatgtcgagaagagtcagatagatagttcacactcaacctgaatggagttatcaa
catggttaatgccagggtgaattataaaaaacttcgcaaaaccccacgttgccttaatcttgaaat
ggcttaaatgatgactaacaaactattgtcttattatagttaggcggaagacaataggggagattg
aggaggagatgacctacaagtggctttgcactgtattgtttttttcggctcccccatggccccaag
acattatccatgagacaaccgaacaaacaagaagcatcaataccggtagcagaagcacacaccgtc
gctcaccctgctaactgctttgtactagccgaccgccactagctgttgctaccgtatccttcatct
agaccacccacgaattaactgaaaccaccgtcgtgtatgtcccataaaatggtctacttaggatta
tatacaagtacacatgttgatcatgaacatgaaattttgaatacaacaatggtatttgatcaaatt
tggataactttacattcatacacaagatataaaataatattgctataatatgttactcataagcat
gaagataataatactagcactacaaaatgtcacttgatgaaaccacaattgatgttaacacataaa
tttcttcccttccaatctgaatgccctagattaacatggagaaaattttatctgcagataacact
aaaccggatccaaaatttcccataccaaggctgtgtttagttcatgtgtcaattttttttaagtat
acggacacacatttaagctattaaatgtatactaataacaaaaaaaattggtcacgcgatttacat
gcaaactgtgcaatttaatatacattattagtatattatcaaatcatggcgtaattaggctcaaaa
gattcgtcacgtgatttacatgcaaactgtgcaattgatttttttttcgtccacatttaatactct
atgtatgtgtccaaacatttgatgtgacagaaaagttggaagttcgaagaaaaatatttgaatcta
aacgaggcctgaatggaaataatcaaaaccgcaatgggctggcaaactgtcgatttcagataattt
ttttagtacggacaaactgcagggacctaaacgaaaaagaaagaaaaccgtgacgtcgctcgcttc
cagagatctTcagatcagatcagaaatccccaaaaaaaaaaaacacaacaaaaccaaacccgacag
atcttctcttcttcctcctccctttcccatcttcgacgaggcgacccggcgcgagagaagaagaga
tcgatcgatcgatcaaccgatctcgccggagaaggaagaggagcaaagcaggtaatctccgccatc
cctcttcctcttcccccgatcaagcgattaggtgtagaaagctccagtttttccaatcaaagtcgc
catctttttctttcccccatctggttgatcctgcgatttggttcgatggtgatggaggtccacgcc
cctccgattcgcgcgatctgtgacgccctgagtgtgaatttcttcttcgcgtggctagatttgac
ccgattggagatcggatttgtggggaaaaaaagttgggagctttggattctgttcttgatgggggg
atttgcttatttgctttcattcgatctgttgcaggt

Figure 139 (SEQ ID NO: 139) Os01g16890, +intron tttggacacatgcatggagtattaaatgtggacgaaaaaaacaaattacacagtttgcgtgtaaat
tgcgagatgaatcttttaagcctaattgcgccatgatttgacaatgtggtgctacattaaacactt
gctaatgacggattaattaggcttaataaattcgtctcgcagtttacaggcagattatgtaatttg
ttttgttattagactacgtttaatacttcaaatgtgtgtccgtatatctgatgtgacacgccaaaa
ctttacacccctagatctaaacatcgcctttggcttcaaaccaaaatggcccaatcattttgatta
aaaaaaacttgatatgcagtaatctatatttttagaaattcctcaatgggccttgagaaaataagg
cataaacactacaaggttagttccaactacttaactttctataatcttccattccttgtcagcttg
cttcctatcgaggattgtactaatgaataagaagaccatgaatgaaaggatgccacacccttatat
cctgtgtctttaatttttaagaattataccatccttcttagactacttcggtagtaggaggggtt
gcataatagatatatcaaaggataagatcccaactggtttgctatgggtcacagacattttttttt
ggatttctgttttaaaaataattttaggagaaattattacttattttcttatcaatcatgaaaagg
gagtcaaacagcgaaaaggttactaagaaaaccacaaacattaatcataacatcatatgaatcaag
catgctctagccaaattttactatacatcagtcaatgttggttcgttcgtttcttaatcatccagc
atttgataaactttggcacatttcttaagcacatgcgtgtggcaagacagaattgttcacaggaag
aaaaaaaaacccacatctcgttaaccatatttttttactgtttaaacatttttatttttattattt
ttttaaacgaactattccaaaacttattttcaaaacgcgtttggcgtggcaaaacaacagttcacg
tcactccgcagcgggcatgacaattttgtcctgccacgccagcaagacaacgttatcacgctagcc
agactgacatggcaatattatttttgccatgccaacctgcattacatggacaaaggttcatatcat
ggaaataaaatttagaagaatttatttttaaaactaaaaattaaaatgctcaaaaaataaaaaata
tattcttaactaacctggtgaaacaaaagaagcccaacagtcaggccttatccaggaaagcggagc
ccaagcccaacaaacccatttacccccagcgtgggcaggcgaaccctttccctcccgtgcctatat
aaggccacaaaccctaacgccccccActcttccacctcgcagtcgccaccccgagcagaagccgccg
ccgccgcccgaaaccctcgccgccgtcgcttctcctcggggcgcagccaggtaacgttgtcctcct
cccggtctctccctccatcacctcggtccgccgcgcaagcgagcgagcgagcgagatcctgcattt
ctcatggcgctaacgcctctctgttcgtcgtggtgatggtgtgatggtggttgtgtttgcaggt

Figure 140 (SEQ ID NO: 140) Os03g58430, +intron cggcgcaagtggttgcgttggtaggcttctcggcactgaggagtggacagagcagtgcccagatta
ggttgcaagggtacatggacgataacaaggttgtctcgacatagcaacatgctcatcagtgttggc
cctagggttcccttaccgtttttggcgtggttattggacccccacggcaaggtggttatcgcgaaa
ccgcgcggtaaccccgagagataccgtggttttaaaaactgaaaaggttaccgtgcatggtaatcg
cgcggttttgtgtggctccctgatagtggtgagcctagggacaatgactaccaatgggggttctac
acctagatttgactgagtgatgatgggacagtattgtctttacggcgtgttggtgtggacaatgat
ggtggtggtacaggtgatggccctaggagcagtggctactagtggaaacttttcatccatatctga
ctgtgtgacggtgagggtgatgactattgtggcggtgcttttcggcatggtagtggcaatgaccct
aggggcagtggctgctaaatcgtcggtttataggcctaaatcgaaccatgtggattgggaggtggc
tctagctagtacgacaatgacaagcttggtggctgtgctagtggcaactggagaggaaggatccaa
cctaaagtcagacccgacgctcttttaatgagcaagacgaggagcggacatagggcttgttggagg
tgctggcaacggttaggaagcgatgctgaatttgagacctaaacagggtttacaaaaccgcgcagt
tatcgcggttaccatgcacggtaatcttttcaatttttaaaaccacggtttatctcgtggttacca
cgccaaaaatggtaagaggaacctagcatccatttccacgccattcacatccatgccagatttgga
acgatggtctacacatgaattctacctggactgcactgtttcatataaaaatccacttatccataa
tatactattttgcatacataccatagtcaagagattgaatctgctggtattgtgaaaccagggtcg
caactttcttttctgcaagtaaccggattggatgttaatccatccatttacacagtattttaaagt
acggaatctagctgacgcaaccgtccagtgcacaaagcaaaccatgcaattcgtcttctttttca
aatagaaaagcaaaatgtcaacacaacgccgctgaccacgagcggcagcgttcactctgggcccga
gtctgcaggcttgcagcggaaggcctcgttacagcgtcgaaatggccaggccaggccgggccgga
acacgtgggcctagcccactcaaacagcccttgacgcgcaccaccaaccactatataagcttccga
gagctcttcccccaaaccCtaaccgccgccgccgccgtctcctcctcctcatccaagcagctcgcg
cctccgacccctcgcctcgagctccagctctccccaacccttcaacaggtgagtcgccgcctctc
ccgcaaccctagccgcgtgtcggcgcgttcgctcgtgatgcctgacgccgcgcgtggtggtgtttt
ttttttttttgggtggtggtggtaggt

Figure 141 (SEQ ID NO: 141) Os06g37440 gtgcttggtgttaggcaagacataggcgggcctagggtagctagagcttgaacccttggcttgcct
acaaaatcatgttaaaattcttcagaatcaccatgtaattttattgaaaatgaacagcttattag
ttacagtctttgataatttctgactccgccaatggtgttaggtagttggtgaatttgcttttagcg
tcttctataaccatacctcggatgaaaactaacaagaattagagaatgaagaggggtgagaagata
tgcagctttttttaatctcatttttcagtcctgaattatctttaaaatatttgaactttgctaaag
ttatgacatgaggtatgtgatctcctatgaaaaatcacatagagtgttgttgatgaggtgcaataa
atgaggaggaaaaaaaccatatcctatagatagattgaaattgtagggaaaattgtgataatgttg
gataatatgtttgcaaaatttatgccattactagatgatgccccgcgctttgctgcgggatatata
ttagatattggagaaataatgaaataatttggattgaaatatcatggaaatgatttaagaatgatg
atttagcatgtgtatgtttagtttaaaatgaaataaattgtaggcttaattactatatacttgcat
gttgagttttgtgtgtttaatgggttgatgtggcatgcttacatataggttttaggagtgctaata
aatactatacttgcatgttaagctttaggtatttagtgaatatattagatttatagaaagaagaca
attagcttccactcgtagaacaatatggtcaagtttagttccgaactaacacacaaacttccaact
tttccatcacatcaaaactttattacacacataaactttcaactttaccgtcacattattccaatt
tcaactaaacttccaattttggtgtgaactaaacacaccctatataccagagactgcaaaatttaa
ttctgaatttacacatagaggctgcaaaggactcattctgaattccgggacaaccgcaggatccca
acgccaagaaaaccaccaccccatcatccgagcaatctcggccgtccaatctccccacccccacca
tccggacggccgccgccacacccgcaaccctagatagcagcgtgcgcccttccttctccttcAtcc
tcctcctcctcgcgccgccataaatcctcgtctcccgtaccaactaaacccccttctctctccgct
ggggttctcgccgccgccgccgccgccgacgatctcgtctcgcaccgcctctctctcggtgtaaga
gctcgccccgactcatctcgtcgtgggaagttcgcgtggttgcggcttctccgcccgcgcttggtc
tcgctgtgtttttttttttgttcggtggatttaattttgttttgctttttttttttctctggtgtt
gcagatctgagatttggatcgggcgcgaggccggcggctccagtcggc Figure 142 (SEQ ID NO: 142) Os10g30580, +intron aaaaaaaaaaaaaacatcgctgcatggccacacgcattcctaacattgcgcattgatcaaggaggt
ttaatctaaaaggaaggatttttttttggctcggtaccatttgcaaatatgatgattaaattggaa
tggggtgagtatatatttgtcaaggtcttttagctatattgatagtgttctgcacttttttttttt
aatggaaacacagatgagtgtatatacctcacgtcagtaaattagaaagaagaatctgttctataa
ttctattccatgtcaagctaaggaaaaagagaaggaaaaaccgaaaaagaaagataactaatcaac
ttttcttaatgggccagcccaaaaggtgcacacctcagtccttgtttcactatttgtgagtcatga
tccatgtttttgggggaaaaggaacaatgtccatgtaacaatgactgtgacgggaatatacaatgg
caaagaattcaaagttcgcccagactaaagtgaaacaaagaaaaacatagtttatgtaggaaaaga
aaaaaggattggagtagacaagatcgtaaaattctgatctccaaattttgtttctgtgtttattac
tttattaggcagatagttcctgccgcttgatcatgggctgcgttctaaggagccgattcagttcag
cctctcttattttcctttagcgcatttgttttaaattattaaatgatgatatatttcgtatgaatt
ttttatatagtatatgttttctaaataaataaaaaaaatctattttttaaatttttaataattaat
actcaattaatgatatgtttcctcgttaattagctataaatcaatcaatcatttgagtagaacgca
gatcgatgggttgacacatgttctcacttttatactagaccaatcctaaaaggaacagctaatatt
tttcatggaattcttgctccctttccctgtcgaaatttctggattcagttcctgtgtttgagtttg
atgctgattttactcgattttactttcggtgttttgagtttgcgactgatttttattcaatttcgc
atcacaattcatacacccctgctctccttcgggtacaagttcgggaccggataccaaaccccctct
cgcaatccgtccccaaccacacccatccaccctcggggcccacctccctctcgcttccatgtgggt
cccaagccggctactctgacctccggaagagcccggaacgttccatgccaggtgggccccacctcc
cccgtggccccactcctcagtgacccccaccgccgtacccgaacccgatagcgagagagagagaga
gagaaaaaaaaacaaaccaaaccaaacccccccgctGcaagaaagaggcttataaaagaacacttta
atccccctcctctcgcctctctctcttctcccaaatctcatcgccttctccgccgcgacgcggacg
cgctcgaattaacgccgccgccgccaaccaccgcccgccgccaccgcgcaggtaagttccgccccc
cgatctggcctgctagggtttcgtttctttccccgatctgggtattggggggtgcttagggtttg
atggttttggtgggtgcaggt

Figure 143 (SEQ ID NO: 143) Os02g27769, +intron atggttgttcaattaagcaacaacatgaatgtatgatttatatatttgtatacactagcatattgc
ctgtgcgttgcaacgaaattttaattgatgaaaatgatcattaacctttgctattatcattatttt
attatcatctcttaaattctacatatatttgtaactaaaccctatcacctcacaatataattctta
cttcccacaaaaaatagaggtggtggggtggttgacatgtgggaccttatcttttcttcactctaa
aagggtaaggactaaggaggtggtggtggggcgcgatcgctaatcggtgcgcgcgccggcggcgcg
cgtttcaggcccatagggcccagcaccggcgcgcgcgcctccttcgacgctttttttttcgtttttc
tttagcgatttttttttcgttttcttttccactttttttctgattatttttttttaatctttagcatgt
tttgagtttgaaagtttttaaattttgagttgaaaatttttaaatctgaatttgaaagttttcaaa
tctcgagttgaaagttttcaaatatggacttgaaagttttcaaatctcgagttggaagttttctaa
tttttcaaatctggacttgaaagttttcgaatctcgagttgaaagttttcgtatctcgagttgaaa
gtttttaaaatttgactttaaagtttaaaattaaaatcgaaaattttcaaatctaacttaaaaaat
tttcaatctgttagtaaaaaaatctccaaaatctttcttaattactatcattagtgttaagtatat
attaactaatggagatagttaagtatattaactaatagtgttaatagagtaggttaataagggagg
agtgctcgctagctagtagaagcgcgtcgcgtgtcgcatgggccgggccaaccgcgggggagggg
gtgggggcaacagccgcgcgctagttaatttgctcgcgcgagctaggaccctccgtggtggggtgg
cagattcaccacctaccaccaccactactcctttttcaaagaagtataggtttaaatctccaaaaga
tacataatattataaaatacctatatatatttgcgttatatttccatataatactgattaatctta
tgcatttcgattaatctgtaaacgatactcttttcattctacaaccgtattccctcttgtacggca
ctgatgtaaagttagatgatcctttttttacctttatacagtatgttcagtccaaagtgaaagtgtt
cagctgcccgaaggcccagcccacgggaaaaaagaacactgcccaaaggcccagataactagacat
cccgatcagacggcccagattcaccagatccagctataaaaatccggaccacgcccaccacccAaa
accctccggctcattcttgcccacgccgcgccgccgcctcctcctcctcctcctcctcctcctcct
agggcttcttcttcttcccctcctccgagcgccgccgccgccgacgagcaggtacgatccgttcct
taccttcaccgcctcatgaccctcaccctcaagccgatacgattcgagtgctctctctcccctcgc
gccagcgcctctgatctgactaatttttctcttttcgtttggatgtgcgacgcggtgcgcaggt

Figure 144 (SEQ ID NO: 144) Os07g08660, +intron ctgaccgaatacggctccgtcggctttgtatcggccaccccgagcaacaccatcccggccaccaga
gggccggtctgactgcgcatgtgccgccggtcaaaccggccttatgcaccggtcagaccaccgtct
tgtggccggtcagactggccaaggcacgccggtcagaccgccactatgtggccggtctgaccgccc
ctggtcaggccgaacacagtgaaactgtgtgtgataagtgtgtgtggtgaaaagtgagcacaagtc
taaatgcataatgacataatgtggcaattaaaatcatctcatttgctaggtcattaccccttgat
agtacggcaaaactaaaaataaactagcaaatttgatcgcccttcacctcgatcaattttaaaact
aaagcactagttttaccgttttcttttcttcgcttcgcgccatcaaattttaatccgtcgataatc
atccatgcgcacacatgacgtggacctaacttaaaatatatcttaatagcaacggttagtccacaa
ttagcgcttgtcattaattaccaaattaacaacgggggcctagatgcttcagcgtcgcagcggcg
tccgcgggctggcgcaccaccgcacggagcggctgtggatgctggccttcccgcctccggcggtgg
gggtttccgcttacatcgcactgcctcgccgttgcctaggatgacgcaggtgaagacgaccccgat
cttggcggcgaggttgacccagcgcaggaggtgggcgccgacaaggcggtggcgcacgacgtcgca
gaagtggttgcagttgcggagaatgaggttgtaagcgtcgccggggaaatcggaggtccgccatga
ccgcggatttgggtctgagaggtcatgagcgagagaggagaggatggggaaagagagaggtagaag
atgagggtatttccgtccaatacatgcaaaatatgtagcttagtggcatcactaaaattacaaaca
agcagcagtgtatggttacaaatacttaaatagtaatggcatatttctaaactggcaaatttttaa
tggcacgtatccaattaaccctttcaggaacgcttgggacgtatcggcgaggtatcttttttttat
ttaactgaaaatcgcgaaaatctgggatacgtatcgaagtgtatccaatatgtatccatatccata
cacgtatccgatactgatacgccacttttgtgctgtatccaggtaacatagattatagataatcgg
attcgttgacatacctcagatgaacttattcctagggcaaattagtcccagccgaaactccacaca
gcccaactatcattcagcccaacccatcagtacaacgagaatggccttcgcaaccacgcgcactat
ataacctacccacctcactcgccctctcccCtctaaaccctacccgccagcctccgcctccgcctc
cgcctccgccgccgccgccgagctcctcccgcgcgctccgagcccatcaggtgagttcctcgctct
cgaactttcctccgttggtgatcccccgtgcatgtctccgtcggtgaccgcgtcgttttccgcag
gt

Figure 145 (SEQ ID NO: 145) Os04g47220, +intron tcacatgtatggcacgtacaatgtgtcaaatttcaggtacagataacttactgagaaatttgtata
tacctgttatatgaactcatctatatcacatttgttaggaaaccctcataatcttagtcacctttt
tttttacaaaacctactatacaccttcccaacgtgagcgccgcaaacatcaacaccatcgctgcc
accgcctccttacccctagtgtgtcgccacacggtctcacctgctggttggaagacaccaatggca
ttggcaaggcccctcggctggtttcctccctatctccactctctgactctgccctcccctgcccta
tgttccttctcaagccggcggcaataaggtgcccctgctccaccatcttccatgtctctagtggct
atctgtcgttggatccgtcacccccgattgccgcctcctaaccagtgggtttgttttgcccctgt
cagtcatcctccgtcacacacggttatctctctaagctttgggaaacccttcctcttcctcctcc
tcctacccccctcccatcccaaaaataacctagaaccctaactgatgggggacgttgctgccttgc
tagagctagaggagaagaaagccgacacaaatcttggcatggaccctatggtctgaaattcgacga
aaatctttccaaatttctgccatatgaaggttagcgattccgtaaaaattatgaatgagcctgtac
aatttacctaaatggatggtccggatttggaacttatctacccttaaggatggtcaaaattctcat
ggttacacgaagaatgtcaaatacactcacacatctcgctaaggaaaaacagaacagccaatcaga
gcataaatttcaaacttttcttgaaaactcaagcaatttttcactgatattggacaattttttta
tcaaccataatcactagtgtcacaaacaccttgaaattcaaatacattcaaaacttttgtccaaaa
gcacatccgaccgggggacctcaagatagaaccgaaatttcaaattttcaaccgaaatttatgaac
tagatgagagtgatgcgtaaggggaccatcagggagcaaacaaccgtgaccgaattgcataggag
ttatggctgatcacttgagaaattaaccatccattcccggtttccctccaatattgcacccatcca
tcatccaccagggatgataccgttgccgttgctctaaaaaacgttaaaacagcggcaggcaacacg
acagcacatcgcatcgtacgtacgtcgttcgtcccgctctcctccgtcgtcctccctgcccaccgt
cccccacacccactccccgccgtcacgtccttccagaaccacctccacgactcttCcaatcccccg
ctataagacgcttctccactcaccactgcaaccctcacccagccagctcgagcgagcgaagccagc
agcagaagcagtagagagaaagtagagagttggaggggaaggaggaggcaggttagtataccaact
actactgcagtaaagattcagagatggaagtatttttactgttttctgagtgattgatttttgttt
taatttgcgcgatcttccacaggt

Figure 146 (SEQ ID NO: 146) Os05g07700, +intron gagctttgacttaaaagacaactaaaacacttcgatgatcgaaaccttgaattaaatatatatgtt
ctaaacagacatatattagaaggtatataatgcacattaataaataaataaaacttgaataaccca
tatatatattttaaaaaattaacatattactgtcaactgatgacttggctgtattagaaggtatg
agttgggaaccataccctgatattcaaaatgataggatgaatcagcgtataattaattaaatatta
tattaaaaaactctaaaaatgatcatatagattttaaagtaatttatctataaaatattttaaaa
cacaccgaaatgtaggcacgaaaaaacagaaatgagttggaaacatgagaacacacccgagtggac
tctgaccagcaatatccactcccataaaaaacgaaaagaaaaaaaaataatgacaggaagaggtgg
cccaattgcaatgggcttccatgggctcctcaagcccaacacgcaatcaccaccatcggtcacgcg
tgacgcaaaccccacagccccccctcccctctatataagcctctgcgccgcgctcctccGaaccta
gccgcacatccccgcctcttcccgccgccgtccgccgcgcgcacgccgccgccgccaggtaagtct
aaccatttcctgctctaccgctcgttgtcttgctgtttgttccacggttgcgctggatcggtcgcc
gcggctccctgatttcaggcgcgttttgggcgtttggtttagatccatagtagctgggcgctgctg
gattgttgctgttcccggtgttgatctgtgttttgctttgatgaatttaggtgtagatagattttg
tagttgtttcgttgcatatctcgttagtttgcttactcaacctgaaggagtcatgttggacttaat
aggatgtgaatattgttggggaactgtaccgatctttgattttcacagataatggtagtatgata
tgattagtggttctctgtgaatctaaatgatttattctgatgtagctagcagatgtagatgcattt
atcctagctagaaatggcttgtttgtggtggttttgttgtttgaagcgaatccctgtaatggattt
agttacttcatggctatttctatatccactattttcttgttcatcgatcaattatgattatttaga
ttaatgtaatggatttagtttctttcatgactttgtatattcactatttgcgtgttcatcgatcag
ttatgaatagtattcagattaacagtgatggggctgtaggtgctttagggtgtttctgagtaacta
acttgactttgtggcttgctttggttaggt

Figure 147 (SEQ ID NO: 147) Os11g26850, +intron tctctagggctccgcgtcccctgtctcagcaaatttcactaaatttaaaagactttttgagtaaa
attcaactcaaacatatctgagtggcaagtgcgtgggtccgccatgatctacaccaacaagctccc
cggtttggatcgtgtgtgcatgacggtgcagccgccgacgcggcgcgccgacgcgatctgaaaccc
atccccctctctctctctctgtgtgtccgaaggagatatttttcgcatcgaatggagcagcgacaa
gtcatgtgaaacagtgactgtccaaaccagcacgcgtggattcttcagatctcgatgtcctcctcc
tcagatgggccatgatgggccggcccccgcaaccaacggcccggatcacctcttcccccaccccc
atcacaaaaccccaaacccatcaccaacttcccaatctcacccaccccaccaatccccaccagatc
caacggcccagatctccccctcacccagatccaacgcctccccttcgtcttctccctccataaaac
cccacctcacccccaccctcccActccgcctcctcctcctgcctgcctcctctctacccacccacc
ctctcgccgtcgcagatccgatccaggaagagctcgccgccgccgctgccttggcgctctccgtgg
agaagacctcgtcggggagggagtttcaaggtgaaggacctctcccaagcggacttcggccgcctc
gagatcgagctcgccgaggtcgagcaggtgaagcatcccctccctccctttctaatcccattatat
ttcagatctgaagctgtttgcgttagcctagcctgctgcttgtactgttcttaccttagtactact
tgattttgccgttattatggatttgattatgctactactgtggatctggatctggtttatctgctt
cggttgattcagtagatctggtgggctattacgcataaaaaaagtttatgctataggagtggtggt
taggtggattatacatgtgtctttaacattttagattcctgatgtttgtggcatgttgaatatgga
tctgtcatctagatctccttttgtgacacaaactaaaaagacagggttaaaaaggtttagttgatt
ttacctaagcaacactaacaattgggggaaatttgcacctgatgtagtgcgcgaattttgcttttc
gtgatcgtttggttgcttgatttagacgggatgcttgtagttcctttatttagtgtctcctgtgtt
ataggagtaggagcgtcgaatttaagtcttaggttactgcggttggatctaaatcttggtctaatt
gttgcgtagctgtcaaagatgtctagttttgttgttagcttgcatgttttgcggatctgatgacag
aatatggaataaaatattggtaccaaactgcttgccatttgttttattttactcgttattgtgcac
ttgtgtagcttgattgtttaatggcattttactggactccttagtacacccttcatctgtagtgaa
atattactgaatgctgggaattacaatctgttatattttgcaatgattttatcatttttgcttgag
atatattaactctgtgtttcttctgaacaggt

Figure 148 (SEQ ID NO: 148) Os12g38000, +intron aatagttcgggggtcgatatatccggttctgtggtttagggtcgtggattagattcgggtaacttt
taagggagtcaaagcgaacttattttccccccatcgctcagaagaaaaatcgaaaaagcccaacca
caacgacgcggcccattacagcccaagtccattacactgacaaatccgcccccacgaatccaacgg
cccagatcaaccccaccctccatcccagccgtccacgctagggctatccctccccgaaaccccca
cgccgacctctatataaaccggagaccttctccctcctccAaccctagccacccccgcctccccca
ttctccccgccgccgccgccgccgtctcgccgccgacgaggagcaggtgatccccatctctctcgc
ttcttcttttttttgcctgaattgatgagatgttttgtgttagatctgtttgttagtctcgtagtt
gtgtggtagtaactactattattggatctgaattgatttgttcgcgtgattagaagaactcatcta
ttggaaatgatctcggctcaatctaaatatggatgatgcgatttaatgttgctttaattatttgtt
atttagtagagacccaaagtaaatatatgtgccatttgtttagagatgattcgaatgccttggatg
tagctactttagtgtattttcgaacatttgcttctgttgatactgtgtaatagagcaccacaaaca
actagttttgttcaataatcctgctgtttttctatcgttataatatagttgtatatgcactactt
gatattgttgcccatggatgctttccatttgttctaccatcaagattgtggtggcatatgtactag
atattgtttgtctatgcatgattaatatgattggccaattcgctctttcaagtggtgaattatgtt
tatgcttatgattttgctatcaagtgatgtatgtatgctaacatagaagataatcctttacatatg
cgccttgtttgatccgcatgcttgcttctgttggagagatgtccttggccttgtgaagtatttta
ttcctgcaatttttttgtaatgttcagtgcaaataaactgtattgctcatgcaactagttgatatt
atttcttgcaggt

Figure 149 (SEQ ID NO: 149) Os03g56241, +intron
gtcactgccgcctgttacaagaacattcttcctgactattttctgggttttctgttctctgctgct
tggaagaataagattgttgtctgtgttaaaaaaacacacaataatttagtttcatattactacagt
agaaaacaataagttactcgcgaacggatattttagcactaaaagagaattaaagaaaaaaagagg
tcccaccgagatttgaactcgggttactggattcagagtccaatgtcctaaccgctagaccatggg
gccattttgaacacacggattttaatctctatatatccatacttgcatctagtctagcatgggcc
ccggcccatgatacgttcacctgaaagcccactcatgcgacgacttgtcaaagcccaacaagcgaa
gaagccgatgcttatagaggaagcccggctaccaccacGccaacgcgctcatttcgttcattctag
ggtttacaactcacgacctccgccgccgccgccag<u>gtaatcctctctactctactcgcgatccccc</u>
<u>gcgccgtgttttcattcagttcggtgacgaaccataggagtatttcttctatctgtgtgcgtagca</u>
<u>tcgggtcagatttgtcagattttgtggcgtgaattcgcatgttgctagattttatactgtagtagt</u>
<u>ttatctcttgcttccggtagaaaggttcgtgcgccttttttcttggattgcttgacgagtgcttac</u>
<u>ggatttgtggtgtggatttgttgttgcag</u>gt

Figure 150 (SEQ ID NO: 150) Os02g27760 gcactccctccatgggaagcccgtccaagatgcaggtgtggtgatcgttgtcaggttcttcgttcc
ataaatcctacaacattgggttgaaggttctttgtttgtccaaatattcttgacgacgatttcatg
gtaagaatattttgattacatgaatccttattttctcacaacatttactaactttgcttgctttac
atctattctttcctcccaggaaccaccaaggagatgtcaatacagagaatggatagacaccagaag
ggttctaactccacctagccgtgttgtgcagcttgaactaccagagcaatacaaggttactaaagc
gcggtttgagagaggagagggatcctcacgtaggggttagctattatcggacaacttggcatattg
aaatttttactgtcatgtttccttgtcccattactacatcgtcgttgtgttcaactattgcactac
ctccctcctagttcgaatctaatatcatctatgtaaccgcaatgcaaataattgtatcatgttcaa
attgtactactatttcttcatgttacataattctccttgtttaagtccatataatgtttctacgac
ccagactgcgataggcctatataaattatccgagtactaatacgtcgaataaggtacaaaataata
cctcacttaacatatgaaattgcgcaacaaccaacttcaatacattttataacaatattaacaag
ttttaccaataaatacttctttataacaatattaacaagttttgccccaataaggacggcaaggga
cccagatgaaaaaagtacggccgcaagttctttatgggcggccaaaattgcaattagcctatgggc
ggcaagggcctaatcgcaattttggccgacggcggcagacggcgcggtcgacccaccgtctgccac
gtcagcttgccgcccaccattagggcggcaggggctatttctgcaatttttttggtcgatagatta
tttctgtaaatattaaaaaaaatctaaaaacgaaaaaacttcggcaatcgctttctgtattctgta
aaagaagcccaacgaagctacggagcccggcccaccaagaagcaacccccctggtaagccccagat
gaagcgacaacccgatcggacggtccagattcacgcgatgccaatataagacagtcaccacgccca
cgcgcaaaaccCtcgagacctagggcttcctccttcccctccgagcaccgccgccgccgccgccac
cgccaccgcagcctgaccgctcggtctccggcaaccaggtgcgagtcccccccccccttcctga
ccccagctcaagcgaggcatttctcgtgttcgtcagttctatccatgtggttgcgctcgagtgtgt
tgttcctttcgtctgatctgaaggcccccgtacctgattttgtttgtgagctacgtgctgttctt
gagtctgctgggttatactgtaatcattccgaccatccgggttagctaagagtttttggttgctag
atgttgagagtggcatcgctggtggttgggtggatctccagtaaccatgtattttgttagtatag
tatttatctgcgatttagttgttggtcttggtggacaatttcgagtcctttcgatttgggaatgac
tcgcaactaggatgttggtgcttttgtacggtcgatttgcaatgtagcgactagcgagctatccat
ttcaacagattatttttactacctgggggtttcgtggggcagaaatgtgtagtgtcttcatgaaca
cttaatctgctgactaactattgacacagtgggagaagttttggtttaaaggaaatctggttttca
tgttgctttgttggcatttcaaggtagcagcttcgtatgggattttatttaggaatgtgttctttc
tgttagattcagaatgctaaatgtagcagttaaaagtgtgacactgattttgttggtttcttaat
gaagcagctgacggttgcaatttcatttgctagaaactacgatgtaatgcttaggaagtccaacag
ccaattaattttagaccattgttctaaaatggtatgatgtggtagtctgatggatcctttagttgc
atgcattatatacttgttcacatgttacaaatcatgcattcatctgtgatagttgtccatacttat
ataatgatgtttggcatccttgaggtcatttttctataaaaaaggctatttgctatcttttgaaa
gtacattcaaatgtttgtagttgaactctgtattagtgatatacatttagtcattaagttgtctta
tgctcggtttggacagatgcctacctgtttctttttttttttggtagctattgtttgtgtgtcaat
tattcagtgtttaccagttggagctatgttacaaatgtgaaatggttttactactgtctttattga
agcttgtagtttttaaggtgtgtttgttgccaacggtacttatcttttgcagacaaa Figure 151 (SEQ ID NO: 151) Os03g05980, +intron acgatattctttcatgtagtcctgcatagatgacaagaatgagcagtgttagatttgtcaaagtgg
gggtgaagctgagcccttgttcaaccttggagagcaccttgtcttctttgaaacatgcatgaaatc
ggattcgcttggagcaggtggcaatgccatttcaactctgtgcacatgtgtgaaaggacaaagaaa
atatcatttcaatggtgattcatcctcgattgaacaaaagtatcaaatcattttaaaacagaaaac
acccatgtagccactaagatatgcaaacatcaacagaaaaaaaaaatccaaatcatctgcatctat
gactcagctgcatctgccaactttgtcaccacgcactgccctctatgacaaagaggataacaattg
acaagcaaagcgtgcccggaactagaagctagcaaccgagtgatgcggatttctctgattttgttt
acacttcagttcacccaaaaaaaatcctactagttgaatggagatttctctgttttaagacagtgt
gtacttgttaacggcaaaattgcttgctccaagcaatacttgttacagctagaagcatttcaagcg
atctattccaattcgaacattttgctgcaaatatcatatcaagtatcatatgattcagcacataca
cacatccctcacctctgctacaaacacccccagtgaatgaacaaaaacacacagaaaaaagagaga
gagtattagcttactttgatttcaatttggatgtgatatgatgagccccatccaaagattagtgat
tcaacaaaccctagaaaatgcaaaaatgaagagatgttaaatcaaaatcaggaaatcgatgaaaaa
agaggaatgagagaaaggggtatcgtgcgcaccggctctgccgcagatgccaccggctccgccgca
gacaccgccgccacagccgccaccaccacgctcacgccactctccctctctggcacaactgacctt
gtgcgcatcggcgccgctgaagaggaggagccgcaagaaggctccgccgccggcgactccgccgcc
gcagccatgctcgtgacgatttgggagctgcaggtgtctgtttgggagtgactcaatgtttctcga
gtgtgtgtatctgatccgtgagggtgtgtgtttgatccgtgggaaattgtcctgtccgggaccgac
tcgaaacagtataccggtgactagcatttctgttataaaaataaggaaaaaagaacgagaaaaaga
ccatttaacgagcggtgtaaatatggcccctgcaccgaaggcccattcgatatgtgggcctaattc
ccacccgtccgttaatggccgggaaatctcggcccatttaacctagccctaaagctagggtttcc
tctcgccgccgcactAtaaacgcgctctcctcctcactcctcctcccctcgagaaaccaaagctcc
agcaatcggcggcggcggcggcggcccgtgagaggcggtccggcgacgcaggtgcgtagctcctcc
tcctcctcctctccctctctctcgtccaagaacggcgggccttacctgttgtgttcttcgtcgtcg
tcttggttggtgctagtgcgatttgacgcagcgagagaatgttctccttttatttccctcttctc
ttgcttatgtgtcttagttgattagcgagtgtcggttaggtgattaggcgatggctggttcggttg
gcgagatgatctggatcaagatttgcctcgatgcgttctgttcccgtagctttgttcattttctcg
tttccactgcgttggatccgtatctatgccgattagttcgtgctgatttcgactgactgcgcattc
tgtagttgaaacttgtgtgtggtccggatttaatttcgagatatgtagtagattatttggggggttc
taactagaatgctaatatgtgttgtatagtactgaggaatgaggacatgttttactctggcatttg
gtattatgtagctcgaaaatgtttatttctgttatggtacaaaatttgataatttaccggttttaa
ggactggaaatatgatattcattaactagagtttttttgttctcaaatactctgtttgatcactcat
tttggtggaatggagttatgcataagcttgtgaatttttttatgaaaatgaataatggcgcttaat
atagaggactatatacttgtaatgcactaactgtatgtttgtccatagagtgatccatcgagaact
atatttgttaatttttttttaaaatttctgtgtaagttgtagtatactaattgcattctatatgtat
atttcttaaatatattatatgatagtccctgataagatctttcaagtattgtcgctttaggtcat
gaattccatttacagcaggacaaataatttaggtatgtatgatatgggcaaccagggataacaca
gcaaaactaaatctggcatgtaagctattcttgggttaatcagacacaatgttatgaattgttttt
taaatccttgtcaaacatggttgtatatctgaagctcttagtatttactgtacacaagatccctac
tactatttgtcttgaatatccatactattattgggcgtaatctcaacaactactgtagttttcttt
atttgtattgttgcattgtctttccgggttgtgtgtgcagtttctttcttgctttgtatatttttg
gggtcaggatataaggaatttgggactgtagggcttctttctatgttattgtttggttcctcatga
acaactatgctatctgcagtggtttctttctctgtcatgtgttgtgaacaaatttattacttcatt
gcaggt

Figure 152 (SEQ ID NO: 152) Os03g05730, +intron
tggctaacctcaaacagacagaaacttttgccttttacgctctacaatttgtgcagtataatgaat
taatgccacgatcgcatacgaacacgggacactttccttacaatcgaaggcagcaaaagatgcgaa
acttctcttccgagccgaacacatgctcctattcctgcacgagcaggcacaagtgaacaacaacta
cctgatacactgacatgtcgggcccacactctctcaactcggcacggggccccctccatcttccgg
gacccacctcatccgaactctatgtcgcgtgggccacgggcctcgtgggacccacatgtcatggac
ctccggggactcccgaaccgagcccaacccgtaggacggtaggaggtcgaatcccaaaccccttcg
gcaagaaaggagctatttaaggtagactaatcccctcgtcttccccCacaatcacttctccccccg
gaatatctccgccaagagaagagaagagacacccaacaacccaaaacctagcgcctctgcgctcga
ggcccccccgaatccgcgaatccgccgactcccaggtaagtttccccccttcctgatctagccttt
tcgatctggtagattatcgaatttttgcgatttttttgcgatttttttgggtgatttaatgttcg
tggggtggtggtggtgttgtgagcaggt

Figure 153 (SEQ ID NO: 153) Os05g01262, +intron
ttttatatttttttaaaaaaaattatttatccattatatactgcaagaatttttttttgctgttt
ttaatgtaactttttcgagaacatacctcatttctaatgtaaattatcttttgcgtaagtaattt
ctctctcataaaaaactcaaaaatatttttttaaaaaagtgaaaacttgaaatttatatataaac
tttcatgttgggtaagtaagctacataaacaattcatattttaaaccccttagatgaataaattaa
ttgttaaccttatatgtattttgagtatttttaaaactaggacctgagtaaatatttttcttgag
ttttaggttataagacttcacattcatatatgtctagatctattaacacatatataaatatggaca
atgctaaaaaataagaataggaggtggtattattttttttttggtagagaggggagggggccgcat
aggaggcaggaggtagtaaaatgggctgatgggcatagtattcacgggggcccatgtaAtagttgg
gttgggcttgaacacacttgtattgtaacaatagcctcggtcgaggtgaggtggaagaagcaaagc
aatctccgtgagcggtgcaggtcagtcccctccccatctcatctccctcttcccccagatttagat
ccacatctctctctccctctcttcactttgttaacctattattgctctatccgcctttccttattg
attaattcgcataggtcaaaaacaacgggaattcctactgttagctagacttgatagatagccgcg
agcccatgtttccctttctctgtgtaataatgtcaagctgactcacttgttgataacacaaattat
cacgctactattgtgcatatatactactcctacatgacatgacatgattgatagtcacatacacac
acatcaatcgctaatccatttctccatctatctaaccacactgctattttagggaaggggaaccgg
aatcctcattatggggggtgtttacatccagggttgtaaagttttggcgtttccgggtattatatag
ggtgtcgcattgggtgttcggcactaataaaaaaactaattacagtaaaccgcgagacgaatttat
taagcctaattaatccatcattaccatatgtttactgtagcaccacattgtcaaatcttagagcaa
ttaggcttaaaagatttcgtctcgcaaagtagtcgcaatctgtgcaattggttatttttttagcct
atatttaatacttcatacaggtgttcaaacgttcgatgtgatagggtgtaaaattttagggtggga
tctaaacaggccctatattcttcactgccagtgccatcaaccattcatcttctattcttctatcat
gttgtttactactctctctctctctctctcatttttacaggt

Figure 154 (SEQ ID NO: 154) Os07g46670 taggttttatcaatagtctatgtttaatatttttaattagtgtcaaacatctggttggactgaaaa
gtcccatccaaacagccccatcttatccgataactacaagcaaaccgtacacgatttacacattaa
acacaccctctctctctctctctctctctccataggagcacttcaatatctctatcgccaggaa
acttccacccgaattattatatccctcgcccacagaaaatcccgcccaagcatcaccacactcccc
attggccccacccccccatgtgaaaaagggacccaaaccgaccagtcaccaactcaccatccacccc
caccccaacccaccccacccacacgccaacccggccccacacgtcagccactcccactgacaaccc
ggccccaccaccccacccgctcgtactcctcccctctcgcctattaaacgcgctccccctccacca
ccgcgcAgccaagccaaacaagaaacccaccgtttctctctcaaaaccgcgggaatcaatcaatcg
ccgttcgcgtcgcgccacgagatattttcccccaagaaaaggtagtagtaatcttcgacgatcttg
atcgatcgccatgagctagctagctagcgaatttcttgttgtttctttttgggttattgatggcg
ttgttgttcttgttcttgtttgttgcagttggagtgaggg Figure 155 (SEQ ID NO: 155) Os05g01560, +intron tattctgtgaatcatatggacaacaatgtaaaatctcatagtaattcttatttaggttgtttgcag
aaagttaatttgggtcaactgaaatgaaagcttgtctgttggctctctcactgaattgaccccatt
gtaattaatgcatataattggcctatatattacactttcaatatcgtaaaacctttttctttgtac
acttcacctagttgatctagtatctgccgggctcatcgggcttatcttgtcaatgaacagtaataa
gagctatgtcgggctgtttgctgtgtgcttctgttcaaccaatttcgacacagtgtactttgcgaa
attgggaattgagatgcttggtgtgaaaattggctgtgctatcatgatgatggcccatgagcccac
gaaacctcacgactcttaattcatttacttgtttccggttaagagaaattgtttcagatatttaca
atgtttttgaaatataagtttaatccgtctcaaaggttgttttaataactatttttttctctgtaga
aattctgataaaattataatattatgaaactttttttaggaaagttctatgcatataattgtcatg
aatttaatagaaatgtttatagtgaaattaatgtcctaagattcaaacttttctcttacaaatata
ctccatgctatgtttttaccaaaagatcaatgaggtattagcatatagtaaccggctcacaggcgc
tcgtgtccgtcagggcgctctaaacctccatcgcacagtttctatccgatcaccttcaccctccgt
ctccagtagtaggatccaatctttcccaagtttttttttatctttatttaagttcctatagaattag
gtctattaggttgtctagggtttgtctttcaaatttttcatggatcagatgtgtagtcttttgttt
cttctatttatttattctagttaccttattgaggttctcggtgaaaaactagtaagatttgtatgt
cgggttgtcgatgatcaagccagtgacacgctttaaggcttgagtcgctaacttttcgtggtgat
ggttagttgttttgttgtaggaatagagatggtagcatatactttcatattcaatgcttttgtatg
tgctggaatttgtcaatggtgttggcttcacatttgctaatgtataggaatttcaagacgtggaat
ctctttgggctgtgttgccagatcaaaacaggcccaaaaagttttagagttagacaaatatataat
acgtttattctgtgttgaaaatattattatattttttataaacttaattaaacttaaaaatgttt
gattataaaaaaaattaaagtgattgtaatatgaagagagcaagtaaatataaatgaagtGaggtc
cacacacgttgacgaggcaacgagatacggcaccaataccaatctctgactcctccggcctccggc
ggccggcgagagagatcccaccctcaccgacgacggcgagcgaccaccaggtaagctcccaatctt
ccccttcactttctcggggccagatctgatctgagatgaggttgacacacgacgcatgcaaggt

Figure 156 (SEQ ID NO: 156) Os07g08330, +intron agattaatgattacagtggtactattttgataaattattttgttcccagtttatatgaattttaaa
attttagatcacaattttacatataaactacaaatctatggtggatctgagatctgtagttatgcc
aaagaatacctcatattgctgatcctttctcgtatgctttctaatggagctagtatctgcagctgt
attatcagaaatacatttaaatgagatatgttttgtatgacccagttgacggcctcacaaaccta
aacaggagggaaccaagcctgagctctaggcttggctcctaaatcccattcaaatattcttaaaaa
aatcacatatttctttttttaaaaaaaatagtaggatgattaggccgaatatgtcagttgagcct
taggcgtggagaattttaatttggctctgtcaccaccatcaggaattgaagcagggaaatgagagc
tataaccgttgaataacctctcaaaaaatccctgaattttagctgcatgagcagcttaaatgtggg
atcaatattcattaagctcaagttactaacttgaaaaatatacagcatgtgtgtgttgttttgaac
tctaaaaatacctagacggagttatgcattattgaaaacataacatatgaatgcaaacttatacta
gaaaaacccatgaattctaaccttagtggtttttcaccaatatttctaataaggggtcaacctttg
gaagatgagaactctaccatttgaacacatgaatagtgaaaaatcaaactattaaagcttgacggg
ctagggccataactgagcattgccacgtcagattattgtacaattatactactctagcagtacata
cactcttggctgtgtactgttgtacgaaacggagagtccaaagtagtagactgtccatatagttca
gtttgatggatttcacccggagatacaccgtacgatttaattgtaataatacatagaaccatttgt
tttttttttgaactgaagaaccatttgtttttcatttactttttactttaaaacatggacaatgaat
ttgtttttgaacagggcttgaaactcttaactccgagcaaatgaaaattcaaacagcagtggattc
aatattcaactcgaaacccctcctttttttcaactaaaaagtccgcaaaacttcccaataattaaa
ccgtgaaatttcagcgagacctgtatttaaaaatatgggccaaattcaaaatccaaagcaataaac
aactgggctacacacaacatgcgacggcccatctcatcaagcaacaaggcccagcccactcgacac
ccaccgaatccacgccgctcaatcgaaaccgacggtccagatctcgccgcgccaaccccatcacac
aaaccctagcaacccccccacctatataacctctctccctcacgccccgcctcCattcgcacgcccg
cgccaccacaaaaccctagccgccgccgccgccgccgccgccgccaggtataacttactctcc
tctcaattttgttgattcagttattataaaatgatgactaggttgtagaataatccgattagctat
gtagatctatagttgactctcatggtaacaagaacaaccatttggatgcttgtctaatgtgttagc
tggtactgctttggatgatctatttgtttagatgacattctagtttacttagttagcctgcacttg
ctgtttgtgctgctatgttgcttcatgggctgttaatttgttagtattgctcggaattgatactac
ctggtgttaattcttgctgttattaggtacattcgtttctatattcatgcttctaatgtgccattt
tctccatgtttagttgagtagtattttgttctatgatctctctggtaagccaaggttgtattactt
gttataagttattgacctcattgttgtagctcagtgtctgtcttatttctacattgtgttcctaga
agcctttgaatgtgttaattgattcatgataacatacagttgtgcaaggtcatttagttatttttc
ttaaattatgtctctatgcattcaagtttaggtttcatgtaatgttaatattctagattggctcct
tgtccttggtgaaatggtggctgagttcttggcattagaaggtcatttatttggctgtgttttata
tttatcatagcatgtgtggtttgttgttgacttgtcgtagctgtttatttacactgatcttaggtt
ctactatcatttttttgtctggtttattctgccattgatatttcatttgctgtattgcccttagtgt
ttttagtgggatacttgtttagtcctcaaccatttggagacttcaatctcttggtgcctttttgttc
taactgaaaattcctgttgattcattgtaggt

Figure 157 (SEQ ID NO: 157) Os03g58204, +intron catttttattttatagatattgttggttaaagtagcatctcgaagactgtgtcaaagtctaaaata
cttatattttaggacggagggagtatatttcagcactatcgaactttggcgttgagaaactgtcca
tctctacaaatagtagtttttgacatggtctattttaaaaatatatttttaaaagaattaatttat
caaattttcgggagacaacgaggccaagaagaagatgcgaaaccaccgggcccaactcagagagaa
ctacaaaggacaggcccagcccaacccacgacaaagatccaaccgtccaatctaaaccgacggctc
agatctcacctaattccaaacccaaaccctagccactacgcccctagacagatataagctcgtctc
cttctctcgccgccctctccttccctcgccgccgcccgagccactacactatccacctcgccgccg
ccgccgccgccggaaatggccgccgccgcgcgccccctggtgtccgtgaaggccctggagggcgac
atggcgacggactcggccggcatccagatgccgcaggtgctccgcgcgccgatccgccccgacgtg
gtcaccttcacccacaagctcctctcctgcaaccgccgccagccgtacgccgtgtcgcgccgcgcg
gggcaccagacctccgcggagtcgtggggcacgggccgcgccgtgtcccgcatcccgcgcgtcccc
ggcggcggcacgcaccgcgcggggcagggcgcgttcggcaacatgtgccgcggcgggcgcatgttc
gcgcccaccaagatctggcgccgctggcaccgccgcgtcaacatccgcctccgccgcatagccgtc
gcgtccgcgctcgccgccaccgccgtcccgtccctcgtcctcgcccgcggccaccgcatcgagggc
gtccccgagttcccgctcgtcgtctcggactccatcgagtccatcgagaagactgcgcagtccatc
aaggtcctcaagcagattggtgcctacgctgatgccgagaagaccaaggattcggtggccatccgc
gctggcaaggggaagatgcgcaaccgccggtacatcaatcgcaagggcccccctcatcgtctacggc
accgagggttccaaggtcgtcaaggctttccgcaacctccccggcgttgatgttgccaatgtggag
cgcctcaacctgctcgaccttgcccctggtggccaccttggccgcttcgtgatctggaccgagtgc
gcgttcaagaagctcgacgaggtgtatggtggcttcgacacaccggcgctgaagaagaagggcttc
gtgctcccgaggccgaagatggcgaatgccgacctgtccaggctgatcaactccgatgaggtccag
tcggtggtgaagcccatcaacaaggaggtgaagctcagggaggcgagaaggaaccctctgaagaat
gtggccgctgtgctcaagctgaaccccTacttcggcactgcgcgcaagcaggtatgatcatccatt
cctatgctagttgtcttatattcgtaaatcataatattatcacatcacagcttttatgatttgta
tgtgattaattgtatagtttttgtgtgatcatatatgctataatgtgttagctatatcaataatga
ctatccatctttgttcatgcattgtttcttttacttggtatgtcgaccctttcgatttccgcagta
ttattatattatatatagggtataatgctttggtgttgcatcatagcaatggtgagatggtggttg
tagtcaattgtgtcctactgcagtagtttcataccgtctttcattaaatgcgttgcgccaaattgc
ttcgattgatagttttatgctgcattttgtgaatggttcaagctgattatttcattaagttgtaac
ttgctttagttccgtgagggacgtgtatgatactacgacgattgtttcttagattcatatatttgt
aacatattattgtgatgctttactcaaatttatcgcgttcattttcttatgtgacaaatgtgttta
tctttggttaagtgattttcttgttcagcttagtttatgtcatggtgctattttgtataatgttac
acattgttgtttattggttacattaggtctaatttgtagttatttttcttcatatttgtttagtat
gacgttttcattgattctggtttgtcgtcccattttgtgtatggttttggtttgttcagccatgtt
gtattcattttttgtgtttagtcctgtcatgttgatattcatgtatggaggttggtggtttcaatca
acttggctgtaatgctagttcctttgtttcttgtgcttattatgtcatgctttatgtccttctatt
gcctggactgttaatacttggttgttaatattacttatcttattggaatctcactttactttata
tactaatcttgtaggt

Figure 158  (SEQ ID NO: 158) Os01g62420, +intron
aggtttcgtttgttggttgttgacaattccttaaattctttagcatcttctgtactcgctgaagct
ctgttagaacaacgttgcagaggctaatcatatgcttgtgttcgttcttacttgatgctagttgta
tgatatgattcagctgtattactggccctgtttgggtgagcttaatttagagaaactggaatatgt
ttctagattctaattctatatctatagtaactatacatatcagaatatgtatgaaaaattagacta
tgtaagaagggtgtgttcacactaaaattggaagtttggttaaaattggaacgatgtgatggaaaa
attggaagtttgtgtgtgtaagagttttgatgtgatgaaaaagttgaaagtttgaagaaaaatttt
ggaactaaactcggccgaagttttttgtttagagcatcaccaatgtatatggcaaagtgatctata
tagatgggacccacataaatagtttatccctatgataatgtccacaatgtatagatacaaggtatc
attaggagaaggagaagagagaggagtagagatagataatataatttatttcatatgggtagtcca
tatgtatatgggtattttttgctattttttttatatggactagttgcacaatgataataggtggct
gaatggaatattctattgtttatagactacttttatattgtggatgcccttaggaaaagctaaacc
cctatcggcgccttcctatgcctctctatcaccttttggtcattcggttcatcgcggatcgacgag
aaaccaggttggcccgaatcaatcggcgccGgcggcctccgcggtttccgccttcgggtaggcgcc
tgcggcatcaacaaagcacacagccgaaaccgaagccttttctttcttccgccccaagaagctgtg
ccacgtgtttcctccttcccctcctcgatttaaccgccccatctcgagtcccccatcacagcttc
cactccacgaaaaccctctgcctccttcgctcgctgcaccctcgtctcggcgatccatccttggct
gccaggaagttcttcgtcggcggcaactggaacag<u>gtaagtattcccccagcactagtcgtctca</u>
<u>caatccagattccggatgagccggagacgctgctgatgagtgatgaggcttgggttttatcgatgc</u>
<u>gctgcgctgttgctgcgtgcagaatgggacaggggaggacgtgaagaagatcgtcaccgtcctcaa</u>
<u>cgaggccgaggtgccctccgaggacgtcgtcggtgagccgtcgtcccctcccgagggcgttgtttg</u>
<u>gagttggatcgattcatgaatcgatctggtgctgatctgtgggtttgtttatttattttaattttt</u>
<u>tttgggtgcag</u>gt

Figure 159 (SEQ ID NO: 159) Os01g14580, +intron cgctcgcggcgactcacccggttgcatcgttcgcccatgctgtgccactccacgcttgcccacgca
gctccttgcccgctgttcgcccattcacaccgctccttgcccgtcagttgccagtcggccgcctat
ctacatcatgccgctcctcgtcccaaccacgccactcaccagccctcctccagcagctacttgcct
ccttcatctgccagattccgccgctacgcccaccacctggttgctgtcgagctctagtgctctacc
acgtcgtcggaactggacgtggactgacggtagctgcaaaagtttcacatcccatcccaccctcat
tccttccactaaaagaaaaaaaattgaatcatcccatcctataaatcaaacagttgagtgagatc
gtaccatccctagaatcaaggacaagttcaacctatcacatctcgcttctaaaccaaacacacact
gacagaacagagggccctgaggattcggctcctctgcctttaggggctaaagactgaggcgcatag
caaaatgagtttgccgctacaatataaaatattaattttgcagttatttactgtagatacagtata
aaaagtaaaacgtattgtgccaaggtactgttcatgatgtattgtattatatgtagcaattaatca
cattcgttcgctataaatccgatggttgagaataatttaaaaccctaagggcttgttcggaataga
gggattacacaggattcttgtaggattggcaattcctttggatttggcactgtttatgcattcggt
tcataggaaccatgcgtaggaatttcgtagaaatactgtagcaaccttgtgaaaacataggaattt
cataagattctaaacatccactcacacctcatttttttcattagctatcatgggatagatgctaat
cacgttgaagtgactagatgggaactaatattttattgcttaattatactataatatactacctca
atgcatgaatgtatgacgttggttagttcaattttgagctaaccaacgtcaaacaaaaaaatatgg
agggagtatgagattaatactaattgaaaaattcatgtggtttatatattcttgtgttccgaatgc
ttcatagcatcaaattccttttcctatcctgcgatccgaacaagccctaaattctgaggatcccaa
tccgggccatgaccgcctcctatcatcggacggctatagtggtccaaagctgacgtggccaagact
ggcccacatggcccatgtagtccgtcctggaccgagtccacggacggcgcGgccgaacgcccgcgc
cgtgtctgcttttgttgcttcgttctctccgcgctccgtgtccgaccttcttcagacttcacacct
cgcgcgccgccgcagctccgatcggaagaagctcgattcgtctccgactccgacgaccagaagcta
ccggcgacgcgagcggagaagcgcggagggaggggcgcgcgccgccaggtgagaacccccacct
cccctctccttccccccgcttccgatcggaactcgctcgtgattagcctcgctatctccgctgat
atctacgggggagcctttgcctcttgtctggtgccgtgattgctttggttctgctataccattgg
tggtgggatggattaggctgctctacgtactggatctaaaatttgtaggtgtttggaggaagaagg
ggagtcgtcctgagtagaacgtgcggctgaaattagctaaatggtcctgttttgtgggaacagagt
tcaacacatttgatgtgctgaaagctgctctacttggcctttctgaaattctaggtgttacaagga
atagtggtagtcatccttaggcgtagaaagtgtgctgaaattagttaaatagccatcttcttggga
ggacaaaatgttcaaccttagatgcgcggaatagtcggttttaaagggtaaatctaaaataactgt
tttagtgcattgtcattggtaaaaaagaaaagattattcatgtgaagaatatagtaaaaaaataaa
gaataaaattgaacccacagcatcgcttagttacaagttccaaggtgaactgtatcagtaaacaca
tatgccaatttcagaacttatcatctacaatgttcaagtgggctgaaaagtttttctgttgacagt
ctttctgcttcatttgaagttctgtgctgaaaagttccatcatcgaacttaagtaactttaaattg
catatttagaaagtataccatacttttggctagcccaatcatcctttgcttacctcagattgtagt
ggttatatatgactgtatgtgctttttacttaggt

Figure 160 (SEQ ID NO: 160) Os02g57040, +intron agctcaggactgactgactacagacttacagttacaacttcagaggatgtgaattattcatttctc
ttgcgcactaacagttagttcttcagtggttttgggatgagatcctaaaaatatcacatcaactag
attattaagaacaaattgattaatatttatacatgctgaaaagcttaaatttgttactactgcggg
cttgtttggcacagctcacctctcctggagctgaagctcagccaaacagtttcaactccacctaaa
atgagagcgaagttgggtggaactctcttacaaaatgaactagagaggtggagctggatttaggct
gcttcacaactacattctagacccgactcctagaactaaatttaggagttggagctctgccaaaca
gccctgctactactacatggttaagggggtgtttaaatctaggggtgtaaagtttttttgtttca
catcgggtattatatagggtgtcgtatggggtgttcaggcactaataaaaaaaaataattacagaa
tttgtcagtaaactacgagacatttttaagcctaattaatccgtcattagcaaatgtttactgta
gcaccacattatcaaatcatggagcaattaggcttaaaagattcgtctcgcaaattagtcgcaatc
tgtgcaattagttatttttttaccctatatttaatattccatacagatattcaaacatggtgaaaa
atttagggtgggatctaaacagggcctaggaacaaaacgagcatcacatgctgatctgccaagct
ggctagccctaataatttggaaatgcaatattccaatatccaaagtggacccggcccaattaaccc
aaccaaaacccacgcccacctcCtctccccttctcggctgctcttctcccccctccctatcctctcc
tctcacctcgcaatcacatcctcttcccttctcttctccatcgcatctaccaccgagcgtgcaagg
aggggggggggggggggggggtgaaacaggtaacctcttggttcccctctcttagtatcgtggatt
cgtggtggtagatttgctagtgtgctagagttggatgtatggttgctgtttcttggagtgttcttg
gtttgatctggagtgggggatccccggtgtggtggtgggtgcaggt

Figure 161 (SEQ ID NO: 161) Os06g06980 ttaatttgaaatactctgaaatattaaaatacgcaatgtaccgggcggacgactggtattattact
gatcttgctcaaaatggtcatcgtaatttcagaacgaactgatcgttcaaacgttcctcatgttgc
gcgtgtgctgcaactactgcacggtaaaagtgataggaatcggtcggaaacagtattaatgttttt
attattttacaaaaacgaattgaaataattggaaattttcatatttatatattaaactattcagt
atcaacttcaattcgacgtcaatagaaattagaaaagcataattatacacagtaataggcgttcaa
gatattattgttattatttagttttgtggaaatggtatcaacgtgatcggaaaattttgtacatgt
tttcaccctgcgggatatctcaattccttctcctccctctaccgccatatcagcacacgttttaga
gcaccaatcataacccataaatccgtgggctactcacttatttaatttatatgtgaattcgtgacc
tgactcactcacatactatcaaaaatttgtctcagtcacccatctccttctttcctggtccgataa
gggtttatcctacggttcgacggttatcacgatagtcgtgcggttactgaggtataccgtgattta
aaaatatgataaagttaccgcaggttttaactgcgcggtttggtaaacctgttcctcctcaccaac
cttctcctccggtctccttatgtgtctcaccgaggcgagccgccgcgagaccgcatggacgcggtc
cacgcacctggcggtgcacctcctcctccccggcgaagaagacgtggaggagagtaaatgagcaat
caggcccacggcccaatcgccgtccaccacccaccaccctcagcgacccaaaaccacctcaccaac
ccaactctgtaccgtactgtacccgccctcccctcccactgacactccgggcccacctgtcggcgc
gactcttccacggtccccttctctcctcagagatttttccacgcatttttaattttttttttttctg
cagttcacatgctcttctcccactcttccgccgcgctatataaaccgcgcgaggcgtcgttgcctc
Gtcggcgaagtcaatccggcgatccccggcgagcgagagatcgaagcaagctgctacacagatctc
acgacttggccgaggcggcgtcggcggcggcggcggcgacgacggagcaggcgattgggagcagcg
gcggcgagcagaagacgcggcactcggaggtcggccacaagagcctcctcaagagcgacgatctct
accaggtaacccgccgtctccggccatcccctcctcgccggaaaacctccgccgccgtggctgacc
ttgcctgactggctgactcggtgcttcgtttccgcagtacatcctggagacgagcgtgtacccgcg
cgagcacgagtgcttgaaggagctccgcgaggtcaccgccaaccaccc Figure 162 (SEQ ID NO: 162) Os08g38920, +intron taggcttgtgaaaagaattacaaaacttgctttgcgcaaaagaactatagccatcctttgaattcc
cctgtcatgtgcattattgctgtggtggcttgctgagtacggttggtactcacccttgcaatatac
aaatttaatcagaggtcggagatgaagcttcggaggatccctacgcttactaacaggagggtgatg
aagacgatggcgcccagtaggtcttagttacggtcattgcctgtggcaatggcgtgccgctgcctt
aactccgctgccttaccttcttctgtttttggaatgtattccggaccgctcggtccgatgatttaa
gactatgcctgcgggcttatgatgcaatgattcatactagacactcgtgtatgtgcacttgatatt
tcagctaagaattcgtgtgtaccagactacttgatccagggaaatggtactgtttacacgattgat
tcctgttataaaaacggggggtccacatagatccgccactgctccctcctttccttcatatttagac
tttaataatttggattttcacaaatgttatctaaataattaaataaatatcatgctatcgaagtat
attacataaacataagtattaaactttctttcattatgatttaacaaaattgctagaatgctagaa
aatttttgtcaaaactttcagatttgttattattggatcattttaagatgggtgcattgaatagaa
aaataattgctagaaagaaatttcacataggctacggataagatcccggtgctagtcaactaaact
agtcttaaatacaggtttatatcagttatactgtagctataacatagccacggtataaattaatgt
aattacaatgcggttatagtgcagttacaatgtaattacactcaattacattatagttacatttga
aagttttccctcaaaaaacttgatagttatttttttaagatactctaacgatttaatcatctcaaa
atttttaataattaaagttatagatgaaccggtaacaattattacctctgtttcaggttaatatgt
caaagtcaaactactttaagtttgactaaattatagaaaataaacattttcaacccatgttagatt
tattataaaaatatatttaattattgatttaataaaactaatttggtattataaatattactatag
ttatctacaaacttagtaaaattgaaagtagtttgattttaactaaagttaaaacttctaataacc
taaaatggagggagcacaccatatttataccaaagtactgtcagcaattagctgatcggtagaga
cgctgagtaactgcacgttcaggtcatcacgcgacctaccaatttaacaaaacgccGtgtcgtctt
gttcttcttcttatctttttttttagtcattaattgatctgcaatactcttgtaagaggtccagat
agctagagaggccattgagagatcatcatcggagctagctagctagccaggtacgtatagactcgc
ggatgtgtaagcgcgatgtacgtgtgcagtggtgtgtgtttcatgttcgtttttttggaggaagag
atcgaaaaaatgatggagagatgcatatttgtgtgtgcactttgcaggt

Figure 163 (SEQ ID NO: 163) Os09g01640 aataatggtagaatgaaagacttaggtggagattttaacatatatatccaatgcatatgtcacata
gttaaactcttccaacgtatatgtaaattagaataaaatcattttacaaaaacatattaagtttta
atatgaaatggtgttgtataatttgcaagttgaatatatgattttaaagtttagggtgctagataa
accttgaatcaaactttgaagggttatttatataaaaaaatatggtagtattttaacccaaaaca
aacatattatcaaaatatattcaatattagattctaatattttcgatgttgctgaatttttctaaa
aaggttaaacttaacagaatttgactagaaaaaaatcaaacggctattaataatagcgaagtgagt
aatatttttttcatatggtacaacgaagttaatatatttttttcctaacaaaaaatagtacattac
aactattctaatgaaatagttgacgttatgatacctaggtacagggtatgatgtctggtaccctaa
cactaaatctgatacatacgataccataggtatgtcagcatgatatatatgtactttaggtactaa
agagtatcatgtctcataccatagtaccagatccatgaactatatatggtaccacacgtatcaaat
ctagtaccacctacaataccgtgctaacgttagcacataattactctgttctataatgtactccct
ccggttctataataattgacgttttggacaaggttgagatcaaacttttataactttgaccattaa
taacttcaaaagtatttagttttaaaaaactagaacaaatgaatctttgtggaagaagaagcggtt
cgccagccgctacattcagggaaacatatatagatttgtctttcaaaacactataataaaagttaa
catgcatttatttattgtgtatattataatagaaaaataaggtcaaaggtatatttgtagaccgt
gtcattgtccaaaacgtcaattaaaatgaaattggagggagtaagtatttttagttgtgtagaaat
attaagaaagtagataaaagtgattagagaatgttgattagagaatgtttgtgattggcggagaag
aaaaaatagatgaagaaattggttttgattgtttgagagaagtgggtagataaagaataaaactta
attttggaacaagctagtgagctaaaaatagctagtacattgtaaaacagaggtagttcaaactat
tccgttggaacggcgtaacaacaattaacccaattttcctagtagtaataaatataaatataaaac
caattcagagaaattcagggaagaaaacgcgtcggctctcgaaccttcttGcattgtgtcgtcgaa
ggcggttggaccattcggcggccgcaccctcgatccaaaatccccaattcgccttccacgaaaccc
taaccctagttctccgtctccggcgggctctaccggcggcgaggcaag Figure 164 (SEQ ID NO: 164) Os07g10720 ggccgctgcttccatcgcgctggatgcagtgcccaccatcaccggccgctcgtcgccctgccccttg
aatgcccagcctaacgccgttcccgccggagatgacgccgccgccgccgccgtggggactcgccgc
ggcggcgggggatcgttttttttttttgttgttttttgtgtgcgtgttcatttcttttctcgaaaa
aaatggcccatgaaagattccagcccggcccactaagaaactactcctcgtaaagtcgtaaggccc
agatgacgcgagagcccgatcggacggtccagatagacctgatcgcgctataagaggggcgcacca
cgcactcgtcgcAaaaccctcagccgccgccgcccgagcagagaagccgccttcgccgccgccgcc
gcactccaccgcgcgctctccgtctccggccgccgccaggtgaggaggatctcccttaccctaccc
tctctcccctctcttcctcgtgtgcgtggctttactttacccccctgtgatcgatcgcgctcgagga
cgacgtccctttcgcgtgatcttggttcttggtgtgggtctgatttgctgctgggttgaacccttg
tgattcctaccaactggggtagacgatgagagtgagagtgcgtgcgctctgtggtatttggatgga
actagaattcgggaagtgcttggtcatatccttttttattccgcatgaattgttgctgtgttaggct
agtgaggcagatttgttaatttattttgaatctaggtatacaacgtcgagtcctttcagtttgaa
atgtctcgcagctagaacctgagtttttttgttgggtcgatgtgcagtagaacgaagagaacttt
ttttaacaaaaaatttggtaggtactaccatgttagatggagtagttgtagttttagtgaaggttt
tttgttactcatattgtttagaaaccagtaaggcagccatttcgtttttcatcgtcagattggcag
cttggtctggtttttgcttagatatgttctttttctttgttggattcttaatgctcaagaacctgca
gcttgatcagatcgctgtttctgaagaagcccatgatagtagttgcaattacttgatttgataac
agttatgatgtaaaatgcttatgattaccattaggcaacttctttcaggccattcctcaaatgtga
tccttgattatttgtgtgttgcatgtatatgttatacactcatcacaaaacagacatgcatttgtg
attgttatttgtagttaaggtgttttgtctataattatatctgtcatattgagcttagtgatcatc
tattttttagaccatttctacctgtggaaaatacaatggaaaaacatttggtagttgcactgtctt
taggtttgttgttaacaaaatatttaagtaatacaaatttcttctcatattttgcagacaaggt

Figure 165 (SEQ ID NO: 165) Os07g12650 attacacctgttttaatagttggggggttaagatatcggtatcgtggttcagggaaacaaatcagat
ccggtcactagttaagggagtaaaagtaaacttattcgtagtgaagcccagaagcgggagatcaag
gcccatctaggcccgacacgagagagccatataaaccccaccattctcccacccgcctcttCCccca
cctgccctcctcgcgaaaaccctaaccctcctcctcctccgccgccgccgctctcccaaggtggcg
gcgctgcccttccccccttgttcttcttccttgcatctgcttccctcccgtttgcttctaattgta
tttctctttcgtttccgcagatccctcccgtcgtcgtcgctgtcggcccctcgggtctttctagcg
caggagac Figure 166 (SEQ ID NO: 166) Os08g38900
ctgttttgactcctttttggctgcccatccacagtcgccaccagaaaattcactgtgcccaaatc
aatggaagcgcctactagatccatccatcttcgtgacagctccgagctttctcctggttattttc
tcccaaaaatacattcagaacacgatctcaaatttaaactaatggagtgctactgcatttcttaat
tataagtcgcagcaccactcattaatcatttccatcacaggtaaatcgtggtgagctggtggttgc
tactgtactactagtactacctgtcgcagctttgtagaagccgttttcgctgaagcttcttcttct
tccctgggcaaaataattttaagcaggcggaataatattgggataaacagggtggacaaaagcgtg
cgatccctttctttaaccaaaccacgacgaaagcaggttaggtcgcggcaggtggtggtggtagga
agaagaagaaagagaggggaaaaaaaacaaaaatttcacatgcatcatgcatgaagtagtacatgt
agtactgagtactgtaataatgttcagtttactggaccgtctcaacgggaagaccaaattaacgct
tataaaatacccttttttgggcactgatcTtggccactacgtttggtggctcaacaaccaggtca
ccgtgcgatcgatcgattgctaatttatttttgaaaaggaagggaggaaaaaagaccgggtgttt
ggtggcgccaccaaccctgctctcgtgagccgataaatattgctcgccggagctctcggttgacga
cccaaccaatcgactcgcaccaccaccagcagctcaagcagcaacagctcaaacggaggaagatct
catcgccttgacgaccggcattggcgacgcaccggtgatcaagaacgcccacagcgacatcgacag
caccaacaagacgctgctcaagagcgacgccctgtacaaggtacgtgctgctgatgattcttgatc
agctcgccggattgtgtttaggatgatctctctgttttaattaatttgctgatggttgctgtgttc
gtcgccggtgaacttgcagtttgtcctggacacgacggtgctgccacgggagccggagtgcttgcg
cgatctgcgcctcatcacggacaagcaccagtggtaagaaaccacgatctctgctaattaatctgc
ttaattaagctagatcttggggttgattaactaattagcccattaattcttgcaggggggttc Figure 167 (SEQ ID NO: 167) Os12g05430
aacacggtcatcttatatagaactttcactaatattttgaaaatgttctagagccaatctaaccat
atcatttttgattaattaaaacttgaatcaaaatatttaaagagtgttagctgcacgtattttaa
aacatttattatttcttgagatagtatataatacattcgttcttttgtgcgcgaacacgcaaaaga
ttacacatcaatatattagaagaaacgcgcaaaagattataaagatcatgtgtgtgtgagggagct
gatcattttcacggcggaggtaaagtggtacagtcacatgtacatacactcattggaccatatgtg
catatctcacacatactgcacgtaaaatacgtatggtgcatatgccaacgtgaaatagcatcaacg
gtacaggtagccaccagctacacgtaataattcccaatcaattaaacgagacgagtcattagcaag
catcaacattcaacggtactcccaaaaaaaaaaaaaaaaacggtactaccatcatatcgacctccc
agccgtctatgtatgcgtgtacgtatgcacgatcgtacgagattttctactatacatccttgcgtc
agcgtcaacaaagacgggcgtatacgttgcatcatctatctatctatattgtgccacgaggaaatt
ggcaatagatcgggccatgaaatgggcccaatgacagacttagtaaggccgtgcgttacctcgcaa
tgtggcctggttaggccttgttcggataaaccgaaattccggcccatctactactaaagttgaagc
ccacaaaaatgaccgggccgaaattgaggcccataaaaacgagacctagttgaaggccgaagccca
cagacgcttccatccttccaacgaatccacgccgtccattCgccatcgccgtcgggtatataaacc
ctccctccgcggcattccaccctctcacccacccccaaaccctagctccccccgcgccgccgccgc
cgccgccgcc Figure 168 (SEQ ID NO: 168) Os12g04924, +intron ctattatcggacaacttggcatattgaaatttctactgtcatgcttccttgtcccattactacatc
gtcgttgtgttcaactattgcactacctccctcctagttcaaatctaatatcatatatgtaaccgc
aatggaaatagttgtatcatgttcaaattgtactactatttcttcatgttacataattctccttgt
ttaagtccatataatgtttctacaaccgagactgcgataggcctattaattatccgagtactaata
cgtcgaataagttacaaaataataccttccttaacatatgaaattgcgaaacaaccaacttcaata
catttttataacaatattaacaagttttaccaataaatacttctttatttattattaacataaaat
agaaaaatcgtttggccgtacttttttgcatctgggtcccttgccgccctctactggggcagcaagg
ggcccaaatgcaaaaagtacgagcgcaacctctttatgggcggcaaaaattgcaattagccccttg
ccgccctctgggggtaattgcaattttggccgacggcggcagacggcacggtcgacccgccgtctg
ccacgtcagcttgccgcccaccactggggcggcagggtctattttttgtatttttttttggccgatag
attatttctgtaaatattaaaaaaaatctaaaaatgaaaaaaattcGtgctacactgctactgctc
cggtgctccctcatctccttctcgattcttctgctcctccaccgagagcggggcgagcaggcgagg
ccacacgattctcctctcccttgccgcttccaacaccaagtctcgccgtggccaggactgagctag
ggtttgcgtgatcttcgggaggagggagcaggagagagttcgaggaggaggaggaggaggagaagc
aggtaatttcaatttttcagttcttgtttggcccttcctttgatgctaggtaaggttcttggttga
tcaaatagtgttgtggattgagaattgaggactaggtacgcttaattttgactaggaatcatgaat
tgggcggcctttatttgggtatcaaatgttccgctttggccaattgattaggatgattctttctgg
tgttgtagtcattcgtgtcctcatcatttgtcgaatagagggatatgatgaattctcgcatgctga
ctgattactggcgacgtaattaggaggattaattgtgcgctcctgtaattctacattctttggttc
caatgtaagttgtgggtcaatcaactagacattgatgactggatatttgctggtactgttagctac
aaaatgggtctagattattttatgatgtttcatgtttgtaatgacccctggcaaattgtgttgtat
tcattggtgtccccaatttcccctcttgttatctttgtcaactgttggttgggttttagctttgtg
gctttagaaatttgtgaggatatgctcaacaccgtgtggtgccttccccctcccagcctgtattta
gagatttcactaattcagtcatttagtgcattttccaatgcatagcatttgtttcttgtttgaatg
cattagaatatcgagattggcaggttaattagggtgtaatttgagaatctcttgggacctgagtta
gtatagggttgtcttggtttgttggctagttatgattaatatgaatgaacatgtaagtatgtaacc
atgtgccataaatatgatgtccaggaaaggaaaatcctggtagccggtacattcagtactggaaaa
aaaaatctgatttgcaagttttgctgttcagttattgtacttacattagctttttttatgttgcata
agacagaggtgcaggctgaaaaccatagaagcaagcatcctcctattttattatgttgtatcctta
taatttcaaatagtttcatctgtttttggtgttgtcggttgtggccagtcactcatacatcattat
tttatcacatattcagttgttcatgcattgcgagttgtctagttgttgatattggaaattgtagct
aaacgcactgtggataaaatagtttgattagtggtgttattcttgtgttgatggtcgcattatcct
tcatattcctgtgatgatgtttaaacctatagtttccattcctttggcatgtaatgggttagcatc
gatatgccaaagtaacttgttgaactttgagcatggacacaaaaaaacctggcatataggcgttta
agaaattgctttgtccttttctgtagcagcatgctagtattgactggatatagctgaatggttata
tggatgaagcagttagcatttgatcacatgtataatgatcacacctgaggcctgacaaatctggtt
ttccactggctgcatcatagcttgtgttagttactggagaaagatctgaaaaaacgaaccacactt
gttgctgattttgttcaacgaaagtgttctctatggactgcggagcagaacaatttatacaaatgg
gctagttggtgaatgcttgaattcaagtatgccacattgaacaataaactggagatgcactcctac
ctgatattgatatgtataagtatatggactgtttgttttgttcccctatctagaattattcacttt
tatgcttctattgttgtaggaaaggctaaatcaactttggtatgcaagtatgataccagggaaacc
acaaaccatttcacatgttactgttagcatgtttttttttttttgctgagacgtgtgattatatg
cttttgtatttgtttttttatctcaactaatatttgttcaactgcaatgcaggt

Figure 169 (SEQ ID NO: 169) Os01g73990, +intron ttcgtaaaaataaaaaacgaagaacgaactcgaccaaactagcctctctctctctcttaaaatc
tttcgatcatctcagttctggtcttattatagtttgcttttcagtttctgttagtttcccatcttt
agaaagccgaaaaatcaaccttcttcccacatcgatccccatgttatatcgtcttcactgttgctt
ttaaaaaaaatatagaatgtgaaaatgtctggttacgataaaaaggaaaacacccggatacgatta
ttgaaccatgtcgatattagctagagagataacaactgagtagagcataataaagcaattagatcg
ccatatccaacaaaatatggatggccatatcctatccatgcatgaccgtgaaccaaacacactcta
agttatgtatgttatccaagaagacaaaaaaaaaagatataaatatagctgaatgagagatactcc
atccgtccctaaaatataagagattttggttggaagtgacacatcctagtccaacgaatttggaca
tgcttctgtccagattcattgtaataagatatatcacatcccaccaaaatctcttatatttaggga
cgtggggagtagttcataattatagagttagtggcacatgatgggaagcaagtgagagttgcatag
gatttgggcagacttggcaggttggcttccgtcccataatatagcaatctaggatgggatggaatc
tattataggacaatgtatctagacatgactcgtaatatagcaacctaggatgggatgagatccatc
ctaggactagatatattatgggacggagggagtagtttatactttgggtaaaaacataaaccagta
ggaaaaaagaagcaattatttttgcacatttttctcttttacgtgaataagttttggtggtcgttc
agaaagagaatttgaatttccaaaagactgtataaaccgtgtagtataactgtaaaccaattggcc
accactacttctgttggacagaaaagcatgaagtacagtagtaccgtatttgtacaacatacagat
acagggagggagggcccacacaccagactagtctagtcgcatacggatcggatccacagactagct
ggctagctgctacggttgttggtgtggagtacacagaaaagaaaaaaaaaaggaaccatgtggttg
gggtcggtgagacaagcgcccttacccaccaaccaaactgactatgactggtgggcccttcgacct
actcccactatacaactctactgctcctcaatcctctcCtcctcctcctcctcctcattcgcgatc
tctctctctctctttctttcgtcgttggatccaaagctcctcctcctcctcgcctcgcgctcctcg
tcccttctctcgtcccatctctcatctcatctcttggtagttgccagttgggacttgggagagaga
ggagcaggaggcaggagcaagaggagggcaagatcgatcaagatcaacaggtcttctccctttct
cttctcttctcttttcttttgattagtatgacacacggtcttgctgggaacttttagggacaaact
tttcatcactgtgcggatatggctttccagataggataggatagcaaacatccctcataaattagc
ctatcctgaccttaattttgttgagaatctcctactgcacatttttttcctgtaatgttcctga
acatcttttcttaaccagtcattttcatggagcctatataagaatgtacctcactagtcctggtat
aaatattttgtggtttaatgcgagaaactgttctttgtaatctaaatgtgcagctcttgtttcatc
ttttattccataggattcacaattctgttgatatgtcaaacgctaaagaataatgcaagatctttt
acttcatagagccaaggaaaaatcagttttgcttacttctctatttccagttcaatcagatgaaca
agcctgtttaaaatatgctcagaactttagggagcttatatgttctcgtgtagtatatgtcaagaa
gctattttgactctgtgaacatgatgttggctgatcaaaagatatgtatttttttcaacaaactgtt
ctataagggaggttgctagggtcatttgctcattttttatacactgaaatgtgcttggttattgttg
cttttatattgacgaggccttatatggtgaaaaaaaaatcccctttacacaaatcaaactcataga
agtatttgttttgctacttgcaggt

Figure 170 (SEQ ID NO: 170) Os01g01307, +intron tatgcttgttcgtcagttgtgtttgtgtcaaatgagcaagtttgtaactgtggacaggatgacaag
tgggaactcgatggacaatgcatttgctttggtgcggaggcccatcaaatgcagcccagcccaggg
aggtccctatcgagtagtaagtgagtagaagaaaagtctgatctccacccacgggcggagTtgaca
tactagtagtagtagtactagtacacgaggagaagaagcaagaggaagggcatccagaatcagatc
cacaaggcagcagctgcagcagcatcgaccaggtttcgctctcccgccccaagcctggcgtcgagc
gcctcgccgtctccctcgacctctacaaccagggatccgcgtaactactctcctctcctcctcctc
ctcctcctccgatctctcctctcctctcctcgttgttgcaagggaacttcacttgtctttttcttc
tcggatctgcatctgaggatccgtcctctatttctatagatagatccagaccccttccatgtcgta
attgccaactaatcaaccattactctgctactgctttcttttctacgcttaaaacaaacaagcaat
taactagaaagccaaaagattcactgcatatgctagtatctttaaattgcatgggcttgtgctcca
tctcatcatctactgttatgtctttcttgccagattatgttatgctaataggattctacttgtaat
aaaccacacatggtttagcctatttacaatggtttcactctctgttatattcgccttattttgctg
aaattacatactaggtgacttgccagcttattcaccctatgcctttttttgttccctccatatgttc
ttacaatgcctgctatcaacatttctctctctcaagtccaaacttttccatgctgcccaaagcacc
agctttgcccaaaactaacaacttaactttcttccccgagaagtaataacaatttcaagctaaagt
tggtagttcggacacaacaacataactgactctttttatgtacagaaatatggattattgctaaat
tttagcttggaattatttactggatcttggtggaaattctgttaaagattagcttagcagcccatg
gagaatgagaatgttttaaatattatttttgccagtgtttacctggacaccaacacaggcctcaaa
ctctgccttggattcgcgtgtctgattcggcagaaaagaattgtacatgcaacgggtgcccgaatc
ctactcagactcaggatgtcagactcgacaaaaaaacatctgccattctgatatgatgtcaaaggg
tgttctggtttatctattcttttccctgaaagtgcattacctatagactacagttgcattaaattg
ccaaaatctgccattgtttttcttttcctatttggattagtttactttctctatgtgatatgatg
gcaagcaactatgtatatcacatagtaataaactgaccgtaaaatttattgcagaactgcctatga
tgtgagcattaatgatgatacttggccaaaggaggcatttgagcttgtctctggagaggt

Figure 171 (SEQ ID NO: 171) Os11g04880, +intron gatctcaaccctacgattaaatacgatcaacggcgcggattactttctactgcaaatagaaagcat
tggagtggggctctttcttctttcgtttctattcatgtacagtttagaaatgatttttaaatttg
aaattttatttattgaaatttaaaaaataatttttggtttcaaagttttacaaatctacacccta
aacctttctatgacgttacaacgcaccaatgaatatgtgcccgtcataaaaaaaaacctgtttgga
agagagagcgttaggggtgtaaatttataaaactttgagaaaaatattttgtaaatattttaataa
ataaaattaaaacttgaaaaaaaatcctgaaaaaaccggggaactgtctactggagtacagcccat
caaagagacgaggcccatagcccatcggccaccacAatccttctcgattcttctgctctccaccga
gaggagcaaggcgaactgcaggcggagaggctgggccacacgataccctcctctcccttcccttcc
cttgccgcttccaactccaagtctcgctgtgatcaggagctagggtttgtgcgatcttcgggagga
ggggaagcaggtaatttctgttttgcagttcttgttaggccctttctttttttgatgctaggctctt
ggttgatcaaatcgtgctgtggattgagaaacgcttcgttcgtacttggaattgaggactaggtac
gcttaatttttgtctaggaatcatgaattgggcgggctttatttgggtatcaagtcgtgtactaat
actctgatagcaacttctgttccgctatttagttcagtctgtgcttgcatatgctgtagctctggc
cgattgattaggatgcttctttctggtattgtagtcattcgtgtcctcatcatttgcagaatagag
ggatatgatgaactctcgcatgctgactgattactggcgaggcaattaggaggattaaatgcgcgc
tcttgtaattctacattctttggttccaatataagctatgggtcaatcaactagacattgatgagt
ggatatttgctggtactgttagttacaaaatgggtttagattattttatgatgtttcatgtttgta
atgacctctggcaaattgtgttgtattcactggtgtccccaatttcccctcttgttatcttttgtc
aactattggtcaggttttagctttgtggctttagaaatttgtgaggatatgctcaacaccgtgtga
tgcctccccccctcccagcctctatttagagatttcctaatccagtaatttagtgcattatccaatg
cataccatttgtttcttgtttgaatgcattagaatatcgagattggcaggttaattagggtgtaat
ttgagaatctgttgggacctgagttagtatagggtattagggttgtcttggtttgttggctagtta
tgattaatatgaatggacatgtaagtatgtaaccatgtgccataaatataatatccaggaaaggaa
aatcctggcagccggtacattcggtactagaaaaaaaaattctgatttgcaagttctgctgttcag
ttattgtacttacattagccttttaatgttgcataagtaacataggtgcaggctgaaaactataga
agcaaagcatcctcctttttttattctgttatatccttataatttcaaacagtgtcatctgtcttt
ggtgttgtctgttgtggccagtcactcatacatcattattttatcacatattcagttgttcatgca
ttgtgagttgtctagttattgatatcggaaattgtagctaaatgcagcgtggataaagtagtttga
ttagtggtgttattcttgtgttgatgatctcattatccttcatattcctgtgatgatggttaaacc
tatagtttccattcctttggcatgtaatgggttagcatcgatatgccaaagtaacttgttaaactt
tgagcatggacacgaaaaaaacctggcatataggtgtttaagatattgctttgtcctttctgtag
cagcatgctaagtattgactggatatagctgaatggttatatggataaaacagttagcatttgatc
acatatatagtgatcacacctgaggcctgacaaatctggttttccactggctgcatcatagcatgt
gttagttactggagaaagatctgaaaaaacgaatcatacttgttgctgattttgttcaacgaaagg
gttctctgtggactgtggagcagaacaatttatacaaacgggctagttggtgaatgcttgaattcg
agtatgccacattgaacaataagctggagatgtactcctacctgatattgatatgtacaagtgtat
ggactgttttgttttgttcccctagctagaattattcacttttaggcttctattgttgtaggaaag
gctaaatcaactttggtatgcagtaggataccagggaaatcataaaccatttcacttgttagcatg
tgtttttttgctgagacatgtgattatatgctgttgtatttgtttttttatctcaactaatatttg
ttcaactgcaatgcaggt

Figure 172 (SEQ ID NO: 172) Os02g34510, +intron cttgtgtggaaggaactggcaggccaatggatgagggaccagatgcaagaggggaagagacggga
gaaggatatgcaggcagctacaggtggagaattcgcatgccttccctacatgagcaccgacagagt
cgaacccctagctcatctgaaattaggaacatgtccaactcaacaggaagtacattttggggaaaa
acagaatacggaccaacgggatagggggagagcatgtgggaggagggaggagagtaagacctata
atgtcggccgaggcagccgccgaccgtcgactccctggcatcactggagcttggagtagccaattt
ggggatggattttgaatcggagccctgcccctgtgcatttgggcagtgggtagagtgaggggtta
acgtgctaaatgtctggatgagacggggtcgtttctgaaagtttcaacacgtacgacgtagatact
ccctccatcccagaatataacaacctaaaatgagacgagacctatcttaggacaatgtatttggac
acgcctcatatataaatacattgtccatcctagattgatacattctgagattggaggtagtagatc
acagacgtacattttatatttaacagaaatttactatagtttacacggtagatgtagaggctgttt
ggttcttaactaacattgccataactcactttaggcaatgttagataagtgtggcttgtcacagtt
tttatgacctacaaattataagccacaattgtggcaaagttagacaaagaattgagtctataacat
gtggggtaagatggtaagaaagtacgacttgtcataaccatggcaataaaccaaacataagactct
aaagacatgtgacagcctaaaatatggtgtgacaagttgaagcattgagccccgtAgtctccgcca
catatctctttccttcttcctcacccccaccaccacctcttctctttcccccaccaacaccaaccc
cacgcgaccacccccaatcctcgatcaaacgccctaggatttcatcgcaagcaaggaaggaggaga
ccaaatccaatccaatcccccaggttatccccatcccgaaatccccccacccaaaatgtgttaaa
ctttttttgatgtggatttgttaataatactccggaatgaggtaaaattgctgaactgctatagtg
cctaatgccattaaattgtgatttgtttggagtcatgagaaaagaagagaaatcctttactcattc
tcacatgtctacatccttagaatcttagagctttctaatgtgatatgcggatatgagcaatgatcc
taaacccactttacagctgttatggatgtaatttatgtttgatatgttaatttagttagaaatagc
catcatgtttcacttcactaataactttacaatagttactgtaactgaactttacataaattgtat
catcaatttttgatggcattgcatttttcttaaaggaaaaaaagaatacaaaggggaaacatctcta
tgcttatgattctcagagtttgggcagcaaagtcaatcccatgcatatcaggggttcagcgccatg
taaatgttgacccttattctagggggctattgttctagaatgcaaaattcttccgttactaaataa
cagagtttcacttggctccaagtaattgaccctttctttaataaattaaaactggctatatgtatg
gtatggataggtctatgtgctatttaaatgcctagcagaaatattcaaatgtctcaggtaattgag
gttcttaatgagttgagttttgtattttaaaatttgctctgatagtcaagtttgactttccttgac
tttattattatttagtgaacacttttggcccttctaggaacgtaccaatggatgcggttatacttt
ttttttcctttttcaatgcaaagttatgtccttgtagttcagccaaactttacaagccattttgtc
aatctacattactgcacaattcatgcctgcggtcagttcatgtgatcgcagctaagattcttttgg
tatactgacctactggataactggatgttgcatgatctatgattaaatttcaaatcatgatttaca
gtaatttatcgttgtaccttgatttgtgacaaaggaaaccatgcatgtatgtctctcaatggttat
atgttccttctacagtttcatggattatatgatcgcatttagtaccatttcatgacactttgtgca
gcttgattggaaccacaggaattttgatttttatgctttgcttggtgcgctgttctaacataatct
acttttgctctcaggt

Figure 173 (SEQ ID NO: 173) Os02g44630, +intron taacttttatatagaaaatttttaaaaaacacatcgtttagccgtttgaaaagcatgcgcatgga
atactagtaagagcggttgggagtcctttgcaacgaaaacagccttagtagcaagcacaaactaac
tcagctttagaggcccctcatattgatgtttaacttgttatggggcatttatttctacacagtctc
atttatcaactgaaactaaaaaggttgtccaattccgtcctccttttgtaacggctcgcaaataca
atgggttgtttagattcatgtcattttaaatcatattatttttataaagttatcaaaatgtacat
atatttatttattttaccaaactttactaaatgagataatccaacaaatggcatttaaagcgttc
aaatccaagaaatgccatcgccgttatgcttccgtccgtttcacgccgttaaaatacaatgttcat
cctataacacttaatggtgtggaatggacggaaccctaacggcgatggcattttgggataaagtc
gtttgtacgatggcatttcttagaactcatatttgtcgatggcatttttgaatttggatgattgt
caatggtatttttggattatctcttagtaaatacataaggaatcatgccaaaacttgacaatatt
gtcaacttatcaaaatttaattgggattattttggcgataatatgaacagcccttacatttctgaa
gaattatagctcaaatatggctatggccctgtttggattcggagggctatttaatagccctccgga
atcttgctatttaagagtattaaacgtagattactgataaaactcattccataacccctacgctat
tctacgagacgaatctaacgaggtatattaatccatgatttgctacagtaatcagccgctaatcgt
ggattaatatacatcattagattcgtctcgtaaaataggctagggattatggaatcggttttatcg
gtaatctatgtttaatacttctaaatagcaagattccgaagggctatttaatagctcggagcatcc
aaacaaggcctatgtttagatccaaacttccaactttttctatcacattaaactgtcatacataca
taacttttcagtcacatcgtaccaatttcaacccaaactttcaactttggaagaactaaacacagc
atatgacagtgcagttcagctcaattttgttcggagcctaaaaaaaagaaaagaaaaaaagctcaa
tttggataaggctatgaataaactcaaaaaagcatccaacctaaccaccacactggcccaccaggg
cccacgctccactcccgtgatcatcacctccttccctttccagaaccAccttctccttccttcctc
ctcttcttcttcagtgtactctgcctttataacaccctactcctctctctcacctccaccatctag
ctcactcacacagtctccactcacacgcattgcagaggagaggcgacaggtcagttcactctcctt
tggcttcctcccccaccttcaagatctcaagtcttcaactttgtcatgattttgccttggtttgtc
ttgctagttgatacttacttgttacctgcactttgcttggctcagtagtttcttcatactagcatg
ctcactttagtaaagcatgaggtatagaatcatgtgtactactactgctccttccataagtagcaa
gactttgaggcatatggcattaacactgaataattgatgaaagacttttagttacctgcttttggg
gtgttagatcagtattagtaactggaaattcactaaatttgttgtccatgctcttgtagttttaaa
gaattattatagctttctacaggtgttgaatgcaccaaaaatttatgacactaccttttgctcttg
taccatcatgtaccttgtctgcgcaaagatttgtcgctggcatattgtactgctgtggtatgtgaa
ttttgttcttatgcaaaggtttgatttacgactagaagattaaggatttaaggtcatccgattgat
ttaactcttaacccagcattttcttcggtagtgttctaactgttgatgctgaaaccacacaaatta
tcacacaaaaatatattatttttagttcatcaaaattgaatgtgcacttggagccttggaggcaaa
gaaatatgtgatgccaaaatttctccttggttaatcttcctaccagaatattaacaaaactatat
gaacaagtaaatatcttgtgttgtcaacttatacagtctatcacaactcgcaatcttagaagttaa
tttctgtaccagttttatataatgcttcaaaatctcaaatactaccttgttaatctcaaaatatga
atacatgagggtacactatacagtcttacttcaactgtcatgacaactgaccacaaaacaactacg
gcaattaagggcactactaatatccattatattgtctgttactgcaacaggt

Figure 174 (SEQ ID NO: 174) Os04g32710
ttgggtcatttgtcttcaatttttttatcaatttaatgttttatttttttgggtcatttgtcttc
aatttttttgtgttttatttttgggtttttgggtcatttgtcttcaatttttttatcaattta
atgttttatttctgggtcatttgtcttcaatttttttgtgttttatttttgggtcatttgtct
tcaatttttttatcaatttaatttttgggtcatttgattctcttcggaaagaaaccaacattct
ggactaaatcaacattctggataaaatccttgggaagtaatagtcactactagaaaaattatttgt
cacttcgtagaagttctgaattaaagtgagatctctttaaaagaaaccaacgttctggataaaatc
cttgggaagtaataggtactcccagataccaacattcaacagcacagcaattcgcccttgtatcat
ccgaaacgcacccttacatatattcatcattaagaagtccaaaatttaaatttgaaaaaaaaaacc
agaccatattcgctccactttatgttctatattccttgtgcaaatacaacagagatggcagaagat
gaacaaaaaagaaaaaatcagagacggcccaacaataaacagcccatccctttttgggcctccact
atccagacccacggcccagcagtagaagcccccacgggagatctcgtcgcgtcccatccatccgac
ggcgcagaccacctcacgcctcccctataaataccacgcctccaaccctaaAccctctcactct
cttcctccgccgccgccctcctctccgggaagaagagaccagagcgagcgcgcgcgccgccggagc
aaacccctcctcctacccttcagcc Figure 175 (SEQ ID NO: 175) Os04g30730
atttttcctgtaaaataccattgactattatgtaggagtatgtattattgtttgtcattagcaatc
ttaagttatgcatagacaatcttgaaagctcttctacggcgtggattcaaagtgagccaaaatgcg
tcacaaaaataagaacaagggttaaaacattaaaaaaataatcctgctatatgcaatgatttagag
aggcaatgcacaatgatttagttctccttcaggctttagtcactttatacaaaaacacaaaaaaga
ccaaaaaggaaaaaagaaaaccaaaactattttatatataaaaggcccactacaagtaattaccca
ctaggcccataaaggaccactacaagtcattacccattaggcccatcaaggcccatctaaaatttc
tagggtttcctcatcctcgatggggtttatccTtcgagcacatatataatccgcacgccgccgcct
ccctctctgcttcgcactccattttccctctccccgctcgccgccgccgccgccgccagccaagct
cgccgctcgcc Figure 176 (SEQ ID NO: 176) Os02g30050
taaaatacaatcgtaaccgactaggatcttgggtattaccttgacatacaagtttagaatttaacc
caagtcattttaaagatattctatctatatatagcactccatacccagtcaaactatacatgccgt
gtatgtatggggtatccatgatctccacaattcatttgtcaagtaagtacttcaatagtacaattc
tgatagtgcgagcatagtcgtgaaatacgacattcacaaaaccgatgataactgctcgaaaaccac
aggtatcatcagctttattgctccggctcaagctaaaagttcactaaaatccggtcaagtatataa
aaactcaagctaaaacttaaattttgcattaaactgtcatctccgagctgttaacatcaaaaccga
caaatccaaatcctcgaatccttatgggaagcccatttcaactcaccttaaacagtcaatgggccc
agccatctatcataaagcccaacaaggcccatgaaagcccatctcaactcagcctagggttttttt
ccactccgcggcgtctcgctgtctctctctcctctatatataagcctccgccgccgcctcctcacc
tcTtccccttcctagcaccgccgccgccgccgccgccgccgccgcccgccgcgccgcctccgtcgc
c Figure 177 (SEQ ID NO: 177) Os01g05490
atttatatttattccctaatacaatgaagcatgcatttatttctagactagagacatttaattatt
ttgccactcttaaatgtggtaagtaaccatttaccatgtatacccacatgtcatagacacgtaagg
atccaaatgttaacacataggtgtcagatagttaaacgtctaacctaaaagtaacaaatatttaaa
tatcccttatatctatgattgaaaggaaaaaagtctaagtacaattgtcgagatatggcaggtttg
gtaggtctctaacttctcaacttaactcaaataattaagtttagagtggaattatggagcaccttg
aatccagattcatctctctaatttgttttaatagcactgctctactccctttttagatggaattgaa
atcgtttggttggacttcatccctaacctccataagaggtgaaattggagctagaagtatgtcaaa
catggccatataatctaagaacagcttatcgagatatccaacaaaaaataatcgttctcctatttc
agtgagtaaaaacctgatggtccaaacgagttgggctgaaaatgggacagtgtttcggtgagacgg
gcccagcaagaacataggcctggttggcccctattcccccctacgttttctcggcccacccaccgt
tgggctcggctcgggcctaccatcgggcggagaggaggcccaactcgggaaaaaggagaaacagaa
aagaggccgaaaaggcgaaagggatcgatgaggtggggaccaccggaccagcgagagatgcgcatc
ccgatgcagcacgatgccgcggcgccctctgttccgctccgcgccgcggccacgaaaaccacgacg
ccgccgggatcatctgcgtccgccttaccagtggccgtcgctgctatggatgacttaagcagtttt
ttttatgtgtataaataaaacagggtagttaacgagtcatactttggttctggaagagaatatctt
tttaggaaaaaagcaataggtcatcttactctttgctacaggtgcaataatttgcccggacaatag
acctgagtatagtttatttagttctaaacaatgcatcagaatatggaggaaaaagatggccttagt
ataggatcaattgagatgtacagttaaacaaaaaagtagatatggatttacaaaattgatgcggaa
tattatatccatgtagtagctcccatgtactagtttcttttgcttgaaaaaataaaagaagcagat
aatttctagagaagtccagagaataaaaagattggtggtgggagtgggacccacctgtcattgtcg
gaggagcctgcctcgcctcatgtgatcccatcggaggccacacctctgctccccctAtattatcct
gtccttggtgtttttcttcctcctccacaaaaaccaaaatccaatctccagctctcttcccccccc
ccccccccccccgcgtccagttccatctaatcagcttctcgtcgag Figure 178 (SEQ ID NO: 178) Os01g61814
ccagccccaccaaggggtagagatctcttgaacggacctgtgcagagaaaagctggaccgagtcca
agtgagaggaaaaaaaacctcatcaatggcgacgggacagggtagacgtaggccatgtcccctgct
agcagtaggcatgtgcagacagcgccctgtcctatgcctgtccgccgtcacatccgtcattcctgc
tgctagtggcctgtcagtgtgcatgctcgccacattaaatacagcgtgccacggccgacaggacct
cattaaacacagtagttgggcgctgggaacgcctgcccagggcgcacacacgaatcacgaatcaga
gcgaggaggggtcccaactcggaaacagccaccacttcaacacccccctcccggagggggggg
ggggcggcacgtgggtttgaggcggcttcctccctttgtatgggggtaccctgggcccatatcac
tgacactcactttcttgttcgaactaaattgaccactaacaaatatttctattatagggagcatag
gtgcgcatccctgtacaataaggaaccacacctctgatagaactataaggatcatgcgccttaatg
cttgatctaaagttaggcgccagttccacattgcattgattttcgtcaaaacttttcacaactata
gtttaatgaaaggcatgcaaacagttttaacaagcaaaaaataacgataactacgttcaaaattag
atgcacttagatacaaaccaagaatcctagttcatccccactaagtgtagataatgctacttctct
cttctctcattaagccacatcaccccaataatttatagcctttggatgatagatctatggtttaaa
ttgtctcttctttcttctctcttaaaaatatgcaatatcaattattttagtctcaaaattatatc
aaattattttagttttgataatcaaattacgtcttatttgtacatattatgcaacttaattttccg
cagcacacggcgggtagtcatctagtaatattatatacgagagatagtcgtagttgaaacaaagcg
actagtaattaggcatttaaatatttaacgtgcacaactaatgctacaaaaaaaggactcataatt
cttaaatgaaaaataatttgtgtataaaatatttatatacgtgttcttagcaatttaaaaacaaat
actaaaaaataaacttcgaaatttaaattttaactgataagtataagcaaaagcgaaaaatgtgag
gcccagaaactcccgcgatccacttctcaacatctgggccgtcgtccatccagcacggatcttgaa
gcaggaaggcccattagcaaaccctagacagcaacgccaccgcaaataaatagcttcgctgccctt
ccccctatccctcTcctctattgccgccgccgccgctcccagctcgtgctcccctcgccgccgccg
ccgccgccgcctcgcctcctcggagatcttcgctgcccttccgccaac Figure 179 (SEQ ID NO: 179) Os05g11780
atttatagtctcatgctaaattaaattgttgaccgaaatatgaacaactatcttagtcctcattgg
ttacatgcatagtataattcattagtttctggtgggttttgtttttataatttttagaagtctcgt
caaacactatcactatagtccgctacggtccatccgctgccttatctatttattgtcattgtgatt
ttaaaaattgaacataattatcgtttgagtttattatttttactctctataagtctagtaaaatcat
tagcggcttcgtcattatactcctctacagcttgcccgctgcttccgctctttattgcttttgaga
ttgtaaaagtccaacattattatcattggggtttattttttactttccagaagttccactaatcg
tcgtgactggtgctgcttaatggcatgctcgttgttcctcctcttaatcatcatagggattcaatt
tgggactctgtttatagtttttagatgttccatcaatcaccactaccctgcttcattaccttctcc
catcttttattgccatttgtcattactgttctagatgttttttttttgaaaatttcatatttttca
ttcctatatttttttatttatataaattgtattcctacataaactcttataattattcttctatttt
ctaaatttattttatttattatttcgaattttattgatcgtgttttagatggtcatttctttcaat
agtttttatttttttaattataaattttagctatttataaattgtattcctagttgaactcttattt
attttaaattttggaattcatttttatttttttatttcaaattttaatttaacaataactgaaattca
caattaaaaataagcaatatttaatcccaaattttaatttccgagtcgtaactgcggcggcaacg
acactccgacggcgacggcagcaaatcccccctcccccgccgccgtccggtgacgtggccttcctc
ctcttcccaccgcagcctcaagttgggggcgtggcccacgcactgggccccacacccgcccaccat
agctggtgcccacactccaacctcccaattcctccatgaacgtagcccaccatacaccacccctct
cacaagttcacaacacctcacccacgggcccacctgtcagtcactcaaccatccccacccatccgt
agagcgggtccacccgcccagtccaccatcgtcgtcacccacgaggagacgccgcagcacgggaac
actctttttttcttcaatttcacaggaaataacattttttGtaatttcttttataatttttttatt
gcgcgtcggcgttaataaagcgcaacggcaggcagcgatctaggcgcccgtcgtccactcctcctc
gccttcctcgccttcctcgcttttatcgccgccgccgccgccgccgcctccgccgccgccgaggag
taggagtagtaggaggaggaagccggtagccggaggaggagcggggag Figure 180 (SEQ ID NO: 180) Os03g14450
tgttccaaattcagagcagcttcatatctgtatgagcattattcaggaatgcagactgccatagcc
catagactaccgacaggtaaaacaaaatactgctccgtgatgttattaagcaactagacacctgaa
atctgaattcgatgatacacatttgaacatctccaagcacgaggagatatcgatccgtccaagtac
caacagtgcagtgtgcaccatatgcaggttggatatgcatattttgacaactatagacttggaaaa
cccgtttcagtggaacctgtgaaaaaacggtgcagatccttatgctttttttgaatccacaagtgtg
ctcaagctaagagatggaagcgtctctatgctcgactgagcggccatgtttttctccgtttcagaa
ggattggaattcggaggaggttgcaaagaaacagccaagcaaatggcaggagtccaggagatatca
gtagcagatcctcgggttttctcactcgatgcagtgacatgtgtgtgcttcccatctgtgtactcc
aatcttaccaagatcagataaatattcgacgtgattcaaatttcgaagtaccaaaagaaaaaactt
aacttgcaacatcacgtatagtgaccccagattggcattcatcgacacgaacgaacagtaatacag
cccaagatgtgaagctgcggccctgctgcggcggttccccgtgggctggactaccagctgcaagga
gataggaataagttcagatatcatccctcaactttacgtcgagtttgtatgacatccctaatcttc
aataccagaaatcttcacccataaactatacaaaaccgtgtggttctcacagcagtatgattaggg
atgaagatttgaagagtgaagatttctggtattagggattagggatgtcatactgattcagcataa
agttgagcgatgaaaggtgaacttattcccaaggagatacgcatgcaacgacgccAccacaaacgg
gccaccacaccaacggcccggcaattgcggcgttgcagtccccgcggcgcgggcgaatttgctctc
cgcaggacggcgttgccacttcttcggttatcgggtgggccctcacttcctccgccgaaagccacg
cacacgctgcccataaaaaggcgacgctgttctcaaaacctcagaaaattcctatatcctctgttc
gtcactgccttcctctccaagtccatccccttccccgatctaagatccatccgatccaggcc Figure 181 (SEQ ID NO: 181) Os01g17190
gctagagcatgtctttgcactgctcgttttaagttgctatgtagcttgtgcatggaccctacttga
gaccacatacattatggagtatatgtctgttcgatcagtgtattggccctacatcttgttgaggtc
tagctaaagcatatcttgcattgttcttgccctaagttgctctagacaatgtgtacatggacttgt
tgacctcgtctgatgcacatgacacatgctaatttttgttttaattactaaagcccatataggag
aaatgacgtcacccccctagcccaatagttagagcaaatcgtgtgctatcagactgcagaatgaaaa
agcccatcaagtagcctagaatggccagacacgcactaaagaacaaaagatgcctgctcgatcgag
ttctcttcttcttcgtctaggcaagaagatgaaggcaaggagtctccttttctttcctacaccact
gaccagcaagctctcaatttgcaaagagaacacaccactttaagtgacaacgtgatcaatctcagc
gaaggatcctatagacccctagcaccctcctcccaccttggccacccagtttacactatattttat
gtcgacgacaacatctagctatttcttatgcagagaaacaagtttcaagcattcaaattgaatgta
gtttcaatttatttataatagctatctttatctcagtttcttaattagggatttcatttaatcagt
tttcccccaaaacatagggtttctaatttgacaattcatttgaaagcaattgataaacaaatggta
gagtttggaggatgaatgcttgaagcttgataaacatgtactaccaaacttttgctaaggcaacat
ttagctctacaataacaaaccctacaaatcactattaaatataaattgcttgatatgtcaagtact
agatagttttattgtgatatactattatgtttgggacaccagatcattttcgttttggatttacta
tgattgtttaggatcctacttgagaccacatacacataatacatagtatttgagacctagctagtg
catgtactctgtccattcccattccaaaatagaggccgcttttggattaaaaagttttcaaaaaaa
aaggagtttagaagtaccttttatcacatcaattcaaaatttctctatcctaccccttaaatata
ggtattacagtaatttttttaagcattatttttctatataacttggatcgataactatagaatag
aaggtagtaccgaaccgttcctcctacaggcaattccctcaacctaaaccattggaagaacgtgcc
aagttggaagcctaacctagcactagtcttagaaaaaacagtagaaatcgtgagttatctctgcaa
taaaaaaGgaggtaagcctacccacactgcaagtctccaactcgggcaagctctcctcccccacga
ctcccctctccttcctctctctctcgctcgcgcgcgcctgcgtcgcca Figure 182 (SEQ ID NO: 182) Os10g17280
gccggaaccacgctggcagaccagcaggggtcggtgcccgaagcaatagatatgaaattacatttg
cttagcttagataattaaaacccatagaaagtcctctctagcctagcctgcctaccatctgttgtt
gttcttggatagtcttagccttatgtagattacacacgttctctgagtttgatatccttttggagt
cacccgaaggtgaagtgctacagcggtattccgtgcgcttgcggatttatcagtggtcgtaagaaa
taccaacacgggccggccaaacaagggaacggcatgggaaaggagttgggccgacggcccaagaaa
gaaaaagaagaaaaggaaaaagaggaaaaagaaaaagggattcatgtgatttatatattgcataga
attgattttaatcggttaaaattatttccgaggcgctgaaaatttcgctaaaaatcctgttaatgt
attgtgacatgtggaacttaagaaaaattccacgataccaattgcatttattagttaaggttcatc
tctaggttaaattaaacaatttcttcagataatttattaaataaattttaaagctagaaaggggaa
ctttaggggcatgatacatgaccataggatatagggtatgcattatcccctgacagaaaactctat
tcatcccttaagggaatatacccttatttttgcatgtcacttaaaagttatcaaaaagaatttgaa
acaaattagtaagatagatcattatgtgatatgtcactccacaaacatgcacgttcaaattcaact
tatacaagtagaaacaaaaataaaaaattttgactattcaatatgaataaaatgtgtaatttgcga
tcaaaattgttagaattgtataagtcgaaattcaacttgcatgttcgtggaaaaatatatcatatg
ttgatctatatatttttattttttttatgactttttttatgattactgcaattgttttaaaattgaga
aagtaccaaaataacaaataatgatacagaaggtggtaatcagggaaataaactagtaaaacattg
ataagtgtgaaataaaataatacaaaagttgatatgaagaataaactagtagtacatattgtggta
gttgggaaataaattaataatgtgtctaaatcacaaaatttatatattgtgacaaatttgaaagat
aaaatcatctatcctgagacagactgacggagggatcggagtaccccgtaacaaataaagaagaag
aagaaaataataacaataatagtaatagtaaaagaagaaaaaggcctatttcacttcttggaggcc
cattagcaacaagcggcccattcccaagctggcatgaggcatcttagggcttgtgccggtgtgccc
tcacctGctgccctcccaccccaccactctccctcctctctctttcctcccaacctcttgcggcca
cacgagccaagcagcgagacccccggatcgaaacgcacaccggcggcg Figure 183 (SEQ ID NO: 183) Os11g06890 tacttgatatgttgattttgagatgtttggtagcactctaaatccataatatgctatattagaaat
ttatggcttcctcaatacaaagattggatgacaaaatatctccaccaccgtcaaatcttaggagta
caatctgcattcatgtcgagaagagtcagatagatagttcacactcaacctgaatggagttatcaa
catggttaatgccagggtgaattataaaaaacttcgcaaaaccccacgttgccttaatcttgaaat
ggcttaaatgatgactaacaaactattgtcttattatagttaggcggaagacaataggggagattg
aggaggagatgacctacaagtggctttgcactgtattgtttttttcggctcccccatggccccaag
acattatccatgagacaaccgaacaaacaagaagcatcaataccggtagcagaagcacacaccgtc
gctcaccctgctaactgctttgtactagccgaccgccactagctgttgctaccgtatccttcatct
agaccacccacgaattaactgaaaccaccgtcgtgtatgtcccataaaatggtctacttaggatta
tatacaagtacacatgttgatcatgaacatgaaattttgaatacaacaatggtatttgatcaaatt
tggataactttacattcatacacaagatataaaataatattgctataatatgttactcataagcat
gaagataataatactagcactacaaaatgtcacttgatgaaaccacaattgatgttaacacataaa
tttcttcccttccaatctgaatgccctagattaacatggagaaaattttatctgcagataacact
aaaccggatccaaaatttcccataccaaggctgtgtttagttcatgtgtcaatttttttttaagtat
acggacacacatttaagctattaaatgtatactaataacaaaaaaaattggtcacgcgatttacat
gcaaactgtgcaatttaatatacattattagtatattatcaaatcatggcgtaattaggctcaaaa
gattcgtcacgtgatttacatgcaaactgtgcaattgatttttttttcgtccacatttaatactct
atgtatgtgtccaaacatttgatgtgacagaaaagttggaagttcgaagaaaaatatttgaatcta
aacgaggcctgaatggaaataatcaaaaccgcaatgggctggcaaactgtcgatttcagataattt
ttttagtacggacaaactgcagggacctaaacgaaaaagaaagaaaaccgtgacgtcgctcgcttc
cagagatctTcagatcagatcagaaatccccaaaaaaaaaaaaacacaacaaaaccaaacccgacag
atcttctcttcttcctcctccctttcccatcttcgacgaggcgacccggcgcgagagaagaagaga
tcgatcgatcgatcaaccgatctcgccggagaaggaagaggagcaaag Figure 184 (SEQ ID NO: 184) Os01g16890 tttggacacatgcatggagtattaaatgtggacgaaaaaaacaaattacacagtttgcgtgtaaat
tgcgagatgaatcttttaagcctaattgcgccatgatttgacaatgtggtgctacattaaacactt
gctaatgacggattaattaggcttaataaattcgtctcgcagtttacaggcagattatgtaatttg
ttttgttattagactacgtttaatacttcaaatgtgtgtccgtatatctgatgtgacacgccaaaa
ctttacacccctagatctaaacatcgcctttggcttcaaaccaaaatggcccaatcattttgatta
aaaaaaacttgatatgcagtaatctatattttagaaattcctcaatgggccttgagaaaataagg
cataaacactacaaggttagttccaactacttaactttctataatcttccattccttgtcagcttg
cttcctatcgaggattgtactaatgaataagaagaccatgaatgaaaggatgccacacccttatat
cctgtgtctttaatttttaagaattataccatccttcttagactacttcggtagtaggaggggtt
gcataatagatatatcaaaggataagatcccaactggtttgctatgggtcacagacattttttttt
ggatttctgttttaaaaataattttaggagaaattattacttattttcttatcaatcatgaaaagg
gagtcaaacagcgaaaaggttactaagaaaaccacaaacattaatcataacatcatatgaatcaag
catgctctagccaaattttactatacatcagtcaatgttggttcgttcgtttcttaatcatccagc
atttgataaactttggcacatttcttaagcacatgcgtgtggcaagacagaattgttcacaggaag
aaaaaaaaacccacatctcgttaaccatattttttactgtttaaacatttttatttttattattt
ttttaaacgaactattccaaaacttattttcaaaacgcgtttggcgtggcaaaacaacagttcacg
tcactccgcagcgggcatgacaattttgtcctgccacgccagcaagacaacgttatcacgctagcc
agactgacatggcaatattatttttgccatgccaacctgcattacatggacaaaggttcatatcat
ggaaataaaatttagaagaatttatttttaaaactaaaaattaaaatgctcaaaaaataaaaaata
tattcttaactaacctggtgaaacaaaagaagcccaacagtcaggccttatccaggaaagcggagc
ccaagcccaacaaacccatttacccccagcgtgggcaggcgaaccctttccctcccgtgcctatat
aaggccacaaaccctaacgccccccActcttccacctcgcagtcgccaccccgagcagaagccgccg
ccgccgcccgaaaccctcgccgccgtcgcttctcctcggggcgcagcc Figure 185 (SEQ ID NO: 185) Os03g58430
cggcgcaagtggttgcgttggtaggcttctcggcactgaggagtggacagagcagtgcccagatta
ggttgcaagggtacatggacgataacaaggttgtctcgacatagcaacatgctcatcagtgttggc
cctagggttcccttaccgtttttggcgtggttattggacccccacggcaaggtggttatcgcgaaa
ccgcgcggtaaccccgagagataccgtggttttaaaaactgaaaaggttaccgtgcatggtaatcg
cgcggttttgtgtggctccctgatagtggtgagcctagggacaatgactaccaatggggggttctac
acctagatttgactgagtgatgatgggacagtattgtctttacggcgtgttggtgtggacaatgat
ggtggtggtacaggtgatggccctaggagcagtggctactagtggaaacttttcatccatatctga
ctgtgtgacggtgagggtgatgactattgtggcggtgcttttcggcatggtagtggcaatgacccct
aggggcagtggctgctaaatcgtcggtttataggcctaaatcgaaccatgtggattgggaggtggc
tctagctagtacgacaatgacaagcttggtggctgtgctagtggcaactggagaggaaggatccaa
cctaaagtcagacccgacgctcttttaatgagcaagacgaggagcggacatagggcttgttggagg
tgctggcaacggttaggaagcgatgctgaatttgagacctaaacagggtttacaaaaccgcgcagt
tatcgcggttaccatgcacggtaatcttttcaatttttaaaaccacggtttatctcgtggttacca
cgccaaaaatggtaagaggaacctagcatccatttccacgccattcacatccatgccagatttgga
acgatggtctacacatgaattctacctggactgcactgtttcatataaaaatccacttatccataa
tatactattttgcatacataccatagtcaagagattgaatctgctggtattgtgaaaccagggtcg
caactttcttttctgcaagtaaccggattggatgttaatccatccatttacacagtattttaaagt
acggaatctagctgacgcaaccgtccagtgcacaaagcaaaccatgcaattcgtcttctttttca
aatagaaaagcaaaatgtcaacacaacgccgctgaccacgagcggcagcgttcactctgggcccga
gtctgcaggcttgcagcggaaggcctcgttacagcgtcgaaatgggccaggccaggccgggccgga
acacgtgggcctagcccactcaaacagcccttgacgcgcaccaccaaccactatataagcttccga
gagctcttcccccaaaccCtaaccgccgccgccgccgtctcctcctcctcatccaagcagctcgcg
cctccgacccctcgcctcgagctccagctctccccaaccccttcaaca Figure 186 (SEQ ID NO: 186) Os10g30580
aaaaaaaaaaaaaaacatcgctgcatggccacacgcattcctaacattgcgcattgatcaaggaggt
ttaatctaaaaggaaggatttttttttggctcggtaccatttgcaaatatgatgattaaattggaa
tggggtgagtatatatttgtcaaggtctttttagctatattgatagtgttctgcacttttttttt
aatggaaacacagatgagtgtatatacctcacgtcagtaaattagaaagaagaatctgttctataa
ttctattccatgtcaagctaaggaaaaagagaaggaaaaaccgaaaaagaaagataactaatcaac
ttttcttaatgggccagcccaaaaggtgcacacctcagtccttgtttcactatttgtgagtcatga
tccatgtttttggggggaaaaggaacaatgtccatgtaacaatgactgtgacgggaatatacaatgg
caaagaattcaaagttcgcccagactaaagtgaaacaaagaaaaacatagtttatgtaggaaaaga
aaaaaggattggagtagacaagatcgtaaaattctgatctccaaattttgtttctgtgtttattac
tttattaggcagatagttcctgccgcttgatcatgggctgcgttctaaggagccgattcagttcag
cctctcttattttcctttagcgcatttgttttaaattattaaatgatgatatatttcgtatgaatt
ttttatatagtatatgttttctaaataaataaaaaaaatctatttttttaaatttttaataattaat
actcaattaatgatatgtttcctcgttaattagctataaatcaatcaatcatttgagtagaacgca
gatcgatgggttgacacatgttctcactttatactagaccaatcctaaaaggaacagctaatatt
tttcatggaattcttgctccctttccctgtcgaaatttctggattcagttcctgtgtttgagtttg
atgctgattttactcgattttactttcggtgttttgagtttgcgactgatttttattcaatttcgc
atcacaattcatacacccctgctctccttcgggtacaagttcgggaccggataccaaaccccctct
cgcaatccgtccccaaccacacccatccaccctcggggcccacctccctctcgcttccatgtgggt
cccaagccggctactctgacctccggaagagcccggaacgttccatgccaggtgggccccacctcc
cccgtggccccactcctcagtgaccccccaccgccgtacccgaacccgatagcgagagagagagaga
gagaaaaaaaaacaaaccaaaccaaacccccccgctGcaagaaagaggcttataaaagaacacttta
atccccctcctctcgcctctctctcttctcccaaatctcatcgccttctccgccgcgacgcggacg
cgctcgaattaacgccgccgccgccaaccaccgcccgccgccaccgcg Figure 187 (SEQ ID NO: 187) Os02g27769
atggttgttcaattaagcaacaacatgaatgtatgatttatatatttgtatacactagcatattgc
ctgtgcgttgcaacgaaattttaattgatgaaaatgatcattaacctttgctattatcattatttt
attatcatctcttaaattctacatatatttgtaactaaaccctatcacctcacaatataattctta
cttcccacaaaaaatagaggtggtggggtggttgacatgtgggaccttatcttttcttcactctaa
aagggtaaggactaaggaggtggtggtggggcgcgatcgctaatcggtgcgcgcgccggcggcgcg
cgtttcaggcccatagggcccagcaccggcgcgcgcgcctccttcgacgctttttttttcgtttttc
tttagcgatttttttttcgttttcttttccactttttttctgattatttttttttaatctttagcatgt
tttgagtttgaaagtttttaaattttgagttgaaaatttttaaatctgaatttgaaagttttcaaa
tctcgagttgaaagttttcaaatatggacttgaaagttttcaaatctcgagttggaagttttctaa
tttttcaaatctggacttgaaagttttcgaatctcgagttgaaagttttcgtatctcgagttgaaa
gtttttaaaatttgactttaaagtttaaaattaaaatcgaaaattttcaaatctaacttaaaaaat
tttcaatctgttagtaaaaaaatctccaaaatctttcttaattactatcattagtgttaagtatat
attaactaatggagatagttaagtatattaactaatagtgttaatagagtaggttaataagggagg
agtgctcgctagctagtagaagcgcgtcgcgtgtcgcatgggccgggccaaccgcgggggggagggg
gtgggggcaacagccgcgcgctagttaatttgctcgcgcgagctaggaccctccgtggtggggtgg
cagattcaccacctaccaccaccactactccttttcaaagaagtataggtttaaatctccaaaaga
tacataatattataaaatacctatatatatttgcgttatatttccatataatactgattaatctta
tgcatttcgattaatctgtaaacgatactcttttcattctacaaccgtattccctcttgtacggca
ctgatgtaaagttagatgatcctttttttacctttatacagtatgttcagtccaaagtgaaagtgtt
cagctgcccgaaggcccagcccacgggaaaaaagaacactgcccaaaggcccagataactagacat
cccgatcagacggcccagattcaccagatccagctataaaaatccggaccacgcccaccaccccAaa
accctccggctcattcttgcccacgccgcgccgccgcctcctcctcctcctcctcctcctcctcct
agggcttcttcttcttcccctcctccgagcgccgccgccgccgacgag Figure 188 (SEQ ID NO: 188) Os07g08660 ctgaccgaatacggctccgtcggctttgtatcggccaccccgagcaacaccatcccggccaccaga
gggccggtctgactgcgcatgtgccgccggtcaaaccggccttatgcaccggtcagaccaccgtct
tgtggccggtcagactggccaaggcacgccggtcagaccgccactatgtggccggtctgaccgccc
ctggtcaggccgaacacagtgaaactgtgtgtgataagtgtgtgtggtgaaaagtgagcacaagtc
taaatgcataatgacataatgtggcaattaaaatcatctcatttgctaggtcattaccccttgat
agtacggcaaaactaaaaataaactagcaaatttgatcgcccttcacctcgatcaattttaaaact
aaagcactagttttaccgttttcttttcttcgcttcgcgccatcaaattttaatccgtcgataatc
atccatgcgcacacatgacgtggacctaacttaaaatatatcttaatagcaacggttagtccacaa
ttagcgcttgtcattaattaccaaaattaacaacggggcctagatgcttcagcgtcgcagcggcg
tccgcgggctggcgcaccaccgcacggagcggctgtggatgctggccttcccgcctccggcggtgg
gggtttccgcttacatcgcactgcctcgccgttgcctaggatgacgcaggtgaagacgaccccgat
cttggcggcgaggttgacccagcgcaggaggtgggcgccgacaaggcggtggcgcacgacgtcgca
gaagtggttgcagttgcggagaatgaggttgtaagcgtcgccggggaaatcggaggtccgccatga
ccgcggatttgggtctgagaggtcatgagcgagagaggagaggatggggaaagagagaggtagaag
atgagggtatttccgtccaatacatgcaaaatatgtagcttagtggcatcactaaaattacaaaca
agcagcagtgtatggttacaaatacttaaatagtaatggcatatttctaaactggcaaattttttaa
tggcacgtatccaattaaccctttcaggaacgcttgggacgtatcggcgaggtatcttttttttat
ttaactgaaaatcgcgaaaatctgggatacgtatcgaagtgtatccaatatgtatccatatccata
cacgtatccgatactgatacgccacttttgtgctgtatccaggtaacatagattatagataatcgg
attcgttgacatacctcagatgaacttattcctagggcaaattagtcccagccgaaactccacaca
gcccaactatcattcagcccaacccatcagtacaacgagaatggccttcgcaaccacgcgcactat
ataacctacccacctcactcgccctctcccCtctaaaccctacccgccagcctccgcctccgcctc
cgcctccgccgccgccgccgagctcctcccgcgcgctccgagcccatc Figure 189 (SEQ ID NO: 189) Os04g47220 tcacatgtatggcacgtacaatgtgtcaaatttcaggtacagataacttactgagaaatttgtata
tacctgttatatgaactcatctatatcacatttgttaggaaaccctcataatcttagtcacctttt
tttttacaaaacctactatacaccttcccaacgtgagcgccgcaaacatcaacaccatcgctgcc
accgcctccttaccccctagtgtgtcgccacacggtctcacctgctggttggaagacaccaatggca
ttggcaaggcccctcggctggtttcctccctatctccactctctgactctgccctcccctgcccta
tgttccttctcaagccggcggcaataaggtgcccctgctccaccatcttccatgtctctagtggct
atctgtcgttggatccgtcacccccccgattgccgcctcctaaccagtgggtttgttttgcccctgt
cagtcatcctccgtcacacacggttatctctctaagctttgggaaaacccttcctcttcctcctcc
tcctacccccctcccatcccaaaaataacctagaaccctaactgatgggggacgttgctgccttgc
tagagctagaggagaagaaagccgacacaaatcttggcatggaccctatggtctgaaattcgacga
aaatctttccaaatttctgccatatgaaggttagcgattccgtaaaaattatgaatgagcctgtac
aatttacctaaatggatggtccggatttggaacttatctacccttaaggatggtcaaaattctcat
ggttacacgaagaatgtcaaatacactcacacatctcgctaaggaaaaacagaacagccaatcaga
gcataaatttcaaacttttcttgaaaactcaagcaatttttcactgatattggacaattttttta
tcaaccataatcactagtgtcacaaacaccttgaaattcaaatacattcaaaacttttgtccaaaa
gcacatccgaccgggggacctcaagatagaaccgaaatttcaaattttcaaccgaaatttatgaac
tagatgagagtgatgcgtaaggggaccatcagggagcaaacaaccgtgaccgaattgcataggag
ttatggctgatcacttgagaaattaaccatccattcccggtttccctccaatattgcacccatcca
tcatccaccagggatgataccgttgccgttgctctaaaaaacgttaaaacagcggcaggcaacacg
acagcacatcgcatcgtacgtacgtcgttcgtcccgctctcctccgtcgtcctccctgcccaccgt
cccccacacccactccccgccgtcacgtccttccagaaccacctccacgactcttCcaatcccccg
ctataagacgcttctccactcaccactgcaaccctcacccagccagctcgagcgagcgaagccagc
agcagaagcagtagagagaaagtagagagttggaggggaaggaggagg Figure 190 (SEQ ID NO: 190) Os05g07700 gagctttgacttaaaagacaactaaaacacttcgatgatcgaaaccttgaattaaatatatatgtt
ctaaacagacatatattagaaggtatataatgcacattaataaataaataaaacttgaataaccca
tatatatattttaaaaaattaacatattactgtcaactgatgacttggctgtattagaaggtatg
agttgggaaccataccctgatattcaaaatgataggatgaatcagcgtataattaattaaatatta
tattaaaaaactctaaaaatgatcatatagatttttaaagtaatttatctataaaatattttaaaa
cacaccgaaatgtaggcacgaaaaaacagaaatgagttggaaacatgagaacacacccgagtggac
tctgaccagcaatatccactcccataaaaaacgaaaagaaaaaaaaataatgacaggaagaggtgg
cccaattgcaatgggcttccatgggctcctcaagcccaacacgcaatcaccaccatcggtcacgcg
tgacgcaaaccccacagccccccctcccctctatataagcctctgcgccgcgctcctccGaaccta
gccgcacatccccgcctcttcccgccgccgtccgccgcgcgcacgccgccgccgcc Figure 191 (SEQ ID NO: 191) Os11g26850
tctctagggctccgcgtcccctgtctcagcaaatttcactaaatttaaaagactttttttgagtaaa
attcaactcaaacatatctgagtggcaagtgcgtgggtccgccatgatctacaccaacaagctccc
cggtttggatcgtgtgtgcatgacggtgcagccgccgacgcggcgcgccgacgcgatctgaaaccc
atccccctctctctctctctgtgtgtccgaaggagatatttttcgcatcgaatggagcagcgacaa
gtcatgtgaaacagtgactgtccaaaccagcacgcgtggattcttcagatctcgatgtcctcctcc
tcagatgggccatgatgggccggcccccgcaaccaacggcccggatcacctcttccccccaccccc
atcacaaaaccccaaacccatcaccaacttcccaatctcacccaccccaccaatccccaccagatc
caacggcccagatctccccctcacccagatccaacgcctccccttcgtcttctccctccataaaac
cccacctcacccccaccctcccActccgcctcctcctcctgcctgcctcctctctacccacccacc
ctctcgccgtcgcagatccgatccaggaagagctcgccgccgccgctgccttggcgctctccgtgg
agaagacctcgtcggggagggagtttcaaggtgaaggacctctcccaagcggacttcggccgcctc
gagatcgagctcgccgaggtcgag Figure 192 (SEQ ID NO: 192) Os12g38000
aatagttcgggggtcgatatatccggttctgtggtttagggtcgtggattagattcgggtaacttt
taagggagtcaaagcgaacttattttcccccccatcgctcagaagaaaaatcgaaaaagcccaacca
caacgacgcggcccattacagcccaagtccattacactgacaaatccgcccccacgaatccaacgg
cccagatcaaccccaccctccatcccagccgtccacgctagggctatccctccccgaaaccccccca
cgccgacctctatataaaccggagaccttctccctcctccAaccctagccaccccccgcctcccca
ttctccccgccgccgccgccgccgtctcgccgccgacgaggag Figure 193 (SEQ ID NO: 193) Os03g56241
gtcactgccgcctgttacaagaacattcttcctgactattttctgggttttctgttctctgctgct
tggaagaataagattgttgtctgtgttaaaaaaacacacaataatttagtttcatattactacagt
agaaaacaataagttactcgcgaacggatattttagcactaaaagagaattaaagaaaaaaagagg
tcccaccgagatttgaactcgggttactggattcagagtccaatgtcctaaccgctagaccatggg
gccattttgaacacacggatttttaatctctatatatccatacttgcatctagtctagcatgggcc
ccggcccatgatacgttcacctgaaagcccactcatgcgacgacttgtcaaagcccaacaagcgaa
gaagccgatgcttatagaggaagcccggctaccaccacGccaacgcgctcatttcgttcattctag
ggtttacaactcacgacctccgccgccgccgcc Figure 194 (SEQ ID NO: 194) Os03g05980 acgatattctttcatgtagtcctgcatagatgacaagaatgagcagtgttagatttgtcaaagtgg
gggtgaagctgagcccttgttcaaccttggagagcaccttgtcttctttgaaacatgcatgaaatc
ggattcgcttggagcaggtggcaatgccatttcaactctgtgcacatgtgtgaaaggacaaagaaa
atatcatttcaatggtgattcatcctcgattgaacaaaagtatcaaatcattttaaaacagaaaac
acccatgtagccactaagatatgcaaacatcaacagaaaaaaaaaatccaaatcatctgcatctat
gactcagctgcatctgccaactttgtcaccacgcactgccctctatgacaaagaggataacaattg
acaagcaaagcgtgcccggaactagaagctagcaaccgagtgatgcggatttctctgattttgttt
acacttcagttcacccaaaaaaaatcctactagttgaatggagatttctctgttttaagacagtgt
gtacttgttaacggcaaaattgcttgctccaagcaatacttgttacagctagaagcatttcaagcg
atctattccaattcgaacattttgctgcaaatatcatatcaagtatcatatgattcagcacataca
cacatccctcacctctgctacaaacacccccagtgaatgaacaaaaacacacagaaaaaagagaga
gagtattagcttactttgatttcaatttggatgtgatatgatgagccccatccaaagattagtgat
tcaacaaaccctagaaaatgcaaaaatgaagagatgttaaatcaaaatcaggaaatcgatgaaaaa
agaggaatgagagaaaggggtatcgtgcgcaccggctctgccgcagatgccaccggctccgccgca
gacaccgccgccacagccgccaccaccacgctcacgccactctccctctctggcacaactgacctt
gtgcgcatcggcgccgctgaagaggaggagccgcaagaaggctccgccgccggcgactccgccgcc
gcagccatgctcgtgacgatttgggagctgcaggtgtctgtttgggagtgactcaatgtttctcga
gtgtgtgtatctgatccgtgagggtgtgtgtttgatccgtgggaaattgtcctgtccgggaccgac
tcgaaacagtataccggtgactagcatttctgttataaaaataaggaaaaaagaacgagaaaaaga
ccatttaacgagcggtgtaaatatggcccctgcaccgaaggcccattcgatatgtgggcctaattc
ccacccgtccgttaatgggccgggaaatctcggcccatttaacctagccctaaagctagggtttcc
tctcgccgccgcactAtaaacgcgctctcctcctcactcctcctcccctcgagaaaccaaagctcc
agcaatcggcggcggcggcggcggcccgtgagaggcggtccggcgacg Figure 195 (SEQ ID NO: 195) Os03g05730 tggctaacctcaaacagacagaaactttttgcctttttacgctctacaatttgtgcagtataatgaat
taatgccacgatcgcatacgaacacgggacactttccttacaatcgaaggcagcaaaagatgcgaa
acttctcttccgagccgaacacatgctcctattcctgcacgagcaggcacaagtgaacaacaacta
cctgatacactgacatgtcgggcccacactctctcaactcggcacgggggcccccctccatcttccgg
gacccacctcatccgaactctatgtcgcgtgggccacgggcctcgtgggacccacatgtcatggac
ctccggggactcccgaaccgagcccaacccgtaggacggtaggaggtcgaatcccaaaccccttcg
gcaagaaaggagctatttaaggtagactaatcccctcgtcttccccCacaatcacttctccccccg
gaatatctccgccaagagaagagaagagacacccaacaacccaaaacctagcgcctctgcgctcga
ggcccccccgaatccgcgaatccgccgactccc Figure 196 (SEQ ID NO: 196) Os05g01262 ttttatatttttttaaaaaaaattatttatccattatatactgcaagaattttttttttgctgttt
ttaatgtaactttttttcgagaacatacctcatttctaatgtaaattatcttttgcgtaagtaattt
ctctctcataaaaaactcaaaaatattttttttaaaaaagtgaaaacttgaaatttatatataaac
tttcatgttgggtaagtaagctacataaacaattcatatttttaaacccttagatgaataaattaa
ttgttaaccttatatgtattttgagtattttttaaaactaggacctgagtaaatatttttcttgag
ttttaggttataagacttcacattcatatatgtctagatctattaacacatatataaatatggaca
atgctaaaaaataagaataggaggtggtattattttttttttggtagagaggggagggggccgcat
aggaggcaggaggtagtaaaatgggctgatgggcatagtattcacgggggcccatgtaAtagttgg
gttgggcttgaacacacttgtattgtaacaatagcctcggtcgaggtgaggtggaagaagcaaagc
aatctccgtgagcggtg Figure 197 (SEQ ID NO: 197) Os01g05650 tatttaagtaagacaaataatgaaatgttatttttaaaagtcaatagttttaaaactgagaaaata
tatgttagaataaaaaggattagaaaatttttcgatgcaaaagatcagcagattgatatggagctta
ttttatttgtcacgattatctcttcctagttcccagcgagtggtggtgactaataacttcacaaaa
atagagaaaacataaaataacaataatagcttttcagtaaacaaccattgatagagtagacatgaa
cctgctttatgcctacctacgaccttaccatccgggccatttccaggccattttcagtgttatcaa
gtgcttgacataatggcatggcccaacacatcaataagcaccatgaatttgtgatcttctgaatct
cctctgtgctgcgagcgatgcggcgtggtattttgattcttccttgaacgtgcattatacacctct
agcgcgccgaatgtatgatgacatattataaagaaatgcataaactttgtggaagaaatatataaa
gcacatgaatgatgagaatgaaatctatcccataatatagggcatattcggcaagctggttgcggc
tgcgcttttcggcactgtcggtgtcagctacgccgtttgcgcaaaacagacagccaaacatacccg
taatttatagttccaatattttctttctttagaaaatatttttcgataaagtttaaaaaatatttg
ctgaagtttaataggacatctacttttagataagccatgactaggctaggtgattgtgtacctgat
ctatcactaacttattagtatgtccacaagcacatatgtaaaagaatgtaaactttagtaccataa
atgttataacatatattgtaaaccctacacatatcatcgccaggcacgtaaataaccctatgttgg
tatagttgttaataggttgatgcttgacaagtctattctcgttgatgtttttttttaattatactc
attcaaaataaaatataattgatagttctgtgctgatttagtttagaaaaatatacacgaactccc
aacaactcaacaaacaaacacgtacacaaccttctcaattctcactatgaactagaggccacaaac
cagacgccaaactcgcggatcatacgtgatcacgccatgcatatgcgttcggttgtccgcgagcga
cggacggacggttgagtcccgaagaatcgctcaatcaatgaggggcaaaaccgtaaactcactcac
ccccacaggaggtgacttcccccccttccccaaatcgacgatttgttcacggcaggtctcccgatg
cgtgccacgtgtacggcggatggcctccctccctctctataagtagcaaccctctccgccccccctc
cCtgcgtgtggttcaggtgctgaaggtgatattcagattttcagagtgagtgctcgtgtgttgtgc
gatcagtgcccgcagttcgatcgatccgtgttgatctttgaaagaaag Figure 198 (SEQ ID NO: 198) Os05g01560
tattctgtgaatcatatggacaacaatgtaaaatctcatagtaattcttatttaggttgtttgcag
aaagttaatttgggtcaactgaaatgaaagcttgtctgttggctctctcactgaattgaccccatt
gtaattaatgcatataattggcctatatattacactttcaatatcgtaaaacctttttctttgtac
acttcacctagttgatctagtatctgccgggctcatcgggcttatcttgtcaatgaacagtaataa
gagctatgtcgggctgtttgctgtgtgcttctgttcaaccaatttcgacacagtgtactttgcgaa
attgggaattgagatgcttggtgtgaaaattggctgtgctatcatgatgatggcccatgagcccac
gaaacctcacgactcttaattcatttacttgtttccggttaagagaaattgtttcagatatttaca
atgtttttgaaatataagtttaatccgtctcaaaggttgttttaataactatttttctctgtaga
aattctgataaaattataatattatgaaactttttttaggaaagttctatgcatataattgtcatg
aatttaatagaaatgtttatagtgaaattaatgtcctaagattcaaacttttctcttacaaatata
ctccatgctatgtttttaccaaaagatcaatgaggtattagcatatagtaaccggctcacaggcgc
tcgtgtccgtcagggcgctctaaacctccatcgcacagtttctatccgatcaccttcaccctccgt
ctccagtagtaggatccaatctttcccaagtttttttatctttatttaagttcctatagaattag
gtctattaggttgtctagggtttgtctttcaatttttcatggatcagatgtgtagtcttttgttt
cttctatttatttattctagttaccttattgaggttctcggtgaaaaactagtaagatttgtatgt
cgggttgtcgatgatcaagccagtgacacgctttaaggcttgagtcgctaactttttcgtggtgat
ggttagttgttttgttgtaggaatagagatggtagcatatactttcatattcaatgcttttgtatg
tgctggaatttgtcaatggtgttggcttcacatttgctaatgtataggaatttcaagacgtggaat
ctctttgggctgtgttgccagatcaaaacaggcccaaaaagttttagagttagacaaatatataat
acgtttattctgtgttgaaaatattattatatttttttataaacttaattaaacttaaaaatgttt
gattataaaaaaaattaaagtgattgtaatatgaagagagcaagtaaatataaatgaagtGaggtc
cacacacgttgacgaggcaacgagatacggcaccaataccaatctctgactcctccggcctccggc
ggccggcgagagagatcccaccctcaccgacgacggcgagcgaccacc Figure 199 (SEQ ID NO: 199) Os07g08330
agattaatgattacagtggtactattttgataaattattttgttcccagtttatatgaattttaaa
atttagatcacaattttacatataaactacaaatctatggtggatctgagatctgtagttatgcc
aaagaatacctcatattgctgatcctttctcgtatgctttctaatggagctagtatctgcagctgt
attatcagaaatacatttaaatgagatatgttttgtatgacccagttgacggcctcacaaaccta
aacaggagggaaccaagcctgagctctaggcttggctcctaaatcccattcaaatattcttaaaaa
aatcacatatttctttttttaaaaaaaatagtaggatgattaggccgaatatgtcagttgagcct
taggcgtggagaattttaatttggctctgtcaccaccatcaggaattgaagcagggaaatgagagc
tataaccgttgaataacctctcaaaaaatccctgaattttagctgcatgagcagcttaaatgtggg
atcaatattcattaagctcaagttactaacttgaaaaatatacagcatgtgtgtgttgttttgaac
tctaaaaatacctagacggagttatgcattattgaaaacataacatatgaatgcaaacttatacta
gaaaaacccatgaattctaaccttagtggtttttcaccaatatttctaataaggggtcaacctttg
gaagatgagaactctaccatttgaacacatgaatagtgaaaaatcaaactattaaagcttgacggg
ctagggccataactgagcattgccacgtcagattattgtacaattatactactctagcagtacata
cactcttggctgtgtactgttgtacgaaacggagagtccaaagtagtagactgtccatatagttca
gtttgatggatttcacccggagatacaccgtacgatttaattgtaataatacatagaaccatttgt
tttttttttgaactgaagaaccatttgtttttcatttacttttactttaaaacatggacaatgaat
ttgtttttgaacagggcttgaaactcttaactccgagcaaatgaaaattcaaacagcagtggattc
aatattcaactcgaaacccctccttttttttcaactaaaaagtccgcaaaacttcccaataattaaa
ccgtgaaatttcagcgagacctgtatttaaaaatatgggccaaattcaaaatccaaagcaataaac
aactgggctacacacaacatgcgacggcccatctcatcaagcaacaaggcccagcccactcgacac
ccaccgaatccacgccgctcaatcgaaaccgacggtccagatctcgccgcgccaaccccatcacac
aaaccctagcaaccccccacctatataacctctctccctcacgccccgcctcCattcgcacgcccg
cgccaccacaaaaccctagccgccgccgccgccgccgccgccgcc Figure 200 (SEQ ID NO: 200) Os03g58204 cattttattttatagatattgttggttaaagtagcatctcgaagactgtgtcaaagtctaaaata
cttatatttaggacggagggagtatatttcagcactatcgaactttggcgttgagaaactgtcca
tctctacaaatagtagtttttgacatggtctattttaaaaatatatttttaaaagaattaatttat
caaattttcgggagacaacgaggccaagaagaagatgcgaaaccaccgggcccaactcagagagaa
ctacaaaggacaggcccagcccaacccacgacaaagatccaaccgtccaatctaaaccgacggctc
agatctcacctaattccaaacccaaaccctagccactacgcccctagacagatataagctcgtctc
cttctctcgccgccctctccttccctcgccgccgcccgagccactacactatccacctcgccgccg
ccgccgccgccggaaatggccgccgccgcgcgccccctggtgtccgtgaaggccctggagggcgac
atggcgacggactcggccggcatccagatgccgcaggtgctccgcgcgccgatccgccccgacgtg
gtcaccttcacccacaagctcctctcctgcaaccgccgccagccgtacgccgtgtcgcgcccgcgcg
gggcaccagacctccgcggagtcgtggggcacgggccgcgcccgtgtcccgcatcccgcgcgtcccc
ggcggcggcacgcaccgcgcggggcagggcgcgttcggcaacatgtgccgcggcgggcgcatgttc
gcgcccaccaagatctggcgccgctggcaccgccgcgtcaacatccgcctccgccgcatagccgtc
gcgtccgcgctcgccgccaccgccgtcccgtccctcgtcctcgcccgcggccaccgcatcgagggc
gtccccgagttcccgctcgtcgtctcggactccatcgagtccatcgagaagactgcgcagtccatc
aaggtcctcaagcagattggtgcctacgctgatgccgagaagaccaaggattcggtggccatccgc
gctggcaaggggaagatgcgcaaccgccggtacatcaatcgcaagggcccccctcatcgtctacggc
accgagggttccaaggtcgtcaaggctttccgcaacctccccggcgttgatgttgccaatgtggag
cgcctcaacctgctcgaccttgcccctggtggccaccttggccgcttcgtgatctggaccgagtgc
gcgttcaagaagctcgacgaggtgtatggtggcttcgacacaccggcgctgaagaagaagggcttc
gtgctcccgaggccgaagatggcgaatgccgacctgtccaggctgatcaactccgatgaggtccag
tcggtggtgaagcccatcaacaaggaggtgaagctcagggaggcgagaaggaaccctctgaagaat
gtggccgctgtgctcaagctgaacccccTacttcggcactgcgcgcaag Figure 201 (SEQ ID NO: 201) Os01g62420 aggtttcgtttgttggttgttgacaattccttaaattctttagcatcttctgtactcgctgaagct
ctgttagaacaacgttgcagaggctaatcatatgcttgtgttcgttcttacttgatgctagttgta
tgatatgattcagctgtattactggccctgtttgggtgagcttaatttagagaaactggaatatgt
ttctagattctaattctatatctatagtaactatacatatcagaatatgtatgaaaaattagacta
tgtaagaagggtgtgttcacactaaaattggaagtttggttaaaattggaacgatgtgatggaaaa
attggaagtttgtgtgtgtaagagttttgatgtgatgaaaaagttgaaagtttgaagaaaaatttt
ggaactaaactcggccgaagtttttgtttagagcatcaccaatgtatatggcaaagtgatctata
tagatgggacccacataaatagtttatccctatgataatgtccacaatgtatagatacaaggtatc
attaggagaaggagaagagagaggagtagagatagataatataatttatttcatatgggtagtcca
tatgtatatgggtatttttttgctattttttttatatggactagttgcacaatgataataggtggct
gaatggaatattctattgtttatagactacttttatattgtggatgcccttaggaaaagctaaacc
cctatcggcgcctttctatgcctctctatcacctttggtcattcggttcatcgcggatcgacgag
aaaccaggttggcccgaatcaatcggcgccGgcggcctccgcggtttccgccttcgggtaggcgcc
tgcggcatcaacaaagcacacagccgaaaccgaagccttttctttcttccgccccaagaagctgtg
ccacgtgtttcctccttcccctcctcgatttaaccgccccatctcgagtccccccatcacagcttc
cactccacgaaaaccctctgcctccttcgctcgctgcaccctcgtctcggcgatccatccttggct
gccaggaagttcttcgtcggcggcaactggaa Figure 202 (SEQ ID NO: 202) Os01g14580
cgctcgcggcgactcacccggttgcatcgttcgcccatgctgtgccactccacgcttgcccacgca
gctccttgcccgctgttcgcccattcacaccgctccttgcccgtcagttgccagtcggccgcctat
ctacatcatgccgctcctcgtcccaaccacgccactcaccagccctcctccagcagctacttgcct
ccttcatctgccagattccgccgctacgcccaccacctggttgctgtcgagctctagtgctctacc
acgtcgtcggaactggacgtggactgacggtagctgcaaaagtttcacatcccatcccaccctcat
tccttccactaaaaagaaaaaaaattgaatcatcccatcctataaatcaaacagttgagtgagatc
gtaccatccctagaatcaaggacaagttcaacctatcacatctcgcttctaaaccaaacacacact
gacagaacagagggccctgaggattcggctcctctgcctttaggggctaaagactgaggcgcatag
caaaatgagtttgccgctacaatataaaatattaatttgcagttatttactgtagatacagtata
aaaagtaaaacgtattgtgccaaggtactgttcatgatgtattgtattatatgtagcaattaatca
cattcgttcgctataaatccgatggttgagaataatttaaaccctaagggcttgttcggaataga
gggattacacaggattcttgtaggattggcaattcctttggatttggcactgtttatgcattcggt
tcataggaaccatgcgtaggaatttcgtagaaatactgtagcaaccttgtgaaaacataggaattt
cataagattctaaacatccactcacacctcatttttttcattagctatcatgggatagatgctaat
cacgttgaagtgactagatgggaactaatattttattgcttaattatactataatatactacctca
atgcatgaatgtatgacgttggttagttcaattttgagctaaccaacgtcaaacaaaaaaatatgg
agggagtatgagattaatactaattgaaaaattcatgtggtttatatattcttgtgttccgaatgc
ttcatagcatcaaattccttttcctatcctgcgatccgaacaagccctaaattctgaggatcccaa
tccgggccatgaccgcctcctatcatcggacggctatagtggtccaaagctgacgtggccaagact
ggcccacatggcccatgtagtccgtcctggaccgagtccacggacggcgcGgccgaacgcccgcgc
cgtgtctgcttttgttgcttcgttctctccgcgctccgtgtccgaccttcttcagacttcacacct
cgcgcgccgccgcagctccgatcggaagaagctcgattcgtctccgactccgacgaccagaagcta
ccggcgacgcgagcggagaagcgcggaggggaggggcgcgcgccgcc Figure 203 (SEQ ID NO: 203) Os02g57040
agctcaggactgactgactacagacttacagttacaacttcagaggatgtgaattattcatttctc
ttgcgcactaacagttagttcttcagtggttttgggatgagatcctaaaaatatcacatcaactag
attattaagaacaaattgattaatatttatacatgctgaaaagcttaaatttgttactactgcggg
cttgtttggcacagctcacctctcctggagctgaagctcagccaaacagtttcaactccacctaaa
atgagagcgaagttgggtggaactctcttacaaaatgaactagagaggtggagctggatttaggct
gcttcacaactacattctagacccgactcctagaactaaatttaggagttggagctctgccaaaca
gccctgctactactacatggttaagggggtgtttaaatctaggggtgtaaagtttttttgtttca
catcgggtattatatagggtgtcgtatggggtgttcaggcactaataaaaaaaaataattacagaa
tttgtcagtaaactacgagacatttttaagcctaattaatccgtcattagcaaatgtttactgta
gcaccacattatcaaatcatggagcaattaggcttaaaagattcgtctcgcaaattagtcgcaatc
tgtgcaattagttattttttaccctatatttaatattccatacagatattcaaacatggtgaaaa
atttagggtgggatctaaacagggcctaggaacaaaacgagcatcacatgctgatctgccaagct
ggctagccctaataatttggaaatgcaatattccaatatccaaagtggacccggcccaattaaccc
aaccaaaacccacgcccacctcCtctccccttctcggctgctcttctccccctccctatcctctcc
tctcacctcgcaatcacatcctcttcccttctcttctccatcgcatctaccaccgagcgtgcaagg
aggggggggggggggggggtgaaa Figure 204 (SEQ ID NO: 204) Os08g38920
taggcttgtgaaaagaattacaaaacttgctttgcgcaaaagaactatagccatcctttgaattcc
cctgtcatgtgcattattgctgtggtggcttgctgagtacggttggtactcacccttgcaatatac
aaatttaatcagaggtcggagatgaagcttcggaggatccctacgcttactaacaggagggtgatg
aagacgatggcgcccagtaggtcttagttacggtcattgcctgtggcaatggcgtgccgctgcctt
aactccgctgccttaccttcttctgtttttggaatgtattccggaccgctcggtccgatgatttaa
gactatgcctgcgggcttatgatgcaatgattcatactagacactcgtgtatgtgcacttgatatt
tcagctaagaattcgtgtgtaccagactacttgatccagggaaatggtactgtttacacgattgat
tcctgttataaaaacgggggtccacatagatccgccactgctccctcctttccttcatatttagac
tttaataatttggattttcacaaatgttatctaaataattaaataaatatcatgctatcgaagtat
attacataaacataagtattaaactttctttcattatgatttaacaaaattgctagaatgctagaa
aatttttgtcaaaactttcagatttgttattattggatcattttaagatgggtgcattgaatagaa
aaataattgctagaaagaaatttcacataggctacggataagatcccggtgctagtcaactaaact
agtcttaaatacaggtttatatcagttatactgtagctataacatagccacggtataaattaatgt
aattacaatgcggttatagtgcagttacaatgtaattacactcaattacattatagttacatttga
aagttttccctcaaaaaacttgatagttatttttttaagatactctaacgatttaatcatctcaaa
atttttaataattaaagttatagatgaaccggtaacaattattacctctgtttcaggttaatatgt
caaagtcaaactactttaagtttgactaaattatagaaaataaacattttcaacccatgttagatt
tattataaaaatatatttaattattgatttaataaaactaatttggtattataaatattactatag
ttatctacaaacttagtaaaattgaaagtagtttgattttaactaaagttaaaacttctaataacc
taaaatggagggagcacaccatatttataccaaagtactgtcagcaattagctgatcggtagaga
cgctgagtaactgcacgttcaggtcatcacgcgacctaccaatttaacaaaacgccGtgtcgtctt
gttcttcttcttatctttttttttagtcattaattgatctgcaatactcttgtaagaggtccagat
agctagagaggccattgagagatcatcatcggagctagctagctagcc Figure 205 (SEQ ID NO: 205) Os03g60400 tttcctcctcctccttcctcgagctgctctaatggcggcgtgggtgattagcgatgtggatgtctc
atactcgccatcaccactttagctcccgccgccgctgccgcttcaactcctgcccgtgctccctgg
ctccccgcagccggccgaaggactgagaaagagaaagaaagagagaagggaggaagaggggatgga
aggcccgcgcgacgagctattagctcagtggtagagcgtgcccctgataattgcgtcgttgtacca
tggctgtgagggctctcagccacatggatagttcaatgtgctcatcagcgcctgacacgaagatgt
ggatcatccaaggcacattagcatggcgtactcctcctgtttgaatcggagtttgaaaccaaacaa
acttctcctcaggaggatagatggggcaattcaggtgagatcccatgtagatctaactttctattc
actcgtgggttccgggcggtccgggggcactacggctcctctcttctcaagaatccatacatccct
tatcagtgtatggagagctatctctcgagcacagattgaggttcgtcctcgatgggaaaatagagc
acccaacaacgcatcttcacagaccaagaactacgagatcatgttggggaagaagaaagagatgat
gacatgtggggccacatgtcagtgtgtcccacaatttttaatgtgtgtgaatgacacggatccca
cgtatatgtttttaattcaaataccacctaagcgccacgttaactaaacatactaggtcaacaccg
ccatgtcagcgccacgtcagcgaaaccgccctccaaaaccacgaagggagtcaaactgcaccggtt
tcaatagttcggcgtcgaaatatctggttttgcggtttagggtcatggattagattcgggtcactt
ttaagggagtccaagtggacttattccgaaaatatctggtcatttagcccataaaaaacaggtcca
taagattctctcctaagctaagccacttatacttgagcacgtatcgtaaggaaaatccaCcggtcg
tcgcaagcccgcatcaacgagcaggagggatataaaccctccgcccctcctcccccaaaccctt
ccgccgccgccgtcgccgtcgcctgctccagcgcgctcgccgccggccgccctactcccgctccag
gcccgtcaccgccgtcgccgatccaac Figure 206 (SEQ ID NO: 206) Os02g57720 cagtagaccttgttcgtgagtggttgcggcttctgttgtgtttggtcgcctttgttcgctagtgca
tctggattccatgatcatgatcatgatgtccatgcagattgatgtggtgactgactgactgaatga
atgaacagctgcagctatagctgagggtgtgtttagttaacgctaaaattagaagtttggttaaaa
ttggaatgatacgacggaaaagttggaagtttgtgtatgtaggaaagttttgatgtaatagaaaag
ttgaaagtttgaagaaaaaatttggaagtgaataaacgagtgagctctccttttccttttgaccca
ctctgctagctgcccttcttcccctagtggccatttttcccccatactagccgactttgctactact
tgatagtcttatcactgagaggaatggacgcacattattatatgctagattgttaaatcgagaggg
gattactgttgcaagtgagacagtacctagcacataatatgaaggtatatattcattcttcttggg
tcgagttgttagcaatgctgaattatcaatgtttgccaactgctagcaattaggaagaatggctag
tttgtggctatgattgatcgatcatcaagctaaagataatgctatgcaagtcgagacagctcgatg
agctcacacaaaggataatcttccaaactgaccactctgtccgtggtcttgtttggatcctccgag
ctattaaatagtcctctgaaattttgctatttaggattattaaacgtagattaccgacaaaaccga
ttccatagcccctaggctattttgcgagacgaatctaatgatgtatattaatccataattagcagc
tgattactgtagtattactgtagcaaatcatggattaatatacctcgttagattcgtctcgcaaaa
tagcctagtggttatggaatgagttttgtcagtaatttacgtttaatactcttaaataacgaaatt
ccggagggctatttaatagccctccggatccaaacagggcccgtgtcacctaaacaaaaatggctt
taatttccagaacctgccccgtagcaaacgaacccatactactaatctatcatatcatcttgtgaa
ttatttatctctcgctgacaataaccgatgaaccatcaaattcaagcttagtaacagtagcgcttc
ctgtcatccacagattaatcaaggtaaaacaaaaacccctaccatcatcgttgtcgtccactaatt
actaaattgccgactgctaaaacaaaatgaataattaattaattaattaattagtaaagaggaaga
gaaagagaaggccattggtgcagacgtagtaGtggagcaggagctataaaaagaagcaggaagcca
ctcgctctcctcacagccacagctcgccatcgtcgtcgtcgtcgtcgtctccggctccggcaa
gagagctagtagtgagtagtagaaagaagaagaggcaaattaatagta Figure 207 (SEQ ID NO: 207) Os12g04924 ctattatcggacaacttggcatattgaaatttctactgtcatgcttccttgtcccattactacatc
gtcgttgtgttcaactattgcactacctccctcctagttcaaatctaatatcatatatgtaaccgc
aatggaaatagttgtatcatgttcaaattgtactactatttcttcatgttacataattctccttgt
ttaagtccatataatgtttctacaaccgagactgcgataggcctattaattatccgagtactaata
cgtcgaataagttacaaaataataccttccttaacatatgaaattgcgaaacaaccaacttcaata
catttttataacaatattaacaagttttaccaataaatacttctttatttattattaacataaaat
agaaaaatcgtttggccgtactttttgcatctgggtcccttgccgccctctactggggcagcaagg
ggcccaaatgcaaaaagtacgagcgcaacctctttatgggcggcaaaaattgcaattagccccttg
ccgccctctgggggtaattgcaatttggccgacggcggcagacggcacggtcgacccgccgtctg
ccacgtcagcttgccgcccaccactggggcggcagggtctattttgtatttttttggccgatag
attatttctgtaaatattaaaaaaaatctaaaaatgaaaaaaattcGtgctacactgctactgctc
cggtgctccctcatctccttctcgattcttctgctcctccaccgagagcggggcgagcaggcgagg
ccacacgattctcctctcccttgccgcttccaacaccaagtctcgccgtggccaggactgagctag
ggtttgcgtgatcttcgggaggagggagcaggagagagttcgaggaggaggaggaggaggagaag Figure 208 (SEQ ID NO: 208) Os01g73990 ttcgtaaaaataaaaaacgaagaacgaactcgaccaaactagcctctctctctctctcttaaaatc
tttcgatcatctcagttctggtcttattatagtttgcttttcagtttctgttagtttcccatcttt
agaaagccgaaaaatcaaccttcttcccacatcgatccccatgttatatcgtcttcactgttgctt
ttaaaaaaaatatagaatgtgaaaatgtctggttacgataaaaaggaaaacacccggatacgatta
ttgaaccatgtcgatattagctagagagataacaactgagtagagcataataaagcaattagatcg
ccatatccaacaaaatatggatggccatatcctatccatgcatgaccgtgaaccaaacacactcta
agttatgtatgttatccaagaagacaaaaaaaaaagatataaatatagctgaatgagagatactcc
atccgtccctaaaatataagagattttggttggaagtgacacatcctagtccaacgaatttggaca
tgcttctgtccagattcattgtaataagatatatcacatcccaccaaaatctcttatatttaggga
cgtggggagtagttcataattatagagttagtggcacatgatgggaagcaagtgagagttgcatag
gatttgggcagacttggcaggttggcttccgtcccataatatagcaatctaggatgggatggaatc
tattataggacaatgtatctagacatgactcgtaatatagcaacctaggatgggatgagatccatc
ctaggactagatatattatgggacggagggagtagtttatactttgggtaaaaacataaaccagta
ggaaaaaagaagcaattatttttgcacatttttctcttttacgtgaataagttttggtggtcgttc
agaaagagaatttgaatttccaaaagactgtataaaccgtgtagtataactgtaaaccaattggcc
accactacttctgttggacagaaaagcatgaagtacagtagtaccgtatttgtacaacatacagat
acagggagggagggcccacacaccagactagtctagtcgcatacggatcggatccacagactagct
ggctagctgctacggttgttggtgtggagtacacagaaaagaaaaaaaaaaggaaccatgtggttg
gggtcggtgagacaagcgcccttacccaccaaccaaactgactatgactggtgggcccttcgacct
actcccactatacaactctactgctcctcaatcctctcCtcctcctcctcctcctcattcgcgatc
tctctctctctctttctttcgtcgttggatccaaagctcctcctcctcctcgcctcgcgctcctcg
tcccttctctcgtcccatctctcatctcatctcttggtagttgccagttgggacttgggagagaga
ggagcaggaggcaggagcaagaggagggcaagatcgatcaagatcaac Figure 209 (SEQ ID NO: 209) Os01g01307 tatgcttgttcgtcagttgtgtttgtgtcaaatgagcaagtttgtaactgtggacaggatgacaag
tgggaactcgatggacaatgcatttgctttggtgcggaggcccatcaaatgcagcccagcccaggg
aggtccctatcgagtagtaagtgagtagaagaaaagtctgatctccacccacgggcggagTtgaca
tactagtagtagtagtactagtacacgaggagaagaagcaagaggaagggcatccagaatcagatc
cacaaggcagcagctgcagcagcatcgacc Figure 210 (SEQ ID NO: 210) Os11g04880
gatctcaaccctacgattaaatacgatcaacggcgcggattactttctactgcaaatagaaagcat
tggagtggggctctttcttctttcgtttctattcatgtacagtttagaaatgatttttaaatttg
aaattttatttattgaaatttaaaaaataattttggtttcaaagttttacaaatctacacccta
aacctttctatgacgttacaacgcaccaatgaatatgtgcccgtcataaaaaaaaacctgtttgga
agagagagcgttaggggtgtaaatttataaaactttgagaaaaatattttgtaaatattttaataa
ataaaattaaaacttgaaaaaaaatcctgaaaaaaccggggaactgtctactggagtacagcccat
caaagagacgaggcccatagcccatcggccaccacAatccttctcgattcttctgctctccaccga
gaggagcaaggcgaactgcaggcggagaggctgggccacacgataccctcctctcccttcccttcc
cttgccgcttccaactccaagtctcgctgtgatcaggagctagggtttgtgcgatcttcgggagga
ggggaag Figure 211 (SEQ ID NO: 211) Os02g34510
cttgtgtggaaggaactggcaggccaatggatgagggaccagatgcaagagggggaagagacggga
gaaggatatgcaggcagctacaggtggagaattcgcatgccttccctacatgagcaccgacagagt
cgaacccctagctcatctgaaattaggaacatgtccaactcaacaggaagtacattttggggaaaa
acagaatacggaccaacgggatagggggagagcatgtgggaggagggaggagagtaagacctata
atgtcggccgaggcagccgccgaccgtcgactccctggcatcactggagcttggagtagccaattt
ggggatggattttgaatcggagccctgcccctgtgcatttgggcagtgggtagagtgaggggtta
acgtgctaaatgtctggatgagacggggtcgtttctgaaagtttcaacacgtacgacgtagatact
ccctccatcccagaatataacaacctaaaatgagacgagacctatcttaggacaatgtatttggac
acgcctcatatataaatacattgtccatcctagattgatacattctgagattggaggtagtagatc
acagacgtacattttatatttaacagaaatttactatagtttacacggtagatgtagaggctgttt
ggttcttaactaacattgccataactcactttaggcaatgttagataagtgtggcttgtcacagtt
tttatgacctacaaattataagccacaattgtggcaaagttagacaaagaattgagtctataacat
gtggggtaagatggtaagaaagtacgacttgtcataaccatggcaataaaccaaacataagactct
aaagacatgtgacagcctaaaatatggtgtgacaagttgaagcattgagccccgtAgtctccgcca
catatctctttccttcttcctcaccccaccaccacctcttctctttcccccaccaacaccaaccc
cacgcgaccaccccccaatcctcgatcaaacgccctaggatttcatcgcaagcaaggaaggaggaga
ccaaatccaatccaatccccc Figure 212  (SEQ ID NO: 212) Os02g44630
taacttttatatagaaaattttttaaaaaacacatcgtttagccgtttgaaaagcatgcgcatgga
atactagtaagagcggttgggagtcctttgcaacgaaaacagccttagtagcaagcacaaactaac
tcagctttagaggcccctcatattgatgtttaacttgttatggggcatttatttctacacagtctc
atttatcaactgaaactaaaaaggttgtccaattccgtcctccttttgtaacggctcgcaaataca
atgggttgtttagattcatgtcatttt aaatcatattattttttataaagttatcaaaatgtacat
atatttatttattttt accaaactttactaaatgagataatccaacaaatggcatttaaagcgttc
aaatccaagaaatgccatcgccgttatgcttccgtccgtttcacgccgttaaaatacaatgttcat
cctataacacttaatggtgtggaatggacggaaccctaacggcgatggcattttt gggataaagtc
gtttgtacgatggcatttcttagaactcatatttgtcgatggcatttttt gaatttggatgattgt
caatggtattttttggattatctcttagtaaatacataaggaatcatgccaaaacttgacaatatt
gtcaacttatcaaaatttaattgggattattttggcgataatatgaacagcccttacatttctgaa
gaattatagctcaaatatggctatggccctgtttggattcggagggctatttaatagccctccgga
atcttgctatttaagagtattaaacgtagattactgataaaactcattccataaccccta cgctat
tctacgagacgaatctaacgaggtatattaatccatgatttgctacagtaatcagccgctaatcgt
ggattaatatacatcattagattcgtctcgtaaaataggctagggattatggaatcggttttatcg
gtaatctatgtttaatacttctaaatagcaagattccgaagggctatttaatagctcggagcatcc
aaacaaggcctatgtttagatccaaacttccaacttttt ctatcacattaaactgtcatacataca
taacttttcagtcacatcgtaccaatttcaacccaaactttcaactttggaagaactaaacacagc
atatgacagtgcagttcagctcaattttgttcggagcctaaaaaaaagaaaagaaaaaaagctcaa
tttggataaggctatgaataaactcaaaaaagcatccaacctaaccaccacactgcccaccaggg
cccacgctccactcccgtgatcatcacctccttcccttt ccagaaccActtctccttccttcctc
ctcttcttcttcagtgtactctgcctttataacaccctactcctctctctcacctccaccatctag
ctcactcacacagtctccactcacacgcattgcagaggagaggcgaca

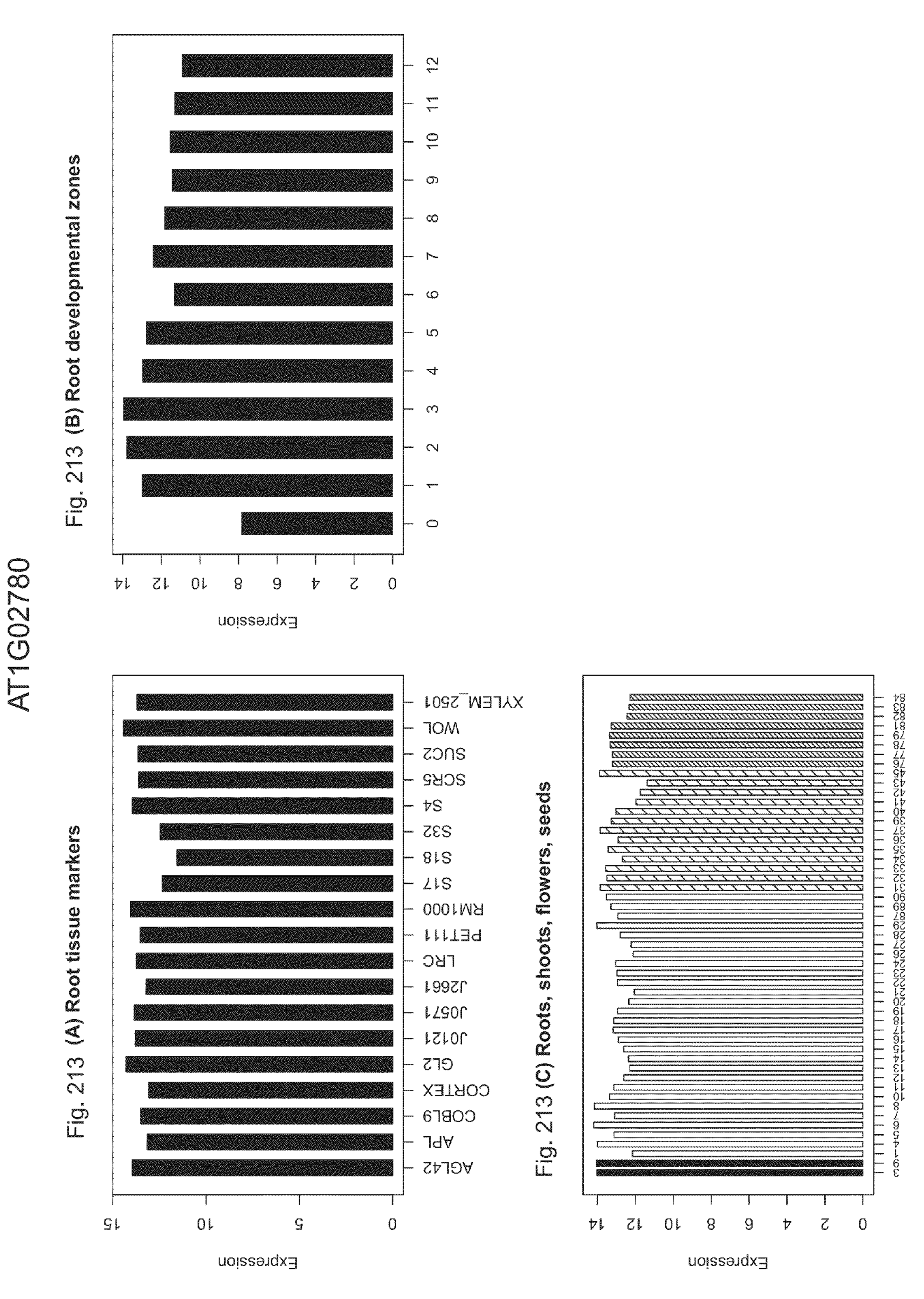
AT1G02780
Fig. 213 (A) Root tissue markers
Expression
AGL42
APL
COBL9
CORTEX
GL2
J0121
J0571
J2661
LRC
PET111
RM1000
S17
S18
S32
S4
SCR5
SUC2
WOL
XYLEM_2501
Fig. 213 (B) Root developmental zones
Fig. 213 (C) Roots, shoots, flowers, seeds AT1G02780
Fig. 213 (D) Abiotic stresses
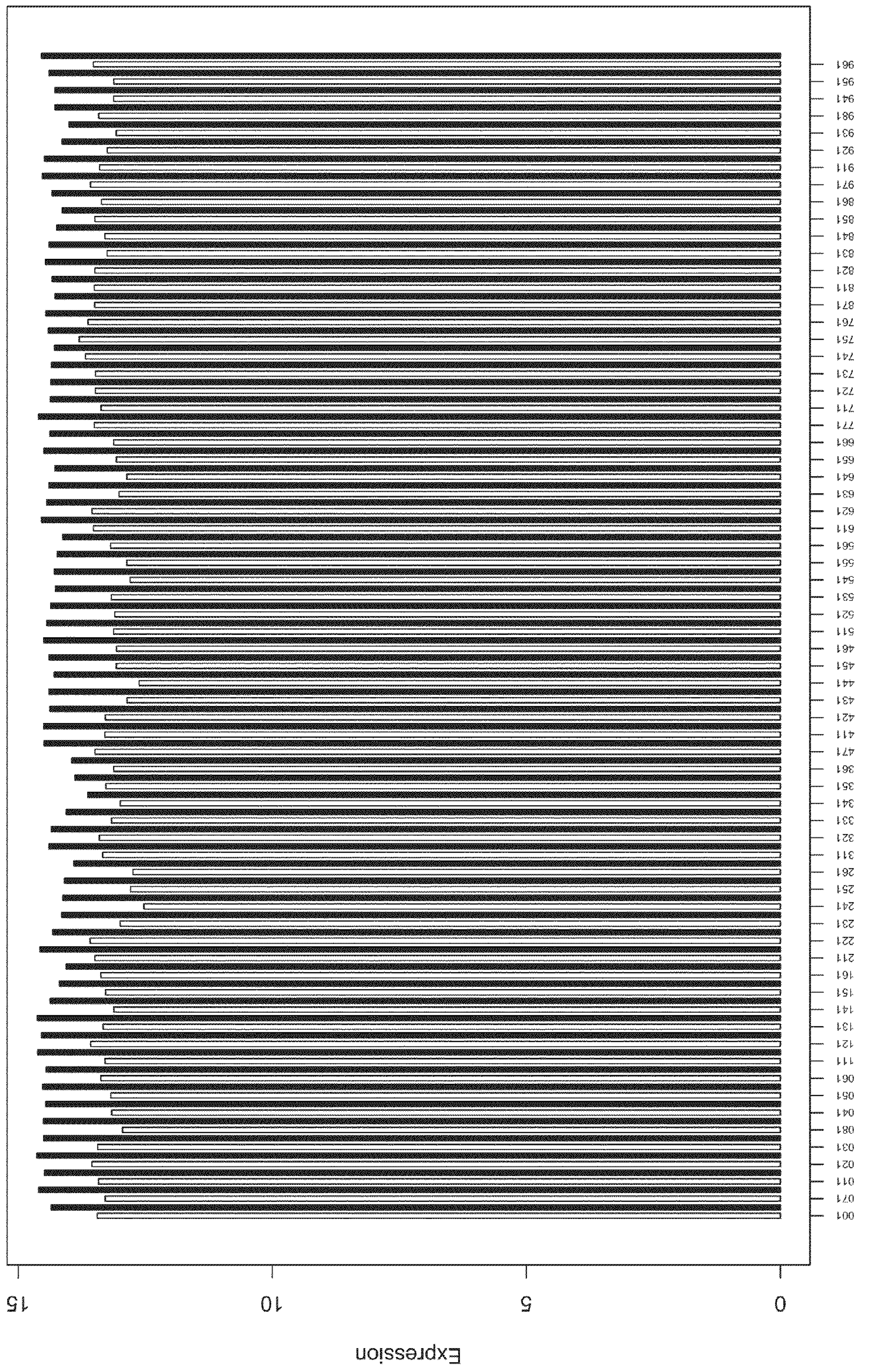

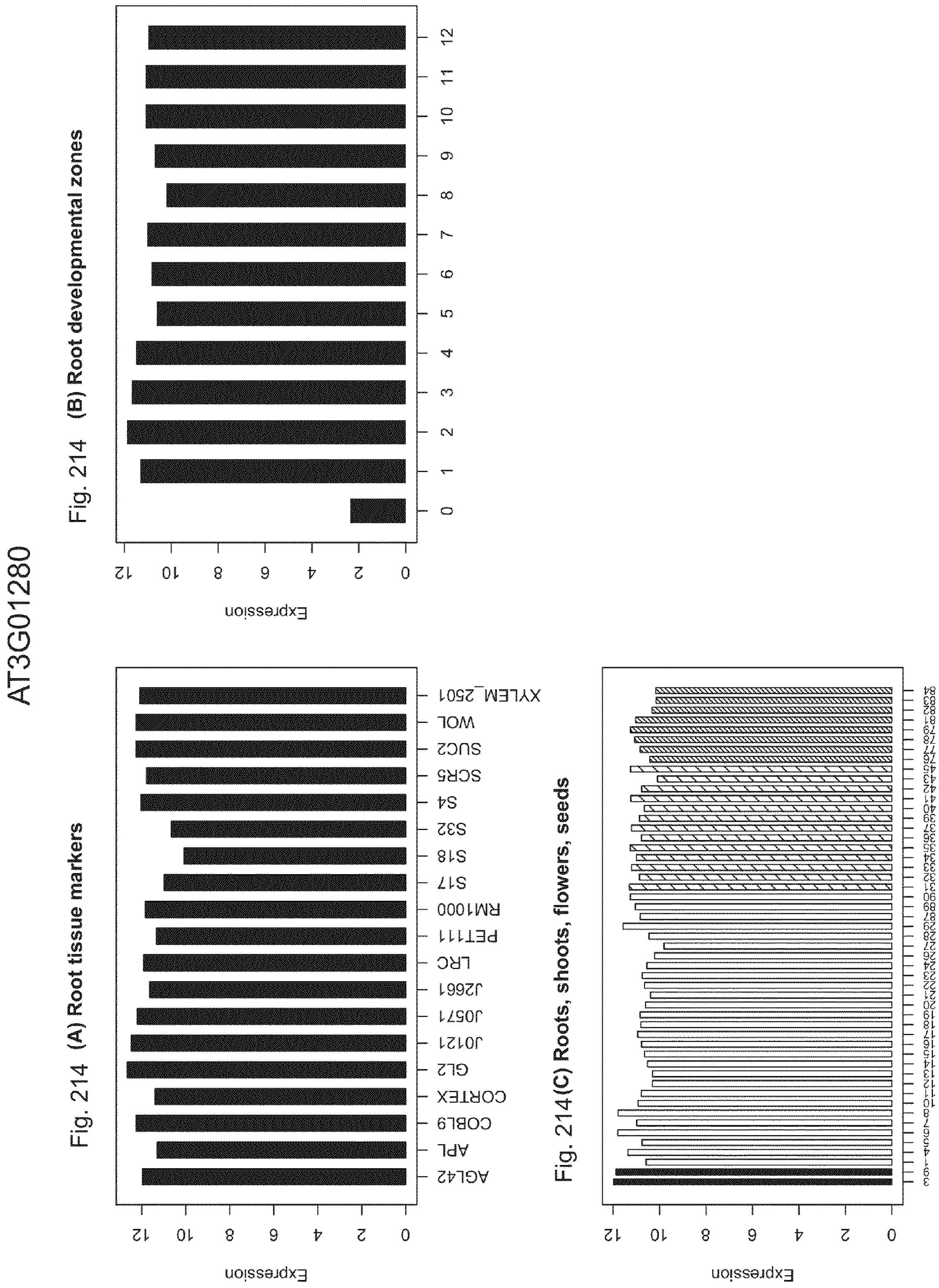
Fig. 214 (A) Root tissue markers
Fig. 214 (B) Root developmental zones
Fig. 214(C) Roots, shoots, flowers, seeds Fig. 214 (D) Abiotic stresses
AT3G01280
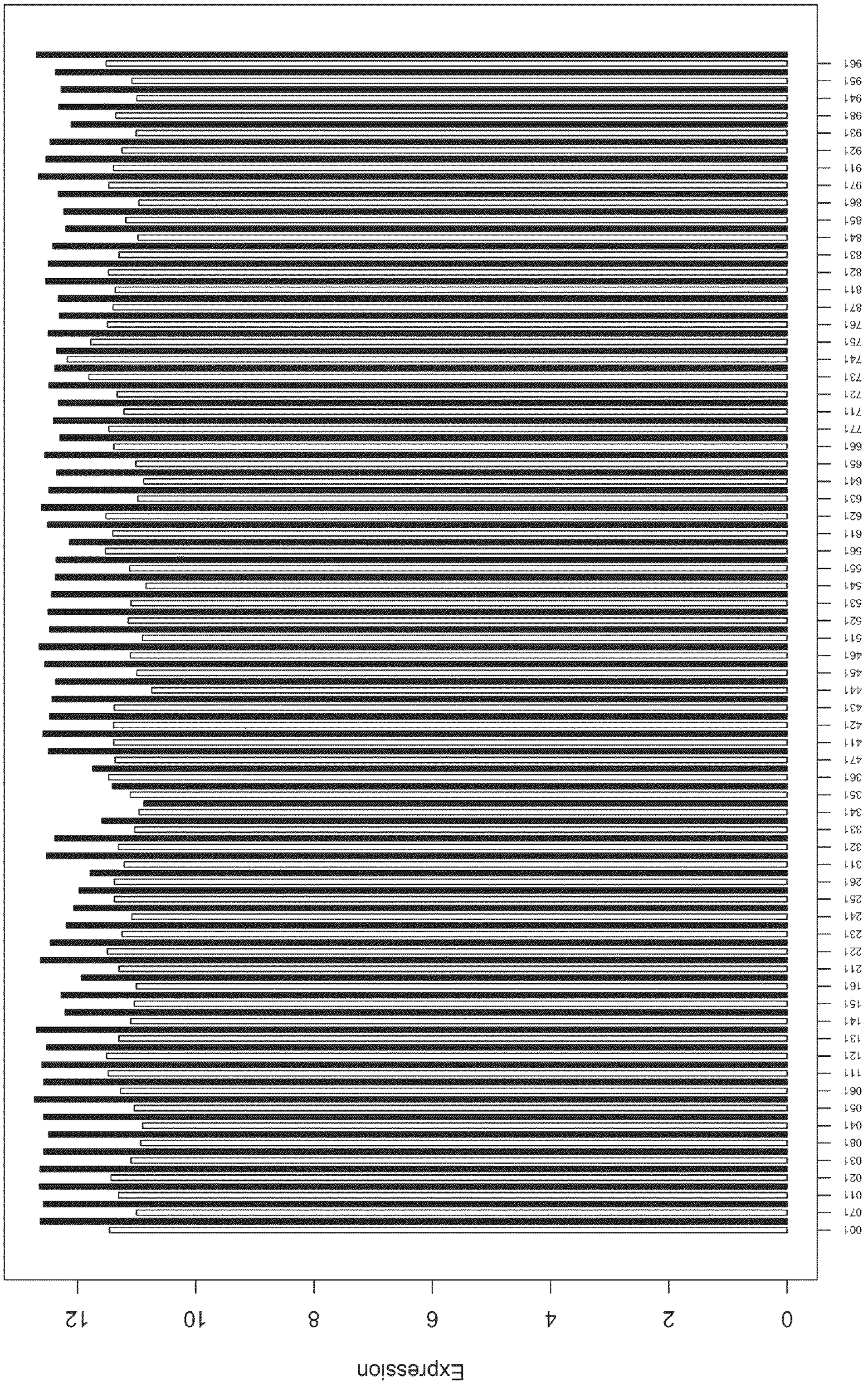

AT1G43170
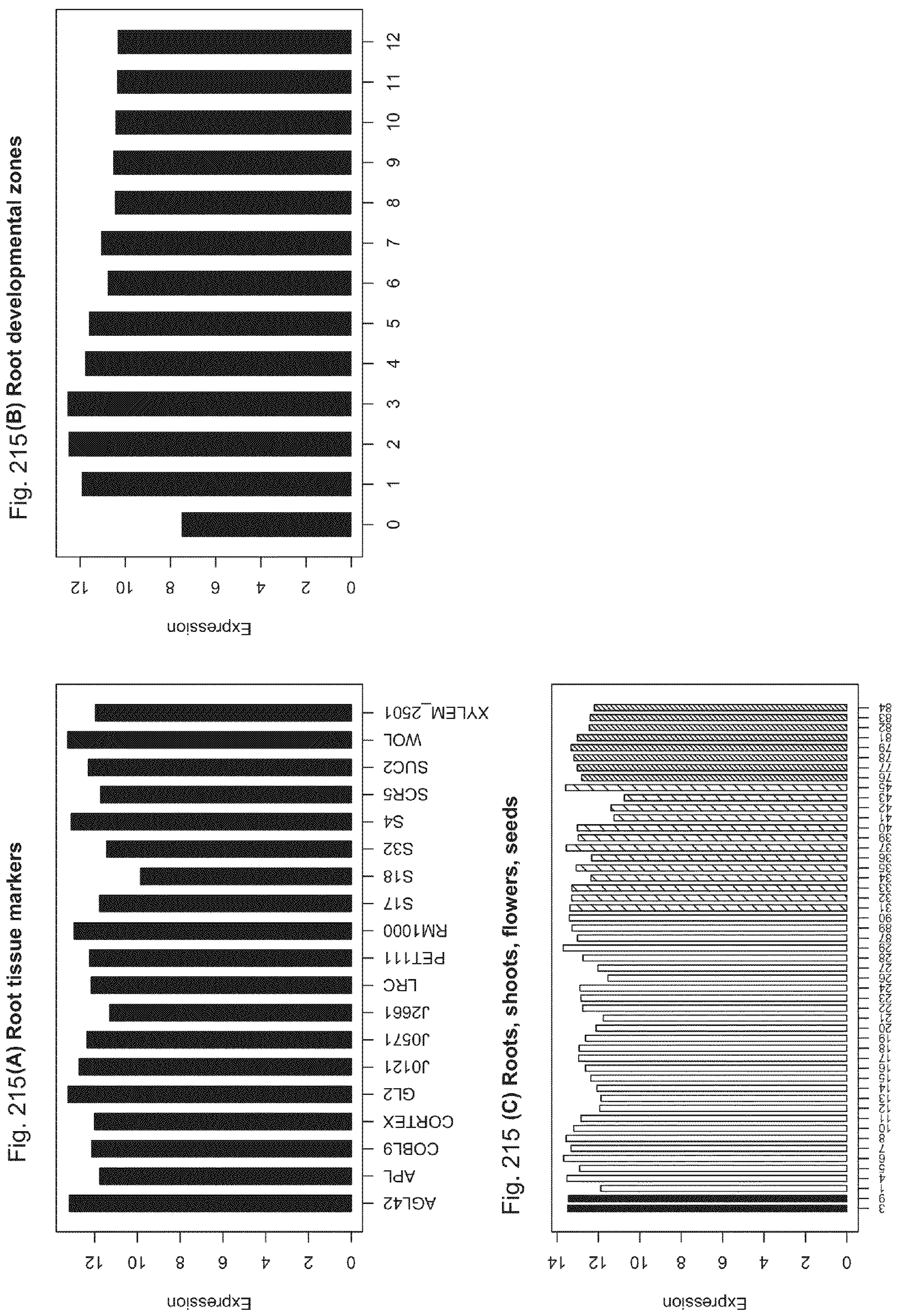
Fig. 215(A) Root tissue markers
Fig. 215(B) Root developmental zones
Fig. 215 (C) Roots, shoots, flowers, seeds AT1G43170
Fig. 215 (D) Abiotic stresses
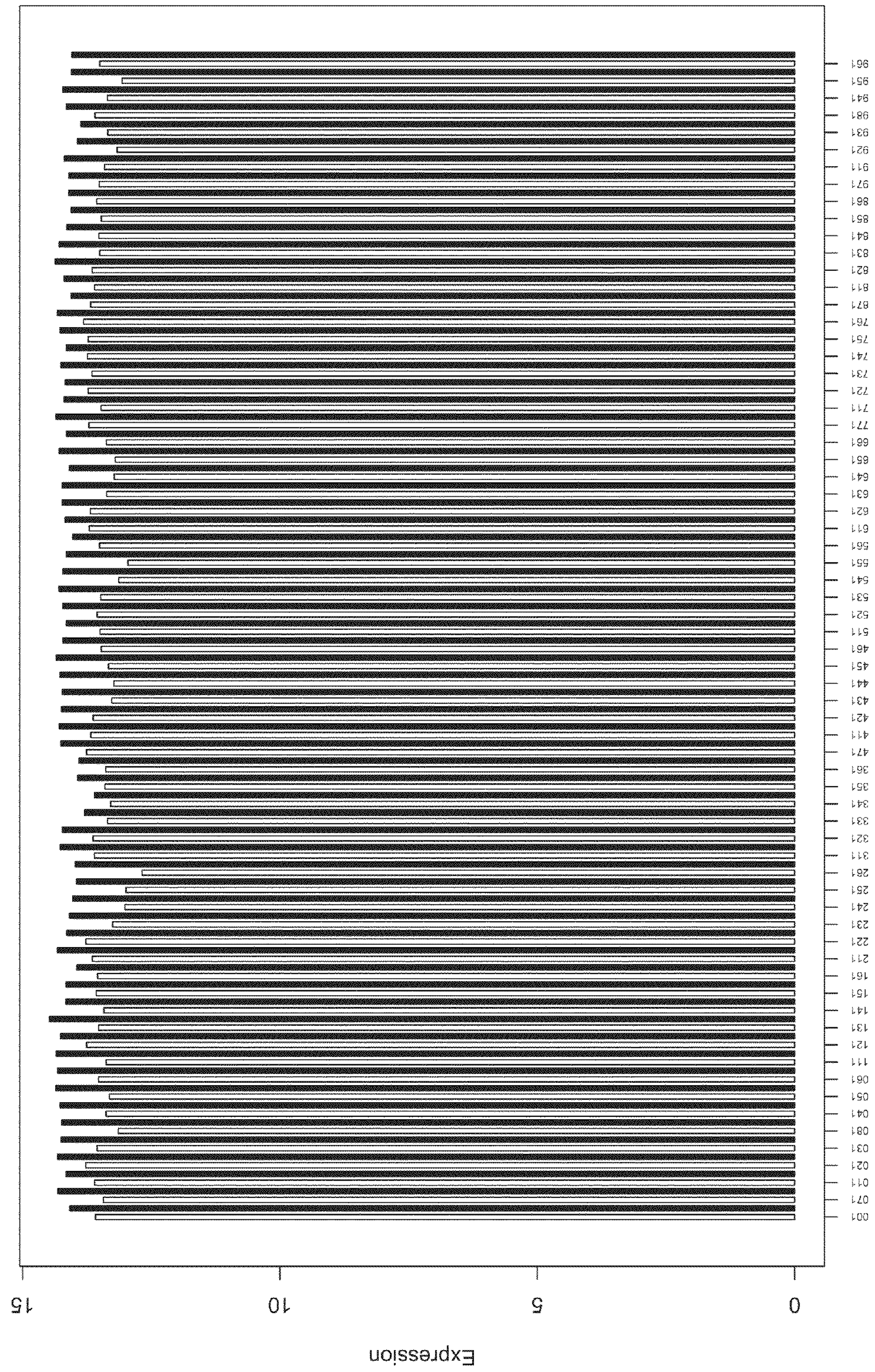

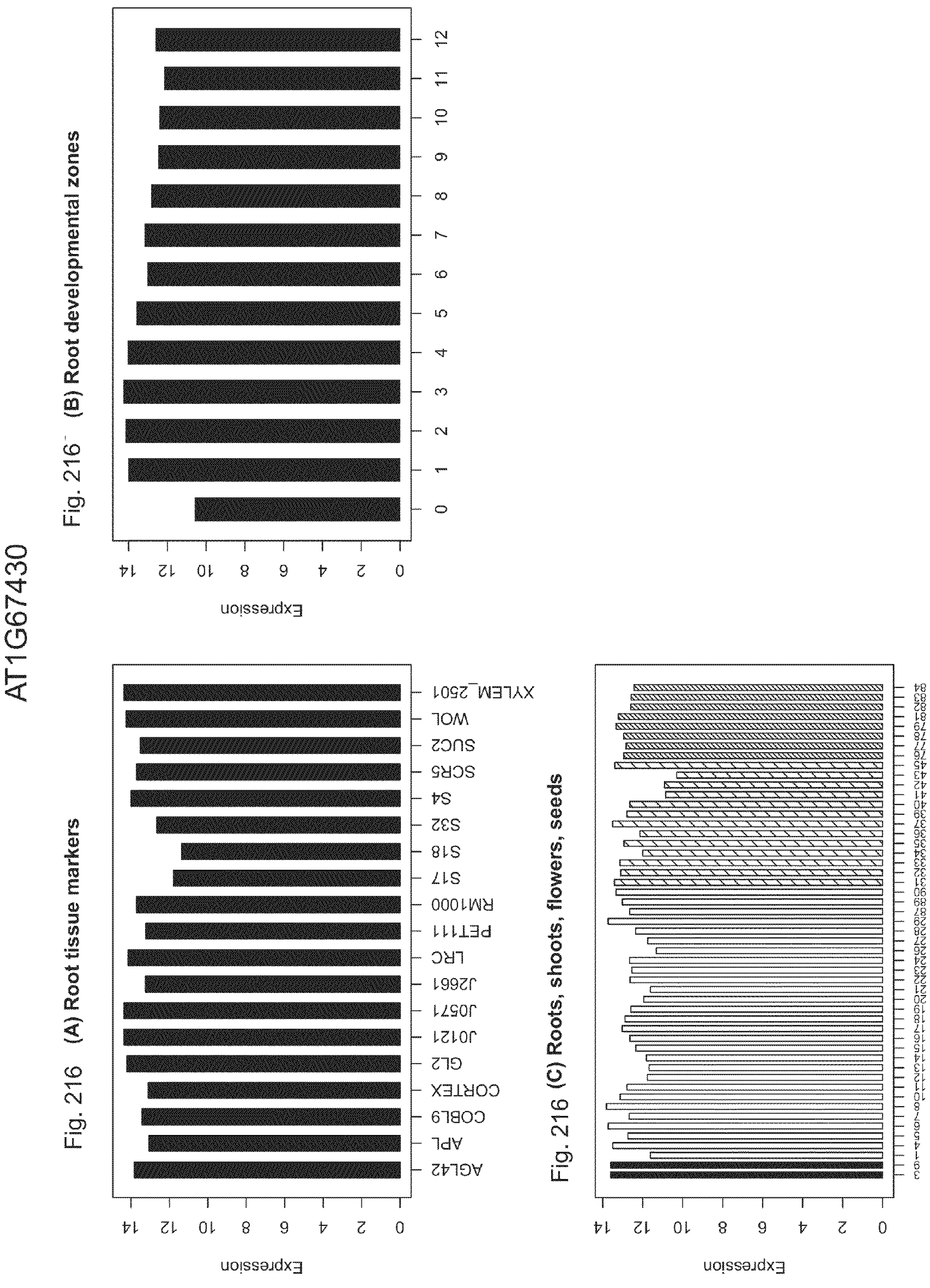
Fig. 216 (A) Root tissue markers
Fig. 216 (B) Root developmental zones
Fig. 216 (C) Roots, shoots, flowers, seeds AT1G67430
Fig. 216 (D) Abiotic stresses
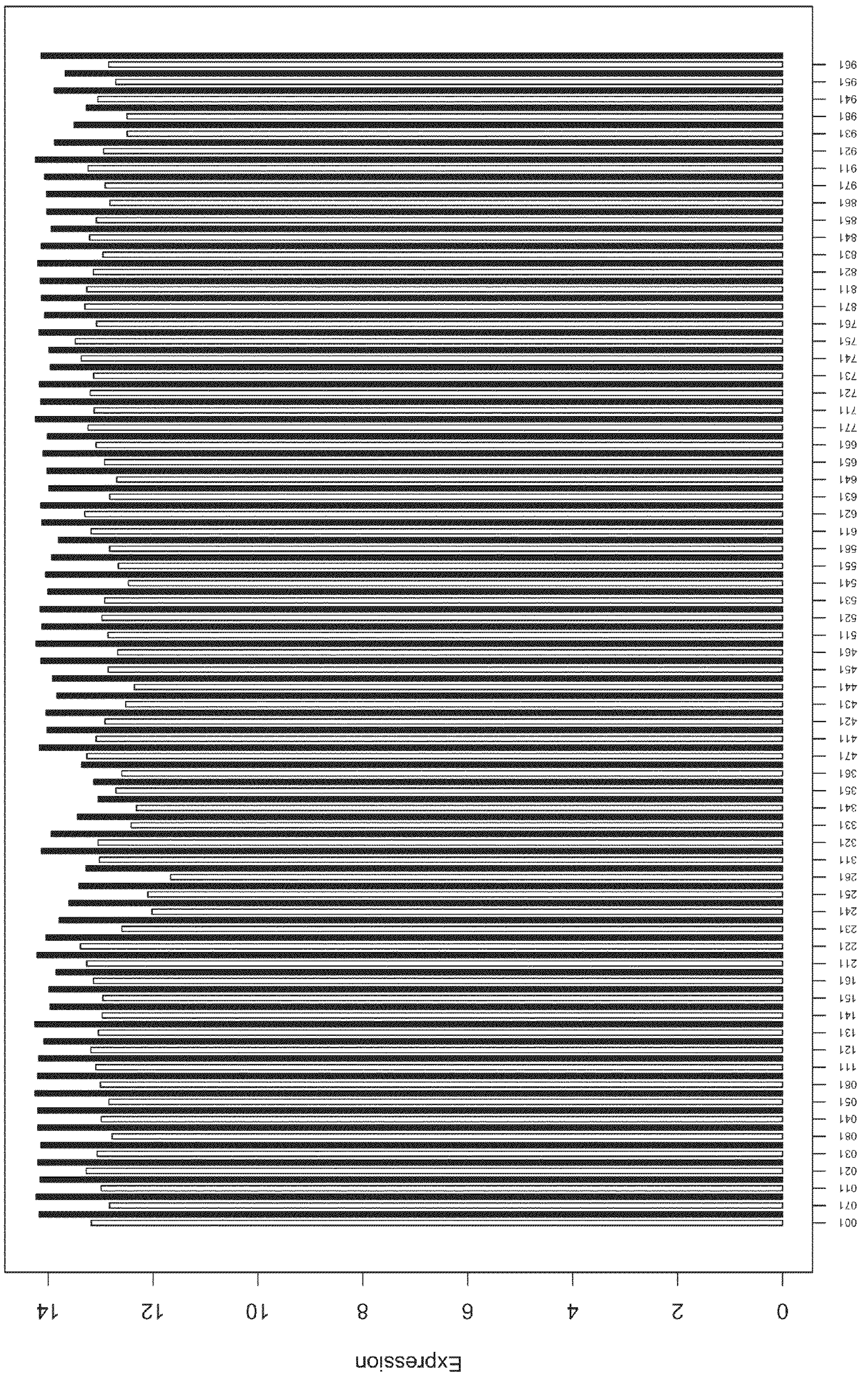

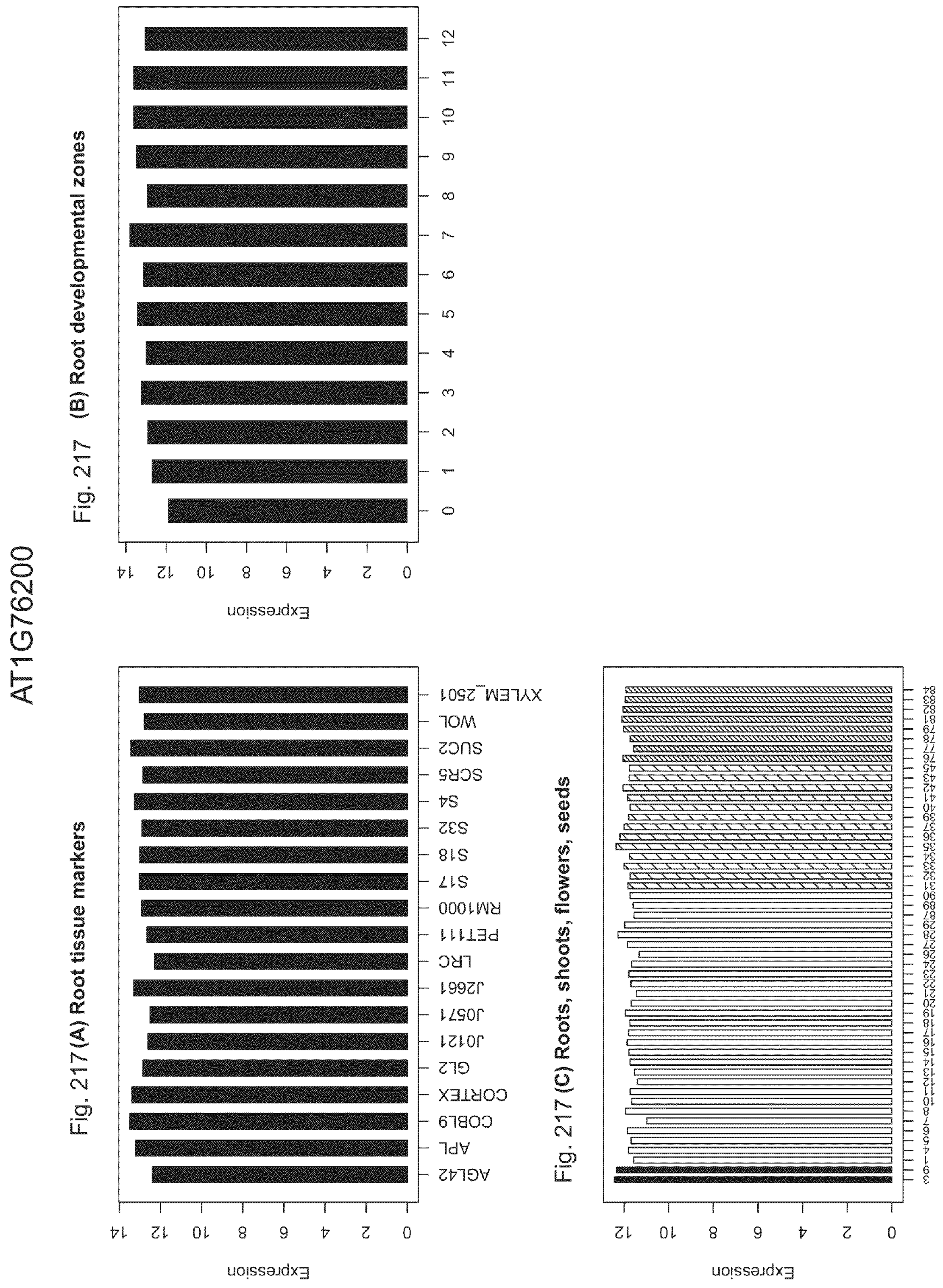
AT1G76200
Fig. 217 (A) Root tissue markers
AGL42
APL
COBL9
CORTEX
GL2
J0121
J0571
J2661
LRC
PET111
RM1000
S17
S18
S32
S4
SCR5
SUC2
WOL
XYLEM_2501
Expression
Fig. 217 (B) Root developmental zones
Expression
Fig. 217 (C) Roots, shoots, flowers, seeds
Expression AT1G76200
Fig. 217 (D) Abiotic stresses
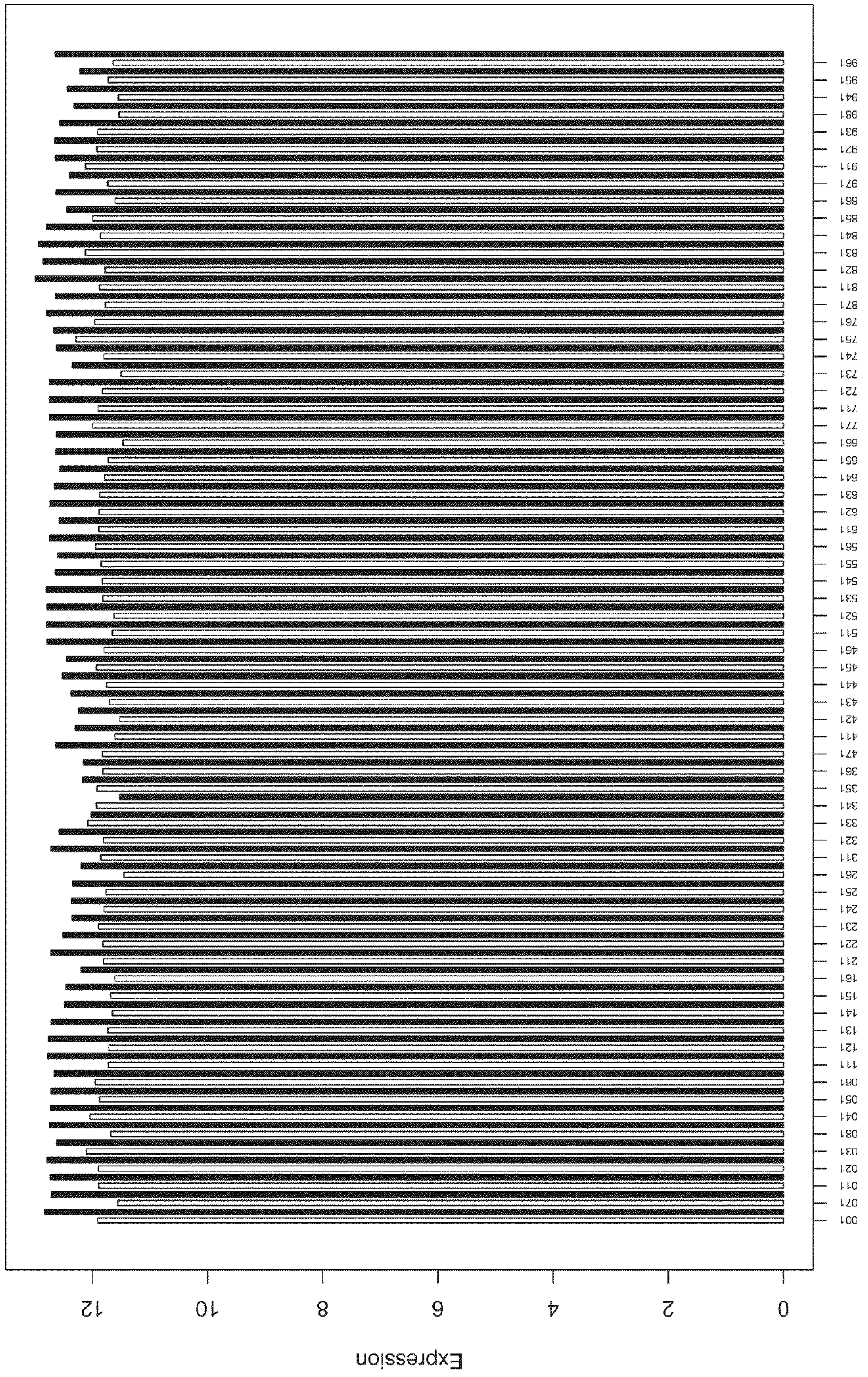

AT2G16850
Fig. 218 (B) Root developmental zones
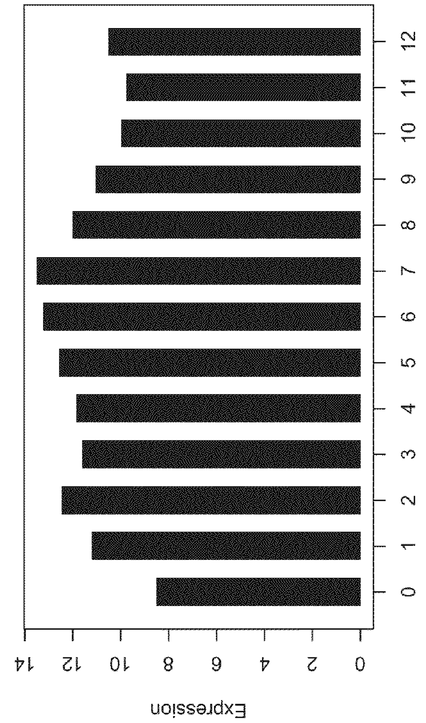
Fig. 218 (A) Root tissue markers
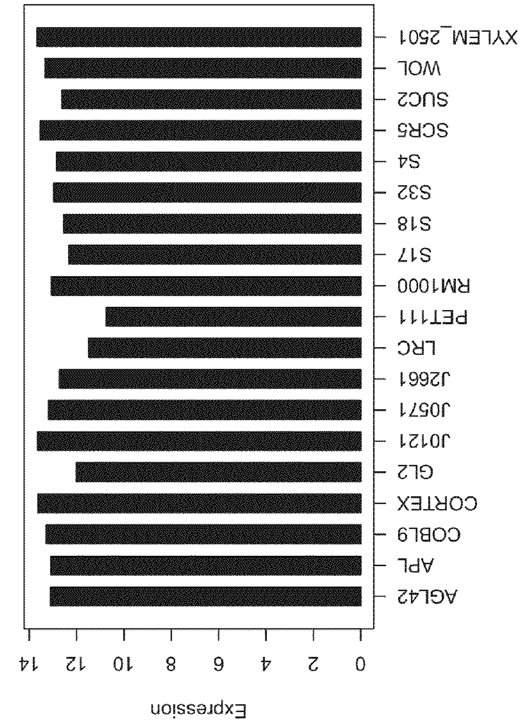
Fig. 218 (C) Roots, shoots, flowers, seeds
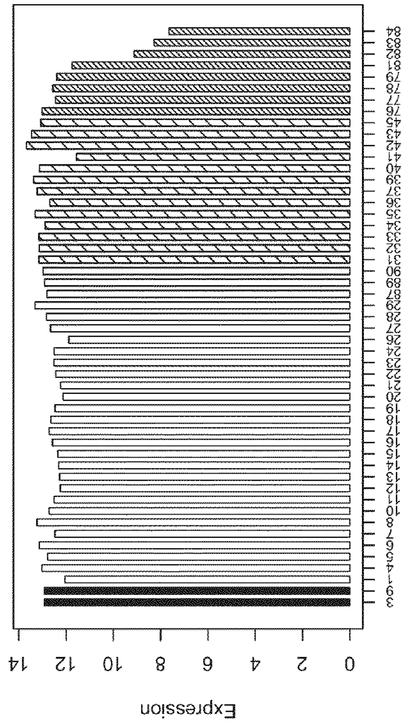

AT2G16850
Fig. 218 (D) Abiotic stresses
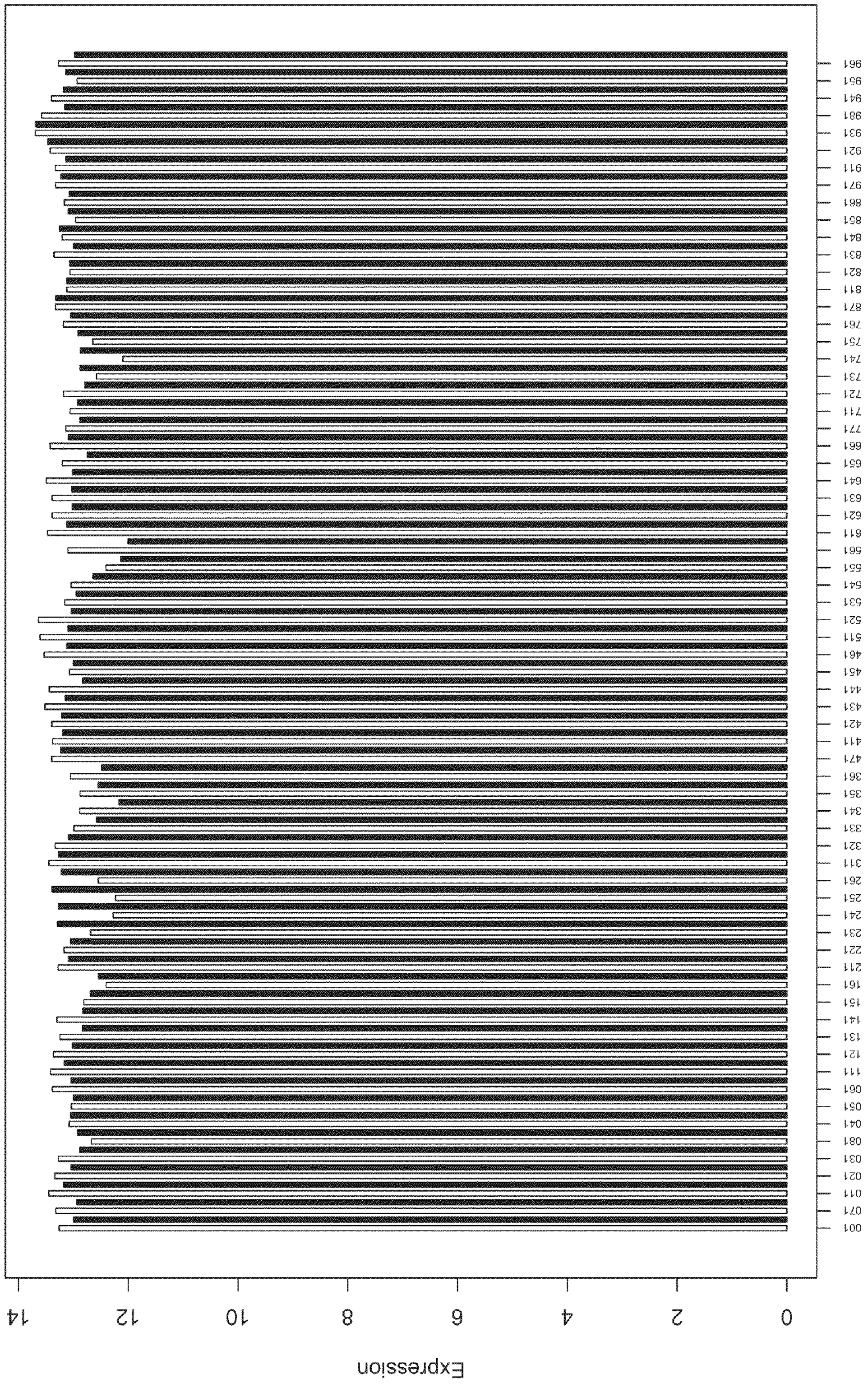

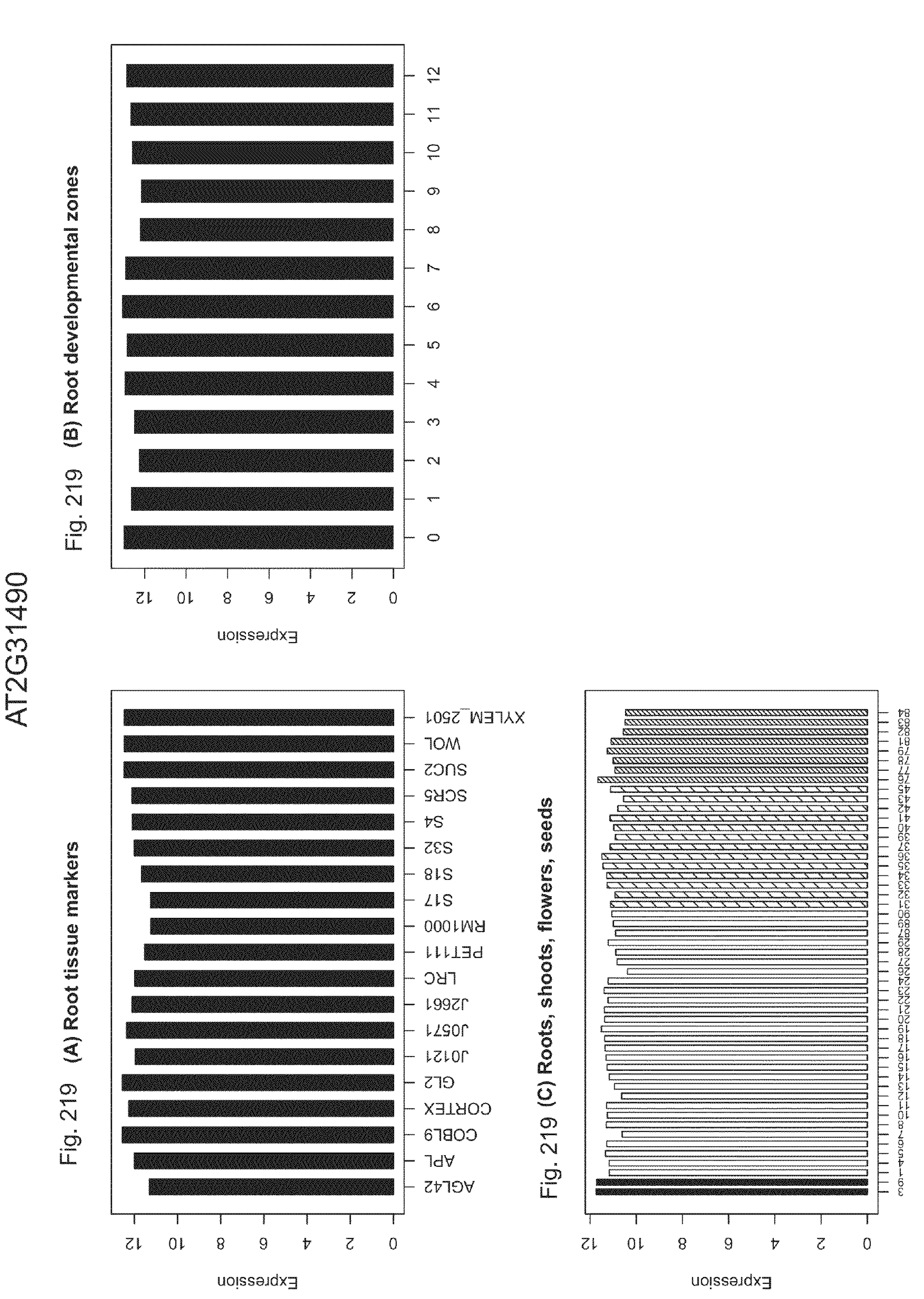
AT2G31490
Fig. 219 (B) Root developmental zones
Expression
0 2 4 6 8 10 12
0 1 2 3 4 5 6 7 8 9 10 11 12
Fig. 219 (A) Root tissue markers
AGL42
APL
COBL9
CORTEX
GL2
J0121
J0571
J2661
LRC
PET111
RM1000
S17
S18
S32
S4
SCR5
SUC2
WOL
XYLEM_2501
Fig. 219 (C) Roots, shoots, flowers, seeds AT2G31490
Fig. 219 (D) Abiotic stresses
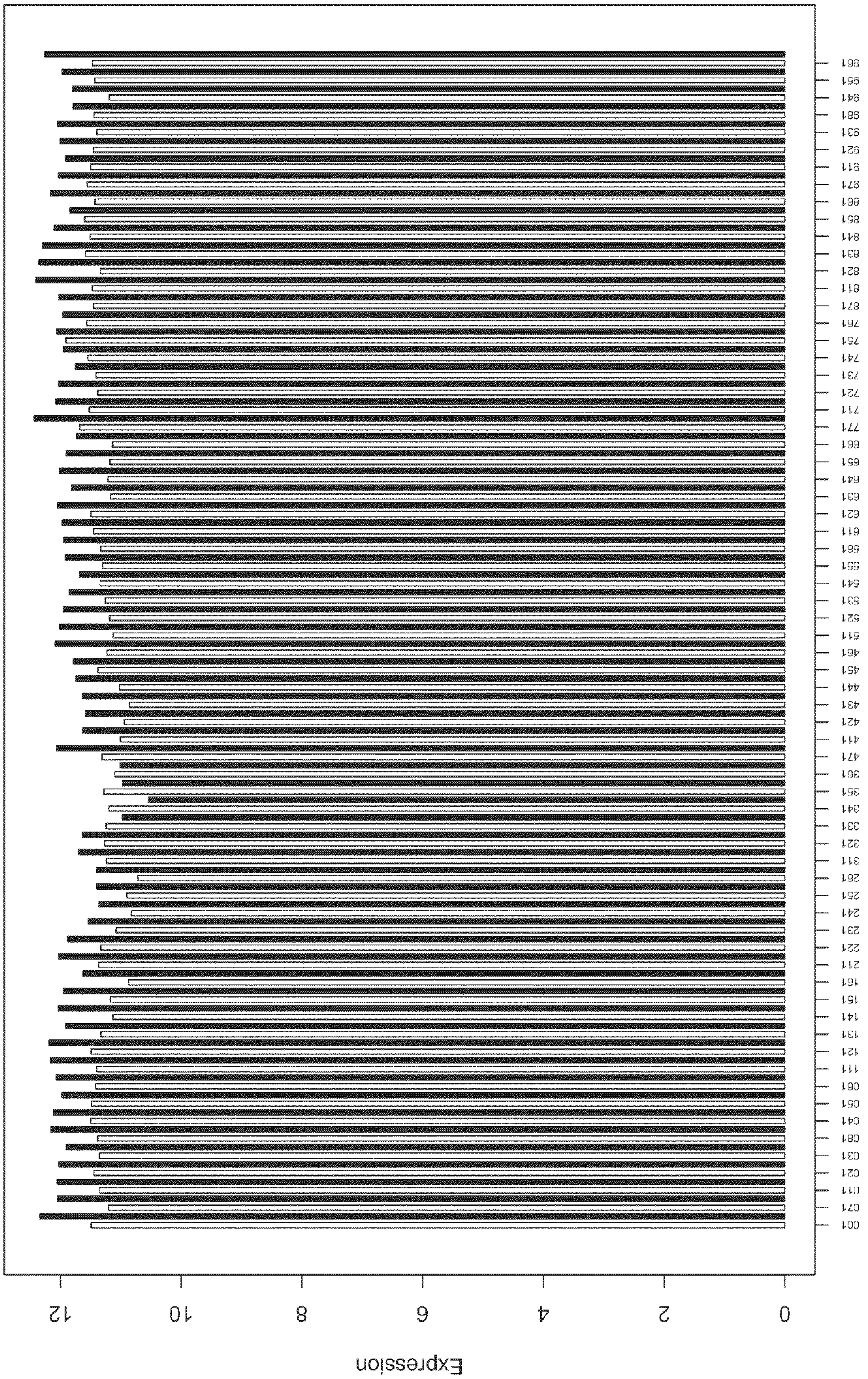

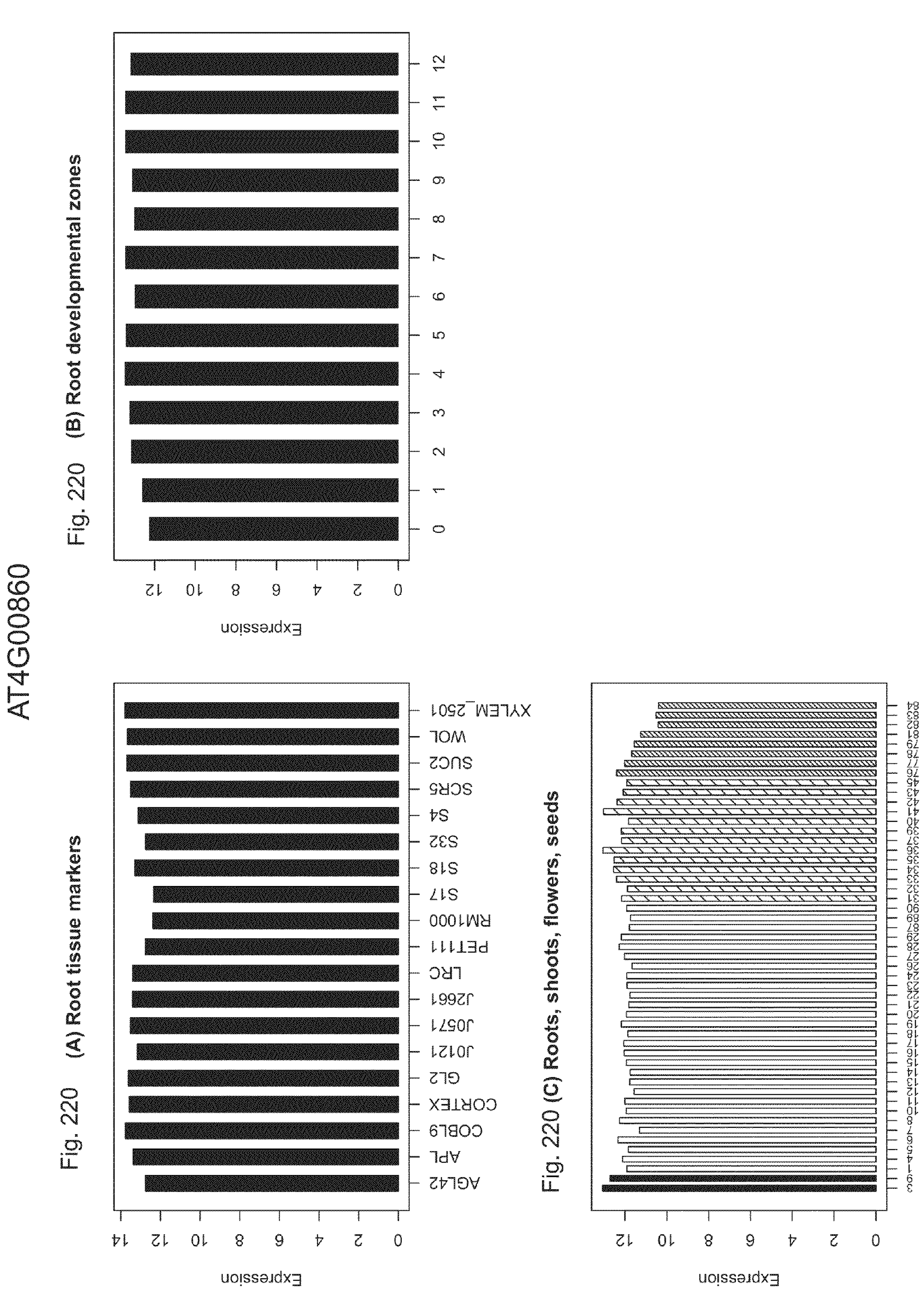
AT4G00860
Fig. 220 (A) Root tissue markers
Expression
0 2 4 6 8 10 12 14
AGL42
APL
COBL9
CORTEX
GL2
J0121
J0571
J2661
LRC
PET111
RM1000
S17
S18
S32
S4
SCR5
SUC2
WOL
XYLEM_2501
Fig. 220 (B) Root developmental zones
Expression
0 2 4 6 8 10 12
0 1 2 3 4 5 6 7 8 9 10 11 12
Fig. 220 (C) Roots, shoots, flowers, seeds
Expression
0 2 4 6 8 10 12

AT4G00860

(D) Abiotic stresses

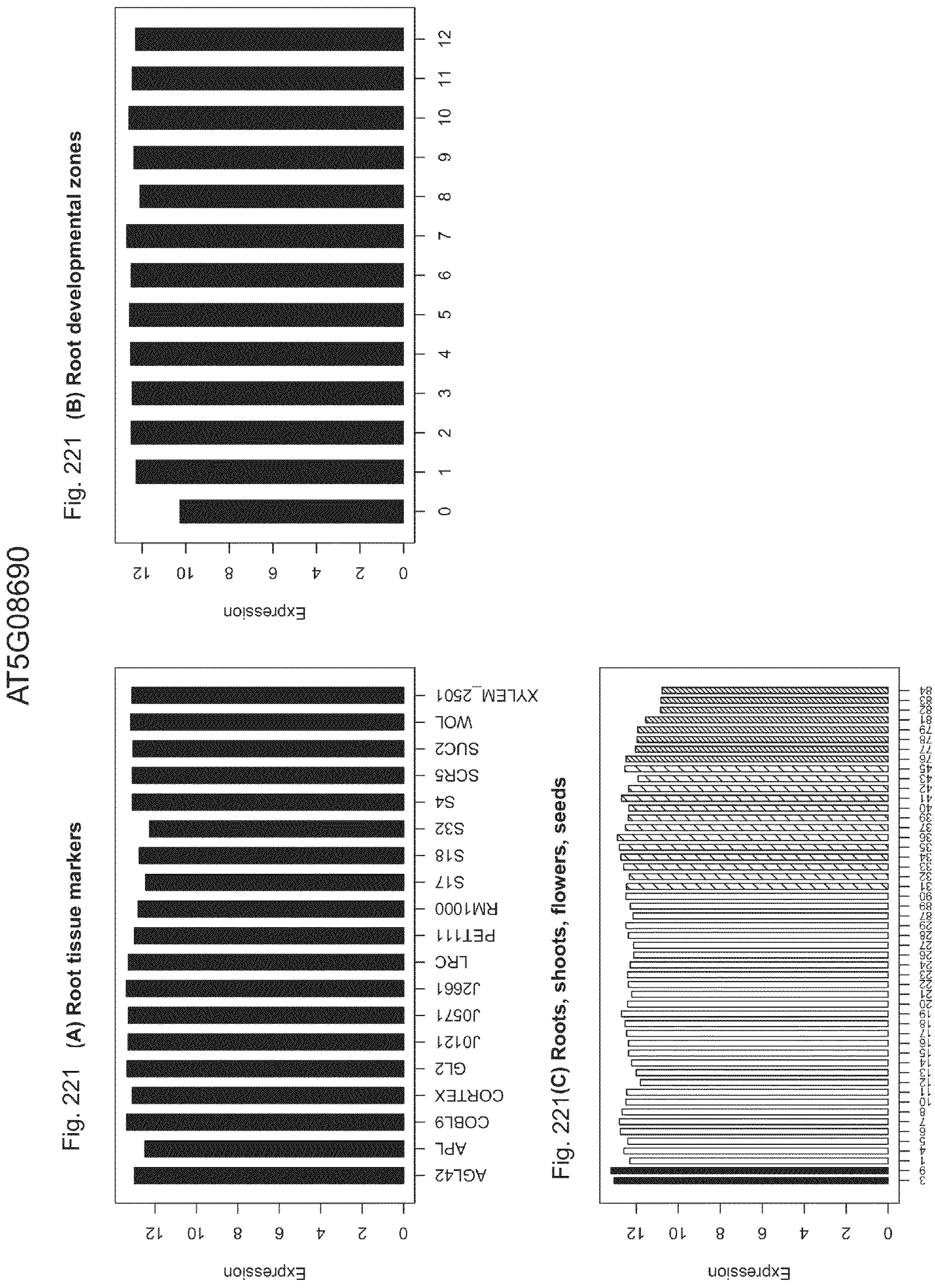
AT5G08690
Fig. 221 (A) Root tissue markers
Expression
AGL42
APL
COBL9
CORTEX
GL2
J0121
J0571
J2661
LRC
PET111
RM1000
S17
S18
S32
S4
SCR5
SUC2
WOL
XYLEM_2501
Fig. 221 (B) Root developmental zones
Expression
Fig. 221(C) Roots, shoots, flowers, seeds
Expression AT5G08690
Fig. 221 (D) Abiotic stresses
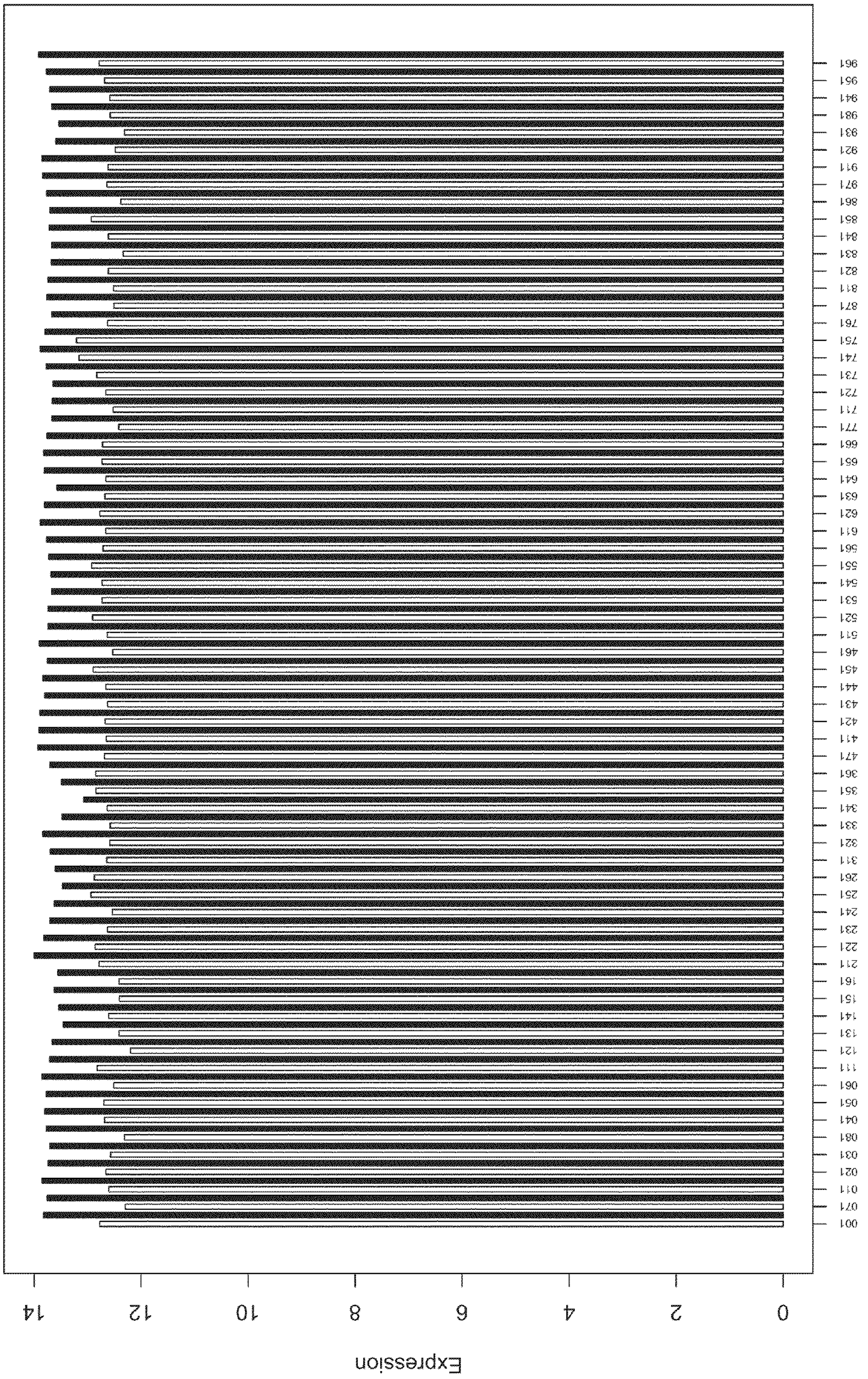

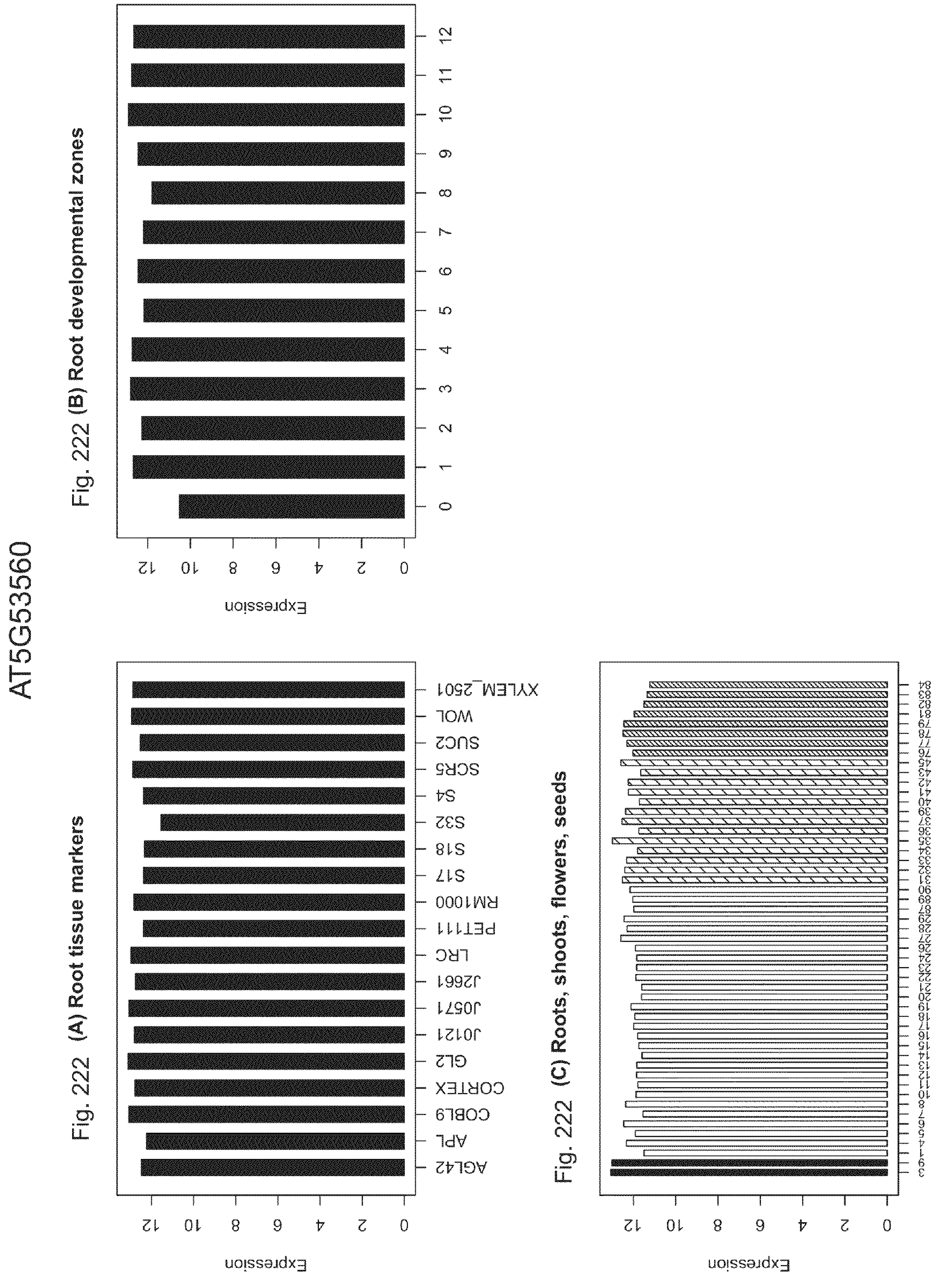
Fig. 222 (A) Root tissue markers
Fig. 222 (B) Root developmental zones
Fig. 222 (C) Roots, shoots, flowers, seeds AT5G53560
Fig. 222 (D) Abiotic stresses
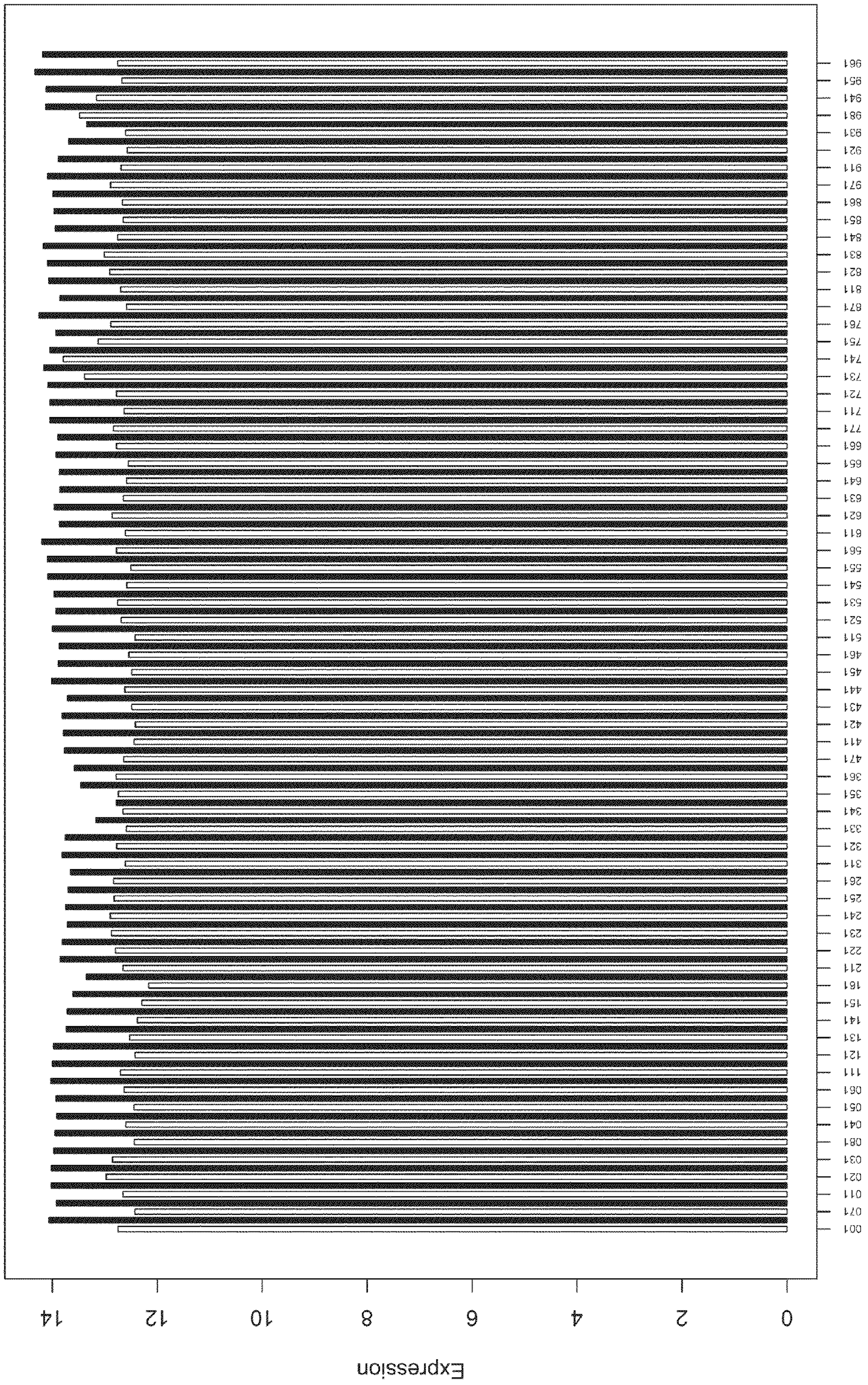

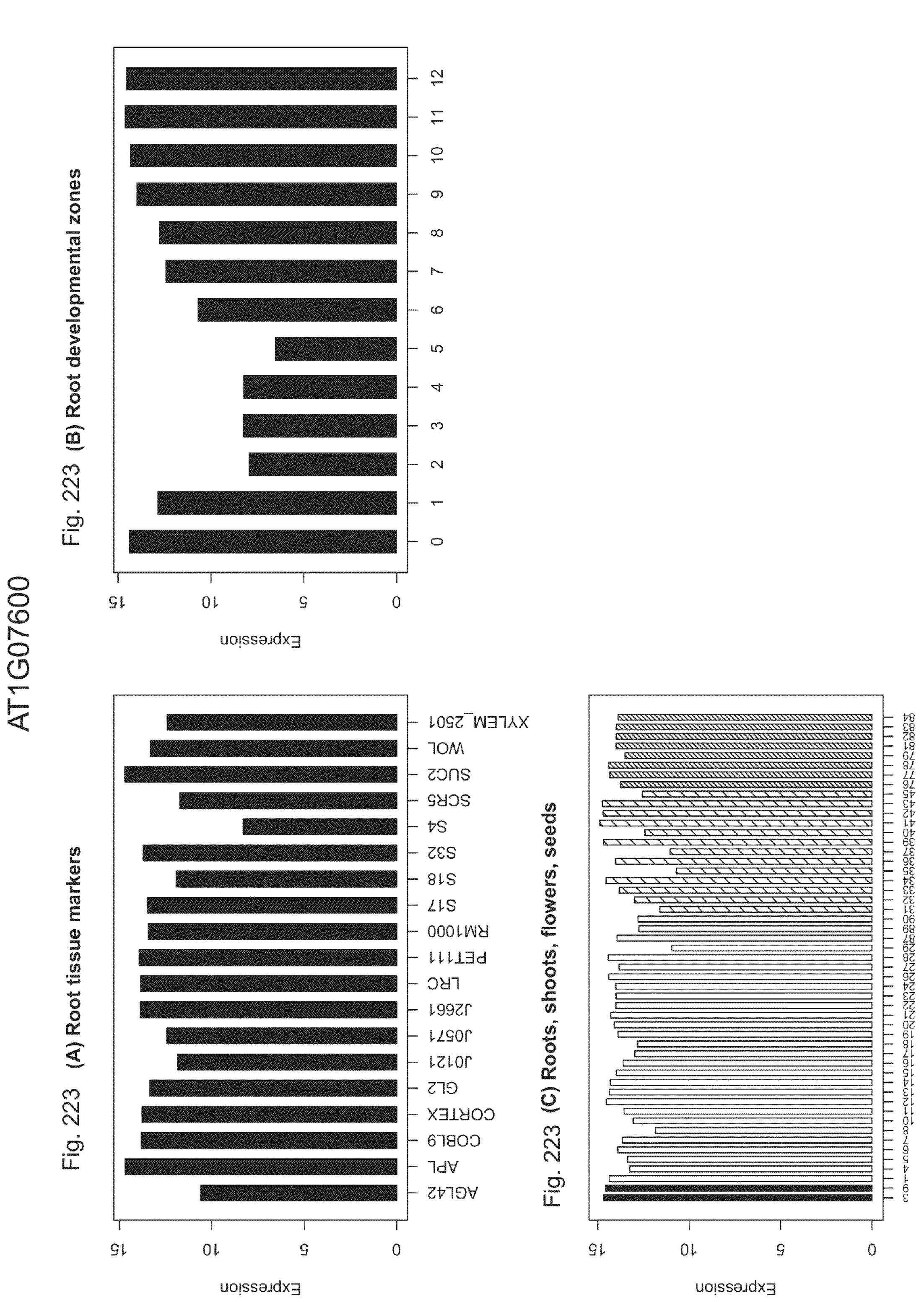
Fig. 223 (A) Root tissue markers
Fig. 223 (B) Root developmental zones
Fig. 223 (C) Roots, shoots, flowers, seeds AT1G07600
Fig. 223 (D) Abiotic stresses
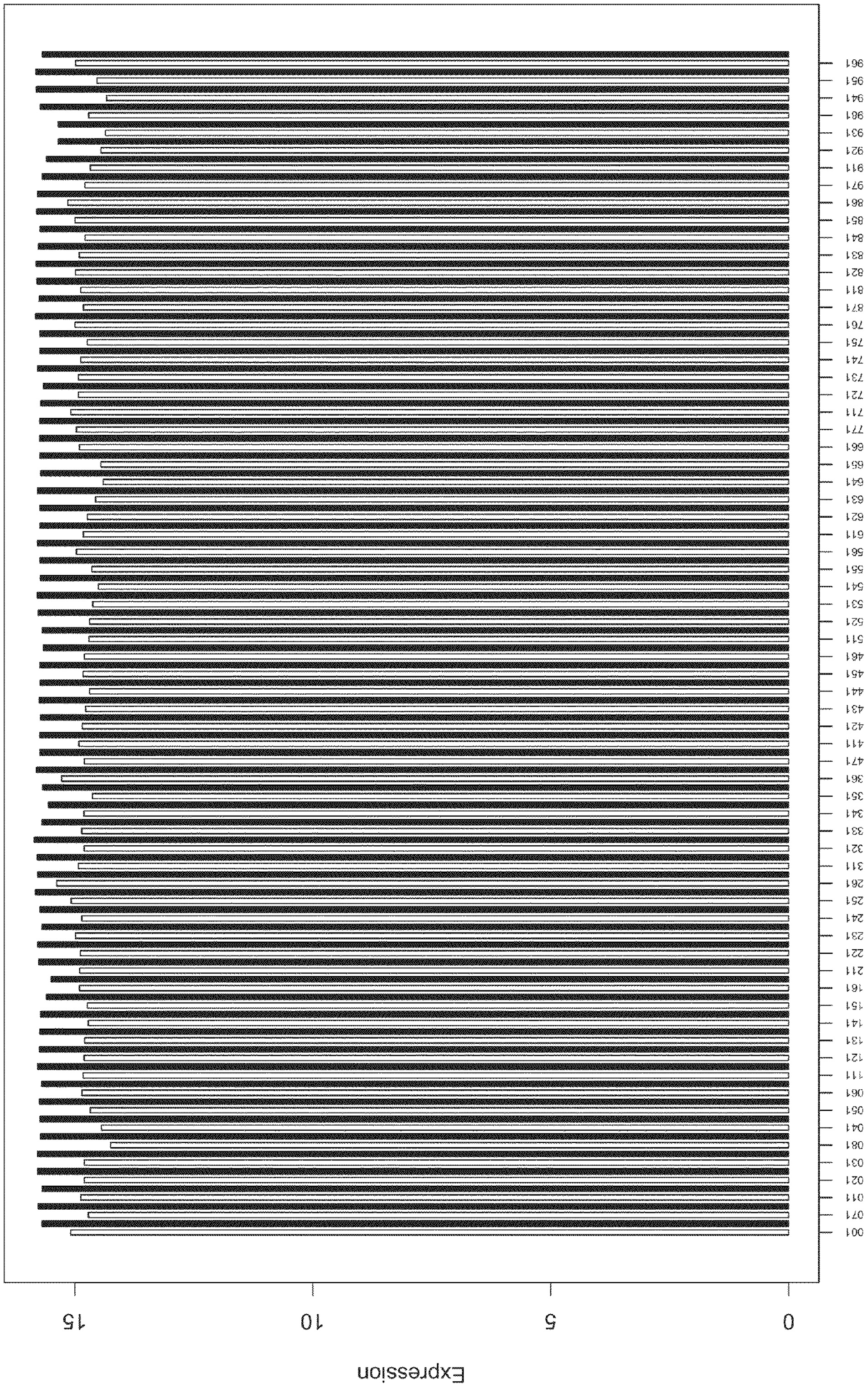

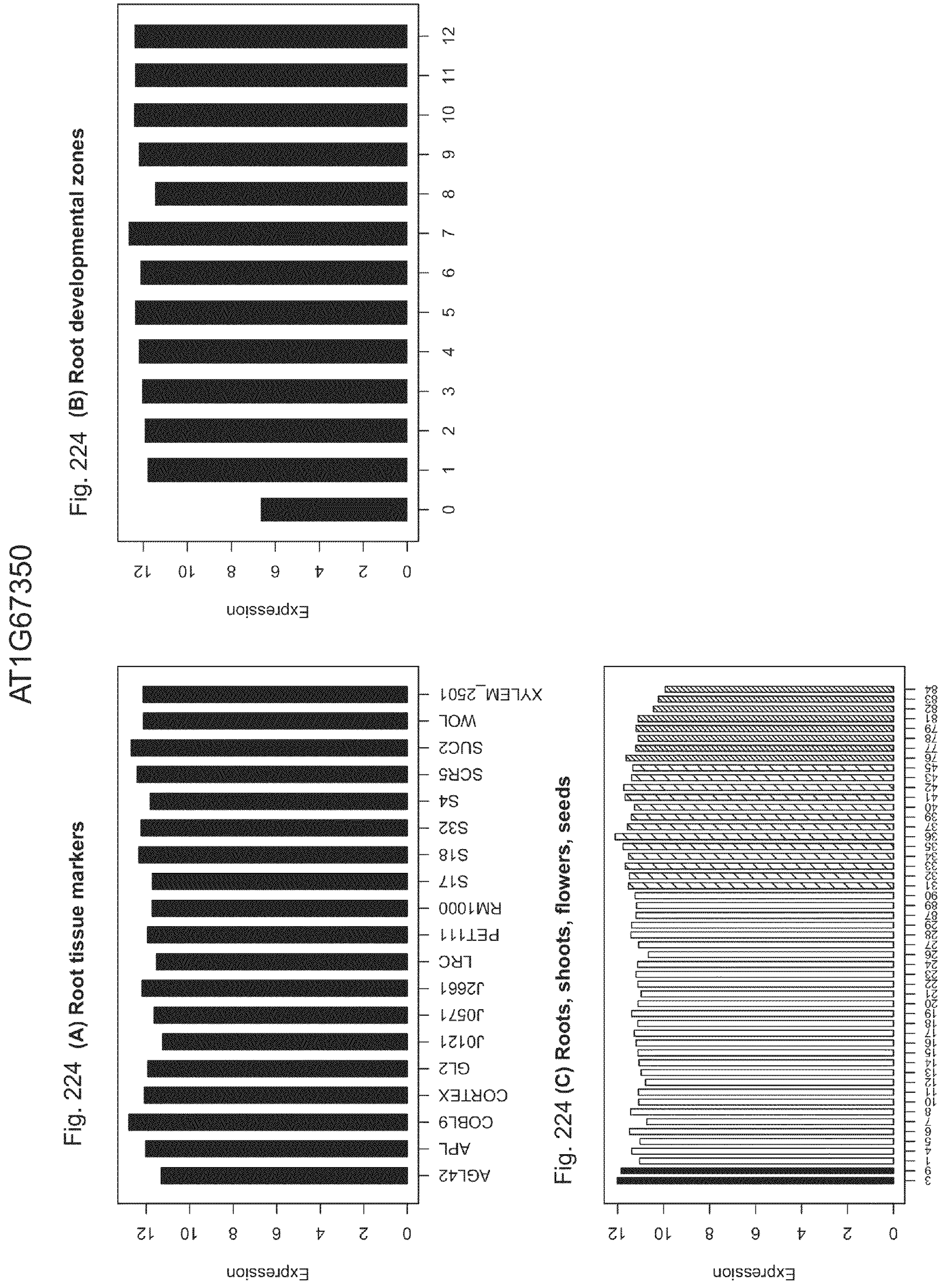
AT1G67350
Fig. 224 (A) Root tissue markers
AGL42
APL
COBL9
CORTEX
GL2
J0121
J0571
J2661
LRC
PET111
RM1000
S17
S18
S32
S4
SCR5
SUC2
WOL
XYLEM_2501
Expression
Fig. 224 (B) Root developmental zones
Expression
Fig. 224 (C) Roots, shoots, flowers, seeds
Expression

AT1G67350

(D) Abiotic stresses

AT1G78380
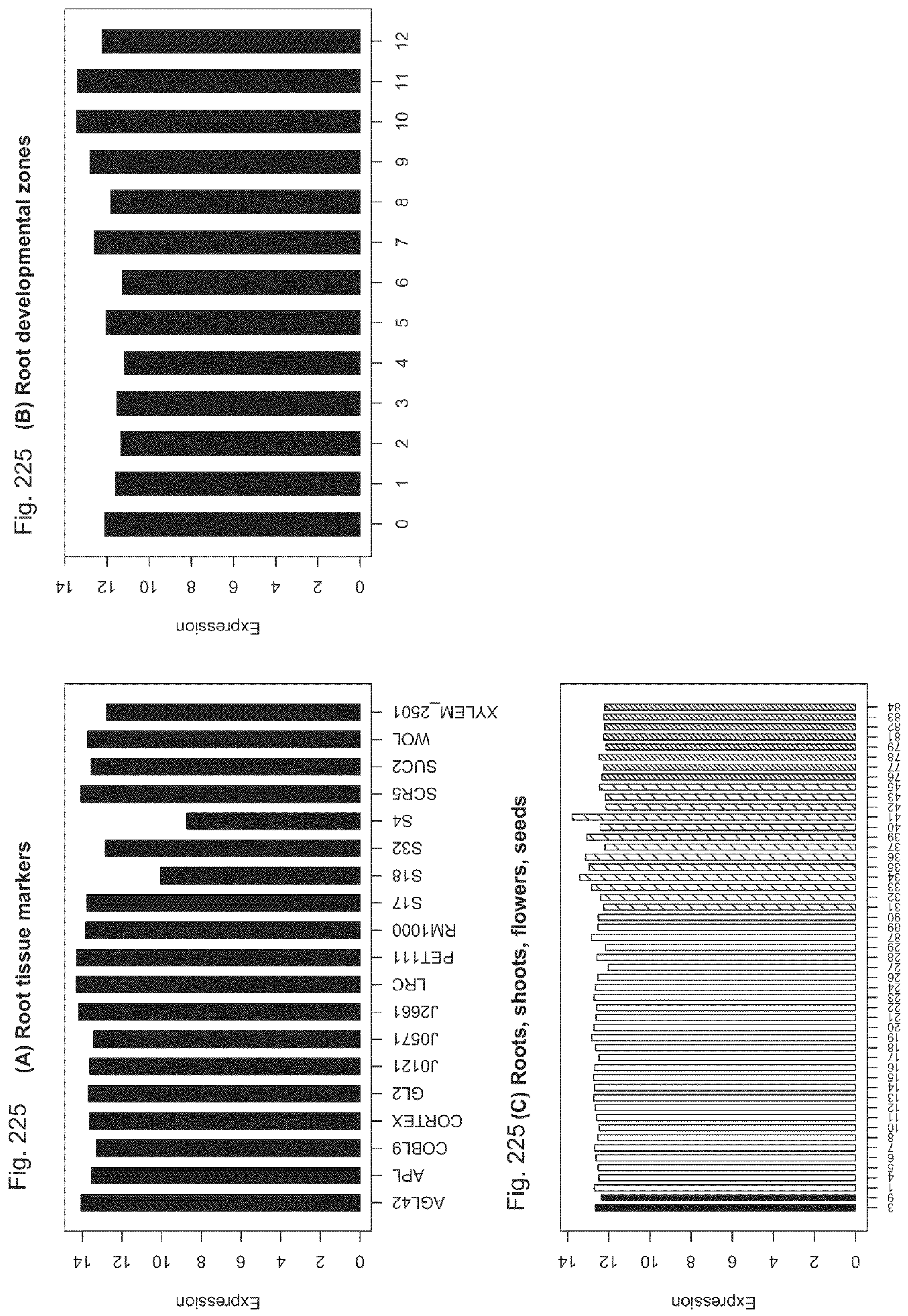
Fig. 225 (A) Root tissue markers
Fig. 225 (B) Root developmental zones
Fig. 225 (C) Roots, shoots, flowers, seeds AT1G78380
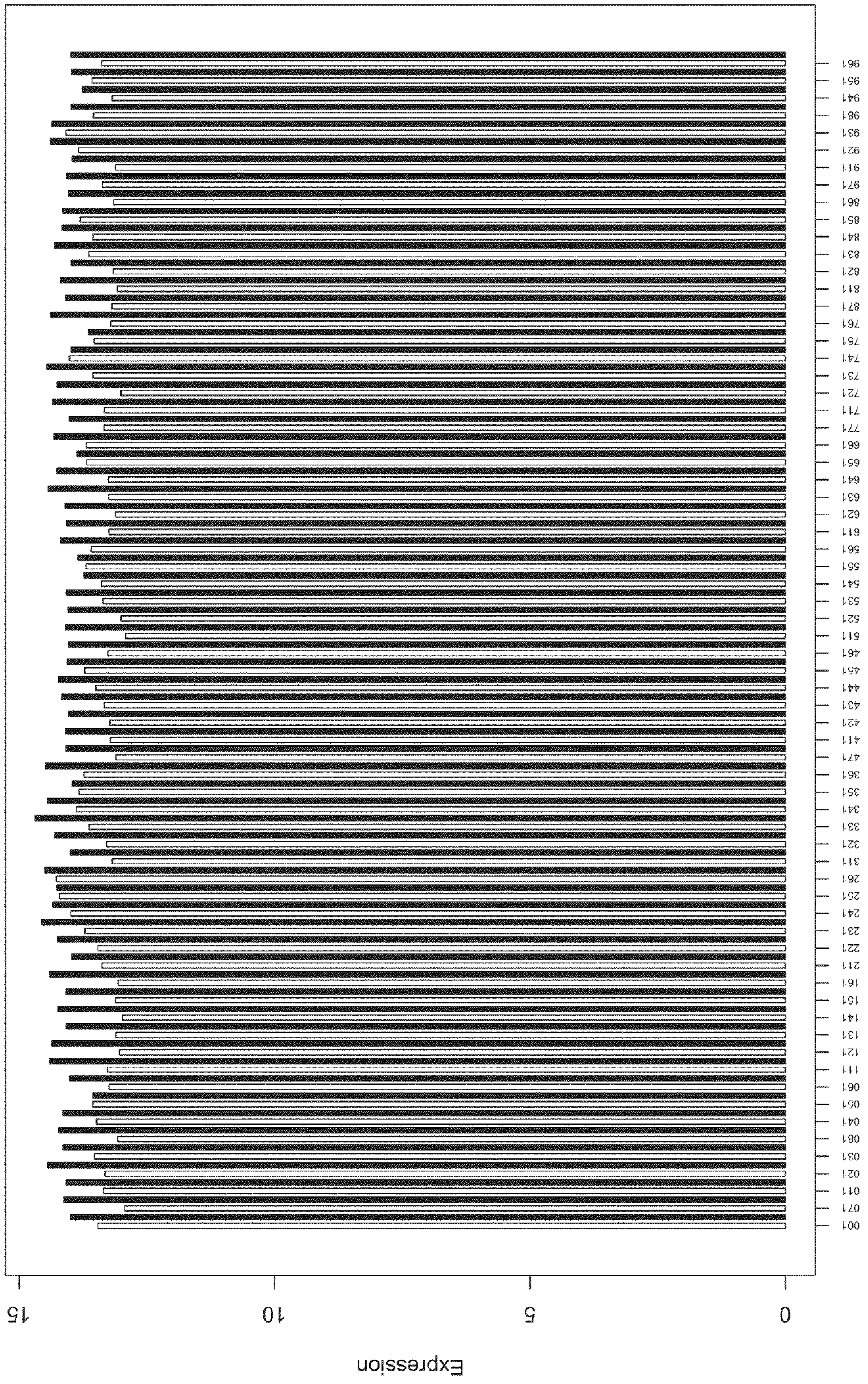
Fig. 225 (D) Abiotic stresses AT4G05320
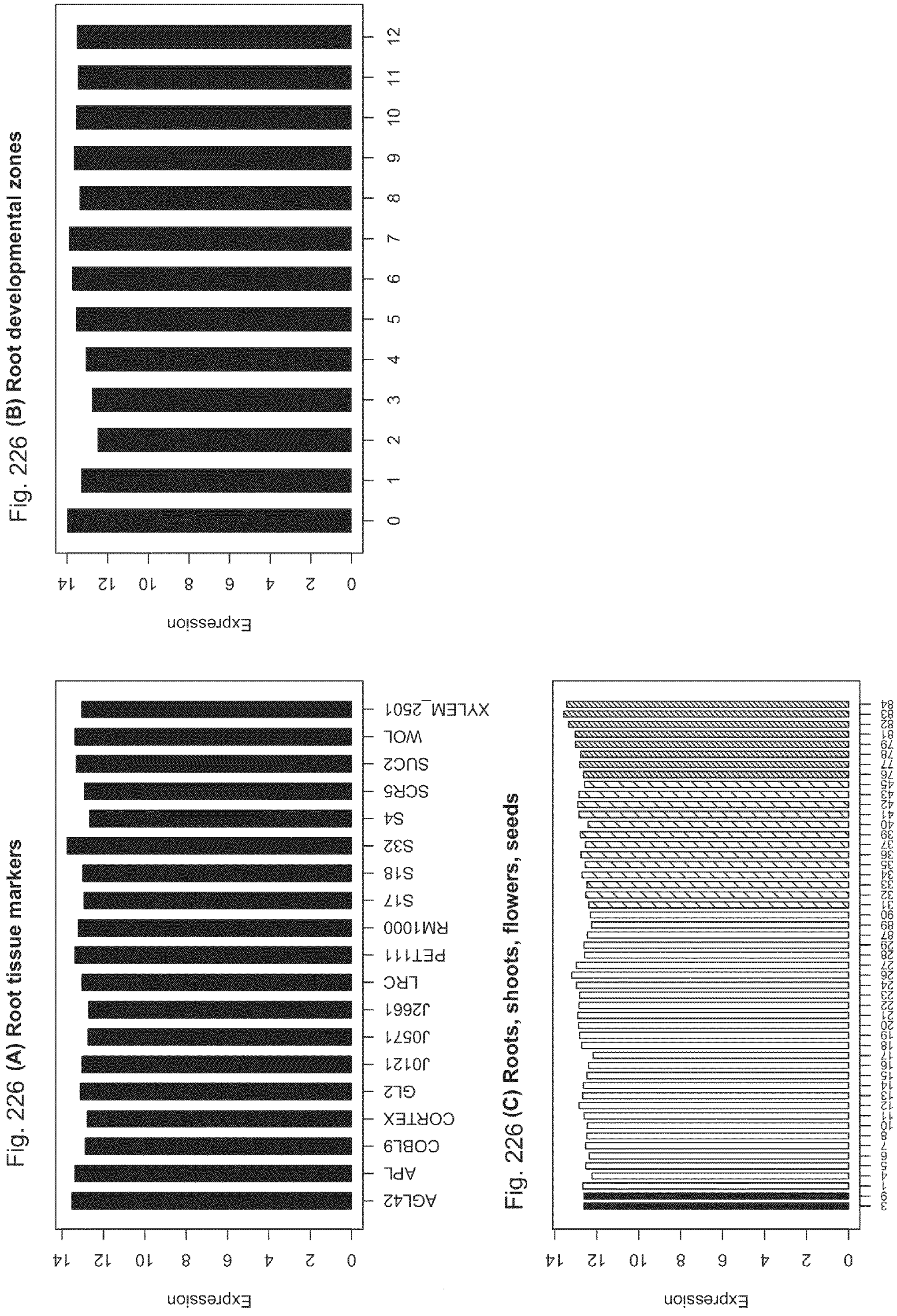
Fig. 226 (A) Root tissue markers
Fig. 226 (B) Root developmental zones
Fig. 226 (C) Roots, shoots, flowers, seeds AT4G05320
Fig. 226 (D) Abiotic stresses
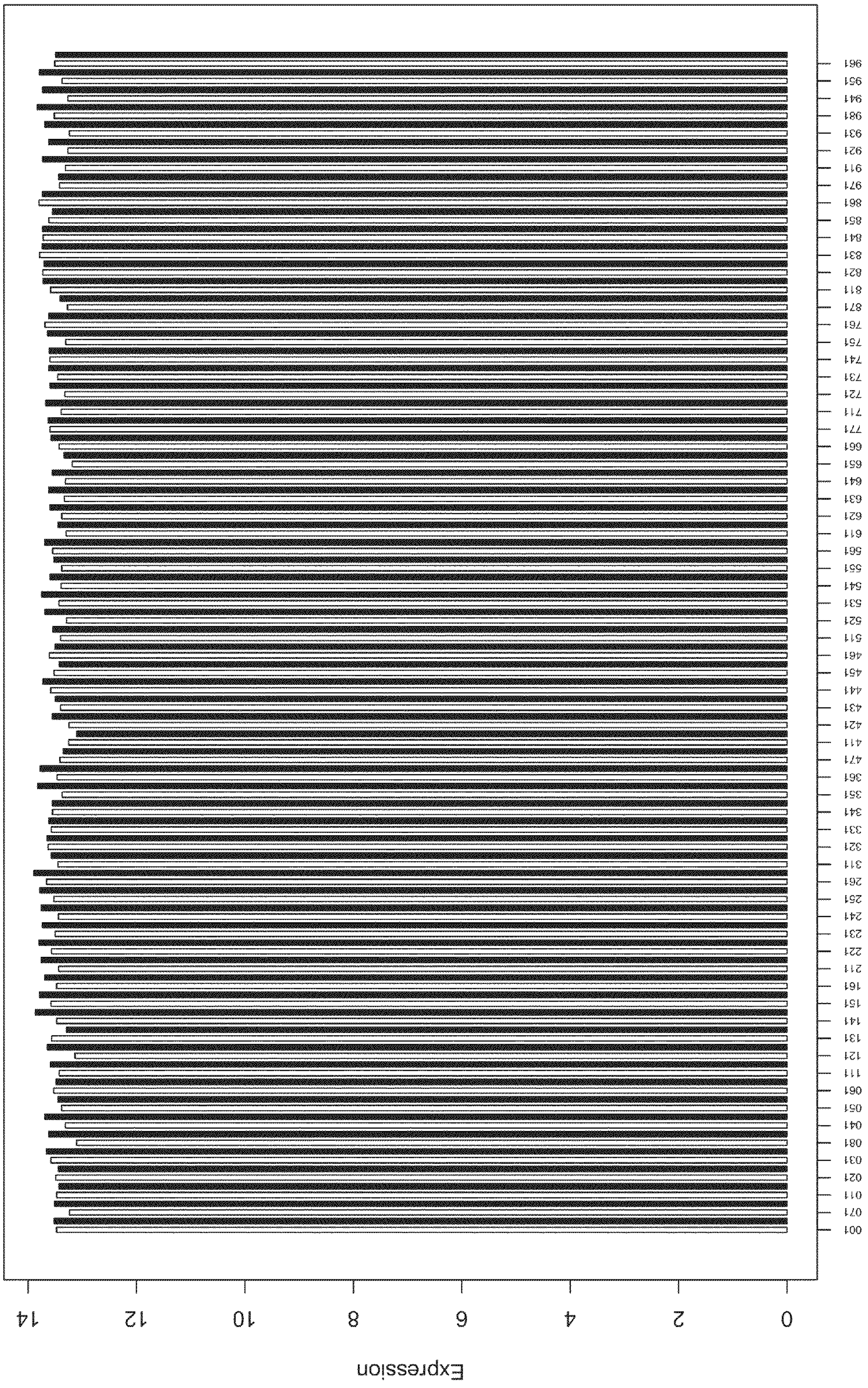

AT5G20290
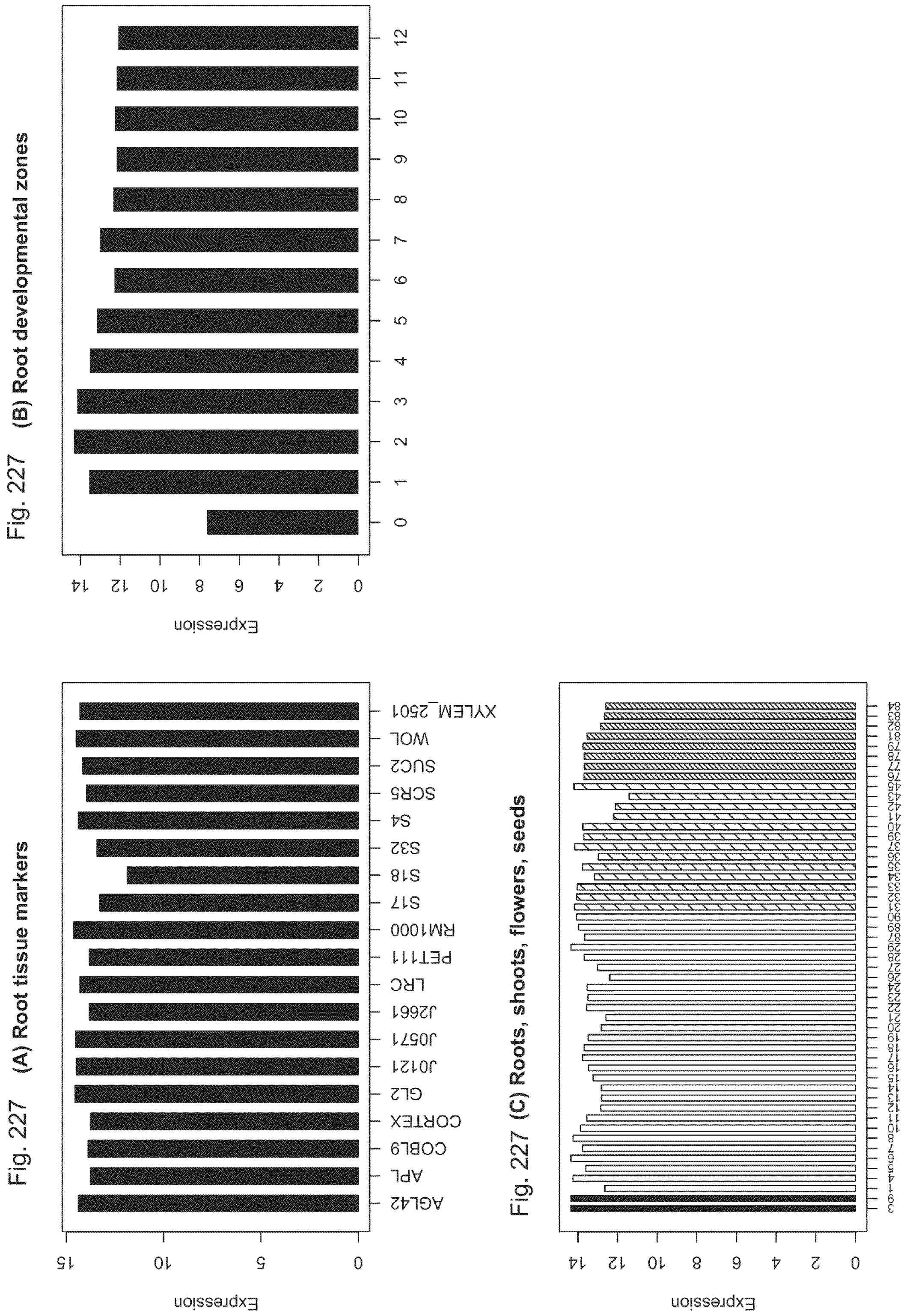
Fig. 227 (A) Root tissue markers
Fig. 227 (B) Root developmental zones
Fig. 227 (C) Roots, shoots, flowers, seeds AT5G20290
Fig. 227 (D) Abiotic stresses
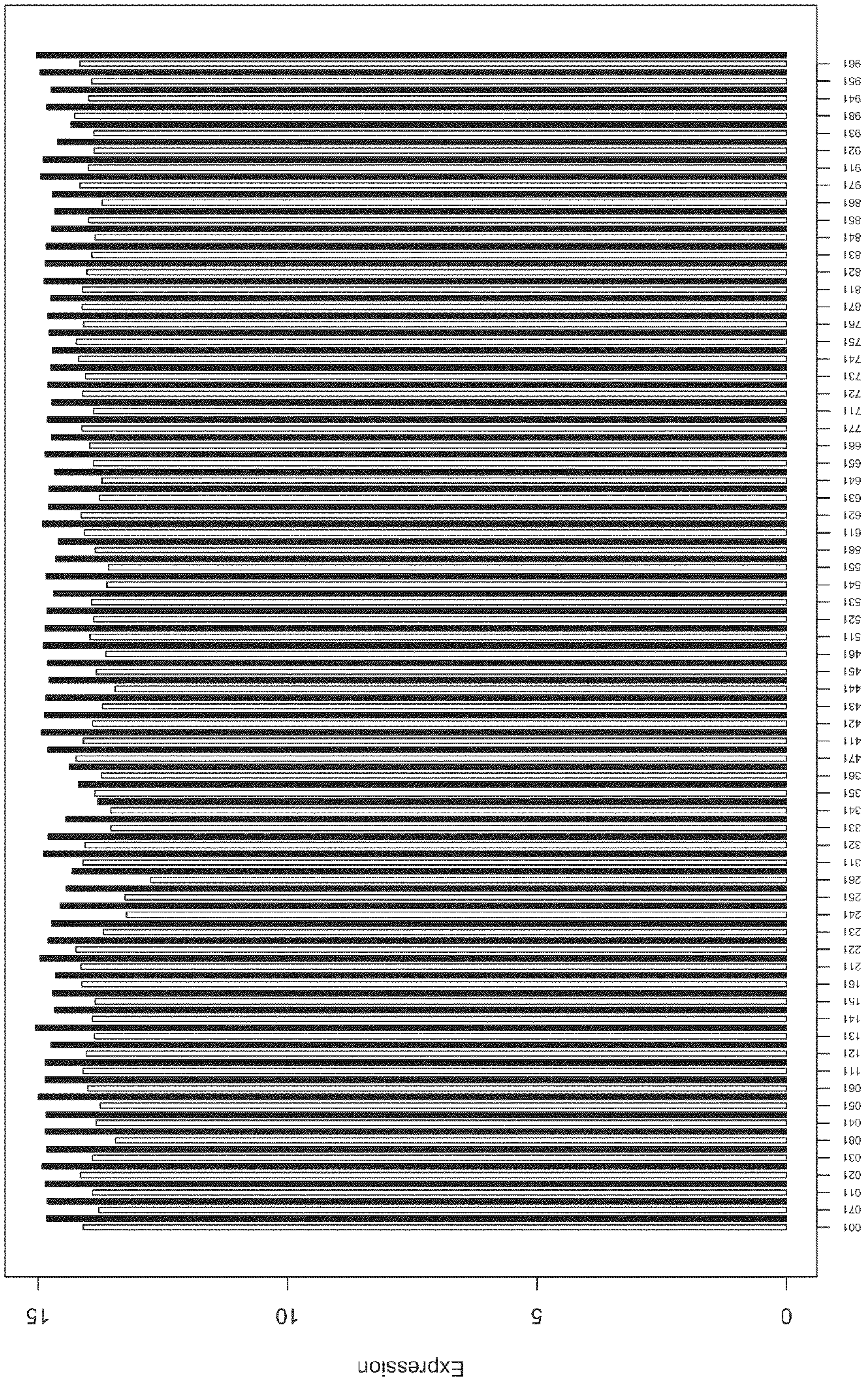

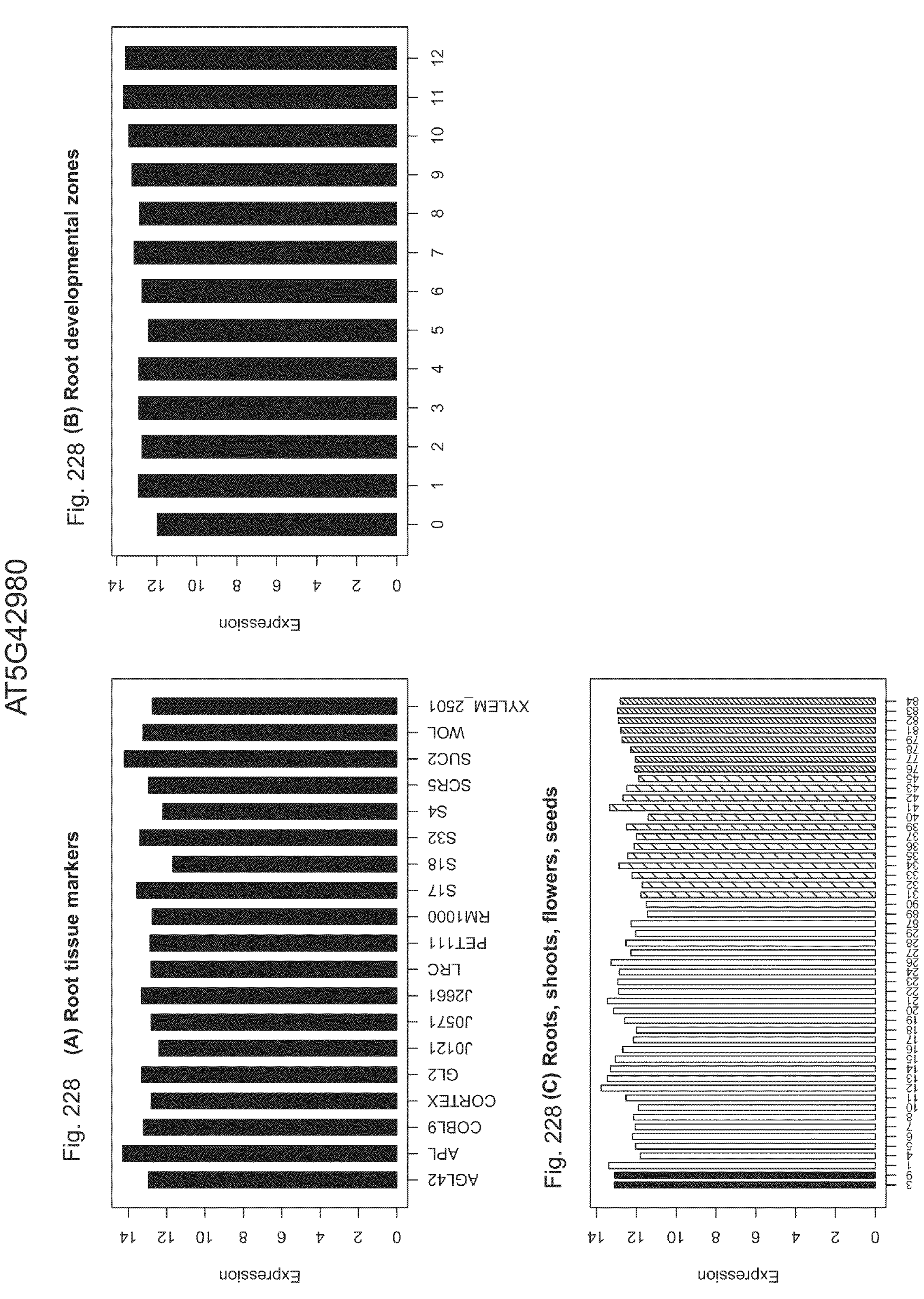
AT5G42980
Fig. 228 (A) Root tissue markers
Expression
AGL42
APL
COBL9
CORTEX
GL2
J0121
J0571
J2661
LRC
PET111
RM1000
S17
S18
S32
S4
SCR5
SUC2
WOL
XYLEM_2501
Fig. 228 (B) Root developmental zones
Expression
Fig. 228 (C) Roots, shoots, flowers, seeds
Expression AT5G42980
Fig. 228 (D) Abiotic stresses
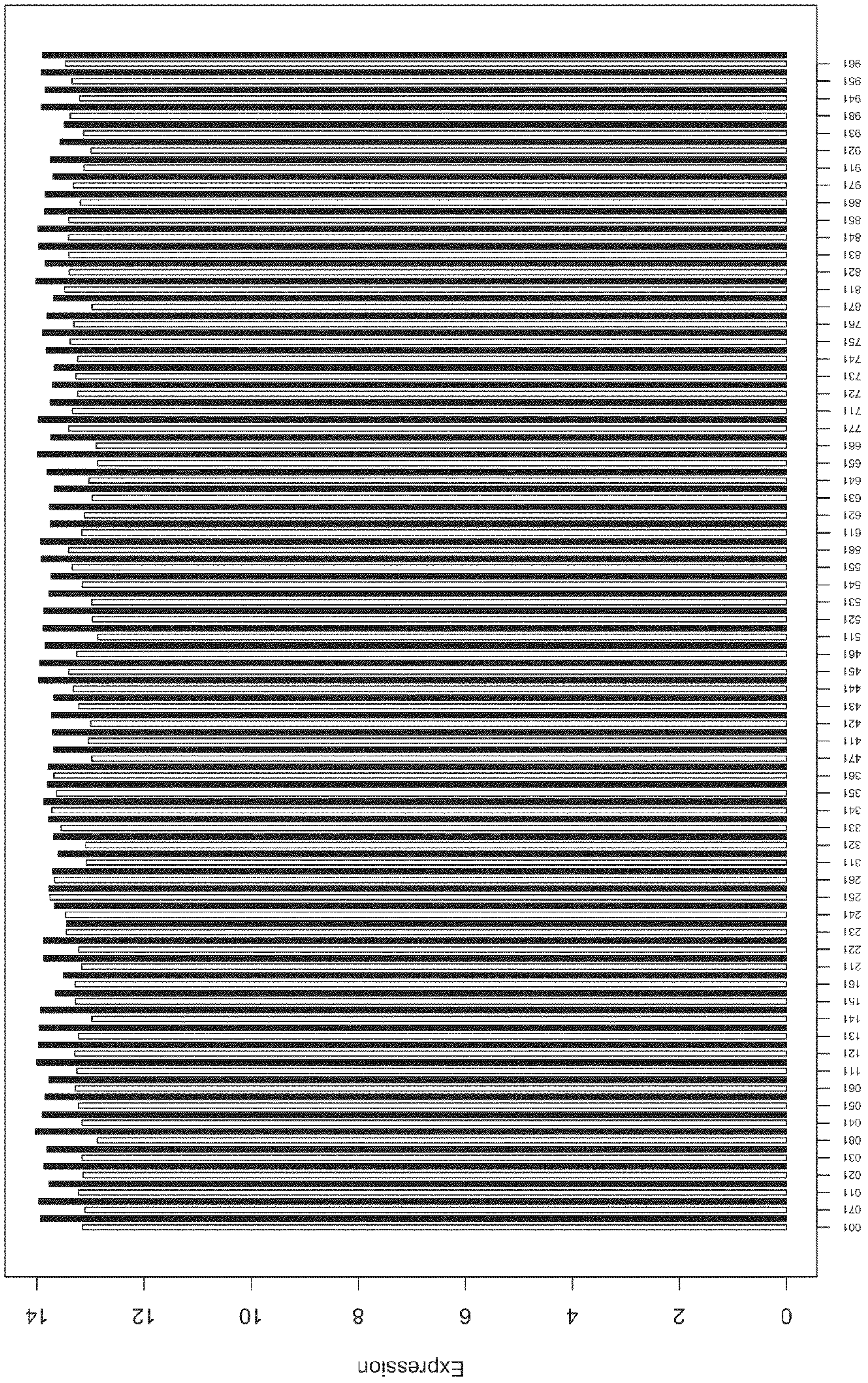

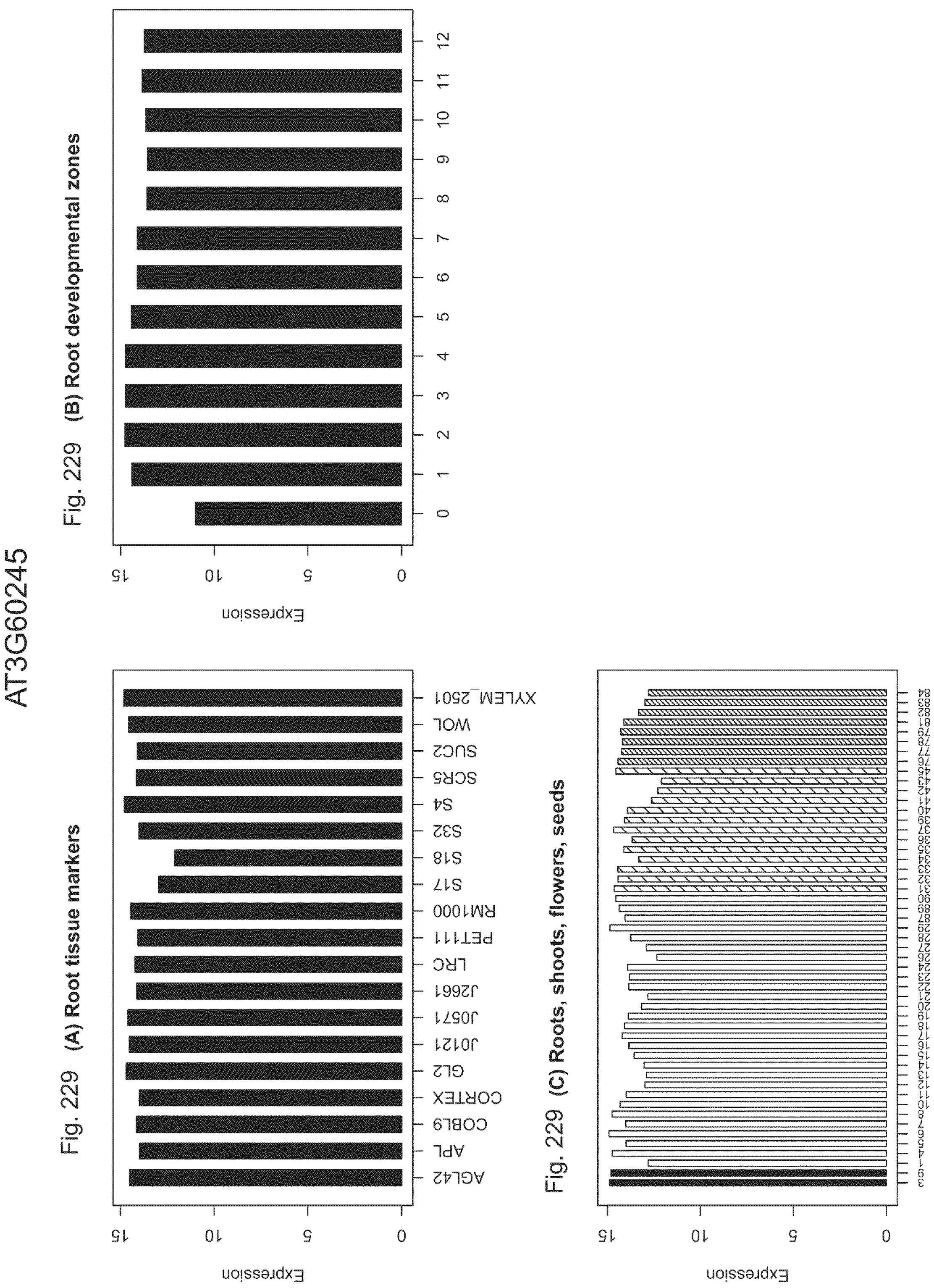
AT3G60245
Fig. 229 (A) Root tissue markers
AGL42
APL
COBL9
CORTEX
GL2
J0121
J0571
J2661
LRC
PET111
RM1000
S17
S18
S32
S4
SCR5
SUC2
WOL
XYLEM_2501
Fig. 229 (B) Root developmental zones
0
1
2
3
4
5
6
7
8
9
10
11
12
Fig. 229 (C) Roots, shoots, flowers, seeds
Expression
0
5
10
15

AT3G60245
Fig. 229 (D) Abiotic stresses
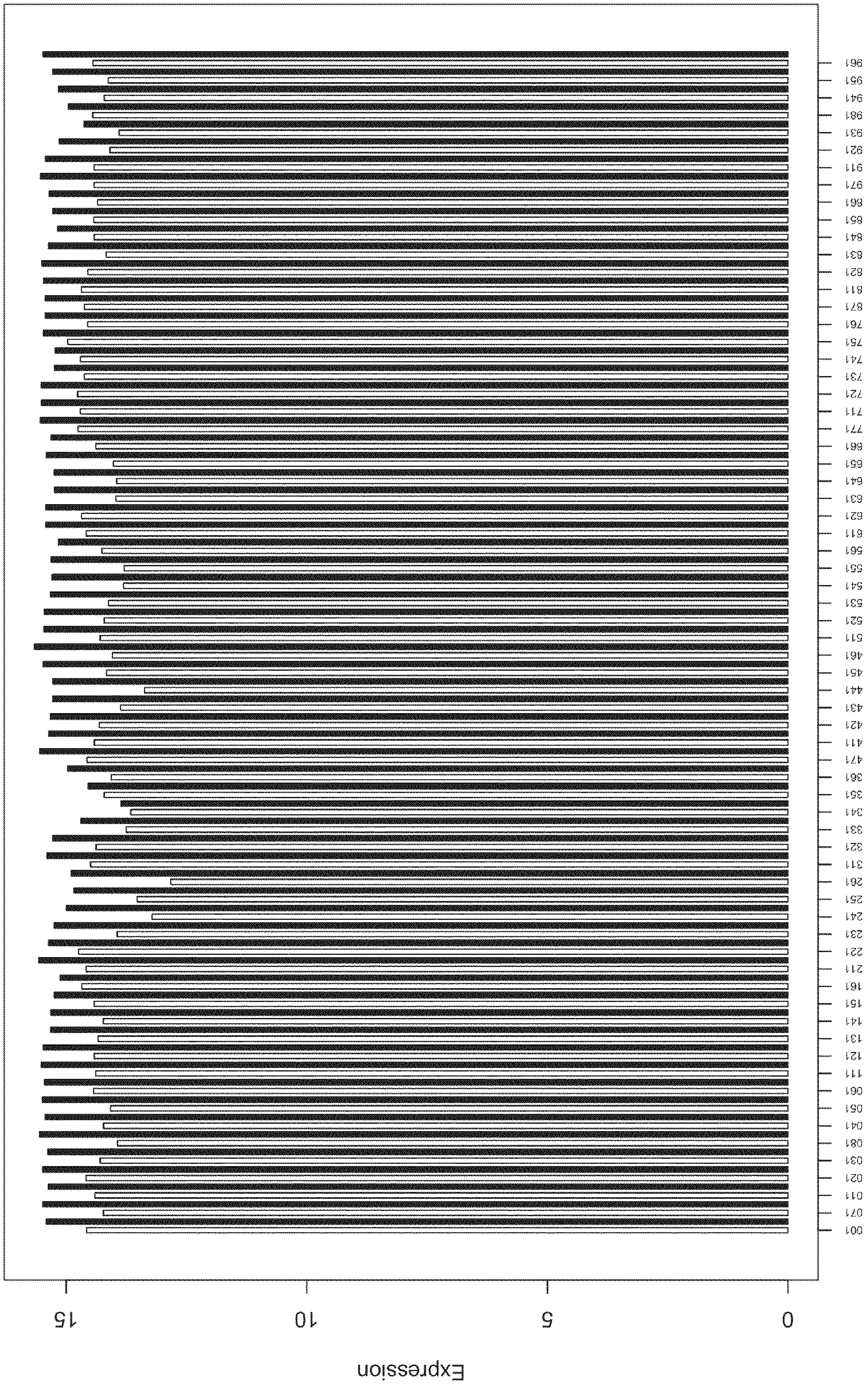

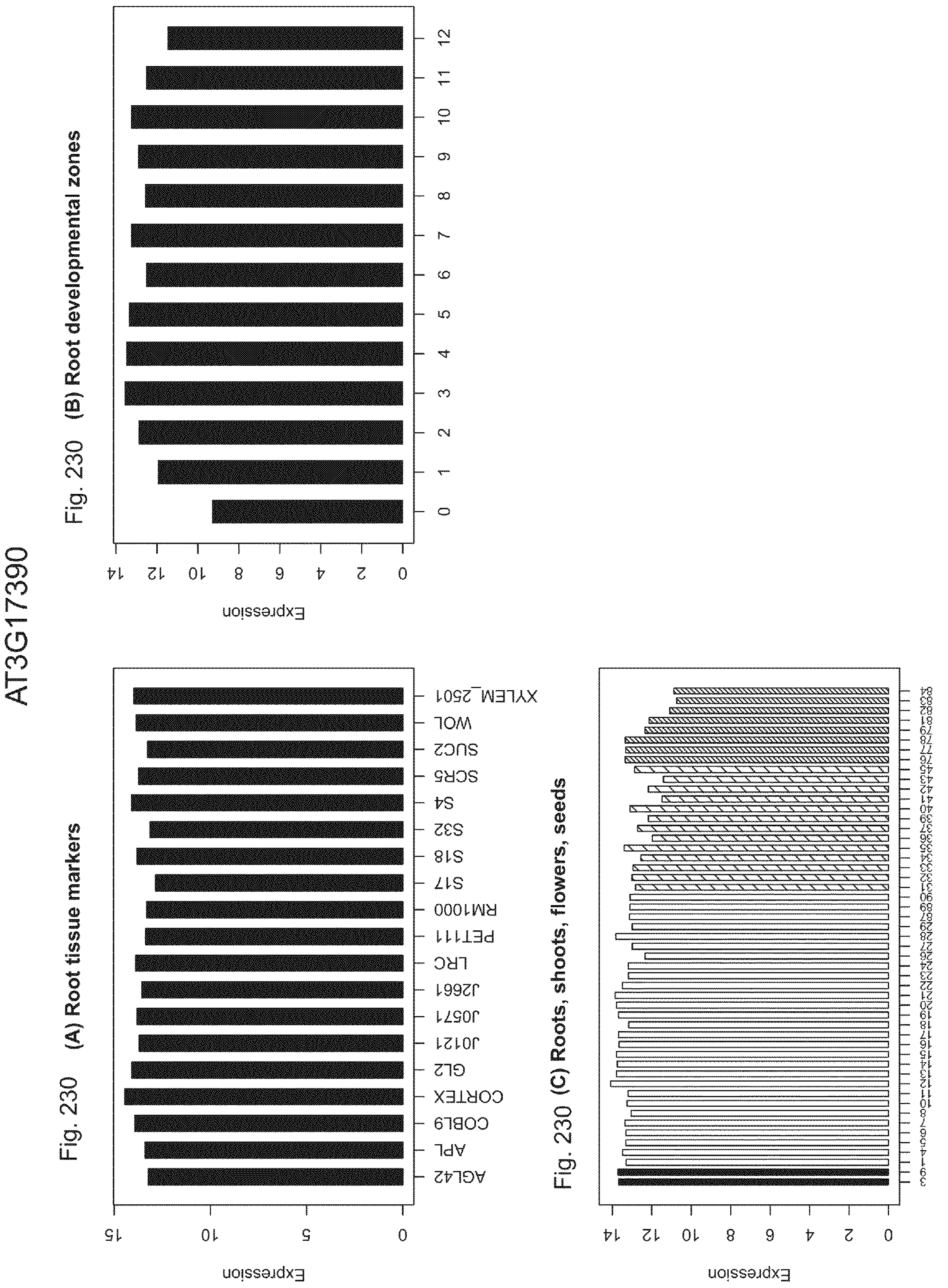
AT3G17390
Fig. 230 (A) Root tissue markers
Expression
AGL42
APL
COBL9
CORTEX
GL2
J0121
J0571
J2661
LRC
PET111
RM1000
S17
S18
S32
S4
SCR5
SUC2
WOL
XYLEM_2501
0
5
10
15
Fig. 230 (B) Root developmental zones
Expression
0
1
2
3
4
5
6
7
8
9
10
11
12
0
2
4
6
8
10
12
14
Fig. 230 (C) Roots, shoots, flowers, seeds
Expression
0
2
4
6
8
10
12
14

AT3G17390
Fig. 230 (D) Abiotic stresses
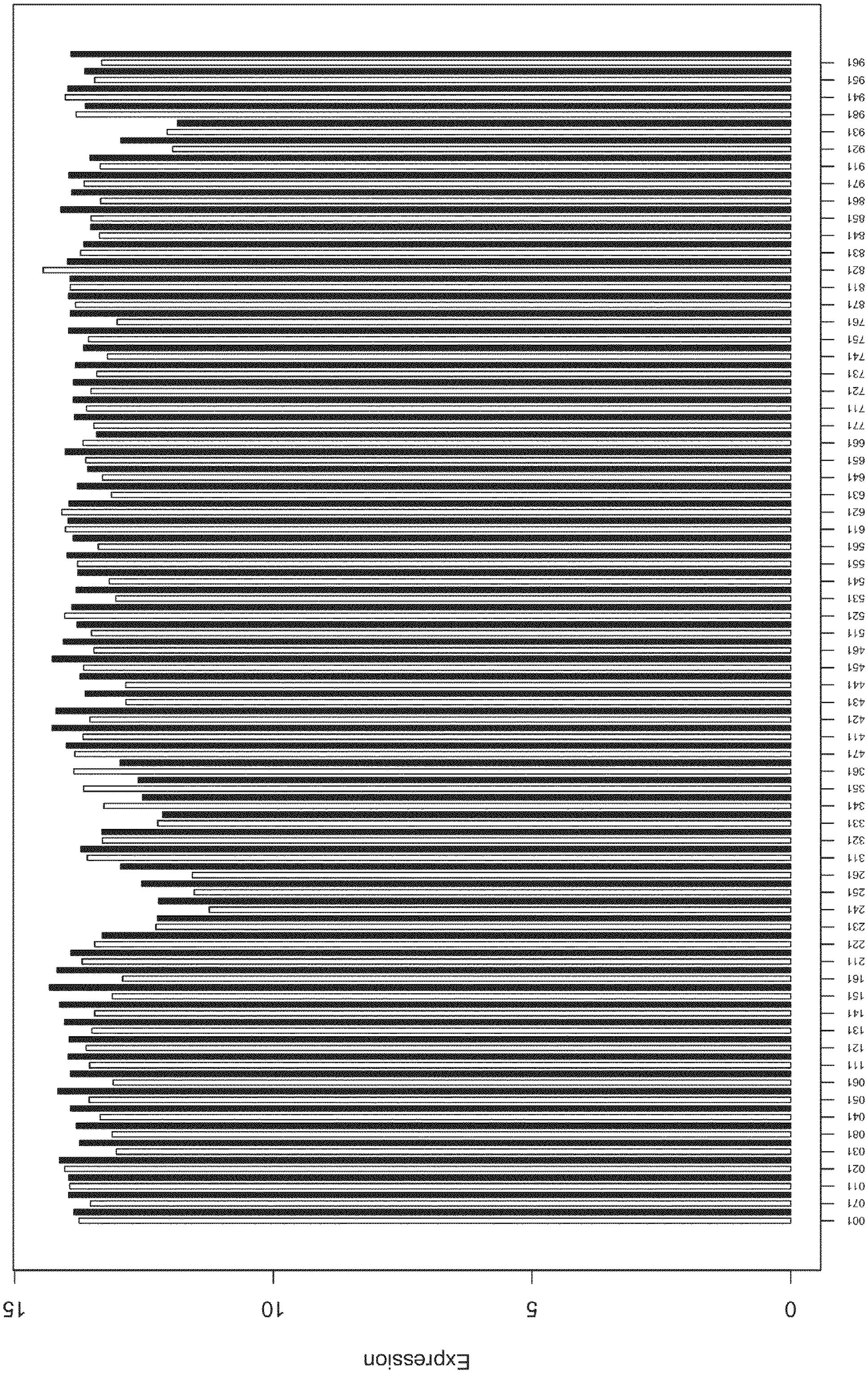

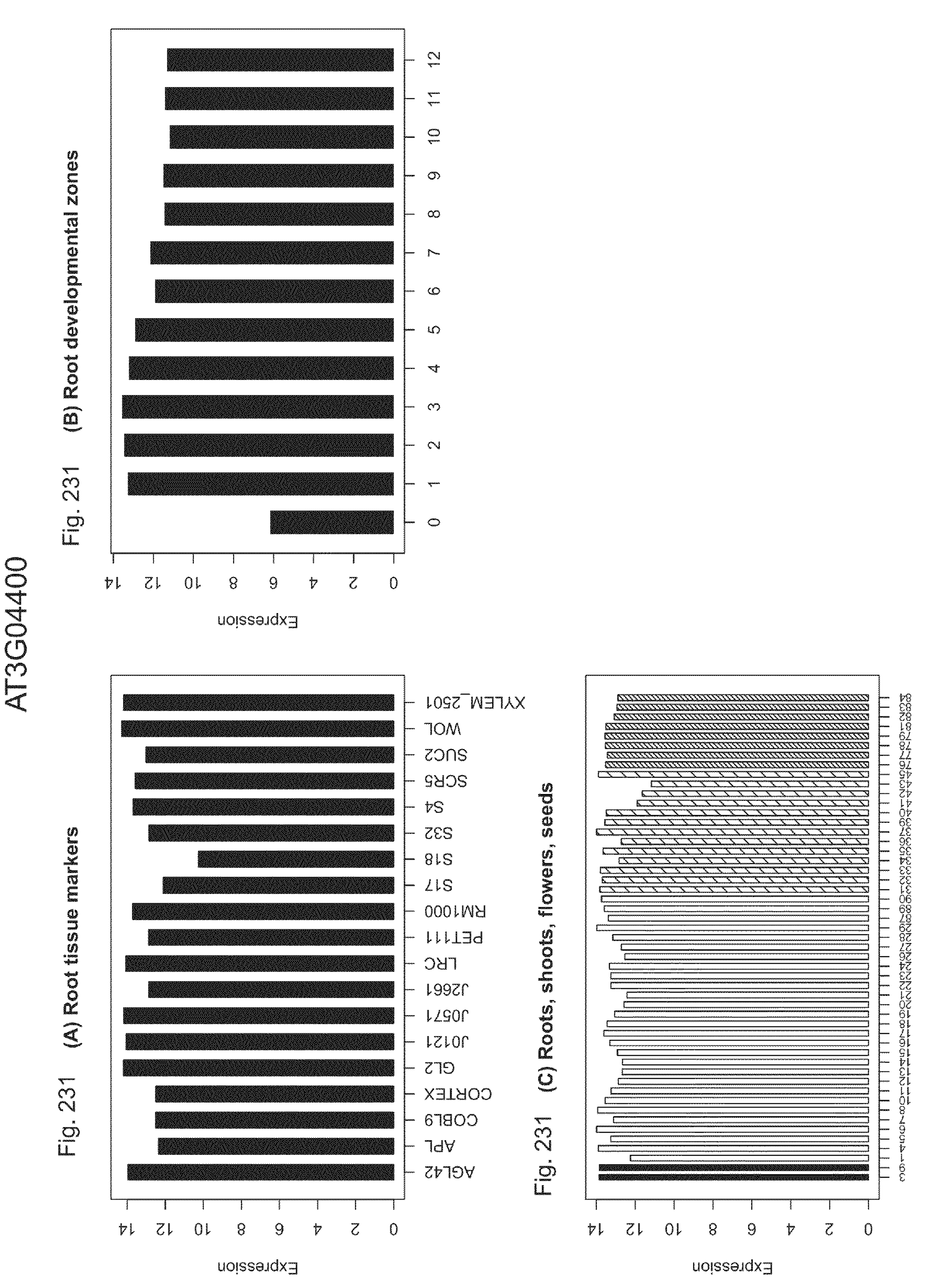
AT3G04400
Fig. 231 (A) Root tissue markers
Fig. 231 (B) Root developmental zones
Fig. 231 (C) Roots, shoots, flowers, seeds
Expression
AGL42
APL
COBL9
CORTEX
GL2
J0121
J0571
J2661
LRC
PET111
RM1000
S17
S18
S32
S4
SCR5
SUC2
WOL
XYLEM_2501

AT3G04400
Fig. 231 (D) Abiotic stresses
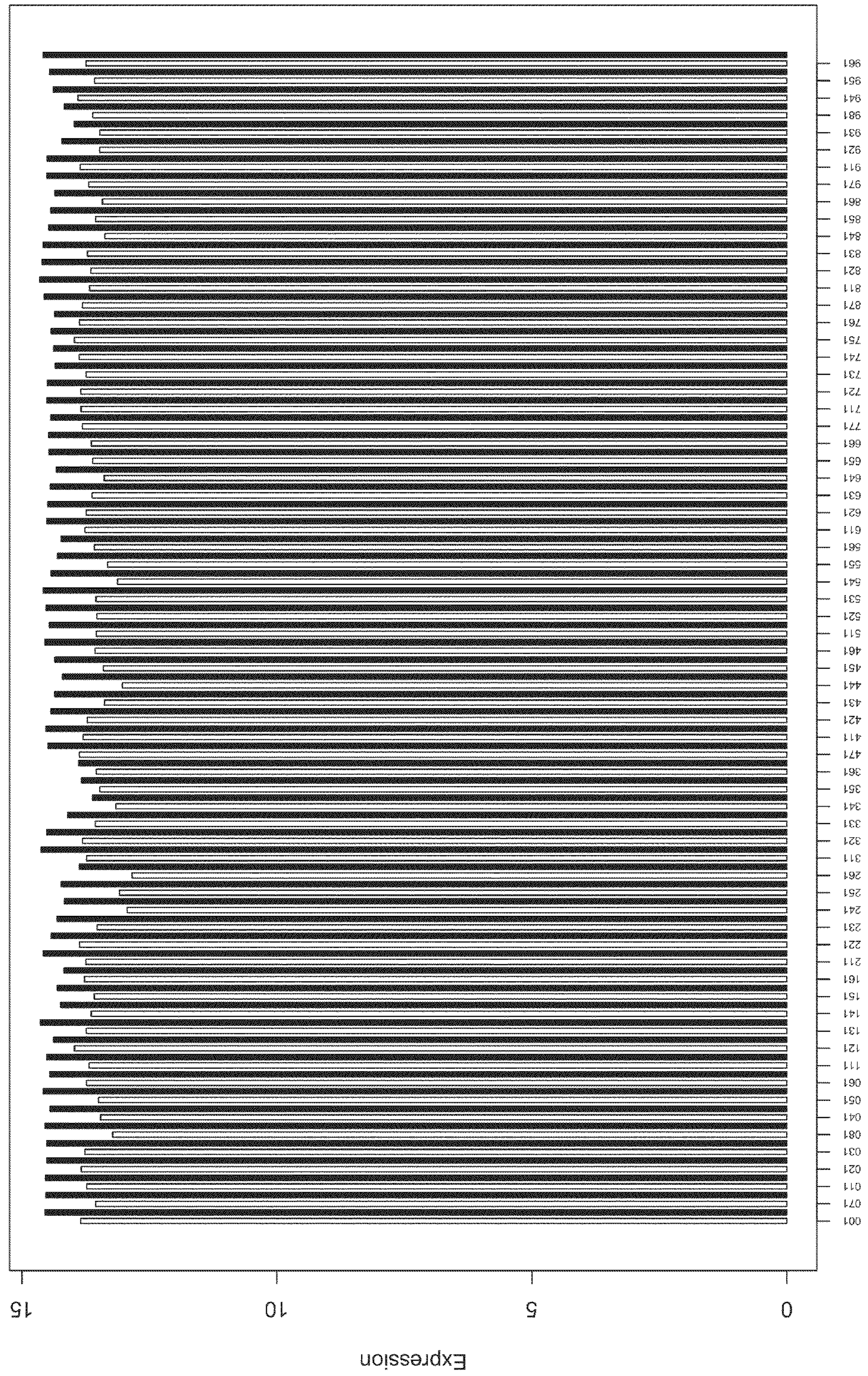

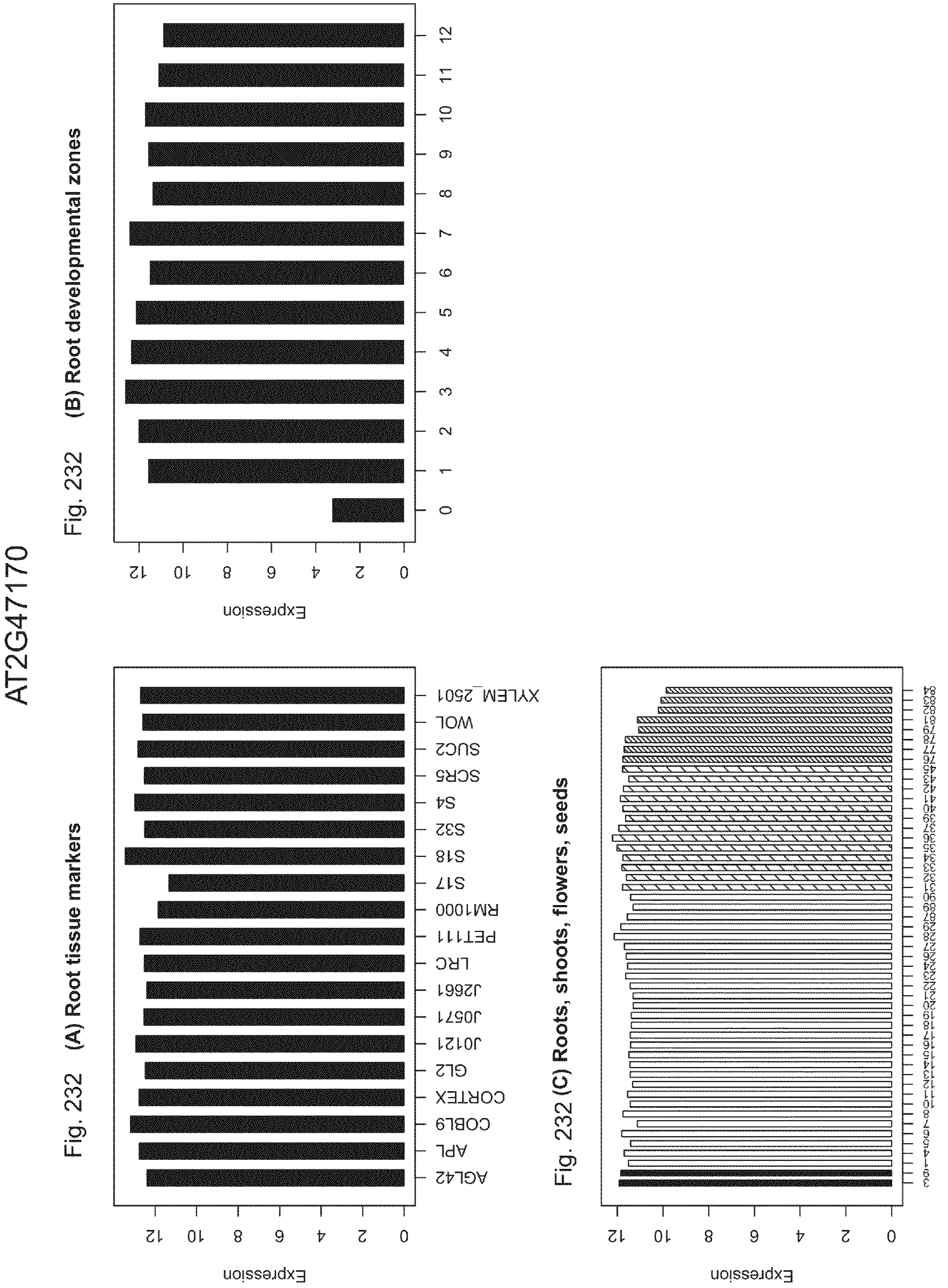
AT2G47170
Fig. 232 (A) Root tissue markers
Fig. 232 (B) Root developmental zones
Fig. 232 (C) Roots, shoots, flowers, seeds
Expression
AGL42
APL
COBL9
CORTEX
GL2
J0121
J0571
J2661
LRC
PET111
RM1000
S17
S18
S32
S4
SCR5
SUC2
WOL
XYLEM_2501

AT2G47170
Fig. 232 (D) Abiotic stresses
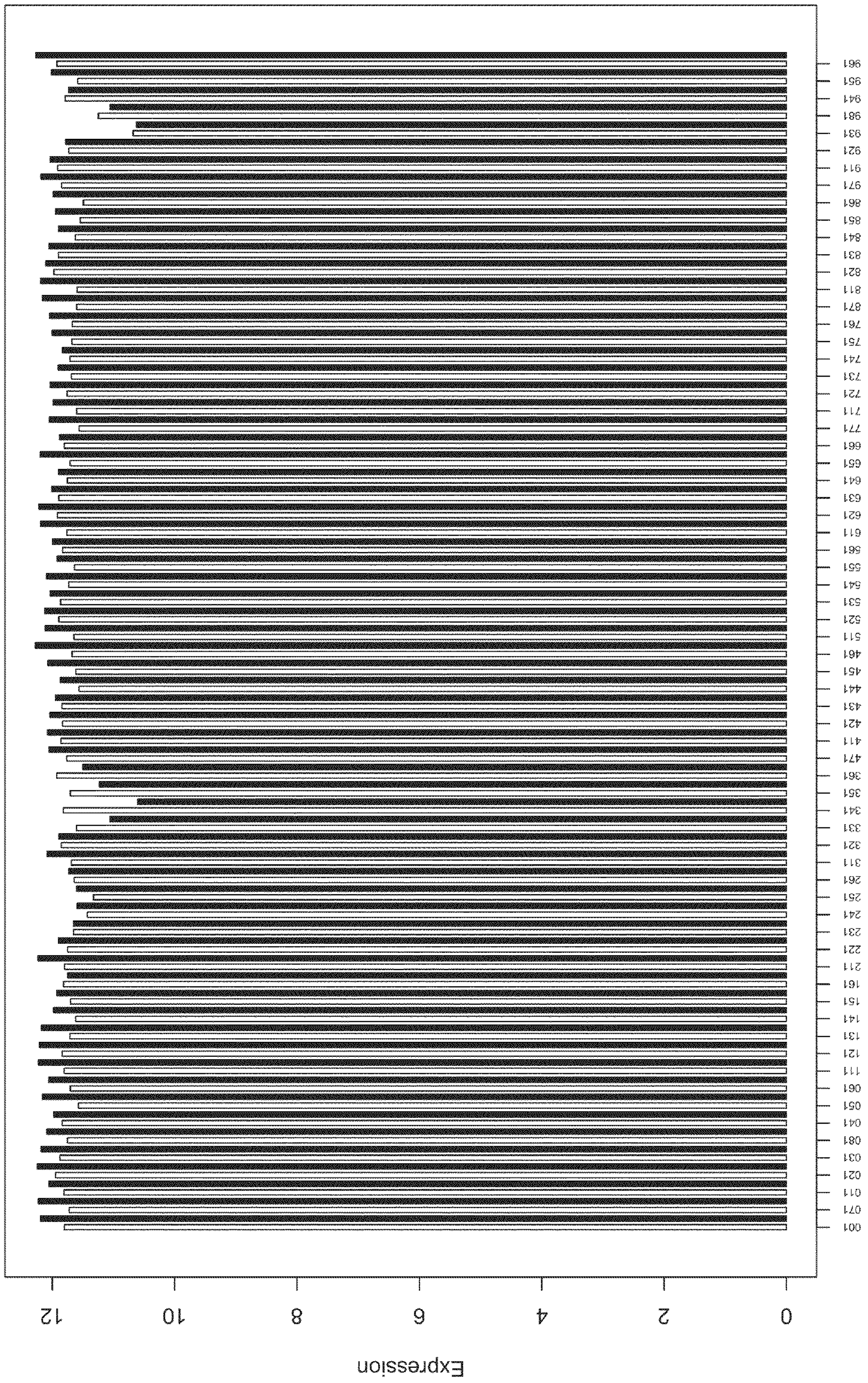

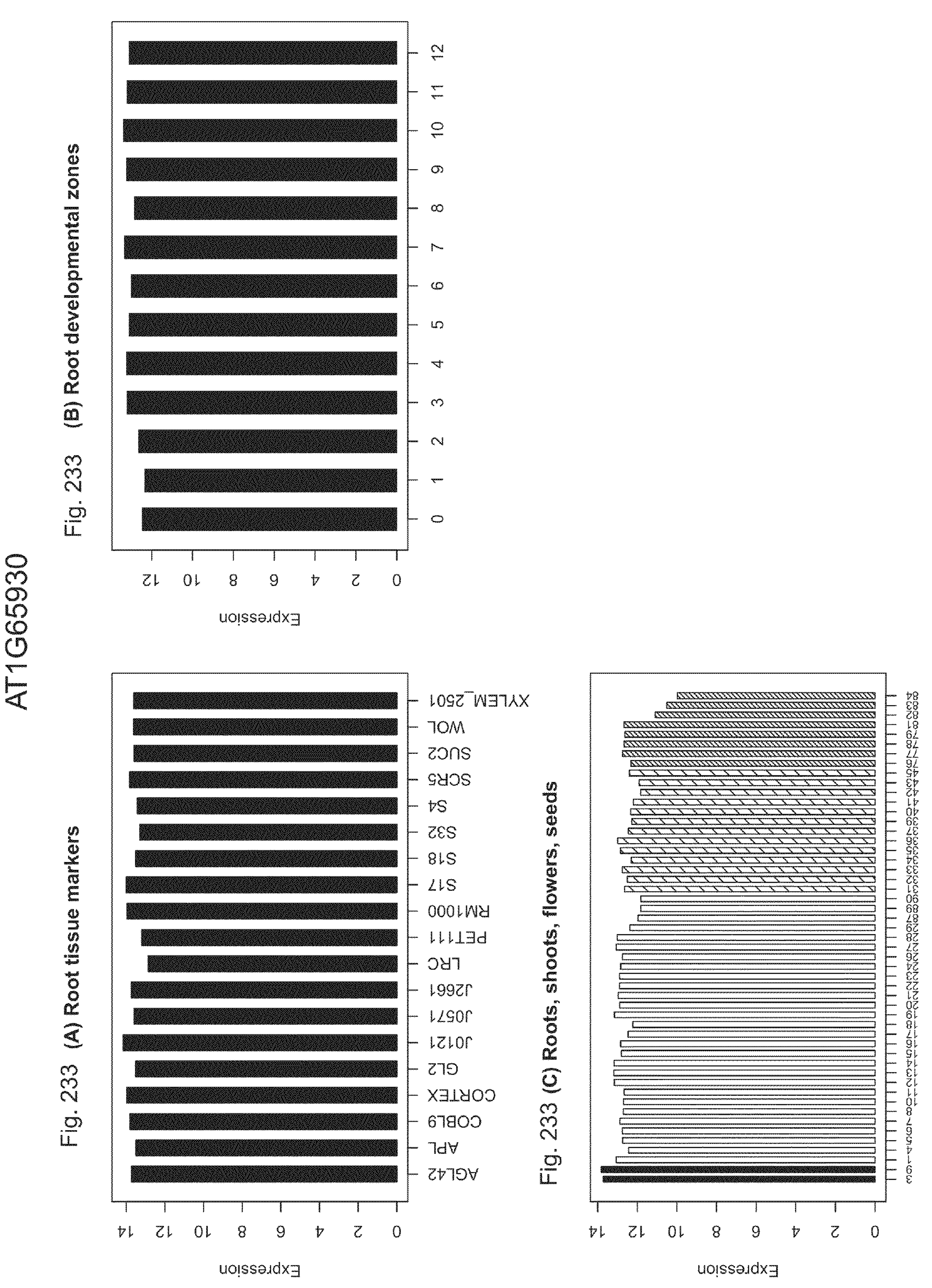
AT1G65930
Fig. 233 (A) Root tissue markers
Expression
0
2
4
6
8
10
12
14
AGL42
APL
COBL9
CORTEX
GL2
J0121
J0571
J2661
LRC
PET111
RM1000
S17
S18
S32
S4
SCR5
SUC2
WOL
XYLEM_2501
Fig. 233 (B) Root developmental zones
Expression
0
2
4
6
8
10
12
0
1
2
3
4
5
6
7
8
9
10
11
12
Fig. 233 (C) Roots, shoots, flowers, seeds
Expression
0
2
4
6
8
10
12
14

AT1G65930

(D) Abiotic stresses

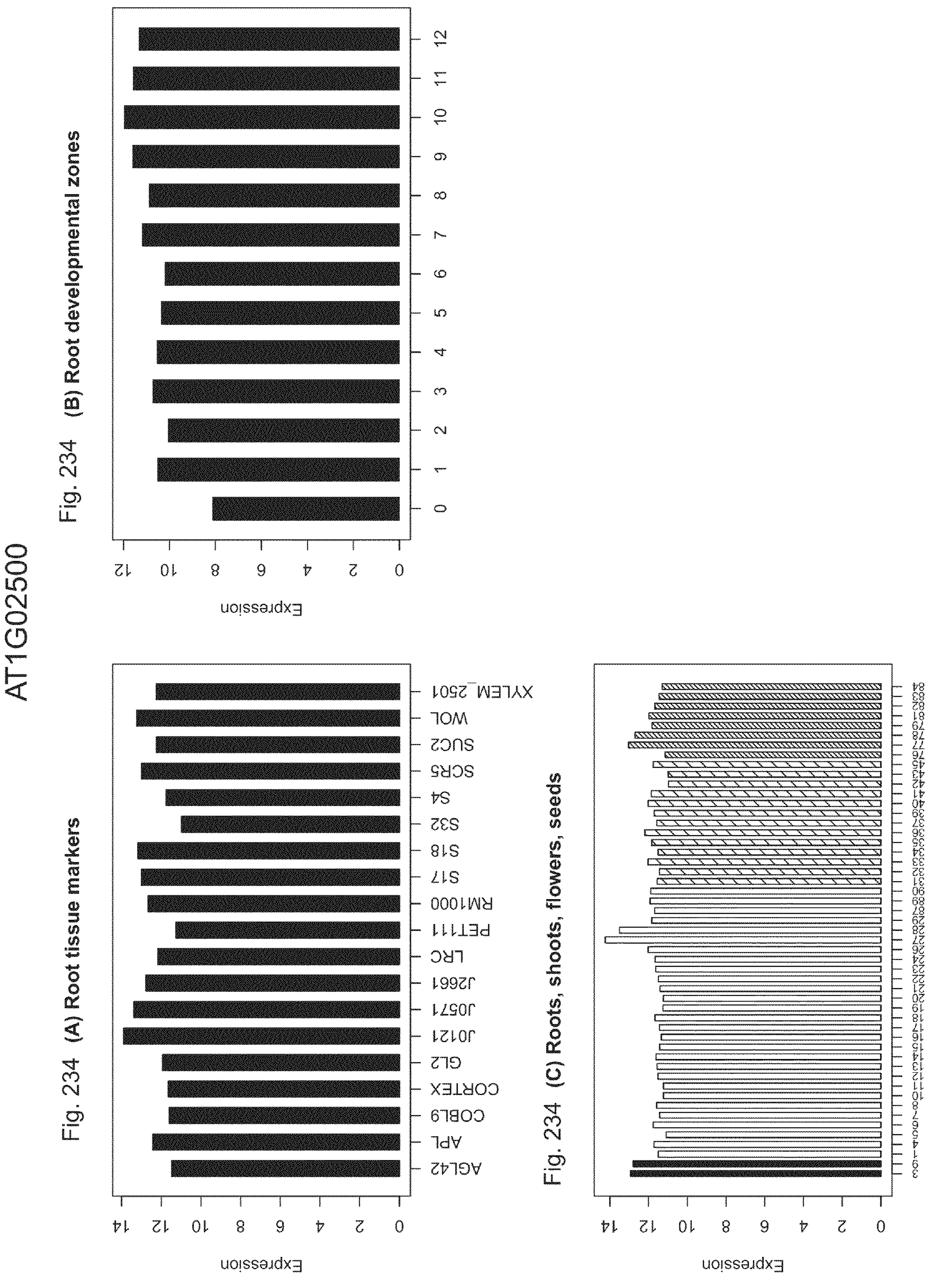
AT1G02500
Fig. 234 (A) Root tissue markers
AGL42
APL
COBL9
CORTEX
GL2
J0121
J0571
J2661
LRC
PET111
RM1000
S17
S18
S32
S4
SCR5
SUC2
WOL
XYLEM_2501
Expression
Fig. 234 (B) Root developmental zones
Expression
Fig. 234 (C) Roots, shoots, flowers, seeds
Expression AT1G02500
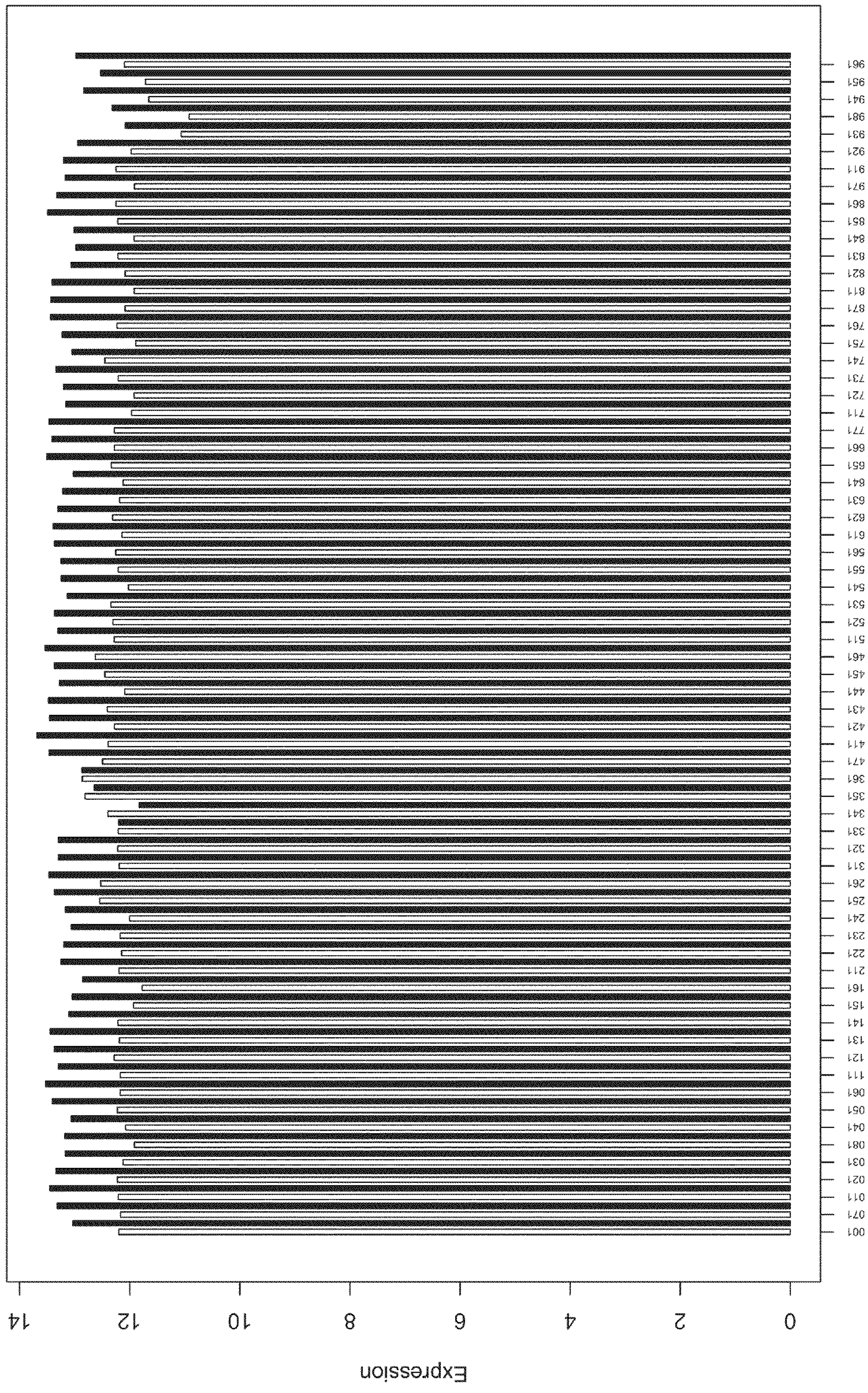
Fig. 234 (D) Abiotic stresses

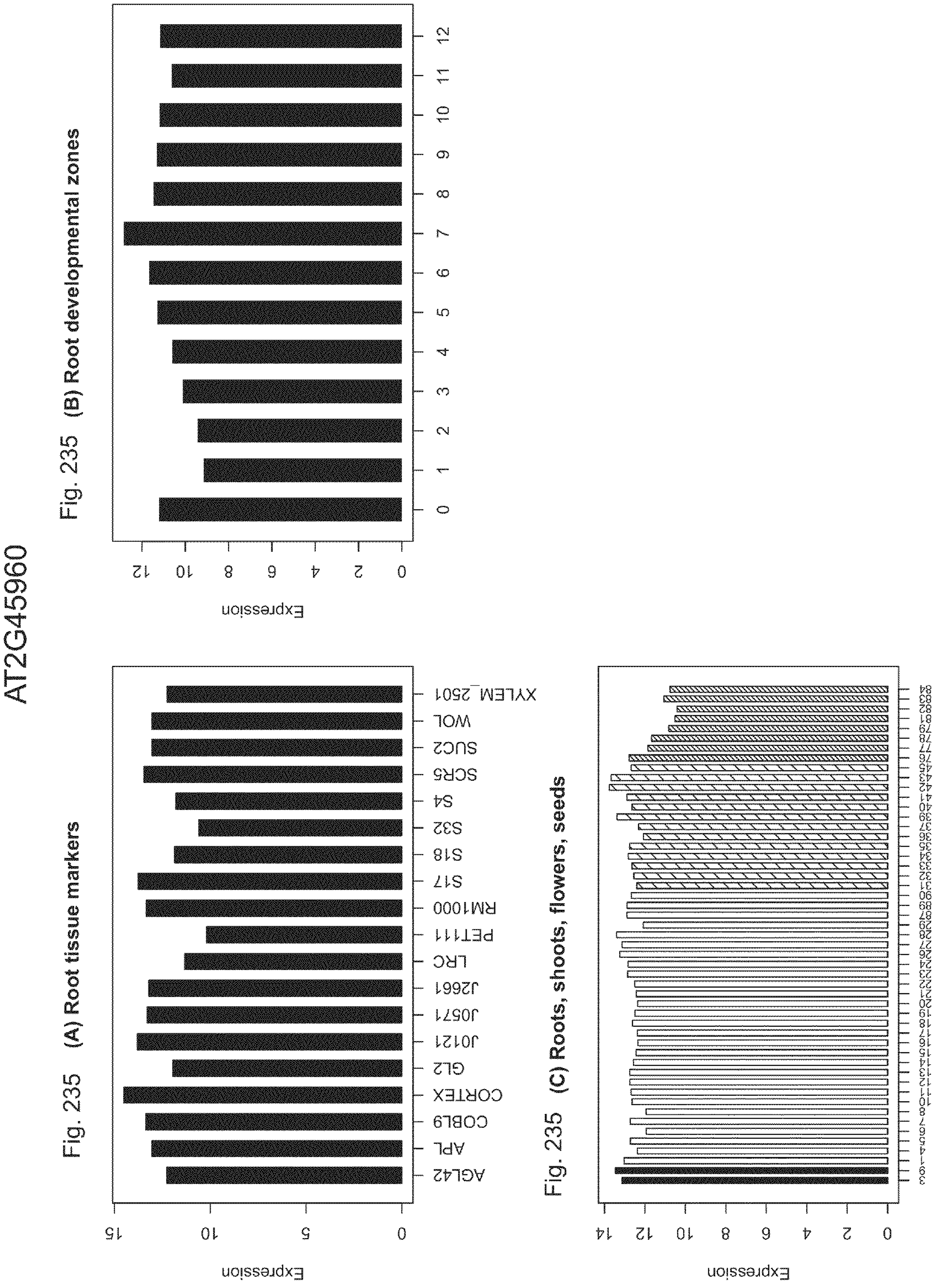
AT2G45960
Fig. 235 (A) Root tissue markers
Expression
AGL42
APL
COBL9
CORTEX
GL2
J0121
J0571
J2661
LRC
PET111
RM1000
S17
S18
S32
S4
SCR5
SUC2
WOL
XYLEM_2501
Fig. 235 (B) Root developmental zones
Expression
Fig. 235 (C) Roots, shoots, flowers, seeds
Expression AT2G45960
Fig. 235 (D) Abiotic stresses
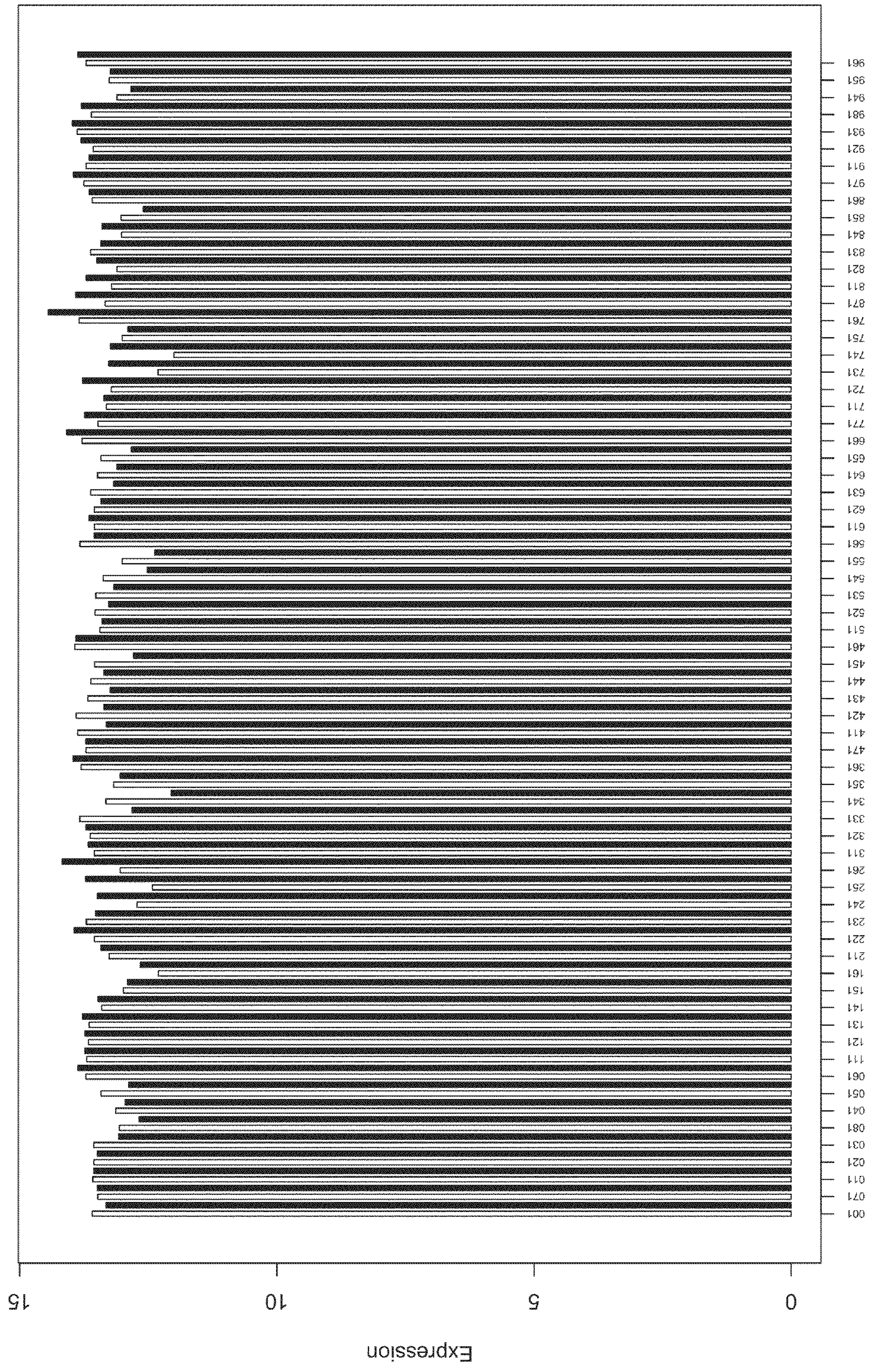

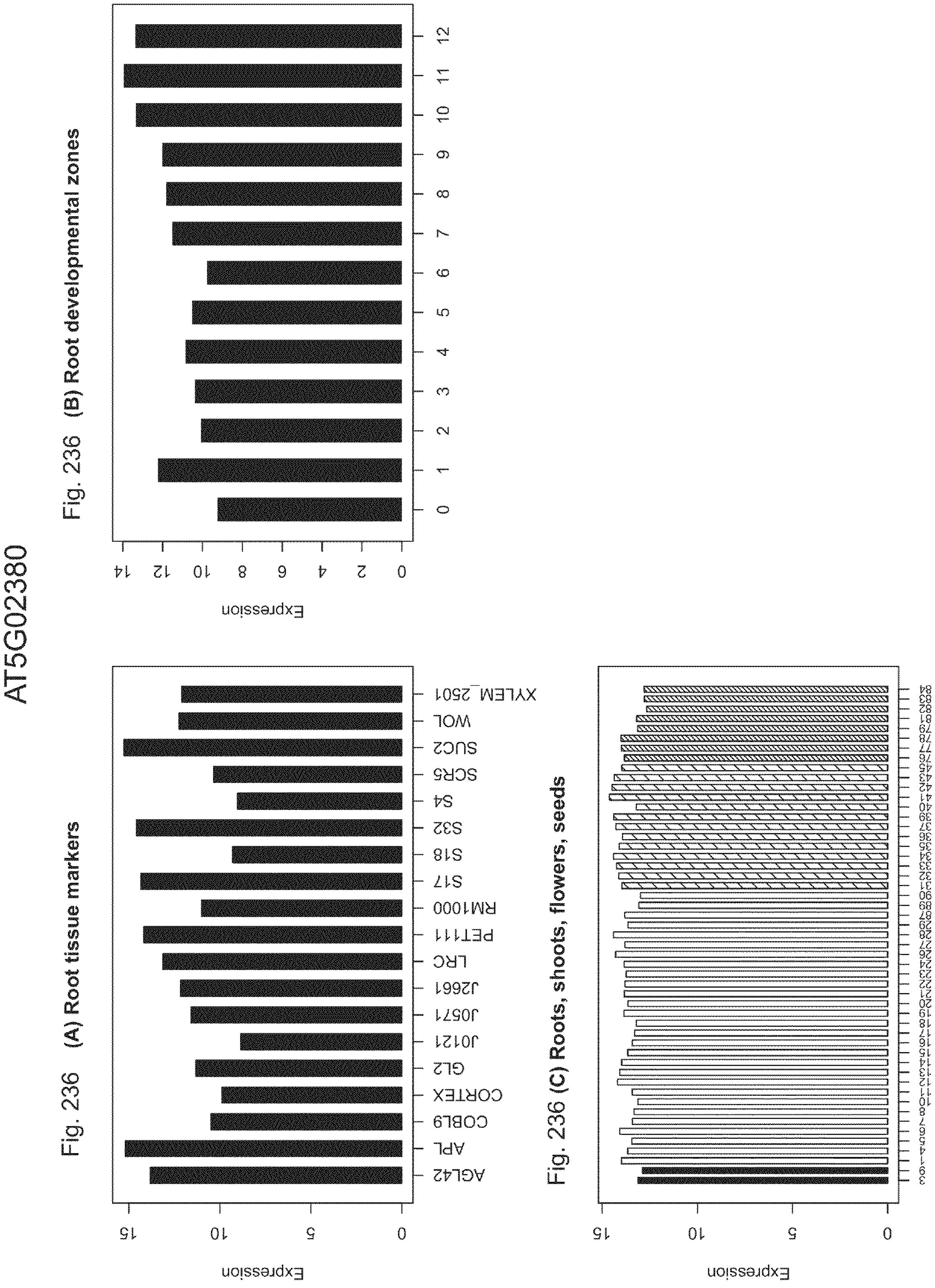
AT5G02380
Fig. 236 (A) Root tissue markers
Expression
AGL42
APL
COBL9
CORTEX
GL2
J0121
J0571
J2661
LRC
PET111
RM1000
S17
S18
S32
S4
SCR5
SUC2
WOL
XYLEM_2501
Fig. 236 (B) Root developmental zones
Expression
Fig. 236 (C) Roots, shoots, flowers, seeds
Expression AT5G02380
Fig. 236 (D) Abiotic stresses
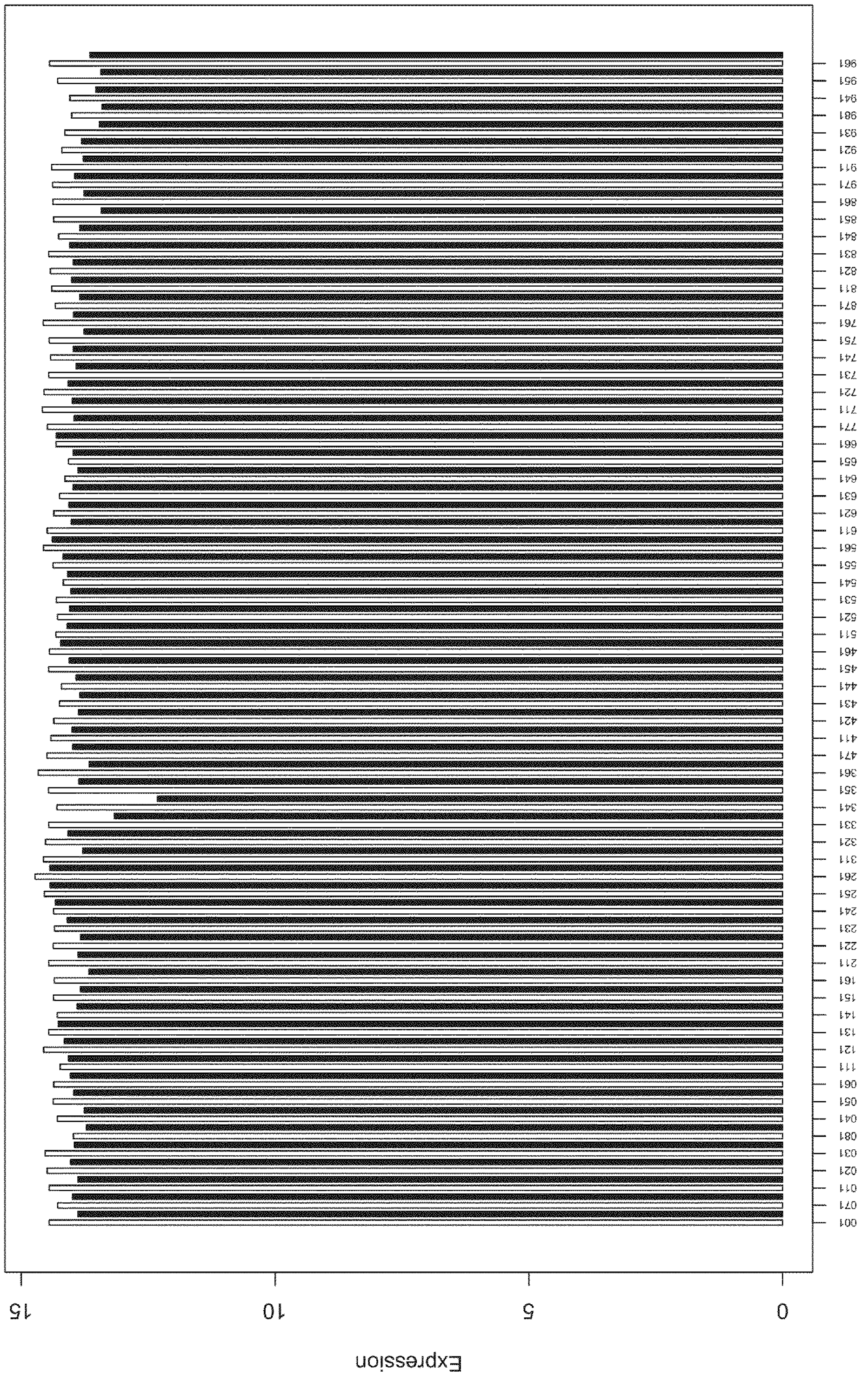

AT1G15930
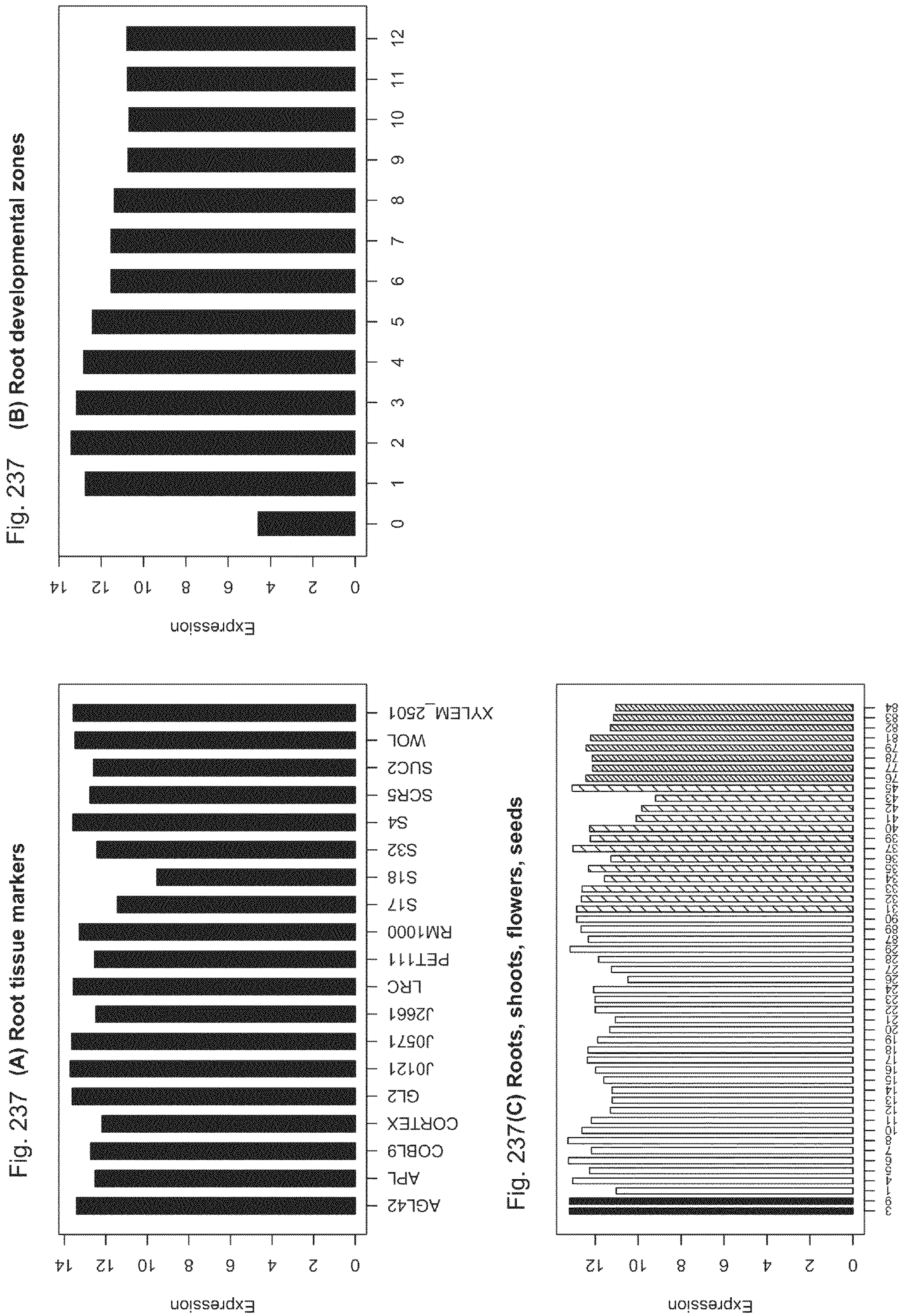
Fig. 237 (A) Root tissue markers
Fig. 237 (B) Root developmental zones
Fig. 237(C) Roots, shoots, flowers, seeds AT1G15930
Fig. 237 (D) Abiotic stresses
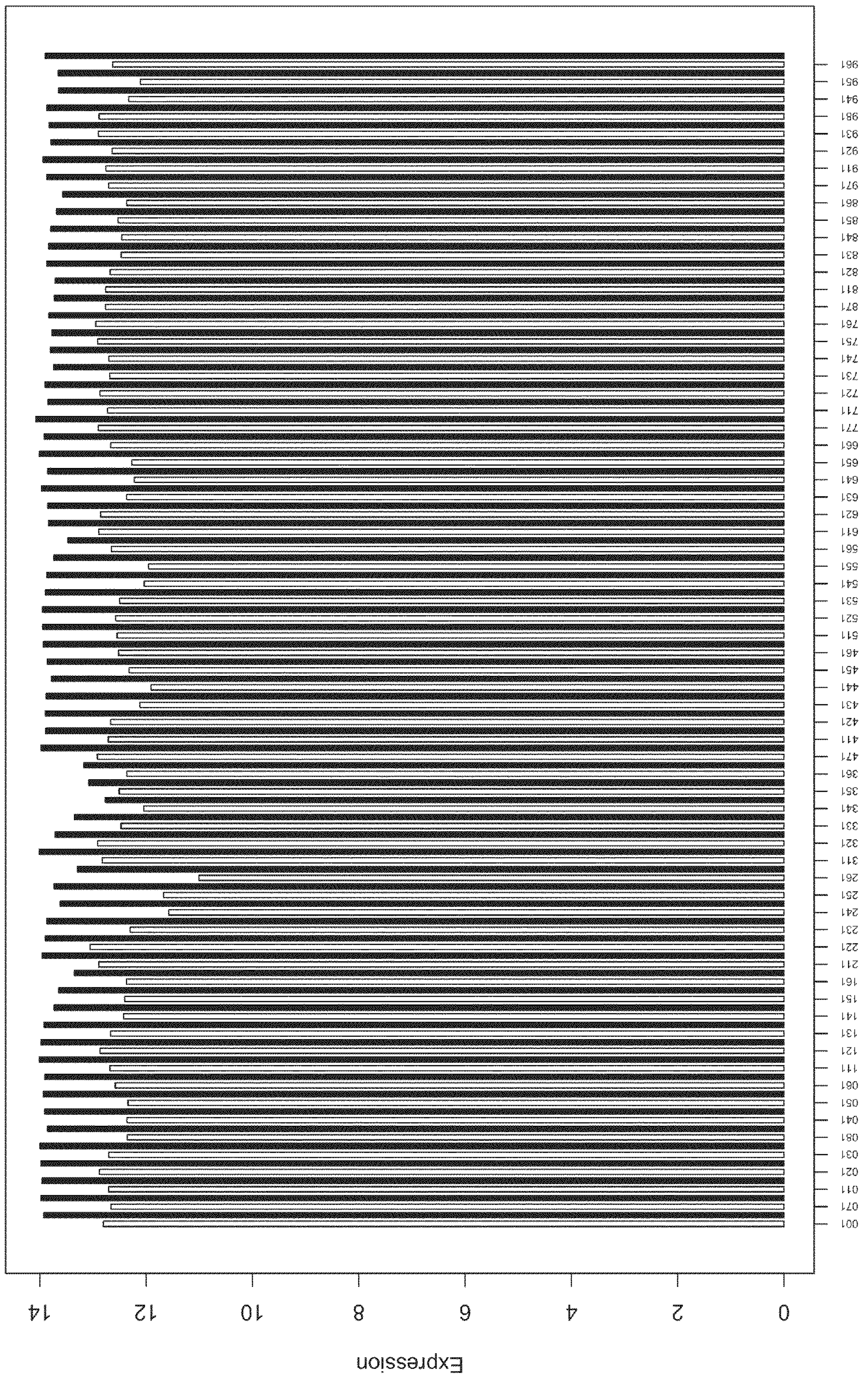

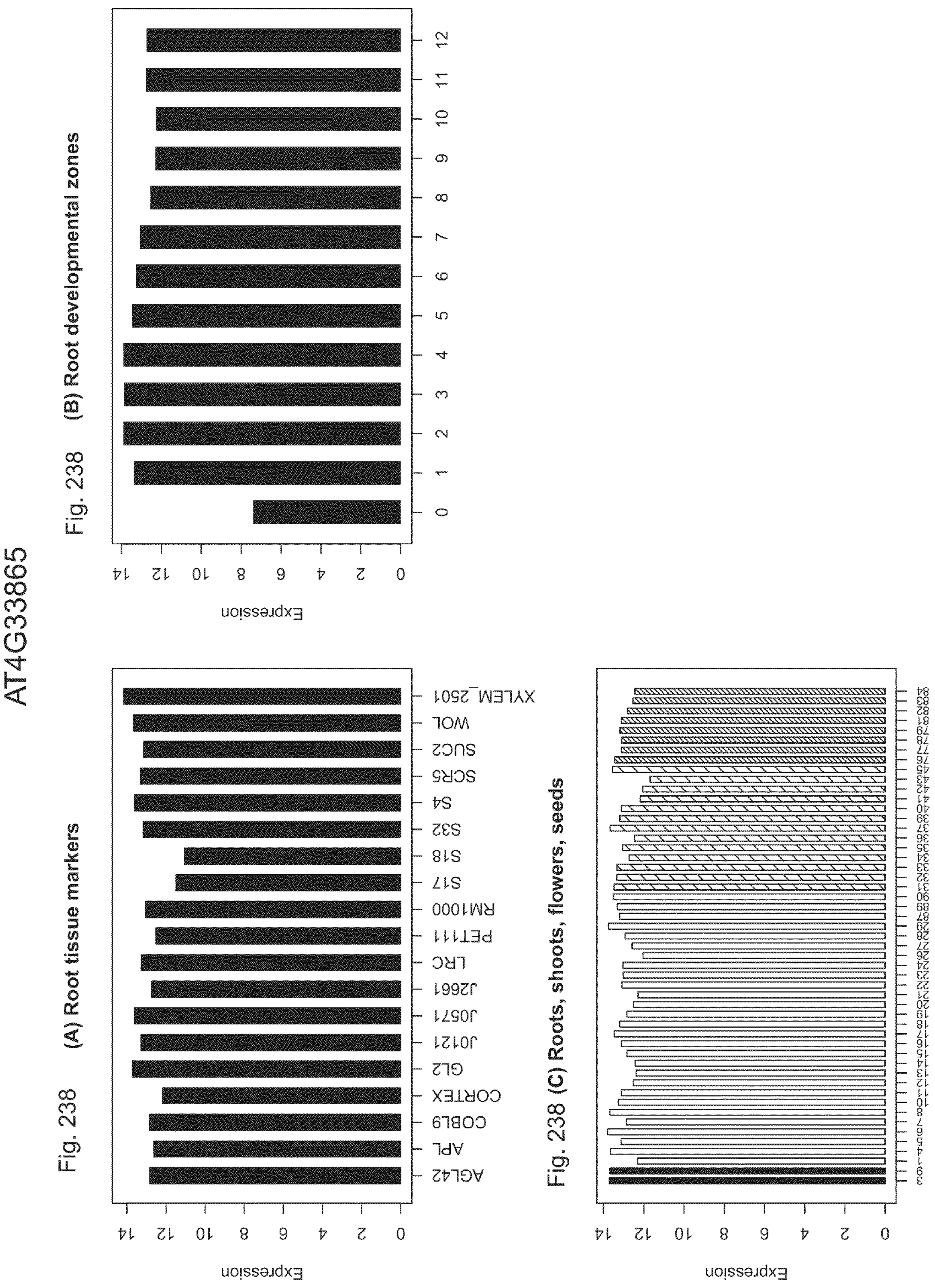
AT4G33865
Fig. 238 (A) Root tissue markers
AGL42
APL
COBL9
CORTEX
GL2
J0121
J0571
J2661
LRC
PET111
RM1000
S17
S18
S32
S4
SCR5
SUC2
WOL
XYLEM_2501
Expression
Fig. 238 (B) Root developmental zones
0 1 2 3 4 5 6 7 8 9 10 11 12
Expression
Fig. 238 (C) Roots, shoots, flowers, seeds
Expression
0 2 4 6 8 10 12 14

AT4G33865
Fig. 238 (D) Abiotic stresses
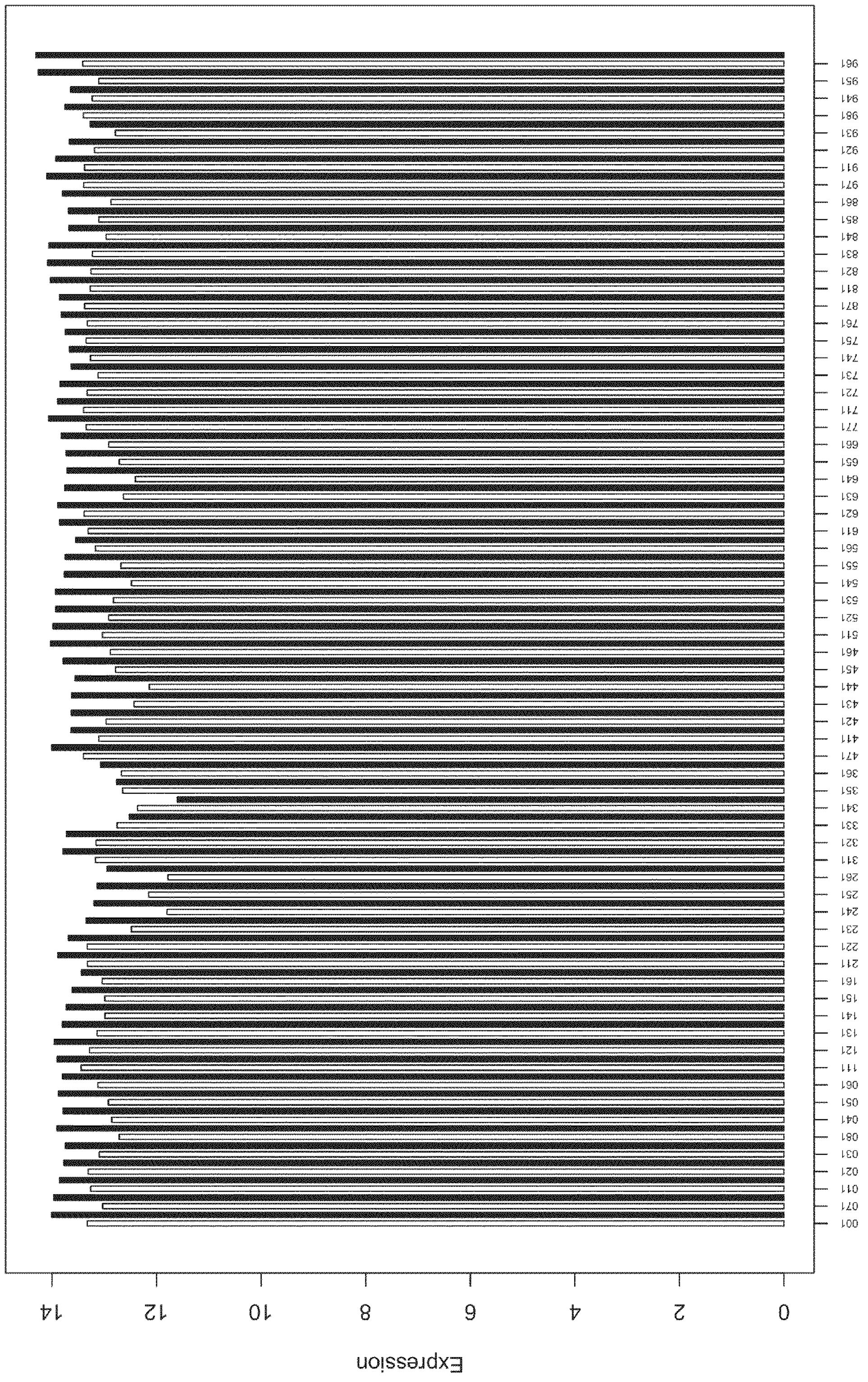

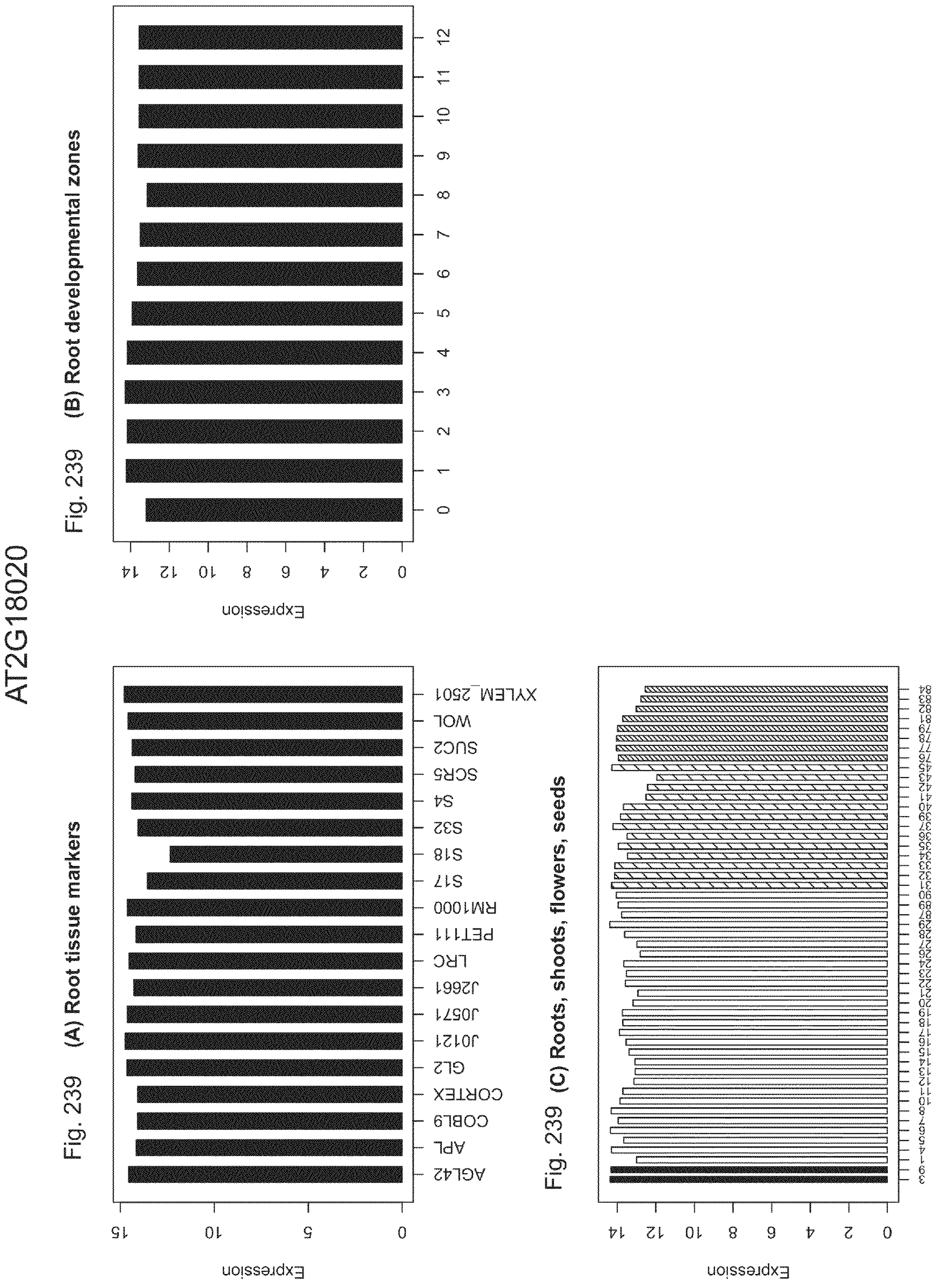
AT2G18020
Fig. 239 (A) Root tissue markers
Expression
AGL42
APL
COBL9
CORTEX
GL2
J0121
J0571
J2661
LRC
PET111
RM1000
S17
S18
S32
S4
SCR5
SUC2
WOL
XYLEM_2501
Fig. 239 (B) Root developmental zones
Expression
Fig. 239 (C) Roots, shoots, flowers, seeds
Expression AT2G18020
Fig. 239 (D) Abiotic stresses
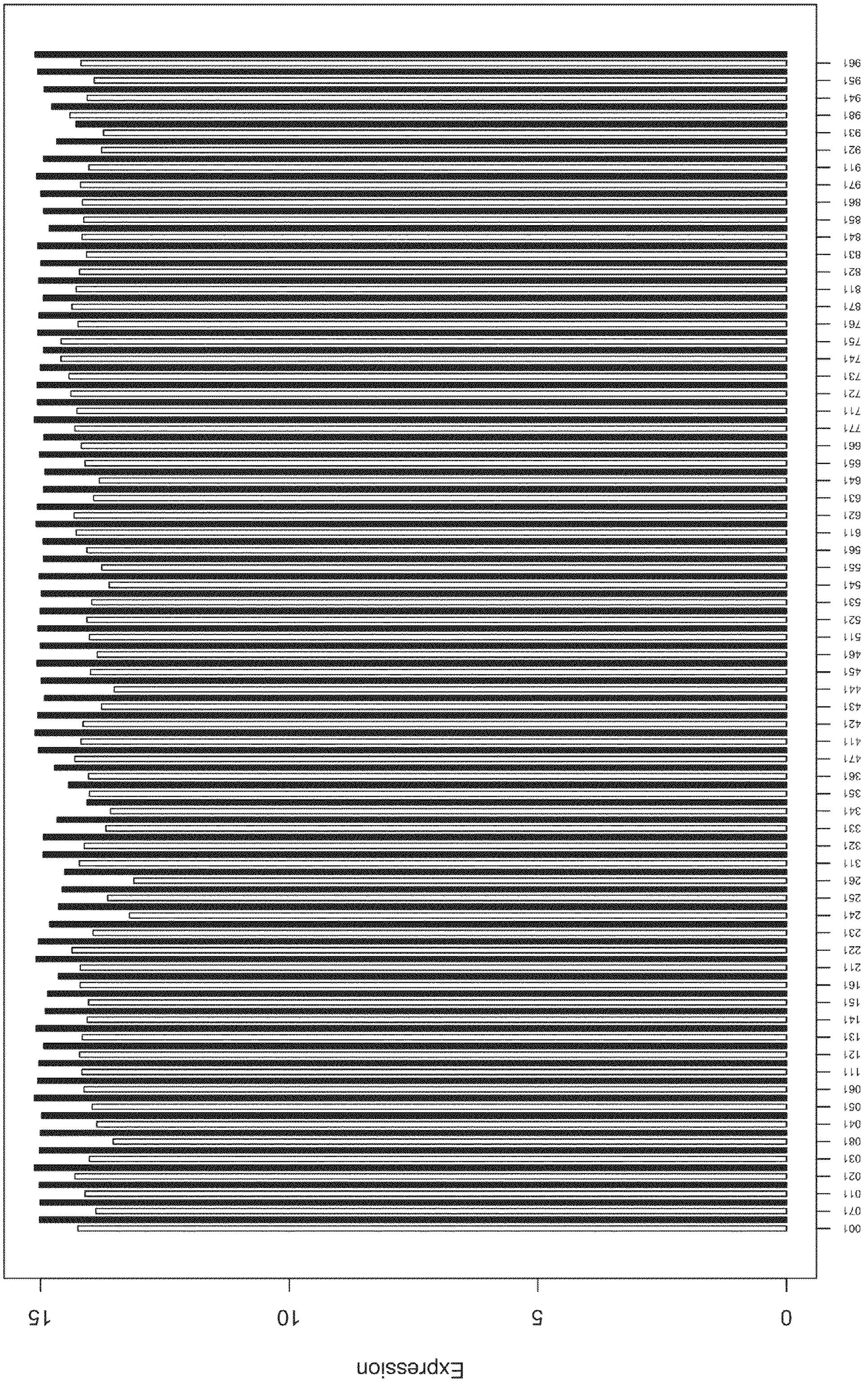

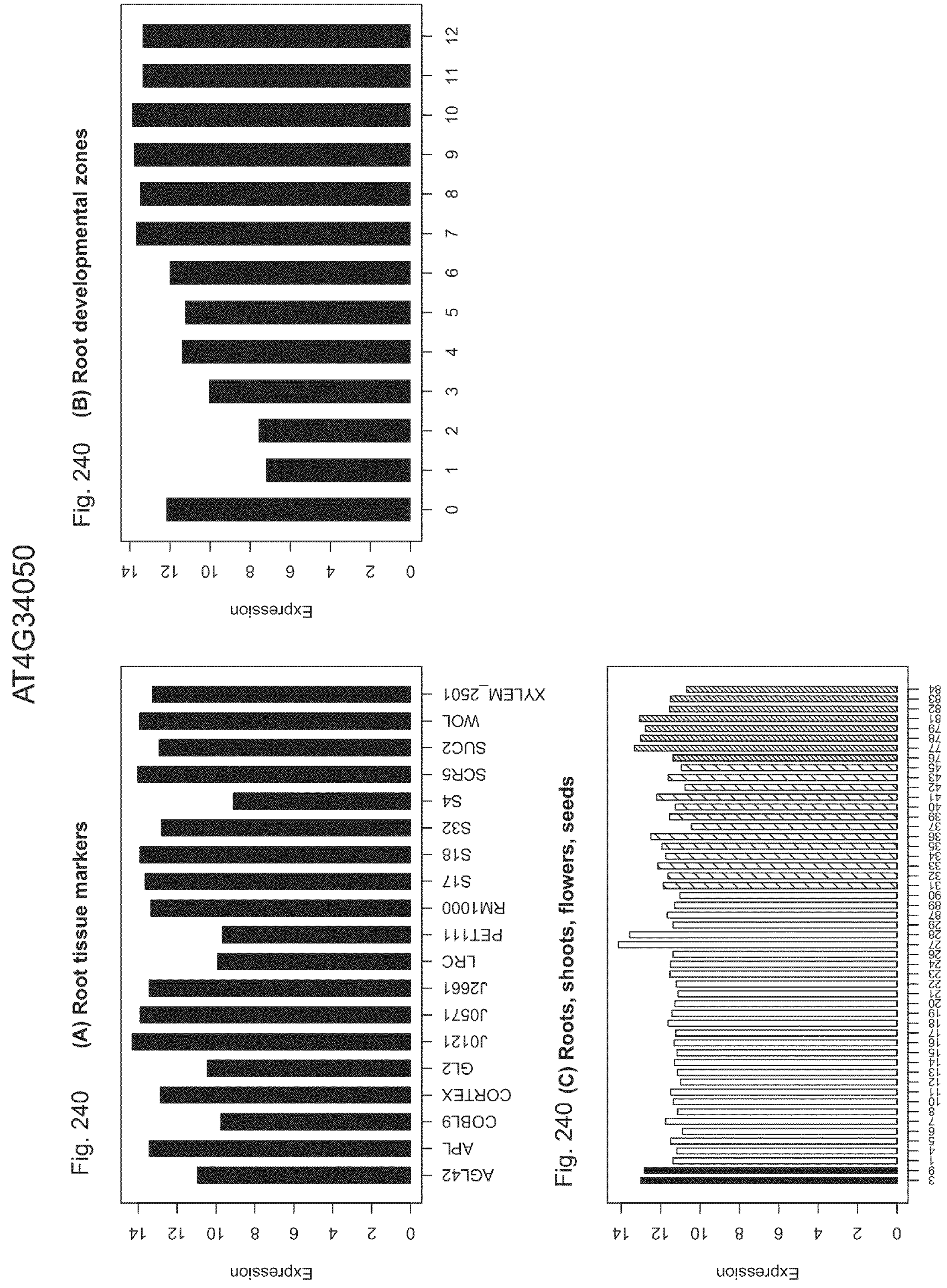
Fig. 240 (A) Root tissue markers
Fig. 240 (B) Root developmental zones
Fig. 240 (C) Roots, shoots, flowers, seeds AT4G34050
Fig. 240 (D) Abiotic stresses
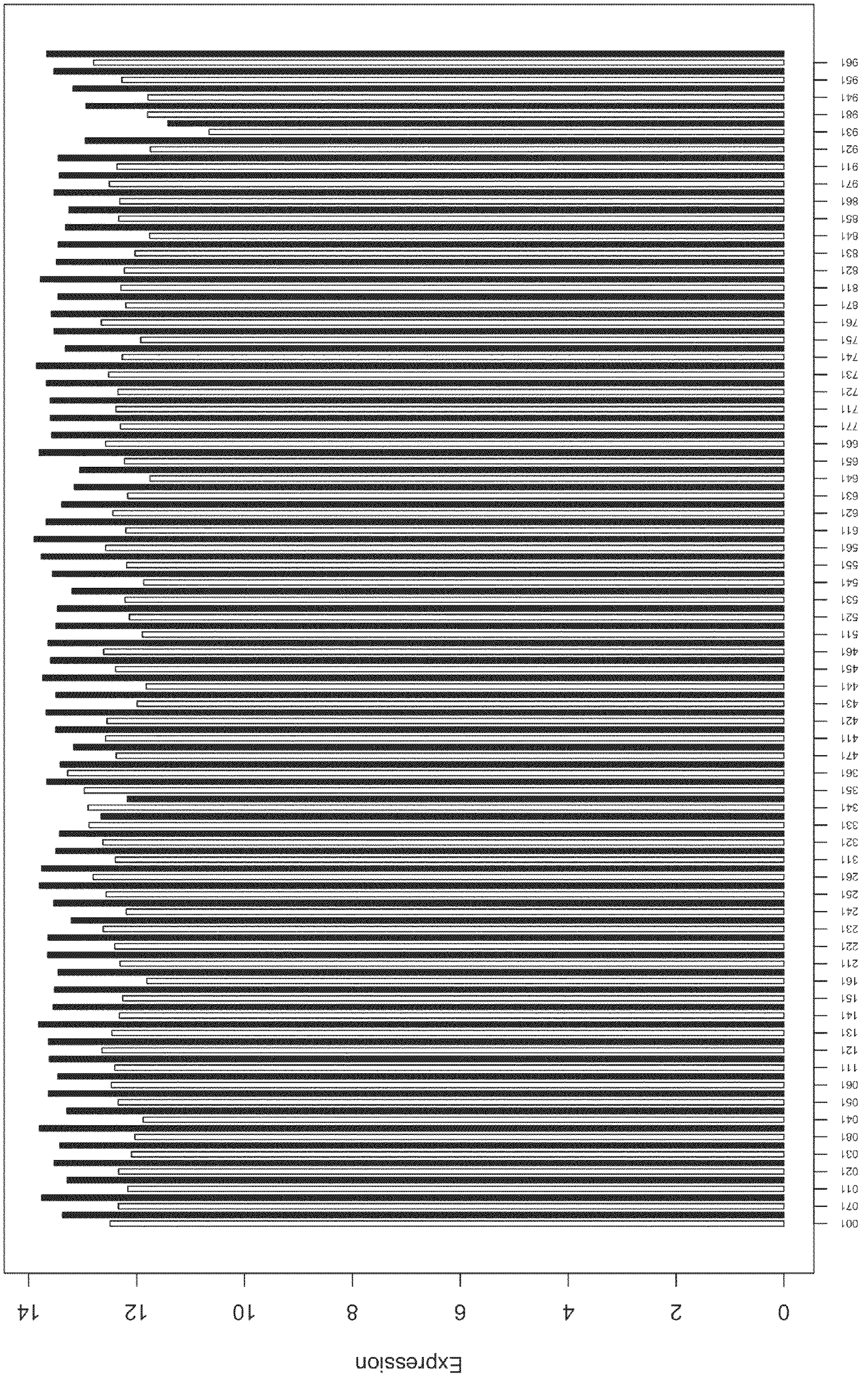

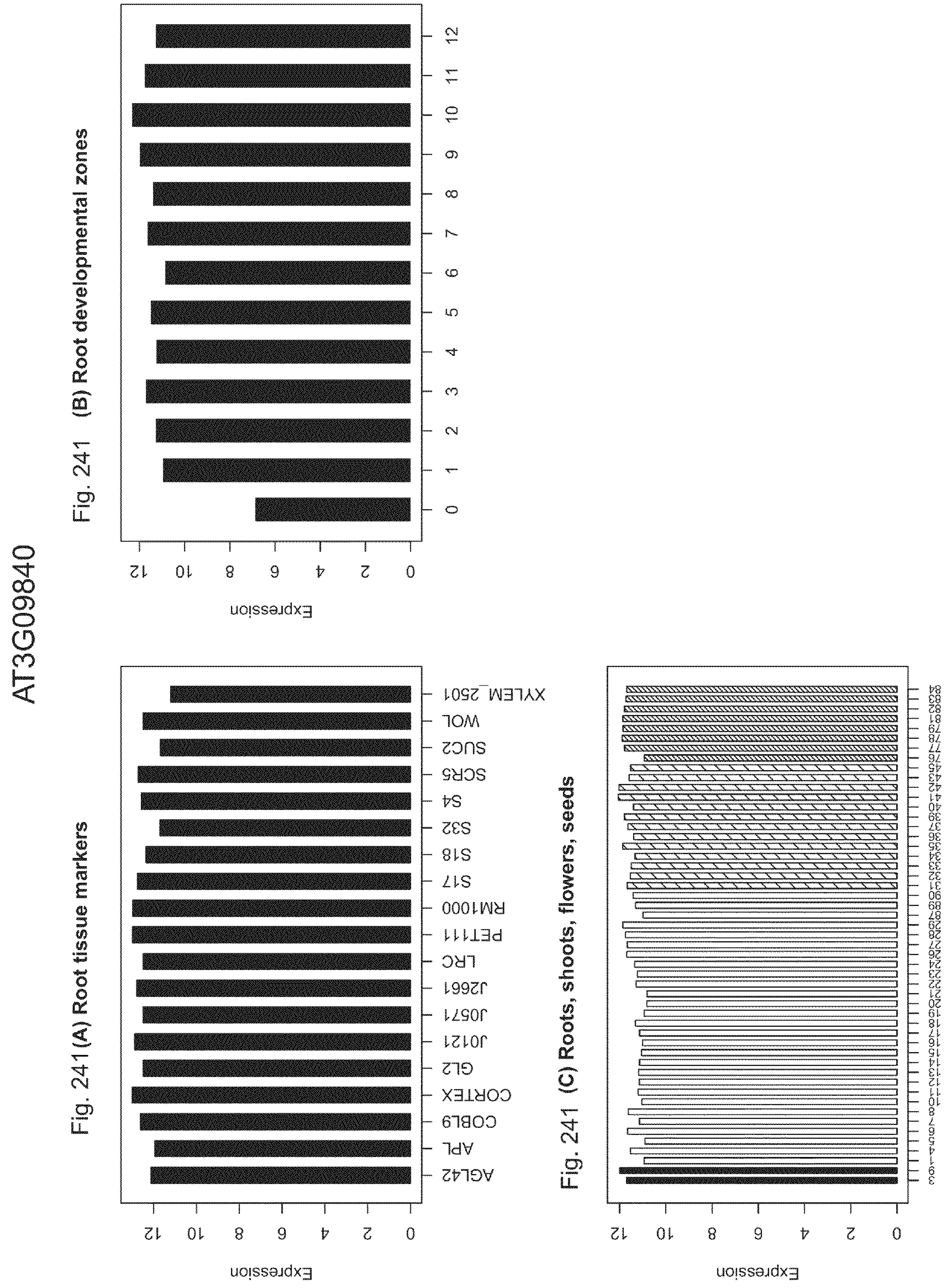
AT3G09840
Fig. 241 (A) Root tissue markers
Fig. 241 (B) Root developmental zones
Fig. 241 (C) Roots, shoots, flowers, seeds
Expression
AGL42
APL
COBL9
CORTEX
GL2
J0121
J0571
J2661
LRC
PET111
RM1000
S17
S18
S32
S4
SCR5
SUC2
WOL
XYLEM_2501
0
1
2
3
4
5
6
7
8
9
10
11
12

AT3G09840
Fig. 241 (D) Abiotic stresses
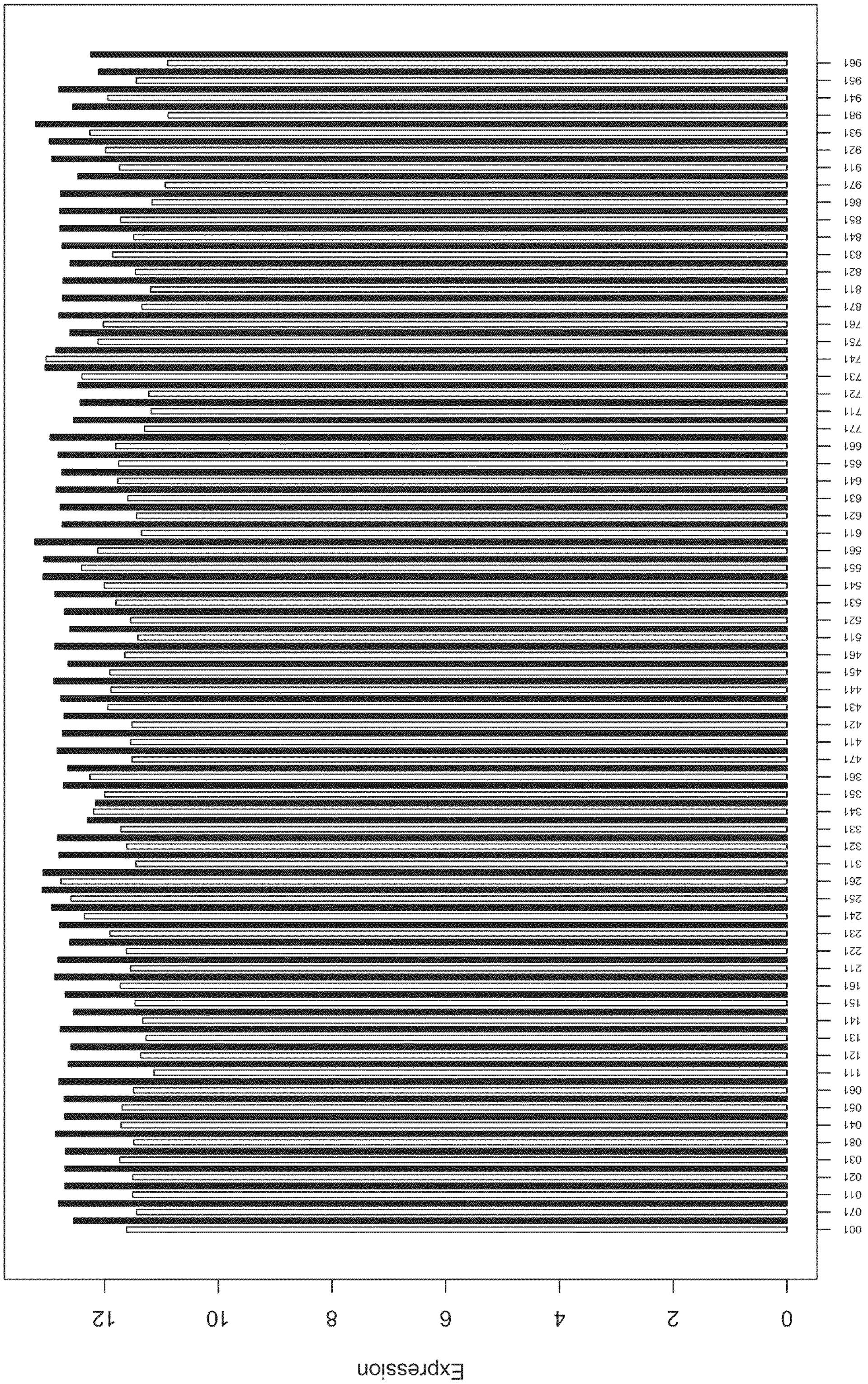

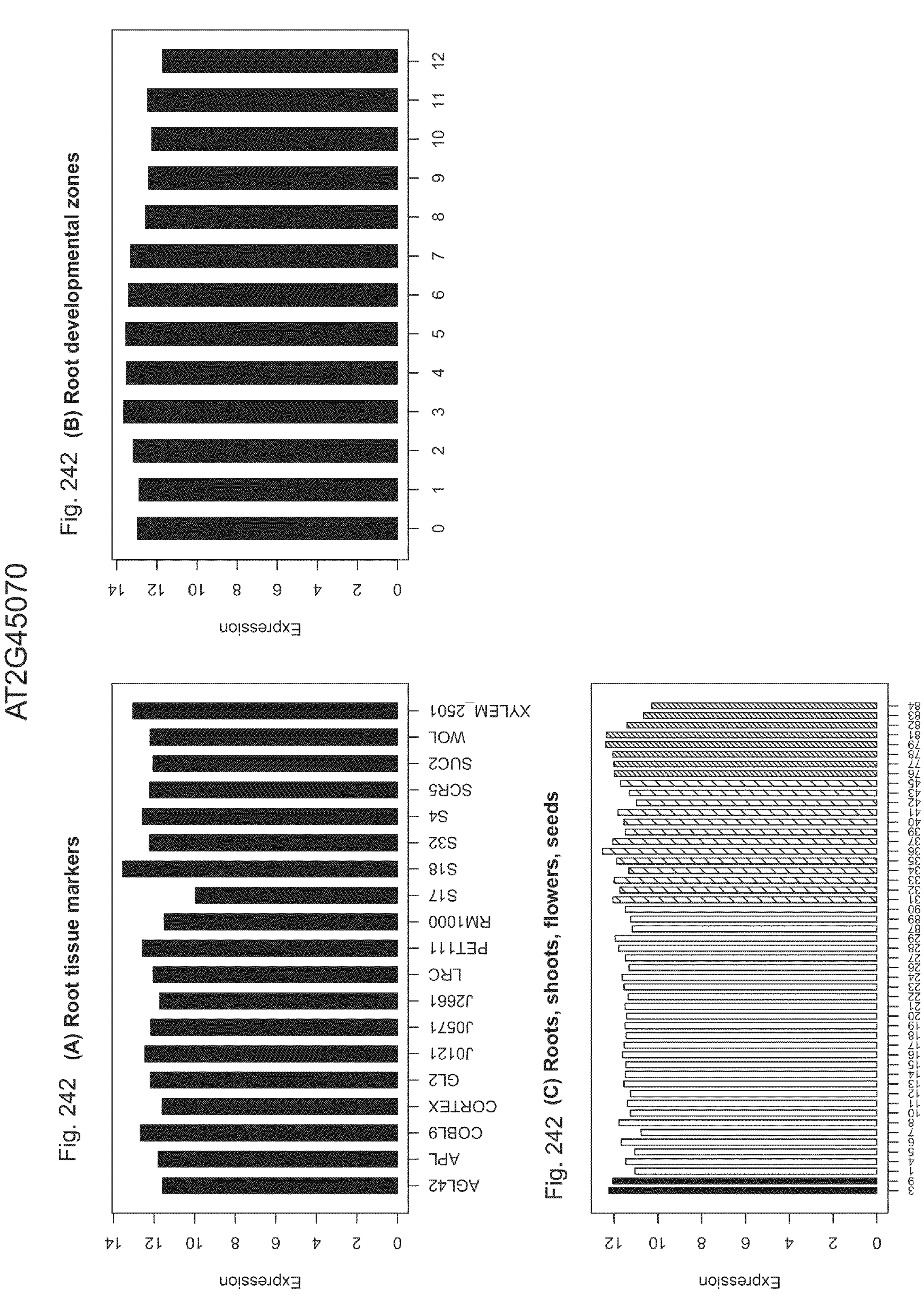
AT2G45070
Fig. 242 (A) Root tissue markers
Expression
0 2 4 6 8 10 12 14
AGL42
APL
COBL9
CORTEX
GL2
J0121
J0571
J2661
LRC
PET111
RM1000
S17
S18
S32
S4
SCR5
SUC2
WOL
XYLEM_2501
Fig. 242 (B) Root developmental zones
Expression
0 2 4 6 8 10 12 14
0 1 2 3 4 5 6 7 8 9 10 11 12
Fig. 242 (C) Roots, shoots, flowers, seeds
Expression
0 2 4 6 8 10 12

Fig. 242 (D) Abiotic stresses
AT2G45070
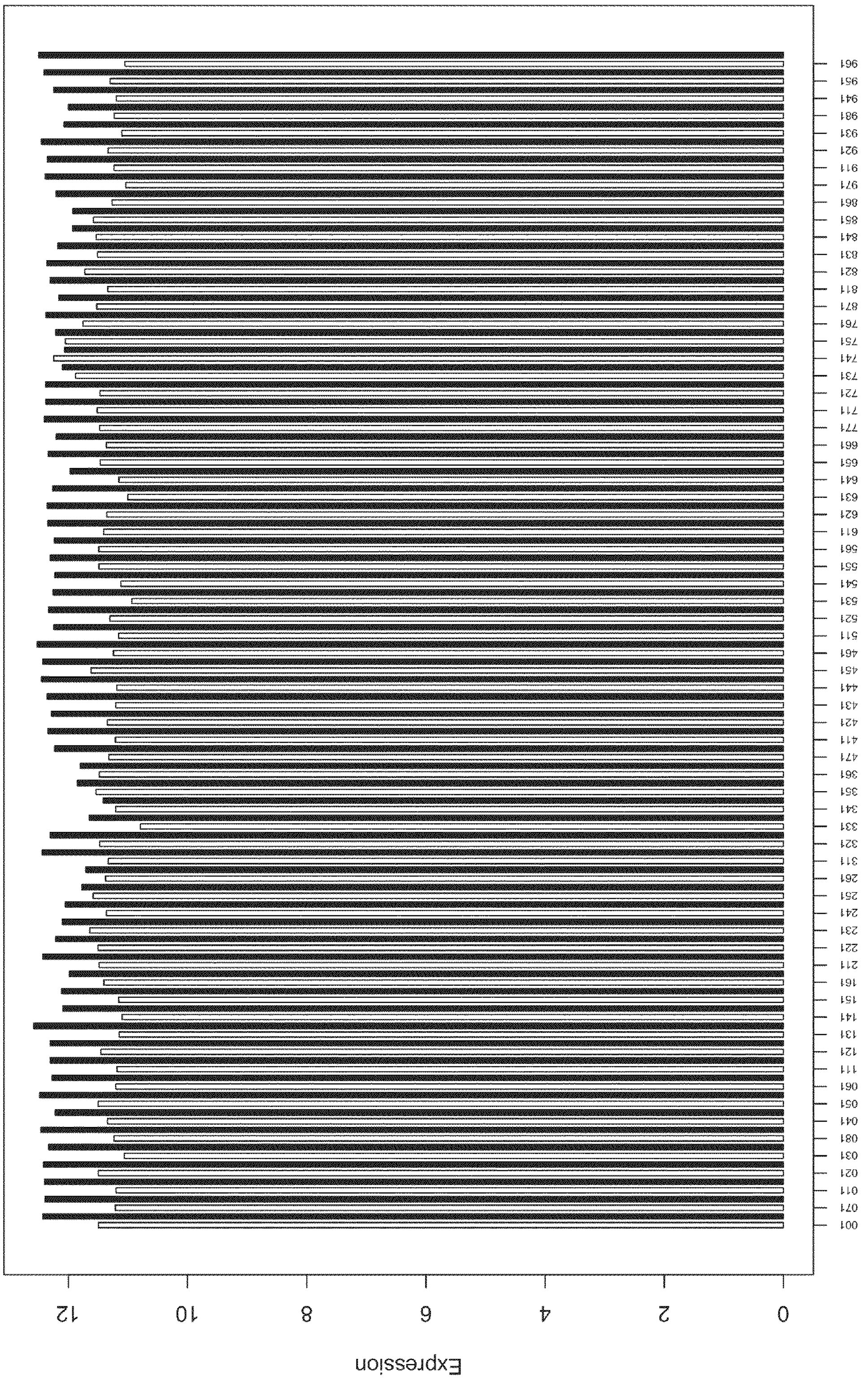

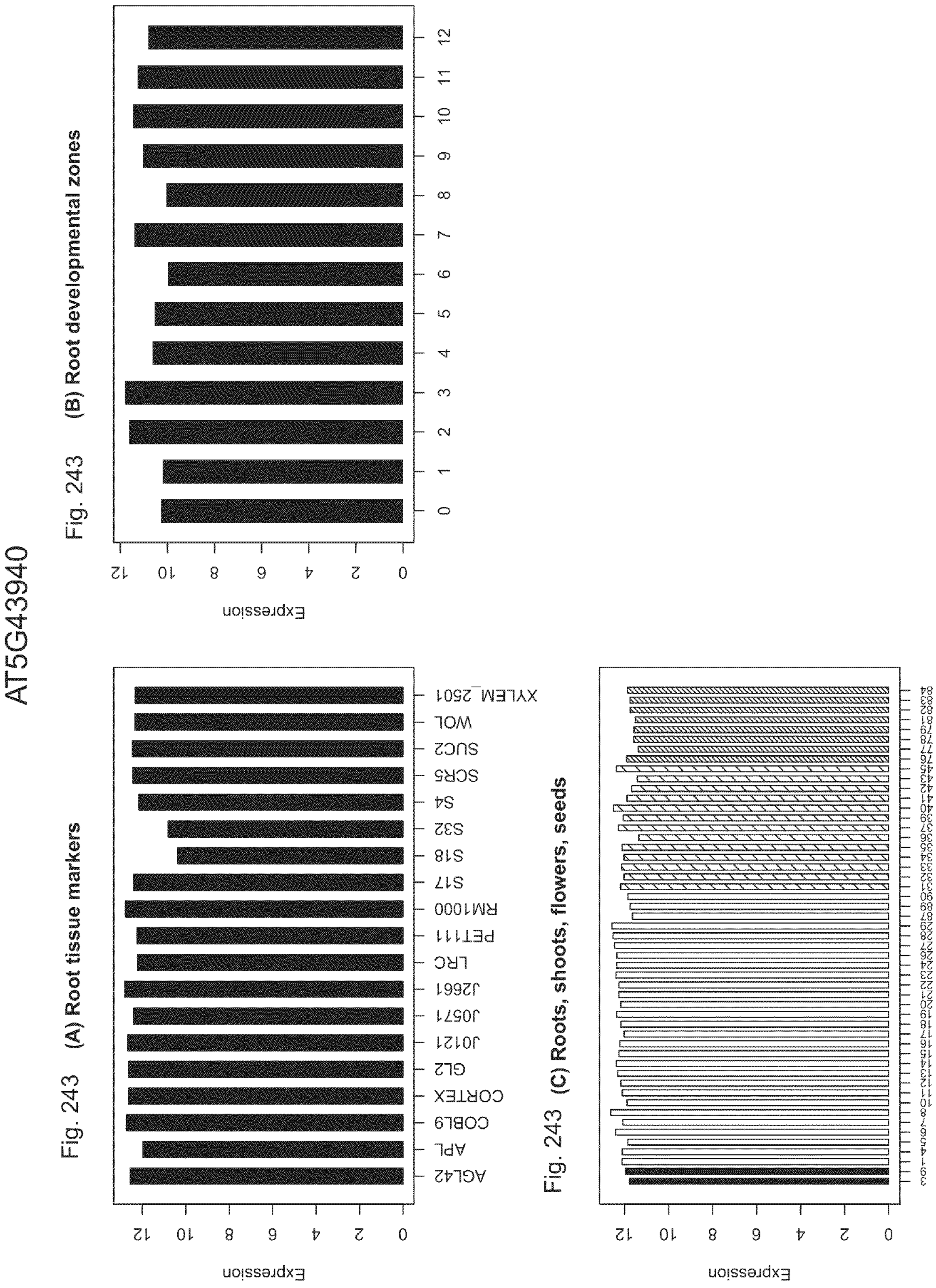
AT5G43940
Fig. 243 (A) Root tissue markers
Expression
0 2 4 6 8 10 12
AGL42 APL COBL9 CORTEX GL2 J0121 J0571 J2661 LRC PET111 RM1000 S17 S18 S32 S4 SCR5 SUC2 WOL XYLEM_2501
Fig. 243 (B) Root developmental zones
Expression
0 2 4 6 8 10 12
0 1 2 3 4 5 6 7 8 9 10 11 12
Fig. 243 (C) Roots, shoots, flowers, seeds
Expression
0 2 4 6 8 10 12

AT5G43940
Fig. 243 (D) Abiotic stresses
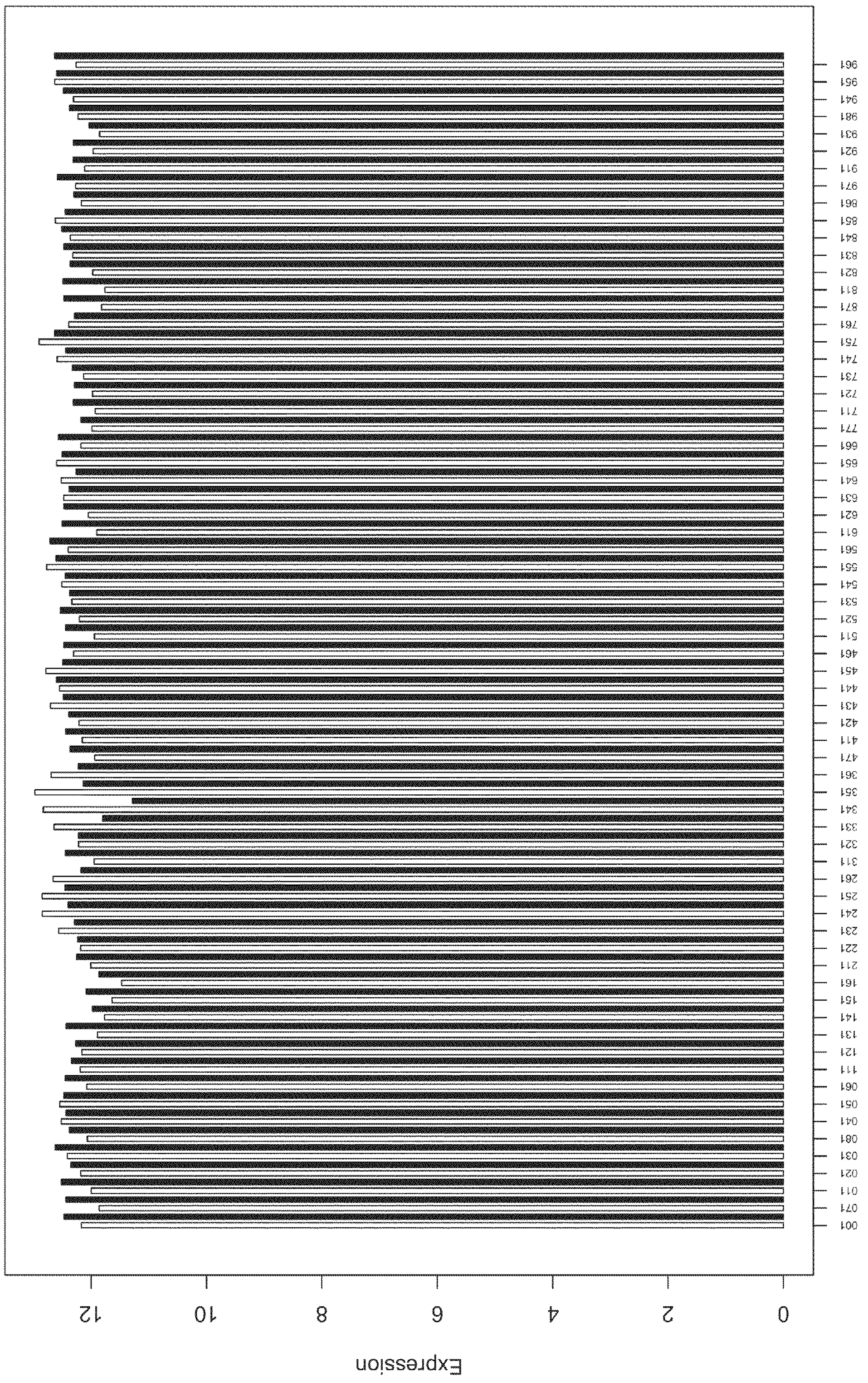

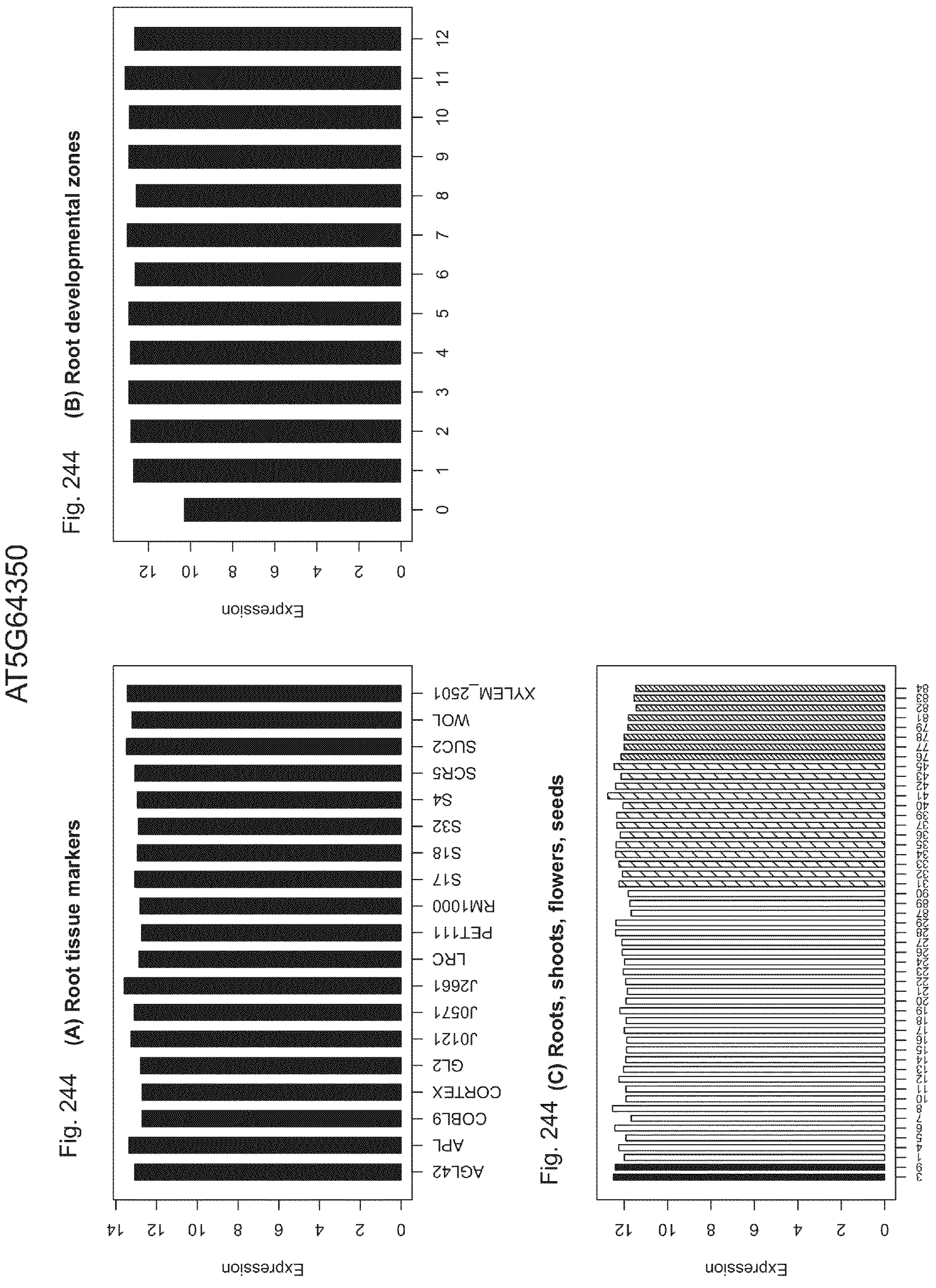
AT5G64350
Fig. 244 (A) Root tissue markers
Fig. 244 (B) Root developmental zones
Fig. 244 (C) Roots, shoots, flowers, seeds
Expression
AGL42
APL
COBL9
CORTEX
GL2
J0121
J0571
J2661
LRC
PET111
RM1000
S17
S18
S32
S4
SCR5
SUC2
WOL
XYLEM_2501

AT5G64350
Fig. 244 (D) Abiotic stresses
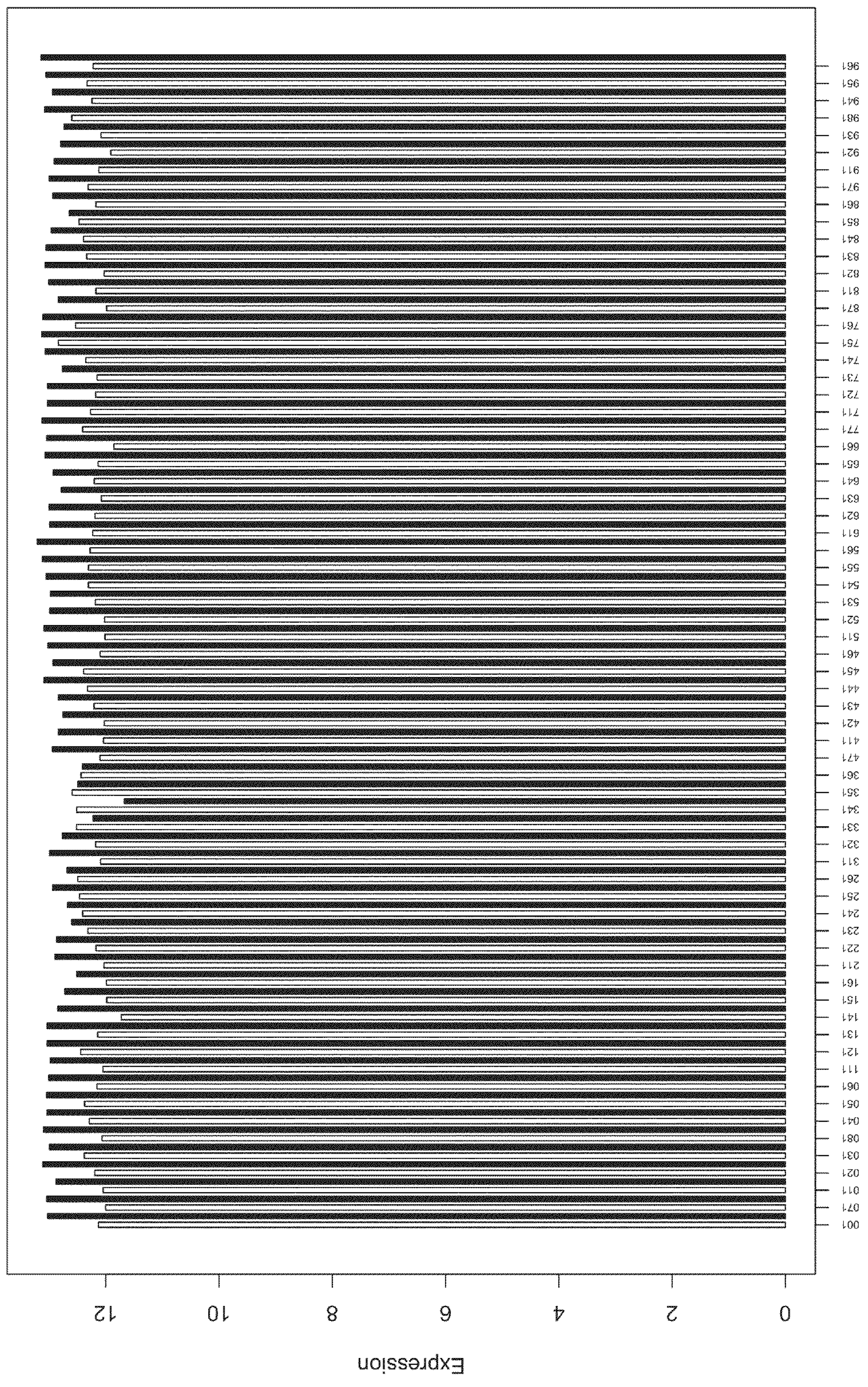

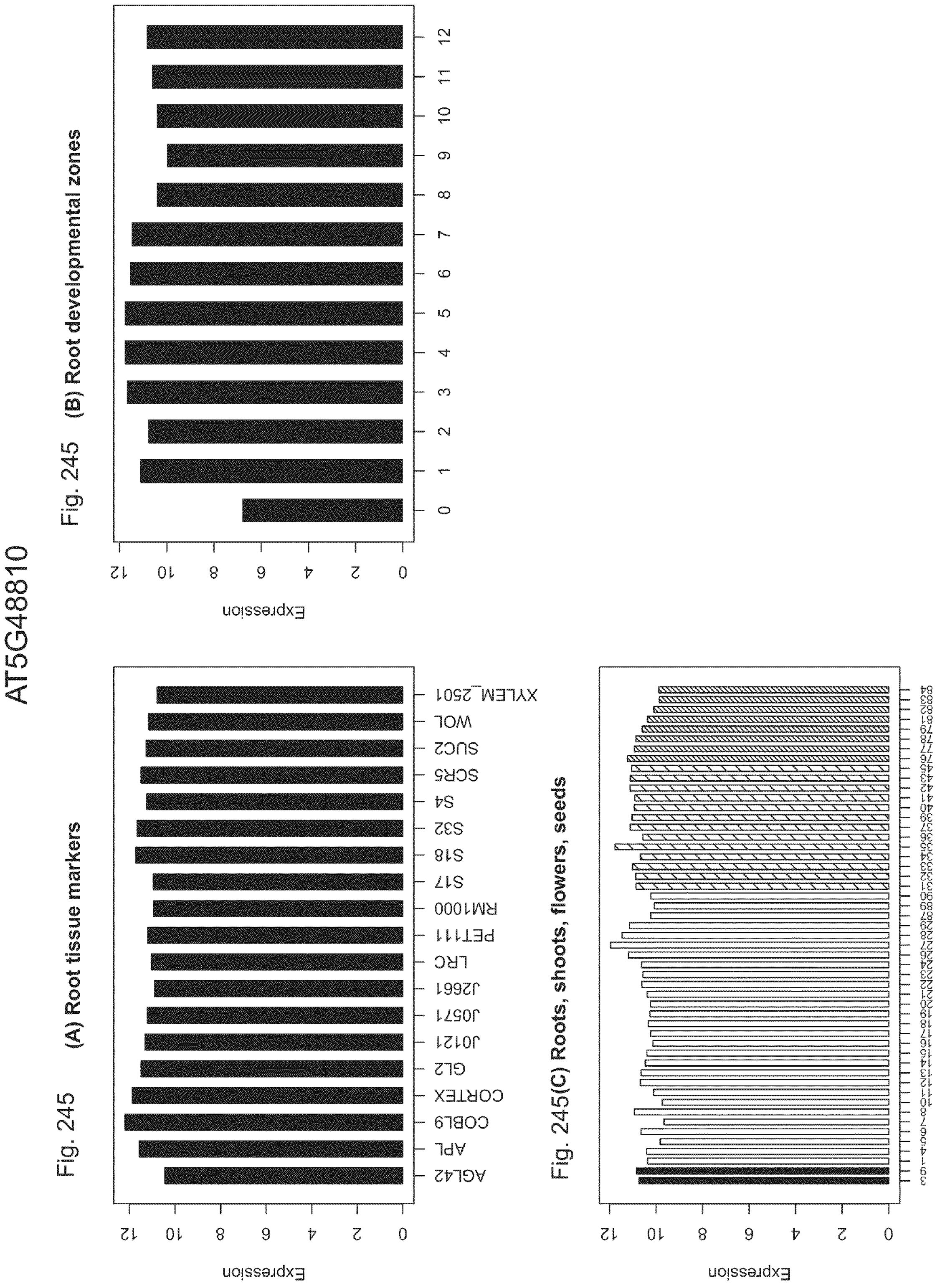
Fig. 245 (A) Root tissue markers
Fig. 245 (B) Root developmental zones
Fig. 245(C) Roots, shoots, flowers, seeds

AT5G48810

(D) Abiotic stresses

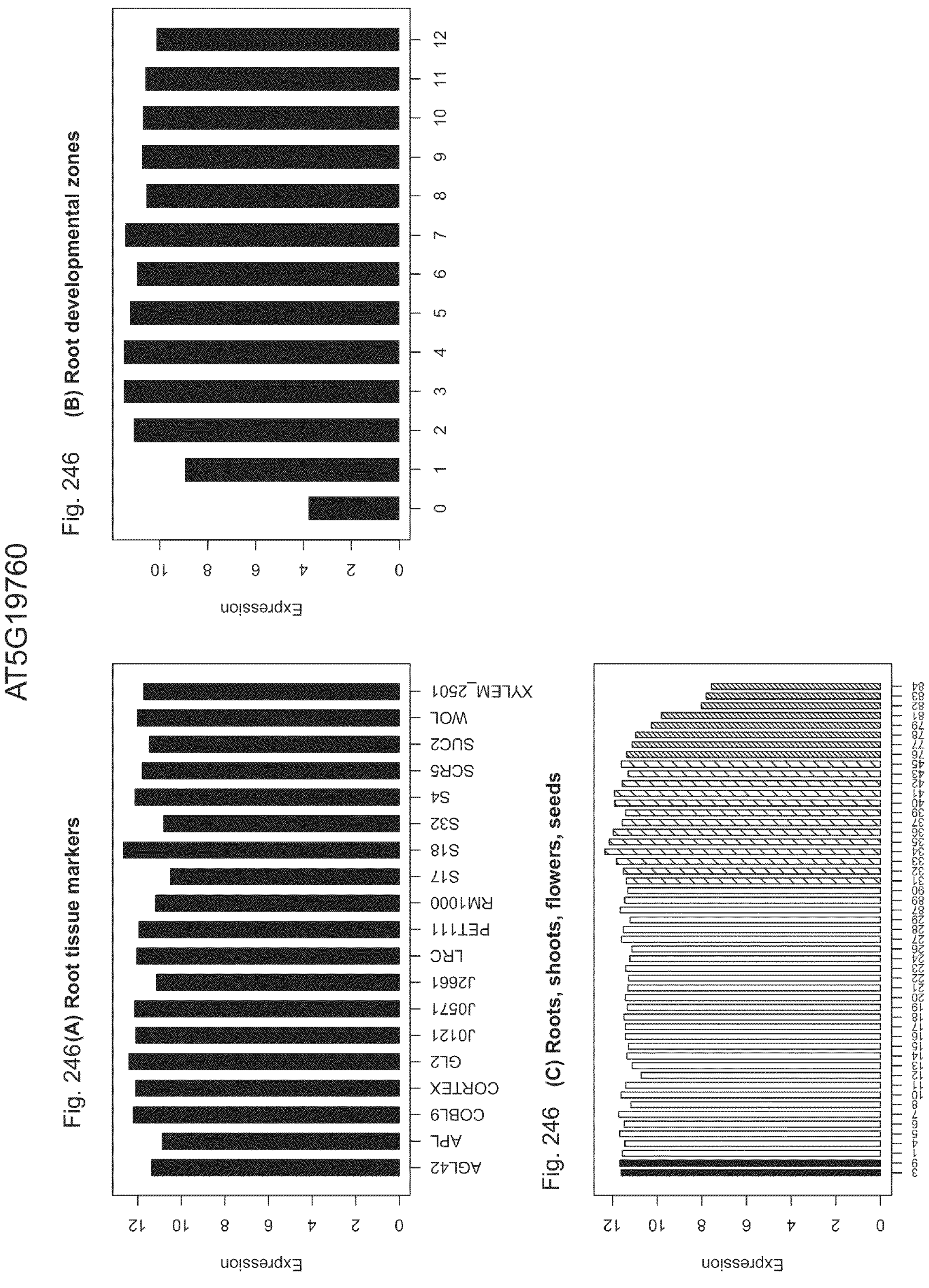
AT5G19760
Fig. 246(A) Root tissue markers
Expression
0 2 4 6 8 10 12
AGL42
APL
COBL9
CORTEX
GL2
J0121
J0571
J2661
LRC
PET111
RM1000
S17
S18
S32
S4
SCR5
SUC2
WOL
XYLEM_2501
Fig. 246 (B) Root developmental zones
Expression
0 2 4 6 8 10
0 1 2 3 4 5 6 7 8 9 10 11 12
Fig. 246 (C) Roots, shoots, flowers, seeds
Expression
0 2 4 6 8 10 12

AT5G19760

(D) Abiotic stresses

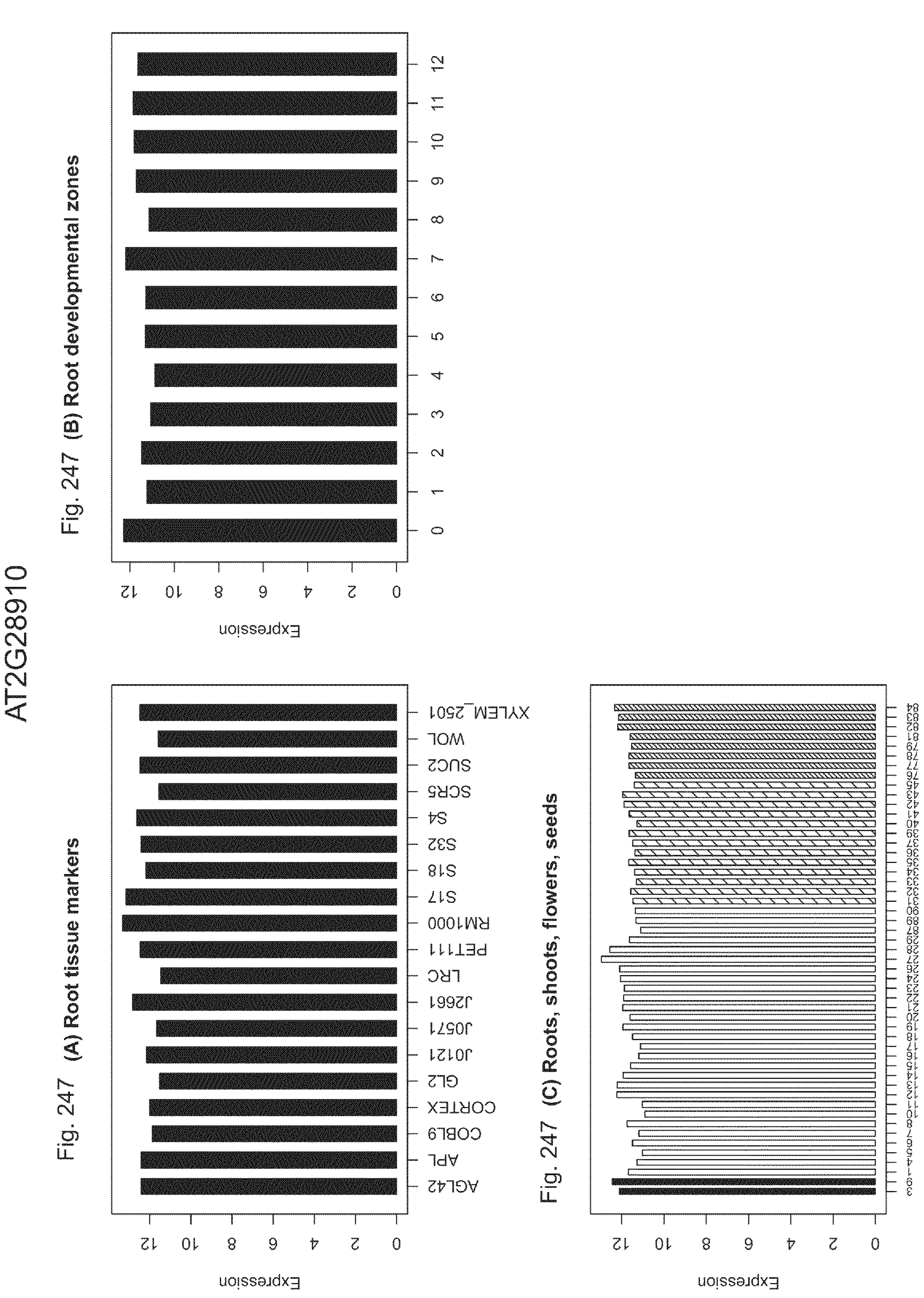
AT2G28910
Fig. 247 (A) Root tissue markers
Expression
AGL42
APL
COBL9
CORTEX
GL2
J0121
J0571
J2661
LRC
PET111
RM1000
S17
S18
S32
S4
SCR5
SUC2
WOL
XYLEM_2501
Fig. 247 (B) Root developmental zones
Fig. 247 (C) Roots, shoots, flowers, seeds Fig. 247 (D) Abiotic stresses
AT2G28910
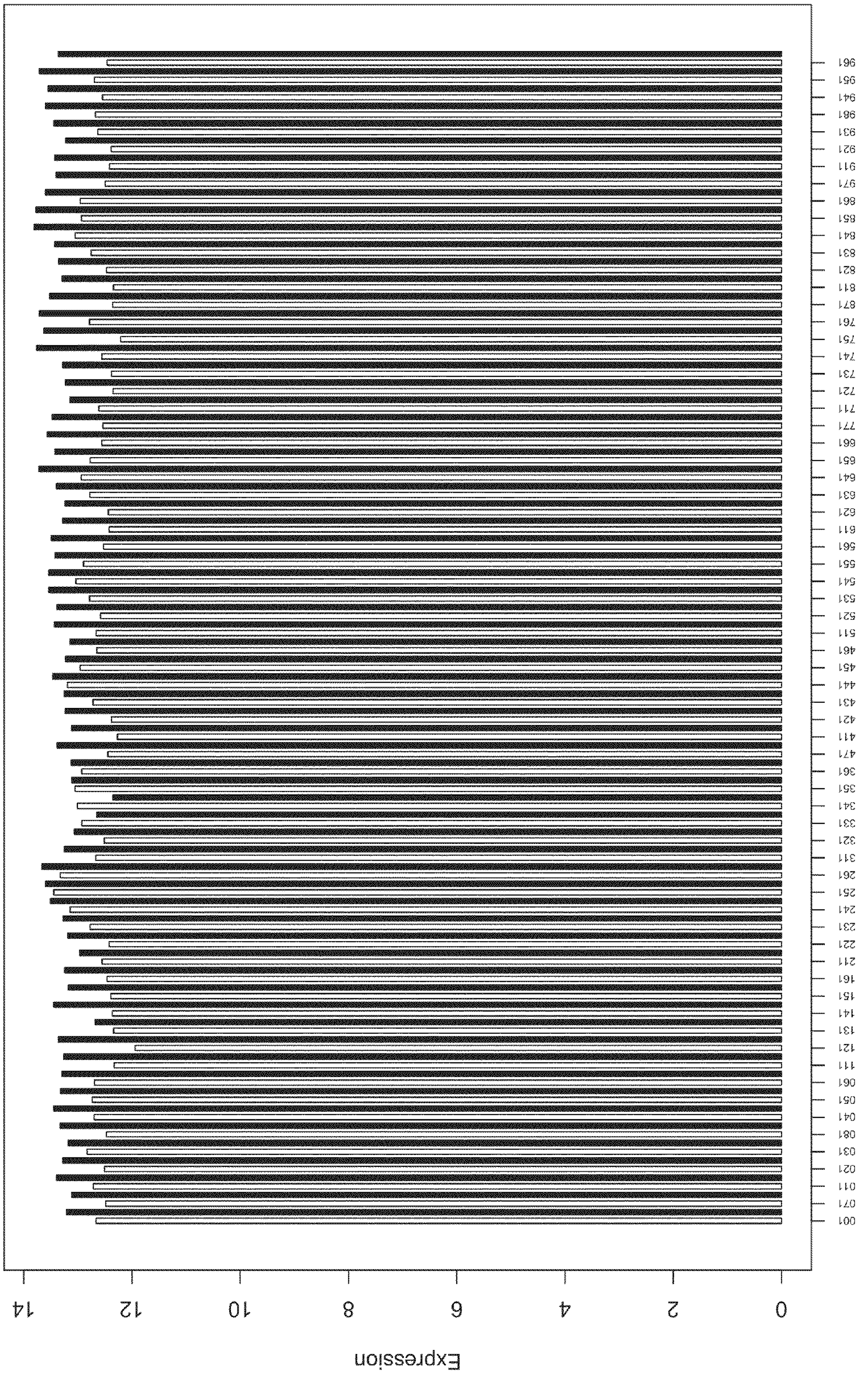

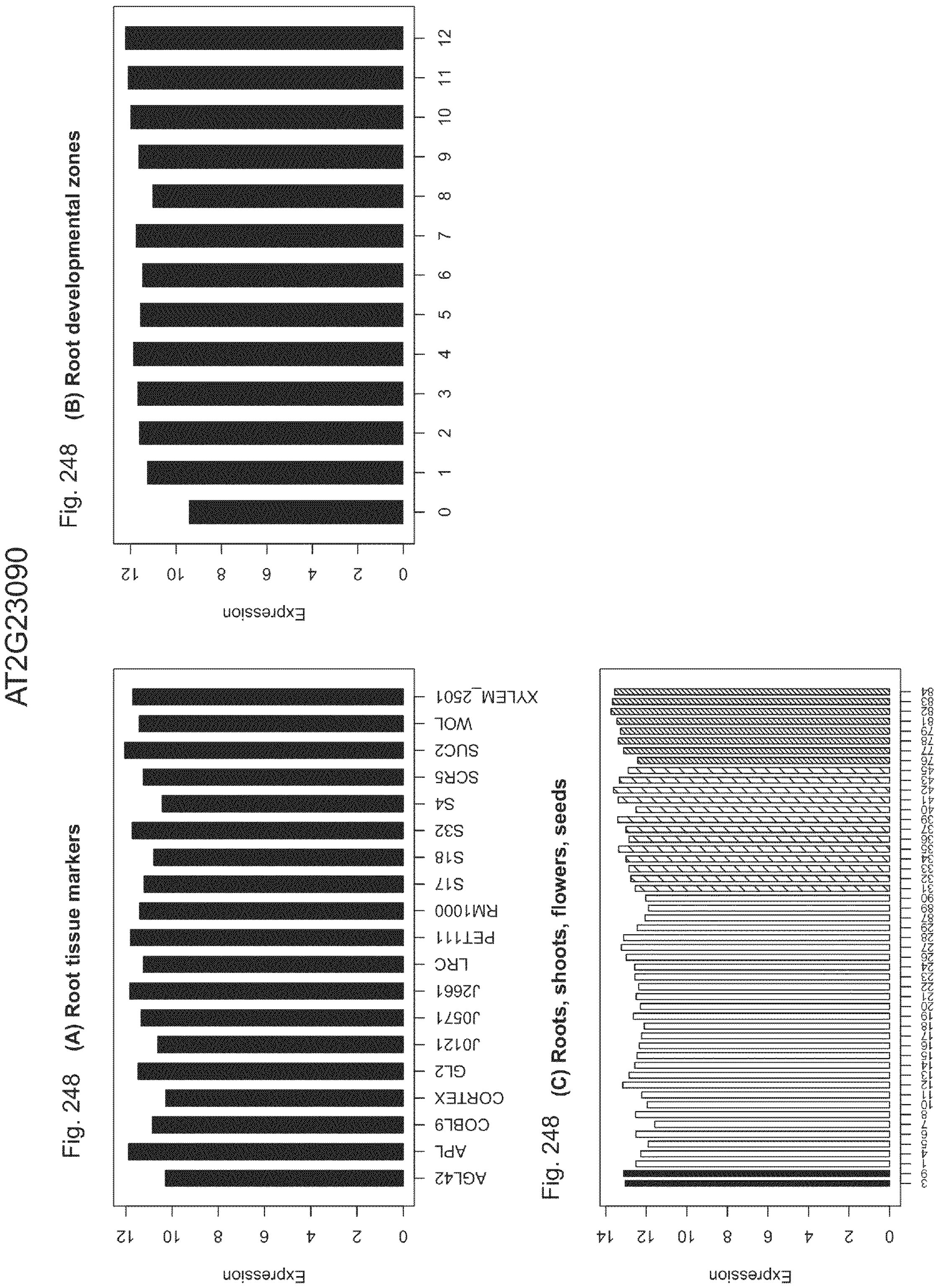
Fig. 248 (A) Root tissue markers
Fig. 248 (B) Root developmental zones
Fig. 248 (C) Roots, shoots, flowers, seeds

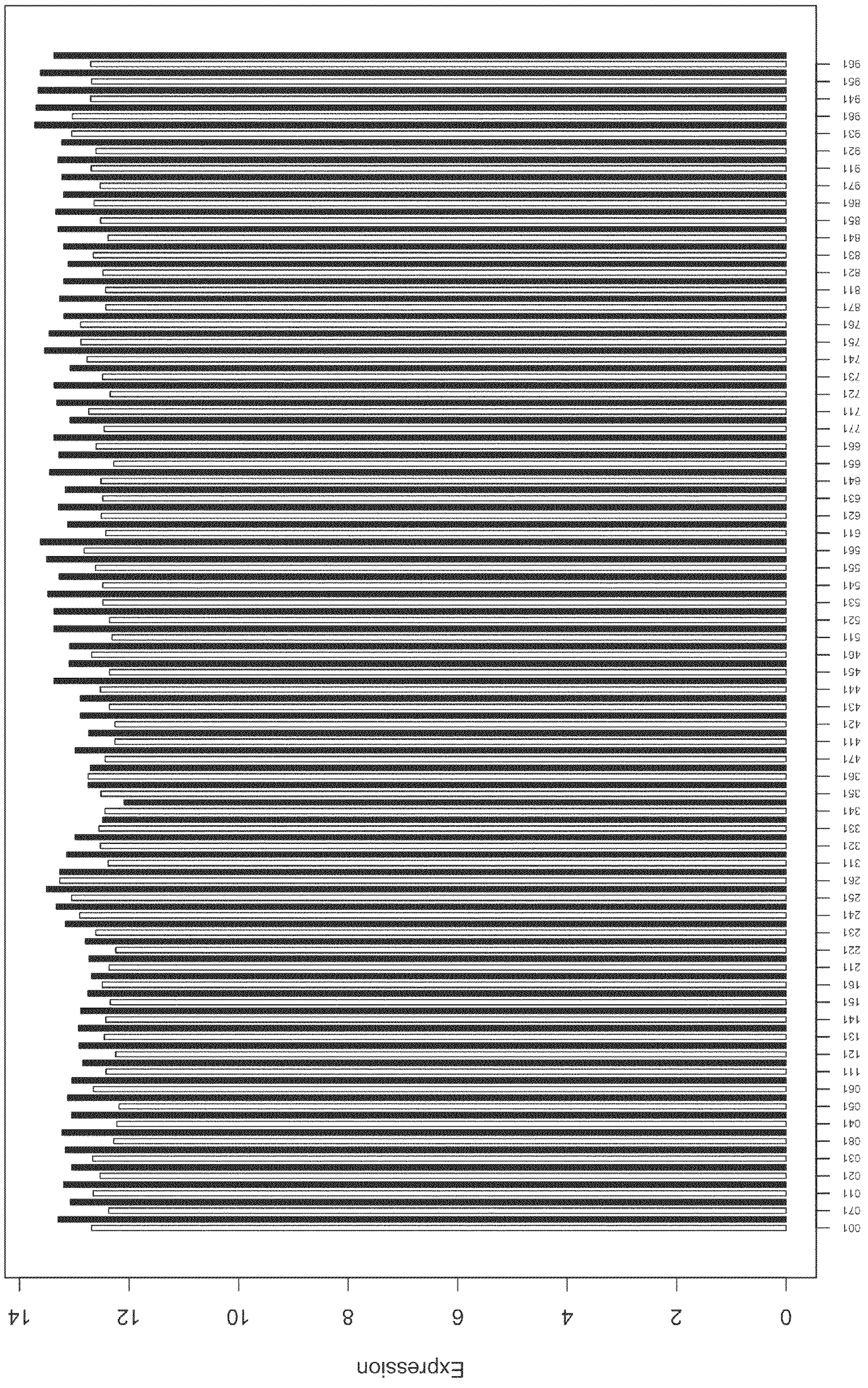
AT2G23090
Fig. 248 (D) Abiotic stresses

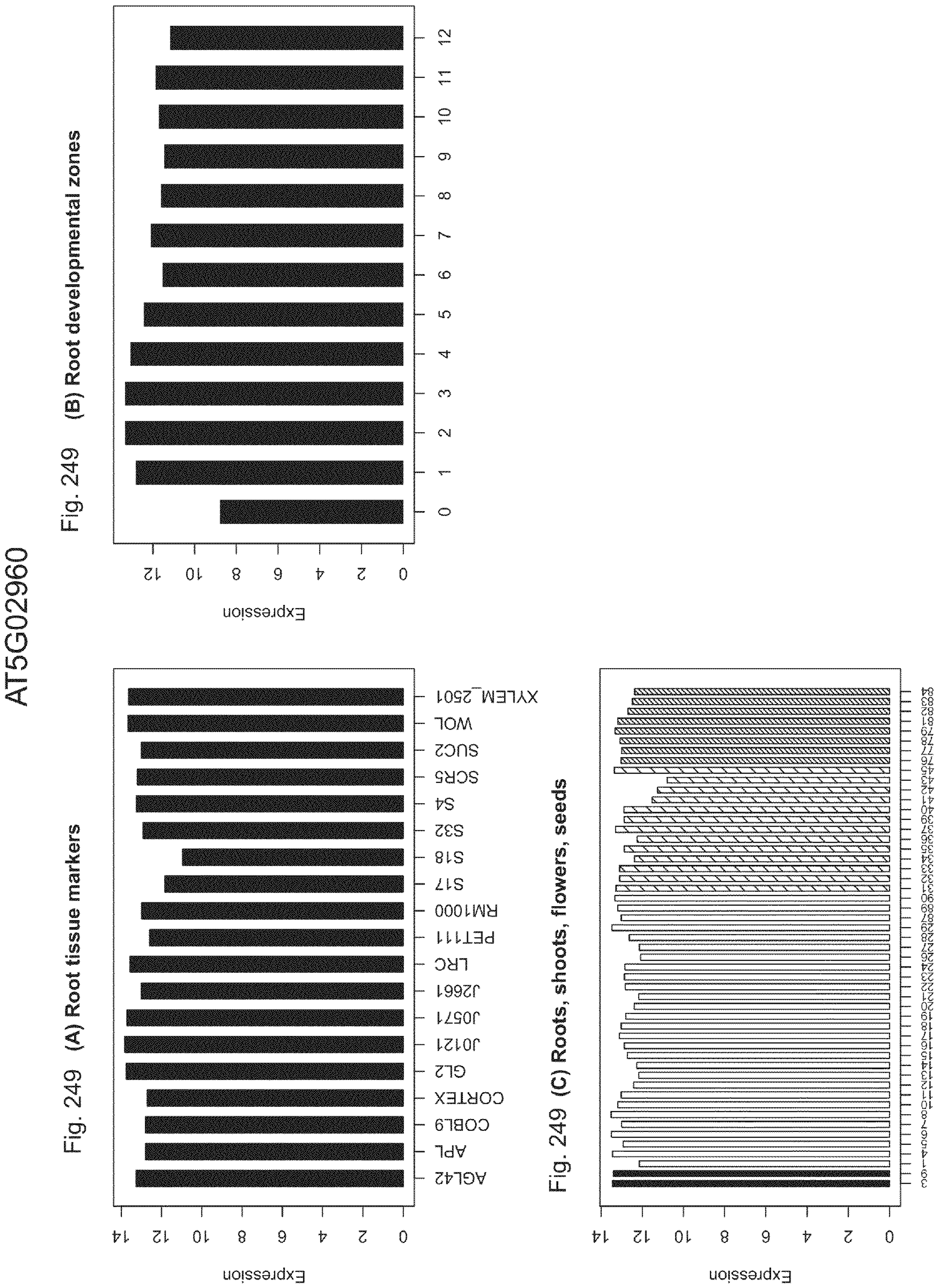
AT5G02960
Fig. 249 (A) Root tissue markers
Fig. 249 (B) Root developmental zones
Fig. 249 (C) Roots, shoots, flowers, seeds
Expression
AGL42
APL
COBL9
CORTEX
GL2
J0121
J0571
J2661
LRC
PET111
RM1000
S17
S18
S32
S4
SCR5
SUC2
WOL
XYLEM_2501

AT5G02960

(D) Abiotic stresses

AT3G09500
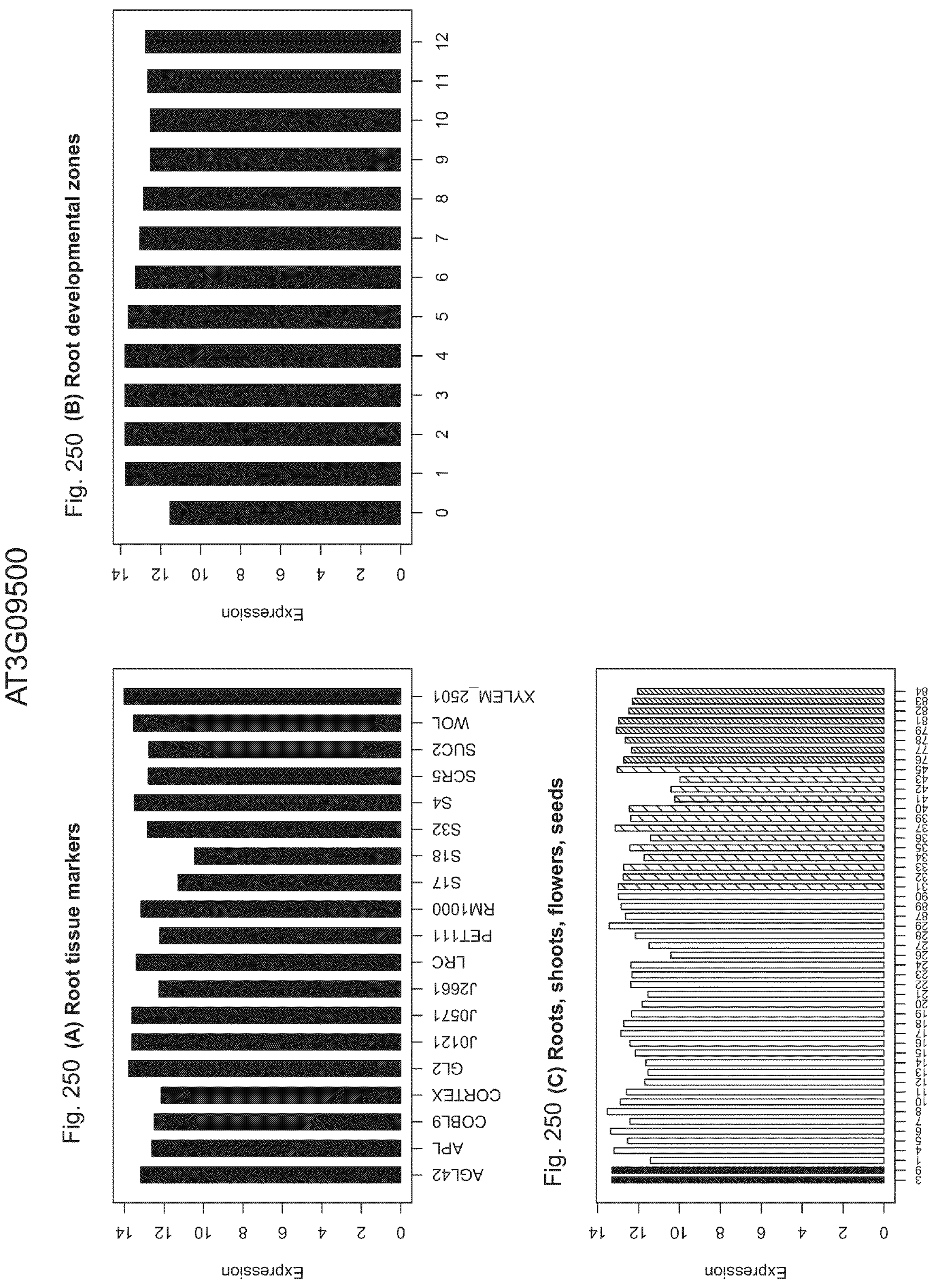
Fig. 250 (A) Root tissue markers
Fig. 250 (B) Root developmental zones
Fig. 250 (C) Roots, shoots, flowers, seeds

AT3G09500

(D) Abiotic stresses

AT1G66410
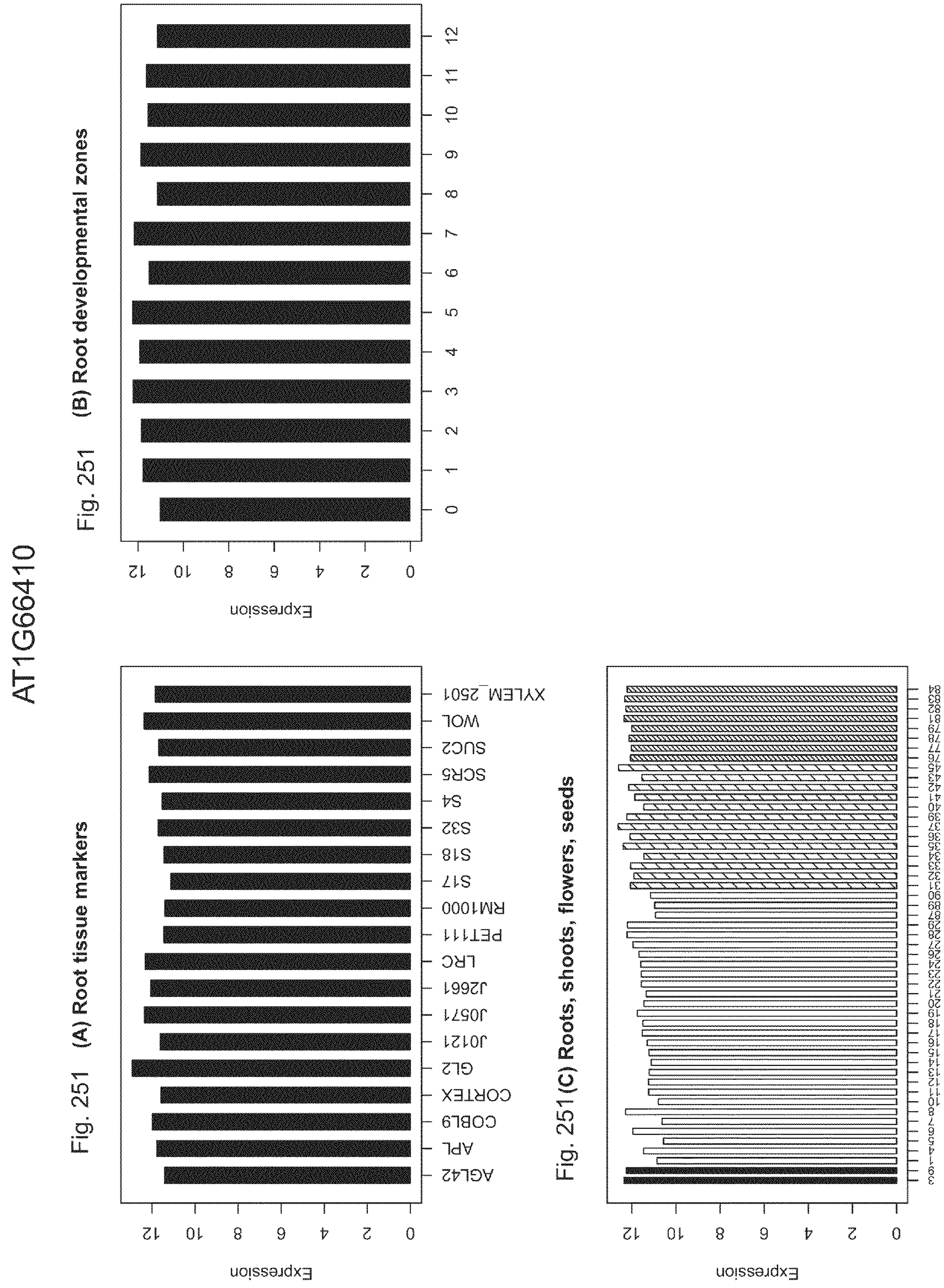
Fig. 251 (A) Root tissue markers
Fig. 251 (B) Root developmental zones
Fig. 251 (C) Roots, shoots, flowers, seeds AT1G66410
Fig. 251 (D) Abiotic stresses
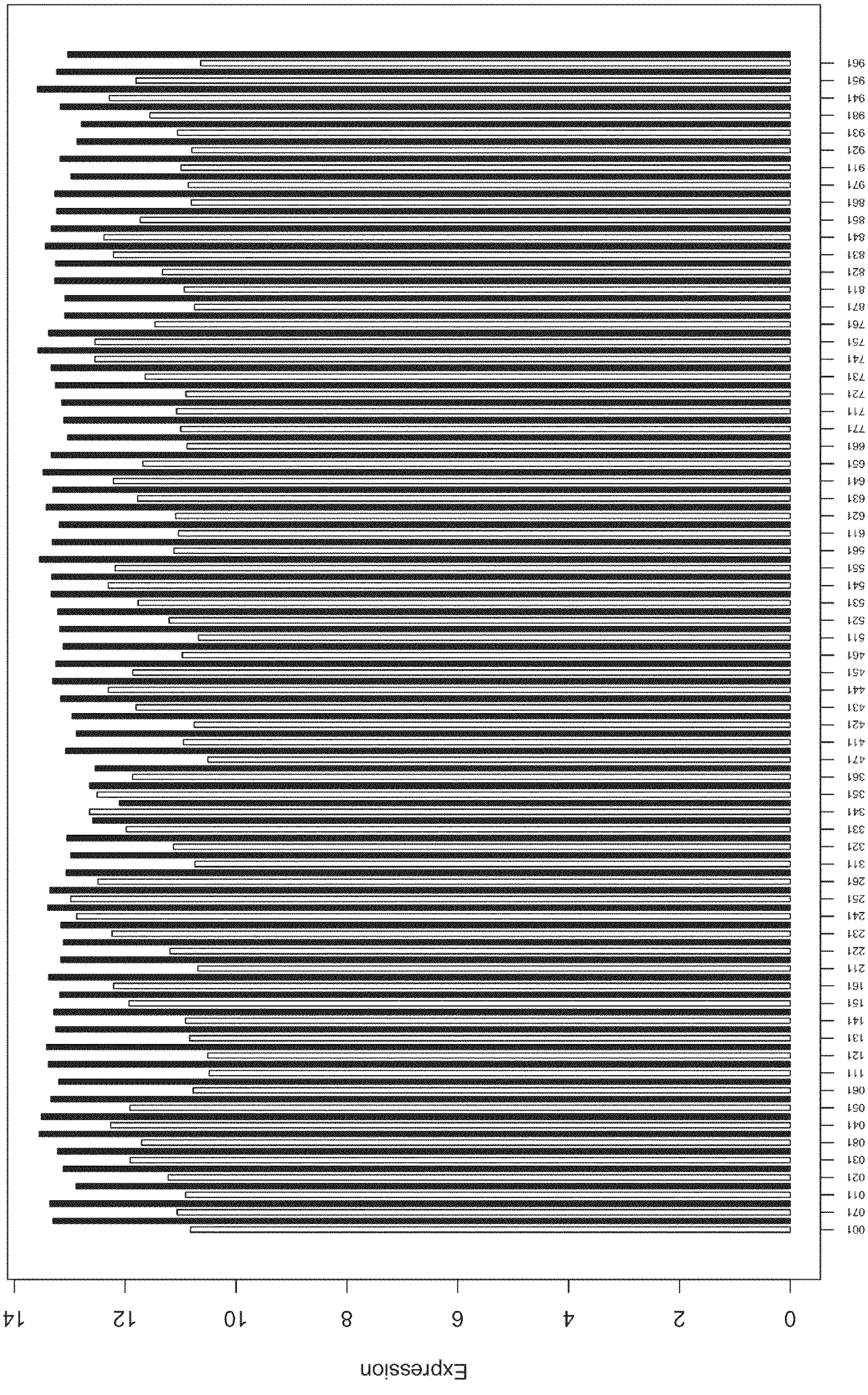

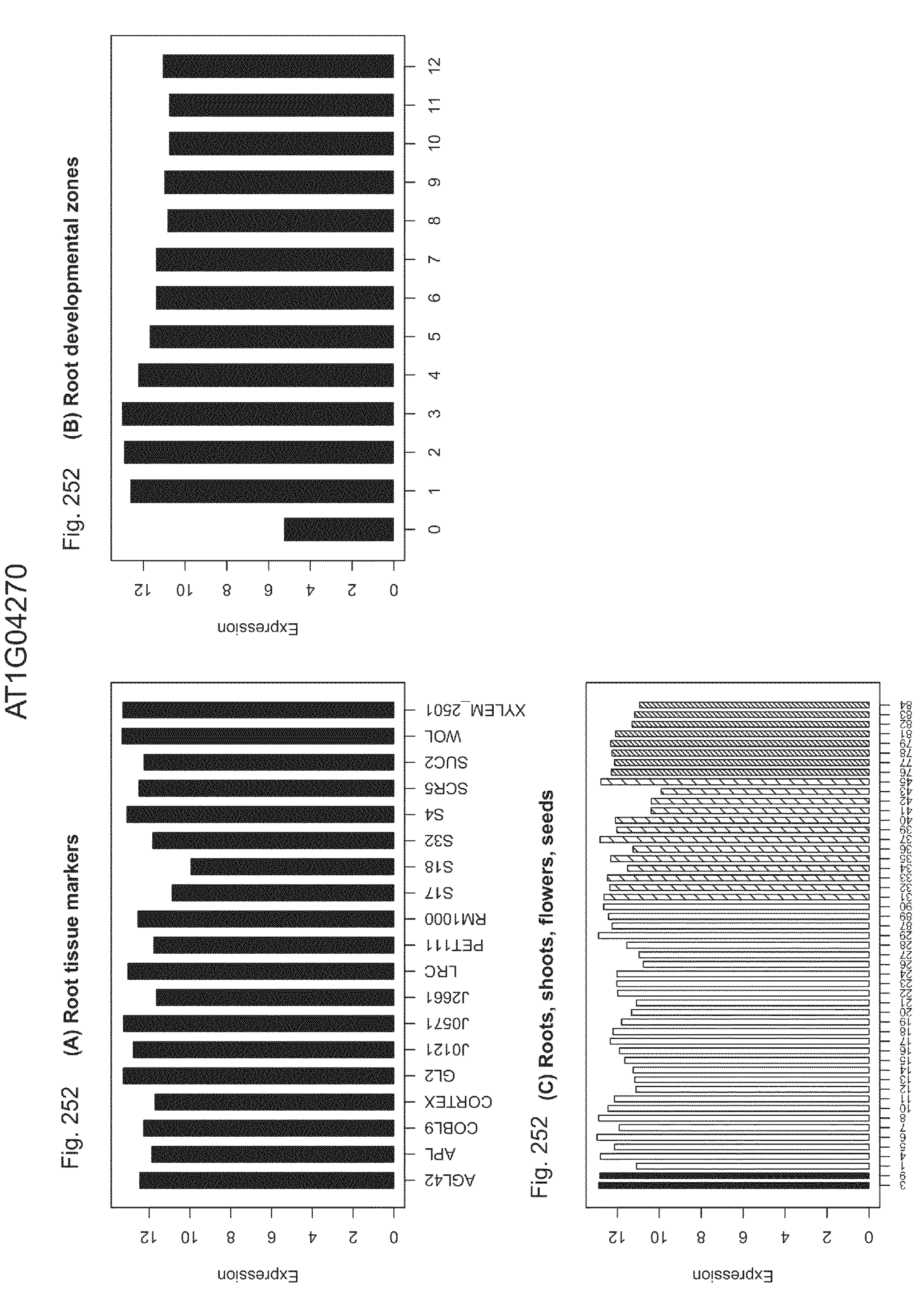
AT1G04270
Fig. 252 (A) Root tissue markers
AGL42
APL
COBL9
CORTEX
GL2
J0121
J0571
J2661
LRC
PET111
RM1000
S17
S18
S32
S4
SCR5
SUC2
WOL
XYLEM_2501
Expression
Fig. 252 (B) Root developmental zones
Expression
Fig. 252 (C) Roots, shoots, flowers, seeds
Expression AT1G04270
Fig. 252 (D) Abiotic stresses
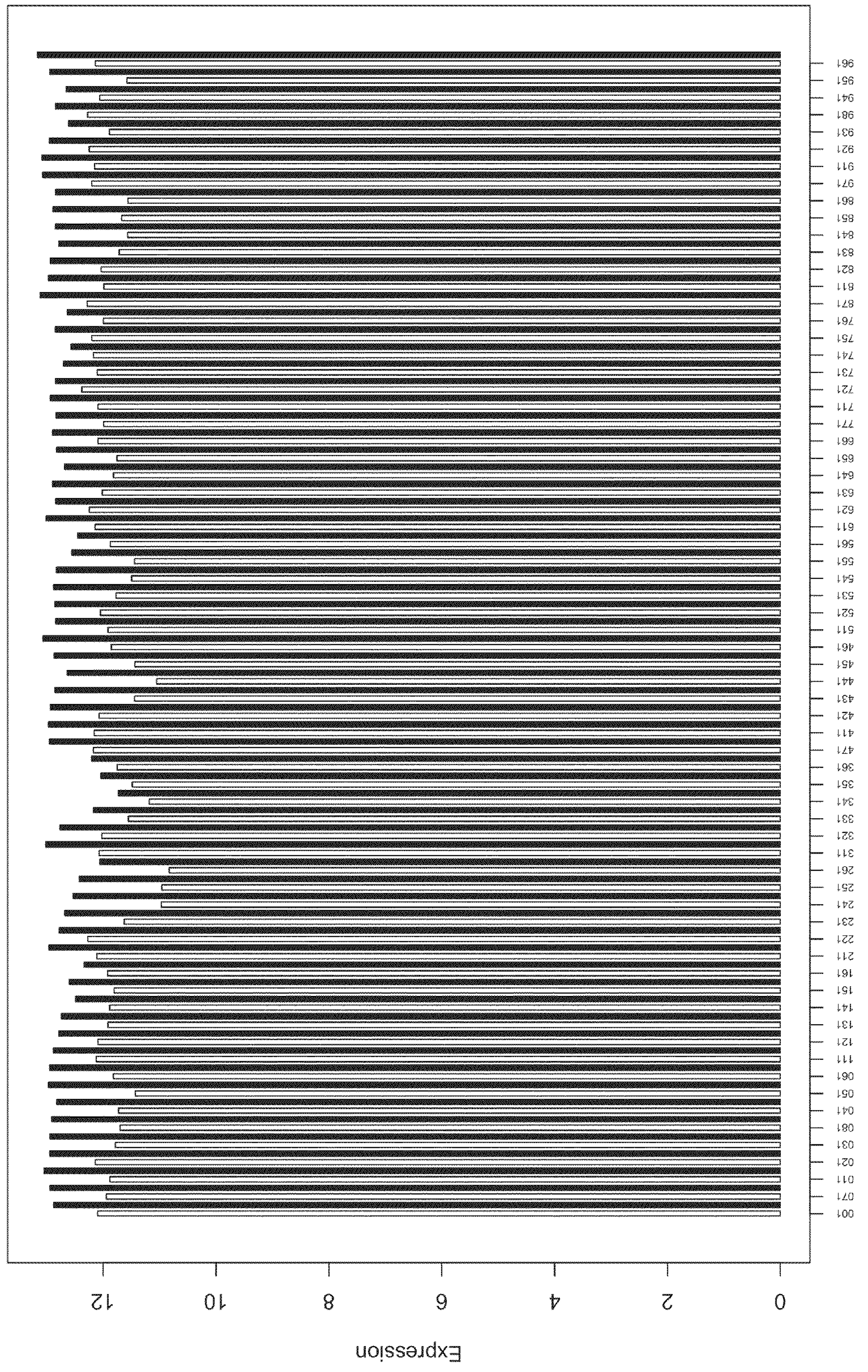

AT2G46330
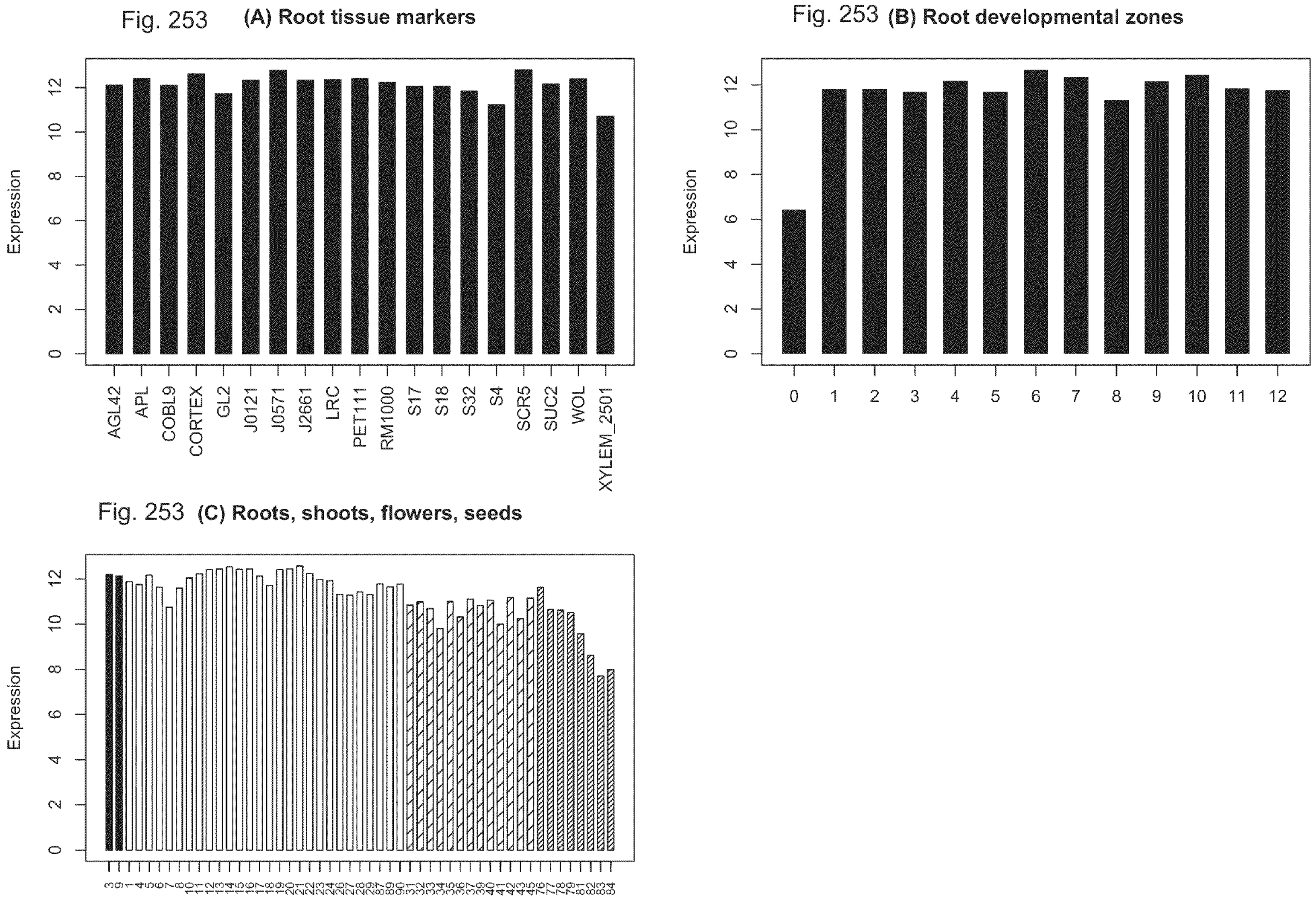

AT2G46330
Fig. 253 (D) Abiotic stresses
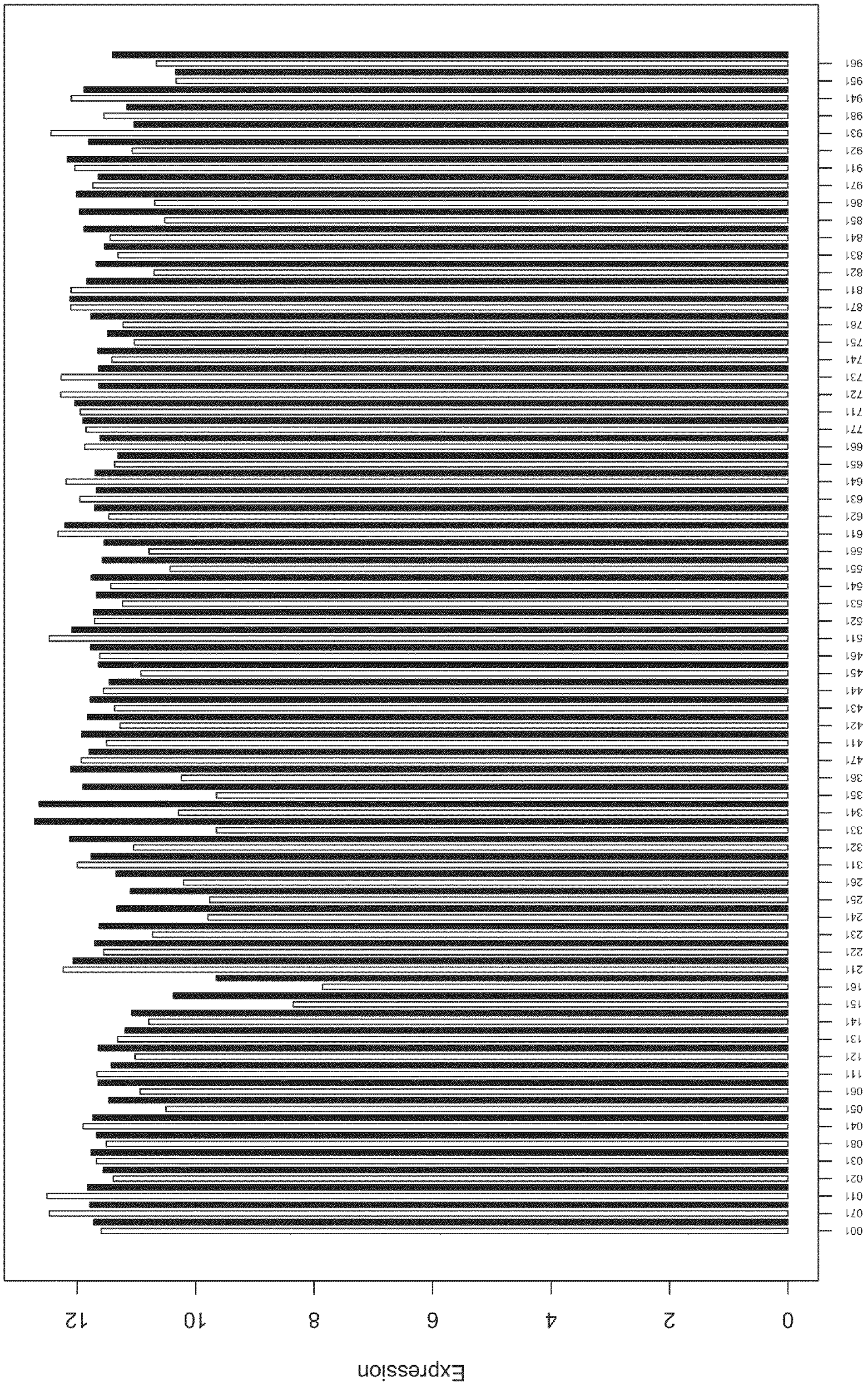

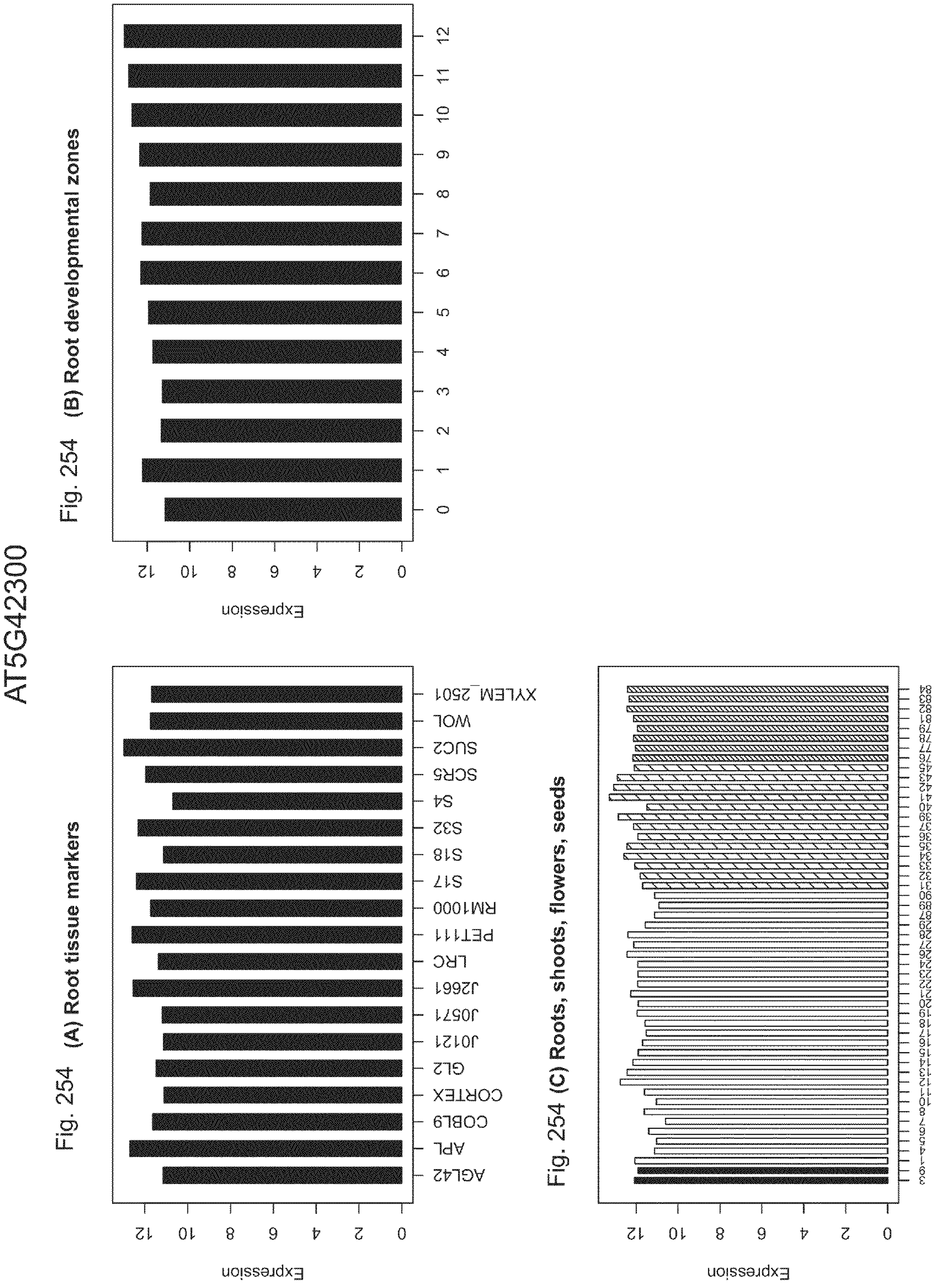
AT5G42300
Fig. 254 (A) Root tissue markers
Fig. 254 (B) Root developmental zones
Fig. 254 (C) Roots, shoots, flowers, seeds
Expression
AGL42
APL
COBL9
CORTEX
GL2
J0121
J0571
J2661
LRC
PET111
RM1000
S17
S18
S32
S4
SCR5
SUC2
WOL
XYLEM_2501
0 2 4 6 8 10 12

AT5G42300
Fig. 254 (D) Abiotic stresses
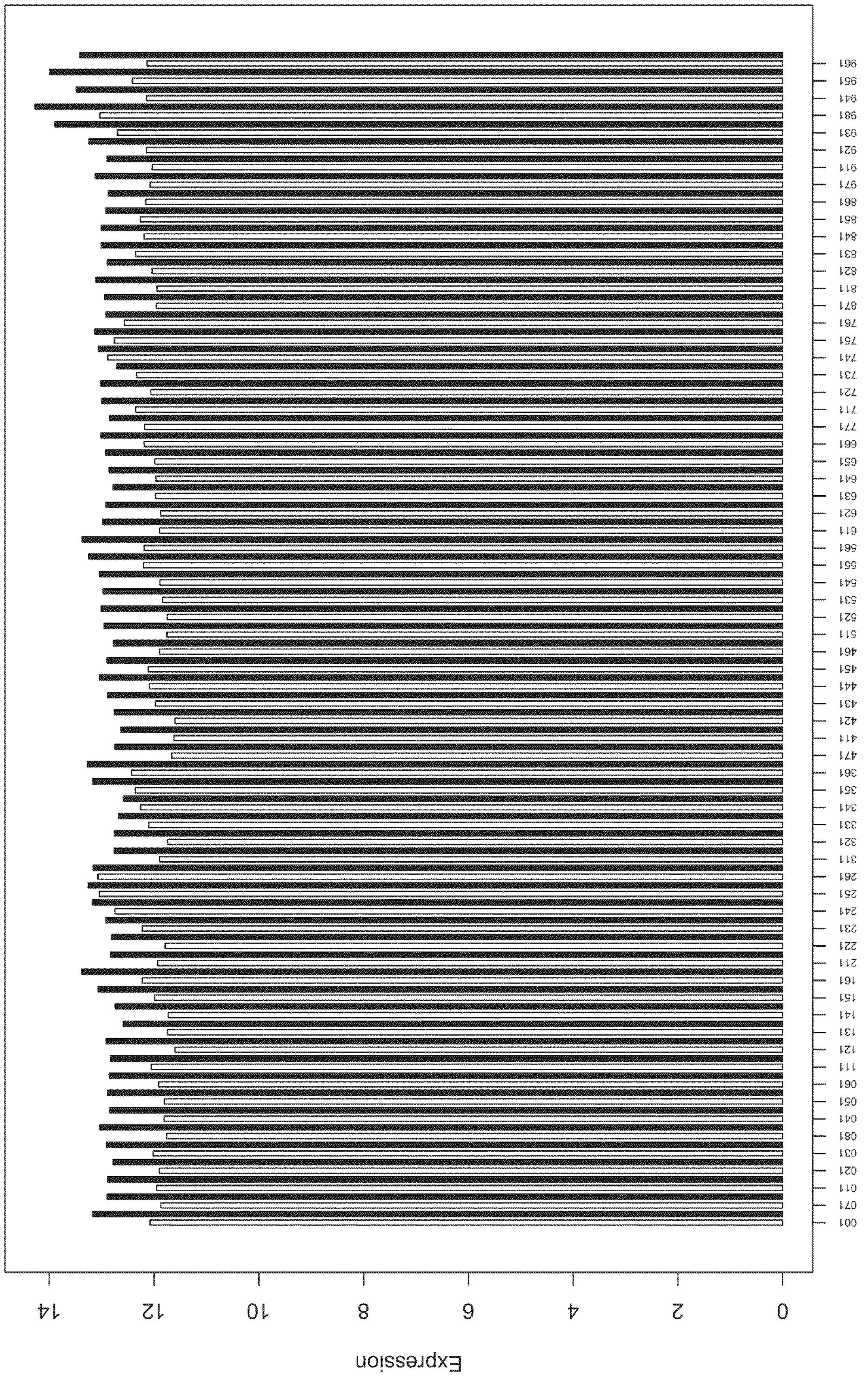

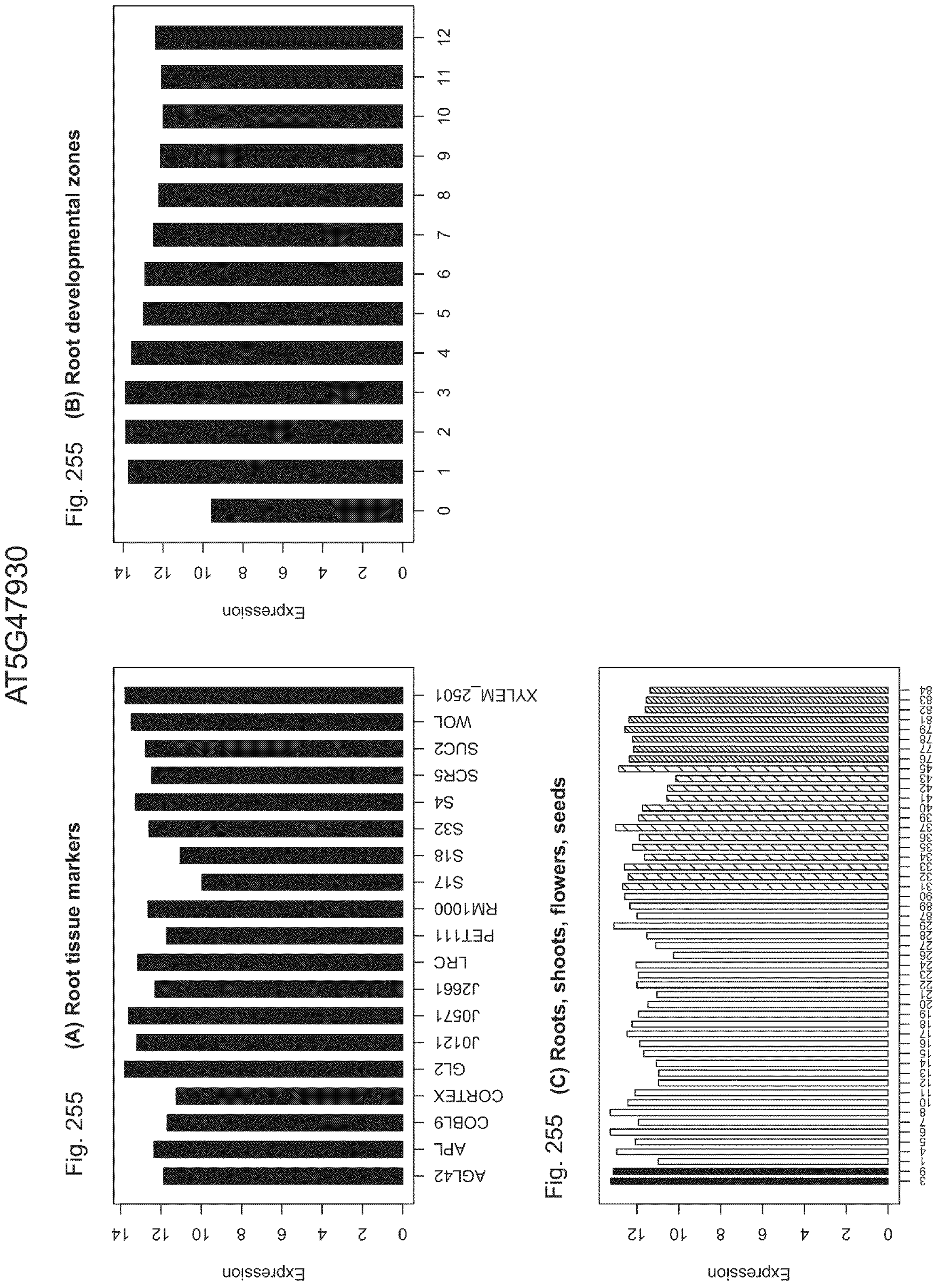
AT5G47930
Fig. 255 (B) Root developmental zones
Expression
0 1 2 3 4 5 6 7 8 9 10 11 12
Fig. 255 (A) Root tissue markers
AGL42
APL
COBL9
CORTEX
GL2
J0121
J0571
J2661
LRC
PET111
RM1000
S17
S18
S32
S4
SCR5
SUC2
WOL
XYLEM_2501
Fig. 255 (C) Roots, shoots, flowers, seeds AT5G47930
Fig. 255 (D) Abiotic stresses
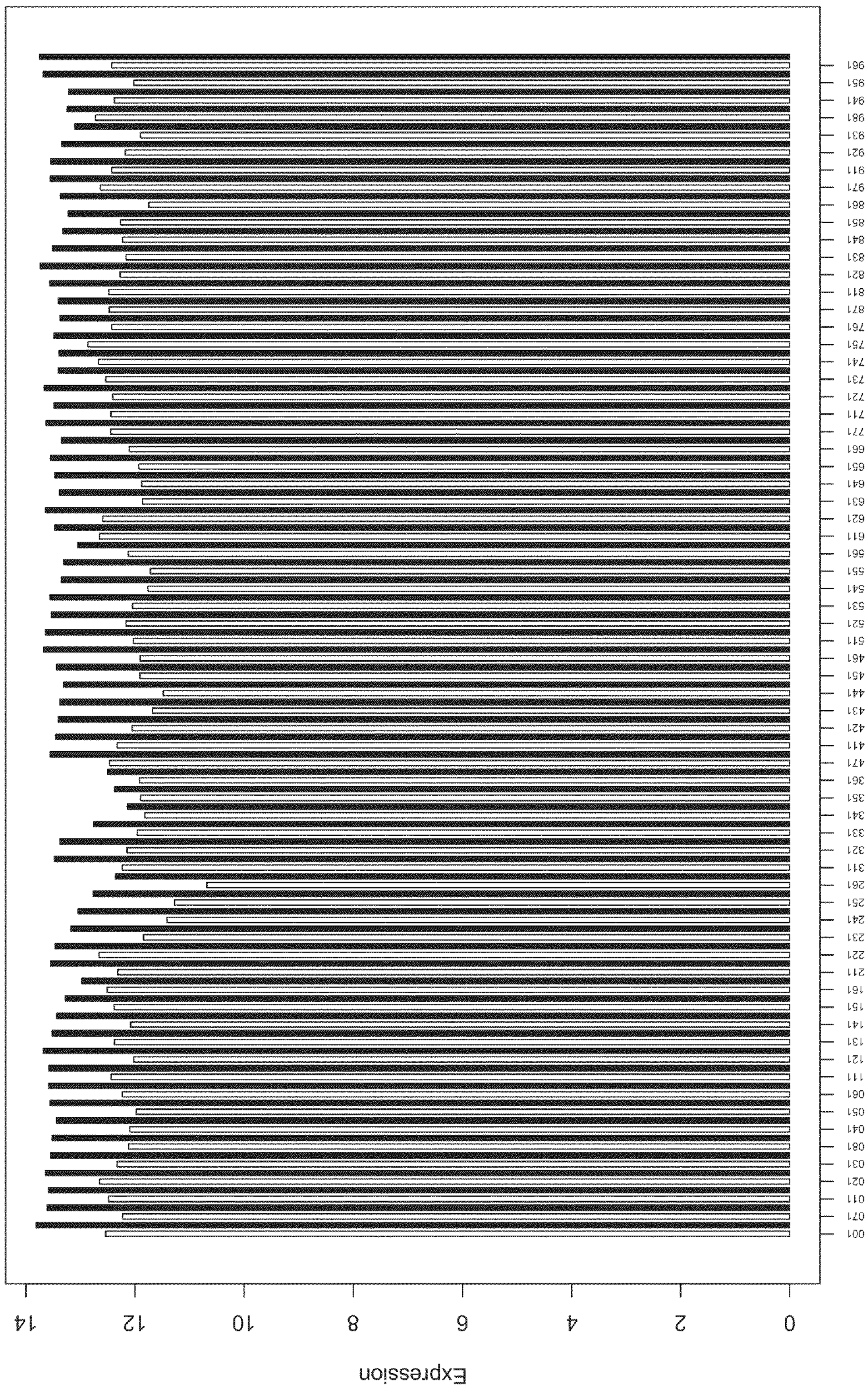

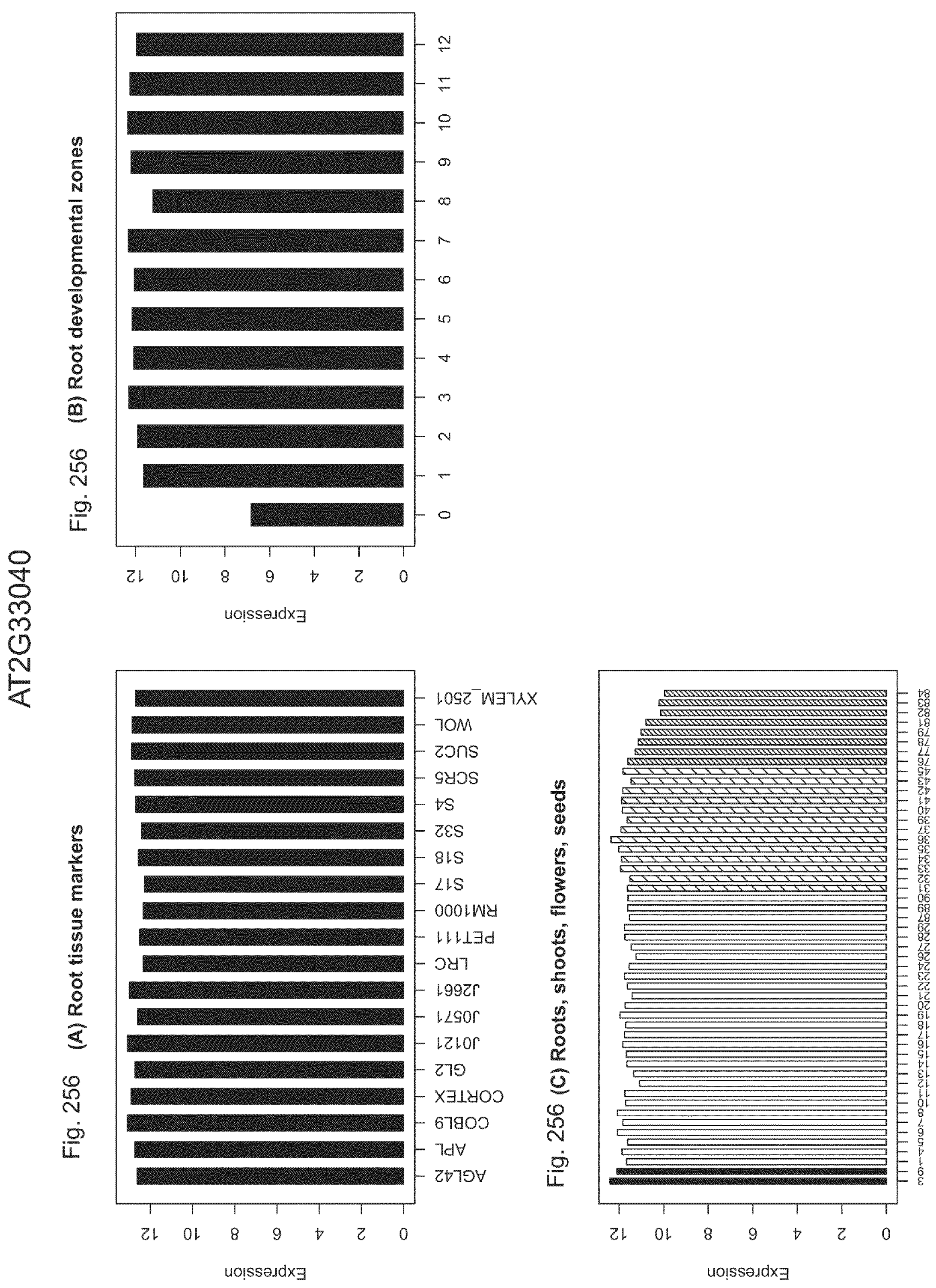
AT2G33040
Fig. 256 (A) Root tissue markers
Expression
0 2 4 6 8 10 12
AGL42 APL COBL9 CORTEX GL2 J0121 J0571 J2661 LRC PET111 RM1000 S17 S18 S32 S4 SCR5 SUC2 WOL XYLEM_2501
Fig. 256 (B) Root developmental zones
Expression
0 2 4 6 8 10 12
0 1 2 3 4 5 6 7 8 9 10 11 12
Fig. 256 (C) Roots, shoots, flowers, seeds
Expression
0 2 4 6 8 10 12

AT2G33040
Fig. 256 (D) Abiotic stresses
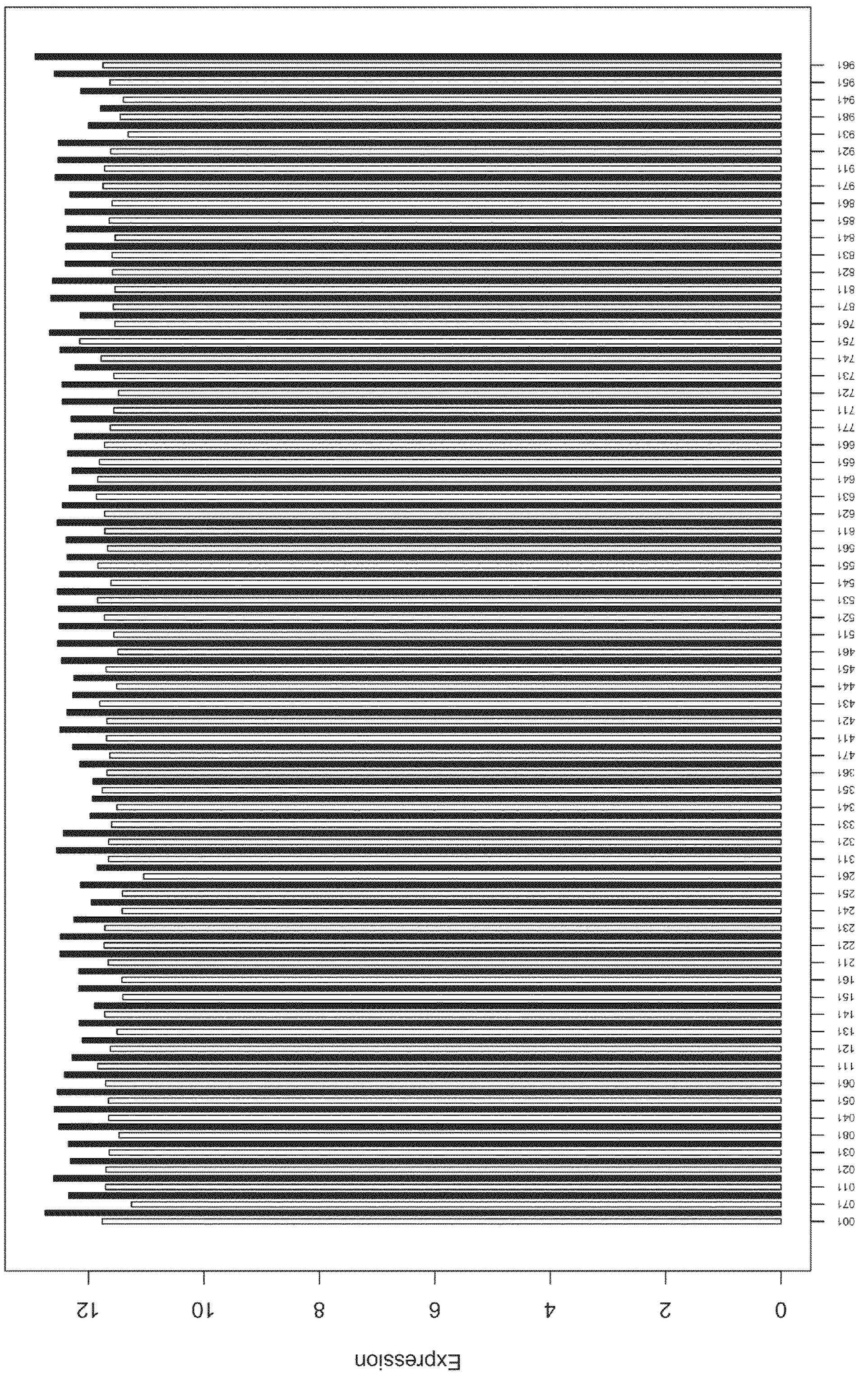

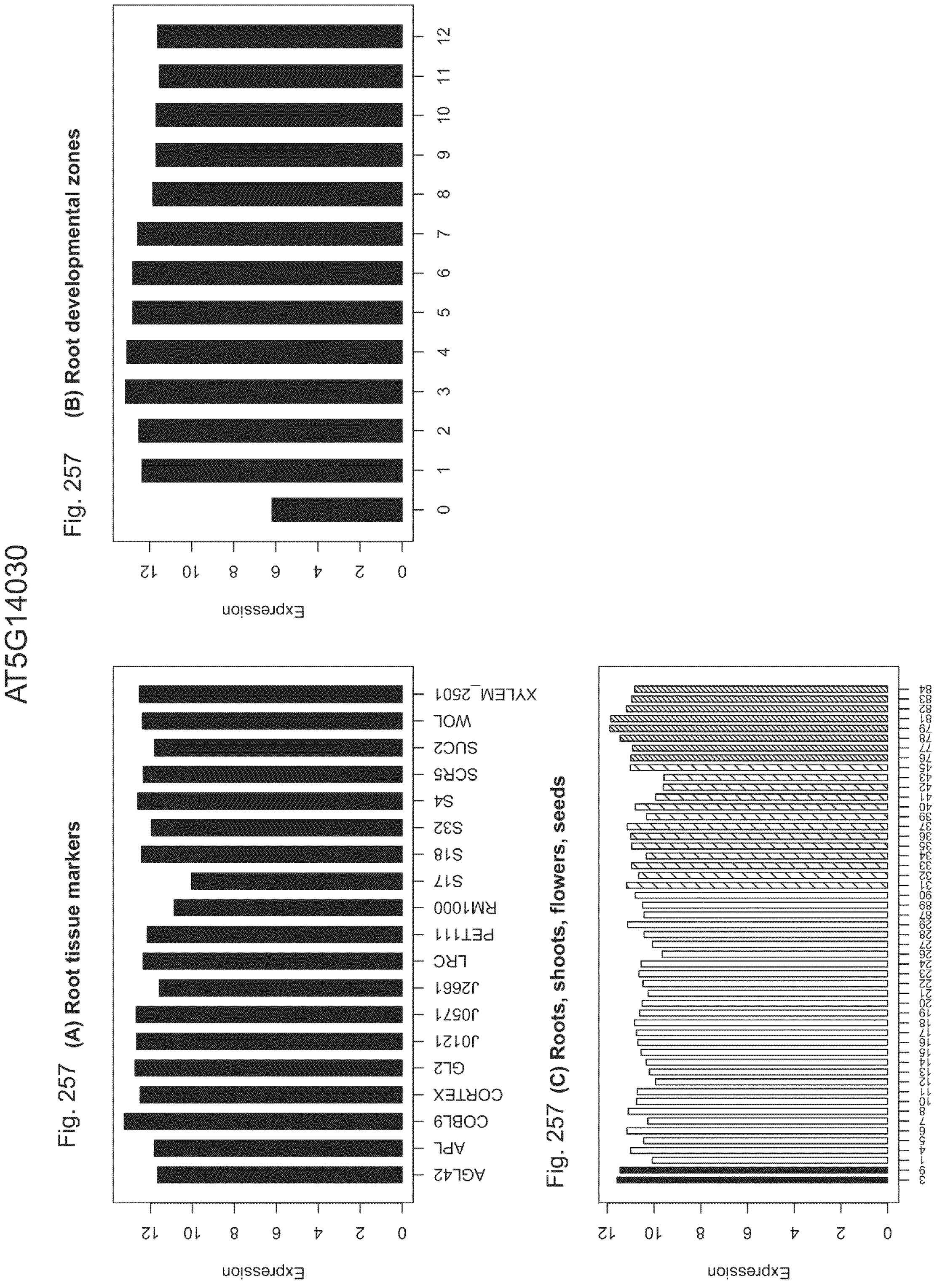
Fig. 257 (A) Root tissue markers
Fig. 257 (B) Root developmental zones
Fig. 257 (C) Roots, shoots, flowers, seeds AT5G14030
Fig. 257 (D) Abiotic stresses
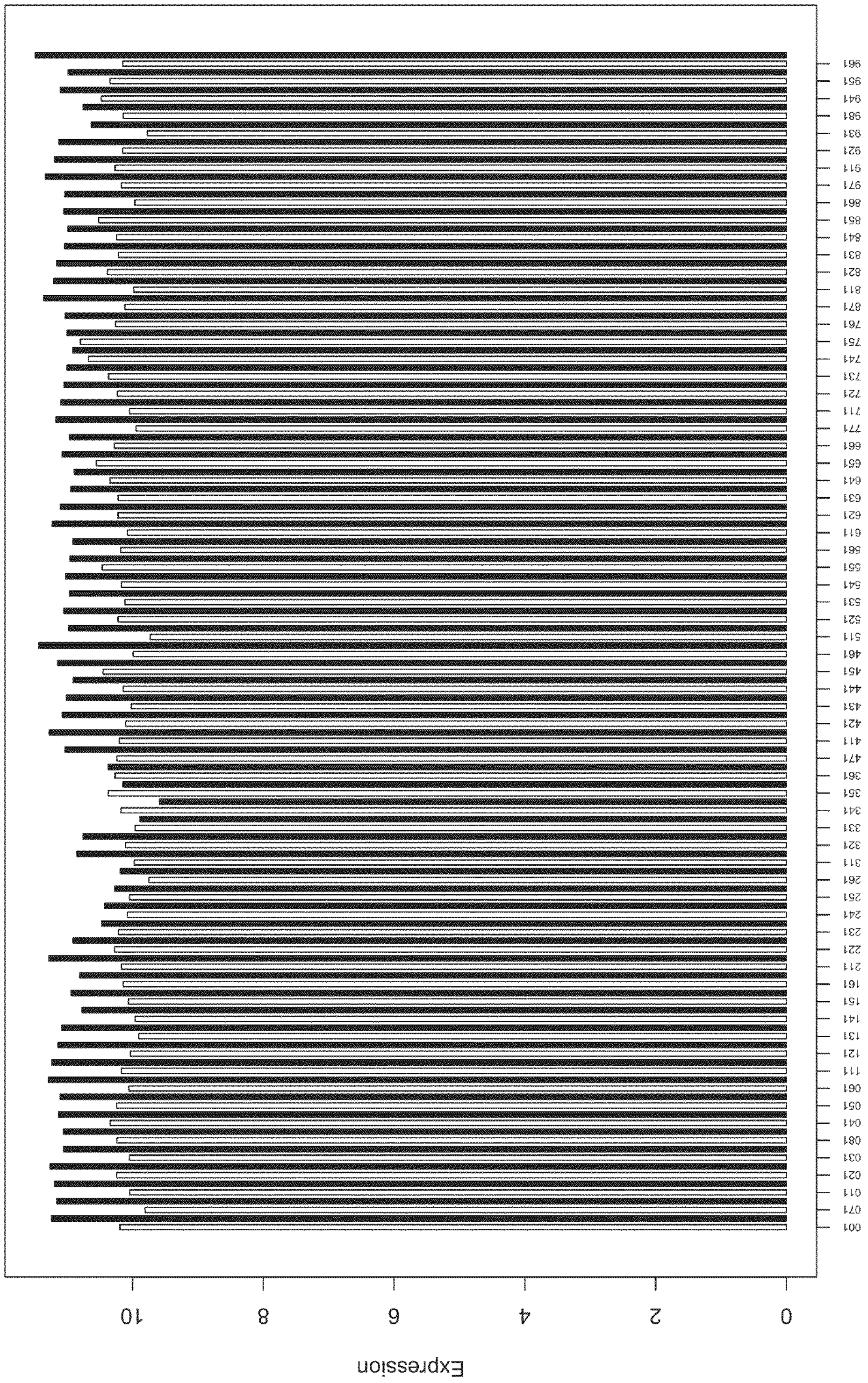

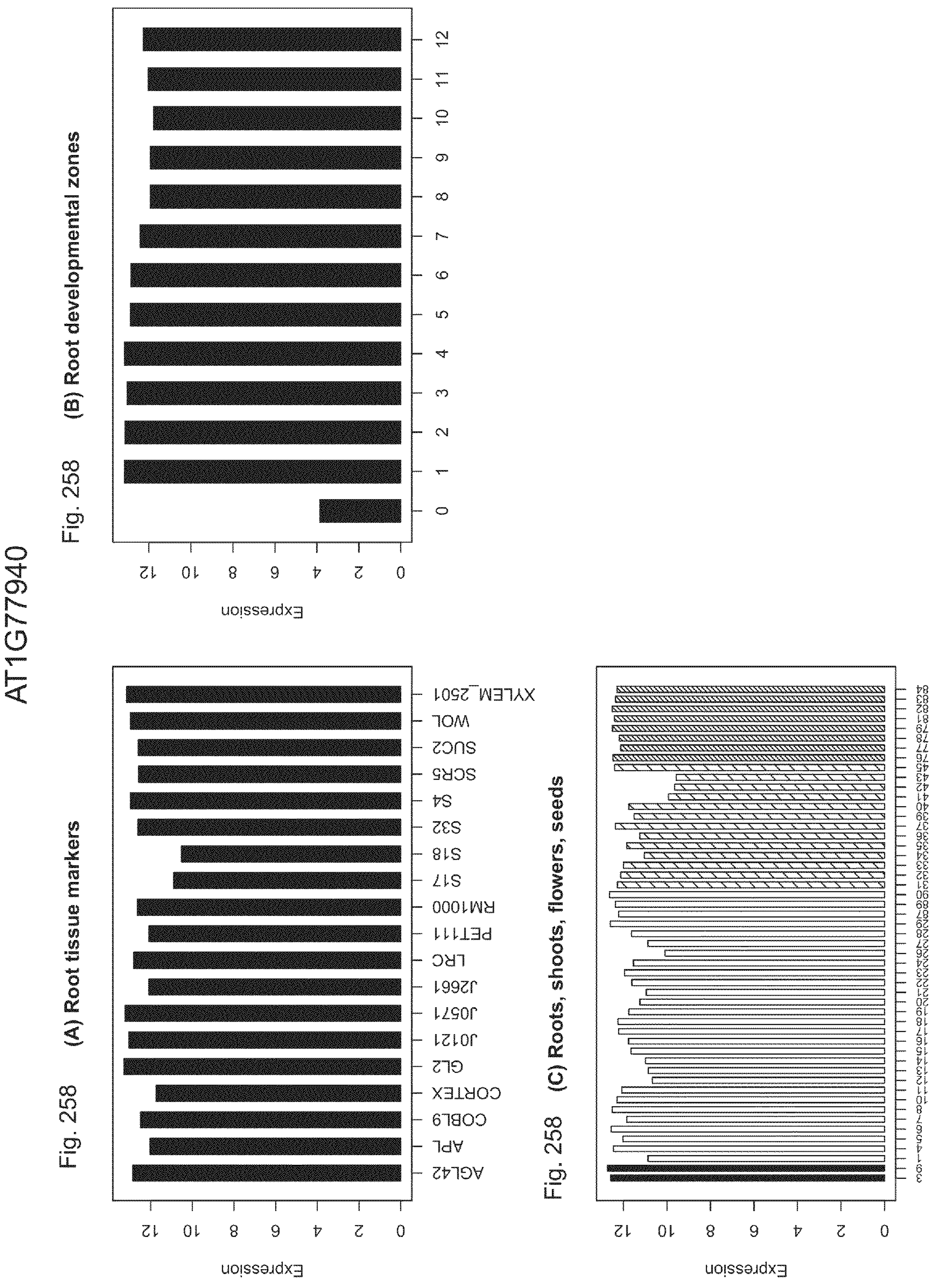
AT1G77940
Fig. 258 (A) Root tissue markers
AGL42
APL
COBL9
CORTEX
GL2
J0121
J0571
J2661
LRC
PET111
RM1000
S17
S18
S32
S4
SCR5
SUC2
WOL
XYLEM_2501
Expression
0
2
4
6
8
10
12
Fig. 258 (B) Root developmental zones
0
1
2
3
4
5
6
7
8
9
10
11
12
Expression
Fig. 258 (C) Roots, shoots, flowers, seeds
Expression AT1G77940
Fig. 258 (D) Abiotic stresses
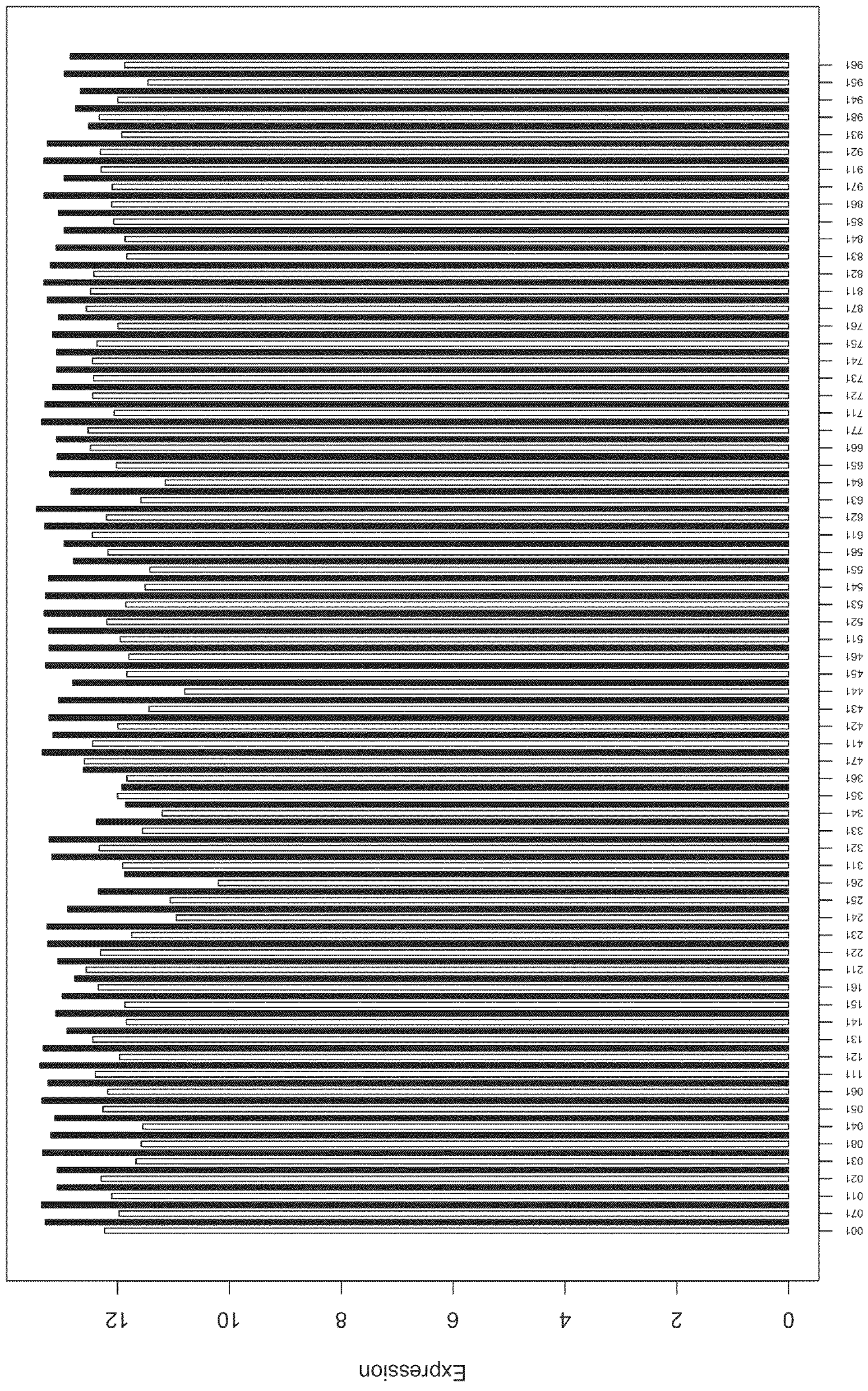

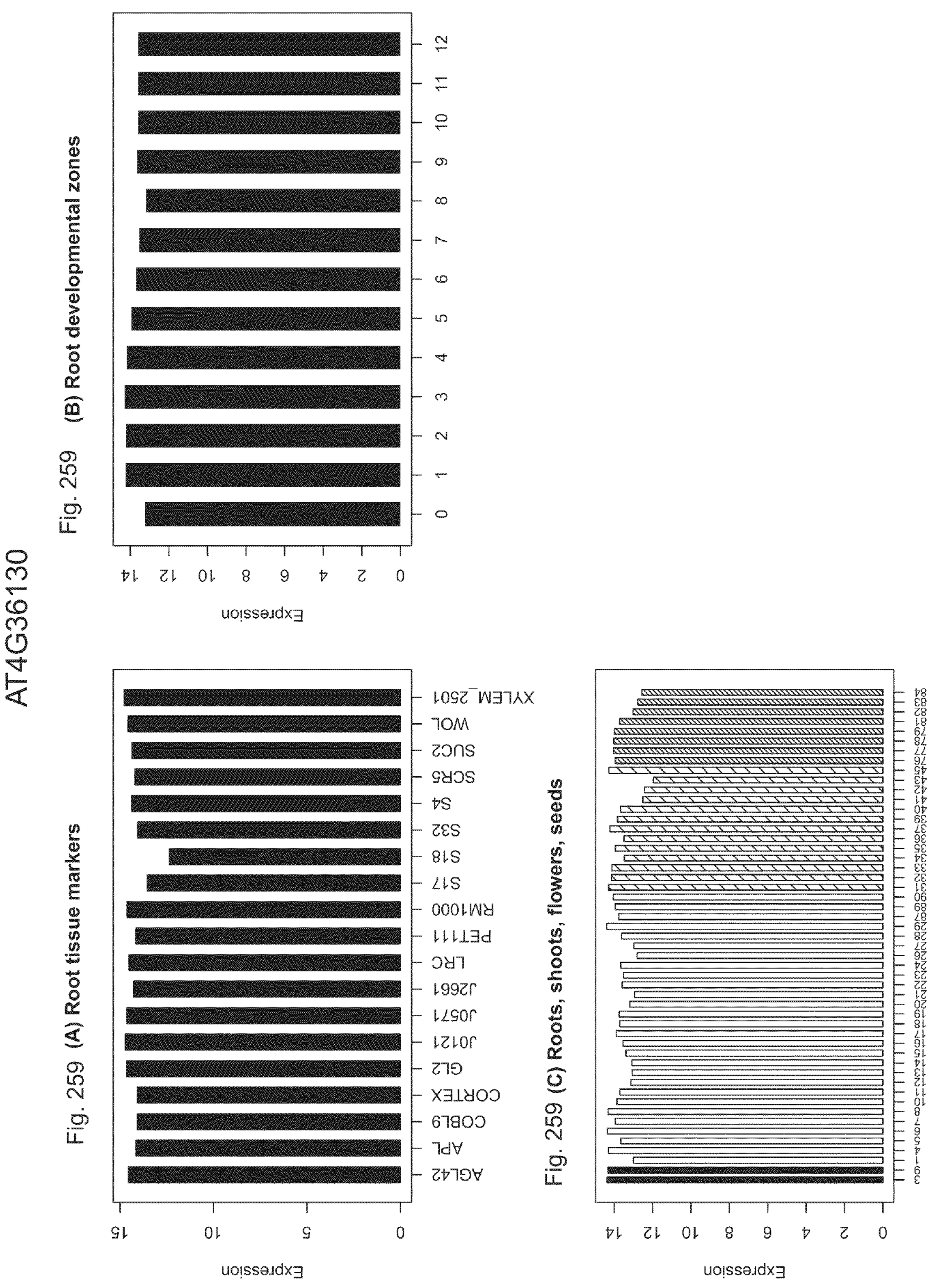
Fig. 259 (A) Root tissue markers
Fig. 259 (B) Root developmental zones
Fig. 259 (C) Roots, shoots, flowers, seeds AT4G36130
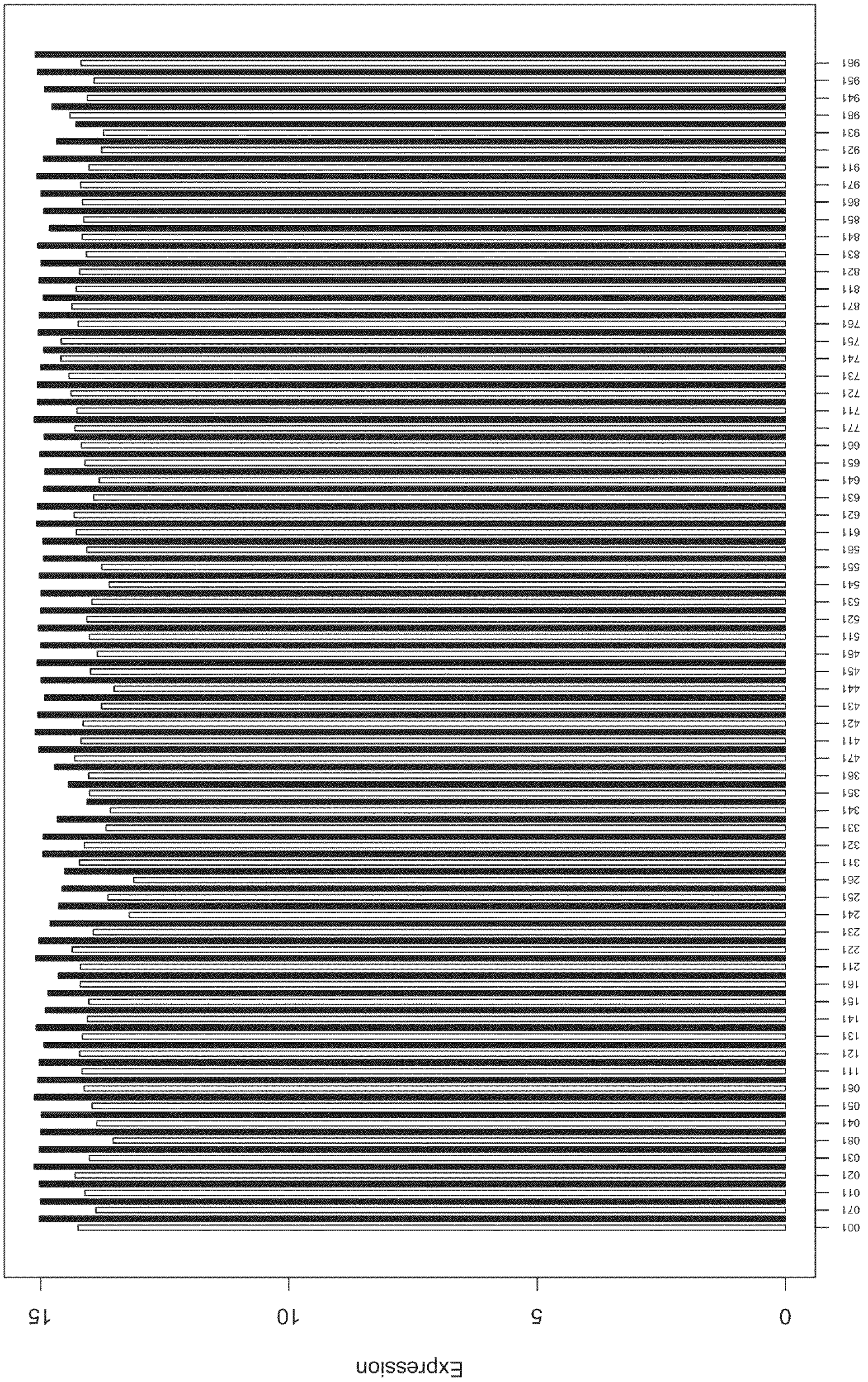
Fig. 259 (D) Abiotic stresses

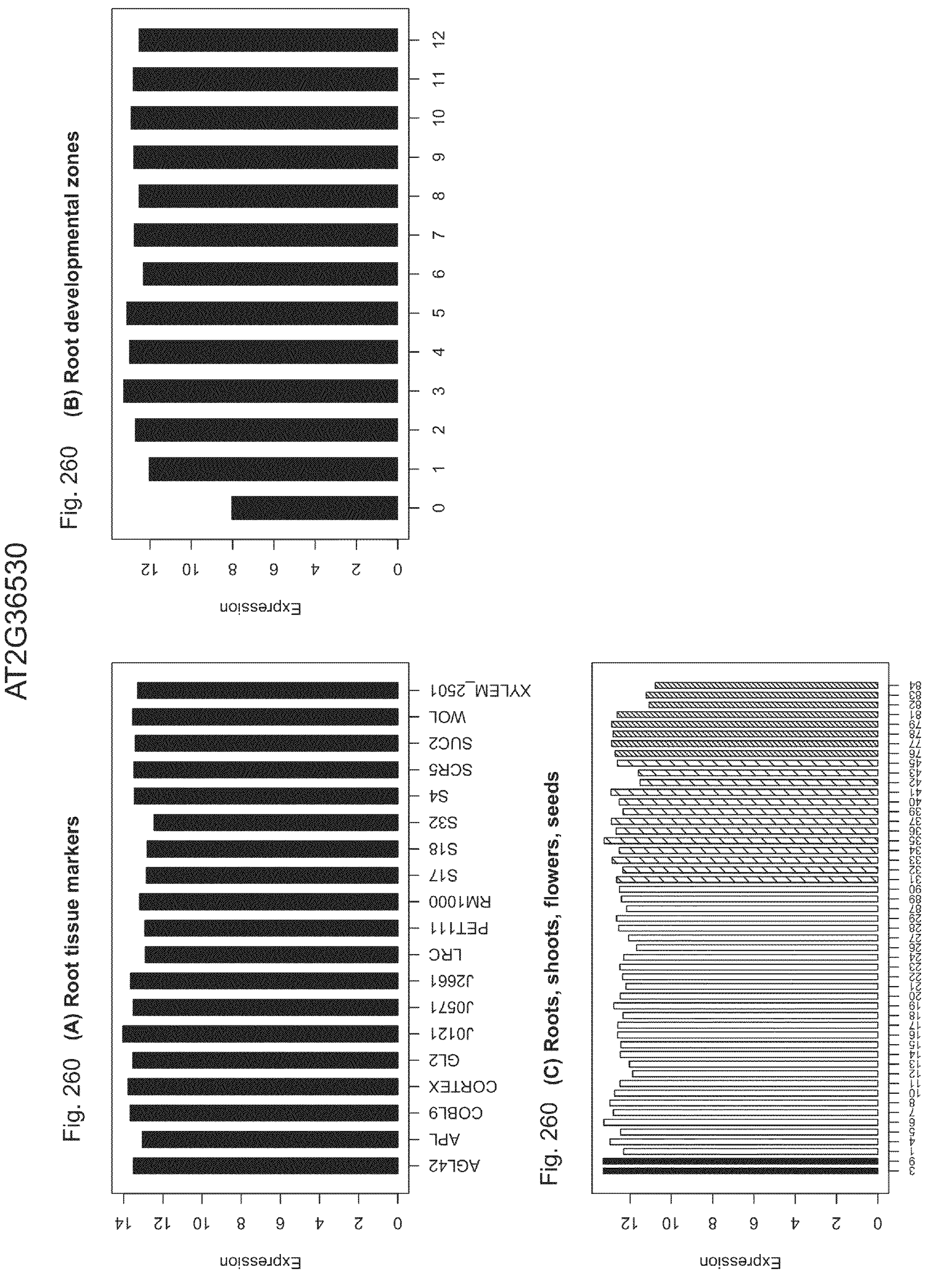
AT2G36530
Fig. 260 (A) Root tissue markers
AGL42
APL
COBL9
CORTEX
GL2
J0121
J0571
J2661
LRC
PET111
RM1000
S17
S18
S32
S4
SCR5
SUC2
WOL
XYLEM_2501
Expression
0
2
4
6
8
10
12
14
Fig. 260 (B) Root developmental zones
0
1
2
3
4
5
6
7
8
9
10
11
12
Fig. 260 (C) Roots, shoots, flowers, seeds Fig. 260 AT2G36530
(D) Abiotic stresses
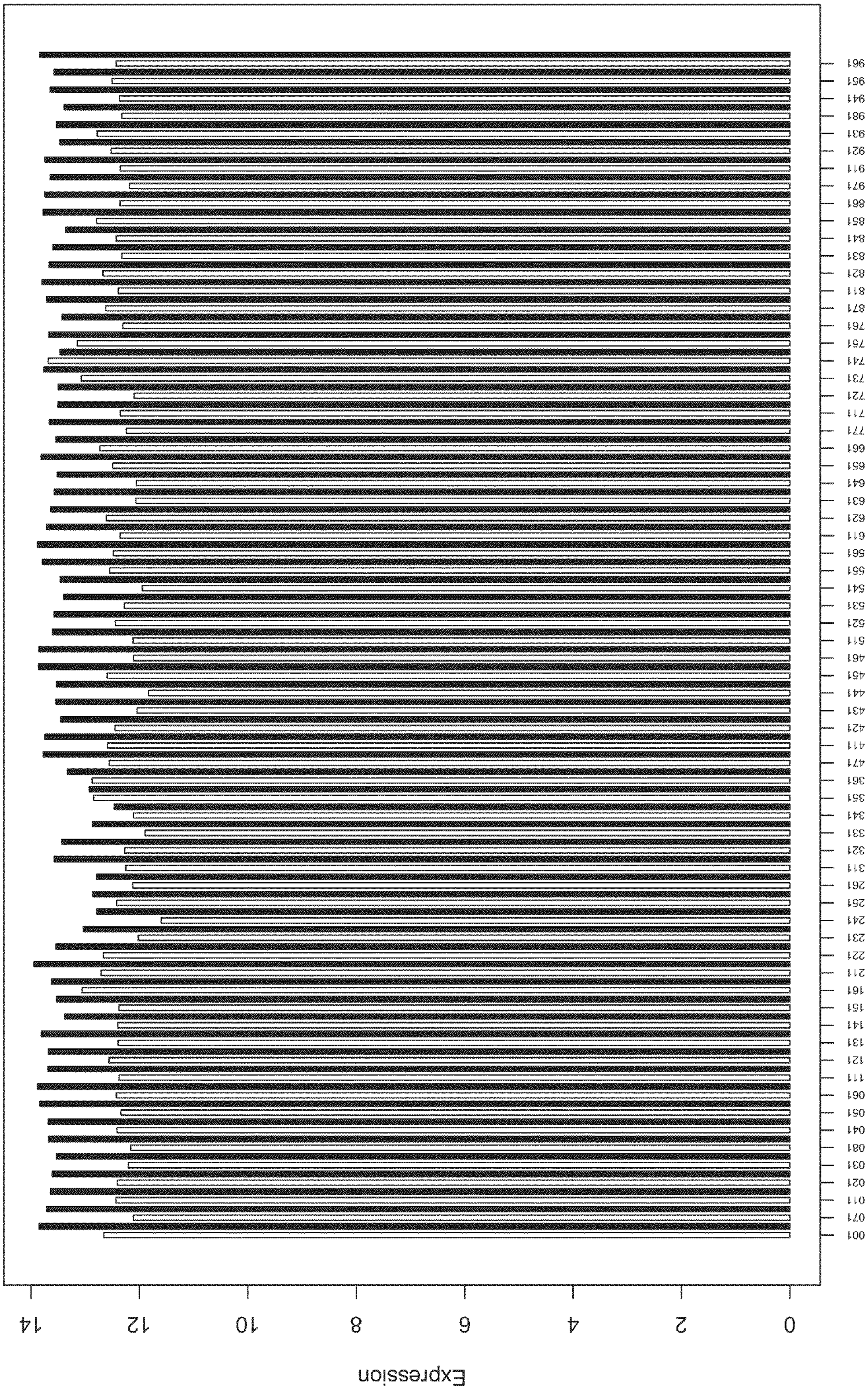

AT5G15200
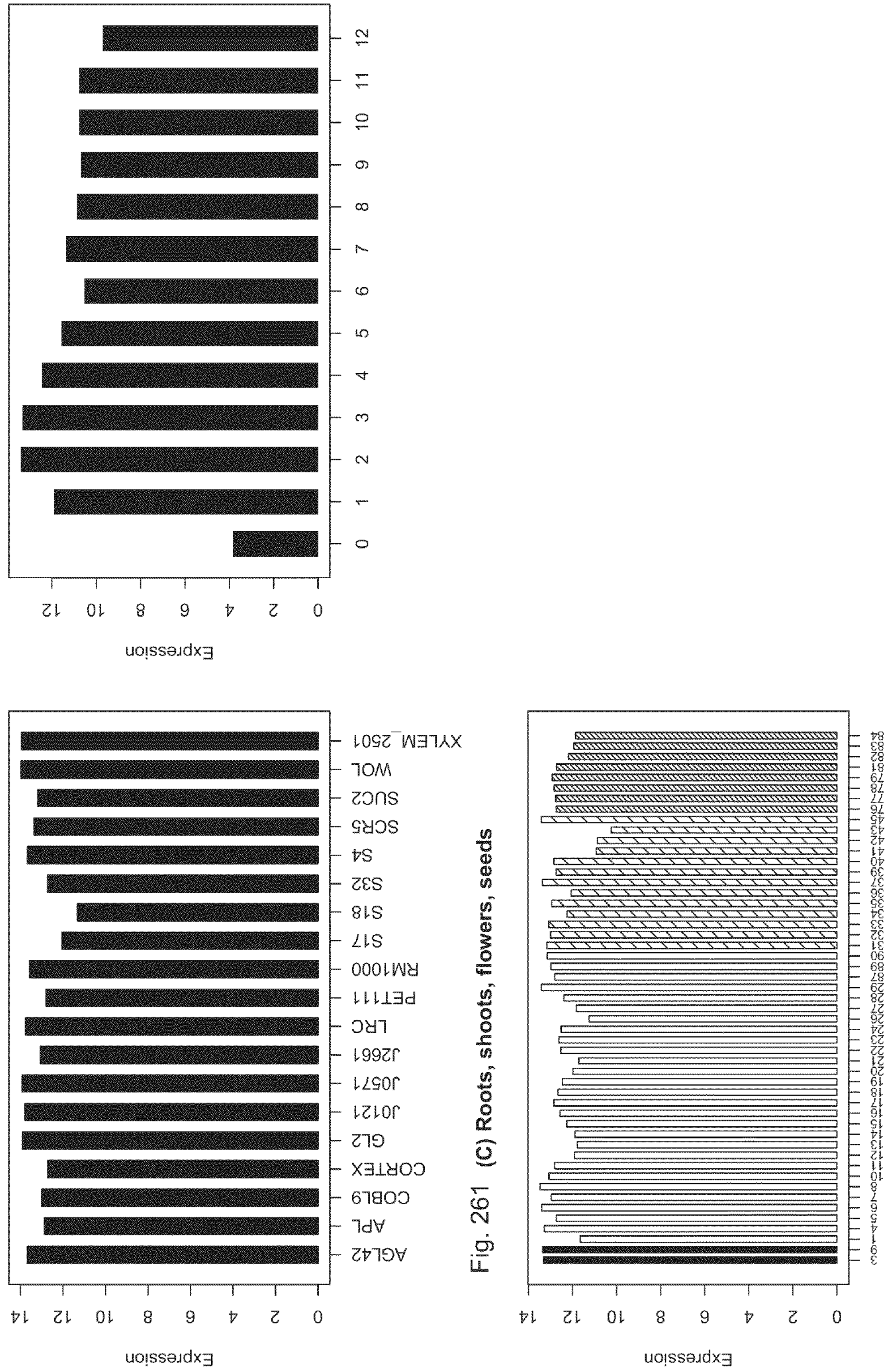
Fig. 261 (A) Root tissue markers
Fig. 261(B) Root developmental zones
Fig. 261 (C) Roots, shoots, flowers, seeds AT5G15200
Fig. 261 (D) Abiotic stresses
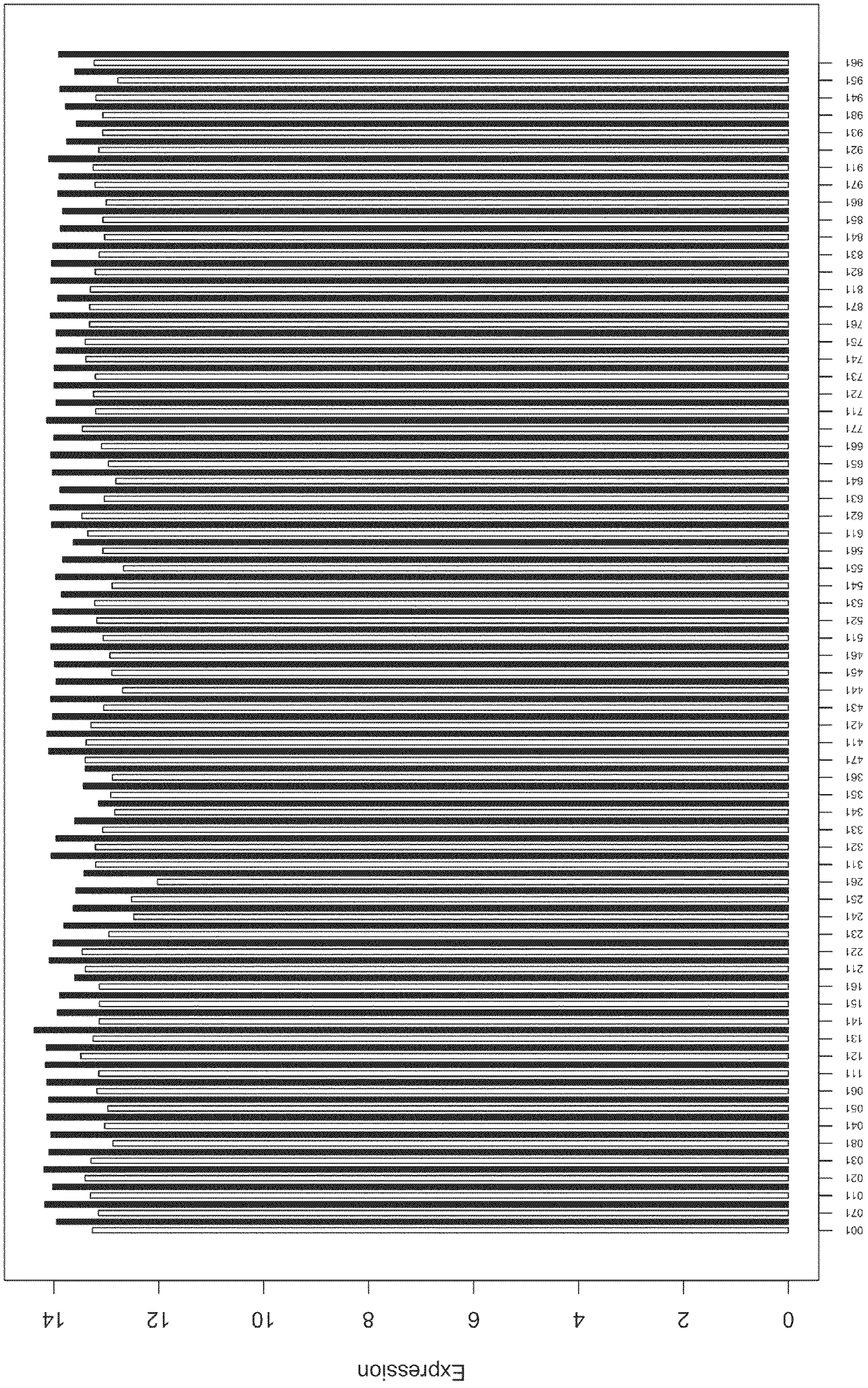

Os04g35300

Os04g35300

Os05g45950

Os05g47980

Os01g46610

Os02g52290

Os05g01820

Os05g01820

Os07g46750

Os07g02210

Os12g07010

Os09g08430

Os08g03290

Os10g22590

Os03g45280

Os03g45280

Os07g30970

Os09g33500

Os11g38959

Os11g38959

Os10g08550

Os04g32710

Os04g30730

Os05g11780

Os05g11780

Os01g17190

Os10g17280

Os11g06890

Os01g16890

Os03g58430

Os06g37440

Os02g27769

Os04g47220

Os05g07700

Os05g07700

Os05g07700

Os12g38000

Os02g27760

Os03g05730

Os05g01262

Os07g46670

Os07g46670

Os05g01560

Os03g58204

Os03g58204

Os01g62420

Os01g14580

Os09g01640

Os07g10720

Os07g12650

Os08g38900

Os12g05430

Os12g04924

Os01g73990

Os11g04880

Os11g04880

Os02g34510

Os02g44630

Figure 328A (SEQ ID NO: 213), AT4G05320 (UBQ10)

gttttgtgtatcattcttgttacattgttattaatgaaaaaatattattggtcattggactgaaca
cgagtgttaaatatggaccaggccccaaataagatccattgatatatgaattaaataacaagaata
aatcgagtcaccaaaccacttgcctttttttaacgagacttgttcaccaacttgatacaaaagtcat
tatcctatgcaaatcaataatcatacaaaaatatccaataacactaaaaaattaaaagaaatggat
aatttcacaatatgttatacgataaagaagttacttttccaagaaattcactgattttataagccc
acttgcattagataaatggcaaaaaaaaacaaaaaggaaaagaaataaagcacgaagaattctaga
aaatacgaaatacgcttcaatgcagtgggacccacggttcaattattgccaattttcagctccacc
gtatatttaaaaaataaaacgataatgctaaaaaaatataaatcgtaacgatcgttaaatctcaac
ggctggatcttatgacgaccgttagaaattgtggttgtcgacgagtcagtaataaacggcgtcaaa
gtggttgcagccggcacacacgagtcgtgtttatcaactcaaagcacaaatacttttcctcaacct
aaaaataaggcaattagccaaaaacaactttgcgtgtaaacaacgctcaatacacgtgtcattta
ttattagctattgcttcaccgccttagctttctcgtgacctagtcgtcctcgtcttttcttcttct
tcttctataaaacaataccCaaagagctcttcttcttcacaattcagatttcaatttctcaaaatc
ttaaaaactttctctcaattctctctaccgtgatcaaggtaaatttctgtgttccttattctctca
aaatcttcgattttgttttcgttcgatcccaatttcgtatatgttctttggtttagattctgttaa
tcttagatcgaagacgattttctgggtttgatcgttagatatcatcttaattctcgattagggttt
catagatatcatccgatttgttcaaataatttgagttttgtcgaataattactcttcgatttgtga
tttctatctagatctggtgttagtttctagtttgtgcgatcgaatttgtcgattaatctgagtttt
tctgattaacag*gt*

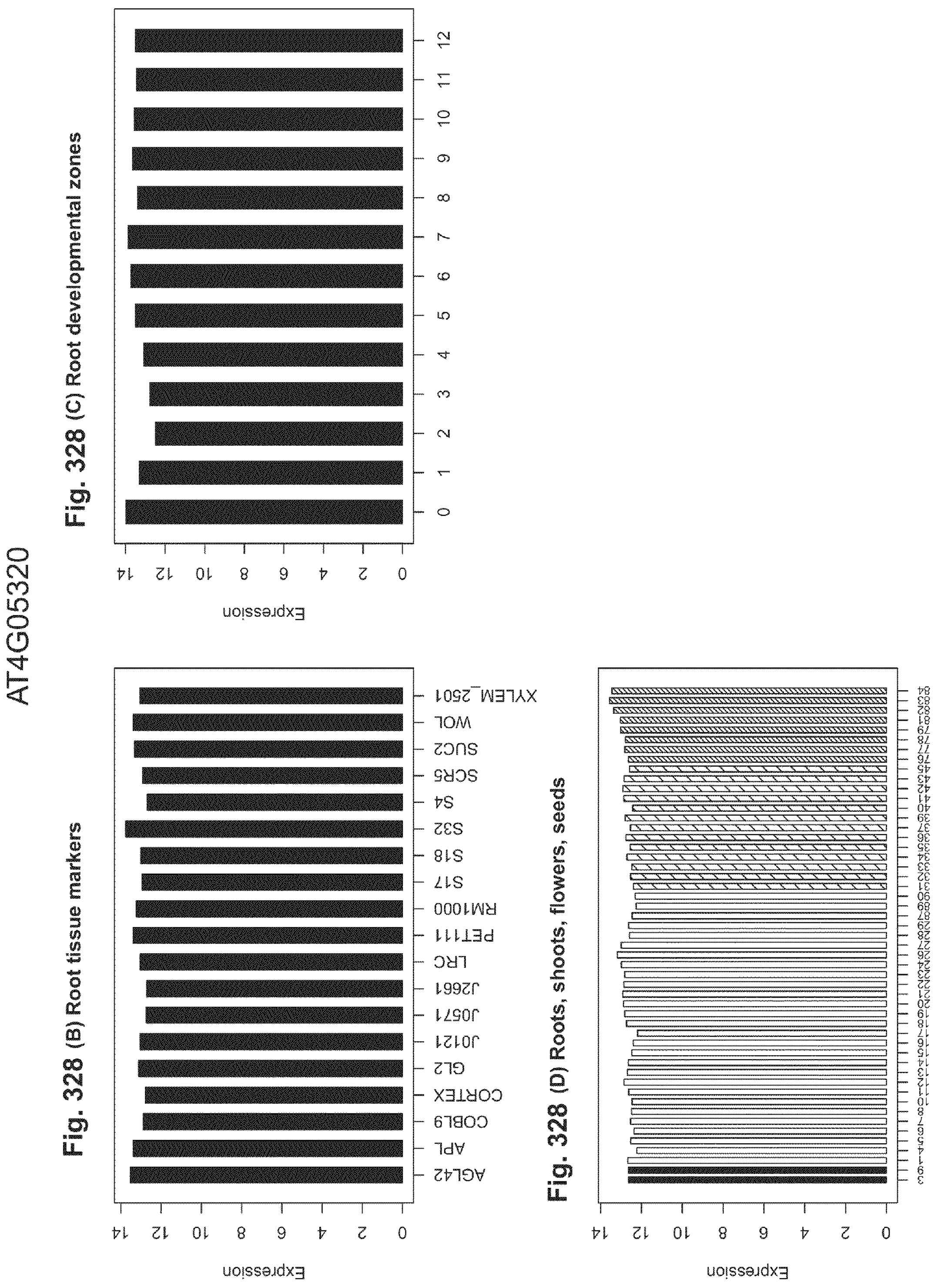
Fig. 328 (C) Root developmental zones
Fig. 328 (B) Root tissue markers
Fig. 328 (D) Roots, shoots, flowers, seeds AT4G05320
Fig. 328 (E) Abiotic stresses
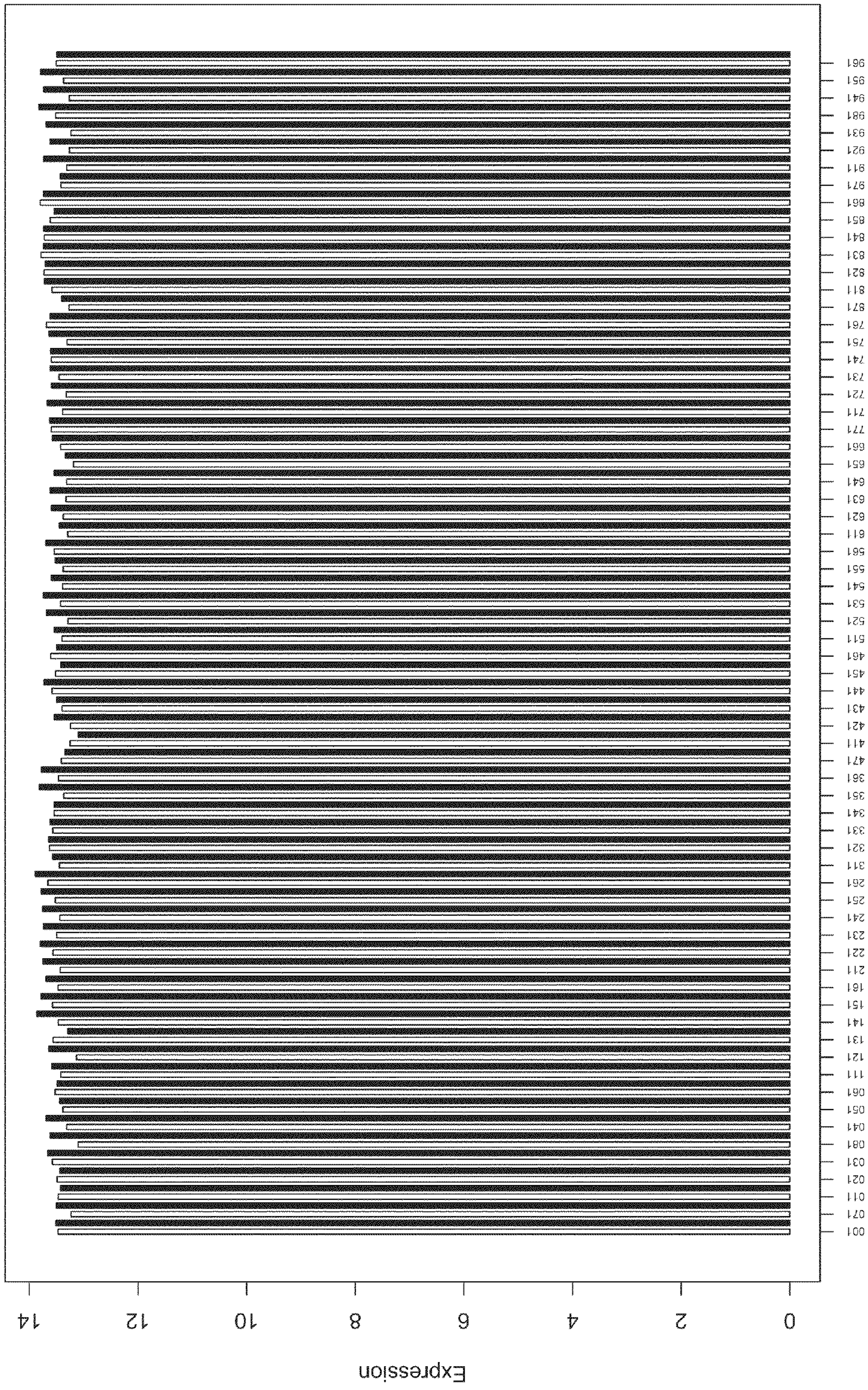

Construct A GFP Expression Index
in maturation zone
Maturation Zone
Control @ 0 hrs
Control @ 24 hrs
High Salt @ 0 hrs
High Salt @ 24 hrs
Low Nitrogen @ 0 hrs
Low Nitrogen @ 24 hrs
Low pH @ 0 hrs
Low pH @ 24 hrs
GFP Index
0
0.1
0.2
0.3
0.4
0.5
0.6
0.7
0.8
0.9
1
Epidermis
Cortex
Endodermis
Stele

REGULATORY POLYNUCLEOTIDES AND USES THEREOF

This application is a continuation application of PCT/US2010/61793 filed Dec. 22, 2010, which claims the benefit of U.S. Provisional Patent Application No. 61/289,771 filed Dec. 23, 2009; U.S. Provisional Patent Application No. 61/298,765 filed Jan. 27, 2010; U.S. Provisional Patent Application No. 61/299,053 filed Jan. 28, 2010; and U.S. Provisional Patent Application No. 61/385,243 filed Sep. 22, 2010; the entire contents of these applications are hereby incorporated herein by reference.

FIELD

The present invention relates to polynucleotide molecules for regulating expression of transcribable polynucleotides in cells (including plant tissues and plants) and uses thereof.

BACKGROUND

The development of transgenic plants having agronomically desirable characteristics often depends on the ability to control the spatial and temporal expression of the polynucleotide responsible for the desired trait. The control of the expression is largely dependent on the availability and use of regulatory control sequences that are responsible for the expression of the operably linked polynucleotide. Where expression in specific tissues or organs is desired, tissue-preferred regulatory elements may be used. Where expression in response to a stimulus is desired, inducible regulatory polynucleotides are the regulatory element of choice. In contrast, where continuous expression is desired throughout the cells of a plant, constitutive regulatory polynucleotides are utilized.

The proper regulatory elements typically must be present and be in the proper location with respect to the polynucleotide in order to obtain expression of the newly inserted transcribable polynucleotide in the plant cell. These regulatory elements may include a promoter region, various cis-elements, regulatory introns, a 5' non-translated leader sequence and a 3' transcription termination/polyadenylation sequence.

Since the patterns of expression of transcribable polynucleotides introduced into a plant are controlled using regulatory elements, there is an ongoing interest in the isolation and identification of novel regulatory elements which are capable of controlling expression of such transcribable polynucleotides.

SUMMARY

In one aspect, an isolated regulatory polynucleotide is provided that comprises a polynucleotide molecule selected from the group consisting of: (a) a polynucleotide molecule comprising a nucleic acid molecule having a sequence selected from the group consisting of SEQ ID NOS: 1-212 that is capable of regulating transcription of an operably linked transcribable polynucleotide molecule; (b) a polynucleotide molecule having at least about 70% sequence identity to a sequence selected from the group consisting of SEQ ID NOS:1-212 that is capable of regulating transcription of an operably linked transcribable polynucleotide molecule; and (c) a fragment of the polynucleotide molecule of (a) or (b) capable of regulating transcription of an operably linked transcribable polynucleotide molecule. In some aspects, the isolated regulatory polynucleotide is capable of regulating constitutive transcription. The isolated regulatory polynucleotide may comprise an intron.

In another aspect, a recombinant polynucleotide construct is provided comprising a regulatory polynucleotide described herein operably linked to a heterologous transcribable polynucleotide molecule. The transcribable polynucleotide molecule may encode a protein of agronomic interest.

In other aspects, such a recombinant polynucleotide construct is used to provide a transgenic host cell comprising the recombinant polynucleotide construct and to provide a transgenic plant stably transformed with the recombinant polynucleotide construct. Seed produced by such transgenic plants are also provided.

In a further aspect, a chimeric polynucleotide molecule is provided that comprises:

(1) a first polynucleotide molecule selected from the group consisting of (a) a polynucleotide molecule comprising a nucleic acid molecule having a sequence selected from the group consisting of SEQ ID NOS: 1-212 that is capable of regulating transcription of an operably linked transcribable polynucleotide molecule;

(b) a polynucleotide molecule having at least about 70% sequence identity to a sequence selected from the group consisting of SEQ ID NOS:1-212 that is capable of regulating transcription of an operably linked transcribable polynucleotide molecule; and (c) a fragment of the polynucleotide molecule of (a) or (b) capable of regulating transcription of an operably linked transcribable polynucleotide molecule, and (2) a second polynucleotide molecule capable of regulating transcription of an operably linked polynucleotide molecule, wherein the first polynucleotide molecule is operably linked to the second polynucleotide molecule.

In yet a further aspect, an isolated polynucleotide molecule is provided that comprises a regulatory element derived from SEQ ID NOS: 1-212, wherein the regulatory element is capable of regulating transcription of an operably linked transcribable polynucleotide molecule.

In another aspect, a method of directing expression of a transcribable polynucleotide molecule in a host cell is provided that comprises:

(a) introducing the recombinant nucleic acid construct described herein into a host cell to produce a transgenic host cell; and (b) selecting a transgenic host cell exhibiting expression of the transcribable polynucleotide molecule.

In a further aspect, a method of directing expression of a transcribable polynucleotide molecule in a plant is provided that comprises:

(a) introducing the recombinant nucleic acid construct described herein into a plant cell;

(b) regenerating a plant from the plant cell; and (c) selecting a transgenic plant exhibiting expression of the transcribable polynucleotide molecule.

BRIEF DESCRIPTION OF THE DRAWINGS

FIGS. 1-86 each provide the nucleotide sequence of a regulatory polynucleotide corresponding to the *Arabidopsis* gene having the accession number specified in the Figure. Where the regulatory polynucleotide has been modified to include the first intron from the coding sequence of the specified gene attached at the 3' end of the 5' UTR, the Figure indicates the gene accession number followed by the indicia "+intron". The nucleic acid sequences are annotated to indicate one transcription start site capital letter in bold the endogenous 5'-UTR intron sequences (double underlining), the first intron from the coding sequence (single underlining), and any added intron splice sequences (bold italics).

FIGS. 87-212 each provide the nucleotide sequence of a regulatory polynucleotide of a rice ortholog having the identified accession number specified in the Figure. Where the regulatory polynucleotide has been modified to include the first intron from the coding sequence of the specified gene attached at the 3' end of the 5' UTR, the Figure indicates the gene accession number followed by the indicia "+intron". The nucleic acid sequences are annotated to indicate one transcription start site (capital letter in bold), the endogenous 5'-UTR intron sequences (double underlining), the first intron from the coding sequence (single underlining), and any added intron splice sequences (bold italics).

FIGS. 213-261 provide a schematic representation of the endogenous expression data for the *Arabidopsis* gene having the specified accession number (corresponding to FIGS. 1-86). Panels (A) provide the expression values of the gene in different cell types which were sorted on the basis of expressing the indicated GFP markers. Panels (B) provide the expression values of the gene from root sections along the longitudinal axis of the root. Panels (C) provide the developmental specific expression of the gene. Panels (D) provide the expression of the gene in response to various abiotic stresses.

FIG. 328 provides the nucleotide sequence and expression data of the *Arabidopsis* regulatory polynucleotide having gene Accession No. AT4G05320 (UBQ10). Panel (A) shows the nucleotide sequence indicating the endogenous 5'-UTR intron sequences (double underlining) and an added intron splice sequence (bold italics). Panel (B) provides the expression values of this gene in different cell types which were sorted on the basis of expressing the indicated GFP markers. Panel (C) provides the expression values of this gene from root sections along the longitudinal axis of the root. Panel (D) provides the developmental specific expression of AT4G05320. Panel (E) provides the expression of AT4G05320 in response to various abiotic stresses.

DETAILED DESCRIPTION

Figure 220:
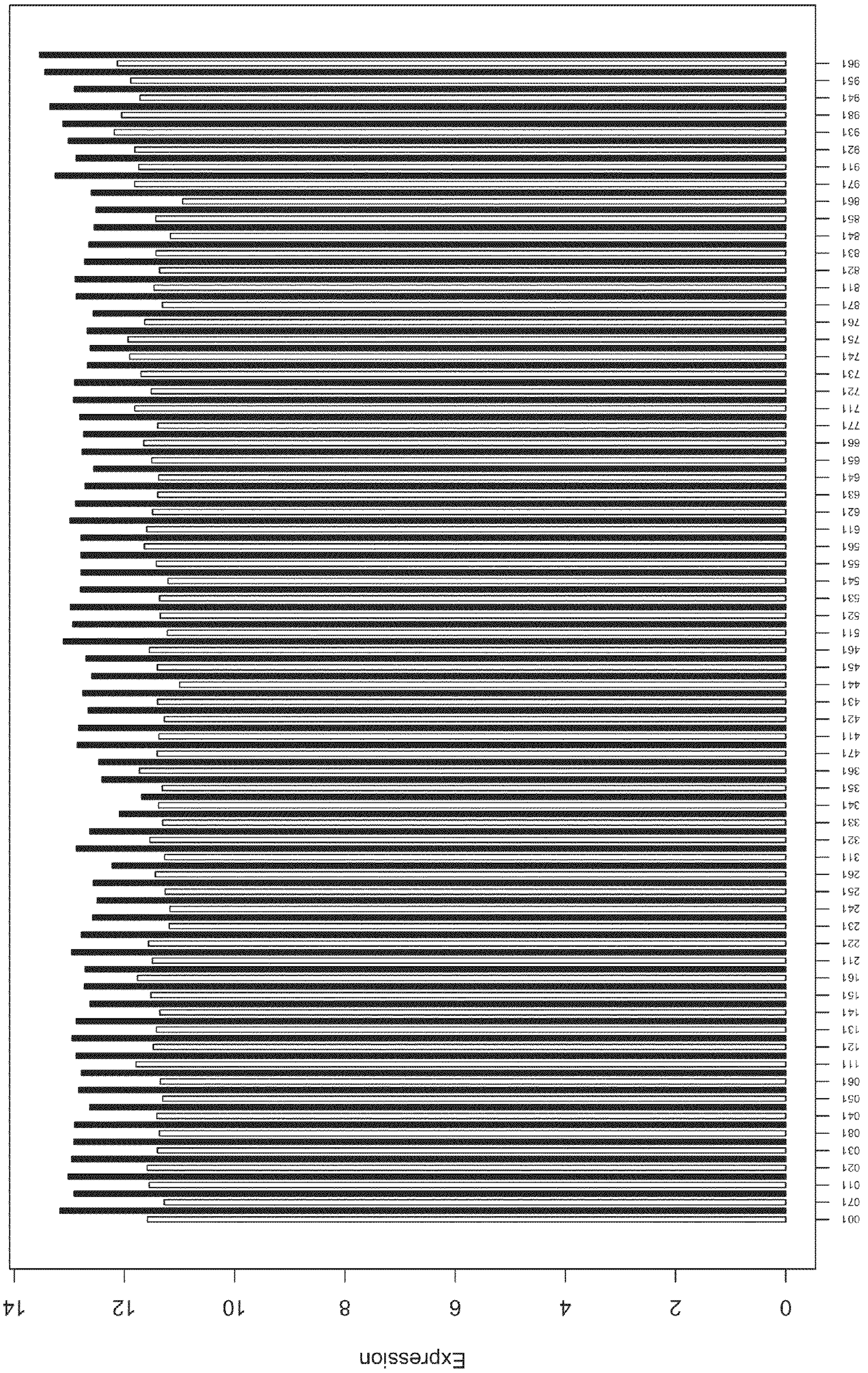
Figure 224:
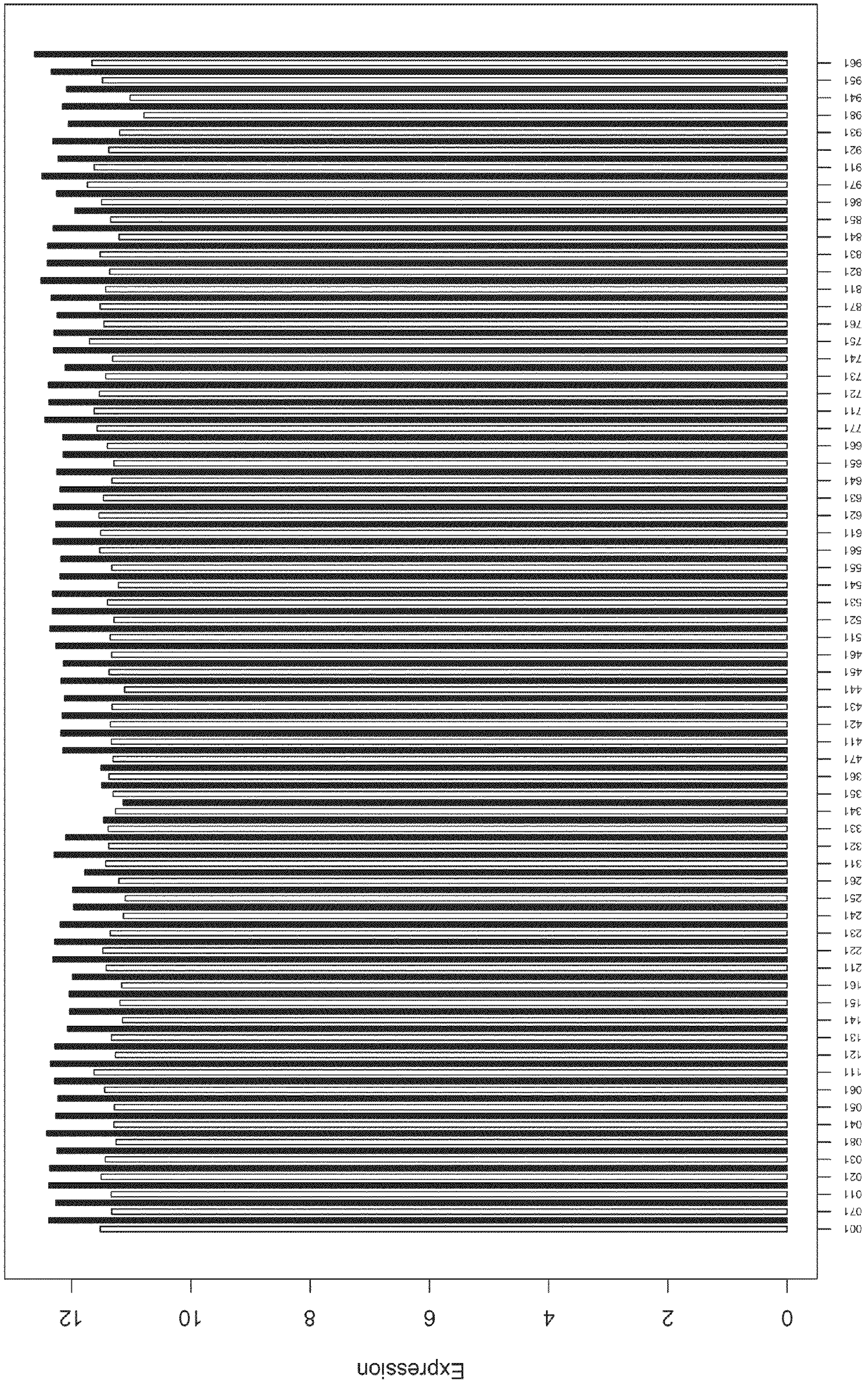
Figure 233:
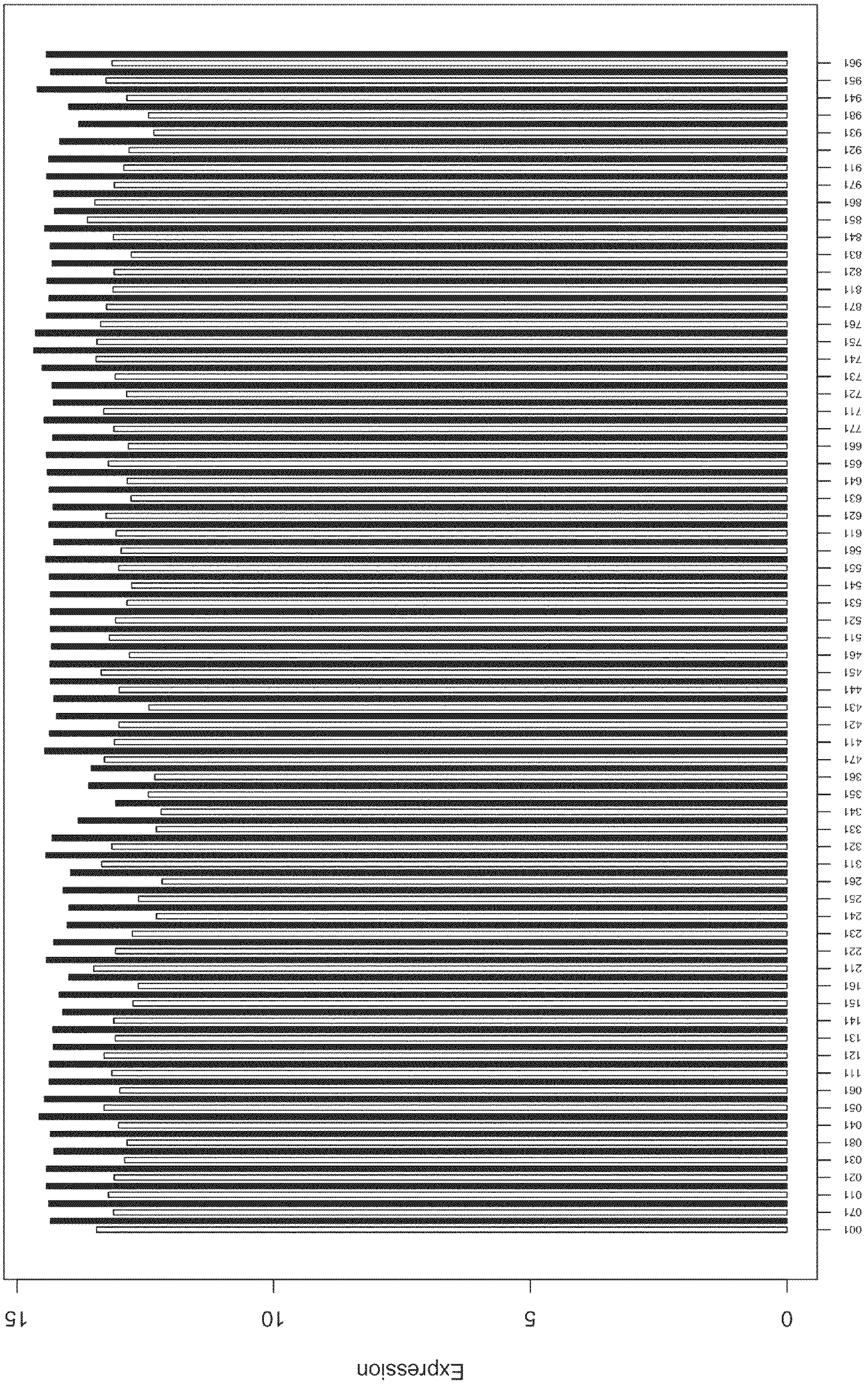
Figure 245:
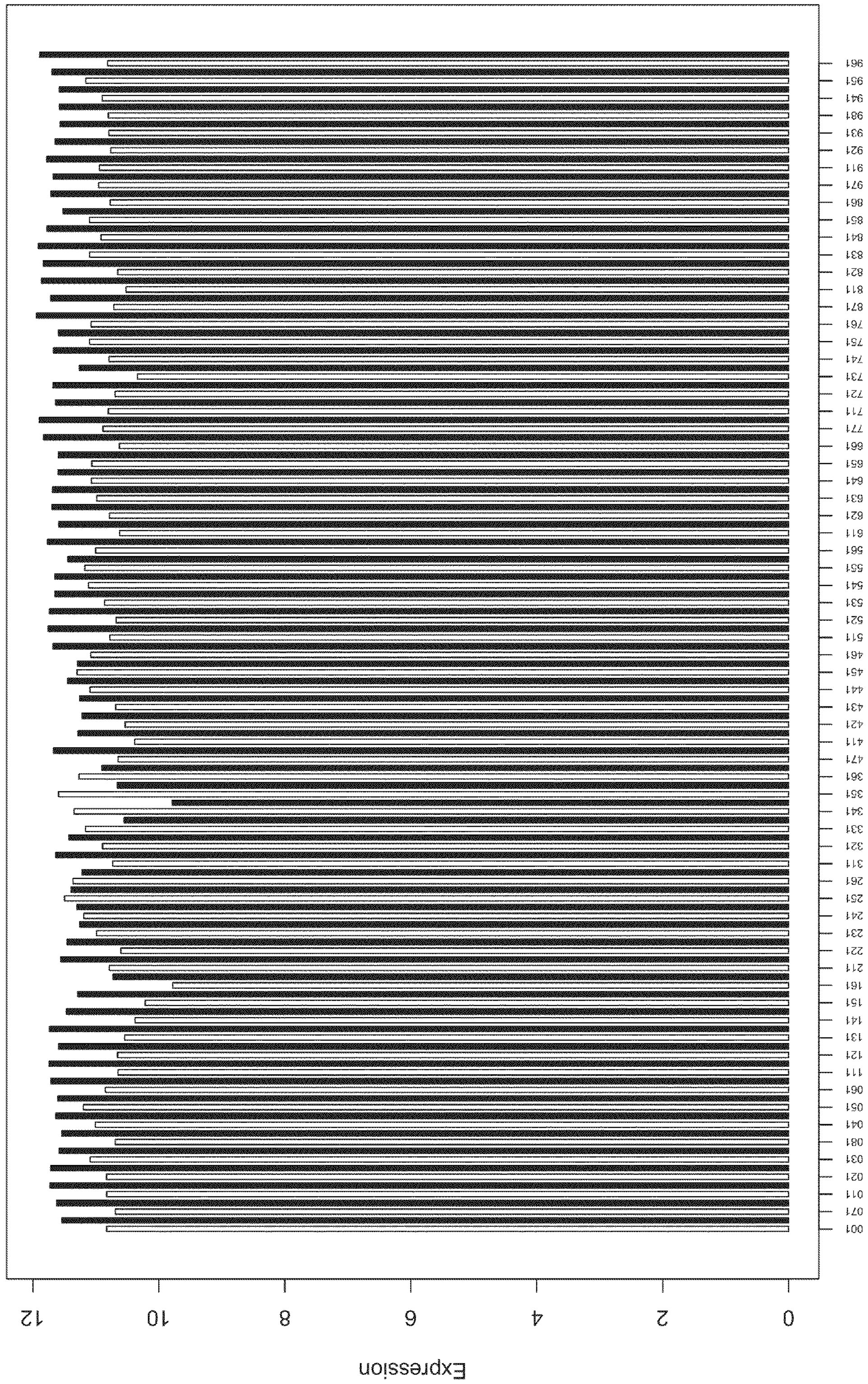
Figure 246:
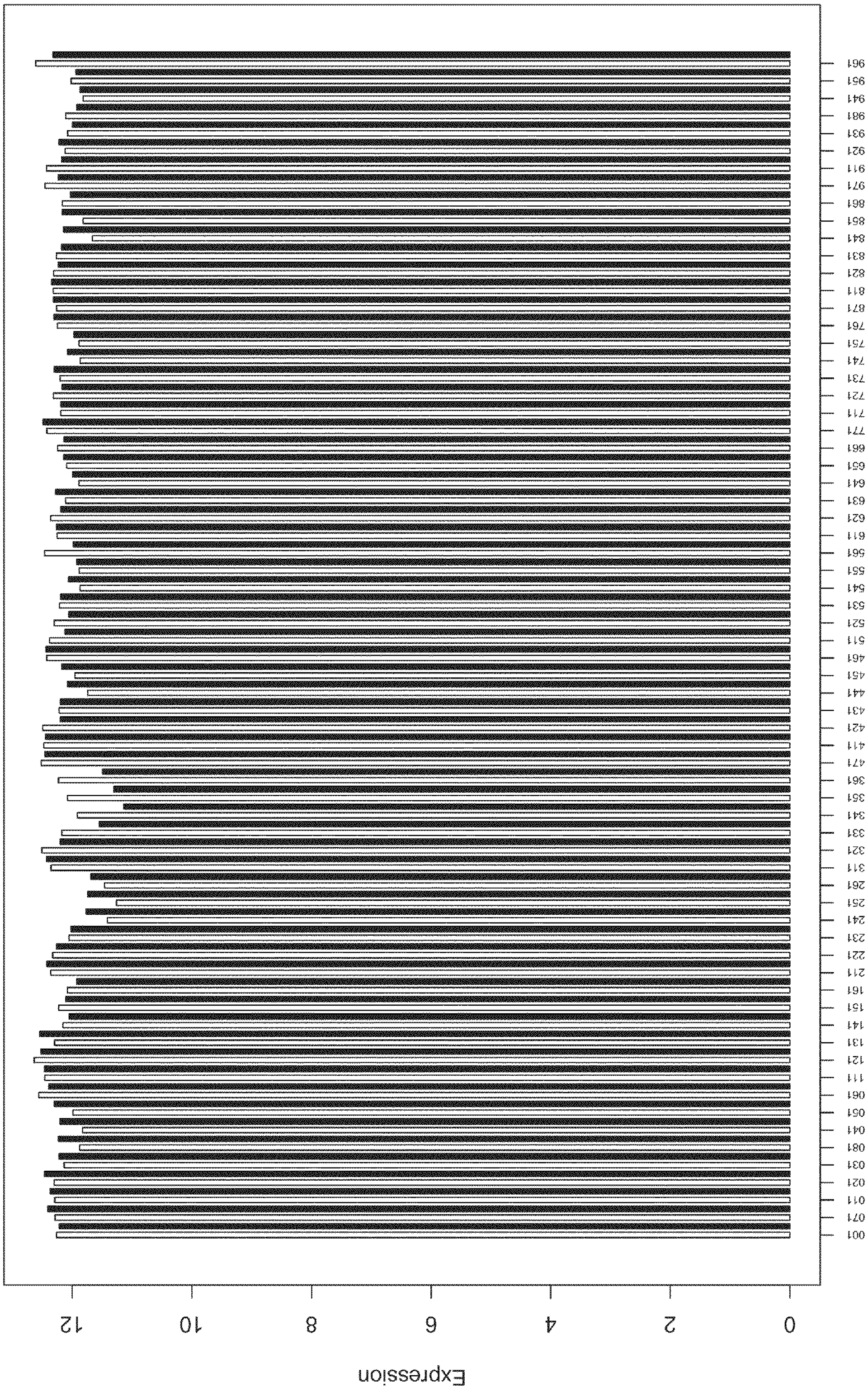
Figure 249:
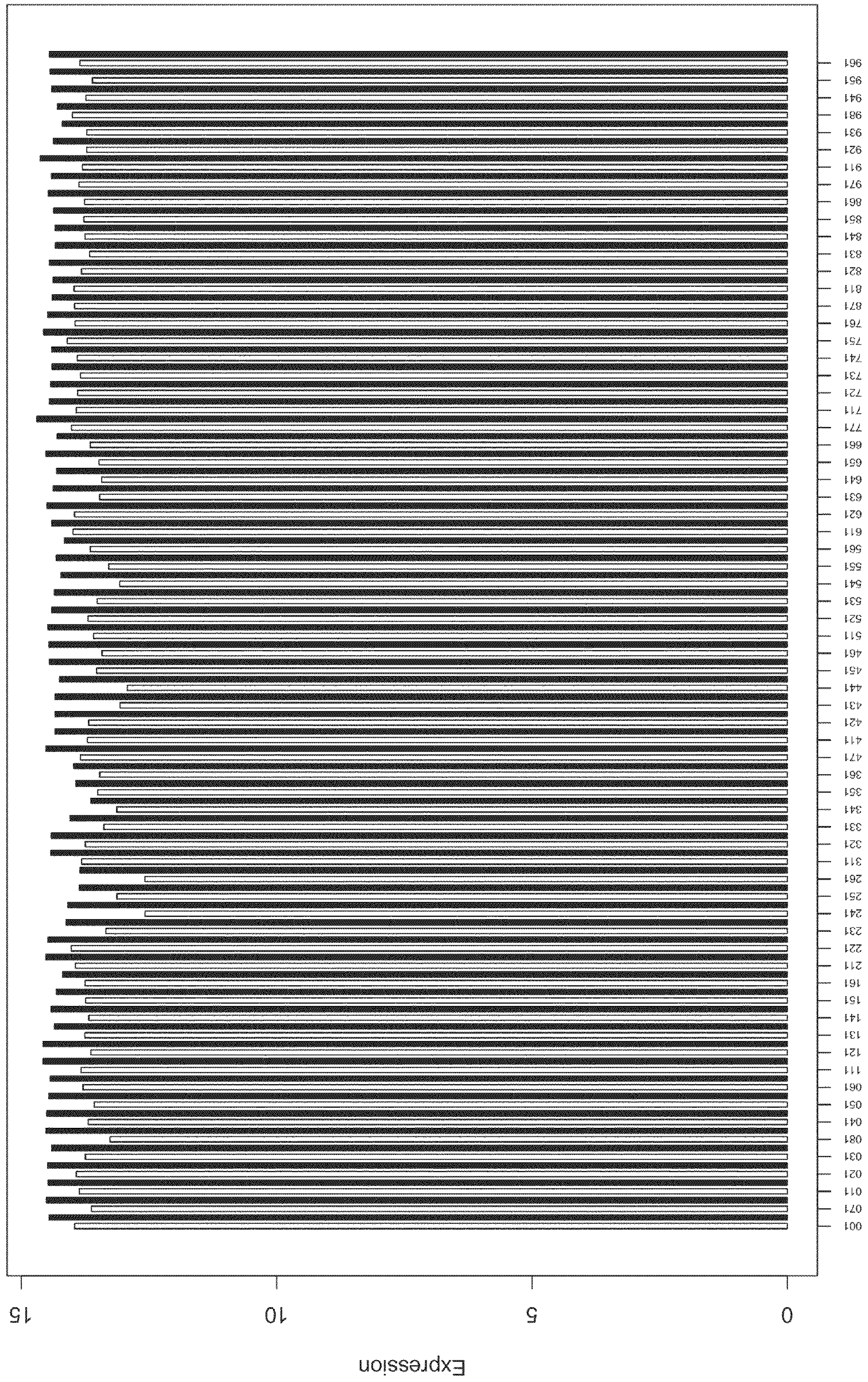
Figure 250:
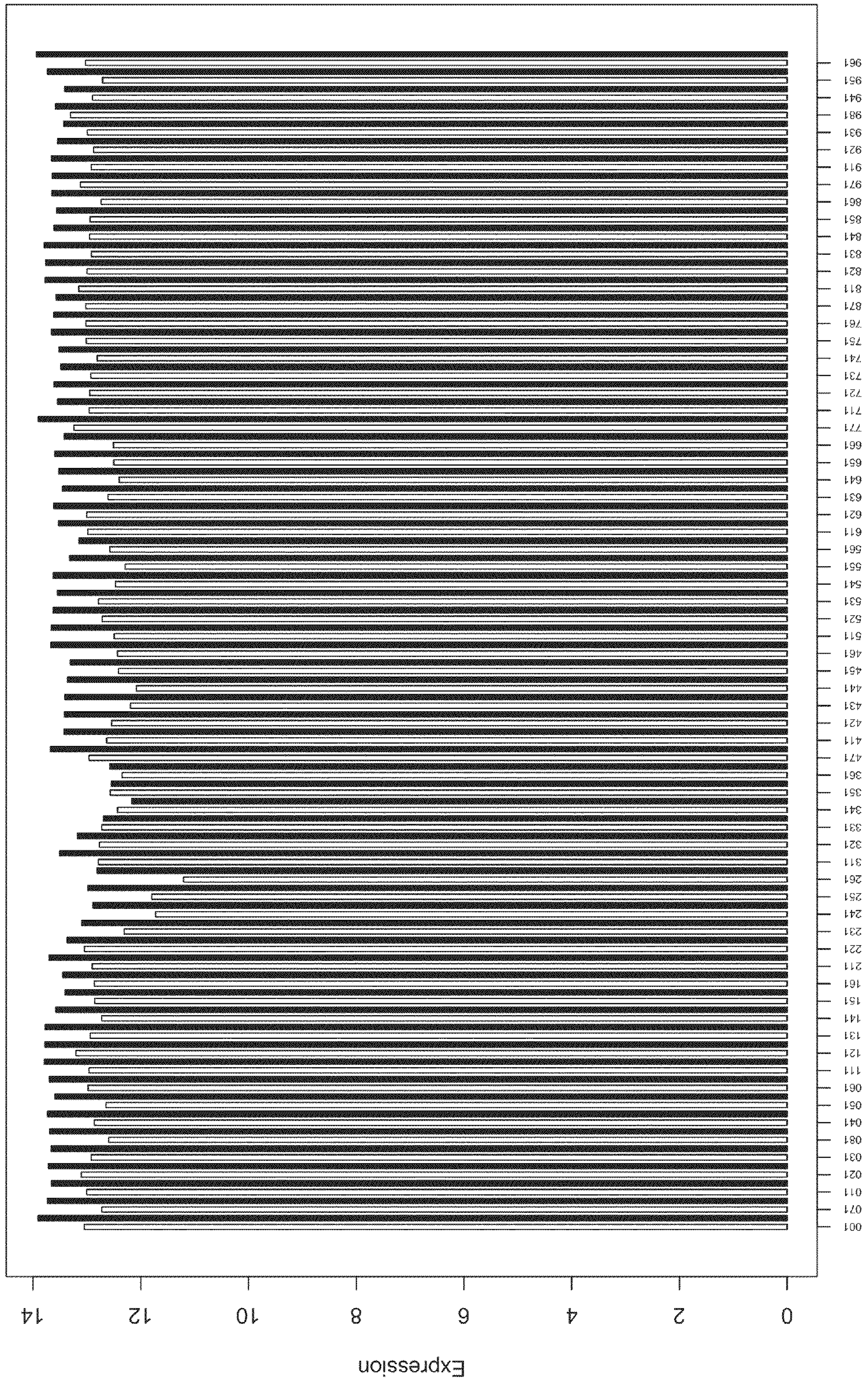

The present disclosure relates to regulatory polynucleotides that are capable of regulating expression of a transcribable polynucleotide in a host cell. In some embodiments, the regulatory polynucleotides are capable of regulating expression of a transcribable polynucleotide in a plant cell, plant tissue, plant, or plant seed. In other embodiments, the regulatory polynucleotides are capable of providing for constitutive expression of an operably linked polynucleotide in plants and plant tissues.

The present disclosure also provides recombinant constructs comprising such regulatory polynucleotides, as well as transgenic host cells, and organisms containing such recombinant constructs. Also provided are methods of directing expression of a transcribable polynucleotide in a host cell or organism.

Prior to describing this invention in further detail, however, the following terms will first be defined.

Definitions

As used herein, the phrase "polynucleotide molecule" refers to a single- or double-stranded DNA or RNA of any origin (e.g., genomic or synthetic origin), i.e., a polymer of deoxyribonucleotide or ribonucleotide bases, respectively, read from the 5' (upstream) end to the 3' (downstream) end.

As used herein, the phrase "polynucleotide sequence" refers to the sequence of a polynucleotide molecule. The nomenclature for DNA bases as set forth at 37 CFR §1.822 is used.

As used herein, the term "transcribable polynucleotide molecule" refers to any polynucleotide molecule capable of being transcribed into a RNA molecule including, but not limited to, protein coding sequences (e.g., transgenes) and functional RNA sequences (e.g., a molecule useful for gene suppression).

As used herein, the terms "regulatory element" and "regulatory polynucleotide" refer to polynucleotide molecules having regulatory activity (i.e., one that has the ability to affect the transcription of an operably linked transcribable polynucleotide molecule). The terms refer to a polynucleotide molecule containing one or more elements such as core promoter regions, cis-elements, leaders or UTRs, enhancers, introns, and transcription termination regions, all of which have regulatory activity and may play a role in the overall expression of nucleic acid molecules in living cells. The "regulatory elements" determine if, when, and at what level a particular polynucleotide is transcribed. The regulatory elements may interact with regulatory proteins or other proteins or be involved in nucleotide interactions, for example, to provide proper folding of a regulatory polynucleotide.

As used herein, the terms "core promoter" and "minimal promoter" refer to a minimal region of a regulatory polynucleotide required to properly initiate transcription. A core promoter typically contains the transcription start site (TSS), a binding site for RNA polymerase, and general transcription factor binding sites. Core promoters can include promoters produced through the manipulation of known core promoters to produce artificial, chimeric, or hybrid promoters, and can be used in combination with other regulatory elements, such as cis-elements, enhancers, or introns, for example, by adding a heterologous regulatory element to an active core promoter with its own partial or complete regulatory elements.

As used herein, the term "cis-element" refers to a cis-acting transcriptional regulatory element that confers an aspect of the overall control of the expression of an operably linked transcribable polynucleotide. A cis-element may function to bind transcription factors, which are trans-acting protein factors that regulate transcription. Some cis-elements bind more than one transcription factor, and transcription factors may interact with different affinities with more than one cis-element. Cis-elements can confer or modulate expression, and can be identified by a number of techniques, including deletion analysis (i.e., deleting one or more nucleotides from the 5' end or internal to a promoter), DNA binding protein analysis using DNase I footprinting, methylation interference, electrophoresis mobility-shift assays, in vivo genomic footprinting by ligation-mediated PCR, and other conventional assays; or by DNA sequence similarity analysis with known cis-element motifs by conventional DNA sequence comparison methods. The fine structure of a cis-element can be further studied by mutagenesis (or substitution) of one or more nucleotides or by other conventional methods. Cis-elements can be obtained by chemical synthesis or by isolation from regulatory polynucleotides that include such elements, and they can be synthesized with additional flanking nucleotides that contain useful restriction enzyme sites to facilitate subsequence manipulation.

As used herein, the term "enhancer" refers to a transcriptional regulatory element, typically 100-200 base pairs in length, which strongly activates transcription, for example, through the binding of one or more transcription factors. Enhancers can be identified and studied by methods such as those described above for cis-elements. Enhancer sequences can be obtained by chemical synthesis or by isolation from regulatory elements that include such elements, and they can be synthesized with additional flanking nucleotides that contain useful restriction enzyme sites to facilitate subsequence manipulation.

As used herein, the term "intron" refers to a polynucleotide molecule that may be isolated or identified from the intervening sequence of a genomic copy of a transcribed polynucleotide which is spliced out during mRNA processing prior to translation. Introns may themselves contain sub-elements such as cis-elements or enhancer domains that affect the transcription of operably linked polynucleotide molecules. Some introns are capable of increasing gene expression through a mechanism known as intron mediated enhancement (IME). IME, as distinguished from the effects of enhancers, is based on introns residing in the transcribed region of a polynucleotide. In general, IME is mediated by the first intron of a gene, which can reside in either the 5'-UTR sequence of a gene or between the first and second protein coding (CDS) exons of a gene. Without being limited by theory, IME may be particularly important in highly expressed, constitutive genes.

As used herein, the terms "leader" or "5'-UTR" refer to a polynucleotide sequence between the transcription and translation start sites of a gene. 5'-UTRs may themselves contain sub-elements such as cis-elements, enhancer domains, or introns that affect the transcription of operably linked polynucleotide molecules.

As used herein, the term "ortholog" refers to a polynucleotide from a different species that encodes a similar protein that performs the same biological function. For example, the ubiquitin genes from, for example, *Arabidopsis* and rice, are orthologs. Orthologs may also exhibit similar tissue expression patterns (for example, constitutive expression in plant cells or plant tissues). Typically, orthologous nucleotide sequences are characterized by significant sequence similarity. A nucleotide sequence of an ortholog in one species (for example, *Arabidopsis*) can be used to isolate the nucleotide sequence of the ortholog in another species (for example, rice) using standard molecular biology techniques.

The term "expression" or "gene expression" means the transcription of an operably linked polynucleotide. The term "expression" or "gene expression" in particular refers to the transcription of an operably linked polynucleotide into structural RNA (rRNA, tRNA) or mRNA with or without subsequent translation of the latter into a protein. The process includes transcription of DNA and processing of the resulting mRNA product.

"Constitutive expression" refers to the transcription of a polynucleotide in all or substantially all tissues and stages of development and being minimally responsive to abiotic stimuli. "Constitutive plant regulatory polynucleotides" are regulatory polynucleotides that have regulatory activity in all or substantially all tissues of a plant throughout plant development. It is understood that for the terms "constitutive expression" and "constitutive plant regulatory polynucleotide" that some variation in absolute levels of expression or activity can exist among different plant tissues and stages of development.

As used herein, the term "chimeric" refers to the product of the fusion of portions of two or more different polynucleotide molecules. As used herein, the term "chimeric regulatory polynucleotide" refers to a regulatory polynucleotide produced through the manipulation of known promoters or other polynucleotide molecules, such as cis-elements. Such chimeric regulatory polynucleotides may combine enhancer domains that can confer or modulate expression from one or more regulatory polynucleotides, for example, by fusing a heterologous enhancer domain from a first regulatory polynucleotide to a promoter element (e.g. a core promoter) from a second regulatory polynucleotide with its own partial or complete regulatory elements.

As used herein, the term "operably linked" refers to a first polynucleotide molecule, such as a core promoter, connected with a second polynucleotide molecule, such as a transcribable polynucleotide (e.g., a polynucleotide encoding a protein of interest), where the polynucleotide molecules are so arranged that the first polynucleotide molecule affects the transcription of the second polynucleotide molecule. The two polynucleotide molecules may be part of a single contiguous polynucleotide molecule and may be adjacent. For example, a promoter is operably linked to a polynucleotide encoding a protein of interest if the promoter modulates transcription of the polynucleotide of interest in a cell.

An "isolated" or "purified" polynucleotide or polypeptide molecule, refers to a molecule that is not in its native environment such as, for example, a molecule not normally found in the genome of a particular host cell, or a DNA not normally found in the host genome in an identical context, or any two sequences adjacent to each other that are not normally or naturally adjacent to each other.

Regulatory Polynucleotide Molecules

The regulatory polynucleotide molecules described herein were discovered using bioinformatic screening techniques of databases containing expression and sequence data for genes in various plant species. Such bioinformatic techniques are described in more detail in the Examples set forth below.

In one embodiment, isolated regulatory polynucleotide molecules are provided. The regulatory polynucleotides provided herein include polynucleotide molecules having transcription regulatory activity in host cells, such as plant cells. In some embodiments, the regulatory polynucleotides are capable of regulating constitutive transcription of an operably linked transcribable polynucleotide molecule in transgenic plants and plant tissues.

The isolated regulatory polynucleotide molecules comprise a polynucleotide molecule selected from the group consisting of a) a polynucleotide molecule comprising a nucleic acid molecule having a sequence selected from the group consisting of SEQ ID NOs: 1-212 that is capable of regulating transcription of an operably linked transcribable polynucleotide molecule; b) a polynucleotide molecule having at least about 70% sequence identity to the sequence of SEQ ID NOs:1-212 that is capable of regulating transcription of an operably linked transcribable polynucleotide molecule; and c) a fragment of the polynucleotide molecule of a) or b) capable of regulating transcription of an operably linked transcribable polynucleotide molecule. Such fragments can be a UTR, a core promoter, an intron, an enhancer, a cis-element, or any other regulatory element.

Thus, the regulatory polynucleotide molecules include those molecules having sequences provided in SEQ ID NO: 1 through SEQ ID NO: 212. These polynucleotide molecules are capable of affecting the expression of an operably linked transcribable polynucleotide molecule in plant cells and plant tissues and therefore can regulate expression in transgenic plants. The present disclosure also provides methods of modifying, producing, and using such regulatory polynucleotides. Also included are compositions, transformed host cells, transgenic plants, and seeds containing the regulatory polynucleotides, and methods for preparing and using such regulatory polynucleotides.

The disclosed regulatory polynucleotides are capable of providing for expression of operably linked transcribable polynucleotides in any cell type, including, but not limited to plant cells. For example, the regulatory polynucleotides may be capable of providing for the expression of operably linked heterologous transcribable polynucleotides in plants and plant cells. In one embodiment, the regulatory polynucleotides are capable of directing constitutive expression in a transgenic plant, plant tissue(s), or plant cell(s).

In one embodiment, the regulatory polynucleotides may comprise multiple regulatory elements, each of which confers a different aspect to the overall control of the expression of an operably linked transcribable polynucleotide. In another embodiment, regulatory elements may be derived from the polynucleotide molecules of SEQ ID NOs:1-212. Thus, regulatory elements of the disclosed regulatory polynucleotides are also provided.

The disclosed polynucleotides include, but are not limited to, nucleic acid molecules that are between about 0.1 Kb and about 5 Kb, between about 0.1 Kb and about 4 Kb, between about 0.1 Kb and about 3 Kb, and between about 0.1 Kb and about 2 Kb, about 0.25 Kb and about 2 Kb, or between about 0.10 Kb and about 1.0 Kb.

The regulatory polynucleotides as provided herein also include fragments of SEQ ID NOs: 1-212. The fragment polynucleotides include those polynucleotides that comprise at least 50, at least 75, at least 100, at least 125, at least 150, at least 175, or at least 200 contiguous nucleotide bases where the fragment's complete sequence in its entirety is identical to a contiguous fragment of the referenced polynucleotide molecule. In some embodiments, the fragments contain one or more regulatory elements capable of regulating the transcription of an operably linked polynucleotide. Such fragments may include regulatory elements such as introns, enhancers, core promoters, leaders, and the like.

Thus also provided are regulatory elements derived from the polynucleotides having the sequences of SEQ ID NOs: 1-212. In some embodiments, the regulatory elements are capable of regulating transcription of operably linked transcribable polynucleotides in plants and plant tissues. The regulatory elements that may be derived from the polynucleotides of SEQ ID NOs:1-212 include, but are not limited to introns, enhancers, leaders, and the like. In addition, the regulatory elements may be used in recombinant constructs for the expression of operably linked transcribable polynucleotides of interest.

The present disclosure also includes regulatory polynucleotides that are substantially homologous to SEQ ID NOs:1-212. As used herein, the phrase "substantially homologous" refers to polynucleotide molecules that generally demonstrate a substantial percent sequence identity with the regulatory polynucleotides provided herein. Substantially homologous polynucleotide molecules include polynucleotide molecules that function in plants and plant cells to direct transcription and have at least about 70% sequence identity, at least about 80% sequence identity, at least about 90% sequence identity, or even greater sequence identity, specifically including about 73%, 75%, 78%, 83%, 85%, 88%, 92%, 94%, 95%, 96%, 97%, 98%, 99% or greater sequence identity with the regulatory polynucleotide molecules provided in SEQ ID NOs:1-212. Polynucleotide molecules that are capable of regulating transcription of operably linked transcribable polynucleotide molecules and are substantially homologous to the polynucleotide sequences of the regulatory polynucleotides provided herein are encompassed herein.

As used herein, the "percent sequence identity" is determined by comparing two optimally aligned sequences over a comparison window, where the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, divided by the number of matched positions by the total number of positions in the window of comparison and multiplying the result by 100 to yield the percentage of sequence identity. Alignment for the purposes of determining the percentage identity can be achieved in various ways that are within the skill in the art, for example, using publicly available computer software such as BLAST. Those skilled in the art can determine appropriate parameters for measuring alignment, including any algorithms needed to achieve optimal alignment over the full length of the sequences being compared.

Additional regulatory polynucleotides substantially homologous to those identified herein may be identified by a variety of methods. For example, cDNA libraries may be constructed using cells or tissues of interest and screened to identify genes having an expression pattern similar to that of the regulatory elements described herein. The cDNA sequence for the identified gene may then be used to isolate the gene's regulatory sequences for further characterization. Alternately, transcriptional profiling or electronic northern techniques may be used to identify genes having an expression pattern similar to that of the regulatory polynucleotides described herein. Once these genes have been identified, their regulatory polynucleotides may be isolated for further characterization. The electronic northern technique refers to a computer-based sequence analysis which allows sequences from multiple cDNA libraries to be compared electronically based on parameters the researcher identifies including abundance in EST populations in multiple cDNA libraries, or exclusively to EST sets from one or combinations of libraries. The transcriptional profiling technique is a high-throughput method used for the systematic monitoring of expression profiles for thousands of genes. This DNA chip-based technology arrays thousands of oligonucleotides on a support surface. These arrays are simultaneously hybridized to a population of labeled cDNA or cRNA probes prepared from RNA samples of different cell or tissue types, allowing direct comparative analysis of expression. This approach may be used for the isolation of regulatory sequences such as promoters associated with those sequences.

In some embodiments, substantially homologous polynucleotide molecules may be identified when they specifically hybridize to form a duplex molecule under certain conditions. Under these conditions, referred to as stringency conditions, one polynucleotide molecule can be used as a probe or primer to identify other polynucleotide molecules that share homology. Accordingly, the nucleotide sequences of the present invention may be used for their ability to selectively form duplex molecules with complementary stretches of polynucleotide molecule fragments. Substantially homologous polynucleotide molecules may also be determined by computer programs that align polynucleotide sequences and estimate the ability of polynucleotide molecules to form duplex molecules under certain stringency conditions or show sequence identity with a reference sequence.

In some embodiments, the regulatory polynucleotides disclosed herein can be modified from their wild-type sequences to create regulatory polynucleotides that have variations in the polynucleotide sequence. The polynucleotide sequences of the regulatory elements of SEQ ID NOs: 1-212 may be modified or altered. One method of alteration of a polynucleotide sequence includes the use of polymerase chain reactions (PCR) to modify selected nucleotides or regions of sequences. These methods are well known to those of skill in the art. Sequences can be modified, for example, by insertion, deletion, or replacement of template sequences in a PCR-based DNA modification approach. In the context of the present invention, a "variant" is a regulatory polynucleotide containing changes in which one or more nucleotides of an original regulatory polynucleotide is deleted, added, and/or substituted. In one example, a variant regulatory polynucleotide substantially maintains its regulatory function. For example, one or more base pairs may be deleted from the 5' or 3' end of a regulatory polynucleotide to produce a "truncated" polynucleotide. One or more base pairs can also be inserted, deleted, or substituted internally to a regulatory polynucleotide. Variant regulatory polynucleotides can be produced, for example, by standard DNA mutagenesis techniques or by chemically synthesizing the variant regulatory polynucleotide or a portion thereof.

The methods and compositions provided for herein may be used for the efficient expression of transgenes in plants. The regulatory polynucleotide molecules useful for directing expression (including constitutive expression) of transcribable polynucleotides, may provide enhancement of expression (including enhancement of constitutive expression) (e.g., through the use of IME with the introns of the regulatory polynucleotides disclosed herein), and/or may provide for increased levels of expression of transcribable polynucleotides operably linked to a regulatory polynucleotide described herein. In addition, the introns identified in the regulatory polynucleotide molecules provided herein may also be included in conjunction with any other plant promoter (or plant regulatory polynucleotide) for the enhancement of the expression of selected transcribable polynucleotides.

Also provided are chimeric regulatory polynucleotide molecules. Such chimeric regulatory polynucleotides may contain one or more regulatory elements disclosed herein in operable combination with one or more additional regulatory elements. The one or more additional regulatory elements can be any additional regulatory elements from any source, including those disclosed herein, as well as those known in the art, for example, the actin 2 intron. In addition, the chimeric regulatory polynucleotide molecules may comprise any number of regulatory elements such as, for example, 2, 3, 4, 5, or more regulatory elements.

In some embodiments, the chimeric regulatory polynucleotides contain at least one core promoter molecule provided herein operably linked to one or more additional regulatory elements, such as one or more regulatory introns and/or enhancer elements. Alternatively, the chimeric regulatory polynucleotides may contain one or more regulatory elements as provided herein in combination with a minimal promoter sequence, for example, the CaMV 35S minimal promoter. Thus, the design, construction, and use of chimeric regulatory polynucleotides according to the methods disclosed herein for modulating the expression of operably linked transcribable polynucleotide molecules are also provided.

The chimeric regulatory polynucleotides as provided herein can be designed or engineered using any method. Many regulatory regions contain elements that activate, enhance, or define the strength and/or specificity of the regulatory region. Thus, for example, chimeric regulatory polynucleotides of the present invention may comprise core promoter elements containing the site of transcription initiation (e.g., RNA polymerase II binding site) combined with heterologous cis-elements located upstream of the transcription initiation site that modulate transcription levels. Thus, in one embodiment, a chimeric regulatory polynucleotide may be produced by fusing a core promoter fragment polynucleotide described herein to a cis-element from another regulatory polynucleotide; the resultant chimeric regulatory polynucleotide may cause an increase in expression of an operably linked transcribable polynucleotide molecule. Chimeric regulatory polynucleotides can be constructed such that regulatory polynucleotide fragments or elements are operably linked, for example, by placing such a fragment upstream of a minimal promoter. The core promoter regions, regulatory elements and fragments of the present invention can be used for the construction of such chimeric regulatory polynucleotides.

Thus, also provided are chimeric regulatory polynucleotide molecules comprising (1) a first polynucleotide molecule selected from the group consisting of a) a polynucleotide molecule comprising a nucleic acid molecule having the sequence of SEQ ID NOs: 1-212 that is capable of regulating transcription of an operably linked transcribable polynucleotide molecule; b) a polynucleotide molecule having at least about 70% sequence identity to the sequence of SEQ ID NOs:1-212 that is capable of regulating transcription of an operably linked transcribable polynucleotide molecule; and c) a fragment of the polynucleotide molecule of a) or b) capable of regulating transcription of an operably linked transcribable polynucleotide molecule, and (2) a second polynucleotide molecule capable of regulating transcription of an operably linked polynucleotide molecule, wherein the first polynucleotide molecule is operably linked to the second polynucleotide molecule. The chimeric regulatory polynucleotide molecules may further comprise at least a third, fourth, fifth, or more additional polynucleotide molecules capable of regulating transcription of an operably linked polynucleotide, where the at least a third, fourth, fifth, or more additional polynucleotide molecules is/are operably linked to the first and second polynucleotide molecules.

The first and second polynucleotide molecules may be any combination of regulatory elements, including those provided herein. In one embodiment, the first polynucleotide comprises at least a core promoter element and the second polynucleotide comprises at least one additional regulatory element, including, but not limited to, an enhancer, an intron, and a leader molecule.

Methods for construction of chimeric and variant regulatory polynucleotides include, but are not limited to, combining elements of different regulatory polynucleotides or duplicating portions or regions of a regulatory polynucleotide. Those of skill in the art are familiar with the standard resource materials that describe specific conditions and procedures for the construction, manipulation, and isolation of macromolecules (e.g., polynucleotide molecules, plasmids, etc.), as well as the generation of recombinant organisms and the screening and isolation of polynucleotide molecules.

Thus, also provided are novel methods and compositions for the efficient expression of transcribable polynucleotides in plants through the use of the regulatory polynucleotides described herein. The regulatory polynucleotides described herein include constitutive promoters which may find wide utility in directing the expression of potentially any polynucleotide which one desires to have expressed in a plant. The regulatory elements disclosed herein may be used as promoters within expression constructs in order to increase the level of expression of transcribable polynucleotides operably linked to any one of the disclosed regulatory polynucleotides. Alternatively, the regulatory elements disclosed herein may be included in expression constructs in conjunction with any other plant promoter for the enhancement of the expression of one or more selected polynucleotides.

Recombinant Constructs

The disclosed regulatory polynucleotide molecules find use in the production of recombinant polynucleotide constructs, for example to express transcribable polynucleotides encoding proteins of interest in a host cell.

The recombinant constructs comprise (1) an isolated regulatory polynucleotide molecule comprising a polynucleotide molecule selected from the group consisting of a) a polynucleotide molecule comprising a nucleic acid molecule having the sequence of SEQ ID NOs: 1-212 that is capable of regulating transcription of an operably linked transcribable polynucleotide molecule; b) a polynucleotide molecule having at least about 70% sequence identity to the sequence of SEQ ID NOs:1-212 that is capable of regulating transcription of an operably linked transcribable polynucleotide molecule; and c) a fragment of the polynucleotide molecule of a) or b) capable of regulating transcription of an operably linked transcribable polynucleotide molecule operably linked to (2) a transcribable polynucleotide molecule.

The constructs provided herein may contain any recombinant polynucleotide molecule having a combination of regulatory elements linked together in a functionally operative manner. For example, the constructs may contain a regulatory polynucleotide operably linked to a transcribable polynucleotide molecule operably linked to a 3' transcription termination polynucleotide molecule. In addition, the constructs may include, but are not limited to, additional regulatory polynucleotide molecules from the 3'-untranslated region (3' UTR) of plant genes (e.g., a 3' UTR to increase mRNA stability, such as the PI-II termination region of potato or the octopine or nopaline synthase 3' termination regions). Constructs may also include but are not limited to the 5' untranslated regions (5' UTR) of an mRNA polynucleotide molecule which can play an important role in translation initiation and can also be a regulatory component in a plant expression construct. For example, non-translated 5' leader polynucleotide molecules derived from heat shock protein genes have been demonstrated to enhance expression in plants. These additional upstream and downstream regulatory polynucleotide molecules may be derived from a source that is native or heterologous with respect to the other elements present on the promoter construct.

Thus, constructs generally comprise regulatory polynucleotides such as those provided herein (including modified and chimeric regulatory polynucleotides), operatively linked to a transcribable polynucleotide molecule so as to direct transcription of the transcribable polynucleotide molecule at a desired level or in a desired tissue or developmental pattern upon introduction of the construct into a plant cell. In some cases, the transcribable polynucleotide molecule comprises a protein-coding region, and the promoter provides for transcription of a functional mRNA molecule that is translated and expressed as a protein product. Constructs may also be constructed for transcription of antisense RNA molecules or other similar inhibitory RNA in order to inhibit expression of a specific RNA molecule of interest in a target host cell.

Exemplary transcribable polynucleotide molecules for incorporation into the disclosed constructs include, for example, transcribable polynucleotides from a species other than the target species, or even transcribable polynucleotides that originate with or are present in the same species, but are incorporated into recipient cells by genetic engineering methods rather than classical reproduction or breeding techniques. Exogenous polynucleotide or regulatory element is intended to refer to any polynucleotide molecule or regulatory polynucleotide that is introduced into a recipient cell. The type of polynucleotide included in the exogenous polynucleotide can include polynucleotides that are already present in the plant cell, polynucleotides from another plant, polynucleotides from a different organism, or polynucleotides generated externally, such as a polynucleotide molecule containing an antisense message of a protein-encoding molecule, or a polynucleotide molecule encoding an artificial or modified version of a protein.

The disclosed regulatory polynucleotides can be incorporated into a construct using marker genes and can be tested in transient analyses that provide an indication of expression in stable plant systems. As used herein, the term "marker gene" refers to any transcribable polynucleotide molecule whose expression can be screened for or scored in some way.

Methods of testing for marker expression in transient assays are known to those of skill in the art. Transient expression of marker genes has been reported using a variety of plants, tissues, and DNA delivery systems. For example, types of transient analyses include but are not limited to direct DNA delivery via electroporation or particle bombardment of tissues in any transient plant assay using any plant species of interest. Such transient systems would include but are not limited to electroporation of protoplasts from a variety of tissue sources or particle bombardment of specific tissues of interest. Any transient expression system may be used to evaluate regulatory polynucleotides or regulatory polynucleotide fragments operably linked to any transcribable polynucleotide molecule including, but not limited to, selected reporter genes, marker genes, or polynucleotides encoding proteins of agronomic interest. Any plant tissue may be used in the transient expression systems and include but are not limited to leaf base tissues, callus, cotyledons, roots, endosperm, embryos, floral tissue, pollen, and epidermal tissue.

Any scorable or screenable marker can be used in a transient assay as provided herein. For example, markers for transient analyses of the regulatory polynucleotides or regulatory polynucleotide fragments of the present invention include GUS or GFP. The constructs containing the regulatory polynucleotides or regulatory polynucleotide fragments of the present invention operably linked to a marker are delivered to the tissues and the tissues are analyzed by the appropriate mechanism, depending on the marker. The quantitative or qualitative analyses are used as a tool to evaluate the potential expression profile of the promoters or promoter fragments when operatively linked to polynucleotides encoding proteins of agronomic interest in stable plants.

Thus, in one embodiment, a regulatory polynucleotide molecule, or a variant, or derivative thereof, capable of regulating transcription, is operably linked to a transcribable polynucleotide molecule that provides for a selectable, screenable, or scorable marker. Markers for use in the practice of the present invention include, but are not limited to, transcribable polynucleotide molecules encoding β-glucuronidase (GUS), green fluorescent protein (GFP), luciferase (LUC), proteins that confer antibiotic resistance, or proteins that confer herbicide tolerance. Useful antibiotic resistance markers, including those encoding proteins conferring resistance to kanamycin (nptII), hygromycin B (aph IV), streptomycin or spectinomycin (aad, spec/strep), and gentamycin (aac3 and aacC4), are known in the art. Herbicides for which transgenic plant tolerance has been demonstrated and for which the methods disclosed herein can be applied include, but are not limited to, glyphosate, glufosinate, sulfonylureas, imidazolinones, bromoxynil, delapon, cyclohezanedione, protoporphyrionogen oxidase inhibitors, and isoxasflutole herbicides. Polynucleotide molecules encoding proteins involved in herbicide tolerance are known in the art, and include, but are not limited to, a polynucleotide molecule encoding 5-enolpyruvylshikimate-3-phosphate synthase (EPSP synthase); and aroA for glyphosate tolerance; a polynucleotide molecule encoding bromoxynil nitrilase (Bxn) for Bromoxynil tolerance; a polynucleotide molecule encoding phytoene desaturase (crtl) for norflurazon tolerance; a polynucleotide molecule encoding acetohydroxyacid synthase (AHAS, aka ALS) for tolerance to sulfonylurea herbicides; and the bar gene for glufosinate and bialaphos tolerance.

The regulatory polynucleotide molecules can be operably linked to any transcribable polynucleotide molecule of interest. Such transcribable polynucleotide molecules include, for example, polynucleotide molecules encoding proteins of agronomic interest. Proteins of agronomic interest can be any protein desired to be expressed in a host cell, such as, for example, proteins that provide a desirable characteristic associated with plant morphology, physiology, growth and development, yield, nutritional content, disease or pest resistance, or environmental or chemical tolerance. The expression of a protein of agronomic interest is desirable in order to confer an agronomically important trait on the plant containing the polynucleotide molecule. Proteins of agronomic interest that provide a beneficial agronomic trait to crop plants include, but are not limited to for example, proteins conferring herbicide resistance, insect control, fungal disease resistance, virus resistance, nematode resistance, bacterial disease resistance, starch production, modified oils production, high oil production, modified fatty acid content, high protein production, fruit ripening, enhanced animal and human nutrition, biopolymers, environmental stress resistance, pharmaceutical peptides, improved processing traits, improved digestibility, low raffinose, industrial enzyme production, improved flavor, nitrogen fixation, hybrid seed production, and biofuel production.

In other embodiments, the transcribable polynucleotide molecules can affect an agronomically important trait by encoding an RNA molecule that causes the targeted inhibition, or substantial inhibition, of expression of an endogenous gene (e.g., via antisense, RNAi, and/or cosuppression-mediated mechanisms). The RNA could also be a catalytic RNA molecule (i.e., a ribozyme) engineered to cleave a desired endogenous RNA product. Thus, any polynucleotide molecule that encodes a protein or mRNA that expresses a phenotype or morphology change of interest is useful for the practice of the present invention.

The constructs of the present invention may be double Ti plasmid border DNA constructs that have the right border (RB) and left border (LB) regions of the Ti plasmid isolated from *Agrobacterium tumefaciens* comprising a transfer DNA (T-DNA), that along with transfer molecules provided by the *Agrobacterium* cells, permits the integration of the T-DNA into the genome of a plant cell. The constructs also may contain the plasmid backbone DNA segments that provide replication function and antibiotic selection in bacterial cells, for example, an *E. coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker. For plant transformation, the host bacterial strain is often *Agrobacterium tumefaciens* ABI, C58, or LBA4404, however, other strains known to those skilled in the art of plant transformation can function in the present invention.

Transgenic Cells, Host Cells, Plants and Plant Cells

The polynucleotides and constructs as provided herein can be used in the preparation of transgenic host cells, tissues, organs, and organisms. Thus, also provided are transgenic host cells, tissues, organs, and organisms that contain an introduced regulatory polynucleotide molecule as provided herein.

The transgenic host cells, tissues, organs, and organisms disclosed herein comprise a recombinant polynucleotide construct having (1) an isolated regulatory polynucleotide molecule comprising a polynucleotide molecule selected from the group consisting of a) a polynucleotide molecule comprising a nucleic acid molecule having the sequence of SEQ ID NOs: 1-212 that is capable of regulating transcription of an operably linked transcribable polynucleotide molecule; b) a polynucleotide molecule having at least about 70% sequence identity to the sequence of SEQ ID NOs:1-212 that is capable of regulating transcription of an operably linked transcribable polynucleotide molecule; and c) a fragment of the polynucleotide molecule of a) or b) capable of regulating transcription of an operably linked transcribable polynucleotide molecule, operably linked to (2) a transcribable polynucleotide molecule.

A plant transformation construct containing a regulatory polynucleotide as provided herein may be introduced into plants by any plant transformation method. The polynucleotide molecules and constructs provided herein may be introduced into plant cells or plants to direct transient expression of operably linked transcribable polynucleotides or be stably integrated into the host cell genome. Methods and materials for transforming plants by introducing a plant expression construct into a plant genome in the practice of this invention can include any of the well-known and demonstrated methods including electroporation; microprojectile bombardment; *Agrobacterium*-mediated transformation; and protoplast transformation.

Plants and plant cells for use in the production of the transgenic plants and plant cells include both monocotyledonous and dicotyledonous plants and plant cells. Methods for specifically transforming monocots and dicots are well known to those skilled in the art. Transformation and plant regeneration using these methods have been described for a number of crops including, but not limited to, soybean (*Glycine max*), *Brassica* sp., *Arabidopsis thaliana*, cotton (*Gossypium hirsutum*), peanut (*Arachis hypogae*), sunflower (*Helianthus annuus*), potato (*Solanum tuberosum*), tomato (*Lycopersicon esculentum* L.), rice, (*Oryza sativa*), corn (*Zea mays*), and alfalfa (*Medicago sativa*). It is apparent to those of skill in the art that a number of transformation methodologies can be used and modified for production of stable transgenic plants from any number of target crops of interest.

The transformed plants may be analyzed for the presence of the transcribable polynucleotides of interest and the expression level and/or profile conferred by the regulatory polynucleotides of the present invention. Those of skill in the art are aware of the numerous methods available for the analysis of transformed plants. For example, methods for plant analysis include, but are not limited to Southern blots or northern blots, PCR-based approaches, biochemical analyses, phenotypic screening methods, field evaluations, and immunodiagnostic assays.

The seeds of this invention can be harvested from fertile transgenic plants and be used to grow progeny generations of the transformed plants disclosed herein. The terms "seeds" and "kernels" are understood to be equivalent in meaning. In the context of the present invention, the seed refers to the mature ovule consisting of a seed coat, embryo, aleurone, and an endosperm.

Thus, also provided are methods for expressing transcribable polynucleotides in host cells, plant cells, and plants. In some embodiments, such methods comprise stably incorporating into the genome of a host cell, plant cell, or plant, a regulatory polynucleotide operably linked to a transcribable polynucleotide molecule of interest and regenerating a stably transformed plant that expresses the transcribable polynucleotide molecule. In other embodiments, such methods comprise the transient expression of a transcribable polynucleotide operably linked to a regulatory polynucleotide molecule provided herein in a host cell, plant cell, or plant.

Such methods of directing expression of a transcribable polynucleotide molecule in a host cell, such as a plant cell, include: A) introducing a recombinant nucleic acid construct into a host cell, the construct having (1) an isolated regulatory polynucleotide molecule comprising a polynucleotide molecule selected from the group consisting of a) a polynucleotide molecule comprising a nucleic acid molecule having the sequence of SEQ ID NOs: 1-212 that is capable of regulating transcription of an operably linked transcribable polynucleotide molecule; b) a polynucleotide molecule having at least about 70% sequence identity to the sequence of SEQ ID NOs:1-212 that is capable of regulating transcription of an operably linked transcribable polynucleotide molecule; and c) a fragment of the polynucleotide molecule of a) or b) capable of regulating transcription of an operably linked transcribable polynucleotide molecule, operably linked to (2) a transcribable polynucleotide molecule; and B) selecting a transgenic host cell exhibiting expression of the transcribable polynucleotide molecule.

The articles "a" and "an" are used herein to refer to one or more than one (i.e., to at least one) of the grammatical object of the article. By way of example, "an element" means one or more elements.

As used herein, the word "comprising," or variations such as "comprises" or "comprising," will be understood to imply the inclusion of a stated element, integer or step, or group of elements, integers or steps, but not the exclusion of any other element, integer or step, or group of elements, integers or steps.

The following examples are offered by way of illustration and not by way of limitation.

EXAMPLES

Example 1

Identification of *Arabidopsis* Constitutive Regulatory Sequences

A bioinformatics approach was used to identify regulatory polynucleotides that have putative constitutive activity. Most plant regulatory polynucleotides (such as promoters) that are considered to have constitutive expression have been identified by their expression characteristics at the organ level (i.e., roots, shoots, leaves, seeds) and may not be truly constitutive at the cell type/tissue level. The method used to identify the regulatory polynucleotides described herein was used to identify regulatory polynucleotides having constitutive expression activity at the cell type and/or tissue level.

Using existing microarray expression data, a bioinformatics analysis method was used to identify genes from this data collection that are highly expressed in all cell types and longitudinal zones of the *Arabidopsis* root.

Such existing data includes microarray expression profiles of all cell-types and developmental stages within *Arabidopsis* root tissue (Brady et al., *Science,* 318:801-806 (2007)). The radial dataset comprehensively profiles expression of 14 non-overlapping cell-types in the root, while the longitudinal data set profiles developmental stages by measuring expression in 13 longitudinal sections. This detailed expression profiling has mapped the spatiotemporal expression patterns of nearly all genes in the *Arabidopsis* root.

The bioinformatics analysis method identified genes based on their published absolute expression level (see Brady et al, 2007, Science. 318: 801-6). This selection process used expression values that are similar to the Robust Microchip Average (RMA) expression values where a value of approximately 1.0 corresponds to the gene being expressed. The identified genes were then filtered with expression values above a certain threshold in every expression measurement. The selection resulted in *Arabidopsis* gene candidates that are broadly expressed in all cell-types and development stages of root tissue.

A second statistical approach was then used that determined the probability of classifying each gene as highly expressed by mistake. This method looked at the expression levels of each gene in each sample and assigns a p-value to that gene corresponding to how likely its expression pattern is not the result of being a constitutively and highly expressed gene. Therefore, genes with very low probabilities are likely to be constitutive and highly expressed. Using this approach, candidate genes with p-values of less than 0.005 were selected.

The two lists of candidate genes were combined to yield a master list of *Arabidopsis* gene candidates that are broadly expressed in all cell-types and development stages of root tissue.

To assess expression in aerial tissue and responsiveness to abiotic stress, the expression profiles of these candidates were also analyzed in the AtGenExpress Development and Abiotic Stress datasets (available on the World Wide Web at the site weigelworld.org/resources/microarray/AtGenExpress). Candidates were further selected that showed significant expression in aerial tissue throughout development and also demonstrated little or no response to abiotic stresses according to these databases.

To identify regulatory polynucleotide molecules responsible for driving high constitutive expression of these candidate genes, upstream sequences of 1500 bp or less of the selected gene candidates were determined. Because transcription start sites are not always known, sequences upstream of the translation start site were used in all cases. Therefore, the selected regulatory polynucleotide molecules contain an endogenous 5'-UTR, and some of the endogenous 5'-UTRs contain introns. The use of such introns in expression constructs containing these regulatory sequences may increase expression through IME. Without being limited by theory, IME may be important for highly expressed constitutive genes, such as those identified here. To capture these regulatory molecules in genes that do not contain a 5'-UTR intron, chimeric regulatory polynucleotide molecules may be constructed wherein the first intron from the gene of interest is fused to the 3'-end of the 5'-UTR of the regulatory polynucleotide (which may be from the same or a different (e.g., exogenous) gene). To ensure efficient intron splicing, the introns in these chimeric molecules may be flanked by consensus splice sites.

The regulatory polynucleotides listed in Table 1 below were selected. Sequences including the regulatory polynucleotides plus the first intron from the coding region added at the 3' end of the 5' UTR are indicated by the corresponding gene accession number and the indicator "+intron":

TABLE 1

| FIG. | SEQ ID NO: | Corresponding Gene Accession No. |
|---|---|---|
| 1 | 1 | AT1G02780 |
| 2 | 2 | AT3G01280 |
| 3 | 3 | AT1G43170 |
| 4 | 4 | AT1G67430 |
| 5 | 5 | AT1G76200 |
| 6 | 6 | AT2G16850 |
| 7 | 7 | AT2G31490 |
| 8 | 8 | AT4G00860 |
| 9 | 9 | AT5G08690 |
| 10 | 10 | AT5G53560 |
| 11 | 11 | AT1G07600 |
| 12 | 12 | AT1G67350 |
| 13 | 13 | AT1G78380 |
| 14 | 14 | AT1G76200 (+intron) |
| 15 | 15 | AT1G78380 (+intron) |
| 16 | 16 | AT1G02780 (+intron) |
| 17 | 17 | AT5G08690 (+intron) |
| 18 | 18 | AT1G67430 (+intron) |
| 19 | 19 | AT2G16850 (+intron) |
| 20 | 20 | AT2G31490 (+intron) |
| 21 | 21 | AT3G01280 (+intron) |
| 22 | 22 | AT1G07600 (+intron) |
| 23 | 23 | AT4G05320 |
| 24 | 24 | AT5G20290 |
| 25 | 25 | AT5G42980 |
| 26 | 26 | AT3G60245 |
| 27 | 27 | AT3G17390 |
| 28 | 28 | AT3G04400 |
| 29 | 29 | AT5G20290 (+intron) |
| 30 | 30 | AT5G42980 (+intron) |
| 31 | 31 | AT3G60245 (+intron) |
| 32 | 32 | AT3G04400 (+intron) |
| 33 | 33 | AT2G47170 |
| 34 | 34 | AT1G65930 |
| 35 | 35 | AT1G02500 |
| 36 | 36 | AT2G45960 |
| 37 | 37 | AT5G02380 |
| 38 | 38 | AT1G15930 |
| 39 | 39 | AT4G33865 |
| 40 | 40 | AT2G18020 |
| 41 | 41 | AT4G34050 |
| 42 | 42 | AT3G09840 |
| 43 | 43 | AT2G45070 |
| 44 | 44 | AT5G43940 |
| 45 | 45 | AT5G64350 |
| 46 | 46 | AT5G48810 |
| 47 | 47 | AT5G19760 |
| 48 | 48 | AT2G28910 |
| 49 | 49 | AT2G23090 |
| 50 | 50 | AT5G02960 |
| 51 | 51 | AT3G09500 |
| 52 | 52 | AT1G66410 |
| 53 | 53 | AT1G04270 |
| 54 | 54 | AT2G46330 |
| 55 | 55 | AT5G42300 |
| 56 | 56 | AT5G47930 |
| 57 | 57 | AT2G33040 |
| 58 | 58 | AT5G14030 |
| 59 | 59 | AT1G77940 |
| 60 | 60 | AT4G36130 |
| 61 | 61 | AT2G36530 |
| 62 | 62 | AT5G15200 |
| 63 | 63 | AT1G65930, +intron |
| 64 | 64 | AT2G45960, +intron |
| 65 | 65 | AT5G02380, +intron |
| 66 | 66 | AT4G33865, +intron |
| 67 | 67 | AT2G18020, +intron |
| 68 | 68 | AT4G34050, +intron |
| 69 | 69 | AT3G09840, +intron |
| 70 | 70 | AT5G43940, +intron |
| 71 | 71 | AT5G64350, +intron |
| 72 | 72 | AT5G48810, +intron |
| 73 | 73 | AT5G19760, +intron |
| 74 | 74 | AT2G23090, +intron |
| 75 | 75 | AT5G02960, +intron |
| 76 | 76 | AT3G09500, +intron |
| 77 | 77 | AT1G66410, +intron |
| 78 | 78 | AT1G04270, +intron |
| 79 | 79 | AT5G42300, +intron |
| 80 | 80 | AT5G47930, +intron |
| 81 | 81 | AT2G33040, +intron |
| 82 | 82 | AT5G14030, +intron |
| 83 | 83 | AT1G77940, +intron |
| 84 | 84 | AT4G36130, +intron |
| 85 | 85 | AT2G36530, +intron |
| 86 | 86 | AT5G15200, +intron |

The nucleic acid sequences provided in FIGS. 1 through 86 are annotated to indicate one transcription start site (Capital letter in bold), the endogenous 5'-UTR intron sequences (double underlining), the first intron from the coding sequence (single underlining), and any added intron splice sequences (bold italics). All *Arabidopsis* genome sequences and annotations (i.e. transcription start sites, translation start sites, and introns) are from the *Arabidopsis* Information Resource (TAIR, available on the worldwide web at the address *Arabidopsis*.org/index.jsp).

Example 2

Endogenous Expression of Candidate *Arabidopsis* Genes

This example shows the endogenous expression data of the genes identified through the bioinformatics filtering of Example 1. Endogenous gene expression data is provided for each gene corresponding to each of the identified *Arabidopsis* regulatory polynucleotides is provided in FIGS. 213-261. All data shown in the figures are GC-RMA (GeneChip-RMA) normalized expression values (log 2 scale) from Affymetrix ATH1 microarrays which allow the detection of about 24,000 protein-encoding genes from *Arabidopsis thaliana*. For each gene, four plots labeled A-D are shown in the figures. Table 2 below shows the correspondence between the regulatory polynucleotides in Example 1 and the expression plots of FIGS. 213-261.

TABLE 2

| Expression FIG. (Gene Accession No.) | Regulatory Polynucleotide SEQ ID NOS (Corresponding Gene Accession No.) |
|---|---|
| 213A-D (AT1G02780) | 1 (AT1G02780) |
| | 16 (AT1G02780 + intron) |
| 214A-D (AT3G01280) | 2 (AT3G01280) |
| | 21 (AT3G01280 + intron) |
| 215A-D (AT1G43170) | 3 (AT1G43170) |

TABLE 2-continued

| Expression FIG. (Gene Accession No.) | Regulatory Polynucleotide SEQ ID NOS (Corresponding Gene Accession No.) |
|---|---|
| 216A-D (AT1G67430) | 4 (AT1G67430)<br>18 (AT1G67430 + intron) |
| 217A-D (AT1G76200) | 5 (AT1G76200)<br>14 (AT1G76200 + intron) |
| 218A-D (AT2G16850) | 6 (AT2G16850)<br>19 (AT2G16850 + intron) |
| 219A-D (AT2G31490) | 7 (AT2G31490)<br>20 (AT2G31490 + intron) |
| 220A-D (AT4G00860) | 8 (AT4G00860) |
| 221A-D (AT5G08690) | 9 (AT5G08690)<br>17 (AT5G08690 + intron) |
| 222A-D (AT5G53560) | 10 (AT5G53560) |
| 223A-D (AT1G07600) | 11 (AT1G07600)<br>22 (AT1G07600 + intron) |
| 224A-D (AT1G67350) | 12 (AT1G67350) |
| 225A-D (AT1G78380) | 13 (AT1G78380)<br>15 (AT1G78380 + intron) |
| 226A-D (AT4G05320) | 23 (AT4G05320) |
| 227A-D (AT5G20290) | 24 (AT5G20290)<br>29 (AT5G20290 + intron) |
| 228A-D (AT5G42980) | 25 (AT5G42980)<br>30 (AT5G42980 + intron) |
| 229A-D (AT3G60245) | 26 (AT3G60245)<br>31 (AT3G60245 + intron) |
| 230A-D (AT3G17390) | 27 (AT3G17390) |
| 231A-D (AT3G04400) | 28 (AT3G04400)<br>32 (AT3G04400 + intron) |
| 232A-D (AT2G47170) | 33 (AT2G47170) |
| 233A-D (AT1G65930) | 34 (AT1G65930)<br>63 (AT1G65930 + intron) |
| 234A-D (AT1G02500) | 35 (AT1G02500) |
| 235A-D (AT2G45960) | 36 (AT2G45960)<br>64 (AT2G45960 + intron) |
| 236A-D (AT5G02380) | 37 (AT5G02380)<br>65 (AT5G02380 + intron) |
| 237A-D (AT1G15930) | 38 (AT1G15930) |
| 238A-D (AT4G33865) | 39 (AT4G33865)<br>66 (AT4G33865 + intron) |
| 239A-D (AT2G18020) | 40 (AT2G18020)<br>67 (AT2G18020 + intron) |
| 240A-D (AT4G34050) | 41 (AT4G34050)<br>68 (AT4G34050 + intron) |
| 241A-D (AT3G09840) | 42 (AT3G09840)<br>69 (AT3G09840 + intron) |
| 242A-D (AT2G45070) | 43 (AT2G45070) |
| 243A-D (AT5G43940) | 44 (AT5G43940)<br>70 (AT5G43940 + intron) |
| 244A-D (AT5G64350) | 45 (AT5G64350)<br>71 (AT5G64350 + intron) |
| 245A-D (AT5G48810) | 46 (AT5G48810)<br>72 (AT5G48810 + intron) |
| 246A-D (AT5G19760) | 47 (AT5G19760)<br>73 (AT5G19760 + intron) |
| 247A-D (AT2G28910) | 48 (AT2G28910) |
| 248A-D (AT2G23090) | 49 (AT2G23090)<br>74 (AT2G23090 + intron) |
| 249A-D (AT5G02960) | 50 (AT5G02960)<br>75 (AT5G02960 + intron) |
| 250A-D (AT3G09500) | 51 (AT3G09500)<br>76 (AT3G09500 + intron) |
| 251A-D (AT1G66410) | 52 (AT1G66410)<br>77 (AT1G66410 + intron) |
| 252A-D (AT1G04270) | 53 (AT1G04270)<br>78 (AT1G04270 + intron) |
| 253A-D (AT2G46330) | 54 (AT2G46330) |
| 254A-D (AT5G42300) | 55 (AT5G42300)<br>79 (AT5G42300 + intron) |
| 255A-D (AT5G47930) | 56 (AT5G47930)<br>80 (AT5G47930 + intron) |
| 256A-D (AT2G33040) | 57 (AT2G33040)<br>81 (AT2G33040 + intron) |
| 257A-D (AT5G14030) | 58 (AT5G14030)<br>82 (AT5G14030 + intron) |
| 258A-D (AT1G77940) | 59 (AT1G77940)<br>83 (AT1G77940 + intron) |
| 259A-D (AT4G36130) | 60 (AT4G36130)<br>84 (AT4G36130 + intron) |

TABLE 2-continued

| Expression FIG. (Gene Accession No.) | Regulatory Polynucleotide SEQ ID NOS (Corresponding Gene Accession No.) |
|---|---|
| 260A-D (AT2G36530) | 61 (AT2G36530)<br>85 (AT2G36530 + intron) |
| 261A-D (AT5G15200) | 62 (AT5G15200)<br>86 (AT5G15200 + intron) |

Plots A and B are derived from data published by Brady et al. (*Science,* 318:801-806 (2007)). Plot A in each figure shows expression values from cells sorted on the basis of expressing the indicated GFP marker. Table 3 contains a key showing the specific cell types in which each marker is expressed. The table provides a description of cell types together with the associated markers. This table defines the relationship between cell-type and marker line, including which longitudinal sections of each cell-type are included. Lateral Root Primordia is included as a cell-type in this table, even though it may be a collection of multiple immature cell types. There are also no markers that differentiate between metaxylem and protoxylem or between metaphloem and protophloem, so those cell types are labeled Xylem and Phloem respectively. Together, these data provide expression information for virtually all cell-types found in the *Arabidopsis* root.

TABLE 3

| Cell Type | Markers | Longitudinal Section |
|---|---|---|
| Lateral root cap | LRC | 0-5 |
| Columella | PET111 | 0 |
| Quiescent centre | AGL42 | 1 |
| | RM1000 | 1 |
| | SCR5 | 1 |
| Hair cell | N/A | 1-6 |
| | COBL9 | 7-12 |
| Non-hair cell | GL2 | 1-12 |
| Cortex | J0571 | 1-12 |
| | CORTEX | 6-12 |
| Endodermis | J0571 | 1-12 |
| | SCR5 | 1-12 |
| Xylem pole pericycle | WOL | 1-8 |
| | JO121 | 8-12 |
| | J2661 | 12 |
| Phloem pole pericycle | WOL | 1-8 |
| | S17 | 7-12 |
| | J2661 | 12 |
| Phloem | S32 | 1-12 |
| | WOL | 1-8 |
| Phloem ccs | SUC2 | 9-12 |
| | WOL | 1-8 |
| Xylem | S4 | 1-6 |
| | S18 | 7-12 |
| | WOL | 1-8 |
| Lateral root primordial | RM1000 | 11 |
| Procambium | WOL | 1-8 |

Plot B in each figure shows expression values from root sections along the longitudinal axis. Different regions along this axis correspond to different developmental stages of root cell development. In particular, section 0 corresponds to the columella, sections 1-6 correspond to the meristematic zone, sections 7-8 correspond to the elongation zone, and sections 9-12 correspond to the maturation zone.

Plots C and D in each figure are derived from publically available expression data of the AtGeneExpress project (available on the World Wide Web at weigelworld.org/resources/microarray/AtGenExpress). Plot C shows developmental specific expression as described by Schmid et al. (Nat. Genet., 37: 501-506 (2005)). A key for the samples in this dataset is provided in Table 4. For ease of visualization, root expression values are indicated with black bars, shoot expression with white bars, flower expression with coarse hatched bars, and seed expression with fine hatched bars.

TABLE 4

| No | Sample ID | Experiment Description | Genotype | Tissue | Age | Photoperiod | Substrate |
|---|---|---|---|---|---|---|---|
| 1 | ATGE_1 | development baseline | Wt | cotyledons | 7 days | continuous light | soil |
| 2 | ATGE_2 | development baseline | Wt | hypocotyl | 7 days | continuous light | soil |
| 3 | ATGE_3 | development baseline | Wt | roots | 7 days | continuous light | soil |
| 4 | ATGE_4 | development baseline | Wt | shoot apex, vegetative + young leaves | 7 days | continuous light | soil |
| 5 | ATGE_5 | development baseline | Wt | leaves 1 + 2 | 7 days | continuous light | soil |
| 6 | ATGE_6 | development baseline | Wt | shoot apex, vegetative | 7 days | continuous light | soil |
| 7 | ATGE_7 | development baseline | Wt | seedling, green parts | 7 days | continuous light | soil |
| 8 | ATGE_8 | development baseline | Wt | shoot apex, transition (before bolting) | 14 days | continuous light | soil |
| 9 | ATGE_9 | development baseline | Wt | roots | 17 days | continuous light | soil |
| 10 | ATGE_10 | development baseline | Wt | rosette leaf #4, 1 cm long | 10 days | continuous light | soil |
| 11 | ATGE_11 | development baseline | gl1-T | rosette leaf #4, 1 cm long | 10 days | continuous light | soil |
| 12 | ATGE_12 | development baseline | Wt | rosette leaf #2 | 17 days | continuous light | soil |
| 13 | ATGE_13 | development baseline | Wt | rosette leaf #4 | 17 days | continuous light | soil |
| 14 | ATGE_14 | development baseline | Wt | rosette leaf #6 | 17 days | continuous light | soil |
| 15 | ATGE_15 | development baseline | Wt | rosette leaf #8 | 17 days | continuous light | soil |
| 16 | ATGE_16 | development baseline | Wt | rosette leaf # 10 | 17 days | continuous light | soil |
| 17 | ATGE_17 | development baseline | Wt | rosette leaf # 12 | 17 days | continuous light | soil |
| 18 | ATGE_18 | development baseline | gl1-T | rosette leaf # 12 | 17 days | continuous light | soil |
| 19 | ATGE_19 | development baseline | Wt | leaf 7, petiole | 17 days | continuous light | soil |
| 20 | ATGE_20 | development baseline | Wt | leaf 7, proximal half | 17 days | continuous light | soil |
| 21 | ATGE_21 | development baseline | Wt | leaf 7, distal half | 17 days | continuous light | soil |
| 22 | ATGE_22 | development baseline | Wt | developmental drift, entire rosette after transition to flowering, but before bolting | 21 days | continuous light | soil |
| 23 | ATGE_23 | development baseline | Wt | as above | 22 days | continuous light | soil |
| 24 | ATGE_24 | development baseline | Wt | as above | 23 days | continuous light | soil |
| 25 | ATGE_25 | development baseline | Wt | senescing leaves | 35 days | continuous light | soil |
| 26 | ATGE_26 | development baseline | Wt | cauline leaves | 21+ days | continuous light | soil |
| 27 | ATGE_27 | development baseline | Wt | stem, 2nd internode | 21+ days | continuous light | soil |
| 28 | ATGE_28 | development baseline | Wt | 1st node | 21+ days | continuous light | soil |
| 29 | ATGE_29 | development baseline | Wt | shoot apex, inflorescence (after bolting) | 21 days | continuous light | soil |
| 30 | ATGE_31 | development baseline | Wt | flowers stage 9 | 21+ days | continuous light | soil |
| 31 | ATGE_32 | development baseline | Wt | flowers stage 10/11 | 21+ days | continuous light | soil |
| 32 | ATGE_33 | development baseline | Wt | flowers stage 12 | 21+ days | continuous light | soil |
| 33 | ATGE_34 | development baseline | Wt | flowers stage 12, sepals | 21+ days | continuous light | soil |

TABLE 4-continued

| No | Sample ID | Experiment Description | Geno-type | Tissue | Age | Photo-period | Substrate |
|---|---|---|---|---|---|---|---|
| 34 | ATGE_35 | development baseline | Wt | flowers stage 12, petals | 21+ days | continuous light | soil |
| 35 | ATGE_36 | development baseline | Wt | flowers stage 12, stamens | 21+ days | continuous light | soil |
| 36 | ATGE_37 | development baseline | Wt | flowers stage 12, carpels | 21+ days | continuous light | soil |
| 37 | ATGE_39 | development baseline | Wt | flowers stage 15 | 21+ days | continuous light | soil |
| 38 | ATGE_40 | development baseline | Wt | flowers stage 15, pedicels | 21+ days | continuous light | soil |
| 39 | ATGE_41 | development baseline | Wt | flowers stage 15, sepals | 21+ days | continuous light | soil |
| 40 | ATGE_42 | development baseline | Wt | flowers stage 15, petals | 21+ days | continuous light | soil |
| 41 | ATGE_43 | development baseline | Wt | flowers stage 15, stamen | 21+ days | continuous light | soil |
| 42 | ATGE_45 | development baseline | Wt | flowers stage 15, carpels | 21+ days | continuous light | soil |
| 43 | ATGE_46 | development baseline | clv3-7 | shoot apex, inflorescence (after bolting) | 21+ days | continuous light | soil |
| 44 | ATGE_47 | development baseline | lfy-12 | shoot apex, inflorescence (after bolting) | 21+ days | continuous light | soil |
| 45 | ATGE_48 | development baseline | ap1-15 | shoot apex, inflorescence (after bolting) | 21+ days | continuous light | soil |
| 46 | ATGE_49 | development baseline | ap2-6 | shoot apex, inflorescence (after bolting) | 21+ days | continuous light | soil |
| 47 | ATGE_50 | development baseline | ap3-6 | shoot apex, inflorescence (after bolting) | 21+ days | continuous light | soil |
| 48 | ATGE_51 | development baseline | ag-12 | shoot apex, inflorescence (after bolting) | 21+ days | continuous light | soil |
| 49 | ATGE_52 | development baseline | ufo-1 | shoot apex, inflorescence (after bolting) | 21+ days | continuous light | soil |
| 50 | ATGE_53 | development baseline | clv3-7 | flower stage 12; multi-carpel gynoeceum; enlarged meristem; increased organ number | 21+ days | continuous light | soil |
| 51 | ATGE_54 | development baseline | lfy-12 | flower stage 12; shoot characteristics; most organs leaf-like | 21+ days | continuous light | soil |
| 52 | ATGE_55 | development baseline | ap1-15 | flower stage 12; sepals replaced by leaf-like organs, petals mostly lacking, 2° flowers | 21+ days | continuous light | soil |
| 53 | ATGE_56 | development baseline | ap2-6 | flower stage 12; no sepals or petals | 21+ days | continuous light | soil |
| 54 | ATGE_57 | development baseline | ap3-6 | flower stage 12; no petals or stamens | 21+ days | continuous light | soil |
| 55 | ATGE_58 | development baseline | ag-12 | flower stage 12; no stamens or carpels | 21+ days | continuous light | soil |
| 56 | ATGE_59 | development baseline | ufo-1 | flower stage 12; filamentous organs in whorls two and three | 21+ days | continuous light | soil |

TABLE 4-continued

| No | Sample ID | Experiment Description | Geno-type | Tissue | Age | Photo-period | Substrate |
|---|---|---|---|---|---|---|---|
| 57 | ATGE_73 | pollen | Wt | mature pollen | 6 wk | continuous light | soil |
| 58 | ATGE_76 | seed & silique development | Wt | siliques, w/ seeds stage 3; mid globular to early heart embryos | 8 wk | long day (16/8) | soil |
| 59 | ATGE_77 | seed & silique development | Wt | siliques, w/ seeds stage 4; early to late heart embryos | 8 wk | long day (16/8) | soil |
| 60 | ATGE_78 | seed & silique development | Wt | siliques, w/ seeds stage 5; late heart to mid torpedo embryos | 8 wk | long day (16/8) | soil |
| 61 | ATGE_79 | seed & silique development | Wt | seeds, stage 6, w/o siliques; mid to late torpedo embryos | 8 wk | long day (16/8) | soil |
| 62 | ATGE_81 | seed & silique development | Wt | seeds, stage 7, w/o siliques; late torpedo to early walking-stick embryos | 8 wk | long day (16/8) | soil |
| 63 | ATGE_82 | seed & silique development | Wt | seeds, stage 8, w/o siliques; walking-stick to early curled cotyledons embryos | 8 wk | long day (16/8) | soil |
| 64 | ATGE_83 | seed & silique development | Wt | seeds, stage 9, w/o siliques; curled cotyledons to early green cotyledons embryos | 8 wk | long day (16/8) | soil |
| 65 | ATGE_84 | seed & silique development | Wt | seeds, stage 10, w/o siliques; green cotyledons embryos | 8 wk | long day (16/8) | soil |
| 66 | ATGE_87 | phase change | Wt | vegetative rosette | 7 days | short day (10/14) | soil |
| 67 | ATGE_89 | phase change | Wt | vegetative rosette | 14 days | short day (10/14) | soil |
| 68 | ATGE_90 | phase change | Wt | vegetative rosette | 21 days | short day (10/14) | soil |
| 69 | ATGE_91 | comparison with CAGE | Wt | leaf | 15 days | long day (16/8) | 1x MS agar, 1% sucrose |
| 70 | ATGE_92 | comparison with CAGE | Wt | flower | 28 days | long day (16/8) | Soil |
| 71 | ATGE_93 | comparison with CAGE | Wt | root | 15 days | long day (16/8) | 1x MS agar, 1% sucrose |
| 72 | ATGE_94 | development on MS agar | Wt | root | 8 days | continuous light | 1x MS agar |
| 73 | ATGE_95 | development on MS agar | Wt | root | 8 days | continuous light | 1x MS agar, 1% sucrose |
| 74 | ATGE_96 | development on MS agar | Wt | seedling, green parts | 8 days | continuous light | 1x MS agar |
| 75 | ATGE_97 | development on MS agar | Wt | seedling, green parts | 8 days | continuous light | 1x MS agar, 1% sucrose |
| 76 | ATGE_98 | development on MS agar | Wt | root | 21 days | continuous light | 1x MS agar |

TABLE 4-continued

| No | Sample ID | Experiment Description | Genotype | Tissue | Age | Photoperiod | Substrate |
|---|---|---|---|---|---|---|---|
| 77 | ATGE_99 | development on MS agar | Wt | root | 21 days | continuous light | 1x MS agar, 1% sucrose |
| 78 | ATGE_100 | development on MS agar | Wt | seedling, green parts | 21 days | continuous light | 1x MS agar |
| 79 | ATGE_101 | development on MS agar | Wt | seedling, green parts | 21 days | continuous light | 1x MS agar, 1% sucrose |

Plot D in each figure shows expression in response to abiotic stress as described by Kilian et al. (*Plant J.,* 50: 347-363 (2007)). The data are presented as expression values from pairs of shoots (white bars) and roots (black bars) per treatment. A key for the samples in this dataset is presented in Table 5. The table identifies the codes that are used along the x-axis in plot D in each figure. The codes are presented in 4 digit format, where the first digit represents the treatment (i.e., control=0, cold=1, osmotic stress=2, etc.), the second digit represents the time point, the third digit represents the tissue (1=shoot and 2=root), and the fourth digit represents the replication number. Since the figures provide the averages of the first and second replication, the last digit is not shown in the figures.

TABLE 5

Abiotic Stress Key

| Code | Treatment | Time point | Organ | Sample |
|---|---|---|---|---|
| 0011 | Control | 0 h | Shoots | 1 |
| 0012 | Control | 0 h | Shoots | 2 |
| 0021 | Control | 0 h | Roots | 1 |
| 0022 | Control | 0 h | Roots | 2 |
| 0711 | Control | 0.25 h | Shoots | 1 |
| 0712 | Control | 0.25 h | Shoots | 2 |
| 0721 | Control | 0.25 h | Roots | 1 |
| 0722 | Control | 0.25 h | Roots | 2 |
| 0111 | Control | 0.5 h | Shoots | 1 |
| 0112 | Control | 0.5 h | Shoots | 2 |
| 0121 | Control | 0.5 h | Roots | 1 |
| 0122 | Control | 0.5 h | Roots | 2 |
| 0211 | Control | 1.0 h | Shoots | 1 |
| 0212 | Control | 1.0 h | Shoots | 2 |
| 0221 | Control | 1.0 h | Roots | 1 |
| 0222 | Control | 1.0 h | Roots | 2 |
| 0311 | Control | 3.0 h | Shoots | 1 |
| 0312 | Control | 3.0 h | Shoots | 2 |
| 0321 | Control | 3.0 h | Roots | 1 |
| 0322 | Control | 3.0 h | Roots | 2 |
| 0811 | Control | 4.0 h | Shoots | 1 |
| 0812 | Control | 4.0 h | Shoots | 2 |
| 0821 | Control | 4.0 h | Roots | 1 |
| 0822 | Control | 4.0 h | Roots | 2 |
| 0411 | Control | 6.0 h | Shoots | 1 |
| 0412 | Control | 6.0 h | Shoots | 2 |
| 0421 | Control | 6.0 h | Roots | 1 |
| 0422 | Control | 6.0 h | Roots | 2 |
| 0511 | Control | 12.0 h | Shoots | 1 |
| 0512 | Control | 12.0 h | Shoots | 2 |
| 0521 | Control | 12.0 h | Roots | 1 |
| 0522 | Control | 12.0 h | Roots | 2 |
| 0611 | Control | 24.0 h | Shoots | 1 |
| 0612 | Control | 24.0 h | Shoots | 2 |
| 0621 | Control | 24.0 h | Roots | 1 |
| 0622 | Control | 24.0 h | Roots | 2 |
| 1111 | Cold (4° C.) | 0.5 h | Shoots | 1 |
| 1112 | Cold (4° C.) | 0.5 h | Shoots | 2 |

TABLE 5-continued

Abiotic Stress Key

| Code | Treatment | Time point | Organ | Sample |
|---|---|---|---|---|
| 1121 | Cold (4° C.) | 0.5 h | Roots | 1 |
| 1122 | Cold (4° C.) | 0.5 h | Roots | 2 |
| 1211 | Cold (4° C.) | 1.0 h | Shoots | 1 |
| 1212 | Cold (4° C.) | 1.0 h | Shoots | 2 |
| 1221 | Cold (4° C.) | 1.0 h | Roots | 1 |
| 1222 | Cold (4° C.) | 1.0 h | Roots | 2 |
| 1311 | Cold (4° C.) | 3.0 h | Shoots | 1 |
| 1312 | Cold (4° C.) | 3.0 h | Shoots | 2 |
| 1321 | Cold (4° C.) | 3.0 h | Roots | 1 |
| 1322 | Cold (4° C.) | 3.0 h | Roots | 2 |
| 1411 | Cold (4° C.) | 6.0 h | Shoots | 1 |
| 1412 | Cold (4° C.) | 6.0 h | Shoots | 2 |
| 1421 | Cold (4° C.) | 6.0 h | Roots | 1 |
| 1422 | Cold (4° C.) | 6.0 h | Roots | 2 |
| 1511 | Cold (4° C.) | 12.0 h | Shoots | 1 |
| 1512 | Cold (4° C.) | 12.0 h | Shoots | 2 |
| 1521 | Cold (4° C.) | 12.0 h | Roots | 1 |
| 1522 | Cold (4° C.) | 12.0 h | Roots | 2 |
| 1611 | Cold (4° C.) | 24.0 h | Shoots | 1 |
| 1612 | Cold (4° C.) | 24.0 h | Shoots | 2 |
| 1621 | Cold (4° C.) | 24.0 h | Roots | 1 |
| 1622 | Cold (4° C.) | 24.0 h | Roots | 2 |
| 2111 | Osmotic stress | 0.5 h | Shoots | 1 |
| 2112 | Osmotic stress | 0.5 h | Shoots | 2 |
| 2121 | Osmotic stress | 0.5 h | Roots | 1 |
| 2122 | Osmotic stress | 0.5 h | Roots | 2 |
| 2211 | Osmotic stress | 1.0 h | Shoots | 1 |
| 2212 | Osmotic stress | 1.0 h | Shoots | 2 |
| 2221 | Osmotic stress | 1.0 h | Roots | 1 |
| 2222 | Osmotic stress | 1.0 h | Roots | 2 |
| 2311 | Osmotic stress | 3.0 h | Shoots | 1 |
| 2312 | Osmotic stress | 3.0 h | Shoots | 2 |
| 2321 | Osmotic stress | 3.0 h | Roots | 1 |
| 2322 | Osmotic stress | 3.0 h | Roots | 2 |
| 2411 | Osmotic stress | 6.0 h | Shoots | 1 |
| 2412 | Osmotic stress | 6.0 h | Shoots | 2 |
| 2421 | Osmotic stress | 6.0 h | Roots | 1 |
| 2422 | Osmotic stress | 6.0 h | Roots | 2 |
| 2511 | Osmotic stress | 12.0 h | Shoots | 1 |
| 2512 | Osmotic stress | 12.0 h | Shoots | 2 |
| 2521 | Osmotic stress | 12.0 h | Roots | 1 |
| 2522 | Osmotic stress | 12.0 h | Roots | 2 |
| 2611 | Osmotic stress | 24.0 h | Shoots | 1 |
| 2612 | Osmotic stress | 24.0 h | Shoots | 2 |
| 2621 | Osmotic stress | 24.0 h | Roots | 1 |
| 2622 | Osmotic stress | 24.0 h | Roots | 2 |
| 3111 | Salt stress | 0.5 h | Shoots | 1 |
| 3112 | Salt stress | 0.5 h | Shoots | 2 |
| 3121 | Salt stress | 0.5 h | Roots | 1 |
| 3122 | Salt stress | 0.5 h | Roots | 2 |
| 3211 | Salt stress | 1.0 h | Shoots | 1 |
| 3212 | Salt stress | 1.0 h | Shoots | 2 |
| 3221 | Salt stress | 1.0 h | Roots | 1 |
| 3222 | Salt stress | 1.0 h | Roots | 2 |
| 3311 | Salt stress | 3.0 h | Shoots | 1 |
| 3312 | Salt stress | 3.0 h | Shoots | 2 |

TABLE 5-continued

Abiotic Stress Key

| Code | Treatment | Time point | Organ | Sample |
|---|---|---|---|---|
| 3321 | Salt stress | 3.0 h | Roots | 1 |
| 3322 | Salt stress | 3.0 h | Roots | 2 |
| 3411 | Salt stress | 6.0 h | Shoots | 1 |
| 3412 | Salt stress | 6.0 h | Shoots | 2 |
| 3421 | Salt stress | 6.0 h | Roots | 1 |
| 3422 | Salt stress | 6.0 h | Roots | 2 |
| 3511 | Salt stress | 12.0 h | Shoots | 1 |
| 3512 | Salt stress | 12.0 h | Shoots | 2 |
| 3521 | Salt stress | 12.0 h | Roots | 1 |
| 3522 | Salt stress | 12.0 h | Roots | 2 |
| 3611 | Salt stress | 24.0 h | Shoots | 1 |
| 3612 | Salt stress | 24.0 h | Shoots | 2 |
| 3621 | Salt stress | 24.0 h | Roots | 1 |
| 3622 | Salt stress | 24.0 h | Roots | 2 |
| 4711 | Drought stress | 0.25 h | Shoots | 1 |
| 4712 | Drought stress | 0.25 h | Shoots | 2 |
| 4721 | Drought stress | 0.25 h | Roots | 1 |
| 4722 | Drought stress | 0.25 h | Roots | 2 |
| 4111 | Drought stress | 0.5 h | Shoots | 1 |
| 4112 | Drought stress | 0.5 h | Shoots | 2 |
| 4121 | Drought stress | 0.5 h | Roots | 1 |
| 4122 | Drought stress | 0.5 h | Roots | 2 |
| 4211 | Drought stress | 1.0 h | Shoots | 1 |
| 4212 | Drought stress | 1.0 h | Shoots | 2 |
| 4221 | Drought stress | 1.0 h | Roots | 1 |
| 4222 | Drought stress | 1.0 h | Roots | 2 |
| 4311 | Drought stress | 3.0 h | Shoots | 1 |
| 4312 | Drought stress | 3.0 h | Shoots | 2 |
| 4321 | Drought stress | 3.0 h | Roots | 1 |
| 4322 | Drought stress | 3.0 h | Roots | 2 |
| 4411 | Drought stress | 6.0 h | Shoots | 1 |
| 4412 | Drought stress | 6.0 h | Shoots | 2 |
| 4421 | Drought stress | 6.0 h | Roots | 1 |
| 4422 | Drought stress | 6.0 h | Roots | 2 |
| 4511 | Drought stress | 12.0 h | Shoots | 1 |
| 4512 | Drought stress | 12.0 h | Shoots | 2 |
| 4521 | Drought stress | 12.0 h | Roots | 1 |
| 4522 | Drought stress | 12.0 h | Roots | 2 |
| 4611 | Drought stress | 24.0 h | Shoots | 1 |
| 4612 | Drought stress | 24.0 h | Shoots | 2 |
| 4621 | Drought stress | 24.0 h | Roots | 1 |
| 4622 | Drought stress | 24.0 h | Roots | 2 |
| 5111 | Genotoxic stress | 0.5 h | Shoots | 1 |
| 5112 | Genotoxic stress | 0.5 h | Shoots | 2 |
| 5121 | Genotoxic stress | 0.5 h | Roots | 1 |
| 5122 | Genotoxic stress | 0.5 h | Roots | 2 |
| 5211 | Genotoxic stress | 1.0 h | Shoots | 1 |
| 5212 | Genotoxic stress | 1.0 h | Shoots | 2 |
| 5221 | Genotoxic stress | 1.0 h | Roots | 1 |
| 5222 | Genotoxic stress | 1.0 h | Roots | 2 |
| 5311 | Genotoxic stress | 3.0 h | Shoots | 1 |
| 5312 | Genotoxic stress | 3.0 h | Shoots | 2 |
| 5321 | Genotoxic stress | 3.0 h | Roots | 1 |
| 5322 | Genotoxic stress | 3.0 h | Roots | 2 |
| 5411 | Genotoxic stress | 6.0 h | Shoots | 1 |
| 5412 | Genotoxic stress | 6.0 h | Shoots | 2 |
| 5421 | Genotoxic stress | 6.0 h | Roots | 1 |
| 5422 | Genotoxic stress | 6.0 h | Roots | 2 |
| 5511 | Genotoxic stress | 12.0 h | Shoots | 1 |
| 5512 | Genotoxic stress | 12.0 h | Shoots | 2 |
| 5521 | Genotoxic stress | 12.0 h | Roots | 1 |
| 5522 | Genotoxic stress | 12.0 h | Roots | 2 |
| 5611 | Genotoxic stress | 24.0 h | Shoots | 1 |
| 5612 | Genotoxic stress | 24.0 h | Shoots | 2 |
| 5621 | Genotoxic stress | 24.0 h | Roots | 1 |
| 5622 | Genotoxic stress | 24.0 h | Roots | 2 |
| 6111 | Oxidative stress | 0.5 h | Shoots | 1 |
| 6112 | Oxidative stress | 0.5 h | Shoots | 2 |
| 6124 | Oxidative stress | 0.5 h | Roots | 1 |
| 6122 | Oxidative stress | 0.5 h | Roots | 2 |
| 6211 | Oxidative stress | 1.0 h | Shoots | 1 |
| 6212 | Oxidative stress | 1.0 h | Shoots | 2 |
| 6223 | Oxidative stress | 1.0 h | Roots | 1 |
| 6224 | Oxidative stress | 1.0 h | Roots | 2 |
| 6311 | Oxidative stress | 3.0 h | Shoots | 1 |

TABLE 5-continued

Abiotic Stress Key

| Code | Treatment | Time point | Organ | Sample |
|---|---|---|---|---|
| 6312 | Oxidative stress | 3.0 h | Shoots | 2 |
| 6323 | Oxidative stress | 3.0 h | Roots | 1 |
| 6322 | Oxidative stress | 3.0 h | Roots | 2 |
| 6411 | Oxidative stress | 6.0 h | Shoots | 1 |
| 6412 | Oxidative stress | 6.0 h | Shoots | 2 |
| 6421 | Oxidative stress | 6.0 h | Roots | 1 |
| 6422 | Oxidative stress | 6.0 h | Roots | 2 |
| 6511 | Oxidative stress | 12.0 h | Shoots | 1 |
| 6512 | Oxidative stress | 12.0 h | Shoots | 2 |
| 6523 | Oxidative stress | 12.0 h | Roots | 1 |
| 6524 | Oxidative stress | 12.0 h | Roots | 2 |
| 6611 | Oxidative stress | 24.0 h | Shoots | 1 |
| 6612 | Oxidative stress | 24.0 h | Shoots | 2 |
| 6621 | Oxidative stress | 24.0 h | Roots | 1 |
| 6622 | Oxidative stress | 24.0 h | Roots | 2 |
| 7711 | UV-B stress | 0.25 h | Shoots | 1 |
| 7712 | UV-B stress | 0.25 h | Shoots | 2 |
| 7721 | UV-B stress | 0.25 h | Roots | 1 |
| 7722 | UV-B stress | 0.25 h | Roots | 2 |
| 7111 | UV-B stress | 0.5 h | Shoots | 1 |
| 7112 | UV-B stress | 0.5 h | Shoots | 2 |
| 7121 | UV-B stress | 0.5 h | Roots | 1 |
| 7122 | UV-B stress | 0.5 h | Roots | 2 |
| 7211 | UV-B stress | 1.0 h | Shoots | 1 |
| 7212 | UV-B stress | 1.0 h | Shoots | 2 |
| 7221 | UV-B stress | 1.0 h | Roots | 1 |
| 7222 | UV-B stress | 1.0 h | Roots | 2 |
| 7311 | UV-B stress | 3.0 h | Shoots | 1 |
| 7312 | UV-B stress | 3.0 h | Shoots | 2 |
| 7321 | UV-B stress | 3.0 h | Roots | 1 |
| 7322 | UV-B stress | 3.0 h | Roots | 2 |
| 7411 | UV-B stress | 6.0 h | Shoots | 1 |
| 7412 | UV-B stress | 6.0 h | Shoots | 2 |
| 7421 | UV-B stress | 6.0 h | Roots | 1 |
| 7422 | UV-B stress | 6.0 h | Roots | 2 |
| 7511 | UV-B stress | 12.0 h | Shoots | 1 |
| 7512 | UV-B stress | 12.0 h | Shoots | 2 |
| 7521 | UV-B stress | 12.0 h | Roots | 1 |
| 7522 | UV-B stress | 12.0 h | Roots | 2 |
| 7611 | UV-B stress | 24.0 h | Shoots | 1 |
| 7612 | UV-B stress | 24.0 h | Shoots | 2 |
| 7621 | UV-B stress | 24.0 h | Roots | 1 |
| 7622 | UV-B stress | 24.0 h | Roots | 2 |
| 8715 | Wounding stress | 0.25 h | Shoots | 1 |
| 8712 | Wounding stress | 0.25 h | Shoots | 2 |
| 8723 | Wounding stress | 0.25 h | Roots | 1 |
| 8724 | Wounding stress | 0.25 h | Roots | 2 |
| 8111 | Wounding stress | 0.5 h | Shoots | 1 |
| 8112 | Wounding stress | 0.5 h | Shoots | 2 |
| 8124 | Wounding stress | 0.5 h | Roots | 1 |
| 8126 | Wounding stress | 0.5 h | Roots | 2 |
| 8211 | Wounding stress | 1.0 h | Shoots | 1 |
| 8214 | Wounding stress | 1.0 h | Shoots | 2 |
| 8224 | Wounding stress | 1.0 h | Roots | 1 |
| 8225 | Wounding stress | 1.0 h | Roots | 2 |
| 8313 | Wounding stress | 3.0 h | Shoots | 1 |
| 8314 | Wounding stress | 3.0 h | Shoots | 2 |
| 8324 | Wounding stress | 3.0 h | Roots | 1 |
| 8325 | Wounding stress | 3.0 h | Roots | 2 |
| 8411 | Wounding stress | 6.0 h | Shoots | 1 |
| 8412 | Wounding stress | 6.0 h | Shoots | 2 |
| 8423 | Wounding stress | 6.0 h | Roots | 1 |
| 8424 | Wounding stress | 6.0 h | Roots | 2 |
| 8511 | Wounding stress | 12.0 h | Shoots | 1 |
| 8512 | Wounding stress | 12.0 h | Shoots | 2 |
| 8524 | Wounding stress | 12.0 h | Roots | 1 |
| 8525 | Wounding stress | 12.0 h | Roots | 2 |
| 8611 | Wounding stress | 24.0 h | Shoots | 1 |
| 8612 | Wounding stress | 24.0 h | Shoots | 2 |
| 8624 | Wounding stress | 24.0 h | Roots | 1 |
| 8624_repl_8623 | Wounding stress | 24.0 h | Roots | 2 |
| 9711 | Heat stress | 0.25 h | Shoots | 1 |
| 9712 | Heat stress | 0.25 h | Shoots | 2 |
| 9721 | Heat stress | 0.25 h | Roots | 1 |
| 9722 | Heat stress | 0.25 h | Roots | 2 |

TABLE 5-continued

Abiotic Stress Key

| Code | Treatment | Time point | Organ | Sample |
|---|---|---|---|---|
| 9111 | Heat stress | 0.5 h | Shoots | 1 |
| 9112 | Heat stress | 0.5 h | Shoots | 2 |
| 9121 | Heat stress | 0.5 h | Roots | 1 |
| 9122 | Heat stress | 0.5 h | Roots | 2 |
| 9211 | Heat stress | 1.0 h | Shoots | 1 |
| 9212 | Heat stress | 1.0 h | Shoots | 2 |
| 9221 | Heat stress | 1.0 h | Roots | 1 |
| 9222 | Heat stress | 1.0 h | Roots | 2 |
| 9311 | Heat stress | 3.0 h | Shoots | 1 |
| 9312 | Heat stress | 3.0 h | Shoots | 2 |
| 9321 | Heat stress | 3.0 h | Roots | 1 |
| 9322 | Heat stress | 3.0 h | Roots | 2 |
| 9811 | Heat stress (3 h) + 1 h | 4.0 h | Shoots | 1 |
| 9812 | Heat stress (3 h) + 1 h | 4.0 h | Shoots | 2 |
| 9821 | Heat stress (3 h) + 1 h | 4.0 h | Roots | 1 |
| 9822 | Heat stress (3 h) + 1 h | 4.0 h | Roots | 2 |
| 9411 | Heat stress (3 h) + 3 h | 6.0 h | Shoots | 1 |
| 9412 | Heat stress (3 h) + 3 h | 6.0 h | Shoots | 2 |
| 9421 | Heat stress (3 h) + 3 h | 6.0 h | Roots | 1 |
| 9422 | Heat stress (3 h) + 3 h | 6.0 h | Roots | 2 |
| 9511 | Heat stress (3 h) + 9 h | 12.0 h | Shoots | 1 |
| 9512 | Heat stress (3 h) + 9 h | 12.0 h | Shoots | 2 |
| 9521 | Heat stress (3 h) + 9 h | 12.0 h | Roots | 1 |
| 9522 | Heat stress (3 h) + 9 h | 12.0 h | Roots | 2 |
| 9611 | Heat stress (3 h) + 21 h | 24.0 h | Shoots | 1 |
| 9612 | Heat stress (3 h) + 21 h | 24.0 h | Shoots | 2 |
| 9621 | Heat stress (3 h) + 21 h | 24.0 h | Roots | 1 |
| 9622 | Heat stress (3 h) + 21 h | 24.0 h | Roots | 2 |
| C0_1 | Control | 0 h | Cell culture | 1 |
| C0_2 | Control | 0 h | Cell culture | 2 |
| C1_1 | Control | 3.0 h | Cell culture | 1 |
| C1_2 | Control | 3.0 h | Cell culture | 2 |
| C2_1 | Control | 6.0 h | Cell culture | 1 |
| C2_2 | Control | 6.0 h | Cell culture | 2 |
| C3_1 | Control | 12.0 h | Cell culture | 1 |
| C3_2 | Control | 12.0 h | Cell culture | 2 |
| C4_1 | Control | 24.0 h | Cell culture | 1 |
| C4_2 | Control | 24.0 h | Cell culture | 2 |
| C5_1 | Heat stress | 0.25 h | Cell culture | 1 |
| C5_2 | Heat stress | 0.25 h | Cell culture | 2 |
| C6_1 | Heat stress | 0.5 h | Cell culture | 1 |
| C6_2 | Heat stress | 0.5 h | Cell culture | 2 |
| C7_1 | Heat stress | 1.0 h | Cell culture | 1 |
| C7_2 | Heat stress | 1.0 h | Cell culture | 2 |
| C8_1 | Heat stress | 3.0 h | Cell culture | 1 |
| C8_2 | Heat stress | 3.0 h | Cell culture | 2 |
| C9_1 | Heat stress (3 h) + 1 h | 4.0 h | Cell culture | 1 |
| C9_2 | Heat stress (3 h) + 1 h | 4.0 h | Cell culture | 2 |
| C10_1 | Heat stress (3 h) + 3 h | 6.0 h | Cell culture | 1 |
| C10_2 | Heat stress (3 h) + 3 h | 6.0 h | Cell culture | 2 |
| C11_1 | Heat stress (3 h) + 9 h | 12.0 h | Cell culture | 1 |
| C11_2 | Heat stress (3 h) + 9 h | 12.0 h | Cell culture | 2 |
| C12_1 | Heat stress (3 h) + 21 h | 24.0 h | Cell culture | 1 |
| C12_2 | Heat stress (3 h) + 21 h | 24.0 h | Cell culture | 2 |

Treatment Codes

0 - Control plants, Group Kudla The plants were treated like the treated plants; e.g.: Transfer of Magenta boxes out of the climate chamber. Opening of the boxes and lifting the raft as long as the treatments last. Then boxes were transferred back to the climate chamber.

1 - old stress (4° C.), Group Kudla The Magenta boxes were placed on ice in the cold room (4° C.). The environmental light intensity was 20 μEinstein/cm2 sec. An extra light which was installed over the plants had 40 μEinstein/cm2 sec. The plants stayed there.

2 - smotic stress, Group Kudla Mannitol was added to a concentration of 300 mM in the Media. To add Mannitol the raft was lifted out A magnetic stir bar and a stirrer were used to mix the media and the added Mannitol. After the rafts were put back in the boxes, they were transferred back to the climate chamber.

3 - Salt stress, Group Kudla NaCl was added to a concentration of 150 mM in the Media. To add NaCl the raft was lifted out. A magnetic stir bar and a stirrer were used to mix the media and the added NaCl. After the rafts were put back in the boxes, they were transferred back to the climate chamber.

4 - Drought stress, Group Kudla The plants were stressed by 15 min. dry air stream (clean bench) until 10% loss of fresh weight; then incubation in closed vessels in the climate chamber.

5 - Genotoxic stress, Group Puchta Bleomycin + mitomycin (1.5 μg/ml bleomycin + 22 μg/ml mitomycin), were added to the indicated concentration in the Media. To add the reagents the raft was lifted out A magnetic stir bar and a stirrer were used to mix the media and the added reagents. After the rafts were put back in the boxes, they were transferred back to the climate chamber.

6 - Oxidative stress, Group Bartels Methyl Viologen was added to a final concentration of 10 μM in the Media. To add the reagent the raft was lifted out A magnetic stir bar and a stirrer were used to mix the media and the added reagent. After the rafts were put back in the boxes, they were transferred back to the climate chamber 7 - UV-B stress, Group Harter 15 min. 1.18 W/m2 Philips TL40W/12

8 - Wounding stress, Group Harter Punctured with pins

9 - Heat stress, Group Nover/von Koskull-Döring 38° C., samples taken at 0.25, 0.5, 1.0, 3.0 h of hs and +1, +3, +9, +21 h recovery at 25° C.

C - Heat stressed suspension culture, Group Nover/von Koskull-Döring 38° C., samples taken at 0.25, 0.5, 1.0, 3.0 h of hs and +1, +3, +9, +21 h recovery at 25° C.

Example 3

Testing Expression Using Identified Regulatory Polynucleotides

Regulatory polynucleotide molecules may be tested using transient expression assays using tissue bombardment and protoplast transfections following standard protocols. Reporter constructs including the respective candidate regulatory polynucleotide molecules linked to GUS are prepared and bombarded into *Arabidopsis* tissue obtained from different plant organs using a PDS-1000 Gene Gun (BioRad). GUS expression is assayed to confirm expression from the candidate promoters.

To further assess the candidate regulatory polynucleotide molecules in stable transformed plants, the candidate molecules are synthesized and cloned into commercially available constructs using the manufacturer's instructions. Regulatory polynucleotide:: GFP fusions are generated in a binary vector containing a selectable marker using commercially available vectors and methods, such as those previously described (J. Y. Lee et al., *Proc Natl Acad Sci USA* 103, 6055 (Apr. 11, 2006)). The final constructs are transferred to *Agrobacterium* for transformation into *Arabidopsis* ecotype plants by the floral dip method (S. J. Clough, A. F. Bent, *Plant J* 16, 735 (December, 1998)). Transformed plants (T1) are selected by growth in the presence of the appropriate antibiotic or herbicide. Following selection, transformants are transferred to MS plates and allowed to recover.

For preliminary analysis, T1 root tips are excised, stained with propidium iodide and imaged for GFP fluorescence with a Zeiss 510 confocal microscope. Multiple T1 plants are analyzed per construct and multiple images along the longitudinal axis are taken in order to assess expression in the meristematic, elongation, and maturation zones of the root. In some cases expression may not be detectable as GFP fluorescence, but may detectable by qRT-PCR due to the higher sensitivity of the latter technique. Thus, qRT-PCR may also be used to detect the expression of GFP.

Example 4

Identification of Rice Regulatory Sequences

The Gramene.org database was queried to identify rice (*Oryza sativa* japonica) orthologs corresponding to the *Arabidopsis* genes whose regulatory elements were selected in Example 1 above. In some cases, the *Arabidopsis* genes may lack a rice ortholog and in other cases the *Arabidopsis* genes may have more than one ortholog.

As the above strategy does not take any rice expression data into consideration, additional bioinformatics analyses were used to further identify rice orthologs, corresponding to the constitutive *Arabidopsis* genes from Example 1, that exhibit constitutive expression. Aerial and root expression of the orthologs was analyzed using two publically available rice Affymetrix datasets (Hirose et al. *Plant Cell Physiol.,* 48: 523-539 (2007) and Jain et al. *Plant Physiol.,* 143: 1467-1483 (2007)). Evaluation cutoffs for the two datasets were defined by analyzing expression profiles of several known constitutive genes including actin, 60S ribosomal protein, 40S ribosomal protein and ubiquitin. The orthologs were filtered by requiring similar expression levels as the control constitutive genes, less than 2-fold difference between root and aerial tissue, and agreement between the two data sets. This resulted in the identification of constitutive and highly expressed rice candidate genes. In some cases where no rice expression data was available, the rice orthologs were chosen based on expression of the corresponding *Arabidopsis* orthologs. To identify regulatory polynucleotide sequences responsible for driving high constitutive expression of these candidate genes, upstream sequences of 1500 bp or less of the selected gene candidates were determined Because transcription start sites are not always known, sequences upstream of the translation start site were used in all cases. Therefore, the identified regulatory polynucleotides contain an endogenous 5'-UTR, and some of the endogenous 5'-UTRs contain introns. The use of such introns in expression constructs containing these regulatory molecules may increase expression through IME. Without being limited by theory, IME may be important for highly expressed constitutive genes, such as those identified here. In order to capture these regulatory sequences in genes that do not contain a 5'-UTR intron, chimeric regulatory polynucleotide molecules may be constructed wherein the first intron from the gene in question is fused to the 3'-end of the 5'-UTR of the regulatory polynucleotide (which may be from the same or a different (e.g. exogenous) gene). In order to ensure efficient intron splicing, the introns in these chimeric sequences may be flanked by consensus splice sites.

This resulted in a list of rice ortholog regulatory sequences listed in Table 6 (sequences including the regulatory polynucleotides plus the first intron from the coding region added at the 3' end of the 5' UTR are indicated by the corresponding gene accession number and the indicator “+intron”):

TABLE 6

| FIG. | SEQ ID NO: | Corresponding Gene Accession No. |
|---|---|---|
| 87 | 87 | Os03g21940 |
| 88 | 88 | Os04g35300 |
| 89 | 89 | Os05g45950 |
| 90 | 90 | Os11g47760 |
| 91 | 91 | Os02g02130 |
| 92 | 92 | Os03g56190 |
| 93 | 93 | Os05g47980 |
| 94 | 94 | Os01g46610 |
| 95 | 95 | Os02g52290 |
| 96 | 96 | Os04g28180 |
| 97 | 97 | Os05g01820 |
| 98 | 98 | Os07g46750 |
| 99 | 99 | Os11g11390 |
| 100 | 100 | Os03g56190 (+intron) |
| 101 | 101 | Os04g35300 (+intron) |
| 102 | 102 | Os02g02130 (+intron) |
| 103 | 103 | Os01g46610 (+intron) |
| 104 | 104 | Os05g01820 (+intron) |
| 105 | 105 | Os07g46750 (+intron) |
| 106 | 106 | Os04g28180 (+intron) |
| 107 | 107 | Os03g21940 (+intron) |
| 108 | 108 | Os05g45950 (+intron) |

TABLE 6-continued

| FIG. | SEQ ID NO: | Corresponding Gene Accession No. |
|---|---|---|
| 109 | 109 | Os02g52290 (+intron) |
| 110 | 110 | Os05g47980 (+intron) |
| 111 | 111 | Os11g11390 (+intron) |
| 112 | 112 | Os11g47760 (+intron) |
| 113 | 113 | Os07g02210 |
| 114 | 114 | Os12g07010 |
| 115 | 115 | Os09g08430 |
| 116 | 116 | Os08g03290 |
| 117 | 117 | Os10g22590 |
| 118 | 118 | Os03g45280 |
| 119 | 119 | Os06g07969 |
| 120 | 120 | Os07g30970 |
| 121 | 121 | Os09g33500 |
| 122 | 122 | Os10g33800 |
| 123 | 123 | Os11g38959 |
| 124 | 124 | Os11g38959 (+intron) |
| 125 | 125 | Os06g07969 (+intron) |
| 126 | 126 | Os09g33500 (+intron) |
| 127 | 127 | Os07g30970 (+intron) |
| 128 | 128 | Os08g03290 (+intron) |
| 129 | 129 | Os09g08430 (+intron) |
| 130 | 130 | Os10g08550 |
| 131 | 131 | Os04g32710, +intron |
| 132 | 132 | Os04g30730, +intron |
| 133 | 133 | Os02g30050, +intron |
| 134 | 134 | Os05g11780, +intron |
| 135 | 135 | Os03g14450, +intron |
| 136 | 136 | Os01g17190, +intron |
| 137 | 137 | Os10g17280, +intron |
| 138 | 138 | Os11g06890, +intron |
| 139 | 139 | Os01g16890, +intron |
| 140 | 140 | Os03g58430, +intron |
| 141 | 141 | Os06g37440 |
| 142 | 142 | Os10g30580, +intron |
| 143 | 143 | Os02g27769, +intron |
| 144 | 144 | Os07g08660, +intron |
| 145 | 145 | Os04g47220, +intron |
| 146 | 146 | Os05g07700, +intron |
| 147 | 147 | Os11g26850, +intron |
| 148 | 148 | Os12g38000, +intron |
| 149 | 149 | Os03g56241, +intron |
| 150 | 150 | Os02g27760 |
| 151 | 151 | Os03g05980, +intron |
| 152 | 152 | Os03g05730, +intron |
| 153 | 153 | Os05g01262, +intron |
| 154 | 154 | Os07g46670 |
| 155 | 155 | Os05g01560, +intron |
| 156 | 156 | Os07g08330, +intron |
| 157 | 157 | Os03g58204, +intron |
| 158 | 158 | Os01g62420, +intron |
| 159 | 159 | Os01g14580, +intron |
| 160 | 160 | Os02g57040, +intron |
| 161 | 161 | Os06g06980 |
| 162 | 162 | Os08g38920, +intron |
| 163 | 163 | Os09g01640 |
| 164 | 164 | Os07g10720 |
| 165 | 165 | Os07g12650 |
| 166 | 166 | Os08g38900 |
| 167 | 167 | Os12g05430 |
| 168 | 168 | Os12g04924, +intron |
| 169 | 169 | Os01g73990, +intron |
| 170 | 170 | Os01g01307, +intron |
| 171 | 171 | Os11g04880, +intron |
| 172 | 172 | Os02g34510, +intron |
| 173 | 173 | Os02g44630, +intron |
| 174 | 174 | Os04g32710 |
| 175 | 175 | Os04g30730 |
| 176 | 176 | Os02g30050 |
| 177 | 177 | Os01g05490 |
| 178 | 178 | Os01g61814 |
| 179 | 179 | Os05g11780 |
| 180 | 180 | Os03g14450 |
| 181 | 181 | Os01g17190 |
| 182 | 182 | Os10g17280 |
| 183 | 183 | Os11g06890 |
| 184 | 184 | Os01g16890 |
| 185 | 185 | Os03g58430 |
| 186 | 186 | Os10g30580 |

TABLE 6-continued

| FIG. | SEQ ID NO: | Corresponding Gene Accession No. |
|---|---|---|
| 187 | 187 | Os02g27769 |
| 188 | 188 | Os07g08660 |
| 189 | 189 | Os04g47220 |
| 190 | 190 | Os05g07700 |
| 191 | 191 | Os11g26850 |
| 192 | 192 | Os12g38000 |
| 193 | 193 | Os03g56241 |
| 194 | 194 | Os03g05980 |
| 195 | 195 | Os03g05730 |
| 196 | 196 | Os05g01262 |
| 197 | 197 | Os01g05650 |
| 198 | 198 | Os05g01560 |
| 199 | 199 | Os07g08330 |
| 200 | 200 | Os03g58204 |
| 201 | 201 | Os01g62420 |
| 202 | 202 | Os01g14580 |
| 203 | 203 | Os02g57040 |
| 204 | 204 | Os08g38920 |
| 205 | 205 | Os03g60400 |
| 206 | 206 | Os02g57720 |
| 207 | 207 | Os12g04924 |
| 208 | 208 | Os01g73990 |
| 209 | 209 | Os01g01307 |
| 210 | 210 | Os11g04880 |
| 211 | 211 | Os02g34510 |
| 212 | 212 | Os02g44630 |

The nucleic acid sequences provided in FIGS. 87 through 212 are annotated to indicate one transcription start site (Capital letter in bold), the endogenous 5'-UTR intron sequences (double underlining), any added intron from the coding sequence (single underlining), and any added intron splice sequences (bold italics). All rice genome sequence and annotation is from the Rice Genome Annotation Project (available on the worldwide web at rice.plantbiology.msu.edu/index.shtml).

Example 5

Endogenous Expression Analysis of Rice Orthologs

This example provides the endogenous expression data of the sequences identified in Example 4, where such data was available. The endogenous expression levels of the rice orthologs are provided in FIGS. 262-327. Expression data presented for the underlying rice genes is shown where available. Also, when more than one set of expression data was available, the further data may also be shown. All data are from Affymetrix GeneChip rice genome arrays which allow the detection of about 51,000 transcripts from *Oryza sativa*. Each figure provides data from two publically available datasets. The four bars on the left of each plot are derived from Hirose et al. (*Plant Cell Physiol.,* 48: 523-539 (2007)) and show expression data from roots (black bars) and leaves (hatched bars). The roots and leaves were excised from 2-week-old seedlings dipped in distilled water containing DMSO for either 30 or 120 minutes. The bars on the right of each plot are derived from Jain et al. (*Plant Physiol.,* 143: 1467-1483 (2007)) and show expression values in various above ground tissues (hatched bars) as well as in root tissue (black bars). Above ground tissue consisted of mature leaf, Y leaf, and different stages of influorescence (up to 0.5 mm, SAM; 0-3 cm, P1; 3-5 cm, P2; 5-10 cm, P3; 10-15 cm, P4; 15-22 cm, P5; 22-30 cm, P6) and seed (0-2 dap, 51; 3-4 dap, S2; 5-10 dap, S3; 11-20 dap, S4; 21-29 dap, S5) development, and was harvested from rice plants grown under greenhouse or field conditions. Roots were harvested from 7-d-old light-grown seedlings grown in reverse-osmosis (RO) water.

Figure 262:
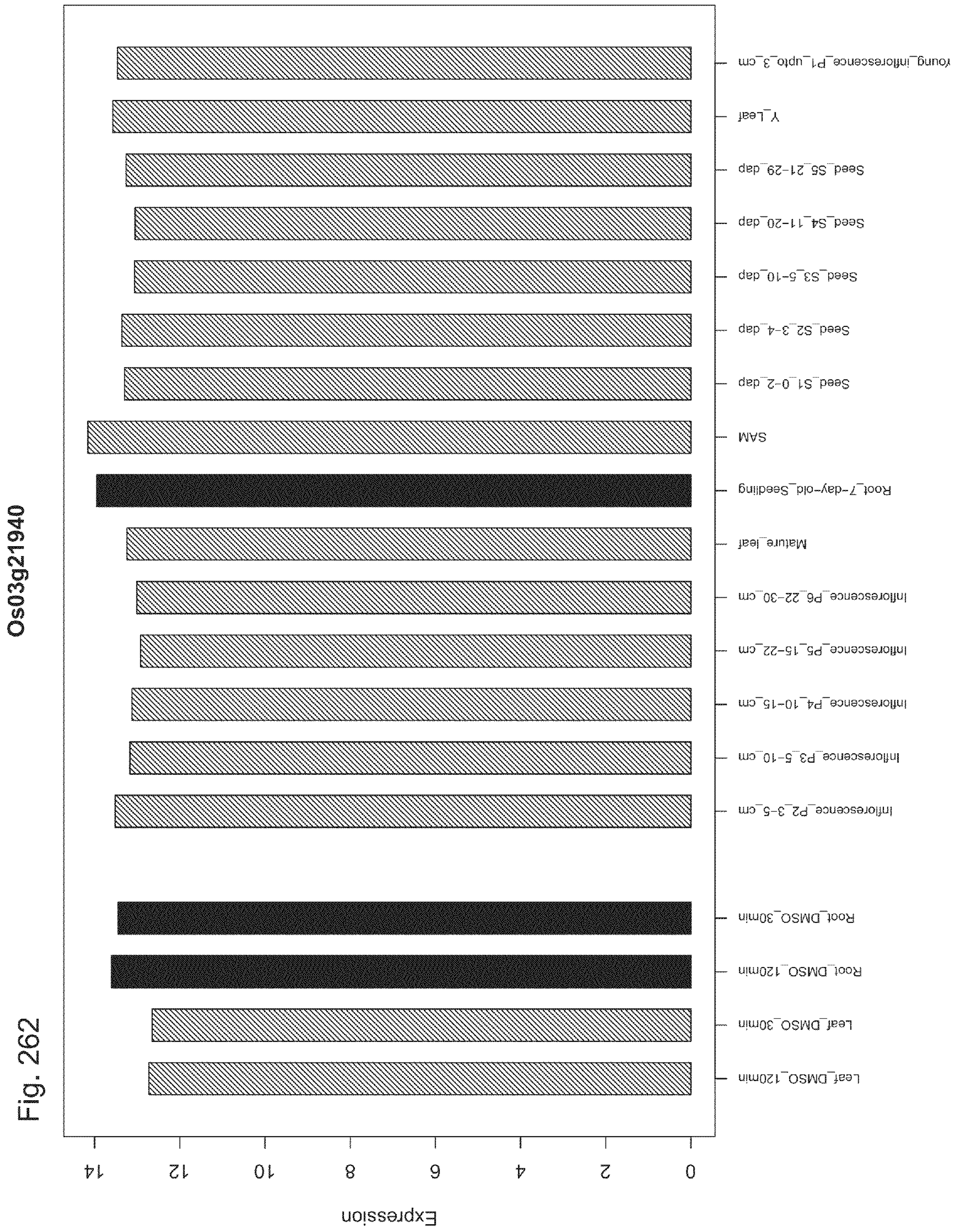
FIGS. 262-327 provide a schematic representation of the endogenous expression data for the rice ortholog having the specified accession number (corresponding to FIGS. 87-212). The black bars represent expression data obtained from root tissue while the hatched bars represent expression.
Figure 263A:
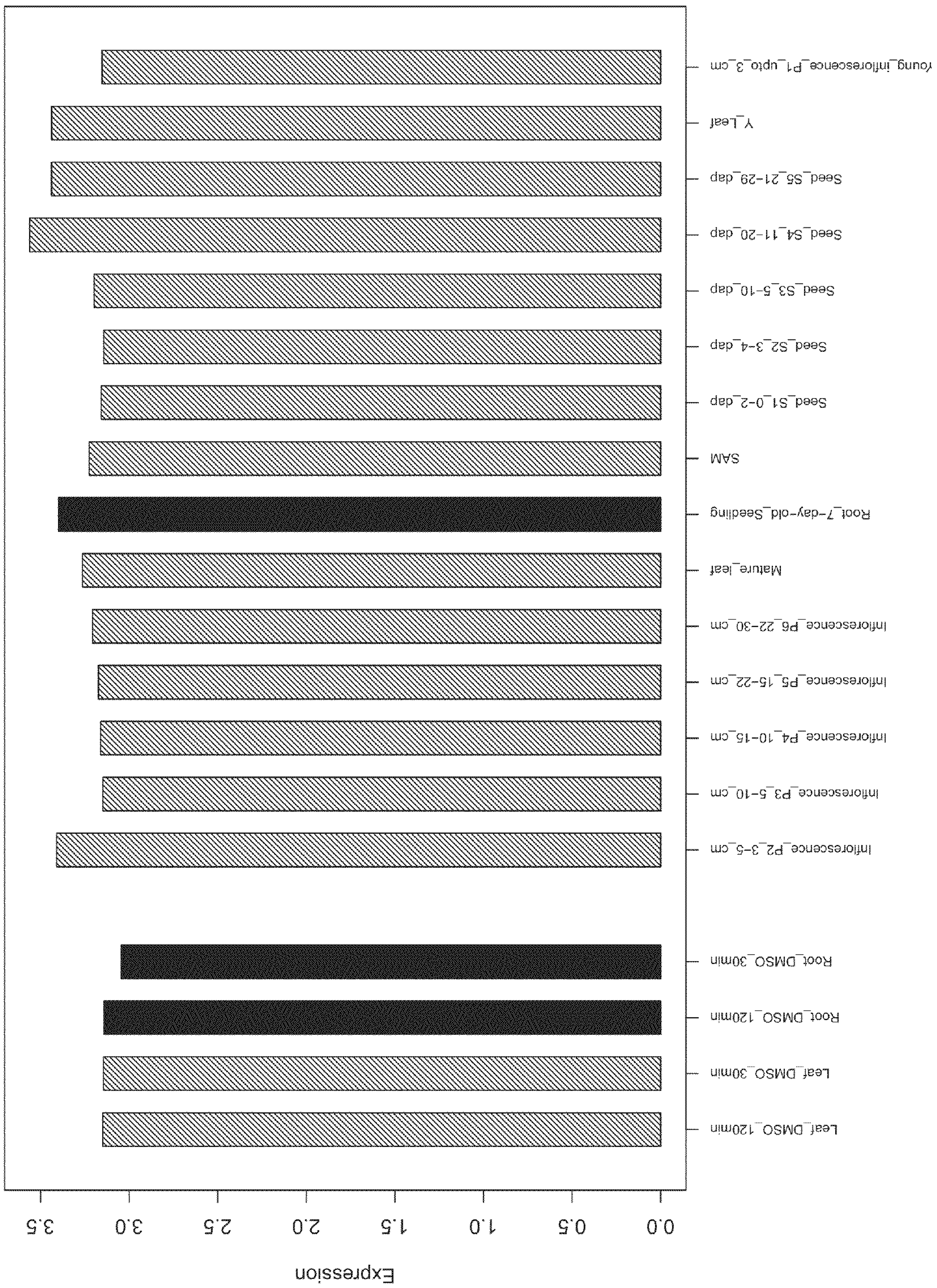
Figure 263B:
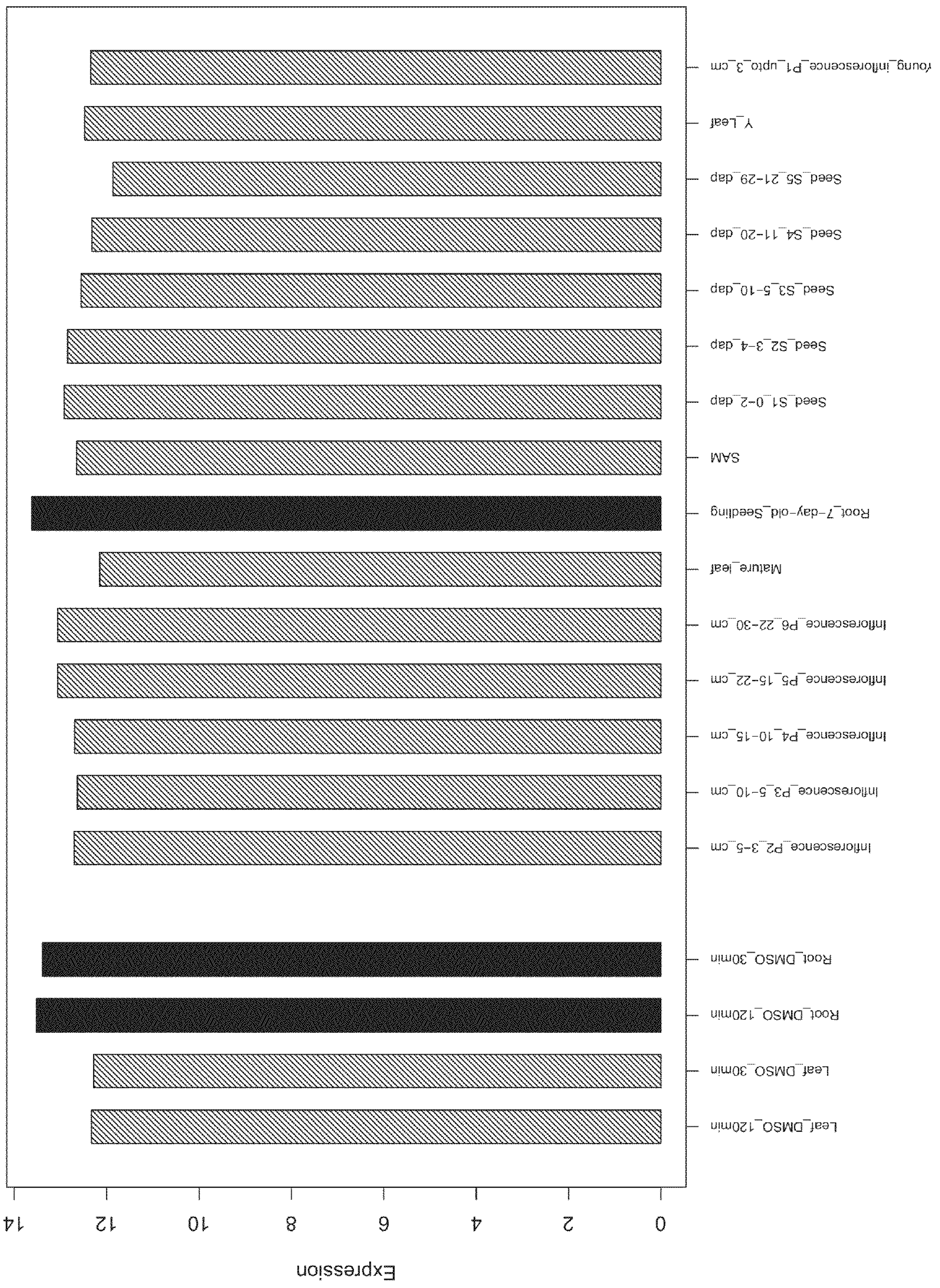
Figure 264:
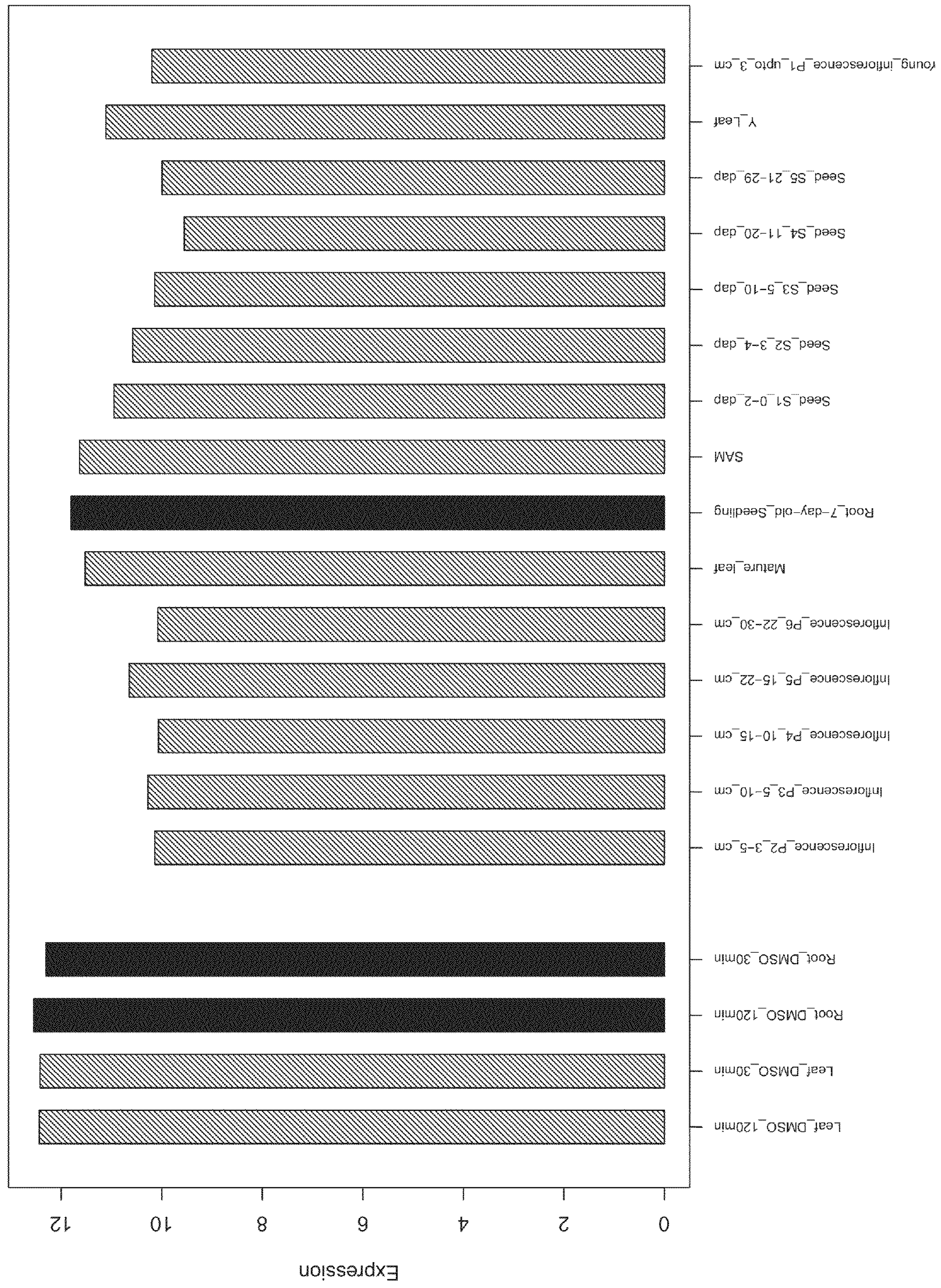
Figure 265A:
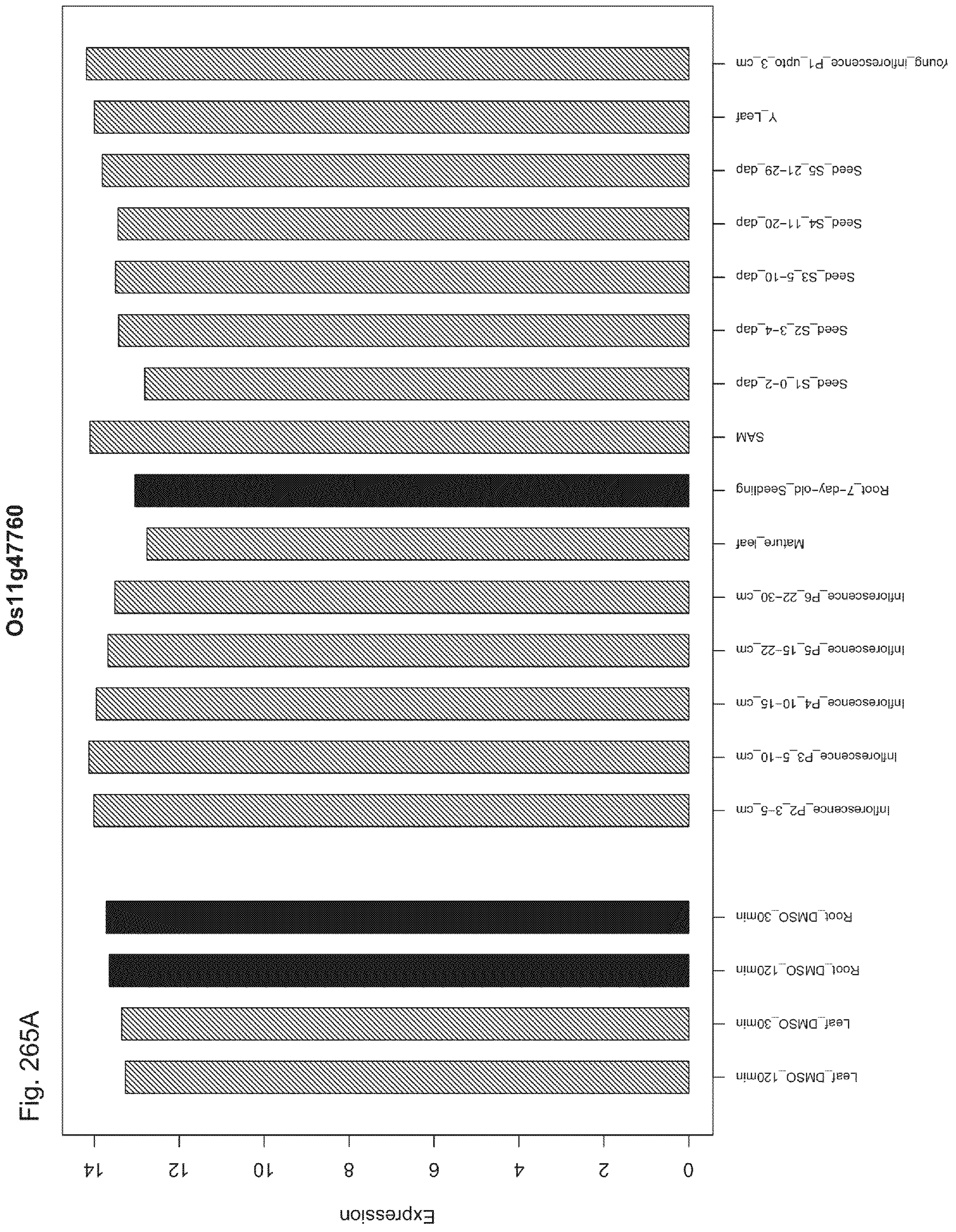
Figure 265B:
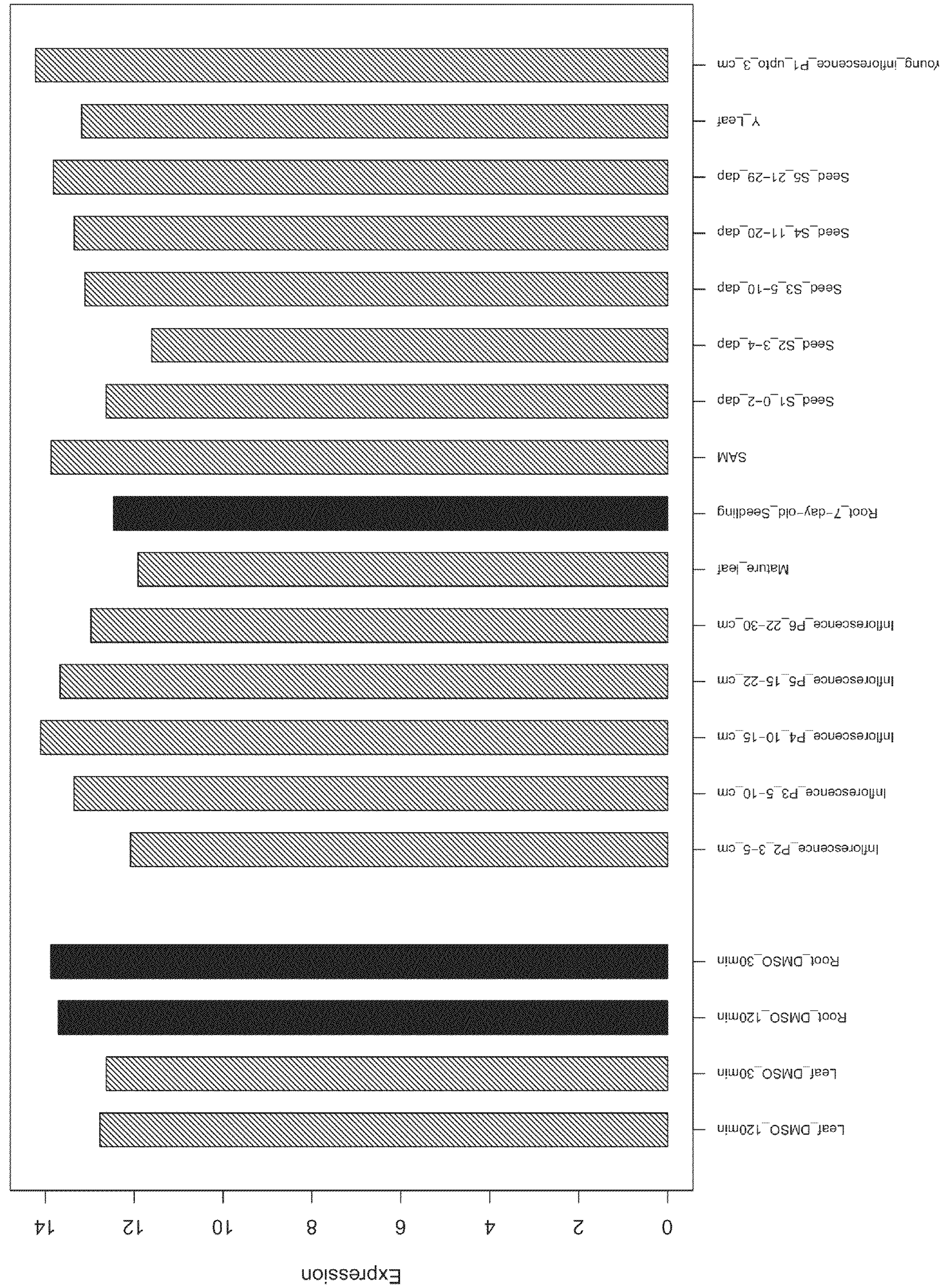
Figure 266:
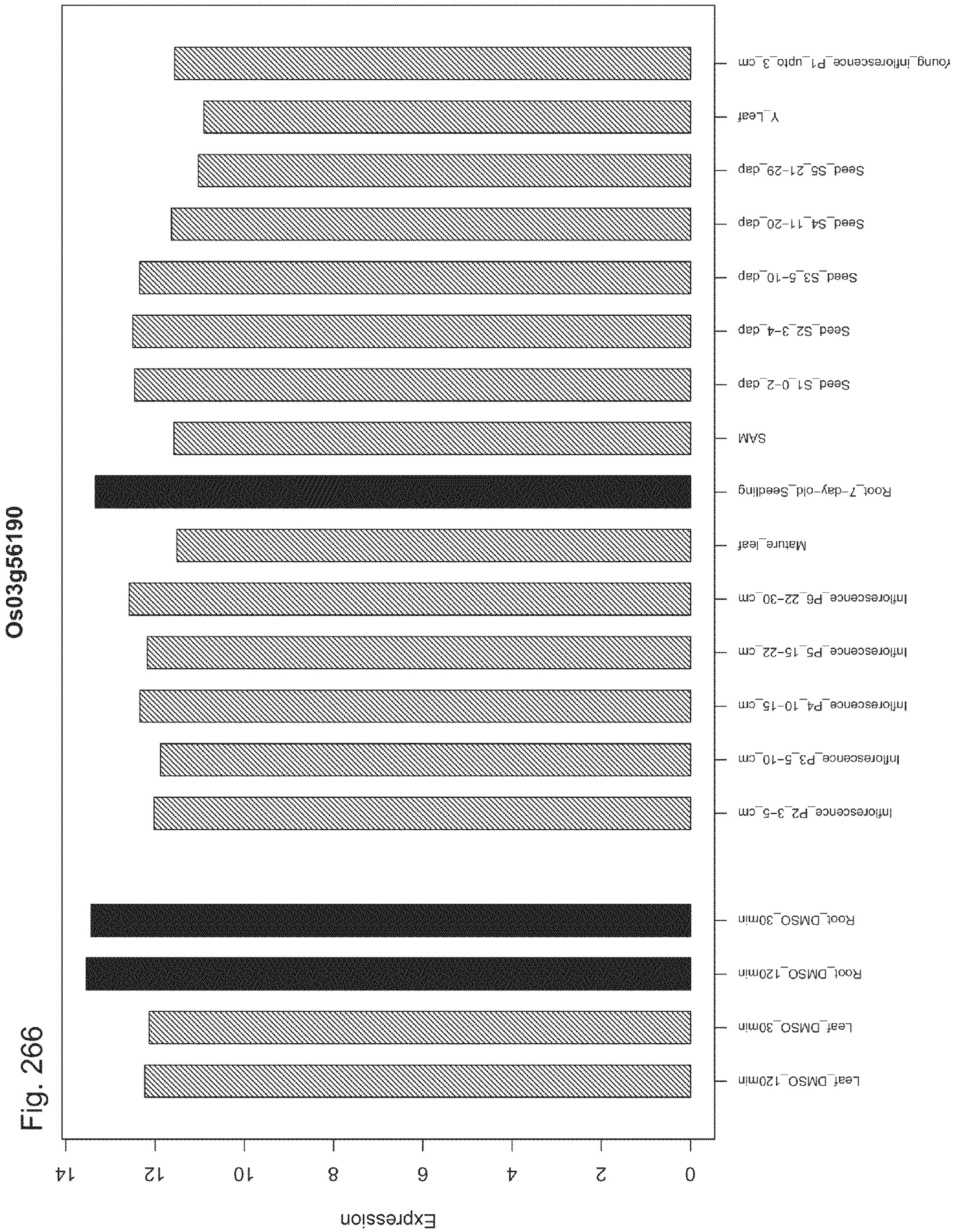
Figure 267A:
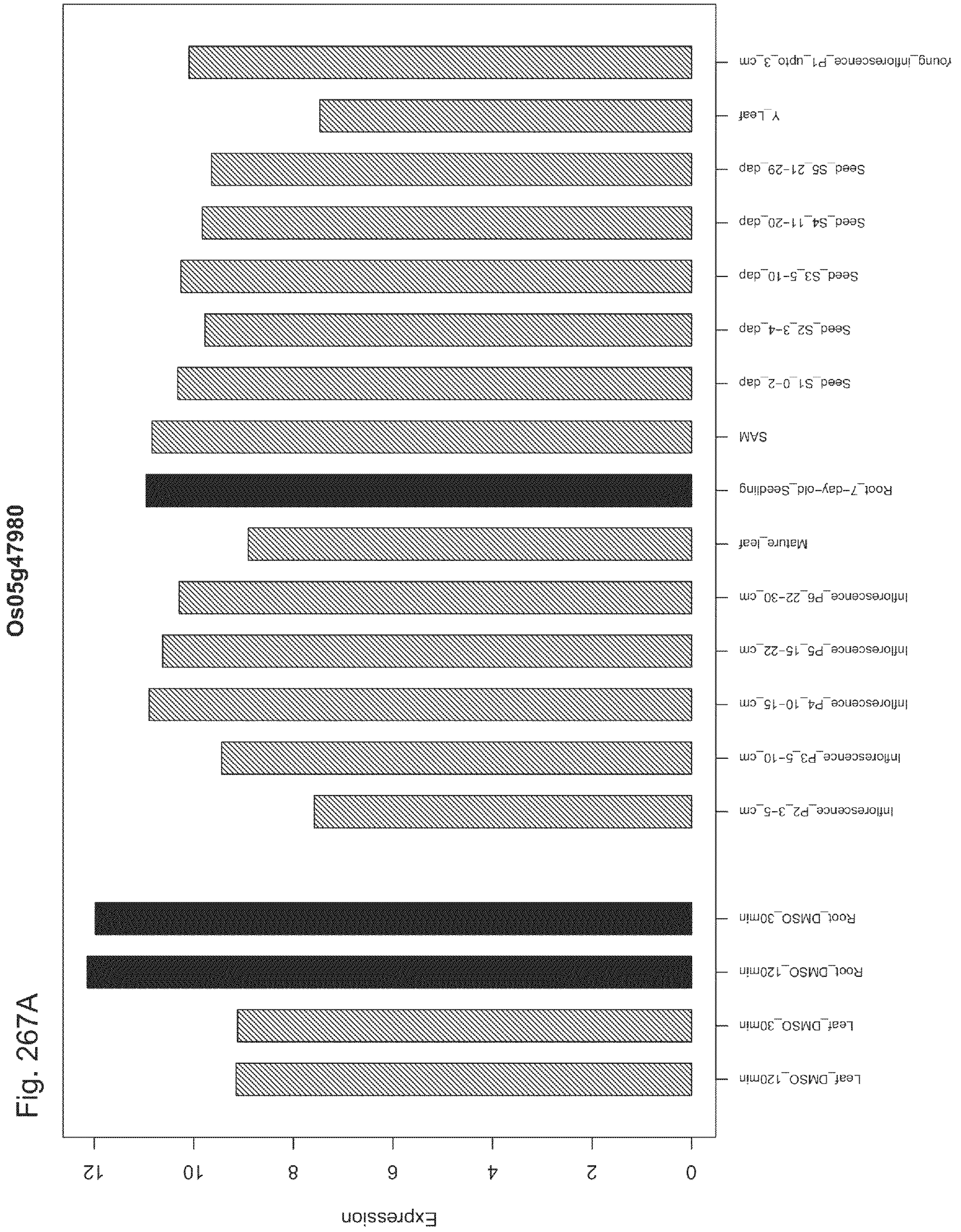
Figure 267B:
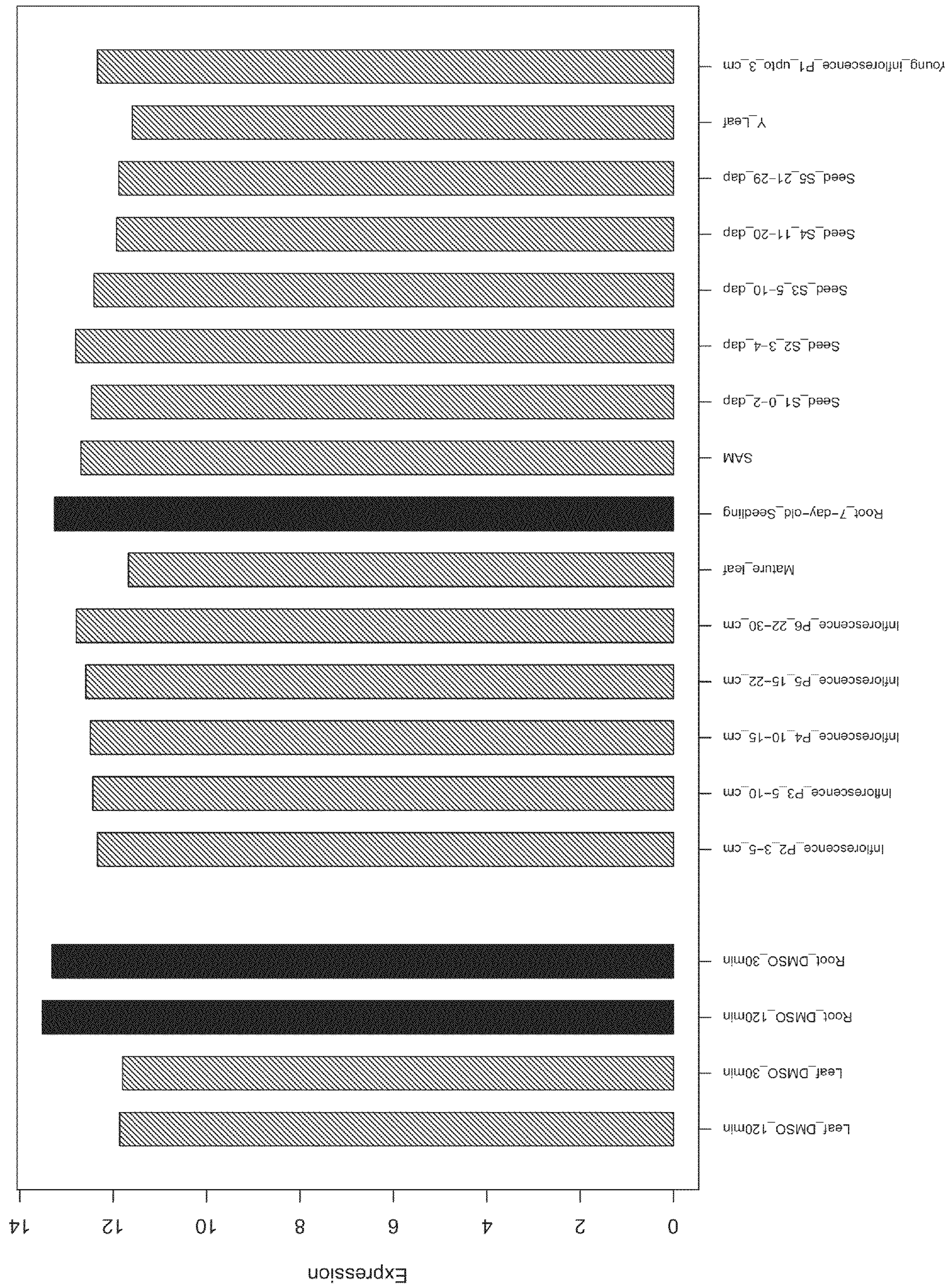
Figure 268:
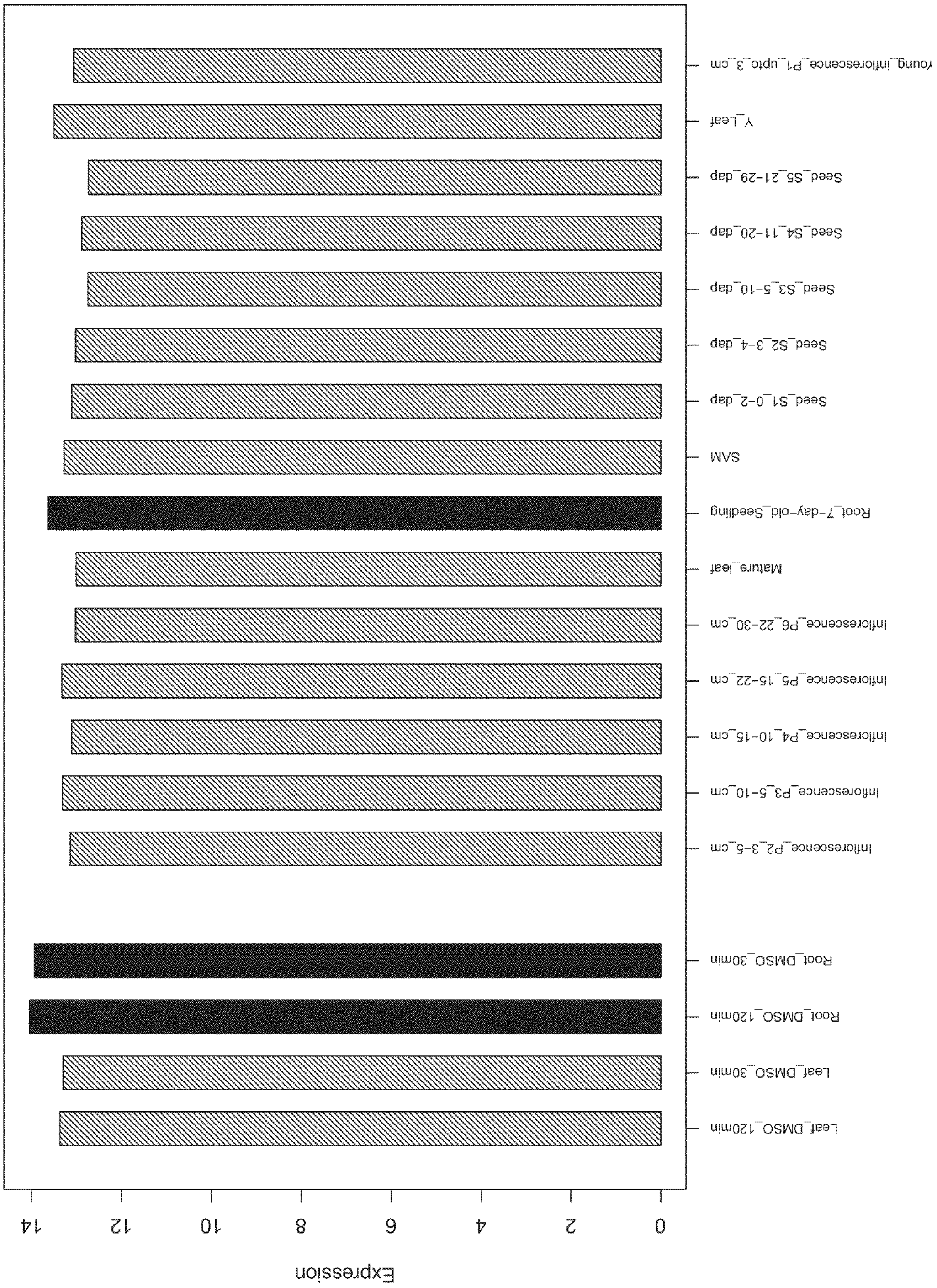
Figure 269:
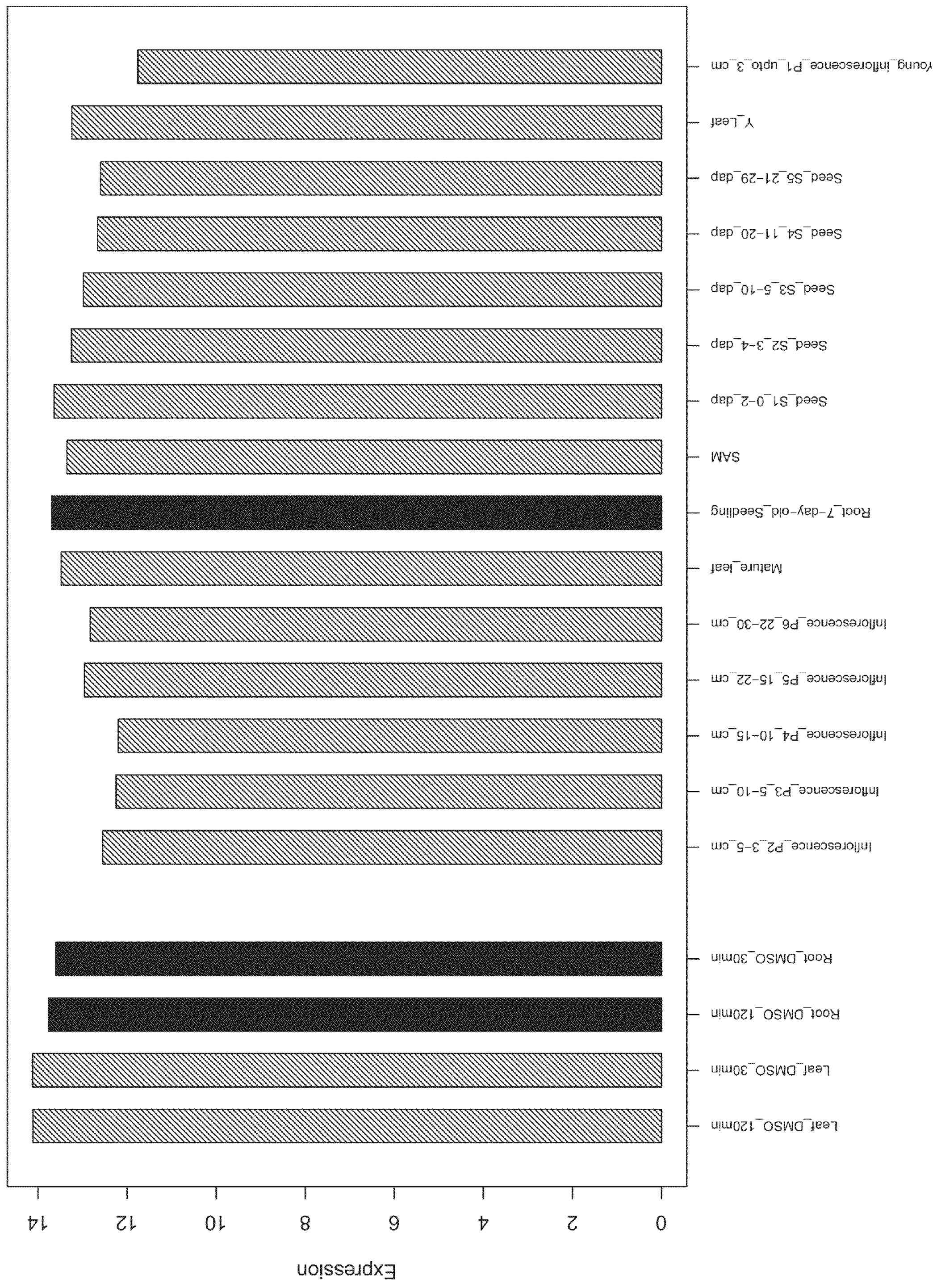
Figure 270:
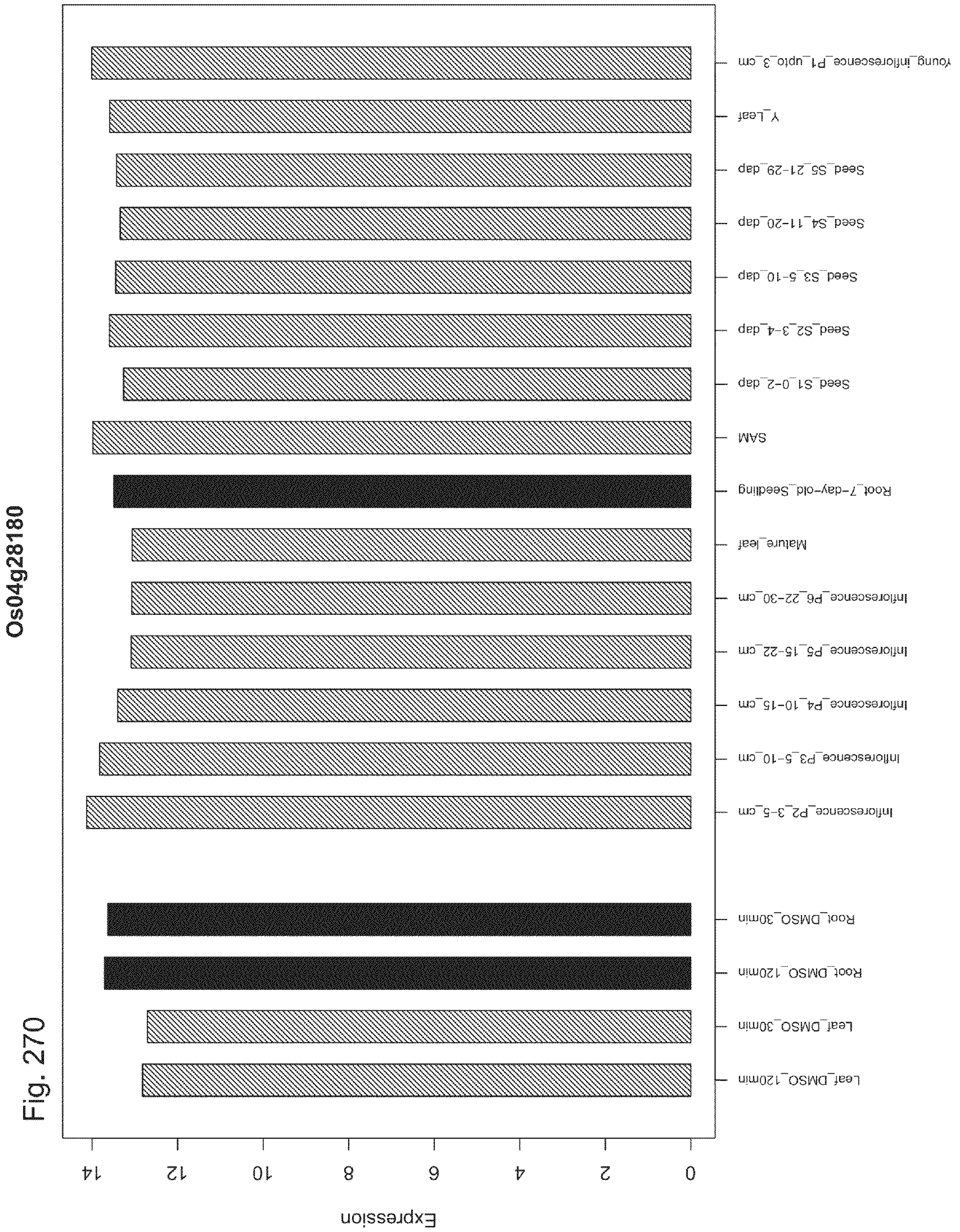
Figure 271A:
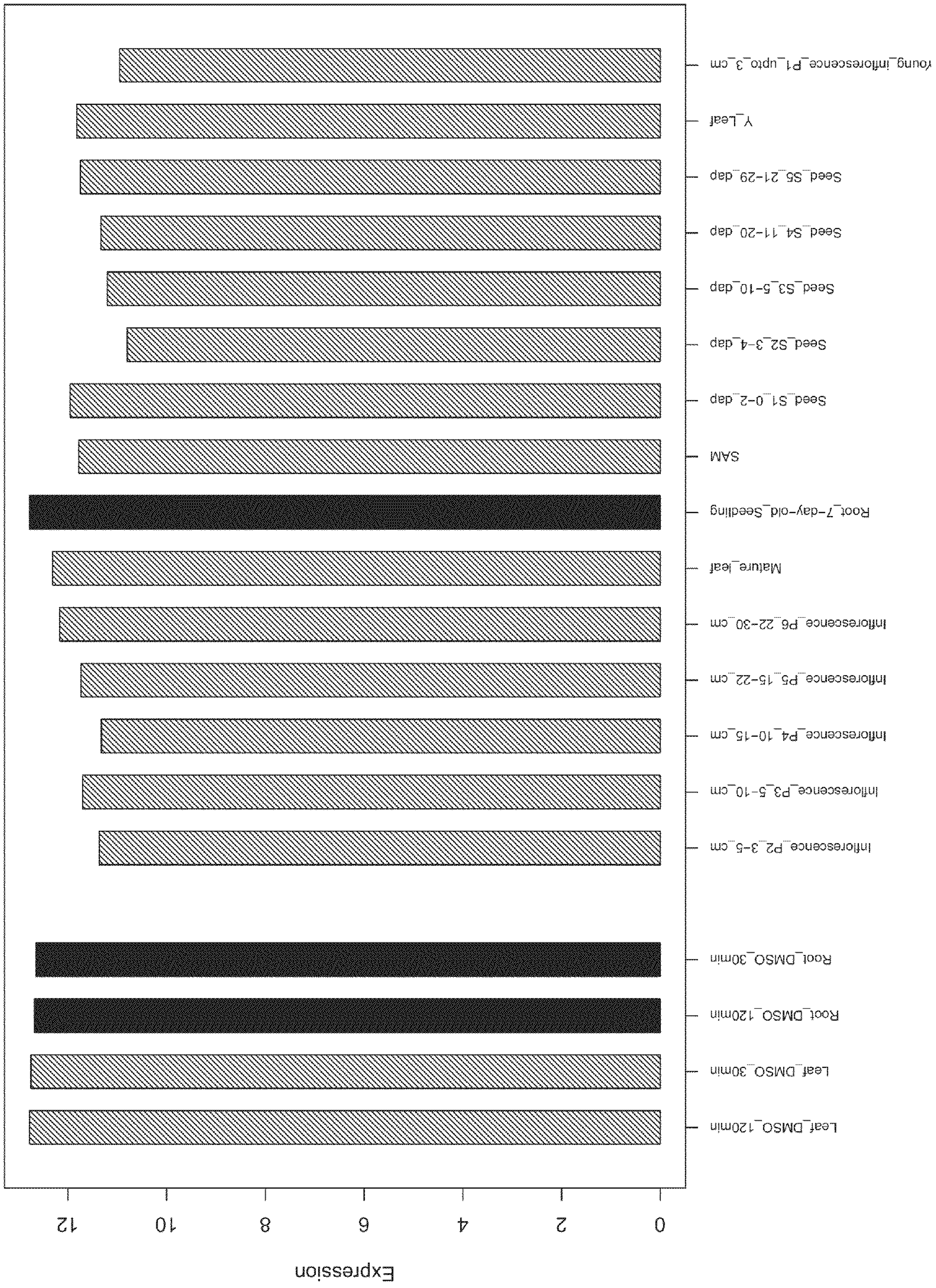
Figure 271B:
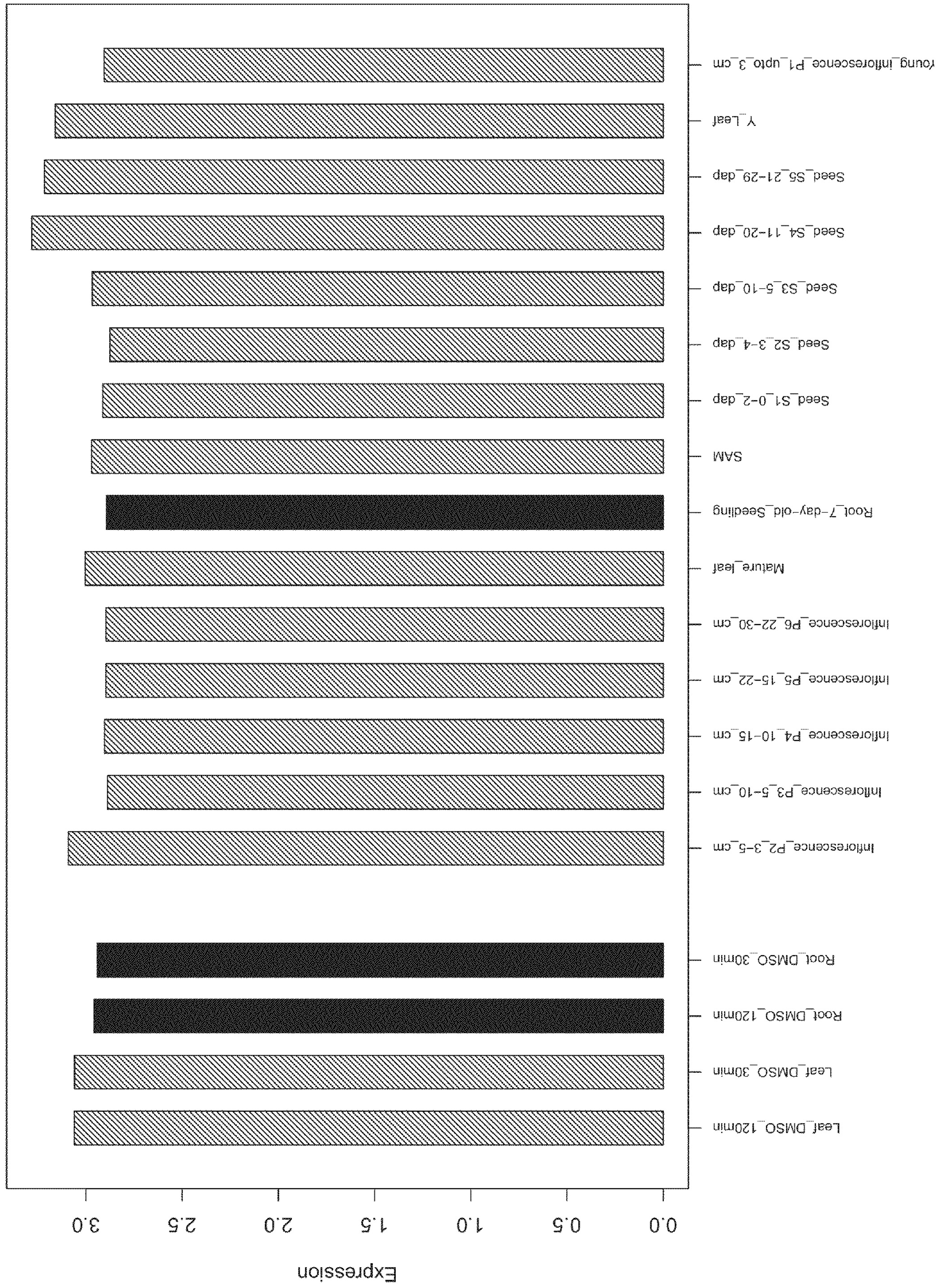
Figure 272:
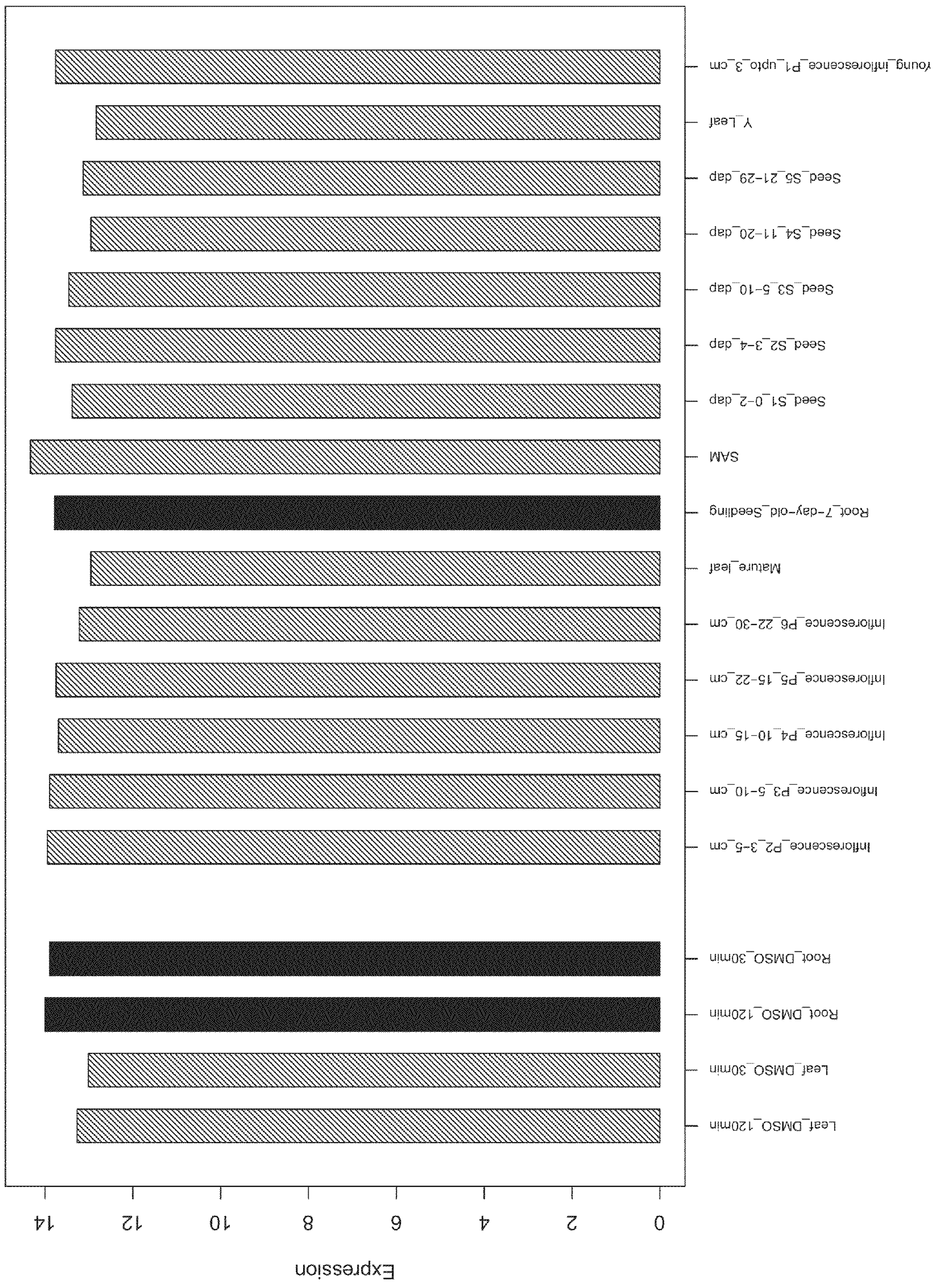
Figure 273:
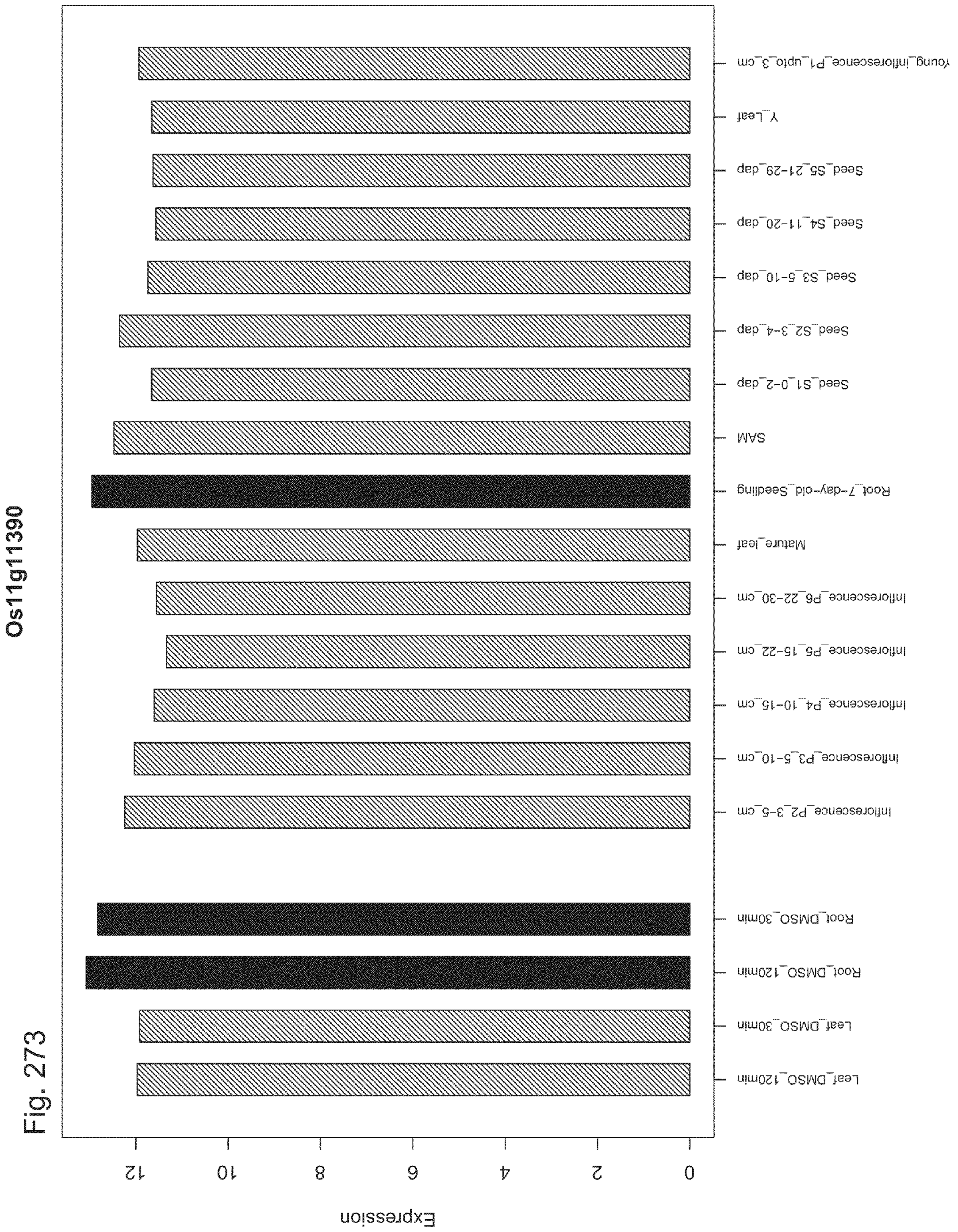
Figure 274:
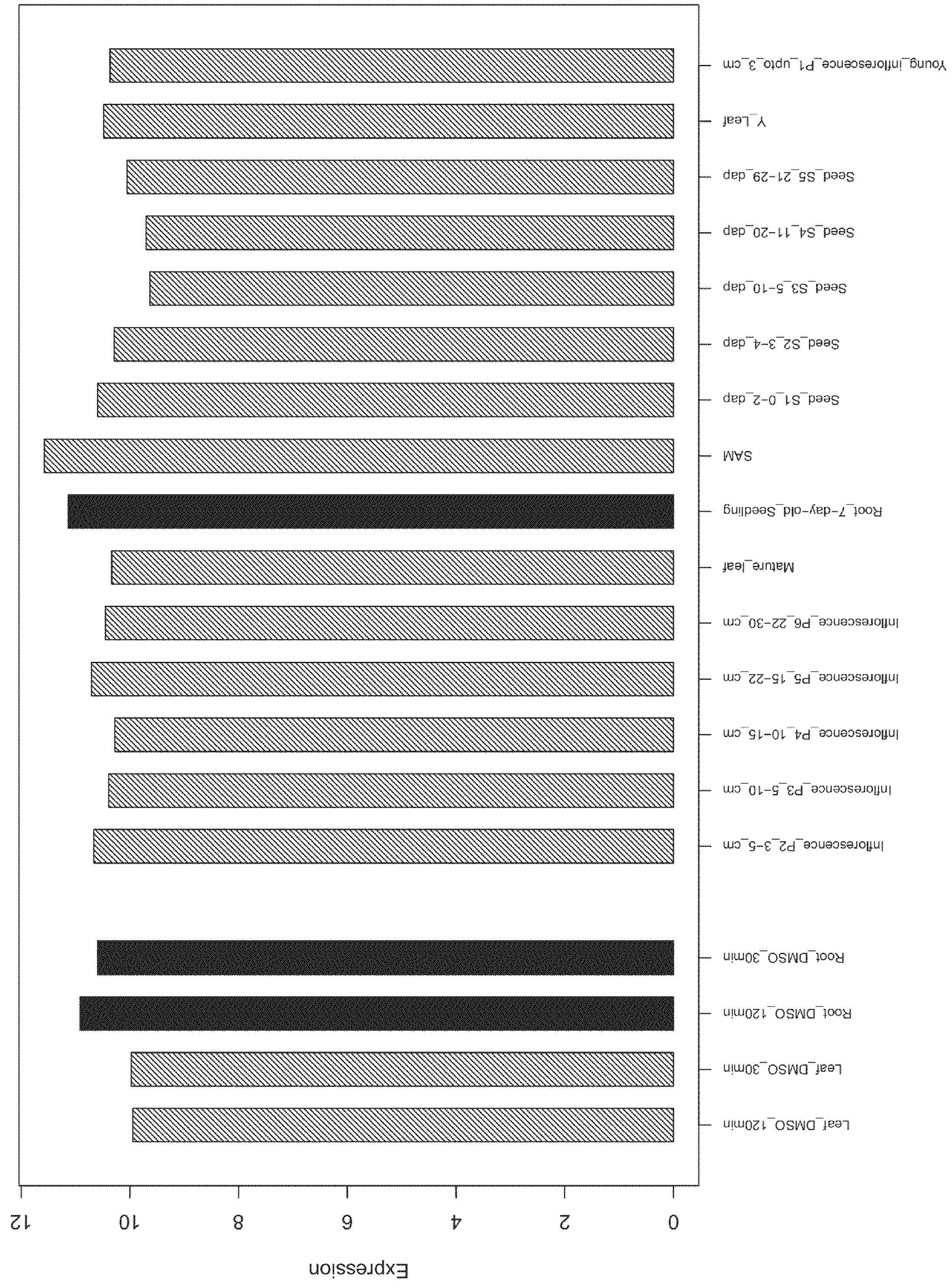
Figure 275:
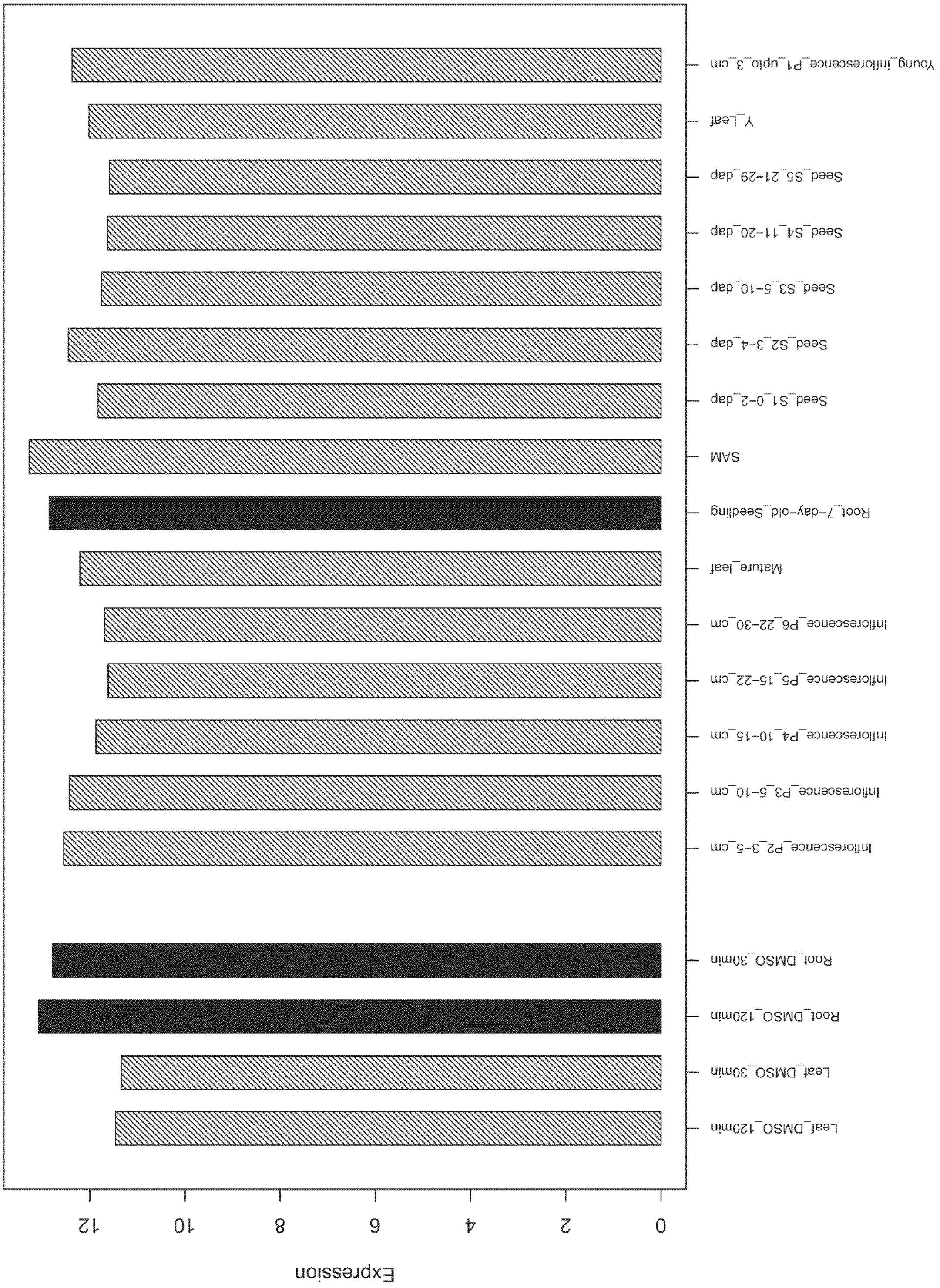
Figure 276A:
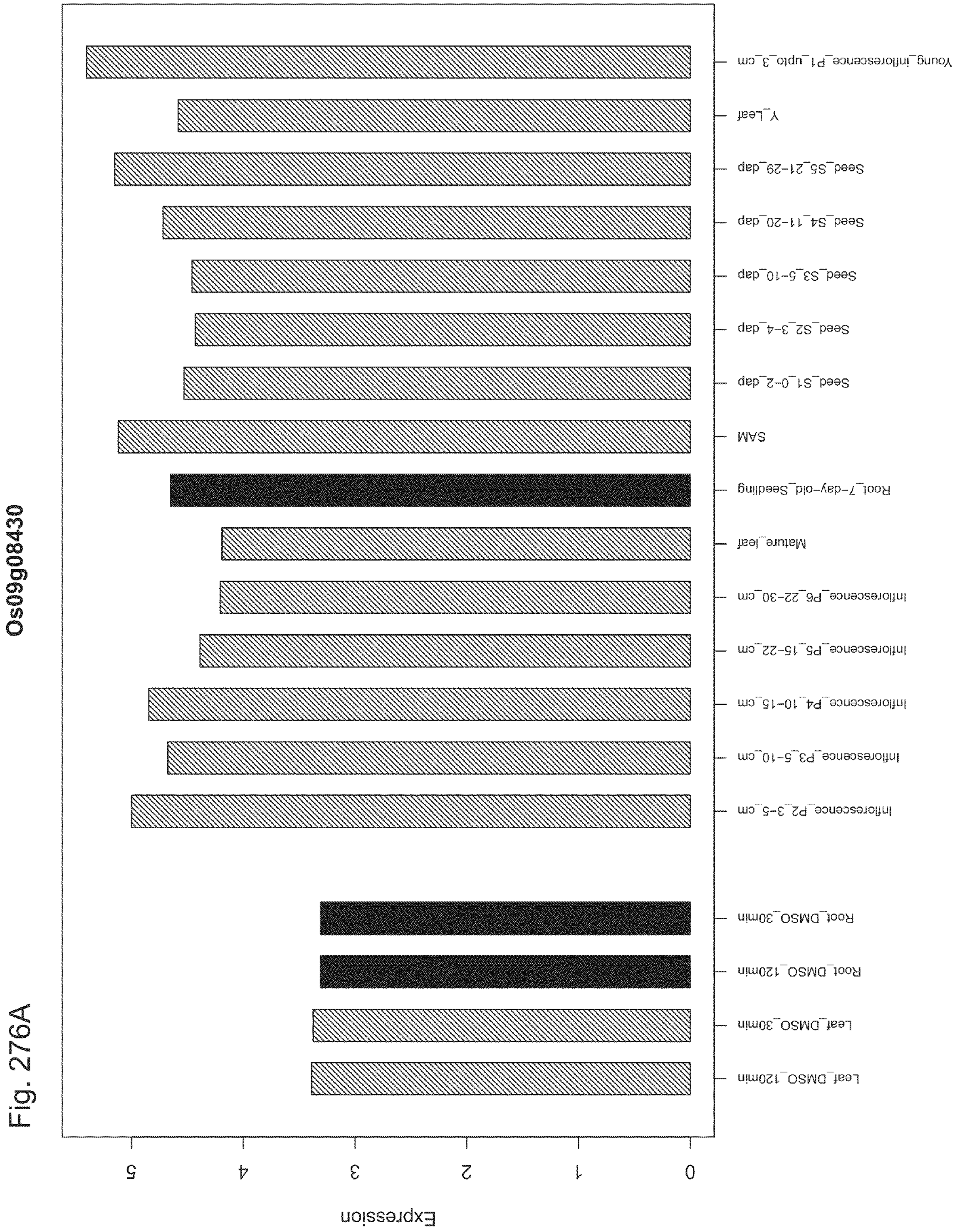
Figure 276B:
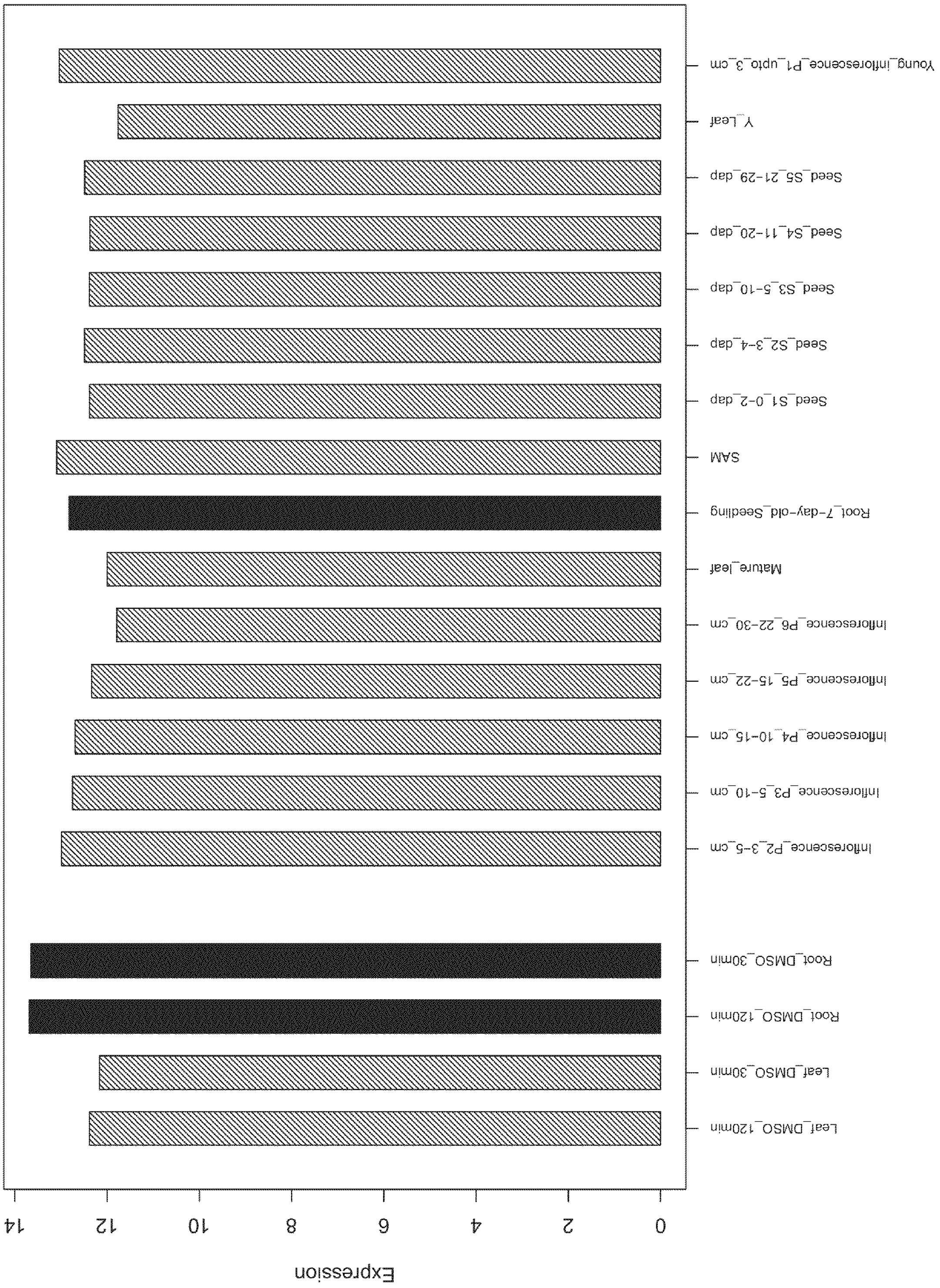
Figure 277:
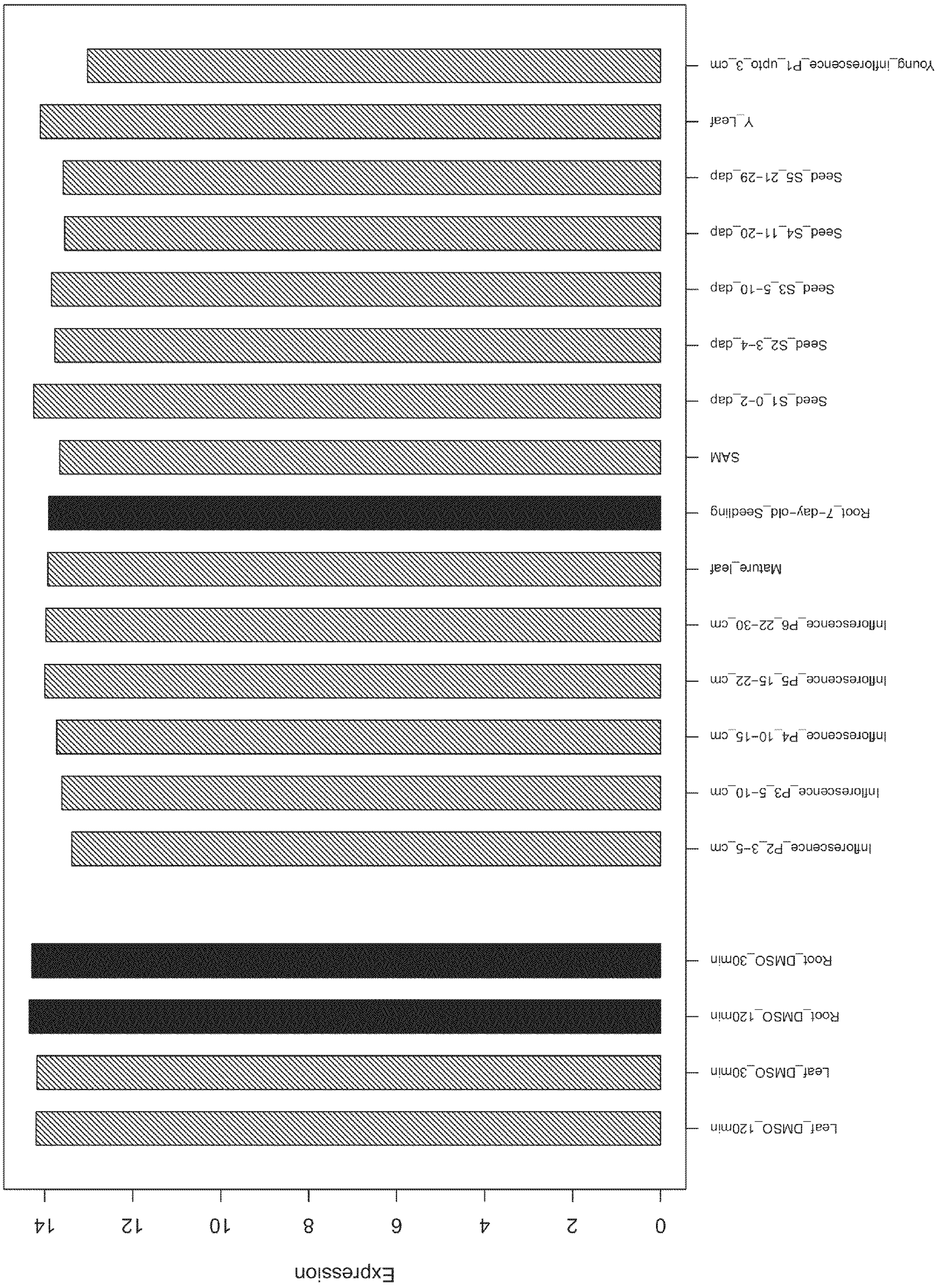
Figure 278:
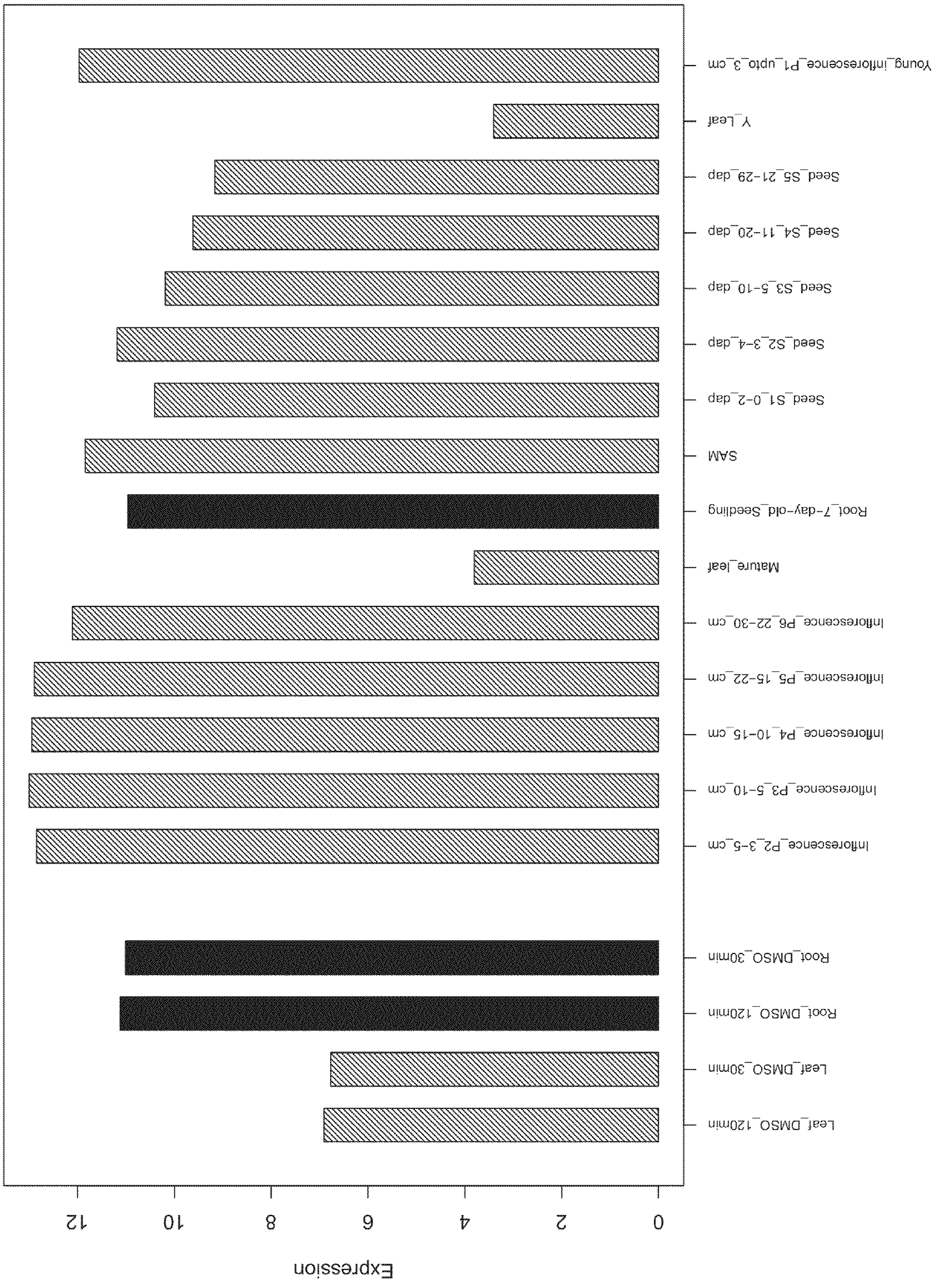
Figure 279A:
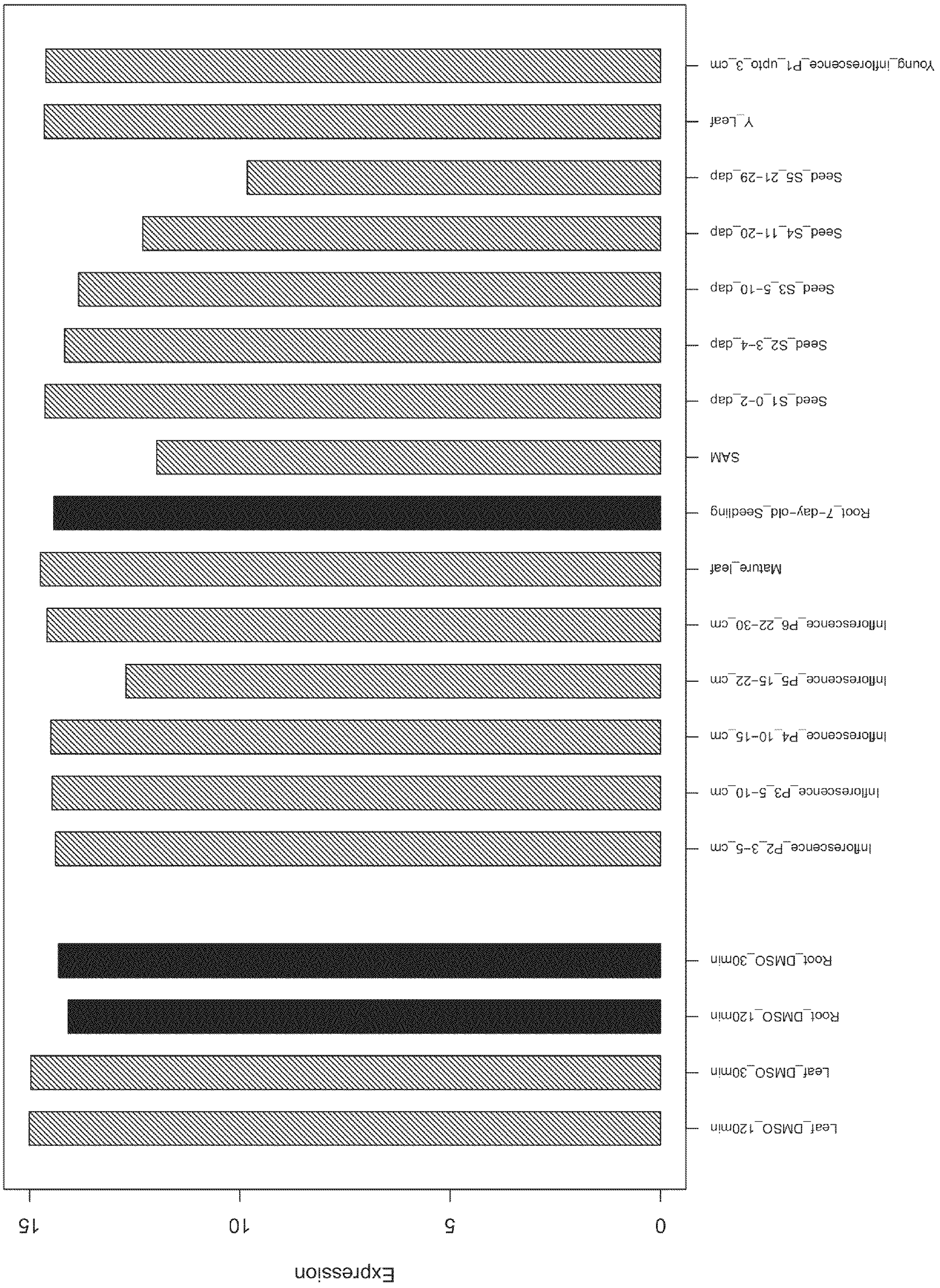
Figure 279B:
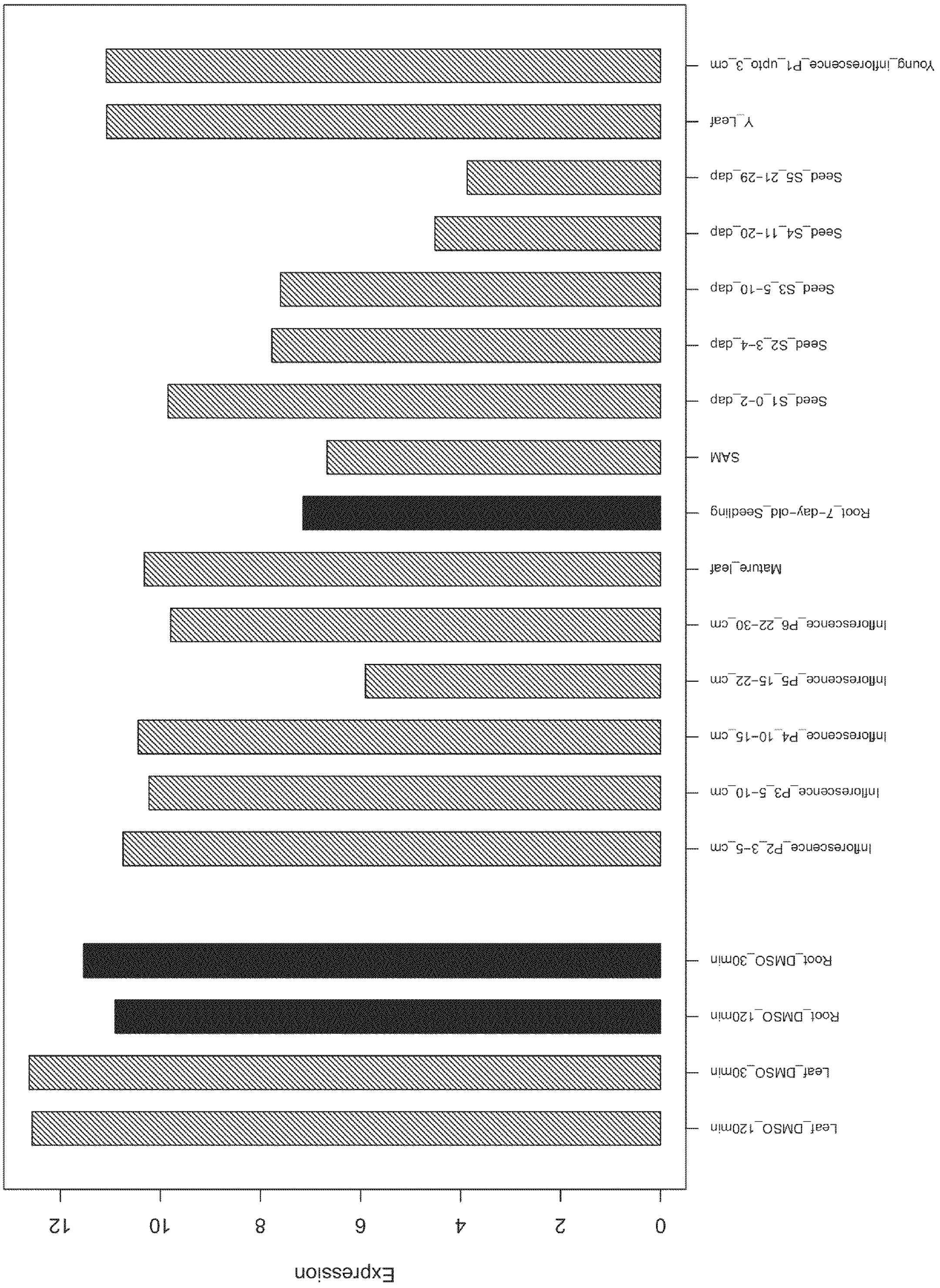
Figure 280:
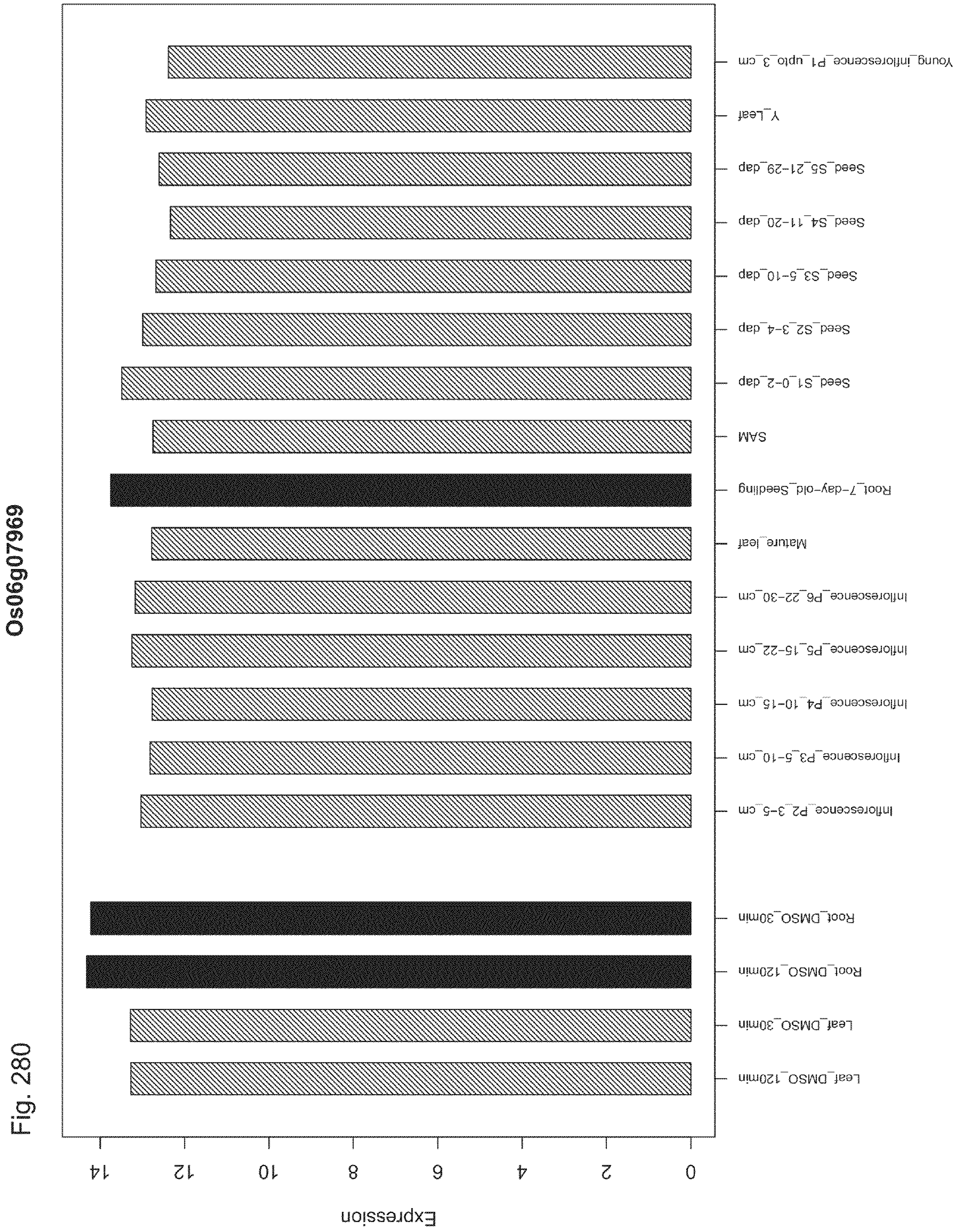
Figure 281:
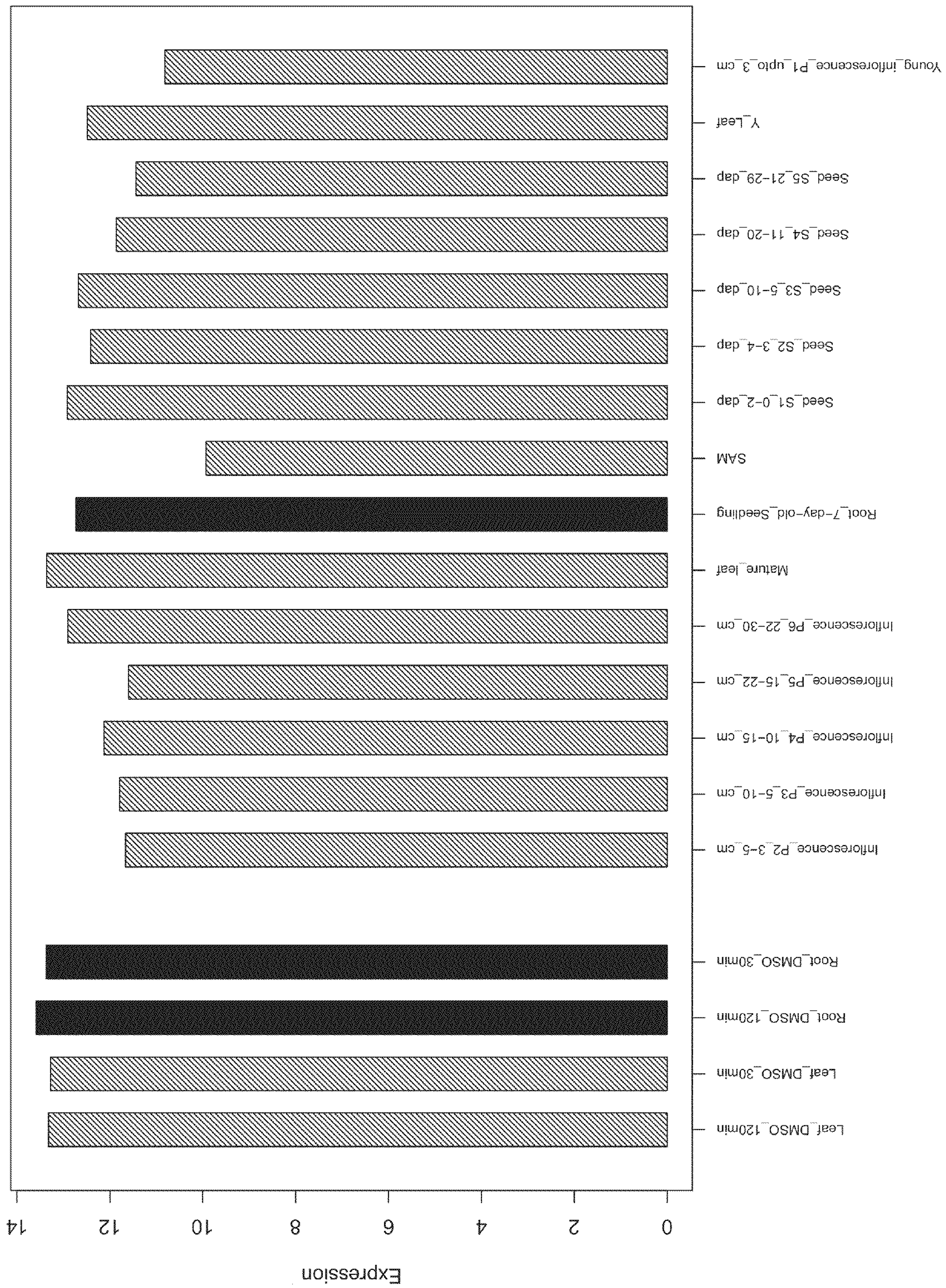
Figure 282:
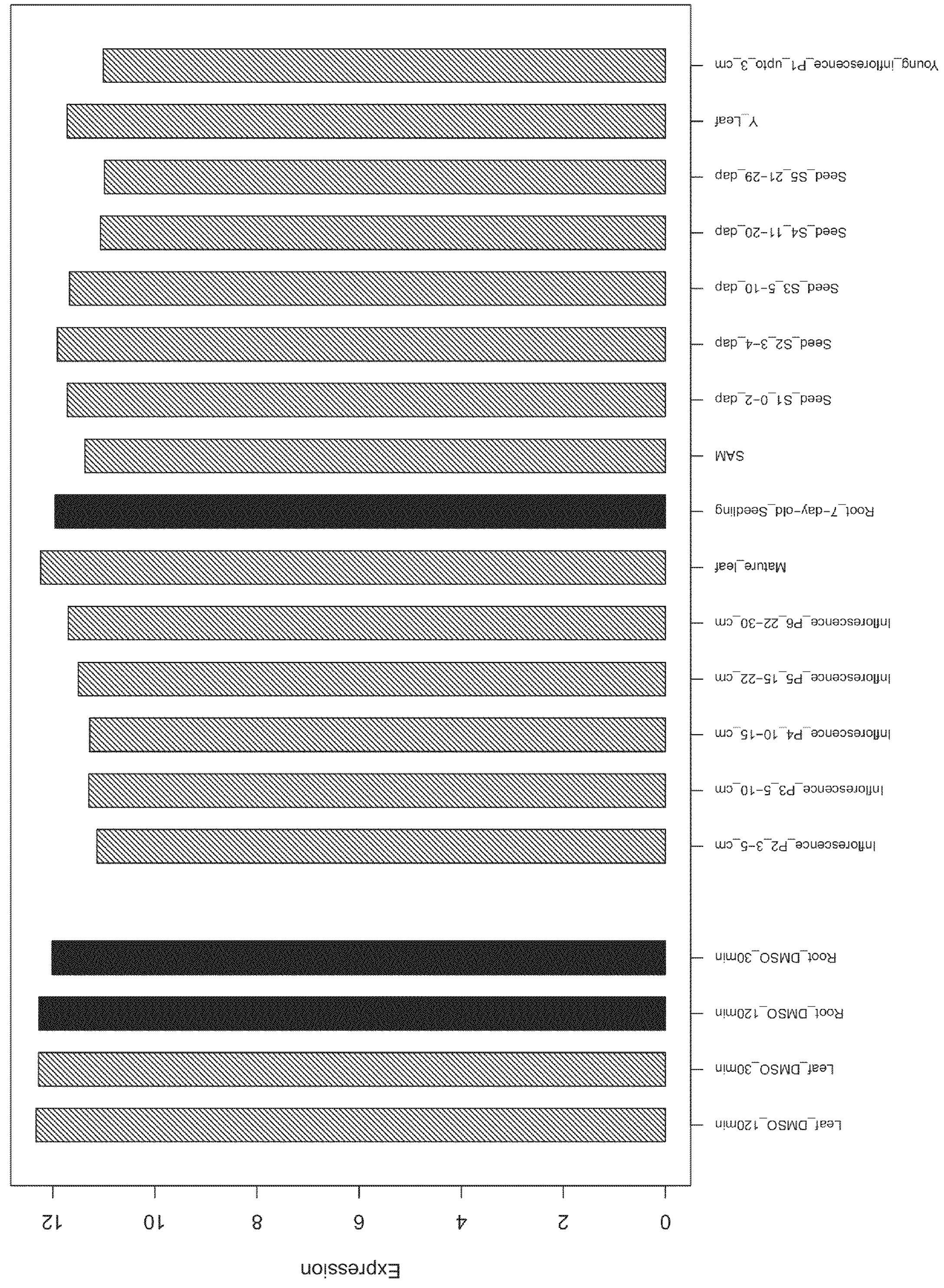
Figure 283:
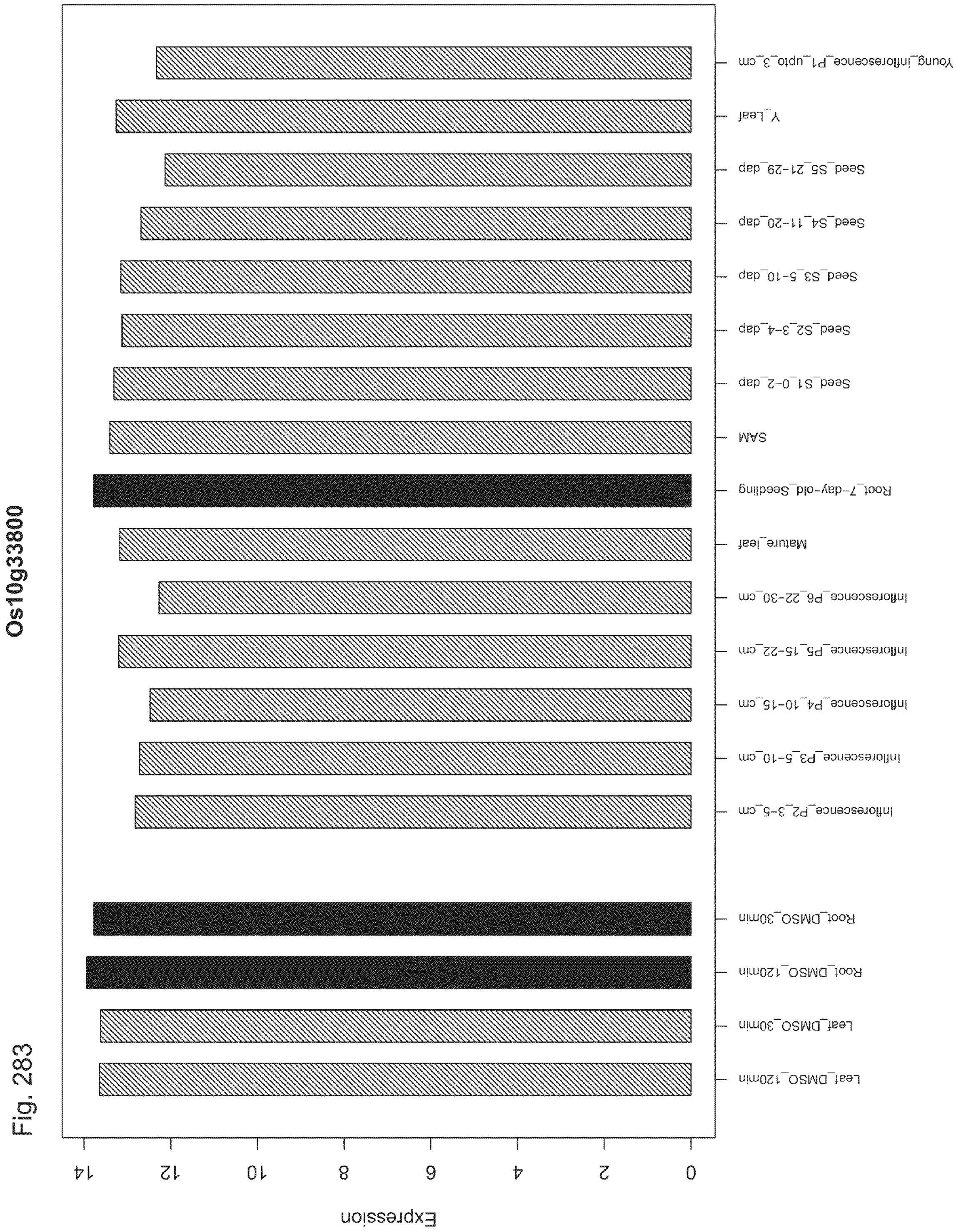
Figure 284A:
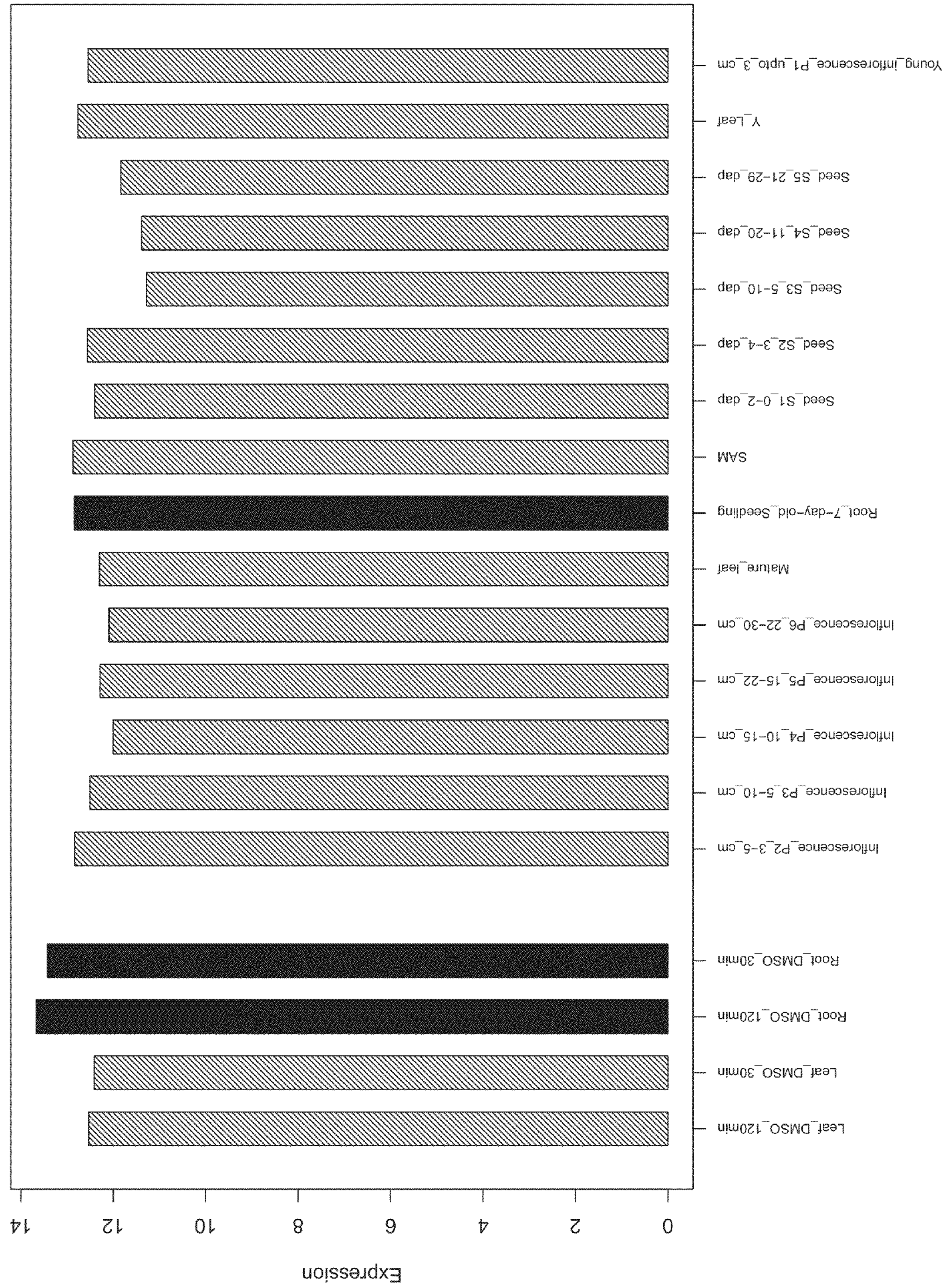
Figure 284B:
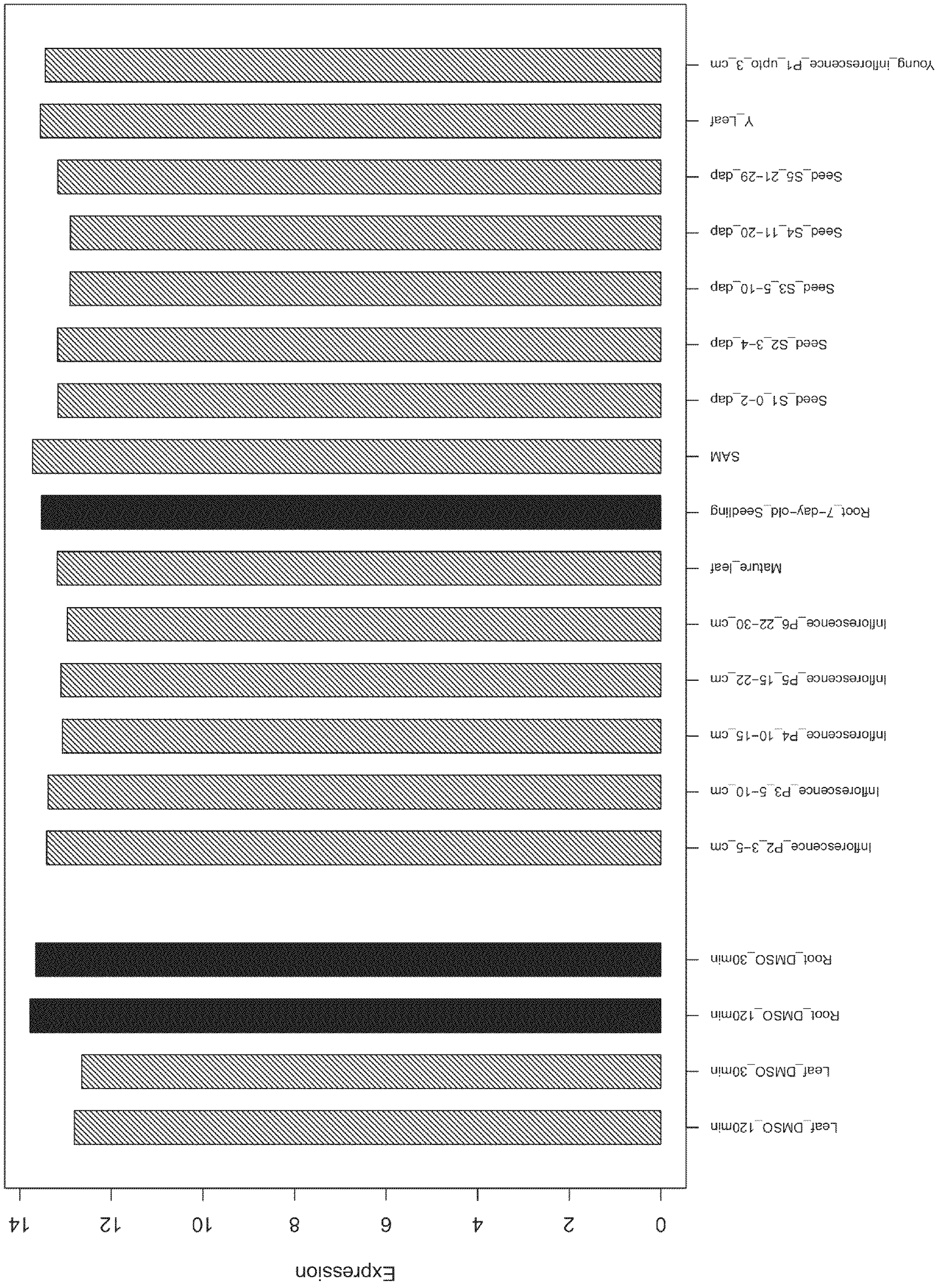
Figure 285A:
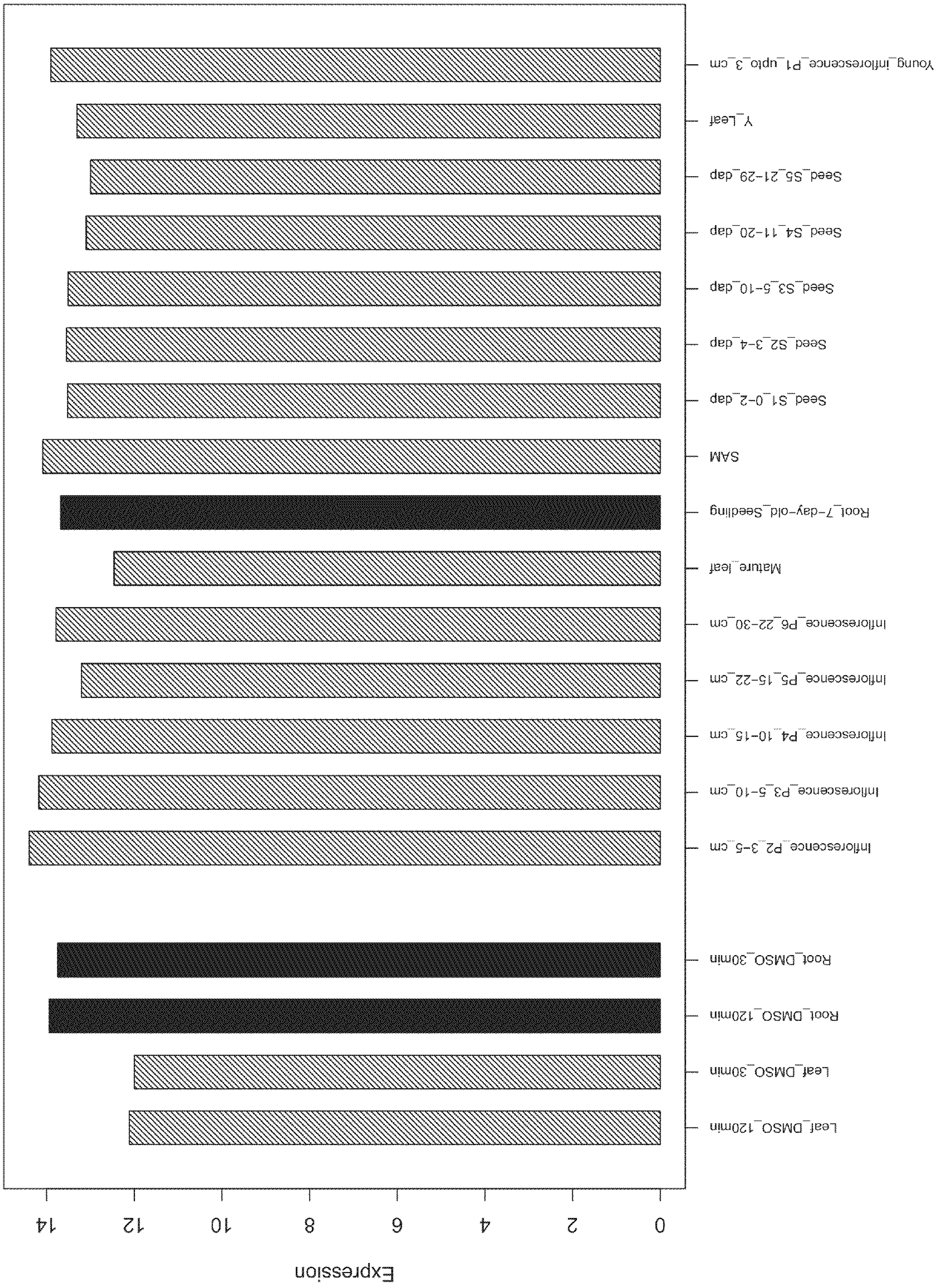
Figure 285B:
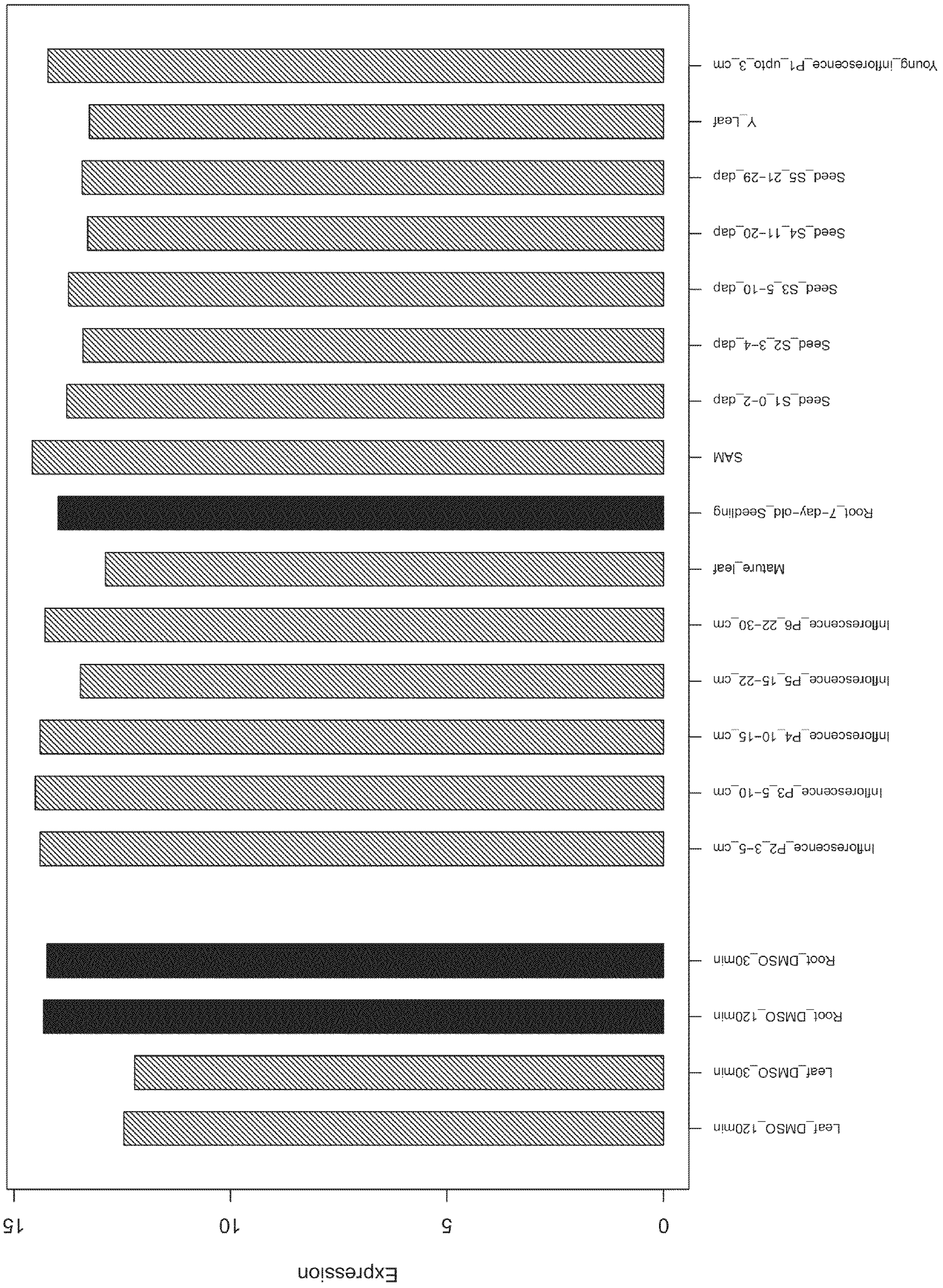
Figure 286:
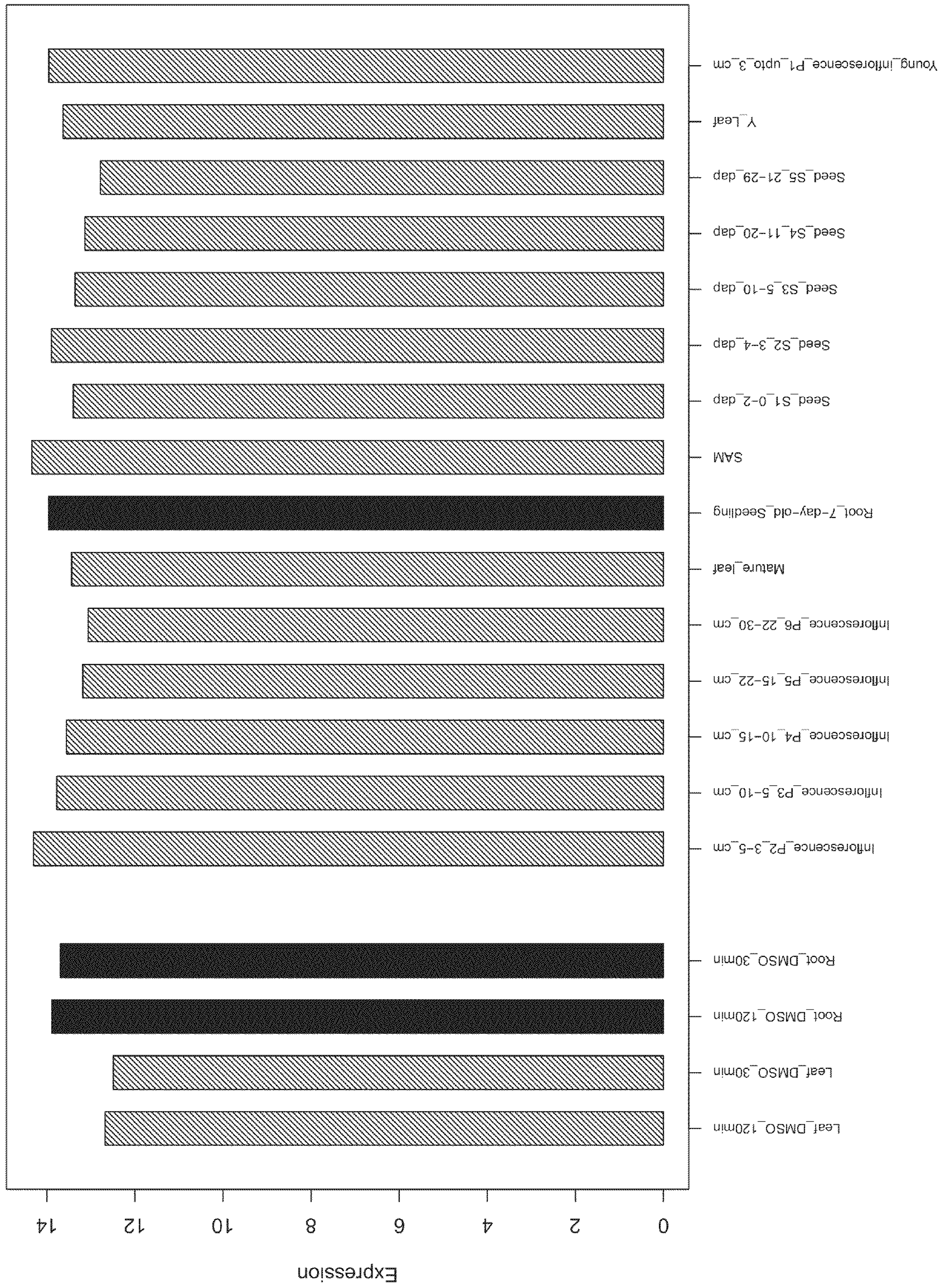
Figure 287:
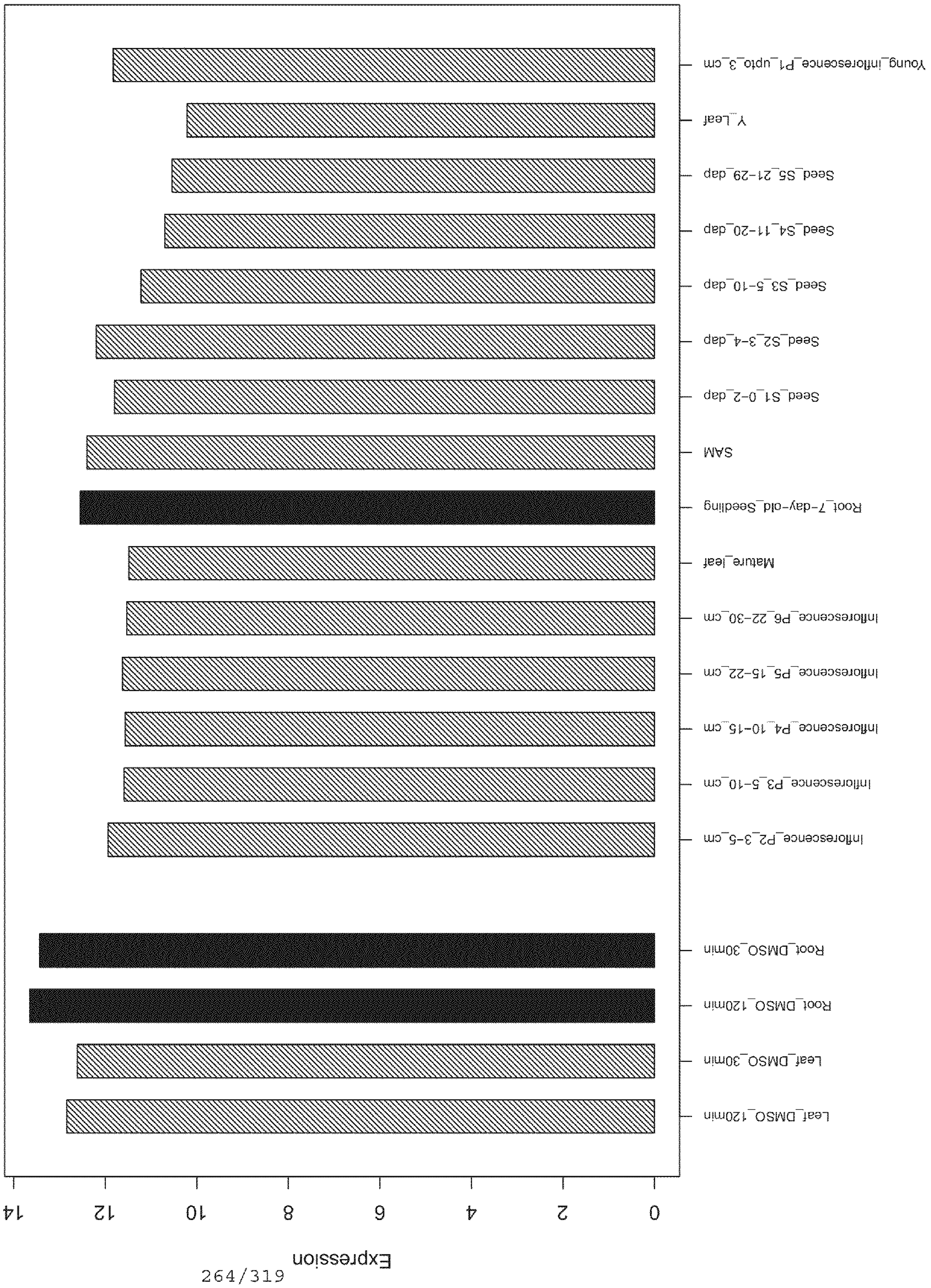
Figure 288:
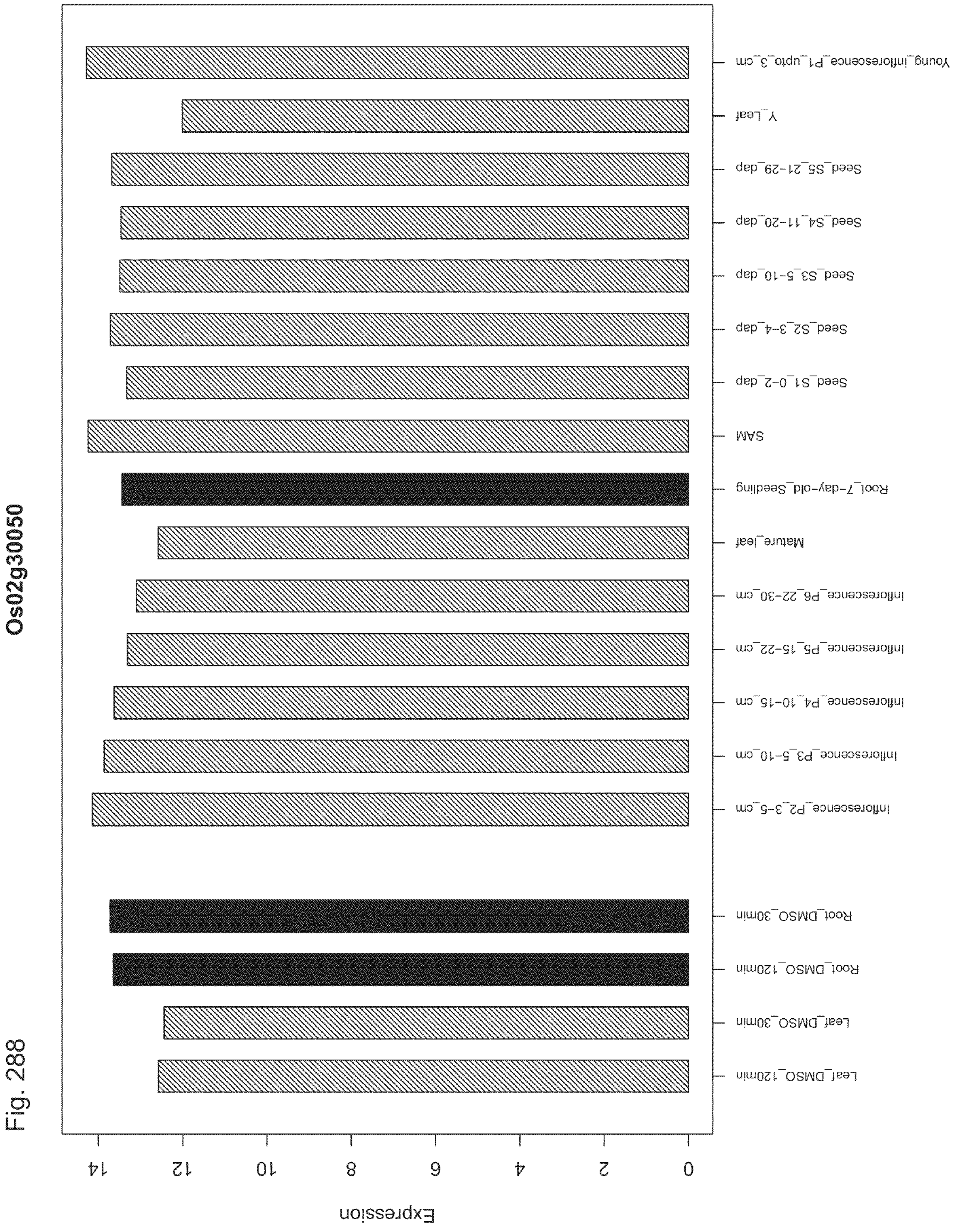
Figure 289A:
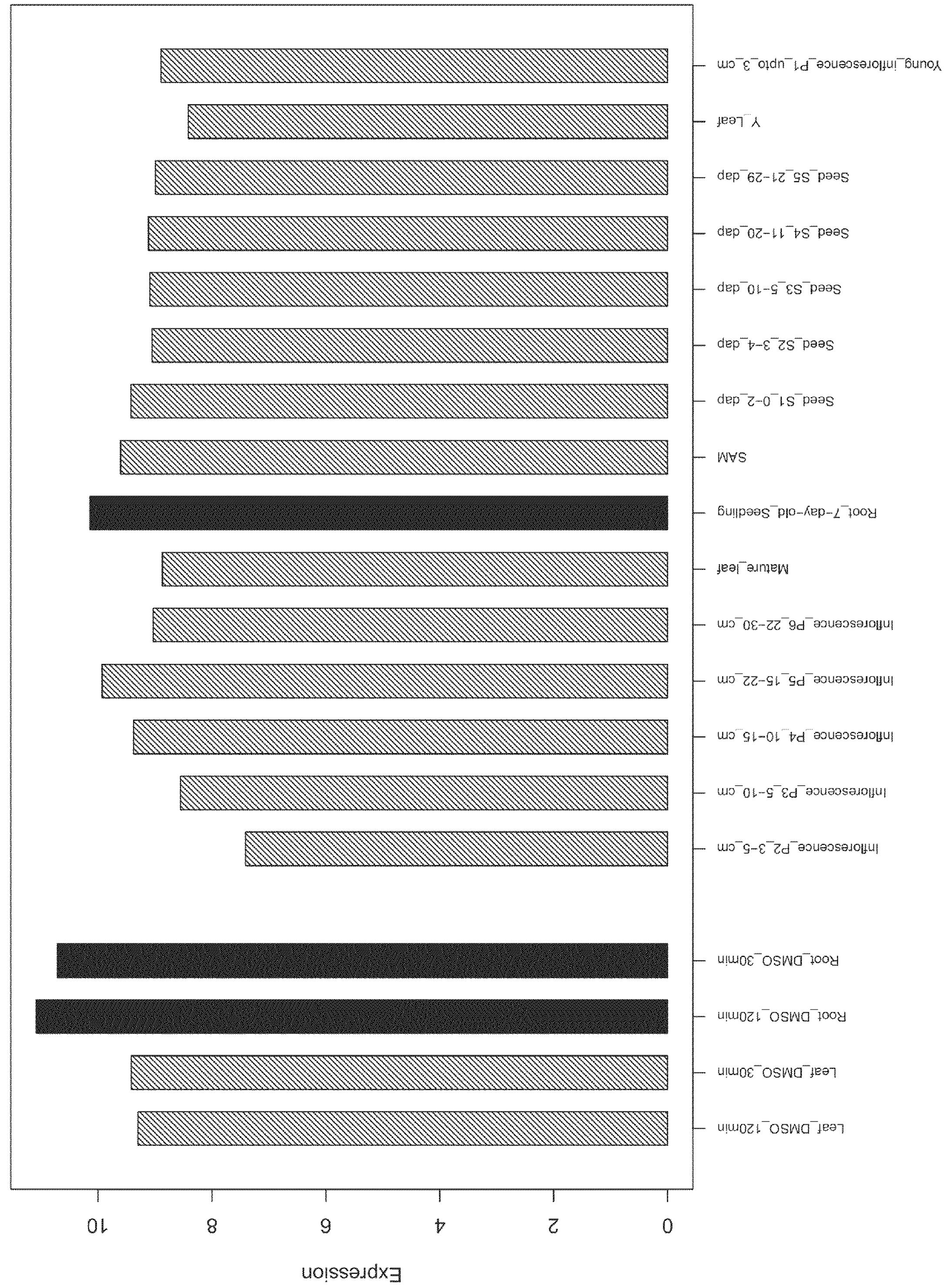
Figure 289B:
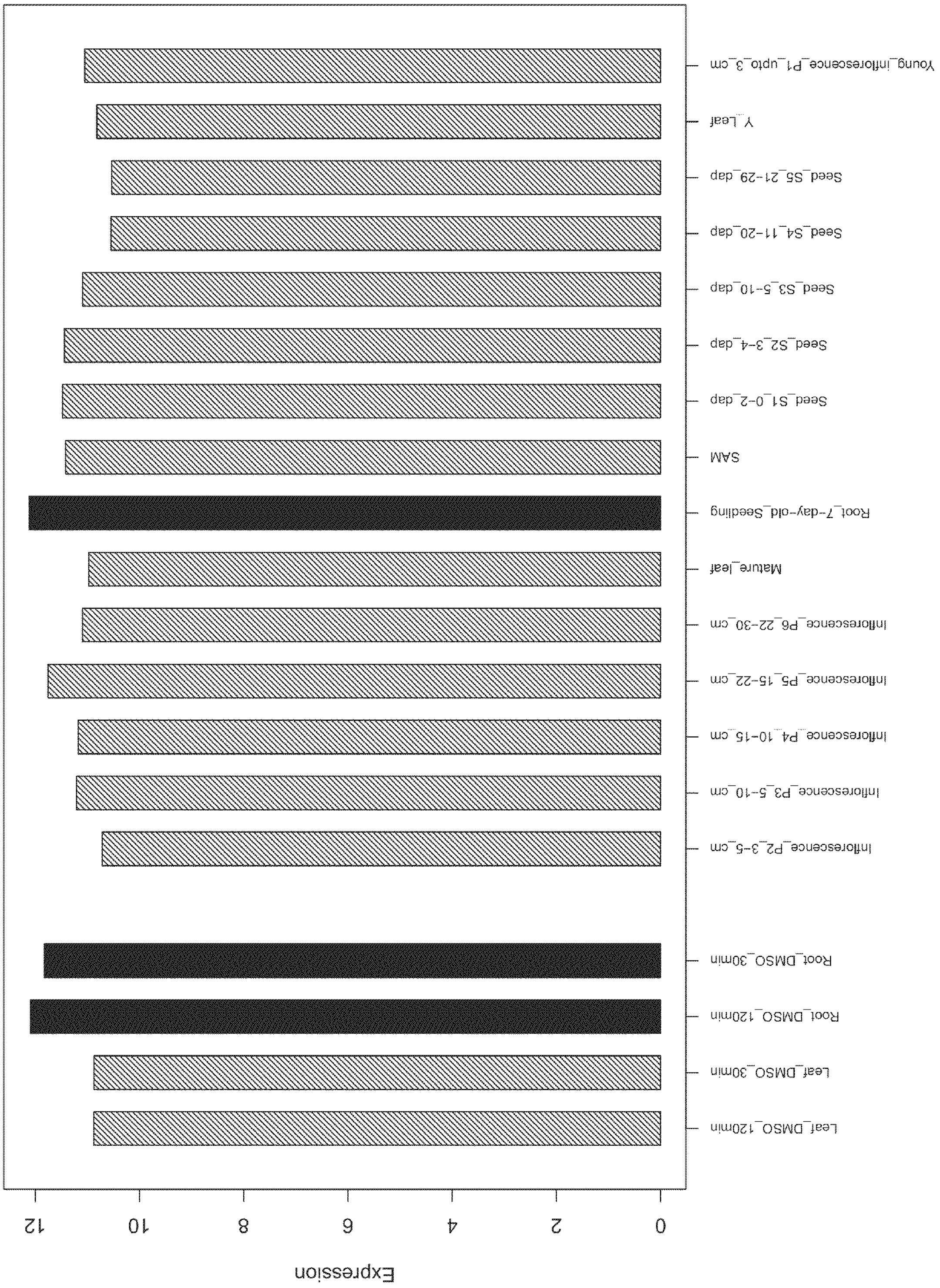
Figure 290:
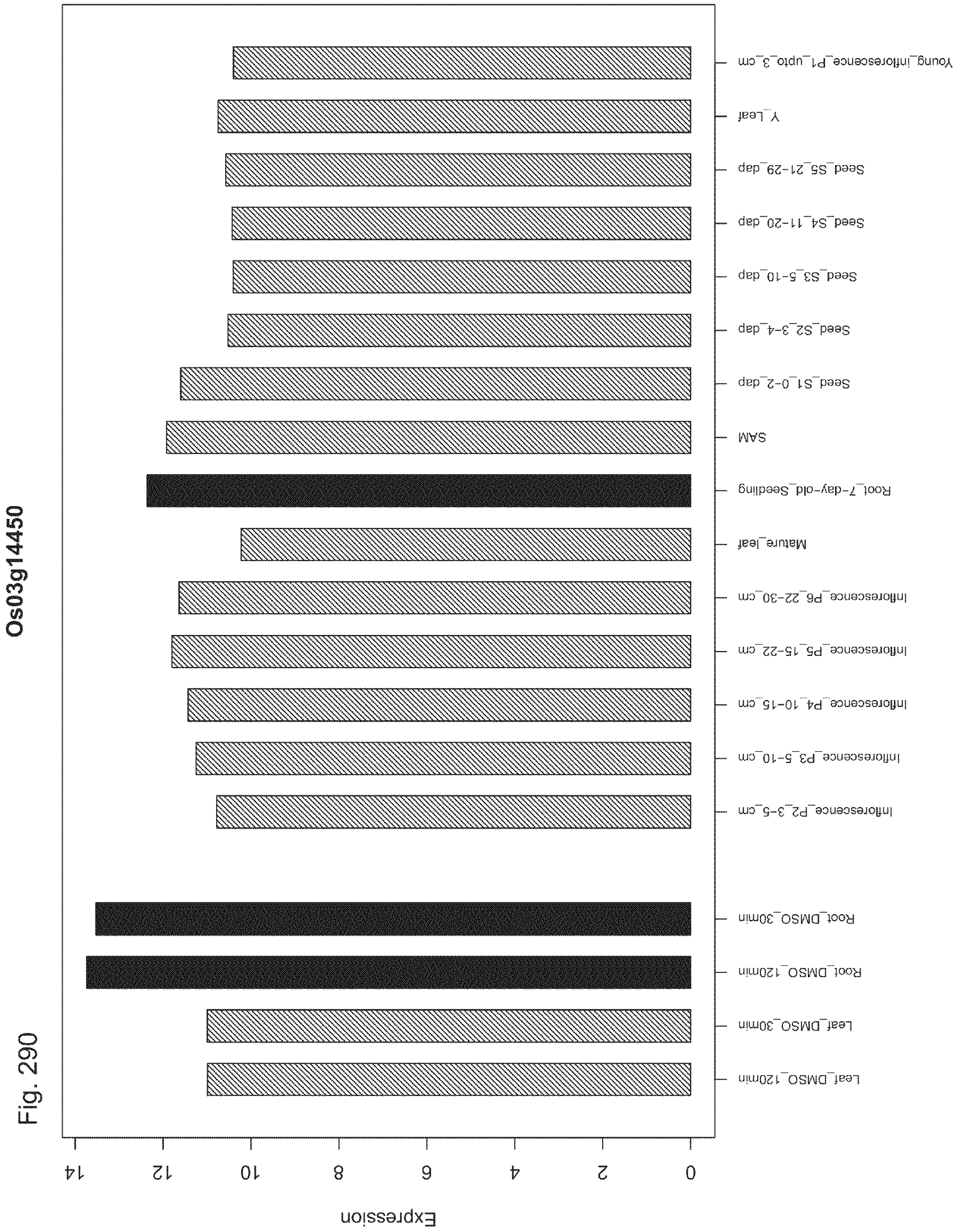
Figure 291:
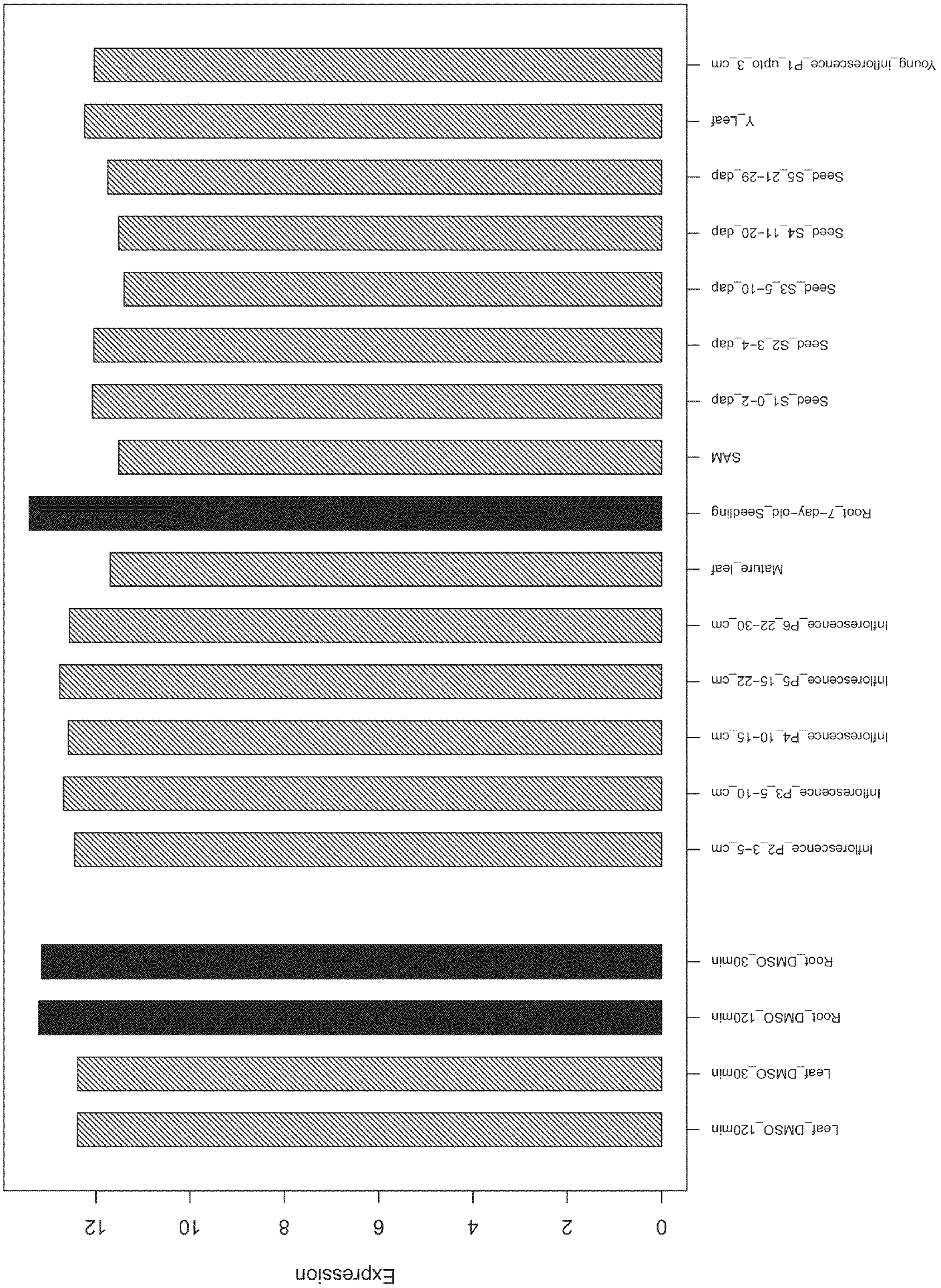
Figure 292:
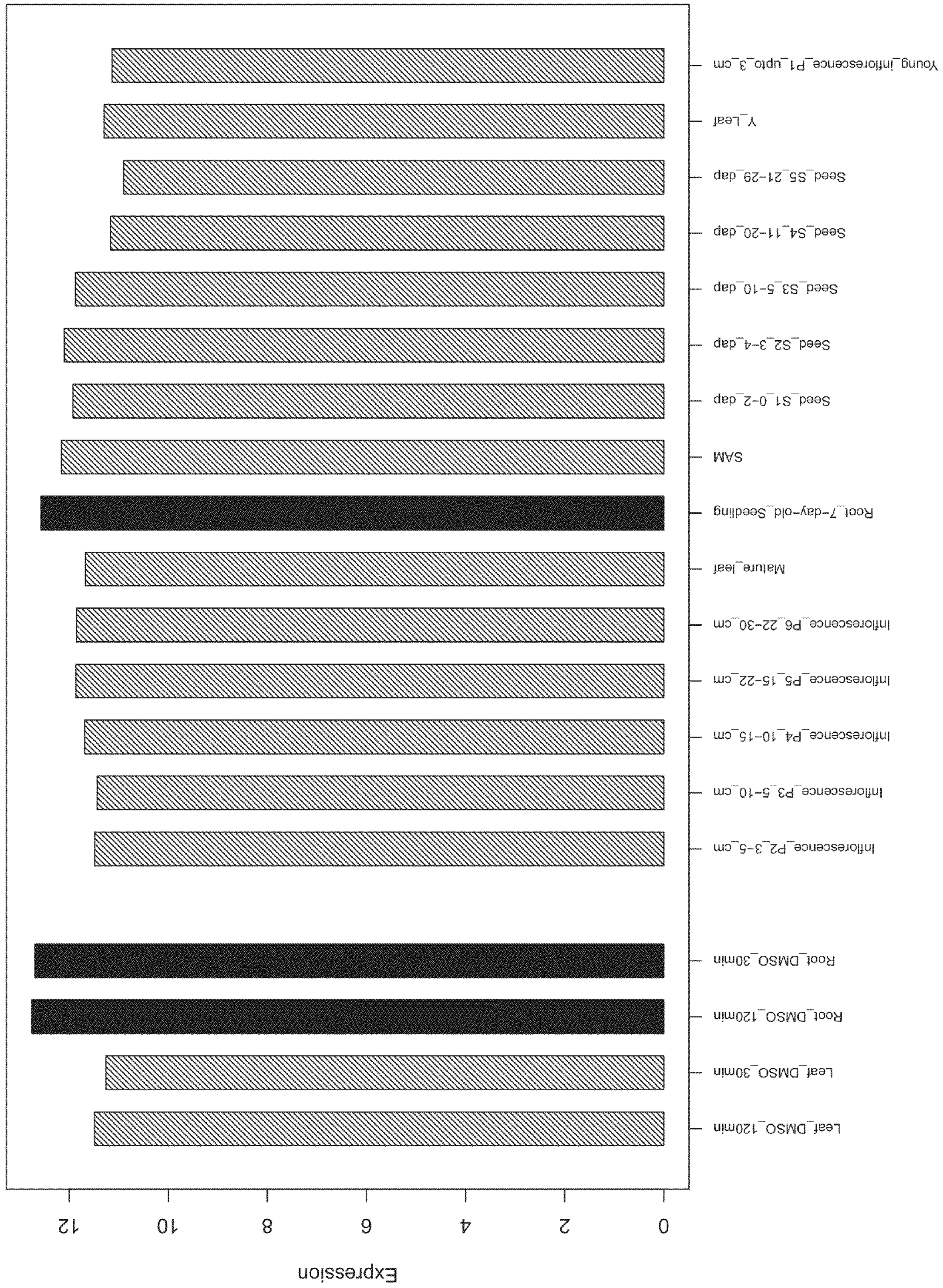
Figure 293:
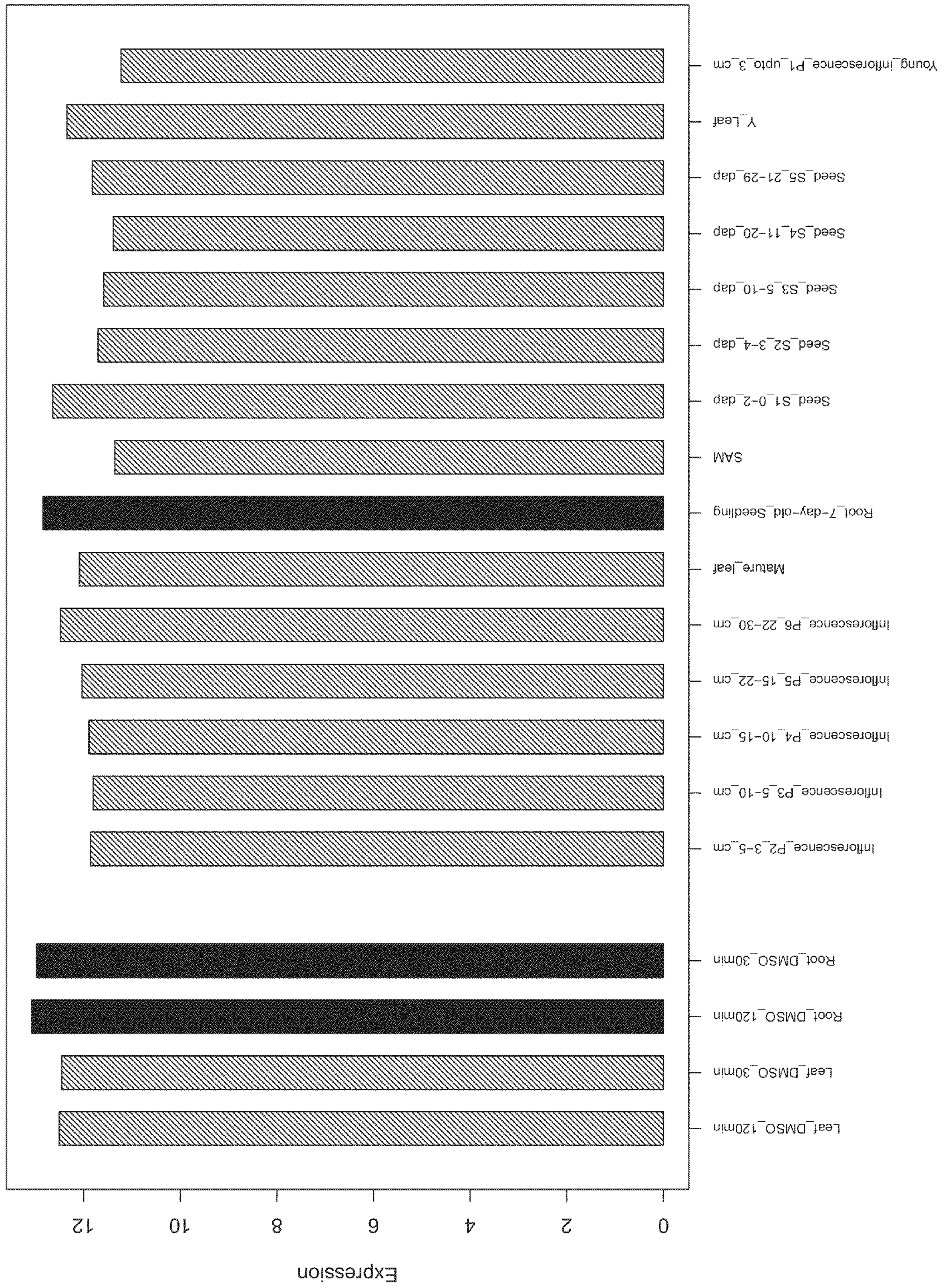
Figure 294:
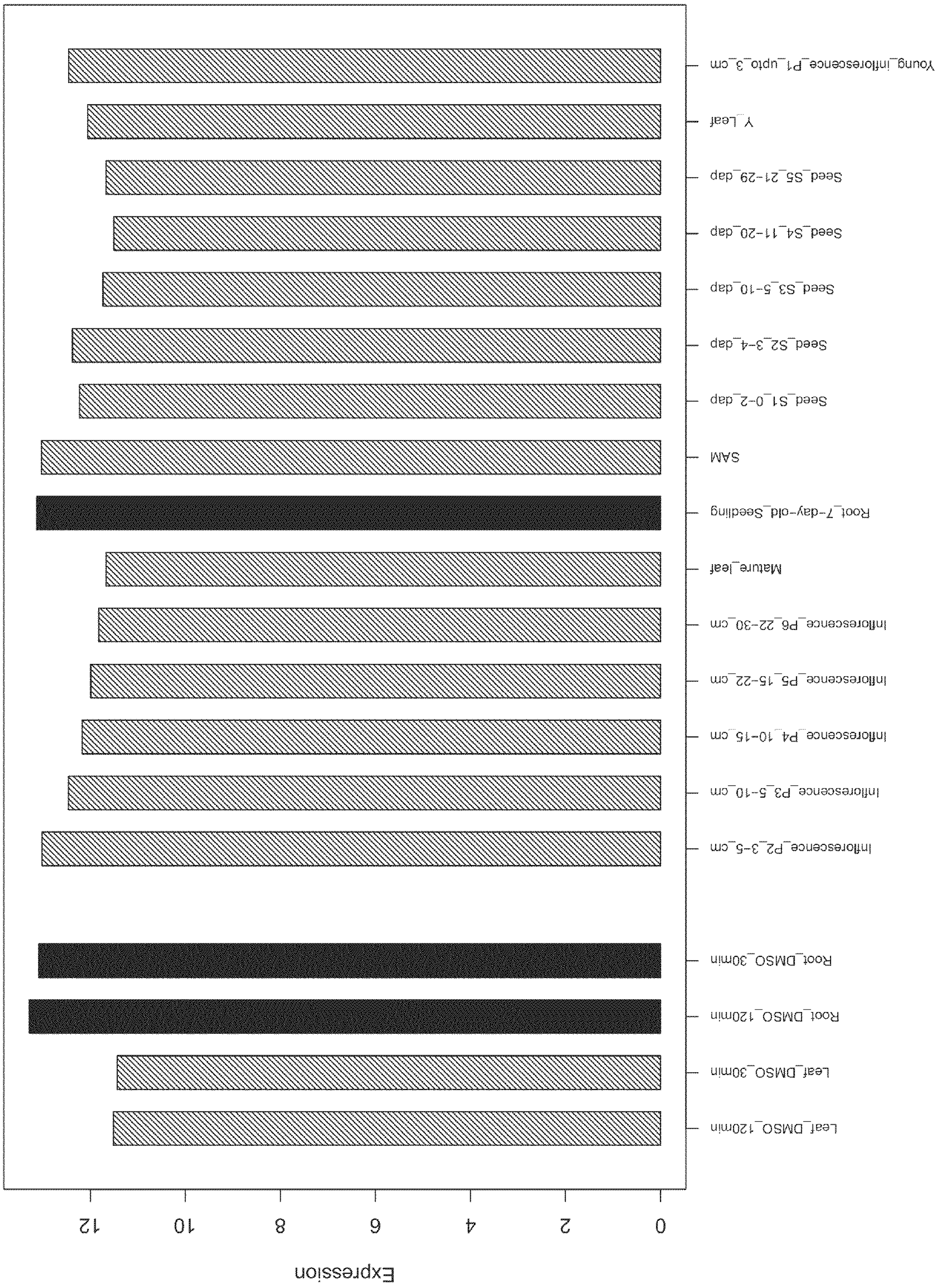
Figure 295:
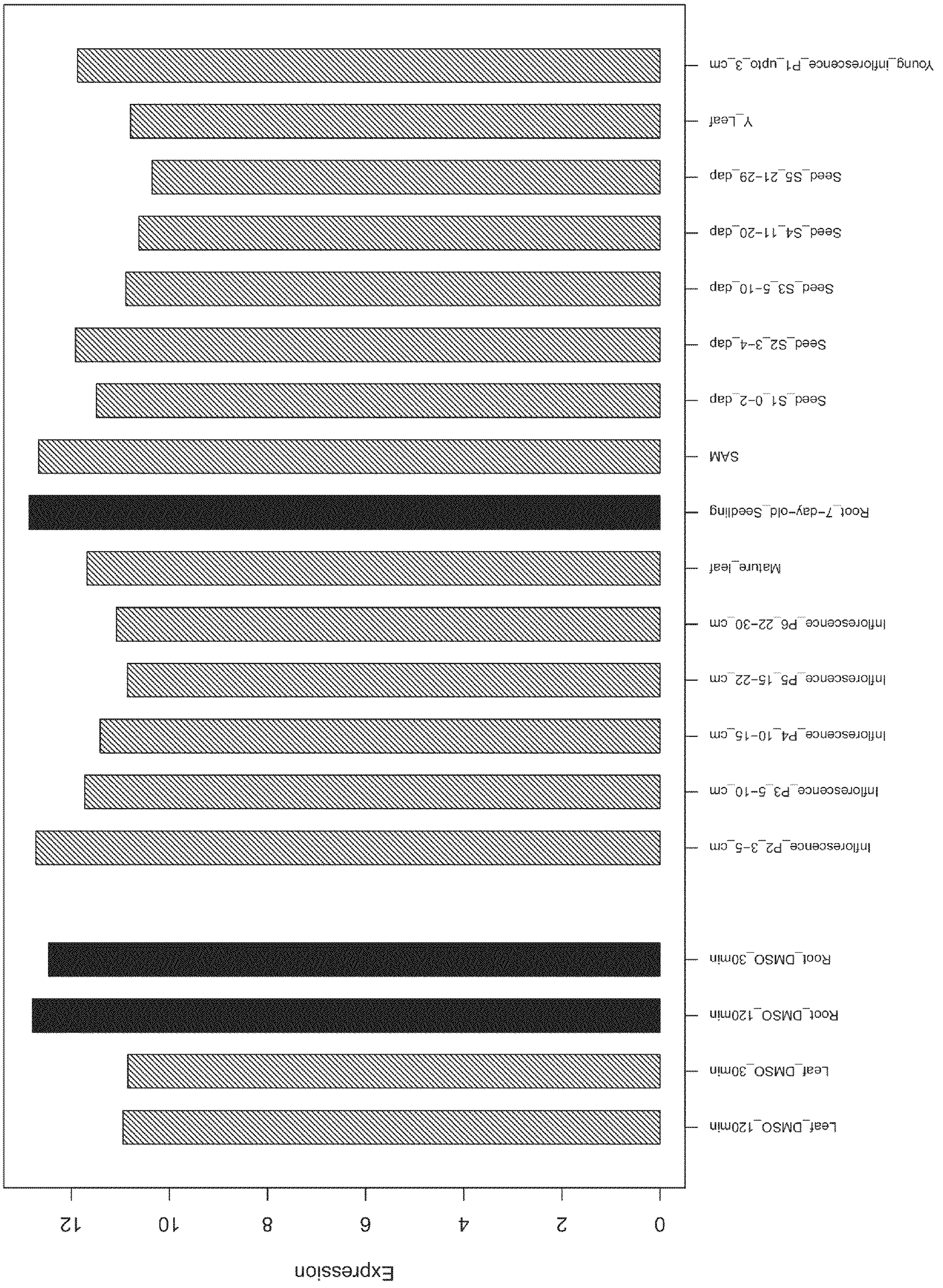
Figure 296:
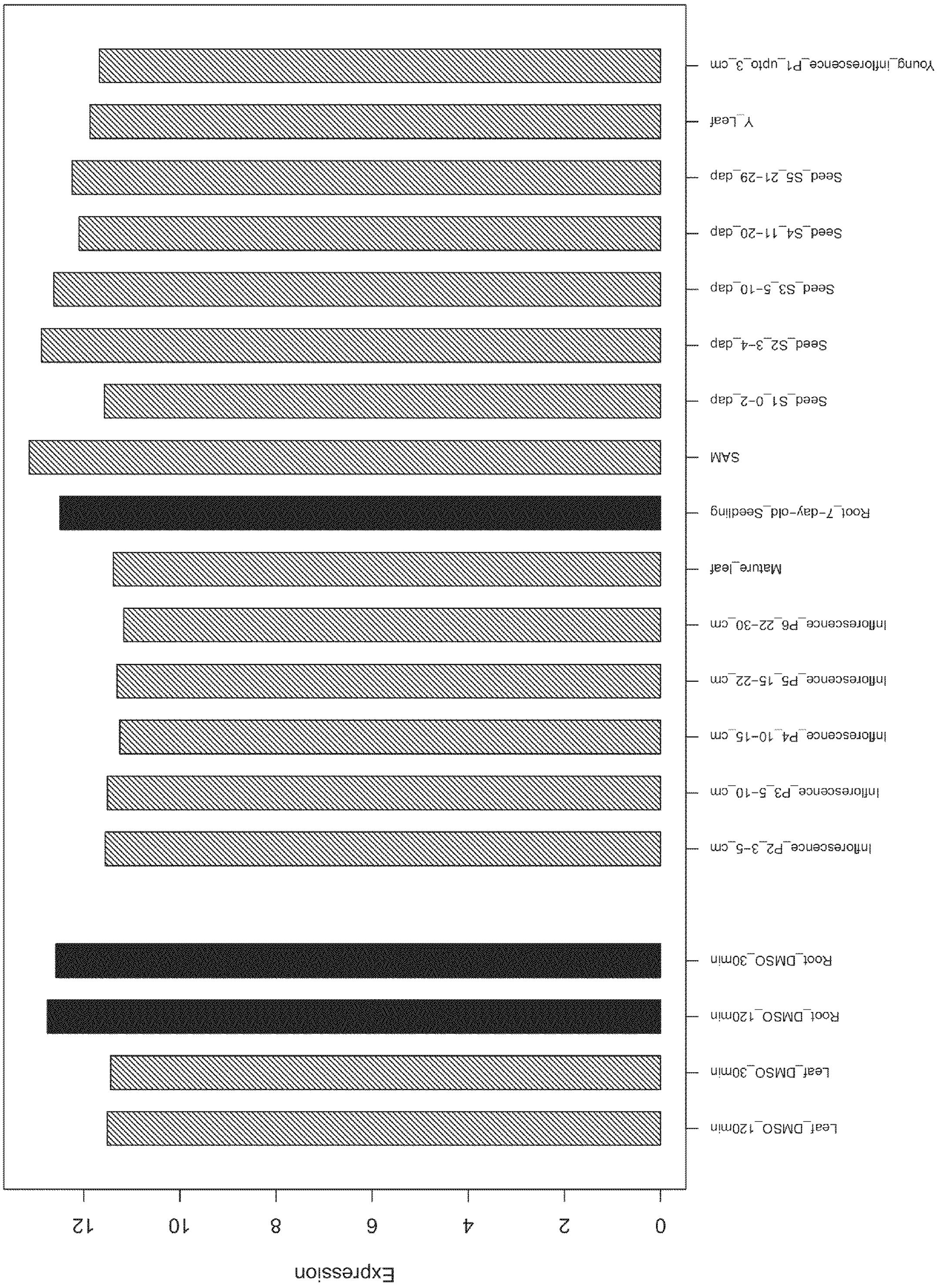
Figure 297:
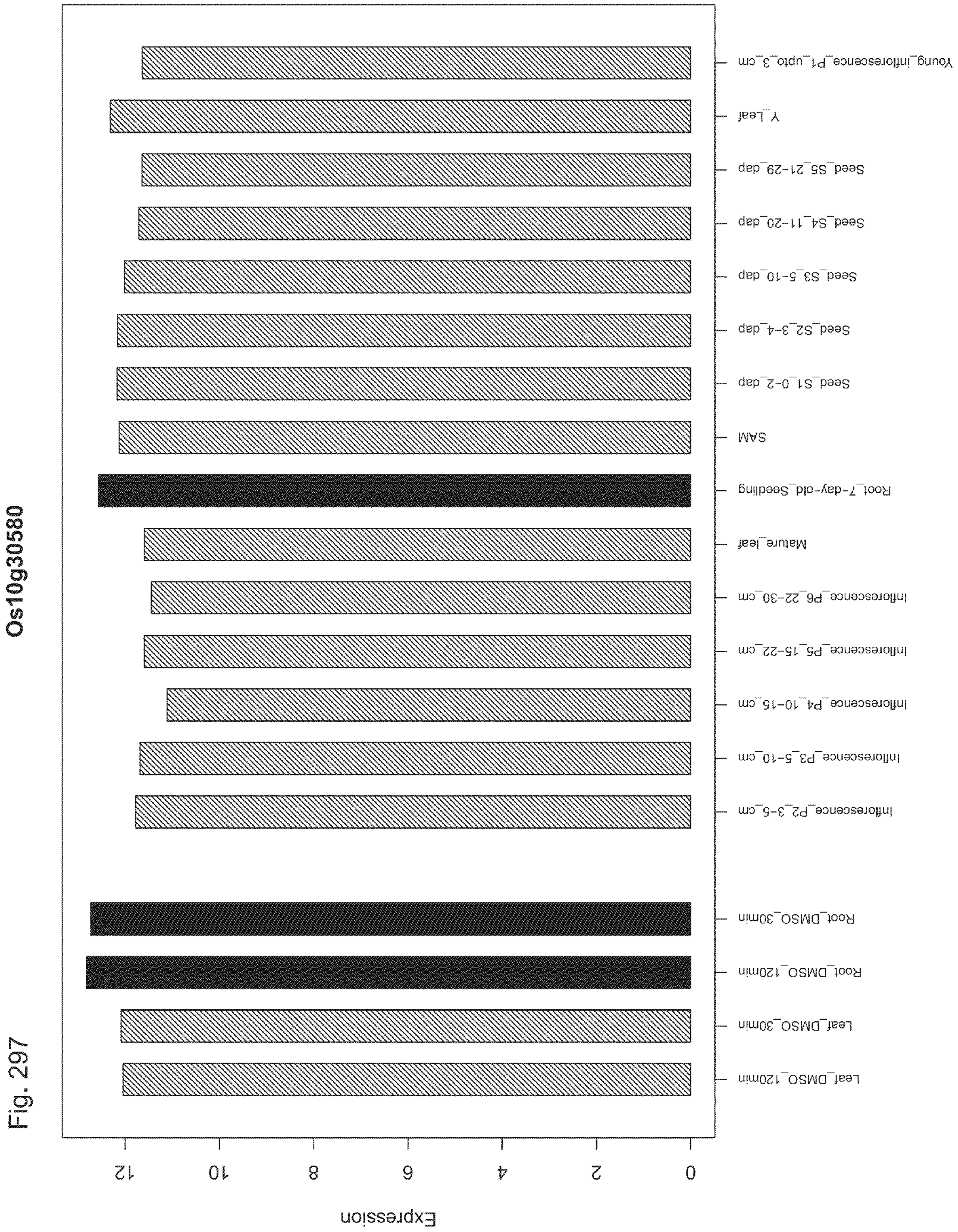
Figure 298:
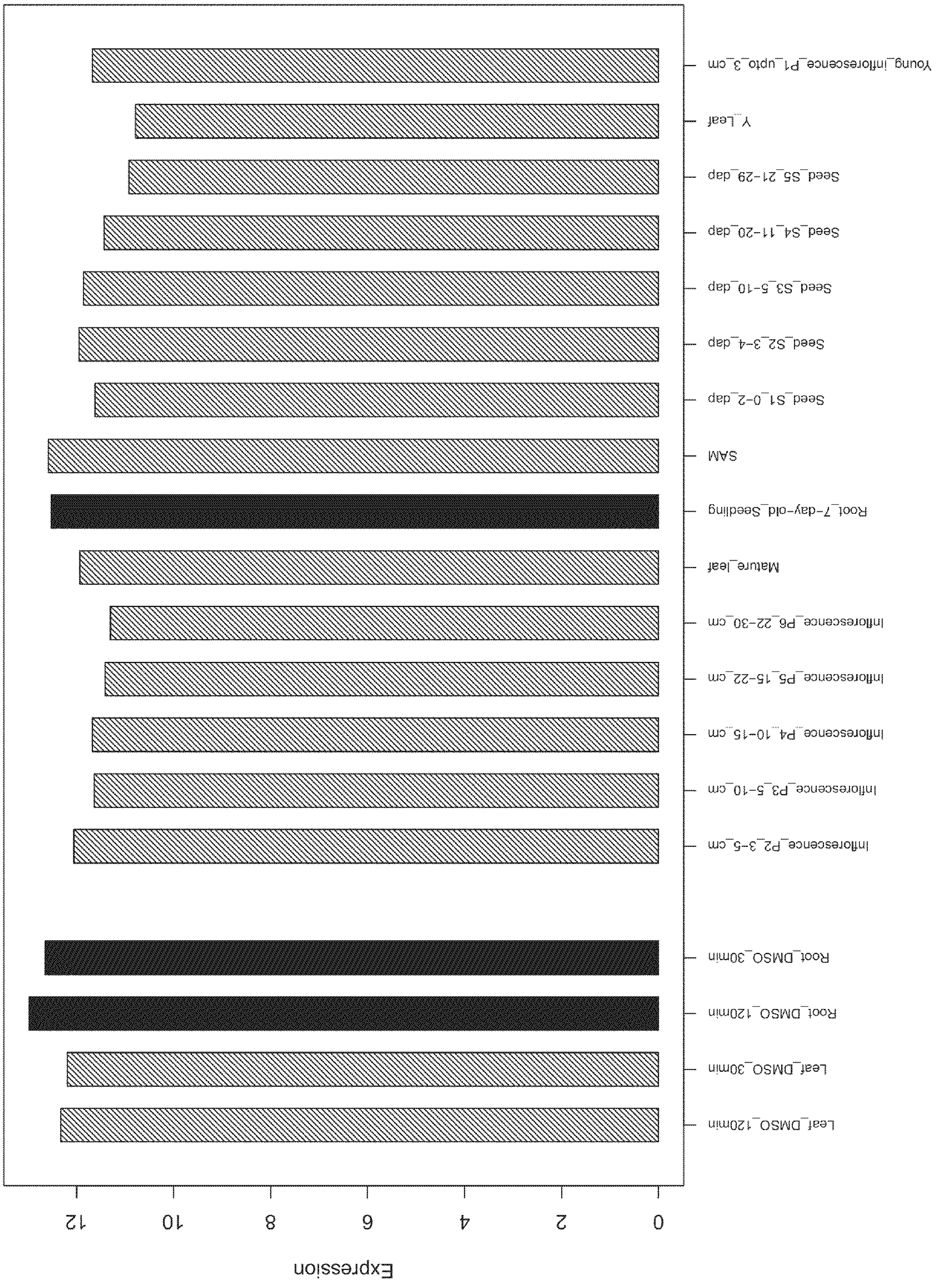
Figure 299:
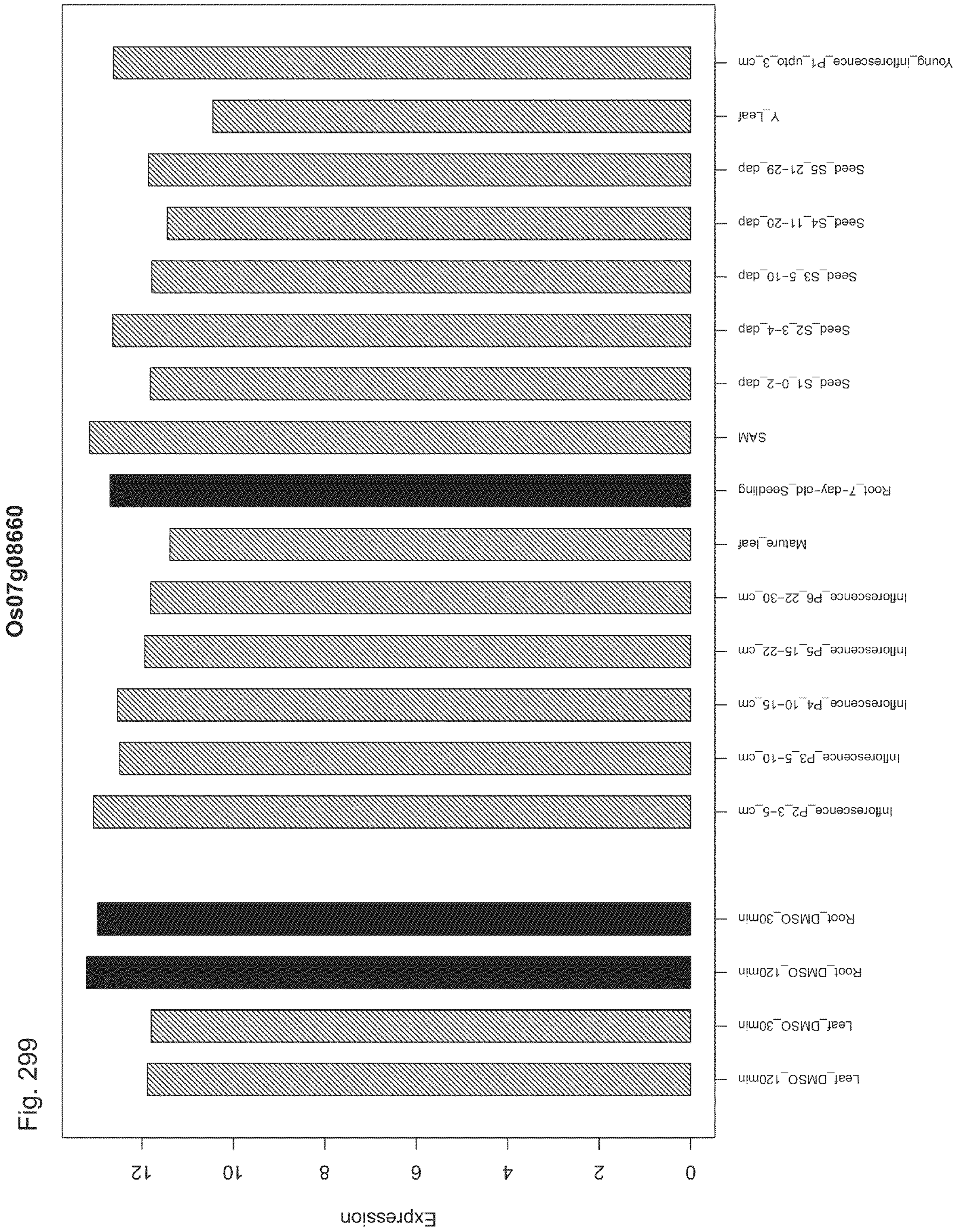
Figure 300:
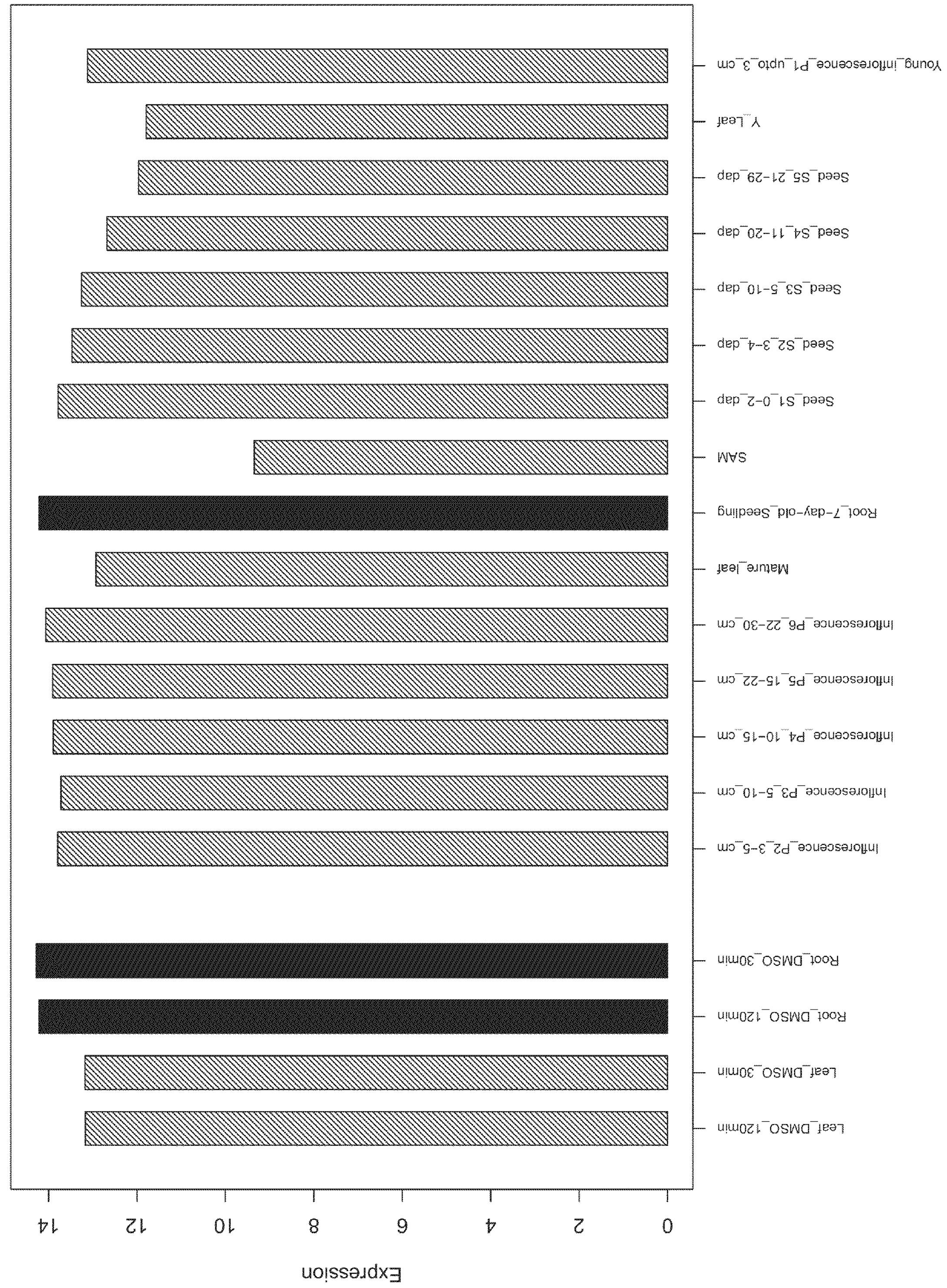
Figure 301A:
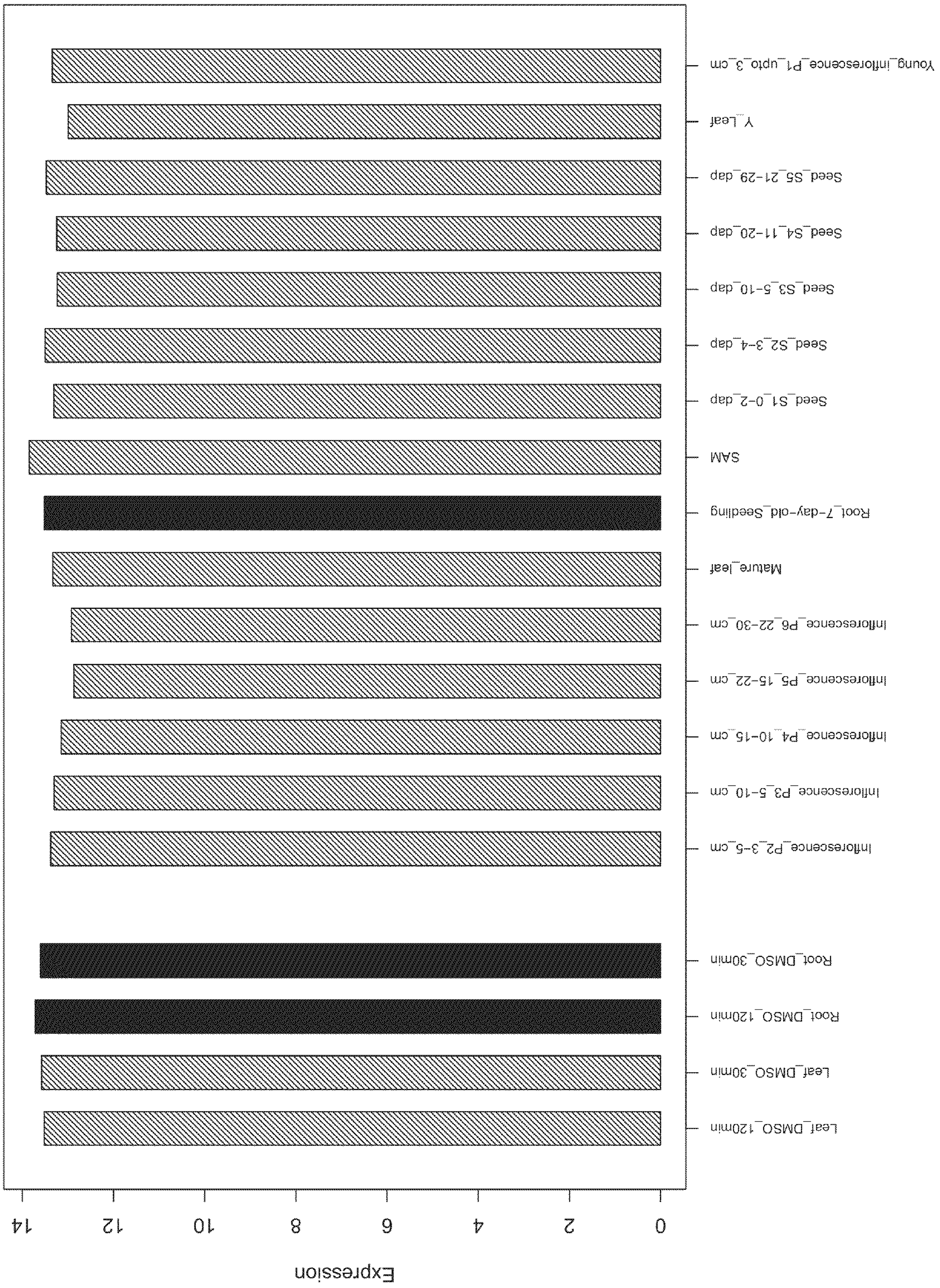
Figure 301B:
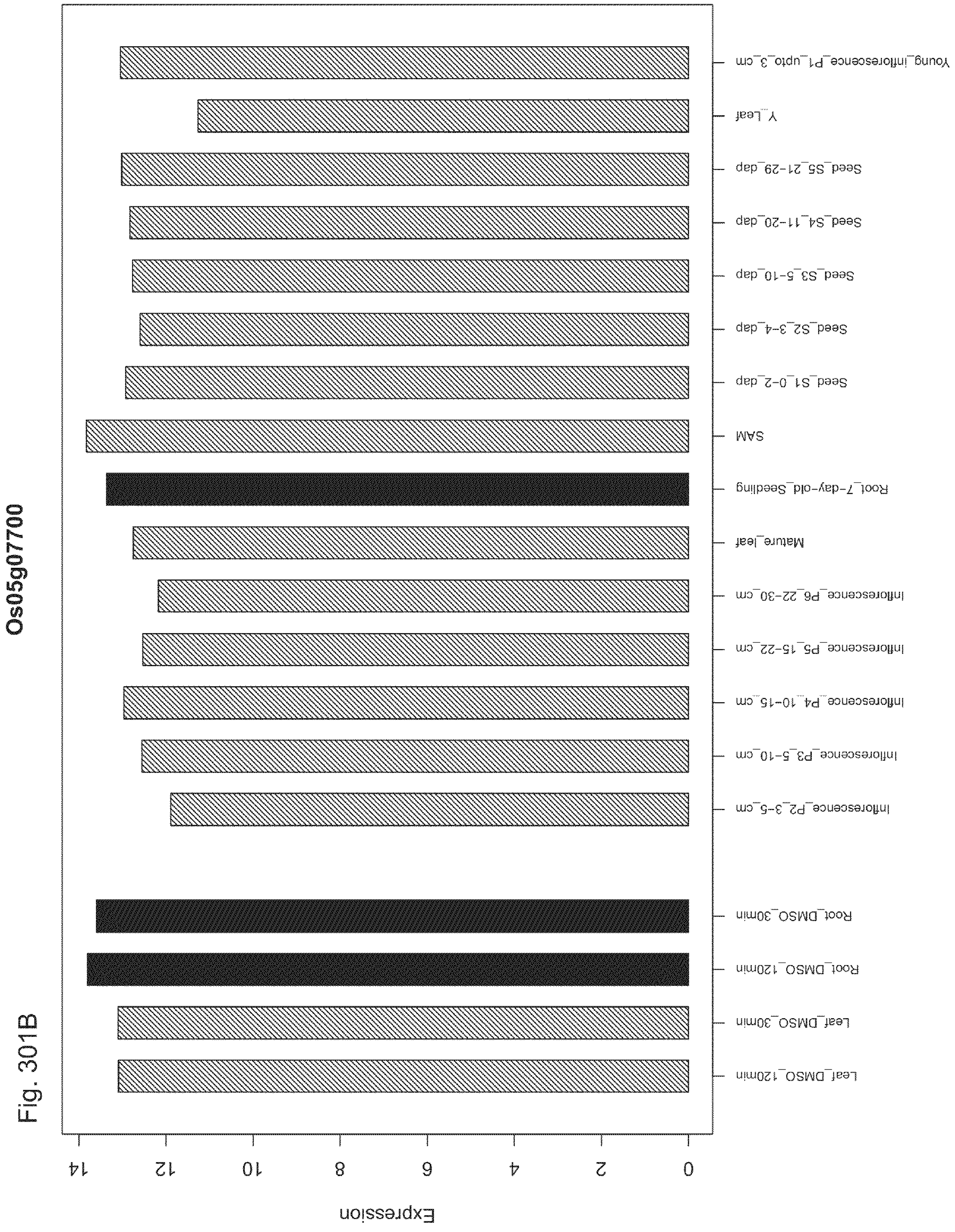
Figure 301C:
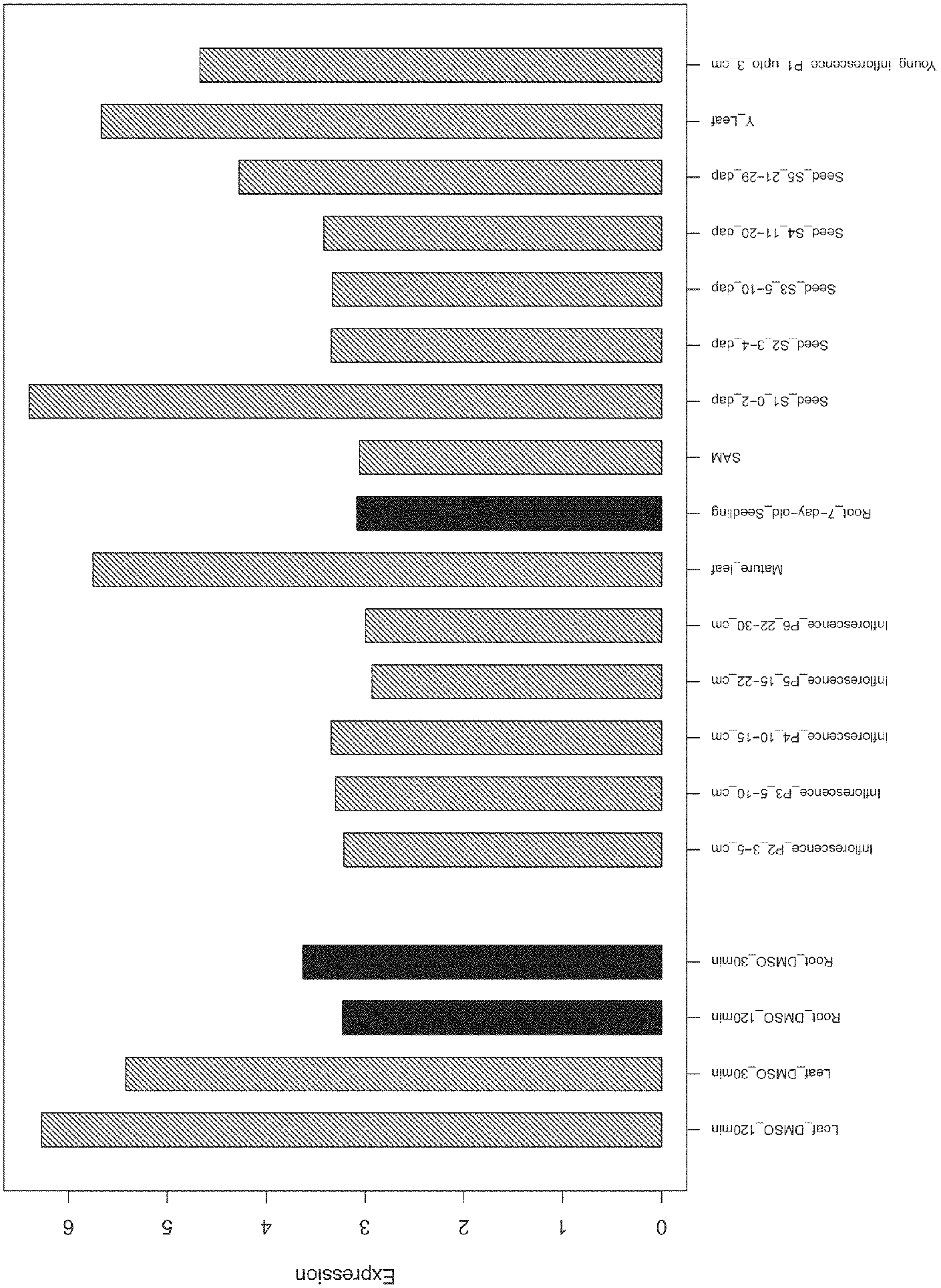
Figure 301D:
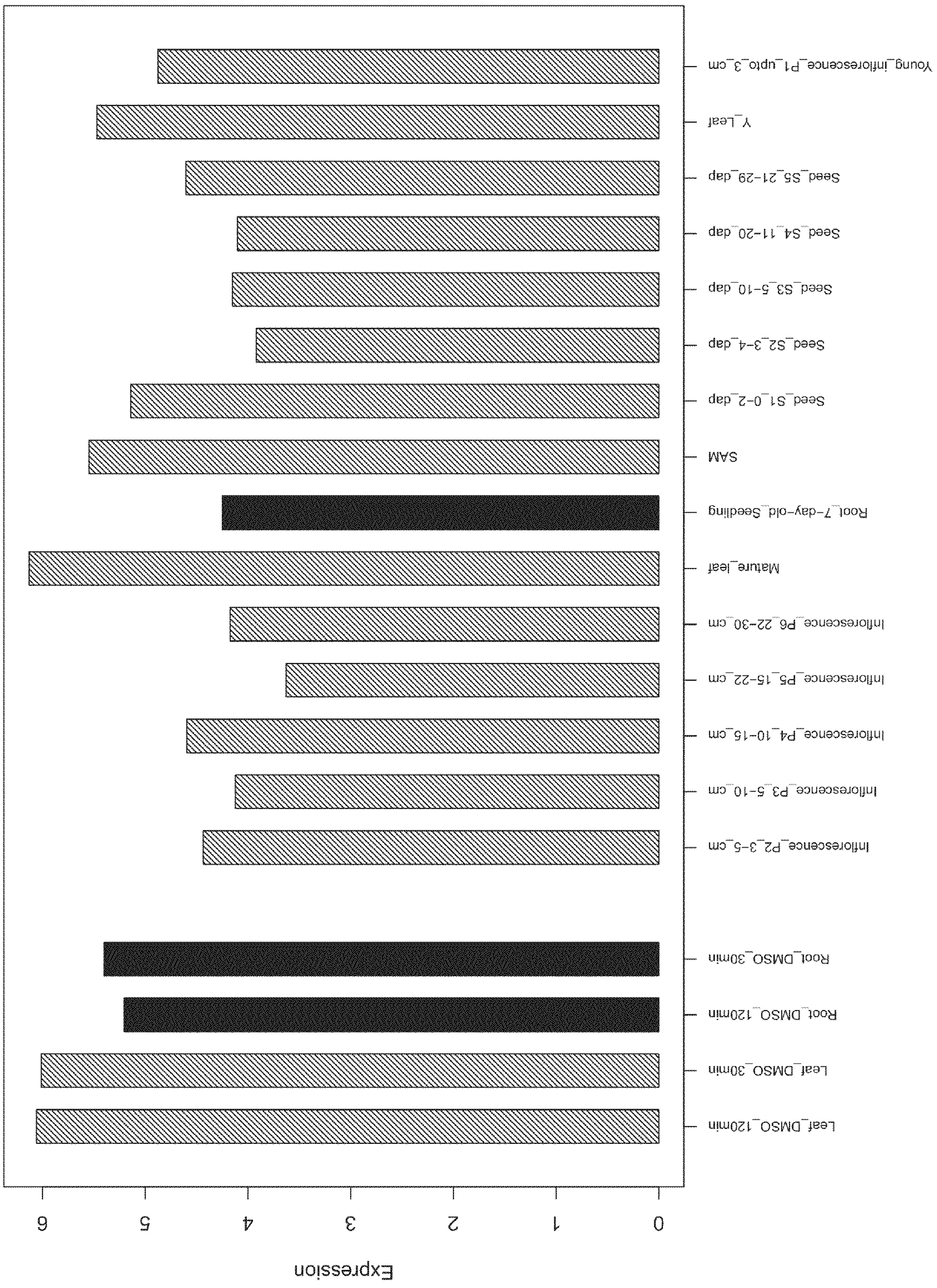
Figure 302:
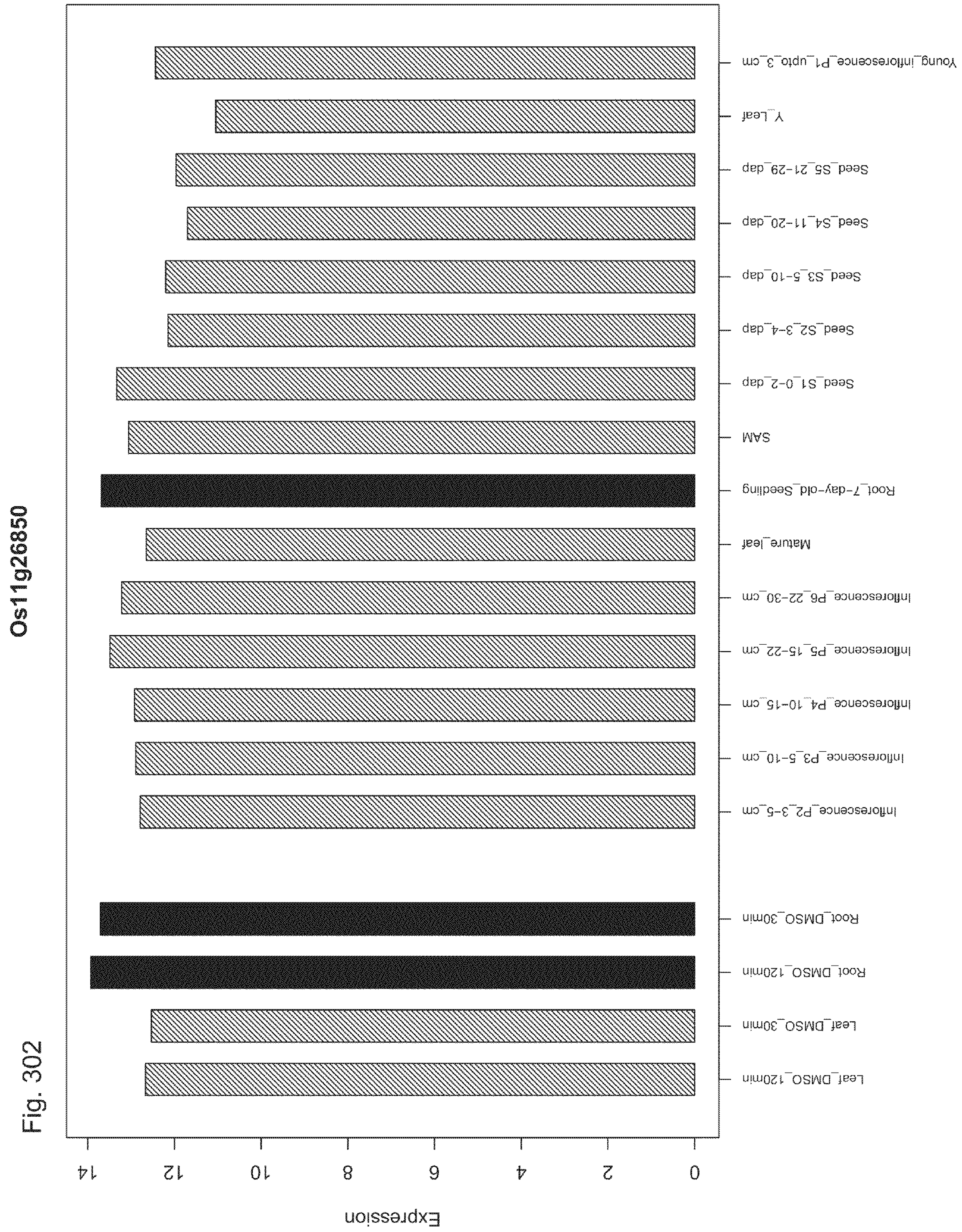
Figure 303:
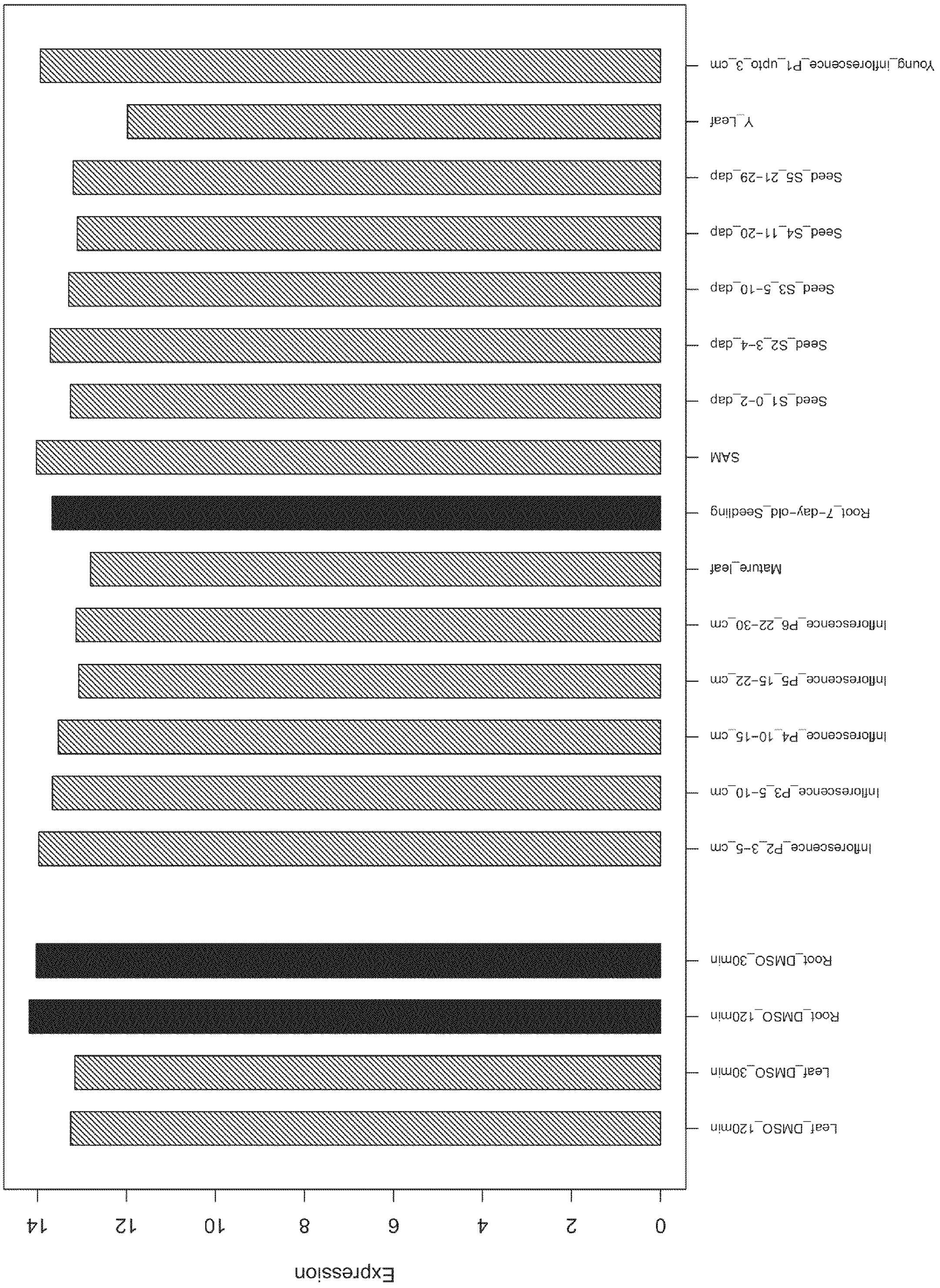
Figure 304:
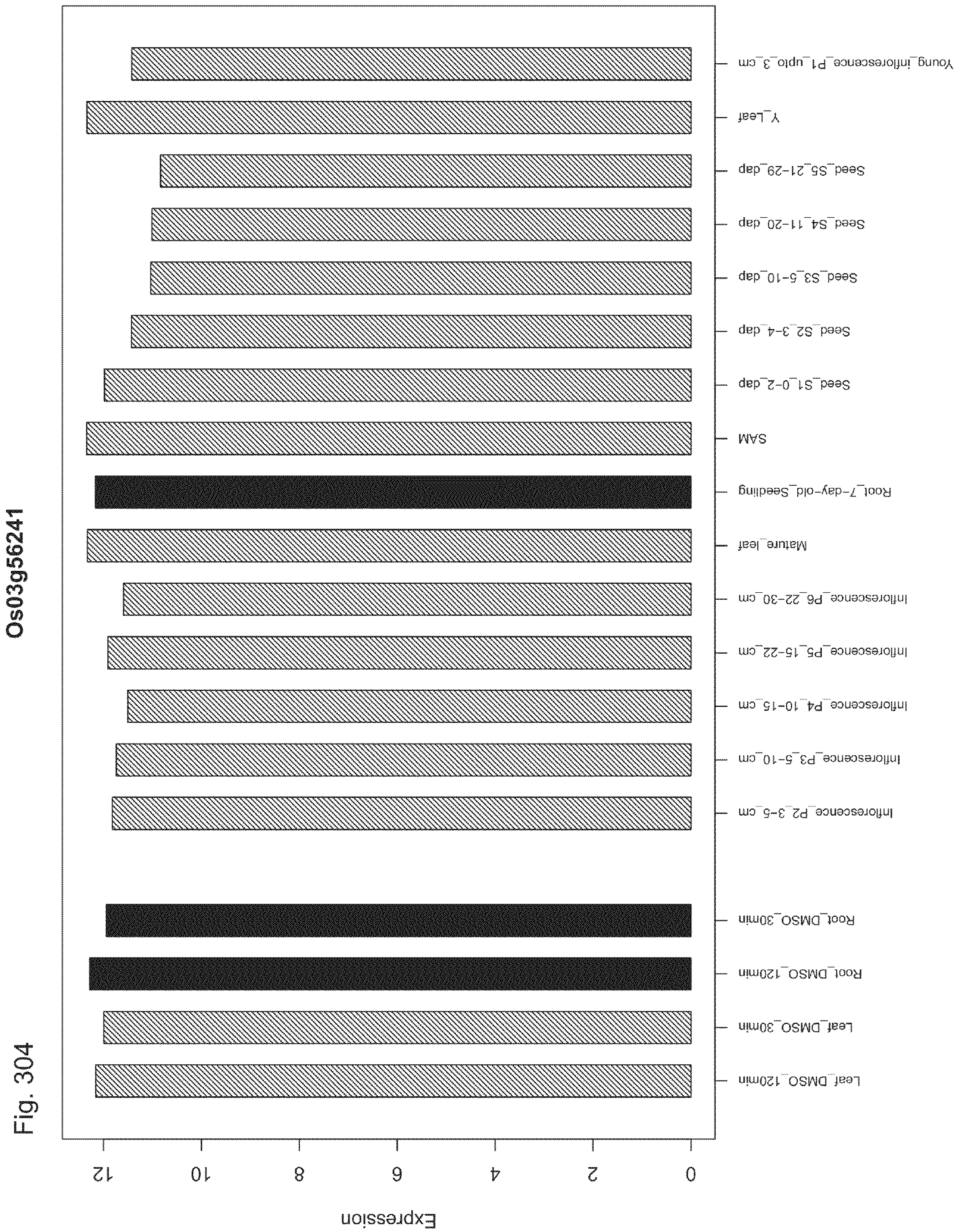
Figure 305:
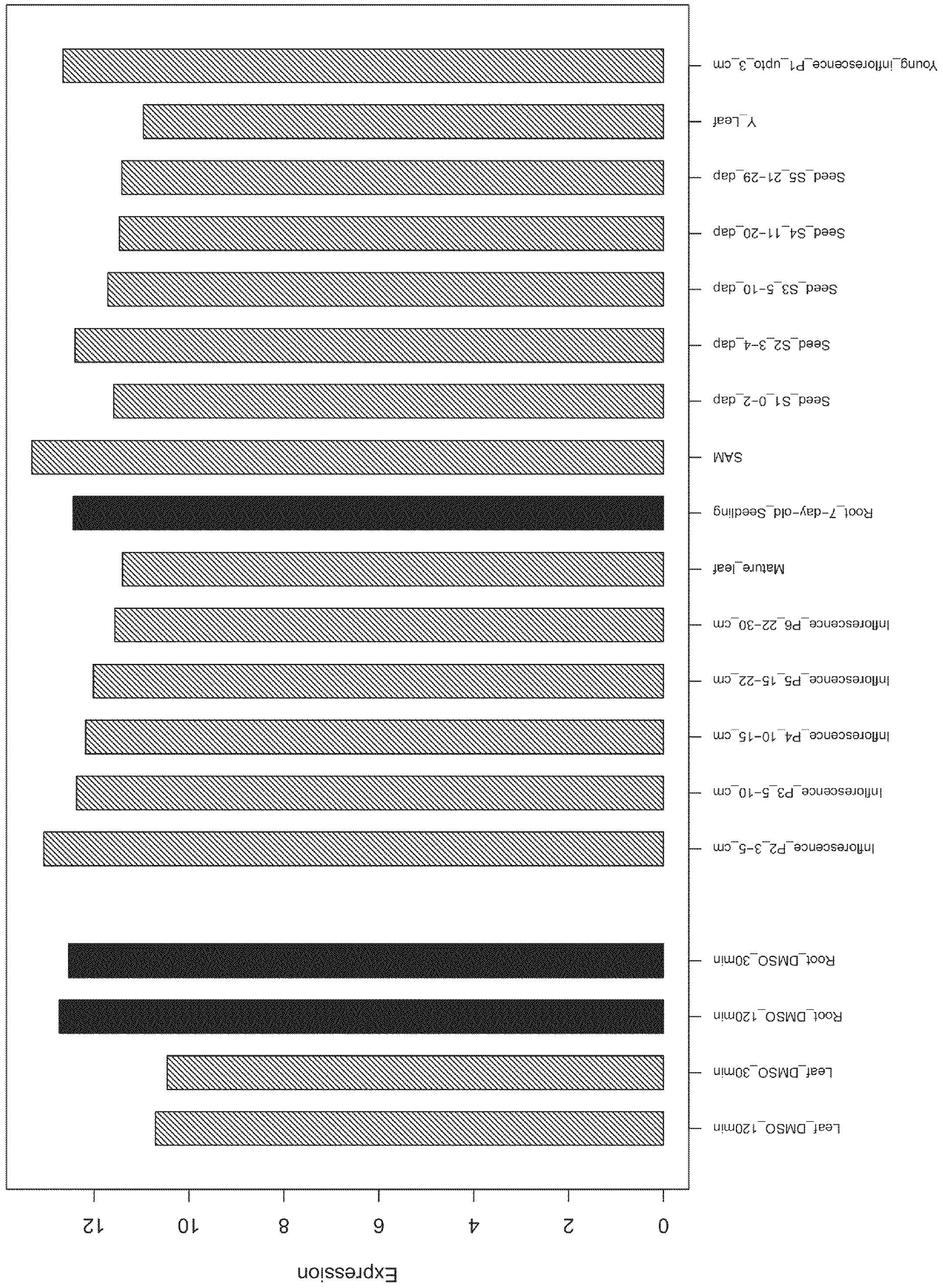
Figure 306:
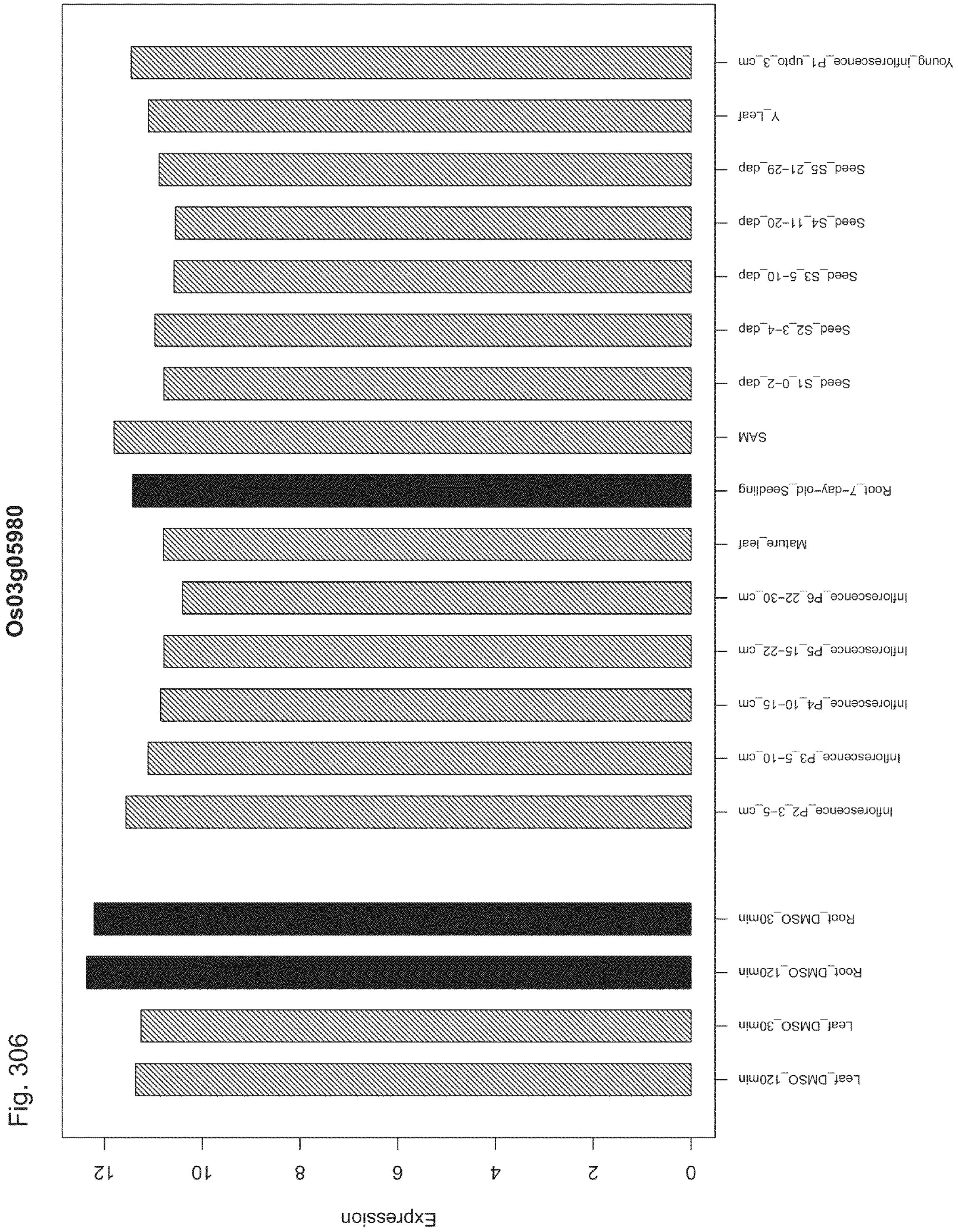
Figure 307:
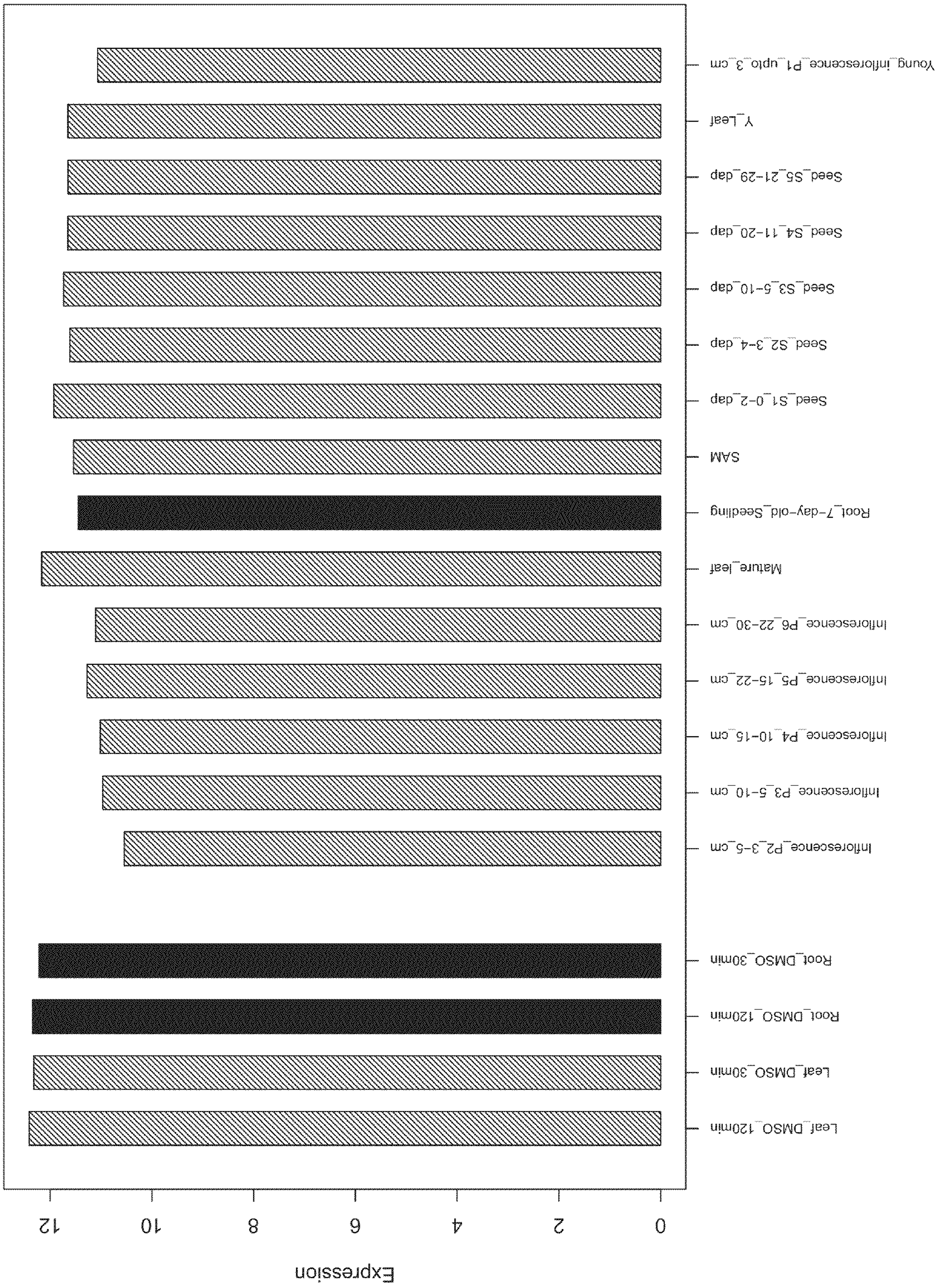
Figure 308:
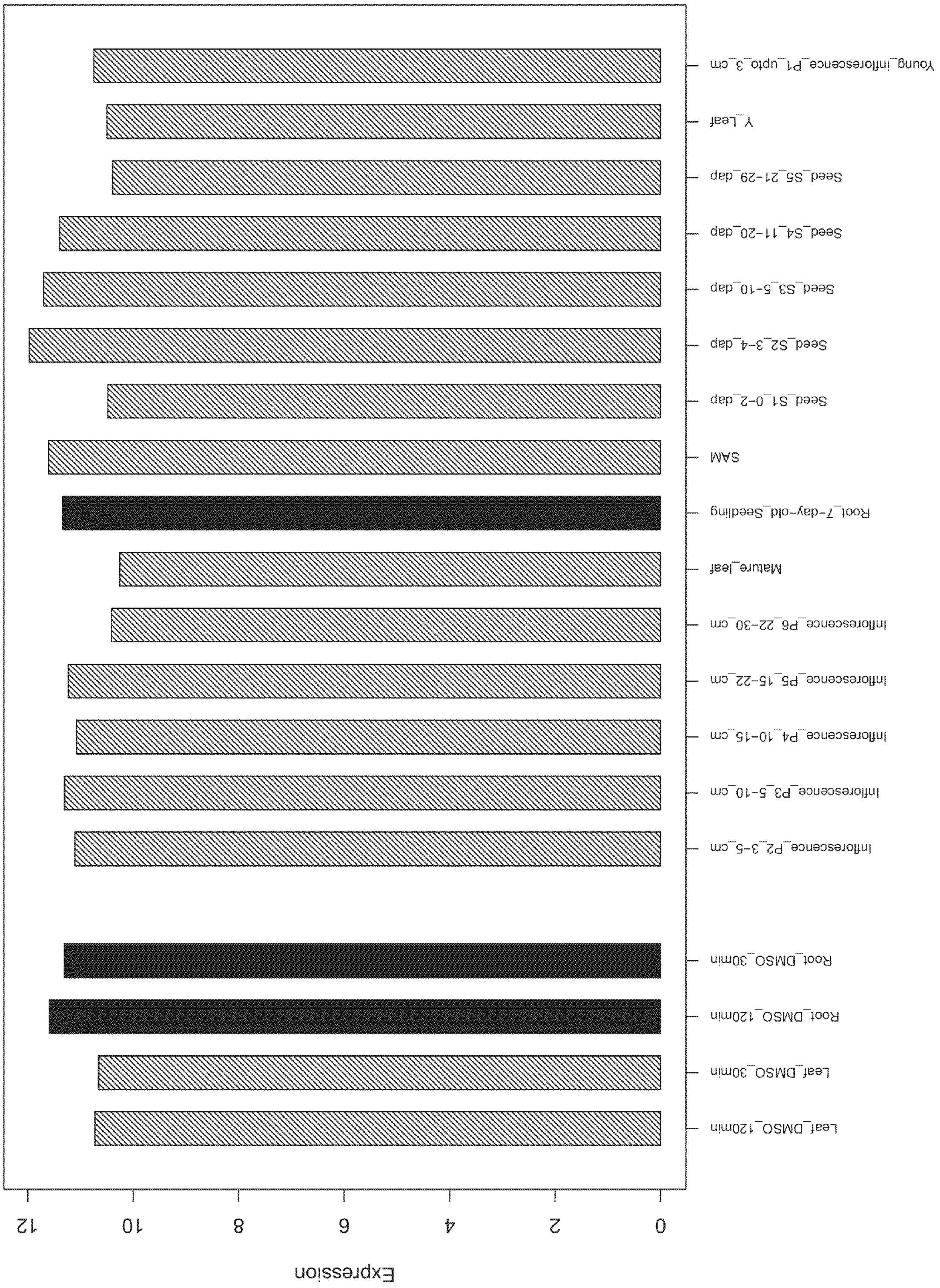
Figure 309A:
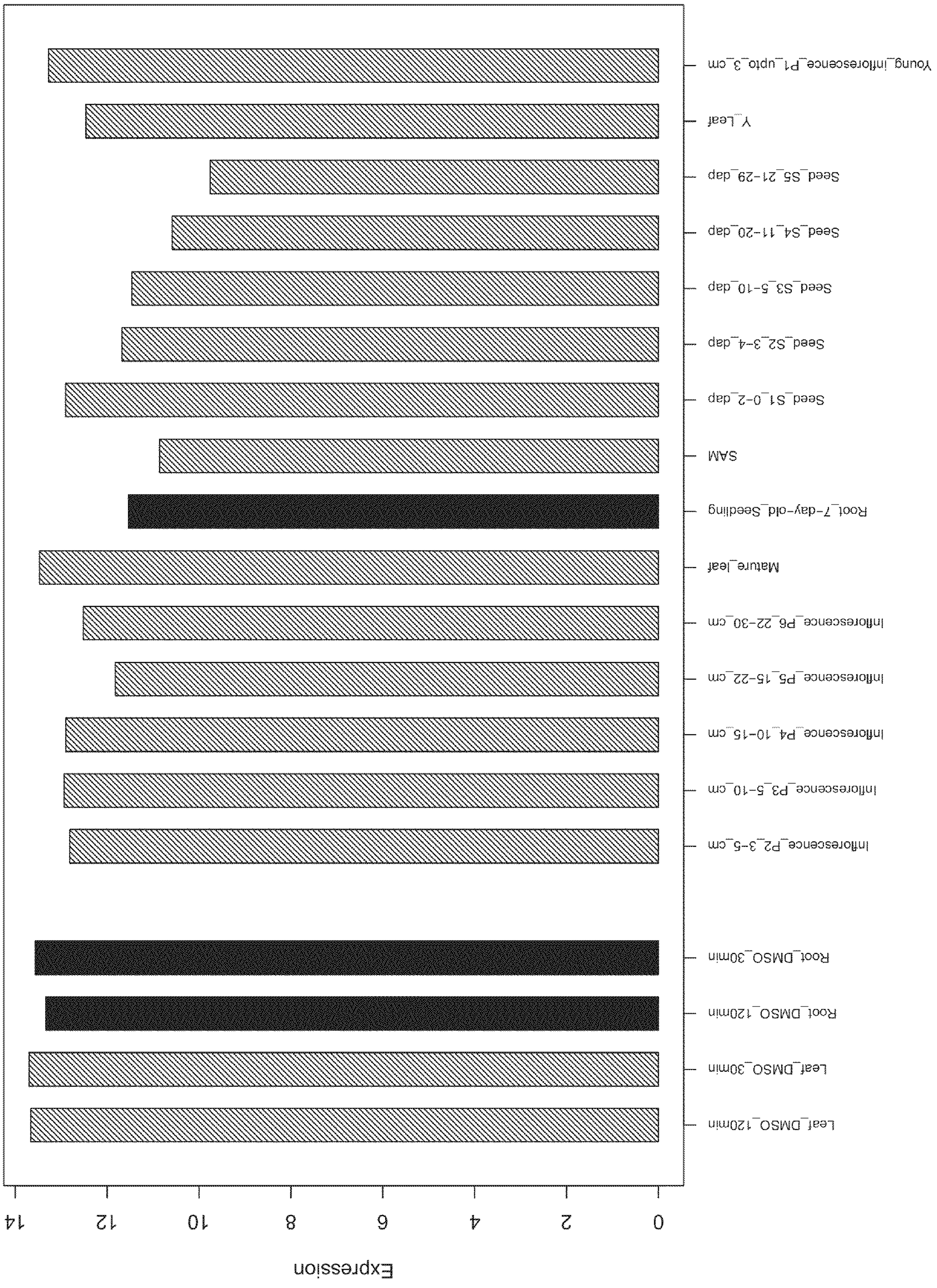
Figure 309B:
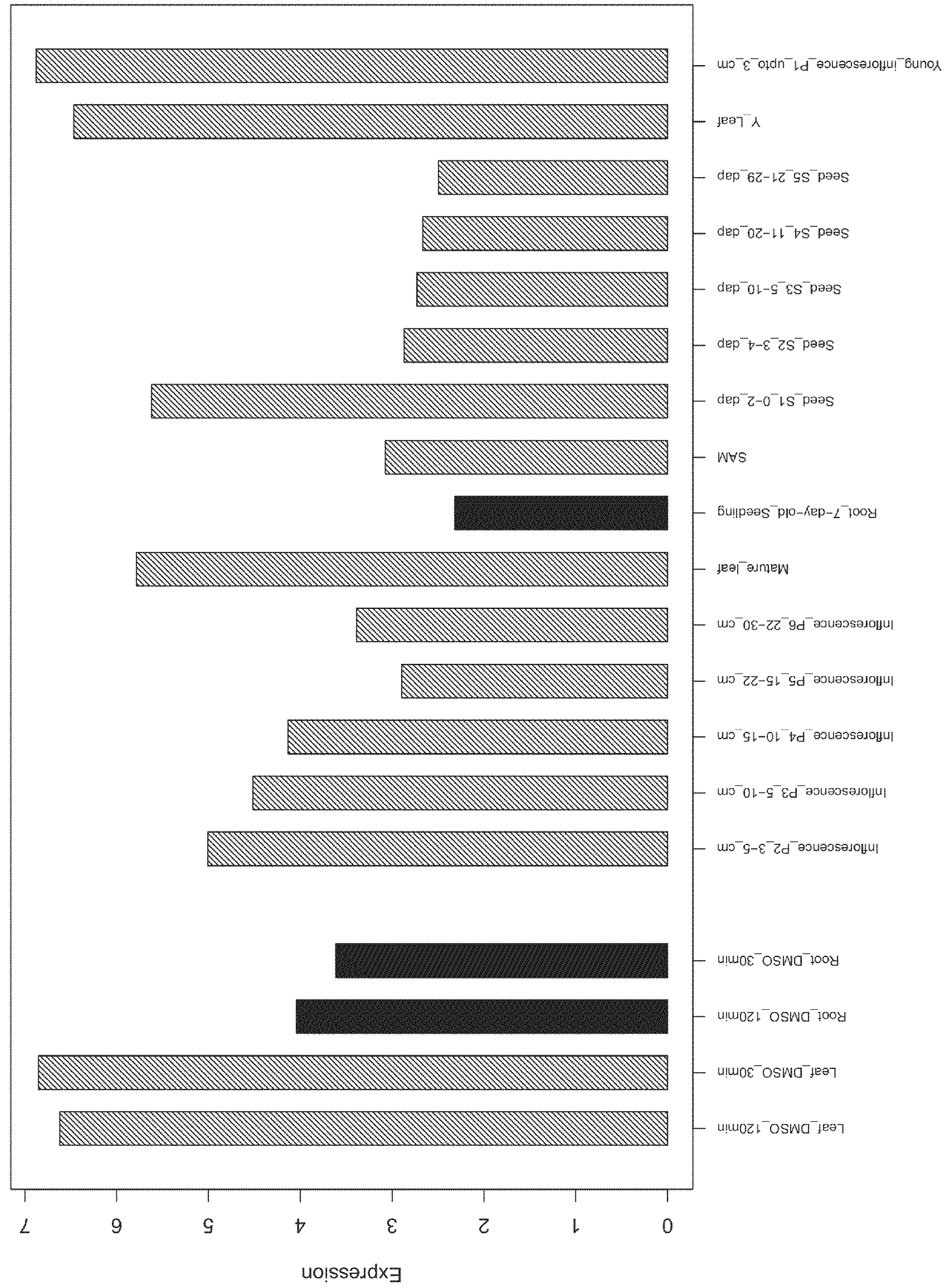
Figure 310:
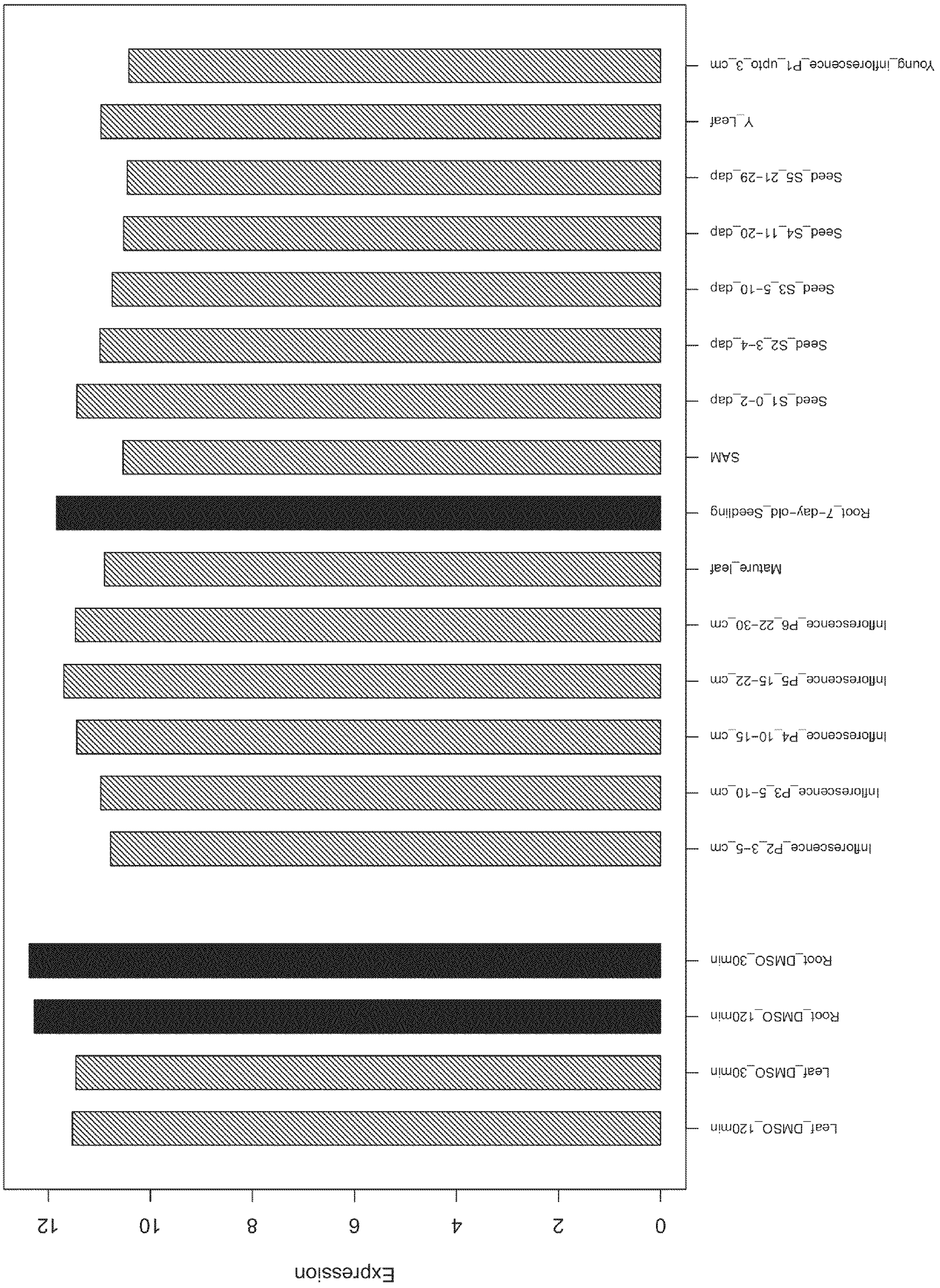
Figure 311:
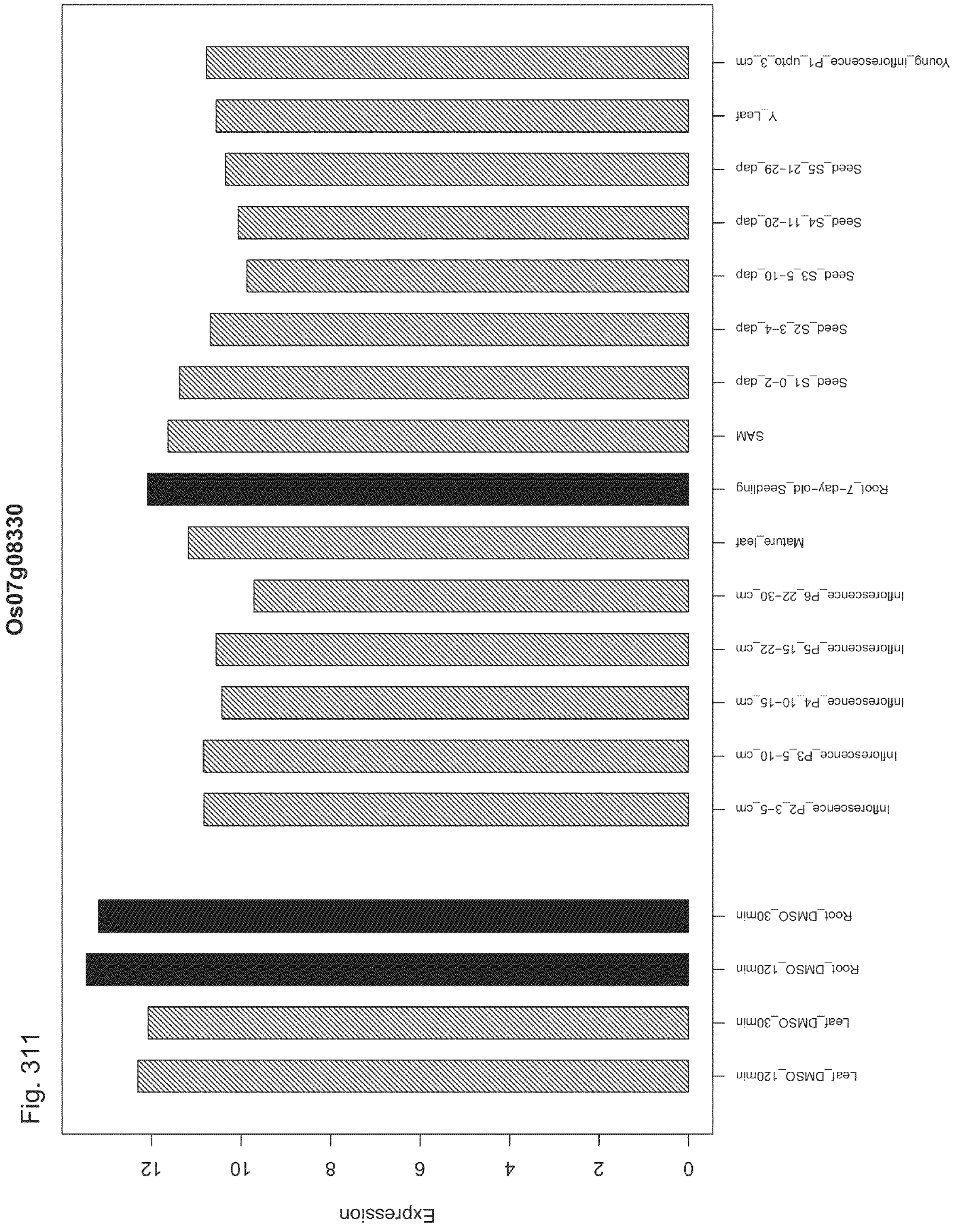
Figure 312A:
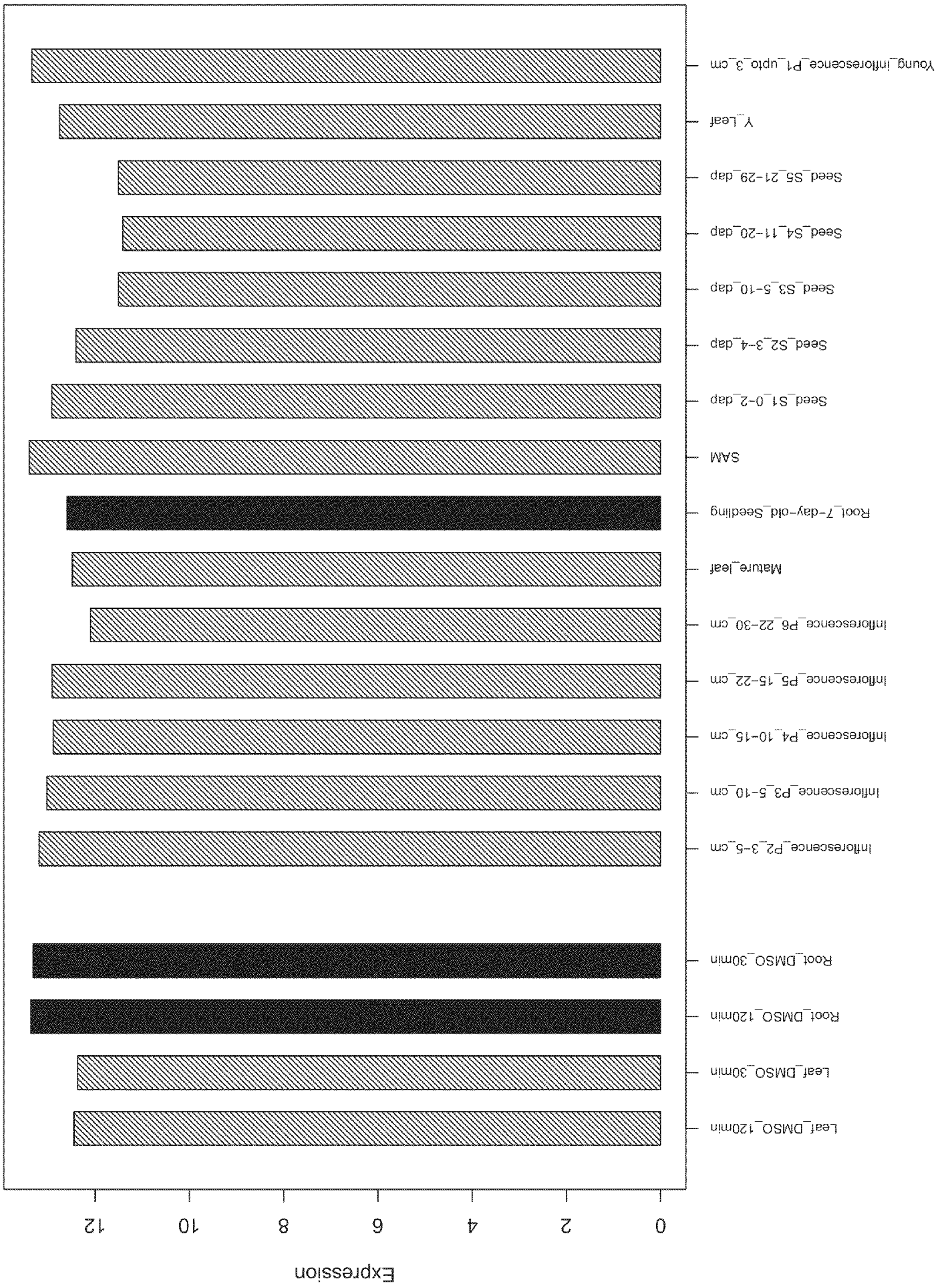
Figure 312B:
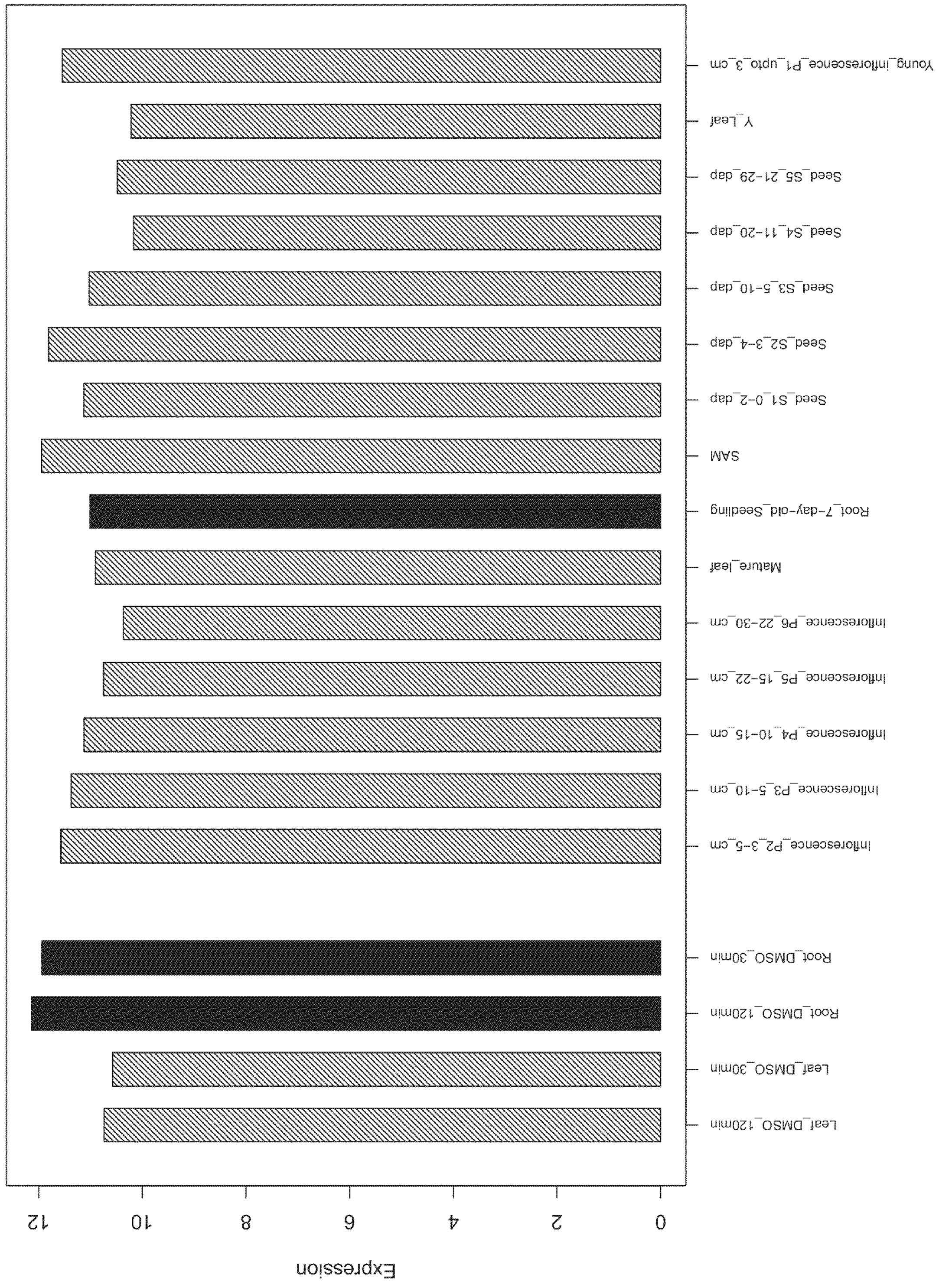
Figure 313:
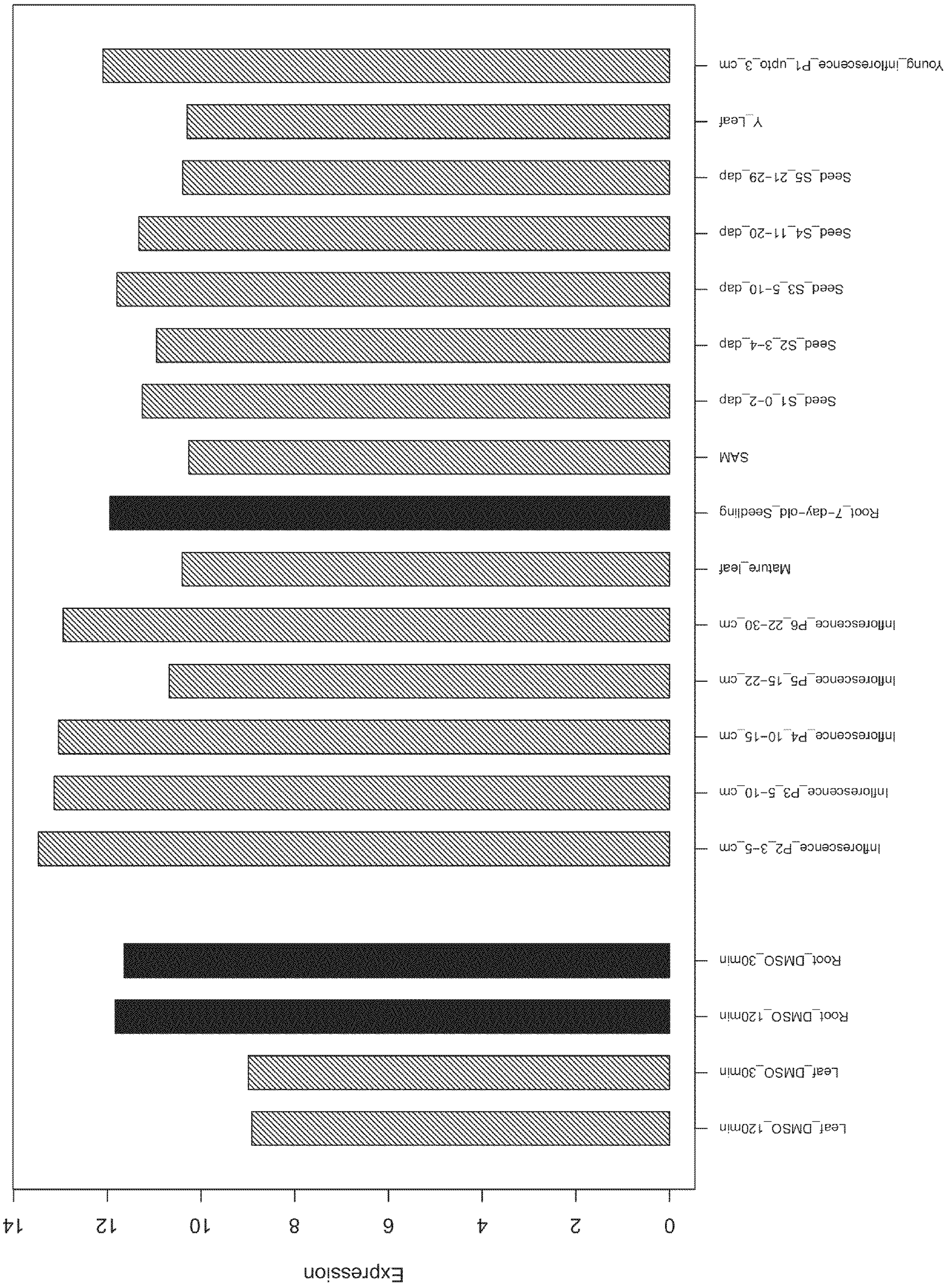
Figure 314:
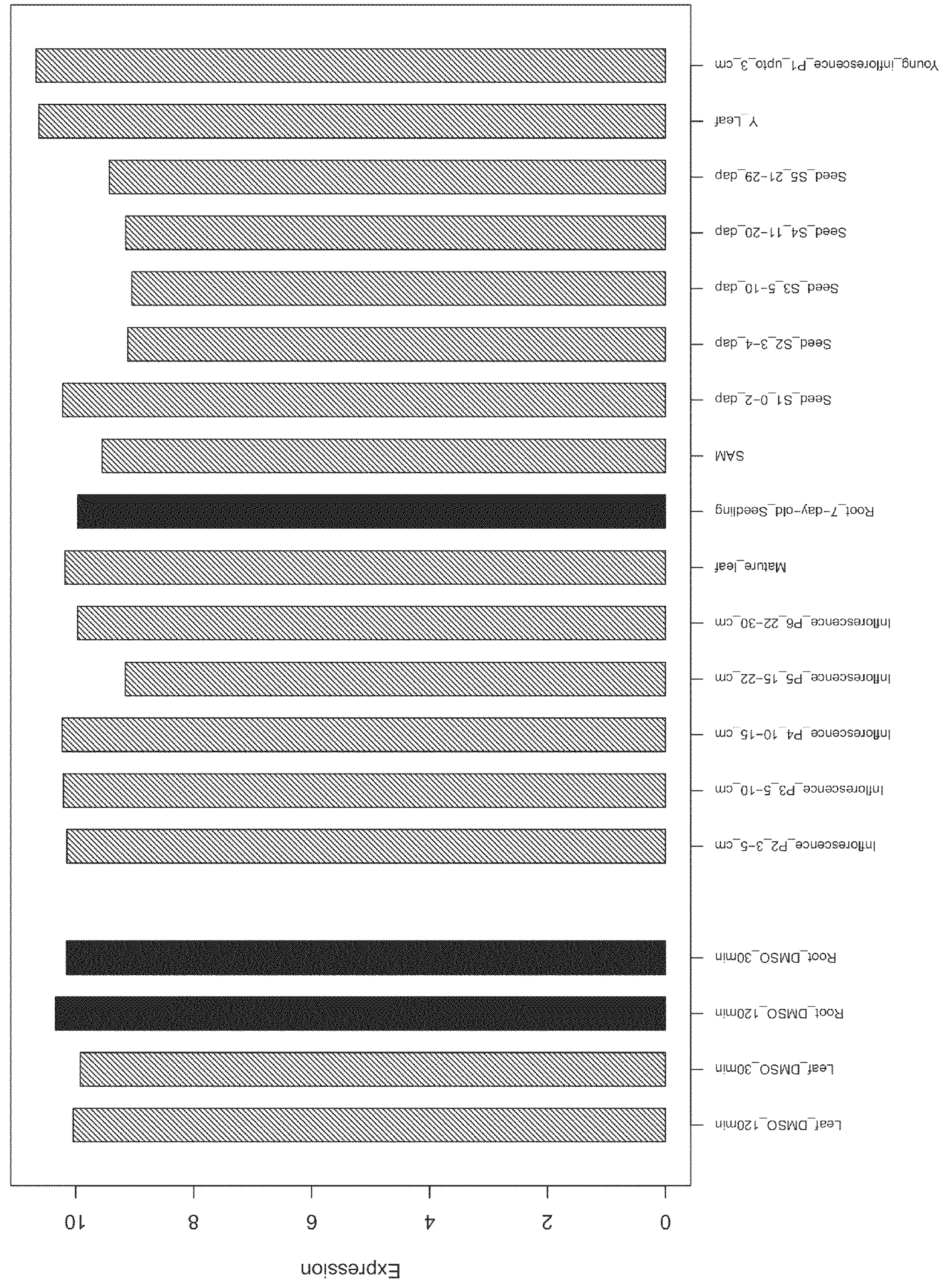
Figure 315:
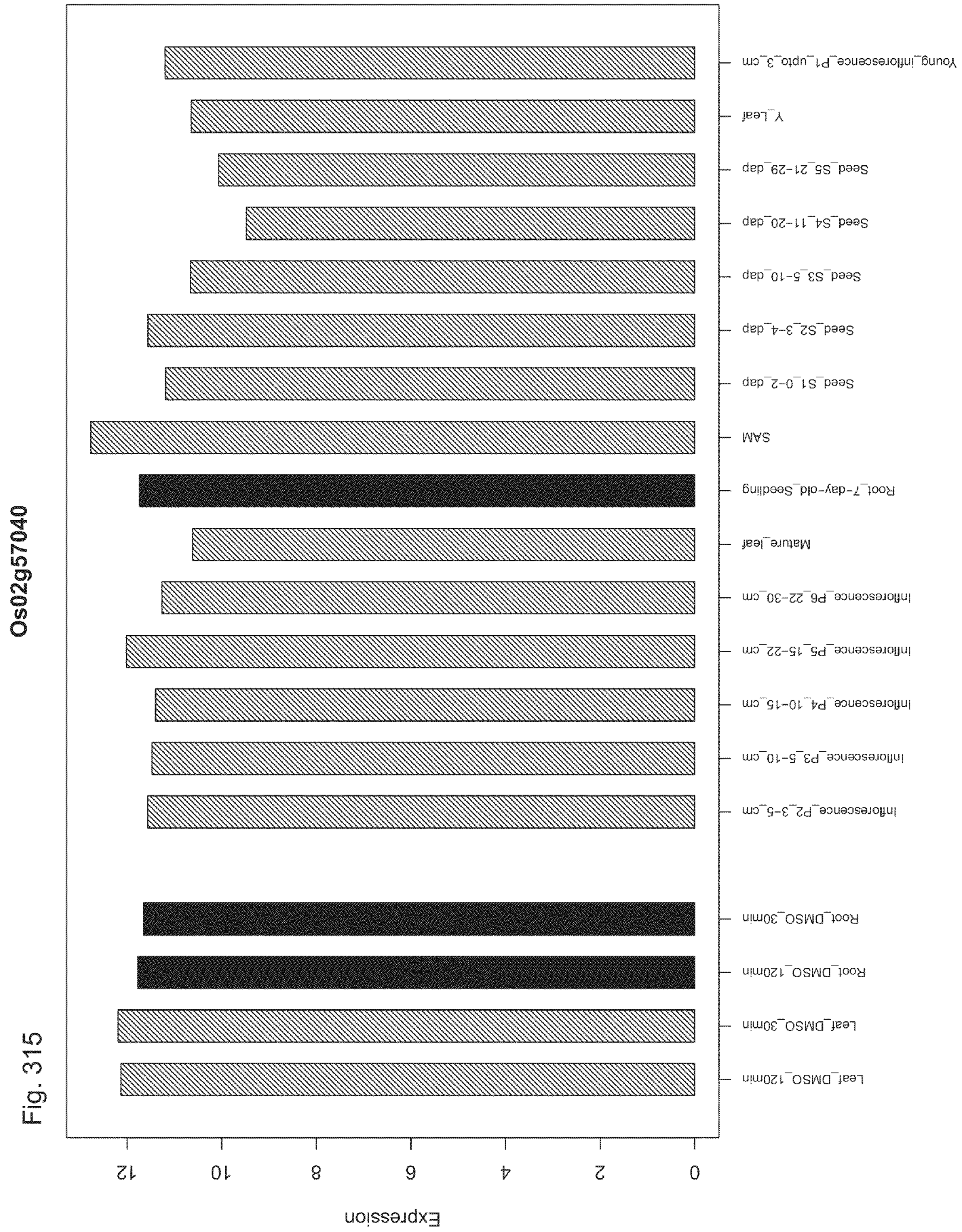
Figure 316A:
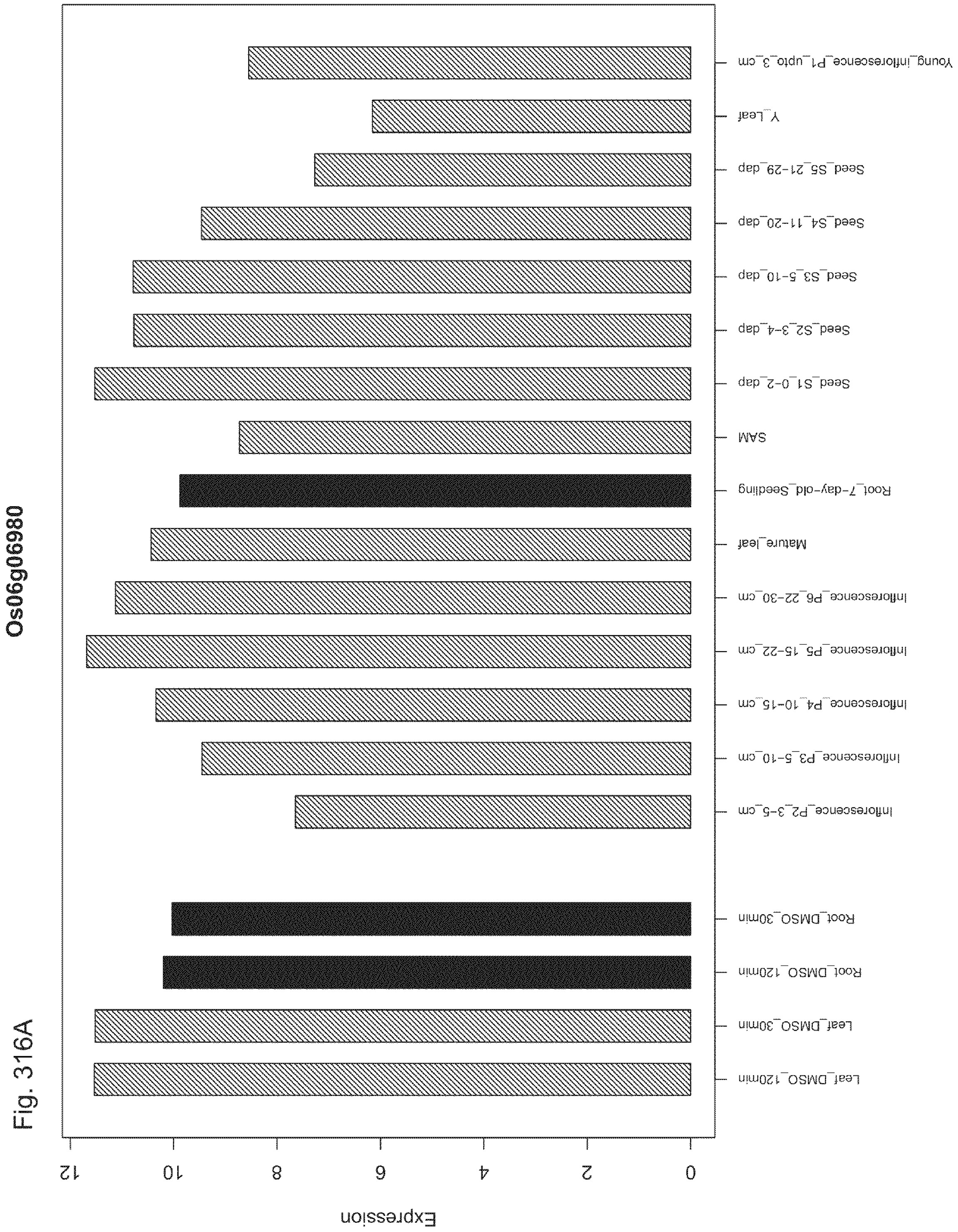
Figure 316B:
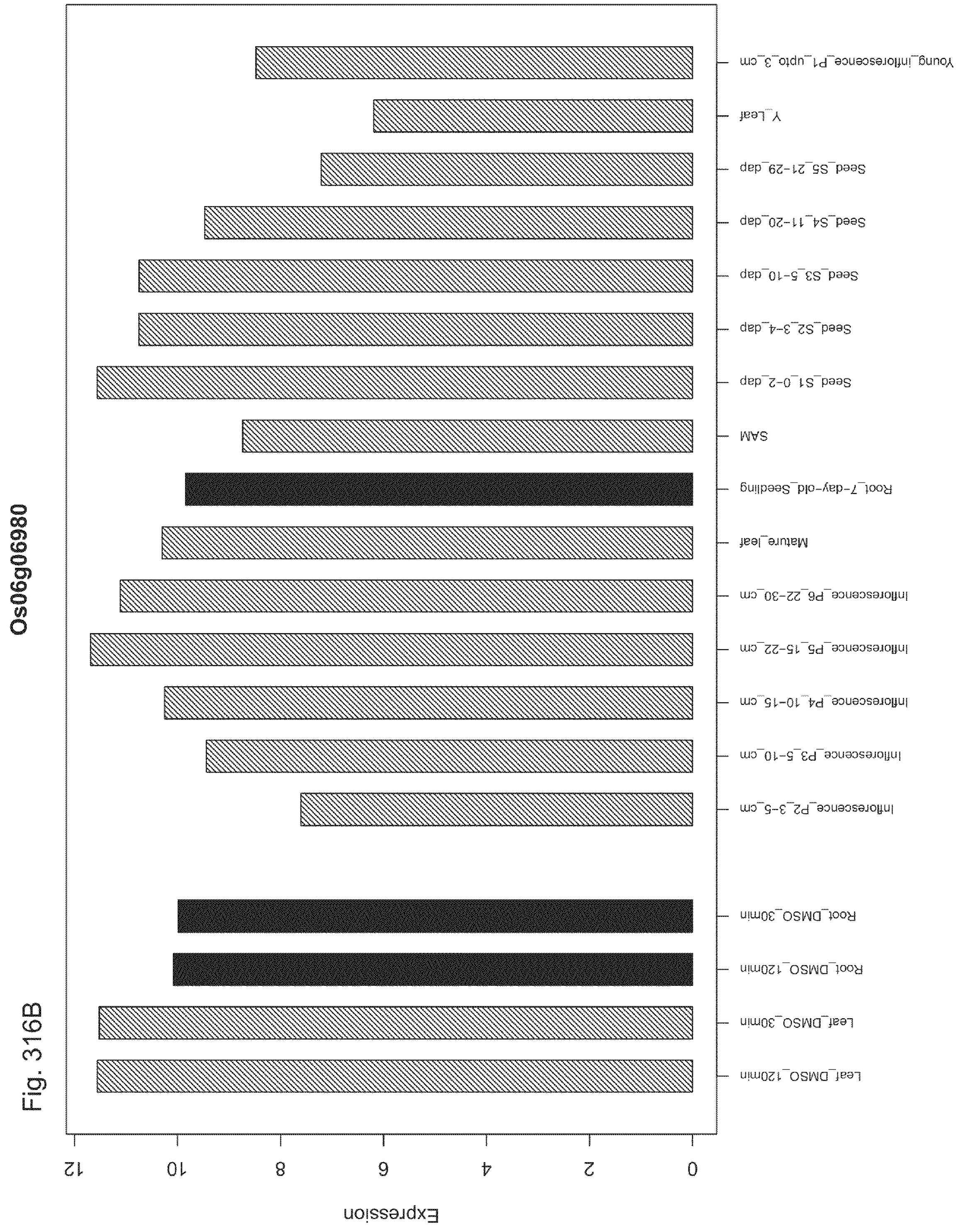
Figure 317:
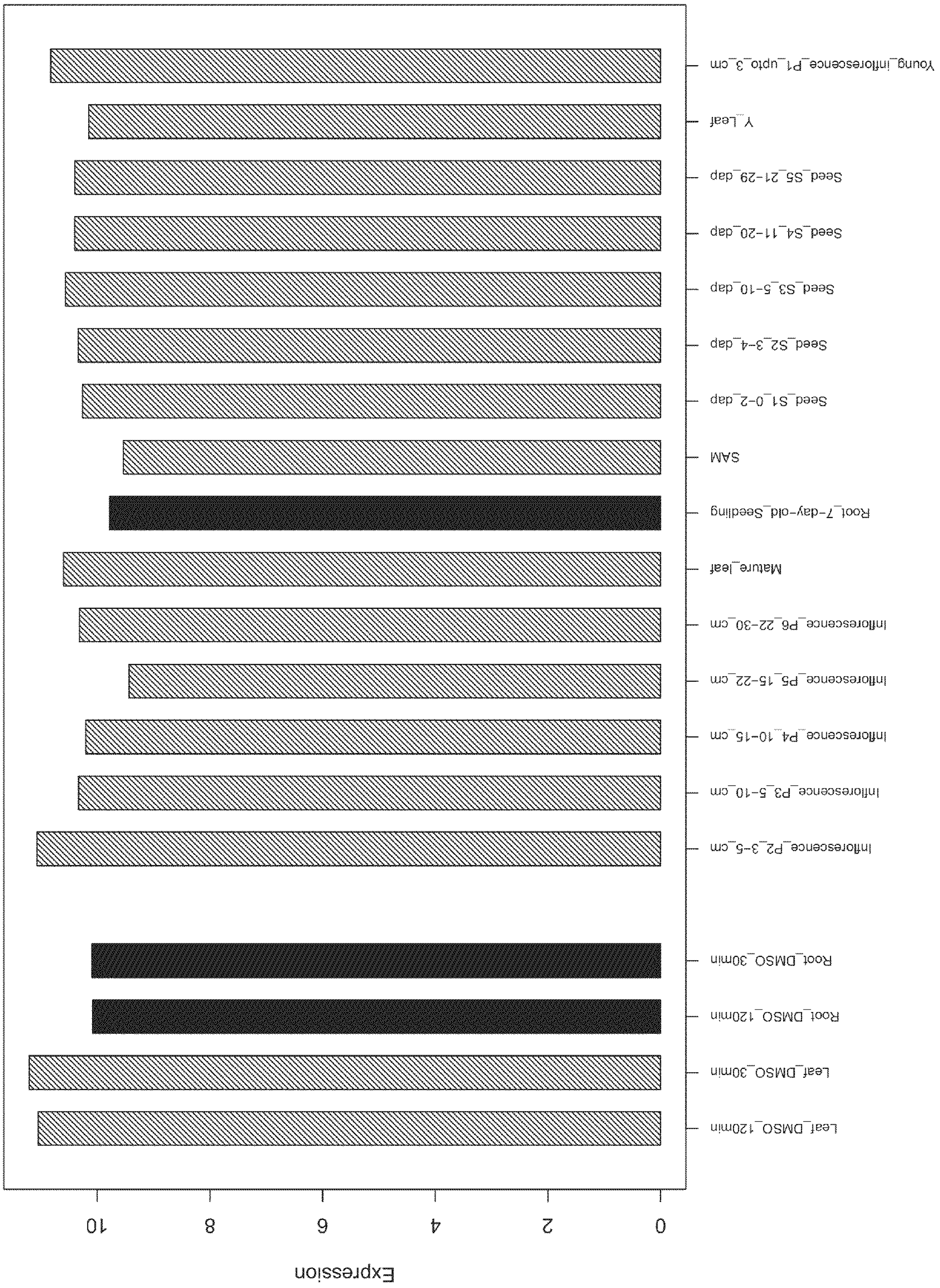
Figure 318:
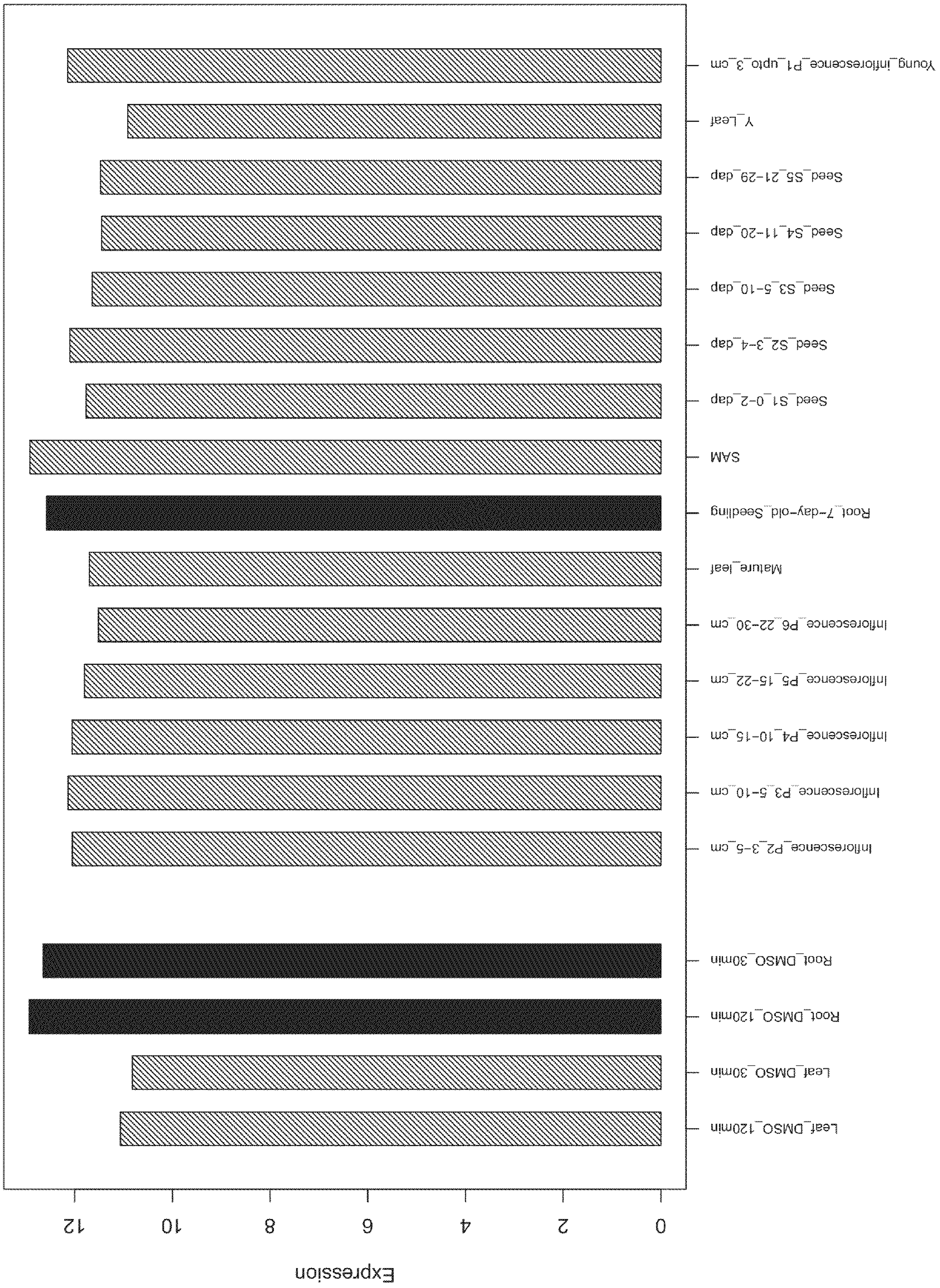
Figure 319A:
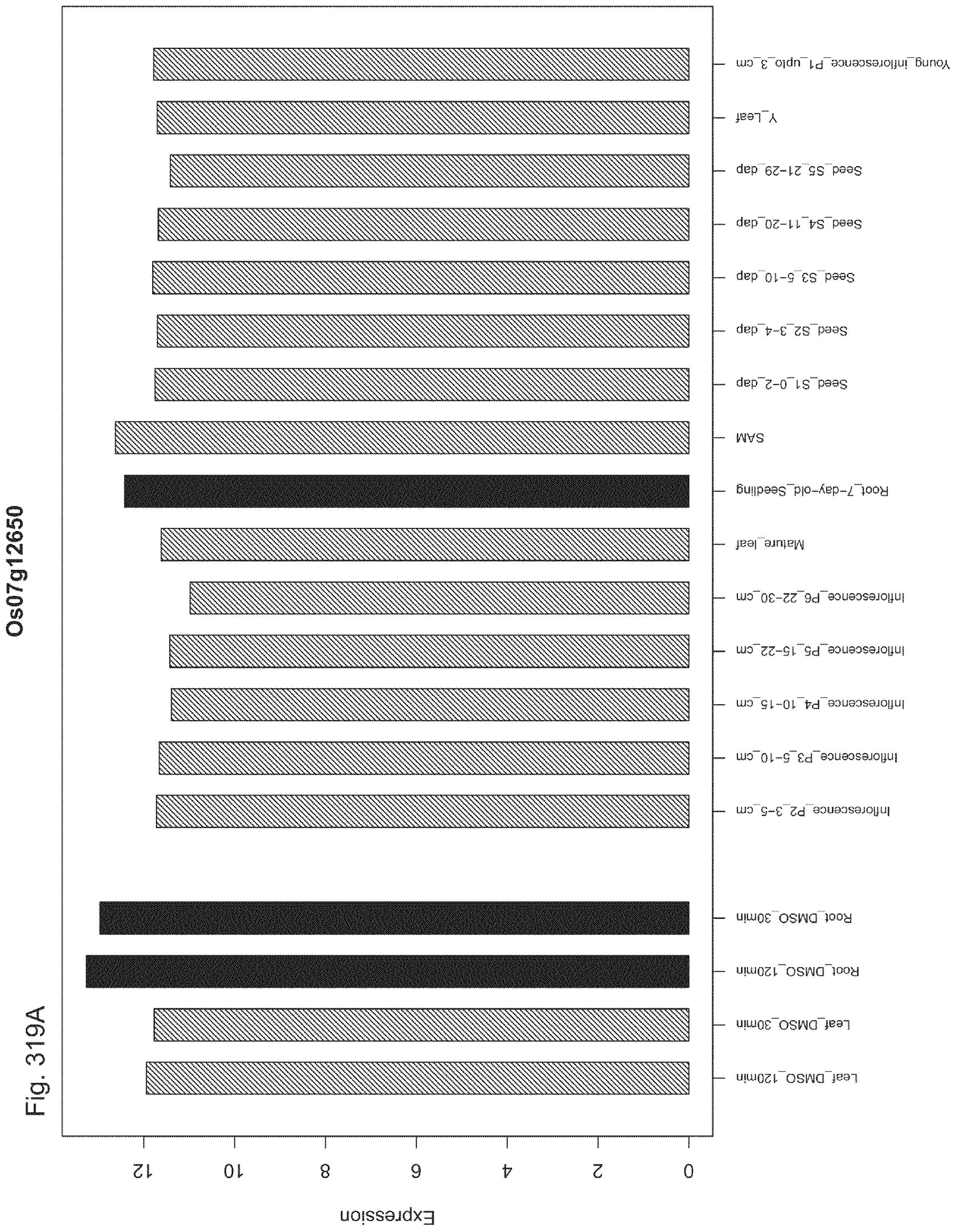
Figure 319B:
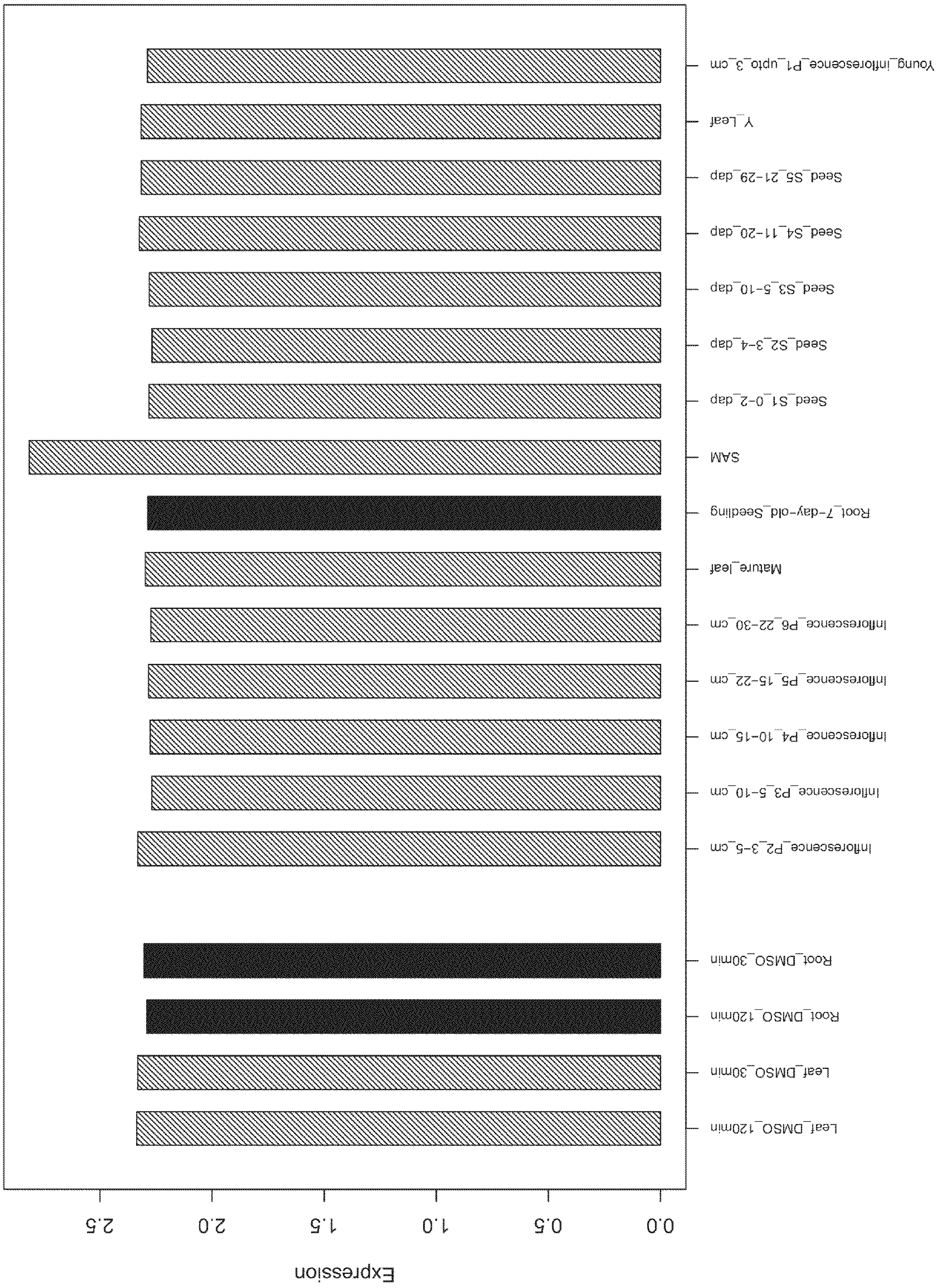
Figure 320:
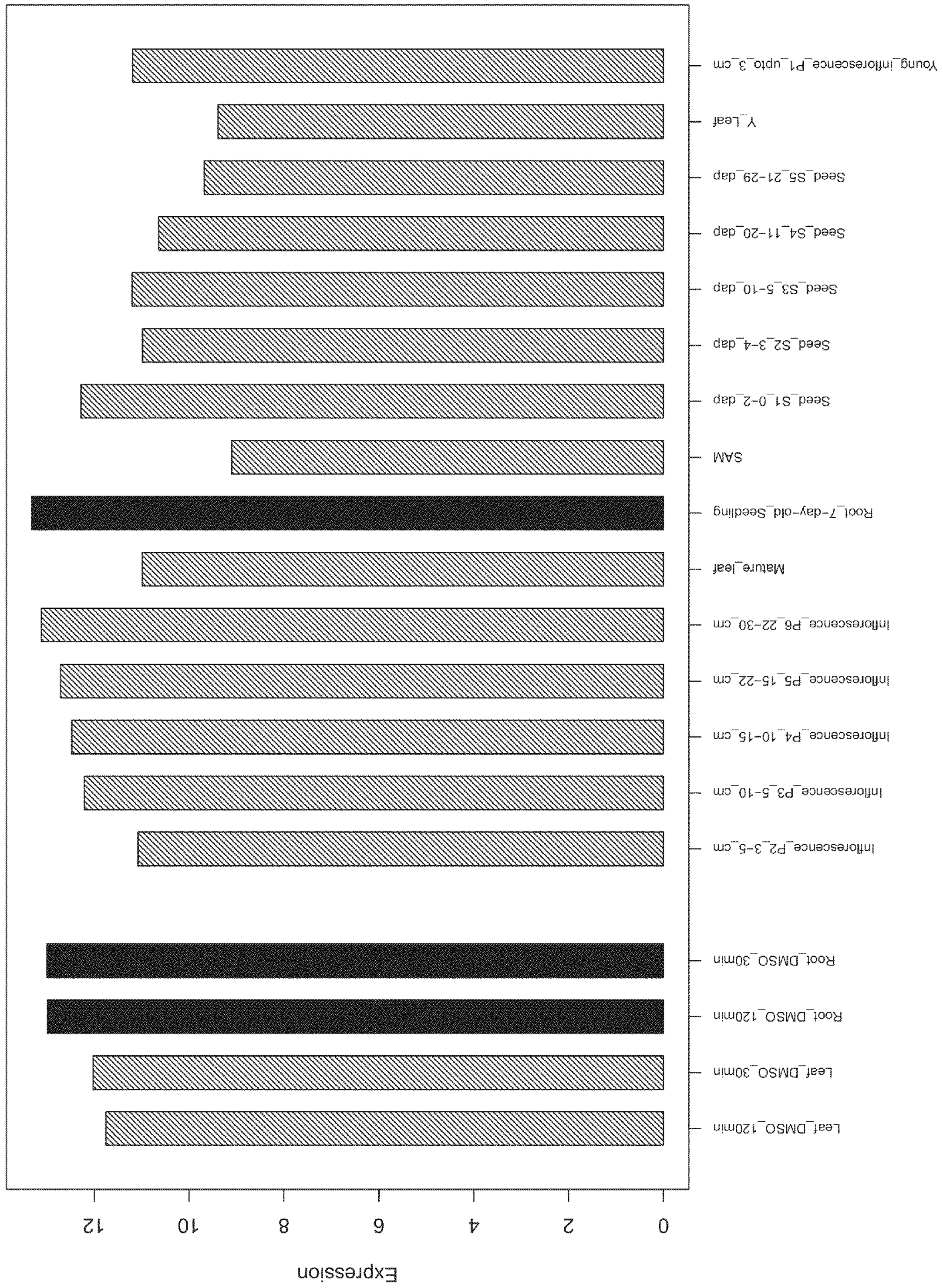
Figure 321:
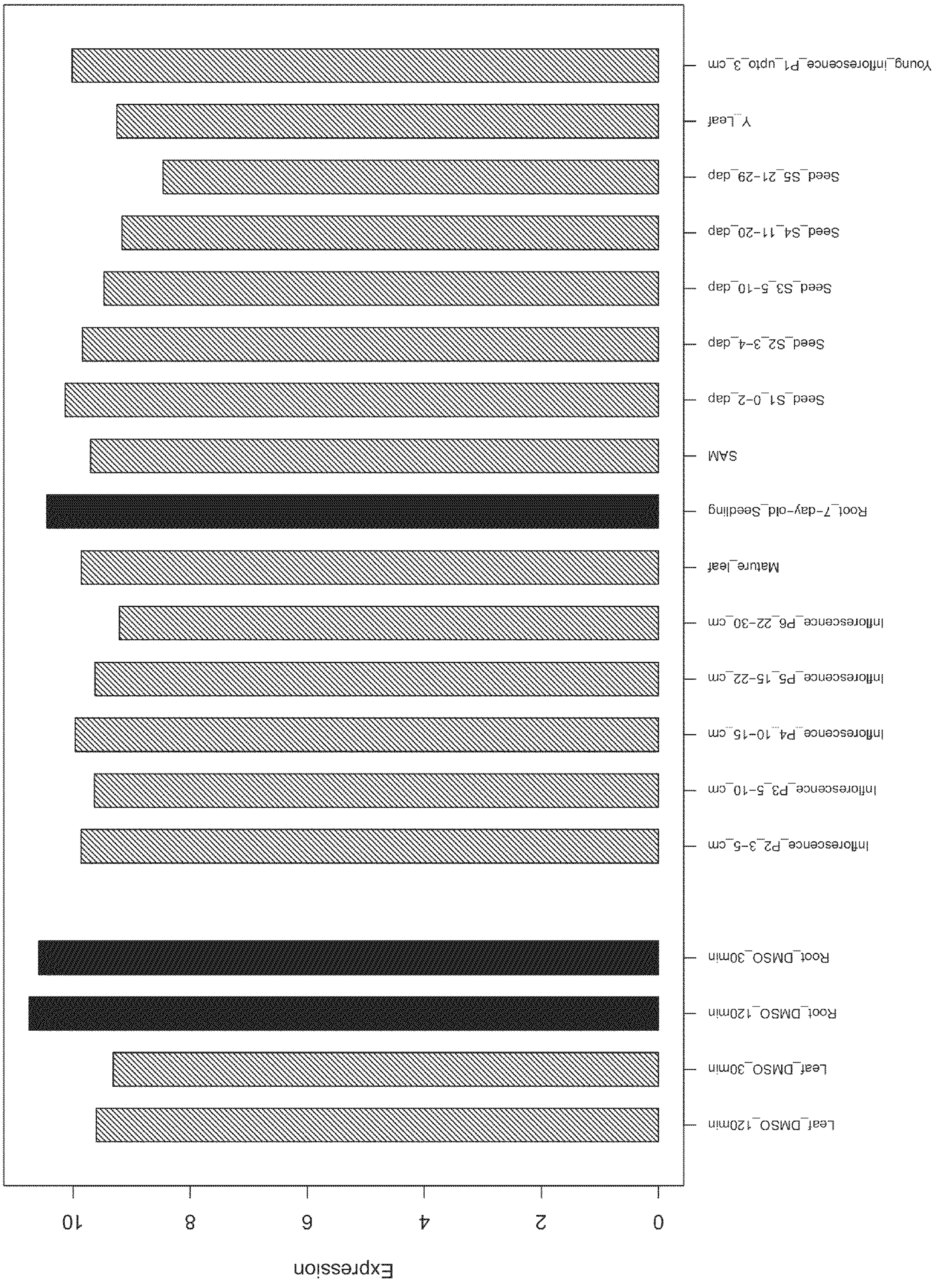
Figure 322:
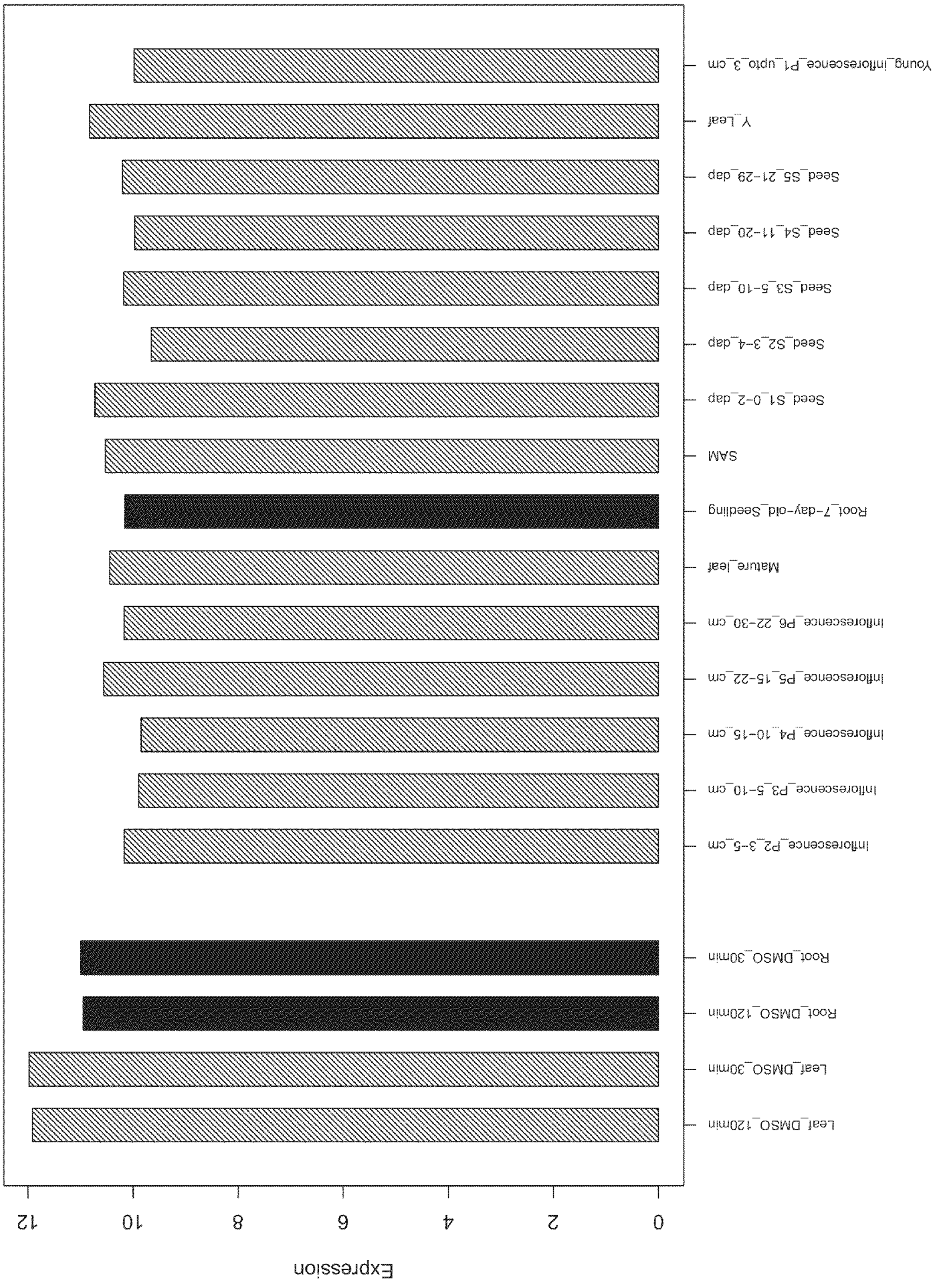
Figure 323:
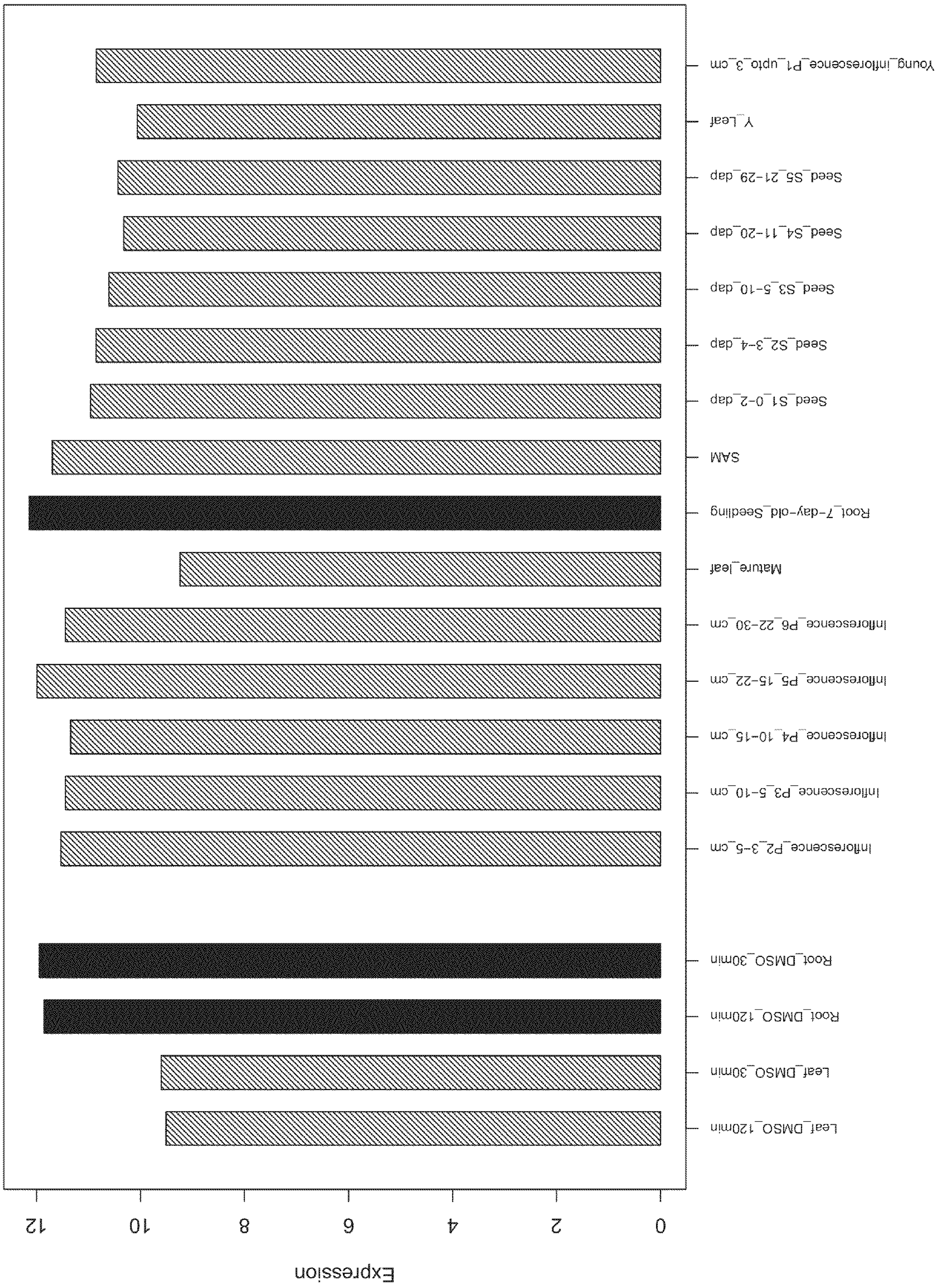
Figure 324:
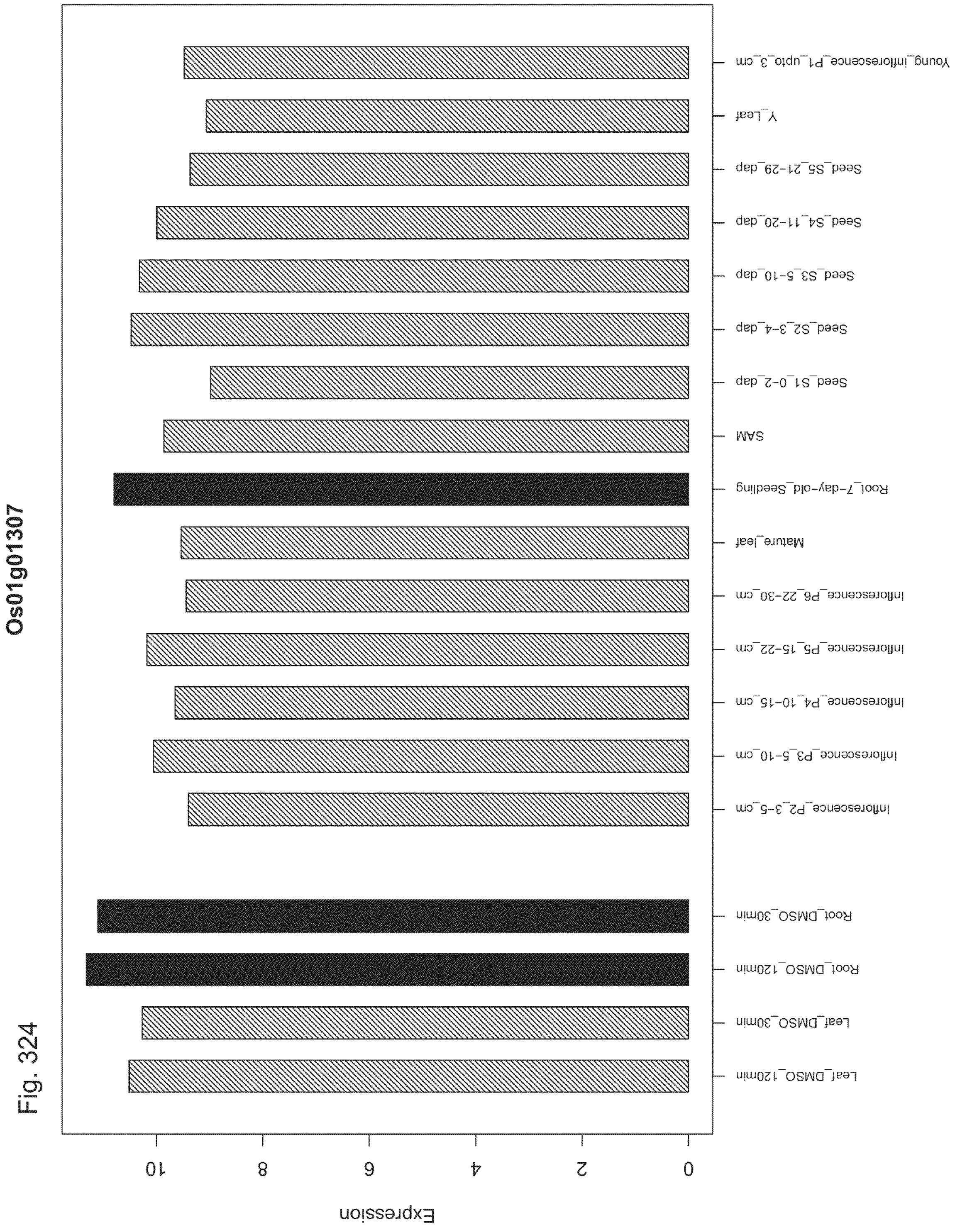
Figure 325A:
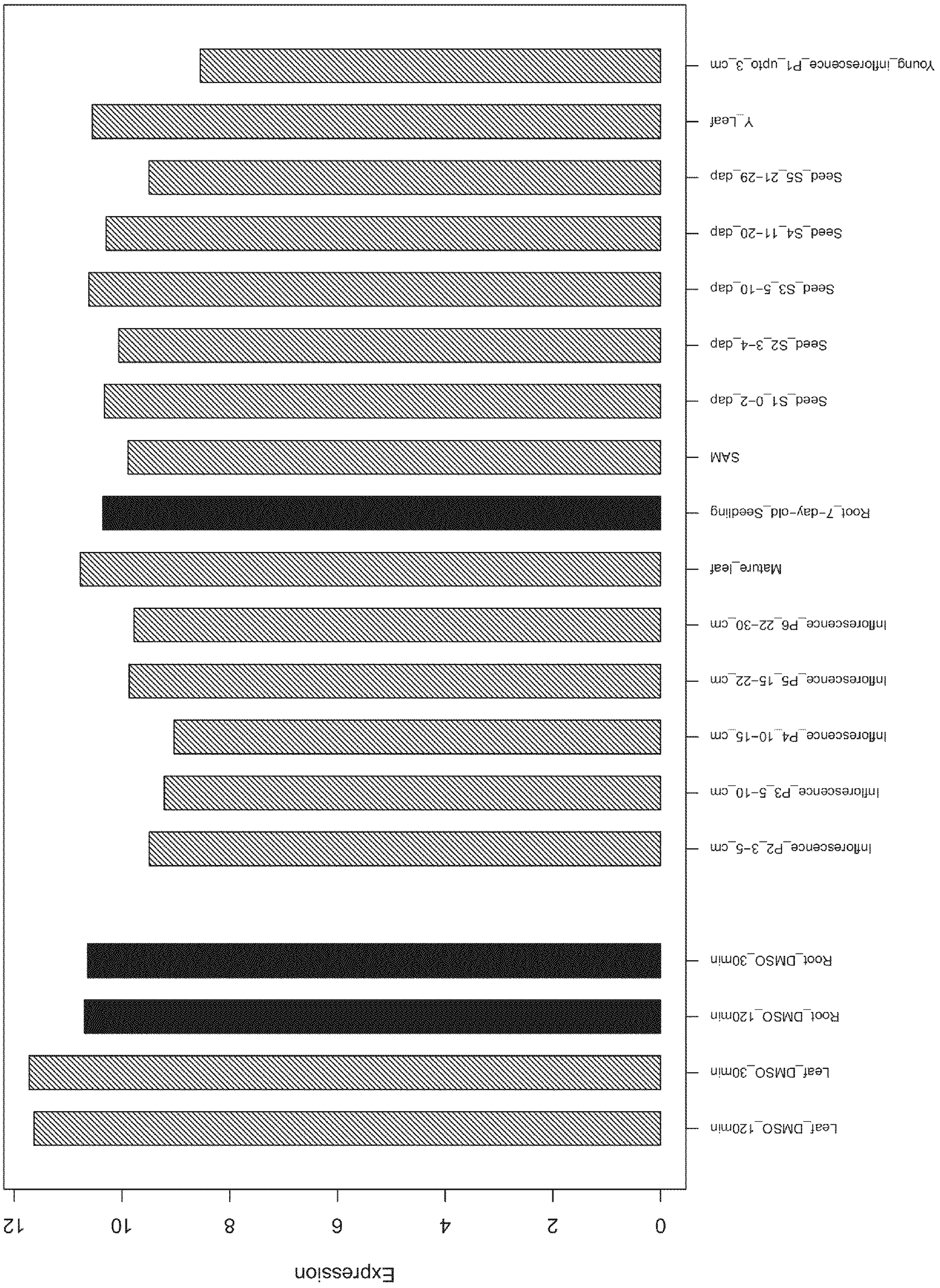
Figure 325B:
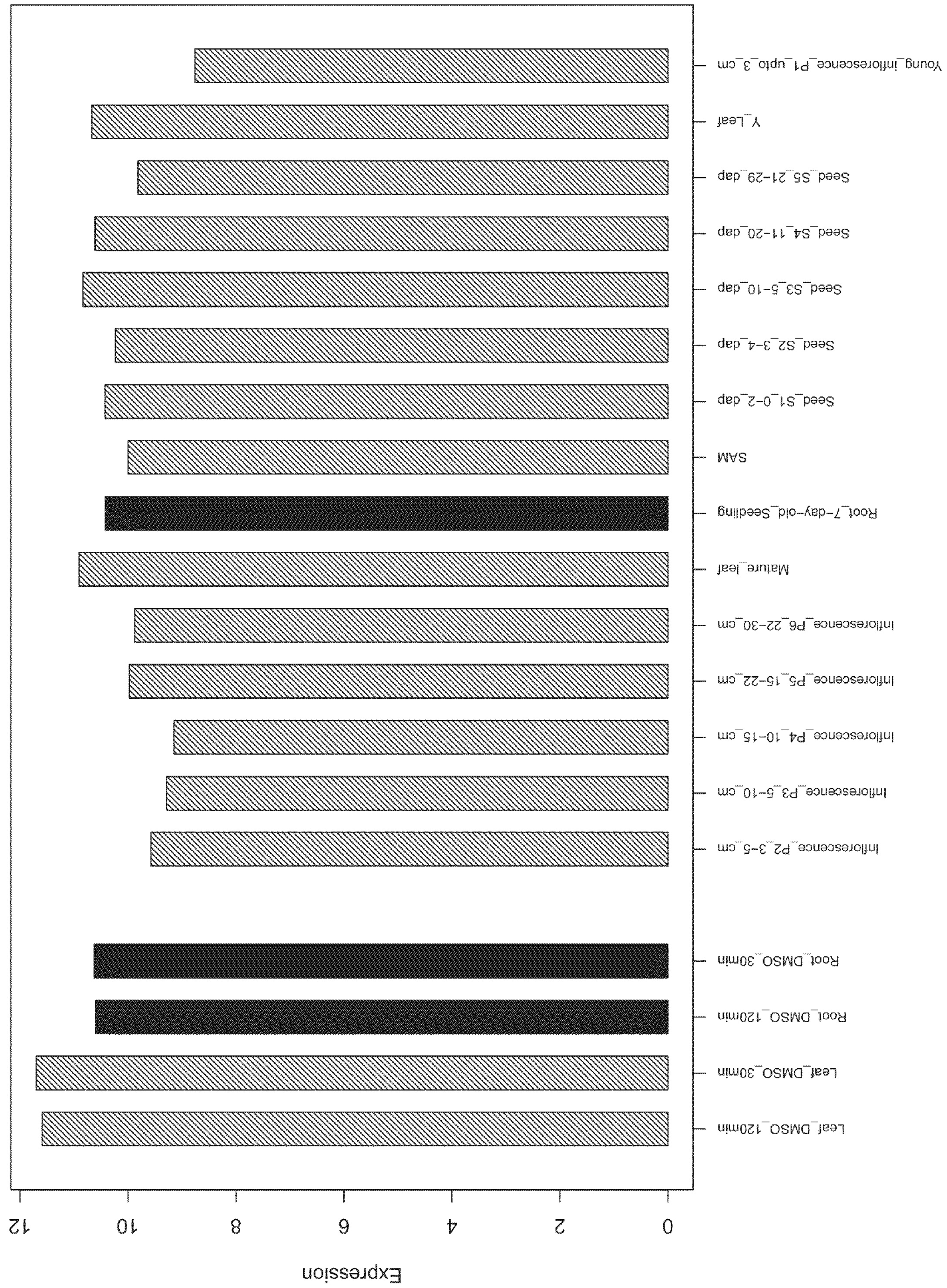
Figure 326:
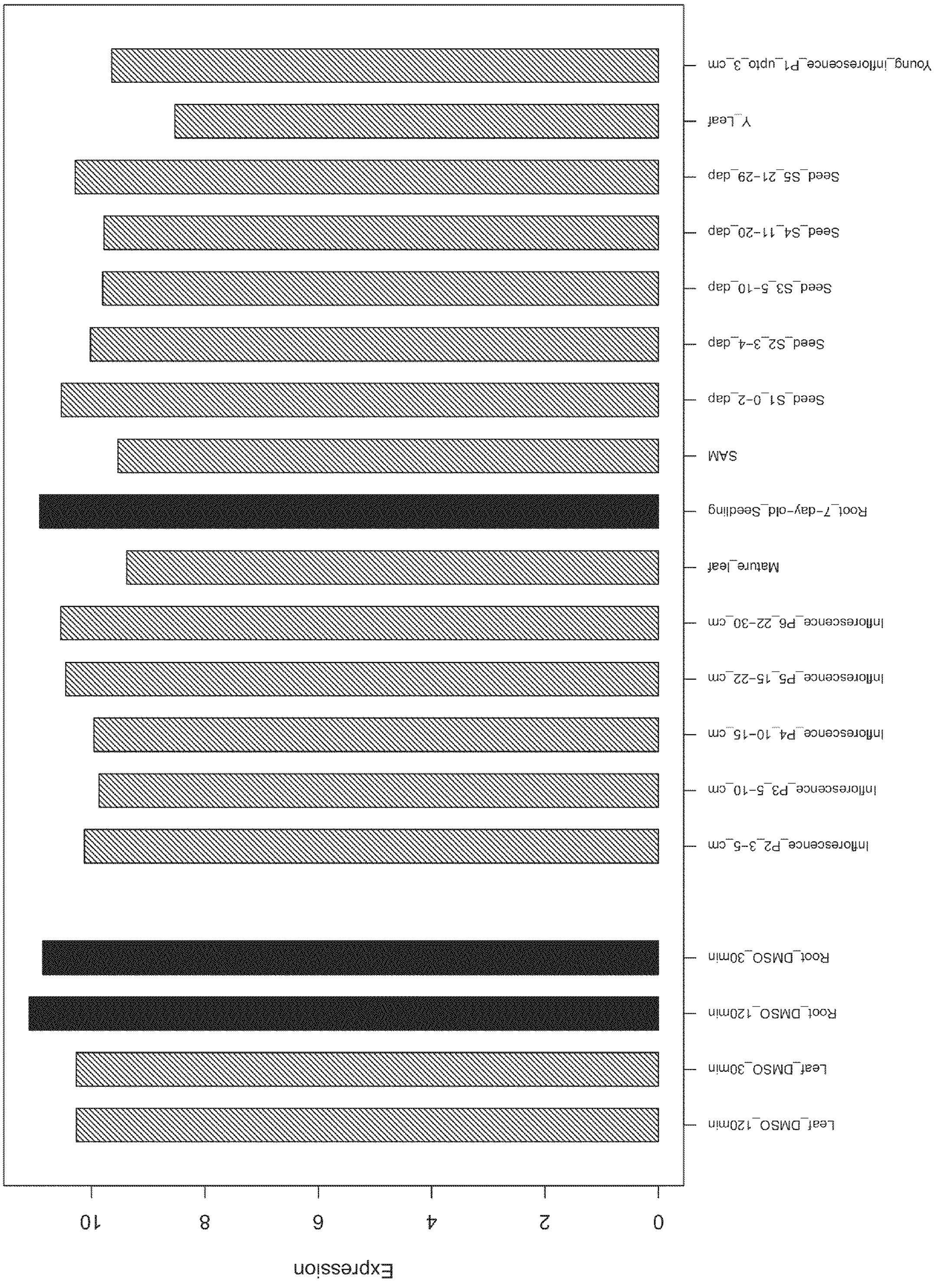
Figure 327:
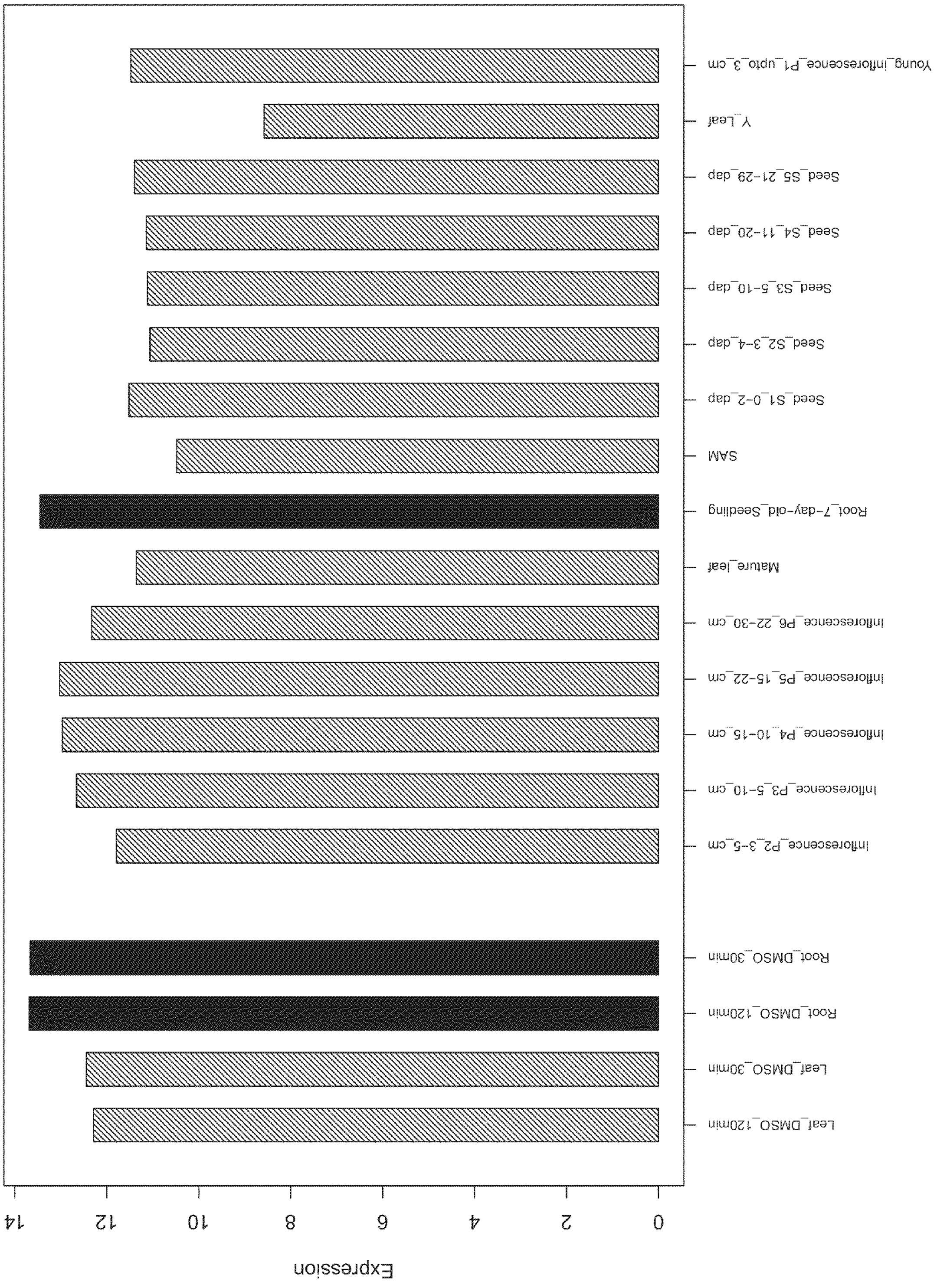

Table 7 below shows the correspondence between the regulatory polynucleotides in Example 4 and the expression plots of FIGS. 262-327 (where data was not available and no Figure is shown, "N/A" (not applicable) is indicated).

TABLE 7

| Expression FIG. (Gene Accession No.) | Regulatory Polynucleotide SEQ ID NOS (Corresponding Gene Accession No.) |
|---|---|
| 262 (Os03g21940) | 87 (Os03g21940)<br>107 (Os03g21940 + intron) |
| 263A, B (Os04g35300) | 88 (Os04g35300)<br>101 (Os04g35300 + intron) |
| 264 (Os05g45950) | 89 (Os05g45950)<br>108 (Os05g45950 + intron) |
| 265A, B (Os11g47760) | 90 (Os11g47760)<br>112 (Os11g47760 + intron) |
| N/A | 91 (Os02g02130)<br>102 (Os02g02130 + intron) |
| 266 (Os03g56190) | 92 (Os03g56190)<br>100 (Os03g56190 + intron) |
| 267A, B (Os05g47980) | 93 (Os05g47980)<br>110 (Os05g47980 + intron) |
| 268 (Os01g46610) | 94 (Os01g46610)<br>103 (Os01g46610 + intron) |
| 269 (Os02g52290) | 95 (Os02g52290)<br>109 (Os02g52290 + intron) |
| 270 (Os04g28180) | 96 (Os04g28180)<br>106 (Os04g28180 + intron) |
| 271A, B (Os05g01820) | 97 (Os05g01820)<br>104 (Os05g01820 + intron) |
| 272 (Os07g46750) | 98 (Os07g46750)<br>105 (Os07g46750 + intron) |
| 273 (Os11g11390) | 99 (Os11g11390)<br>111 (Os11g11390 + intron) |
| 274 (Os07g02210) | 113 (Os07g02210) |
| 275 (Os12g07010) | 114 (Os12g07010) |
| 276 A, B (Os09g08430) | 115 (Os09g08430)<br>129(Os09g08430 + intron) |
| 277 (Os08g03290) | 116 (Os08g03290)<br>128 (Os08g03290 + intron) |
| 278 (Os10g22590) | 117 (Os10g22590) |
| 279 A, B (Os03g45280) | 118 (Os03g45280) |
| 280 (Os06g07969) | 119 (Os06g07969)<br>125 (Os06g07969 + intron) |
| 281 (Os07g30970) | 120 (Os07g30970)<br>127 (Os07g30970 + intron) |
| 282 (Os09g33500) | 121 (Os09g33500)<br>126 (Os09g33500 + intron) |
| 283 (Os10g33800) | 122 (Os10g33800) |
| 284A, B (Os11g38959) | 123 (Os11g38959)<br>124 (Os11g38959 + intron) |
| 285 A, B (Os10g08550) | 130 (Os10g08550) |
| 286 (Os04g32710) | 131 (Os04g32710, +intron)<br>174 (Os04g32710) |
| 287 (Os04g30730) | 132 (Os04g30730, +intron)<br>175 (Os04g30730) |
| 288 (Os02g30050) | 133 (Os02g30050, +intron)<br>176 (Os02g30050) |
| N/A | 177 (Os01g05490) |
| N/A | 178 (Os01g61814) |
| 289 A, B (Os05g11780) | 134 (Os05g11780, +intron)<br>179 (Os05g11780) |
| 290 (Os03g14450) | 135 (Os03g14450, +intron)<br>180 (Os03g14450) |
| 291 (Os01g17190) | 136 (Os01g17190, +intron)<br>181 (Os01g17190) |
| 292 (Os10g17280) | 137 (Os10g17280, +intron)<br>182 (Os10g17280) |
| 293 (Os11g06890) | 138 (Os11g06890, +intron)<br>183 (Os11g06890) |
| 294 (Os01g16890) | 139 (Os01g16890, +intron)<br>184 (Os01g16890) |
| 295 (Os03g58430) | 140 (Os03g58430, +intron)<br>185 (Os03g58430) |
| 296 (Os06g37440) | 141 (Os06g37440) |
| 297 (Os10g30580) | 142 (Os10g30580, +intron)<br>186 (Os10g30580) |
| 298 (Os02g27769) | 143 (Os02g27769, +intron)<br>187 (Os02g27769) |

TABLE 7-continued

| Expression FIG. (Gene Accession No.) | Regulatory Polynucleotide SEQ ID NOS (Corresponding Gene Accession No.) |
|---|---|
| 299 (Os07g08660) | 144 (Os07g08660, +intron) |
| | 188 (Os07g08660) |
| 300(Os04g47220) | 145(Os04g47220, +intron) |
| | 189 (Os04g47220) |
| 301 A-D | 146 (Os05g07700, +intron) |
| (Os05g07700) | 190 (Os05g07700) |
| 302 (Os11g26850) | 147 (Os11g26850, +intron) |
| | 191 (Os11g26850) |
| 303 (Os12g38000) | 148 (Os12g38000, +intron) |
| | 192 (Os12g38000) |
| 304 (Os03g56241) | 149 (Os03g56241, +intron) |
| | 193 (Os03g56241) |
| 305 (Os02g27760) | 150 (Os02g27760) |
| 306 (Os03g05980) | 151 (Os03g05980, +intron) |
| | 194 (Os03g05980) |
| 307 (Os03g05730) | 152 (Os03g05730, +intron) |
| | 195 (Os03g05730) |
| 308 (Os05g01262) | 153 (Os05g01262, +intron) |
| | 196 (Os05g01262) |
| 309 A, B (Os07g46670) | 154 (Os07g46670) |
| N/A | 197 (Os01g05650) |
| 310 (Os05g01560) | 155 (Os05g01560, +intron) |
| | 198 (Os05g01560) |
| 311 (Os07g08330) | 156 (Os07g08330, +intron) |
| | 199 (Os07g08330) |
| 312 A, B (Os03g58204) | 157 (Os03g58204, +intron) |
| | 200 (Os03g58204) |
| 313 (Os01g62420) | 158 (Os01g62420, +intron) |
| | 201 (Os01g62420) |
| 314 (Os01g14580) | 159 (Os01g14580, +intron) |
| | 202 (Os01g14580) |
| 315 (Os02g57040) | 160 (Os02g57040, +intron) |
| | 203 (Os02g57040) |
| 316 A, B (Os06g06980) | 161 (Os06g06980) |
| N/A | 162 (Os08g38920, +intron) |
| | 204 (Os08g38920) |
| 317 (Os09g01640) | 163 (Os09g01640) |
| 318 (Os07g10720) | 164 (Os07g10720) |
| 319 A, B (Os07g12650) | 165 (Os07g12650) |
| 320 (Os08g38900) | 166 (Os08g38900) |
| 321 (Os12g05430) | 167 (Os12g05430) |
| N/A | 205 (Os03g60400) |
| N/A | 206 (Os02g57720) |
| 322 (Os12g04924) | 168 (Os12g04924, +intron) |
| | 207 (Os12g04924) |
| 323 (Os01g73990) | 169 (Os01g73990, +intron) |
| | 208 (Os01g73990) |
| 324(Os01g01307) | 170 (Os01g01307, +intron) |
| | 209 (Os01g01307) |
| 325 A, B (Os11g04880) | 171(Os11g04880, +intron) |
| | 210 (Os11g04880) |
| 326 (Os02g34510) | 172 (Os02g34510, +intron) |
| | 211 (Os02g34510) |
| 327 (Os02g44630) | 173 (Os02g44630, +intron) |
| | 212 (Os02g44630) |

Example 6

Generation of Derivative Regulatory Polynucleotides

This example illustrates the utility of derivatives of the native *Arabidopsis* and rice ortholog regulatory polynucleotides. Derivatives of the *Arabidopsis* and ortholog regulatory polynucleotides are generated by introducing mutations into the nucleotide sequence of the native rice regulatory polynucleotides. A plurality of mutagenized DNA segments derived from the *Arabidopsis* and rice ortholog regulatory polynucleotides including derivatives with nucleotide deletions and modifications are generated and inserted into a plant transformation vector operably linked to a GUS marker gene. Each of the plant transformation vectors are prepared, for example, essentially as described in Example 3 above, except that the full length *Arabidopsis* or rice ortholog polynucleotide is replaced by a mutagenized derivative of the *Arabidopsis* or rice ortholog polynucleotide. *Arabidopsis* plants are transformed with each of the plant transformation vectors and analyzed for expression of the GUS marker to identify those mutagenized derivatives having regulatory activity.

Example 7

Identification of Regulatory Fragments

This example illustrates the utility of modified regulatory polynucleotides derived from the native *Arabidopsis* and rice ortholog polynucleotides. Fragments of the polynucleotides are generated by designing primers to clone fragments of the native *Arabidopsis* and rice regulatory polynucleotide. A plurality of cloned fragments of the polynucleotides ranging in size from 50 nucleotides up to about full length are obtained using PCR reactions with primers designed to amplify various size fragments instead of the full length polynucleotide. 3' fragments from the 3' end of the *Arabidopsis* or rice ortholog regulatory polynucleotide comprising random fragments of about 50, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600 and 1650 nucleotides in length from various parts of the *Arabidopsis* or rice ortholog regulatory polynucleotides are obtained and inserted into a plant transformation vector operably linked to a GUS marker gene. Each of the plant transformation vectors is prepared essentially as described, for example, in Example 3 above, except that the full length *Arabidopsis* or rice polynucleotide is replaced by a fragment of the *Arabidopsis* or rice regulatory polynucleotide or a combination of a 3' fragment and a random fragment. *Arabidopsis* plants are transformed with each of the plant transformation vectors and analyzed for expression of the GUS marker to identify those fragments having regulatory activity.

Example 8

Identification of Additional Orthologs

This example illustrates the identification and isolation of regulatory polynucleotides from organisms other than rice using the native *Arabidopsis* polynucleotide sequences and fragments to query genomic DNA from other organisms in a publicly available nucleotide data bases including GENBANK. Orthologous genes in other organisms can be identified using reciprocal best hit BLAST methods as described in Moreno-Hagelsieb and Latimer, Bioinformatics (2008) 24:319-324. The Gramene.org database could also be queried to identify rice (*Oryza sativa* japonica) orthologs corresponding to the *Arabidopsis* genes whose regulatory elements were identified in Example 1 above. In some cases, the *Arabidopsis* genes may lack a rice ortholog and in other cases the *Arabidopsis* genes may have more than one ortholog.

Once an ortholog gene is identified, its corresponding regulatory polynucleotide sequence can be selected using methods described for *Arabidopsis* and rice in Examples 1 and 4. The full length polynucleotides are cloned and inserted into a plant transformation vector which is used to transform *Arabidopsis* plants essentially as illustrated in Example 3 above to verify regulatory activity and expression patterns.

Example 9

*Arabidopsis* Ubiquitin Regulatory Sequences

One *Arabidopsis* sequence identified using the technique of Example 1 was AT4g05320 (also referred to as the *Arabi-*

*dopsis* polyubiquitin gene UBQ10). FIG. 328A provides the nucleotide sequence of the regulatory polynucleotide of the *Arabidopsis* gene having Accession No. AT4g05320 (SEQ ID NO: 213), with the sequence being annotated as described in Example 1. The expression pattern of the *Arabidopsis* ubiquitin gene was shown to be constitutive at the cell type/tissue level by the methods described in Example 1. Plots B and C (FIGS. 328B and 328C, respectively) are derived from data published by Brady et al. (Science, 318:801-806 (2007)) as discussed in Example 2 above. Plot B (FIG. 328B) provides the expression values of this gene in different cell types which were sorted on the basis of expressing the indicated GFP markers. Plot C (FIG. 328C) provides the expression values of this gene from root sections along the longitudinal axis of the root. FIG. 328D provides the developmental specific expression of AT4G05320. FIG. 328E provides the expression of AT4G05320 in response to various abiotic stresses. Plots D and E in FIG. 328 are derived from publically available expression data of the AtGeneExpress project (available on the World Wide Web at weigelworld.org/resources/microarray/AtGenExpress) also as discussed in Example 2. Plot D (FIG. 328D) shows developmental specific expression as described by Schmid et al. (*Nat. Genet.,* 37: 501-506 (2005)). Plot E (FIG. 328E) shows expression in response to abiotic stress as described by Kilian et al. (*Plant J.,* 50: 347-363 (2007)) as discussed above in Example 2.

A recombinant construct containing an approximately 1.2 kb fragment (including a 304 bp endogenous 5'-UTR intron) of the regulatory region from the *Arabidopsis* ubiquitin gene UBQ10 (corresponding to Accession No. AT4g05320) operably linked to the green fluorescence protein (GFP) coding sequence was prepared, and is referred to as construct A. A summary of the sequence used in Construct A is provided in Table 8.

TABLE 8

| source gene ID | endogenous promoter-UTR seq. used (bp) | endogenous 5'-UTR intron (bp) |
|---|---|---|
| AT4G05320 | 1201 | 304 |

Figure 329A:
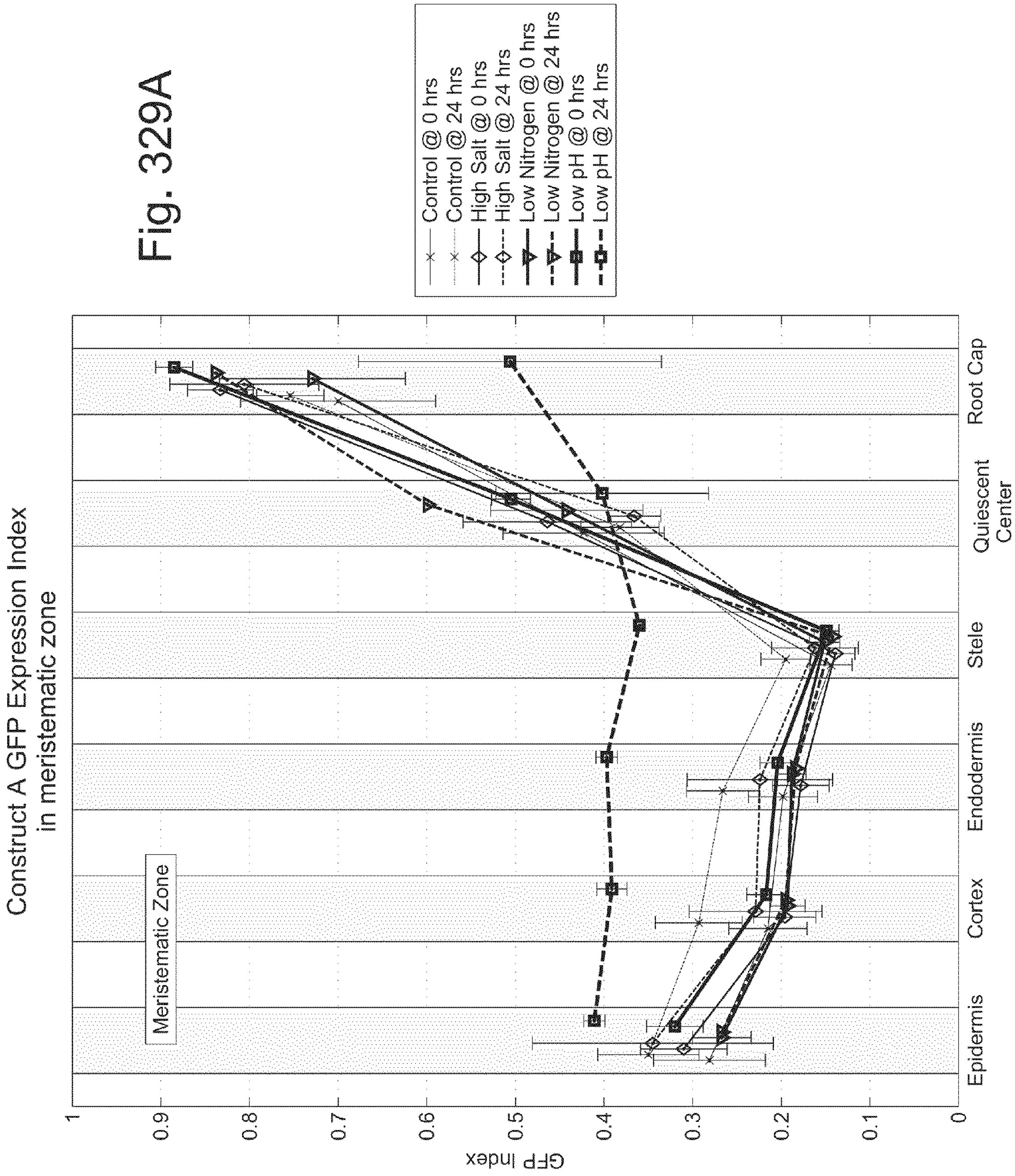
FIG. 329 shows the average GFP Expression Index in different cell-types in 3 longitudinal zones ((A) meristematic zone, (B) elongation zone, and (C) maturation zone) under standard and 3 stress conditions using a regulatory polynucleotide from the *Arabidopsis* polyubiquitin gene UBQ10, which was identified using the methods described herein.
Figure 329B:
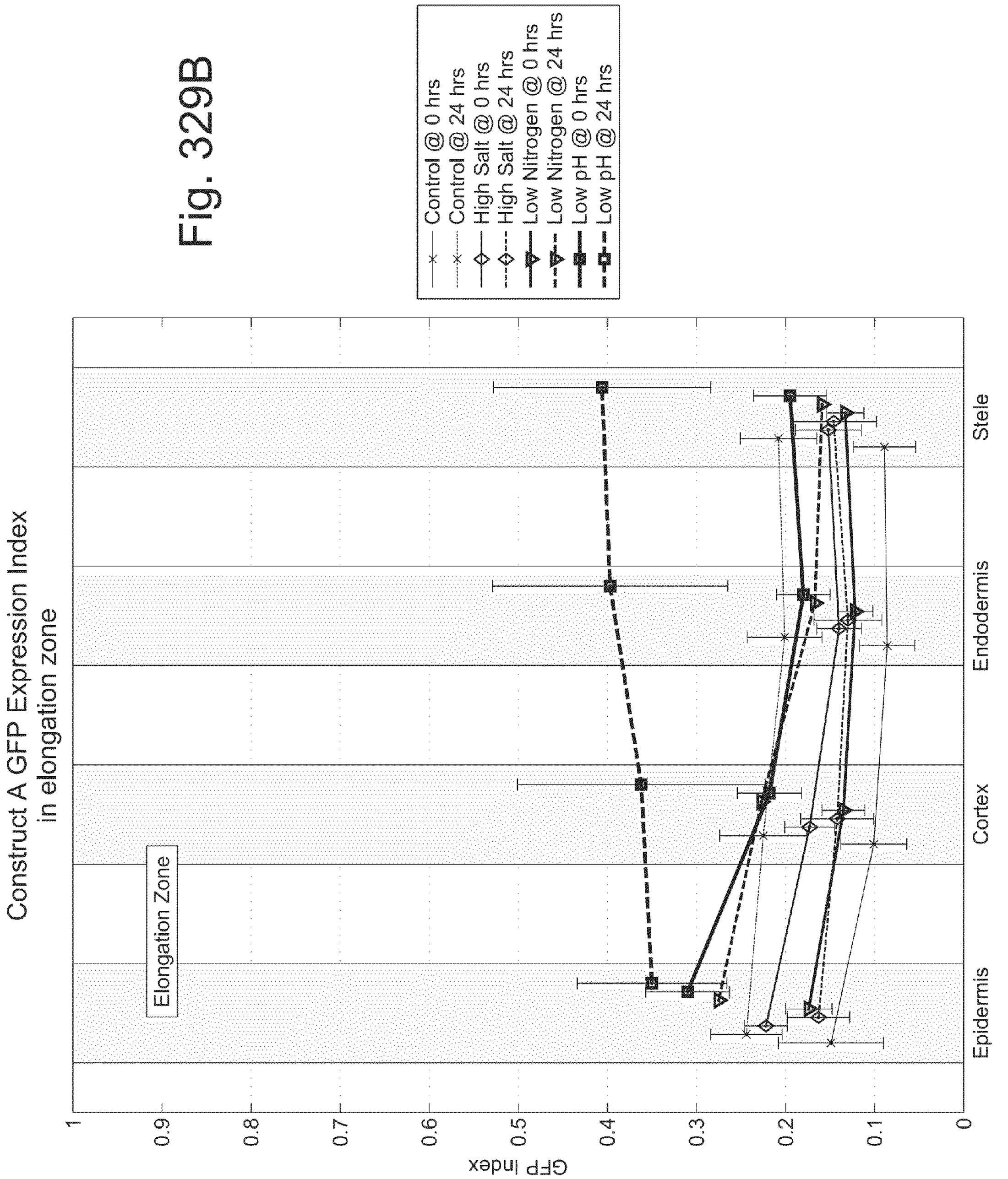
Figure 329C:
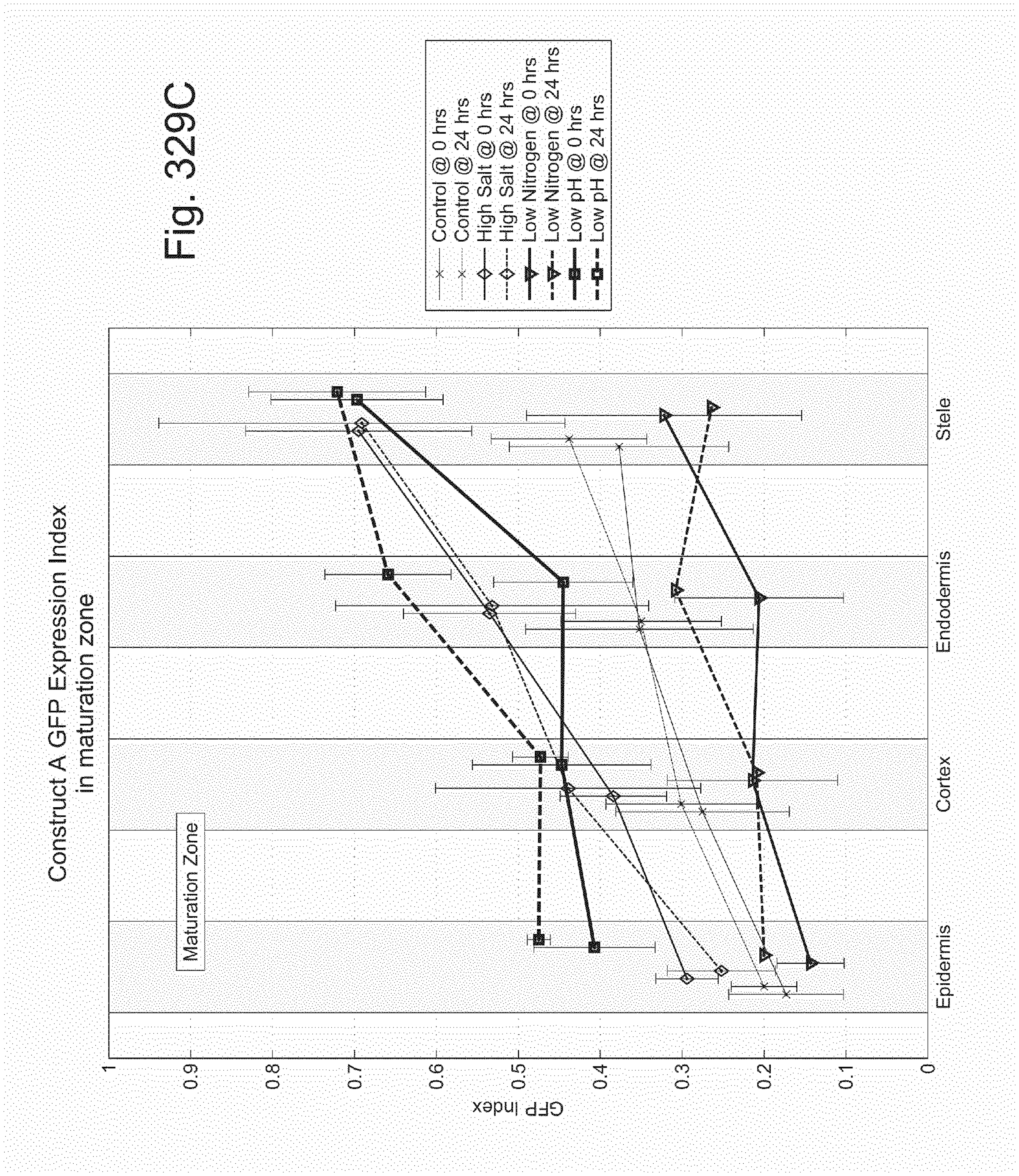

Construct A was transformed into *Arabidopsis* using the *Agrobacterium*-mediated floral dip method as described in Clough and Bent, 1998, Plant J. 16:735-743. Transformed plants (T1) were selected, transferred to soil, and allowed to set seed. T2 seed was harvested from multiple T1 lines and single insertion lines were identified by 3:1 segregation of the selection marker in T2 seedlings. T2 seedlings from single insertion lines were grown under standard Murashige and Skoog (MS) media conditions and roots were analyzed for GFP fluorescence with a Zeiss 510 confocal microscope expression. Seedlings were then kept in MS media or transferred to high salt (MS+20 mM NaCl), low nitrogen (MS containing 0.5 mM N), or low pH (MS pH 4.6) conditions for 24 h. The roots were then again analyzed for GFP fluorescence to test expression responses to abiotic stress. The three stress conditions were validated to confer differential expression of known stress-responsive genes. One to seven T2 seedlings containing the transgene were analyzed per line and multiple images along the longitudinal axis were taken in order to assess expression in the meristematic, elongation and maturation zones of the root. The same sensitivity settings were used in all cases to provide quantitative comparisons between images. GFP expression in different cell-types was determined from the images using a predefined root template. The template was calculated using a series of images manually segmented to find the root's "tissue percentage profile" (TPP), in which each region of interest in the template is a percentage of the root thickness at the specified location relative to the quiescent center (QC). Using different TPPs for each root zone, the images were segmented into different regions of interest (ROI) corresponding to different root cell-types. The average grayscale intensity of each ROI from the GFP fluorescence channel was then calculated and presented as the GFP Expression Index (GEI). The GEI varies from 0 and 1, which corresponds to no GFP expression (GEI=0) and complete saturation of GFP signal (GEI=1), respectively. FIGS. 329A, 329B, and 329C show the average GEI (±SEM) in different cell-types in 3 longitudinal zones under standard and 3 stress conditions. Note that the average GEI across all root regions for non-transgenic *Arabidopsis* seedlings (i.e. the background signal) is 0.0244±0.0011. These data show that the regulatory region used in construct A drives constitutive expression of GFP that was generally unresponsive to abiotic stress.

Thus, the methods disclosed herein are useful to identify regulatory polynucleotides that are capable of regulating constitutive expression of an operably linked polynucleotide.

Example 10

Preparation and Quantitative Root Expression Testing of Identified Regulatory Elements in Stably Transformed *Arabidopsis*

Candidate regulatory elements represented by SEQ ID NOS:1-22, 66, 71-73, 75, 81-82, 100, and 102-112 were sub-cloned into a plant transformation vector containing a right border region from *Agrobacterium tumefaciens*, a first transgene cassette to test the regulatory or chimeric regulatory element comprised of, a regulatory or chimeric regulatory element, operably linked to a coding sequence for Green Fluorescent Protein (GFP), operably linked to the 3' termination region from the fiber Fb Late-2 gene from *Gossypium barbadense* (sea-island cotton, Genbank reference, U34401); a second transgene selection cassette used for selection of transformed plant cells that conferred resistance to the herbicide glyphosate, driven by the *Arabidopsis* Actin 7 promoter (Genbank accession, U27811) and a left border region from *A. tumefaciens*. Final constructs were transferred to *Agrobacterium* and transformed into *Arabidopsis* Columbia ecotype plants by the floral dip method (S. J. Clough, A. F. Bent, *Plant J* 16, 735 (December, 1998)). Transformed plants (T1 generation) were selected by resistance to glyphosate application. Sixteen glyphosate resistant T1s were selected per construct and their relative copy number was determined by qPCR. The six lowest copy T1s were selected for further analysis and allowed to set seed (T2 generation).

For a preliminary assessment of GFP expression, T2 seed from these 6 events was grown for 5 days on agar plates containing Murashige and Skoog (MS) media after which the seedling roots were stained with the lipophilic probe FM4-64 to visualize cell membranes. The roots from 3-5 seedlings of each of the 6 T2 lines per construct were imaged for GFP fluorescence with a Zeiss 510 confocal microscope at the three developmental zones of the root (meristematic, elongation, and maturation). A line was considered to fail expression prescreening if no GFP fluorescence was observed in 5 seedlings of each of the 6 T2 lines per construct. No further analysis of these lines was performed, with regulatory polynucleotides contained in these lines listed in Table 9.

TABLE 9

| Gene | Promoter Sequence |
|---|---|
| AT3G01280 | SEQ ID NO: 2 |
| AT1G76200 | SEQ ID NO: 5 |
| AT2G16850 | SEQ ID NO: 6 |
| AT2G31490 | SEQ ID NO: 7 |
| AT5G08690 | SEQ ID NO: 9 |
| AT2G16850 | SEQ ID NO: 19 |
| Os07g46750 | SEQ ID NO: 105 |
| Os05g45950 | SEQ ID NO: 108 |
| Os01g46610 | SEQ ID NO: 103 |
| Os03g56190 | SEQ ID NO: 100 |
| Os04g28180 | SEQ ID NO: 106 |

The designation of failing expression does not mean that these regulatory polynucleotides are not capable of driving expression since the prescreening procedures have low detection sensitivity. More sensitive detection methods like qRT-PCR were able to detect GFP transcripts in lines that failed to show GFP fluorescence in this presecreening procedure.

For all regulatory polynucleotides that passed prescreening, 3 to 6 of the T2 lines exhibited GFP fluorescence. High resolution, quantitative measurements of GFP fluorescence in roots were then undertaken on two representative lines that exhibited fluorescence. T2 seed from the two representative lines was grown in MS media in the RootArray, a device designed for confocal imaging of living plant roots under controlled conditions, and described in U.S. Patent Publication No. 2008/0141585 which is incorporated herein by reference in its entirety. After 5 days growth, the roots were stained with FM4-64 and imaged for GFP fluorescence in the meristematic zone, elongation zone and maturation zone with approximately 50 seedlings analyzed per line.

In order to yield quantitative results from image pixel intensities, imaging conditions and measurements were strictly controlled. The imaging normalization and calibration methods were based on two key measurements. First, on any day measurements are taken, a dilution series of an external reference fluorophore was quantitatively imaged. Second, the post objective laser intensity was directly measured before and after each RootArray experiment in order to account for variations in laser light intensity that may have occurred.

The dilution series that was imaged each day was prepared from a reference standard. The reference standard was prepared from a concentrated stock of Alexa Fluor 488 in MES buffer (pH 6.0), with its concentration determined by spectrophotometry. Aliquots of the reference standard were stored at −20° C. as a master stock. For calibration use, a dilution series of the stock was prepared in a sealed, modified 96 well plate. The dilution series was stored at 4° C. in the dark and used for up to one month before being replaced. The Alexa Fluor standard was verified to be stable under these conditions. The dilution series was imaged at the beginning of each day to characterize the performance of the detector and optics of the microscope as described below.

Tests have shown that laser light intensity can vary up to 10% at a given setting over the course of a RootArray experiment. To correct for this, laser power is measured before and after each RootArray experiment. The laser intensity is actively adjusted to 355±15 μW at 488 nm at the beginning of each experiment. The change in intensity measured at the end of a RootArray experiment was assumed to be due to a linear transition. Therefore, the estimated light intensity for a specific RootArray image was interpolated from that image's timestamp.

To correct for variations in laser intensity and detector response a model was developed to describe how Alexa Fluor 488 fluorescence varied with laser intensity under the imaging conditions described herein. The laser correction model for Alexa Fluor 488 is based on the relative change of the dilution series slope versus the relative change of laser light intensity. Experiments have demonstrated that this relationship is independent of scan settings. This model was then adapted to GFP in root tissue with the addition of a GFP specific variable. This model is used to calculate a GFP expression index (GEI) as described in Equation 1 below (it is noted that the equation used to calculate the GFP Expression Index (GEI) in this example is slightly different from the equation used to calculate the GFP Expression Index in Example 9).

$$GFP \text{ expression index } (GEI) \qquad \text{Equation 1}$$

$$GEI = \frac{\mu(roi(Img) - bkg(Img))}{\alpha_{AF}^{DS}\beta_{Sat}}\gamma_{AF}^{DS}\gamma_{AF}^{IMG}\delta_{GFP}^{Img}$$

roi (Img): The pixel population for the quantification channel (green channel) over a selected region of interest. In this case each ROI is a tissue type.

bkg (Img): The background pixel value for every experimental image is characterized with a novel statistics based approach.

$\alpha_{AF}^{DS}$: Normalized slope of the dilution series standard.

$\gamma_{AF}^{DS}$: Laser correction factor for Alexa Fluor 488 fluorophore to normalize the dilution series to the reference laser power (355 μW at 488 nm).

$\gamma_{AF}^{Img}$: Laser correction factor for Alexa Fluor 488 fluorophore at the laser power the GFP image was taken.

$\delta_{GFP}^{Img}$: Relative laser correction factor for GFP fluorophore in the experimental image.

$\beta_{Sat}$: Normalization constant to prevent pixel oversaturation of the detector when the image was acquired.

The green channel image signal passes through this function to produce the GEI, a metric of fluorescent intensity that allows for comparison across RootArrays over time. The background of each experimental image was calculated as described below and subsequently subtracted from the pixel population of the region of interest. The negative values were zeroed to create an image with minimal background noise. The mean of corrected pixel intensities was divided by the slope of the dilution series to convert the pixel output to a metric of light intensity relative to the dilution series standard. The first gamma value ($\gamma_{AF}^{DS}$) is a laser correction factor that adjusts the slope of the dilution series to what it would be if the dilution series was imaged at exactly 355 μW. The next gamma ($\gamma_{AF}^{Img}$) and the delta values ($\delta_{GFP}^{Img}$) correct the GFP signal to what it would be if the root was imaged at exactly 355 μW. It is noted that all correction factors typically varied by less than 5% between experiments.

Regions of interest that have a strong signal near the point of pixel oversaturation of the detector did not exhibit a linear relationship with GFP expression. Therefore a normalization constant ($\beta_{Sat}$) was included to limit the scope of the dynamic bit range of the detector and the GEI is capped at 1 to preserve its linear correlation with GFP expression for all reported values <1. To calculate the background of an image (bkg (Img)), the image was first split into a grid of squares and the pixel population of each square is examined. A small number of squares was initially selected based on having the lowest percentile rankings in terms of standard deviation, 95$^{th}$ percentile pixel value, mean, median, and gradient magnitude.

The pixel populations in the initial "seed" squares, which are assumed to be background, were then compared against the pixel populations of all other squares in a one tailed unpaired t test in order to categorize each square as "background" or "non-background". The median pixel intensity of all squares determined to be "background" was then used as the bkg (Img) value in Equation 1. Tests have shown that this algorithm robustly selected background pixel populations even if there were several roots in the field of view.

The correspondence of regions of interest to different cell-types was determined from the images using a predefined root template. The template was calculated using a series of images manually segmented to find the root's "tissue percentage profile" (TPP), in which each region of interest in the template is a percentage of the root thickness at the specified location relative to the quiescent center (QC). Using different TPPs for each root zone, the images were segmented into different regions of interest (ROI) corresponding to different root cell-types. Specifically, the regions determined in all three developmental zones were the epidermis, the cortex, the endodermis, and the stele. In addition to these four regions, the root cap and the quiescent center were also determined in the meristematic zone.

To determine if a particular transgenic line exhibited significant GFP expression in an ROI, the GEI measurements for each of the 14 tissue-zone ROIs were compared to the corresponding values determined from 48 non-transgenic *Arabidopsis* Columbia ecotype seedlings grown under identical conditions. Significance was determined using a one-tailed Welch's t-test with a cutoff of $p<0.01$.

The average GEI for each of the 14 tissue-zone ROIs for 2 representative lines of each regulatory molecule that passed prescreening is shown in Tables 10-12. All values represent significant expression ($p<0.01$) unless indicated by bold italics. The GEIs measured from seedlings containing a 35S promoter-GFP transgene are shown for comparison. The 35S promoter is widely used in plant biotechnology and considered a standard for strong promoters. These data show that the regulatory polynucleotides listed in Tables 10-12 generally drive constitutive expression in the root.

Table 10 shows the GEI values of promoter sequences in regions of the meristematic zone.

TABLE 10

| Gene | Promoter Sequence (SEQ ID NO) | Meristematic Zone | | | | | |
|---|---|---|---|---|---|---|---|
| | | Root Cap | QC | Epidermis | Cortex | Endodermis | Stele |
| | 35S control | 1.00 | 0.96 | 0.40 | 0.28 | 0.24 | 0.23 |
| AT1G02780 | SEQ ID NO: 1 | 0.03 | 0.02 | 0.07 | 0.07 | 0.06 | 0.03 |
| AT1G02780 | SEQ ID NO: 1 | 0.28 | 0.27 | 0.53 | 0.51 | 0.46 | 0.37 |
| AT1G43170 | SEQ ID NO: 3 | 0.16 | 0.17 | 0.19 | 0.17 | 0.16 | 0.14 |
| AT1G43170 | SEQ ID NO: 3 | 0.47 | 0.47 | 0.55 | 0.51 | 0.48 | 0.42 |
| AT1G67430 | SEQ ID NO: 4 | 0.11 | 0.10 | 0.17 | 0.16 | 0.15 | 0.13 |
| AT1G67430 | SEQ ID NO: 4 | 0.04 | 0.03 | 0.10 | 0.10 | 0.07 | 0.06 |
| AT4G00860 | SEQ ID NO: 8 | 0.08 | 0.05 | 0.04 | 0.03 | 0.03 | 0.03 |
| AT4G00860 | SEQ ID NO: 8 | 0.31 | 0.17 | 0.14 | 0.11 | 0.10 | 0.09 |
| AT5G53560 | SEQ ID NO: 10 | 0.01 | 0.01 | 0.01 | ***0.01*** | ***0.01*** | ***0.01*** |
| AT5G53560 | SEQ ID NO: 10 | ***0.01*** | ***0.01*** | ***0.01*** | ***0.01*** | 0.01 | ***0.01*** |
| AT1G07600 | SEQ ID NO: 11 | ***0.02*** | ***0.01*** | ***0.01*** | ***0.01*** | ***0.01*** | ***0.01*** |
| AT1G07600 | SEQ ID NO: 11 | 0.01 | ***0.01*** | ***0.01*** | ***0.01*** | ***0.01*** | ***0.00*** |
| AT1G67350 | SEQ ID NO: 12 | 0.29 | 0.24 | 0.13 | 0.12 | 0.11 | 0.10 |
| AT1G67350 | SEQ ID NO: 12 | 0.14 | 0.13 | 0.07 | 0.06 | 0.06 | 0.05 |
| AT1G78380 | SEQ ID NO: 13 | 0.14 | 0.14 | 0.03 | 0.02 | 0.02 | 0.01 |
| AT1G78380 | SEQ ID NO: 13 | 0.04 | 0.03 | 0.02 | 0.01 | 0.01 | 0.01 |
| AT1G76200 | SEQ ID NO: 14 | 0.10 | 0.07 | 0.05 | 0.05 | 0.05 | 0.04 |
| AT1G76200 | SEQ ID NO: 14 | 0.05 | 0.04 | 0.04 | 0.03 | 0.03 | 0.03 |
| AT1G78380 | SEQ ID NO: 15 | 0.18 | 0.11 | 0.02 | 0.02 | 0.01 | 0.01 |
| AT1G78380 | SEQ ID NO: 15 | 0.31 | 0.28 | 0.04 | 0.03 | 0.03 | 0.03 |
| AT1G02780 | SEQ ID NO: 16 | 0.24 | 0.20 | 0.22 | 0.20 | 0.18 | 0.15 |
| AT1G02780 | SEQ ID NO: 16 | 0.31 | 0.24 | 0.26 | 0.24 | 0.21 | 0.18 |
| AT5G08690 | SEQ ID NO: 17 | 0.01 | ***0.01*** | 0.01 | 0.01 | ***0.01*** | ***0.01*** |

TABLE 10-continued

| Gene | Promoter Sequence (SEQ ID NO) | Meristematic Zone Root Cap | QC | Epidermis | Cortex | Endodermis | Stele |
|---|---|---|---|---|---|---|---|
| AT5G08690 | SEQ ID NO: 17 | 0.07 | 0.03 | 0.05 | 0.05 | 0.04 | 0.03 |
| AT1G67430 | SEQ ID NO: 18 | 0.13 | 0.11 | 0.19 | 0.18 | 0.16 | 0.13 |
| AT1G67430 | SEQ ID NO: 18 | 0.05 | 0.04 | 0.08 | 0.07 | 0.06 | 0.05 |
| AT2G31490 | SEQ ID NO: 20 | 0.07 | 0.05 | 0.04 | 0.04 | 0.03 | 0.03 |
| AT2G31490 | SEQ ID NO: 20 | 0.11 | 0.07 | 0.07 | 0.06 | 0.06 | 0.05 |
| AT3G01280 | SEQ ID NO: 21 | 0.13 | 0.10 | 0.12 | 0.11 | 0.10 | 0.09 |
| AT3G01280 | SEQ ID NO: 21 | 0.35 | 0.31 | 0.32 | 0.29 | 0.26 | 0.23 |
| AT1G07600 | SEQ ID NO: 22 | 0.01 | ***0.01*** | 0.01 | 0.01 | 0.01 | 0.01 |
| AT1G07600 | SEQ ID NO: 22 | ***0.01*** | ***0.01*** | ***0.01*** | ***0.01*** | 0.01 | 0.01 |
| AT4G33865 | SEQ ID NO: 66 | 0.38 | 0.30 | 0.42 | 0.36 | 0.33 | 0.28 |
| AT4G33865 | SEQ ID NO: 66 | 0.41 | 0.31 | 0.42 | 0.35 | 0.31 | 0.27 |
| AT5G64350 | SEQ ID NO: 71 | 0.05 | 0.04 | 0.02 | 0.03 | 0.03 | 0.03 |
| AT5G64350 | SEQ ID NO: 71 | 0.14 | 0.14 | 0.09 | 0.08 | 0.09 | 0.09 |
| AT5G48810 | SEQ ID NO: 72 | 0.02 | 0.01 | 0.01 | 0.01 | 0.01 | 0.01 |
| AT5G48810 | SEQ ID NO: 72 | 0.04 | 0.01 | 0.02 | 0.01 | 0.01 | 0.01 |
| AT5G19760 | SEQ ID NO: 73 | 0.04 | 0.01 | 0.03 | 0.02 | 0.02 | 0.01 |
| AT5G19760 | SEQ ID NO: 73 | 0.05 | 0.01 | 0.02 | 0.01 | 0.01 | 0.01 |
| AT5G02960 | SEQ ID NO: 75 | 0.53 | 0.49 | 0.52 | 0.48 | 0.45 | 0.41 |
| AT5G02960 | SEQ ID NO: 75 | 0.59 | 0.52 | 0.57 | 0.50 | 0.46 | 0.42 |
| AT2G33040 | SEQ ID NO: 81 | 0.06 | 0.05 | 0.08 | 0.07 | 0.06 | 0.05 |
| AT2G33040 | SEQ ID NO: 81 | 0.06 | 0.05 | 0.09 | 0.08 | 0.07 | 0.05 |
| AT5G14030 | SEQ ID NO: 82 | 0.09 | 0.06 | 0.08 | 0.07 | 0.07 | 0.05 |
| AT5G14030 | SEQ ID NO: 82 | 0.11 | 0.06 | 0.10 | 0.09 | 0.08 | 0.06 |
| Os02g02130 | SEQ ID NO: 102 | 0.08 | 0.06 | 0.12 | 0.11 | 0.10 | 0.08 |
| Os02g02130 | SEQ ID NO: 102 | 0.03 | 0.02 | 0.06 | 0.05 | 0.04 | 0.03 |
| Os05g01820 | SEQ ID NO: 104 | 0.02 | 0.02 | 0.01 | 0.02 | 0.01 | 0.01 |
| Os05g01820 | SEQ ID NO: 104 | 0.07 | 0.04 | 0.02 | 0.03 | 0.03 | 0.02 |
| Os03g21940 | SEQ ID NO: 107 | 0.08 | 0.08 | 0.10 | 0.10 | 0.10 | 0.09 |
| Os03g21940 | SEQ ID NO: 107 | 0.01 | 0.02 | 0.03 | 0.02 | 0.02 | 0.02 |
| Os02g52290 | SEQ ID NO: 109 | 0.03 | 0.01 | 0.02 | 0.02 | 0.01 | 0.01 |
| Os02g52290 | SEQ ID NO: 109 | 0.03 | 0.01 | 0.01 | 0.01 | 0.01 | 0.01 |
| Os05g47980 | SEQ ID NO: 110 | 0.02 | 0.02 | 0.01 | 0.02 | 0.02 | 0.01 |
| Os05g47980 | SEQ ID NO: 110 | 0.03 | 0.03 | 0.03 | 0.03 | 0.03 | 0.02 |
| Os11g11390 | SEQ ID NO: 111 | 0.14 | 0.12 | 0.14 | 0.13 | 0.13 | 0.11 |
| Os11g11390 | SEQ ID NO: 111 | 0.25 | 0.22 | 0.27 | 0.25 | 0.25 | 0.22 |
| Os11g47760 | SEQ ID NO: 112 | 0.11 | 0.20 | 0.11 | 0.12 | 0.12 | 0.11 |
| Os11g47760 | SEQ ID NO: 112 | 0.34 | 0.54 | 0.36 | 0.37 | 0.37 | 0.35 |

Table 11 shows the GEI values of promoter sequences in regions of the elongation zone.

TABLE 11

| Gene | Promoter Sequence (SEQ ID NO) | Elongation Zone Epidermis | Elongation Zone Cortex | Elongation Zone Endodermis | Elongation Zone Stele |
|---|---|---|---|---|---|
| | 35S control | 0.24 | 0.08 | 0.08 | 0.20 |
| AT1G02780 | SEQ ID NO: 1 | 0.02 | 0.01 | 0.01 | 0.01 |
| AT1G02780 | SEQ ID NO: 1 | 0.16 | 0.11 | 0.09 | 0.10 |
| AT1G43170 | SEQ ID NO: 3 | 0.08 | 0.05 | 0.05 | 0.05 |
| AT1G43170 | SEQ ID NO: 3 | 0.20 | 0.12 | 0.10 | 0.12 |
| AT1G67430 | SEQ ID NO: 4 | 0.07 | 0.04 | 0.04 | 0.04 |
| AT1G67430 | SEQ ID NO: 4 | 0.05 | 0.03 | 0.03 | 0.03 |
| AT4G00860 | SEQ ID NO: 8 | 0.03 | 0.02 | 0.02 | 0.02 |
| AT4G00860 | SEQ ID NO: 8 | 0.10 | 0.06 | 0.05 | 0.05 |
| AT5G53560 | SEQ ID NO: 10 | 0.01 | 0.01 | 0.01 | 0.01 |
| AT5G53560 | SEQ ID NO: 10 | 0.01 | 0.01 | 0.01 | 0.01 |
| AT1G07600 | SEQ ID NO: 11 | ***0.01*** | ***0.01*** | ***0.01*** | ***0.00*** |
| AT1G07600 | SEQ ID NO: 11 | 0.01 | ***0.01*** | ***0.00*** | ***0.00*** |
| AT1G67350 | SEQ ID NO: 12 | 0.07 | 0.04 | 0.03 | 0.04 |
| AT1G67350 | SEQ ID NO: 12 | 0.04 | 0.02 | 0.02 | 0.02 |
| AT1G78380 | SEQ ID NO: 13 | 0.02 | 0.01 | 0.01 | ***0.01*** |
| AT1G78380 | SEQ ID NO: 13 | 0.02 | 0.01 | 0.00 | 0.00 |
| AT1G76200 | SEQ ID NO: 14 | 0.03 | 0.03 | 0.02 | 0.02 |
| AT1G76200 | SEQ ID NO: 14 | 0.03 | 0.02 | 0.02 | 0.02 |
| AT1G78380 | SEQ ID NO: 15 | 0.01 | 0.00 | ***0.00*** | ***0.00*** |
| AT1G78380 | SEQ ID NO: 15 | 0.02 | 0.01 | ***0.00*** | ***0.00*** |
| AT1G02780 | SEQ ID NO: 16 | 0.12 | 0.07 | 0.06 | 0.07 |
| AT1G02780 | SEQ ID NO: 16 | 0.15 | 0.09 | 0.08 | 0.08 |
| AT5G08690 | SEQ ID NO: 17 | 0.01 | 0.01 | 0.00 | 0.00 |
| AT5G08690 | SEQ ID NO: 17 | 0.04 | 0.02 | 0.02 | 0.02 |
| AT1G67430 | SEQ ID NO: 18 | 0.08 | 0.05 | 0.04 | 0.04 |
| AT1G67430 | SEQ ID NO: 18 | 0.03 | 0.02 | 0.02 | 0.02 |
| AT2G31490 | SEQ ID NO: 20 | 0.03 | 0.03 | 0.02 | 0.02 |
| AT2G31490 | SEQ ID NO: 20 | 0.05 | 0.04 | 0.03 | 0.03 |
| AT3G01280 | SEQ ID NO: 21 | 0.05 | 0.03 | 0.02 | 0.03 |
| AT3G01280 | SEQ ID NO: 21 | 0.12 | 0.07 | 0.06 | 0.07 |
| AT1G07600 | SEQ ID NO: 22 | 0.01 | 0.01 | ***0.00*** | ***0.00*** |
| AT1G07600 | SEQ ID NO: 22 | 0.01 | 0.01 | ***0.00*** | ***0.00*** |
| AT4G33865 | SEQ ID NO: 66 | 0.19 | 0.17 | 0.12 | 0.13 |
| AT4G33865 | SEQ ID NO: 66 | 0.17 | 0.15 | 0.11 | 0.12 |
| AT5G64350 | SEQ ID NO: 71 | 0.01 | 0.01 | 0.01 | 0.01 |
| AT5G64350 | SEQ ID NO: 71 | 0.04 | 0.03 | 0.02 | 0.03 |
| AT5G48810 | SEQ ID NO: 72 | 0.03 | 0.02 | 0.02 | 0.01 |
| AT5G48810 | SEQ ID NO: 72 | 0.03 | 0.03 | 0.02 | 0.01 |
| AT5G19760 | SEQ ID NO: 73 | 0.06 | 0.06 | 0.05 | 0.03 |
| AT5G19760 | SEQ ID NO: 73 | 0.09 | 0.07 | 0.06 | 0.04 |
| AT5G02960 | SEQ ID NO: 75 | 0.17 | 0.13 | 0.11 | 0.12 |
| AT5G02960 | SEQ ID NO: 75 | 0.22 | 0.17 | 0.13 | 0.14 |
| AT2G33040 | SEQ ID NO: 81 | 0.04 | 0.04 | 0.03 | 0.03 |
| AT2G33040 | SEQ ID NO: 81 | 0.04 | 0.04 | 0.03 | 0.03 |
| AT5G14030 | SEQ ID NO: 82 | 0.06 | 0.04 | 0.03 | 0.03 |
| AT5G14030 | SEQ ID NO: 82 | 0.05 | 0.04 | 0.03 | 0.03 |
| Os02g02130 | SEQ ID NO: 102 | 0.05 | 0.03 | 0.03 | 0.03 |
| Os02g02130 | SEQ ID NO: 102 | 0.02 | 0.01 | 0.01 | 0.01 |
| Os05g01820 | SEQ ID NO: 104 | 0.01 | 0.01 | 0.01 | 0.01 |
| Os05g01820 | SEQ ID NO: 104 | 0.02 | 0.03 | 0.03 | 0.02 |
| Os03g21940 | SEQ ID NO: 107 | 0.06 | 0.04 | 0.04 | 0.04 |
| Os03g21940 | SEQ ID NO: 107 | 0.01 | 0.01 | 0.01 | 0.01 |
| Os02g52290 | SEQ ID NO: 109 | 0.01 | 0.01 | 0.01 | 0.01 |
| Os02g52290 | SEQ ID NO: 109 | 0.01 | 0.01 | 0.01 | 0.01 |
| Os05g47980 | SEQ ID NO: 110 | 0.02 | 0.01 | 0.01 | 0.01 |
| Os05g47980 | SEQ ID NO: 110 | 0.02 | 0.02 | 0.02 | 0.02 |
| Os11g11390 | SEQ ID NO: 111 | 0.06 | 0.04 | 0.04 | 0.04 |
| Os11g11390 | SEQ ID NO: 111 | 0.10 | 0.07 | 0.06 | 0.07 |
| Os11g47760 | SEQ ID NO: 112 | 0.05 | 0.03 | 0.03 | 0.04 |
| Os11g47760 | SEQ ID NO: 112 | 0.16 | 0.11 | 0.11 | 0.13 |

Table 12 shows the GEI values of promoter sequences in regions of the maturation zone.

TABLE 12

| Gene | Promoter Sequence (SEQ ID NO) | Maturation Zone Epidermis | Maturation Zone Cortex | Maturation Zone Endodermis | Maturation Zone Stele |
|---|---|---|---|---|---|
| | 35S control | 0.23 | 0.22 | 0.31 | 0.55 |
| AT1G02780 | SEQ ID NO: 1 | ***0.01*** | ***0.01*** | 0.01 | 0.01 |
| AT1G02780 | SEQ ID NO: 1 | 0.04 | 0.03 | 0.04 | 0.10 |
| AT1G43170 | SEQ ID NO: 3 | 0.02 | 0.02 | 0.02 | 0.05 |

TABLE 12-continued

| Gene | Promoter Sequence (SEQ ID NO) | Maturation Zone | | | |
|---|---|---|---|---|---|
| | | Epidermis | Cortex | Endodermis | Stele |
| AT1G43170 | SEQ ID NO: 3 | 0.05 | 0.04 | 0.06 | 0.15 |
| AT1G67430 | SEQ ID NO: 4 | 0.01 | 0.01 | 0.01 | 0.03 |
| AT1G67430 | SEQ ID NO: 4 | 0.01 | 0.01 | 0.01 | 0.02 |
| AT4G00860 | SEQ ID NO: 8 | 0.02 | 0.01 | 0.01 | 0.02 |
| AT4G00860 | SEQ ID NO: 8 | 0.04 | 0.03 | 0.04 | 0.08 |
| AT5G53560 | SEQ ID NO: 10 | 0.01 | 0.01 | 0.01 | 0.01 |
| AT5G53560 | SEQ ID NO: 10 | 0.01 | 0.01 | 0.01 | 0.01 |
| AT1G07600 | SEQ ID NO: 11 | 0.17 | 0.13 | 0.09 | 0.04 |
| AT1G07600 | SEQ ID NO: 11 | 0.56 | 0.39 | 0.27 | 0.10 |
| AT1G67350 | SEQ ID NO: 12 | 0.04 | 0.03 | 0.04 | 0.07 |
| AT1G67350 | SEQ ID NO: 12 | 0.02 | 0.01 | 0.02 | 0.03 |
| AT1G78380 | SEQ ID NO: 13 | 0.03 | 0.01 | 0.02 | 0.02 |
| AT1G78380 | SEQ ID NO: 13 | 0.03 | 0.02 | 0.02 | 0.02 |
| AT1G76200 | SEQ ID NO: 14 | 0.02 | 0.02 | 0.02 | 0.03 |
| AT1G76200 | SEQ ID NO: 14 | 0.01 | 0.01 | 0.02 | 0.02 |
| AT1G78380 | SEQ ID NO: 15 | 0.03 | 0.03 | 0.04 | 0.04 |
| AT1G78380 | SEQ ID NO: 15 | 0.06 | 0.05 | 0.06 | 0.07 |
| AT1G02780 | SEQ ID NO: 16 | 0.03 | 0.02 | 0.03 | 0.06 |
| AT1G02780 | SEQ ID NO: 16 | 0.03 | 0.03 | 0.04 | 0.09 |
| AT5G08690 | SEQ ID NO: 17 | 0.01 | ***0.01*** | ***0.00*** | ***0.01*** |
| AT5G08690 | SEQ ID NO: 17 | 0.01 | 0.01 | 0.01 | 0.02 |
| AT1G67430 | SEQ ID NO: 18 | 0.02 | 0.01 | 0.02 | 0.04 |
| AT1G67430 | SEQ ID NO: 18 | 0.01 | 0.01 | 0.01 | 0.02 |
| AT2G31490 | SEQ ID NO: 20 | 0.01 | 0.01 | 0.02 | 0.02 |
| AT2G31490 | SEQ ID NO: 20 | 0.02 | 0.02 | 0.03 | 0.04 |
| AT3G01280 | SEQ ID NO: 21 | 0.02 | 0.02 | 0.03 | 0.05 |
| AT3G01280 | SEQ ID NO: 21 | 0.06 | 0.06 | 0.06 | 0.13 |
| AT1G07600 | SEQ ID NO: 22 | 0.40 | 0.45 | 0.34 | 0.09 |
| AT1G07600 | SEQ ID NO: 22 | 0.20 | 0.17 | 0.11 | 0.03 |
| AT4G33865 | SEQ ID NO: 66 | 0.05 | 0.06 | 0.07 | 0.17 |
| AT4G33865 | SEQ ID NO: 66 | 0.04 | 0.04 | 0.05 | 0.13 |
| AT5G64350 | SEQ ID NO: 71 | 0.01 | 0.01 | 0.01 | 0.01 |
| AT5G64350 | SEQ ID NO: 71 | 0.01 | 0.01 | 0.02 | 0.04 |
| AT5G48810 | SEQ ID NO: 72 | 0.02 | 0.02 | 0.02 | 0.01 |
| AT5G48810 | SEQ ID NO: 72 | 0.02 | 0.03 | 0.03 | 0.02 |
| AT5G19760 | SEQ ID NO: 73 | 0.02 | 0.03 | 0.03 | 0.03 |
| AT5G19760 | SEQ ID NO: 73 | 0.02 | 0.03 | 0.03 | 0.02 |

TABLE 12-continued

| Gene | Promoter Sequence (SEQ ID NO) | Maturation Zone | | | |
|---|---|---|---|---|---|
| | | Epidermis | Cortex | Endodermis | Stele |
| AT5G02960 | SEQ ID NO: 75 | 0.03 | 0.04 | 0.05 | 0.14 |
| AT5G02960 | SEQ ID NO: 75 | 0.06 | 0.06 | 0.07 | 0.14 |
| AT2G33040 | SEQ ID NO: 81 | 0.01 | 0.01 | 0.02 | 0.02 |
| AT2G33040 | SEQ ID NO: 81 | 0.02 | 0.01 | 0.02 | 0.02 |
| AT5G14030 | SEQ ID NO: 82 | 0.02 | 0.02 | 0.02 | 0.03 |
| AT5G14030 | SEQ ID NO: 82 | 0.02 | 0.02 | 0.02 | 0.04 |
| Os02g02130 | SEQ ID NO: 102 | 0.01 | 0.01 | 0.02 | 0.02 |
| Os02g02130 | SEQ ID NO: 102 | ***0.01*** | 0.01 | 0.01 | 0.01 |
| Os05g01820 | SEQ ID NO: 104 | 0.01 | 0.01 | 0.01 | 0.02 |
| Os05g01820 | SEQ ID NO: 104 | 0.01 | 0.02 | 0.04 | 0.05 |
| Os03g21940 | SEQ ID NO: 107 | 0.02 | 0.01 | 0.02 | 0.03 |
| Os03g21940 | SEQ ID NO: 107 | ***0.01*** | ***0.00*** | ***0.00*** | 0.01 |
| Os02g52290 | SEQ ID NO: 109 | ***0.02*** | ***0.02*** | ***0.02*** | ***0.02*** |
| Os02g52290 | SEQ ID NO: 109 | 0.01 | 0.01 | 0.01 | 0.01 |
| Os05g47980 | SEQ ID NO: 110 | 0.01 | 0.01 | 0.01 | 0.01 |
| Os05g47980 | SEQ ID NO: 110 | 0.01 | 0.01 | 0.01 | 0.01 |
| Os11g11390 | SEQ ID NO: 111 | 0.02 | 0.02 | 0.02 | 0.04 |
| Os11g11390 | SEQ ID NO: 111 | 0.03 | 0.02 | 0.03 | 0.07 |
| Os11g47760 | SEQ ID NO: 112 | 0.02 | 0.02 | 0.02 | 0.04 |
| Os11g47760 | SEQ ID NO: 112 | 0.05 | 0.05 | 0.07 | 0.14 |

Example 11

Expression Testing of Regulatory Polynucleotides in Aerial Tissue of Stably Transformed *Arabidopsis*

Expression of GFP in aerial tissue of stably transformed *Arabidopsis* was assessed by qRT-PCR in two representative lines of some of the regulatory polynucleotides that were demonstrated to confer significant expression in all 14 tissue-zone ROIs of the root. T2 seeds from each line were grown on MS agar plates. After 4 days the segregating seedlings were screened for GFP fluorescence to identify those that carried the transgene. The GFP positive seedlings were grown an additional 7 days after which the aerial portions of approximately 10 GFP positive plants were collected in triplicate for RNA extraction and cDNA synthesis. Tissue was homogenized in liquid nitrogen via bead milling and total RNA was extracted using the Allprep DNA/RNA kit (Qiagen). cDNA was generated from total RNA using the Superscript VILO cDNA synthesis kit (Invitrogen) per the manufacturer's instructions. Multiplex qPCR TaqMan assays were conducted using either the CFX96 Real-Time PCR Detection System or the iCycler iQ Real-Time PCR Detection System (both instruments are from Bio-Rad Laboratories) with primers and probes specific for GFP and the "housekeeping" gene UBC9. Three technical qRT-PCR replicates were performed on each biological replicate, and data was processed using CFX Manager software (Bio-Rad).

To determine relative GFP expression level, PCR reaction efficiency was calculated using LinRegPCR software (Ruijter) and verified using a standard curve based method. Ct and baseline threshold values were obtained from the CFX Manager software. Data analysis was performed using the statistics package R, available at the R Project for Statistical Computing. After correcting the Ct values for reaction efficiency, the relative GFP expression was calculated by subtracting the Ct of the UBC control from that of GFP, followed by averaging across all replicates. To assess statistical significance of the data, the relative GFP expression of each line was compared to that determined from non-transgenic *Arabidopsis* ecotype Columbia seedlings using a one-tailed Welch's t-test. All statistical analysis was performed on the corrected Ct values, but these values were exponentiated to a linear expression scale for presentation. To normalize the linear expression scale, the data was expressed relative to a 35S-promoter control that was included in all experiments. The 35S-promoter control value was set to 100 on this scale.

Aerial expression data for regulatory polynucleotides that drove constitutive expression in *Arabidopsis* roots is shown in Table 13. All expression measurements were statistically significant ($p<0.01$). These data show that regulatory polynucleotides that drove constitutive GFP expression in *Arabidopsis* roots also drove GFP expression in *Arabidopsis* aerial tissue.

TABLE 13

| Gene | Promoter Sequence | Relative Expression |
|---|---|---|
| AT1G02780 | SEQ ID NO: 1 | 0.8 |
| AT1G02780 | SEQ ID NO: 1 | 7.4 |
| AT1G43170 | SEQ ID NO: 3 | 8.4 |
| AT1G43170 | SEQ ID NO: 3 | 18.5 |
| AT1G67430 | SEQ ID NO: 4 | 2.2 |
| AT1G67430 | SEQ ID NO: 4 | 1.0 |
| AT4G00860 | SEQ ID NO: 8 | 4.1 |
| AT4G00860 | SEQ ID NO: 8 | 11.7 |
| AT1G67350 | SEQ ID NO: 12 | 17.3 |
| AT1G67350 | SEQ ID NO: 12 | 5.9 |
| AT1G02780 | SEQ ID NO: 16 | 57.1 |
| AT1G02780 | SEQ ID NO: 16 | 40.4 |
| AT5G08690 | SEQ ID NO: 17 | 0.2 |
| AT5G08690 | SEQ ID NO: 17 | 4.6 |
| AT1G67430 | SEQ ID NO: 18 | 13.4 |
| AT1G67430 | SEQ ID NO: 18 | 6.3 |
| AT2G31490 | SEQ ID NO: 20 | 1.2 |
| AT2G31490 | SEQ ID NO: 20 | 4.7 |
| AT3G01280 | SEQ ID NO: 21 | 14.8 |
| AT3G01280 | SEQ ID NO: 21 | 80.4 |
| Os02g02130 | SEQ ID NO: 102 | 2.1 |
| Os02g02130 | SEQ ID NO: 102 | 0.5 |
| Os03g21940 | SEQ ID NO: 107 | 46.0 |
| Os03g21940 | SEQ ID NO: 107 | 9.5 |
| Os05g47980 | SEQ ID NO: 110 | 0.8 |
| Os05g47980 | SEQ ID NO: 110 | 2.0 |
| Os11g11390 | SEQ ID NO: 111 | 7.9 |
| Os11g11390 | SEQ ID NO: 111 | 22.3 |
| Os11g47760 | SEQ ID NO: 112 | 6.7 |
| Os11g47760 | SEQ ID NO: 112 | 12.2 |

Example 12

Expression Testing of Regulatory Polynucleotides in Stably Transformed Corn

Representative regulatory polynucleotides were tested for their ability to drive GUS expression in corn. Regulatory elements represented by SEQ ID NOS: 14, 15, 20, 87-94, 96-100, 102-104, 106-112, 114, and 118 were sub-cloned into a plant transformation vector containing a right border region from *Agrobacterium tumefaciens*, a first transgene cassette to test the regulatory or chimeric regulatory element comprised of, a regulatory or chimeric regulatory element, operably linked to a coding sequence for β-glucuronidase (GUS), operably linked to the 3' termination region from the rice lipid transfer protein gene (Genbank accession, AY466108); a second transgene selection cassette used for selection of transformed plant cells that conferred resistance to the herbicide glyphosate, driven by the rice Actin 1 promoter (McElroy et. al., 1990, Plant Cell, 2: 163-171) and a left border region from *A. tumefaciens*. The resulting constructs were introduced into corn by *agrobacterium* mediated transformation and RO transformants were selected by glyphosate resistance. GUS expression in different tissues of RO plants at various stages of development was quantified with an enzyme activity assay. All tissue samples were collected in a 96-well Nunc box and immediately stored at −70° C. until subjected to further processing. To extract protein from the samples, frozen tissues were subjected to lyophilyzation for sixteen (16) hours. The lyophilized tissues were processed in a mega-grinder with steel beads to powder the tissue. Total soluble protein was extracted from the tissue powder in 100 mM protein extraction buffer. Specifically, about 800 μl of protein extraction buffer was added to the tissue powder and dissolved gently on a shaker. For protein from embryo and cotyledon, after adding the buffer, the extraction buffer containing dissolved protein was incubated in a water bath at 42° C. for fifteen (15) minutes. After completely dissolving the tissue powder, the extraction buffer containing dissolved protein was centrifuged using either Heraeus multifuge 3 S—R (5800 rpm) or Eppendorf centrifuge 5810R (4000 rpm) for 10 min. After centrifugation, 60 μl of the supernatant was transferred to 96 well nunc plates and sealed using a plate mate. The protein extract in the sealed 96 well nunc plates was stored at −70° C. until subjected to further processing.

Protein concentration of the plant extracts was determined using a BSA standard according to the dye-binding method of Bradford (1976) using a kit available from Bio-Rad Laboratories following the manufacturer's instructions. The protein concentration may have been adjusted to 0.4 to 0.8 μg/μl by adding protein extraction buffer.

A fluorometric assay using 4-methylumbelliferyl-beta-D-glucuronide (MUG) as a substrate was used to quantify GUS activity in the plant protein extracts in accordance with Jefferson et al., *EMBO J.,* 6: 3901-3907 (1987). The fluorogenic reaction was carried out in 1 mM MUG extraction buffer using a reaction volume of 50 μl. The reaction was set up in the 96 well black Nunc micro plates.

Approximately 1 to 2 μg (5 μl) of total protein was taken in 20 μl of protein extraction buffer to which 25 μl of 2 mM MUG was added and incubated at 37° C. for 1 hour after sealing the plate with aluminum foil. The reaction was stopped by adding 350 μl of 0.2 M sodium carbonate buffer. Fluorescence was measured with excitation at 365 nm, emission at 445 nm using Fluoromax-3 with Micromax Reader (Jobin—Yvon—Spex, Horiba group), with slit width set at Excitation 2 nm and Emission 3 nm. The fluorescence data (counts/sec) obtained from the Fluoromax-3 reader was processed using the 4-MU standard curve and GUS activity is expressed as pmol of 4-MU/ng protein/hour. The fluorometer was calibrated with freshly prepared MU standard of 10 nM, 320 nM and enzyme blank in the same buffer. Data were pooled for a given tissue across plant lines and replications with the range, mean and standard error (SE) then calculated. Table 14 shows mean GUS activity values associated with representative regulatory polynucleotides in different tissues of RO corn plants at various stages of development. These data demonstrate that some of the regulatory polynucleotides listed in Table 14 drove constitutive expression in stably transformed corn plants.

TABLE 14

| Gene | Promoter Sequence | R0 Corn GUS Expression Data V3-root | V7-root | V3-leaf | V7-leaf | VT-leaf | VT-anther | VT-silk | 21 DAP embryo | 21 DAP-endosperm | |
|---|---|---|---|---|---|---|---|---|---|---|---|
| AT1G76200 | SEQ ID NO: 14 | 7.3 | 0 | 0 | 13.2 | 0 | 0 | 15.5 | 4.1 | 1.8 | 3.4 |
| AT1G78380 | SEQ ID NO: 15 | 6.9 | 0 | 1.6 | 5.9 | 0 | 5.6 | 9.9 | 0 | 2.5 | 4.1 |
| AT2G31490 | SEQ ID NO: 20 | 0 | 0 | 0 | 7.7 | 0 | 0 | 13.9 | 0 | 0 | 0 |
| Os03g21940 | SEQ ID NO: 87 | 0.0 | 0.0 | 0.0 | 34.0 | 30.3 | 78.6 | 83.9 | 157.1 | 23.5 | 21.3 |
| Os04g35300 | SEQ ID NO: 88 | 0.0 | 0.0 | 0.0 | 0.0 | 0.0 | 0.0 | 0.0 | 0.0 | 0.0 | 0.0 |
| Os05g45950 | SEQ ID NO: 89 | 0.0 | 0.0 | 0.0 | 0.0 | 0.0 | 0.0 | 0.0 | 0.0 | 0.0 | 0.0 |
| Os11g47760 | SEQ ID NO: 90 | 0.0 | 0.0 | 0.0 | 21.0 | 0.0 | 18.1 | 13.5 | 0.0 | 4.2 | 4.2 |
| Os02g02130 | SEQ ID NO: 91 | 0.0 | 0.0 | 0.0 | 18.9 | 7.6 | 21.1 | 42.0 | 22.3 | 1.7 | 18.5 |
| Os03g56190 | SEQ ID NO: 92 | 0.0 | 0.0 | 0.0 | 0.0 | 11.1 | 0.0 | 0.0 | 8.8 | 10.6 | 15.6 |
| Os12g07010 | SEQ ID NO: 114 | 11.4 | 0.0 | 24.0 | 84.5 | 25.6 | 42.6 | 220.4 | 35.1 | 55.6 | 29.4 |
| Os05g47980 | SEQ ID NO: 93 | 0.0 | 0.0 | 0.0 | 0.0 | 0.0 | 0.0 | 0.0 | 0.0 | 14.7 | 13.1 |
| Os01g46610 | SEQ ID NO: 94 | 45.5 | 0.0 | 28.1 | 48.1 | 18.4 | 19.9 | 51.3 | 13.7 | 72.2 | 121.0 |
| Os03g45280 | SEQ ID NO: 118 | 16.7 | 0.0 | 0.0 | 19.7 | 0.0 | 0.0 | 69.1 | 16.9 | 0.0 | 0.0 |
| Os04g28180 | SEQ ID NO: 96 | 0.0 | 0.0 | 0.0 | 25.2 | 16.6 | 11.5 | 52.8 | 0.0 | 13.7 | 15.1 |
| Os05g01820 | SEQ ID NO: 97 | 0.0 | 0.0 | 0.0 | 17.8 | 0.0 | 15.2 | 0.0 | 90.4 | 0.0 | 0.0 |
| Os07g46750 | SEQ ID NO: 98 | 0.0 | 0.0 | 17.2 | 19.7 | 0.0 | 20.3 | 174.4 | 11.5 | 11.1 | 19.2 |
| Os11g11390 | SEQ ID NO: 99 | 27.2 | 0.0 | 0.0 | 23.4 | 7.8 | 12.5 | 20.9 | 2.8 | 0.0 | 0.1 |
| Os03g56190 | SEQ ID NO: 100 | 11.2 | 0.0 | 0.0 | 25.0 | 12.1 | 0.0 | 16.4 | 0.0 | 10.1 | 17.6 |
| Os02g02130 | SEQ ID NO: 102 | 11.2 | 15.2 | 1.2 | 37.1 | 26.2 | 14.7 | 41.2 | 16.6 | 34.4 | 33.4 |
| Os01g46610 | SEQ ID NO: 103 | 87.6 | 10.6 | 11.5 | 10.5 | 94.4 | 18.5 | 89.8 | 36.9 | 59.8 | 38.6 |
| Os05g01820 | SEQ ID NO: 104 | 13.3 | 1.2 | 1.4 | 75.0 | 0.0 | 63.0 | 127.4 | 15.3 | ND | ND |
| Os04g28180 | SEQ ID NO: 106 | 0.0 | 10.3 | 29.4 | 40.1 | 41.6 | 53.4 | 133.9 | 19.9 | 86.5 | 45.1 |
| Os03g21940 | SEQ ID NO: 107 | 12.7 | 9.7 | 6.2 | 63.8 | 44.2 | 32.0 | 159.0 | 92.8 | 122.7 | 39.7 |
| Os05g45950 | SEQ ID NO: 108 | 43.1 | 0.0 | 0.0 | 29.6 | 12.3 | 14.0 | 17.0 | 16.9 | 0.0 | 12.5 |
| Os02g52290 | SEQ ID NO: 109 | 0.0 | 0.0 | 27.0 | 35.0 | 29.2 | 32.5 | 32.0 | 24.3 | 35.6 | 21.4 |
| Os05g47980 | SEQ ID NO: 110 | 0.0 | 0.0 | 0.0 | 15.7 | 18.0 | 21.9 | 118.2 | 79.1 | 36.1 | 27.2 |
| Os11g11390 | SEQ ID NO: 111 | 3.4 | ND | 4.5 | 47.3 | 59.0 | 41.7 | 460.4 | 65.9 | 93.7 | 81.0 |
| Os11g47760 | SEQ ID NO: 112 | 31.2 | 93.7 | 81.0 | 48.9 | 46.7 | 100.9 | 481.6 | 301.4 | 170.2 | 155.0 |

While the invention has been described in detail and with reference to specific embodiments thereof, it will be apparent to one skilled in the art that various changes and modifications can be made without departing from the spirit and scope of the invention.

The invention claimed is:

1. A polynucleotide molecule comprising SEQ ID NO: 112 operably linked to a heterologous transcribable polynucleotide molecule.

2. The polynucleotide molecule of claim 1, wherein the polynucleotide molecule is capable of regulating constitutive transcription.

3. The polynucleotide molecule of claim 1, wherein the heterologous transcribable polynucleotide molecule encodes a protein of agronomic interest.

4. The polynucleotide molecule of claim 1, wherein the heterologous transcribable polynucleotide molecule is operably linked to a 3' transcription termination polynucleotide molecule.

5. A transgenic host cell comprising the polynucleotide molecule of claim 1.

6. The transgenic host cell of claim 5, wherein the host cell is a plant cell.

7. A transgenic plant stably transformed with the polynucleotide molecule of claim 1.

8. The transgenic plant of claim 7, wherein the plant is selected from the group consisting of a monocotyledonous and a dicotyledonous plant.

9. The transgenic plant of claim 8, wherein the plant is a monocotyledonous plant selected from the group consisting of wheat, corn, rice, turf grass, millet, sorghum, switchgrass, miscanthus, sugarcane, and Brachypodium.

10. The transgenic plant of claim 8, wherein the plant is a dicotyledonous plant selected from the group consisting of soybean, cotton, canola, and potato.

11. A seed produced by the transgenic plant of claim 7, wherein the seed comprises the polynucleotide molecule.

12. A method of directing expression of a transcribable polynucleotide molecule in a host cell comprising:

(a) introducing the polynucleotide molecule of claim 1 into a host cell to produce a transgenic host cell; and (b) selecting a transgenic host cell exhibiting expression of the heterologous transcribable polynucleotide molecule.

13. The method of claim 12, wherein the heterologous transcribable polynucleotide molecule is selected from the group consisting of a coding sequence and a functional RNA.

14. The method of claim 12, wherein the host cell is a plant cell.

15. The method of claim 14, further comprising regenerating a plant comprising the introduced polynucleotide molecule from the cell.

16. A method of directing expression of a transcribable polynucleotide molecule in a plant comprising:

(a) introducing the polynucleotide molecule of claim 1 into a plant cell;

(b) regenerating a plant from the plant cell; and (c) selecting a transgenic plant exhibiting expression of the heterologous transcribable polynucleotide molecule.

17. The method of claim 16, wherein the heterologous transcribable polynucleotide molecule is selected from the group consisting of a coding sequence and a functional RNA.

* * * * *

SEQUENCE LISTING

```
<160> NUMBER OF SEQ ID NOS: 213

<210> SEQ ID NO 1
<211> LENGTH: 999
<212> TYPE: DNA
```

-continued

<213> ORGANISM: Arabidopsis thaliana

<400> SEQUENCE: 1
tttctaagtg gcaaaatatc tctttcataa aaaaaaaagg aaagaataat aaataaaaat 60
atctctttca ttctaacttg gcattaaaat ttagcaaaaa ctatttgtgg aacttgaaaa 120
aaatattact agctcagact taaacttaaa tagtaacaag catattaaaa gtcatgctaa 180
ctgagatatt gatttcctca tctcaagaaa ctatcttatg aatctgtttc cgattatttt 240
agtttcccat caatcatctt taatttctag gaagtttgat tttttgaaaa tttctccacc 300
tgcttaaatt tcattacaat ttttaatctt agataaacaa ctgtaattta tgcaaaatga 360
actgattata taagtcgtta tgaatattta tattttttaa aaacatttca gcaaaactga 420
tatacttttt tttttttttt ttttgcaagc aaataaacaa acttccttga ataaaacgtg 480
aaaaataata agagtcttta aagataaacg ttgttcatat acattacgtc atataatata 540
tataacaatt aagacaatac aaacatatat acaattctca ttgggttgaa acattataaa 600
gataagataa acatctgtat atatacattg gtatacaata tttttcataa attttttttt 660
ctctaatcga cagttatata tatacagaac cataattttt aaagcatgct ttccaatgcg 720
tttttttttt tttttttttt ttttgtaaac caaagccgtg tttctaaacc tcaatttata 780
aatttggtgt agcttttcaa ccttgatgaa attattacat agaatcattc gttaaaagac 840
ttataattgg gtttagaaaa gcccatttta aatttaaagc ccaatatact gctcgaaaag 900
gaggaaaccc tagaaacatt gtggtatata aattcttttc gtctcgttcg ctaatcagtt 960
ctccgccaca ccaatctcca gaaaagggga gaagcaaaa 999

<210> SEQ ID NO 2
<211> LENGTH: 600
<212> TYPE: DNA
<213> ORGANISM: Arabidopsis thaliana

<400> SEQUENCE: 2
cgtttacatt ctcatgatgc atctaaaagt agtgaaaatg tcagactgct tgtagtataa 60
attgctacca taacggagac ttgactaatc gtttactata tcagccgcta actagttggg 120
atatttttct gaaaatagtt tgataaatat gtaaaaatca cgatttcacc atcacattcg 180
attactcatt catgactaaa ataaaggatg aaatagctaa atttatgcga ctaatcatca 240
agggaaaaaa acgattttct cattttaggc gtggaaagaa aaatgtgtta ttaaacgacg 300
ccgtttagtt gccacgtaat aaatgagaat aaatttcttg gtgagtgggg aataaatata 360
tggacggctg tggataagga atactgaagc aagcgagtct ccatccaacg gctgataaaa 420
ttatgcttga taaacaggaa aactcttctt tctctgataa tattcggaaa taaaaaacat 480
tttagggttt tcctcagtct ctctctctta tagacgccaa ccacgttttc cagctcttgt 540
tctttcgatt ctcagagaag acttttcaga acatcctcca actttctcag ataagcaaca 600

<210> SEQ ID NO 3
<211> LENGTH: 1200
<212> TYPE: DNA
<213> ORGANISM: Arabidopsis thaliana

<400> SEQUENCE: 3
catgagcgga gtaagaggtg ttgtactaga ctaaagatta gtttagcgat ttagaattag 60
caaatagtgt taaaaatgac acaaagaaaa attttgaatg tataatctaa tacatgattc 120
tcaagcctct aaatgagaaa tattaaatct agattaagtt taaatatata aaatttagct 180

```
taaatctaaa tttcaaaatg ataggaacta ctataaaatc atatagtaac aagatacaaa    240

aaaacatcca tgtgttacct taagttatat ttattccctt tagtaaccaa caaattttaa    300

ctttctttca cgacaaaact tttgccgtct acaattcaca cacacttcca actttgaagc    360

ttacatacaa tacggtggca gcagtaacac acaccattat actacaaaca tcgataaatt    420

tttatcaata accatatcga tcatttgaca aaaccaccca cggagtaacc atatcattat    480

aagtaaacat aatgaaattt ttgcttcaag tgaactgtga acatgtgagt gtgttatcgg    540

atttagctgt tgtcttttct ttttatacga aacaaaaaat aaataaaacc tttatcaaat    600

ttgtacaaac ctctgggctt tatttaggcc caataacaaa attcggccca tatttgagaa    660

ttcacaaaac ctagatactc ttactataaa ttggaacatc attgatctaa tacaattaat    720

tactgtgtta atattattta tactcaatct gaaatgtctt tttttagctg tccaccagtt    780

tccaatcttt gaaatacgaa acaaaaaata aataaaagta taaaaccttt atctaatttg    840

taaaaacatt tgttgggctt taggcccaaa acaaaagtcg gcccatattt gagtgttcac    900

aaaacctaga tactcttact ataaattcaa actagggttt taaagctcat ttctctcttg    960

cagtcctcat cgttggagct tagaagccgt cggcacaagg ttcgtctttc tctcatccct   1020

ttcctcttcc tttgcgtgaa ttcaccagaa aatgtatatc taccttagcg agtctgtcta   1080

gtttagcgaa tctaggataa tctccggaag acacttttga atcatcactg tttttgatct   1140

ctgtttcttt ctctaattgt gttgttgtat tactgttgat gtagaagaag aagaagaaga   1200
```

<210> SEQ ID NO 4
<211> LENGTH: 1779
<212> TYPE: DNA
<213> ORGANISM: Arabidopsis thaliana

<400> SEQUENCE: 4

```
tgggaaagtt tttttttttt tgacatcgga accgcatact ctatttatac ctaaatcata     60

ctaacatgag caagtcttaa gtacattttc tttgttgata tagtaattgt gtacatttac    120

ttggttcttt gataatttat aatcttatac tttgattggt gcaactatag tcttatatcc    180

ttaatttaac tttatcctta atttaacttc atgatcaaaa gatatagtct tgttttttgt    240

tttgttgaga agtttcatta gcattattgt ctaccgagag taataccaca aattgatagt    300

ttctctgcat ttttaagaga ataagctaaa taacggacct aaatacaagt ggtccttaca    360

attgcaattt gcaaatgaaa aaatttaaaa gagtaagcta aacaaccgta ctgacctaaa    420

taacaaacac atgaaaaacc acataaataa caaacacatg aaaaaccaat agaagtgtct    480

gttacaatta caaagtccac gtacatgcca cgaggtaatg aataagtcta attgcaacaa    540

aataaataat attgtttcat ataaataatt tttcaaaata ttgtttttat ttttttcgtt    600

atcttttgga ctcaaatatg tgacaagagt aagactctat aaacgacagc tattttatcg    660

tggtgcgcca tcaaataatg tgtcctatca tttctaagtt gagccacgaa ggtcaacgtt    720

tccgatgcat accaccaaaa ctcctccctc gtggtgcacc atcaaataat cgtcaatcca    780

ctcgttaata tgtgtgatga tacgcttatc agcgatatca gtagatgttg aatcaactct    840

tcaggtttca atgatatcga tagtatactt agctagtttc tcccccatga aatcgataga    900

gcttcctccc aaggtattca agatcttatt ggcttctaca tatgaagcaa tcattactca    960

tgtagcaaac ttgttaatct tctatatttt cattacatat aatattttac gtacaagtaa   1020

gtcaaatgac atgacatgac atatgatata actgagtaag taagaaatta cgtataacaa   1080
```

-continued

```
ttaagtcaaa tgacatagta accattcgtg attgttgtct catatttata tatataaaac   1140
aaaaaatgaa gttttaagca aatgatctac aactaaaaca acatactcca ccaatatata   1200
caaaatacgt acactttttt ttgataagta agtagaattc tattgaacct gatgagagtt   1260
gagcataact ctattcttag acccgaaaac tactcaccat gtttatttta gagatttaat   1320
gatggattgg acagttttta ggccatatta catagtaaca actaatttca actaaaagaa   1380
tgcaagttgg ttagtttaat acaaaacaaa atagtgaaaa ttggatctct agctcatttt   1440
ccgattaatt aacttatttt caaaaaaatt gtggttataa gaacgaatta atcaattgca   1500
tttcttataa aaaaaagtaa tgaagagaga ttttacttac ataaaataaa tacatctggc   1560
ctgatgaaac aaaaatgagt aaggatatca acctttgtaa taagtaattg ttaattacca   1620
attcatagtc ttgatgggca ttattagaaa gcccattaaa aatggacaag gcccatttaa   1680
acctaggttt cgcagggttt attgcttcac tcttatataa aaactctcgt cttcacaaat   1740
ctcacatctc ttctgcagcc gattcttcta ttagccgcc                          1779
```

<210> SEQ ID NO 5
<211> LENGTH: 754
<212> TYPE: DNA
<213> ORGANISM: Arabidopsis thaliana

<400> SEQUENCE: 5

```
ccatttggag taattgttaa cttttttttgg agaagggttg ttctattttg tgtataccaa     60
catgatcttg taataaatta attattgtaa tgtatcaatg atacagtatc atcatttgat    120
tttgagtctt tttttgacgg ttaaaacaac gatttgggac gaagttatag gccctgaatg    180
gatgctgatt ttggattcag tttttgaatt tagattttag tttatagatt ttagatttta    240
gtttcagatt tttattatta tatttttgtt tcaaaaaccc caaaaaattg gtttttggtt    300
tttgagaaaa ataacgttga ttgagtaaaa actagatttc ctaaatttta ggagaactaa    360
aaaactaaaa tcatgaatgg aaaactacaa gaaaataatt tttctaaatt gtagggaaac    420
caaaatttta aaatcttgat tggtatgaaa ataagttttt ggaaaacaaa aaccaaaaac    480
tcttacaaaa tctacaaaac attcaattca tgtatccaaa cttcttaaag ggcccaaaaa    540
ggaagaaaac attgtgaaag aaacagatat agaaatgggc ctttggtctt taaattgggc    600
ctaagccttt taattgaggc cttactaaaa gtgacgactc acatggttga atcaaatctc    660
aggtagtaaa ttgtcaaagc tgaggagaaa gaaagctttt tcggtctgaa attgaagtgc    720
gaatcgggga atctagggtt tcgagagaga gata                                754
```

<210> SEQ ID NO 6
<211> LENGTH: 1200
<212> TYPE: DNA
<213> ORGANISM: Arabidopsis thaliana

<400> SEQUENCE: 6

```
gatcaaattt ttgtaaaaaa ttacaaattt gtaaaatatc tccataaatt aataattatt     60
aatttatcga taaattaata tctctctaaa ttaaaaaaaa ttttggtcct gacattatta    120
atttatagag gttttactgt agttacaaac tgcgcatggt ttgtcaaatt ctaaaacatg    180
ctttgtttat tttgaaaata aaataaaatg atactagatg aaacaaatat aatgaaaagg    240
atatttacca attgattatt cttatatttc catatttttt tattttagct actatttttg    300
aaaacttcca ttaactcttt cactaagagc tgtgatagta cacaaaaaaa aaagctgtga    360
ttcaagtttt tctactcata aaatatgtct ttgatttttt gtagtaatta taggccgtag    420
```

```
gccaatcttt caatatcata cacgtaggca cgggctagtg ctggcccaaa ttggagatgg    480

tcttagtggt tagaaacgaa tgtttaaatt cttaattaac ttttgtaaaa caccagatag    540

tttgtaatat acgacgagat agttgaaact tatgtccaaa aaagaaacaa aagaaagaga    600

gtatgttcat atagtaatag ggaaaagaaa gaaatataac cgttggtgat tagtcattta    660

gttggatgac aaatctctct caccttcaca tggaccaacg gcttctatgt cccaccaatt    720

tgtactctca atctccttta ccttatttat tcattacacc aaagctacga cacgacatgg    780

cttttgtttt attttcatta tatttatgtt atttaatgtt acagtacata caatatttag    840

cttttatgtc atgcattggt tattagtatt ttgtattact agtaagattg aaaacggttt    900

taagaatgta ggagtgtgtt tcacaaaatt gagagtattg caattacatg agagtgttca    960

gacttcagag tattacaaac ctaacaaacc tggatattgt gatatgactg gcttttaggt   1020

tttgtaggtc tcccatttga ttataaacaa aatgtattta ttacctatat tccaaaagta   1080

cccttatgtt ccatgttctc ttcttataaa gcaacacaca agatgcaaga aatctccata   1140

actagagaga gaaactaatc tttttagtga gagagaaatc ttagagctga gctaagaaaa   1200


<210> SEQ ID NO 7
<211> LENGTH: 700
<212> TYPE: DNA
<213> ORGANISM: Arabidopsis thaliana

<400> SEQUENCE: 7

gtaagaacca aacctagctt tcaaaacatg aaataacaat aagaaacctt tttcgattga     60

acggcgaaat atatccattg aagatgttga gagtgagaat cgaagacgaa gaggtgcaat    120

tactcgcagt tttttttttt ttgtaagtta attattaatt tttgacttca ttaaagttaa    180

ttatttgctg aaaaaaaaaa aaaaaaaagt taattattta gtatcttcaa atataatatt    240

taaaaaaatc tagccatctt aatgcatttt aatgaaaatc ctacccaagt tttttaaagg    300

tcaatttaaa aagtatcagt tttgattttt aattatattc aatatttgtt aaattttgtt    360

tcatatgtta atattaaaaa cacaatctat ttcctaaaca tttatataca gatctttttt    420

aaaaaaggtt agtcaaaaac tgttggaaaa gctaatcttt ttttaacaaa aatagtaaaa    480

tactcatata cgtaactttg ggcctttctt aaatggcttt gggcctttcg taaatgggct    540

tatgggctta agtacttcaa atctgatagt atttggttta ttgcaacaaa aacaataaat    600

ggaaatagcg atctgagctg accaaccaca gtcgcggaca gagctaaaac caccatttga    660

agaaggagaa gaagaagaag acgattcggt gaaagcgaag                         700


<210> SEQ ID NO 8
<211> LENGTH: 1200
<212> TYPE: DNA
<213> ORGANISM: Arabidopsis thaliana

<400> SEQUENCE: 8

atcttatgcg tgcagaataa atattggtgt tatgtgcatt tgaagcttta ggctttagca     60

ctttctaaaa cctcgttttg agcaaagtca ttcaaaagga actcttaata tttttacaaa    120

ttgaaatagc aattgtaatt taatcagtaa aacctctata aattatcatg tttattaatt    180

tatagagaca atatttgggc taaaatatca atttgagaac ggaagaaaat tattaattta    240

atgagatatt aatttattga atattaattt atagattttt gactgtatat attctaagct    300

ttgttttaag aaaatttaat ccgtttaaaa agatttatct tcattaaccc caaaagaaat    360
```

-continued gatttgtttt agcttggcca atagtcatgt atggcccaat ctggtataaa atctcataaa 420
aagttttatc ttcattaacc caaagaaatg atttgtatta agatgggcca atagtcaagt 480
gtggcccaat taggagtaaa atctcataaa cgaaatgggc ccataatggc ccaatatttg 540
tacaccacaa tcggaaaccc cttttgggtc atttcaagtt tgacgagaaa cgtaaatcgc 600
tatttcttct attcctccct aaaaatctac caacgagatt cttctcgaaa atttcctgcg 660
cctctccgtg tctgtgaaat cgattcaggt aaatcactct tctcgaatcg atgcttgttt 720
tgtgaaatac cgattctatc agatctattt gataaatttg ttgttgttgt tagtcgtctg 780
tgtagtttat tcacctttg tttcgatttt tgggtcctca cgagatctat gaatcgttat 840
ctgaaacaaa actcgaaact agcagatgat atgttattta gcgcgattag gaagaataaa 900
acgagatttg ttggtagcag tgagtttctt agatcggttt ttttatcgat tgtgtgaaaa 960
aattcaccat tcagatgctt ttattgattt gtgtcttcta taattgaatt gaattgtttg 1020
attcagcagc ttaattatct aatggtttta tgtgattgta ttggcttgat tagggttgaa 1080
tatgccttga aacttcattt caatcccact atacactata gctataatct gatataagtt 1140
cgttttctcc ttttgtgtgg cttgattatg tttgatatat ctatgtactt caggttaagg 1200

<210> SEQ ID NO 9
<211> LENGTH: 772
<212> TYPE: DNA
<213> ORGANISM: Arabidopsis thaliana

<400> SEQUENCE: 9
aaatgctgca agtcttggta cgccaagcaa gtataattat atctaatgtc cgaaaagaca 60
agcaaaatag catcccataa ttcgaaaaat atcacgatat tcaagtattg catctacgta 120
tatactactg cagcactaca tgcattgttc attataaagt gtgttgtata tagatgactg 180
gttaagcaag tcttgcatat gatgatttat tgatctcagg ctctttgttt tatcaagcaa 240
aatagcatct cataattcga ggaaatatca ccaccatatt aaaatattgc atacaacgac 300
ggcagcacta cattgctcag gataaaatgt gttgcatatc tcggtatttt accaaaaata 360
tgttgatttt tatttgaaaa ataaaataca tactatcatt ttaatattta tcgtgtctaa 420
atgtattttt ttaaaaatta tctttatact tttctaaaga tagttaaatg aaagcaactt 480
ggaaatctta aaaccatcaa aaatatttgt gtttaataaa actttgacct tgcaaaatat 540
atttttgtta actaaaaatc tcaaccgatc ccccaaaggt caacctcatc ttttttttt 600 ttttttatcc tttagtttc tattatgata aagacccaaa taaataagcc cattattctg 660
ttttgttcaa aataagccca ttatctgagc ccaccaaaca ttggaaagtt tgagcttaga 720
ttcaggtgct gtagttaccc tagcttgcat ttcctcttcc acacacccac tc 772

<210> SEQ ID NO 10
<211> LENGTH: 710
<212> TYPE: DNA
<213> ORGANISM: Arabidopsis thaliana

<400> SEQUENCE: 10
aattctattt aaaaatccat gtcccaagta acttctcccc aaaaagaaac tcaatatttt 60
agaataaggt caaatggaat taaattccag aagatatttg ccaaaatagt gataaaaata 120
cggttaaatt ggtatatgtt tttactgaca aaaggcaaga ttcttctatt ttaagattta 180
tttctttctt tgaaatctgc taaacgttgt tagatcacac tttatgtgtc tgttttttt 240 tttgtcaatt cagcacacgt catatttgta tttttcaaag taccaaacgt ggaccaaaat 300

-continued

```
aaaatctcgt caaaaatgga aaccaaattt taatttgatt tgcacaaagc ccaatttgat    360
ttgtttaaag tcaaagccca acttgaccaa aactacccct gctcatccaa accctaagca    420
aaatatcgag ggtagtttcg tattttgttt atattgaaca caattaagta ggtgaggaac    480
ctctatttct tccgtcttct gctgatttct gagcttcgga gctatcgaaa attctgaatc    540
tgaaagggta aagatcccat ctttttccaa aaatcgataa gggaattagt atattcgttc    600
attcatcatc gttctgatga tttcgatttg aatctgtatc tagtactctg tattatcaga    660
aattttgatt agtagctttg atgtgttctt gttttgcagt ttgagtgaag              710
```

<210> SEQ ID NO 11
<211> LENGTH: 1500
<212> TYPE: DNA
<213> ORGANISM: Arabidopsis thaliana

<400> SEQUENCE: 11

```
taggaaaaaa gtttatattc ctacccaaac tttcggcacc agagacaaat taggtttgtt     60
cagaaaatca gtcgctcatc gacagactta acaccacaaa atcatcagaa tttctttggg    120
acaaaatgga aaatgttctt cacggctcca cctaccaaaa tttcgatatc aagctcaaaa    180
gcatacacaa actataacta attccatagt tacgtaatct taacttcgaa ttcaacaaca    240
catgcatgca tcgactgaat cttcaacaaa tgcaatcaaa cacacaaaat tgctaccaaa    300
aaaatatgat ttttttttta tgatttcaat tttcatccgg cacttagtcc aaaacttttt    360
ttgtgtgtca acatttttta aaaaaatctt taaacggata tctgatctaa gagcatgttc    420
ataggtgata cttacaaaat atttttaaga aattttttag tattatttat aatgtttgtt    480
taataaatat atataagatt ttttgctttt atcaaatgtg accaatcaga agaaaccacg    540
tcagatgata ctgatatgac aaatatgata ctgatcaaac atattctaat tgctttacta    600
atataaaaat aatttttgga cttgtgatac tctaaaaata tcacccatat acatggtcta    660
atatatggat cgtaaaaaac tcatatataa tattaataag tagtagaaga gcgtagacca    720
tgtcctgggt cgtcgtccaa atgaccacaa gaagatttca aaacagagga aaatatttct    780
cattaaataa gttttcctga cgcataagat aacattatta caagattcag aaaaagaaag    840
gtgaaaggat aatgtttctc ctactatata agatgtgtac atctgaaaaa atatgaatat    900
atttgtaacg tttgactgtt attacatgat taatacgata taaatattaa catttttttt    960
caaaataaaa gtaatatagt aaggaaatga aaagaggcat gaagcatgcc tctttttttg   1020
gtcggctgcc gtttacaatt gccaattgcg atagttactc ttcttgcgtg tacgactttt   1080
gttttttttt acatattcgc caataatttg acgttttcta ttagtttgtt tgatactctg   1140
ttgtcttgct aaaactcaat aaaacattaa attactttct tgaatgaagc tggaacaaat   1200
ctaacataaa tagaaaatga tgggcaagtt gatgttattc gtaaatttat ttagattata   1260
ttatataaaa agcaatccaa ttatatatct catatataca atttcttatc ttactttgtc   1320
aatgtcatat acgtaactaa aacttgcgga aatagaaaat gccacgtgta tggtggacat   1380
aatccgaatc tctctctttc ttctataaat agtggccatt cccattggtt gaaatcacaa   1440
aagcatcata agaagaagaa gaaactacaa tagttaatca atcaaagaga agtaagagaa   1500
```

<210> SEQ ID NO 12
<211> LENGTH: 1190
<212> TYPE: DNA
<213> ORGANISM: Arabidopsis thaliana -continued

<400> SEQUENCE: 12
attgacacat ttaataagta gctttcgata gcaaacaaat ctattggaac tttctgttca 60
tttaccttct ttttggggtc agaaaataaa tgtatcagct taattgaact ttgaacgata 120
aaaagtagat tcatggtgag ggtggggtgc tacaaagagg tccagcccat ttattgctag 180
ttgttagaat ttgccagctt ttggttcaaa atgatataca cacatatgta gttgttgcat 240
attaagtaga aagagaaatt caatgttgtg aattttcaaa aaagttgtaa taatatatga 300
tactcgatcc ttattaacat gtaatattag gccttggctg aaccggattg ttcggatcgg 360
tttgtttggt ttgggagaaa ttcggttttc aaaaaatctc agatccgtat taaccttttc 420
cggaatagat ccatattaac ctttacccga ctcaaaaatt atatatacct tttttttaaa 480
gacggatact aaatggataa cggatcaaat acttgtaact ggtatatcag tgcccagcag 540
tctagcacta gtttagttgt agccatatat ttgacagctg aataggtttg gtcaaatttt 600
ggccacggca ttccgtaaag ggaggcataa acagggtgga gtttttgtta cagaaaacgt 660
cttgtttctt tattctcagt acaaaacaac acgcagtttc tattcctatc agatttttgt 720
tttcttcttc atcaacactc gctctgcgct gcgttcgaat ccagaactct ctgaccatcc 780
caaagcaaaa gcttcaccga tcttcctcgt ttggtctcga atattaaggt aagttccatt 840
ttattgtatg gatcctagaa acttaaccta gatctagatt aagaacccaa tttgtggaaa 900
tcaatgcgtc gatttgatag aaaccctaat ttctgggtga tttccatggt taagctgttg 960
gcttgcatta agtaaataac gagatggttt cagaaattta ggtcacagag tccaatttat 1020
ggattcaatg cttcgatttg attttaaaaa accaatcttc gggttaaatt gaatgtaaga 1080
agtgtgtgtt tttgagtttg cagtgaaata tgggtttcat aatggaattc gcggagaatt 1140
tggtgttaag gttaatggag aatccagagg aacgagacag gaaagcgagg 1190

<210> SEQ ID NO 13
<211> LENGTH: 1500
<212> TYPE: DNA
<213> ORGANISM: Arabidopsis thaliana

<400> SEQUENCE: 13
agtcaactat tttgtgtata ttgtaagatg tatcatgtta tgacatgagt atgttgctac 60
gtgtcgtgag atatcgaacc caacgcagat atgagtatgt tgagctagtt tcttcttatg 120
aaacaatcat atatgtctat aatgaataga tcacattatc tgcctgaaaa aaatcccgta 180
tattactcga cgaaatataa atacccaatg tagctgattt tgctttctct ggtgacatat 240
ccaatttggc taaatttgtt aactagtcta ttataggttt ataatagatc tagctatgtt 300
aaagatacta aagcatcagt tacataaatt tttggcgcga gtttatatct tttggaatta 360
aaaataagag aatttaaaaa taagaagatc attttgtttg gccacaggag ttctgaaagg 420
tcaggtatga ttttttttctt gctcgctctt atgattttgt ttttattaat gggttttcaa 480
ataagaaaaa ctgtttttcg aagcccggtt cagatccatt gttttttgta aaatataggc 540
ccaattcacc ataagtccat gaccaaaaca aaaataagat agaaccaata ctgaaccagg 600
atcttctctc gctttcgtga tcaatgtcgc caagcttctc gagatcatgt ggtcacgtca 660
attgtataaa tacaattatt gacgtaacac aatctctaca gttccatcga aatatctcga 720
aaatttccag ttaattctgg taacgtgaac gtatcttcca cctcttcaac ctacacagct 780
ttctagaaat ttggctcgct tttctaagtc ctctgtattt ttttgcacgt ttttcaacta 840
agtttcaata tgaatcattt cttctataaa taaatgatat tttcatcagg taatgataca 900
ttgtgccgaa ataaaacgtc aatactcatt agtcaaatta attgttcaca taatttaaaa 960
ctgtgttaat ccatccagtt attttcttac aacaaaataa tcttttccat caacttttaa 1020
aataattaaa cgcagtgcta agaaatctaa aatcttgatt tagaaatcca ttatggtttc 1080
tggtcaactg aaatccataa tttcctttaa catccaaaat ccaaatttgc tactatgata 1140
atagatttca gacgattttt tttctttttt caatcataga gtccacacga atatttgcaa 1200
gttactatat aaaacactat aatggtcaac agataaaaaa aaggcgaatg aagatatgtt 1260
acgtaaaaag aaaatactgt aattataaat tattacttta aaaagcttta aaatctggcc 1320
acatgttttt aaagagtggt gtgacgtaac gactagagtc agcacaatcc attattgtat 1380
cataaatatt ctcatctata aattacctaa acccttacag gtagtgtccc aaccaaacaa 1440
atcgagaaag acgaacactt acaaaaaaaa atctctttgt gagctttagc gatcgtaaca 1500

<210> SEQ ID NO 14
<211> LENGTH: 1075
<212> TYPE: DNA
<213> ORGANISM: Arabidopsis thaliana

<400> SEQUENCE: 14
ccatttggag taattgttaa cttttttgg agaagggttg ttctattttg tgtataccaa 60
catgatcttg taataaatta attattgtaa tgtatcaatg atacagtatc atcatttgat 120
tttgagtctt tttttgacgg ttaaaacaac gatttgggac gaagttatag gccctgaatg 180
gatgctgatt ttggattcag tttttgaatt tagattttag tttatagatt ttagatttta 240
gtttcagatt tttattatta tatttttgtt tcaaaaaccc caaaaaattg gtttttggtt 300
tttgagaaaa ataacgttga ttgagtaaaa actagatttc ctaaatttta ggagaactaa 360
aaaactaaaa tcatgaatgg aaaactacaa gaaaataatt tttctaaatt gtagggaaac 420
caaaatttta aaatcttgat tggtatgaaa ataagttttt ggaaaacaaa aaccaaaaac 480
tcttacaaaa tctacaaaac attcaattca tgtatccaaa cttcttaaag ggcccaaaaa 540
ggaagaaaac attgtgaaag aaacagatat agaaatgggc ctttggtctt taaattgggc 600
ctaagccttt taattgaggc cttactaaaa gtgacgactc acatggttga atcaaatctc 660
aggtagtaaa ttgtcaaagc tgaggagaaa gaaagctttt tcggtctgaa attgaagtgc 720
gaatcgggga atctagggtt tcgagagaga gatacaggta catttctgat ttctctcttt 780
cacctaattc gcttttgatt ttgggaccta gctaatctcg atcgtagcta gatctcgcca 840
tggggatttt gggctaattg atcatctgag gaattttgta tatagaatcc atttgaatca 900
aaaaattgga tttgtcaaat tagtatcgga gctaatcagg tagatgttaa tttgaatcag 960
atattgctta tgtcaatttc agttcgatga gaatggttga agaagtaatc gcacataggt 1020
tttaactttc cctagcattc acatcttaaa aactcaattt ttggtatttt caggt 1075

<210> SEQ ID NO 15
<211> LENGTH: 2006
<212> TYPE: DNA
<213> ORGANISM: Arabidopsis thaliana

<400> SEQUENCE: 15
agtcaactat tttgtgtata ttgtaagatg tatcatgtta tgacatgagt atgttgctac 60
gtgtcgtgag atatcgaacc caacgcagat atgagtatgt tgagctagtt tcttcttatg 120
aaacaatcat atatgtctat aatgaataga tcacattatc tgcctgaaaa aaatcccgta 180

-continued

```
tattactcga cgaaatataa atacccaatg tagctgattt tgctttctct ggtgacatat    240
ccaatttggc taaatttgtt aactagtcta ttataggttt ataatagatc tagctatgtt    300
aaagatacta aagcatcagt tacataaatt tttggcgcga gtttatatct tttggaatta    360
aaaataagag aatttaaaaa taagaagatc attttgtttg gccacaggag ttctgaaagg    420
tcaggtatga tttttttctt gctcgctctt atgattttgt ttttattaat gggttttcaa    480
ataagaaaaa ctgtttttcg aagcccggtt cagatccatt gtttttttgta aaatataggc    540
ccaattcacc ataagtccat gaccaaaaca aaaataagat agaaccaata ctgaaccagg    600
atcttctctc gctttcgtga tcaatgtcgc caagcttctc gagatcatgt ggtcacgtca    660
attgtataaa tacaattatt gacgtaacac aatctctaca gttccatcga aatatctcga    720
aaatttccag ttaattctgg taacgtgaac gtatcttcca cctcttcaac ctacacagct    780
ttctagaaat ttggctcgct tttctaagtc ctctgtattt ttttgcacgt ttttcaacta    840
agtttcaata tgaatcattt cttctataaa taaatgatat tttcatcagg taatgataca    900
ttgtgccgaa ataaaacgtc aatactcatt agtcaaatta attgttcaca taatttaaaa    960
ctgtgttaat ccatccagtt attttcttac aacaaaataa tcttttccat caacttttaa   1020
aataattaaa cgcagtgcta agaaatctaa aatcttgatt tagaaatcca ttatggtttc   1080
tggtcaactg aaatccataa tttcctttaa catccaaaat ccaaatttgc tactatgata   1140
atagatttca gacgattttt tttctttttt caatcataga gtccacacga atatttgcaa   1200
gttactatat aaaacactat aatggtcaac agataaaaaa aaggcgaatg aagatatgtt   1260
acgtaaaaag aaaatactgt aattataaat tattacttta aaaagcttta aaatctggcc   1320
acatgttttt aaagagtggt gtgacgtaac gactagagtc agcacaatcc attattgtat   1380
cataaatatt ctcatctata aattacctaa acccttacag gtagtgtccc aaccaaacaa   1440
atcgagaaag acgaacactt acaaaaaaaa atctctttgt gagctttagc gatcgtaaca   1500
caggtatctt atttcctttg tgcccttgat tgaataatgt tgaaattgaa cttgggattt   1560
cataaaaatt gaaactttag ttgagtttgc tagtgattgg ctcaaattta gggttttgct   1620
tgtagactcg tctttgagct tgtatgggtt tgtctgatgt tataatatta cttgagtttg   1680
tagttgttag ggttagagat ctcacctcca aatttcagat ttttcttgtg gactcatctc   1740
tgagctagtc agggtttgtc ttcttagata gtttaatgtt atgttacttg tgcaatttga   1800
ggtttttaca tactagtttc gctagtagat atcatctttg agctttgttt gggttcatct   1860
tagatagttt gatgatatgt ttcttttgca atttgggggt ctctaggact ggttttgctt   1920
tgtagacatc atctttgagc tttgtttggg ttcgactgag ttctgacata gcttggtgtt   1980
atgttactct gtgcaatgtt tcaggt                                        2006
```

<210> SEQ ID NO 16
<211> LENGTH: 1345
<212> TYPE: DNA
<213> ORGANISM: Arabidopsis thaliana

<400> SEQUENCE: 16

```
tttctaagtg gcaaaatatc tctttcataa aaaaaaaagg aaagaataat aaataaaaat     60
atctctttca ttctaacttg gcattaaaat ttagcaaaaa ctatttgtgg aacttgaaaa    120
aaatattact agctcagact taaacttaaa tagtaacaag catattaaaa gtcatgctaa    180
ctgagatatt gatttcctca tctcaagaaa ctatcttatg aatctgtttc cgattatttt    240
agtttcccat caatcatctt taatttctag gaagtttgat tttttgaaaa tttctccacc    300
```

tgcttaaatt tcattacaat ttttaatctt agataaacaa ctgtaattta tgcaaaatga 360
actgattata taagtcgtta tgaatattta tattttttaa aaacatttca gcaaaactga 420
tatacttttt tttttttttt ttttgcaagc aaataaacaa acttccttga ataaaacgtg 480
aaaaataata agagtcttta aagataaacg ttgttcatat acattacgtc atataatata 540
tataacaatt aagacaatac aaacatatat acaattctca ttgggttgaa acattataaa 600
gataagataa acatctgtat atatacattg gtatacaata tttttcataa attttttttt 660
ctctaatcga cagttatata tatacagaac cataattttt aaagcatgct ttccaatgcg 720
tttttttttt tttttttttt ttttgtaaac caaagccgtg tttctaaacc tcaatttata 780
aatttggtgt agcttttcaa ccttgatgaa attattacat agaatcattc gttaaaagac 840
ttataattgg gtttagaaaa gcccatttta aatttaaagc ccaatatact gctcgaaaag 900
gaggaaaccc tagaaacatt gtggtatata aattcttttc gtctcgttcg ctaatcagtt 960
ctccgccaca ccaatctcca gaaaagggga gaagcaaaac aggtatgttg ttgctttttt 1020
cttcatcctt ttacttttat tgttgtcctg tgtttgtctg cgacggtggt agacggtctt 1080
aggtgttgaa tcactgtgtt tgtttccgat ctgaaaattt agagcttgta ggtgttgtta 1140
cggtttcatt tctctagtta taggccttgt agaactgtga tttgtctcgt gaatcaaagc 1200
tagaggattt gatttctgat attgcttctt aatagactga ggatttgaat gatgttccat 1260
ttcgagtatt gttgttatat atttgaagat ctttgtagct tcaaatatta agaatgtgat 1320
gattggtgtt gaacttattg taggt 1345

<210> SEQ ID NO 17
<211> LENGTH: 1079
<212> TYPE: DNA
<213> ORGANISM: Arabidopsis thaliana

<400> SEQUENCE: 17
aaatgctgca agtcttggta cgccaagcaa gtataattat atctaatgtc cgaaaagaca 60
agcaaaatag catcccataa ttcgaaaaat atcacgatat tcaagtattg catctacgta 120
tatactactg cagcactaca tgcattgttc attataaagt gtgttgtata tagatgactg 180
gttaagcaag tcttgcatat gatgatttat tgatctcagg ctctttgttt tatcaagcaa 240
aatagcatct cataattcga ggaaatatca ccaccatatt aaaatattgc atacaacgac 300
ggcagcacta cattgctcag gataaaatgt gttgcatatc tcggtatttt accaaaaata 360
tgttgatttt tatttgaaaa ataaaataca tactatcatt ttaatattta tcgtgtctaa 420
atgtattttt ttaaaaatta tctttatact tttctaaaga tagttaaatg aaagcaactt 480
ggaaatctta aaaccatcaa aaatatttgt gtttaataaa actttgacct tgcaaaatat 540
atttttgtta actaaaaatc tcaaccgatc ccccaaaggt caacctcatc tttttttttt 600
ttttttatcc tttagttttc tattatgata aagacccaaa taaataagcc cattattctg 660
ttttgttcaa aataagccca ttatctgagc ccaccaaaca ttggaaagtt tgagcttaga 720
ttcaggtgct gtagttaccc tagcttgcat ttcctcttcc acacacccac tccaggtaag 780
tggcttctct gtctagatcc ttctatcttt gttgctgatc cgtaaaacaa gccattacta 840
ggtatagatc tgtgaattcg ttgattggat ttgcatagtc tcgccggtgt ctgttcgtgt 900
ttcctcaacg ttgactttcc ccaatctcac ttttttcttt aaaagtctat tcattaccaa 960
ggaactctac gtccggatga tttcgtgaat ttgaatgact aatcaattcc ttgatacatt 1020

-continued

```
aatctgaata agttgcgatt gtcaaaaatg acttttttgc ttgttctcac tgttaaggt    1079


<210> SEQ ID NO 18
<211> LENGTH: 1893
<212> TYPE: DNA
<213> ORGANISM: Arabidopsis thaliana

<400> SEQUENCE: 18

tgggaaagtt tttttttttt tgacatcgga accgcatact ctatttatac ctaaatcata      60

ctaacatgag caagtcttaa gtacattttc tttgttgata tagtaattgt gtacatttac     120

ttggttcttt gataatttat aatcttatac tttgattggt gcaactatag tcttatatcc     180

ttaatttaac tttatcctta atttaacttc atgatcaaaa gatatagtct tgttttttgt     240

tttgttgaga agtttcatta gcattattgt ctaccgagag taataccaca aattgatagt     300

ttctctgcat ttttaagaga ataagctaaa taacggacct aaatacaagt ggtccttaca     360

attgcaattt gcaaatgaaa aaatttaaaa gagtaagcta aacaaccgta ctgacctaaa     420

taacaaacac atgaaaaacc acataaataa caaacacatg aaaaaccaat agaagtgtct     480

gttacaatta caaagtccac gtacatgcca cgaggtaatg aataagtcta attgcaacaa     540

aataaataat attgtttcat ataaataatt tttcaaaata ttgtttttat tttttcgtt     600

atcttttgga ctcaaatatg tgacaagagt aagactctat aaacgacagc tattttatcg     660

tggtgcgcca tcaaataatg tgtcctatca tttctaagtt gagccacgaa ggtcaacgtt     720

tccgatgcat accaccaaaa ctcctccctc gtggtgcacc atcaaataat cgtcaatcca     780

ctcgttaata tgtgtgatga tacgcttatc agcgatatca gtagatgttg aatcaactct     840

tcaggtttca atgatatcga tagtatactt agctagtttc tcccccatga aatcgataga     900

gcttcctccc aaggtattca agatcttatt ggcttctaca tatgaagcaa tcattactca     960

tgtagcaaac ttgttaatct tctatatttt cattacatat aatattttac gtacaagtaa    1020

gtcaaatgac atgacatgac atatgatata actgagtaag taagaaatta cgtataacaa    1080

ttaagtcaaa tgacatagta accattcgtg attgttgtct catatttata tatataaaac    1140

aaaaaatgaa gttttaagca aatgatctac aactaaaaca acatactcca ccaatatata    1200

caaaatacgt acactttttt ttgataagta agtagaattc tattgaacct gatgagagtt    1260

gagcataact ctattcttag acccgaaaac tactcaccat gtttatttta gagatttaat    1320

gatggattgg acagttttta ggccatatta catagtaaca actaatttca actaaaagaa    1380

tgcaagttgg ttagtttaat acaaaacaaa atagtgaaaa ttggatctct agctcatttt    1440

ccgattaatt aacttatttt caaaaaaatt gtggttataa gaacgaatta atcaattgca    1500

tttcttataa aaaaaagtaa tgaagagaga ttttacttac ataaaataaa tacatctggc    1560

ctgatgaaac aaaaatgagt aaggatatca acctttgtaa taagtaattg ttaattacca    1620

attcatagtc ttgatgggca ttattagaaa gcccattaaa aatggacaag gcccatttaa    1680

acctaggttt cgcagggttt attgcttcac tcttatataa aaactctcgt cttcacaaat    1740

ctcacatctc ttctgcagcc gattcttcta ttagccgccc aggtaattgc ttaattgctt    1800

aagcttctca aactccatct ctcttctcgc tgatttgacc tagaaatctt cttccctaat    1860

tttctttacc ctgtctttgc tgatttcgca ggt                                  1893


<210> SEQ ID NO 19
<211> LENGTH: 1434
<212> TYPE: DNA
<213> ORGANISM: Arabidopsis thaliana
```

<400> SEQUENCE: 19

```
gatcaaattt ttgtaaaaaa ttacaaattt gtaaaatatc tccataaatt aataattatt     60
aatttatcga taaattaata tctctctaaa ttaaaaaaaa ttttggtcct gacattatta    120
atttatagag gttttactgt agttacaaac tgcgcatggt ttgtcaaatt ctaaaacatg    180
ctttgtttat tttgaaaata aaataaaatg atactagatg aaacaaatat aatgaaaagg    240
atatttacca attgattatt cttatatttc catatttttt tattttagct actatttttg    300
aaaacttcca ttaactcttt cactaagagc tgtgatagta cacaaaaaaa aaagctgtga    360
ttcaagtttt tctactcata aaatatgtct ttgatttttt gtagtaatta taggccgtag    420
gccaatcttt caatatcata cacgtaggca cgggctagtg ctggcccaaa ttggagatgg    480
tcttagtggt tagaaacgaa tgtttaaatt cttaattaac ttttgtaaaa caccagatag    540
tttgtaatat acgacgagat agttgaaact tatgtccaaa aaagaaacaa aagaaagaga    600
gtatgttcat atagtaatag ggaaaagaaa gaaatataac cgttggtgat tagtcattta    660
gttggatgac aaatctctct caccttcaca tggaccaacg gcttctatgt cccaccaatt    720
tgtactctca atctccttta ccttatttat tcattacacc aaagctacga cacgacatgg    780
cttttgtttt attttcatta tatttatgtt atttaatgtt acagtacata caatatttag    840
cttttatgtc atgcattggt tattagtatt ttgtattact agtaagattg aaaacggttt    900
taagaatgta ggagtgtgtt tcacaaaatt gagagtattg caattacatg agagtgttca    960
gacttcagag tattacaaac ctaacaaacc tggatattgt gatatgactg gcttttaggt   1020
tttgtaggtc tcccatttga ttataaacaa aatgtattta ttacctatat tccaaaagta   1080
cccttatgtt ccatgttctc ttcttataaa gcaacacaca agatgcaaga aatctccata   1140
actagagaga gaaactaatc tttttagtga gagagaaatc ttagagctga gctaagaaaa   1200
caggtaaata tttccacaaa aaccacaaaa atttccataa acttcagttt caagatctta   1260
atatgaagtt gtttagcaat gatacattta taattcaaag atacattttt agcaagtttt   1320
tgtttggtaa aatacctttt tagcaagttg gtaaaatatt tcaacaaaac tttatcctaa   1380
aattactaaa ccttaatctt caacaactta atatggagtt gttaacttgc aggt         1434
```

<210> SEQ ID NO 20
<211> LENGTH: 1432
<212> TYPE: DNA
<213> ORGANISM: Arabidopsis thaliana

<400> SEQUENCE: 20

```
gtaagaacca aacctagctt tcaaaacatg aaataacaat aagaaacctt tttcgattga     60
acggcgaaat atatccattg aagatgttga gagtgagaat cgaagacgaa gaggtgcaat    120
tactcgcagt tttttttttt ttgtaagtta attattaatt tttgacttca ttaaagttaa    180
ttatttgctg aaaaaaaaaa aaaaaaaagt taattattta gtatcttcaa atataatatt    240
taaaaaaatc tagccatctt aatgcatttt aatgaaaatc ctacccaagt tttttaaagg    300
tcaatttaaa aagtatcagt tttgattttt aattatattc aatatttgtt aaattttgtt    360
tcatatgtta atattaaaaa cacaatctat ttcctaaaca tttatataca gatctttttt    420
aaaaaaggtt agtcaaaaac tgttggaaaa gctaatcttt ttttaacaaa aatagtaaaa    480
tactcatata cgtaactttg ggcctttctt aaatggcttt gggcctttcg taaatgggct    540
tatgggctta agtacttcaa atctgatagt atttggttta ttgcaacaaa aacaataaat    600
```

-continued ggaaatagcg atctgagctg accaaccaca gtcgcggaca gagctaaaac caccatttga 660
agaaggagaa gaagaagaag acgattcggt gaaagcgaag caggtgagtt taaatctctc 720
tatctctatc tcattctcga tcctatttgc atttcgaatc ctcccgagtt agatatctgt 780
tttgtgccct aatttttcat gtatcgtatg gaattggatc gtttgataca tttgaaattg 840
gggtttaatt ttagctgtag atgcatttga attagattag ttcttttgct gcaacgattg 900
gattcggaac tggatttcaa ttttcacctc catactagta ttcttaggtg atgatggttc 960
gatttcagat tgattataac tcaaaatttt cgagaccgac caatgaaagt ctaagattgg 1020
agttagggca gaagaaattt agttctcttt tagcttgtaa aaattggatc tttggctaaa 1080
aaaatggttt taactgcttt ctattgttct gagtttgagt ctgagctgat ttggttatga 1140
aaaattatgt atagtggact ttcaaggttc ttaatctctc agcagttcat tgctacaatc 1200
cttgaggatt cttcctccat agtagtttct actctgtgtc cttgaatata gattcttgtt 1260
aggaccatgt ttatgtggtt gatgatctat gccatccctt gttagtggaa tttgtctatg 1320
acgattgaga tggaaatttt ttttatgtgt tacttccaat acaattgtgt agttattgtg 1380
attaatatac taagttcaat ctaatggact ctaaactcat tttttgatag gt 1432

<210> SEQ ID NO 21
<211> LENGTH: 1104
<212> TYPE: DNA
<213> ORGANISM: Arabidopsis thaliana

<400> SEQUENCE: 21
cgtttacatt ctcatgatgc atctaaaagt agtgaaaatg tcagactgct tgtagtataa 60
attgctacca taacggagac ttgactaatc gtttactata tcagccgcta actagttggg 120
atatttttct gaaaatagtt tgataaatat gtaaaaatca cgatttcacc atcacattcg 180
attactcatt catgactaaa ataaaggatg aaatagctaa atttatgcga ctaatcatca 240
agggaaaaaa acgattttct cattttaggc gtggaaagaa aaatgtgtta ttaaacgacg 300
ccgtttagtt gccacgtaat aaatgagaat aaatttcttg gtgagtgggg aataaatata 360
tggacggctg tggataagga atactgaagc aagcgagtct ccatccaacg gctgataaaa 420
ttatgcttga taaacaggaa aactcttctt tctctgataa tattcggaaa taaaaaacat 480
tttagggttt tcctcagtct ctctctctta tagacgccaa ccacgttttc cagctcttgt 540
tctttcgatt ctcagagaag acttttcaga acatcctcca actttctcag ataagcaaca 600
caggtatctt tttattatct ccctcacttc ttctctttca tttcgttcaa ttaaatctgt 660
ttatggcgta gacgatctga ttgttgctac ttagtgtccc gttctgtctt ctaatctgga 720
ctttcttttg attccttagg atttttgatt catttgctca tctcttagat tttccttttc 780
ccggtcccga tttggctacc gggatagatc atagatgcat gcgtagattt cgagtattcg 840
atcgggtaga gattcataag taatggattt caatcattgg tgctgatatg agtaattcct 900
tgggttcaat gtctccgtca ctctcgttta agctctctac ctttctcaat agaccctgtt 960
ttgtttatcg ttgatctgga atagccaatt tgaatgctgt gattctcttt catgtttagc 1020
atttctcacc atttaagtcc cctttgagaa tgttttgtta ataagctgtc taaaactgtt 1080
gctctgctct gtgtatttgc aggt 1104

<210> SEQ ID NO 22
<211> LENGTH: 1785
<212> TYPE: DNA
<213> ORGANISM: Arabidopsis thaliana

<400> SEQUENCE: 22
taggaaaaaa gtttatattc ctacccaaac tttcggcacc agagacaaat taggtttgtt 60
cagaaaatca gtcgctcatc gacagactta acaccacaaa atcatcagaa tttctttggg 120
acaaaatgga aaatgttctt cacggctcca cctaccaaaa tttcgatatc aagctcaaaa 180
gcatacacaa actataacta attccatagt tacgtaatct taacttcgaa ttcaacaaca 240
catgcatgca tcgactgaat cttcaacaaa tgcaatcaaa cacacaaaat tgctaccaaa 300
aaaatatgat tttttttta tgatttcaat tttcatccgg cacttagtcc aaaacttttt 360
ttgtgtgtca acatttttta aaaaaatctt taaacggata tctgatctaa gagcatgttc 420
ataggtgata cttacaaaat atttttaaga aattttttag tattatttat aatgtttgtt 480
taataaatat atataagatt ttttgctttt atcaaatgtg accaatcaga agaaaccacg 540
tcagatgata ctgatatgac aaatatgata ctgatcaaac atattctaat tgctttacta 600
atataaaaat aatttttgga cttgtgatac tctaaaaata tcacccatat acatggtcta 660
atatatggat cgtaaaaaac tcatatataa tattaataag tagtagaaga gcgtagacca 720
tgtcctgggt cgtcgtccaa atgaccacaa gaagatttca aaacagagga aaatatttct 780
cattaaataa gttttcctga cgcataagat aacattatta caagattcag aaaaagaaag 840
gtgaaaggat aatgtttctc ctactatata agatgtgtac atctgaaaaa atatgaatat 900
atttgtaacg tttgactgtt attacatgat taatacgata taaatattaa cattttttt 960 caaaataaaa gtaatatagt aaggaaatga aaagaggcat gaagcatgcc tcttttttg 1020 gtcggctgcc gtttacaatt gccaattgcg atagttactc ttcttgcgtg tacgactttt 1080 gtttttttt acatattcgc caataatttg acgttttcta ttagtttgtt tgatactctg 1140
ttgtcttgct aaaactcaat aaaacattaa attactttct tgaatgaagc tggaacaaat 1200
ctaacataaa tagaaaatga tgggcaagtt gatgttattc gtaaatttat ttagattata 1260
ttatataaaa agcaatccaa ttatatatct catatataca atttcttatc ttactttgtc 1320
aatgtcatat acgtaactaa aacttgcgga aatagaaaat gccacgtgta tggtggacat 1380
aatccgaatc tctctctttc ttctataaat agtggccatt cccattggtt gaaatcacaa 1440
aagcatcata agaagaagaa gaaactacaa tagttaatca atcaaagaga agtaagagaa 1500
caggtaaacc cctagattct ctcttcttta catttatatg catatatgta gactatgtag 1560
ttcgagcttc atggtacaaa attcaataaa ctcttcttat gacttcgttt acaattgtgt 1620
ttgtgaatag acacaaaaga ttagttttgt ttactttaga ttcaaaacac ttcgggccta 1680
tcctgtatat atgctgatca gatgcatgtg gttgattaat ctttaatctc atcatattaa 1740
ttactaattt tttgtttgtt tgattaattt gtgtgtggta aaggt 1785

<210> SEQ ID NO 23
<211> LENGTH: 1202
<212> TYPE: DNA
<213> ORGANISM: Arabidopsis thaliana

<400> SEQUENCE: 23
gttttgtgta tcattcttgt tacattgtta ttaatgaaaa aatattattg gtcattggac 60
tgaacacgag tgttaaatat ggaccaggcc ccaaataaga tccattgata tatgaattaa 120
ataacaagaa taaatcgagt caccaaacca cttgcctttt ttaacgagac ttgttcacca 180
acttgataca aaagtcatta tcctatgcaa atcaataatc atacaaaaat atccaataac 240

-continued

```
actaaaaaat taaaagaaat ggataatttc acaatatgtt atacgataaa gaagttactt    300
ttccaagaaa ttcactgatt ttataagccc acttgcatta gataaatggc aaaaaaaaac    360
aaaaaggaaa agaaataaag cacgaagaat tctagaaaat acgaaatacg cttcaatgca    420
gtgggaccca cggttcaatt attgccaatt ttcagctcca ccgtatattt aaaaaataaa    480
acgataatgc taaaaaaata taaatcgtaa cgatcgttaa atctcaacgg ctggatctta    540
tgacgaccgt tagaaattgt ggttgtcgac gagtcagtaa taaacggcgt caaagtggtt    600
gcagccggca cacacgagtc gtgtttatca actcaaagca caaatacttt tcctcaacct    660
aaaaataagg caattagcca aaaacaactt tgcgtgtaaa caacgctcaa tacacgtgtc    720
attttattat tagctattgc ttcaccgcct tagctttctc gtgacctagt cgtcctcgtc    780
ttttcttctt cttcttctat aaaacaatac ccaaagagct cttcttcttc acaattcaga    840
tttcaatttc tcaaaatctt aaaaactttc tctcaattct ctctaccgtg atcaaggtaa    900
atttctgtgt tccttattct ctcaaaatct tcgattttgt tttcgttcga tcccaatttc    960
gtatatgttc tttggtttag attctgttaa tcttagatcg aagacgattt tctgggtttg   1020
atcgttagat atcatcttaa ttctcgatta gggtttcata gatatcatcc gatttgttca   1080
aataatttga gttttgtcga ataattactc ttcgatttgt gatttctatc tagatctggt   1140
gttagtttct agtttgtgcg atcgaatttg tcgattaatc tgagtttttc tgattaacag   1200
gt                                                                  1202
```

<210> SEQ ID NO 24
<211> LENGTH: 403
<212> TYPE: DNA
<213> ORGANISM: Arabidopsis thaliana

<400> SEQUENCE: 24

```
tgataactta tgtgcaagag tctctcgttg gtcagtgtga aatgtttatg ttgttagaac     60
agattttggc tctcaaaccc aacacgtttt caataaaata tgcacggtta gattcaccca    120
accctagttc aatctgccag gatctatctc tttttttttt acgattttct tcaaccaaaa    180
caatgaaata acacacaaaa ttattatcac tagaccaaat tttatttata acataaaacg    240
gccggaagct gatgcttcat gggcttggcc caaaggccgg ctctggatgg gccagatgat    300
aacctagggt ttatactccc tatatattta tatttaagct cttcgttcac tcctctcaac    360
tccgcgcagc taaactttat tggagaaacc ctaatcggcg aca                      403
```

<210> SEQ ID NO 25
<211> LENGTH: 1000
<212> TYPE: DNA
<213> ORGANISM: Arabidopsis thaliana

<400> SEQUENCE: 25

```
caaaactttt ttggaatggt agacatccca ttgaaagaaa acaaattgcc atggtatgga     60
attcatgata atgatttaac tcgttatagt ctggacaaat tgtcatggta gggtttcatt    120
gctctttctt tgggtagtta cctcaagata tctctttgtt cttccttgtg atagttccac    180
cttgatatgt acaaccccac attaatctgc tcatttcaac attaattttc tctattgttt    240
ttaaattgtg tgtataagat tatttcacta actaggaaaa caatccattt ctttgacaca    300
tgggctttac ttaaacaaaa gcccaataac ttgtgtttag aagtcacatg atcaaatctc    360
aagacctatt ataaattaac aaatttcata ttgataaatt ttaaaagatt tcctattaca    420
atatttaaag ttgctacaaa ttatagattc ttttgatctt ttctgatatt gtttctcaaa    480
```

```
taaaatatag gaataccaaa ttacaatatg aaagttgctt caaattatag attcttttct    540

gattttgttt ctcaaataaa atataggact gaactaccaa aggcaataat attcaatgtg    600

accaacaaaa aaaaaataaa aaataaaaag aaatactcaa atctcataac ctttttgact    660

aaatatatca atttcttcta ttttcaatga gcataaatta cacgcgtcct cagaagctga    720

atccgatttg caattcttca atctcaaccg ttagatcaac aaatccggca tcgaattcct    780

ccgcgtggtt tggtccattt ttttaatttg agtattaatt cttttcctat ttgacaactt    840

gttttattaa ttattattat tattccattt gcattaaaat ataataaaaa gttgtaagat    900

tctctccgcc tccttctctc tataagaacc gacacagaga cgaagaagaa taatcactcg    960

aaaactcatc aaatcaaaaa tcaaacacag agaagagaaa                          1000
```

<210> SEQ ID NO 26
<211> LENGTH: 347
<212> TYPE: DNA
<213> ORGANISM: Arabidopsis thaliana

<400> SEQUENCE: 26

```
atttctgtgt ttaacctttt cgtacatcag ttttaaagca cagagagctc aatgttcttc     60

caatatcgtt attaataaat tttgattaaa ttcaatcaaa tcggagttat attaccacat    120

gaggttaaag ggccatatta aaaagtctgc acttcatatg agcaacaagg cttttatgtc    180

tttatggttg atttgatggc ccatatatga tagttcaaag gcccatatta aaaaatgccc    240

taacatgatt cgattcgtat ataaagacgc ttaatgtgac aagcgaactt gctcattagg    300

gtttctcatc tacgacggcg tggtgttcct ccttcctgct ctgaaaa                  347
```

<210> SEQ ID NO 27
<211> LENGTH: 818
<212> TYPE: DNA
<213> ORGANISM: Arabidopsis thaliana

<400> SEQUENCE: 27

```
ccgacactac taaaaagcaa acaaaagaag aattctatgt tgtcatttta ccggtggcaa     60

gtggaccctt ctataaaaga gtaaagagac agcctgtgtg tgtataatct ctaattatgt    120

tcaccgacac aatcacacaa acccttctct aatcacacaa cttcttcatg atttacgaca    180

ttaattatca ttaactcttt aaattcactt tacatgctca aaaatatcta atttgcagca    240

ttaatttgag taccgataac tattattata atcgtcgtga ttcgcaatct tcttcattag    300

atgctgtcaa gttgtactcg cacgcggtgg tccagtgaag caaatccaac ggtttaaaac    360

cttcttacat ttctagatct aatctgaacc gtcagatatc tagatctcat tgtctgaaca    420

cagttagttg aaactgggat tgaatctgga cgaaattacg atcttacacc aaccccctcg    480

acgagctcgt atatataaag cttatacgct cctccttcac cttcgtacta ctactaccac    540

cacatttctt tagctcaacc ttcattacta atctcctttt aaggtatgtt cacttttctt    600

cgattcatac tttctcaaga ttcctgcatt tctgtagaat ttgaaccaag tgtcgatttt    660

tgtttgagag aagtgttgat ttatagatct ggttattgaa tctagattcc aatttttaat    720

tgattcgagt ttgttatgtg tgtttatact acttctcatt gatcttgttt gatttctctg    780

ctctgtatta ggtttctttc gtgaatcaga tcggaaaa                            818
```

<210> SEQ ID NO 28
<211> LENGTH: 1000
<212> TYPE: DNA

<213> ORGANISM: Arabidopsis thaliana

<400> SEQUENCE: 28
agattgaagg aggacttaat aattagaaca aggttatata attagatata ttcttttttt 60
ttttaaggtt atataattag atatattcgt ttttttaaaa ggttatagaa taagatttca 120
ttgcatctta aaaccagaca actttcagaa ctgaagaatg acgaaaaatt aataatagag 180
gaggagagga ggagctacat caacattatt tctatttttt cagccaatca gagcgctccg 240
gacttcgccc actcgcacca acctcgcgcc acgcgctcca ttccatgccc actcgcacca 300
acctcgcgtt gaacgcgtgt cgtcgatttc tgtaggggta aacccacaaa atcatgccta 360
ttttacatct actcgctttg tttccaaaac agcctcgagt gactttttttc ttttgttttt 420 tttctcaaaa ccgtattaat tctaatgcaa accgaaccaa aattaatttt tatttcaaaa 480
ccatctaaac caaacagaaa tcacatgtaa tttcaaaccc gaaccgaaat caattgtcat 540
ttcatcaaaa ccatgtaaaa agcttctacg attgttttaa cttgcaactg aaaatagcaa 600
tcctaattta tcaacagata aagatagata catgcaacac tttacttttt tatttttggt 660
tttgagaaga tgattacagt tgtgattttg gtggagacaa aaatgtccat ctctgtatgt 720
tgctagccga tcaaatttta cattcaaaat ccttttttgat aaaaaaaata aaaaaattca 780
aaatccttta tgatatattg ggcctaagat gatttccaaa aaaaagatga tgagaaaaga 840
aagagaacat tattgggctt attgttaaat tatttcggcc cataaaataa agtccaggtc 900
agctcacaat acatgaagaa aaccctagtt caagcgtata taaaccctct cggcgctgcc 960
attgaaactc tttcaaggag agagctgcta ctctgcaacc 1000

<210> SEQ ID NO 29
<211> LENGTH: 520
<212> TYPE: DNA
<213> ORGANISM: Arabidopsis thaliana

<400> SEQUENCE: 29
tgataactta tgtgcaagag tctctcgttg gtcagtgtga aatgtttatg ttgttagaac 60
agattttggc tctcaaaccc aacacgtttt caataaaata tgcacggtta gattcaccca 120
accctagttc aatctgccag gatctatctc tttttttttt acgattttct tcaaccaaaa 180
caatgaaata acacacaaaa ttattatcac tagaccaaat tttatttata acataaaacg 240
gccggaagct gatgcttcat gggcttggcc caaaggccgg ctctggatgg gccagatgat 300
aacctagggt ttatactccc tatatattta tatttaagct cttcgttcac tcctctcaac 360
tccgcgcagc taaactttat tggagaaacc ctaatcggcg acacaggtac gaacaatctc 420
tcctcgcttt ctctttgatt tctccactcc ttcgatctcg tttctgtgtt atgctattgt 480
tgtttagatt ctgatatatg gattctggtt tctcttaggt 520

<210> SEQ ID NO 30
<211> LENGTH: 1497
<212> TYPE: DNA
<213> ORGANISM: Arabidopsis thaliana

<400> SEQUENCE: 30
caaaactttt ttggaatggt agacatccca ttgaaagaaa acaaattgcc atggtatgga 60
attcatgata atgatttaac tcgttatagt ctggacaaat tgtcatggta gggtttcatt 120
gctctttctt tgggtagtta cctcaagata tctctttgtt cttccttgtg atagttccac 180
cttgatatgt acaaccccac attaatctgc tcatttcaac attaattttc tctattgttt 240

```
ttaaattgtg tgtataagat tatttcacta actaggaaaa caatccattt ctttgacaca    300
tgggctttac ttaaacaaaa gcccaataac ttgtgtttag aagtcacatg atcaaatctc    360
aagacctatt ataaattaac aaatttcata ttgataaatt ttaaaagatt tcctattaca    420
atatttaaag ttgctacaaa ttatagattc ttttgatctt ttctgatatt gtttctcaaa    480
taaaatatag gaataccaaa ttacaatatg aaagttgctt caaattatag attcttttct    540
gattttgttt ctcaaataaa atataggact gaactaccaa aggcaataat attcaatgtg    600
accaacaaaa aaaaaataaa aaataaaaag aaatactcaa atctcataac ctttttgact    660
aaatatatca atttcttcta ttttcaatga gcataaatta cacgcgtcct cagaagctga    720
atccgatttg caattcttca atctcaaccg ttagatcaac aaatccggca tcgaattcct    780
ccgcgtggtt tggtccattt ttttaatttg agtattaatt cttttcctat ttgacaactt    840
gttttattaa ttattattat tattccattt gcattaaaat ataataaaaa gttgtaagat    900
tctctccgcc tccttctctc tataagaacc gacacagaga cgaagaagaa taatcactcg    960
aaaactcatc aaatcaaaaa tcaaacacag agaagagaaa caggtaaaaa ctctcgatct   1020
aaggttttaa atgtttcttt ctgattgatt tcgctgcttt atcgtttctg atcttggtcc   1080
ttttgattag aatatgacgg attcagaatt aggtttgaat tgtccccaat cgaatttttg   1140
agctccttaa tgtcaaattt atgaacccta atagtttaat tgattgttta ggaacccaga   1200
atctcagaaa ttgaaaccct aagaacttga tagaagcatc attggataaa aacatgttat   1260
gtgaatctct caactatgca tattcaattt tatgaatcat ctgctagaga tcacatgaaa   1320
attgtcttta gtgaacccat tttgtatcta tgtttgtatt attatccatg ttctgtgaag   1380
cacatgaaat gcatacattt gttatcttaa tgatgaaccg atgtcgtatc tattgtttga   1440
attatcgatc ggtgtagctt gttttcttaa atatggttgt gtggaaatga cacaggt      1497
```

<210> SEQ ID NO 31
<211> LENGTH: 555
<212> TYPE: DNA
<213> ORGANISM: Arabidopsis thaliana

<400> SEQUENCE: 31

```
atttctgtgt ttaacctttt cgtacatcag ttttaaagca cagagagctc aatgttcttc     60
caatatcgtt attaataaat tttgattaaa ttcaatcaaa tcggagttat attaccacat    120
gaggttaaag ggccatatta aaaagtctgc acttcatatg agcaacaagg cttttatgtc    180
tttatggttg atttgatggc ccatatatga tagttcaaag gcccatatta aaaaatgccc    240
taacatgatt cgattcgtat ataaagacgc ttaatgtgac aagcgaactt gctcattagg    300
gtttctcatc tacgacggcg tggtgttcct ccttcctgct ctgaaaacag gtgaaaaacc    360
taatcctttc tttttgttat tgttcttgaa tctctgtaat tccatagcaa gttattcgag    420
tatacttcct tctgtctcgt tctagctttc gttttgagat ttcaagtttc atagttgatc    480
tgtggattct gatagaagtc tagttttgtg attttgtctt ttgactctat tactcttttt    540
cgatgtttca caggt                                                     555
```

<210> SEQ ID NO 32
<211> LENGTH: 1232
<212> TYPE: DNA
<213> ORGANISM: Arabidopsis thaliana

<400> SEQUENCE: 32

```
agattgaagg aggacttaat aattagaaca aggttatata attagatata ttcttttttt      60
ttttaaggtt atataattag atatattcgt ttttttaaaa ggttatagaa taagatttca     120
ttgcatctta aaaccagaca actttcagaa ctgaagaatg acgaaaaatt aataatagag     180
gaggagagga ggagctacat caacattatt tctatttttt cagccaatca gagcgctccg     240
gacttcgccc actcgcacca acctcgcgcc acgcgctcca ttccatgccc actcgcacca     300
acctcgcgtt gaacgcgtgt cgtcgatttc tgtaggggta aacccacaaa atcatgccta     360
ttttacatct actcgctttg tttccaaaac agcctcgagt gacttttttc ttttgttttt     420
tttctcaaaa ccgtattaat tctaatgcaa accgaaccaa aattaatttt tatttcaaaa     480
ccatctaaac caaacagaaa tcacatgtaa tttcaaaccc gaaccgaaat caattgtcat     540
ttcatcaaaa ccatgtaaaa agcttctacg attgttttaa cttgcaactg aaaatagcaa     600
tcctaattta tcaacagata aagatagata catgcaacac tttacttttt tatttttggt     660
tttgagaaga tgattacagt tgtgattttg gtggagacaa aaatgtccat ctctgtatgt     720
tgctagccga tcaaatttta cattcaaaat cctttttgat aaaaaaaata aaaaaattca     780
aaatccttta tgatatattg ggcctaagat gatttccaaa aaaaagatga tgagaaaaga     840
aagagaacat tattgggctt attgttaaat tatttcggcc cataaaataa agtccaggtc     900
agctcacaat acatgaagaa aaccctagtt caagcgtata taaaccctct cggcgctgcc     960
attgaaactc tttcaaggag agagctgcta ctctgcaacc caggtaaaaa aacgtttctt    1020
catctctaat tcgcttaacc taatctgtgt acatctcgta tgaatcatat cctgttttcg    1080
cttattttct tcatttcact ttcaatgaca atggttttac cctaatttct attagtaaag    1140
cttctggatc atgaatatta gtcttatatg tctctacttt ggttgatagt gtttagatct    1200
gtaacttttg tgtttgtttt ttgtgaatag gt                                  1232
```

<210> SEQ ID NO 33
<211> LENGTH: 1000
<212> TYPE: DNA
<213> ORGANISM: Arabidopsis thaliana

<400> SEQUENCE: 33

```
ttcagacaca aggaccgacc aattcgaaaa caatgaatgg atatgattca tccttatgaa      60
agcttgacaa caaactcggt tttggctggt taacctagac tcggtttatt taaaccagac     120
aataatttct ttcgtcgtcg ttttatttga ataggtgcgt caaaaataaa agctgaaatt     180
cttggttgca aaagcccaac aggcctgtgg agatagcttt ttagattgat taaatgggcc     240
gaattgggct gacacatgac gagaatgtgg ctatagaaat tgttagtgag agggtccggg     300
tccaaaaatg ttgcagaagt gatatagtat ttatttaatt aaaaacatat tattcgacgt     360
atttttaacg ctcactggat ttataagtag agattttttg tgtctcacaa aaacaaaaaa     420
atcatcgtga aacgttcgaa ggccattttc tttggacgac catcggcgtt aaggagagag     480
cttagatctc gtgccgtcgt gcgacgttgt tttccggtac gtttattcct gttgattcct     540
tctctgtctc tctcgattca ctgctacttc tgtttggatt cctttcgcgc gatctctgga     600
tccgtgcgtt attcattggc tcgtcgtttt cagatctgtt gcgtttcttc tgttttctgt     660
tatgagtgga tgcgttttct tgtgattcgc ttgtttgtaa tgctggatct gtatctgcgt     720
cgtgggaatt caaagtgata gtagttgata ttttttccag atcaggcatg ttctcgtata     780
atcaggtcta atggttgatg attctgcgga attatagatc taagatcttg attgatttag     840
atttgaggat atgaatgaga ttcgtaggtc cacaaaggtc ttgttatctc tgctgctaga     900
```

tagatgatta tccaattgcg tttcgtagtt atttttatgg attcaaggaa ttgcgtgtaa 960
ttgagagttt tactctgttt tgtgaacagg cttgatcaaa 1000

<210> SEQ ID NO 34
<211> LENGTH: 1000
<212> TYPE: DNA
<213> ORGANISM: Arabidopsis thaliana

<400> SEQUENCE: 34
aataacaata tatatatata tatatattta tttatttata gatattcata tatatatata 60
agaaaatata tagatatggt catatggata tggttgtgga cttgtgatgc gacaaaaaaa 120
aattgaacaa agtggatctg gttaggtggc cagcatcttt tacggaaggg aaaagttgga 180
tatattacaa tatttttggt ggaccatgag caaccccacc acaaagtgca tgtgaagtga 240
ccacttttct gcgagctgat ccaactaatc aataatggta acaaatacaa aaaataaacg 300
ctctaatttt atttcagtca aatgttttta ataattttcc atgtccgaaa actttaaaat 360
cttttattat tactaagtta agaaaattgc aaatgtaaga attatttgtt tctaaataga 420
taatattaat accaaattga tattccaaaa catattattt tcttgtttga tttgattgat 480
aatctattaa ctgataaaca acaatgatag aaatatgttc tctaattctt cttctctagc 540
attcaaaaat tcacatccaa caaaaccata aattttgtaa ttttagatac aattttacac 600
taaaaattaa taattgtaaa gcttgtaatt atattcccaa actttattct ataaattaaa 660
acttagcatt catattgttg aatatgactt ttgaattttg ttagtgggac ccttttatac 720
aataagtggc ggctacaacg aaaaatcaaa gtagggacca aaatgataca aatcgtaata 780
acggggtcaa aataacataa tccaaacttt taaatagcat aaatacaaca actctcaaga 840
cctgtacaag ctatttcacc tacttcatca ctcatcacca gcttcgcatc ttcttctccg 900
gcttgatctt ctctcgtttc tagatctccg acgatcggaa tatcaaatcc gatcgattaa 960
ttctgtcaat cacacaaaaa ccgaaaacca aaaaaaaacc 1000

<210> SEQ ID NO 35
<211> LENGTH: 1200
<212> TYPE: DNA
<213> ORGANISM: Arabidopsis thaliana

<400> SEQUENCE: 35
tgaaaacgtt ttccttatct cacttgtatc aaaccaaacg aaactaaaaa agactattgt 60
ttgatataat ttttgatgtg taacccggtc caacaatttc atatggtatt tatttgaatt 120
tttatagtcc ttttttccta aattacagtc ttacagacac aattattttc tttgaaatga 180
aaaatccgat tggttcacgt tatataacaa gtcggaccaa tcggtcccca atagtcagaa 240
aattttgaaa ataatgccaa aaaatagtaa atattggtag gccaactcca aagccaaata 300
catatatatt tctttacaag tccaaagtag ggtggtttaa ccaaataaac cggtgaccag 360
tcattagtga accgtaaaag gcctataaat aaccaacgtg ttctgactca ctttctcgtc 420
tcaaaccgtt ccttctcttt taacacttgt tcttttaagg caaaaaggct cgagccacag 480
agatctgagt ttctcttctt cgagatctga tcgccgaatc tcataatctc ccatcgaagc 540
aggtattgtt cttcgtattc gcttctcgtt tctctctcga tgtattgttc atttttgttt 600
tccagttgat tttcaagtct gacgtgcgta ttttttccga tttgacgatg gaagtagatt 660
taagggacta ttgactgtat ctatggtttt taattagatt tcagctactc tttaaccatt 720

-continued

```
ttgttattgg atcagcagcg atttcgttat agattctcaa aaatattctc agatgtgtgg    780

gatttgagta gagtttatgt tgcgttggca tgatttgaat agtatgcaag atttttgaga    840

ttttgaattc gttcatgtgt gtatgtgtga ttgtagcttg atatgattta acctgttagt    900

taaatgtgca tagacaataa gtaacatacg aagcgagtca ctaagcataa gagtcaactt    960

gttttgctga aaagatatca cttatgattt tcgaatcatt ttagcttttt tgtcacttga   1020

gcttaatgat tcttctgaaa ttcgattctt tgtttggttt atgtcacatt ctttagaatt   1080

gagaatctaa gaaaagctta caggatatgg tgaaactatt cttttaagat agcatgatgc   1140

ttcttttatg attctacagt ggctaagtca ttttttttt gttctattct ttgtagcaga   1200
```

<210> SEQ ID NO 36
<211> LENGTH: 1000
<212> TYPE: DNA
<213> ORGANISM: Arabidopsis thaliana

<400> SEQUENCE: 36

```
atttacaca ttcatggtga aactacttgg tatatatatg caaatgaata tgcatgtgga      60

tggtacatgg cgtttgattt tgcatatagg caatttattg atcaatactt ggtgtagttg    120

gtacattaaa gttgcattat agacaaacaa aattcggctg tcatgcttga ttgatctata    180

gatgatttca taataaaaaa atattgtcat ggataaaaat agtgaagatg ataacaaaaa    240

gaacagaaca caaagaagaa tctcatttct tttttgatta ataaaaggat ataaagtcat    300

tagtttttt attcgtctca ctcgacacta ataataacta aaattgttgg agaattaaaa    360

gtaagaaagc aatgctataa aataaagtaa ttgttgggaa tggagcatgt aaaattatca    420

ctcataacta aaattagcaa tgttataaag tatttaagta agaaaatgtt gtagataatt    480

tgttaaatga ggtgtcccta tgtcttttag gtgcggtgag tccatgtgct tatcctgaca    540

gcggtccaac ttaaccggcg gttcatctcg accacatatt caactgcttt tttaatatga    600

ttttctgtat tttcttacct gtcataatct acatttaaac gttaaaaaat gtccacaatt    660

ttatttattt tattagggta caataacgac atttgattag agtaaagaaa atagttgcaa    720

agcgggattt gaaactctgt ccacatactt taattatcat taatcaataa caagcattat    780

cagtattcag cagcagcaaa gatgataacg ttaattatac tatcatgcaa ttaagttaac    840

taattaacta tcatcttgtt tttgttttaa ttttgtttcc atcatcttcc aaccttgagt    900

ttcggtcact ataaaaagcc accactctct ctgcttctct gcaacacata acccactcac    960

agaaaaacct agaaagctct agagagaaag agagagagag                         1000
```

<210> SEQ ID NO 37
<211> LENGTH: 1000
<212> TYPE: DNA
<213> ORGANISM: Arabidopsis thaliana

<400> SEQUENCE: 37

```
cgaaaaaaga ggagagattc gattcaaata cccacataga acggacaagg tcaataatgg     60

gcccactatt cttttgagag cccatctcaa caagttgaat catctttttt gtgtactctc    120

acttcacctt ttgacaaaaa gtcatggaag ccaaactttg gaacactact ttactttgcc    180

aacatcttgt tttgttgaat acctttttca aattggaaac caaagacata tctaaaggga    240

aaacctgtag gacaataaaa caaagaagtg atagctaaag tctaaactaa tctcaatata    300

tgtaaatcaa agagataact aatgaaaaat atgaaaattt tcgcgaggat taatgaacaa    360

aggaattttt ttttttcctt ctaaaatttt ttattagaca attggtatta caatgacaac    420
```

```
tacgaagcta atacaaaact tcggaaacca acttattaca taagcaaaat tatgtgtcat    480

atactgaaaa ttacgaaact gaaaaagtga atttaacgat ttttcctttc gataagcttt    540

attcgctaac atgttaacat gttagaacat agaaaatatt gaaaaaaaat ttatgtttaa    600

attgtcaaat ggaaatatac tttacacttt tatttgtatt aattgttact ttgctctcct    660

agttataaag aagtaaagtc tatgattttg ttacttcttt ttttcttgta aatctttata    720

catgtaaaaa gcttttgttt ccaactctaa tcctcaatat tttatttttc tgtttattgg    780

aaaagggctg taaactaaaa ttatttactt gaggaacgat tatttaggtg ataagagtgg    840

acaaagatcg ttgacacgtg gacggtctac aaattctaat tttgcctata aatatcaaag    900

ctcctgaata tgtaagtttc attcactgat tatcgtttaa ggcaaattaa gatcatcttc    960

ataaatcttc tcagatctct tccaattttc tagaaaaaac                         1000


<210> SEQ ID NO 38
<211> LENGTH: 552
<212> TYPE: DNA
<213> ORGANISM: Arabidopsis thaliana

<400> SEQUENCE: 38

agttgtttac accctttgtt tgtcaaccac aacttttcca atgattccac taatccacgt     60

tgctgccaat gtctaatatc gtatcaatta tcaaaattgt gggagagaag ggaaccaccg    120

aaataataat gtccttacac aacgtcgtct agcccaatta ataggcccat ttaagcccaa    180

ataatacaga attgtggccc tggtccgcta cgatccgtta aaatctgaaa ttagggtttt    240

agtttaactc tccatataaa ttgttccaaa tttcattcgt atcctttccg ctgctgccgt    300

cttcgtctct gaggtcagtg tttcagctcc ttgaacgata tatacgatct tatcgatttc    360

gcattattct atcttaggct atgtatatga ctgtcgaact tagttttacc gccgccgatt    420

tggcttcgtt atattttccc tagtagaatt aattgtttag gtgtttgcta agctcatttg    480

catgacttat attggcagat aataaggact tgtgtatttt tccatcgtta aaaggcattt    540

caaagagaca at                                                        552


<210> SEQ ID NO 39
<211> LENGTH: 555
<212> TYPE: DNA
<213> ORGANISM: Arabidopsis thaliana

<400> SEQUENCE: 39

tctctctttt accactttag cggactcctg ttgataagat ttgattttgt tttcgaatat     60

atgtagtaac tgaattgagg attttgagtt tgatttcaga aggctgataa ataagttgag    120

agttcaatcc ctcattgtgt atgataacca tcaccaattt ttctactaca ttttttggct    180

ctgacctcat ttatcaaatt ttgataggaa aatgtcactt tggtttgtgc caaaaaaggg    240

caggctctgt tatattattg acggcagaaa atggtaggca tgcttaaacg tatgagttag    300

tgttaaatta ggtagaaaaa tgacaagctt ggtatataac gttcaataat ataaggaaga    360

tgtggcagag ttagtgttga gaatgggcta gtctacttgt gtttaggccc atatatataa    420

ggcccatata tatttgaaga ccacaaataa ctagggttta caaatttggt tatatagctc    480

tctctctcga gccgcacata tttcgtcttc ttgatctaat cgctttgagc tgttagcaga    540

gagcagtcga caatc                                                     555


<210> SEQ ID NO 40
```

<211> LENGTH: 1000
<212> TYPE: DNA
<213> ORGANISM: Arabidopsis thaliana

<400> SEQUENCE: 40
atcatcattt tatatatcaa tctatatatt tatcatatga ctcagactat catgagacgc 60 attttttta agtattatga ataatatacc acttgttcac gttttaacgt ttgaaaaaca 120
tgattttgct actttttacg attcaaagta tttattaaga atttacgttc ttgaaaagtg 180
attatactgt atatataact ataagtaaat aaaacttttt tcgacgaaat ttctgatgat 240
aaataaaagg tcggatatat ttgacttttt tttttttttt aattattttt tgacgataaa 300
tttttcgttg aaaaatcatc gaaattttcg acggattcca atgatcaaaa attcgtcaat 360
aatttccaac gatattctga ctaaactaaa tctgatgaaa tatttttgac ggctttccaa 420
ccaaaatatt tcgttgtgac ttgtcaaaaa tccgttagaa tactaagcaa cttttcgaca 480
gattttcagc aaaaatattc ggtaatataa cgtgttaaaa atatgataaa aaaaaaaact 540
tgatgaatct actaaaacta aattttcaat catatatatc tattattcat atatttcatt 600
cattttatta tttttctctt aacaattatt tagttattct ggtatcgtgt aattatattc 660
atatgattta ttctgatatt gattcggtta gcatccggat aaatctgggt tgggcttttt 720
aacttggttt ttctaagaaa aattctaata tgatttggtt agcatccgga ttagtctagt 780
ttggtaggcc tgcctttgtg attcttaact cggtcttttg tatgggtttg aacaattact 840
acaccattta gattcttctg acccatatca aataaagatc cacttaggcc cattagggtt 900
agaacaaaca tgaggttgca gaataaaaag ggttcatttt cctcactctc aagttggatc 960
tcaaaaccct aatatctgaa cttcgccgtc gagagcatcc 1000

<210> SEQ ID NO 41
<211> LENGTH: 1000
<212> TYPE: DNA
<213> ORGANISM: Arabidopsis thaliana

<400> SEQUENCE: 41
taaaaaaatt tgttcggaaa atatcacatt tctttcacta gacaagcctt gttaccacac 60
aatgtatcaa tatgatctaa agggcaaacg aaagatcctg acatgaaacg tttaattctc 120
attttctcca aattttattt tttatgtgaa gtagataaat tagtatatat atatatatac 180
caaactagtg tgttatgtta tggcaaatgt tatatcaatt cgaaggttcc gctattgcaa 240
tattcattaa ttttttcata ccaatactat ttttctttct cttttatttt gtttttttaat 300 aaataaaaga aattaaggat gattagtaag gaagtcgcct accaagagat tcacctacca 360
cggtacactt caacaccgaa gcagagttgt tgaatccact tttttattccc ttctctaatc 420 tctactcacc aagtctccac ttttttttct ctttattata tacatttaaa ttatttaata 480
tacgccaact acatacatat ccagtgtaat ttctcgttac gtcacacccc tttcgtaatc 540
gtctaatttc agaaaaatat ccagaggttt aaatacatat tcccatcatt aaatctagac 600
ataaacacat catactcaca aaatttggca gcaaacagtt actacagacc cataaatgaa 660
aaaacgtatt cacttgtttt caattttcac ataaccactt ccctgagttt ggtctcaatt 720
tgattgcccc gccgaggcat tactacgcca agtgcgatta aggtcccata cagtgtaacg 780
ggacccacta taagacagcg accgaccaat tgcgtgttag gagagtttca ccaaccccgg 840
accggttttt accggatata acagaaccgg tacgaaccgg tctcattatc ttccatcttc 900
tttatataga cctcatgcca tgtgtgtgac tcaccaagaa aaacacaatc gtttaatctc 960
acccaagaag acaaaaacac agagagagaa agagagagaa 1000

<210> SEQ ID NO 42
<211> LENGTH: 510
<212> TYPE: DNA
<213> ORGANISM: Arabidopsis thaliana

<400> SEQUENCE: 42
atatttgtgg taatgtgtta agagttccta ttaattacca taagtaaatc acaaacataa 60
ataaaatgaa aataattatg ggctttaagg tctggaggac tactgaaatt tgggagaagt 120
agttggaaaa agaatattag tcgataggta ggaaattgat attgcttgtg gaatggagga 180
aaaaattgaa cgaaaaagaa gtttctagaa ttctaatcac ataacataaa tagggtgaat 240
atttgggaaa agtaaaacaa taggggtcgg tttgatatta ctagaagata agaaacaaaa 300
aggaaaataa gaataaagga aaaaaaaaga gctctctttt ccaacaagaa acgtagagag 360
atataattag agaaaatctg tgctctttca gatcccatta tcacaaatcc atctctctct 420
ctctctcaga gaagaaacca aagaagaaga aaaagctctc aactttcttc gatttctcag 480
ggaactcttt cgttaatctc aaactcaatc 510

<210> SEQ ID NO 43
<211> LENGTH: 1300
<212> TYPE: DNA
<213> ORGANISM: Arabidopsis thaliana

<400> SEQUENCE: 43
gaaacaatga tgtggaccta atttcggttg gaagatattt tgtttatctg gcttagattt 60
tgtcctttga tttagggaat caaaagaaag tcataaacat taattttgcc tgtaaaatca 120
cacatttcag atttgttctc gtatgaccta caaataaagt atatgattac acaatcaatc 180
tttagattca agaactttgt ccctacttca ttatattcag ctaacatttc tttttaattc 240
tctgtcgtgc gaaaggttgt tgacaatata aatgatatat gtacttgtac gcgtaatgct 300
gctaatacat tttaatttgg gcttcttctg ggccttaata tttgggcttt aaataagtta 360
tctctcccac ttacgcatgt aaacacagct ctgataatta cgctgaggtg gcattttta 420 attggctatt gcattaagag ttgcgtggcg agaaatttcc cctcctataa aaattgttga 480
agagtccggt caactccgaa agtcttcaaa tctctccgtc acgaatcgtt ctctcgtcgt 540
catcaaaatc tgttagccga atcaggtgag ccctttgtta tttttgttgt ttatgatctg 600
gatctctgtt gattgaggaa attggtagat ctatggattt gttagatgag cgtgtgcgta 660
gatctgaaaa tgagatctcg atgttgaatc tgaatcgcgg ctggtatacg attcccgatc 720
tggatacgat tcaacatgca tagcatctga gaattttaca tagaattttg catgttcaat 780
ttttgtctcg ctgatttgag aattttagga ttgcttcatc taatttagtt ttgttgactc 840
gatgctgaaa ttagttttct gcgtttgaga gtttcgaatc ttccatctcc tgaaaatgca 900
gctcaaactc atatagtata tgtcaaattg aaacaagttt tttcaattac gtttctaaga 960
actcttgcta accagaacag gattgtacca agtaatttac atgattaaac ctgaatttgt 1020
actgatttga gcttacggat aaatggaaac aatgtgatag tagtatataa atttgggtat 1080
acgtagttgc cttgtgggaa gcaaatcttt taccagaggt ttctagtatc atatagaatg 1140
tatgaccatg gaaaactaaa catgagctta atggtgttta gatgtctcct attatttcat 1200
ttgcttaata attctctgtt ttttttata tatgatcgct cttttgcttc cgatttccta 1260

-continued aaggccaacc attattctca gatagagaaa agaagaaaga 1300

<210> SEQ ID NO 44
<211> LENGTH: 818
<212> TYPE: DNA
<213> ORGANISM: Arabidopsis thaliana

<400> SEQUENCE: 44
tgctaaacct cagcaaaatc atgtgttgtg ataagacagt ggcattagcc aatagcttaa 60
acaaaaaaaa gtactagagt acaacctctt attattgttt tcaatgtttt gtttttatat 120
ttttttcaga ataaaatata taatggttcg acgcatattt ttcaattttc ttttggttta 180
attaatgata aaatgattgc aactctataa atatacataa ttgtgaaata aacctaattg 240
ctatgttctt aattgtcaag aatttatctt cgaatgacac gaaaatcgaa tttgaagtac 300
gagacatgat ttgatctgtg tatattgtac atgtcctgga tcgataaggt tcccagtcta 360
gctacgtaca ctagtttggt cagggatagc tttatggtaa cgagaaagaa aggaagtgta 420
tccaatcacg atgaatcgtt ttctaatcta tttctttcag tcctattcaa ctgattacac 480
atgtcacatg tgcgccaatt ggatgctgtt gaaactttga aaatgcacca ctatagtgtt 540
aacaatgagc cggcgtgata ccatgttttc tttattttcg aaaggtgtat ccattattgt 600
aattttggac caaagcatat gacattgatg tgtctctggg cctactttaa atcaaatcgg 660
acttttctca ctcgattatt aacgacccga cccgactcga cccggctcgg accggataat 720
tacatttgta gctatgagaa gaaaaagaag accacactac tctctctatc tctctttctc 780
tctatctctc tctatctctc tcatttcttc ctgcgtca 818

<210> SEQ ID NO 45
<211> LENGTH: 349
<212> TYPE: DNA
<213> ORGANISM: Arabidopsis thaliana

<400> SEQUENCE: 45
atattgctct gtcttcttga ccatgtatct ttcaaaaatg cgaaggaaat tttgatagct 60
acaagtctgg gcttgaattt gatgaatccg aagtaaaaaa tagttttggg ctagattctg 120
cttcttaatt cggtctggta cagtattata ttatccacct ttgagaaaga ataaataatg 180
ggcctaaatt tcatcgaatt gggttttgga ttattgttag gcccagatag ggtttagatc 240
aaacagcatg ataattgata aataacaaaa tatataggca aaagctactc cgagattcga 300
agctgcaaag aacgcgaaac agtgagagag acagagagaa gatatagag 349

<210> SEQ ID NO 46
<211> LENGTH: 1000
<212> TYPE: DNA
<213> ORGANISM: Arabidopsis thaliana

<400> SEQUENCE: 46
ttttaaaatg aatcactaaa caagattcat tttctttcta aatagtgtaa agacgagtga 60
tgcatgcaac tgctctcctt tccgttggtc ccttgtcaaa atatacgacc gtgaataatt 120
cttcccatca tatttatctg tcggagagtt ccaacctcaa aacattctcc ttctcttatc 180
aattctttct aaaatcataa accaacaaac tgggcctatg atcaattatt catattcaat 240
ttagcctata actaaaacca cactgctttc gttacactgg ccttccgaca agtctctttg 300
actgttttta tcttaagcgc catcaagttt taaagaagac aaccccatat ctttcctccc 360
atgaatcatc gtgtccatat tgctatagtt catgaaaaaa ctaaatacta tcgacaactg 420

-continued aagaaaagat ccggatcttg tggaccgagt gaatggttgg gcccaattag aatggtctac 480
cctaacatct agccgtctac acgattgatc atacgtctaa gagggcgaaa ccaccaaacg 540
tttggatttt atctaaattg atgtacataa agctaacatg attttagtat aaacattata 600
agcatcatgg aaatcaataa gctaacatga ttttagtaga aacattatca gctaacatga 660
attactaaaa acatttattt tattttaagg aaaaacatac aatactaaga ttttttataa 720 catttttct ttgtaacatt ataaattgtt ttagtttcta cattaattaa atatataaaa 780
taaattcatt taaataatat aagaaaacgg aatctttgat taactgctga ttattggcca 840
ctgattaatt tccgacccca tcaatagttg agatcagaca tacacaactt aagtagacca 900
aaaaagcggt tggtgtaaga tcccaaactc acagattccc aaataatagt aatactcttc 960
ctcttctcaa ctctcaccag tcaccagcag atcatcggag 1000

<210> SEQ ID NO 47
<211> LENGTH: 647
<212> TYPE: DNA
<213> ORGANISM: Arabidopsis thaliana

<400> SEQUENCE: 47
aacgttctgt atatgctttg ttgtcgtatc agctaataat acatttatga gattcaacta 60
atgttaacaa accacgttga tcttcacaaa agggcatcag aattatcaaa ttgcatcaga 120
aatactgctc cactggtcca ctatctaaaa tacggcgtga aaaatgccaa aaattattga 180
acaaatacaa aatacaaata cagaagatca atttttttaa aaaattagaa tttattggac 240
ccaaaaaatt cagaatacta acgattttca acttcatact agaaaattag aaatggacga 300
atgtcaaatc taaaattcat atgaatgcgt aataaataac tctaaatatt tggattgcgt 360
aaaatccgaa tggtgaaaag taaagtccaa attaataaat ttagaaaata tgtctggctt 420
agatcagatc tcatatgcaa atggaaaaaa ataaaaatta aaaaggcaag ggtttggtgc 480
aatttagttt cagttgggtg gtgttaatat aaaaggccca taagcttcac acttcatcgt 540
ctcctctcca ccaagtgaat ctctttctct ctctcttttt ctccgcggaa ggaatctctt 600
cttctggttg cgtttgagtc cgtacgaaaa caaaagaaaa gagagag 647

<210> SEQ ID NO 48
<211> LENGTH: 687
<212> TYPE: DNA
<213> ORGANISM: Arabidopsis thaliana

<400> SEQUENCE: 48
taagctaatg cgcagttttg tttgtttttt atctggagtt ttttttgttt cagttactat 60
ttgatgatgg atgattacag cagtaaaaaa gaaaaacaca tattaactac tcagccaggc 120
ccagcccaaa tccctctcaa cgcagccagg cccagccgaa ttatgtgaca aaactaaaaa 180
tgatgaaata cacaaaattt ggaggatata aatgtaaaat aacaaaagct aaagggcggt 240
tccaactatt tcccaatctt tataatatac cctcgagact ttccaatctt tcctttttgc 300
ctcagaggcc attggcgaag aacaaagttt gaaccttttc ttcatccatc tctctccgtc 360
gcttcttcct aacgattcct tcactcgaat caggtaaact atttactctt ctctttctct 420
ttaggatcga ttggaaccct aggatctctg agtttttctt tcacatttag gatctatccc 480
tttaatcggc aaattagtat gtgagctttt gatgatttgg ggcttgaaac cctagatttc 540
agcttaatct gggtaatttc attgggttgt gaaatttctg tgtaattgta ttttggagaa 600

-continued gatattgatt tggttaggta ttaatcaatc tatatttctc tgttattggt ttaggtttgt 660
gaaggttttt tctagggttt cgaaaag 687

<210> SEQ ID NO 49
<211> LENGTH: 1000
<212> TYPE: DNA
<213> ORGANISM: Arabidopsis thaliana

<400> SEQUENCE: 49
gttttggccg aaaagaatat gatgaaatca tatgttagat gtcaaaatta cggaatcatc 60
tagaaaaaat caaaatgaat tcttctagaa gttaacaata gaaaccactc attcgccggg 120
tgaaatcaat tgactgacga gttgtctact aaacgagcgt tagtgtgagt taaacctcta 180
aagtttgata gctcgaacta ctatcgagat tcttcggaca atctttctta gtatcatctc 240
gatgttcatt gctataccat catttgctct cttatactca atagacaagg tagtagttag 300
ctcgtgcaat caataaaaag cggtcatatt ttgtgtgagt gagtgactca ttttttttga 360
agaagataaa tcgtgtaggt tatagcttat agagacctaa taaaattgac atttactaga 420
gtctgtccta aaacaacaaa aaaataattt tcctttattt ttaatttttt aattgtaaat 480
tctgttttgt tttagttttt ttagaagtta acaatataaa ccactcactc cctgaataat 540
attaatccta tcattttgca tgaatgagtg agtgtctcaa ttcctttgaa taagataaac 600
tgtacaggtt atcaattagc aaaaaagaat ctttttcttg gtttagattg aaaacatatt 660
tgtgtgttgg tcaactgatt tattcagacc aaaaaaaaaa aaaaaacctc agtcgtttaa 720
acgttaaagg ttcttgtttt aacgggcctt aaatggataa taagtccgaa ggcccattat 780
gttgaattat ctagaatcca aaataacttt aggtgattgg tgagtaggcg aattaaatgt 840
aagtggacat tacagaaaaa gaatcaagtg gcatcgtttt tttctttctc atataaatct 900
tttcacatta gagtcggcat aaaaattcca tttcgtattt ttctcttctt cctcttctga 960
aaaattaggg tttgagttct tcttctaatc gatcagaaag 1000

<210> SEQ ID NO 50
<211> LENGTH: 383
<212> TYPE: DNA
<213> ORGANISM: Arabidopsis thaliana

<400> SEQUENCE: 50
tacagccggt tccgtaagga ttacgggtta tgctgatgtg gcggaagtat ttattcccag 60
tattaattag catcagagta tacgtgtatg tcatctaatg cgtccattag atccaacggt 120
ttagagttca gcttttaaaa gcccaaaaga atgatgagaa gttgagacaa ttatagtcaa 180
ttttttaaaa gcccatgact taatgggcct actaattgat gggccaagta ttagaaatcc 240
gcggaggtag aaccagcttc gcatatatta agagtcactg ccttcactag gtttagggtt 300
ttctcagccg cttaagagct tatcatcttt gtgcttcctg caaatagctc tttgctgttg 360
atctttctcc tccatcaaca aac 383

<210> SEQ ID NO 51
<211> LENGTH: 373
<212> TYPE: DNA
<213> ORGANISM: Arabidopsis thaliana

<400> SEQUENCE: 51
tattgatttt tgtttgtgat tttaacactt tgtacaaaga ttgggtgagt atttgtcatt 60
tgagaagcgg aagcttcatt gtgataataa agacaagatg aaattagatg atgcaatgtg 120
actgaaacca taaaggtcac gtgcgtttat ttgctttagg cttctcgtaa tgaaagtgat 180
aatacatggg ctaaggccca ttaagtattt ctcttaagtt aagctattgg gtatgaataa 240
tgagctttat accacccaat aaggagactc gtcatatata attgaccact cctccgttat 300
tagggtttct gattctcgga gctaaaagaa gagcaagcag cggcgcagaa gttgaacaca 360
agtgaagctc aca 373

<210> SEQ ID NO 52
<211> LENGTH: 825
<212> TYPE: DNA
<213> ORGANISM: Arabidopsis thaliana

<400> SEQUENCE: 52
aatgttcaca cacattgatg gaaaacatgc cattacaaaa gatgtatata gataattttg 60
aaatcagtta acatacctat aagtgttcaa atgatagtat taggttagtt aaaatgttgg 120
cttaactaat tttgttttta gtaaatcata gatttggagg taaattttgt agtccccgag 180
atttaaaata ataacagatt ttaatcttca tctgaagaaa attgaacagt tgttttgttc 240
ctatctttag aaactactag ttcaatcctt tttttattat acagtaagta atgtcaactt 300
ttactataag attaggtctt tactctttag gataaaactg tttttaagta aacacaattt 360
tattttaaac tcaaaagtaa atatttgctt ttcagggatg tcaaataaaa tgatgatctg 420
aataataaaa caatggtaat tttggaaaac ttacagctta aaacttaagt actattgtat 480
tattgaggat tgtcttattt atcattcaaa attgaaaaat cattactttt taaatatgta 540
aattgtttta ttaaaacatt tttaagcctt aatgtgtatc caagggccct ttgggcttcc 600
tctcaagtcc cacatccact aatcacatga ttagctaaaa acccaactag taaattatta 660
ttattatctt ccgtaaacat ttaatttcgt tttaactttt tcctcattgt cgtataattg 720
tttttgtcgg tcgctaagat attttcacag cttcggagac ttcaggaaaa aaaaaaatca 780
tttcttctct gaaacgaaaa accaaagaaa cgagaagaag aagct 825

<210> SEQ ID NO 53
<211> LENGTH: 475
<212> TYPE: DNA
<213> ORGANISM: Arabidopsis thaliana

<400> SEQUENCE: 53
ttgatcctat cgtatataac ttcgatttaa caaacacaag tcgtaatttc taaaaaacaa 60
ttaactcaat ttgtttgaaa ataaaagttt cctttttctt cgtaacaagt gaagtcaaat 120
gtttttcact cgtatctctt acaacgtttt gatgagatga taagagaaga gtgggcccac 180
atatttgctt aacaatacac gttttagggt tacgtgtcac taatgttatt gggttcattt 240
aatctgggct taaaagaggc gtgtatcatg ttgtaatatt cccatttggg ctttcatata 300
atgaagttgg gccgacaaaa aaaaaaagga ctagggttcc caagtatccc actatatata 360
attttagtcg aagaaaattc ttttattttt ctcttgcaaa gacctctcag cagccaacga 420
cagttatcaa agcttaagcc gttttagggt tttatccttt tgctgagatc caatc 475

<210> SEQ ID NO 54
<211> LENGTH: 1000
<212> TYPE: DNA
<213> ORGANISM: Arabidopsis thaliana

<400> SEQUENCE: 54

-continued

```
atagagagag agagagactg actaatgagt cacatatgac gaatgagtcc agtttggctg      60
ccagtctgtc agcccctacc attacaccac ctctaaagat ttgtatttta tcataatcca     120
accaaacaat gcttacaaaa aaaagataat cacatcacat cacatggcct tcttcgtcgc     180
tgtaacgttt aattaaacta gccgccaatt tcttttaaag atttttttgt tttgtttttg     240
ggcttatgtt taaaccatat aatccataac ttcatttcta ttgctatttt tgaatttacc     300
ctataaagct accaatattg aatttttgta attcatttaa gtttattaca taaataattt     360
atttacttat atgattataa ttttttttat cggctatatg attgtaattt agatcagtac     420
ctaatcaagt ttctatcttt ttctatccgt tgacagaaaa aagaaaacaa ttttctatca     480
acaattcaca aatcaaattg gattagagat acaacaactt tagtcaaaat tctaacacaa     540
caattcatac ttttgatcat tcaaacatga ttttattttt tatttatcta gaaacatagt     600
aatgtcaatt ttgacaatta ttcattcaaa aaaaaatgtc aattttgaca agaaaactag     660
gaaaaaaaag aacaatagag gaatggtcaa aaaagaataa aagaaaattc gaggaaaatc     720
atgcttctta gaagtttttt gtttaattag cttgactagt aaatagattt gaccggataa     780
ataaccggtt gaaaccggta acctttaacc ggtcttcata ctataagaac accttaaaca     840
agtcgtctcc ttccacttct tgctttattc ctctcatacc gtttctctc tctcctccgt     900
cgtctctgca gaatcactct ctcgccggag tttttcacct gcagagctct cgattttttc     960
tctcgagcat catcatttc gtcggatcaa tcaccaagag                          1000
```

<210> SEQ ID NO 55
<211> LENGTH: 1000
<212> TYPE: DNA
<213> ORGANISM: Arabidopsis thaliana

<400> SEQUENCE: 55

```
atccggagtt gatatggcgg tgaatgatag ttggttcgat ttgatggtgt tcttgttcgt      60
gagacagatt tttttcgagt agttaagctt cgctccttgt ctttgatttg catatttggt     120
agtgatttga tagcgttttg tagaatttta tttagacgta aattggtggc atatttattg     180
taattttaca tatcagatta tgagtttgaa tggtaacaca atacagcttt atataatttt     240
gtacaacttt cacagttacc aataacaaaa actttattaa aagtgttata aaaagtttac     300
tctcagcttt tttgtacaac tctttctaac agctttgcac tattcaaata aagctaacag     360
ctaaaaaact tgtacagctt ttggttacca atcagacact atgtaaattt ttggtttttg     420
cttttgttac ttttgagagg tcggctcttt tcttgatagg ataaaattgt tgttattttt     480
gagtttgcta gcatcaataa tcacaattaa gatgtatctt attttgagag gtcggctctt     540
tctttgatag gataaaattg ttgttatttt taagtttgct gagagaattc aagatgataa     600
aaaaattaaa aaaatcacaa tcacaaggtt ttaataataa ggtttcaaat ataaactttt     660
tttttttgc acaaactttc aaatataaac aaaaaaataa ttttaataca aagtctatat     720
atggagaaaa taggaagcca aaattgataa ttcacaaaat taaagtaaaa tctattagcc     780
gacaaaaaaa aaggtaaaat ctattaaaat atagataagg ttctagaaat taaataaatc     840
tattaccaat tctcaaaccg acataagtac gaccaaaaaa aagtttataa ataaaagtca     900
caacgagcct taacgcgtag aatcttcccg tactttactt ttccggagga atagaaaatt     960
gggggctagg gttcgcaatt gtagttttcg agcgaagaag                          1000
```

<210> SEQ ID NO 56
<211> LENGTH: 675

<212> TYPE: DNA
<213> ORGANISM: Arabidopsis thaliana

<400> SEQUENCE: 56
tactctgttg aaagaagttg taagctttaa tgataccatg gattactgtg ttctatatgc 60
gacaaatgca agtgtagata ttagaaccaa ttgtggcaga aatccaatga cgtggagaaa 120
aaaagttatg cgctaggact cagaccagta cgttgccact cgacttctta gtacgatttg 180
ttaggataga tagactatag caaagaattg accatcttga ggaagggtta ggggagttgg 240
tctgccgcat agagtaaacc aacgtgactt ggagctatga gggaacacta atgtgacata 300
aagacaactc tcagtgagac ctaagtttaa gttgtacata ttgagaggat atctagttta 360
ttgttacaaa tctatccttt tcaattaatc ttttggggtt aatggtgata aatattcaac 420
tatacataac actttttgtt tacgtttttt agttttccaa agtaagagca tacaaattgc 480
taagccgaat ttctcccact cctacttgtt tatatgtaca atgggctggg cctataaggc 540
ccaatgtttt gtgtgtcaca tttcgtcacc cacagacata tatacttaga ttgaagctaa 600
agctgcagtc tccgtctctt cgcttctagg gtttcatcaa ccaaattcgc tttcgccgcc 660
tttccacaag caatc 675

<210> SEQ ID NO 57
<211> LENGTH: 550
<212> TYPE: DNA
<213> ORGANISM: Arabidopsis thaliana

<400> SEQUENCE: 57
ggatcaaatg aacgcacatt aatatgacgt aacgatgatg acaattctgt ttaatagtat 60
cttattgttt acagatacag aaaaataaat taagtgggcc tttcaataat taataggttg 120
gtgaaatgtt accttctctt gatatttttt taattttcat ttattatgag tatgttgcgt 180
tatgaaacaa ctcgcattaa tttggttata gattggagaa agaagaagtc atggtcaaaa 240
ctcaaaaatg taaaaggaaa caagacgtgt atgacgacgt gattgataat ctgaggagat 300
acctttgggc cttataagat gggccgaaaa agtaatagta ttagcctcta ttcggcccga 360
ttaatttcag gggaaatttt ggtaataaag tggaaacgac gtcgtgacaa aactactgtg 420
tagactgaga aataaagaag cccttgattt tgcccattgc agtcatctct ctcgaatctc 480
tctctataat ccgatctgag aaatttcgcc ggagctaggt tttgttgttt accgatcaat 540
cctttaatca 550

<210> SEQ ID NO 58
<211> LENGTH: 679
<212> TYPE: DNA
<213> ORGANISM: Arabidopsis thaliana

<400> SEQUENCE: 58
tgtgaattct tattctatgt ccccacccac ttgcctactt tttattggct ctcctgtttt 60
agttttagta cttccttcct cgttgacttc tttccttaac tttcccgcca ccttgattaa 120
ttgaatcaaa tcaactttat cagtttttac cctcttttct tactccaacc aaaagattgt 180
tagaaatgaa aatgagatta tggtaacaaa acctccattg attcgagtca atatgtcttt 240
tgaatgatat gaatcgttgg ctattacatc ttaagtagac tttataatta gacgagataa 300
ttaatagaca aagtcatcta tgattataaa agtattagag aatatttgga tccaatcgaa 360
atgtggtgtg ggaaaagaaa catgttagat tgtggcagga gacaggctgt gttatcttca 420
ttgttctact gcaagtgcaa acacacttcc cttctttaat ttggacggta tattaataca 480
ctttattatt agaatgggct tttataagta ggcccattat caggtgaaaa acaattgggc 540
ccatcattga cttttttttgt taatgggtgg tggtggtggt gattaatatc gtcgtcggag 600
gtttcttgag ctgaagaaaa cattcgtaga tctatttccg catctgctta aacacctaca 660
tcgtcgtaga tcgcaaacc 679

<210> SEQ ID NO 59
<211> LENGTH: 1000
<212> TYPE: DNA
<213> ORGANISM: Arabidopsis thaliana

<400> SEQUENCE: 59
aacgaaggtg cctctcgatg aaggagcttc aaaaggaagc aaattaggtt agggctctat 60
ggaataattc ttgatgttac catatatttt atagaaatat tgtacatgac gaccacctgg 120
tctcagttta cgacacgtgg gggatttgtt tgtttgtgtt gtctcggtcg ttgttgttac 180
gtgccgacaa ggggaatgat attaacatag agggggaaaa aagagagaga tcttcaatgt 240
gaagtttgct ctgtgtatat aaatattttt acatctttcg acttattcta ttaattcttc 300
aaatcataat aaaaattaaa ccacttttga ttacttgttt cttaatttcc aagataatta 360
attataattt atctattaat atttgtctac caaaatctaa cacttaaaat tagcaattta 420
tcttaattaa ataaatattg ttaaactttg tcttttgtca cactagtcat aactgagatt 480
gatcagttcg ttccatttct atagaattca acttatacgt tgaatccgat agaaagaaaa 540
tagaaaagta atttgaattt tttttcatcc acaaacaaaa cttgttgaaa cttgaaacat 600
tgaataatct aataaaagta taaaaaaaaa tataaaaaat atatgtttac caattatcca 660
atttatttct gcatattttg taaattaaaa agtaattcaa atacgtttca tgtcgacaaa 720
atgttgaatg tacaagtggt ttatgctaat ttaatcactg tcaattcact gaaacgaata 780
aatcgagtaa ttactttttt aattgacaaa ttacaaaact atagaaacat taagggcata 840
attgaaattt ccaataaatt gaagagcaaa aaccctagaa aattgacacg gactataaaa 900
aggtgacgaa gcggcgcttt ttcggtttgg tcatcgtgct cctcttctcc tccaccgcac 960
agatccaaga cattttgatt acactccatc gccggcgaaa 1000

<210> SEQ ID NO 60
<211> LENGTH: 696
<212> TYPE: DNA
<213> ORGANISM: Arabidopsis thaliana

<400> SEQUENCE: 60
cgagtccttc acattaaacc tgatcataat catcatcagc taccacagta tcgcacttag 60
aacacacaca atcaaattca aacaaacttt cgcttgacaa tttcaatcga aaccatatct 120
tttcaagttt agctaactat cggaaagaaa ttacataccg agactaatga ttccacagac 180
ttgagagagc gcaaagatcg aagaacattc gtcgagagaa agaagaagaa agtgggagga 240
gcgtgtatgt gccagagaag aaggagcagt ggatgattta tgcgcttggg ctgtcgcttt 300
ttttcaactt tgacgctcca caaagacaca acaacgacat ctctctattt caaaaaagtt 360
ttattttttt attcatttta aatacatttt aaaaaaatta acaaataaat cgccatttgt 420
tgttcttttt tcaaaaacgg aatacgaggg tgcagttatc ctctacgagc aggtgcatgt 480
aataccatct gatggatttg acttatcgtt tatccacaaa agattcaaaa tcttcccggt 540
ttttaagttt gggcttcata aggcccaatt agtggcaaat ccatcacagt ccactagggt 600
ttttgagaga ctggatataa aatttgattt tgttcattgt tgtcattcgc cgtaatctga 660
agaagacgaa gcaaatcctc ccacaaagaa tcatcc 696

<210> SEQ ID NO 61
<211> LENGTH: 700
<212> TYPE: DNA
<213> ORGANISM: Arabidopsis thaliana

<400> SEQUENCE: 61
aacaccacat tttgataaga attatagaac tagtgatttg cattttaaat gttgatacat 60
atagaataag cataatcaaa caatgattac tgaaaaatat ggtccattaa tatcgtataa 120
aaatggttga tggacattga aaccctagtg gagaatttgt cacataagta aggcccaaag 180
tttttgaccc acaaacatat ccattaagtt atagtttagc gaaacccctt taacaaaaaa 240
gaaaattttc aactagtgaa ttgtttctag agagttctgt acaaccatcc aaatttcaaa 300
catggtataa aagatgttat tgacaaaata aaaatggaaa cagtgaaacg tatagtcgga 360
aaatggaata aaatctagat gccatatatt attcttactt gttctaaagt ctttaataaa 420
aatagtcggt attacttgga caaggagcaa aacaatatgg aaaaaactct tctattctgc 480
aaaaggcgtg cagcgcatcg ttttggcttc ttgcatcaga gctgactgtt ctcatccaac 540
ggctgttatt aaaacaatcc aacggttttg gctaaatccg tgacgtcttt atatatcgaa 600
ccagaccacc aacccatttc ctcagctact actgttgaag cgattctcac taaaaccctc 660
gaacacatcg cctttatctc tttctctaga tctactcgct 700

<210> SEQ ID NO 62
<211> LENGTH: 500
<212> TYPE: DNA
<213> ORGANISM: Arabidopsis thaliana

<400> SEQUENCE: 62
acgttaggtt aatatgattg gagacaccac tcacttataa tatattcttg ctgttctatt 60
aaggcaagac tggtaaaaca tctcaacaaa atattgcaat tatttgtttt tacgatataa 120
tctttttttt ttcatcaact tttttaatga tataatctaa atgccaaaag acatgtaaaa 180
tgacattttt ttttttgttc aaatgacatt tctaggtacc actattcagt gcataaaaat 240
aattttatga ttaagaaaat aaattcgagc ccaagcgcaa gactcaaaaa taaatcgaca 300
tctcaaaacg ggcccaatat aaagccataa ttcgtaaagg cccaatataa agccttaatt 360
cgtaaaggcc caataaagaa agtgagagtg tagcgttagg gttttaagaa atcctataaa 420
ttagttcatt cgtctctttc gttcctctct gcgtgcccta gttattcaga tcgccgaatt 480
tgcagtaagg agacgaaaat 500

<210> SEQ ID NO 63
<211> LENGTH: 1359
<212> TYPE: DNA
<213> ORGANISM: Arabidopsis thaliana

<400> SEQUENCE: 63
aataacaata tatatatata tatatattta tttatttata gatattcata tatatatata 60
agaaaatata tagatatggt catatggata tggttgtgga cttgtgatgc gacaaaaaaa 120
aattgaacaa agtggatctg gttaggtggc cagcatcttt tacggaaggg aaaagttgga 180
tatattacaa tatttttggt ggaccatgag caaccccacc acaaagtgca tgtgaagtga 240

-continued

```
ccacttttct gcgagctgat ccaactaatc aataatggta acaaatacaa aaaataaacg    300

ctctaatttt atttcagtca aatgttttta ataattttcc atgtccgaaa actttaaaat    360

cttttattat tactaagtta agaaaattgc aaatgtaaga attatttgtt tctaaataga    420

taatattaat accaaattga tattccaaaa catattattt tcttgtttga tttgattgat    480

aatctattaa ctgataaaca acaatgatag aaatatgttc tctaattctt cttctctagc    540

attcaaaaat tcacatccaa caaaaccata aattttgtaa ttttagatac aattttacac    600

taaaaattaa taattgtaaa gcttgtaatt atattcccaa actttattct ataaattaaa    660

acttagcatt catattgttg aatatgactt ttgaattttg ttagtgggac ccttttatac    720

aataagtggc ggctacaacg aaaaatcaaa gtagggacca aaatgataca aatcgtaata    780

acggggtcaa aataacataa tccaaacttt taaatagcat aaatacaaca actctcaaga    840

cctgtacaag ctatttcacc tacttcatca ctcatcacca gcttcgcatc ttcttctccg    900

gcttgatctt ctctcgtttc tagatctccg acgatcggaa tatcaaatcc gatcgattaa    960

ttctgtcaat cacacaaaaa ccgaaaacca aaaaaaaacc aggtgagatc ttacttctcc   1020

ttctcctctc tcgatctctt tcgctatcta taatcagata ttttcgttga ttggatacga   1080

aatgatttac tttcgcttgc ctagattgta acgaagtttc gttgtttgtt ctgatctgat   1140

ctctggaatc tacgcatgtg taaactcgtt gattgatttg gttttggtgt atgattacgt   1200

tacagatcga taaaatcgat aaaacctta agctctgttc atgagattga ttgatttatg   1260

aaaaatctgg actcgatttc aagtgtggat ttgatttaca gctttgattc ggcgaaatag   1320

tttcgatatt taagcttcat tggtttgtgt aatgtaggt                          1359
```

<210> SEQ ID NO 64
<211> LENGTH: 1230
<212> TYPE: DNA
<213> ORGANISM: Arabidopsis thaliana

<400> SEQUENCE: 64

```
attttacaca ttcatggtga aactacttgg tatatatatg caaatgaata tgcatgtgga     60

tggtacatgg cgtttgattt tgcatatagg caatttattg atcaatactt ggtgtagttg    120

gtacattaaa gttgcattat agacaaacaa aattcggctg tcatgcttga ttgatctata    180

gatgatttca taataaaaaa atattgtcat ggataaaaat agtgaagatg ataacaaaaa    240

gaacagaaca caaagaagaa tctcatttct tttttgatta ataaaaggat ataaagtcat    300

tagttttttt attcgtctca ctcgacacta ataataacta aaattgttgg agaattaaaa    360

gtaagaaagc aatgctataa aataaagtaa ttgttgggaa tggagcatgt aaaattatca    420

ctcataacta aaattagcaa tgttataaag tatttaagta agaaaatgtt gtagataatt    480

tgttaaatga ggtgtcccta tgtcttttag gtgcggtgag tccatgtgct tatcctgaca    540

gcggtccaac ttaaccggcg gttcatctcg accacatatt caactgcttt tttaatatga    600

ttttctgtat tttcttacct gtcataatct acatttaaac gttaaaaaat gtccacaatt    660

ttatttattt tattagggta caataacgac atttgattag agtaaagaaa atagttgcaa    720

agcgggattt gaaactctgt ccacatactt taattatcat taatcaataa caagcattat    780

cagtattcag cagcagcaaa gatgataacg ttaattatac tatcatgcaa ttaagttaac    840

taattaacta tcatcttgtt tttgttttaa ttttgtttcc atcatcttcc aaccttgagt    900

ttcggtcact ataaaaagcc accactctct ctgcttctct gcaacacata acccactcac    960

agaaaaacct agaaagctct agagagaaag agagagagag caggtaagtt cactggtttc   1020
```

tccgatctaa cgatttcgaa tatagatcct gtgttagcta ggtagcgtaa ttcaaatctt 1080
agcatgttta ggattcaatc aggaacaaat tagggtttac aaactcagta aatgggggac 1140
tttgatgtta gttccagctt tgttctgctt ggaatcattt gatttgcaga tgttttaatc 1200
tgtgtttgtg tatgttatga cctttcaggt 1230

<210> SEQ ID NO 65
<211> LENGTH: 1180
<212> TYPE: DNA
<213> ORGANISM: Arabidopsis thaliana

<400> SEQUENCE: 65
cgaaaaaaga ggagagattc gattcaaata cccacataga acggacaagg tcaataatgg 60
gcccactatt cttttgagag cccatctcaa caagttgaat catctttttt gtgtactctc 120
acttcacctt ttgacaaaaa gtcatggaag ccaaactttg gaacactact ttactttgcc 180
aacatcttgt tttgttgaat accttttca aattggaaac caaagacata tctaaaggga 240
aaacctgtag gacaataaaa caaagaagtg atagctaaag tctaaactaa tctcaatata 300
tgtaaatcaa agagataact aatgaaaaat atgaaaattt tcgcgaggat taatgaacaa 360
aggaattttt tttttcctt ctaaaatttt ttattagaca attggtatta caatgacaac 420
tacgaagcta atacaaaact tcggaaacca acttattaca taagcaaaat tatgtgtcat 480
atactgaaaa ttacgaaact gaaaaagtga atttaacgat ttttcctttc gataagcttt 540
attcgctaac atgttaacat gttagaacat agaaaatatt gaaaaaaaat ttatgtttaa 600
attgtcaaat ggaaatatac tttacacttt tatttgtatt aattgttact ttgctctcct 660
agttataaag aagtaaagtc tatgattttg ttacttcttt ttttcttgta aatctttata 720
catgtaaaaa gcttttgttt ccaactctaa tcctcaatat tttatttttc tgtttattgg 780
aaaagggctg taaactaaaa ttatttactt gaggaacgat tatttaggtg ataagagtgg 840
acaaagatcg ttgacacgtg gacggtctac aaattctaat tttgcctata aatatcaaag 900
ctcctgaata tgtaagtttc attcactgat tatcgtttaa ggcaaattaa gatcatcttc 960
ataaatcttc tcagatctct tccaattttc tagaaaaaac aggtacgcgt ttctcgatct 1020
ctcataattc tgattcttct ggtgtttctt gtgattttct gaatcaaaaa ccctaatttc 1080
tcgatgagat tataatacaa ttttaatcaa atctttctgg ttttaattat tcatcatttt 1140
taacccatga tctttatttt ttttggggct ttgtacaggt 1180

<210> SEQ ID NO 66
<211> LENGTH: 1009
<212> TYPE: DNA
<213> ORGANISM: Arabidopsis thaliana

<400> SEQUENCE: 66
tctctctttt accactttag cggactcctg ttgataagat ttgattttgt tttcgaatat 60
atgtagtaac tgaattgagg attttgagtt tgatttcaga aggctgataa ataagttgag 120
agttcaatcc ctcattgtgt atgataacca tcaccaattt ttctactaca ttttttggct 180
ctgacctcat ttatcaaatt ttgataggaa aatgtcactt tggtttgtgc caaaaaaggg 240
caggctctgt tatattattg acggcagaaa atggtaggca tgcttaaacg tatgagttag 300
tgttaaatta ggtagaaaaa tgacaagctt ggtatataac gttcaataat ataaggaaga 360
tgtggcagag ttagtgttga gaatgggcta gtctacttgt gtttaggccc atatatataa 420

-continued

```
ggcccatata tatttgaaga ccacaaataa ctagggttta caaatttggt tatatagctc    480
tctctctcga gccgcacata tttcgtcttc ttgatctaat cgctttgagc tgttagcaga    540
gagcagtcga caatcaggta ctatcttttt ctcatctctc ggctttcttt tcttttaaaa    600
taaaaattct gtttagttta gagaaattgg gattgcctaa gaacttttat catgtttatc    660
attcgaaaga ttttcaacat aggaagattt tttatctgaa cctgatcctt attgattatg    720
tgaaactttt gatgtgaaat tttgcttagg gatagttaag tgtggtggtt taggtgtgta    780
aagcagaaca ctttatccat gaagatcttg tattaatctt aatagtttcc atgggataga    840
aaattgatat gttcctccgc tctgtttgag ttgacttgtt agatttcttc attccatttt    900
ttactttagt ttacgttaaa acattgtttt gtgaataaat atatggatta ctgttaatag    960
ttgtgttgat ttggagcatc ttaaacattc atgtatttgt tttgtaggt              1009
```

<210> SEQ ID NO 67
<211> LENGTH: 1237
<212> TYPE: DNA
<213> ORGANISM: Arabidopsis thaliana

<400> SEQUENCE: 67

```
atcatcattt tatatatcaa tctatatatt tatcatatga ctcagactat catgagacgc     60
atttttttta agtattatga ataatatacc acttgttcac gttttaacgt ttgaaaaaca    120
tgattttgct actttttacg attcaaagta tttattaaga atttacgttc ttgaaaagtg    180
attatactgt atatataact ataagtaaat aaaacttttt tcgacgaaat ttctgatgat    240
aaataaaagg tcggatatat ttgacttttt tttttttttt aattattttt tgacgataaa    300
tttttcgttg aaaaatcatc gaaattttcg acggattcca atgatcaaaa attcgtcaat    360
aatttccaac gatattctga ctaaactaaa tctgatgaaa tatttttgac ggctttccaa    420
ccaaaatatt tcgttgtgac ttgtcaaaaa tccgttagaa tactaagcaa cttttcgaca    480
gattttcagc aaaaatattc ggtaatataa cgtgttaaaa atatgataaa aaaaaaaact    540
tgatgaatct actaaaacta aattttcaat catatatatc tattattcat atatttcatt    600
cattttatta tttttctctt aacaattatt tagttattct ggtatcgtgt aattatattc    660
atatgattta ttctgatatt gattcggtta gcatccggat aaatctgggt tgggcttttt    720
aacttggttt ttctaagaaa aattctaata tgatttggtt agcatccgga ttagtctagt    780
ttggtaggcc tgcctttgtg attcttaact cggtcttttg tatgggtttg aacaattact    840
acaccattta gattcttctg acccatatca aataaagatc cacttaggcc cattagggtt    900
agaacaaaca tgaggttgca gaataaaaag ggttcatttt cctcactctc aagttggatc    960
tcaaaaccct aatatctgaa cttcgccgtc gagagcatcc aggtttgttt ctcttatcca   1020
aaaatcttct gaggcttata aacattttca gatctgttga ttgtttgttg tagattatga   1080
tgatcttaat cagattaatt agaaaatgct tatgtatcat tggttattta gtgtagttta   1140
tgatgatgtt aatggaatca tttcgttaat tagaaatgct tgtggtatag ttgttgtagt   1200
cttgtgaatg atgatttgag tatatgtttg cgcaggt                            1237
```

<210> SEQ ID NO 68
<211> LENGTH: 1088
<212> TYPE: DNA
<213> ORGANISM: Arabidopsis thaliana

<400> SEQUENCE: 68

```
taaaaaaatt tgttcggaaa atatcacatt tctttcacta gacaagcctt gttaccacac     60
```

aatgtatcaa tatgatctaa agggcaaacg aaagatcctg acatgaaacg tttaattctc 120
attttctcca aattttattt tttatgtgaa gtagataaat tagtatatat atatatatac 180
caaactagtg tgttatgtta tggcaaatgt tatatcaatt cgaaggttcc gctattgcaa 240
tattcattaa ttttttcata ccaatactat ttttcttttct cttttatttt gtttttttaat 300 aaataaaaga aattaaggat gattagtaag gaagtcgcct accaagagat tcacctacca 360
cggtacactt caacaccgaa gcagagttgt tgaatccact ttttattccc ttctctaatc 420
tctactcacc aagtctccac ttttttttct ctttattata tacatttaaa ttatttaata 480
tacgccaact acatacatat ccagtgtaat ttctcgttac gtcacacccc tttcgtaatc 540
gtctaatttc agaaaaatat ccagaggttt aaatacatat tcccatcatt aaatctagac 600
ataaacacat catactcaca aaatttggca gcaaacagtt actacagacc cataaatgaa 660
aaaacgtatt cacttgtttt caattttcac ataaccactt ccctgagttt ggtctcaatt 720
tgattgcccc gccgaggcat tactacgcca agtgcgatta aggtcccata cagtgtaacg 780
ggacccacta taagacagcg accgaccaat tgcgtgttag gagagtttca ccaaccccgg 840
accggttttt accggatata acagaaccgg tacgaaccgg tctcattatc ttccatcttc 900
tttatataga cctcatgcca tgtgtgtgac tcaccaagaa aaacacaatc gtttaatctc 960
acccaagaag acaaaaacac agagagagaa agagagagaa caggtctgtt tttttgtttt 1020
actcaaaaac tctgcttttc aattcaattt cagcaatcta aatctcaatt aaaaaaatca 1080
acacaggt 1088

<210> SEQ ID NO 69
<211> LENGTH: 663
<212> TYPE: DNA
<213> ORGANISM: Arabidopsis thaliana

<400> SEQUENCE: 69
atatttgtgg taatgtgtta agagttccta ttaattacca taagtaaatc acaaacataa 60
ataaaatgaa aataattatg ggctttaagg tctggaggac tactgaaatt tgggagaagt 120
agttggaaaa agaatattag tcgataggta ggaaattgat attgcttgtg gaatggagga 180
aaaaattgaa cgaaaaagaa gtttctagaa ttctaatcac ataacataaa tagggtgaat 240
atttgggaaa agtaaaacaa taggggtcgg tttgatatta ctagaagata agaaacaaaa 300
aggaaaataa gaataaagga aaaaaaaaga gctctctttt ccaacaagaa acgtagagag 360
atataattag agaaaatctg tgctctttca gatcccatta tcacaaatcc atctctctct 420
ctctctcaga gaagaaacca aagaagaaga aaaagctctc aactttcttc gatttctcag 480
ggaactcttt cgttaatctc aaactcaatc aggtaagtac ccagatctct gattttggtt 540
ttccgatcgg gattttttttc ggatcttctt aaagtctggg tttttcgatt ttggggatta 600
gggttttggt tgatcttgtg tttctatagt tgaatcttaa tcttctttgt tgttgttaca 660
ggt 663

<210> SEQ ID NO 70
<211> LENGTH: 936
<212> TYPE: DNA
<213> ORGANISM: Arabidopsis thaliana

<400> SEQUENCE: 70
tgctaaacct cagcaaaatc atgtgttgtg ataagacagt ggcattagcc aatagcttaa 60

-continued

```
acaaaaaaaa gtactagagt acaacctctt attattgttt tcaatgtttt gtttttatat    120

tttttcaga ataaaatata taatggttcg acgcatattt ttcaattttc ttttggttta    180

attaatgata aaatgattgc aactctataa atatacataa ttgtgaaata aacctaattg    240

ctatgttctt aattgtcaag aatttatctt cgaatgacac gaaaatcgaa tttgaagtac    300

gagacatgat ttgatctgtg tatattgtac atgtcctgga tcgataaggt tcccagtcta    360

gctacgtaca ctagtttggt cagggatagc tttatggtaa cgagaaagaa aggaagtgta    420

tccaatcacg atgaatcgtt ttctaatcta tttctttcag tcctattcaa ctgattacac    480

atgtcacatg tgcgccaatt ggatgctgtt gaaactttga aaatgcacca ctatagtgtt    540

aacaatgagc cggcgtgata ccatgttttc tttattttcg aaaggtgtat ccattattgt    600

aattttggac caaagcatat gacattgatg tgtctctggg cctactttaa atcaaatcgg    660

acttttctca ctcgattatt aacgacccga cccgactcga cccggctcgg accggataat    720

tacatttgta gctatgagaa gaaaaagaag accacactac tctctctatc tctctttctc    780

tctatctctc tctatctctc tcatttcttc ctgcgtcagg tacctttatc ctcgatcctc    840

gcactctcac tatctgtaga catgttattg aaaaacccta tctccgatta ttagttttct    900

gattttcatt tcattttgac gccgattcac ataggt                              936
```

<210> SEQ ID NO 71
<211> LENGTH: 753
<212> TYPE: DNA
<213> ORGANISM: Arabidopsis thaliana

<400> SEQUENCE: 71

```
atattgctct gtcttcttga ccatgtatct ttcaaaaatg cgaaggaaat tttgatagct     60

acaagtctgg gcttgaattt gatgaatccg aagtaaaaaa tagttttggg ctagattctg    120

cttcttaatt cggtctggta cagtattata ttatccacct ttgagaaaga ataaataatg    180

ggcctaaatt tcatcgaatt gggttttgga ttattgttag gcccagatag ggtttagatc    240

aaacagcatg ataattgata aataacaaaa tatataggca aaagctactc cgagattcga    300

agctgcaaag aacgcgaaac agtgagagag acagagagaa gatatagagc aggtaacttt    360

cctctgcata tttatatctt tgaaaattcc atgataggct aaatcgatct atacaaatct    420

gctttgttga agagctattt gatgtgttgt ggtagtcgta ctcgctattt gtttgttttc    480

tatgatgtga aatagattta attagggttt atgttctatt ctgggtggtg atagtaacac    540

ttaggtcata attaatctgt aattttgctg ttctgcgaga ttatttgtct gctcatctga    600

aacttcatac gaatagatct cttgtttaga ttttctattt gtaggtttaa ttaaagaatc    660

ttgtttatct tataatccag tttcttgtgt ggaattgaaa tgaatttgtt tgagaatctt    720

atttctcttg tgtgtgtgtt ttttttggca ggt                                 753
```

<210> SEQ ID NO 72
<211> LENGTH: 1440
<212> TYPE: DNA
<213> ORGANISM: Arabidopsis thaliana

<400> SEQUENCE: 72

```
ttttaaaatg aatcactaaa caagattcat tttctttcta aatagtgtaa agacgagtga     60

tgcatgcaac tgctctcctt tccgttggtc ccttgtcaaa atatacgacc gtgaataatt    120

cttcccatca tatttatctg tcggagagtt ccaacctcaa aacattctcc ttctcttatc    180

aattctttct aaaatcataa accaacaaac tgggcctatg atcaattatt catattcaat    240
```

```
ttagcctata actaaaacca cactgctttc gttacactgg ccttccgaca agtctctttg     300
actgttttta tcttaagcgc catcaagttt taaagaagac aaccccatat ctttcctccc     360
atgaatcatc gtgtccatat tgctatagtt catgaaaaaa ctaaatacta tcgacaactg     420
aagaaaagat ccggatcttg tggaccgagt gaatggttgg gcccaattag aatggtctac     480
cctaacatct agccgtctac acgattgatc atacgtctaa gagggcgaaa ccaccaaacg     540
tttggatttt atctaaattg atgtacataa agctaacatg attttagtat aaacattata     600
agcatcatgg aaatcaataa gctaacatga ttttagtaga aacattatca gctaacatga     660
attactaaaa acatttattt tattttaagg aaaaacatac aatactaaga ttttttataa     720
catttttct ttgtaacatt ataaattgtt ttagtttcta cattaattaa atatataaaa      780
taaattcatt taaataatat aagaaaacgg aatctttgat taactgctga ttattggcca     840
ctgattaatt tccgacccca tcaatagttg agatcagaca tacacaactt aagtagacca     900
aaaaagcggt tggtgtaaga tcccaaactc acagattccc aaataatagt aatactcttc     960
ctcttctcaa ctctcaccag tcaccagcag atcatcggag caggtcctac atctccgatc    1020
ccagtttctc attcgatttt ccgttttccc ttagattttg catcttatct tcgtgagatc    1080
cgaaattctt gagttgtgtt gacttggatt tataaatcta gagttatgta gtaacaagtt    1140
tggggataga tctgatctga tttgctagat taatgttact tttctaagtc taaatcacag    1200
agaaattgct aaaaacttac gtctttataa ttgaatgtga tagttggtgc tgcttaagat    1260
gtctctgtgt gatcttgtat ctgtagttaa agctagtaag gttcatgtag ttcatgtatg    1320
ttctgatgta tgaacttttg ataacccact taatctaggt ctctgattgt gtggaattag    1380
ggacttatat gacaaagttt acatttttg tgtgtttcat tttgatggtt atatataggt     1440
```

<210> SEQ ID NO 73
<211> LENGTH: 1056
<212> TYPE: DNA
<213> ORGANISM: Arabidopsis thaliana

<400> SEQUENCE: 73

```
aacgttctgt atatgctttg ttgtcgtatc agctaataat acatttatga gattcaacta      60
atgttaacaa accacgttga tcttcacaaa agggcatcag aattatcaaa ttgcatcaga     120
aatactgctc cactggtcca ctatctaaaa tacggcgtga aaaatgccaa aaattattga     180
acaaatacaa aatacaaata cagaagatca attttttaa aaaattagaa tttattggac      240
ccaaaaaatt cagaatacta acgattttca acttcatact agaaaattag aaatggacga     300
atgtcaaatc taaaattcat atgaatgcgt aataaataac tctaaatatt tggattgcgt     360
aaaatccgaa tggtgaaaag taaagtccaa attaataaat ttagaaaata tgtctggctt     420
agatcagatc tcatatgcaa atggaaaaaa ataaaaatta aaaaggcaag ggtttggtgc     480
aatttagttt cagttgggtg gtgttaatat aaaaggccca taagcttcac acttcatcgt     540
ctcctctcca ccaagtgaat ctctttctct ctctcttttt ctccgcggaa ggaatctctt     600
cttctggttg cgtttgagtc cgtacgaaaa caaaagaaaa gagagagcag gtctgtcaaa     660
tgtttacgga tacacgtttc tgtatcaccc atctctatgt ctaagctcgt tagtattaac     720
aattcttgct tgatttgctg gtattgatac ctacgaaatc cgtaaatgtt gttcatcaga     780
tccgagtctg tagattttat ctctcagatc tgagtttttg ttttggctta ttataatcaa     840
atttcattgc tcggaacata gtcagactcg tttgagtgtg aattgttgct attgatacat     900
```

gtttagatga aatgttctag ttcagatctg gattttgatt agaataacgt tcttaggttc 960
atcacaatgt gtgattcttc gcctgtgttc ataggatttt taaatgatgt gaatgtaatt 1020
aactaatact ttgttttgtt tctggttggt gaaggt 1056

<210> SEQ ID NO 74
<211> LENGTH: 1112
<212> TYPE: DNA
<213> ORGANISM: Arabidopsis thaliana

<400> SEQUENCE: 74
gttttggccg aaaagaatat gatgaaatca tatgttagat gtcaaaatta cggaatcatc 60
tagaaaaaat caaaatgaat tcttctagaa gttaacaata gaaaccactc attcgccggg 120
tgaaatcaat tgactgacga gttgtctact aaacgagcgt tagtgtgagt taaacctcta 180
aagtttgata gctcgaacta ctatcgagat tcttcggaca atctttctta gtatcatctc 240
gatgttcatt gctataccat catttgctct cttatactca atagacaagg tagtagttag 300
ctcgtgcaat caataaaaag cggtcatatt ttgtgtgagt gagtgactca ttttttttga 360
agaagataaa tcgtgtaggt tatagcttat agagacctaa taaaattgac atttactaga 420
gtctgtccta aaacaacaaa aaaataattt tcctttattt ttaatttttt aattgtaaat 480
tctgttttgt tttagttttt ttagaagtta acaatataaa ccactcactc cctgaataat 540
attaatccta tcattttgca tgaatgagtg agtgtctcaa ttcctttgaa taagataaac 600
tgtacaggtt atcaattagc aaaaaagaat ctttttcttg gtttagattg aaaacatatt 660
tgtgtgttgg tcaactgatt tattcagacc aaaaaaaaaa aaaaaacctc agtcgtttaa 720
acgttaaagg ttcttgtttt aacgggcctt aaatggataa taagtccgaa ggcccattat 780
gttgaattat ctagaatcca aaataacttt aggtgattgg tgagtaggcg aattaaatgt 840
aagtggacat tacagaaaaa gaatcaagtg gcatcgtttt tttctttctc atataaatct 900
tttcacatta gagtcggcat aaaaattcca tttcgtattt ttctcttctt cctcttctga 960
aaaattaggg tttgagttct tcttctaatc gatcagaaag caggtaacaa ccagattcaa 1020
ttttaggggt ttttagtcaa tttcaaagat ggagatttta gccgtaaaat cgtgtttctt 1080
aatgattttt gtatttgatc tctcttatag gt 1112

<210> SEQ ID NO 75
<211> LENGTH: 889
<212> TYPE: DNA
<213> ORGANISM: Arabidopsis thaliana

<400> SEQUENCE: 75
tacagccggt tccgtaagga ttacgggtta tgctgatgtg gcggaagtat ttattcccag 60
tattaattag catcagagta tacgtgtatg tcatctaatg cgtccattag atccaacggt 120
ttagagttca gcttttaaaa gcccaaaaga atgatgagaa gttgagacaa ttatagtcaa 180
ttttttaaaa gcccatgact taatgggcct actaattgat gggccaagta ttagaaatcc 240
gcggaggtag aaccagcttc gcatatatta agagtcactg ccttcactag gtttagggtt 300
ttctcagccg cttaagagct tatcatcttt gtgcttcctg caaatagctc tttgctgttg 360
atctttctcc tccatcaaca aacaggtacg tttctcctct attagatcta tccttcgtgt 420
tcctatctca tttctctgtt tagcgtttta tttatctgat tcacttgctg tttccatgaa 480
ttatgaagga ttctatagag tctgctgtgt ttttttttg tttgaaattg ttacatgttt 540
tcgacttttg attgtggttt ttgattggaa ctgattctat agcaaatgcg tcttcatttc 600

-continued

```
tggatatgtt tgctaaatgt tttttatgta tagatccaca atagattgtg taaattttga    660

gctactctgg agttctagta tggttgataa ctggagattt aaaattcgct gtatgagtat    720

ctatggtctc ttgggttttg aagctcactt ttgctgatgt attagagata aatcttctat    780

cgtcttgtta ttatttagat gaatttctta ttgattttct gagttttaac tatggtttat    840

cgagtgaagt tgttctcaaa tgttattttg tgatgatttg ttaacaggt                889
```

<210> SEQ ID NO 76
<211> LENGTH: 471
<212> TYPE: DNA
<213> ORGANISM: Arabidopsis thaliana

<400> SEQUENCE: 76

```
tattgatttt tgtttgtgat tttaacactt tgtacaaaga ttgggtgagt atttgtcatt     60

tgagaagcgg aagcttcatt gtgataataa agacaagatg aaattagatg atgcaatgtg    120

actgaaacca taaaggtcac gtgcgtttat ttgctttagg cttctcgtaa tgaaagtgat    180

aatacatggg ctaaggccca ttaagtattt ctcttaagtt aagctattgg gtatgaataa    240

tgagctttat accacccaat aaggagactc gtcatatata attgaccact cctccgttat    300

tagggtttct gattctcgga gctaaaagaa gagcaagcag cggcgcagaa gttgaacaca    360

agtgaagctc acaggtatgg caatggctaa tccctaaatg tcttctaatc tgtttcgttt    420

tcatcggaga attacgtcta attaatattt gtttggttct gttttgtagg t             471
```

<210> SEQ ID NO 77
<211> LENGTH: 1735
<212> TYPE: DNA
<213> ORGANISM: Arabidopsis thaliana

<400> SEQUENCE: 77

```
aatgttcaca cacattgatg gaaaacatgc cattacaaaa gatgtatata gataattttg     60

aaatcagtta acatacctat aagtgttcaa atgatagtat taggttagtt aaaatgttgg    120

cttaactaat tttgttttta gtaaatcata gatttggagg taaattttgt agtccccgag    180

atttaaaata ataacagatt ttaatcttca tctgaagaaa attgaacagt tgttttgttc    240

ctatctttag aaactactag ttcaatcctt tttttattat acagtaagta atgtcaactt    300

ttactataag attaggtctt tactctttag gataaaactg tttttaagta aacacaattt    360

tattttaaac tcaaaagtaa atatttgctt ttcagggatg tcaaataaaa tgatgatctg    420

aataataaaa caatggtaat tttggaaaac ttacagctta aaacttaagt actattgtat    480

tattgaggat tgtcttattt atcattcaaa attgaaaaat cattactttt taaatatgta    540

aattgtttta ttaaaacatt tttaagcctt aatgtgtatc caagggccct ttgggcttcc    600

tctcaagtcc cacatccact aatcacatga ttagctaaaa acccaactag taaattatta    660

ttattatctt ccgtaaacat ttaatttcgt tttaactttt tcctcattgt cgtataattg    720

tttttgtcgg tcgctaagat attttcacag cttcggagac ttcaggaaaa aaaaaaatca    780

tttcttctct gaaacgaaaa accaaagaaa cgagaagaag aagctcaggt tagtctcaat    840

ctcatcttct tcttttaaat ctctcttgat cgttgttaaa accataacgg atctcatttt    900

ttccgatttc gtctgcgatc agcttcagat tcagaaaata tttgagtctg attctttgat    960

acgctttgga tttggtctaa tctctggttt tgctagattc gatctctgat tcaggtgatt   1020

cgtgtggtga attgttactt cgttgttgat tgaatcgttt gattgtctct tttgatgtag   1080
```

-continued

```
ttttgttcca tctctaagca tggatttgtg attttgatgt ttctttgaag gtgacttata   1140

ttgaaatgtt actagctttg tgcagaatat catgttcctg attcttgttc tgaatcgtct   1200

ttttgtgtca ttcttctgta gtttaagtag gtatattgct atagatttca gttcaaagat   1260

actgtttagt tttagcacct gtcatgcttt ttccatagcc aaagatattc agattctagt   1320

gtttttatga gattcattta atggtcatgt ttttggttga ttagtggctt ttttttgctc   1380

aaaaacgttt aaacaaaaga cctggtttca ttcatgtttc gtatgtatat caatctgact   1440

ttgttatggg aatctacttg taaggtggta tgtagctaca ggtttaagtt ctctgataat   1500

atttagtttc gtatgagaag caaacagtca tgtatagtca tgtatgtttt agaacagatc   1560

atgagttttc cataatgaaa gattccagag tctagtgctt tttttttctg gcatccattg   1620

atggtcatgt gtttagctgt ttgttggctc ttgtagctta aaaaagtttt attggagact   1680

tatttatcac aagacctggt ttttattcat gttatctttt actgattgaa caggt        1735
```

<210> SEQ ID NO 78
<211> LENGTH: 567
<212> TYPE: DNA
<213> ORGANISM: Arabidopsis thaliana

<400> SEQUENCE: 78

```
ttgatcctat cgtatataac ttcgatttaa caaacacaag tcgtaatttc taaaaaacaa     60

ttaactcaat ttgtttgaaa ataaaagttt ccttttttctt cgtaacaagt gaagtcaaat   120

gtttttcact cgtatctctt acaacgtttt gatgagatga taagagaaga gtgggcccac    180

atatttgctt aacaatacac gttttagggt tacgtgtcac taatgttatt gggttcattt    240

aatctgggct taaaagaggc gtgtatcatg ttgtaatatt cccatttggg ctttcatata    300

atgaagttgg gccgacaaaa aaaaaaagga ctagggttcc caagtatccc actatatata    360

attttagtcg aagaaaattc ttttattttt ctcttgcaaa gacctctcag cagccaacga    420

cagttatcaa agcttaagcc gttttagggt tttatccttt tgctgagatc caatcaggtg    480

agttcttcag tctcaatatc tgactgaatc ttcttctctg atttacattt tccgattgct    540

gaacaattaa tggtgaatgt tgtaggt                                        567
```

<210> SEQ ID NO 79
<211> LENGTH: 1993
<212> TYPE: DNA
<213> ORGANISM: Arabidopsis thaliana

<400> SEQUENCE: 79

```
atccggagtt gatatggcgg tgaatgatag ttggttcgat ttgatggtgt tcttgttcgt     60

gagacagatt tttttcgagt agttaagctt cgctccttgt ctttgatttg catatttggt    120

agtgatttga tagcgttttg tagaatttta tttagacgta aattggtggc atatttattg    180

taattttaca tatcagatta tgagtttgaa tggtaacaca atacagcttt atataatttt    240

gtacaacttt cacagttacc aataacaaaa actttattaa aagtgttata aaaagtttac    300

tctcagcttt tttgtacaac tctttctaac agctttgcac tattcaaata aagctaacag    360

ctaaaaaact tgtacagctt ttggttacca atcagacact atgtaaattt ttggtttttg    420

cttttgttac ttttgagagg tcggctcttt tcttgatagg ataaaattgt tgttattttt    480

gagtttgcta gcatcaataa tcacaattaa gatgtatctt attttgagag gtcggctctt    540

tctttgatag gataaaattg ttgttatttt taagtttgct gagagaattc aagatgataa    600

aaaaattaaa aaaatcacaa tcacaaggtt ttaataataa ggtttcaaat ataaactttt    660
```

```
tttttttgc acaaactttc aaatataaac aaaaaaataa ttttaataca aagtctatat     720
atggagaaaa taggaagcca aaattgataa ttcacaaaat taaagtaaaa tctattagcc    780
gacaaaaaaa aaggtaaaat ctattaaaat atagataagg ttctagaaat taaataaatc    840
tattaccaat tctcaaaccg acataagtac gaccaaaaaa aagtttataa ataaaagtca    900
caacgagcct taacgcgtag aatcttcccg tactttactt ttccggagga atagaaaatt    960
gggggctagg gttcgcaatt gtagttttcg agcgaagaag caggttttac atctttctta   1020
ttgtttgcga ttacgattga ttatctttcg gtttttgtgg tatgtgattt gtttgagtat   1080
ggagctttat ttttggctta agattttgat ttttctgaag attttgcgga attgagatgt   1140
tgttgttagt tgtggaccct gtgattgcag aatttggaga tttaattgga attttggaac   1200
cttgaaaagc cattgttatt aaaaactgaa gcttgttatt gtttgatttt gtagtaagta   1260
aacccttaag gagaatccaa acctttaatt ataatgtttt ggaatagcct agttgctaaa   1320
ccttaagaga cgccataagt gaatagctga ccaatgtgtt tccttaaagt tttggtttt    1380
tcagaaactt tagcaaattc agaggttgta gttagttgca gacctgtgaa aagtagaact   1440
ctaaagcttt agttggaccc atcaaaatcc attgttatac aaaattgaag cttttaagga   1500
ttttgatttt gttccacagt atcctaagca tagatagata tgttgaggct cctttagtac   1560
aaagaagata tgattgctcg taatgaaata gattggttgg ttaaaaagat tctctattat   1620
cattcttctt ccactgaaat gtgttttgat ctttcctaat cgtttgtgta atgagaaggt   1680
cttagaaaga catggaacct ttgcttcctc ccattgagac acccccttgt ctctattgga   1740
acatgattga taactctgaa taagttgcta ttaatactga acagtaaagt cgccaaacat   1800
tccattcaat tgttttatat aataaataac tcacatggta acttgaggta gacaatatgc   1860
agttttccaa tgaacctctg acatgtctat tttcatgatc gtttgcgcat tgtcctaatc   1920
tgattatgat tctattcttc gattggtata cacgagcttc attgtttatt tgctttttct   1980
atctggtcca ggt                                                       1993
```

<210> SEQ ID NO 80
<211> LENGTH: 769
<212> TYPE: DNA
<213> ORGANISM: Arabidopsis thaliana

<400> SEQUENCE: 80

```
tactctgttg aaagaagttg taagctttaa tgataccatg gattactgtg ttctatatgc     60
gacaaatgca agtgtagata ttagaaccaa ttgtggcaga aatccaatga cgtggagaaa    120
aaaagttatg cgctaggact cagaccagta cgttgccact cgacttctta gtacgatttg    180
ttaggataga tagactatag caaagaattg accatcttga ggaagggtta ggggagttgg    240
tctgccgcat agagtaaacc aacgtgactt ggagctatga gggaacacta atgtgacata    300
aagacaactc tcagtgagac ctaagtttaa gttgtacata ttgagaggat atctagttta    360
ttgttacaaa tctatccttt tcaattaatc ttttggggtt aatggtgata aatattcaac    420
tatacataac actttttgtt tacgtttttt agttttccaa agtaagagca tacaaattgc    480
taagccgaat ttctcccact cctacttgtt tatatgtaca atgggctggg cctataaggc    540
ccaatgtttt gtgtgtcaca tttcgtcacc cacagacata tatacttaga ttgaagctaa    600
agctgcagtc tccgtctctt cgcttctagg gtttcatcaa ccaaattcgc tttcgccgcc    660
tttccacaag caatcaggtg aaatatctct ccttgttctt gatttcctc tctctttcac     720
```

tttcctctgt aatctctgag ttttttttt atggatctgt tgattaggt 769

<210> SEQ ID NO 81
<211> LENGTH: 954
<212> TYPE: DNA
<213> ORGANISM: Arabidopsis thaliana

<400> SEQUENCE: 81
ggatcaaatg aacgcacatt aatatgacgt aacgatgatg acaattctgt ttaatagtat 60
cttattgttt acagatacag aaaaataaat taagtgggcc tttcaataat taataggttg 120
gtgaaatgtt accttctctt gatatttttt taattttcat ttattatgag tatgttgcgt 180
tatgaaacaa ctcgcattaa tttggttata gattggagaa agaagaagtc atggtcaaaa 240
ctcaaaaatg taaaaggaaa caagacgtgt atgacgacgt gattgataat ctgaggagat 300
acctttgggc cttataagat gggccgaaaa agtaatagta ttagcctcta ttcggcccga 360
ttaatttcag gggaaatttt ggtaataaag tggaaacgac gtcgtgacaa aactactgtg 420
tagactgaga aataaagaag cccttgattt tgcccattgc agtcatctct ctcgaatctc 480
tctctataat ccgatctgag aaatttcgcc ggagctaggt tttgttgttt accgatcaat 540
cctttaatca ggtgagatct ctttctcatt catcttatcc ttgcgtataa acacacattt 600
cgctgttcct ctgtgatgct tttctgaatt tgaaatcgtt tgatttaatt gagtcgttga 660
tgttttcatt tccttgaaat tcgaatcgac gaaaatttat ggaaattgtg ttgtttgact 720
cgggagctgc taatgagtga ggtgtttttg ttcgtctatt tggagttttg agactcggaa 780
atgtcctgtt aagctcgttt cgttgaattt cctattgcaa gaccaatttg attttcctcg 840
tagaagagac tttgtgatat gttgtctaag ctcgtcagat ttaatcagct tttacctgca 900
aaactttgtg atatttagga tgatgaggac taaacttgta tttgatttgt aggt 954

<210> SEQ ID NO 82
<211> LENGTH: 991
<212> TYPE: DNA
<213> ORGANISM: Arabidopsis thaliana

<400> SEQUENCE: 82
tgtgaattct tattctatgt ccccacccac ttgcctactt tttattggct ctcctgtttt 60
agttttagta cttccttcct cgttgacttc tttccttaac tttcccgcca ccttgattaa 120
ttgaatcaaa tcaactttat cagtttttac cctcttttct tactccaacc aaaagattgt 180
tagaaatgaa aatgagatta tggtaacaaa acctccattg attcgagtca atatgtcttt 240
tgaatgatat gaatcgttgg ctattacatc ttaagtagac tttataatta gacgagataa 300
ttaatagaca aagtcatcta tgattataaa agtattagag aatatttgga tccaatcgaa 360
atgtggtgtg ggaaaagaaa catgttagat tgtggcagga gacaggctgt gttatcttca 420
ttgttctact gcaagtgcaa acacacttcc cttctttaat ttggacggta tattaataca 480
ctttattatt agaatgggct tttataagta ggcccattat caggtgaaaa acaattgggc 540
ccatcattga cttttttgt taatgggtgg tggtggtggt gattaatatc gtcgtcggag 600
gtttcttgag ctgaagaaaa cattcgtaga tctatttccg catctgctta aacacctaca 660
tcgtcgtaga tcgcaaacca ggttagttct ctatccttca tctagttatt tcccgaatcc 720
gtttgatttc tccattttca tttccgatcc gtgttaattt ctgattgcat ggagagattg 780
gtcaatgtag aattaggaga ttatgcttga gctatcatta gatctaccgt atgcgtatca 840
gttaaacgaa acgccatttg atctgatctc attgtttatc ggaattttgg atttggtttg 900
tgaattttgt atctgccggc tacgatgact ttgagatttt taatgaatgt cagctaaaag 960
cgtcagatat ttgtggtgtt tgctctcagg t 991

<210> SEQ ID NO 83
<211> LENGTH: 1114
<212> TYPE: DNA
<213> ORGANISM: Arabidopsis thaliana

<400> SEQUENCE: 83
aacgaaggtg cctctcgatg aaggagcttc aaaaggaagc aaattaggtt agggctctat 60
ggaataattc ttgatgttac catatatttt atagaaatat tgtacatgac gaccacctgg 120
tctcagttta cgacacgtgg gggatttgtt tgtttgtgtt gtctcggtcg ttgttgttac 180
gtgccgacaa ggggaatgat attaacatag agggggaaaa aagagagaga tcttcaatgt 240
gaagtttgct ctgtgtatat aaatattttt acatctttcg acttattcta ttaattcttc 300
aaatcataat aaaaattaaa ccacttttga ttacttgttt cttaatttcc aagataatta 360
attataattt atctattaat atttgtctac caaaatctaa cacttaaaat tagcaattta 420
tcttaattaa ataaatattg ttaaactttg tcttttgtca cactagtcat aactgagatt 480
gatcagttcg ttccatttct atagaattca acttatacgt tgaatccgat agaaagaaaa 540
tagaaaagta atttgaattt tttttcatcc acaaacaaaa cttgttgaaa cttgaaacat 600
tgaataatct aataaaagta taaaaaaaaa tataaaaaat atatgtttac caattatcca 660
atttatttct gcatattttg taaattaaaa agtaattcaa atacgtttca tgtcgacaaa 720
atgttgaatg tacaagtggt ttatgctaat ttaatcactg tcaattcact gaaacgaata 780
aatcgagtaa ttactttttt aattgacaaa ttacaaaact atagaaacat taagggcata 840
attgaaattt ccaataaatt gaagagcaaa aaccctagaa aattgacacg gactataaaa 900
aggtgacgaa gcggcgcttt ttcggtttgg tcatcgtgct cctcttctcc tccaccgcac 960
agatccaaga cattttgatt acactccatc gccggcgaaa caggtgcgcc ttattctctc 1020
ccatcaaagt tttatccctt ttcctcatca tctagatatc gtttacgatc tcaatgtact 1080
aatatgtttc tgggtttatt gcttaattgc aggt 1114

<210> SEQ ID NO 84
<211> LENGTH: 967
<212> TYPE: DNA
<213> ORGANISM: Arabidopsis thaliana

<400> SEQUENCE: 84
cgagtccttc acattaaacc tgatcataat catcatcagc taccacagta tcgcacttag 60
aacacacaca atcaaattca aacaaacttt cgcttgacaa tttcaatcga aaccatatct 120
tttcaagttt agctaactat cggaaagaaa ttacataccg agactaatga ttccacagac 180
ttgagagagc gcaaagatcg aagaacattc gtcgagagaa agaagaagaa agtgggagga 240
gcgtgtatgt gccagagaag aaggagcagt ggatgattta tgcgcttggg ctgtcgcttt 300
ttttcaactt tgacgctcca caaagacaca acaacgacat ctctctattt caaaaaagtt 360
ttattttttt attcatttta aatacatttt aaaaaaatta acaaataaat cgccatttgt 420
tgttcttttt tcaaaaacgg aatacgaggg tgcagttatc ctctacgagc aggtgcatgt 480
aataccatct gatggatttg acttatcgtt tatccacaaa agattcaaaa tcttcccggt 540
ttttaagttt gggcttcata aggcccaatt agtggcaaat ccatcacagt ccactagggt 600

```
ttttgagaga ctggatataa aatttgattt tgttcattgt tgtcattcgc cgtaatctga    660

agaagacgaa gcaaatcctc ccacaaagaa tcatccaggt ttgttgtatt caataccttt    720

tctggtgatt cgattgatta atgatgtata atgtaatgtt ttgttctact gaattgtttt    780

gtgtgactga atatgatata tatctcatag accagttggc ttagctctgc tgaattgtat    840

catgaaaatt gtgtttagta taccatttca gttttctgat tgcgtagaat tgcagtgaac    900

acaattttta cttacgagca ttgttctcag tctcacagtt acgaatttgc gcatgatttt    960

gataggt                                                              967


<210> SEQ ID NO 85
<211> LENGTH: 1060
<212> TYPE: DNA
<213> ORGANISM: Arabidopsis thaliana

<400> SEQUENCE: 85

aacaccacat tttgataaga attatagaac tagtgatttg cattttaaat gttgatacat     60

atagaataag cataatcaaa caatgattac tgaaaaatat ggtccattaa tatcgtataa    120

aaatggttga tggacattga aaccctagtg gagaatttgt cacataagta aggcccaaag    180

tttttgaccc acaaacatat ccattaagtt atagtttagc gaaacccctt taacaaaaaa    240

gaaaattttc aactagtgaa ttgtttctag agagttctgt acaaccatcc aaatttcaaa    300

catggtataa aagatgttat tgacaaaata aaaatggaaa cagtgaaacg tatagtcgga    360

aaatggaata aaatctagat gccatatatt attcttactt gttctaaagt ctttaataaa    420

aatagtcggt attacttgga caaggagcaa aacaatatgg aaaaaactct tctattctgc    480

aaaaggcgtg cagcgcatcg ttttggcttc ttgcatcaga gctgactgtt ctcatccaac    540

ggctgttatt aaaacaatcc aacggttttg gctaaatccg tgacgtcttt atatatcgaa    600

ccagaccacc aacccatttc ctcagctact actgttgaag cgattctcac taaaaccctc    660

gaacacatcg cctttatctc tttctctaga tctactcgct caggttagtt tctccgatca    720

cttttgtatt tcccagtcac tttccggctt tgtacagtat tcgtgacgga tctgtttgtt    780

tgatgactat ccgatgctaa aaccactatt caatcgtttt tttgtaaacc tgaattgatc    840

tagtagtcgt acgtgaatga gatttggttt ttgtgaacga tgatcggtga tttgatctcg    900

gcgatttgga tcgtgagttg tcgatgatgg agttgatttt gtttatatga tttttgcgac    960

ggatctattt atttccatct ggtttttacg atttcgattg tttgctaatg acgaatttga   1020

aaagaaagct aatgatttct ctgatgatgt tggtttaggt                         1060


<210> SEQ ID NO 86
<211> LENGTH: 767
<212> TYPE: DNA
<213> ORGANISM: Arabidopsis thaliana

<400> SEQUENCE: 86

acgttaggtt aatatgattg gagacaccac tcacttataa tatattcttg ctgttctatt     60

aaggcaagac tggtaaaaca tctcaacaaa atattgcaat tatttgtttt tacgatataa    120

tctttttttt ttcatcaact tttttaatga tataatctaa atgccaaaag acatgtaaaa    180

tgacattttt ttttttgttc aaatgacatt tctaggtacc actattcagt gcataaaaat    240

aattttatga ttaagaaaat aaattcgagc ccaagcgcaa gactcaaaaa taaatcgaca    300

tctcaaaacg ggcccaatat aaagccataa ttcgtaaagg cccaatataa agccttaatt    360

cgtaaaggcc caataaagaa agtgagagtg tagcgttagg gttttaagaa atcctataaa    420
```

-continued

```
ttagttcatt cgtctctttc gttcctctct gcgtgcccta gttattcaga tcgccgaatt    480

tgcagtaagg agacgaaaat caggtaagct tcttctctcc ttttcgtcgt ttatatcaca    540

gctcattttc gattcgatct acgtagtgat ttctctcaat atcaaatgat agattaggga    600

ttatctgagg tttttgattg tgttatatat atagattgtg aatctgggtt gttgtaactt    660

ttgaggtttt agtttctgaa atgaatcaat cttagatacg agcctcaaag atctaacctt    720

tatgctgata attttgtatg aatgtgtgtg tttgttgttg aataggt                 767


<210> SEQ ID NO 87
<211> LENGTH: 1500
<212> TYPE: DNA
<213> ORGANISM: Oryza sativa

<400> SEQUENCE: 87

ctgcatgtaa taagttaatg tagcaaccat gcccgtggaa atattatcac atttgacttg     60

agaacaaatg aatgaaatat atttggatta tgtttatttt ttaagaaaat agattaaacc    120

tgcctctaca accatagtgg atgtacacaa ccaaggatta tatgtttcta tgtctgtcgt    180

ttcacttttc tgaatataag ctagtataaa atgcaggtgt ggttcaatgt gtagtaaaat    240

gcacctgagg taccaaaact tatgctgccg attagttact aatcctgcaa acaatttaga    300

gtttagatga gttacaggca tgggcagaaa atgacatact ggtctactac tacatcgata    360

tcaccttgac taatctacgc tcacttctaa atgctccctc cgattcatgt taagacgtta    420

taactttcaa aagttaaact tatttaagat tacgagaaat atagcaacct ttttaataca    480

aaacaaataa aaacatgtta tcaacttcta ctttcttatt tttcacgtgc acacttttca    540

aactgttaaa tattataatt ttttttaggg acaacgcaga cactcacaac acgcgcacgc    600

taaccaaagg cacacgctaa ccttctaaga gcacattcag aagactagat atatctatga    660

gcacatccga aaggctaggc atatcttaag attaatgaag ttaccacgga cgtctcgttg    720

tcgatgattg tattgtctat cactgaaaaa aaattagccg taaatgtgaa tacccgtgct    780

aaatttagaa ttttgaaggc ccacttcgca gtgtcacagt tttaaaaaca tattaatcaa    840

tttttaagtt tttataacta atacttaatt actgatctgt taatgagcca ttcgttttaa    900

tgtgcacgtt agagaagttt ctaatcttcg cttctgaacc cacactgatc ctgatactgt    960

aatgcaaaag agagagtaca ttttaagtat ctcttttcat ttttttttc agaaaaaact   1020

tttaagtatc tcacagaaat tggagccatc aaatcatcaa tatagtttac tcatttatga   1080

aagcttcaaa tgtccggcgt ccagagtttc agaaaattca ctcaggagta tgctagacta   1140

ttctcttctc catgattccg caaaaagctt tttcgttaaa acctaaataa acctcgtcaa   1200

aaaaaaaaag ccggcgacaa atccaagtcc tccacgtcat cccatccccg acagcgacac   1260

gctccactca ctcgagcctt ctgggcggtg gaacctacac caaccactga tgggccgacg   1320

gcccagccca gccagctcgc gctgaaaccc tagccccatc acaggagggg ggctatataa   1380

gccctccgcg ccgcccctcg ccaacccttg caccccctcg cgcctccacc acacactccc   1440

acccaggtaa ggagagggag gaggaaggga acctcgaagg cggcggcggc ggcggcggag   1500


<210> SEQ ID NO 88
<211> LENGTH: 470
<212> TYPE: DNA
<213> ORGANISM: Oryza sativa

<400> SEQUENCE: 88
```

```
tcgttctggg ttatcaaaac tcaaaaagga actctcaagg tatcagtgtc agtgtgtcaa      60

gtgtgatcgt tccatggcat atatggcttc aaacatttgg ttcttggcac ttggcagaat     120

tgaagtgtgc agtgaaaaga actgaaattg caatgtgctg gaagcatgga gcagacgagg     180

aggaagagaa ggaaggaaag gaagcctttc aactcgtctg gtttgttttc ctttcttctt     240

ttattttcag gcccatggag gcccacacgg cccatgttac agcgctgggg cccaaggtac     300

gaagcccact cacactcccc ccgcatctct cgggagtggt gagattgacc taaccggtag     360

tggagccaag atcagcgaaa ccgcggcacc caaccccaac ccaaaccacc agaccggcgg     420

cggcgggggc gacctaaggc gagaacacga gcgaaaccag agagggggcg                470
```

<210> SEQ ID NO 89
<211> LENGTH: 1500
<212> TYPE: DNA
<213> ORGANISM: Oryza sativa

<400> SEQUENCE: 89

```
ggcgatggtc agaattaggc atctacaatt ctacatggca aagccagcat acatggcaat      60

ttgattctaa ggtattgatc agatcagatt tgatgcaacc tgtttggaag tcaggcccct     120

ttgactttga ggtgcaaatt aatcttttgc ttgtctccta gcttagaatc gcctatggac     180

tgttgctgtt tataacttaa ggctggccaa acaattagtt ttgtcctcta tgcatcaaac     240

cttgagacat ctcatcattt gttcatgaag agtagattag tttcaagcca tccggacagg     300

aataagcctg tgcttaactg aagtttcttc agcaagcctc cttcggcctg ttcagtattg     360

gaatggtggt gtcacaagac ttcatcagaa aagatgcaaa gaaaagggct caggaccctc     420

ttcttgctgg tctgctgggg aatttggacg gaacgaaaca atagaaactt cgagaaagag     480

ggatggtcaa ttcagcgaat tgtcgacaaa ttctttttta tgagatcaag cagtggacca     540

gctacagaga aaaaaggctg gtatagttct ctcgaagaga gagctgtttt tttgttagtt     600

tgtaactttg tatagcctct ggcttcagtt ctattttgtt ccctcctatc aaaattcgta     660

caaaacagac agatcatacc cataattaca agtaccgatt atgttggtta tatctttttt     720

acaattacac aggatatata ttttataaat tttggttgaa taaattattt ttggtagata     780

tagtttccaa actttcaatg tatccctatg atatatttta tgaaaaacgt gtattgcacg     840

tgcacgatta ctagtgccca gataaattag tactgatctt gtcccgctca aggcctcaaa     900

cctcggtaaa aataatttca cggcggtaaa aataaaacat ggcaccatct ttttactcaa     960

gaaagaaggc aaaaatcctg tcgctattca ccaatcacgc aaaacccttc tctccaagaa    1020

cacggcgccc tcacctcaca tctcacatca attttgatac cattttcaac cttaccaaat    1080

tttaataaag ttataaaaaa atggctgcat ttagtttgtt accatatttt aatacttata    1140

gaaatcctac taaaatttta gcaagttatc aaaatttgac aactatattg ctaaaatttg    1200

gtaaggtttt ttttacatca aagtgaacag tcccaaaagt tcaccctgcg caacaattaa    1260

attaagcaaa ttaaatcatt tttggcatct tcttcctccc caagaaaaag ggccaggata    1320

agcccatccg acggcgcagg cgagccgaga gccccgcgag cgcagatctg ggccgtccgc    1380

ccgccgataa ataccagctc tctcctccac tccgcttcac ccccaaatca aatccccttc    1440

tcccattttt cctctcctcg cttctcgccg cagccgccgc cgcctcctcc tcctctcgcc    1500
```

<210> SEQ ID NO 90
<211> LENGTH: 716
<212> TYPE: DNA
<213> ORGANISM: Oryza sativa

<400> SEQUENCE: 90
agcaccatca gacgccgcca catctccggc gcccgtcgcc tcctccatcc ctcccaactc 60
gcttgagcgg acacgagcag ccgcaggagc tcctccagct ccggccaccg gcgtggtgct 120
cgtgctccgc cgcggcactc tcgccggaaa aagaacgaag agaagagaga gagaggagga 180
accgaggaag aggagaggga ggggagagat gacatggcat atatgtgggg gtcccacgct 240
gactcaactg tcacatagga caaaaccaag atcaaaacca tagaggatct attgtgaacg 300
ggttttgatt agttaagaga ccccaaatat tttttcagtt gaggtacgat tttgtaactc 360
gatgacaagt tgagggacct ttggtgtact ttttcctagc caaaaggcct cggcccatgt 420
attaaggtga cggcccactt gtgccgtcct cgaagacggc cgacagacca acattcattt 480
acagcccaaa aattacgaaa acctagctgc atcgcatctt cttctccttt ccccaggcgg 540
agcaccgtcc gatgagcatc caacggctac ggtcagcacc ctcggaacct tcgagaacac 600
cctccccgct ataaattccc gcctttccgg tagcatctag tcttcctctc ccactcttcc 660
tcctccccaa accctagccg ccgccgccgg cgtactcgag agaaacatca gcatcc 716

<210> SEQ ID NO 91
<211> LENGTH: 1500
<212> TYPE: DNA
<213> ORGANISM: Oryza sativa

<400> SEQUENCE: 91
tatttagctc gttaagaaaa gtatataaaa attttattca taaattattt ttaatttgca 60
aatatatcgt tccgttcttt cgtccaatat gctaaacagg gccggagaga tttgccggac 120
ccaatggtat ccatgttgcc ttcgattggg tcaagtcatg ggaagaagaa tccaaaagag 180
ggagactgat gaccattggc atcgatgatt aaagagaggg ctcgtactaa gtgctagtga 240
tagacattga cgccaattga tagagcaact tttgaccaca agttgatccc gcttgccgat 300
tgtaaagaaa ttgagcatag tgtgctctct ctgtcctata agtacaacct aatataaatg 360
tgatcacatc tatattatat tgtatttata ttagagcgga aggagtactc cctccattcc 420
attttaaaca taaccatgag tttccgtgtc ctagcgatca aggtgctaac tcgagcctac 480
ccttcaagca gactgatgtt gtagatctcc actcggcttg tggagttatg cataaaagtg 540
cggttatact cacatgaaac gtcgaaacct tctttgtaga agcaaccagt atcaatgccg 600
aacgggtagg gacgagctaa caataatgct gaactggtct tgagattcat gctatttcca 660
cgcgttgcgt gatgctattt ggcatctacg cggatacaaa caaactgaat tttggaagac 720
tcgtagactt gcgttttgcc gtgaagtact tgaaggcgga tcgctattga aggacgacgg 780
caagacgcgc ttcgcgaagg ttacgagtca attttcagga ctttagtact gtaggtctaa 840
ttgggtcaag tcgttgcctt tgtgtgatat ctttcgtccg aaagagcgtc gttgttttac 900
ttatgtttat aggtaggatt taaattttaa aatttaattt taaagttgac ttagggagtt 960
tttttctaat ttattttaca ccatttgctt ttgaatatcc gaaaacatat atatagaagt 1020
tttatataca aattaagttt tagttgctaa taagataaac ataagagaat gctatgaatg 1080
taacatctcc tatcaggcta tcactccaaa aataatgaac aacaaattgt agatagcttg 1140
tttgtgcata atccttttgt tttgtttacg gtgaatctgg atttaaaatt actaaaacaa 1200
tgtgatcatc atatgcaggc ttcggccatt cggagcgacc caactttcgt tgacgggccg 1260
acgtcgctgg ctgaaggtga atggaacagc ccatgttcca ttatattggc ccagaacgga 1320

-continued

```
atcgtaacta ttggttccta atatcggccc aatcaattgc gttggttatg aatggcccat   1380

ggaagcccac tattgctgct cccgtgctcc ctataaatag ctagggtttt acgccacttc   1440

ccccatctcc gccgccgccg ccccactctc caaccctagc cgagaggagc agaccaagca   1500
```

<210> SEQ ID NO 92
<211> LENGTH: 1500
<212> TYPE: DNA
<213> ORGANISM: Oryza sativa

<400> SEQUENCE: 92

```
aattgtaaat ttgaatatga ttgaattcta tgtgttttaa atatttctgt ttgaattatt     60

ttggtgctaa actaggtata aatatagtgt atacaaaata gaagagaatg agaaatgtgg    120

cctgagaaat gggggttgtt gctgaagtac aagtcaactt ttggatcctc ggacagcctc    180

cattagatct tttaagggct ttacaattta caatataagt tattgctgga gatgcttggc    240

agcatcatag tttctcccac cttcgtcgga aagtagattc cgccaaatgc atggtttatt    300

tgatttgcca ttataccaaa atgttgcagt gctaaaatct aggtaatttt aagtactgct    360

atttttttaa accggtgtat attatcggca catcttaata gcaaattaaa caataacaaa    420

atactcttta aagtgctaac aattcaacac ggcacatttt ggattcaaac gagaatgctt    480

gcatgggcat aatcacttaa cgtgtatttg gtctggtgac aagatgagat gggttaggct    540

catccctctt tttttttttt tttaaggata tgttttcatc agtacacgtt tggtagataa    600

ctttctcttt aaagaaatga gagaatgtgg cccaatgaga gagagtggat tagattagtt    660

atgtcgattt ttaagtacaa aactgaaccc gatctagaga gtattccctt ttagggatca    720

atgtatccca cctatccccg aatcaaatac actgaagaat aagttcaccc ttattgatca    780

tcccattatg tccctttcaa cttaaaaata tgtttatagt tggaattagg gtagtatgat    840

ttaaaggtga aaaaaatgta ttcaacgtag ctttgaaaag gtaaagaaaa gtgtattcgg    900

acttgttctt gtcaaacact ttatattagt caattgccgt tgcattgtat tttgaaaaca    960

gttatactcc taccttagga attactacta ggagttaggt cctaacttca ataactccta   1020

tggagatttt agcgcacaca aaaagagaaa actcattaac atatgattaa ttaactatta   1080

actattataa acttgaagat caaatttatt taatttttct taagaaaaca tttttttatat   1140

attaaaaaat tcgtatattt taaatattta aaaatcgtgc taacagaaaa cgagtacagg   1200

ttagagtttg aagttgaaga aaaaaacaat gacagtggtt gaaatttcct acttcctctg   1260

tcctaaaata ttgctacatg acccacaaat tcgttgtttt acgatggtag caacattttg   1320

ggaccgatgt agtatctgtg atttcaactc aacggcccaa caattgaagc ccacaaaccg   1380

caaagcccac gaagaccacc agcaaaaata aagaagaaac cggaggtcag tttcctatct   1440

aatctcgatc tctccacccg tttcccccaa aaccagcggc gccaccaccc accttccccc   1500
```

<210> SEQ ID NO 93
<211> LENGTH: 936
<212> TYPE: DNA
<213> ORGANISM: Oryza sativa

<400> SEQUENCE: 93

```
tgtgggtccc atctttttta ttattatttt atgtgactga catgtgggtc ccacagattt     60

tattattttt ctagatcgga ttgccacgta agcaccacgt cagtaccaca tcaaatgaag    120

accgagtcaa aatggacacg taggcgctac gtcagccaaa accaccctta aaatcgtcaa    180

ggtacctcgt ttgtccggtt ttcgtaagtt ggggacgggt cgtaccggtt ttgcagttca    240
```

```
gggacgaaaa tcagactggg cgacaaatag agggacctaa aatgaactta ttccttcaac    300

gtttgtgtgc tgacagagtg acgagcctcg attttctaaa aaagaaaagg ttacaggcct    360

cgaacaagat gctgttacca aagttagcca cgaatttgga ctagaaaata gctaaacatg    420

acggcttgat cgaagattac gcaaagtttt agttcgactt tcgaacttat aatagttcaa    480

aataatcatc tgctgtcatc atctactcaa taaaaaccga aatcctctgt caccatcaaa    540

acatagcaaa aatcaaatgc cattaaaaag tgccaaatga cagttgacag cccaaaataa    600

aaaagaagaa aaaaaaagga acactattat attccagatt tccagctgca atatcaagct    660

accaaatgga tccccaaaaa aattgcaatc cattccatga actgagccca ccatgcacca    720

cacaaccccc gctcctccac gcttctcggg ctcccgtaga ccgggtccac ccgccaatcc    780

ccccacacgt cgatatctcc agcacccacc gcacccactc tcctcctcac tccgctcccc    840

tcctctcctc ctcccttctc gcggaggccg ccgcaaccaa aaaaaaaaaa gtctaaccct    900

agatccaggc cccgcgtctc cggcgatctc ccggcc                              936


<210> SEQ ID NO 94
<211> LENGTH: 1500
<212> TYPE: DNA
<213> ORGANISM: Oryza sativa

<400> SEQUENCE: 94

gtgacaaatg tttctttcat tctatctttt ttttttgaga ggtttcattc tatcgttttc     60

ccctttgagt ttgagaggag agcagtgttt ttgttttaca cgtaggaatg ggctatggag    120

tatggagtat ggagttggta acgtggcaac tgggaaggaa atagtaggag taggtgggaa    180

atttgctttg cgctgcatga ctgcatccca cttgatagag atgttaattg acttgatgtt    240

gtttgcacat gaatactgac acatggggcc actaccttgt gggcctactt ctcagttctc    300

agtcccacct aaactgattt tacgaacgga tttcacgtag gattaggggc ccaaaaaggt    360

cgtttttacg attttatttc tgatcagagg ctttcagcta ataaaattaa attgctgaga    420

ggtttagtag agtctataca tattcttttg cagtttgttg taacagcaat gcagaggatc    480

ctcgttgata gtactacaca caaacacatt ttgtgagctg tgtgacgata attaggggcc    540

tgttcacttt gatgctattt ttaaccttac caaattttgg taaagataaa aaaaagtggc    600

tatatttaat ttgctgccaa attttaatta ctatataaaa aatcctgtta aaatttagac    660

aagttgtcaa aattttgaca cctataccaa gtgaacaggc cctaggtgca gacaataacc    720

tacctccccg gcccaaaatg ctcgtggagt cgttgtgttc atgtcatttg agaatctcat    780

acccgtgacg tgctaatgct agggttaaac gcctaaacta cggcgcggcc atgcatgtgc    840

gcggcggatt ggtcacgcgc tgcgtgtcgg gtgctatcaa ttttgttgga tttgattgca    900

atctcacact ctcacagggt cacaccgttt ttggatttgg gaagaaaaat actgaggatt    960

agagagagag agattaattt cgaggtgtca cgagagagag actactattt ctccagatag   1020

tagtagtaac tcttacgtca tggacactcc aatacaccaa atggagtttc tactagtacc   1080

acctaatcca aatgattggt caaacaagag acatctacca aaactaatcg ctgcaaaaat   1140

caccactcct cgaataatac tcgccgtgcc aaacgctttg gccgccggag tccatcgccc   1200

tacattgccc accaaccgca cgcacccaga ttcacattca agtgggcccc acgctctgat   1260

cccataacca acaattatgc aggcgaaaaa tattactaac aaatgtagtg tctcaatgac   1320

aggtgggacc catacctccc acccgtctgt tctttaaatg cgctcgccca actgctcgca   1380
```

tctttctctc tgcccgtgcc aatcttcctt tcccacatcc tcctccgccg ccggctgctt 1440
cccaccggct cccgatctcc gaggcaagca gcgccgcacc cggccgctgc cgccgccgcc 1500

<210> SEQ ID NO 95
<211> LENGTH: 1500
<212> TYPE: DNA
<213> ORGANISM: Oryza sativa

<400> SEQUENCE: 95
aaaagttttt ttaatgtgtt tgtattatga gcgtctgcgt ttacacaata gaagttatta 60
atcatgcatt gatcattgta tatttgtatt gtaccatggt gcagttaatt ttagagaaaa 120
aattcaaaga aaaactagcg atccaaacca atatattggt gttgatactt gttctaccac 180
cataacgata tattggtgtt ggacgtgcta gtgtgttttg aacaagattt ttttagcgag 240
gttaaaaatc ccatattcaa gccttgttac ttctttctta ggttaagcac atcatttatt 300
aatattgcca tctattactg gataggatac atcatagtac tacgaatcgg atacatcact 360
atattatata gtactaaatt gttatattat gggatggaga gagtattcta taacacacat 420
tttgttttct cataagcaat tatcatttct tcttttgtta tgacgatcaa gcaagagaga 480
ttacatgaga ggcatcatat gttgttatta ggaagattat gggttgtttg gttgatacct 540
aactttgaca taactaaggt tagacaagta atatgtctaa gaaatagttg gttatagccc 600
gcagggggga tttacaatta tgacattgca aacattaacc tttgctataa taacactagg 660
ctcacatttt atagacacag atggacccat ttgtcatcca ctcggagtgt caaaacagcg 720
aagctctcgt gtttgcagtc ccaatattac aaatttctcg cccgcatgtg tgatatgttt 780
agttacaaat ttgaaagtgc gggtaggtct taagagtaag aaagtgtgca taattgtgaa 840
gtgaaacaat cacatgacta aataatcgtg atatgactaa agtgtggtat ggtaaagtga 900
gacaaccaac ccatcacccc cttagtcaat ggccggtcag cagcttaata cggcatttgt 960
agcctcacga ctaatattgt atggttcttt taataggttt ttcataggac gacacaaaat 1020
atatttttcg agatcgttat aggaatgtaa caaaatatcg tacgcatagt attttccgtt 1080
atgtttaccg ttatgtttat gttattccag tttctttccc atgtttttat tttttgagcg 1140
gtttcccatg tttttatggt tgtgcgcaac ctatatacgt agaggtcgga tgcaatttta 1200
ttgcgaaaaa aaagaagaaa accattgaag ctggaccgta ggactgaaaa gatcgtctct 1260
ccatccaacg gcccaggaga cgccggaaca attacaccac cagaaagtcg tgtaataaaa 1320
aaaagtagtg gattggtggt gtaataaaaa aggaatctac tagcgctcta taagggcgag 1380
ccgcacggca ccaccaatcc accactgatc atactagcac agagcgccgc cgccgaggag 1440
agtccaatcg agaagaaggg aggagaggca agcggagagg aagaagaaga agaagagagg 1500

<210> SEQ ID NO 96
<211> LENGTH: 1500
<212> TYPE: DNA
<213> ORGANISM: Oryza sativa

<400> SEQUENCE: 96
atcggcttat actaagggga gaatatatgc tgggaagaga acttgaaggg gactaattct 60
gattatttat tgctaaattc caaagactag ctaaataccc tatatataga gccgacacct 120
gcaactcaat ctaatctaat cctactttta agcaacagag tatatgtaac acgcgctgca 180
ttggaggcat ggaggcatta tatctaacac ccaccttgtt tccctgcatg gaggcattcc 240
ctagtttact agcttgctca gtccgttttg ctcctttcaa tctcaaaatt atatagatcc 300
ttatgtttga tgttattttt gtcattaccg gtctcttcac gttattccat tatgttaggt 360
gccaagaaga gtatgttgga ccattagagt ggacatgatt agggatgcaa gtggatagtt 420
cctctactcg caaaaaaacc cgtttgctag ttcatttctt acatgatagt ataaaattta 480
gaagaaaaaa tgaagtagaa gtgagattag cgggctaaag aaacccgctt gcatccctag 540
acatgatcca tccaccttct tattattagg ttgtaggctg ccatttttct accagccatt 600
tacaagattg ccaaccagat tcgctctgct ctcgtagcca ctttacacca ctacgcagaa 660
ctacaaatct acaggatgga tttgcattgc gagcatgatg tccccaactt taatacaaaa 720
ctgccaatat ataatgagtt cagcaacgtg ttagggtaaa gttttttttt tttttttgcg 780
cagaggcagt tggaaaaaaa aacctaagac ccctatccca tataaaaaaa accaacttgt 840
agcttacaaa cctagataat aagctagaag tttatttttt atgagtaaaa caggtggctt 900
gacagtaatt ctgatggcag tgttcttttg aagggattgg agcatatccc actcgcacgc 960
aaacaaagtg acaaattaat gcacgattaa ttaagtatta gcttaaaaag tttgaaaaat 1020
gaattaattt gatttttaca gtaacttttg tgtaattttt tttaaaaaaa gtgcaccatt 1080
taaccgtttg ggatatgtgc atgtggaaaa caagaaatat gtggttgaaa ccttgaggga 1140
gaacacagcc aaaacaaaaa aaaatctgat ggaatcaaga aggccaacgt tggtgtgggc 1200
cgggcccaat gcatcatttc cttcgtacgt tgcaatctag gcccaacgga ctgcccacca 1260
ccccccctcgc ctgaagaatg gggtggatca gatggcaggc tcattcccag ccgtcggatc 1320
gacccgatca ccgcctgcga agtaaaccct aagccacggc cgcctcccta tataagccca 1380
cccactaggg tttcgcccgc ctctcctccc ccccgctagt tcccaaccag cagctgcggc 1440
ggcgcgagca cacgaagagg aggcggagca gccggagcca cctccgccgc cgccgccacc 1500

<210> SEQ ID NO 97
<211> LENGTH: 1500
<212> TYPE: DNA
<213> ORGANISM: Oryza sativa

<400> SEQUENCE: 97
cttccaaatt atgatctact cactccagaa gcttctgttg tcctgttaac tgatagcatc 60
ttctcttcta atgttctgtg gactgtgttt aatttagcac tagcatttaa tttggggcct 120
acttgaatat cattatatta tattgctaaa atttgatggt ttgccattta atttgtttgt 180
aagttcactg aatcatgtgt aatctagata gtactaagtt agtggtaggt gtgttagctc 240
cctccaactg aagaagatga gacatgcaaa gcaccctgcg tcatgtacaa cccacaaagt 300
tctaattaac gttcttaact atatataaaa tatcataaca ataactcctt aatgtgaaag 360
gtaaatagcc tctttgagta atccacatga agatgtggat ctgaaagaca aatgaggatg 420
tagatctgaa aacaattgta aataaattca taggataaga aaaagacaat gcttgatttg 480
atactgctat ggtcactagt cataagagaa aatgacttca aagttggaat atgttttgga 540
ttgtcaatag gtgcttcaat tggactctca gctgagccac caaccttaca actttttgagc 600
ggctaacata atattccttt ctccaaataa gcaagaataa aaaccagagt tcaaatacaa 660
ttagaaaaga ttaacattta cttgctcggt tttacgattc caaaaagaaa aaaaattcta 720
ctatgttttc tcgcatggtt attacgacaa cgtctaccac atcatgcatg cttttttttc 780
attaacggtt tgggtgggac aaatatactc cttccgtcct caaatataag agattttgat 840
attttccttg tactgtttca ccattcgtct tatttaaaat tttttaaaat tattatttat 900

```
tttatttgtg acttacttta ttatccaaaa tacttaaacc acaacttttc gttttatatt    960
tgtacaattt ttttagaata agatgagtgg tcaaacgtta taagaaaata gtgaatattc   1020
cttatattag gggacggagc tagtagcata tattcgatta aggattttaa gcagtgacag   1080
tgattataga ccaatccctt tggaattatg ataatagaaa ttgaattgaa aagggaaaag   1140
gtgaaggaaa agaggtgtgg gtttagccgt ttattgaaag gtgagatggg ggtaggtaag   1200
ctaatataag ctctccactc ctacaccaac acaacacaaa ctccgatctt gtttctctct   1260
ctctctctcc cttgtttcag tggctcagaa attttcctct tttcttatta ttgctttcct   1320
ttatttaagg aaggagttgg gctctctctc tttctctgag tctgaatccc cacgagacga   1380
gaaacctagc aaaaatctcg tctttcgccg cgctctccct cctctgattc ctgctgttct   1440
tgatcttgga tctcaattcc caaccaagaa cacacagaca gagaaaggaa ggagaagaag   1500
```

<210> SEQ ID NO 98
<211> LENGTH: 1338
<212> TYPE: DNA
<213> ORGANISM: Oryza sativa

<400> SEQUENCE: 98

```
cgcataaaca gatactaggg ggtgggaggt agagacgacc ttgcgttgga tttcgcagat     60
gcgatgtaga ccgttgcgtg aggaacgaaa gaacgagtga ccagtaaaat catttgttgg    120
gtagattact ttttcttcgt attctttttt ttactttttt ttcttatttt tacttctatt    180
agaaaaaatg cacgtgcgtt gcatcgggat aaaaacgttt ttatgataca accgttatta    240
gaaactgagc aatgaagaaa cattaggatc actattcatt ataattgaaa aaattaatga    300
aaattatttc ttggttttgg gcctacagcc cattatttcc ttccttttct atcctaaccc    360
agcccgctac ctctctcgcc tgcctctttt ctatccagcc cacaagtgga actacatgct    420
cctccctatt aaattcggtc gaatcttttt tttatctctc aaaattggtt aagaacttat    480
acactcaata tcctcttttc gttttcccaa aaccaaaatg aattcacaaa gttgggataa    540
aaaggtcggc caaccataat tagtgactga taaatctaga tatttaaaac cgaatcgaaa    600
ggagaagtca tgagaaaaat gatgagagag gagtggagaa tcgattttta caatcagttg    660
aaggagaaaa cacatgggga gacagatcaa agtggcggcg gcgtaagggt ttggtccagc    720
gacggaagca tgcaacagat cggatgagat aaaaaaaccgg gtaaaaaaag cgaaaaagaa    780
acctagaaaa aaaccgaata gggaaaaatc aaacaacgaa gaaaaagaaa ccggataaaa    840
acagcaaaaa aaaaacacga caaaacgaat cgaaaaaaaa ggagacacga aaaaaaacga    900
atagtaggcg acgatgcgtt atggtcatga gaaaaaaaaa agggaacata tgcttaggct    960
gaaaaaaaac gacgacggaa gcgattggga ttctaattga cggaccaaat aatctggcaa   1020
aaacattaaa cttttataat aggtaaagaa aaggtaattc aagtgatgat gaaaagctca   1080
gaatccgggc cgtacactgc ctcgagatcc gatccgacgg ccaggaggct cccagcggtg   1140
cccccgggaa tatccccacc gtagatgcct catcccacgg gtagaaggct agatgccgcg   1200
ggagccgggg tataaatagg ccactcgtcc ttctcctctc ggtctctagg gtttgggatt   1260
ttagccgccg ccgccgccgc cgccgctcac ccgcgccttc gacgagctcc agcccgtaga   1320
cctcgccgga tctccccg                                                 1338
```

<210> SEQ ID NO 99
<211> LENGTH: 1500
<212> TYPE: DNA
<213> ORGANISM: Oryza sativa

<400> SEQUENCE: 99
cacatgcatg ctatcccatg aggtgggttt ttgtgatatt tcaaagaatt aattttcgaa 60
taggccttag cccatctatt aattccaata ttaattccaa cagtaataag ctagctgatg 120
ctatagcatc gatcggatgt aacagtcccc aaaacaccga tctcctttgg gacagtgcac 180
ctccgggtgt tgagggtttg gtcgccagtg attctgccgc gtccatgggt taatggaaac 240
atgaagtctt ctttaaaaaa aactattggg ttaatcggta cgcacccata tgtccatctc 300
actcccacct ctagtcgaga tcccatttga tttagattat tgaatggacc atttacttga 360
atattgggat atattaagta ttttaagaga taatcttaac aaatagctta caacaaatga 420
cctaagcaag cagtaaaatt tctgttaaga aaatgtattt tttgaagtgg aggctagaga 480
gcaaacatat atccggttgg atgtagaggc cgggtaaaaa aaaaagttat tactgcttat 540
ctttttcacc gtatgtctct gggtaaaaaa aaaaacttct cttaaaaaag tgttatcgct 600
gcttatcatt ttcaccgtat gtctctgagt aaaaaaaaaa ccttctctaa aaaatccggt 660
tggatgtaga ggccgggtaa aaaaataccc ttctccagaa aaagtattat tgctgcttat 720
ctttttcacc gtatgtctct gggtaaaaca aaaaacccct tctttaaaaa aattcggttg 780
gatatagaga ccgggtaaaa taaataaaaa acccttctct taaaaaaagt gatttgctac 840
ttatcttttt caccgtatgt gttaggttaa aaaaaaaccc cttctctaaa acaaggtaaa 900
aatgtgttat tgatgtttat ctttttcacc gtatgtctct aagttaaaaa aaaaccattc 960
tcttaaaaaa atgtattatt actgcttatc gcttatgtgt cttggatcca actggtaacg 1020
gtggtgggaa aggaggcaag aagcatagca aaattcctga tgcaaatgcg caacaccctg 1080
aaaatattga aagtaggaat gcccccccttt tttttaaaac aataaaaatc atttcaacga 1140
aaatttgact aactggtaca caatacaaga aaatttattt caccgtctct tgcgtcatga 1200
tagaaaccat cgaaaaaaca agttttagac attcgcgaaa gaggactacc agctcactct 1260
tttacggaat tgcccttttt gaggaaccgt tgttatggtt atgggcctta tgaactgggc 1320
ccaatatcca cgcggccata cggcccgaag cccaggccca tttcgcaggc agccacacct 1380
attgctcccc ctccgcagta tttaagcttc acccccctcca accctagcgc ccccattcct 1440
caggtttccc ctcgccgacg cctccatcgc cctccgggct ccgcctccgc cgccgccgcc 1500

<210> SEQ ID NO 100
<211> LENGTH: 1617
<212> TYPE: DNA
<213> ORGANISM: Oryza sativa

<400> SEQUENCE: 100
aattgtaaat ttgaatatga ttgaattcta tgtgttttaa atatttctgt ttgaattatt 60
ttggtgctaa actaggtata aatatagtgt atacaaaata gaagagaatg agaaatgtgg 120
cctgagaaat gggggttgtt gctgaagtac aagtcaactt ttggatcctc ggacagcctc 180
cattagatct tttaagggct ttacaattta caatataagt tattgctgga gatgcttggc 240
agcatcatag tttctcccac cttcgtcgga aagtagattc cgccaaatgc atggtttatt 300
tgatttgcca ttataccaaa atgttgcagt gctaaaatct aggtaatttt aagtactgct 360
attttttttaa accggtgtat attatcggca catcttaata gcaaattaaa caataacaaa 420
atactcttta aagtgctaac aattcaacac ggcacatttt ggattcaaac gagaatgctt 480
gcatgggcat aatcacttaa cgtgtatttg gtctggtgac aagatgagat gggttaggct 540
catccctctt tttttttttt tttaaggata tgttttcatc agtacacgtt tggtagataa 600
ctttctcttt aaagaaatga gagaatgtgg cccaatgaga gagagtggat tagattagtt 660
atgtcgattt ttaagtacaa aactgaaccc gatctagaga gtattccctt ttagggatca 720
atgtatccca cctatccccg aatcaaatac actgaagaat aagttcaccc ttattgatca 780
tcccattatg tccctttcaa cttaaaaata tgtttatagt tggaattagg gtagtatgat 840
ttaaaggtga aaaaaatgta ttcaacgtag ctttgaaaag gtaaagaaaa gtgtattcgg 900
acttgttctt gtcaaacact ttatattagt caattgccgt tgcattgtat tttgaaaaca 960
gttatactcc taccttagga attactacta ggagttaggt cctaacttca ataactccta 1020
tggagatttt agcgcacaca aaaagagaaa actcattaac atatgattaa ttaactatta 1080
actattataa acttgaagat caaatttatt taatttttct taagaaaaca tttttttatat 1140
attaaaaaat tcgtatattt taaatattta aaaatcgtgc taacagaaaa cgagtacagg 1200
ttagagtttg aagttgaaga aaaaaacaat gacagtggtt gaaatttcct acttcctctg 1260
tcctaaaata ttgctacatg acccacaaat tcgttgtttt acgatggtag caacattttg 1320
ggaccgatgt agtatctgtg atttcaactc aacggcccaa caattgaagc ccacaaaccg 1380
caaagcccac gaagaccacc agcaaaaata aagaagaaac cggaggtcag tttcctatct 1440
aatctcgatc tctccacccg tttcccccaa aaccagcggc gccaccaccc accttccccc 1500
caggtgagtc gtcccacctc ccgtctcctc ttccccgttt tgtgtggttt tctcgttgac 1560
ccatgattgg cttctgattc gcgtttcgat ctccctatcc ccctccccct cgcaggt 1617

<210> SEQ ID NO 101
<211> LENGTH: 1888
<212> TYPE: DNA
<213> ORGANISM: Oryza sativa

<400> SEQUENCE: 101
tcgttctggg ttatcaaaac tcaaaaagga actctcaagg tatcagtgtc agtgtgtcaa 60
gtgtgatcgt tccatggcat atatggcttc aaacatttgg ttcttggcac ttggcagaat 120
tgaagtgtgc agtgaaaaga actgaaattg caatgtgctg gaagcatgga gcagacgagg 180
aggaagagaa ggaaggaaag gaagcctttc aactcgtctg gtttgttttc ctttcttctt 240
ttattttcag gcccatggag gcccacacgg cccatgttac agcgctgggg cccaaggtac 300
gaagcccact cacactcccc ccgcatctct cgggagtggt gagattgacc taaccggtag 360
tggagccaag atcagcgaaa ccgcggcacc caaccccaac ccaaaccacc agaccggcgg 420
cggcgggggc gacctaaggc gagaacacga gcgaaaccag agagggggcg caggtgcaag 480
cgctccctac ccctcccttc tcctccccaa tcccctcgag ctgcgtcgcg ttgaccgcgc 540
gaggcggcct ggttagggtt tcggcgccgg gcggcgagcg attcgcctcg atggatgcat 600
atgttcccgt ttctctttgt tcgggtggtg gtttggatgc gttggacggt agatccgcga 660
ctcctggaaa agcgaatcgg gggtttggcg atcgaaatgt ttctagggct gatggatctt 720
gggccgctgt gatttggttt gcgtaggcgt ttattagatc aatcgctaca tcattctcgt 780
ttggatgaat cccgcgatgg accatgttgg tggttgattt ttgggctagc ctgtggtgac 840
tgaatcgacc gtaggccggt ggaatgtgaa tctgcgatat gccgtcactg tgaaatgatc 900
aaacggatgg ccatcttgtg aactgtgatg aaattctgat gtccaaattc tgtgcgtcgg 960
gcggcggcgg tgacgtgcgc gtgcgttgct ggctgcggcg gtgcgcgtgt gcgtcggacg 1020
gcagcggcgg cggcggcgcg cgtacgtcag gcggtggcgg cggcgcgttc gcctccgccg 1080

-continued cctcctgccg gtgccgccgc tcgccgaacg ccaccgtcac tgtcgttcgc cgaaagccgc 1140
tgtgccagcg acgtcctcgc tgctccgtgc catggactga cccaacagca agcagctcca 1200
catgcccagg cgaggagaac gagggtaatt tggtcccgta tagcattgta gcttgtagcc 1260
acgggttgag attggcattt taacgaatcc cttttgcgga gtggcatttt ggcaaaacct 1320
agttttggca atggcagaat gtccaatttc tcgttttggt tgccctggtt tcatctgtgc 1380
agaggagagt attgtgcaaa taacctgttt ttctcacaaa atgtctagtc acctgctcgc 1440
tgccgttttt taactagttt atttgtctgt gatgttaatg atgagcagta ttactaatgg 1500
ttttctgcca agggtcgaaa tacgtgtcca tcttgtcatg ctatatgtat ctatggtgca 1560
ttctagcgaa tcttagagat aatcagagta gcttggatgg gggaagagtg gagacctgga 1620
attgttggct attggattgg atgtgtattt gcgtttcaga tgtttggctt gttcttcttt 1680
ttaatgttta gtagtatcat caaatatatc tttgatgttt ggcttgttct ttttttattg 1740
tttagtagta tcttcaaata tagttattgg tttggatgtg tatttgcctt cgagatgttt 1800
ggcttgttcc tgtatcatca aattgtgaac tctactattt tagttcactt ctgattgctg 1860
aattctcttc tctgtgcata taacaggt 1888

<210> SEQ ID NO 102
<211> LENGTH: 1588
<212> TYPE: DNA
<213> ORGANISM: Oryza sativa

<400> SEQUENCE: 102
tatttagctc gttaagaaaa gtatataaaa attttattca taaattattt ttaatttgca 60
aatatatcgt tccgttcttt cgtccaatat gctaaacagg gccggagaga tttgccggac 120
ccaatggtat ccatgttgcc ttcgattggg tcaagtcatg ggaagaagaa tccaaaagag 180
ggagactgat gaccattggc atcgatgatt aaagagaggg ctcgtactaa gtgctagtga 240
tagacattga cgccaattga tagagcaact tttgaccaca agttgatccc gcttgccgat 300
tgtaaagaaa ttgagcatag tgtgctctct ctgtcctata agtacaacct aatataaatg 360
tgatcacatc tatattatat tgtatttata ttagagcgga aggagtactc cctccattcc 420
attttaaaca taaccatgag tttccgtgtc ctagcgatca aggtgctaac tcgagcctac 480
ccttcaagca gactgatgtt gtagatctcc actcggcttg tggagttatg cataaaagtg 540
cggttatact cacatgaaac gtcgaaacct tctttgtaga agcaaccagt atcaatgccg 600
aacgggtagg gacgagctaa caataatgct gaactggtct tgagattcat gctatttcca 660
cgcgttgcgt gatgctattt ggcatctacg cggatacaaa caaactgaat tttggaagac 720
tcgtagactt gcgttttgcc gtgaagtact tgaaggcgga tcgctattga aggacgacgg 780
caagacgcgc ttcgcgaagg ttacgagtca attttcagga ctttagtact gtaggtctaa 840
ttgggtcaag tcgttgcctt tgtgtgatat ctttcgtccg aaagagcgtc gttgttttac 900
ttatgtttat aggtaggatt taaattttaa aatttaattt taaagttgac ttagggagtt 960
tttttctaat ttattttaca ccatttgctt ttgaatatcc gaaaacatat atatagaagt 1020
tttatataca aattaagttt tagttgctaa taagataaac ataagagaat gctatgaatg 1080
taacatctcc tatcaggcta tcactccaaa aataatgaac aacaaattgt agatagcttg 1140
tttgtgcata atccttttgt tttgtttacg gtgaatctgg atttaaaatt actaaaacaa 1200
tgtgatcatc atatgcaggc ttcggccatt cggagcgacc caactttcgt tgacgggccg 1260

```
acgtcgctgg ctgaaggtga atggaacagc ccatgttcca ttatattggc ccagaacgga   1320
atcgtaacta ttggttccta atatcggccc aatcaattgc gttggttatg aatggcccat   1380
ggaagcccac tattgctgct cccgtgctcc ctataaatag ctagggtttt acgccacttc   1440
ccccatctcc gccgccgccg ccccactctc caaccctagc cgagaggagc agaccaagca   1500
caggtaacct tcgcgccgcc gccgcctcat tgcttcttcc tcgtctactc ctagctctaa   1560
catggtgatc ttcttgtggc tcgcaggt                                      1588
```

```
<210> SEQ ID NO 103
<211> LENGTH: 2230
<212> TYPE: DNA
<213> ORGANISM: Oryza sativa

<400> SEQUENCE: 103

gtgacaaatg tttctttcat tctatctttt ttttttgaga ggtttcattc tatcgttttc     60
ccctttgagt ttgagaggag agcagtgttt ttgttttaca cgtaggaatg ggctatggag    120
tatggagtat ggagttggta acgtggcaac tgggaaggaa atagtaggag taggtgggaa    180
atttgctttg cgctgcatga ctgcatccca cttgatagag atgttaattg acttgatgtt    240
gtttgcacat gaatactgac acatggggcc actaccttgt gggcctactt ctcagttctc    300
agtcccacct aaactgattt tacgaacgga tttcacgtag gattaggggc ccaaaaaggt    360
cgtttttacg attttatttc tgatcagagg ctttcagcta ataaaattaa attgctgaga    420
ggtttagtag agtctataca tattcttttg cagtttgttg taacagcaat gcagaggatc    480
ctcgttgata gtactacaca caaacacatt ttgtgagctg tgtgacgata attaggggcc    540
tgttcacttt gatgctattt ttaaccttac caaattttgg taaagataaa aaaaagtggc    600
tatatttaat ttgctgccaa attttaatta ctatataaaa aatcctgtta aaatttagac    660
aagttgtcaa aattttgaca cctataccaa gtgaacaggc cctaggtgca gacaataacc    720
tacctccccg gcccaaaatg ctcgtggagt cgttgtgttc atgtcatttg agaatctcat    780
acccgtgacg tgctaatgct agggttaaac gcctaaacta cggcgcggcc atgcatgtgc    840
gcggcggatt ggtcacgcgc tgcgtgtcgg gtgctatcaa ttttgttgga tttgattgca    900
atctcacact ctcacagggt cacaccgttt ttggatttgg gaagaaaaat actgaggatt    960
agagagagag agattaattt cgaggtgtca cgagagagag actactattt ctccagatag   1020
tagtagtaac tcttacgtca tggacactcc aatacaccaa atggagtttc tactagtacc   1080
acctaatcca aatgattggt caaacaagag acatctacca aaactaatcg ctgcaaaaat   1140
caccactcct cgaataatac tcgccgtgcc aaacgctttg gccgccggag tccatcgccc   1200
tacattgccc accaaccgca cgcacccaga ttcacattca agtgggcccc acgctctgat   1260
cccataacca acaattatgc aggcgaaaaa tattactaac aaatgtagtg tctcaatgac   1320
aggtgggacc catacctccc acccgtctgt tctttaaatg cgctcgccca actgctcgca   1380
tctttctctc tgcccgtgcc aatcttcctt tcccacatcc tcctccgccg ccggctgctt   1440
cccaccggct cccgatctcc gaggcaagca gcgccgcacc cggccgctgc cgccgccgcc   1500
caggttagat cccccgcttc cctctccgca ccagcagatc tgtcccgcgg acgaggcgcc   1560
gttcgcatgc gctgggtttt gatatttttt ggttcgtggg tgtcgcggag agatccgcgt   1620
gatccggcaa atcgctgttg ttttcccgtc gaggttgctt ttgtttaggc taggcgatgg   1680
tgcgtcgagt tcgtgcgcgt aggattttag cgcgtaatca ctctgtggag ccgagctgcc   1740
gctgtattag tttgtggaca cgcgggagac gatttgctgc cgtgttagag gccggattta   1800
```

agcatgtaga gatatatgca tatatgcgat gccccgatgg atgatctatg tgcagctgac 1860
gaaagtattg tgaattggat gcatgatgtg aaaattttga atagtgggtt tggagtccag 1920
aattctggtt gtcgtttaga tattggttat gtacttttgt gaggctattt ccatatgcaa 1980
ttgatcatgt ttgatgtcca aacatcatca ggactcgtcc gaactgttcc tttgtttttt 2040
aaatataacg aagggaagat ctctaatgaa aaattgttgc aaacactgca catacttata 2100
agtatatcag gaattaaggg tatacggcac tgtgtttgta atgagtcaga gattatttgc 2160
acataatata tcagtgagcc tctgtttcat cttatggaac taactgattt gtaattcacc 2220
tactccaggt 2230

<210> SEQ ID NO 104
<211> LENGTH: 2455
<212> TYPE: DNA
<213> ORGANISM: Oryza sativa

<400> SEQUENCE: 104
cttccaaatt atgatctact cactccagaa gcttctgttg tcctgttaac tgatagcatc 60
ttctcttcta atgttctgtg gactgtgttt aatttagcac tagcatttaa tttggggcct 120
acttgaatat cattatatta tattgctaaa atttgatggt ttgccattta atttgtttgt 180
aagttcactg aatcatgtgt aatctagata gtactaagtt agtggtaggt gtgttagctc 240
cctccaactg aagaagatga gacatgcaaa gcaccctgcg tcatgtacaa cccacaaagt 300
tctaattaac gttcttaact atatataaaa tatcataaca ataactcctt aatgtgaaag 360
gtaaatagcc tctttgagta atccacatga agatgtggat ctgaaagaca aatgaggatg 420
tagatctgaa aacaattgta aataaattca taggataaga aaaagacaat gcttgatttg 480
atactgctat ggtcactagt cataagagaa aatgacttca aagttggaat atgttttgga 540
ttgtcaatag gtgcttcaat tggactctca gctgagccac caaccttaca actttgagc 600 ggctaacata atattccttt ctccaaataa gcaagaataa aaaccagagt tcaaatacaa 660
ttagaaaaga ttaacattta cttgctcggt tttacgattc caaaaagaaa aaaaattcta 720
ctatgttttc tcgcatggtt attacgacaa cgtctaccac atcatgcatg cttttttttc 780
attaacggtt tgggtgggac aaatatactc cttccgtcct caaatataag agattttgat 840
attttccttg tactgtttca ccattcgtct tatttaaaat tttttaaaat tattatttat 900
tttatttgtg acttacttta ttatccaaaa tacttaaacc acaacttttc gttttatatt 960
tgtacaattt ttttagaata agatgagtgg tcaaacgtta taagaaaata gtgaatattc 1020
cttatattag gggacggagc tagtagcata tattcgatta aggattttaa gcagtgacag 1080
tgattataga ccaatcccct tggaattatg ataatagaaa ttgaattgaa aagggaaaag 1140
gtgaaggaaa agaggtgtgg gtttagccgt ttattgaaag gtgagatggg ggtaggtaag 1200
ctaatataag ctctccactc ctacaccaac acaacacaaa ctccgatctt gtttctctct 1260
ctctctctcc cttgtttcag tggctcagaa attttcctct tttcttatta ttgctttcct 1320
ttatttaagg aaggagttgg gctctctctc tttctctgag tctgaatccc cacgagacga 1380
gaaacctagc aaaaatctcg tctttcgccg cgctctccct cctctgattc ctgctgttct 1440
tgatcttgga tctcaattcc caaccaagaa cacacagaca gagaaaggaa ggagaagaag 1500
caggtctcat cttttgtttt tcttttcttt tcacgctttt acttacttgt actattcgat 1560
ttcatgtttc gattcgtttc gttggttctt ggttccctat cctccaacaa cgtcctgaga 1620

-continued

```
cctcgatctg gtcggagtcc acgaccagat cttggccgcg gcgcagatct ggccctccag   1680

ccgccggcgt ggggaccttg ccagatctgg tcttctccga cggtggccaa cttctcttgt   1740

cccttggttg cagccaccaa acctcttcct cccctcctcg atccaacctt ggtcttgttc   1800

atcgactggc cactaaaccc caaataagcg agatagaatt tggattcgtt tcgttggtta   1860

ttgtttctct gatgctgtga tggtggctag atcatggcag atctgcccag taaagtcgaa   1920

ttttgtttga ttccaccgca cctcctgagg aatcggtcca atcctgtgaa ttcttctctt   1980

ctttcctgct gattggattg tctacatggg ctttacctgg aaacaggggt gagtgctagc   2040

agattcaaac atcatggact gactgctcct aaacaagttc catatgaaaa cctgttctac   2100

atgctttttt tcttttactc ttcactcgtt gtcagtcaaa cactgcaaaa tttgtccctg   2160

cgcctattct gcaagagctt cttgttagta caactgaaga atcaatcctc tgttccaact   2220

tggcatctgg acagaataat gaatgtttca taggaaaggc tcagctcaac taagtaaatc   2280

atgttgattg gccttaaaac acacttcatt aagagtctgt ttttttata ttggacatga   2340

taagaataat atggctgttt tttattatta atgtttttc ttggtaacag tgcttctatt   2400

gatgaaccta ccctgtttac ctgatctcac cagtgttctg caatactatc caggt        2455
```

<210> SEQ ID NO 105
<211> LENGTH: 1737
<212> TYPE: DNA
<213> ORGANISM: Oryza sativa

<400> SEQUENCE: 105

```
cgcataaaca gatactaggg ggtgggaggt agagacgacc ttgcgttgga tttcgcagat     60

gcgatgtaga ccgttgcgtg aggaacgaaa gaacgagtga ccagtaaaat catttgttgg    120

gtagattact ttttcttcgt attctttttt ttactttttt ttcttatttt tacttctatt    180

agaaaaaatg cacgtgcgtt gcatcgggat aaaaacgttt ttatgataca accgttatta    240

gaaactgagc aatgaagaaa cattaggatc actattcatt ataattgaaa aaattaatga    300

aaattatttc ttggttttgg gcctacagcc cattatttcc ttccttttct atcctaaccc    360

agcccgctac ctctctcgcc tgcctctttt ctatccagcc cacaagtgga actacatgct    420

cctccctatt aaattcggtc gaatcttttt tttatctctc aaaattggtt aagaacttat    480

acactcaata tcctcttttc gttttcccaa aaccaaaatg aattcacaaa gttgggataa    540

aaaggtcggc caaccataat tagtgactga taaatctaga tatttaaaac cgaatcgaaa    600

ggagaagtca tgagaaaaat gatgagagag gagtggagaa tcgattttta caatcagttg    660

aaggagaaaa cacatgggga gacagatcaa agtggcggcg gcgtaagggt ttggtccagc    720

gacggaagca tgcaacagat cggatgagat aaaaaaccgg gtaaaaaaag cgaaaaagaa    780

acctagaaaa aaaccgaata gggaaaaatc aaacaacgaa gaaaaagaaa ccggataaaa    840

acagcaaaaa aaaaacacga caaaacgaat cgaaaaaaaa ggagacacga aaaaaaacga    900

atagtaggcg acgatgcgtt atggtcatga gaaaaaaaaa agggaacata tgcttaggct    960

gaaaaaaaac gacgacggaa gcgattggga ttctaattga cggaccaaat aatctggcaa   1020

aaacattaaa cttttataat aggtaaagaa aaggtaattc aagtgatgat gaaaagctca   1080

gaatccgggc cgtacactgc ctcgagatcc gatccgacgg ccaggaggct cccagcggtg   1140

cccccgggaa tatccccacc gtagatgcct catcccacgg gtagaaggct agatgccgcg   1200

ggagccgggg tataaatagg ccactcgtcc ttctcctctc ggtctctagg gtttgggatt   1260

ttagccgccg ccgccgccgc cgccgctcac ccgcgccttc gacgagctcc agcccgtaga   1320
```

```
cctcgccgga tctccccgca ggtgagcccc caatttcaca cccttcgcgc ttgcaatttg   1380
gtgattagat ctgttgacga cgacgacgac gatgcgcttg ttgtgttgac gcgtgctgat   1440
ttgcgtgggc atattaaatt ggatgatgtt gtgtgttttt gccatgatga tatcgtacgg   1500
gggtaggatt agatcttgct gcgtccattt caatttagta aatatggtga ttcgcgatgc   1560
gggcgtgctc acttggtagt gtttgttctt gtgatctagt atttgttgtg gtgattgtgc   1620
agcaattggt agtatttgtt gtggtgattg tgcagcaatt ggtgtggtgg tatctgttct   1680
ggcaatctgc gatgaggctg tgctcacttt ttacttatct gtgatgattg aacaggt      1737
```

<210> SEQ ID NO 106
<211> LENGTH: 1648
<212> TYPE: DNA
<213> ORGANISM: Oryza sativa

<400> SEQUENCE: 106

```
atcggcttat actaagggga gaatatatgc tgggaagaga acttgaaggg gactaattct     60
gattatttat tgctaaattc caaagactag ctaaataccc tatatataga gccgacacct    120
gcaactcaat ctaatctaat cctactttta agcaacagag tatatgtaac acgcgctgca    180
ttggaggcat ggaggcatta tatctaacac ccaccttgtt tccctgcatg gaggcattcc    240
ctagtttact agcttgctca gtccgttttg ctcctttcaa tctcaaaatt atatagatcc    300
ttatgtttga tgttattttt gtcattaccg gtctcttcac gttattccat tatgttaggt    360
gccaagaaga gtatgttgga ccattagagt ggacatgatt agggatgcaa gtggatagtt    420
cctctactcg caaaaaaacc cgtttgctag ttcatttctt acatgatagt ataaaattta    480
gaagaaaaaa tgaagtagaa gtgagattag cgggctaaag aaacccgctt gcatccctag    540
acatgatcca tccaccttct tattattagg ttgtaggctg ccatttttct accagccatt    600
tacaagattg ccaaccagat tcgctctgct ctcgtagcca ctttacacca ctacgcagaa    660
ctacaaatct acaggatgga tttgcattgc gagcatgatg tccccaactt taatacaaaa    720
ctgccaatat ataatgagtt cagcaacgtg ttagggtaaa gttttttttt tttttttgcg    780
cagaggcagt tggaaaaaaa aacctaagac ccctatccca tataaaaaaa accaacttgt    840
agcttacaaa cctagataat aagctagaag tttatttttt atgagtaaaa caggtggctt    900
gacagtaatt ctgatggcag tgttcttttg aagggattgg agcatatccc actcgcacgc    960
aaacaaagtg acaaattaat gcacgattaa ttaagtatta gcttaaaaag tttgaaaaat   1020
gaattaattt gatttttaca gtaacttttg tgtaattttt tttaaaaaaa gtgcaccatt   1080
taaccgtttg ggatatgtgc atgtggaaaa caagaaatat gtggttgaaa ccttgaggga   1140
gaacacagcc aaaacaaaaa aaaatctgat ggaatcaaga aggccaacgt tggtgtgggc   1200
cgggcccaat gcatcatttc cttcgtacgt tgcaatctag gcccaacgga ctgcccacca   1260
ccccccctcgc ctgaagaatg gggtggatca gatggcaggc tcattcccag ccgtcggatc   1320
gacccgatca ccgcctgcga agtaaaccct aagccacggc cgcctcccta tataagccca   1380
cccactaggg tttcgcccgc ctctcctccc ccccgctagt tcccaaccag cagctgcggc   1440
ggcgcgagca cacgaagagg aggcggagca gccggagcca cctccgccgc cgccgccacc   1500
caggtaaggc acgcccgcaa cccgggtgct caaccttcct cctccgctta cccccatccg   1560
cgtggggggt tgtggagttc gttgtttggg ttttttgcgt gtgtgtgtgc tgatggattg   1620
atgggggtgc ggtgatggct gtgcaggt                                      1648
```

<210> SEQ ID NO 107
<211> LENGTH: 2484
<212> TYPE: DNA
<213> ORGANISM: Oryza sativa

<400> SEQUENCE: 107
ctgcatgtaa taagttaatg tagcaaccat gcccgtggaa atattatcac atttgacttg 60
agaacaaatg aatgaaatat atttggatta tgtttatttt ttaagaaaat agattaaacc 120
tgcctctaca accatagtgg atgtacacaa ccaaggatta tatgtttcta tgtctgtcgt 180
ttcacttttc tgaatataag ctagtataaa atgcaggtgt ggttcaatgt gtagtaaaat 240
gcacctgagg taccaaaact tatgctgccg attagttact aatcctgcaa acaatttaga 300
gtttagatga gttacaggca tgggcagaaa atgacatact ggtctactac tacatcgata 360
tcaccttgac taatctacgc tcacttctaa atgctccctc cgattcatgt taagacgtta 420
taactttcaa aagttaaact tatttaagat tacgagaaat atagcaacct ttttaataca 480
aaacaaataa aaacatgtta tcaacttcta ctttcttatt tttcacgtgc acacttttca 540
aactgttaaa tattataatt ttttttaggg acaacgcaga cactcacaac acgcgcacgc 600
taaccaaagg cacacgctaa ccttctaaga gcacattcag aagactagat atatctatga 660
gcacatccga aaggctaggc atatcttaag attaatgaag ttaccacgga cgtctcgttg 720
tcgatgattg tattgtctat cactgaaaaa aaattagccg taaatgtgaa tacccgtgct 780
aaatttagaa ttttgaaggc ccacttcgca gtgtcacagt tttaaaaaca tattaatcaa 840
tttttaagtt tttataacta atacttaatt actgatctgt taatgagcca ttcgttttaa 900
tgtgcacgtt agagaagttt ctaatcttcg cttctgaacc cacactgatc ctgatactgt 960
aatgcaaaag agagagtaca ttttaagtat ctcttttcat tttttttttc agaaaaaact 1020
tttaagtatc tcacagaaat tggagccatc aaatcatcaa tatagtttac tcatttatga 1080
aagcttcaaa tgtccggcgt ccagagtttc agaaaattca ctcaggagta tgctagacta 1140
ttctcttctc catgattccg caaaaagctt tttcgttaaa acctaaataa acctcgtcaa 1200
aaaaaaaaag ccggcgacaa atccaagtcc tccacgtcat cccatccccg acagcgacac 1260
gctccactca ctcgagcctt ctgggcggtg gaacctacac caaccactga tgggccgacg 1320
gcccagccca gccagctcgc gctgaaaccc tagccccatc acaggagggg ggctatataa 1380
gccctccgcg ccgcccctcg ccaacccttg cacccccctcg cgcctccacc acacactccc 1440
acccaggtaa ggagagggag gaggaaggga acctcgaagg cggcggcggc ggcggcggag 1500
caggtaagaa ctcccctcaa ctcccgtttg atatcatctt tgtgtgcgat tggtagtttg 1560
tgttgcgcgt gatttccttt agatctggag ctatagtgct agtctgcggc gcgaaactgt 1620
tgccgtggcg attccgatgt ggagtttcgt ttggttcgct tagtcggagt agttttgatg 1680
tgttctaggt agtgtgttgt ttaatttagt tgcggaggaa gttgcttcat gggacttaaa 1740
ccgttgcctg ttgcagtttt tctaggttcg tttttgtgat ggatgcatag aggtagaaaa 1800
gtttcgagaa atgatttata catggaactt agggttaggg tttagattga tcttaggggt 1860
tctgtcaaat ccacggtgct gttctgggga tgtgtgtgct tattatcctc cattagatga 1920
aaaatagaca tgatatagac atgatatgtg atgcttgatg tattacttat tcttgttcgt 1980
cacctatgcc aggtaggatg aagactgcaa ttcatgcaca caggattatt aatagggaat 2040
gcccacacgg ttatcaatag gggaacattc ctttgtctgt tgaaattaca attctataac 2100
atctaagttc attcggttca tttcgattgt tcatcaccat ttgtagaact gcagtatgat 2160

```
actgtgtaaa tgtatgcatt gtggtttgtt tacttgcaag ttttgttgtg ctaattataa   2220

gatatattgt ttgctatgct atgttgggta tcgtgcatac tttcataaac aaagtctatg   2280

ttctgttctg tttggagtat aaatactcat ttccgatggt ctagtaatta tttactatcg   2340

tcttgaaaag ctgttctaga tacttggttt tatttccctg tgacttgtat atgtgcttgc   2400

atggtgatga actttgattt ctataacacg ttcctgaaat gctgggaaag ctatctgatg   2460

ttctgttcct tcctacttgc aggt                                           2484
```

<210> SEQ ID NO 108
<211> LENGTH: 1658
<212> TYPE: DNA
<213> ORGANISM: Oryza sativa

<400> SEQUENCE: 108

```
ggcgatggtc agaattaggc atctacaatt ctacatggca aagccagcat acatggcaat     60

ttgattctaa ggtattgatc agatcagatt tgatgcaacc tgtttggaag tcaggcccct    120

ttgactttga ggtgcaaatt aatcttttgc ttgtctccta gcttagaatc gcctatggac    180

tgttgctgtt tataacttaa ggctggccaa acaattagtt ttgtcctcta tgcatcaaac    240

cttgagacat ctcatcattt gttcatgaag agtagattag tttcaagcca tccggacagg    300

aataagcctg tgcttaactg aagtttcttc agcaagcctc cttcggcctg ttcagtattg    360

gaatggtggt gtcacaagac ttcatcagaa aagatgcaaa gaaaagggct caggaccctc    420

ttcttgctgg tctgctgggg aatttggacg gaacgaaaca atagaaactt cgagaaagag    480

ggatggtcaa ttcagcgaat tgtcgacaaa ttctttttta tgagatcaag cagtggacca    540

gctacagaga aaaaaggctg gtatagttct ctcgaagaga gagctgtttt tttgttagtt    600

tgtaactttg tatagcctct ggcttcagtt ctattttgtt ccctcctatc aaaattcgta    660

caaaacagac agatcatacc cataattaca agtaccgatt atgttggtta tatctttttt    720

acaattacac aggatatata ttttataaat tttggttgaa taaattattt ttggtagata    780

tagtttccaa actttcaatg tatccctatg atatatttta tgaaaaacgt gtattgcacg    840

tgcacgatta ctagtgccca gataaattag tactgatctt gtcccgctca aggcctcaaa    900

cctcggtaaa aataatttca cggcggtaaa aataaaacat ggcaccatct ttttactcaa    960

gaaagaaggc aaaaatcctg tcgctattca ccaatcacgc aaaacccttc tctccaagaa   1020

cacggcgccc tcacctcaca tctcacatca attttgatac cattttcaac cttaccaaat   1080

tttaataaag ttataaaaaa atggctgcat ttagtttgtt accatatttt aatacttata   1140

gaaatcctac taaaatttta gcaagttatc aaaatttgac aactatattg ctaaaatttg   1200

gtaaggtttt ttttacatca aagtgaacag tcccaaaagt tcaccctgcg caacaattaa   1260

attaagcaaa ttaaatcatt tttggcatct tcttcctccc caagaaaaag ggccaggata   1320

agcccatccg acggcgcagg cgagccgaga gccccgcgag cgcagatctg ggccgtccgc   1380

ccgccgataa ataccagctc tctcctccac tccgcttcac ccccaaatca aatccccttc   1440

tcccattttt cctctcctcg cttctcgccg cagccgccgc cgcctcctcc tcctctcgcc   1500

caggttcggg gatgctgcgt cgttgctggt tctttttgtg gggtgttttt gtggttgggg   1560

ttttgtgatt ttgttgccct tttgcttggg gttgtttctt ggtttcttgg gtgtttgctg   1620

acgctggttg ttttttttt ctggtgggat ttgcaggt                              1658
```

<210> SEQ ID NO 109

```
<211> LENGTH: 1811
<212> TYPE: DNA
<213> ORGANISM: Oryza sativa

<400> SEQUENCE: 109

aaaagttttt ttaatgtgtt tgtattatga gcgtctgcgt ttacacaata gaagttatta      60

atcatgcatt gatcattgta tatttgtatt gtaccatggt gcagttaatt ttagagaaaa     120

aattcaaaga aaaactagcg atccaaacca atatattggt gttgatactt gttctaccac     180

cataacgata tattggtgtt ggacgtgcta gtgtgttttg aacaagattt ttttagcgag     240

gttaaaaatc ccatattcaa gccttgttac ttctttctta ggttaagcac atcatttatt     300

aatattgcca tctattactg gataggatac atcatagtac tacgaatcgg atacatcact     360

atattatata gtactaaatt gttatattat gggatggaga gagtattcta taacacacat     420

tttgttttct cataagcaat tatcatttct tcttttgtta tgacgatcaa gcaagagaga     480

ttacatgaga ggcatcatat gttgttatta ggaagattat gggttgtttg gttgatacct     540

aactttgaca taactaaggt tagacaagta atatgtctaa gaaatagttg gttatagccc     600

gcagggggga tttacaatta tgacattgca aacattaacc tttgctataa taacactagg     660

ctcacatttt atagacacag atggacccat ttgtcatcca ctcggagtgt caaaacagcg     720

aagctctcgt gtttgcagtc ccaatattac aaatttctcg cccgcatgtg tgatatgttt     780

agttacaaat ttgaaagtgc gggtaggtct taagagtaag aaagtgtgca taattgtgaa     840

gtgaaacaat cacatgacta aataatcgtg atatgactaa agtgtggtat ggtaaagtga     900

gacaaccaac ccatcacccc cttagtcaat ggccggtcag cagcttaata cggcatttgt     960

agcctcacga ctaatattgt atggttcttt taataggttt ttcataggac gacacaaaat    1020

atatttttcg agatcgttat aggaatgtaa caaaatatcg tacgcatagt attttccgtt    1080

atgtttaccg ttatgtttat gttattccag tttctttccc atgtttttat tttttgagcg    1140

gtttcccatg tttttatggt tgtgcgcaac ctatatacgt agaggtcgga tgcaatttta    1200

ttgcgaaaaa aaagaagaaa accattgaag ctggaccgta ggactgaaaa gatcgtctct    1260

ccatccaacg gcccaggaga cgccggaaca attacaccac cagaaagtcg tgtaataaaa    1320

aaaagtagtg gattggtggt gtaataaaaa aggaatctac tagcgctcta taagggcgag    1380

ccgcacggca ccaccaatcc accactgatc atactagcac agagcgccgc cgccgaggag    1440

agtccaatcg agaagaaggg aggagaggca agcggagagg aagaagaaga agaagagagg    1500

caggttcgcc gctttcctcc ctccctatct cccccagaac atttcctttc atgctttttc    1560

ttttcttgga tccgtgcgtg tgcttagctg aatcaacctg agcggtaaga acaaggtggt    1620

tcgttcccag atccatttct tgttggatct catgtttgat gccaggattg tcttttggat    1680

agatggttta gattcaaatc gcagctgcta gtttacctct gtccggtttg tggatagatt    1740

tctgagtttc tgttttggag tagttaagcc taacttggtt tccttgccat gctgctttct    1800

tttctgcagg t                                                         1811


<210> SEQ ID NO 110
<211> LENGTH: 1555
<212> TYPE: DNA
<213> ORGANISM: Oryza sativa

<400> SEQUENCE: 110

tgtgggtccc atcttttta ttattatttt atgtgactga catgtgggtc ccacagattt      60

tattattttt ctagatcgga ttgccacgta agcaccacgt cagtaccaca tcaaatgaag     120
```

```
accgagtcaa aatggacacg taggcgctac gtcagccaaa accacccttta aaatcgtcaa    180
ggtacctcgt ttgtccggtt ttcgtaagtt ggggacgggt cgtaccggtt ttgcagttca    240
gggacgaaaa tcagactggg cgacaaatag agggacctaa aatgaactta ttccttcaac    300
gtttgtgtgc tgacagagtg acgagcctcg attttctaaa aaagaaaagg ttacaggcct    360
cgaacaagat gctgttacca aagttagcca cgaatttgga ctagaaaata gctaaacatg    420
acggcttgat cgaagattac gcaaagtttt agttcgactt tcgaacttat aatagttcaa    480
aataatcatc tgctgtcatc atctactcaa taaaaaccga aatcctctgt caccatcaaa    540
acatagcaaa aatcaaatgc cattaaaaag tgccaaatga cagttgacag cccaaaataa    600
aaaagaagaa aaaaaaagga acactattat attccagatt tccagctgca atatcaagct    660
accaaatgga tccccaaaaa aattgcaatc cattccatga actgagccca ccatgcacca    720
cacaaccccc gctcctccac gcttctcggg ctcccgtaga ccgggtccac ccgccaatcc    780
ccccacacgt cgatatctcc agcacccacc gcacccactc tcctcctcac tccgctcccc    840
tcctctcctc ctcccttctc gcggaggccg ccgcaaccaa aaaaaaaaaa gtctaaccct    900
agatccaggc cccgcgtctc cggcgatctc ccggcccagg taatgccccc ccgcccgtct    960
tctcatcctt gtttgcgatc gtacatttca tttcgtgttg tctccgacca gatctgacga   1020
aatgtggatc tactgctgtc agatttgatc taggtgtaca gttctgagtg gcgagcgatc   1080
gcccttccat ttcgttcatt ttatcggtag actgttggct gctttgtggt ggtctgttcg   1140
tgctagtgaa gaaattgact ttttttcccc tataaagtgc tgccttttgg tttgtggtgg   1200
tcatctagag tctattagaa ttcattatgt tcaccagtgt tgcatttccg tattggcgta   1260
ttgtgaggtt aacatgcatt ggttggtata acttttccac tgtttgcttg aatgaaaatt   1320
gtcgtcatag tctaggaatc cattccagtt tttgtttatt taatacccct gccaattgtt   1380
tagcataaaa tgggcattac tgaattcaga gaactgctga tgcattcgtg taaattctga   1440
ttataattag agttgctgaa ccttgtatct gtagcattgt cttggaagtt gaaactaatc   1500
atatataatg tgttctacta tgtttttgac ttggaagtta ttcttctttg taggt        1555
```

<210> SEQ ID NO 111
<211> LENGTH: 2800
<212> TYPE: DNA
<213> ORGANISM: Oryza sativa

<400> SEQUENCE: 111

```
cacatgcatg ctatcccatg aggtgggttt ttgtgatatt tcaaagaatt aattttcgaa     60
taggccttag cccatctatt aattccaata ttaattccaa cagtaataag ctagctgatg    120
ctatagcatc gatcggatgt aacagtcccc aaaacaccga tctcctttgg gacagtgcac    180
ctccgggtgt tgagggtttg gtcgccagtg attctgccgc gtccatgggt taatggaaac    240
atgaagtctt ctttaaaaaa aactattggg ttaatcggta cgcacccata tgtccatctc    300
actcccacct ctagtcgaga tcccatttga tttagattat tgaatggacc atttacttga    360
atattgggat atattaagta ttttaagaga taatcttaac aaatagctta caacaaatga    420
cctaagcaag cagtaaaatt tctgttaaga aaatgtattt tttgaagtgg aggctagaga    480
gcaaacatat atccggttgg atgtagaggc cgggtaaaaa aaaaagttat tactgcttat    540
ctttttcacc gtatgtctct gggtaaaaaa aaaaacttct cttaaaaaag tgttatcgct    600
gcttatcatt ttcaccgtat gtctctgagt aaaaaaaaaa ccttctctaa aaaatccggt    660
```

-continued

```
tggatgtaga ggccgggtaa aaaaataccc ttctccagaa aaagtattat tgctgcttat    720
ctttttcacc gtatgtctct gggtaaaaca aaaaacccct tctttaaaaa aattcggttg    780
gatatagaga ccgggtaaaa taaataaaaa acccttctct taaaaaaagt gatttgctac    840
ttatcttttt caccgtatgt gttaggttaa aaaaaaaccc cttctctaaa acaaggtaaa    900
aatgtgttat tgatgtttat ctttttcacc gtatgtctct aagttaaaaa aaaaccattc    960
tcttaaaaaa atgtattatt actgcttatc gcttatgtgt cttggatcca actggtaacg   1020
gtggtgggaa aggaggcaag aagcatagca aaattcctga tgcaaatgcg caacaccctg   1080
aaaatattga aagtaggaat gcccccccct tttttaaaac aataaaaatc atttcaacga   1140
aaatttgact aactggtaca caatacaaga aaatttattt caccgtctct tgcgtcatga   1200
tagaaaccat cgaaaaaaca agttttagac attcgcgaaa gaggactacc agctcactct   1260
tttacggaat tgcccttttt gaggaaccgt tgttatggtt atgggcctta tgaactgggc   1320
ccaatatcca cgcggccata cggcccgaag cccaggccca tttcgcaggc agccacacct   1380
attgctcccc ctccgcagta tttaagcttc accccctcca accctagcgc ccccattcct   1440
caggtttccc ctcgccgacg cctccatcgc cctccgggct ccgcctccgc cgccgccgcc   1500
caggtaagct cgctcgctcg ctcgatctct cacatccctt catcatctct ccctctccct   1560
ctctcgctcg ctcgctcgta cggttgctct ctcttcgatc ggctgcgcgg tgtcttggct   1620
cggctctgcg ctagggtttc gctccggtga actaggtccg tgtcttagat cccgtggcgc   1680
gcgcgcctcc tcggtgcgag atttgcgaaa ttcggtcggg gtaatcgagc ggattgtagg   1740
atttgtttct cgtggtggtg ttgactcggt gggcggtttg acttttcttg ttttcgtgaa   1800
tgttataagg cgagtaatcg ggaaatctcc gggtttgttc agtttagcat gttaaatttg   1860
gtctataatc ggttatgtag ggcgtgtaag agctgcagga tcagcaatat acatgtatag   1920
gattgctttc ttagaagata tgtttggtgg cgtgtgattt gttgcgccat gtaatgcata   1980
aacttgttag gttagtattg gtcgttgttg ggatgccaca gtatcttgta attttggcaa   2040
tctgttgtgg tgctacatgt cctagtattg tagatttaca tctgacaaac tagatataaa   2100
tggtttctgt tgaattttgt ttatggcata cgttcatgta gtttgattgt cattctgtgg   2160
cttatattac ggtacatcat gtgtatactt ttcatttacg gtgtattccc attcctaaga   2220
atgtttcatg ttgtgaatca ccctcaatct caaaattatg atgagatatg gactaactag   2280
gatttttatt atctattagt gatacacata tgtgctattt agggtttaat ctttttggta   2340
ctatctttga agcttaattt gcatcattga ctccatactt aatgtaatct gctgagaatc   2400
tgtctcgaac atcacatgtt tctttcttgt ttttgctatt gtcaagattg ttttgttgtc   2460
tttgctacct ttgtatgtat ttcaaattat aatgcaatca ttgtcatgta tgcatatatg   2520
cctggttatg atgtatgatg cagatacaca ttttacttga gctttttttgg ccaatttgtt  2580
gaatttcact tttctttttg attctgtact catgatttcc tcagctagaa acattgcctt   2640
gttcagatta tactgagata cttaatatct ttcattttca tctttggatg ctggtcacta   2700
gtttagacct attatcttgt taattagagt ttgtatactt gaatgaacca catgtgagtt   2760
gtgttattct aacttgtgca ctgctgttct cttaccaggt                         2800
```

<210> SEQ ID NO 112
<211> LENGTH: 2635
<212> TYPE: DNA
<213> ORGANISM: Oryza sativa

<400> SEQUENCE: 112

-continued

```
agcaccatca gacgccgcca catctccggc gcccgtcgcc tcctccatcc ctcccaactc     60
gcttgagcgg acacgagcag ccgcaggagc tcctccagct ccggccaccg gcgtggtgct    120
cgtgctccgc cgcggcactc tcgccggaaa aagaacgaag agaagagaga gagaggagga    180
accgaggaag aggagaggga ggggagagat gacatggcat atatgtgggg gtcccacgct    240
gactcaactg tcacatagga caaaaccaag atcaaaacca tagaggatct attgtgaacg    300
ggttttgatt agttaagaga ccccaaatat tttttcagtt gaggtacgat tttgtaactc    360
gatgacaagt tgagggacct ttggtgtact ttttcctagc caaaaggcct cggcccatgt    420
attaaggtga cggcccactt gtgccgtcct cgaagacggc cgacagacca acattcattt    480
acagcccaaa aattacgaaa acctagctgc atcgcatctt cttctccttt ccccaggcgg    540
agcaccgtcc gatgagcatc caacggctac ggtcagcacc ctcggaacct tcgagaacac    600
cctccccgct ataaattccc gcctttccgg tagcatctag tcttcctctc ccactcttcc    660
tcctccccaa accctagccg ccgccgccgg cgtactcgag agaaacatca gcatcccagg    720
taactactta ttccctgctc ctcagtcctc tctctttctc tctctccccc cttagatctc    780
atctctaagg tcttcgtcgt cgtcgtatgc tagatctact cttgcccagc tcgttcagat    840
ctgttagatt tgtgtgggat gctctaatta attactacca acttagtaga tctggaactc    900
ttttgacttg cagatcttgc tccactcctg ttgcattttg aatctgtgtt gatgtgattt    960
aagttgttgg cagtgctttt tgcatactat ttgaatttgt ggatggttag cagtcagtac   1020
actaggattt attactggat ctggacagat atgctcgttt caatcggctc gatttgctat   1080
gttgatagct aacatgttgt gcttgtccta ctgccctggc gcaaatttga tccatgcatt   1140
cttttcgtta aatgatttgt caagtagtaa tgcttgtttg aaaatgatat tattattatt   1200
attattattt taaataaata tagcctgaaa cattcttagt ttcgaggaga agtgatgatg   1260
tcttatccat accacatgtc tgcatctcat atgatgatta atctacatca tgcactacca   1320
tctgatctcc tctagctcat acagctttta acaagttagg cgatagatgt ttgctacaaa   1380
cagtcaactg gatttgcttt cttgaaagaa aaaaaatgaa ccgtgtagtt tgcaacctgt   1440
gatgtaaatt aacccattta ctgaactaca ttgattattt cagtaaaatc accatctttc   1500
ggctgaggtt gcatgcttag ttattatatt tttaccaatg atgattttgt tatgtagcca   1560
gatactgtac tttcttatgc catttggtat ctgactcatt gtctactttt gtgactatgt   1620
gtctcgaaat atggcatata ataaggggga acggatcttg cgacattgat ggctcctgta   1680
tgagcctcca attactatat agccgtttac atgttcttat catgttactt ttccaaatta   1740
gtgctgcaca tcttgtctgt ttgcaagttt gggttcattc atattgctgt gggcatttta   1800
atacatctta actataatgt aaatttcttg tacatcgcta aaattttctg ccttgattga   1860
gtagactctt agatgacatc tatcttacct tatgcacttg attcgtattt ctgttacaac   1920
atttgatta cttgatgtag ttcacacaag catgacacat ctctttgaaa aaaagatttc   1980
attttttaaa gcaagcctaa tgctttaggg tgggagaagt gatgatactt aatccataca   2040
acatttctgc atctcagatg atgatcaatc tacatcatgc actaccatct gatctcccca   2100
tcatacaatt ttttattttg ttttgttgga ttatataact ttaacatttg ataaagtgcc   2160
aacagatttt tatacacaat ttcttataga tattaccatg acagcttgca gcctgtgatg   2220
caaaagtacc cattaaactg aattacactg attattccaa acaaatcacc atctttcggc   2280
tgaggttgct tgcttgttta aaattatgaa tgcttcttgc acaaccattt aggactttcg   2340
```

```
gtagtttgta atgccatttg gtatctgaca catggtctgc gcttgtgact atttgtcttg   2400
aaatatggca taaaacaagg gggaacggat cttgcgacat tggtggttcc tctatgatcc   2460
tccaattact atatagctgt ttacaatttg ttaagttagg agcatacctt ttgctttgtc   2520
atcaaagtct tggttccttt gtatttctag ttcagattca tttttcttca gcttttgaaa   2580
cataaactca gtatattttt actgtaattg ctgacattga gtcttctctg caggt        2635
```

```
<210> SEQ ID NO 113
<211> LENGTH: 1500
<212> TYPE: DNA
<213> ORGANISM: Oryza sativa

<400> SEQUENCE: 113

atatgttcaa ccattttcta ttgacaaaaa tgaattctag accttgtgct agcgtttcgt     60
attttccagt acaaaacatg agtaaaaaac taagaacttc ctcgcattcc agattttact    120
ctaactgttg tactagtagc cccatttgga gaacaaagtt taactaaaaa ctgtatgaag    180
caattaaact ctcacacaat caaatcaaga tagatataca attgtaaaaa aaaacatatc    240
tttaacctgg aagtgaggag gagatccaag gtcaatgaaa gaagacaggt agggagggcc    300
atgtgaggag atgcctctcc atttgcccct ttatttccga caatgccact caagttgatc    360
agtatcttct tcatggcacc agtagctgtg tactccatga gtgtaattaa ctttcttctt    420
ctctccaact gcttcagcta actttcttat taatgagcac cattttctg ctctcattat     480
atcatgtggt ttgcttctgt tacctgctga cctgtgtttg tgtgtgatct actatctgca    540
gactgcagct accacttggg cttgctttgt cacatgcagt tttacacctt ttatttctcc    600
ttaatacaag gtaagtgttg gatcagtagc ttgctcaatg ctcactcatc ctgccaaaga    660
gagactacag acttgttctg aactgtaaag tctgttgttt ggatcctctg catattgttc    720
agtcttgtcc ttttgcttta cagccctttt gcaaatgcag gaaccgtgtg ataaaacagt    780
agtagaagtt tcatcaggct catggttgaa gtaacagtga ggatggagcc agggcgaagc    840
catgattctt cgagtgcatg gctagaaaat aataaaatgc atttttttca tttagatatt    900
cttagcttaa aatcgcttac tctgcattgg aaaattctgc tgccacatgt agtgttactc    960
tgcattagcc aaaaaaaaag aagcaaaagc aaaaattaac aggtgcctca agatttgtgt   1020
taagtgatat cacagtaatg ttaacctatc caatgtagta ttagttagtc atattctaac   1080
tggatgattg gattgattat ggacagattt aaatttgctc gtatggatga ataaagcaag   1140
ggacgtgtga aaattgtaca aaattttgat gggcctgatc tgggccactt tgggccttga   1200
cactctaggc ggactagtgc aacatatgcc ccggcccatt tacaccgccc cgcgataaaa   1260
actgggtgag ggcgaccaag aaccctaggc tgtcgcggat ccatcccatc ccatctcttc   1320
ctcgtctccc actcctccgg tgagccttgc ctcccttttt cctcgattca gttcatcaga   1380
tctttcggta aatccaatcg agttgatagg gtttgatgtc ctaatctatc tatctctctc   1440
tgtgctgctg ctgttgttgg gggtggcagg attctttctg ttcttggttg attgccggag   1500
```

```
<210> SEQ ID NO 114
<211> LENGTH: 1500
<212> TYPE: DNA
<213> ORGANISM: Oryza sativa

<400> SEQUENCE: 114

ggtgttcgtc atgttggcga ggatgatgca gagggagacg aacaaaagca gtcgcacgta     60
gcgctcccca aaaacttaat cgcccgccta cccgtgcagg ttctcaagcg gatgaagttt    120
```

```
cggaggcacc tgctcgttcc gatctaccgt acgtgcggga tggacagaac cggggaaaca    180
gagagacaac gcaggaacaa aaggagaata tcgccaagga acatcagcag gaggaagact    240
caatctttga gagccttttc ctttgcgtta tttatataga gagatctcca ttaccacaca    300
aataaatctc atttgttgtg aaggttacca cacaatgaat ctatttgttg tagaggttac    360
aacaaataaa tctctatttg ttgtggaggt tacaacacaa tgaatctctc atttgttgtg    420
taggttacaa cacacaatga atttcatttg ttaatggtga ctttattttc gtctgttaca    480
aaacggaaga gcaacaagag gcttggctcg gcaggccgcc tcgcctcgcc acgcccacgg    540
ccgaggccga ctcggcgcgc gcgcgtgtgg cagtccaacc atcacctcaa ccggtcaaca    600
tggattctcc aatatcactc tatttaagtt gaggttattc cacataaatt ttcaaggtag    660
tattattgtc tctaacaata cttatgggat cttaagattt taattaaatt aaatttggcc    720
taacctattt attccaacag aatataaaca attttagttt tttttagcag atattagact    780
tgaggataaa aaggctttga catgtatcat aaaatgaagt atgtttggga ttagaaggat    840
tactgagagt aagatggaaa gaaattaaaa cgtgaggtga ttgatgaagc aattactatt    900
ctaaaaatct ttatatctgt gaacaaattt aaaaaacata aaatgtttat atttgtgaac    960
agataaagta cacaatattc cactgtcata atacaaaaca ctcagaaaga gacgtatttg   1020
ggccgtaagc aagttggtgt ggtcgtgtcc aagcgatcca gtccaaaagc ccattcgctt   1080
tacctagtgt gaggcccagt ctgcgacctc cacacaaagc cctagcattc aagcccattc   1140
ctacatttcc gcccgaccca gcgaaaccct ccattcggta gccgcctata aataccaccc   1200
ctagggttta cctccctcgc ctctgcactc agctcgcgcc gccgccgccg tcgccgtcac   1260
tctcctcagg taagctcctc ccctcctcat cctccaatcc ccgcttcgat tcagattttg   1320
cctccgctcc gtgtccgcaa tccgccatta gttgttagtg agctagctgg gagatcgaat   1380
tctcgtcgct ggtgctgtag tttgatcgct gtggcttgcg attggtgatt ttacgggcat   1440
tttcttggtt gcggatctca tggcttgtgt gggtttcgtt tgcaggtaag gaggaggaag   1500
```

<210> SEQ ID NO 115
<211> LENGTH: 1500
<212> TYPE: DNA
<213> ORGANISM: Oryza sativa

<400> SEQUENCE: 115

```
acttcaccac cacaccaaag ggtgttgtac tctcttactc tgcacctttt aaaatactct     60
tactccgcac ctttcaaaat acatgcccat atcttctctt tgcaaaattt cagcttttct    120
gtagttaaat gatttaacca ataaaatgtg gttgtatcat acaaagaaat taatggtgta    180
aaatgaattt ggacgtattc tagtcatgtt acttacataa tcgagcttat gaggtatttg    240
agcttaagaa agattatgag ttgggacata ggctatggtc aaaagtgaca agtaatctga    300
acatcaagta tgtgatttca actcttggca attgacattt gacaactact tctatacagc    360
atgtaaagct atgttgtcca tctgtagtac tattagttgg cagatcaagt tgctaggagc    420
ccgttgttcg ttgatgatta agattgtgat cgcacggtca tctagcctaa aaggacggtt    480
gaacacatat gattttatcc aggttcaggt cttccagaag ataataggtc tactcactaa    540
ctagagatat tatcttgatg ggattgcttg ggtacccctg ttcgctcaag gtggctaagc    600
tctacactcc tatagcttct ctgtgttgta atgaaccaaa cctctggtgt agaccagact    660
ggtcctcata atcgctcaag gtggctaacc cttgcaatct tatatatccc caggtctacc    720
```

-continued

```
taaccaccat agagacactg agctactgtc acgctgcttg tcctggtcat tcttctttgc    780

catgttggca tgttgcacgg taccaccttg agcttccatt ttgatggaaa ggggagcttg    840

agagatatat tattttccgt gaggaattta gttttattta tgtatatgaa atttaaaatt    900

agttattagc aagatgcagt tacacggact ttttctccta aactatcatt atacaattag    960

aaaataaacc aatatattta tcaatcataa gattaatatt ttaatattta atatatttat   1020

catatgacta aaattttaat attttatcaa taataattgc ccgtgcaaag catgagttga   1080

tggcataaat aattattcaa aataaatagt atttatatat atagtagtgg gtggcaataa   1140

ccaggagggg aaatttgaac gccatagttt tctctcatct acacattttt caatacaatg   1200

aaaaaaatac agtaacataa attggcaatc ccttaaaaat gatttacaga aattacctca   1260

cattgttttt gaaaagaaag aatgtacagc atcggtttgg gctgagggag tcgttgccat   1320

cttgggccgc gcgcaaacag cccatacctt ggcccattag ggttttgctc cctaggtttc   1380

gtctcccccc tatataaatg cttctcctgc gccgtcgttt ccctcttcca tccttcgctc   1440

gctccgccgc cgccgccgcc gcctcctcct cctcggcgcc tctccgccgc cgcctcagcc   1500
```

<210> SEQ ID NO 116
<211> LENGTH: 1500
<212> TYPE: DNA
<213> ORGANISM: Oryza sativa

<400> SEQUENCE: 116

```
gacaaccgat gtagatgaat acttcctcgg tttaggaatt gggattttat ttataagtta     60

tacaaagtaa atataaaatg gacggtgcat attgattgag gtagaatatt agtactactg    120

tttcttcttt ttggaatata ctgcaaaaca acactaatgt aatgttcgga caaaacttaa    180

acgtcattat gaatattatt agctcttaat aatcggcaat agccaatagg tcagagacaa    240

acacccatca gaggatccgg attcgatcag gtgagtgccg gacaaacagt atgcggcgcc    300

atcgcccgtc gccgccgccg gctactttct gttagagcac gggcctgttt agttcaagaa    360

aaaaaaatta tttttgaatg tcacattgga cgtttaacta gatatcgaaa tagatttttg    420

gacacgaata aaaaaactaa tttcataact cgtctggaaa cagcgagacg aatcatttga    480

gcctaattaa tccgtcgtta gtatacgtag gttaatgtag cacttatggc taatcatgaa    540

ctaattagac tcaaaagatt cgtctcgtga tttcctccct aactgtgcaa ttagtttttg    600

tttttatcta tatttaatgt ttcatgtatg tgtccaaaga ttcgatgtaa tgtttttagg    660

aaaaaaatct gtgaactaaa cagggcccaa gtttagccaa ctactaactc caaatcacat    720

atagtcaact taatagttaa ttcatacaat agttacatac tacactatta atacctgatc    780

ccacctgtca tacatacact gtctcttgaa gtccatgcta cagctggcta caaatcttta    840

gctcgctgct cttctctttc ttattttatt ttcttaaaat atgttaccaa acgacgacac    900

gtagccagaa acacctcgac acgaacaccc ccatgtcaca ccacaccaca acacgatcag    960

ttcaactttt tttttctctt ttttcaaaat ttcacatcct tttccatcaa tttttcttta   1020

ccccgcatta ttgcagaagc aagaaggagc aaatatgccc ttttctattt ctttcacctc   1080

ccctgattct ttcttgggcg acaaaccaca acctgccacg tactctactc tacccgccgc   1140

gcgtcactag ctaatgacac gtgggcctcg cccatgcccg ggcccacacg tcagcgggac   1200

acctcacctg cctgcccctg cgctgcgccg gctgcgcctt ctggagaaaa ggtaaagaaa   1260

gacaggtcac ccacgcacct cgcgcttaat ttatttgttt ccatttttat ttttaatttt   1320

ttttcctcac gctttctcgg ttccatttgg ctttattaat aattaattag actttttcct   1380
```

cttggcttta taaaagagag cgcttaaacc ctctccacct ctccatatcc ggcttccaga 1440
cgcttctctc ctcctctaat ctcaagtctc tgtctcgtcg tcctcgcatc tccactcgcc 1500

<210> SEQ ID NO 117
<211> LENGTH: 1500
<212> TYPE: DNA
<213> ORGANISM: Oryza sativa

<400> SEQUENCE: 117
agacatacct tctatcctag aagtcataaa gtatgcggat acattatatc ttcaagtaaa 60
cggaaaggat ccatttgaat taaggaaatt gatgagtcct tacgaaaata atatctacga 120
acaggggata tcagagtcct acttataggg gataattaat gacgttgtca tatcgtgcgg 180
ggtctgttgt ctccaagttc tacttggaga ccaaggtgat ctgcggtata aatagatacc 240
ccctgagagg tatagggcat cgaatcttag tgcaagacac ccgccaccac ataagcaatc 300
cggaggactt gaagccaatt catcgataga tctcgtcgag gctctctcga caagaatctc 360
gtcggtaatc ttggagttat gttgttctct gttgtactct gtggattctt ctataatccc 420
atataaactg gattaagaat attaccttgt gaggtgcctg aaccagtata attcctatct 480
ttttatgtgc tcgatgtcgt atcgtgtaga tcctcgtacc aacatacccc gatacccata 540
gaatacggtc cgtgggaatc ccgtcgacat tataaattta tagagttcaa gaaaacttag 600
atccagtgtt gtgctaaaac aatcttaata tgacttatat ttacaatatc ttattaaaca 660
ttgcttgtgt taaaacttag ccaaagttta acagtagaca accaaaccga cactaagtat 720
atctttaaga gcgagtaagt aataactttg gtatatggcg ttattccaca tttcctaagt 780
tcgaaaacta ttttgtaata atacacgtaa gttcaaaaac tatgtctaca acattcaacg 840
ttacaatgtc atataacctc acaaattatt gctgctgtag cggttccaat cgaaaaacat 900
caaatttcgt cttggagcaa ctcgatagat tatggagaaa atctcaaacc cctaagtaga 960
atcataaaaa aaagaatgcg agagaccaga tcagataaag agtctatttg agagagttta 1020
tggtcctgta gtttcctatc tggccttagg ttataagtcc tcagctattt gtcatcttgc 1080
ttaaaactgt aatctttctc agactgtaat cttttatgaa ttaataaagc tccttgtatt 1140
cgtcgaaaaa aaaagctttc tcaaaaaatt tagattttcg ttcaaattaa aaaatatata 1200
gtcaaataaa aataattgta cgatagaaac cgagaaaccc aatttgttag attttcagaa 1260
aatgattagc aacgagcttt gcctttgatt ctcctgggtc ctggccatca ccgactcacc 1320
gtgcggtgct cgcaccccca caaaaccggt cacatgctgc gcataaatcc atccacccca 1380
tcacgcgacc ccacacgacc attattcctc ctcctctctg gagtctagtc tcctctcctc 1440
actcctcact cgccccactc cgccgcttca ctcgcgagct cgtcgttggc gccggcggca 1500

<210> SEQ ID NO 118
<211> LENGTH: 1500
<212> TYPE: DNA
<213> ORGANISM: Oryza sativa

<400> SEQUENCE: 118
tgtaaattgt gtaattagtt ttttatttta tctatattta atgctctatg catgtattta 60
aagattcgat gtggtgtttt taaaaaaata aaattgagaa gtaaacaagg ccttacattt 120
gagaaagctt ccattggagc tagccgtgga agtccaacct gcaggctcag gctgcagatc 180
gcccaaggcg cacttgcctc cacgatggct tgtcctcaac cgctcggaag gcgagatcca 240
attggcaatt tgttcaacgc agggagagag gaggagactg gaacgggatc attggacatt 300
ggttgatgaa ttgcaatttg gatgacgagg ccgcgagggt cagaccgtcg gagagtgaga 360
tgatggttat acaagtgtac tagtaggacg gacggtggca ccggccagaa gcagcagatt 420
ttgtgcaaac gttgagcccg caacacgtgg ccggcatcga cccgctacga cggacgcagc 480
gccccccccc cccccccccc cccccgcgga cccacgcggg ccggccgcgc tgtcgccgtg 540
ctgccgacta cgccgtcgaa atcaacgcgt ccgcctcgat cctcccctgc cgacgctgta 600
caagtggcga ccagaaaaca ccatgtagta tttgatctcg tctaagagca agtttaatac 660
tatagtccac tattagctcc aatttattta taactgatct aatagccaat tcacacaata 720
attgcttact atactattaa tatatggtct cacatgtcat acacatattc cgtcttggag 780
ttcgtgctgc agctggctac agatctgtag cccgctgctc ttctctctca gagcgagtat 840
aatagtacaa actggactgg cgataggaga aacacgtcag ctacagtgtt gagctggatg 900
agtgagaaga ggagagagag tgagagtggg cgacaatttt atcgccggct ctagcaccag 960
cttcgagaga aaagtggtga gcgcagaggt tgtgagctgc atgtgtgaga cgaagcttaa 1020
gttattttat tatgatgtga agttgatggg tccagcgttg caggtcattt attgtattca 1080
caagatgcaa agagagctac tagctgagtt ggatggaatt aacgccggct gtctacgcta 1140
ctattaacct tgctctcatc ttttatctca tcaaaatata tttatagctg gctaatagtc 1200
tgctatcgta cctgctctaa tgcatacgtt ttttctctct gtggcaaaac ggttggtgcg 1260
ttacacgggg tgcacgaagc catgcatcac cctgctcaac ccgtctcctt ttttagccta 1320
atcttttcct ccttatccga tgggccttcc gtttctcaag acaccccccac accgccccgg 1380 ccctctataa ataccaacca cgacgagcca agcgaacatc accacagcta gatcattagc 1440
aatccattcc gatccatcaa atttctcttg agaccgtaga gagagagaga ggcgccaacc 1500

<210> SEQ ID NO 119
<211> LENGTH: 875
<212> TYPE: DNA
<213> ORGANISM: Oryza sativa

<400> SEQUENCE: 119
ggtttctttg aactgcaatt ttgcaaccac tgacagtgat gcaaggattg aaagaacagt 60
gtttgtacat accattggat gttagcctct taccttgcac gcaacttgtt tgtctacatt 120
gcatatttgc atgtgagctt tggtcaacct tgttgagttg tttgtgaggc aacaagggat 180
ttcacaaata tgttaacaat cctaagaagt gagaactcta atgctaggtt tggaatacaa 240
gaactatgca gaaattcata gggaactgac tgtaattccc acgcgaatca atgccaagtt 300
ccaagtggta aggtgtctta ggtgaccaag tttatgaaaa aagatagcaa cattctaaac 360
atattcaata gtaggtataa ttaaattaat ttggtgtttt tctataaact tggttaaact 420
tgaggatgtt taactcaaga caaaaacaaa acaccttaca ttttaaaaat gatttcgaaa 480
aactaatata attctttttc ccagtgaaca atcatgctac caaaccgcat ctgcacagtt 540
aggtctacca gtatcgttta tcaaggtctt cagagttcac atctacgatt tggttgcttg 600
cattctcgcc atggtagaga ttataattcg ctcttctgaa atttactcaa aaaatcgctg 660
tgtaattggg ccgggcccaa gaggccaagt ttgtgattgg gccaaagccc aatacccccaa 720 cacacgacga cttctatcca tcctatatac cgaaccctag ctgacgaaca atccagaagc 780
ccatcgatcg atcggcgtgt agaggtgatc ggaggcgagc gcaccggagc acaccaccga 840
ggcggcggcg gcggcggcga gggagggaga ggaag 875

<210> SEQ ID NO 120
<211> LENGTH: 1348
<212> TYPE: DNA
<213> ORGANISM: Oryza sativa

<400> SEQUENCE: 120
cttttcactg cttgaacctg caggggacac atgatttcaa gctcagtctc agaattggga 60
ccatatatac agcaacgctg gtgaaagttc ctcatattaa ctgtacatgc tgtacatatc 120
gatgtacttt tcccgtggac atggtgtggt tagagcaaac gtcttgttac attaccaggc 180
tgttcttggg ccacaagggc caaccaagaa acgaaccggg ccttctcttt ggggaatctg 240
gctcggccca caaaataacc agctatggga gactcagtca catccctcat gcaacgtaca 300
tcctccgtct tgtaaaaaaa atatcaactt ctagctatgt actttatggg atggattgag 360
tacgggttat gtgatcattg cctcttgttt ttgcgatgat ccttgtacgc tagtgcctag 420
tggtataaaa tgagctttgt atataatttg gtccattttt tttaaaaaaa taaacctgca 480
ataaaacgtt ttctagaaac tggacctaca atatggggcc gtgatattca atgtgatgtg 540
catacagcat ggtgttgtat aatttggacg tcgatgtagg atattttgtg agaccattat 600
acgcggttgc ctacatagcc tcaaattatg tgacacggtg ccaatgtgcc ataaacatct 660
ctatctctaa aatgctaccg acggtctaga atatatatga tgtttaggag aaccaaaatt 720
gacttaaatg ttgttatatt tttctgtcct aaacgtcgta tatgatcatg attggatgga 780
gtattttatt agaggcccac atgtaaaaga tatttaagaa aaaaaaagac taaattacca 840
aaactacccc gctatgtact cctatactgc ccagtctgcc ctacaagaaa ctcgtgcgtg 900
aacttctact gtcactgcac tcttcctctg cacacacgtt tcagtctctc atcagcccga 960
cgtttctgct gcaaaaccac ggcctgattc cgattcacgc aaatcgcggc caaatctcgc 1020
aaaccaaaac caaaatcgcc acctgtaatg taaagaaaag aaaaacaaaa acaaacaaaa 1080
gtgaaaaaca gccaaaccga cggcccaaaa agaagccgca gcggtgcgtt tccatgtggc 1140
gaatatttcc aggatgattc caatcggcgc acggcacctc agcacatcac accagatata 1200
taattaacca ccccgtctct ttcacgaccc actccgcctc gcctccactc ctctcctctc 1260
cgcatcctcc tcatcgcctc cgcttctgct tttttttttc ttttttctcg ttgatcggtt 1320
tgttcgatca gatcggttct ttggagag 1348

<210> SEQ ID NO 121
<211> LENGTH: 1500
<212> TYPE: DNA
<213> ORGANISM: Oryza sativa

<400> SEQUENCE: 121
tacaaaataa tttatgagta aaacttttat atgtgtctct agcgacttaa agatcaatgc 60
tgaaaagaaa acaaagtcca aaatacctta aaatcaactc cacaatcaag ctttaaattt 120
taaattttgg ccgcgactga ttcgttgtaa gataaacgat gatgcttgag acaaatggcc 180
tccctgaact ggagagagag aaaaaaaact tttgcagctt tcaagaggcg aaatgagaag 240
tttgatcagc ggaaggaagg aagggaggaa agaaggacgg gtccccctgg ctcgagcgag 300
tcaagtgaga gtgagtgaca gacacctgcg aatccaccgc gagatcctgg cgttgaatcg 360
cggggcgctc tgccgatcac gtcgccaaca gtgtgacagt tcagcaaaga tggcgatctt 420
tcttttgctc tcgagtggcc tcggtactct gaactcttct gaagtctgaa gtctgaactc 480
cttcaagtgg cgatctgcat atagatacta gaggttgtct cattatttat ttgctcccga 540
ttactgtgaa tagtaacaag aagtagtatt atagtagtat gaatatattt ttctgaagaa 600
ttgtgacatc tagtatagaa aagaacgcag taaaagttga gaaaccagaa gtttgcaggc 660
attatttttt atccagaggc aaatgcatat aaggaagtga gggagaaggt ttggtctgta 720
cagttaaact gattccgctc cctttgtcgt gaaaatacaa tctcaaagac atgtttatgt 780
tcttacatta aaaaaaacct caaaaacttg tttatgttct taagacaaaa attactcgtc 840
cctacacaaa agtcaatcca cgaattactc ctttaaatat tccttatggt ggttttctaa 900
atgtatagtt gtagcggtag agtcacgagt gcatgattct actcaccaga gtttaattcc 960
ttgtgtccat aaatatggtt atgttcatcc tcgttgatgt agagatggga gttatacatt 1020 tttcccccttt tttttgggga tatacagttc ccctcgcaaa attcaggtcg ttaattggaa 1080
aaacatttat gctaaacagg ccgtcattac ggtgatagca atacgaaagc ccatcacagc 1140
agtctcccct ttgacgggcc ggcccaatta ctcccacaaa ccaggctggg cctttgggcc 1200
aatatgtaat tacagtaatt attccttata ctaataataa atgcgcatta agctgggggg 1260
ctttcctgca aaagagcgcg gaaaataaaa atctcgcaca gaggcgtatc cacgctttcc 1320
ttctcccctc ccaccaacta atcgatctcc tctctctctc tctctctccc tctctatccc 1380
attcgcgagg cggcgtctcc tcctcctccc cgtctctctc gcttcccccc caaatccggc 1440
ggcgaatcca gggccccgcg ccgcgccgac gaccaccgcc gatcgcgacc aggagggagg 1500

<210> SEQ ID NO 122
<211> LENGTH: 1500
<212> TYPE: DNA
<213> ORGANISM: Oryza sativa

<400> SEQUENCE: 122
tgtgtagcca tatatatagg acatcttcaa ctagtggttc ccttatcatc gttgtacccc 60
tcctcggtaa taggttagtt accgagcaaa acagataaaa gctaaaatgc tagaaaaggt 120
taattaaaaa ctttttttaaa ttcgtaacaa acatttttcg ttatttagcc ttggtggtaa 180
actatggtga ccgatggtca aaccttggtt tcaacgaagc cacccattgt agtgtaaaaa 240
tatttctgta gcttaattta ggggttgttt ggttggtgac cgcaatttgc tataccaaaa 300
tcttagacac agttgaatta agctacactt tattagcaca ttggcccgtg cgttatattg 360
tcattttcta gccaaagttt gccataattg tggctaacaa attgttggcc acattttggc 420
tacgttcgat aggacatgtt cccaacttct ccttctcgtt tttcgcgcgt acgctttttc 480
aaactgttaa acggtgtgtt ttttgcaaaa tattttttta cgaaagttgc ttaaaaaatt 540
atattaatct atttttttta aaaaaagtag ctaaaactta attaatctca cgctagacgc 600
tgcttcgttt tacgtgtcgg gtacccaacc ctcactcccg aacacagcct ttgtgtggtt 660
tactacagtt atagtaaagc tagtctccat ccaaacaatc ctttagtcca tataacttcg 720
tatactccaa aattccactc gttctacgga catcactaat acgaagatca agtggaagat 780
agatattttt aatgacatgt tattttcagt gaacacttga ggtcctcacg atccacaaac 840
acacattttc gtagataagt tctgaaatac tccatacggc ggttgtcacg atgtcatgat 900
cgtcgttacc caaggaagaa gaaaagagtg gcatcttctc cacgccagtg ttcccaacgg 960
agcatctttt cttcccccac acggcatcga cgtcacactt tctggtgcaa actttaataa 1020
ttagtccaaa aacaaaaaaa gaatttcggc cacatcttct cccgaaacgc caggtgggcc 1080
ccacctgcat cactgacagc ctgtccccac aacgcgcagt cgtgtcccca cctgtcagga 1140

-continued tgttagcgtc tccgttgcag gtttcccaga tcccatcgcc gatctgtggg ccagcgccca 1200
cggtgtcacg cccgcgcaca cctggctcca acccacccac cccacgcgct ccgtcgccga 1260
cagcgtggac ccacctaggt ggggcccacc gtcagtggga gatgggtagg ggagccccca 1320
cgtgggagca acgggggttc tccgggctcc ccgtcgccgc gaggttaaat aacggccacc 1380
cgtttccccc tctctcgcaa aactcaccca aaagagcagc gtcgcctctc ctcctcctcc 1440 ctaacccta cgcttccaga accttctcga agctcccgct cccccccccc ttccgctcca 1500

<210> SEQ ID NO 123
<211> LENGTH: 1500
<212> TYPE: DNA
<213> ORGANISM: Oryza sativa

<400> SEQUENCE: 123
atgtgatcga caaattttga agaagtgtca tcaaaatcca tcgaattcca tcaaaaacct 60
gttactgatg gcattattca gaagattttt cctcctgttc tttttgcgtt tcaatactct 120
gctcgaaatt tttttcccct cctatttttt tgtatttcaa ctgatatcac catcatcctg 180
atgtgataat cagagcaatg tacaaaattc tctcaaacat taatgaggtt cagaaaattt 240
ctccttttgc atttcaaaat cagtaaacaa caatgattca ttcactatgc atcctgggaa 300
gaaaagaaaa gaggaggcag cggcgaacgg gtagcagcag catagccaac accggctggt 360
catgtaggcg tatggcctcc tatgcacata tagcaaagga ggaaaatgag cagctaacca 420
ttcatacatg caaagatatt ttttaaagca taggcaagaa atcaccacag taggcaagaa 480
aaaatggttg ccagatttgc caggtccgcg taacatagaa cacatgtcag gcagatggga 540
gcaacactgc tattacagca tcaaaattca ccggctcgac ggcgatcgcc gcgcgcggcc 600
gcggcagtcg cccgtcgagc aggtaagctg cgaccccgga ggtggaggtg gagcccgtgg 660
aagatggagc gaggtgccgg aggagcatga ggccgtggcg gctgccccga ccgcgagctc 720
catggatgcc cgtgatctgg aagaagaagt cgaggcaggg gttgtcggag tcggcatagg 780
tggcggatcg agtcgttctc ggtgcaggcc ttccatggct tttggtttct atccggaggt 840
cctcccgctc cttcgcggcc tgtccgtcgc cgccaagaag ctcgcttacg gctgccatgg 900
cgcctgcctc cacctctgcg cccgtcgccg cggcgcccgg cctcgcctta gcctccacac 960
ccaccgccgc ggcgccccac ctgcgcccgg ccagccgtcg ccaccgctcc accgcgccgc 1020
ccgtatgttg taaaaaatga gagagaggag gaagggagag aagggagaga gatgatgacg 1080
tggtcacatg acgtgtggga ctcatgctga ctctgttgct acgtaggata aaaccggggt 1140
caaaaccagc caagaatata aagtgaacgg ttttgttagt tgagggacgt atctgctttt 1200
acggttgagg cacgattttg tatctggatg ataagttgag ggaccttttg gtgtactttt 1260
tccttgcaaa tatgggcctt ctcaccgaag gcccatttat gatctcgata tgtgggccta 1320
attgccaccc gtgcgttaat gggccgagaa atctcggccc atttaaccta gccctcaagc 1380
tagggtttcc tctcgtcgcc gcatataaaa gcgctctcct cttcactcct cctcccctcg 1440
ggaaaccata gctccagcaa tcggcggcgg cggcgacgcg ggagaggcgg tccggcgacg 1500

<210> SEQ ID NO 124
<211> LENGTH: 2817
<212> TYPE: DNA
<213> ORGANISM: Oryza sativa

<400> SEQUENCE: 124

-continued

```
atgtgatcga caaattttga agaagtgtca tcaaaatcca tcgaattcca tcaaaaacct     60
gttactgatg gcattattca gaagattttt cctcctgttc tttttgcgtt tcaatactct    120
gctcgaaatt tttttcccct cctatttttt tgtatttcaa ctgatatcac catcatcctg    180
atgtgataat cagagcaatg tacaaaattc tctcaaacat taatgaggtt cagaaaattt    240
ctccttttgc atttcaaaat cagtaaacaa caatgattca ttcactatgc atcctgggaa    300
gaaaagaaaa gaggaggcag cggcgaacgg gtagcagcag catagccaac accggctggt    360
catgtaggcg tatggcctcc tatgcacata tagcaaagga ggaaaatgag cagctaacca    420
ttcatacatg caaagatatt ttttaaagca taggcaagaa atcaccacag taggcaagaa    480
aaaatggttg ccagatttgc caggtccgcg taacatagaa cacatgtcag gcagatggga    540
gcaacactgc tattacagca tcaaaattca ccggctcgac ggcgatcgcc gcgcgcggcc    600
gcggcagtcg cccgtcgagc aggtaagctg cgaccccgga ggtggaggtg gagcccgtgg    660
aagatggagc gaggtgccgg aggagcatga ggccgtggcg gctgccccga ccgcgagctc    720
catggatgcc cgtgatctgg aagaagaagt cgaggcaggg gttgtcggag tcggcatagg    780
tggcggatcg agtcgttctc ggtgcaggcc ttccatggct tttggtttct atccggaggt    840
cctcccgctc cttcgcggcc tgtccgtcgc cgccaagaag ctcgcttacg gctgccatgg    900
cgcctgcctc cacctctgcg cccgtcgccg cggcgcccgg cctcgcctta gcctccacac    960
ccaccgccgc ggcgccccac ctgcgcccgg ccagccgtcg ccaccgctcc accgcgccgc   1020
ccgtatgttg taaaaaatga gagagaggag gaagggagag aagggagaga gatgatgacg   1080
tggtcacatg acgtgtggga ctcatgctga ctctgttgct acgtaggata aaaccggggt   1140
caaaaccagc caagaatata aagtgaacgg ttttgttagt tgagggacgt atctgctttt   1200
acggttgagg cacgattttg tatctggatg ataagttgag ggaccttttg gtgtactttt   1260
tccttgcaaa tatgggcctt ctcaccgaag gcccatttat gatctcgata tgtgggccta   1320
attgccaccc gtgcgttaat gggccgagaa atctcggccc atttaaccta gccctcaagc   1380
tagggtttcc tctcgtcgcc gcatataaaa gcgctctcct cttcactcct cctcccctcg   1440
ggaaaccata gctccagcaa tcggcggcgg cggcgacgcg ggagaggcgg tccggcgacg   1500
caggtacgta gctcctcctc ctcctctccc tctctctcgt ccaagaacgg cgcgtcgtct   1560
tggttggtgc tagtgcgatt tggcgcagcg agagaatgtt cttttctttt tttttatct    1620
cttttcttgc ttcggtgtgt tagttgatta gcgagtggcg gttagttaat gaggggatgg   1680
ctggttcggt tggcgagatg atctggatca agatttgcct cgacgcggtc tgttcccgta   1740
gctttgttca tattctcgtt tccattgcgt tggatccgta cctatgccga ttagttcgtg   1800
ctgatttcga ctgactgcgc attctgttgt tgaaacttgt gtggtgcgga tttaatttcg   1860
agatatgtag attttggggg ggttttaact agaatgctaa gatgtgttga ttagtactga   1920
ggaatgagga catgtttact catttggcat ttggtactat gtagcttgaa aatggttgtt   1980
tctgttatgg tacaaaattt gataatttac ctgttttaag gactggaaat atgagtttca   2040
ttagctagag tttttttgtt ctcaagtatt ctgtttgatc actcatttgg tggaatggag   2100
ttatgcataa gcttgtgaat tttgttacga aaatgaatca tggagcttaa tatagaggac   2160
tatatacttg taatgcacta actgtttgtt tatacataga gtggtccatc gagaactata   2220
tttgttattt tttttaaaat ttctgtgtaa gttgtagtat gctaattgta ttctatatgt   2280
atattttctt aaatatatta tatgatagtt cctgatgaga tctttcaagt attgtcgctt   2340
taggtcatga attccatttt acagtagaac aaataattta ggtatgtatg atatggctaa   2400
```

```
ccagggataa cacagcaaaa ctaaatctgg catgtaagct atttatgggt taatcagaca   2460
caatgttatg aattgtttta taaatccttg tcaaacatgg ttgtatatct gaagctctta   2520
tagtatttac tgtacacaag atccctacta ctatttgtct tgaatatcca tactattatt   2580
gggcgtaatc tcaacaacta ctgtagtttt ctttatttgt gttgttgcat tgtctttctg   2640
ggttgtgtgt gcagttgctt tcttgctttg tatatttttg gggtcaggat ataaggaatt   2700
tgggactgta gggcttcttt ctatgttatt gtttggttct tatgaacaac tatactatct   2760
acagtggttt ctttctctgt caagtgttat gaacaaattt attacttcat tgcaggt      2817
```

<210> SEQ ID NO 125
<211> LENGTH: 2369
<212> TYPE: DNA
<213> ORGANISM: Oryza sativa

<400> SEQUENCE: 125

```
ggtttctttg aactgcaatt ttgcaaccac tgacagtgat gcaaggattg aaagaacagt     60
gtttgtacat accattggat gttagcctct taccttgcac gcaacttgtt tgtctacatt    120
gcatatttgc atgtgagctt tggtcaacct tgttgagttg tttgtgaggc aacaagggat    180
ttcacaaata tgttaacaat cctaagaagt gagaactcta atgctaggtt tggaatacaa    240
gaactatgca gaaattcata gggaactgac tgtaattccc acgcgaatca atgccaagtt    300
ccaagtggta aggtgtctta ggtgaccaag tttatgaaaa aagatagcaa cattctaaac    360
atattcaata gtaggtataa ttaaattaat ttggtgtttt tctataaact tggttaaact    420
tgaggatgtt taactcaaga caaaaacaaa acaccttaca ttttaaaaat gatttcgaaa    480
aactaatata attctttttc ccagtgaaca atcatgctac caaaccgcat ctgcacagtt    540
aggtctacca gtatcgttta tcaaggtctt cagagttcac atctacgatt tggttgcttg    600
cattctcgcc atggtagaga ttataattcg ctcttctgaa atttactcaa aaaatcgctg    660
tgtaattggg ccgggcccaa gaggccaagt ttgtgattgg gccaaagccc aataccccaa    720
cacacgacga cttctatcca tcctatatac cgaaccctag ctgacgaaca atccagaagc    780
ccatcgatcg atcggcgtgt agaggtgatc ggaggcgagc gcaccggagc acaccaccga    840
ggcggcggcg gcggcggcga gggagggaga ggaagcaggt acgcctcccc catcctcttc    900
cctccactcc cccctcctct cgcgcgcatg cggtttcggc ggatctgggc ggatctaggg    960
ttgttaggca tggttagctt cggtggctct ggttggatcg gtcttctcgt tgcggtttcg   1020
gttgattcgt taggtctgcg atgcggggat gagtttctct gtatttgctc ccatttcgtc   1080
ggaattattg tgcagatttc gcgtgaattg atgcgtgtca acgttgcatc gggttgtcat   1140
ttgactcggg aaacgcgtgc cccgtcgatc caattaggtt aggcagaatt tggagcagtg   1200
gactcgctgc aaattatttg ctgtgaggtt atatttgtat ttgttctcac aacgattttg   1260
ctgtttcaat cgagagttcc agacccaaat tgatttggta ttctgtatgg tcatgatgct   1320
gatccaatca tgttagctaa gtacttctct tgtactgtat tatttagttg aatttgcctc   1380
taatattgat tggctttgtt actgtttcca aactgaatgt tttgagcgcc acatatagct   1440
tttgtactca catgtctcct ggagaatcta tgcccaagct tgagatatgc aaaactagat   1500
tatgtcttcg gatgaatgcc tgaatgatca gttagcctat tatactattt ttttccaaca   1560
tggatttttc agtgatttag ctttatgtga acttgttaaa ctgcatgtta cagcttgttg   1620
gcgttgtgag ctcactatgt gtcgaagcct gaagaaatac catctgaatg ttgtttgttt   1680
```

accttgtacc ataggatttt tgggaagttg tcttaagtag atgcaatatg ctatgttttg 1740
accattgatg cagcttatca tatagtctcc atggttctta gtactgatga gttacctttt 1800
tttttttttt gcctggcagt tataggcatg cttgtttttc ctaatatcag gaaaccctca 1860
cctcggattg tgaattattg aaaacaatga gcctaacgat tgaaatgttt tttgagaact 1920
tgaattgaaa agaggagttg ggttggcagg gctggcctct taagttccta gtgctgccta 1980
ggtactccaa gagattagca acatattaca tgctaaacaa tatagcacta aaatagtaac 2040
acaagagcac tctagccgcc tattgcacca tctaattgct aaacacggtg gctacctggc 2100
gcctgctaac ttttagaaca ctgagtcgct gacagcattc actctttttg cctttcgtga 2160
gggaaatgca agtaggcctt cttttcaatc caaggatgga ggaacatggt ggagtgtgta 2220
tactgctggt tcacgttgta aacaattgat gacttccttt tgtgtttctt tgtgtgcagt 2280
aacactgttt ccttgacatt gatgactatc agttttcttg acagcatcac aaacaatata 2340
acctggtcta ttttgatggc tatgcaggt 2369

<210> SEQ ID NO 126
<211> LENGTH: 1655
<212> TYPE: DNA
<213> ORGANISM: Oryza sativa

<400> SEQUENCE: 126
tacaaaataa tttatgagta aaacttttat atgtgtctct agcgacttaa agatcaatgc 60
tgaaaagaaa acaaagtcca aaatacctta aaatcaactc cacaatcaag ctttaaattt 120
taaattttgg ccgcgactga ttcgttgtaa gataaacgat gatgcttgag acaaatggcc 180
tccctgaact ggagagagag aaaaaaaact tttgcagctt tcaagaggcg aaatgagaag 240
tttgatcagc ggaaggaagg aagggaggaa agaaggacgg gtccccctgg ctcgagcgag 300
tcaagtgaga gtgagtgaca gacacctgcg aatccaccgc gagatcctgg cgttgaatcg 360
cggggcgctc tgccgatcac gtcgccaaca gtgtgacagt tcagcaaaga tggcgatctt 420
tcttttgctc tcgagtggcc tcggtactct gaactcttct gaagtctgaa gtctgaactc 480
cttcaagtgg cgatctgcat atagatacta gaggttgtct cattatttat ttgctcccga 540
ttactgtgaa tagtaacaag aagtagtatt atagtagtat gaatatattt ttctgaagaa 600
ttgtgacatc tagtatagaa aagaacgcag taaaagttga gaaaccagaa gtttgcaggc 660
attatttttt atccagaggc aaatgcatat aaggaagtga gggagaaggt ttggtctgta 720
cagttaaact gattccgctc cctttgtcgt gaaaatacaa tctcaaagac atgtttatgt 780
tcttacatta aaaaaaacct caaaaacttg tttatgttct taagacaaaa attactcgtc 840
cctacacaaa agtcaatcca cgaattactc ctttaaatat tccttatggt ggttttctaa 900
atgtatagtt gtagcggtag agtcacgagt gcatgattct actcaccaga gtttaattcc 960
ttgtgtccat aaatatggtt atgttcatcc tcgttgatgt agagatggga gttatacatt 1020
tttccccttt ttttttggga tatacagttc ccctcgcaaa attcaggtcg ttaattggaa 1080
aaacatttat gctaaacagg ccgtcattac ggtgatagca atacgaaagc ccatcacagc 1140
agtctcccct ttgacgggcc ggcccaatta ctcccacaaa ccaggctggg cctttgggcc 1200
aatatgtaat tacagtaatt attccttata ctaataataa atgcgcatta agctgggggg 1260
ctttcctgca aaagagcgcg gaaaataaaa atctcgcaca gaggcgtatc cacgctttcc 1320
ttctcccctc ccaccaacta atcgatctcc tctctctctc tctctctccc tctctatccc 1380
attcgcgagg cggcgtctcc tcctcctccc cgtctctctc gcttcccccc caaatccggc 1440
ggcgaatcca gggccccgcg ccgcgccgac gaccaccgcc gatcgcgacc aggagggagg 1500
caggtgagtg ccgacgacct cctcggtttt ttttcctcgc tcgctcgccc gcccgccatc 1560
cctcggattt cccggggttt ggtgcggttg ggtttcgatc tgtgatttgg ggggtcgctg 1620
acgggtaatg gatggcgtgt gtgggggttg caggt 1655

<210> SEQ ID NO 127
<211> LENGTH: 1551
<212> TYPE: DNA
<213> ORGANISM: Oryza sativa

<400> SEQUENCE: 127
cttttcactg cttgaacctg caggggacac atgatttcaa gctcagtctc agaattggga 60
ccatatatac agcaacgctg gtgaaagttc ctcatattaa ctgtacatgc tgtacatatc 120
gatgtacttt tcccgtggac atggtgtggt tagagcaaac gtcttgttac attaccaggc 180
tgttcttggg ccacaagggc caaccaagaa acgaaccggg ccttctcttt ggggaatctg 240
gctcggccca caaaataacc agctatggga gactcagtca catccctcat gcaacgtaca 300
tcctccgtct tgtaaaaaaa atatcaactt ctagctatgt actttatggg atggattgag 360
tacgggttat gtgatcattg cctcttgttt ttgcgatgat ccttgtacgc tagtgcctag 420
tggtataaaa tgagctttgt atataatttg gtccattttt tttaaaaaaa taaacctgca 480
ataaaacgtt ttctagaaac tggacctaca atatggggcc gtgatattca atgtgatgtg 540
catacagcat ggtgttgtat aatttggacg tcgatgtagg atattttgtg agaccattat 600
acgcggttgc ctacatagcc tcaaattatg tgacacggtg ccaatgtgcc ataaacatct 660
ctatctctaa aatgctaccg acggtctaga atatatatga tgtttaggag aaccaaaatt 720
gacttaaatg ttgttatatt tttctgtcct aaacgtcgta tatgatcatg attggatgga 780
gtattttatt agaggcccac atgtaaaaga tatttaagaa aaaaaaagac taaattacca 840
aaactacccc gctatgtact cctatactgc ccagtctgcc ctacaagaaa ctcgtgcgtg 900
aacttctact gtcactgcac tcttcctctg cacacacgtt tcagtctctc atcagcccga 960
cgtttctgct gcaaaaccac ggcctgattc cgattcacgc aaatcgcggc caaatctcgc 1020
aaaccaaaac caaaatcgcc acctgtaatg taaagaaaag aaaaacaaaa acaaacaaaa 1080
gtgaaaaaca gccaaaccga cggcccaaaa agaagccgca gcggtgcgtt tccatgtggc 1140
gaatatttcc aggatgattc caatcggcgc acggcacctc agcacatcac accagatata 1200
taattaacca ccccgtctct ttcacgaccc actccgcctc gcctccactc ctctcctctc 1260
cgcatcctcc tcatcgcctc cgcttctgct tttttttttc ttttttctcg ttgatcggtt 1320
tgttcgatca gatcggttct ttggagagca ggtaatctga cttctttttt tcttttaatg 1380
ttcttcttgt cgttttggcc atcgattttc gagaggaatt ttgcggtttc ggatcggtta 1440
aatagcgtag ttgattggtg tttgtttgtg agattttgag ttgttttggt aactttttgt 1500
accgttttgc gtggttttta atggggaatt ttgattttct gttctgcagg t 1551

<210> SEQ ID NO 128
<211> LENGTH: 1638
<212> TYPE: DNA
<213> ORGANISM: Oryza sativa

<400> SEQUENCE: 128
gacaaccgat gtagatgaat acttcctcgg tttaggaatt gggattttat ttataagtta 60

```
tacaaagtaa atataaaatg gacggtgcat attgattgag gtagaatatt agtactactg    120
tttcttcttt ttggaatata ctgcaaaaca acactaatgt aatgttcgga caaaacttaa    180
acgtcattat gaatattatt agctcttaat aatcggcaat agccaatagg tcagagacaa    240
acacccatca gaggatccgg attcgatcag gtgagtgccg gacaaacagt atgcggcgcc    300
atcgcccgtc gccgccgccg gctactttct gttagagcac gggcctgttt agttcaagaa    360
aaaaaaatta tttttgaatg tcacattgga cgtttaacta gatatcgaaa tagatttttg    420
gacacgaata aaaaaactaa tttcataact cgtctggaaa cagcgagacg aatcatttga    480
gcctaattaa tccgtcgtta gtatacgtag gttaatgtag cacttatggc taatcatgaa    540
ctaattagac tcaaaagatt cgtctcgtga tttcctccct aactgtgcaa ttagtttttg    600
tttttatcta tatttaatgt ttcatgtatg tgtccaaaga ttcgatgtaa tgtttttagg    660
aaaaaaatct gtgaactaaa cagggcccaa gtttagccaa ctactaactc caaatcacat    720
atagtcaact taatagttaa ttcatacaat agttacatac tacactatta atacctgatc    780
ccacctgtca tacatacact gtctcttgaa gtccatgcta cagctggcta caaatcttta    840
gctcgctgct cttctctttc ttattttatt ttcttaaaat atgttaccaa acgacgacac    900
gtagccagaa acacctcgac acgaacaccc ccatgtcaca ccacaccaca acacgatcag    960
ttcaactttt tttttctctt ttttcaaaat ttcacatcct tttccatcaa tttttcttta   1020
ccccgcatta ttgcagaagc aagaaggagc aaatatgccc ttttctattt ctttcacctc   1080
ccctgattct ttcttgggcg acaaaccaca acctgccacg tactctactc tacccgccgc   1140
gcgtcactag ctaatgacac gtgggcctcg cccatgcccg ggcccacacg tcagcgggac   1200
acctcacctg cctgcccctg cgctgcgccg gctgcgcctt ctggagaaaa ggtaaagaaa   1260
gacaggtcac ccacgcacct cgcgcttaat ttatttgttt ccatttttat ttttaatttt   1320
ttttcctcac gctttctcgg ttccatttgg ctttattaat aattaattag actttttcct   1380
cttggcttta taaaagagag cgcttaaacc ctctccacct ctccatatcc ggcttccaga   1440
cgcttctctc ctcctctaat ctcaagtctc tgtctcgtcg tcctcgcatc tccactcgcc   1500
caggtaatta tgctcacctc cgaatcgaat taattccccc gtttgattac tgctggtgct   1560
tcgcgtcctg atctgattga tgtttttttt tctgattttt ttggtgaatt ttctggtggt   1620
gtttttgggg acgcaggt                                                 1638
```

<210> SEQ ID NO 129
<211> LENGTH: 1634
<212> TYPE: DNA
<213> ORGANISM: Oryza sativa

<400> SEQUENCE: 129

```
acttcaccac cacaccaaag ggtgttgtac tctcttactc tgcacctttt aaaatactct     60
tactccgcac ctttcaaaat acatgcccat atcttctctt tgcaaaattt cagcttttct    120
gtagttaaat gatttaacca ataaaatgtg gttgtatcat acaaagaaat taatggtgta    180
aaatgaattt ggacgtattc tagtcatgtt acttacataa tcgagcttat gaggtatttg    240
agcttaagaa agattatgag ttgggacata ggctatggtc aaaagtgaca agtaatctga    300
acatcaagta tgtgatttca actcttggca attgacattt gacaactact tctatacagc    360
atgtaaagct atgttgtcca tctgtagtac tattagttgg cagatcaagt tgctaggagc    420
ccgttgttcg ttgatgatta agattgtgat cgcacggtca tctagcctaa aaggacggtt    480
gaacacatat gattttatcc aggttcaggt cttccagaag ataataggtc tactcactaa    540
```

```
ctagagatat tatcttgatg ggattgcttg ggtacccctg ttcgctcaag gtggctaagc    600
tctacactcc tatagcttct ctgtgttgta atgaaccaaa cctctggtgt agaccagact    660
ggtcctcata atcgctcaag gtggctaacc cttgcaatct tatatatccc caggtctacc    720
taaccaccat agagacactg agctactgtc acgctgcttg tcctggtcat tcttctttgc    780
catgttggca tgttgcacgg taccaccttg agcttccatt ttgatggaaa ggggagcttg    840
agagatatat tattttccgt gaggaattta gttttattta tgtatatgaa atttaaaatt    900
agttattagc aagatgcagt tacacggact ttttctccta aactatcatt atacaattag    960
aaaataaacc aatatattta tcaatcataa gattaatatt ttaatattta atatatttat   1020
catatgacta aaattttaat attttatcaa taataattgc ccgtgcaaag catgagttga   1080
tggcataaat aattattcaa aataaatagt atttatatat atagtagtgg gtggcaataa   1140
ccaggagggg aaatttgaac gccatagttt tctctcatct acacattttt caatacaatg   1200
aaaaaaatac agtaacataa attggcaatc ccttaaaaat gatttacaga aattacctca   1260
cattgttttt gaaaagaaag aatgtacagc atcggtttgg gctgagggag tcgttgccat   1320
cttgggccgc gcgcaaacag cccatacctt ggcccattag ggttttgctc cctaggtttc   1380
gtctcccccc tatataaatg cttctcctgc gccgtcgttt ccctcttcca tccttcgctc   1440
gctccgccgc cgccgccgcc gcctcctcct cctcggcgcc tctccgccgc cgcctcagcc   1500
caggtgagcc tccctctccc tctctcatct cgccgcgaca tctctctctc tccgccgcct   1560
tctcaccgat gcttctctcg gtatggctct cttctgactc gcgattccgt tgttgttctt   1620
ggtggttcgc aggt                                                     1634
```

<210> SEQ ID NO 130
<211> LENGTH: 2300
<212> TYPE: DNA
<213> ORGANISM: Oryza sativa

<400> SEQUENCE: 130

```
attaaattca agaaagccat taagatgata agttgttgga ttgaaatatg cctatcaaaa     60
ataaattttt cagatttgga aatataacta tcaaaagtag aaaagtagat ggagggagta    120
ttaaataatt tctatttctc cccacatggc cacatgtttc catgttatca tcaatttaca    180
actactggac ccactttgat atgaagtata accgttcaat ttgtgacgga catgtggatc    240
gcactaatat gtagatgcta cgtggcaccc cacgttagtt tacggaaacc catttgaact    300
tgcataacac ccaaaacatg tttaggcact aaaaatattt ttgagagttc aggacctaga    360
tatcacaccc gcttaagttt atgtactgtt catttacttc actctttaaa acattccatg    420
gtttgttatt agacatcttt tctagtctta tttgttctaa caggagttgg atgtaccttt    480
acataccatt cgaacctatg ttatattgat tcatttgtca acaaacgcaa caactctccc    540
ttcggtctat tcacaaatca tgctgagacc aactcaacaa aaccctcttc attttgaaac    600
taaatctcat cgataaaggt gtggagtcac ttcggtgtta ggcgcatgca taggtggaga    660
ttgcaatgat gctatttact catgcgctaa taaacgaaca cactgattag ttgttgatcg    720
tctaaaaaat atgtggccat gaccaaacac atgaataaaa aaactattca cattcaccct    780
ctgtcccaaa atataagagc ttttgagtat acgtggaatc attaatattt cttatcaaaa    840
ttttcagatg acaagggaac attccttttg atttgatgat taaaattgtt tccctaataa    900
tgcttaaatc tttttgtcaa cgaatcagga tcctctatag tcaatgcacc gtgcttttat    960
```

-continued

```
cactaacata taagtctaat gtgttgttgg ctccatgtga taaaagcgcg gtgaaatata   1020

ccgttgagta tttcaaattc tcaatccctt gtcaactgcc caatgcgcca gggcttcatt   1080

cggccttcgc gtccatcgct tccatctggc tggacccacc gtactaatgg cacgaccccc   1140

tcagccgcct agaagcaaga aaaaaaaaac gagaccagcc aggaaaccgg tgctctcctc   1200

tctctcccaa cttttcaaaa tccgacggct ggcgaagacc tccttccatc ggcgggccgc   1260

gacgcgaggg cggcgccgat ttccatcacg cccacaagtt tccgcatcga gaacatcgac   1320

aaccccacct ccacgtggga ccacacccca atcccacccc aaaccgggcc cactgtcagc   1380

gacactgcac gtcgaccctc ctcgtgaccg taactattag ggctgcttcc aactcaccac   1440

cctccattat aaatgggcgg tctgccctaa ttgtctcgca tccatcgaaa ccccacttta   1500

ttagcaccaa ccccgtctcc ttcctccatt cctccgctgc tagaaccttc tagaagctct   1560

cctcctcctc ccttggcggc gacgatcgtg tccgtcaagg cgcgccagat cttcgacagc   1620

aggggcaacc ccaccgtcga ggtacgtacc gccgccgaga cgagctttct ctctccctcc   1680

cgctgccgat ctgatctctt cctcctctcg cggcctccct gcttcgatct ggccagatgg   1740

gccgttccgg tgtggtgatt ccgtcgatct cgcggggtgg ggggcgctga ggccgtcgcg   1800

atgaccgtgg attcgttttt tccggcgagg ttgtttgggg gtttaggcga tttgcggggt   1860

tgtttgcgga atttggtgca gggtttaacc ccttttcgcg aggggttttg tggagggtag   1920

gtgggatctg gagacagtga acgactgttg tgttggattt aaagcgaggg ttaaggtatc   1980

gcctagattt aatgcgaata ttgatttatc gcctagatca attagatgct gcgccgtgca   2040

cgaattcccc cacctgtcat acatttttct acggatttga aggatgcatg gtacagatct   2100

gtgggtcctg cacttgctcg tggcttcatt attgtcgaag cattgttgac cgtgggtgtg   2160

gtaattgtga tgtgggtcga tagttctaaa tccaactctt accatgtata cagtaaatgt   2220

ttcattttgt tttcatgctg ttgcgacaaa atgttatttg gttgctagta taatttatga   2280

tacatatgtg catcaggtcg                                                2300
```

```
<210> SEQ ID NO 131
<211> LENGTH: 984
<212> TYPE: DNA
<213> ORGANISM: Oryza sativa

<400> SEQUENCE: 131
```

```
ttgggtcatt tgtcttcaat ttttttatc aatttaatgt tttatttttt tgggtcattt     60

gtcttcaatt tttttgtgt tttatttttt gggtttttgg gtcatttgtc ttcaattttt    120

tttatcaatt taatgtttta ttttctgggt catttgtctt caattttttt tgtgttttat    180

tttttgggtc atttgtcttc aatttttttt atcaatttaa ttttttgggt catttgattc    240

tcttcggaaa gaaaccaaca ttctggacta aatcaacatt ctggataaaa tccttgggaa    300

gtaatagtca ctactagaaa aattatttgt cacttcgtag aagttctgaa ttaaagtgag    360

atctctttaa aagaaaccaa cgttctggat aaaatccttg ggaagtaata ggtactccca    420

gataccaaca ttcaacagca cagcaattcg cccttgtatc atccgaaacg cacccttaca    480

tatattcatc attaagaagt ccaaaattta aatttgaaaa aaaaaaccag accatattcg    540

ctccacttta tgttctatat tccttgtgca aatacaacag agatggcaga agatgaacaa    600

aaaagaaaaa atcagagacg gcccaacaat aaacagccca tcccttttttg ggcctccact    660

atccagaccc acggcccagc agtagaagcc cccacgggag atctcgtcgc gtcccatcca    720

tccgacggcg cagaccacct cacgcctccc ctataaatac cacgcctcca accctaaacc    780
```

```
ctctctcact ctcttcctcc gccgccgccc tcctctccgg gaagaagaga ccagagcgag    840

cgcgcgcgcc gccggagcaa acccctcctc ctacccttca gccaggtacg ctcgccgcgg    900

tccccacccg tctcttcgcc ggatttcgct ggatcgatga tcggtgtggt tttcaaccgt    960

ttgttttttt ttgcgtttgc aggt                                           984
```

<210> SEQ ID NO 132
<211> LENGTH: 639
<212> TYPE: DNA
<213> ORGANISM: Oryza sativa

<400> SEQUENCE: 132

```
atttttcctg taaaatacca ttgactatta tgtaggagta tgtattattg tttgtcatta     60

gcaatcttaa gttatgcata gacaatcttg aaagctcttc tacggcgtgg attcaaagtg    120

agccaaaatg cgtcacaaaa ataagaacaa gggttaaaac attaaaaaaa taatcctgct    180

atatgcaatg atttagagag gcaatgcaca atgatttagt tctccttcag gctttagtca    240

ctttatacaa aaacacaaaa aagaccaaaa aggaaaaaag aaaaccaaaa ctattttata    300

tataaaaggc ccactacaag taattaccca ctaggcccat aaaggaccac tacaagtcat    360

tacccattag gcccatcaag gcccatctaa aatttctagg gtttcctcat cctcgatggg    420

gtttatcctt cgagcacata tataatccgc acgccgccgc ctccctctct gcttcgcact    480

ccatttcccc tctccccgct cgccgccgcc gccgccgcca gccaagctcg ccgctcgcca    540

ggtaagcctc cccctcctct ccctctctcc ggttcatctc gattagtttt agctctcaat    600

cccttccgga tctgaccgtt tcttggacaa atgtcaggt                           639
```

<210> SEQ ID NO 133
<211> LENGTH: 735
<212> TYPE: DNA
<213> ORGANISM: Oryza sativa

<400> SEQUENCE: 133

```
taaaatacaa tcgtaaccga ctaggatctt gggtattacc ttgacataca agtttagaat     60

ttaacccaag tcattttaaa gatattctat ctatatatag cactccatac ccagtcaaac    120

tatacatgcc gtgtatgtat ggggtatcca tgatctccac aattcatttg tcaagtaagt    180

acttcaatag tacaattctg atagtgcgag catagtcgtg aaatacgaca ttcacaaaac    240

cgatgataac tgctcgaaaa ccacaggtat catcagcttt attgctccgg ctcaagctaa    300

aagttcacta aaatccggtc aagtatataa aaactcaagc taaaacttaa attttgcatt    360

aaactgtcat ctccgagctg ttaacatcaa aaccgacaaa tccaaatcct cgaatcctta    420

tgggaagccc atttcaactc accttaaaca gtcaatgggc ccagccatct atcataaagc    480

ccaacaaggc ccatgaaagc ccatctcaac tcagcctagg gtttttttcc actccgcggc    540

gtctcgctgt ctctctctcc tctatatata agcctccgcc gccgcctcct cacctcttcc    600

ccttcctagc accgccgccg ccgccgccgc cgccgccgcc cgccgcgccg cctccgtcgc    660

caggtaagct acaacattcc gttcttctct cctcccgctc gcctgcggat ctaaccgtgc    720

gtgtgtggtg caggt                                                     735
```

<210> SEQ ID NO 134
<211> LENGTH: 2321
<212> TYPE: DNA
<213> ORGANISM: Oryza sativa -continued

<400> SEQUENCE: 134

```
atttatagtc tcatgctaaa ttaaattgtt gaccgaaata tgaacaacta tcttagtcct     60
cattggttac atgcatagta taattcatta gtttctggtg ggttttgttt ttataatttt    120
tagaagtctc gtcaaacact atcactatag tccgctacgg tccatccgct gccttatcta    180
tttattgtca ttgtgatttt aaaaattgaa cataattatc gtttgagttt attattttac    240
tctctataag tctagtaaaa tcattagcgg cttcgtcatt atactcctct acagcttgcc    300
cgctgcttcc gctctttatt gcttttgaga ttgtaaaagt ccaacattat tatcattggg    360
gtttattttt ttactttcca gaagttccac taatcgtcgt gactggtgct gcttaatggc    420
atgctcgttg ttcctcctct taatcatcat agggattcaa tttgggactc tgtttatagt    480
ttttagatgt tccatcaatc accactaccc tgcttcatta ccttctccca tcttttattg    540
ccatttgtca ttactgttct agatgttttt tttttgaaaa tttcatattt ttcattccta    600
tattttttat ttatataaat tgtattccta cataaactct tataattatt cttctatttt    660
ctaaatttat tttatttatt atttcgaatt ttattgatcg tgttttagat ggtcatttct    720
ttcaatagtt tttatttttt aattataaat tttagctatt tataaattgt attcctagtt    780
gaactcttat ttattttaaa ttttggaatt cattttattt tttatttcaa attttaattt    840
aacaataact gaaattcaca attaaaaata agcaatattt taatcccaaa ttttaatttc    900
cgagtcgtaa ctgcggcggc aacgacactc cgacggcgac ggcagcaaat ccccccctccc    960
ccgccgccgt ccggtgacgt ggccttcctc ctcttcccac cgcagcctca agttgggggc   1020
gtggcccacg cactgggccc cacacccgcc caccatagct ggtgcccaca ctccaacctc   1080
ccaattcctc catgaacgta gcccaccata caccacccct ctcacaagtt cacaacacct   1140
cacccacggg cccacctgtc agtcactcaa ccatccccac ccatccgtag agcgggtcca   1200
cccgcccagt ccaccatcgt cgtcacccac gaggagacgc cgcagcacgg gaacactctt   1260
ttttcttcaa tttcacagga aataacattt tttgtaattt cttttataat ttttttttatt   1320
gcgcgtcggc gttaataaag cgcaacggca ggcagcgatc taggcgcccg tcgtccactc   1380
ctcctcgcct tcctcgcctt cctcgctttt atcgccgccg ccgccgccgc cgcctccgcc   1440
gccgccgagg agtaggagta gtaggaggag gaagccggta gccggaggag gagcggggag   1500
caggtactgg acgctgtgct tcctcctcct ccctagggtc tgaggttggc gacgggatcg   1560
gggttttggg gtgggtcggg ttgcttgctc ggggtggagg gcttggatcc gttgtaatgg   1620
agggggatct ggtgggtagc tgcgtaggag tgggttggat ctgatgatgc gtgggttcga   1680
gtggtgcagt ggagctcgct tatagggggtg gctgggtgtg gatcgcttta gatctgttgc   1740
aatttgtcga tggcgtccgc gcggatgctt gggaactcat ttccgttagc taattattgt   1800
ctcggatgga gttcggtcgc cacgatctat tagatccgtg gagtttgggt tttacgtgat   1860
gcggattgta gtagagccgg gccagtttgg tgttgctcgc tgttctctgt gctttcttga   1920
ggtatttcat atcgccatct taggtaaatt tgtcagtgga ttgtgtagta aattgcctaa   1980
ttggtcgatc ctgagatgat ccattaacat ttaatctgtg aaaattgtag cagtagcaga   2040
tttagtgtat ggctctacat ttgtgcagcg gcatgcaaac gtgctaattt tttagtctgg   2100
tgggcggaga agatgcattc cttgctattc cttttcgtga tctgttatcg attagtagca   2160
caaaatgggg aaaaaaatgt cagcaagatc tgttggaaca tgggaattgg ctagtagcca   2220
tcactatcaa tgtgctgatg gcttggttta tggttggtac ctactttatt tagcacgtga   2280
gcttcctgta cataattctt ccttttattt tgatttcagg t                       2321
```

<210> SEQ ID NO 135
<211> LENGTH: 1878
<212> TYPE: DNA
<213> ORGANISM: Oryza sativa

<400> SEQUENCE: 135
tgttccaaat tcagagcagc ttcatatctg tatgagcatt attcaggaat gcagactgcc 60
atagcccata gactaccgac aggtaaaaca aaatactgct ccgtgatgtt attaagcaac 120
tagacacctg aaatctgaat tcgatgatac acatttgaac atctccaagc acgaggagat 180
atcgatccgt ccaagtacca acagtgcagt gtgcaccata tgcaggttgg atatgcatat 240
tttgacaact atagacttgg aaaacccgtt tcagtggaac ctgtgaaaaa acggtgcaga 300
tccttatgct tttttgaatc cacaagtgtg ctcaagctaa gagatggaag cgtctctatg 360
ctcgactgag cggccatgtt tttctccgtt tcagaaggat tggaattcgg aggaggttgc 420
aaagaaacag ccaagcaaat ggcaggagtc caggagatat cagtagcaga tcctcgggtt 480
ttctcactcg atgcagtgac atgtgtgtgc ttcccatctg tgtactccaa tcttaccaag 540
atcagataaa tattcgacgt gattcaaatt tcgaagtacc aaaagaaaaa acttaacttg 600
caacatcacg tatagtgacc ccagattggc attcatcgac acgaacgaac agtaatacag 660
cccaagatgt gaagctgcgg ccctgctgcg gcggttcccc gtgggctgga ctaccagctg 720
caaggagata ggaataagtt cagatatcat ccctcaactt tacgtcgagt ttgtatgaca 780
tccctaatct tcaataccag aaatcttcac ccataaacta tacaaaaccg tgtggttctc 840
acagcagtat gattagggat gaagatttga agagtgaaga tttctggtat tagggattag 900
ggatgtcata ctgattcagc ataaagttga gcgatgaaag gtgaacttat tcccaaggag 960
atacgcatgc aacgacgcca ccacaaacgg gccaccacac caacggcccg gcaattgcgg 1020
cgttgcagtc cccgcggcgc gggcgaattt gctctccgca ggacggcgtt gccacttctt 1080
cggttatcgg gtgggccctc acttcctccg ccgaaagcca cgcacacgct gcccataaaa 1140
aggcgacgct gttctcaaaa cctcagaaaa ttcctatatc ctctgttcgt cactgccttc 1200
ctctccaagt ccatcccctt ccccgatcta agatccatcc gatccaggcc aggtacgccg 1260
cgggtccagt ttcgttctgt ctagggcgtc gcggcgattg aatcgggtgc tttcttagcg 1320
cgatgccgcg atcttggtct gttggttaga gcggttcgga ttggagtttc cgcgatcttg 1380
gtctgttggt tagagcggtt cggattggag ttcccgtagt agggtttgtt taatcactgt 1440
gtgcgatgtg gctaaccggc ttagagtcct gaattgtgtg gtttgtgaat tgtaaatgtt 1500 gatgcccccct gctccgattt ggccatgcga agggtggatt gggctctgat cggtttattt 1560
ctgtcggctc agtcggcttt ggctttgagt tatgctcgat ccctactcga tccaatctac 1620
tgctgtgtac ctagagatta gttgcacgtc gaactgcgct ttgattttgg aatttgcgct 1680
atatctgcaa cagatggttg ctttgaacat attgccactg ttagatatcg tgttgcttgg 1740
tgcttttgtt ccaggatttc atgatatgag catacagttg ttacagaatt cgtttgtttt 1800
attggactaa atcaatagtt ttgaatggtt ttggcaacta aatggtctta ctaaaatatg 1860
atgcttgtgt tgccaggt 1878

<210> SEQ ID NO 136
<211> LENGTH: 2284
<212> TYPE: DNA
<213> ORGANISM: Oryza sativa

<400> SEQUENCE: 136

```
gctagagcat gtctttgcac tgctcgtttt aagttgctat gtagcttgtg catggaccct     60
acttgagacc acatacatta tggagtatat gtctgttcga tcagtgtatt ggccctacat    120
cttgttgagg tctagctaaa gcatatcttg cattgttctt gccctaagtt gctctagaca    180
atgtgtacat ggacttgttg acctcgtctg atgcacatga cacatgctaa tttttgtttt    240
taattactaa agcccatata ggagaaatga cgtcaccccc tagcccaata gttagagcaa    300
atcgtgtgct atcagactgc agaatgaaaa agcccatcaa gtagcctaga atggccagac    360
acgcactaaa gaacaaaaga tgcctgctcg atcgagttct cttcttcttc gtctaggcaa    420
gaagatgaag gcaaggagtc tccttttctt tcctacacca ctgaccagca agctctcaat    480
ttgcaaagag aacacaccac tttaagtgac aacgtgatca atctcagcga aggatcctat    540
agacccctag caccctcctc ccaccttggc cacccagttt acactatatt ttatgtcgac    600
gacaacatct agctatttct tatgcagaga aacaagtttc aagcattcaa attgaatgta    660
gtttcaattt atttataata gctatcttta tctcagtttc ttaattaggg atttcattta    720
atcagttttc ccccaaaaca tagggtttct aatttgacaa ttcatttgaa agcaattgat    780
aaacaaatgg tagagtttgg aggatgaatg cttgaagctt gataaacatg tactaccaaa    840
cttttgctaa ggcaacattt agctctacaa taacaaaccc tacaaatcac tattaaatat    900
aaattgcttg atatgtcaag tactagatag ttttattgtg atatactatt atgtttggga    960
caccagatca ttttcgtttt ggatttacta tgattgttta ggatcctact tgagaccaca   1020
tacacataat acatagtatt tgagacctag ctagtgcatg tactctgtcc attcccattc   1080
caaaatagag gccgcttttg gattaaaaag ttttcaaaaa aaaaggagtt tagaagtacc   1140
ttttatcaca tcaattcaaa atttctcta tcctacccct taaatatagg tattacagta   1200
attttttaa gcattatttt ttctatataa cttggatcga taactataga atagaaggta   1260
gtaccgaacc gttcctccta caggcaattc cctcaaccta aaccattgga agaacgtgcc   1320
aagttggaag cctaacctag cactagtctt agaaaaaaca gtagaaatcg tgagttatct   1380
ctgcaataaa aaaggaggta agcctaccca cactgcaagt ctccaactcg ggcaagctct   1440
cctcccccac gactcccctc tccttcctct ctctctcgct cgcgcgcgcc tgcgtcgcca   1500
ggtaacccct gcctcacctc cctccctccc tctcgtaatt ttgttgcggg aaccagatcg   1560
ataggctgtc cgaagcgaga tcggcgatct ttttcttggg ggttaattaa atcgaacgcc   1620
ctgatccgtc gtctccgtgt cccgattctt ggtttgctgt agggatccgg ttgggatgcg   1680
tttagctgct ctgaaatctc cggatctttt gataatatag gcgttgctcg tcggtttggg   1740
agtagatgct ggtcggtcaa tcgcgtgatc cagcgtaatt ttctggcctt tttgagattt   1800
ggggcactgg ctagtgcctg ttcgtaatga ttcgtgcttg attaggttta gatgggataa   1860
ttctcacgag tcctcgtttt cattcccatt gcaatagtgt agtaatttgg gttagtcatc   1920
tcgtatgata atacgacgac actgtcctgg tgtttttctt ggatttteta cagaagatct   1980
gtggtggtag aggataagaa gtttacaatt agcactaaca tgagctacta ctgttttcga   2040
taatctttac atatatgatc agggagtaat aattaagcaa ttttagataa cacttcgatt   2100
ctgttcattt caagtagtgc tcagcttttg gtcttgtttc tctttctttt atcagtttgt   2160
aaacagcgac aagccttgat gatctaaagc agtactgtga atactatgta gtgatacact   2220
gacacctcga gttgaacgat ttttagactt tgagtgacat agataaagtt attttcttcc   2280
aggt                                                                 2284
```

<210> SEQ ID NO 137
<211> LENGTH: 2353
<212> TYPE: DNA
<213> ORGANISM: Oryza sativa

<400> SEQUENCE: 137
gccggaacca cgctggcaga ccagcagggg tcggtgcccg aagcaataga tatgaaatta 60
catttgctta gcttagataa ttaaaaccca tagaaagtcc tctctagcct agcctgccta 120
ccatctgttg ttgttcttgg atagtcttag ccttatgtag attacacacg ttctctgagt 180
ttgatatcct tttggagtca cccgaaggtg aagtgctaca gcggtattcc gtgcgcttgc 240
ggatttatca gtggtcgtaa gaaataccaa cacgggccgg ccaaacaagg gaacggcatg 300
ggaaaggagt tgggccgacg gcccaagaaa gaaaaagaag aaaaggaaaa agaggaaaaa 360
gaaaaaggga ttcatgtgat ttatatattg catagaattg attttaatcg gttaaaatta 420
tttccgaggc gctgaaaatt tcgctaaaaa tcctgttaat gtattgtgac atgtggaact 480
taagaaaaat tccacgatac caattgcatt tattagttaa ggttcatctc taggttaaat 540
taaacaattt cttcagataa tttattaaat aaattttaaa gctagaaagg ggaactttag 600
gggcatgata catgaccata ggatataggg tatgcattat cccctgacag aaaactctat 660
tcatccctta agggaatata cccttatttt tgcatgtcac ttaaaagtta tcaaaaagaa 720
tttgaaacaa attagtaaga tagatcatta tgtgatatgt cactccacaa acatgcacgt 780
tcaaattcaa cttatacaag tagaaacaaa aataaaaaat tttgactatt caatatgaat 840
aaaatgtgta atttgcgatc aaaattgtta gaattgtata agtcgaaatt caacttgcat 900
gttcgtggaa aaatatatca tatgttgatc tatatatttt tattttttta tgactttttt 960
atgattactg caattgtttt aaaattgaga aagtaccaaa ataacaaata atgatacaga 1020
aggtggtaat cagggaaata aactagtaaa acattgataa gtgtgaaata aaataataca 1080
aaagttgata tgaagaataa actagtagta catattgtgg tagttgggaa ataaattaat 1140
aatgtgtcta aatcacaaaa tttatatatt gtgacaaatt tgaaagataa aatcatctat 1200
cctgagacag actgacggag ggatcggagt accccgtaac aaataaagaa gaagaagaaa 1260
ataataacaa taatagtaat agtaaaagaa gaaaaaggcc tatttcactt cttggaggcc 1320
cattagcaac aagcggccca ttcccaagct ggcatgaggc atcttagggc ttgtgccggt 1380
gtgccctcac ctgctgccct cccaccccac cactctccct cctctctctt tcctcccaac 1440
ctcttgcggc cacacgagcc aagcagcgag acccccggat cgaaacgcac accggcggcg 1500
caggtaagat cccctttccc ttttcccgct ccgcctcccc cccctctctc tctccgccag 1560
atccgcctcc ggttcgattc gtccgtctcc gctggatctg gctgcggatc tggtgttccc 1620
gtgggcgagt ttattgggcg accagtggat tcattaccct cggatttgag gcgcatctag 1680
ggcgaattgg agttggtgct tgcggctgcg aaatgtatgt gtgggtgtgt tatgggttgt 1740
ggtggtgatt gcgtagacga aggatttgta gtctcctttt cttttcccac ctttagtgga 1800
cgagattgga atccgtatga actttggctg catcccctta tggattatga aatggatgtg 1860
aatgctggaa aagggttctg atgcactgct acaagggaga aaaaaaatcc atatgtagtt 1920
gtaactttaa tctcacatgc tgttgactgg ttcggcatgt tgtttggttt gtgattgtcc 1980
acacggattg caaccgctca taaagtatga cttgtataga aaccactcat gtttctggtg 2040
ggttttactc tcattgtctt gcattgaatg attagtacga aatgtgcagt gtcatagatg 2100

```
tcatttcttg tttgttaaaa ttgtagcctc gtatagctgg ttacttttgt tgcaaacaat   2160

atgacattat attgttaatt gcacattttt atcgtgcatg taagtattta caccaaattc   2220

cttggaatta tctctctgca tgatccatgc ttttgttata catgactgct cgatttctct   2280

ttaaattatt cgcttcttgc ttccactatg tattactttc taactgaata tactgcgtat   2340

ttaaaaacca ggt                                                      2353
```

<210> SEQ ID NO 138
<211> LENGTH: 1818
<212> TYPE: DNA
<213> ORGANISM: Oryza sativa

<400> SEQUENCE: 138

```
tacttgatat gttgattttg agatgtttgg tagcactcta aatccataat atgctatatt     60

agaaatttat ggcttcctca atacaaagat tggatgacaa aatatctcca ccaccgtcaa    120

atcttaggag tacaatctgc attcatgtcg agaagagtca gatagatagt tcacactcaa    180

cctgaatgga gttatcaaca tggttaatgc cagggtgaat tataaaaaac ttcgcaaaac    240

cccacgttgc cttaatcttg aaatggctta aatgatgact aacaaactat tgtcttatta    300

tagttaggcg gaagacaata ggggagattg aggaggagat gacctacaag tggctttgca    360

ctgtattgtt tttttcggct cccccatggc cccaagacat tatccatgag acaaccgaac    420

aaacaagaag catcaatacc ggtagcagaa gcacacaccg tcgctcaccc tgctaactgc    480

tttgtactag ccgaccgcca ctagctgttg ctaccgtatc cttcatctag accacccacg    540

aattaactga aaccaccgtc gtgtatgtcc cataaaatgg tctacttagg attatataca    600

agtacacatg ttgatcatga acatgaaatt ttgaatacaa caatggtatt tgatcaaatt    660

tggataactt tacattcata cacaagatat aaaataatat tgctataata tgttactcat    720

aagcatgaag ataataatac tagcactaca aaatgtcact tgatgaaacc acaattgatg    780

ttaacacata aatttcttcc cttccaatct gaatgcccta gattaacatg gagaaaattt    840

ttatctgcag ataacactaa accggatcca aaatttccca taccaaggct gtgtttagtt    900

catgtgtcaa ttttttttaa gtatacggac acacatttaa gctattaaat gtatactaat    960

aacaaaaaaa attggtcacg cgatttacat gcaaactgtg caatttaata tacattatta   1020

gtatattatc aaatcatggc gtaattaggc tcaaaagatt cgtcacgtga tttacatgca   1080

aactgtgcaa ttgatttttt tttcgtccac atttaatact ctatgtatgt gtccaaacat   1140

ttgatgtgac agaaaagttg gaagttcgaa gaaaaatatt tgaatctaaa cgaggcctga   1200

atggaaataa tcaaaaccgc aatgggctgg caaactgtcg atttcagata atttttttag   1260

tacggacaaa ctgcagggac ctaaacgaaa aagaaagaaa accgtgacgt cgctcgcttc   1320

cagagatctt cagatcagat cagaaatccc caaaaaaaaa aaacacaaca aaaccaaacc   1380

cgacagatct tctcttcttc ctcctccctt tcccatcttc gacgaggcga cccggcgcga   1440

gagaagaaga gatcgatcga tcgatcaacc gatctcgccg gagaaggaag aggagcaaag   1500

caggtaatct ccgccatccc tcttcctctt cccccgatca agcgattagg tgtagaaagc   1560

tccagttttt ccaatcaaag tcgccatctt tttctttccc ccatctggtt gatcctgcga   1620

tttggttcga tggtgatgga ggtccacgcc cctccgattc gcgcgatctg tgacgccctg   1680

agtgtgaatt ttcttcttcg cgtggctaga tttgacccga ttggagatcg gatttgtggg   1740

gaaaaaaagt tgggagcttt ggattctgtt cttgatgggg ggatttgctt atttgctttc   1800

attcgatctg ttgcaggt                                                 1818
```

<210> SEQ ID NO 139
<211> LENGTH: 1648
<212> TYPE: DNA
<213> ORGANISM: Oryza sativa

<400> SEQUENCE: 139
tttggacaca tgcatggagt attaaatgtg gacgaaaaaa acaaattaca cagtttgcgt 60
gtaaattgcg agatgaatct tttaagccta attgcgccat gatttgacaa tgtggtgcta 120
cattaaacac ttgctaatga cggattaatt aggcttaata aattcgtctc gcagtttaca 180
ggcagattat gtaatttgtt ttgttattag actacgttta atacttcaaa tgtgtgtccg 240
tatatctgat gtgacacgcc aaaactttac acccctagat ctaaacatcg cctttggctt 300
caaaccaaaa tggcccaatc attttgatta aaaaaaactt gatatgcagt aatctatatt 360
tttagaaatt cctcaatggg ccttgagaaa ataaggcata aacactacaa ggttagttcc 420
aactacttaa ctttctataa tcttccattc cttgtcagct tgcttcctat cgaggattgt 480
actaatgaat aagaagacca tgaatgaaag gatgccacac ccttatatcc tgtgtcttta 540
attttttaag aattatacca tccttcttag actacttcgg tagtaggagg ggttgcataa 600
tagatatatc aaaggataag atcccaactg gtttgctatg ggtcacagac attttttttt 660
ggatttctgt tttaaaaata attttaggag aaattattac ttattttctt atcaatcatg 720
aaaagggagt caaacagcga aaaggttact aagaaaacca caaacattaa tcataacatc 780
atatgaatca agcatgctct agccaaattt tactatacat cagtcaatgt tggttcgttc 840
gtttcttaat catccagcat ttgataaact ttggcacatt tcttaagcac atgcgtgtgg 900
caagacagaa ttgttcacag gaagaaaaaa aaacccacat ctcgttaacc atattttttt 960
actgtttaaa catttttatt tttattattt ttttaaacga actattccaa aacttatttt 1020
caaaacgcgt ttggcgtggc aaaacaacag ttcacgtcac tccgcagcgg gcatgacaat 1080
tttgtcctgc cacgccagca agacaacgtt atcacgctag ccagactgac atggcaatat 1140
tatttttgcc atgccaacct gcattacatg gacaaaggtt catatcatgg aaataaaatt 1200
tagaagaatt tatttttaaa actaaaaatt aaaatgctca aaaaataaaa aatatattct 1260
taactaacct ggtgaaacaa aagaagccca acagtcaggc cttatccagg aaagcggagc 1320
ccaagcccaa caaacccatt tacccccagc gtgggcaggc gaacccttc cctcccgtgc 1380 ctatataagg ccacaaaccc taacgccccc actcttccac ctcgcagtcg ccaccccgag 1440
cagaagccgc cgccgccgcc cgaaaccctc gccgccgtcg cttctcctcg gggcgcagcc 1500
aggtaacgtt gtcctcctcc cggtctctcc ctccatcacc tcggtccgcc gcgcaagcga 1560
gcgagcgagc gagatcctgc atttctcatg gcgctaacgc ctctctgttc gtcgtggtga 1620
tggtgtgatg gtggttgtgt ttgcaggt 1648

<210> SEQ ID NO 140
<211> LENGTH: 1611
<212> TYPE: DNA
<213> ORGANISM: Oryza sativa

<400> SEQUENCE: 140
cggcgcaagt ggttgcgttg gtaggcttct cggcactgag gagtggacag agcagtgccc 60
agattaggtt gcaagggtac atggacgata acaaggttgt ctcgacatag caacatgctc 120
atcagtgttg gccctagggt tcccttaccg tttttggcgt ggttattgga cccccacggc 180
aaggtggtta tcgcgaaacc gcgcggtaac cccgagagat accgtggttt taaaaactga 240
aaaggttacc gtgcatggta atcgcgcggt tttgtgtggc tccctgatag tggtgagcct 300
agggacaatg actaccaatg ggggttctac acctagattt gactgagtga tgatgggaca 360
gtattgtctt tacggcgtgt tggtgtggac aatgatggtg gtggtacagg tgatggccct 420
aggagcagtg gctactagtg gaaacttttc atccatatct gactgtgtga cggtgagggt 480
gatgactatt gtggcggtgc ttttcggcat ggtagtggca atgaccctag gggcagtggc 540
tgctaaatcg tcggtttata ggcctaaatc gaaccatgtg gattgggagg tggctctagc 600
tagtacgaca atgacaagct tggtggctgt gctagtggca actggagagg aaggatccaa 660
cctaaagtca gacccgacgc tcttttaatg agcaagacga ggagcggaca tagggcttgt 720
tggaggtgct ggcaacggtt aggaagcgat gctgaatttg agacctaaac agggtttaca 780
aaaccgcgca gttatcgcgg ttaccatgca cggtaatctt ttcaattttt aaaaccacgg 840
tttatctcgt ggttaccacg ccaaaaatgg taagaggaac ctagcatcca tttccacgcc 900
attcacatcc atgccagatt tggaacgatg gtctacacat gaattctacc tggactgcac 960
tgtttcatat aaaaatccac ttatccataa tatactattt tgcatacata ccatagtcaa 1020
gagattgaat ctgctggtat tgtgaaacca gggtcgcaac tttcttttct gcaagtaacc 1080
ggattggatg ttaatccatc catttacaca gtattttaaa gtacggaatc tagctgacgc 1140
aaccgtccag tgcacaaagc aaaccatgca attcgtcttc tttttcaaa tagaaaagca 1200 aaatgtcaac acaacgccgc tgaccacgag cggcagcgtt cactctgggc ccgagtctgc 1260
aggcttgcag cggaaggcct cgttacagcg tcgaaatggg ccaggccagg ccgggccgga 1320
acacgtgggc ctagcccact caaacagccc ttgacgcgca ccaccaacca ctatataagc 1380
ttccgagagc tcttccccca aaccctaacc gccgccgccg ccgtctcctc ctcctcatcc 1440
aagcagctcg cgcctccgac ccctcgcctc gagctccagc tctccccaac cccttcaaca 1500
ggtgagtcgc cgcctctccc gcaaccctag ccgcgtgtcg gcgcgttcgc tcgtgatgcc 1560
tgacgccgcg cgtggtggtg ttttttttt ttttgggtgg tggtggtagg t 1611

<210> SEQ ID NO 141
<211> LENGTH: 1500
<212> TYPE: DNA
<213> ORGANISM: Oryza sativa

<400> SEQUENCE: 141
gtgcttggtg ttaggcaaga cataggcggg cctagggtag ctagagcttg aacccttggc 60
ttgcctacaa aatcatgtta aaattcttca gaatcaccat gtaattttta ttgaaaatga 120
acagcttatt agttacagtc tttgataatt tctgactccg ccaatggtgt taggtagttg 180
gtgaatttgc ttttagcgtc ttctataacc atacctcgga tgaaaactaa caagaattag 240
agaatgaaga ggggtgagaa gatatgcagc tttttttaat ctcatttttc agtcctgaat 300
tatctttaaa atatttgaac tttgctaaag ttatgacatg aggtatgtga tctcctatga 360
aaaatcacat agagtgttgt tgatgaggtg caataaatga ggaggaaaaa aaccatatcc 420
tatagataga ttgaaattgt agggaaaatt gtgataatgt tggataatat gtttgcaaaa 480
tttatgccat tactagatga tgccccgcgc tttgctgcgg gatatatatt agatattgga 540
gaaataatga aataatttgg attgaaatat catggaaatg atttaagaat gatgatttag 600
catgtgtatg tttagtttaa aatgaaataa attgtaggct taattactat atacttgcat 660
gttgagtttt gtgtgtttaa tgggttgatg tggcatgctt acatataggt tttaggagtg 720

```
ctaataaata ctatacttgc atgttaagct ttaggtattt agtgaatata ttagatttat    780
agaaagaaga caattagctt ccactcgtag aacaatatgg tcaagtttag ttccgaacta    840
acacacaaac ttccaacttt tccatcacat caaaacttta ttacacacat aaactttcaa    900
ctttaccgtc acattattcc aatttcaact aaacttccaa ttttggtgtg aactaaacac    960
accctatata ccagagactg caaaatttaa ttctgaattt acacatagag gctgcaaagg   1020
actcattctg aattccggga caaccgcagg atcccaacgc caagaaaacc accaccccat   1080
catccgagca atctcggccg tccaatctcc ccacccccac catccggacg gccgccgcca   1140
cacccgcaac cctagatagc agcgtgcgcc cttccttctc cttcatcctc ctcctcctcg   1200
cgccgccata aatcctcgtc tcccgtacca actaaacccc cttctctctc cgctggggtt   1260
ctcgccgccg ccgccgccgc cgacgatctc gtctcgcacc gcctctctct cggtgtaaga   1320
gctcgccccg actcatctcg tcgtgggaag ttcgcgtggt tgcggcttct ccgcccgcgc   1380
ttggtctcgc tgtgtttttt tttttgttcg gtggatttaa ttttgttttg cttttttttt   1440
ttctctggtg ttgcagatct gagatttgga tcgggcgcga ggccggcggc tccagtcggc   1500
```

<210> SEQ ID NO 142
<211> LENGTH: 1605
<212> TYPE: DNA
<213> ORGANISM: Oryza sativa

<400> SEQUENCE: 142

```
aaaaaaaaaa aaaacatcgc tgcatggcca cacgcattcc taacattgcg cattgatcaa     60
ggaggtttaa tctaaaagga aggatttttt tttggctcgg taccatttgc aaatatgatg    120
attaaattgg aatggggtga gtatatattt gtcaaggtct ttttagctat attgatagtg    180
ttctgcactt tttttttaa tggaaacaca gatgagtgta tatacctcac gtcagtaaat    240
tagaaagaag aatctgttct ataattctat tccatgtcaa gctaaggaaa aagagaagga    300
aaaaccgaaa aagaaagata actaatcaac ttttcttaat gggccagccc aaaaggtgca    360
cacctcagtc cttgtttcac tatttgtgag tcatgatcca tgtttttggg ggaaaaggaa    420
caatgtccat gtaacaatga ctgtgacggg aatatacaat ggcaaagaat tcaaagttcg    480
cccagactaa agtgaaacaa agaaaaacat agtttatgta ggaaaagaaa aaaggattgg    540
agtagacaag atcgtaaaat tctgatctcc aaattttgtt tctgtgttta ttactttatt    600
aggcagatag ttcctgccgc ttgatcatgg gctgcgttct aaggagccga ttcagttcag    660
cctctcttat tttcctttag cgcatttgtt ttaaattatt aaatgatgat atatttcgta    720
tgaatttttt atatagtata tgttttctaa ataaataaaa aaaatctatt ttttaaattt    780
ttaataatta atactcaatt aatgatatgt ttcctcgtta attagctata aatcaatcaa    840
tcatttgagt agaacgcaga tcgatgggtt gacacatgtt ctcactttta tactagacca    900
atcctaaaag gaacagctaa tatttttcat ggaattcttg ctccctttcc ctgtcgaaat    960
ttctggattc agttcctgtg tttgagtttg atgctgattt tactcgattt tactttcggt   1020
gttttgagtt tgcgactgat ttttattcaa tttcgcatca caattcatac acccctgctc   1080
tccttcgggt acaagttcgg gaccggatac caaaccccct ctcgcaatcc gtccccaacc   1140
acacccatcc accctcgggg cccacctccc tctcgcttcc atgtgggtcc caagccggct   1200
actctgacct ccggaagagc ccggaacgtt ccatgccagg tgggccccac ctcccccgtg   1260
gccccactcc tcagtgaccc ccaccgccgt acccgaaccc gatagcgaga gagagagaga   1320
```

-continued

```
gagaaaaaaa aacaaaccaa accaaacccc ccgctgcaag aaagaggctt ataaaagaac   1380

actttaatcc ccctcctctc gcctctctct cttctcccaa atctcatcgc cttctccgcc   1440

gcgacgcgga cgcgctcgaa ttaacgccgc cgccgccaac caccgcccgc cgccaccgcg   1500

caggtaagtt ccgcccccg atctggcctg ctagggtttc gtttctttcc ccgatctggg   1560

tattgggggg gtgcttaggg tttgatggtt ttggtgggtg caggt                   1605
```

<210> SEQ ID NO 143
<211> LENGTH: 1648
<212> TYPE: DNA
<213> ORGANISM: Oryza sativa

<400> SEQUENCE: 143

```
atggttgttc aattaagcaa caacatgaat gtatgattta tatatttgta tacactagca     60

tattgcctgt gcgttgcaac gaaattttaa ttgatgaaaa tgatcattaa cctttgctat    120

tatcattatt ttattatcat ctcttaaatt ctacatatat ttgtaactaa accctatcac    180

ctcacaatat aattcttact tcccacaaaa aatagaggtg gtggggtggt tgacatgtgg    240

gaccttatct tttcttcact ctaaaagggt aaggactaag gaggtggtgg tggggcgcga    300

tcgctaatcg gtgcgcgcgc cggcggcgcg cgtttcaggc ccatagggcc cagcaccggc    360

gcgcgcgcct ccttcgacgc tttttttcg tttttcttta gcgatttttt ttcgttttct    420

tttccacttt tttctgatta tttttttaa tctttagcat gttttgagtt tgaaagtttt    480

taaattttga gttgaaaatt tttaaatctg aatttgaaag ttttcaaatc tcgagttgaa    540

agttttcaaa tatggacttg aaagttttca aatctcgagt tggaagtttt ctaatttttc    600

aaatctggac ttgaaagttt tcgaatctcg agttgaaagt tttcgtatct cgagttgaaa    660

gtttttaaaa tttgacttta aagtttaaaa ttaaaatcga aaattttcaa atctaactta    720

aaaaattttc aatctgttag taaaaaaatc tccaaaatct ttcttaatta ctatcattag    780

tgttaagtat atattaacta atggagatag ttaagtatat taactaatag tgttaataga    840

gtaggttaat aagggaggag tgctcgctag ctagtagaag cgcgtcgcgt gtcgcatggg    900

ccgggccaac cgcgggggga gggggtgggg gcaacagccg cgcgctagtt aatttgctcg    960

cgcgagctag gaccctccgt ggtggggtgg cagattcacc acctaccacc accactactc   1020

cttttcaaag aagtataggt ttaaatctcc aaaagataca taatattata aaatacctat   1080

atatatttgc gttatatttc catataatac tgattaatct tatgcatttc gattaatctg   1140

taaacgatac tcttttcatt ctacaaccgt attccctctt gtacggcact gatgtaaagt   1200

tagatgatcc ttttttacct ttatacagta tgttcagtcc aaagtgaaag tgttcagctg   1260

cccgaaggcc cagcccacgg gaaaaaagaa cactgcccaa aggcccagat aactagacat   1320

cccgatcaga cggcccagat tcaccagatc cagctataaa aatccggacc acgcccacca   1380

cccaaaaccc tccggctcat tcttgcccac gccgcgccgc cgcctcctcc tcctcctcct   1440

cctcctcctc ctagggcttc ttcttcttcc cctcctccga gcgccgccgc cgccgacgag   1500

caggtacgat ccgttcctta ccttcaccgc ctcatgaccc tcaccctcaa gccgatacga   1560

ttcgagtgct ctctctcccc tcgcgccagc gcctctgatc tgactaattt ttctcttttc   1620

gtttggatgt gcgacgcggt gcgcaggt                                      1648
```

<210> SEQ ID NO 144
<211> LENGTH: 1586
<212> TYPE: DNA
<213> ORGANISM: Oryza sativa

<400> SEQUENCE: 144
ctgaccgaat acggctccgt cggctttgta tcggccaccc cgagcaacac catcccggcc 60
accagagggc cggtctgact gcgcatgtgc cgccggtcaa accggcctta tgcaccggtc 120
agaccaccgt cttgtggccg gtcagactgg ccaaggcacg ccggtcagac cgccactatg 180
tggccggtct gaccgcccct ggtcaggccg aacacagtga aactgtgtgt gataagtgtg 240
tgtggtgaaa agtgagcaca agtctaaatg cataatgaca taatgtggca attaaaatca 300
tctcatttgc taggtcatta ccccttgat agtacggcaa aactaaaaat aaactagcaa 360
atttgatcgc ccttcacctc gatcaatttt aaaactaaag cactagtttt accgttttct 420
tttcttcgct tcgcgccatc aaattttaat ccgtcgataa tcatccatgc gcacacatga 480
cgtggaccta acttaaaata tatcttaata gcaacggtta gtccacaatt agcgcttgtc 540
attaattacc aaaattaaca acgggggcct agatgcttca gcgtcgcagc ggcgtccgcg 600
ggctggcgca ccaccgcacg gagcggctgt ggatgctggc cttcccgcct ccggcggtgg 660
gggtttccgc ttacatcgca ctgcctcgcc gttgcctagg atgacgcagg tgaagacgac 720
cccgatcttg gcggcgaggt tgacccagcg caggaggtgg gcgccgacaa ggcggtggcg 780
cacgacgtcg cagaagtggt tgcagttgcg gagaatgagg ttgtaagcgt cgccggggaa 840
atcggaggtc cgccatgacc gcggatttgg gtctgagagg tcatgagcga gagaggagag 900
gatggggaaa gagagaggta gaagatgagg gtatttccgt ccaatacatg caaaatatgt 960
agcttagtgg catcactaaa attacaaaca agcagcagtg tatggttaca aatacttaaa 1020
tagtaatggc atatttctaa actggcaaat ttttaatggc acgtatccaa ttaacccttt 1080
caggaacgct tgggacgtat cggcgaggta tcttttttt atttaactga aaatcgcgaa 1140
aatctgggat acgtatcgaa gtgtatccaa tatgtatcca tatccataca cgtatccgat 1200
actgatacgc cacttttgtg ctgtatccag gtaacataga ttatagataa tcggattcgt 1260
tgacatacct cagatgaact tattcctagg gcaaattagt cccagccgaa actccacaca 1320
gcccaactat cattcagccc aacccatcag tacaacgaga atggccttcg caaccacgcg 1380
cactatataa cctacccacc tcactcgccc tctcccctct aaaccctacc cgccagcctc 1440
cgcctccgcc tccgcctccg ccgccgccgc cgagctcctc ccgcgcgctc cgagcccatc 1500
aggtgagttc ctcgctctcg aactttcctc cgttggtgat cccccgtgca tgtctccgtc 1560
ggtgaccgcg tcgtttttcc gcaggt 1586

<210> SEQ ID NO 145
<211> LENGTH: 1608
<212> TYPE: DNA
<213> ORGANISM: Oryza sativa

<400> SEQUENCE: 145
tcacatgtat ggcacgtaca atgtgtcaaa tttcaggtac agataactta ctgagaaatt 60
tgtatatacc tgttatatga actcatctat atcacatttg ttaggaaacc ctcataatct 120
tagtcacctt tttttttac aaaacctact atacaccttc ccaacgtgag cgccgcaaac 180
atcaacacca tcgctgccac cgcctcctta cccctagtgt gtcgccacac ggtctcacct 240
gctggttgga agacaccaat ggcattggca aggcccctcg gctggtttcc tccctatctc 300
cactctctga ctctgccctc ccctgcccta tgttccttct caagccggcg gcaataaggt 360
gcccctgctc caccatcttc catgtctcta gtggctatct gtcgttggat ccgtcaccc 420

-continued

```
ccgattgccg cctcctaacc agtgggtttg ttttgcccct gtcagtcatc ctccgtcaca    480
cacggttatc tctctaagct ttgggaaaac ccttcctctt cctcctcctc ctaccccctc    540
ccatcccaaa aataacctag aaccctaact gatgggggga cgttgctgcc ttgctagagc    600
tagaggagaa gaaagccgac acaaatcttg gcatggaccc tatggtctga aattcgacga    660
aaatctttcc aaatttctgc catatgaagg ttagcgattc cgtaaaaatt atgaatgagc    720
ctgtacaatt tacctaaatg gatggtccgg atttggaact tatctaccct taaggatggt    780
caaaattctc atggttacac gaagaatgtc aaatacactc acacatctcg ctaaggaaaa    840
acagaacagc caatcagagc ataaatttca aacttttctt gaaaactcaa gcaatttttc    900
actgatattg gacaattttt tttatcaacc ataatcacta gtgtcacaaa caccttgaaa    960
ttcaaataca ttcaaaactt ttgtccaaaa gcacatccga ccgggggacc tcaagataga   1020
accgaaattt caaattttca accgaaattt atgaactaga tgagagtgat gcgtaagggg   1080
gaccatcagg gagcaaacaa ccgtgaccga attgcatagg agttatggct gatcacttga   1140
gaaattaacc atccattccc ggtttccctc caatattgca cccatccatc atccaccagg   1200
gatgataccg ttgccgttgc tctaaaaaac gttaaaacag cggcaggcaa cacgacagca   1260
catcgcatcg tacgtacgtc gttcgtcccg ctctcctccg tcgtcctccc tgcccaccgt   1320
cccccacacc cactccccgc cgtcacgtcc ttccagaacc acctccacga ctcttccaat   1380
cccccgctat aagacgcttc tccactcacc actgcaaccc tcacccagcc agctcgagcg   1440
agcgaagcca gcagcagaag cagtagagag aaagtagaga gttggagggg aaggaggagg   1500
caggttagta taccaactac tactgcagta aagattcaga gatggaagta tttttactgt   1560
tttctgagtg attgattttt gttttaattt gcgcgatctt ccacaggt                1608
```

<210> SEQ ID NO 146
<211> LENGTH: 1350
<212> TYPE: DNA
<213> ORGANISM: Oryza sativa

<400> SEQUENCE: 146

```
gagctttgac ttaaaagaca actaaaacac ttcgatgatc gaaaccttga attaaatata     60
tatgttctaa acagacatat attagaaggt atataatgca cattaataaa taaataaaac    120
ttgaataacc catatatata tttttaaaaa attaacatat tactgtcaac tgatgacttg    180
gctgtattag aaggtatgag ttgggaacca taccctgata ttcaaaatga taggatgaat    240
cagcgtataa ttaattaaat attatattaa aaaactctaa aaatgatcat atagattttt    300
aaagtaattt atctataaaa tattttaaaa cacaccgaaa tgtaggcacg aaaaaacaga    360
aatgagttgg aaacatgaga acacacccga gtggactctg accagcaata tccactccca    420
taaaaaacga aaagaaaaaa aaataatgac aggaagaggt ggcccaattg caatgggctt    480
ccatgggctc ctcaagccca acacgcaatc accaccatcg gtcacgcgtg acgcaaaccc    540
cacagccccc ctcccctcta tataagcctc tgcgccgcgc tcctccgaac cctagccgca    600
catccccgcc tcttcccgcc gccgtccgcc gcgcgcacgc cgccgccgcc aggtaagtct    660
aaccatttcc tgctctaccg ctcgttgtct tgctgtttgt tccacggttg cgctggatcg    720
gtcgccgcgg ctccctgatt tcaggcgcgt tttgggcgtt tggtttagat ccatagtagc    780
tgggcgctgc tggattgttg ctgttcccgg tgttgatctg tgttttgctt tgatgaattt    840
aggtgtagat agattttgta gttgtttcgt tgcatatctc gttagtttgc ttactcaacc    900
tgaaggagtc atgttggact taataggatg tgaatattgt tgggggaact gtaccgatct    960
```

ttgattttca cagataatgg tagtatgata tgattagtgg ttctctgtga atctaaatga 1020
tttattctga tgtagctagc agatgtagat gcatttatcc tagctagaaa tggcttgttt 1080
gtggtggttt tgttgtttga agcgaatccc tgtaatggat ttagttactt catggctatt 1140
tctatatcca ctattttctt gttcatcgat caattatgat tatttagatt aatgtaatgg 1200
atttagtttc tttcatgact ttgtatattc actatttgcg tgttcatcga tcagttatga 1260
atagtattca gattaacagt gatggggctg taggtgcttt agggtgtttc tgagtaacta 1320
acttgacttt gtggcttgct ttggttaggt 1350

<210> SEQ ID NO 147
<211> LENGTH: 1616
<212> TYPE: DNA
<213> ORGANISM: Oryza sativa

<400> SEQUENCE: 147
tctctagggc tccgcgtccc ctgtctcagc aaatttcact aaatttaaaa gactttttttg 60 agtaaaattc aactcaaaca tatctgagtg gcaagtgcgt gggtccgcca tgatctacac 120
caacaagctc cccggtttgg atcgtgtgtg catgacggtg cagccgccga cgcggcgcgc 180
cgacgcgatc tgaaacccat ccccctctct ctctctctgt gtgtccgaag gagatatttt 240
tcgcatcgaa tggagcagcg acaagtcatg tgaaacagtg actgtccaaa ccagcacgcg 300
tggattcttc agatctcgat gtcctcctcc tcagatgggc catgatgggc cggccccccgc 360 aaccaacggc ccggatcacc tcttcccccc acccccatca caaaacccca aacccatcac 420
caacttccca atctcaccca ccccaccaat ccccaccaga tccaacggcc cagatctccc 480
cctcacccag atccaacgcc tcccccttcgt cttctccctc cataaaaccc cacctcaccc 540
ccaccctccc actccgcctc ctcctcctgc ctgcctcctc tctacccacc caccctctcg 600
ccgtcgcaga tccgatccag gaagagctcg ccgccgccgc tgccttggcg ctctccgtgg 660
agaagacctc gtcggggagg gagtttcaag gtgaaggacc tctcccaagc ggacttcggc 720
cgcctcgaga tcgagctcgc cgaggtcgag caggtgaagc atcccctccc tccctttcta 780
atcccattat atttcagatc tgaagctgtt tgcgttagcc tagcctgctg cttgtactgt 840
tcttacctta gtactacttg attttgccgt tattatggat ttgattatgc tactactgtg 900
gatctggatc tggtttatct gcttcggttg attcagtaga tctggtgggc tattacgcat 960
aaaaaaagtt tatgctatag gagtggtggt taggtggatt atacatgtgt ctttaacatt 1020
ttagattcct gatgtttgtg gcatgttgaa tatggatctg tcatctagat ctccttttgt 1080
gacacaaact aaaaagacag ggttaaaaag gtttagttga ttttacctaa gcaacactaa 1140
caattggggg aaatttgcac ctgatgtagt gcgcgaattt tgcttttcgt gatcgtttgg 1200
ttgcttgatt tagacgggat gcttgtagtt cctttattta gtgtctcctg tgttatagga 1260
gtaggagcgt cgaatttaag tcttaggtta ctgcggttgg atctaaatct tggtctaatt 1320
gttgcgtagc tgtcaaagat gtctagtttt gttgttagct tgcatgtttt gcggatctga 1380
tgacagaata tggaataaaa tattggtacc aaactgcttg ccatttgttt tattttactc 1440
gttattgtgc acttgtgtag cttgattgtt taatggcatt ttactggact ccttagtaca 1500
cccttcatct gtagtgaaat attactgaat gctgggaatt acaatctgtt atattttgca 1560
atgattttat catttttgct tgagatatat taactctgtg tttcttctga acaggt 1616

<210> SEQ ID NO 148

<211> LENGTH: 1136
<212> TYPE: DNA
<213> ORGANISM: Oryza sativa

<400> SEQUENCE: 148
aatagttcgg gggtcgatat atccggttct gtggtttagg gtcgtggatt agattcgggt 60
aacttttaag ggagtcaaag cgaacttatt ttccccccat cgctcagaag aaaaatcgaa 120
aaagcccaac cacaacgacg cggcccatta cagcccaagt ccattacact gacaaatccg 180
cccccacgaa tccaacggcc cagatcaacc ccaccctcca tcccagccgt ccacgctagg 240
gctatccctc cccgaaaccc cccacgccga cctctatata aaccggagac cttctccctc 300
ctccaaccct agccaccccc gcctccccca ttctccccgc cgccgccgcc gccgtctcgc 360
cgccgacgag gagcaggtga tccccatctc tctcgcttct tcttttttt gcctgaattg 420 atgagatgtt ttgtgttaga tctgtttgtt agtctcgtag ttgtgtggta gtaactacta 480
ttattggatc tgaattgatt tgttcgcgtg attagaagaa ctcatctatt ggaaatgatc 540
tcggctcaat ctaaatatgg atgatgcgat ttaatgttgc tttaattatt tgttatttag 600
tagagaccca aagtaaatat atgtgccatt tgtttagaga tgattcgaat gccttggatg 660
tagctacttt agtgtatttt cgaacatttg cttctgttga tactgtgtaa tagagcacca 720
caaacaacta gttttgttca ataatcctgc tgttttttct atcgttataa tatagttgta 780
tatgcactac ttgatattgt tgcccatgga tgctttccat ttgttctacc atcaagattg 840
tggtggcata tgtactagat attgtttgtc tatgcatgat taatatgatt ggccaattcg 900
ctctttcaag tggtgaatta tgtttatgct tatgattttg ctatcaagtg atgtatgtat 960
gctaacatag aagataatcc tttacatatg cgccttgttt gatccgcatg cttgcttctg 1020
ttggagagat gtccttggcc ttgtgaagta tttttattcc tgcaattttt ttgtaatgtt 1080
cagtgcaaat aaactgtatt gctcatgcaa ctagttgata ttattttctt gcaggt 1136

<210> SEQ ID NO 149
<211> LENGTH: 757
<212> TYPE: DNA
<213> ORGANISM: Oryza sativa

<400> SEQUENCE: 149
gtcactgccg cctgttacaa gaacattctt cctgactatt ttctgggttt tctgttctct 60
gctgcttgga agaataagat tgttgtctgt gttaaaaaaa cacacaataa tttagtttca 120
tattactaca gtagaaaaca ataagttact cgcgaacgga tattttagca ctaaaagaga 180
attaaagaaa aaaagaggtc ccaccgagat ttgaactcgg gttactggat tcagagtcca 240
atgtcctaac cgctagacca tggggccatt ttgaacacac ggatttttaa tctctatata 300
tccatacttg catctagtct agcatgggcc ccggcccatg atacgttcac ctgaaagccc 360
actcatgcga cgacttgtca aagcccaaca agcgaagaag ccgatgctta tagaggaagc 420
ccggctacca ccacgccaac gcgctcattt cgttcattct agggtttaca actcacgacc 480
tccgccgccg ccgccaggta atcctctcta ctctactcgc gatcccccgc gccgtgtttt 540
cattcagttc ggtgacgaac cataggagta tttcttctat ctgtgtgcgt agcatcgggt 600
cagatttgtc agattttgtg gcgtgaattc gcatgttgct agattttata ctgtagtagt 660
ttatctcttg cttccggtag aaaggttcgt gcgccctttt tcttggattg cttgacgagt 720
gcttacggat ttgtggtgtg gatttgttgt tgcaggt 757

<210> SEQ ID NO 150
<211> LENGTH: 2500
<212> TYPE: DNA
<213> ORGANISM: Oryza sativa

<400> SEQUENCE: 150
gcactccctc catgggaagc ccgtccaaga tgcaggtgtg gtgatcgttg tcaggttctt 60
cgttccataa atcctacaac attgggttga aggttctttg tttgtccaaa tattcttgac 120
gacgatttca tggtaagaat attttgatta catgaatcct tattttctca caacatttac 180
taactttgct tgctttacat ctattctttc ctcccaggaa ccaccaagga gatgtcaata 240
cagagaatgg atagacacca gaagggttct aactccacct agccgtgttg tgcagcttga 300
actaccagag caatacaagg ttactaaagc gcggtttgag agaggagagg gatcctcacg 360
taggggttag ctattatcgg acaacttggc atattgaaat ttttactgtc atgtttcctt 420
gtcccattac tacatcgtcg ttgtgttcaa ctattgcact acctccctcc tagttcgaat 480
ctaatatcat ctatgtaacc gcaatgcaaa taattgtatc atgttcaaat tgtactacta 540
tttcttcatg ttacataatt ctccttgttt aagtccatat aatgtttcta cgacccagac 600
tgcgataggc ctatataaat tatccgagta ctaatacgtc gaataaggta caaaataata 660
cctcacttaa catatgaaat tgcgcaacaa ccaacttcaa tacattttta taacaatatt 720
aacaagtttt accaataaat acttctttat aacaatatta acaagttttg ccccaataag 780
gacggcaagg gacccagatg aaaaaagtac ggccgcaagt tctttatggg cggccaaaat 840
tgcaattagc ctatgggcgg caagggccta atcgcaattt tggccgacgg cggcagacgg 900
cgcggtcgac ccaccgtctg ccacgtcagc ttgccgccca ccattagggc ggcaggggct 960
atttctgcaa tttttttggt cgatagatta tttctgtaaa tattaaaaaa aatctaaaaa 1020
cgaaaaaact tcggcaatcg ctttctgtat tctgtaaaag aagcccaacg aagctacgga 1080
gcccggccca ccaagaagca accccctgg taagccccag atgaagcgac aacccgatcg 1140
gacggtccag attcacgcga tgccaatata agacagtcac cacgcccacg cgcaaaaccc 1200
tcgagaccta gggcttcctc cttcccctcc gagcaccgcc gccgccgccg ccaccgccac 1260
cgcagcctga ccgctcggtc tccggcaacc aggtgcgagt cccccccccc cccttcctga 1320
ccccagctca agcgaggcat ttctcgtgtt cgtcagttct atccatgtgg ttgcgctcga 1380
gtgtgttgtt cctttcgtct gatctgaagg ccccccgtac ctgattttgt ttgtgagcta 1440
cgtgctgttc ttgagtctgc tgggttatac tgtaatcatt ccgaccatcc gggttagcta 1500
agagtttttg gttgctagat gttgagagtg gcatcgctgg tggttgggtg gatctccagt 1560
aaccatgtat ttttgttagt atagtattta tctgcgattt agttgttggt cttggtggac 1620
aatttcgagt cctttcgatt tgggaatgac tcgcaactag gatgttggtg cttttgtacg 1680
gtcgatttgc aatgtagcga ctagcgagct atccatttca acagattatt tttactacct 1740
gggggtttcg tggggcagaa atgtgtagtg tcttcatgaa cacttaatct gctgactaac 1800
tattgacaca gtgggagaag ttttggttta aaggaaatct ggttttcatg ttgctttgtt 1860
ggcatttcaa ggtagcagct tcgtatggga ttttatttag gaatgtgttc tttctgttag 1920
attcagaatg ctaaatgtag cagttaaaag tgtgacactg attttgttgg ttttcttaat 1980
gaagcagctg acggttgcaa tttcatttgc tagaaactac gatgtaatgc ttaggaagtc 2040
caacagccaa ttaattttag accattgttc taaaatggta tgatgtggta gtctgatgga 2100
tcctttagtt gcatgcatta tatacttgtt cacatgttac aaatcatgca ttcatctgtg 2160

-continued

```
atagttgtcc atacttatat aatgatgttt ggcatccttg aggtcatttt ttctataaaa   2220

aaggctattt gctatctttt gaaagtacat tcaaatgttt gtagttgaac tctgtattag   2280

tgatatacat ttagtcatta agttgtctta tgctcggttt ggacagatgc ctacctgttt   2340

cttttttttt ttggtagcta ttgtttgtgt gtcaattatt cagtgtttac cagttggagc   2400

tatgttacaa atgtgaaatg gttttactac tgtctttatt gaagcttgta gtttttttaag   2460

gtgtgtttgt tgccaacggt acttatcttt tgcagacaaa                         2500
```

```
<210> SEQ ID NO 151
<211> LENGTH: 2844
<212> TYPE: DNA
<213> ORGANISM: Oryza sativa

<400> SEQUENCE: 151

acgatattct ttcatgtagt cctgcataga tgacaagaat gagcagtgtt agatttgtca     60

aagtgggggt gaagctgagc ccttgttcaa ccttggagag caccttgtct tctttgaaac    120

atgcatgaaa tcggattcgc ttggagcagg tggcaatgcc atttcaactc tgtgcacatg    180

tgtgaaagga caaagaaaat atcatttcaa tggtgattca tcctcgattg aacaaaagta    240

tcaaatcatt ttaaaacaga aaacacccat gtagccacta agatatgcaa acatcaacag    300

aaaaaaaaaa tccaaatcat ctgcatctat gactcagctg catctgccaa ctttgtcacc    360

acgcactgcc ctctatgaca aagaggataa caattgacaa gcaaagcgtg cccggaacta    420

gaagctagca accgagtgat gcggatttct ctgattttgt ttacacttca gttcacccaa    480

aaaaaatcct actagttgaa tggagatttc tctgttttaa gacagtgtgt acttgttaac    540

ggcaaaattg cttgctccaa gcaatacttg ttacagctag aagcatttca agcgatctat    600

tccaattcga acattttgct gcaaatatca tatcaagtat catatgattc agcacataca    660

cacatccctc acctctgcta caaacacccc cagtgaatga acaaaaacac acagaaaaaa    720

gagagagagt attagcttac tttgatttca atttggatgt gatatgatga gccccatcca    780

aagattagtg attcaacaaa ccctagaaaa tgcaaaaatg aagagatgtt aaatcaaaat    840

caggaaatcg atgaaaaaag aggaatgaga gaaaggggta tcgtgcgcac cggctctgcc    900

gcagatgcca ccggctccgc cgcagacacc gccgccacag ccgccaccac cacgctcacg    960

ccactctccc tctctggcac aactgacctt gtgcgcatcg gcgccgctga agaggaggag   1020

ccgcaagaag gctccgccgc cggcgactcc gccgccgcag ccatgctcgt gacgatttgg   1080

gagctgcagg tgtctgtttg ggagtgactc aatgtttctc gagtgtgtgt atctgatccg   1140

tgagggtgtg tgtttgatcc gtgggaaatt gtcctgtccg ggaccgactc gaaacagtat   1200

accggtgact agcatttctg ttataaaaat aaggaaaaaa gaacgagaaa aagaccattt   1260

aacgagcggt gtaaatatgg cccctgcacc gaaggcccat tcgatatgtg ggcctaattc   1320

ccacccgtcc gttaatgggc cgggaaatct cggcccattt aacctagccc taaagctagg   1380

gtttcctctc gccgccgcac tataaacgcg ctctcctcct cactcctcct cccctcgaga   1440

aaccaaagct ccagcaatcg gcggcggcgg cggcggcccg tgagaggcgg tccggcgacg   1500

caggtgcgta gctcctcctc ctcctcctct ccctctctct cgtccaagaa cggcgggcct   1560

tacctgttgt gttcttcgtc gtcgtcttgg ttggtgctag tgcgatttga cgcagcgaga   1620

gaatgttctc cttttatttt ccctcttctc ttgcttatgt gtcttagttg attagcgagt   1680

gtcggttagg tgattaggcg atggctggtt cggttggcga gatgatctgg atcaagattt   1740

gcctcgatgc gttctgttcc cgtagctttg ttcattttct cgtttccact gcgttggatc   1800
```

cgtatctatg ccgattagtt cgtgctgatt tcgactgact gcgcattctg tagttgaaac 1860
ttgtgtgtgg tccggattta atttcgagat atgtagtaga ttatttgggg gttctaacta 1920
gaatgctaat atgtgttgta tagtactgag gaatgaggac atgttttact ctggcatttg 1980
gtattatgta gctcgaaaat gtttatttct gttatggtac aaaatttgat aatttaccgg 2040
ttttaaggac tggaaatatg atattcatta actagagttt tttgttctca aatactctgt 2100
ttgatcactc attttggtgg aatggagtta tgcataagct tgtgaatttt tttatgaaaa 2160
tgaataatgg cgcttaatat agaggactat atacttgtaa tgcactaact gtatgtttgt 2220
ccatagagtg atccatcgag aactatattt gttaattttt tttaaaattt ctgtgtaagt 2280
tgtagtatac taattgcatt ctatatgtat attttcttaa atatattata tgatagtccc 2340
tgataagatc tttcaagtat tgtcgcttta ggtcatgaat tccattttac agcaggacaa 2400
ataatttagg tatgtatgat atgggcaacc agggataaca cagcaaaact aaatctggca 2460
tgtaagctat tcttgggtta atcagacaca atgttatgaa ttgtttttta aatccttgtc 2520
aaacatggtt gtatatctga agctcttagt atttactgta cacaagatcc ctactactat 2580
ttgtcttgaa tatccatact attattgggc gtaatctcaa caactactgt agttttcttt 2640
atttgtattg ttgcattgtc tttccgggtt gtgtgtgcag tttctttctt gctttgtata 2700
tttttggggt caggatataa ggaatttggg actgtagggc ttctttctat gttattgttt 2760
ggttcctcat gaacaactat gctatctgca gtggtttctt tctctgtcat gtgttgtgaa 2820
caaatttatt acttcattgc aggt 2844

<210> SEQ ID NO 152
<211> LENGTH: 688
<212> TYPE: DNA
<213> ORGANISM: Oryza sativa

<400> SEQUENCE: 152
tggctaacct caaacagaca gaaacttttg ccttttacgc tctacaattt gtgcagtata 60
atgaattaat gccacgatcg catacgaaca cgggacactt tccttacaat cgaaggcagc 120
aaaagatgcg aaacttctct tccgagccga acacatgctc ctattcctgc acgagcaggc 180
acaagtgaac aacaactacc tgatacactg acatgtcggg cccacactct ctcaactcgg 240
cacggggccc cctccatctt ccgggaccca cctcatccga actctatgtc gcgtgggcca 300
cgggcctcgt gggacccaca tgtcatggac ctccggggac tcccgaaccg agcccaaccc 360
gtaggacggt aggaggtcga atcccaaacc ccttcggcaa gaaaggagct atttaaggta 420
gactaatccc ctcgtcttcc cccacaatca cttctccccc cggaatatct ccgccaagag 480
aagagaagag acacccaaca acccaaaacc tagcgcctct gcgctcgagg cccccccgaa 540
tccgcgaatc cgccgactcc caggtaagtt tccccccttc ctgatctagc cttttcgatc 600
tggtagatta tcgaattttt gcgatttttt tgcgattttt ttgggtgatt ttaatgttcg 660
tggggtggtg gtggtgttgt gagcaggt 688

<210> SEQ ID NO 153
<211> LENGTH: 1431
<212> TYPE: DNA
<213> ORGANISM: Oryza sativa

<400> SEQUENCE: 153
ttttatattt ttttaaaaaa aattatttat ccattatata ctgcaagaat ttttttttg 60

-continued

```
ctgtttttaa tgtaactttt ttcgagaaca tacctcattt ctaatgtaaa ttatcttttg    120

cgtaagtaat ttctctctca taaaaaactc aaaaatattt tttttaaaaa agtgaaaact    180

tgaaatttat atataaactt tcatgttggg taagtaagct acataaacaa ttcatatttt    240

taaaccctta gatgaataaa ttaattgtta accttatatg tattttgagt attttttaaa    300

actaggacct gagtaaatat ttttcttgag ttttaggtta taagacttca cattcatata    360

tgtctagatc tattaacaca tatataaata tggacaatgc taaaaaataa gaataggagg    420

tggtattatt ttttttttgg tagagagggg agggggccgc ataggaggca ggaggtagta    480

aaatgggctg atgggcatag tattcacggg ggcccatgta atagttgggt tgggcttgaa    540

cacacttgta ttgtaacaat agcctcggtc gaggtgaggt ggaagaagca aagcaatctc    600

cgtgagcggt gcaggtcagt cccctcccca tctcatctcc ctcttccccc agatttagat    660

ccacatctct ctctccctct cttcactttg ttaacctatt attgctctat ccgcctttcc    720

ttattgatta attcgcatag gtcaaaaaca acgggaattc ctactgttag ctagacttga    780

tagatagccg cgagcccatg tttccctttc tctgtgtaat aatgtcaagc tgactcactt    840

gttgataaca caaattatca cgctactatt gtgcatatat actactccta catgacatga    900

catgattgat agtcacatac acacacatca atcgctaatc catttctcca tctatctaac    960

cacactgcta ttttagggaa ggggaaccgg aatcctcatt atgggggtgt ttacatccag   1020

ggttgtaaag ttttggcgtt tccgggtatt atatagggtg tcgcattggg tgttcggcac   1080

taataaaaaa actaattaca gtaaaccgcg agacgaattt attaagccta attaatccat   1140

cattaccata tgtttactgt agcaccacat tgtcaaatct tagagcaatt aggcttaaaa   1200

gatttcgtct cgcaaagtag tcgcaatctg tgcaattggt tatttttta gcctatattt   1260

aatacttcat acaggtgttc aaacgttcga tgtgataggg tgtaaaattt tagggtggga   1320

tctaaacagg ccctatattc ttcactgcca gtgccatcaa ccattcatct tctattcttc   1380

tatcatgttg tttactactc tctctctctc tctctctcat tttttacagg t             1431
```

<210> SEQ ID NO 154
<211> LENGTH: 700
<212> TYPE: DNA
<213> ORGANISM: Oryza sativa

<400> SEQUENCE: 154

```
taggttttat caatagtcta tgtttaatat ttttaattag tgtcaaacat ctggttggac     60

tgaaaagtcc catccaaaca gccccatctt atccgataac tacaagcaaa ccgtacacga    120

tttacacatt aaacacaccc tctctctctc tctctctctc tctccatagg agcacttcaa    180

tatctctatc gccaggaaac ttccacccga attattatat ccctcgccca cagaaaatcc    240

cgcccaagca tcaccacact ccccattggc cccacccccc atgtgaaaaa gggacccaaa    300

ccgaccagtc accaactcac catccacccc caccccaacc caccccaccc acacgccaac    360

ccggccccac acgtcagcca ctcccactga caacccggcc ccaccacccc acccgctcgt    420

actcctcccc tctcgcctat taaacgcgct ccccctccac caccgcgcag ccaagccaaa    480

caagaaaccc accgtttctc tctcaaaacc gcgggaatca atcaatcgcc gttcgcgtcg    540

cgccacgaga tattttcccc caagaaaagg tagtagtaat cttcgacgat cttgatcgat    600

cgccatgagc tagctagcta gcgaatttct tgttgtttct tttttgggtt attgatggcg    660

ttgttgttct tgttcttgtt tgttgcagtt ggagtgaggg                          700
```

<210> SEQ ID NO 155
<211> LENGTH: 1582
<212> TYPE: DNA
<213> ORGANISM: Oryza sativa

<400> SEQUENCE: 155
tattctgtga atcatatgga caacaatgta aaatctcata gtaattctta tttaggttgt 60
ttgcagaaag ttaatttggg tcaactgaaa tgaaagcttg tctgttggct ctctcactga 120
attgacccca ttgtaattaa tgcatataat tggcctatat attacacttt caatatcgta 180
aaaccttttt ctttgtacac ttcacctagt tgatctagta tctgccgggc tcatcgggct 240
tatcttgtca atgaacagta ataagagcta tgtcgggctg tttgctgtgt gcttctgttc 300
aaccaatttc gacacagtgt actttgcgaa attgggaatt gagatgcttg gtgtgaaaat 360
tggctgtgct atcatgatga tggcccatga gcccacgaaa cctcacgact cttaattcat 420
ttacttgttt ccggttaaga gaaattgttt cagatattta caatgttttt gaaatataag 480
tttaatccgt ctcaaaggtt gttttaataa ctatttttc tctgtagaaa ttctgataaa 540
attataatat tatgaaactt tttttaggaa agttctatgc atataattgt catgaattta 600
atagaaatgt ttatagtgaa attaatgtcc taagattcaa acttttctct tacaaatata 660
ctccatgcta tgtttttacc aaaagatcaa tgaggtatta gcatatagta accggctcac 720
aggcgctcgt gtccgtcagg gcgctctaaa cctccatcgc acagtttcta tccgatcacc 780
ttcaccctcc gtctccagta gtaggatcca atctttccca agtttttttt atctttattt 840
aagttcctat agaattaggt ctattaggtt gtctagggtt tgtctttcaa atttttcatg 900
gatcagatgt gtagtctttt gtttcttcta tttatttatt ctagttacct tattgaggtt 960
ctcggtgaaa aactagtaag atttgtatgt cgggttgtcg atgatcaagc cagtgacacg 1020
ctttaaggct tgagtcgcta actttttcgt ggtgatggtt agttgttttg ttgtaggaat 1080
agagatggta gcatatactt tcatattcaa tgcttttgta tgtgctggaa tttgtcaatg 1140
gtgttggctt cacatttgct aatgtatagg aatttcaaga cgtggaatct ctttgggctg 1200
tgttgccaga tcaaaacagg cccaaaaagt tttagagtta gacaaatata taatacgttt 1260
attctgtgtt gaaaatatta ttatattttt ttataaactt aattaaactt aaaaatgttt 1320
gattataaaa aaaattaaag tgattgtaat atgaagagag caagtaaata taaatgaagt 1380
gaggtccaca cacgttgacg aggcaacgag atacggcacc aataccaatc tctgactcct 1440
ccggcctccg gcggccggcg agagagatcc caccctcacc gacgacggcg agcgaccacc 1500
aggtaagctc ccaatcttcc ccttcacttt ctcggggcca gatctgatct gagatgaggt 1560
tgacacacga cgcatgcaag gt 1582

<210> SEQ ID NO 156
<211> LENGTH: 2408
<212> TYPE: DNA
<213> ORGANISM: Oryza sativa

<400> SEQUENCE: 156
agattaatga ttacagtggt actattttga taaattattt tgttcccagt ttatatgaat 60
tttaaaattt tagatcacaa ttttacatat aaactacaaa tctatggtgg atctgagatc 120
tgtagttatg ccaaagaata cctcatattg ctgatccttt ctcgtatgct ttctaatgga 180
gctagtatct gcagctgtat tatcagaaat acatttaaat gagatatgtt ttgtatgacc 240
cagttgacgg cctcacaaac cctaaacagg agggaaccaa gcctgagctc taggcttggc 300

-continued

```
tcctaaatcc cattcaaata ttcttaaaaa aatcacatat ttcttttttt taaaaaaaat    360
agtaggatga ttaggccgaa tatgtcagtt gagccttagg cgtggagaat tttaatttgg    420
ctctgtcacc accatcagga attgaagcag ggaaatgaga gctataaccg ttgaataacc    480
tctcaaaaaa tccctgaatt ttagctgcat gagcagctta aatgtgggat caatattcat    540
taagctcaag ttactaactt gaaaaatata cagcatgtgt gtgttgtttt gaactctaaa    600
aatacctaga cggagttatg cattattgaa aacataacat atgaatgcaa acttatacta    660
gaaaaaccca tgaattctaa ccttagtggt ttttcaccaa tatttctaat aaggggtcaa    720
cctttggaag atgagaactc taccatttga acacatgaat agtgaaaaat caaactatta    780
aagcttgacg ggctagggcc ataactgagc attgccacgt cagattattg tacaattata    840
ctactctagc agtacataca ctcttggctg tgtactgttg tacgaaacgg agagtccaaa    900
gtagtagact gtccatatag ttcagtttga tggatttcac ccggagatac accgtacgat    960
ttaattgtaa taatacatag aaccatttgt tttttttttg aactgaagaa ccatttgttt   1020
ttcatttact tttactttaa aacatggaca atgaatttgt ttttgaacag ggcttgaaac   1080
tcttaactcc gagcaaatga aaattcaaac agcagtggat tcaatattca actcgaaacc   1140
cctccttttt ttcaactaaa aagtccgcaa aacttcccaa taattaaacc gtgaaatttc   1200
agcgagacct gtatttaaaa atatgggcca aattcaaaat ccaaagcaat aaacaactgg   1260
gctacacaca acatgcgacg gcccatctca tcaagcaaca aggcccagcc cactcgacac   1320
ccaccgaatc cacgccgctc aatcgaaacc gacggtccag atctcgccgc gccaacccca   1380
tcacacaaac cctagcaacc ccccacctat ataacctctc tccctcacgc cccgcctcca   1440
ttcgcacgcc cgcgccacca caaaacccta gccgccgccg ccgccgccgc cgccgccgcc   1500
aggtataact tactctcctc tcaattttgt tgattcagtt attataaaat gatgactagg   1560
ttgtagaata atccgattag ctatgtagat ctatagttga ctctcatggt aacaagaaca   1620
accatttgga tgcttgtcta atgtgttagc tggtactgct ttggatgatc tatttgttta   1680
gatgacattc tagtttactt agttagcctg cacttgctgt ttgtgctgct atgttgcttc   1740
atgggctgtt aatttgttag tattgctcgg aattgatact acctggtgtt aattcttgct   1800
gttattaggt acattcgttt ctatattcat gcttctaatg tgccattttc tccatgttta   1860
gttgagtagt attttgttct atgatctctc tggtaagcca aggttgtatt acttgttata   1920
agttattgac ctcattgttg tagctcagtg tctgtcttat ttctacattg tgttcctaga   1980
agcctttgaa tgtgttaatt gattcatgat aacatacagt tgtgcaaggt catttagtta   2040
tttttcttaa attatgtctc tatgcattca agtttaggtt tcatgtaatg ttaatattct   2100
agattggctc cttgtccttg gtgaaatggt ggctgagttc ttggcattag aaggtcattt   2160
atttggctgt gttttatatt tatcatagca tgtgtggttt gttgttgact tgtcgtagct   2220
gtttatttac actgatctta ggttctacta tcattttttg tctggtttat tctgccattg   2280
atatttcatt tgctgtattg cccttagtgt ttttagtggg atacttgttt agtcctcaac   2340
catttggaga cttcaatctc ttggtgcctt ttgttctaac tgaaaattcc tgttgattca   2400
ttgtaggt                                                             2408
```

<210> SEQ ID NO 157
<211> LENGTH: 2458
<212> TYPE: DNA
<213> ORGANISM: Oryza sativa

<400> SEQUENCE: 157

-continued

```
cattttattt ttatagatat tgttggttaa agtagcatct cgaagactgt gtcaaagtct     60
aaaatactta tattttagga cggagggagt atatttcagc actatcgaac tttggcgttg    120
agaaactgtc catctctaca aatagtagtt tttgacatgg tctattttaa aaatatattt    180
ttaaaagaat taatttatca aattttcggg agacaacgag gccaagaaga agatgcgaaa    240
ccaccgggcc caactcagag agaactacaa aggacaggcc cagcccaacc cacgacaaag    300
atccaaccgt ccaatctaaa ccgacggctc agatctcacc taattccaaa cccaaaccct    360
agccactacg cccctagaca gatataagct cgtctccttc tctcgccgcc ctctccttcc    420
ctcgccgccg cccgagccac tacactatcc acctcgccgc cgccgccgcc gccggaaatg    480
gccgccgccg cgcgcccct ggtgtccgtg aaggccctgg agggcgacat ggcgacggac    540
tcggccggca tccagatgcc gcaggtgctc cgcgcgccga tccgccccga cgtggtcacc    600
ttcacccaca agctcctctc ctgcaaccgc cgccagccgt acgccgtgtc gcgccgcgcg    660
gggcaccaga cctccgcgga gtcgtggggc acgggccgcg ccgtgtcccg catcccgcgc    720
gtccccggcg gcggcacgca ccgcgcgggg cagggcgcgt tcggcaacat gtgccgcggc    780
gggcgcatgt tcgcgcccac caagatctgg cgccgctggc accgccgcgt caacatccgc    840
ctccgccgca tagccgtcgc gtccgcgctc gccgccaccg ccgtcccgtc cctcgtcctc    900
gcccgcggcc accgcatcga gggcgtcccc gagttcccgc tcgtcgtctc ggactccatc    960
gagtccatcg agaagactgc gcagtccatc aaggtcctca agcagattgg tgcctacgct   1020
gatgccgaga agaccaagga ttcggtggcc atccgcgctg gcaaggggaa gatgcgcaac   1080
cgccggtaca tcaatcgcaa gggccccctc atcgtctacg gcaccgaggg ttccaaggtc   1140
gtcaaggctt tccgcaacct ccccggcgtt gatgttgcca atgtggagcg cctcaacctg   1200
ctcgaccttg cccctggtgg ccaccttggc cgcttcgtga tctggaccga gtgcgcgttc   1260
aagaagctcg acgaggtgta tggtggcttc gacacaccgg cgctgaagaa gaagggcttc   1320
gtgctcccga ggccgaagat ggcgaatgcc gacctgtcca ggctgatcaa ctccgatgag   1380
gtccagtcgg tggtgaagcc catcaacaag gaggtgaagc tcagggaggc gagaaggaac   1440
cctctgaaga atgtggccgc tgtgctcaag ctgaacccct acttcggcac tgcgcgcaag   1500
caggtatgat catccattcc tatgctagtt gtcttatatt cgtaaatcat aatattatca   1560
catcacagct ttttatgatt tgtatgtgat taattgtata gtttttgtgt gatcatatat   1620
gctataatgt gttagctata tcaataatga ctatccatct ttgttcatgc attgtttctt   1680
ttacttggta tgtcgaccct ttcgatttcc gcagtattat tatattatat atagggtata   1740
atgctttggt gttgcatcat agcaatggtg agatggtggt tgtagtcaat tgtgtcctac   1800
tgcagtagtt tcataccgtc tttcattaaa tgcgttgcgc caaattgctt cgattgatag   1860
ttttatgctg cattttgtga atggttcaag ctgattattt cattaagttg taacttgctt   1920
tagttccgtg agggacgtgt atgatactac gacgattgtt tcttagattc atatatttgt   1980
aacatattat tgtgatgctt tactcaaatt tatcgcgttc attttcttat gtgacaaatg   2040
tgtttatctt tggttaagtg attttcttgt tcagcttagt ttatgtcatg gtgctatttt   2100
gtataatgtt acacattgtt gtttattggt tacattaggt ctaatttgta gttatttttc   2160
ttcatatttg tttagtatga cgttttcatt gattctggtt tgtcgtccca ttttgtgtat   2220
ggttttggtt tgttcagcca tgttgtattc atttttgtgt ttagtcctgt catgttgata   2280
ttcatgtatg gaggttggtg gtttcaatca acttggctgt aatgctagtt cctttgtttc   2340
```

-continued ttgtgcttat tatgtcatgc tttatgtcct tctattgcct ggactgttaa tacttggttg 2400
ttaatattac ttatcttatt ggaatctcac ttttacttta tatactaatc ttgtaggt 2458

<210> SEQ ID NO 158
<211> LENGTH: 1399
<212> TYPE: DNA
<213> ORGANISM: Oryza sativa

<400> SEQUENCE: 158
aggtttcgtt tgttggttgt tgacaattcc ttaaattctt tagcatcttc tgtactcgct 60
gaagctctgt tagaacaacg ttgcagaggc taatcatatg cttgtgttcg ttcttacttg 120
atgctagttg tatgatatga ttcagctgta ttactggccc tgtttgggtg agcttaattt 180
agagaaactg gaatatgttt ctagattcta attctatatc tatagtaact atacatatca 240
gaatatgtat gaaaaattag actatgtaag aagggtgtgt tcacactaaa attggaagtt 300
tggttaaaat tggaacgatg tgatggaaaa attggaagtt tgtgtgtgta agagttttga 360
tgtgatgaaa aagttgaaag tttgaagaaa aattttggaa ctaaactcgg ccgaagtttt 420
ttgtttagag catcaccaat gtatatggca aagtgatcta tatagatggg acccacataa 480
atagtttatc cctatgataa tgtccacaat gtatagatac aaggtatcat taggagaagg 540
agaagagaga ggagtagaga tagataatat aatttatttc atatgggtag tccatatgta 600
tatgggtatt ttttgctatt ttttttatat ggactagttg cacaatgata ataggtggct 660
gaatggaata ttctattgtt tatagactac ttttatattg tggatgccct taggaaaagc 720
taaaccccta tcggcgcctt tctatgcctc tctatcacct tttggtcatt cggttcatcg 780
cggatcgacg agaaaccagg ttggcccgaa tcaatcggcg ccggcggcct ccgcggtttc 840
cgccttcggg taggcgcctg cggcatcaac aaagcacaca gccgaaaccg aagccttttc 900
tttcttccgc cccaagaagc tgtgccacgt gtttcctcct tcccctcctc gatttaaccg 960
ccccatctcg agtcccccca tcacagcttc cactccacga aaccctctg cctccttcgc 1020 tcgctgcacc ctcgtctcgg cgatccatcc ttggctgcca ggaagttctt cgtcggcggc 1080
aactggaaca ggtaagtatt ccccccagca ctagtcgtct cacaatccag attccggatg 1140
agccggagac gctgctgatg agtgatgagg cttgggtttt atcgatgcgc tgcgctgttg 1200
ctgcgtgcag aatgggacag gggaggacgt gaagaagatc gtcaccgtcc tcaacgaggc 1260
cgaggtgccc tccgaggacg tcgtcggtga gccgtcgtcc cctcccgagg gcgttgtttg 1320
gagttggatc gattcatgaa tcgatctggt gctgatctgt gggtttgttt atttatttta 1380
attttttttg ggtgcaggt 1399

<210> SEQ ID NO 159
<211> LENGTH: 2345
<212> TYPE: DNA
<213> ORGANISM: Oryza sativa

<400> SEQUENCE: 159
cgctcgcggc gactcacccg gttgcatcgt tcgcccatgc tgtgccactc cacgcttgcc 60
cacgcagctc cttgcccgct gttcgcccat tcacaccgct ccttgcccgt cagttgccag 120
tcggccgcct atctacatca tgccgctcct cgtcccaacc acgccactca ccagccctcc 180
tccagcagct acttgcctcc ttcatctgcc agattccgcc gctacgccca ccacctggtt 240
gctgtcgagc tctagtgctc taccacgtcg tcggaactgg acgtggactg acggtagctg 300
caaaagtttc acatcccatc ccaccctcat tccttccact aaaaagaaaa aaaattgaat 360

```
catcccatcc tataaatcaa acagttgagt gagatcgtac catccctaga atcaaggaca    420
agttcaacct atcacatctc gcttctaaac caaacacaca ctgacagaac agagggccct    480
gaggattcgg ctcctctgcc tttaggggct aaagactgag gcgcatagca aaatgagttt    540
gccgctacaa tataaaatat taattttgca gttatttact gtagatacag tataaaaagt    600
aaaacgtatt gtgccaaggt actgttcatg atgtattgta ttatatgtag caattaatca    660
cattcgttcg ctataaatcc gatggttgag aataatttaa aaccctaagg gcttgttcgg    720
aatagaggga ttacacagga ttcttgtagg attggcaatt cctttggatt tggcactgtt    780
tatgcattcg gttcatagga accatgcgta ggaatttcgt agaaatactg tagcaacctt    840
gtgaaaacat aggaatttca taagattcta aacatccact cacacctcat tttttcatt     900
agctatcatg ggatagatgc taatcacgtt gaagtgacta gatgggaact aatattttat    960
tgcttaatta tactataata tactacctca atgcatgaat gtatgacgtt ggttagttca   1020
attttgagct aaccaacgtc aaacaaaaaa atatggaggg agtatgagat taatactaat   1080
tgaaaaattc atgtggttta tatattcttg tgttccgaat gcttcatagc atcaaattcc   1140
ttttcctatc ctgcgatccg aacaagccct aaattctgag gatcccaatc cgggccatga   1200
ccgcctccta tcatcggacg gctatagtgg tccaaagctg acgtggccaa gactggccca   1260
catggcccat gtagtccgtc ctggaccgag tccacggacg gcgcggccga acgcccgcgc   1320
cgtgtctgct tttgttgctt cgttctctcc gcgctccgtg tccgaccttc ttcagacttc   1380
acacctcgcg cgccgccgca gctccgatcg gaagaagctc gattcgtctc cgactccgac   1440
gaccagaagc taccggcgac gcgagcggag aagcgcggag gggagggggc gcgcgccgcc   1500
aggtgagaac ccccacctcc cctctccttc ccccccgctt ccgatcggaa ctcgctcgtg   1560
attagcctcg ctatctccgc tgatatctac ggggggagcc tttgcctctt gtctggtgcc   1620
gtgattgctt tggttctgct ataccattgg tggtgggatg gattaggctg ctctacgtac   1680
tggatctaaa atttgtaggt gtttggagga agaaggggag tcgtcctgag tagaacgtgc   1740
ggctgaaatt agctaaatgg tcctgttttg tgggaacaga gttcaacaca tttgatgtgc   1800
tgaaagctgc tctacttggc ctttctgaaa ttctaggtgt tacaaggaat agtggtagtc   1860
atccttaggc gtagaaagtg tgctgaaatt agttaaatag ccatcttctt gggaggacaa   1920
aatgttcaac cttagatgcg cggaatagtc ggttttaaag ggtaaatcta aaataactgt   1980
tttagtgcat tgtcattggt aaaaaagaaa agattattca tgtgaagaat atagtaaaaa   2040
aataaagaat aaaattgaac ccacagcatc gcttagttac aagttccaag gtgaactgta   2100
tcagtaaaca catatgccaa tttcagaact tatcatctac aatgttcaag tgggctgaaa   2160
agtttttctg ttgacagtct ttctgcttca tttgaagttc tgtgctgaaa agttccatca   2220
tcgaacttaa gtaactttaa attgcatatt tagaaagtat accatacttt tggctagccc   2280
aatcatcctt tgcttacctc agattgtagt ggttatatat gactgtatgt gctttttact   2340
taggt                                                               2345
```

<210> SEQ ID NO 160
<211> LENGTH: 1168
<212> TYPE: DNA
<213> ORGANISM: Oryza sativa

<400> SEQUENCE: 160

```
agctcaggac tgactgacta cagacttaca gttacaactt cagaggatgt gaattattca     60
```

```
tttctcttgc gcactaacag ttagttcttc agtggttttg ggatgagatc ctaaaaatat    120

cacatcaact agattattaa gaacaaattg attaatattt atacatgctg aaaagcttaa    180

atttgttact actgcgggct tgtttggcac agctcacctc tcctggagct gaagctcagc    240

caaacagttt caactccacc taaaatgaga gcgaagttgg gtggaactct cttacaaaat    300

gaactagaga ggtggagctg gatttaggct gcttcacaac tacattctag acccgactcc    360

tagaactaaa tttaggagtt ggagctctgc caaacagccc tgctactact acatggttaa    420

ggggggtgtt taaatctagg ggtgtaaagt ttttttgttt cacatcgggt attatatagg    480

gtgtcgtatg gggtgttcag gcactaataa aaaaaaataa ttacagaatt tgtcagtaaa    540

ctacgagaca ttttttaagc ctaattaatc cgtcattagc aaatgtttac tgtagcacca    600

cattatcaaa tcatggagca attaggctta aaagattcgt ctcgcaaatt agtcgcaatc    660

tgtgcaatta gttatttttt taccctatat ttaatattcc atacagatat tcaaacatgg    720

tgaaaaattt tagggtggga tctaaacagg gcctaggaac aaaacgagca tcacatgctg    780

atctgccaag ctggctagcc ctaataattt ggaaatgcaa tattccaata tccaaagtgg    840

acccggccca attaacccaa ccaaaaccca cgcccacctc ctctcccctt ctcggctgct    900

cttctccccc tccctatcct ctcctctcac ctcgcaatca catcctcttc ccttctcttc    960

tccatcgcat ctaccaccga gcgtgcaagg aggggggggg ggggggggggg gtgaaacagg   1020

taacctcttg gttcccctct cttagtatcg tggattcgtg gtggtagatt tgctagtgtg   1080

ctagagttgg atgtatggtt gctgtttctt ggagtgttct tggtttgatc tggagtgggg   1140

gatccccggt gtggtggtgg gtgcaggt                                       1168


<210> SEQ ID NO 161
<211> LENGTH: 1500
<212> TYPE: DNA
<213> ORGANISM: Oryza sativa

<400> SEQUENCE: 161

ttaatttgaa atactctgaa atattaaaat acgcaatgta ccgggcggac gactggtatt     60

attactgatc ttgctcaaaa tggtcatcgt aatttcagaa cgaactgatc gttcaaacgt    120

tcctcatgtt gcgcgtgtgc tgcaactact gcacggtaaa agtgatagga atcggtcgga    180

aacagtatta atgtttttat tatttttaca aaaacgaatt gaaataattg gaaattttca    240

tatttatata ttaaactatt cagtatcaac ttcaattcga cgtcaataga aattagaaaa    300

gcataattat acacagtaat aggcgttcaa gatattattg ttattattta gttttgtgga    360

aatggtatca acgtgatcgg aaaattttgt acatgttttc accctgcggg atatctcaat    420

tccttctcct ccctctaccg ccatatcagc acacgtttta gagcaccaat cataacccat    480

aaatccgtgg gctactcact tatttaattt atatgtgaat tcgtgacctg actcactcac    540

atactatcaa aaatttgtct cagtcaccca tctccttctt tcctggtccg ataagggttt    600

atcctacggt tcgacggtta tcacgatagt cgtgcggtta ctgaggtata ccgtgattta    660

aaaatatgat aaagttaccg caggttttaa ctgcgcggtt tggtaaacct gttcctcctc    720

accaaccttc tcctccggtc tccttatgtg tctcaccgag gcgagccgcc gcgagaccgc    780

atggacgcgg tccacgcacc tggcggtgca cctcctcctc cccggcgaag aagacgtgga    840

ggagagtaaa tgagcaatca ggcccacggc ccaatcgccg tccaccaccc accaccctca    900

gcgacccaaa accacctcac caacccaact ctgtaccgta ctgtacccgc cctcccctcc    960

cactgacact ccgggcccac ctgtcggcgc gactcttcca cggtcccctt ctctcctcag   1020
```

```
agatttttc cacgcatttt ttaatttttt tttctgcagt tcacatgctc ttctcccact   1080
cttccgccgc gctatataaa ccgcgcgagg cgtcgttgcc tcgtcggcga agtcaatccg   1140
gcgatccccg gcgagcgaga gatcgaagca agctgctaca cagatctcac gacttggccg   1200
aggcggcgtc ggcggcggcg gcggcgacga cggagcaggc gattgggagc agcggcggcg   1260
agcagaagac gcggcactcg gaggtcggcc acaagagcct cctcaagagc gacgatctct   1320
accaggtaac ccgccgtctc cggccatccc ctcctcgccg gaaaacctcc gccgccgtgg   1380
ctgaccttgc ctgactggct gactcggtgc ttcgtttccg cagtacatcc tggagacgag   1440
cgtgtacccg cgcgagcacg agtgcttgaa ggagctccgc gaggtcaccg ccaaccaccc   1500
```

<210> SEQ ID NO 162
<211> LENGTH: 1633
<212> TYPE: DNA
<213> ORGANISM: Oryza sativa

<400> SEQUENCE: 162

```
taggcttgtg aaaagaatta caaaacttgc tttgcgcaaa agaactatag ccatcctttg     60
aattcccctg tcatgtgcat tattgctgtg gtggcttgct gagtacggtt ggtactcacc    120
cttgcaatat acaaatttaa tcagaggtcg gagatgaagc ttcggaggat ccctacgctt    180
actaacagga gggtgatgaa gacgatggcg cccagtaggt cttagttacg gtcattgcct    240
gtggcaatgg cgtgccgctg ccttaactcc gctgccttac cttcttctgt ttttggaatg    300
tattccggac cgctcggtcc gatgatttaa gactatgcct gcgggcttat gatgcaatga    360
ttcatactag acactcgtgt atgtgcactt gatatttcag ctaagaattc gtgtgtacca    420
gactacttga tccagggaaa tggtactgtt tacacgattg attcctgtta taaaaacggg    480
ggtccacata gatccgccac tgctccctcc tttccttcat atttagactt taataatttg    540
gattttcaca aatgttatct aaataattaa ataaatatca tgctatcgaa gtatattaca    600
taaacataag tattaaactt tctttcatta tgatttaaca aaattgctag aatgctagaa    660
aatttttgtc aaaactttca gatttgttat tattggatca ttttaagatg ggtgcattga    720
atagaaaaat aattgctaga aagaaatttc acataggcta cggataagat cccggtgcta    780
gtcaactaaa ctagtcttaa atacaggttt atatcagtta tactgtagct ataacatagc    840
cacggtataa attaatgtaa ttacaatgcg gttatagtgc agttacaatg taattacact    900
caattacatt atagttacat ttgaaagttt tccctcaaaa aacttgatag ttattttttt    960
aagatactct aacgatttaa tcatctcaaa atttttaata attaaagtta tagatgaacc   1020
ggtaacaatt attacctctg tttcaggtta atatgtcaaa gtcaaactac tttaagtttg   1080
actaaattat agaaaataaa cattttcaac ccatgttaga tttattataa aaatatattt   1140
aattattgat ttaataaaac taatttggta ttataaatat tactatagtt atctacaaac   1200
ttagtaaaat tgaaagtagt ttgattttaa ctaaagttaa aacttctaat aacctaaaat   1260
ggagggagca caccatattt tataccaaag tactgtcagc aattagctga tcggtagaga   1320
cgctgagtaa ctgcacgttc aggtcatcac gcgacctacc aatttaacaa aacgccgtgt   1380
cgtcttgttc ttcttcttat cttttttttt agtcattaat tgatctgcaa tactcttgta   1440
agaggtccag atagctagag aggccattga gagatcatca tcggagctag ctagctagcc   1500
aggtacgtat agactcgcgg atgtgtaagc gcgatgtacg tgtgcagtgg tgtgtgtttc   1560
atgttcgttt ttttggagga agagatcgaa aaaatgatgg agagatgcat atttgtgtgt   1620
```

```
gcactttgca ggt                                                    1633


<210> SEQ ID NO 163
<211> LENGTH: 1500
<212> TYPE: DNA
<213> ORGANISM: Oryza sativa

<400> SEQUENCE: 163

aataatggta gaatgaaaga cttaggtgga gattttaaca tatatatcca atgcatatgt     60

cacatagtta aactcttcca acgtatatgt aaattagaat aaaatcattt tacaaaaaca    120

tattaagttt taatatgaaa tggtgttgta taatttgcaa gttgaatata tgattttaaa    180

gtttagggtg ctagataaac cttgaatcaa actttgaagg gttatttata taaaaaaata    240

tggtagtatt tttaacccaa aacaaacata ttatcaaaat atattcaata ttagattcta    300

atattttcga tgttgctgaa tttttctaaa aaggttaaac ttaacagaat ttgactagaa    360

aaaaatcaaa cggctattaa taatagcgaa gtgagtaata ttttttttca tatggtacaa    420

cgaagttaat atattttttc ctaacaaaaa atagtacatt acaactattc taatgaaata    480

gttgacgtta tgatacctag gtacagggta tgatgtctgg taccctaaca ctaaatctga    540

tacatacgat accataggta tgtcagcatg atatatatgt actttaggta ctaaagagta    600

tcatgtctca taccatagta ccagatccat gaactatata tggtaccaca cgtatcaaat    660

ctagtaccac ctacaatacc gtgctaacgt tagcacataa ttactctgtt ctataatgta    720

ctccctccgg ttctataata attgacgttt tggacaaggt tgagatcaaa cttttataac    780

tttgaccatt aataacttca aaagtattta gttttaaaaa actagaacaa atgaatcttt    840

gtggaagaag aagcggttcg ccagccgcta cattcaggga aacatatata gatttgtctt    900

tcaaaacact ataataaaag ttaacatgca tttatttatt gtgtatatta taatagaaaa    960

ataaggtcaa aggtatattt tgtagaccgt gtcattgtcc aaaacgtcaa ttaaaatgaa   1020

attggaggga gtaagtattt ttagttgtgt agaaatatta agaaagtaga taaaagtgat   1080

tagagaatgt tgattagaga atgtttgtga ttggcggaga agaaaaaata gatgaagaaa   1140

ttggttttga ttgtttgaga gaagtgggta gataaagaat aaaacttaat tttggaacaa   1200

gctagtgagc taaaaatagc tagtacattg taaaacagag gtagttcaaa ctattccgtt   1260

ggaacggcgt aacaacaatt aacccaattt tcctagtagt aataaatata aatataaaac   1320

caattcagag aaattcaggg aagaaaacgc gtcggctctc gaaccttctt gcattgtgtc   1380

gtcgaaggcg gttggaccat tcggcggccg caccctcgat ccaaaatccc caattcgcct   1440

tccacgaaac cctaacccta gttctccgtc tccggcgggc tctaccggcg gcgaggcaag   1500


<210> SEQ ID NO 164
<211> LENGTH: 1450
<212> TYPE: DNA
<213> ORGANISM: Oryza sativa

<400> SEQUENCE: 164

ggccgctgct tccatcgcgc tggatgcagt gcccaccatc accggccgct cgtcgccctg     60

cccttgaatg cccagcctaa cgccgttccc gccggagatg acgccgccgc cgccgccgtg    120

gggactcgcc gcggcggcgg gggatcgttt tttttttttg ttgttttttg tgtgcgtgtt    180

catttctttt ctcgaaaaaa atggcccatg aaagattcca gcccggccca ctaagaaact    240

actcctcgta aagtcgtaag gcccagatga cgcgagagcc cgatcggacg gtccagatag    300

acctgatcgc gctataagag gggcgcacca cgcactcgtc gcaaaaccct cagccgccgc    360
```

```
cgcccgagca gagaagccgc cttcgccgcc gccgccgcac tccaccgcgc gctctccgtc    420
tccggccgcc gccaggtgag gaggatctcc cttaccctac cctctctccc ctctcttcct    480
cgtgtgcgtg gctttacttt accccctgtg atcgatcgcg ctcgaggacg acgtcccttt    540
cgcgtgatct tggttcttgg tgtgggtctg atttgctgct gggttgaacc cttgtgattc    600
ctaccaactg gggtagacga tgagagtgag agtgcgtgcg ctctgtggta tttggatgga    660
actagaattc gggaagtgct tggtcatatc ctttttattc cgcatgaatt gttgctgtgt    720
taggctagtg aggcagattt gttaatttat ttttgaatct aggtatacaa cgtcgagtcc    780
tttcagtttg aaatgtctcg cagctagaac ctgagttttt tttgttgggt cgatgtgcag    840
tagaacgaag agaacttttt ttaacaaaaa atttggtagg tactaccatg ttagatggag    900
tagttgtagt tttagtgaag gttttttgtt actcatattg tttagaaacc agtaaggcag    960
ccatttcgtt tttcatcgtc agattggcag cttggtctgg tttttgctta gatatgttct   1020
tttctttgtt ggattcttaa tgctcaagaa cctgcagctt gatcagatcg ctgttttctg   1080
aagaagccca tgatagtagt tgcaattact tgatttgata acagttatga tgtaaaatgc   1140
ttatgattac cattaggcaa cttctttcag gccattcctc aaatgtgatc cttgattatt   1200
tgtgtgttgc atgtatatgt tatacactca tcacaaaaca gacatgcatt tgtgattgtt   1260
atttgtagtt aaggtgtttt gtctataatt atatctgtca tattgagctt agtgatcatc   1320
tatttttaga ccattttcta cctgtggaaa atacaatgga aaaacatttg gtagttgcac   1380
tgtctttagg tttgttgtta acaaaatatt taagtaatac aaatttcttc tcatattttg   1440
cagacaaggt                                                          1450
```

<210> SEQ ID NO 165
<211> LENGTH: 404
<212> TYPE: DNA
<213> ORGANISM: Oryza sativa

<400> SEQUENCE: 165

```
attacacctg ttttaatagt tgggggttaa gatatcggta tcgtggttca gggaaacaaa     60
tcagatccgg tcactagtta agggagtaaa agtaaactta ttcgtagtga agcccagaag    120
cgggagatca aggcccatct aggcccgaca cgagagagcc atataaaccc caccattctc    180
ccacccgcct cttccccacc tgccctcctc gcgaaaaccc taaccctcct cctcctccgc    240
cgccgccgct ctcccaaggt ggcggcgctg cccttccccc ttgttcttct tccttgcatc    300
tgcttccctc ccgttttgct tctaattgta tttctctttc gtttccgcag atccctcccg    360
tcgtcgtcgc tgtcggcccc tcgggtcttt ctagcgcagg agac                     404
```

<210> SEQ ID NO 166
<211> LENGTH: 1250
<212> TYPE: DNA
<213> ORGANISM: Oryza sativa

<400> SEQUENCE: 166

```
ctgttttgac tcctttttg gctgcccatc cacagtcgcc accagaaaat tcactgtgcc      60
caaatcaatg gaagcgccta ctagatccat ccatcttcgt gacagctccg agctttctcc    120
tggttatttt tctcccaaaa atacattcag aacacgatct caaatttaaa ctaatggagt    180
gctactgcat ttcttaatta taagtcgcag caccactcat taatcatttc catcacaggt    240
aaatcgtggt gagctggtgg ttgctactgt actactagta ctacctgtcg cagctttgta    300
```

gaagccgttt tcgctgaagc ttcttcttct tccctgggca aaataatttt aagcaggcgg 360
aataatattg ggataaacag ggtggacaaa agcgtgcgat ccctttcttt aaccaaacca 420
cgacgaaagc aggttaggtc gcggcaggtg gtggtggtag gaagaagaag aaagagaggg 480
gaaaaaaaac aaaaatttca catgcatcat gcatgaagta gtacatgtag tactgagtac 540
tgtaataatg ttcagtttac tggaccgtct caacgggaag accaaattaa cgcttataaa 600
ataccctttt tttgggcact gatcttggcc actacgtttg gtggctcaac aaccaggtca 660
ccgtgcgatc gatcgattgc taatttattt tttgaaaagg aagggaggaa aaaagaccgg 720
gtgtttggtg gcgccaccaa ccctgctctc gtgagccgat aaatattgct cgccggagct 780
ctcggttgac gacccaacca atcgactcgc accaccacca gcagctcaag cagcaacagc 840
tcaaacggag gaagatctca tcgccttgac gaccggcatt ggcgacgcac cggtgatcaa 900
gaacgcccac agcgacatcg acagcaccaa caagacgctg ctcaagagcg acgccctgta 960
caaggtacgt gctgctgatg attcttgatc agctcgccgg attgtgttta ggatgatctc 1020
tctgttttaa ttaatttgct gatggttgct gtgttcgtcg ccggtgaact tgcagtttgt 1080
cctggacacg acggtgctgc cacgggagcc ggagtgcttg cgcgatctgc gcctcatcac 1140
ggacaagcac cagtggtaag aaaccacgat ctctgctaat taatctgctt aattaagcta 1200
gatcttgggg ttgattaact aattagccca ttaattcttg caggggggttc 1250

<210> SEQ ID NO 167
<211> LENGTH: 1000
<212> TYPE: DNA
<213> ORGANISM: Oryza sativa

<400> SEQUENCE: 167
aacacggtca tcttatatag aactttcact aatattttga aaatgttcta gagccaatct 60
aaccatatca ttttttgatt aattaaaact tgaatcaaaa tatttaaaga gtgttagctg 120
cacgtatttt aaaacattta ttatttcttg agatagtata taatacattc gttcttttgt 180
gcgcgaacac gcaaaagatt acacatcaat atattagaag aaacgcgcaa aagattataa 240
agatcatgtg tgtgtgaggg agctgatcat tttcacggcg gaggtaaagt ggtacagtca 300
catgtacata cactcattgg accatatgtg catatctcac acatactgca cgtaaaatac 360
gtatggtgca tatgccaacg tgaaatagca tcaacggtac aggtagccac cagctacacg 420
taataattcc caatcaatta aacgagacga gtcattagca agcatcaaca ttcaacggta 480
ctcccaaaaa aaaaaaaaaa aacggtacta ccatcatatc gacctcccag ccgtctatgt 540
atgcgtgtac gtatgcacga tcgtacgaga ttttctacta tacatccttg cgtcagcgtc 600
aacaaagacg ggcgtatacg ttgcatcatc tatctatcta tattgtgcca cgaggaaatt 660
ggcaatagat cgggccatga aatgggccca atgacagact tagtaaggcc gtgcgttacc 720
tcgcaatgtg gcctggttag gccttgttcg gataaaccga aattccggcc catctactac 780
taaagttgaa gcccacaaaa atgaccgggc cgaaattgag gcccataaaa acgagaccta 840
gttgaaggcc gaagcccaca gacgcttcca tccttccaac gaatccacgc cgtccattcg 900
ccatcgccgt cgggtatata aaccctccct ccgcggcatt ccaccctctc acccaccccc 960
aaaccctagc tccccccgcg ccgccgccgc cgccgccgcc 1000

<210> SEQ ID NO 168
<211> LENGTH: 2827
<212> TYPE: DNA
<213> ORGANISM: Oryza sativa -continued

<400> SEQUENCE: 168

```
ctattatcgg acaacttggc atattgaaat ttctactgtc atgcttcctt gtcccattac     60
tacatcgtcg ttgtgttcaa ctattgcact acctccctcc tagttcaaat ctaatatcat    120
atatgtaacc gcaatggaaa tagttgtatc atgttcaaat tgtactacta tttcttcatg    180
ttacataatt ctccttgttt aagtccatat aatgtttcta caaccgagac tgcgataggc    240
ctattaatta tccgagtact aatacgtcga ataagttaca aaataatacc ttccttaaca    300
tatgaaattg cgaaacaacc aacttcaata catttttata acaatattaa caagttttac    360
caataaatac ttctttattt attattaaca taaaatagaa aaatcgtttg gccgtacttt    420
ttgcatctgg gtcccttgcc gccctctact ggggcagcaa ggggcccaaa tgcaaaaagt    480
acgagcgcaa cctctttatg ggcggcaaaa attgcaatta gccccttgcc gccctctggg    540
ggtaattgca attttggccg acggcggcag acggcacggt cgacccgccg tctgccacgt    600
cagcttgccg cccaccactg ggcggcaggg gtctattttt gtattttttt tggccgatag    660
attatttctg taaatattaa aaaaaatcta aaaatgaaaa aaattcgtgc tacactgcta    720
ctgctccggt gctccctcat ctccttctcg attcttctgc tcctccaccg agagcggggc    780
gagcaggcga ggccacacga ttctcctctc ccttgccgct tccaacacca agtctcgccg    840
tggccaggac tgagctaggg tttgcgtgat cttcgggagg agggagcagg agagagttcg    900
aggaggagga ggaggaggag aagcaggtaa tttcaatttt tcagttcttg tttggccctt    960
cctttgatgc taggtaaggt tcttggttga tcaaatagtg ttgtggattg agaattgagg   1020
actaggtacg cttaattttg actaggaatc atgaattggg cggcctttat ttgggtatca   1080
aatgttccgc tttggccaat tgattaggat gattctttct ggtgttgtag tcattcgtgt   1140
cctcatcatt tgtcgaatag agggatatga tgaattctcg catgctgact gattactggc   1200
gacgtaatta ggaggattaa ttgtgcgctc ctgtaattct acattctttg gttccaatgt   1260
aagttgtggg tcaatcaact agacattgat gactggatat ttgctggtac tgttagctac   1320
aaaatgggtc tagattattt tatgatgttt catgtttgta atgacccctg gcaaattgtg   1380
ttgtattcat tggtgtcccc aatttcccct cttgttatct ttgtcaactg ttggttgggt   1440
tttagctttg tggctttaga aatttgtgag gatatgctca acaccgtgtg gtgccttccc   1500
cctcccagcc tgtatttaga gatttcacta attcagtcat ttagtgcatt ttccaatgca   1560
tagcatttgt ttcttgtttg aatgcattag aatatcgaga ttggcaggtt aattagggtg   1620
taatttgaga atctcttggg acctgagtta gtatagggtt gtcttggttt gttggctagt   1680
tatgattaat atgaatgaac atgtaagtat gtaaccatgt gccataaata tgatgtccag   1740
gaaaggaaaa tcctggtagc cggtacattc agtactggaa aaaaaaatct gatttgcaag   1800
ttttgctgtt cagttattgt acttacatta gctttttttat gttgcataag acagaggtgc   1860
aggctgaaaa ccatagaagc aagcatcctc ctattttatt atgttgtatc cttataattt   1920
caaatagttt catctgtttt tggtgttgtc ggttgtggcc agtcactcat acatcattat   1980
tttatcacat attcagttgt tcatgcattg cgagttgtct agttgttgat attggaaatt   2040
gtagctaaac gcactgtgga taaaatagtt tgattagtgg tgttattctt gtgttgatgg   2100
tcgcattatc cttcatattc ctgtgatgat gtttaaacct atagtttcca ttcctttggc   2160
atgtaatggg ttagcatcga tatgccaaag taacttgttg aactttgagc atggacacaa   2220
aaaaacctgg catataggcg tttaagaaat tgctttgtcc ttttctgtag cagcatgcta   2280
```

gtattgactg gatatagctg aatggttata tggatgaagc agttagcatt tgatcacatg 2340
tataatgatc acacctgagg cctgacaaat ctggttttcc actggctgca tcatagcttg 2400
tgttagttac tggagaaaga tctgaaaaaa cgaaccacac ttgttgctga ttttgttcaa 2460
cgaaagtgtt ctctatggac tgcggagcag aacaatttat acaaatgggc tagttggtga 2520
atgcttgaat tcaagtatgc cacattgaac aataaactgg agatgcactc ctacctgata 2580
ttgatatgta taagtatatg gactgtttgt tttgttcccc tatctagaat tattcacttt 2640
tatgcttcta ttgttgtagg aaaggctaaa tcaactttgg tatgcaagta tgataccagg 2700
gaaaccacaa accatttcac atgttactgt tagcatgttt tttttttttt tgctgagacg 2760
tgtgattata tgcttttgta tttgtttttt ttatctcaac taatatttgt tcaactgcaa 2820
tgcaggt 2827

<210> SEQ ID NO 169
<211> LENGTH: 2269
<212> TYPE: DNA
<213> ORGANISM: Oryza sativa

<400> SEQUENCE: 169
ttcgtaaaaa taaaaaacga agaacgaact cgaccaaact agcctctctc tctctctctt 60
aaaatctttc gatcatctca gttctggtct tattatagtt tgcttttcag tttctgttag 120
tttcccatct ttagaaagcc gaaaaatcaa ccttcttccc acatcgatcc ccatgttata 180
tcgtcttcac tgttgctttt aaaaaaaata tagaatgtga aaatgtctgg ttacgataaa 240
aaggaaaaca cccggatacg attattgaac catgtcgata ttagctagag agataacaac 300
tgagtagagc ataataaagc aattagatcg ccatatccaa caaaatatgg atggccatat 360
cctatccatg catgaccgtg aaccaaacac actctaagtt atgtatgtta tccaagaaga 420
caaaaaaaaa agatataaat atagctgaat gagagatact ccatccgtcc ctaaaatata 480
agagattttg gttggaagtg acacatccta gtccaacgaa tttggacatg cttctgtcca 540
gattcattgt aataagatat atcacatccc accaaaatct cttatattta gggacgtggg 600
gagtagttca taattataga gttagtggca catgatggga agcaagtgag agttgcatag 660
gatttgggca gacttggcag gttggcttcc gtcccataat atagcaatct aggatgggat 720
ggaatctatt ataggacaat gtatctagac atgactcgta atatagcaac ctaggatggg 780
atgagatcca tcctaggact agatatatta tgggacggag ggagtagttt atactttggg 840
taaaaacata aaccagtagg aaaaaagaag caattatttt tgcacatttt tctcttttac 900
gtgaataagt tttggtggtc gttcagaaag agaatttgaa tttccaaaag actgtataaa 960
ccgtgtagta taactgtaaa ccaattggcc accactactt ctgttggaca gaaaagcatg 1020
aagtacagta gtaccgtatt tgtacaacat acagatacag ggagggaggg cccacacacc 1080
agactagtct agtcgcatac ggatcggatc cacagactag ctggctagct gctacggttg 1140
ttggtgtgga gtacacagaa aagaaaaaaa aaaggaacca tgtggttggg gtcggtgaga 1200
caagcgccct tacccaccaa ccaaactgac tatgactggt gggcccttcg acctactccc 1260
actatacaac tctactgctc ctcaatcctc tcctcctcct cctcctcctc attcgcgatc 1320
tctctctctc tctttctttc gtcgttggat ccaaagctcc tcctcctcct cgcctcgcgc 1380
tcctcgtccc ttctctcgtc ccatctctca tctcatctct tggtagttgc cagttgggac 1440
ttgggagaga gaggagcagg aggcaggagc aagaggaggg caagatcgat caagatcaac 1500
aggtcttctc ccttttctct tctcttctct tttcttttga ttagtatgac acacggtctt 1560

```
gctgggaact tttagggaca aacttttcat cactgtgcgg atatggcttt ccagatagga   1620
taggatagca aacatccctc ataaattagc ctatcctgac cttaattttt gttgagaatc   1680
tcctactgca catttttttt cctgtaatgt tcctgaacat cttttcttaa ccagtcattt   1740
tcatggagcc tatataagaa tgtacctcac tagtcctggt ataaatattt tgtggtttaa   1800
tgcgagaaac tgttctttgt aatctaaatg tgcagctctt gtttcatctt ttattccata   1860
ggattcacaa ttctgttgat atgtcaaacg ctaaagaata atgcaagatc ttttacttca   1920
tagagccaag gaaaaatcag ttttgcttac ttctctattt ccagttcaat cagatgaaca   1980
agcctgttta aaatatgctc agaactttag ggagcttata tgttctcgtg tagtatatgt   2040
caagaagcta ttttgactct gtgaacatga tgttggctga tcaaaagata tgtatttttt   2100
caacaaactg ttctataagg gaggttgcta gggtcatttg ctcattttta tacactgaaa   2160
tgtgcttggt tattgttgct tttatattga cgaggcctta tatggtgaaa aaaaaatccc   2220
ctttacacaa atcaaactca tagaagtatt tgttttgcta cttgcaggt               2269
```

<210> SEQ ID NO 170
<211> LENGTH: 1578
<212> TYPE: DNA
<213> ORGANISM: Oryza sativa

<400> SEQUENCE: 170

```
tatgcttgtt cgtcagttgt gtttgtgtca aatgagcaag tttgtaactg tggacaggat     60
gacaagtggg aactcgatgg acaatgcatt tgctttggtg cggaggccca tcaaatgcag    120
cccagcccag ggaggtccct atcgagtagt aagtgagtag aagaaaagtc tgatctccac    180
ccacgggcgg agttgacata ctagtagtag tagtactagt acacgaggag aagaagcaag    240
aggaagggca tccagaatca gatccacaag gcagcagctg cagcagcatc gaccaggttt    300
cgctctcccg ccccaagcct ggcgtcgagc gcctcgccgt ctccctcgac ctctacaacc    360
agggatccgc gtaactactc tcctctcctc ctcctcctcc tcctccgatc tctcctctcc    420
tctcctcgtt gttgcaaggg aacttcactt gtctttttct tctcggatct gcatctgagg    480
atccgtcctc tatttctata gatagatcca gaccccttcc atgtcgtaat tgccaactaa    540
tcaaccatta ctctgctact gctttctttt ctacgcttaa aacaaacaag caattaacta    600
gaaagccaaa agattcactg catatgctag tatctttaaa ttgcatgggc ttgtgctcca    660
tctcatcatc tactgttatg tctttcttgc cagattatgt tatgctaata ggattctact    720
tgtaataaac cacacatggt ttagcctatt tacaatggtt tcactctctg ttatattcgc    780
cttattttgc tgaaattaca tactaggtga cttgccagct tattcaccct atgccttttt    840
tgttccctcc atatgttctt acaatgcctg ctatcaacat ttctctctct caagtccaaa    900
cttttccatg ctgcccaaag caccagcttt gcccaaaact aacaacttaa ctttcttccc    960
cgagaagtaa taacaatttc aagctaaagt tggtagttcg gacacaacaa cataactgac   1020
tctttttatg tacagaaata tggattattg ctaaatttta gcttggaatt atttactgga   1080
tcttggtgga aattctgtta aagattagct tagcagccca tggagaatga gaatgtttta   1140
aatattattt ttgccagtgt ttacctggac accaacacag gcctcaaact ctgccttgga   1200
ttcgcgtgtc tgattcggca gaaaagaatt gtacatgcaa cgggtgcccg aatcctactc   1260
agactcagga tgtcagactc gacaaaaaaa catctgccat tctgatatga tgtcaaaggg   1320
tgttctggtt tatctattct tttccctgaa agtgcattac ctatagacta cagttgcatt   1380
```

```
aaattgccaa aatctgccat tgtttttctt ttcctatttt ggattagttt actttctcta   1440

tgtgatatga tggcaagcaa ctatgtatat cacatagtaa taaactgacc gtaaaattta   1500

ttgcagaact gcctatgatg tgagcattaa tgatgatact tggccaaagg aggcatttga   1560

gcttgtctct ggagaggt                                                 1578


<210> SEQ ID NO 171
<211> LENGTH: 2592
<212> TYPE: DNA
<213> ORGANISM: Oryza sativa

<400> SEQUENCE: 171

gatctcaacc ctacgattaa atacgatcaa cggcgcggat tactttctac tgcaaataga     60

aagcattgga gtggggctct ttcttctttc gtttctattc atgtacagtt tagaaatgat    120

tttttaaatt tgaaatttta tttattgaaa tttaaaaaat aatttttggt ttcaaagttt    180

tacaaatcta cacccctaaa cctttctatg acgttacaac gcaccaatga atatgtgccc    240

gtcataaaaa aaaacctgtt tggaagagag agcgttaggg gtgtaaattt ataaaacttt    300

gagaaaaata ttttgtaaat attttaataa ataaaattaa aacttgaaaa aaaatcctga    360

aaaaaccggg gaactgtcta ctggagtaca gcccatcaaa gagacgaggc ccatagccca    420

tcggccacca caatccttct cgattcttct gctctccacc gagaggagca aggcgaactg    480

caggcggaga ggctgggcca cacgataccc tcctctccct tcccttccct tgccgcttcc    540

aactccaagt ctcgctgtga tcaggagcta gggtttgtgc gatcttcggg aggaggggaa    600

gcaggtaatt tctgttttgc agttcttgtt aggccctttc tttttgatg ctaggctctt    660

ggttgatcaa atcgtgctgt ggattgagaa acgcttcgtt cgtacttgga attgaggact    720

aggtacgctt aatttttgtc taggaatcat gaattgggcg ggctttattt gggtatcaag    780

tcgtgtacta atactctgat agcaacttct gttccgctat ttagttcagt ctgtgcttgc    840

atatgctgta gctctggccg attgattagg atgcttcttt ctggtattgt agtcattcgt    900

gtcctcatca tttgcagaat agagggatat gatgaactct cgcatgctga ctgattactg    960

gcgaggcaat taggaggatt aaatgcgcgc tcttgtaatt ctacattctt tggttccaat   1020

ataagctatg ggtcaatcaa ctagacattg atgagtggat atttgctggt actgttagtt   1080

acaaaatggg tttagattat tttatgatgt ttcatgtttg taatgacctc tggcaaattg   1140

tgttgtattc actggtgtcc ccaatttccc ctcttgttat cttttgtcaa ctattggtca   1200

ggttttagct ttgtggcttt agaaatttgt gaggatatgc tcaacaccgt gtgatgcctc   1260

ccccctccca gcctctattt agagatttcc taatccagta atttagtgca ttatccaatg   1320

cataccattt gtttcttgtt tgaatgcatt agaatatcga gattggcagg ttaattaggg   1380

tgtaatttga gaatctgttg ggacctgagt tagtataggg tattagggtt gtcttggttt   1440

gttggctagt tatgattaat atgaatggac atgtaagtat gtaaccatgt gccataaata   1500

taatatccag gaaaggaaaa tcctggcagc cggtacattc ggtactagaa aaaaaaattc   1560

tgatttgcaa gttctgctgt tcagttattg tacttacatt agccttttaa tgttgcataa   1620

gtaacatagg tgcaggctga aaactataga agcaaagcat cctccttttt ttattctgtt   1680

atatccttat aatttcaaac agtgtcatct gtctttggtg ttgtctgttg tggccagtca   1740

ctcatacatc attattttat cacatattca gttgttcatg cattgtgagt tgtctagtta   1800

ttgatatcgg aaattgtagc taaatgcagc gtggataaag tagtttgatt agtggtgtta   1860

ttcttgtgtt gatgatctca ttatccttca tattcctgtg atgatggtta aacctatagt   1920
```

ttccattcct ttggcatgta atgggttagc atcgatatgc caaagtaact tgttaaactt 1980
tgagcatgga cacgaaaaaa acctggcata taggtgttta agatattgct ttgtcctttt 2040
ctgtagcagc atgctaagta ttgactggat atagctgaat ggttatatgg ataaaacagt 2100
tagcatttga tcacatatat agtgatcaca cctgaggcct gacaaatctg gttttccact 2160
ggctgcatca tagcatgtgt tagttactgg agaaagatct gaaaaaacga atcatacttg 2220
ttgctgattt tgttcaacga aagggttctc tgtggactgt ggagcagaac aatttataca 2280
aacgggctag ttggtgaatg cttgaattcg agtatgccac attgaacaat aagctggaga 2340
tgtactccta cctgatattg atatgtacaa gtgtatggac tgttttgttt tgttccccta 2400
gctagaatta ttcactttta ggcttctatt gttgtaggaa aggctaaatc aactttggta 2460
tgcagtagga taccagggaa atcataaacc atttcacttg ttagcatgtg ttttttgctg 2520
agacatgtga ttatatgctg ttgtattttg tttttttatc tcaactaata tttgttcaac 2580
tgcaatgcag gt 2592

<210> SEQ ID NO 172
<211> LENGTH: 2326
<212> TYPE: DNA
<213> ORGANISM: Oryza sativa

<400> SEQUENCE: 172
cttgtgtgga aggaactggc aggccaatgg atgagggacc agatgcaaga gggggaagag 60
acgggagaag gatatgcagg cagctacagg tggagaattc gcatgccttc cctacatgag 120
caccgacaga gtcgaacccc tagctcatct gaaattagga acatgtccaa ctcaacagga 180
agtacatttt ggggaaaaac agaatacgga ccaacgggat agggggggaga gcatgtggga 240 ggagggagga gagtaagacc tataatgtcg gccgaggcag ccgccgaccg tcgactccct 300
ggcatcactg gagcttggag tagccaattt ggggatggat tttgaatcgg agccctgccc 360
ctgtgcattt gggcagtggg tagagtgagg gggttaacgt gctaaatgtc tggatgagac 420
ggggtcgttt ctgaaagttt caacacgtac gacgtagata ctccctccat cccagaatat 480
aacaacctaa aatgagacga gacctatctt aggacaatgt atttggacac gcctcatata 540
taaatacatt gtccatccta gattgataca ttctgagatt ggaggtagta gatcacagac 600
gtacatttta tatttaacag aaatttacta tagtttacac ggtagatgta gaggctgttt 660
ggttcttaac taacattgcc ataactcact ttaggcaatg ttagataagt gtggcttgtc 720
acagttttta tgacctacaa attataagcc acaattgtgg caaagttaga caaagaattg 780
agtctataac atgtggggta agatggtaag aaagtacgac ttgtcataac catggcaata 840
aaccaaacat aagactctaa agacatgtga cagcctaaaa tatggtgtga caagttgaag 900
cattgagccc cgtagtctcc gccacatatc tctttccttc ttcctcaccc ccaccaccac 960
ctcttctctt tcccccacca acaccaaccc cacgcgacca cccccaatcc tcgatcaaac 1020
gccctaggat ttcatcgcaa gcaaggaagg aggagaccaa atccaatcca atcccccagg 1080
ttatccccat cccgaaatcc cccccaccca aaatgtgtta aactttttttt gatgtggatt 1140 tgttaataat actccggaat gaggtaaaat tgctgaactg ctatagtgcc taatgccatt 1200
aaattgtgat ttgtttggag tcatgagaaa agaagagaaa tcctttactc attctcacat 1260
gtctacatcc ttagaatctt agagctttct aatgtgatat gcggatatga gcaatgatcc 1320
taaacccact ttacagctgt tatggatgta atttatgttt gatatgttaa tttagttaga 1380

-continued

```
aatagccatc atgtttcact tcactaataa ctttacaata gttactgtaa ctgaacttta   1440
cataaattgt atcatcaatt tttgatggca ttgcattttc ttaaaggaaa aaaagaatac   1500
aaaggggaaa catctctatg cttatgattc tcagagtttg ggcagcaaag tcaatcccat   1560
gcatatcagg ggttcagcgc catgtaaatg ttgaccctta ttctaggggc tattgttcta   1620
gaatgcaaaa ttcttccgtt actaaataaa cagagtttca cttggctcca agtaattgac   1680
cctttcttta ataaattaaa actggctata tgtatggtat ggataggtct atgtgctatt   1740
taaatgccta gcagaaatat tcaaatgtct caggtaattg aggttcttaa tgagttgagt   1800
tttgtatttt aaaatttgct ctgatagtca agtttgactt tccttgactt tattattatt   1860
tagtgaacac ttttggccct tctaggaacg taccaatgga tgcggttata cttttttttt   1920
tcctttcaa tgcaaagtta tgtccttgta gttcagccaa actttacaag ccattttgtc   1980
aatctacatt actgcacaat tcatgcctgc ggtcagttca tgtgatcgca gctaagattc   2040
ttttggtata ctgacctact ggataactgg atgttgcatg atctatgatt aaatttcaaa   2100
tcatgattta cagtaattta tcgttgtacc ttgatttgtg acaaaggaaa ccatgcatgt   2160
atgtctctca atggttatat gttccttcta cagtttcatg gattatatga tcgcatttag   2220
taccatttca tgacactttg tgcagcttga ttggaaccac aggaatttg atttttatgc    2280
tttgcttggt gcgctgttct aacataatct acttttgctc tcaggt                  2326
```

<210> SEQ ID NO 173
<211> LENGTH: 2494
<212> TYPE: DNA
<213> ORGANISM: Oryza sativa

<400> SEQUENCE: 173

```
taacttttat atagaaaatt ttttaaaaaa cacatcgttt agccgtttga aaagcatgcg     60
catggaatac tagtaagagc ggttgggagt cctttgcaac gaaaacagcc ttagtagcaa    120
gcacaaacta actcagcttt agaggcccct catattgatg tttaacttgt tatggggcat    180
ttatttctac acagtctcat ttatcaactg aaactaaaaa ggttgtccaa ttccgtcctc    240
cttttgtaac ggctcgcaaa tacaatgggt tgtttagatt catgtcattt taaatcatat    300
tattttttat aaagttatca aaatgtacat atatttattt atttttacca aactttacta    360
aatgagataa tccaacaaat ggcatttaaa gcgttcaaat ccaagaaatg ccatcgccgt    420
tatgcttccg tccgtttcac gccgttaaaa tacaatgttc atcctataac acttaatggt    480
gtggaatgga cggaacccta acggcgatgg catttttggg ataaagtcgt ttgtacgatg    540
gcatttctta gaactcatat ttgtcgatgg cattttttga atttggatga ttgtcaatgg    600
tattttttgg attatctctt agtaaataca taaggaatca tgccaaaact tgacaatatt    660
gtcaacttat caaaatttaa ttgggattat tttggcgata atatgaacag cccttacatt    720
tctgaagaat tatagctcaa atatggctat ggccctgttt ggattcggag ggctatttaa    780
tagccctccg gaatcttgct atttaagagt attaaacgta gattactgat aaaactcatt    840
ccataacccc tacgctattc tacgagacga atctaacgag gtatattaat ccatgatttg    900
ctacagtaat cagccgctaa tcgtggatta atatacatca ttagattcgt ctcgtaaaat    960
aggctaggga ttatggaatc ggttttatcg gtaatctatg tttaatactt ctaaatagca   1020
agattccgaa gggctattta atagctcgga gcatccaaac aaggcctatg tttagatcca   1080
aacttccaac tttttctatc acattaaact gtcatacata cataactttt cagtcacatc   1140
gtaccaattt caacccaaac tttcaacttt ggaagaacta aacacagcat atgacagtgc   1200
```

```
agttcagctc aattttgttc ggagcctaaa aaaaagaaaa gaaaaaaagc tcaatttgga   1260

taaggctatg aataaactca aaaaagcatc caacctaacc accacactgg cccaccaggg   1320

cccacgctcc actcccgtga tcatcacctc cttccctttc cagaaccacc ttctccttcc   1380

ttcctcctct tcttcttcag tgtactctgc ctttataaca ccctactcct ctctctcacc   1440

tccaccatct agctcactca cacagtctcc actcacacgc attgcagagg agaggcgaca   1500

ggtcagttca ctctcctttg gcttcctccc ccaccttcaa gatctcaagt cttcaacttt   1560

gtcatgattt tgccttggtt tgtcttgcta gttgatactt acttgttacc tgcactttgc   1620

ttggctcagt agtttcttca tactagcatg ctcactttag taaagcatga ggtatagaat   1680

catgtgtact actactgctc cttccataag tagcaagact ttgaggcata tggcattaac   1740

actgaataat tgatgaaaga cttttagtta cctgcttttg ggtgttagaa tcagtattag   1800

taactggaaa ttcactaaat ttgttgtcca tgctcttgta gttttaaaga attattatag   1860

ctttctacag gtgttgaatg caccaaaaat ttatgacact acctttttgct cttgtaccat   1920

catgtacctt gtctgcgcaa agatttgtcg ctggcatatt gtactgctgt ggtatgtgaa   1980

ttttgttctt atgcaaaggt ttgatttacg actagaagat taaggattta aggtcatccg   2040

attgatttaa ctcttaaccc agcattttct tcggtagtgt tctaactgtt gatgctgaaa   2100

ccacacaaat tatcacacaa aaatatatta tttttagttc atcaaaattg aatgtgcact   2160

tggagccttg gaggcaaaga aatatgtgat gccaaaattt tctccttggt taatcttcct   2220

accagaatat taacaaaact atatgaacaa gtaaatatct tgtgttgtca acttatacag   2280

tctatcacaa ctcgcaatct tagaagttaa tttctgtacc agttttatat aatgcttcaa   2340

aatctcaaat actaccttgt taatctcaaa atatgaatac atgagggtac actatacagt   2400

cttacttcaa ctgtcatgac aactgaccac aaaacaacta cggcaattaa gggcactact   2460

aatatccatt atattgtctg ttactgcaac aggt                                2494
```

<210> SEQ ID NO 174
<211> LENGTH: 883
<212> TYPE: DNA
<213> ORGANISM: Oryza sativa

<400> SEQUENCE: 174

```
ttgggtcatt tgtcttcaat ttttttatc aatttaatgt tttattttt tgggtcattt     60

gtcttcaatt ttttttgtgt tttattttt gggtttttgg gtcatttgtc ttcaattttt    120

tttatcaatt taatgtttta ttttctgggt catttgtctt caatttttt tgtgttttat    180

tttttgggtc atttgtcttc aatttttttt atcaatttaa ttttttgggt catttgattc    240

tcttcggaaa gaaaccaaca ttctggacta aatcaacatt ctggataaaa tccttgggaa    300

gtaatagtca ctactagaaa aattatttgt cacttcgtag aagttctgaa ttaaagtgag    360

atctctttaa aagaaaccaa cgttctggat aaaatccttg ggaagtaata ggtactccca    420

gataccaaca ttcaacagca cagcaattcg cccttgtatc atccgaaacg cacccttaca    480

tatattcatc attaagaagt ccaaaattta aatttgaaaa aaaaaaccag accatattcg    540

ctccacttta tgttctatat tccttgtgca aatacaacag agatggcaga agatgaacaa    600

aaaagaaaaa atcagagacg gcccaacaat aaacagccca tcccttttttg ggcctccact    660

atccagaccc acggcccagc agtagaagcc cccacgggag atctcgtcgc gtcccatcca    720

tccgacggcg cagaccacct cacgcctccc ctataaatac cacgcctcca accctaaacc    780
```

ctctctcact ctcttcctcc gccgccgccc tcctctccgg gaagaagaga ccagagcgag 840
cgcgcgcgcc gccggagcaa acccctcctc ctacccttca gcc 883

<210> SEQ ID NO 175
<211> LENGTH: 539
<212> TYPE: DNA
<213> ORGANISM: Oryza sativa

<400> SEQUENCE: 175 attttttcctg taaaatacca ttgactatta tgtaggagta tgtattattg tttgtcatta 60
gcaatcttaa gttatgcata gacaatcttg aaagctcttc tacggcgtgg attcaaagtg 120
agccaaaatg cgtcacaaaa ataagaacaa gggttaaaac attaaaaaaa taatcctgct 180
atatgcaatg atttagagag gcaatgcaca atgatttagt tctccttcag gctttagtca 240
ctttatacaa aaacacaaaa aagaccaaaa aggaaaaaag aaaaccaaaa ctattttata 300
tataaaaggc ccactacaag taattaccca ctaggcccat aaaggaccac tacaagtcat 360
tacccattag gcccatcaag gcccatctaa aatttctagg gtttcctcat cctcgatggg 420
gtttatcctt cgagcacata tataatccgc acgccgccgc ctccctctct gcttcgcact 480
ccattttccc tctccccgct cgccgccgcc gccgccgcca gccaagctcg ccgctcgcc 539

<210> SEQ ID NO 176
<211> LENGTH: 661
<212> TYPE: DNA
<213> ORGANISM: Oryza sativa

<400> SEQUENCE: 176
taaaatacaa tcgtaaccga ctaggatctt gggtattacc ttgacataca agtttagaat 60
ttaacccaag tcattttaaa gatattctat ctatatatag cactccatac ccagtcaaac 120
tatacatgcc gtgtatgtat ggggtatcca tgatctccac aattcatttg tcaagtaagt 180
acttcaatag tacaattctg atagtgcgag catagtcgtg aaatacgaca ttcacaaaac 240
cgatgataac tgctcgaaaa ccacaggtat catcagcttt attgctccgg ctcaagctaa 300
aagttcacta aaatccggtc aagtatataa aaactcaagc taaaacttaa attttgcatt 360
aaactgtcat ctccgagctg ttaacatcaa aaccgacaaa tccaaatcct cgaatcctta 420
tgggaagccc atttcaactc accttaaaca gtcaatgggc ccagccatct atcataaagc 480
ccaacaaggc ccatgaaagc ccatctcaac tcagcctagg gtttttttcc actccgcggc 540
gtctcgctgt ctctctctcc tctatatata agcctccgcc gccgcctcct cacctcttcc 600
ccttcctagc accgccgccg ccgccgccgc cgccgccgcc cgccgcgccg cctccgtcgc 660
c 661

<210> SEQ ID NO 177
<211> LENGTH: 1500
<212> TYPE: DNA
<213> ORGANISM: Oryza sativa

<400> SEQUENCE: 177
atttatattt attccctaat acaatgaagc atgcatttat ttctagacta gagacattta 60
attattttgc cactcttaaa tgtggtaagt aaccatttac catgtatacc cacatgtcat 120
agacacgtaa ggatccaaat gttaacacat aggtgtcaga tagttaaacg tctaacctaa 180
aagtaacaaa tatttaaata tcccttatat ctatgattga aaggaaaaaa gtctaagtac 240
aattgtcgag atatggcagg tttggtaggt ctctaacttc tcaacttaac tcaaataatt 300

```
aagtttagag tggaattatg gagcaccttg aatccagatt catctctcta atttgtttta    360

atagcactgc tctactccct tttagatgga attgaaatcg tttggttgga cttcatccct    420

aacctccata agaggtgaaa ttggagctag aagtatgtca aacatggcca tataatctaa    480

gaacagctta tcgagatatc caacaaaaaa taatcgttct cctatttcag tgagtaaaaa    540

cctgatggtc caaacgagtt gggctgaaaa tgggacagtg tttcggtgag acgggcccag    600

caagaacata ggcctggttg ggcccctatt ccccctacgt tttctcggcc cacccaccgt    660

tgggctcggc tcgggcctac catcgggcgg agaggaggcc caactcggga aaaaggagaa    720

acagaaaaga ggccgaaaag gcgaaaggga tcgatgaggt ggggaccacc ggaccagcga    780

gagatgcgca tcccgatgca gcacgatgcc gcggcgccct ctgttccgct ccgcgccgcg    840

gccacgaaaa ccacgacgcc gccgggatca tctgcgtccg ccttaccagt ggccgtcgct    900

gctatggatg acttaagcag tttttttat gtgtataaat aaaacagggt agttaacgag    960

tcatactttg gttctggaag agaatatctt tttaggaaaa aagcaatagg tcatcttact   1020

ctttgctaca ggtgcaataa tttgcccgga caatagacct gagtatagtt tatttagttc   1080

taaacaatgc atcagaatat ggaggaaaaa gatggcctta gtataggatc aattgagatg   1140

tacagttaaa caaaaaagta gatatggatt tacaaaattg atgcggaata ttatatccat   1200

gtagtagctc ccatgtacta gtttcttttg cttgaaaaaa taaaagaagc agataatttc   1260

tagagaagtc cagagaataa aaagattggt ggtgggagtg ggacccacct gtcattgtcg   1320

gaggagcctg cctcgcctca tgtgatccca tcggaggcca cacctctgct ccccctatat   1380

tatcctgtcc ttggtgtttt tcttcctcct ccacaaaaac caaaatccaa tctccagctc   1440

tcttcccccc cccccccccc ccccccgcgt ccagttccat ctaatcagct tctcgtcgag   1500
```

<210> SEQ ID NO 178
<211> LENGTH: 1500
<212> TYPE: DNA
<213> ORGANISM: Oryza sativa

<400> SEQUENCE: 178

```
ccagccccac caaggggtag agatctcttg aacggacctg tgcagagaaa agctggaccg     60

agtccaagtg agaggaaaaa aaacctcatc aatggcgacg ggacagggta gacgtaggcc    120

atgtcccctg ctagcagtag gcatgtgcag acagcgccct gtcctatgcc tgtccgccgt    180

cacatccgtc attcctgctg ctagtggcct gtcagtgtgc atgctcgcca cattaaatac    240

agcgtgccac ggccgacagg acctcattaa acacagtagt tgggcgctgg gaacgcctgc    300

ccagggcgca cacacgaatc acgaatcaga gcgaggaggg ggtcccaact cggaaacagc    360

caccacttca acaccccccc tcccggaggg gggggggggg cggcacgtgg gtttgaggcg    420

gcttcctccc tttgtatggg gggtaccctg ggcccatatc actgacactc actttcttgt    480

tcgaactaaa ttgaccacta acaaatattt ctattatagg gagcataggt gcgcatccct    540

gtacaataag gaaccacacc tctgatagaa ctataaggat catgcgcctt aatgcttgat    600

ctaaagttag gcgccagttc cacattgcat tgattttcgt caaaactttt cacaactata    660

gtttaatgaa aggcatgcaa acagttttaa caagcaaaaa ataacgataa ctacgttcaa    720

aattagatgc acttagatac aaaccaagaa tcctagttca tccccactaa gtgtagataa    780

tgctacttct ctcttctctc attaagccac atcaccccaa taatttatag cctttggatg    840

atagatctat ggtttaaatt gtctcttctt tcttctctct taaaaatatg caatatcaat    900
```

-continued tatttttagt ctcaaaatta tatcaaatta ttttagtttt gataatcaaa ttacgtctta 960
tttgtacata ttatgcaact taattttccg cagcacacgg cgggtagtca tctagtaata 1020
ttatatacga gagatagtcg tagttgaaac aaagcgacta gtaattaggc atttaaatat 1080
ttaacgtgca caactaatgc tacaaaaaaa ggactcataa ttcttaaatg aaaaataatt 1140
tgtgtataaa atatttatat acgtgttctt agcaatttaa aaacaaatac taaaaaataa 1200
acttcgaaat ttaaatttta actgataagt ataagcaaaa gcgaaaaatg tgaggcccag 1260
aaactcccgc gatccacttc tcaacatctg ggccgtcgtc catccagcac ggatcttgaa 1320
gcaggaaggc ccattagcaa accctagaca gcaacgccac cgcaaataaa tagcttcgct 1380
gcccttcccc ctatccctct cctctattgc cgccgccgcc gctcccagct cgtgctcccc 1440
tcgccgccgc cgccgccgcc gcctcgcctc ctcggagatc ttcgctgccc ttccgccaac 1500

<210> SEQ ID NO 179
<211> LENGTH: 1500
<212> TYPE: DNA
<213> ORGANISM: Oryza sativa

<400> SEQUENCE: 179
atttatagtc tcatgctaaa ttaaattgtt gaccgaaata tgaacaacta tcttagtcct 60
cattggttac atgcatagta taattcatta gtttctggtg ggttttgttt ttataatttt 120
tagaagtctc gtcaaacact atcactatag tccgctacgg tccatccgct gccttatcta 180
tttattgtca ttgtgatttt aaaaattgaa cataattatc gtttgagttt attattttac 240
tctctataag tctagtaaaa tcattagcgg cttcgtcatt atactcctct acagcttgcc 300
cgctgcttcc gctctttatt gcttttgaga ttgtaaaagt ccaacattat tatcattggg 360
gtttattttt ttactttcca gaagttccac taatcgtcgt gactggtgct gcttaatggc 420
atgctcgttg ttcctcctct taatcatcat agggattcaa tttgggactc tgtttatagt 480
ttttagatgt tccatcaatc accactaccc tgcttcatta ccttctccca tcttttattg 540
ccatttgtca ttactgttct agatgttttt tttttgaaaa tttcatattt ttcattccta 600
tattttttat ttatataaat tgtattccta cataaactct tataattatt cttctatttt 660
ctaaatttat tttatttatt atttcgaatt ttattgatcg tgttttagat ggtcatttct 720
ttcaatagtt tttatttttt aattataaat tttagctatt tataaattgt attcctagtt 780
gaactcttat ttattttaaa ttttggaatt cattttattt tttatttcaa attttaattt 840
aacaataact gaaattcaca attaaaaata agcaatattt taatcccaaa ttttaatttc 900
cgagtcgtaa ctgcggcggc aacgacactc cgacggcgac ggcagcaaat ccccccctccc 960 ccgccgccgt ccggtgacgt ggccttcctc ctcttcccac cgcagcctca agttgggggc 1020
gtggcccacg cactgggccc cacacccgcc caccatagct ggtgcccaca ctccaacctc 1080
ccaattcctc catgaacgta gcccaccata caccacccct ctcacaagtt cacaacacct 1140
cacccacggg cccacctgtc agtcactcaa ccatccccac ccatccgtag agcgggtcca 1200
cccgcccagt ccaccatcgt cgtcacccac gaggagacgc cgcagcacgg gaacactctt 1260
ttttcttcaa tttcacagga aataacattt tttgtaattt cttttataat ttttttttatt 1320 gcgcgtcggc gttaataaag cgcaacggca ggcagcgatc taggcgcccg tcgtccactc 1380
ctcctcgcct tcctcgcctt cctcgctttt atcgccgccg ccgccgccgc cgcctccgcc 1440
gccgccgagg agtaggagta gtaggaggag gaagccggta gccggaggag gagcggggag 1500

<210> SEQ ID NO 180
<211> LENGTH: 1250
<212> TYPE: DNA
<213> ORGANISM: Oryza sativa

<400> SEQUENCE: 180

```
tgttccaaat tcagagcagc ttcatatctg tatgagcatt attcaggaat gcagactgcc     60
atagcccata gactaccgac aggtaaaaca aaatactgct ccgtgatgtt attaagcaac    120
tagacacctg aaatctgaat tcgatgatac acatttgaac atctccaagc acgaggagat    180
atcgatccgt ccaagtacca acagtgcagt gtgcaccata tgcaggttgg atatgcatat    240
tttgacaact atagacttgg aaaacccgtt tcagtggaac ctgtgaaaaa acggtgcaga    300
tccttatgct tttttgaatc cacaagtgtg ctcaagctaa gagatggaag cgtctctatg    360
ctcgactgag cggccatgtt tttctccgtt tcagaaggat tggaattcgg aggaggttgc    420
aaagaaacag ccaagcaaat ggcaggagtc caggagatat cagtagcaga tcctcgggtt    480
ttctcactcg atgcagtgac atgtgtgtgc ttcccatctg tgtactccaa tcttaccaag    540
atcagataaa tattcgacgt gattcaaatt tcgaagtacc aaaagaaaaa acttaacttg    600
caacatcacg tatagtgacc ccagattggc attcatcgac acgaacgaac agtaatacag    660
cccaagatgt gaagctgcgg ccctgctgcg gcggttcccc gtgggctgga ctaccagctg    720
caaggagata ggaataagtt cagatatcat ccctcaactt tacgtcgagt ttgtatgaca    780
tccctaatct tcaataccag aaatcttcac ccataaacta tacaaaaccg tgtggttctc    840
acagcagtat gattagggat gaagatttga agagtgaaga tttctggtat tagggattag    900
ggatgtcata ctgattcagc ataaagttga gcgatgaaag gtgaacttat tcccaaggag    960
atacgcatgc aacgacgcca ccacaaacgg gccaccacac caacggcccg gcaattgcgg   1020
cgttgcagtc cccgcggcgc gggcgaattt gctctccgca ggacggcgtt gccacttctt   1080
cggttatcgg gtgggccctc acttcctccg ccgaaagcca cgcacacgct gcccataaaa   1140
aggcgacgct gttctcaaaa cctcagaaaa ttcctatatc ctctgttcgt cactgccttc   1200
ctctccaagt ccatcccctt ccccgatcta agatccatcc gatccaggcc              1250
```

<210> SEQ ID NO 181
<211> LENGTH: 1500
<212> TYPE: DNA
<213> ORGANISM: Oryza sativa

<400> SEQUENCE: 181

```
gctagagcat gtctttgcac tgctcgtttt aagttgctat gtagcttgtg catggaccct     60
acttgagacc acatacatta tggagtatat gtctgttcga tcagtgtatt ggccctacat    120
cttgttgagg tctagctaaa gcatatcttg cattgttctt gccctaagtt gctctagaca    180
atgtgtacat ggacttgttg acctcgtctg atgcacatga cacatgctaa tttttgtttt    240
taattactaa agcccatata ggagaaatga cgtcaccccc tagcccaata gttagagcaa    300
atcgtgtgct atcagactgc agaatgaaaa agcccatcaa gtagcctaga atggccagac    360
acgcactaaa gaacaaaaga tgcctgctcg atcgagttct cttcttcttc gtctaggcaa    420
gaagatgaag gcaaggagtc tccttttctt tcctacacca ctgaccagca agctctcaat    480
ttgcaaagag aacacaccac tttaagtgac aacgtgatca atctcagcga aggatcctat    540
agacccctag caccctcctc ccaccttggc cacccagttt acactatatt ttatgtcgac    600
gacaacatct agctatttct tatgcagaga aacaagtttc aagcattcaa attgaatgta    660
```

gtttcaattt atttataata gctatcttta tctcagtttc ttaattaggg atttcattta 720
atcagttttc ccccaaaaca tagggtttct aatttgacaa ttcatttgaa agcaattgat 780
aaacaaatgg tagagtttgg aggatgaatg cttgaagctt gataaacatg tactaccaaa 840
cttttgctaa ggcaacattt agctctacaa taacaaaccc tacaaatcac tattaaatat 900
aaattgcttg atatgtcaag tactagatag ttttattgtg atatactatt atgtttggga 960
caccagatca ttttcgtttt ggatttacta tgattgttta ggatcctact tgagaccaca 1020
tacacataat acatagtatt tgagacctag ctagtgcatg tactctgtcc attcccattc 1080
caaaatagag gccgcttttg gattaaaaag ttttcaaaaa aaaaggagtt tagaagtacc 1140
ttttatcaca tcaattcaaa attttctcta tcctacccct taaatatagg tattacagta 1200 attttttaa gcattatttt ttctatataa cttggatcga taactataga atagaaggta 1260
gtaccgaacc gttcctccta caggcaattc cctcaaccta aaccattgga agaacgtgcc 1320
aagttggaag cctaacctag cactagtctt agaaaaaaca gtagaaatcg tgagttatct 1380
ctgcaataaa aaaggaggta agcctaccca cactgcaagt ctccaactcg ggcaagctct 1440
cctcccccac gactcccctc tccttcctct ctctctcgct cgcgcgcgcc tgcgtcgcca 1500

<210> SEQ ID NO 182
<211> LENGTH: 1500
<212> TYPE: DNA
<213> ORGANISM: Oryza sativa

<400> SEQUENCE: 182
gccggaacca cgctggcaga ccagcagggg tcggtgcccg aagcaataga tatgaaatta 60
catttgctta gcttagataa ttaaaaccca tagaaagtcc tctctagcct agcctgccta 120
ccatctgttg ttgttcttgg atagtcttag ccttatgtag attacacacg ttctctgagt 180
ttgatatcct tttggagtca cccgaaggtg aagtgctaca gcggtattcc gtgcgcttgc 240
ggatttatca gtggtcgtaa gaaataccaa cacgggccgg ccaaacaagg gaacggcatg 300
ggaaaggagt tgggccgacg gcccaagaaa gaaaaagaag aaaaggaaaa agaggaaaaa 360
gaaaaaggga ttcatgtgat ttatatattg catagaattg attttaatcg gttaaaatta 420
tttccgaggc gctgaaaatt tcgctaaaaa tcctgttaat gtattgtgac atgtggaact 480
taagaaaaat tccacgatac caattgcatt tattagttaa ggttcatctc taggttaaat 540
taaacaattt cttcagataa tttattaaat aaattttaaa gctagaaagg ggaactttag 600
gggcatgata catgaccata ggatataggg tatgcattat cccctgacag aaaactctat 660
tcatccctta agggaatata cccttatttt tgcatgtcac ttaaaagtta tcaaaaagaa 720
tttgaaacaa attagtaaga tagatcatta tgtgatatgt cactccacaa acatgcacgt 780
tcaaattcaa cttatacaag tagaaacaaa aataaaaaat tttgactatt caatatgaat 840
aaaatgtgta atttgcgatc aaaattgtta gaattgtata agtcgaaatt caacttgcat 900
gttcgtggaa aaatatatca tatgttgatc tatatatttt tattttttta tgactttttt 960
atgattactg caattgtttt aaaattgaga aagtaccaaa ataacaaata atgatacaga 1020
aggtggtaat cagggaaata aactagtaaa acattgataa gtgtgaaata aaataataca 1080
aaagttgata tgaagaataa actagtagta catattgtgg tagttgggaa ataaattaat 1140
aatgtgtcta aatcacaaaa tttatatatt gtgacaaatt tgaaagataa aatcatctat 1200
cctgagacag actgacggag ggatcggagt accccgtaac aaataaagaa gaagaagaaa 1260
ataataacaa taatagtaat agtaaaagaa gaaaaaggcc tatttcactt cttggaggcc 1320
cattagcaac aagcggccca ttcccaagct ggcatgaggc atcttagggc ttgtgccggt 1380
gtgccctcac ctgctgccct cccaccccac cactctccct cctctctctt tcctcccaac 1440
ctcttgcggc cacacgagcc aagcagcgag acccccggat cgaaacgcac accggcggcg 1500

<210> SEQ ID NO 183
<211> LENGTH: 1500
<212> TYPE: DNA
<213> ORGANISM: Oryza sativa

<400> SEQUENCE: 183
tacttgatat gttgattttg agatgtttgg tagcactcta aatccataat atgctatatt 60
agaaatttat ggcttcctca atacaaagat tggatgacaa aatatctcca ccaccgtcaa 120
atcttaggag tacaatctgc attcatgtcg agaagagtca gatagatagt tcacactcaa 180
cctgaatgga gttatcaaca tggttaatgc cagggtgaat tataaaaaac ttcgcaaaac 240
cccacgttgc cttaatcttg aaatggctta aatgatgact aacaaactat tgtcttatta 300
tagttaggcg gaagacaata ggggagattg aggaggagat gacctacaag tggctttgca 360
ctgtattgtt tttttcggct cccccatggc cccaagacat tatccatgag acaaccgaac 420
aaacaagaag catcaatacc ggtagcagaa gcacacaccg tcgctcaccc tgctaactgc 480
tttgtactag ccgaccgcca ctagctgttg ctaccgtatc cttcatctag accacccacg 540
aattaactga aaccaccgtc gtgtatgtcc cataaaatgg tctacttagg attatataca 600
agtacacatg ttgatcatga acatgaaatt ttgaatacaa caatggtatt tgatcaaatt 660
tggataactt tacattcata cacaagatat aaaataatat tgctataata tgttactcat 720
aagcatgaag ataataatac tagcactaca aaatgtcact tgatgaaacc acaattgatg 780
ttaacacata aatttcttcc cttccaatct gaatgcccta gattaacatg gagaaaattt 840
ttatctgcag ataacactaa accggatcca aaatttccca taccaaggct gtgtttagtt 900
catgtgtcaa ttttttttaa gtatacggac acacatttaa gctattaaat gtatactaat 960
aacaaaaaaa attggtcacg cgatttacat gcaaactgtg caatttaata tacattatta 1020
gtatattatc aaatcatggc gtaattaggc tcaaaagatt cgtcacgtga tttacatgca 1080
aactgtgcaa ttgatttttt tttcgtccac atttaatact ctatgtatgt gtccaaacat 1140
ttgatgtgac agaaaagttg gaagttcgaa gaaaaatatt tgaatctaaa cgaggcctga 1200
atggaaataa tcaaaaccgc aatgggctgg caaactgtcg atttcagata attttttag 1260 tacggacaaa ctgcagggac ctaaacgaaa aagaaagaaa accgtgacgt cgctcgcttc 1320
cagagatctt cagatcagat cagaaatccc caaaaaaaaa aaacacaaca aaaccaaacc 1380
cgacagatct tctcttcttc ctcctccctt tcccatcttc gacgaggcga cccggcgcga 1440
gagaagaaga gatcgatcga tcgatcaacc gatctcgccg gagaaggaag aggagcaaag 1500

<210> SEQ ID NO 184
<211> LENGTH: 1500
<212> TYPE: DNA
<213> ORGANISM: Oryza sativa

<400> SEQUENCE: 184
tttggacaca tgcatggagt attaaatgtg gacgaaaaaa acaaattaca cagtttgcgt 60
gtaaattgcg agatgaatct tttaagccta attgcgccat gatttgacaa tgtggtgcta 120
cattaaacac ttgctaatga cggattaatt aggcttaata aattcgtctc gcagtttaca 180

```
ggcagattat gtaatttgtt ttgttattag actacgttta atacttcaaa tgtgtgtccg    240
tatatctgat gtgacacgcc aaaactttac acccctagat ctaaacatcg cctttggctt    300
caaaccaaaa tggcccaatc attttgatta aaaaaaactt gatatgcagt aatctatatt    360
tttagaaatt cctcaatggg ccttgagaaa ataaggcata aacactacaa ggttagttcc    420
aactacttaa ctttctataa tcttccattc cttgtcagct tgcttcctat cgaggattgt    480
actaatgaat aagaagacca tgaatgaaag gatgccacac ccttatatcc tgtgtcttta    540
attttttaag aattatacca tccttcttag actacttcgg tagtaggagg ggttgcataa    600
tagatatatc aaaggataag atcccaactg gtttgctatg ggtcacagac attttttttt    660
ggatttctgt tttaaaaata attttaggag aaattattac ttattttctt atcaatcatg    720
aaaagggagt caaacagcga aaaggttact aagaaaacca caaacattaa tcataacatc    780
atatgaatca agcatgctct agccaaattt tactatacat cagtcaatgt tggttcgttc    840
gtttcttaat catccagcat ttgataaact ttggcacatt tcttaagcac atgcgtgtgg    900
caagacagaa ttgttcacag gaagaaaaaa aaacccacat ctcgttaacc atattttttt    960
actgtttaaa catttttatt tttattattt ttttaaacga actattccaa aacttatttt   1020
caaaacgcgt ttggcgtggc aaaacaacag ttcacgtcac tccgcagcgg gcatgacaat   1080
tttgtcctgc cacgccagca agacaacgtt atcacgctag ccagactgac atggcaatat   1140
tatttttgcc atgccaacct gcattacatg gacaaaggtt catatcatgg aaataaaatt   1200
tagaagaatt tatttttaaa actaaaaatt aaaatgctca aaaaataaaa aatatattct   1260
taactaacct ggtgaaacaa aagaagccca acagtcaggc cttatccagg aaagcggagc   1320
ccaagcccaa caaacccatt tacccccagc gtgggcaggc gaaccctttc cctcccgtgc   1380
ctatataagg ccacaaaccc taacgccccc actcttccac ctcgcagtcg ccacccccgag   1440
cagaagccgc cgccgccgcc cgaaaccctc gccgccgtcg cttctcctcg gggcgcagcc   1500
```

<210> SEQ ID NO 185
<211> LENGTH: 1500
<212> TYPE: DNA
<213> ORGANISM: Oryza sativa

<400> SEQUENCE: 185

```
cggcgcaagt ggttgcgttg gtaggcttct cggcactgag gagtggacag agcagtgccc     60
agattaggtt gcaagggtac atggacgata acaaggttgt ctcgacatag caacatgctc    120
atcagtgttg gccctagggt tcccttaccg tttttggcgt ggttattgga cccccacggc    180
aaggtggtta tcgcgaaacc gcgcggtaac cccgagagat accgtggttt taaaaactga    240
aaaggttacc gtgcatggta atcgcgcggt tttgtgtggc tccctgatag tggtgagcct    300
agggacaatg actaccaatg ggggttctac acctagattt gactgagtga tgatgggaca    360
gtattgtctt tacggcgtgt tggtgtggac aatgatggtg gtggtacagg tgatggccct    420
aggagcagtg gctactagtg gaaacttttc atccatatct gactgtgtga cggtgagggt    480
gatgactatt gtggcggtgc ttttcggcat ggtagtggca atgaccctag gggcagtggc    540
tgctaaatcg tcggtttata ggcctaaatc gaaccatgtg gattgggagg tggctctagc    600
tagtacgaca atgacaagct tggtggctgt gctagtggca actggagagg aaggatccaa    660
cctaaagtca gacccgacgc tcttttaatg agcaagacga ggagcggaca tagggcttgt    720
tggaggtgct ggcaacggtt aggaagcgat gctgaatttg agacctaaac agggtttaca    780
aaaccgcgca gttatcgcgg ttaccatgca cggtaatctt ttcaattttt aaaaccacgg    840
```

tttatctcgt ggttaccacg ccaaaaatgg taagaggaac ctagcatcca tttccacgcc 900
attcacatcc atgccagatt tggaacgatg gtctacacat gaattctacc tggactgcac 960
tgtttcatat aaaaatccac ttatccataa tatactattt tgcatacata ccatagtcaa 1020
gagattgaat ctgctggtat tgtgaaacca gggtcgcaac tttcttttct gcaagtaacc 1080
ggattggatg ttaatccatc catttacaca gtattttaaa gtacggaatc tagctgacgc 1140
aaccgtccag tgcacaaagc aaaccatgca attcgtcttc ttttttcaaa tagaaaagca 1200
aaatgtcaac acaacgccgc tgaccacgag cggcagcgtt cactctgggc ccgagtctgc 1260
aggcttgcag cggaaggcct cgttacagcg tcgaaatggg ccaggccagg ccgggccgga 1320
acacgtgggc ctagcccact caaacagccc ttgacgcgca ccaccaacca ctatataagc 1380
ttccgagagc tcttccccca aaccctaacc gccgccgccg ccgtctcctc ctcctcatcc 1440
aagcagctcg cgcctccgac ccctcgcctc gagctccagc tctccccaac cccttcaaca 1500

<210> SEQ ID NO 186
<211> LENGTH: 1500
<212> TYPE: DNA
<213> ORGANISM: Oryza sativa

<400> SEQUENCE: 186
aaaaaaaaaa aaaacatcgc tgcatggcca cacgcattcc taacattgcg cattgatcaa 60
ggaggtttaa tctaaaagga aggatttttt tttggctcgg taccatttgc aaatatgatg 120
attaaattgg aatggggtga gtatatattt gtcaaggtct ttttagctat attgatagtg 180
ttctgcactt tttttttaa tggaaacaca gatgagtgta tatacctcac gtcagtaaat 240
tagaaagaag aatctgttct ataattctat tccatgtcaa gctaaggaaa aagagaagga 300
aaaaccgaaa aagaaagata actaatcaac ttttcttaat gggccagccc aaaaggtgca 360
cacctcagtc cttgtttcac tatttgtgag tcatgatcca tgtttttggg ggaaaaggaa 420
caatgtccat gtaacaatga ctgtgacggg aatatacaat ggcaaagaat tcaaagttcg 480
cccagactaa agtgaaacaa agaaaaacat agtttatgta ggaaaagaaa aaaggattgg 540
agtagacaag atcgtaaaat tctgatctcc aaattttgtt tctgtgttta ttactttatt 600
aggcagatag ttcctgccgc ttgatcatgg gctgcgttct aaggagccga ttcagttcag 660
cctctcttat tttcctttag cgcatttgtt ttaaattatt aaatgatgat atatttcgta 720
tgaatttttt atatagtata tgttttctaa ataaataaaa aaaatctatt ttttaaattt 780
ttaataatta atactcaatt aatgatatgt ttcctcgtta attagctata aatcaatcaa 840
tcatttgagt agaacgcaga tcgatgggtt gacacatgtt ctcactttta tactagacca 900
atcctaaaag gaacagctaa tatttttcat ggaattcttg ctccctttcc ctgtcgaaat 960
ttctggattc agttcctgtg tttgagtttg atgctgattt tactcgattt tactttcggt 1020
gttttgagtt tgcgactgat ttttattcaa tttcgcatca caattcatac acccctgctc 1080
tccttcgggt acaagttcgg gaccggatac caaacccccct ctcgcaatcc gtccccaacc 1140
acacccatcc accctcgggg cccacctccc tctcgcttcc atgtgggtcc caagccggct 1200
actctgacct ccggaagagc ccggaacgtt ccatgccagg tgggccccac ctccccccgtg 1260 gccccactcc tcagtgaccc ccaccgccgt acccgaaccc gatagcgaga gagagagaga 1320
gagaaaaaaa aacaaaccaa accaaacccc ccgctgcaag aaagaggctt ataaaagaac 1380
actttaatcc ccctcctctc gcctctctct cttctcccaa atctcatcgc cttctccgcc 1440
gcgacgcgga cgcgctcgaa ttaacgccgc cgccgccaac caccgcccgc cgccaccgcg 1500

<210> SEQ ID NO 187
<211> LENGTH: 1500
<212> TYPE: DNA
<213> ORGANISM: Oryza sativa

<400> SEQUENCE: 187
atggttgttc aattaagcaa caacatgaat gtatgattta tatatttgta tacactagca 60
tattgcctgt gcgttgcaac gaaattttaa ttgatgaaaa tgatcattaa cctttgctat 120
tatcattatt ttattatcat ctcttaaatt ctacatatat ttgtaactaa accctatcac 180
ctcacaatat aattcttact tcccacaaaa aatagaggtg gtggggtggt tgacatgtgg 240
gaccttatct tttcttcact ctaaaagggt aaggactaag gaggtggtgg tggggcgcga 300
tcgctaatcg gtgcgcgcgc cggcggcgcg cgtttcaggc ccatagggcc cagcaccggc 360
gcgcgcgcct ccttcgacgc tttttttttcg tttttcttta gcgatttttt ttcgttttct 420
tttccacttt tttctgatta ttttttttaa tctttagcat gttttgagtt tgaaagtttt 480
taaattttga gttgaaaatt tttaaatctg aatttgaaag ttttcaaatc tcgagttgaa 540
agttttcaaa tatggacttg aaagttttca aatctcgagt tggaagtttt ctaatttttc 600
aaatctggac ttgaaagttt tcgaatctcg agttgaaagt tttcgtatct cgagttgaaa 660
gtttttaaaa tttgacttta aagtttaaaa ttaaaatcga aaattttcaa atctaactta 720
aaaaattttc aatctgttag taaaaaaatc tccaaaatct ttcttaatta ctatcattag 780
tgttaagtat atattaacta atggagatag ttaagtatat taactaatag tgttaataga 840
gtaggttaat aagggaggag tgctcgctag ctagtagaag cgcgtcgcgt gtcgcatggg 900
ccgggccaac cgcgggggga gggggtgggg gcaacagccg cgcgctagtt aatttgctcg 960
cgcgagctag gaccctccgt ggtggggtgg cagattcacc acctaccacc accactactc 1020
cttttcaaag aagtataggt ttaaatctcc aaaagataca taatattata aaatacctat 1080
atatatttgc gttatatttc catataatac tgattaatct tatgcatttc gattaatctg 1140
taaacgatac tcttttcatt ctacaaccgt attccctctt gtacggcact gatgtaaagt 1200
tagatgatcc ttttttacct ttatacagta tgttcagtcc aaagtgaaag tgttcagctg 1260
cccgaaggcc cagcccacgg gaaaaaagaa cactgcccaa aggcccagat aactagacat 1320
cccgatcaga cggcccagat tcaccagatc cagctataaa aatccggacc acgcccacca 1380
cccaaaaccc tccggctcat tcttgcccac gccgcgccgc cgcctcctcc tcctcctcct 1440
cctcctcctc ctagggcttc ttcttcttcc cctcctccga gcgccgccgc cgccgacgag 1500

<210> SEQ ID NO 188
<211> LENGTH: 1500
<212> TYPE: DNA
<213> ORGANISM: Oryza sativa

<400> SEQUENCE: 188
ctgaccgaat acggctccgt cggctttgta tcggccaccc cgagcaacac catcccggcc 60
accagagggc cggtctgact gcgcatgtgc cgccggtcaa accggcctta tgcaccggtc 120
agaccaccgt cttgtggccg gtcagactgg ccaaggcacg ccggtcagac cgccactatg 180
tggccggtct gaccgcccct ggtcaggccg aacacagtga aactgtgtgt gataagtgtg 240
tgtggtgaaa agtgagcaca agtctaaatg cataatgaca taatgtggca attaaaatca 300
tctcatttgc taggtcatta ccccccttgat agtacggcaa aactaaaaat aaactagcaa 360

```
atttgatcgc ccttcacctc gatcaatttt aaaactaaag cactagtttt accgttttct    420

tttcttcgct tcgcgccatc aaattttaat ccgtcgataa tcatccatgc gcacacatga    480

cgtggaccta acttaaaata tatcttaata gcaacggtta gtccacaatt agcgcttgtc    540

attaattacc aaaattaaca acgggggcct agatgcttca gcgtcgcagc ggcgtccgcg    600

ggctggcgca ccaccgcacg gagcggctgt ggatgctggc cttcccgcct ccggcggtgg    660

gggtttccgc ttacatcgca ctgcctcgcc gttgcctagg atgacgcagg tgaagacgac    720

cccgatcttg gcggcgaggt tgacccagcg caggaggtgg gcgccgacaa ggcggtggcg    780

cacgacgtcg cagaagtggt tgcagttgcg gagaatgagg ttgtaagcgt cgccggggaa    840

atcggaggtc cgccatgacc gcggatttgg gtctgagagg tcatgagcga gagaggagag    900

gatggggaaa gagagaggta gaagatgagg gtatttccgt ccaatacatg caaaatatgt    960

agcttagtgg catcactaaa attacaaaca agcagcagtg tatggttaca aatacttaaa   1020

tagtaatggc atatttctaa actggcaaat ttttaatggc acgtatccaa ttaacccttt   1080

caggaacgct tgggacgtat cggcgaggta tctttttttt atttaactga aaatcgcgaa   1140

aatctgggat acgtatcgaa gtgtatccaa tatgtatcca tatccataca cgtatccgat   1200

actgatacgc cacttttgtg ctgtatccag gtaacataga ttatagataa tcggattcgt   1260

tgacatacct cagatgaact tattcctagg gcaaattagt cccagccgaa actccacaca   1320

gcccaactat cattcagccc aacccatcag tacaacgaga atggccttcg caaccacgcg   1380

cactatataa cctacccacc tcactcgccc tctcccctct aaaccctacc cgccagcctc   1440

cgcctccgcc tccgcctccg ccgccgccgc cgagctcctc ccgcgcgctc cgagcccatc   1500


<210> SEQ ID NO 189
<211> LENGTH: 1500
<212> TYPE: DNA
<213> ORGANISM: Oryza sativa

<400> SEQUENCE: 189

tcacatgtat ggcacgtaca atgtgtcaaa tttcaggtac agataactta ctgagaaatt     60

tgtatatacc tgttatatga actcatctat atcacatttg ttaggaaacc ctcataatct    120

tagtcacctt tttttttac aaaacctact atacaccttc ccaacgtgag cgccgcaaac    180

atcaacacca tcgctgccac cgcctcctta cccctagtgt gtcgccacac ggtctcacct    240

gctggttgga agacaccaat ggcattggca aggcccctcg gctggtttcc tccctatctc    300

cactctctga ctctgccctc ccctgcccta tgttccttct caagccggcg gcaataaggt    360

gcccctgctc caccatcttc catgtctcta gtggctatct gtcgttggat ccgtcacccc    420

ccgattgccg cctcctaacc agtgggtttg ttttgcccct gtcagtcatc ctccgtcaca    480

cacggttatc tctctaagct ttgggaaaac ccttcctctt cctcctcctc ctaccccctc    540

ccatcccaaa aataacctag aaccctaact gatgggggga cgttgctgcc ttgctagagc    600

tagaggagaa gaaagccgac acaaatcttg gcatggaccc tatggtctga aattcgacga    660

aaatctttcc aaatttctgc catatgaagg ttagcgattc cgtaaaaatt atgaatgagc    720

ctgtacaatt tacctaaatg gatggtccgg atttggaact tatctaccct taaggatggt    780

caaaattctc atggttacac gaagaatgtc aaatacactc acacatctcg ctaaggaaaa    840

acagaacagc caatcagagc ataaatttca aacttttctt gaaaactcaa gcaatttttc    900

actgatattg gacaattttt tttatcaacc ataatcacta gtgtcacaaa caccttgaaa    960
```

ttcaaataca ttcaaaactt ttgtccaaaa gcacatccga ccgggggacc tcaagataga 1020
accgaaattt caaattttca accgaaattt atgaactaga tgagagtgat gcgtaagggg 1080
gaccatcagg gagcaaacaa ccgtgaccga attgcatagg agttatggct gatcacttga 1140
gaaattaacc atccattccc ggtttccctc caatattgca cccatccatc atccaccagg 1200
gatgataccg ttgccgttgc tctaaaaaac gttaaaacag cggcaggcaa cacgacagca 1260
catcgcatcg tacgtacgtc gttcgtcccg ctctcctccg tcgtcctccc tgcccaccgt 1320
cccccacacc cactccccgc cgtcacgtcc ttccagaacc acctccacga ctcttccaat 1380
cccccgctat aagacgcttc tccactcacc actgcaaccc tcacccagcc agctcgagcg 1440
agcgaagcca gcagcagaag cagtagagag aaagtagaga gttggagggg aaggaggagg 1500

<210> SEQ ID NO 190
<211> LENGTH: 650
<212> TYPE: DNA
<213> ORGANISM: Oryza sativa

<400> SEQUENCE: 190
gagctttgac ttaaaagaca actaaaacac ttcgatgatc gaaaccttga attaaatata 60
tatgttctaa acagacatat attagaaggt atataatgca cattaataaa taaataaaac 120
ttgaataacc catatatata tttttaaaaa attaacatat tactgtcaac tgatgacttg 180
gctgtattag aaggtatgag ttgggaacca taccctgata ttcaaaatga taggatgaat 240
cagcgtataa ttaattaaat attatattaa aaaactctaa aaatgatcat atagattttt 300
aaagtaattt atctataaaa tattttaaaa cacaccgaaa tgtaggcacg aaaaaacaga 360
aatgagttgg aaacatgaga acacacccga gtggactctg accagcaata tccactccca 420
taaaaaacga aaagaaaaaa aaataatgac aggaagaggt ggcccaattg caatgggctt 480
ccatgggctc ctcaagccca acacgcaatc accaccatcg gtcacgcgtg acgcaaaccc 540
cacagccccc ctcccctcta tataagcctc tgcgccgcgc tcctccgaac cctagccgca 600
catccccgcc tcttcccgcc gccgtccgcc gcgcgcacgc cgccgccgcc 650

<210> SEQ ID NO 191
<211> LENGTH: 750
<212> TYPE: DNA
<213> ORGANISM: Oryza sativa

<400> SEQUENCE: 191
tctctagggc tccgcgtccc ctgtctcagc aaatttcact aaatttaaaa gacttttttg 60
agtaaaattc aactcaaaca tatctgagtg gcaagtgcgt gggtccgcca tgatctacac 120
caacaagctc cccggtttgg atcgtgtgtg catgacggtg cagccgccga cgcggcgcgc 180
cgacgcgatc tgaaacccat ccccctctct ctctctctgt gtgtccgaag gagatatttt 240
tcgcatcgaa tggagcagcg acaagtcatg tgaaacagtg actgtccaaa ccagcacgcg 300
tggattcttc agatctcgat gtcctcctcc tcagatgggc catgatgggc cggccccccgc 360 aaccaacggc ccggatcacc tcttcccccc acccccatca caaaacccca aacccatcac 420
caacttccca atctcaccca ccccaccaat ccccaccaga tccaacggcc cagatctccc 480
cctcacccag atccaacgcc tccccttcgt cttctccctc cataaaaccc cacctcaccc 540
ccaccctccc actccgcctc ctcctcctgc ctgcctcctc tctacccacc caccctctcg 600
ccgtcgcaga tccgatccag gaagagctcg ccgccgccgc tgccttggcg ctctccgtgg 660
agaagacctc gtcggggagg gagtttcaag gtgaaggacc tctcccaagc ggacttcggc 720
cgcctcgaga tcgagctcgc cgaggtcgag 750

<210> SEQ ID NO 192
<211> LENGTH: 373
<212> TYPE: DNA
<213> ORGANISM: Oryza sativa

<400> SEQUENCE: 192
aatagttcgg gggtcgatat atccggttct gtggtttagg gtcgtggatt agattcgggt 60
aacttttaag ggagtcaaag cgaacttatt ttccccccat cgctcagaag aaaaatcgaa 120
aaagcccaac cacaacgacg cggcccatta cagcccaagt ccattacact gacaaatccg 180
cccccacgaa tccaacggcc cagatcaacc ccaccctcca tcccagccgt ccacgctagg 240
gctatccctc cccgaaaccc cccacgccga cctctatata aaccggagac cttctccctc 300
ctccaaccct agccaccccc gcctccccca ttctccccgc cgccgccgcc gccgtctcgc 360
cgccgacgag gag 373

<210> SEQ ID NO 193
<211> LENGTH: 495
<212> TYPE: DNA
<213> ORGANISM: Oryza sativa

<400> SEQUENCE: 193
gtcactgccg cctgttacaa gaacattctt cctgactatt ttctgggttt tctgttctct 60
gctgcttgga agaataagat tgttgtctgt gttaaaaaaa cacacaataa tttagtttca 120
tattactaca gtagaaaaca ataagttact cgcgaacgga tattttagca ctaaaagaga 180
attaaagaaa aaaagaggtc ccaccgagat ttgaactcgg gttactggat tcagagtcca 240
atgtcctaac cgctagacca tggggccatt ttgaacacac ggatttttaa tctctatata 300
tccatacttg catctagtct agcatgggcc ccggcccatg atacgttcac ctgaaagccc 360
actcatgcga cgacttgtca aagcccaaca agcgaagaag ccgatgctta tagaggaagc 420
ccggctacca ccacgccaac gcgctcattt cgttcattct agggtttaca actcacgacc 480
tccgccgccg ccgcc 495

<210> SEQ ID NO 194
<211> LENGTH: 1500
<212> TYPE: DNA
<213> ORGANISM: Oryza sativa

<400> SEQUENCE: 194
acgatattct ttcatgtagt cctgcataga tgacaagaat gagcagtgtt agatttgtca 60
aagtgggggt gaagctgagc ccttgttcaa ccttggagag caccttgtct tctttgaaac 120
atgcatgaaa tcggattcgc ttggagcagg tggcaatgcc atttcaactc tgtgcacatg 180
tgtgaaagga caaagaaaat atcatttcaa tggtgattca tcctcgattg aacaaaagta 240
tcaaatcatt ttaaaacaga aaacacccat gtagccacta agatatgcaa acatcaacag 300
aaaaaaaaaa tccaaatcat ctgcatctat gactcagctg catctgccaa ctttgtcacc 360
acgcactgcc ctctatgaca aagaggataa caattgacaa gcaaagcgtg cccggaacta 420
gaagctagca accgagtgat gcggatttct ctgattttgt ttacacttca gttcacccaa 480
aaaaaatcct actagttgaa tggagatttc tctgttttaa gacagtgtgt acttgttaac 540
ggcaaaattg cttgctccaa gcaatacttg ttacagctag aagcatttca agcgatctat 600

-continued

```
tccaattcga acattttgct gcaaatatca tatcaagtat catatgattc agcacataca    660

cacatccctc acctctgcta caaacacccc cagtgaatga acaaaaacac acagaaaaaa    720

gagagagagt attagcttac tttgatttca atttggatgt gatatgatga gccccatcca    780

aagattagtg attcaacaaa ccctagaaaa tgcaaaaatg aagagatgtt aaatcaaaat    840

caggaaatcg atgaaaaaag aggaatgaga gaaaggggta tcgtgcgcac cggctctgcc    900

gcagatgcca ccggctccgc cgcagacacc gccgccacag ccgccaccac cacgctcacg    960

ccactctccc tctctggcac aactgacctt gtgcgcatcg gcgccgctga agaggaggag   1020

ccgcaagaag gctccgccgc cggcgactcc gccgccgcag ccatgctcgt gacgatttgg   1080

gagctgcagg tgtctgtttg ggagtgactc aatgtttctc gagtgtgtgt atctgatccg   1140

tgagggtgtg tgtttgatcc gtgggaaatt gtcctgtccg ggaccgactc gaaacagtat   1200

accggtgact agcatttctg ttataaaaat aaggaaaaaa gaacgagaaa aagaccattt   1260

aacgagcggt gtaaatatgg cccctgcacc gaaggcccat tcgatatgtg ggcctaattc   1320

ccacccgtcc gttaatgggc cgggaaatct cggcccattt aacctagccc taaagctagg   1380

gtttcctctc gccgccgcac tataaacgcg ctctcctcct cactcctcct cccctcgaga   1440

aaccaaagct ccagcaatcg gcggcggcgg cggcggcccg tgagaggcgg tccggcgacg   1500
```

<210> SEQ ID NO 195
<211> LENGTH: 561
<212> TYPE: DNA
<213> ORGANISM: Oryza sativa

<400> SEQUENCE: 195

```
tggctaacct caaacagaca gaaacttttg ccttttacgc tctacaattt gtgcagtata     60

atgaattaat gccacgatcg catacgaaca cgggacactt tccttacaat cgaaggcagc    120

aaaagatgcg aaacttctct tccgagccga acacatgctc ctattcctgc acgagcaggc    180

acaagtgaac aacaactacc tgatacactg acatgtcggg cccacactct ctcaactcgg    240

cacggggccc cctccatctt ccgggaccca cctcatccga actctatgtc gcgtgggcca    300

cgggcctcgt gggacccaca tgtcatggac ctccggggac tcccgaaccg agcccaaccc    360

gtaggacggt aggaggtcga atcccaaacc ccttcggcaa gaaaggagct atttaaggta    420

gactaatccc ctcgtcttcc cccacaatca cttctccccc cggaatatct ccgccaagag    480

aagagaagag acacccaaca acccaaaacc tagcgcctct gcgctcgagg cccccccgaa    540

tccgcgaatc cgccgactcc c                                              561
```

<210> SEQ ID NO 196
<211> LENGTH: 611
<212> TYPE: DNA
<213> ORGANISM: Oryza sativa

<400> SEQUENCE: 196

```
ttttatattt ttttaaaaaa aattatttat ccattatata ctgcaagaat tttttttttg     60

ctgtttttaa tgtaactttt ttcgagaaca tacctcattt ctaatgtaaa ttatcttttg    120

cgtaagtaat ttctctctca taaaaaactc aaaaatattt tttttaaaaa agtgaaaact    180

tgaaatttat atataaactt tcatgttggg taagtaagct acataaacaa ttcatatttt    240

taaaccctta gatgaataaa ttaattgtta accttatatg tattttgagt attttttaaa    300

actaggacct gagtaaatat ttttcttgag ttttaggtta taagacttca cattcatata    360

tgtctagatc tattaacaca tatataaata tggacaatgc taaaaaataa gaataggagg    420
```

```
tggtattatt tttttttgg tagagagggg agggggccgc ataggaggca ggaggtagta    480
aaatgggctg atgggcatag tattcacggg ggcccatgta atagttgggt tgggcttgaa    540
cacacttgta ttgtaacaat agcctcggtc gaggtgaggt ggaagaagca aagcaatctc    600
cgtgagcggt g                                                         611

<210> SEQ ID NO 197
<211> LENGTH: 1500
<212> TYPE: DNA
<213> ORGANISM: Oryza sativa

<400> SEQUENCE: 197

tatttaagta agacaaataa tgaaatgtta tttttaaaag tcaatagttt taaaactgag     60
aaaatatatg ttagaataaa aaggattaga aaattttcga tgcaaaagat cagcagattg    120
atatggagct tattttattt gtcacgatta tctcttccta gttcccagcg agtggtggtg    180
actaataact tcacaaaaat agagaaaaca taaaataaca ataatagctt ttcagtaaac    240
aaccattgat agagtagaca tgaacctgct ttatgcctac ctacgacctt accatccggg    300
ccatttccag gccattttca gtgttatcaa gtgcttgaca taatggcatg gcccaacaca    360
tcaataagca ccatgaattt gtgatcttct gaatctcctc tgtgctgcga gcgatgcggc    420
gtggtatttt gattcttcct tgaacgtgca ttatacacct ctagcgcgcc gaatgtatga    480
tgacatatta taaagaaatg cataaacttt gtggaagaaa tatataaagc acatgaatga    540
tgagaatgaa atctatccca taatataggg catattcggc aagctggttg cggctgcgct    600
tttcggcact gtcggtgtca gctacgccgt ttgcgcaaaa cagacagcca aacatacccg    660
taatttatag ttccaatatt ttctttcttt agaaaatatt tttcgataaa gtttaaaaaa    720
tatttgctga agtttaatag gacatctact tttagataag ccatgactag gctaggtgat    780
tgtgtacctg atctatcact aacttattag tatgtccaca agcacatatg taaaagaatg    840
taaactttag taccataaat gttataacat atattgtaaa ccctacacat atcatcgcca    900
ggcacgtaaa taaccctatg ttggtatagt tgttaatagg ttgatgcttg acaagtctat    960
tctcgttgat gtttttttt aattatactc attcaaaata aaatataatt gatagttctg   1020
tgctgattta gtttagaaaa atatacacga actcccaaca actcaacaaa caaacacgta   1080
cacaaccttc tcaattctca ctatgaacta gaggccacaa accagacgcc aaactcgcgg   1140
atcatacgtg atcacgccat gcatatgcgt tcggttgtcc gcgagcgacg gacggacggt   1200
tgagtcccga agaatcgctc aatcaatgag gggcaaaacc gtaaactcac tcaccccac    1260
aggaggtgac ttcccccct tccccaaatc gacgatttgt tcacggcagg tctcccgatg   1320
cgtgccacgt gtacggcgga tggcctccct ccctctctat aagtagcaac cctctccgcc   1380
cccctccctg cgtgtggttc aggtgctgaa ggtgatattc agattttcag agtgagtgct   1440
cgtgtgttgt gcgatcagtg cccgcagttc gatcgatccg tgttgatctt tgaaagaaag   1500

<210> SEQ ID NO 198
<211> LENGTH: 1500
<212> TYPE: DNA
<213> ORGANISM: Oryza sativa

<400> SEQUENCE: 198

tattctgtga atcatatgga caacaatgta aaatctcata gtaattctta tttaggttgt     60
ttgcagaaag ttaatttggg tcaactgaaa tgaaagcttg tctgttggct ctctcactga    120
```

```
attgacccca ttgtaattaa tgcatataat tggcctatat attacacttt caatatcgta    180

aaaccttttt ctttgtacac ttcacctagt tgatctagta tctgccgggc tcatcgggct    240

tatcttgtca atgaacagta ataagagcta tgtcgggctg tttgctgtgt gcttctgttc    300

aaccaatttc gacacagtgt actttgcgaa attgggaatt gagatgcttg gtgtgaaaat    360

tggctgtgct atcatgatga tggcccatga gcccacgaaa cctcacgact cttaattcat    420

ttacttgttt ccggttaaga gaaattgttt cagatattta caatgttttt gaaatataag    480

tttaatccgt ctcaaaggtt gttttaataa ctatttttc tctgtagaaa ttctgataaa    540

attataatat tatgaaactt tttttaggaa agttctatgc atataattgt catgaattta    600

atagaaatgt ttatagtgaa attaatgtcc taagattcaa acttttctct tacaaatata    660

ctccatgcta tgtttttacc aaaagatcaa tgaggtatta gcatatagta accggctcac    720

aggcgctcgt gtccgtcagg gcgctctaaa cctccatcgc acagtttcta tccgatcacc    780

ttcaccctcc gtctccagta gtaggatcca atctttccca agtttttttt atctttattt    840

aagttcctat agaattaggt ctattaggtt gtctagggtt tgtctttcaa atttttcatg    900

gatcagatgt gtagtctttt gtttcttcta tttatttatt ctagttacct tattgaggtt    960

ctcggtgaaa aactagtaag atttgtatgt cgggttgtcg atgatcaagc cagtgacacg   1020

ctttaaggct tgagtcgcta actttttcgt ggtgatggtt agttgttttg ttgtaggaat   1080

agagatggta gcatatactt tcatattcaa tgcttttgta tgtgctggaa tttgtcaatg   1140

gtgttggctt cacatttgct aatgtatagg aatttcaaga cgtggaatct ctttgggctg   1200

tgttgccaga tcaaaacagg cccaaaaagt tttagagtta gacaaatata taatacgttt   1260

attctgtgtt gaaaatatta ttatattttt ttataaactt aattaaactt aaaaatgttt   1320

gattataaaa aaaattaaag tgattgtaat atgaagagag caagtaaata taaatgaagt   1380

gaggtccaca cacgttgacg aggcaacgag atacggcacc aataccaatc tctgactcct   1440

ccggcctccg gcggccggcg agagagatcc caccctcacc gacgacggcg agcgaccacc   1500
```

<210> SEQ ID NO 199
<211> LENGTH: 1500
<212> TYPE: DNA
<213> ORGANISM: Oryza sativa

<400> SEQUENCE: 199

```
agattaatga ttacagtggt actattttga taaattattt tgttcccagt ttatatgaat     60

tttaaaattt tagatcacaa ttttacatat aaactacaaa tctatggtgg atctgagatc    120

tgtagttatg ccaaagaata cctcatattg ctgatccttt ctcgtatgct ttctaatgga    180

gctagtatct gcagctgtat tatcagaaat acatttaaat gagatatgtt ttgtatgacc    240

cagttgacgg cctcacaaac cctaaacagg agggaaccaa gcctgagctc taggcttggc    300

tcctaaatcc cattcaaata ttcttaaaaa aatcacatat ttcttttttt taaaaaaaat    360

agtaggatga ttaggccgaa tatgtcagtt gagccttagg cgtggagaat tttaatttgg    420

ctctgtcacc accatcagga attgaagcag ggaaatgaga gctataaccg ttgaataacc    480

tctcaaaaaa tccctgaatt ttagctgcat gagcagctta aatgtgggat caatattcat    540

taagctcaag ttactaactt gaaaaatata cagcatgtgt gtgttgtttt gaactctaaa    600

aatacctaga cggagttatg cattattgaa aacataacat atgaatgcaa acttatacta    660

gaaaaaccca tgaattctaa ccttagtggt ttttcaccaa tatttctaat aaggggtcaa    720

cctttggaag atgagaactc taccatttga acacatgaat agtgaaaaat caaactatta    780
```

```
aagcttgacg ggctagggcc ataactgagc attgccacgt cagattattg tacaattata    840
ctactctagc agtacataca ctcttggctg tgtactgttg tacgaaacgg agagtccaaa    900
gtagtagact gtccatatag ttcagtttga tggatttcac ccggagatac accgtacgat    960
ttaattgtaa taatacatag aaccatttgt tttttttttg aactgaagaa ccatttgttt   1020
ttcatttact tttactttaa aacatggaca atgaatttgt ttttgaacag ggcttgaaac   1080
tcttaactcc gagcaaatga aaattcaaac agcagtggat tcaatattca actcgaaacc   1140
cctccttttt ttcaactaaa aagtccgcaa aacttcccaa taattaaacc gtgaaatttc   1200
agcgagacct gtatttaaaa atatgggcca aattcaaaat ccaaagcaat aaacaactgg   1260
gctacacaca acatgcgacg gcccatctca tcaagcaaca aggcccagcc cactcgacac   1320
ccaccgaatc cacgccgctc aatcgaaacc gacggtccag atctcgccgc gccaacccca   1380
tcacacaaac cctagcaacc ccccacctat ataacctctc tccctcacgc cccgcctcca   1440
ttcgcacgcc cgcgccacca caaaacccta gccgccgccg ccgccgccgc cgccgccgcc   1500
```

<210> SEQ ID NO 200
<211> LENGTH: 1500
<212> TYPE: DNA
<213> ORGANISM: Oryza sativa

<400> SEQUENCE: 200

```
cattttattt ttatagatat tgttggttaa agtagcatct cgaagactgt gtcaaagtct     60
aaaatactta tattttagga cggagggagt atatttcagc actatcgaac tttggcgttg    120
agaaactgtc catctctaca aatagtagtt tttgacatgg tctattttaa aaatatattt    180
ttaaaagaat taatttatca aattttcggg agacaacgag gccaagaaga agatgcgaaa    240
ccaccgggcc caactcagag agaactacaa aggacaggcc cagcccaacc cacgacaaag    300
atccaaccgt ccaatctaaa ccgacggctc agatctcacc taattccaaa cccaaaccct    360
agccactacg cccctagaca gatataagct cgtctccttc tctcgccgcc ctctccttcc    420
ctcgccgccg cccgagccac tacactatcc acctcgccgc cgccgccgcc gccggaaatg    480
gccgccgccg cgcgcccccct ggtgtccgtg aaggccctgg agggcgacat ggcgacggac    540
tcggccggca tccagatgcc gcaggtgctc cgcgcgccga tccgccccga cgtggtcacc    600
ttcacccaca agctcctctc ctgcaaccgc cgccagccgt acgccgtgtc gcgccgcgcg    660
gggcaccaga cctccgcgga gtcgtggggc acgggccgcg ccgtgtcccg catcccgcgc    720
gtccccggcg gcggcacgca ccgcgcgggg cagggcgcgt tcggcaacat gtgccgcggc    780
gggcgcatgt tcgcgcccac caagatctgg cgccgctggc accgccgcgt caacatccgc    840
ctccgccgca tagccgtcgc gtccgcgctc gccgccaccg ccgtcccgtc cctcgtcctc    900
gcccgcggcc accgcatcga gggcgtcccc gagttcccgc tcgtcgtctc ggactccatc    960
gagtccatcg agaagactgc gcagtccatc aaggtcctca agcagattgg tgcctacgct   1020
gatgccgaga agaccaagga ttcggtggcc atccgcgctg gcaaggggaa gatgcgcaac   1080
cgccggtaca tcaatcgcaa gggccccctc atcgtctacg gcaccgaggg ttccaaggtc   1140
gtcaaggctt tccgcaacct ccccggcgtt gatgttgcca atgtggagcg cctcaacctg   1200
ctcgaccttg cccctggtgg ccaccttggc cgcttcgtga tctggaccga gtgcgcgttc   1260
aagaagctcg acgaggtgta tggtggcttc gacacaccgg cgctgaagaa gaagggcttc   1320
gtgctcccga ggccgaagat ggcgaatgcc gacctgtcca ggctgatcaa ctccgatgag   1380
```

gtccagtcgg tggtgaagcc catcaacaag gaggtgaagc tcagggaggc gagaaggaac 1440
cctctgaaga atgtggccgc tgtgctcaag ctgaacccct acttcggcac tgcgcgcaag 1500

<210> SEQ ID NO 201
<211> LENGTH: 1088
<212> TYPE: DNA
<213> ORGANISM: Oryza sativa

<400> SEQUENCE: 201
aggtttcgtt tgttggttgt tgacaattcc ttaaattctt tagcatcttc tgtactcgct 60
gaagctctgt tagaacaacg ttgcagaggc taatcatatg cttgtgttcg ttcttacttg 120
atgctagttg tatgatatga ttcagctgta ttactggccc tgtttgggtg agcttaattt 180
agagaaactg gaatatgttt ctagattcta attctatatc tatagtaact atacatatca 240
gaatatgtat gaaaaattag actatgtaag aagggtgtgt tcacactaaa attggaagtt 300
tggttaaaat tggaacgatg tgatggaaaa attggaagtt tgtgtgtgta agagttttga 360
tgtgatgaaa aagttgaaag tttgaagaaa aattttggaa ctaaactcgg ccgaagtttt 420
ttgtttagag catcaccaat gtatatggca aagtgatcta tatagatggg acccacataa 480
atagtttatc cctatgataa tgtccacaat gtatagatac aaggtatcat taggagaagg 540
agaagagaga ggagtagaga tagataatat aatttatttc atatgggtag tccatatgta 600
tatgggtatt ttttgctatt ttttttatat ggactagttg cacaatgata ataggtggct 660
gaatggaata ttctattgtt tatagactac ttttatattg tggatgccct taggaaaagc 720
taaaccccta tcggcgcctt tctatgcctc tctatcacct tttggtcatt cggttcatcg 780
cggatcgacg agaaaccagg ttggcccgaa tcaatcggcg ccggcggcct ccgcggtttc 840
cgccttcggg taggcgcctg cggcatcaac aaagcacaca gccgaaaccg aagccttttc 900
tttcttccgc cccaagaagc tgtgccacgt gtttcctcct tcccctcctc gatttaaccg 960
ccccatctcg agtcccccca tcacagcttc cactccacga aaccctctg cctccttcgc 1020 tcgctgcacc ctcgtctcgg cgatccatcc ttggctgcca ggaagttctt cgtcggcggc 1080
aactggaa 1088

<210> SEQ ID NO 202
<211> LENGTH: 1500
<212> TYPE: DNA
<213> ORGANISM: Oryza sativa

<400> SEQUENCE: 202
cgctcgcggc gactcacccg gttgcatcgt tcgcccatgc tgtgccactc cacgcttgcc 60
cacgcagctc cttgcccgct gttcgcccat tcacaccgct ccttgcccgt cagttgccag 120
tcggccgcct atctacatca tgccgctcct cgtcccaacc acgccactca ccagccctcc 180
tccagcagct acttgcctcc ttcatctgcc agattccgcc gctacgccca ccacctggtt 240
gctgtcgagc tctagtgctc taccacgtcg tcggaactgg acgtggactg acggtagctg 300
caaaagtttc acatcccatc ccaccctcat tccttccact aaaaagaaaa aaaattgaat 360
catcccatcc tataaatcaa acagttgagt gagatcgtac catccctaga atcaaggaca 420
agttcaacct atcacatctc gcttctaaac caaacacaca ctgacagaac agagggccct 480
gaggattcgg ctcctctgcc tttaggggct aaagactgag gcgcatagca aaatgagttt 540
gccgctacaa tataaaatat taattttgca gttatttact gtagatacag tataaaaagt 600
aaaacgtatt gtgccaaggt actgttcatg atgtattgta ttatatgtag caattaatca 660
cattcgttcg ctataaatcc gatggttgag aataatttaa aaccctaagg gcttgttcgg 720
aatagaggga ttacacagga ttcttgtagg attggcaatt cctttggatt tggcactgtt 780
tatgcattcg gttcatagga accatgcgta ggaatttcgt agaaatactg tagcaacctt 840
gtgaaaacat aggaatttca taagattcta aacatccact cacacctcat ttttttcatt 900
agctatcatg ggatagatgc taatcacgtt gaagtgacta gatgggaact aatattttat 960
tgcttaatta tactataata tactacctca atgcatgaat gtatgacgtt ggttagttca 1020
attttgagct aaccaacgtc aaacaaaaaa atatggaggg agtatgagat taatactaat 1080
tgaaaaattc atgtggttta tatattcttg tgttccgaat gcttcatagc atcaaattcc 1140
ttttcctatc ctgcgatccg aacaagccct aaattctgag gatcccaatc cgggccatga 1200
ccgcctccta tcatcggacg gctatagtgg tccaaagctg acgtggccaa gactggccca 1260
catggcccat gtagtccgtc ctggaccgag tccacggacg gcgcggccga acgcccgcgc 1320
cgtgtctgct tttgttgctt cgttctctcc gcgctccgtg tccgaccttc ttcagacttc 1380
acacctcgcg cgccgccgca gctccgatcg gaagaagctc gattcgtctc cgactccgac 1440
gaccagaagc taccggcgac gcgagcggag aagcgcggag gggagggggc gcgcgccgcc 1500

<210> SEQ ID NO 203
<211> LENGTH: 1016
<212> TYPE: DNA
<213> ORGANISM: Oryza sativa

<400> SEQUENCE: 203
agctcaggac tgactgacta cagacttaca gttacaactt cagaggatgt gaattattca 60
tttctcttgc gcactaacag ttagttcttc agtggttttg ggatgagatc ctaaaaatat 120
cacatcaact agattattaa gaacaaattg attaatattt atacatgctg aaaagcttaa 180
atttgttact actgcgggct tgtttggcac agctcacctc tcctggagct gaagctcagc 240
caaacagttt caactccacc taaaatgaga gcgaagttgg gtggaactct cttacaaaat 300
gaactagaga ggtggagctg gatttaggct gcttcacaac tacattctag acccgactcc 360
tagaactaaa tttaggagtt ggagctctgc caaacagccc tgctactact acatggttaa 420
ggggggtgtt taaatctagg ggtgtaaagt ttttttgttt cacatcgggt attatatagg 480
gtgtcgtatg gggtgttcag gcactaataa aaaaaaataa ttacagaatt tgtcagtaaa 540
ctacgagaca ttttttaagc ctaattaatc cgtcattagc aaatgtttac tgtagcacca 600
cattatcaaa tcatggagca attaggctta aaagattcgt ctcgcaaatt agtcgcaatc 660
tgtgcaatta gttatttttt taccctatat ttaatattcc atacagatat tcaaacatgg 720
tgaaaaattt tagggtggga tctaaacagg gcctaggaac aaaacgagca tcacatgctg 780
atctgccaag ctggctagcc ctaataattt ggaaatgcaa tattccaata tccaaagtgg 840
acccggccca attaacccaa ccaaaaccca cgcccacctc ctctcccctt ctcggctgct 900
cttctccccc tccctatcct ctcctctcac ctcgcaatca catcctcttc ccttctcttc 960
tccatcgcat ctaccaccga gcgtgcaagg aggggggggg gggggggggg gtgaaa 1016

<210> SEQ ID NO 204
<211> LENGTH: 1500
<212> TYPE: DNA
<213> ORGANISM: Oryza sativa

<400> SEQUENCE: 204

-continued

```
taggcttgtg aaaagaatta caaaacttgc tttgcgcaaa agaactatag ccatcctttg      60
aattcccctg tcatgtgcat tattgctgtg gtggcttgct gagtacggtt ggtactcacc     120
cttgcaatat acaaatttaa tcagaggtcg gagatgaagc ttcggaggat ccctacgctt     180
actaacagga gggtgatgaa gacgatggcg cccagtaggt cttagttacg gtcattgcct     240
gtggcaatgg cgtgccgctg ccttaactcc gctgccttac cttcttctgt ttttggaatg     300
tattccggac cgctcggtcc gatgatttaa gactatgcct gcgggcttat gatgcaatga     360
ttcatactag acactcgtgt atgtgcactt gatatttcag ctaagaattc gtgtgtacca     420
gactacttga tccagggaaa tggtactgtt tacacgattg attcctgtta taaaaacggg     480
ggtccacata gatccgccac tgctccctcc tttccttcat atttagactt taataatttg     540
gattttcaca aatgttatct aaataattaa ataaatatca tgctatcgaa gtatattaca     600
taaacataag tattaaactt tctttcatta tgatttaaca aaattgctag aatgctagaa     660
aatttttgtc aaaactttca gatttgttat tattggatca ttttaagatg ggtgcattga     720
atagaaaaat aattgctaga aagaaatttc acataggcta cggataagat cccggtgcta     780
gtcaactaaa ctagtcttaa atacaggttt atatcagtta tactgtagct ataacatagc     840
cacggtataa attaatgtaa ttacaatgcg gttatagtgc agttacaatg taattacact     900
caattacatt atagttacat ttgaaagttt tccctcaaaa aacttgatag ttattttttt     960
aagatactct aacgatttaa tcatctcaaa atttttaata attaaagtta tagatgaacc    1020
ggtaacaatt attacctctg tttcaggtta atatgtcaaa gtcaaactac tttaagtttg    1080
actaaattat agaaaataaa cattttcaac ccatgttaga tttattataa aaatatattt    1140
aattattgat ttaataaaac taatttggta ttataaatat tactatagtt atctacaaac    1200
ttagtaaaat tgaaagtagt ttgattttaa ctaaagttaa aacttctaat aacctaaaat    1260
ggagggagca caccatattt tataccaaag tactgtcagc aattagctga tcggtagaga    1320
cgctgagtaa ctgcacgttc aggtcatcac gcgacctacc aatttaacaa aacgccgtgt    1380
cgtcttgttc ttcttcttat cttttttttt agtcattaat tgatctgcaa tactcttgta    1440
agaggtccag atagctagag aggccattga gagatcatca tcggagctag ctagctagcc    1500
```

<210> SEQ ID NO 205
<211> LENGTH: 1215
<212> TYPE: DNA
<213> ORGANISM: Oryza sativa

<400> SEQUENCE: 205

```
tttcctcctc ctccttcctc gagctgctct aatggcggcg tgggtgatta gcgatgtgga      60
tgtctcatac tcgccatcac cactttagct cccgccgccg ctgccgcttc aactcctgcc     120
cgtgctccct ggctccccgc agccggccga aggactgaga aagagaaaga aagagagaag     180
ggaggaagag gggatggaag gcccgcgcga cgagctatta gctcagtggt agagcgtgcc     240
cctgataatt gcgtcgttgt accatggctg tgagggctct cagccacatg gatagttcaa     300
tgtgctcatc agcgcctgac acgaagatgt ggatcatcca aggcacatta gcatggcgta     360
ctcctcctgt ttgaatcgga gtttgaaacc aaacaaactt ctcctcagga ggatagatgg     420
ggcaattcag gtgagatccc atgtagatct aactttctat tcactcgtgg gttccgggcg     480
gtccgggggc actacggctc ctctcttctc aagaatccat acatccctta tcagtgtatg     540
gagagctatc tctcgagcac agattgaggt tcgtcctcga tgggaaaata gagcacccaa     600
caacgcatct tcacagacca agaactacga gatcatgttg ggaagaagaa aagagatgat     660
```

```
gacatgtggg gccacatgtc agtgtgtccc acaatttttt aatgtgtgtg aatgacacgg    720

atcccacgta tatgttttta attcaaatac cacctaagcg ccacgttaac taaacatact    780

aggtcaacac cgccatgtca gcgccacgtc agcgaaaccg ccctccaaaa ccacgaaggg    840

agtcaaactg caccggtttc aatagttcgg cgtcgaaata tctggttttg cggtttaggg    900

tcatggatta gattcgggtc acttttaagg gagtccaagt ggacttattc cgaaaatatc    960

tggtcattta gcccataaaa aacaggtcca taagattctc tcctaagcta agccacttat   1020

acttgagcac gtatcgtaag gaaaatccac cggtcgtcgc aagcccgcat caacgagcag   1080

gagggatata aaaccctccg ccccctcctc ccccaaaccc ttccgccgcc gccgtcgccg   1140

tcgcctgctc cagcgcgctc gccgccggcc gccctactcc cgctccaggc ccgtcaccgc   1200

cgtcgccgat ccaac                                                    1215
```

<210> SEQ ID NO 206
<211> LENGTH: 1500
<212> TYPE: DNA
<213> ORGANISM: Oryza sativa

<400> SEQUENCE: 206

```
cagtagacct tgttcgtgag tggttgcggc ttctgttgtg tttggtcgcc tttgttcgct     60

agtgcatctg gattccatga tcatgatcat gatgtccatg cagattgatg tggtgactga    120

ctgactgaat gaatgaacag ctgcagctat agctgagggt gtgtttagtt aacgctaaaa    180

ttagaagttt ggttaaaatt ggaatgatac gacggaaaag ttggaagttt gtgtatgtag    240

gaaagttttg atgtaataga aaagttgaaa gtttgaagaa aaaatttgga agtgaataaa    300

cgagtgagct ctccttttcc ttttgaccca ctctgctagc tgcccttctt cccctagtgg    360

ccattttccc ccatactagc cgactttgct actacttgat agtcttatca ctgagaggaa    420

tggacgcaca ttattatatg ctagattgtt aaatcgagag gggattactg ttgcaagtga    480

gacagtacct agcacataat atgaaggtat atattcattc ttcttgggtc gagttgttag    540

caatgctgaa ttatcaatgt ttgccaactg ctagcaatta ggaagaatgg ctagtttgtg    600

gctatgattg atcgatcatc aagctaaaga taatgctatg caagtcgaga cagctcgatg    660

agctcacaca aaggataatc ttccaaactg accactctgt ccgtggtctt gtttggatcc    720

tccgagctat taaatagtcc tctgaaattt tgctatttag gattattaaa cgtagattac    780

cgacaaaacc gattccatag cccctaggct attttgcgag acgaatctaa tgatgtatat    840

taatccataa ttagcagctg attactgtag tattactgta gcaaatcatg gattaatata    900

cctcgttaga ttcgtctcgc aaaatagcct agtggttatg gaatgagttt tgtcagtaat    960

ttacgtttaa tactcttaaa taacgaaatt ccggagggct atttaatagc cctccggatc   1020

caaacagggc ccgtgtcacc taaacaaaaa tggctttaat ttccagaacc tgccccgtag   1080

caaacgaacc catactacta atctatcata tcatcttgtg aattatttat ctctcgctga   1140

caataaccga tgaaccatca aattcaagct tagtaacagt agcgcttcct gtcatccaca   1200

gattaatcaa ggtaaaacaa aaacccctac catcatcgtt gtcgtccact aattactaaa   1260

ttgccgactg ctaaaacaaa atgaataatt aattaattaa ttaattagta aagaggaaga   1320

gaaagagaag gccattggtg cagacgtagt agtggagcag gagctataaa aagaagcagg   1380

aagccactcg ctctcctcac agccacagct cgccatcgtc gtcgtcgtcg tcgtcgtctc   1440

cggctccggc aagagagcta gtagtgagta gtagaaagaa gaagaggcaa attaatagta   1500
```

<210> SEQ ID NO 207
<211> LENGTH: 923
<212> TYPE: DNA
<213> ORGANISM: Oryza sativa

<400> SEQUENCE: 207
ctattatcgg acaacttggc atattgaaat ttctactgtc atgcttcctt gtcccattac 60
tacatcgtcg ttgtgttcaa ctattgcact acctccctcc tagttcaaat ctaatatcat 120
atatgtaacc gcaatggaaa tagttgtatc atgttcaaat tgtactacta tttcttcatg 180
ttacataatt ctccttgttt aagtccatat aatgtttcta caaccgagac tgcgataggc 240
ctattaatta tccgagtact aatacgtcga ataagttaca aaataatacc ttccttaaca 300
tatgaaattg cgaaacaacc aacttcaata catttttata acaatattaa caagttttac 360
caataaatac ttctttattt attattaaca taaaatagaa aaatcgtttg gccgtacttt 420
ttgcatctgg gtcccttgcc gccctctact ggggcagcaa ggggcccaaa tgcaaaaagt 480
acgagcgcaa cctctttatg ggcggcaaaa attgcaatta gccccttgcc gccctctggg 540
ggtaattgca attttggccg acggcggcag acggcacggt cgacccgccg tctgccacgt 600
cagcttgccg cccaccactg ggcggcaggg gtctattttt gtattttttt tggccgatag 660
attatttctg taaatattaa aaaaaatcta aaaatgaaaa aaattcgtgc tacactgcta 720
ctgctccggt gctccctcat ctccttctcg attcttctgc tcctccaccg agagcggggc 780
gagcaggcga ggccacacga ttctcctctc ccttgccgct tccaacacca agtctcgccg 840
tggccaggac tgagctaggg tttgcgtgat cttcgggagg agggagcagg agagagttcg 900
aggaggagga ggaggaggag aag 923

<210> SEQ ID NO 208
<211> LENGTH: 1500
<212> TYPE: DNA
<213> ORGANISM: Oryza sativa

<400> SEQUENCE: 208
ttcgtaaaaa taaaaaacga agaacgaact cgaccaaact agcctctctc tctctctctt 60
aaaatctttc gatcatctca gttctggtct tattatagtt tgcttttcag tttctgttag 120
tttcccatct ttagaaagcc gaaaaatcaa ccttcttccc acatcgatcc ccatgttata 180
tcgtcttcac tgttgctttt aaaaaaaata tagaatgtga aaatgtctgg ttacgataaa 240
aaggaaaaca cccggatacg attattgaac catgtcgata ttagctagag agataacaac 300
tgagtagagc ataataaagc aattagatcg ccatatccaa caaaatatgg atggccatat 360
cctatccatg catgaccgtg aaccaaacac actctaagtt atgtatgtta tccaagaaga 420
caaaaaaaaa agatataaat atagctgaat gagagatact ccatccgtcc ctaaaatata 480
agagattttg gttggaagtg acacatccta gtccaacgaa tttggacatg cttctgtcca 540
gattcattgt aataagatat atcacatccc accaaaatct cttatattta gggacgtggg 600
gagtagttca taattataga gttagtggca catgatggga agcaagtgag agttgcatag 660
gatttgggca gacttggcag gttggcttcc gtcccataat atagcaatct aggatgggat 720
ggaatctatt ataggacaat gtatctagac atgactcgta atatagcaac ctaggatggg 780
atgagatcca tcctaggact agatatatta tgggacggag ggagtagttt atactttggg 840
taaaaacata aaccagtagg aaaaaagaag caattatttt tgcacatttt tctcttttac 900
gtgaataagt tttggtggtc gttcagaaag agaatttgaa tttccaaaag actgtataaa 960

-continued ccgtgtagta taactgtaaa ccaattggcc accactactt ctgttggaca gaaaagcatg 1020
aagtacagta gtaccgtatt tgtacaacat acagatacag ggagggaggg cccacacacc 1080
agactagtct agtcgcatac ggatcggatc cacagactag ctggctagct gctacggttg 1140
ttggtgtgga gtacacagaa aagaaaaaaa aaaggaacca tgtggttggg gtcggtgaga 1200
caagcgccct tacccaccaa ccaaactgac tatgactggt gggcccttcg acctactccc 1260
actatacaac tctactgctc ctcaatcctc tcctcctcct cctcctcctc attcgcgatc 1320
tctctctctc tctttctttc gtcgttggat ccaaagctcc tcctcctcct cgcctcgcgc 1380
tcctcgtccc ttctctcgtc ccatctctca tctcatctct tggtagttgc cagttgggac 1440
ttgggagaga gaggagcagg aggcaggagc aagaggaggg caagatcgat caagatcaac 1500

<210> SEQ ID NO 209
<211> LENGTH: 294
<212> TYPE: DNA
<213> ORGANISM: Oryza sativa

<400> SEQUENCE: 209
tatgcttgtt cgtcagttgt gtttgtgtca aatgagcaag tttgtaactg tggacaggat 60
gacaagtggg aactcgatgg acaatgcatt tgctttggtg cggaggccca tcaaatgcag 120
cccagcccag ggaggtccct atcgagtagt aagtgagtag aagaaaagtc tgatctccac 180
ccacgggcgg agttgacata ctagtagtag tagtactagt acacgaggag aagaagcaag 240
aggaagggca tccagaatca gatccacaag gcagcagctg cagcagcatc gacc 294

<210> SEQ ID NO 210
<211> LENGTH: 601
<212> TYPE: DNA
<213> ORGANISM: Oryza sativa

<400> SEQUENCE: 210
gatctcaacc ctacgattaa atacgatcaa cggcgcggat tactttctac tgcaaataga 60
aagcattgga gtggggctct ttcttctttc gtttctattc atgtacagtt tagaaatgat 120
tttttaaatt tgaaatttta tttattgaaa tttaaaaaat aatttttggt ttcaaagttt 180
tacaaatcta cacccctaaa cctttctatg acgttacaac gcaccaatga atatgtgccc 240
gtcataaaaa aaaacctgtt tggaagagag agcgttaggg gtgtaaattt ataaaacttt 300
gagaaaaata ttttgtaaat attttaataa ataaaattaa aacttgaaaa aaaatcctga 360
aaaaaccggg gaactgtcta ctggagtaca gcccatcaaa gagacgaggc ccatagccca 420
tcggccacca caatccttct cgattcttct gctctccacc gagaggagca aggcgaactg 480
caggcggaga ggctgggcca cacgataccc tcctctccct tcccttccct tgccgcttcc 540
aactccaagt ctcgctgtga tcaggagcta gggtttgtgc gatcttcggg aggaggggaa 600
g 601

<210> SEQ ID NO 211
<211> LENGTH: 1077
<212> TYPE: DNA
<213> ORGANISM: Oryza sativa

<400> SEQUENCE: 211
cttgtgtgga aggaactggc aggccaatgg atgagggacc agatgcaaga gggggaagag 60
acgggagaag gatatgcagg cagctacagg tggagaattc gcatgccttc cctacatgag 120

```
caccgacaga gtcgaacccc tagctcatct gaaattagga acatgtccaa ctcaacagga    180
agtacatttt ggggaaaaac agaatacgga ccaacgggat agggggggaga gcatgtggga    240
ggagggagga gagtaagacc tataatgtcg gccgaggcag ccgccgaccg tcgactccct    300
ggcatcactg gagcttggag tagccaattt ggggatggat tttgaatcgg agccctgccc    360
ctgtgcattt gggcagtggg tagagtgagg gggttaacgt gctaaatgtc tggatgagac    420
ggggtcgttt ctgaaagttt caacacgtac gacgtagata ctccctccat cccagaatat    480
aacaacctaa aatgagacga gacctatctt aggacaatgt atttggacac gcctcatata    540
taaatacatt gtccatccta gattgataca ttctgagatt ggaggtagta gatcacagac    600
gtacatttta tatttaacag aaatttacta tagtttacac ggtagatgta gaggctgttt    660
ggttcttaac taacattgcc ataactcact ttaggcaatg ttagataagt gtggcttgtc    720
acagttttta tgacctacaa attataagcc acaattgtgg caaagttaga caaagaattg    780
agtctataac atgtggggta agatggtaag aaagtacgac ttgtcataac catggcaata    840
aaccaaacat aagactctaa agacatgtga cagcctaaaa tatggtgtga caagttgaag    900
cattgagccc cgtagtctcc gccacatatc tctttccttc ttcctcaccc ccaccaccac    960
ctcttctctt tcccccacca acaccaaccc cacgcgacca cccccaatcc tcgatcaaac   1020
gccctaggat ttcatcgcaa gcaaggaagg aggagaccaa atccaatcca atccccc      1077
```

<210> SEQ ID NO 212
<211> LENGTH: 1500
<212> TYPE: DNA
<213> ORGANISM: Oryza sativa

<400> SEQUENCE: 212

```
taacttttat atagaaaatt ttttaaaaaa cacatcgttt agccgtttga aaagcatgcg     60
catggaatac tagtaagagc ggttgggagt cctttgcaac gaaaacagcc ttagtagcaa    120
gcacaaacta actcagcttt agaggcccct catattgatg tttaacttgt tatggggcat    180
ttatttctac acagtctcat ttatcaactg aaactaaaaa ggttgtccaa ttccgtcctc    240
cttttgtaac ggctcgcaaa tacaatgggt tgtttagatt catgtcattt taaatcatat    300
tattttttat aaagttatca aaatgtacat atatttattt atttttacca aactttacta    360
aatgagataa tccaacaaat ggcatttaaa gcgttcaaat ccaagaaatg ccatcgccgt    420
tatgcttccg tccgtttcac gccgttaaaa tacaatgttc atcctataac acttaatggt    480
gtggaatgga cggaacccta acggcgatgg catttttggg ataaagtcgt ttgtacgatg    540
gcatttctta gaactcatat ttgtcgatgg cattttttga atttggatga ttgtcaatgg    600
tatttttttgg attatctctt agtaaataca taaggaatca tgccaaaact tgacaatatt    660
gtcaacttat caaaatttaa ttgggattat tttggcgata atatgaacag cccttacatt    720
tctgaagaat tatagctcaa atatggctat ggccctgttt ggattcggag ggctatttaa    780
tagccctccg gaatcttgct atttaagagt attaaacgta gattactgat aaaactcatt    840
ccataacccc tacgctattc tacgagacga atctaacgag gtatattaat ccatgatttg    900
ctacagtaat cagccgctaa tcgtggatta atatacatca ttagattcgt ctcgtaaaat    960
aggctaggga ttatggaatc ggttttatcg gtaatctatg tttaatactt ctaaatagca   1020
agattccgaa gggctattta atagctcgga gcatccaaac aaggcctatg tttagatcca   1080
aacttccaac tttttctatc acattaaact gtcatacata cataactttt cagtcacatc   1140
gtaccaattt caacccaaac tttcaacttt ggaagaacta aacacagcat atgacagtgc   1200
```

-continued

```
agttcagctc aattttgttc ggagcctaaa aaaaagaaaa gaaaaaaagc tcaatttgga   1260

taaggctatg aataaactca aaaaagcatc caacctaacc accacactgg cccaccaggg   1320

cccacgctcc actcccgtga tcatcacctc cttccctttc cagaaccacc ttctccttcc   1380

ttcctcctct tcttcttcag tgtactctgc ctttataaca ccctactcct ctctctcacc   1440

tccaccatct agctcactca cacagtctcc actcacacgc attgcagagg agaggcgaca   1500


<210> SEQ ID NO 213
<211> LENGTH: 1202
<212> TYPE: DNA
<213> ORGANISM: Arabidopsis thaliana

<400> SEQUENCE: 213

gttttgtgta tcattcttgt tacattgtta ttaatgaaaa aatattattg gtcattggac     60

tgaacacgag tgttaaatat ggaccaggcc ccaaataaga tccattgata tatgaattaa    120

ataacaagaa taaatcgagt caccaaacca cttgcctttt ttaacgagac ttgttcacca    180

acttgataca aaagtcatta tcctatgcaa atcaataatc atacaaaaat atccaataac    240

actaaaaaat taaaagaaat ggataatttc acaatatgtt atacgataaa gaagttactt    300

ttccaagaaa ttcactgatt ttataagccc acttgcatta gataaatggc aaaaaaaaac    360

aaaaaggaaa agaaataaag cacgaagaat tctagaaaat acgaaatacg cttcaatgca    420

gtgggaccca cggttcaatt attgccaatt ttcagctcca ccgtatattt aaaaaataaa    480

acgataatgc taaaaaaata taaatcgtaa cgatcgttaa atctcaacgg ctggatctta    540

tgacgaccgt tagaaattgt ggttgtcgac gagtcagtaa taaacggcgt caaagtggtt    600

gcagccggca cacacgagtc gtgtttatca actcaaagca caaatacttt tcctcaacct    660

aaaaataagg caattagcca aaaacaactt tgcgtgtaaa caacgctcaa tacacgtgtc    720

attttattat tagctattgc ttcaccgcct tagctttctc gtgacctagt cgtcctcgtc    780

ttttcttctt cttcttctat aaaacaatac ccaaagagct cttcttcttc acaattcaga    840

tttcaatttc tcaaaatctt aaaaactttc tctcaattct ctctaccgtg atcaaggtaa    900

atttctgtgt tccttattct ctcaaaatct tcgattttgt tttcgttcga tcccaatttc    960

gtatatgttc tttggtttag attctgttaa tcttagatcg aagacgattt tctgggtttg   1020

atcgttagat atcatcttaa ttctcgatta gggtttcata gatatcatcc gatttgttca   1080

aataatttga gttttgtcga ataattactc ttcgatttgt gatttctatc tagatctggt   1140

gttagtttct agtttgtgcg atcgaatttg tcgattaatc tgagtttttc tgattaacag   1200

gt                                                                  1202
```